US012559494B2

(12) United States Patent
Canney et al.

(10) Patent No.: US 12,559,494 B2
(45) **Date of Patent: *Feb. 24, 2026**

(54) FUNCTIONALIZED LACTAMS AS MODULATORS OF THE 5-HYDROXYTRYPTAMINE RECEPTOR 7 AND THEIR METHOD OF USE

(71) Applicants: Temple University - Of The Commonwealth System of Higher Education, Philadelphia, PA (US); Praeventix, LLC, Exton, PA (US)

(72) Inventors: Daniel J. Canney, Philadelphia, PA (US); Benjamin E. Blass, Philadelphia, PA (US); Kevin M. Blattner, Exton, PA (US); Douglas A. Pippin, Exton, PA (US)

(73) Assignees: Temple University-Of The Commonwealth System of Higher Education, Philadelphia, PA (US); Praeventix, LLC, Exton, PA (US)

( * ) Notice: Subject to any disclaimer, the term of this patent is extended or adjusted under 35 U.S.C. 154(b) by 751 days.

This patent is subject to a terminal disclaimer.

(21) Appl. No.: 17/054,468

(22) PCT Filed: May 10, 2019

(86) PCT No.: PCT/US2019/031824

§ 371 (c)(1),
(2) Date: Nov. 10, 2020

(87) PCT Pub. No.: WO2019/217890

PCT Pub. Date: Nov. 14, 2019

(65) Prior Publication Data

US 2022/0306629 A1 Sep. 29, 2022

Related U.S. Application Data

(60) Provisional application No. 62/670,116, filed on May 11, 2018.

(51) Int. Cl.

| | |
|---|---|
| ***C07D 401/06*** | (2006.01) |
| ***C07D 471/10*** | (2006.01) |
| ***C07D 487/04*** | (2006.01) |

(52) U.S. Cl.

CPC ......... *C07D 471/10* (2013.01); *C07D 401/06* (2013.01); *C07D 487/04* (2013.01)

(58) Field of Classification Search

CPC .. C07D 207/20; C07D 209/96; C07D 401/06; C07D 401/12; C07D 471/10; A61K 31/4015; A61K 31/497

See application file for complete search history.

(56) References Cited

U.S. PATENT DOCUMENTS

| | | | |
|---|---|---|---|
| 5,066,651 | A | 11/1991 | Gilbert et al. |
| 5,455,348 | A | 10/1995 | Thomae |
| 9,802,924 | B2 | 10/2017 | Canney et al. |
| 2004/0229874 | A1 | 11/2004 | Bright et al. |
| 2010/0069390 | A1 | 3/2010 | Breder et al. |
| 2010/0197700 | A1 | 8/2010 | Badescu et al. |
| 2015/0291539 | A1 | 10/2015 | Canney et al. |
| 2016/0016941 | A1 | 1/2016 | Canney et al. |
| 2017/0298037 | A1 | 10/2017 | Canney et al. |
| 2018/0221365 | A1 | 8/2018 | Canney et al. |
| 2019/0367528 | A1 | 12/2019 | Canney et al. |
| 2020/0039985 | A1 | 2/2020 | Blass et al. |
| 2020/0331915 | A1 | 10/2020 | Blass et al. |
| 2021/0238189 | A1 | 8/2021 | Canney et al. |

FOREIGN PATENT DOCUMENTS

| | | | |
|---|---|---|---|
| CN | 103570722 | A | 2/2014 |
| CN | 110272425 | A | 9/2019 |
| EP | 1875899 | A1 | 1/2008 |
| JP | 2003020259 | A | 1/2003 |
| JP | 2003500488 | A | 1/2003 |
| JP | 2005533011 | A | 11/2005 |
| JP | 2006025227 | A | 1/2006 |

(Continued)

OTHER PUBLICATIONS

Bhandare et al. "Bioisosteric Replacement and Related Analogs in the Design, Synthesis and Evaluation of Ligands for Muscarinic Acetylcholine Receptors," Med. Chem. 2014, 10:361-375.

(Continued)

*Primary Examiner* — Brian E Mcdowell
(74) *Attorney, Agent, or Firm* — Proskauer Rose LLP

(57) ABSTRACT

Pharmaceutical compositions of the invention comprise functionalized lactam derivatives of formula (I) having a disease-modifying action in the treatment of diseases associated with dysregulation of 5-hydroxytryptamine receptor 7 activity, wherein A is selected from a group consisting of:

(I)

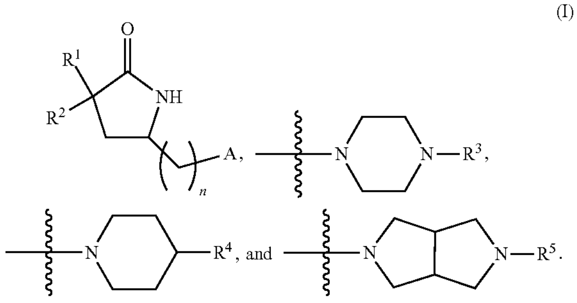

and

19 Claims, No Drawings

(56) References Cited

FOREIGN PATENT DOCUMENTS

| | | | |
|---|---|---|---|
| WO | 2002070523 | A1 | 9/2002 |
| WO | WO 2003/087057 | A1 | 10/2003 |
| WO | WO 2011/098776 | A1 | 8/2011 |
| WO | WO 2012/058769 | A1 | 5/2012 |
| WO | WO 2014/085413 | | 6/2014 |
| WO | WO 2014/164756 | | 10/2014 |
| WO | WO 2016/040554 | | 3/2016 |
| WO | WO 2016/183150 | | 11/2016 |
| WO | WO 2018/093818 | | 5/2018 |
| WO | WO 2018/175188 | | 9/2018 |
| WO | WO 2018/175190 | | 9/2018 |
| WO | WO 2019/217890 | | 11/2019 |
| WO | WO 2021/097116 | | 5/2021 |
| WO | WO 2021/097117 | | 5/2021 |

OTHER PUBLICATIONS

Bhandare, et al: "Modifications to five-substituted 3,3-diethyl-4,5-dihydro-2(3H}-furanones en route to 4 novel muscarinic receptor ligands.", Medicinal Chemistry Research, (2011) vol. 20, No. 5, 2011, pp. 558-565, KP055283393.

Bian, Z. X et al. "5-Hydroxytryptamine promotes hepatocellular carcinoma proliferation by influencing B-catenin." Molecular Oncology, 2016, 10, 195-212.

Cowen, Philip J., and Irwin Lucki. "Serotonin revisited." Psychopharmacology (2011) 213: 167-169.

Díaz-Cervantes et al. "In vitro and in silica evaluation of twelve newly-synthesized 1-acetamide-5-methoxy-2-oxindoles as 5-Ht? receptor ligands." Bioorganic & Medicinal Chemistry Letters, Pergamon, Amsterdam, NL, vol. 25, No. 7, Feb. 13, 2015 (Feb. 13, 2015), pp. 1580-1585, XP029148565.

Gao et al., "Hornologation as a lead modification approach en route to a series of lactone-based muscarinic igands;" (Mar. 14, 2013) Med. Chem. Res. 23:1023-1030.

Gautam, J. et al.: "Tryptophan hydroxylase 1 and 5-HT7 receptor preferentially expressed in triple-negative breast cancer promote cancer progression through autocrine serotonin signaling." Molecular Cancer, 2016, 15, 75, 1-14.

Gautam, J. et al: "Up-regulation of cathepsin S expression by HSP90 and 5-HT 7 receptor-dependent serotonin signaling correlates with triple negativity of human breast cancer." Breast Cancer Research and Treatment, 2017, 161, 29-40.

Halici, Z. et al.: "Liver 5-HT7 receptors: A novel regulator target of fibrosis and inflammation-induced chronic liver injury in vivo and in vitro." International Immunopharmacology, 2017, 43, 227-235.

Halici, Z. et al.: "Peripheral 5-HT7 receptors as a new target for prevention of lung injury andmortality in septic rats." Immunology, 2013, 1271-1283.

Hauser, S. R. et al. "The 5-HT7 receptor as a potential target for treating drug and alcohol abuse." Frontiers in Neuroscience, 2015, 8, 1-9.

International Preliminary Report on Patentability and Written Opinion of the International Searching Authority for PCT/US19/31824, 7 pages, dated Nov. 17, 2020.

International Search Report for PCT/US19/31824, 5 pages, dated Jul. 23, 2019.

Kim, Janice J., et al. "Targeted inhibition of serotonin type 7 (5-HT7) receptor function modulates immune responses and reduces the severity of intestinal inflammation." The Journal of Immunology 190.9 (2013): 4795-4804.

Modlin, J. M. et al., "Serotonin and the 5-HT7 receptor: The link between hepatocytes, IGF-1 and small intestinal neuroendocrine tumors." Cancer Science, 2013, 104, 7, 844-855.

Pytliak, Marek, et al. "Serotonin receptors—from molecular biology to clinical applications." Physiological research 60.1 (2011): 15-25.

Vanhoenacker, P. et al. Trends in Pharmacological Sciences, 2000, 21, 2, 70-77.

Volk et al. "Optimization of the (Arylpiperazinylbutyl) oxindoles Exhibiting Selective 5-HT7 Receptor Antagonist Activity," J .Med. Chem., vol. 54, 2011, pp. 6657-6669, XP002793163.

Witkin, Jeffrey M., et al. "Constitutive deletion of the serotonin-7 (5-HT7) receptor decreases electrical and chemical seizure thresholds." Epilepsy research 75.1 (2007): 39-45.

U.S. Appl. No. 17/709,847, filed Mar. 31, 2022, Canney et al.

U.S. Appl. No. 17/776,531, filed May 12, 2022, Canney et al.

U.S. Appl. No. 17/776,533, filed May 12, 2022, Canney et al.

Chen et al., "Rational Drug Design Leading to the Identification of a Potent 5-HT2C Agonist Lacking 5-HT2B Activity," ACS Medicinal Chemistry Letters, 2011, 2, 929-932.

Hedlund, P. et al., "Functional, molecular and pharmacological advances in 5-HT7 receptor research," Trends in Pharmacological Sciences vol. 25, No. 9, 481-486, Sep. 2004.

International Preliminary Report on Patentability dated May 21, 2019 for PCT/US2017/061677. 7 pages.

International Preliminary Report on Patentability dated May 17, 2022 for PCT/US20/60271. 10 pages.

International Preliminary Report on Patentability dated May 17, 2022 for PCT/US20/60270. 11 pages.

International Search Report and Written Opinion dated Feb. 23, 2018 for PCT/US2017/061677. 10 pages.

International Search Report and Written Opinion dated Jun. 4, 2021 for PCT/US20/60271. 15 pages.

International Search Report and Written Opinion dated Feb. 2, 2021 for PCT/US20/60270. 17 pages.

Naumenko et al., "Interplay between Serotonin 5-HT1A and 5-HT7 Receptors in Depressive Disorders," CNS Neuroscience & Therapy, p. 582-590, Jun. 30, 2014.

International Search Report for PCT/US2019/031824 dated Aug. 5, 2019 (5 pages).

Search Report for CN Application No. 201980046137.1 dated May 10, 2019 (2 pages).

Nozaki, Masakatsu et al., Medicinal Chemistry, 1st edition, Japan, Kagaku-Dojin Publishing Co., Inc., 1995, (pp. 98-99) (5 pages).

FUNCTIONALIZED LACTAMS AS MODULATORS OF THE 5-HYDROXYTRYPTAMINE RECEPTOR 7 AND THEIR METHOD OF USE

CROSS REFERENCE TO RELATED APPLICATIONS

This application is a 35 U.S.C. § 371 National Stage Application of International Application No. PCT/US19/31824, filed on May 10, 2019, which claims the benefit of U.S. Provisional Application No. 62/670,116, filed May 11, 2018, which is herein incorporated by reference in its entirety.

STATEMENT OF FEDERALLY FUNDED RESEARCH

This invention was made with government support under HHSN271200800025C and DK115254 awarded by the National Institutes of Health. The government has certain rights in the invention.

FIELD OF INVENTION

Embodiments of the invention are directed to novel compounds useful as modulators of 5-hydroxytryptamine receptor 7 (5-$HT_7$) activity and their method of use. Embodiments are further directed to a novel chemotype useful for the treatment diseases that are associated with dysregulation of 5-hydroxytryptamine receptor 7 activity.

BACKGROUND OF THE INVENTION

Serotonin was discovered in the late 1940s and is present in both the peripheral and central nervous systems [Physiol. Res, 60 (2011) 15-25; Psychopharmacology 213 (2011) 167-169]. Serotonin or 5-hydroxytryptamine (5-HT) is a monoamine neurotransmitter of the indolalkylamine group that acts at synapses of nerve cells. Seven distinct families of serotonin receptors have been identified and at least 20 subpopulations have been cloned on the basis of sequence similarity, signal transduction coupling and pharmacological characteristics. The seven families of 5-HT receptor are named 5-$HT_1$, 5-$HT_2$, 5-$HT_3$, 5-$HT_4$, 5-$HT_5$, 5-$HT_6$, and 5-$HT_7$ and each of these receptors in turn has subfamilies or subpopulations. The signal transduction mechanism for all seven families have been studied and it is known that activation of 5-$HT_1$ and 5-$HT_5$ receptors causes a decrease in intracellular cAMP whereas activation of 5-$HT_2$, 5-$HT_3$, 5-$HT_4$, 5-$HT_6$, and 5-$HT_7$ results in an increase in intracellular IP3 and DAG. The 5-HT pathways in the brain are important targets for drug development in the area of CNS disorders. The neurotransmitter binds to its a G-protein coupled receptor and is involved in a wide variety of actions including cognition, mood, anxiety, attention, appetite, cardiovascular function, vasoconstriction, sleep (ACS Medicinal Chemistry Letters, 2011, 2, 929-932; Physiological Research, 2011, 60, 15-25), inflammatory bowel disease (IBD), and intestinal inflammation (WO 2012058769, Khan, W. I., et. al. Journal of Immunology, 2013, 190, 4795-4804), epilepsy, seizure disorders (Epilepsy Research (2007) 75, 39), drug addiction, and alcohol addiction (Hauser, S. R. et. al. Frontiers in Neuroscience, 2015, 8, 1-9) among others.

SUMMARY OF THE INVENTION

The present invention is directed toward novel 5-hydroxytryptamine receptor 7 (5-$HT_7$) activity modulators, compounds of formula (I),

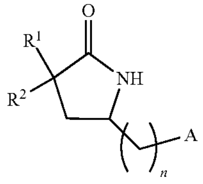

(I)

Including enantiomers, diastereomers, hydrates, solvates, pharmaceutically acceptable salts, prodrugs and complexes thereof, wherein:

A is selected from a group consisting of

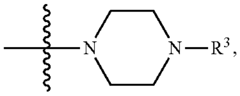
,
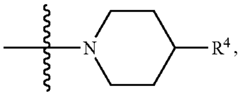
, and
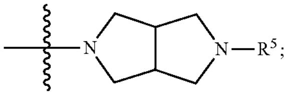
;

$R^1$ is selected from the group consisting of hydrogen, $C_{1-6}$ linear alkyl, $C_{3-7}$ branched alkyl;

$R^2$ is selected from the group consisting of hydrogen, $C_{1-6}$ linear alkyl, $C_{3-7}$ branched alkyl;

Or $R^1$ and $R^2$ are taken together with the atoms to which they are bound to form a ring having from 5 to 7 ring atoms, optionally containing a double bond;

Or $R^1$ and $R^2$ are taken together with the atoms to which they are bound to form a ring having from 6 to 8 ring atoms containing a moiety selected from the group consisting of O, S, SO, $SO_2$, and $NR^7$;

$R^3$ is selected from the group consisting of optionally substituted phenyl, optionally substituted naphthylen-1-yl, optionally substituted naphthylen-2-yl, optionally substituted 2-pyridyl, optionally substituted 3-pyridyl, optionally substituted 4-pyridyl, and

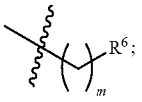
;

$R^4$ is selected from the group consisting of optionally substituted phenyl, optionally substituted naphthylen-1-yl, optionally substituted naphthylen-2-yl, optionally substituted 2-pyridyl, optionally substituted 3-pyridyl, optionally substituted 4-pyridyl and

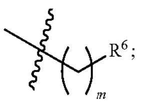
;

$R^5$ is selected from the group consisting of optionally substituted phenyl, optionally substituted naphthylen-1-yl, optionally substituted naphthylen-2-yl, optionally substituted 2-pyridyl, optionally substituted 3-pyridyl, optionally substituted 4-pyridyl and

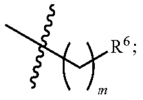

$R^6$ is selected from the group consisting of optionally substituted phenyl, optionally substituted naphthylen-1-yl, optionally substituted naphthylen-2-yl, optionally substituted 2-pyridyl, optionally substituted 3-pyridyl, and optionally substituted 4-pyridyl;

$R^7$ is selected from the group consisting of H, $C_{1-6}$ linear alkyl, $C_{3-7}$ branched alkyl, $C_{3-7}$ cycloalkyl, optionally substituted phenyl, optionally substituted benzyl, $COR^8$, $CO_2R^9$, $CONR^{10a}R^{10b}$, $SO_2NR^{10a}R^{10b}$, and $SO_2R^{10c}$;

$R^8$ is selected from the group consisting of H, $C_{1-6}$ linear alkyl, $C_{3-7}$ branched alkyl, and $C_{3-7}$ cycloalkyl;

$R^9$ is selected from the group consisting of $C_{1-6}$ linear alkyl, $C_{3-7}$ branched alkyl, and $C_{3-7}$ cycloalkyl;

$R^{10a}$ is selected from the group consisting of H, $C_{1-6}$ linear alkyl, $C_{3-7}$ branched alkyl, and $C_{3-7}$ cycloalkyl;

$R^{10b}$ is selected from the group consisting of H, $C_{1-6}$ linear alkyl, $C_{3-7}$ branched alkyl, and $C_{3-7}$ cycloalkyl;

$R^{10c}$ is selected from the group consisting of $C_{1-6}$ linear alkyl, $C_{3-7}$ branched alkyl, $C_{3-7}$ cycloalkyl, $C_{1-6}$ linear haloalkyl, $C_{3-7}$ branched haloalkyl, $—(CH_2)_qCN$, $—(CH_2)_qSO_2R^{11}$, $—(CH_2)_qOR^{12}$,

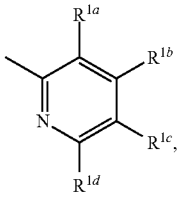

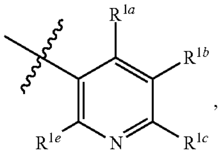
,

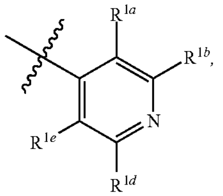

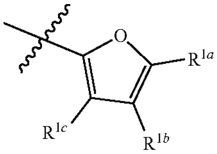
,

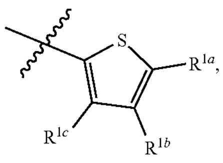

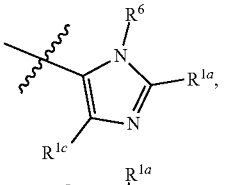

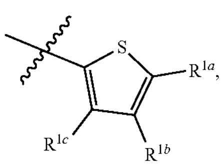

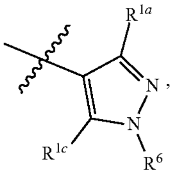

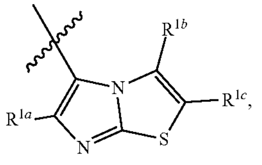

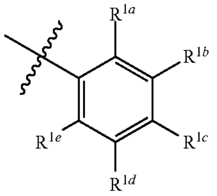

-continued

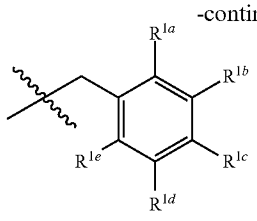

and

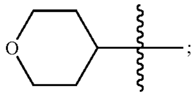
;

$R^{11}$ is selected from the group consisting of $C_{1-6}$ linear alkyl, $C_{3-7}$ branched alkyl, and $C_{3-7}$ cycloalkyl;

$R^{12}$ is selected from the group consisting of $C_{1-6}$ linear alkyl, $C_{3-7}$ branched alkyl, and $C_{3-7}$ cycloalkyl;

$R^{1a}$, $R^{1b}$, $R^{1c}$, $R^{1d}$, and $R^{1e}$ are at each occurrence independently selected from the group consisting of H, OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $—S(C_{1-6}$ linear alkyl), $S(C_{3-7}$ branched alkyl), $—S(C_{3-7}$ cycloalkyl), $COR^{13}$, $CO_2R^{14}$, $CONR^{15a}R^{15b}$, $SO_2NR^{15a}R^{15b}$, $NR^{16a}R^{16b}$, $NR^{16a}COR^{17}$, $NR^{16a}SO_2R^{18}$, and $NR^{16a}SO_2NR^{19a}R^{19b}$;

$R^{13}$ is at each occurrence independently selected from the group consisting of H, $C_{1-6}$ linear alkyl, $C_{3-7}$ branched alkyl, and $C_{3-7}$ cycloalkyl;

$R^{14}$ is at each occurrence independently selected from the group consisting of $C_{1-6}$ linear alkyl, $C_{3-7}$ branched alkyl, and $C_{3-7}$ cycloalkyl;

$R^{15a}$ is at each occurrence independently selected from the group consisting of H, $C_{1-6}$ linear alkyl, $C_{3-7}$ branched alkyl, and $C_{3-7}$ cycloalkyl;

$R^{15b}$ is at each occurrence independently selected from the group consisting of H, $C_{1-6}$ linear alkyl, $C_{3-7}$ branched alkyl, and $C_{3-7}$ cycloalkyl;

$R^{16a}$ is at each occurrence independently selected from the group consisting of H, $C_{1-6}$ linear alkyl, $C_{3-7}$ branched alkyl, and $C_{3-7}$ cycloalkyl;

$R^{16b}$ is at each occurrence independently selected from the group consisting of H, $C_{1-6}$ linear alkyl, $C_{3-7}$ branched alkyl, and $C_{3-7}$ cycloalkyl;

$R^{17}$ is at each occurrence independently selected from the group consisting of H, $C_{1-6}$ linear alkyl, $C_{3-7}$ branched alkyl, and $C_{3-7}$ cycloalkyl;

$R^{18}$ is at each occurrence independently selected from the group consisting of $C_{1-6}$ linear alkyl, $C_{3-7}$ branched alkyl, and $C_{3-7}$ cycloalkyl;

$R^{19a}$ is at each occurrence independently selected from the group consisting of $C_{1-6}$ linear alkyl, $C_{3-7}$ branched alkyl, and $C_{3-7}$ cycloalkyl;

$R^{19b}$ is at each occurrence independently selected from the group consisting of $C_{1-6}$ linear alkyl, $C_{3-7}$ branched alkyl, and $C_{3-7}$ cycloalkyl;

n is 1, 2, 3, or 4;

m is 1, 2, or 3.

In embodiments, A is

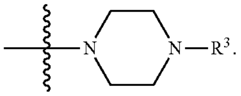

In embodiments, n is 1, 2, or 3. In embodiments, n is 1 or 2. In embodiments, n is 1. In embodiments, n is 2. In embodiments, each of $R^1$ and $R^2$ is unsubstituted $C_{1-6}$ alkyl (e.g., each of $R^1$ and $R^2$ is methyl or each of $R^1$ and $R^2$ is ethyl). In embodiments, $R^1$ and $R^2$ are taken together with the atoms to which they are bound to form a 5- to 8-membered ring (e.g., a $C_3$-$C_8$ cycloalkyl, a $C_5$-$C_8$ cycloalkenyl, or a 5- to 8-membered ring containing a ring atom that is $NR^7$). In embodiments, $R^1$ and $R^2$ are taken together with the atoms to which they are bound to form cyclopropyl, cyclobutyl, cyclopentyl, cyclopentenyl, cyclohexyl, cyclohexenyl, cycloheptyl, cycloheptenyl, cyclooctyl, cyclooctenyl, pyrrolidinyl, or piperidinyl, wherein the nitrogen atom in said pyrrolidinyl or piperidinyl group is $NR^7$. In embodiments, $R^7$ is an alkylsulfonyl —$SO_2R^{10c}$ (e.g., —$SO_2$Me) or an acyl —$COR^8$ (e.g., acetyl). In embodiments, $R^3$ is phenyl or a pyridyl. In embodiments, $R^3$ is unsubstituted. In embodiments, $R^3$ is substituted (e.g., a phenyl substituted by 1, 2, 3, 4, or 5 substituents or a pyridyl substituted by 1, 2, 3, or 4 substituents). In embodiments, substituents are selected from the group consisting of —OH, —F, —Cl, —Br, —I, —CN, —OMe, —OEt, —O$^n$Pr, —O$^i$Pr, —$OCF_3$, -Me, -Et, -$^n$Pr, -$^i$Pr, —$CF_3$, cyclopentyl, cyclohexyl, pyrrolidinyl, piperidinyl, and morpholino.

In embodiments, A is

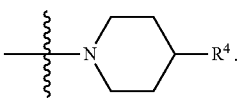

In embodiments, n is 1, 2, or 3. In embodiments, n is 1 or 2. In embodiments, n is 1. In embodiments, n is 2. In embodiments, each of $R^1$ and $R^2$ is unsubstituted $C_{1-6}$ alkyl (e.g., each of $R^1$ and $R^2$ is methyl or each of $R^1$ and $R^2$ is ethyl). In embodiments, $R^1$ and $R^2$ are taken together with the atoms to which they are bound to form a 5- to 8-membered ring (e.g., a $C_3$-$C_8$ cycloalkyl, a $C_5$-$C_8$ cycloalkenyl, or a 5- to 8-membered ring containing a ring atom that is $NR^7$). In embodiments, $R^1$ and $R^2$ are taken together with the atoms to which they are bound to form cyclopropyl, cyclobutyl, cyclopentyl, cyclopentenyl, cyclohexyl, cyclohexenyl, cycloheptyl, cycloheptenyl, cyclooctyl, cyclooctenyl, pyrrolidinyl, or piperidinyl, wherein the nitrogen atom in said pyrrolidinyl or piperidinyl group is $NR^7$. In embodiments, $R^7$ is an alkylsulfonyl —$SO_2R^{10c}$ (e.g., —$SO_2$Me) or an acyl —$COR^8$ (e.g., acetyl). In embodiments, $R^4$ is phenyl or a pyridyl. In embodiments, $R^4$ is unsubstituted. In embodiments, $R^4$ is substituted (e.g., a phenyl substituted by 1, 2, 3, 4, or 5 substituents or a pyridyl substituted by 1, 2, 3, or 4 substituents). In embodiments, substituents are selected from the group consisting of —OH, —F, —Cl, —Br, —I, —CN, —OMe, —OEt, —O$^n$Pr, —O$^i$Pr, —$OCF_3$, -Me, -Et, -$^n$Pr, -$^i$Pr, —$CF_3$, cyclopentyl, cyclohexyl, pyrrolidinyl, piperidinyl, and morpholino.

In embodiments, A is

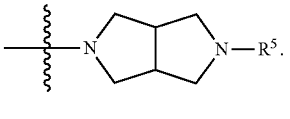

In embodiments, n is 1, 2, or 3. In embodiments, n is 1 or 2. In embodiments, n is 1. In embodiments, n is 2. In embodiments, each of $R^1$ and $R^2$ is unsubstituted $C_{1-6}$ alkyl (e.g., each of $R^1$ and $R^2$ is methyl or each of $R^1$ and $R^2$ is ethyl). In embodiments, $R^1$ and $R^2$ are taken together with the atoms to which they are bound to form a 5- to 8-membered ring (e.g., a $C_3$-$C_8$ cycloalkyl, a $C_5$-$C_8$ cycloalkenyl, or a 5- to 8-membered ring containing a ring atom that is $NR^7$). In embodiments, $R^1$ and $R^2$ are taken together with the atoms to which they are bound to form cyclopropyl, cyclobutyl, cyclopentyl, cyclopentenyl, cyclohexyl, cyclohexenyl, cycloheptyl, cycloheptenyl, cyclooctyl, cyclooctenyl, pyrrolidinyl, or piperidinyl, wherein the nitrogen atom in said pyrrolidinyl or piperidinyl group is $NR^7$. In embodiments, $R^7$ is an alkylsulfonyl —$SO_2R^{10c}$ (e.g., —$SO_2$Me) or an acyl —$COR^8$ (e.g., acetyl). In embodiments, $R^5$ is phenyl or a pyridyl. In embodiments, $R^5$ is unsubstituted. In embodiments, $R^5$ is substituted (e.g., a phenyl substituted by 1, 2, 3, 4, or 5 substituents or a pyridyl substituted by 1, 2, 3, or 4 substituents). In embodiments, substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

In embodiments, a compound is according to any formula described herein, or a pharmaceutically acceptable salt thereof. In embodiments, a compound is any compound described herein or a pharmaceutically acceptable salt thereof (e.g., a compound as described in any of Tables 1-39 described herein, or a pharmaceutically acceptable salt thereof). In embodiments, a compound is any of the compounds described in any of Tables 34-39, or a pharmaceutically acceptable salt thereof.

In embodiments, a compound has the S-configuration at the nitrogen-substituted carbon of the lactam. In embodiments, a compound has the R-configuration at the nitrogen-substituted carbon of the lactam.

The present invention further relates to compositions comprising: an effective amount of one or more compounds according to the present invention and an excipient.

The present invention also relates to a method for treating or preventing diseases that involve dysregulation of 5-hydroxytryptamine receptor 7 activity, including, for example, circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation, epilepsy, seizure disorders, drug addiction, alcohol addiction, breast cancer, liver fibrosis, chronic liver injury, hepatocellular carcinoma, small intestine neuroendocrine tumors, and lung injury said method comprising administering to a subject an effective amount of a compound or composition according to the present invention.

The present invention yet further relates to a method for treating or preventing diseases that involve dysregulation of 5-hydroxytryptamine receptor 7 activity, including, for example, circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar, disorder inflammatory bowel disease (IBD), intestinal inflammation, epilepsy, seizure disorders, drug addiction, alcohol addiction breast cancer, liver fibrosis, chronic liver injury, hepatocellular carcinoma, small intestine neuroendocrine tumors, and lung injury wherein said method comprises administering to a subject a composition comprising an effective amount of one or more compounds according to the present invention and an excipient.

The present invention also relates to a method for treating or preventing diseases or conditions associated with circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation, epilepsy, seizure disorders, drug addiction, alcohol addiction, breast cancer, liver fibrosis, chronic liver injury, hepatocellular carcinoma, small intestine neuroendocrine tumors, and lung injury, and diseases that involve dysregulation of 5-hydroxytryptamine receptor 7 activity. Said methods comprise administering to a subject an effective amount of a compound or composition according to the present invention.

The present invention yet further relates to a method for treating or preventing diseases or conditions associated with circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, and bipolar disorder, inflammatory bowel disease (IBD), intestinal inflammation, epilepsy, seizure disorders, drug addiction, alcohol addiction, breast cancer, liver fibrosis, chronic liver injury, hepatocellular carcinoma, small intestine neuroendocrine tumors, and lung injury, and diseases that involve dysregulation of 5-hydroxytryptamine receptor 7 activity, wherein said method comprises administering to a subject a composition comprising an effective amount of one or more compounds according to the present invention and an excipient.

The present invention also relates to a method for treating or preventing diseases or conditions associated with dysregulation of 5-hydroxytryptamine receptor 7 activity. Said methods comprise administering to a subject an effective amount of a compound or composition according to the present invention.

The present invention yet further relates to a method for treating or preventing diseases or conditions associated with dysregulation of 5-hydroxytryptamine receptor 7 activity, wherein said method comprises administering to a subject a composition comprising an effective amount of one or more compounds according to the present invention and an excipient.

The present invention further relates to a process for preparing the 5-hydroxytryptamine receptor 7 activity modulators of the present invention.

In embodiments, a disease or condition is inflammatory bowel disease (IBD).

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

There is evidence that suggests a role for the 5-$HT_7$ receptor in a number of medical disorders. 5-$HT_7$ receptor activity modulators are likely to have a beneficial effect on patients suffering from these disorders. The disorders in which 5-$HT_7$ dysregulation plays a role and modulation of 5-$HT_7$ receptor activity by a therapeutic agent may be a viable approach to therapeutic relief include, but are not limited to, circadian rhythm disorder, depression, schizophrenia, neurogenic inflammation, hypertension, peripheral, vascular diseases, migraine (Vanhoenacker, P. et al. Trends in Pharmacological Sciences, 2000, 21, 2, 70-77), neuropathic pain, peripheral pain, allodynia (EP1875899), thermoregulation disorder, learning disorder, memory disorder, hippocampal signaling disorder, sleep disorder (WO20100197700) attention deficit/hyperactivity disorder (ADHD) (WO20100069390), anxiety, avoidant personality disorder, premature ejaculation, eating disorder, premenstrual syndrome, premenstrual dysphonic disorder, seasonal affective disorder, bipolar disorder (WO20040229874), inflammatory bowel disease (IBD), intestinal inflammation (WO 2012058769, Khan, W. I., et. al. Journal of Immunology, 2013, 190, 4795-4804), epilepsy, seizure disorders (Epilepsy Research (2007) 75, 39), drug addiction, alcohol addiction (Hauser, S. R. et. al. Frontiers in Neuroscience, 2015, 8, 1-9), breast cancer (Gautam, J. Molecular Cancer, 2016, 15, 75, 1-14, Gautam, J. Breast Cancer Research and Treatment, 2017, 161, 29-40), liver fibrosis, chronic liver injury (Halici, Z. International Immunopharmacology, 2017, 43, 227-235), hepatocellular carcinoma (Bian, Z. X. Molecular Oncology, 2016, 10, 195-212), small intestine neuroendocrine tumors (Modlin, I. M. Cancer Science, 2013, 104, 7, 844-855), and lung injury (Halici, Z. Immunology, 2013, 1271-1283.).

There is a long felt need for new 5-$HT_7$ modulators that will provide therapeutic relief from patients suffering from diseases associated with dysregulation of 5-hydroxytryptamine receptor 7 activity. The invention addresses the need to identify novel 5-$HT_7$ modulators capable of treating disease associated with dysregulation of 5-hydroxytryptamine receptor 7 activity. The present invention addresses the need to develop new therapeutic agents for the treatment and prevention of circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation epilepsy, seizure disorders, drug addiction, alcohol addiction, breast cancer, liver fibrosis, chronic liver injury, hepatocellular carcinoma, small intestine neuroendocrine tumors, and lung injury.

The 5-hydroxytryptamine receptor 7 activity modulators of the present invention are capable of treating and preventing diseases associated with dysregulation of 5-hydroxytryptamine receptor 7 activity, for example circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation, epilepsy, seizure disorders, drug addiction, alcohol addiction, breast cancer, liver fibrosis, chronic liver injury, hepatocellular carcinoma, small intestine neuroendocrine tumors, and lung injury. It has been discovered that the 5-hydroxytryptamine receptor 7 play a role in a number of medical disorders, and therefore, 5-$HT_7$ receptor activity modulators are likely to have a beneficial effect on patients suffering from these disorders. The disorders in which 5-$HT_7$ dysregulation plays a role and modulation of 5-$HT_7$ receptor activity by a therapeutic agent may be a viable approach to therapeutic relief include, but are not limited to, circadian rhythm disorder, depression, schizophrenia, neurogenic inflammation, hypertension, peripheral, vascular diseases, migraine (Vanhoenacker, P. et. al. Trends in Pharmacological Sciences, 2000, 21, 2, 70-77), neuropathic pain, peripheral pain, allodynia (EP1875899), thermoregulation disorder, learning disorder, memory disorder, hippocampal signaling disorder, sleep disorder (WO20100197700) attention deficit/hyperactivity disorder (ADHD) (WO20100069390), anxiety, avoidant personality disorder, premature ejaculation, eating disorder, premenstrual syndrome, premenstrual dysphonic disorder, seasonal affective disorder, bipolar disorder (WO20040229874), inflammatory bowel disease (IBD), intestinal inflammation (WO 2012058769) epilepsy, seizure disorders (Epilepsy Research (2007) 75, 39), drug addiction, alcohol addiction (Hauser, S. R. et. al. Frontiers in Neuroscience, 2015, 8, 1-9), breast cancer (Gautam, J. Molecular Cancer, 2016, 15, 75, 1-14, Gautam, J. Breast Cancer Research and Treatment, 2017, 161, 29-40), liver fibrosis, chronic liver injury (Halici, Z. International Immunopharmacology, 2017, 43, 227-235), hepatocellular carcinoma (Bian, Z. X. Molecular Oncology, 2016, 10, 195-212), small intestine neuroendocrine tumors (Modlin, I. M. Cancer Science, 2013, 104, 7, 844-855), and lung injury (Halici, Z. Immunology, 2013, 1271-1283.).

Without wishing to be limited by theory, it is believed that 5-hydroxytryptamine receptor 7 receptor activity modulators of the present invention can ameliorate, abate, otherwise cause to be controlled, diseases associated with dysregulation of 5-hydroxytryptamine receptor 7 activity. The diseases include, but are not limited to circadian rhythm disorder, depression, schizophrenia, neurogenic inflammation, hypertension, peripheral, vascular diseases, migraine, neuropathic pain, peripheral pain, allodynia, thermoregulation disorder, learning disorder, memory disorder, hippocampal signaling disorder, sleep disorder, attention deficit/hyperactivity disorder, anxiety, avoidant personality disorder, premature ejaculation, eating disorder, premenstrual syndrome, premenstrual dysphonic disorder, seasonal affective disorder, bipolar disorder, inflammatory bowel disease (IBD), intestinal inflammation, epilepsy, seizure disorders, drug addiction, alcohol addiction, breast cancer, liver fibrosis, chronic liver injury, hepatocellular carcinoma, small intestine neuroendocrine tumors, and lung injury.

In embodiments, a disease is depression, schizophrenia, anxiety, or bipolar disorder. In embodiments, a disease is depression. In embodiments, a disease is schizophrenia. In embodiments, a disease is anxiety. In embodiments, a disease is bipolar disorder.

In embodiments, a disease is attention deficit/hyperactivity disorder.

In embodiments, a disease is avoidant personality disorder.

In embodiments, a disease is seasonal affective disorder.

In embodiments, a disease is circadian rhythm disorder or hippocampal signaling disorder. In embodiments, a disease is circadian rhythm disorder. In embodiments, a disease is hippocampal signaling disorder.

In embodiments, a disease is neurogenic inflammation.

In embodiments, a disease is neuropathic pain, peripheral pain, or allodynia. In embodiments, a disease is neuropathic pain. In embodiments, a disease is peripheral pain. In embodiments, a disease is allodynia.

In embodiments, a disease is migraine.

In embodiments, a disease is epilepsy or a seizure disorder. In embodiments, a disease is epilepsy. In embodiments, a disease is a seizure disorder.

In embodiments, a disease is a learning disorder or a memory disorder. In embodiments, a disease is a learning disorder. In embodiments, a disease is a memory disorder.

In embodiments, a disease is an eating disorder.

In embodiments, a disease is drug addiction or alcohol addiction.

In embodiments, a disease is a sleep disorder.

In embodiments, a disease is hypertension or peripheral vascular disease. In embodiments, a disease is hypertension. In embodiments, a disease is peripheral vascular disease.

In embodiments, a disease is thermoregulation disorder.

In embodiments, a disease is premature ejaculation.

In embodiments, a disease is premenstrual syndrome or premenstrual dysphonic disorder. In embodiments, a disease is premenstrual syndrome. In embodiments, a disease is premenstrual dysphonic disorder.

In embodiments, a disease is inflammatory bowel disease (IBD) or intestinal inflammation. In embodiments, a disease is inflammatory bowel disease (IBD). In embodiments, a disease is intestinal inflammation.

In embodiments, a disease is breast cancer.

In embodiments, a disease is liver fibrosis, chronic liver injury, or hepatocellular carcinoma. In embodiments, a disease is liver fibrosis. In embodiments, a disease is chronic liver injury. In embodiments, a disease is hepatocellular carcinoma.

In embodiments, a disease is a small intestine neuroendocrine tumor.

In embodiments, a disease is lung injury.

In embodiments, a disease is inflammatory bowel disease (IBD).

In embodiments, a compound described herein is a selective modulator of the serotonin 5HT7 receptor. In embodiments, a compound described herein can more potently bind a serotonin 5HT7 receptor as compared to other targets (e.g., other serotonin receptors). In embodiments, a compound may selectively bind a serotonin 5HT7 receptor in a particular tissue or organ.

In embodiments, compounds described herein may have particularly favorable properties for effective therapy (e.g., of any of the diseases or conditions described herein). For example, in the treatment of CNS or mental disorders, a compound described herein may exhibit favorably effective blood-brain barrier permeability. Alternatively, in the treatment of non-CNS or -mental disorders, a compound described herein will not have high blood-brain barrier permeability (e.g., off-target effects will be reduced). Without being bound by theory, molecular elements of a compound may be an effective strategy for obtaining the desired biological targeting.

For example, a compound described herein may selectively bind serotonin 5HT7 receptors in the intestine of a subject. Accordingly, a compound may be used to treat or prevent inflammatory bowel disease (IBD) or intestinal inflammation.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, isobutyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $—CF_3$, $—CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "haloalkoxy" refers to the group —O-haloalkyl, wherein the haloalkyl group is as defined above. Examples of haloalkoxy groups include, but are not limited to, fluoromethoxy, difluoromethoxy, trifluoromethoxy, and pentafluoroethoxyl.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, 1H-benzo[d]imidazol-2(3H)-onyl, 1H-benzo[d]imidazolyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

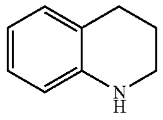

is, for the purposes of the present invention, considered a heterocyclic unit. 6,7-Dihydro-5H-cyclopentapyrimidine having the formula:

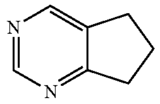

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

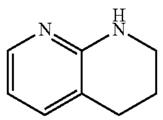

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, $—NO_2$, oxo (=O), $—OR^{26}$, $—SR^{26}$, $—N(R^{26})_2$, $—NR^{26}C(O)R^{26}$, $—SO_2R^{26}$, $—SO_2OR^{26}$, $—SO_2N(R^{26})_2$, $—C(O)R^{26}$, $—C(O)OR^{26}$, $—C(O)N(R^{26})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, $—NO_2$, oxo, and $R^{26}$; wherein $R^{26}$, at each occurrence, independently is hydrogen, $—OR^{27}$, $—SR^{27}$, $—C(O)R^{27}$, $—C(O)OR^{27}$, $—C(O)N(R^{27})_2$, $—SO_2R^{27}$, $—S(O)_2OR^{27}$, $—N(R^{27})_2$, $—NR^{27}C(O)R^{27}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{26}$ units taken together with the atom(s) to which they are bound form an optionally substituted carbocycle or heterocycle wherein said carbocycle or heterocycle has 3 to 7 ring atoms; wherein $R^{27}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{27}$ units taken together with the atom(s) to which they are bound form an optionally substituted carbocycle or heterocycle wherein said carbocycle or heterocycle preferably has 3 to 7 ring atoms.

In some embodiments, the substituents are selected from i) $—OR^{28}$; for example, —OH, $—OCH_3$, $—OCH_2CH_3$, $—OCH_2CH_2CH_3$;

ii) $—C(O)R^{28}$; for example, $—COCH_3$, $—COCH_2CH_3$, $—COCH_2CH_2CH_3$;

iii) $—C(O)OR^{28}$; for example, $—CO_2CH_3$, $—CO_2CH_2CH_3$, $—CO_2CH_2CH_2CH_3$;

iv) $—C(O)N(R^{28})_2$; for example, $—CONH_2$, $—CONHCH_3$, $—CON(CH_3)_2$;

v) $—N(R^{28})_2$; for example, $—NH_2$, $—NHCH_3$, $—N(CH_3)_2$, $—NH(CH_2CH_3)$;

vi) halogen: —F, —Cl, —Br, and —I;

vii) $—CH_eX_g$; wherein X is halogen, m is from 0 to 2, e+g=3; for example, $—CH_2F$, $—CHF_2$, $—CF_3$, $—CCl_3$, or $—CBr_3$;

viii) $—SO_2R^{28}$; for example, $—SO_2H$; $—SO_2CH_3$; $—SO_2C_6H_5$;

ix) $C_1$-$C_6$ linear, branched, or cyclic alkyl;

x) Cyano xi) Nitro;

xii) $N(R^{28})C(O)R^{28}$;

xiii) Oxo (=O);

xiv) Heterocycle; and xv) Heteroaryl.

wherein each $R^{28}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g., optionally substituted $C_3$-$C_4$ cycloalkyl); or two $R^{28}$ units can be taken together to form a ring comprising 3-7 ring atoms. In certain aspects, each $R^{28}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the 5-hydroxytryptamine receptor 7 activity modulators described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^9)_2$, each $R^9$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The 5-Hydroxytryptamine Receptor 7 Activity Modulators

The present invention is directed toward novel 5-hydroxytryptamine receptor 7 (5-HT7) activity modulators, compounds of formula (I),

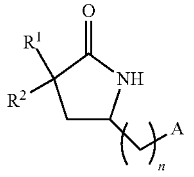

(I)

Including enantiomers, diastereomers, hydrates, solvates, pharmaceutically acceptable salts, prodrugs and complexes thereof, wherein:

A is selected from a group consisting of

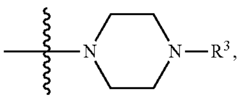
,
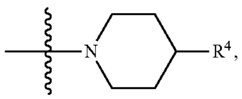
, and
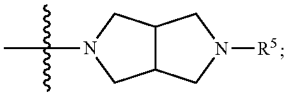
;

$R^1$ is selected from the group consisting of hydrogen, $C_{1-6}$ linear alkyl, $C_{3-7}$ branched alkyl;

$R^2$ is selected from the group consisting of hydrogen, $C_{1-6}$ linear alkyl, $C_{3-7}$ branched alkyl;

Or $R^1$ and $R^2$ are taken together with the atoms to which they are bound to form a ring having from 5 to 7 ring atoms, optionally containing a double bond;

Or $R^1$ and $R^2$ are taken together with the atoms to which they are bound to form a ring having from 6 to 8 ring atoms containing a moiety selected from the group consisting of O, S, SO, $SO_2$, and $NR^7$;

$R^3$ is selected from the group consisting of optionally substituted phenyl, optionally substituted naphthylen-1-yl, optionally substituted naphthylen-2-yl, optionally substituted 2-pyridyl, optionally substituted 3-pyridyl, optionally substituted 4-pyridyl, and

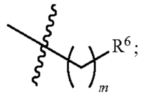
;

$R^4$ is selected from the group consisting of optionally substituted phenyl, optionally substituted naphthylen-1-yl, optionally substituted naphthylen-2-yl, optionally substituted 2-pyridyl, optionally substituted 3-pyridyl, optionally substituted 4-pyridyl and

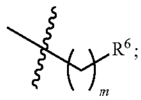
;

$R^5$ is selected from the group consisting of optionally substituted phenyl, optionally substituted naphthylen-1-yl, optionally substituted naphthylen-2-yl, optionally substituted 2-pyridyl, optionally substituted 3-pyridyl, optionally substituted 4-pyridyl and

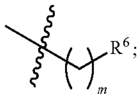;

$R^6$ is selected from the group consisting of optionally substituted phenyl, optionally substituted naphthylen-1-yl, optionally substituted naphthylen-2-yl, optionally substituted 2-pyridyl, optionally substituted 3-pyridyl, and optionally substituted 4-pyridyl;

$R^7$ is selected from the group consisting of H, $C_{1-6}$ linear alkyl, $C_{3-7}$ branched alkyl, $C_{3-7}$ cycloalkyl, optionally substituted phenyl, optionally substituted benzyl, $COR^8$, $CO_2R^9$, $CONR^{10a}R^{10b}$, $SO_2NR^{10a}R^{10b}$, and $SO_2R^{10c}$;

$R^8$ is selected from the group consisting of H, $C_{1-6}$ linear alkyl, $C_{3-7}$ branched alkyl, and $C_{3-7}$ cycloalkyl;

$R^9$ is selected from the group consisting of $C_{1-6}$ linear alkyl, $C_{3-7}$ branched alkyl, and $C_{3-7}$ cycloalkyl;

$R^{10a}$ is selected from the group consisting of H, $C_{1-6}$ linear alkyl, $C_{3-7}$ branched alkyl, and $C_{3-7}$ cycloalkyl;

$R^{10b}$ is selected from the group consisting of H, $C_{1-6}$ linear alkyl, $C_{3-7}$ branched alkyl, and $C_{3-7}$ cycloalkyl;

$R^{10c}$ is selected from the group consisting of $C_{1-6}$ linear alkyl, $C_{3-7}$ branched alkyl, $C_{3-7}$ cycloalkyl, $C_{1-6}$ linear haloalkyl, $C_{3-7}$ branched haloalkyl, $—(CH_2)_qCN$, $—(CH_2)_qSO_2R^{11}$, $—(CH_2)_qOR^{12}$,

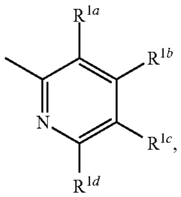,
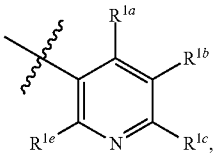,
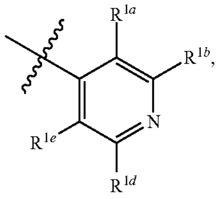,
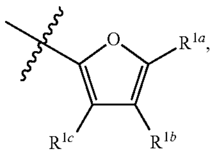,
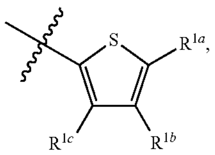,
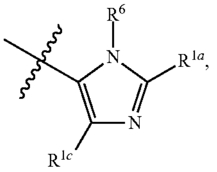,
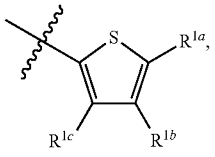,
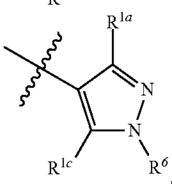,
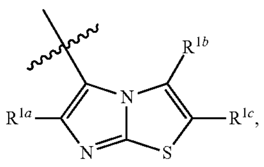,
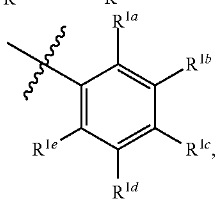, -continued

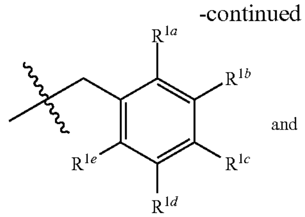
and
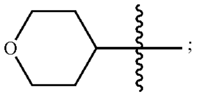;

$R^{11}$ is selected from the group consisting of $C_{1-6}$ linear alkyl, $C_{3-7}$ branched alkyl, and $C_3$-7 cycloalkyl;

$R^{12}$ is selected from the group consisting of $C_{1-6}$ linear alkyl, $C_{3-7}$ branched alkyl, and $C_{3-7}$ cycloalkyl;

$R^{1a}$, $R^{1b}$, $R^{1c}$, $R^{1d}$, and $R^{1e}$ are at each occurrence independently selected from the group consisting of H, OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, —S($C_{1-6}$ linear alkyl), S($C_{3-7}$ branched alkyl), —S($C_{3-7}$ cycloalkyl), $COR^{13}$, $CO_2R^{14}$, $CONR^{15a}R^{15b}$, $SO_2NR^{15a}R^{15b}$, $NR^{16a}R^{16b}$, $NR^{16a}COR^{17}$, $NR^{16a}SO_2R^{18}$, and $NR^{16a}SO_2NR^{19a}R^{19b}$;

$R^{13}$ is at each occurrence independently selected from the group consisting of H, $C_{1-6}$ linear alkyl, $C_{3-7}$ branched alkyl, and $C_{3-7}$ cycloalkyl;

$R^{14}$ is at each occurrence independently selected from the group consisting of $C_{1-6}$ linear alkyl, $C_{3-7}$ branched alkyl, and $C_{3-7}$ cycloalkyl;

$R^{15a}$ is at each occurrence independently selected from the group consisting of H, $C_{1-6}$ linear alkyl, $C_{3-7}$ branched alkyl, and $C_{3-7}$ cycloalkyl;

$R^{15b}$ is at each occurrence independently selected from the group consisting of H, $C_{1-6}$ linear alkyl, $C_{3-7}$ branched alkyl, and $C_{3-7}$ cycloalkyl;

$R^{16a}$ is at each occurrence independently selected from the group consisting of H, $C_{1-6}$ linear alkyl, $C_{3-7}$ branched alkyl, and $C_{3-7}$ cycloalkyl;

$R^{16b}$ is at each occurrence independently selected from the group consisting of H, $C_{1-6}$ linear alkyl, $C_{3-7}$ branched alkyl, and $C_{3-7}$ cycloalkyl;

$R^{17}$ is at each occurrence independently selected from the group consisting of H, $C_{1-6}$ linear alkyl, $C_{3-7}$ branched alkyl, and $C_{3-7}$ cycloalkyl;

$R^{18}$ is at each occurrence independently selected from the group consisting of $C_{1-6}$ linear alkyl, $C_{3-7}$ branched alkyl, and $C_{3-7}$ cycloalkyl;

$R^{19a}$ is at each occurrence independently selected from the group consisting of $C_{1-6}$ linear alkyl, $C_{3-7}$ branched alkyl, and $C_{3-7}$ cycloalkyl;

$R^{19b}$ is at each occurrence independently selected from the group consisting of $C_{1-6}$ linear alkyl, $C_{3-7}$ branched alkyl, and $C_{3-7}$ cycloalkyl;

n is 1, 2, 3, or 4;

m is 1, 2, or 3.

In embodiments,

A is

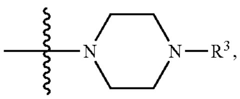,
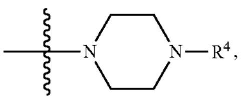, or
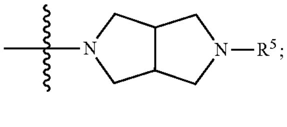;

each $R^1$ and $R^2$ is independently $C_{1-6}$ linear alkyl or $C_{3-7}$ branched alkyl; or $R^1$ and $R^2$ are taken together with the atoms to which they are bound to form a 5- to 8-membered ring, wherein said 5- to 8-membered ring is saturated or comprises a carbon-carbon double bond, and/or a ring atom that is O, S, SO, $SO_2$, or $NR^7$ each $R^3$, $R^4$, and $R^5$ is independently optionally substituted phenyl, optionally optionally substituted 2-pyridyl, optionally substituted 3-pyridyl, or optionally substituted 4-pyridyl;

$R^6$ is independently optionally substituted phenyl, optionally optionally substituted 2-pyridyl, optionally substituted 3-pyridyl, or optionally substituted 4-pyridyl;

$R^7$ is independently H, $C_{1-6}$ linear alkyl, $C_{3-7}$ branched alkyl, $COR^8$, or $SO_2R^{10c}$;

$R^8$ is selected from the group consisting of H, $C_{1-6}$ linear alkyl, $C_{3-7}$ branched alkyl, and $C_{3-7}$ cycloalkyl;

$R^{10c}$ is $C_{1-6}$ linear alkyl or $C_{3-7}$ branched alkyl;

n is 1, 2, 3, or 4; and m is 1, 2, or 3.

In embodiments, n is 1, 2, or 3. In embodiments, n is 1. In embodiments, n is 2. In embodiments, n is 3.

The embodiments of the present invention include compounds having formula (II):

(II)

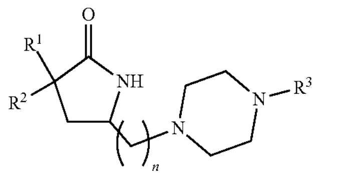

Including hydrates, solvates, enantiomers, diastereomers, pharmaceutically acceptable salts, and complexes thereof.

In embodiments, a compound has the formula (XLII):

(XLII)

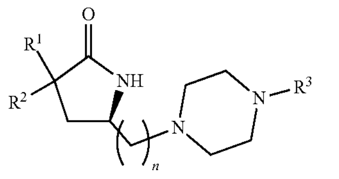

or a pharmaceutically acceptable salt thereof.

In embodiments, a compound has the formula (XLIII):

(XLIII)

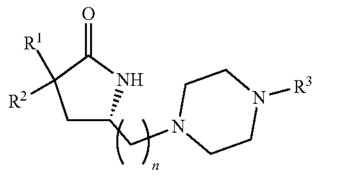

or a pharmaceutically acceptable salt thereof.

In embodiments, n is 1, 2, or 3. In embodiments, n is 1. In embodiments, n is 2. In embodiments, n is 3. In embodiments, n is 1 or 2.

In embodiments, each of $R^1$ and $R^2$ is unsubstituted $C_{1-6}$ alkyl. In embodiments, each of $R^1$ and $R^2$ is ethyl. In embodiments, each of $R^1$ and $R^2$ is methyl.

In embodiments, $R^1$ and $R^2$ are taken together with the atoms to which they are bound to form a 5- to 8-membered ring, optionally containing one carbon-carbon double bonds and/or a ring atom selected from the group consisting of O, S, SO, $SO_2$, and $NR^7$.

In embodiments, $R^1$ and $R^2$ are taken together with the atoms to which they are bound to form a $C_3$-$C_8$ cycloalkyl or a $C_5$-$C_8$ cycloalkenyl.

In embodiments, $R^1$ and $R^2$ are taken together with the atoms to which they are bound to form a $C_3$-$C_8$ cycloalkyl or $C_5$-$C_8$ cycloalkenyl selected from the group consisting of cyclopropyl, cyclobutyl, cyclopentyl, cyclopentenyl, cyclohexyl, cyclohexenyl, cycloheptyl, cycloheptenyl, cyclooctyl, and cyclooctenyl. In embodiments, said $C_3$-$C_8$ cycloalkyl or $C_5$-$C_8$ cycloalkenyl is unsubstituted. In embodiments, said $C_3$-$C_8$ cycloalkyl or $C_5$-$C_8$ cycloalkenyl is substituted by 1, 2, 3, or 4 substituents (e.g., 1 or 2 substituents as described herein). In embodiments, said substituents are selected from oxo (=O), hydroxyl, halo, cyano, $C_{1-6}$ alkoxy, $C_{1-6}$ linear alkyl, $C_{3-7}$ branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —$O^nPr$, —$O^iPr$, —OCF3, -Me, -Et, -nPr, -$^iPr$, —$CF_3$, cyclopentyl, cyclohexyl, pyrrolidinyl, piperidinyl, and morpholino.

In embodiments, a compound has a structure according to formula (XXXXIIIa):

(XXXXIIIa)

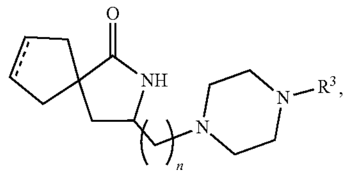

or a pharmaceutically acceptable salt thereof, wherein ⎓ represents a single or double bond.

In embodiments, ⎓ represents a single bond.

In embodiments, ⎓ represents a double bond.

In embodiments, the lactam stereocenter substituted by nitrogen has the R-configuration.

In embodiments, the lactam stereocenter substituted by nitrogen has the S-configuration.

In embodiments, $R^1$ and $R^2$ are taken together with the atoms to which they are bound to form a 5- to 8-membered ring containing a ring atom that is $NR^7$. In embodiments, said 5- to 8-membered ring is not further substituted. In embodiments, said 5- to 8-membered ring further comprises 1, 2, 3, or 4 substituents (e.g., 1 or 2 substituents as described herein). In embodiments, said substituents are selected from oxo (=O), hydroxyl, halo, cyano, $C_{1-6}$ alkoxy, $C_{1-6}$ linear alkyl, $C_{3-7}$ branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —$O^nPr$, —OiPr, —OCF3, -Me, -Et, -nPr, -$^iPr$, —$CF_3$, cyclopentyl, cyclohexyl, pyrrolidinyl, piperidinyl, and morpholino.

In embodiments, $R^1$ and $R^2$ are taken together to form a pyrrolidinyl or piperidinyl group where the nitrogen atom is $NR^7$. In embodiments, said pyrrolidinyl or piperidinyl group is not further substituted. In embodiments, said pyrrolidinyl or piperidinyl group further comprises 1, 2, 3, or 4 substituents as described herein.

In embodiments, a compound has the formula (XLIIIb)

(XLIIIb)

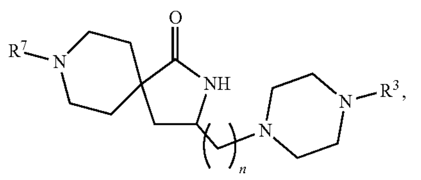

or a pharmaceutically acceptable salt thereof.

In embodiments, a compound has the formula (XLIV)

(XLIV)

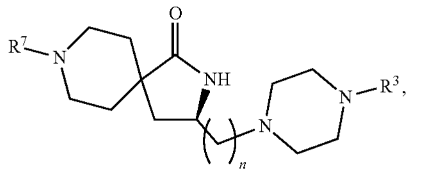

or a pharmaceutically acceptable salt thereof.

In embodiments, a compound has the formula (XLV)

(XLV)

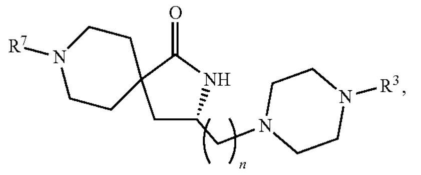

or a pharmaceutically acceptable salt thereof.

In embodiments, n is 1, 2, or 3. In embodiments, n is 1. In embodiments, n is 2. In embodiments, n is 3. In embodiments, n is 1 or 2.

In embodiments, $R^7$ is $COR^8$, and $R^8$ is $C_{1-6}$ linear alkyl.

In embodiments, $R^7$ is acetyl.

In embodiments, $R^7$ is $SO_2R^{10c}$, and $R^{10c}$ is $C_{1-6}$ linear alkyl.

In embodiments, $R^{10c}$ is methyl (i.e., $R^7$ is $SO_2Me$).

In embodiments, $R^3$ is unsubstituted phenyl.

In embodiments, $R^3$ is substituted phenyl. In embodiments, $R^3$ is phenyl substituted by 1, 2, 3, 4, or 5 substituents (e.g., phenyl substituted by 1 or 2 substituents as described herein). In embodiments, the substitutents are selected from the group consisting of hydroxyl, halo, cyano, $C_{1-6}$ alkoxy, $C_{1-6}$ linear alkyl, $C_{3-7}$ branched alkyl, $C_{1-6}$haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —$O^n$Pr, —$O^i$Pr, —OCF3, -Me, -Et, -$^n$Pr, -$^i$Pr, —$CF_3$, cyclopentyl, cyclohexyl, pyrrolidinyl, piperidinyl, and morpholino.

In embodiments, $R^3$ is selected from the group consisting of hydroxylphenyl, fluorophenyl, chlorophenyl, bromophenyl, cyanophenyl, tolyl, methoxylphenyl, difluorophenyl, dichlorophenyl, chloro-fluorophenyl, dimethylphenyl, trifluoromethylphenyl, di(trifluoromethyl)phenyl, In embodiments, $R^3$ is selected from the group consisting of 4-hydroxyphenyl, 3-fluorophenyl, 4-fluorophenyl, 3-chlorophenyl, 4-chlorophenyl, 3,4-dichlorophenyl, 4-fluoro-3-chlorophenyl, 4-cyanophenyl, 2-methoxyphenyl, 2-methylphenyl, 3-methylphenyl, 4-methylphenyl, 2-isopropylphenyl, 4-trifluoromethylphenyl, 2-morpholinophenyl, and 4-methyl-2-morpholinophenyl.

In embodiments, $R^3$ is 2-pyridyl. In embodiments, $R^3$ is 3-pyridyl. In embodiments, $R^3$ is 4-pyridyl. In embodiments, said pyridyl is unsubstituted. In embodiments, said pyridyl is substituted by 1, 2, 3, or 4 substituents (e.g., pyridyl substituted by 1 or 2 substituents as described herein). In embodiments, the substitutents are selected from the group consisting of hydroxyl, halo, cyano, $C_{1-6}$ alkoxy, $C_{1-6}$ linear alkyl, $C_{3-7}$ branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —$O^n$Pr, —$O^i$Pr, —OCF3, -Me, -Et, -$^n$Pr, -$^i$Pr, —$CF_3$, cyclopentyl, cyclohexyl, pyrrolidinyl, piperidinyl, and morpholino.

The embodiments of the present invention include compounds having formula (IIa):

(IIa)

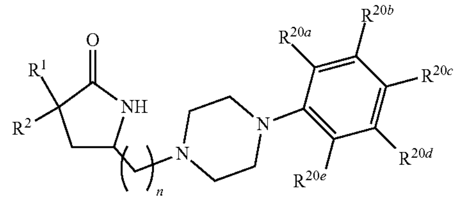

Including hydrates, solvates, enantiomers, diastereomers, pharmaceutically acceptable salts, and complexes thereof wherein $R^{20a}$, $R^{20b}$, $R^{20c}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

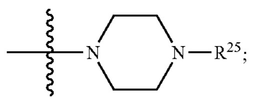

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl; and at least 3 of $R^{20a}$, $R^{20b}$, $R^{20c}$, $R^{20d}$, and $R^{20c}$ are hydrogen.

The embodiments of the present invention include compounds having formula (IIb):

(IIb)

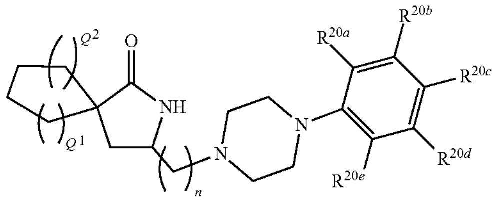

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIc):

(IIc)

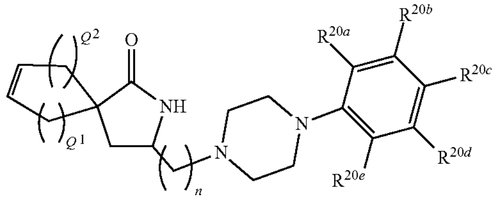

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IId):

(IId)

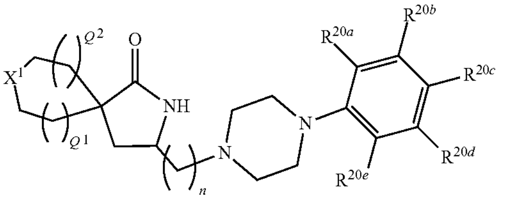

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IId-1):

(IId-1)

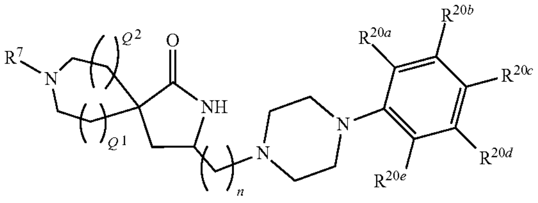

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IId-2):

(IId-2)

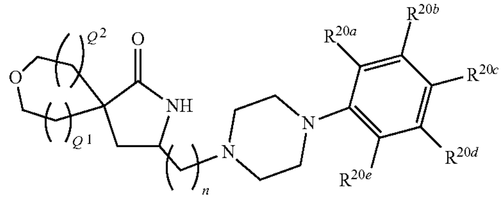

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IId-3):

(IId-3)

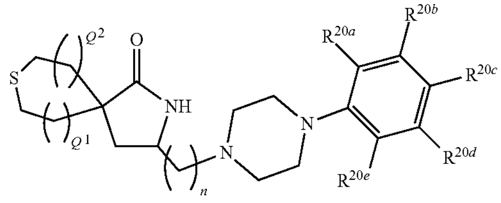

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IId-4):

(IId-4)

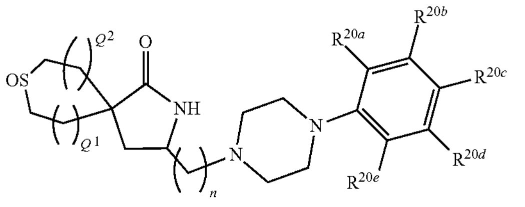

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IId-5):

(IId-5)

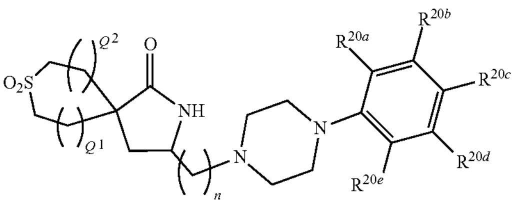

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIe):

(IIe)

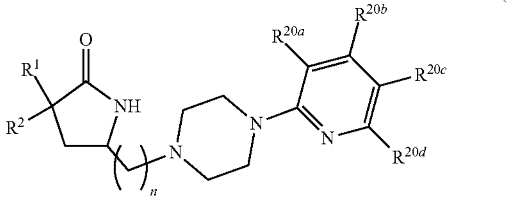

Including hydrates, solvates, enantiomers, diastereomers, pharmaceutically acceptable salts, and complexes thereof wherein $R^{20a}$, $R^{20b}$, $R^{20c}$, and $R^{20d}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

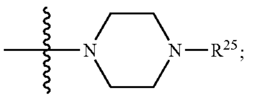
;

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl; and at least 3 of $R^{20a}$, $R^{20b}$, $R^{20c}$, and $R^{20d}$ are hydrogen.

The embodiments of the present invention include compounds having formula (IIf):

(IIf)

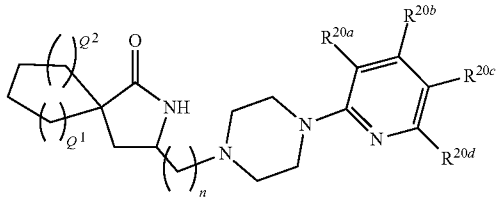

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIg):

(IIg)

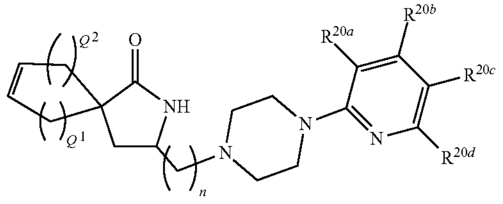

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIh):

(IIh)

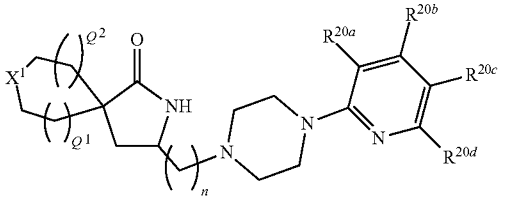

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIh-1):

(IIh-1)

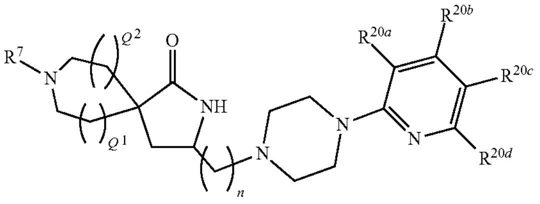

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIh-2):

(IIh-2)

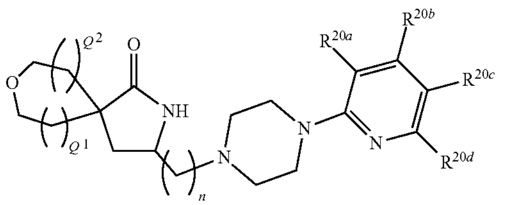

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIh-3):

(IIh-3)

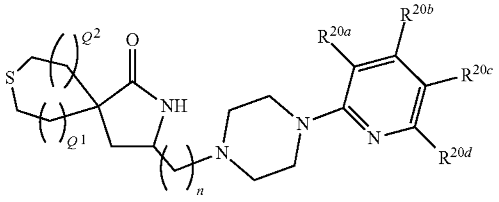

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIh-4):

(IIh-4)

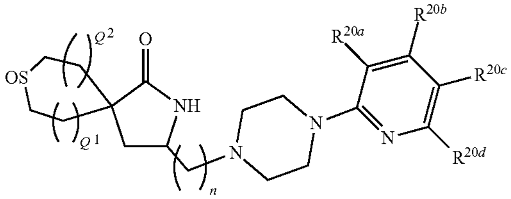

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIh-5):

(IIh-5)

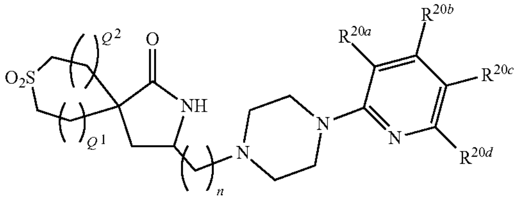

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIi):

(IIi)

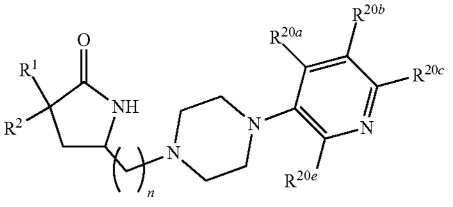

Including hydrates, solvates, enantiomers, diastereomers, pharmaceutically acceptable salts, and complexes thereof wherein $R^{20a}$, $R^{20b}$, $R^{20c}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7 cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

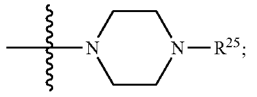

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20e}$ are hydrogen.

The embodiments of the present invention include compounds having formula (IIj):

(IIj)

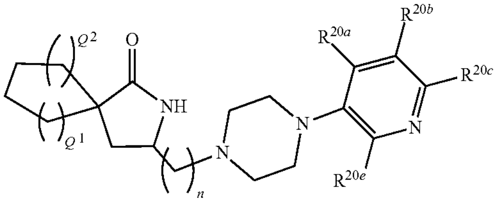

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIk):

(IIk)

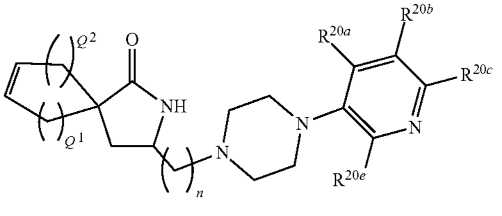

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIL):

(IIL)

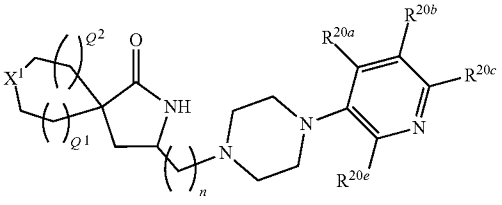

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIL-1):

(IIL-1)

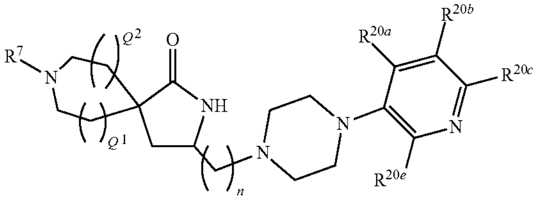

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIL-2):

(IIL-2)

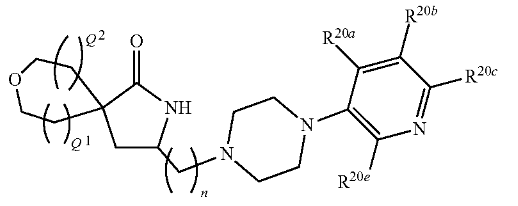

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIL-3):

(IIL-3)

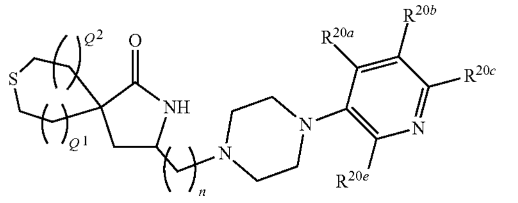

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIL-4):

(IIL-4)

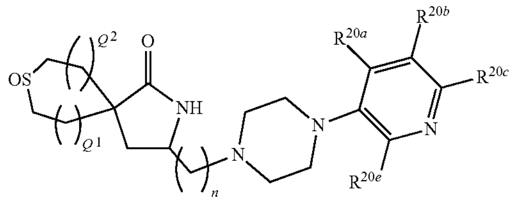

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIL-5):

(IIL-5)

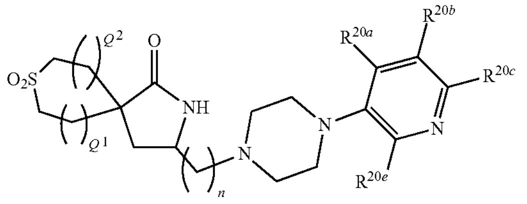

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIm):

(IIm)

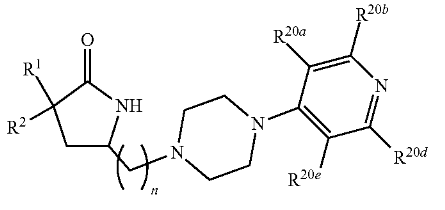

Including hydrates, solvates, enantiomers, diastereomers, pharmaceutically acceptable salts, and complexes thereof wherein $R^{20a}$, $R^{20b}$, $R^{20cd}$ and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

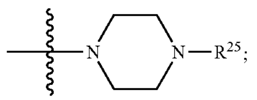

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 3 of $R^{20a}$, $R^{20b}$, $R^{20c}$, and $R^{20d}$ are hydrogen.

The embodiments of the present invention include compounds having formula (IIn):

(IIn)

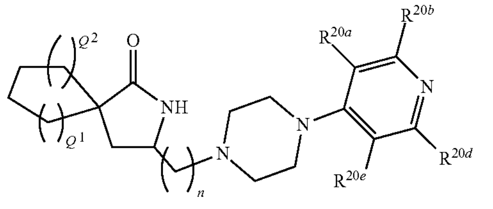

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIo):

(IIo)

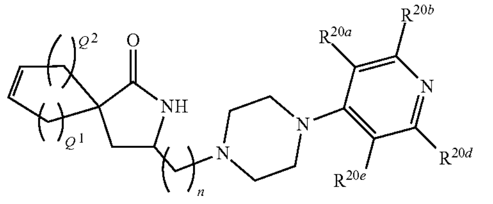

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIp):

(IIp)

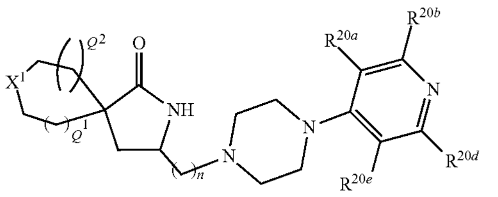

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIp-1):

(IIp-1)

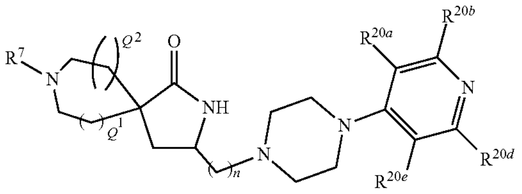

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIp-2):

(IIp-2)

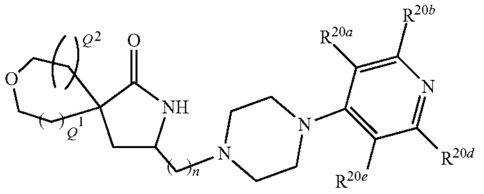

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIp-3):

(IIp-3)

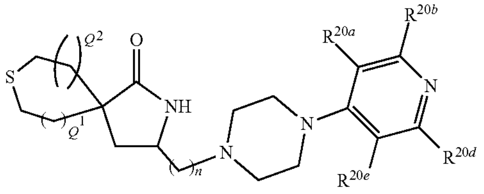

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIp-4):

(IIp-4)

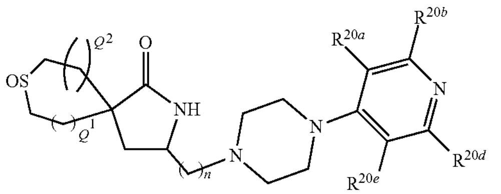

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIp-5):

(IIp-5)

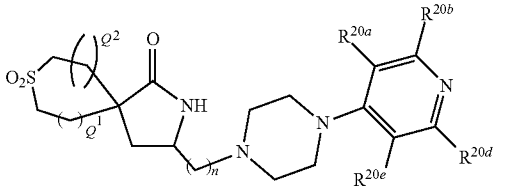

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIq):

(IIq)

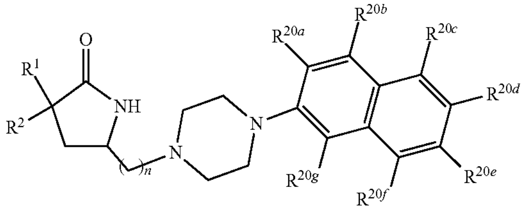

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7 cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

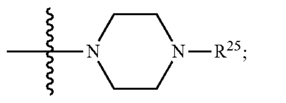

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl; and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (IIr):

(IIr)

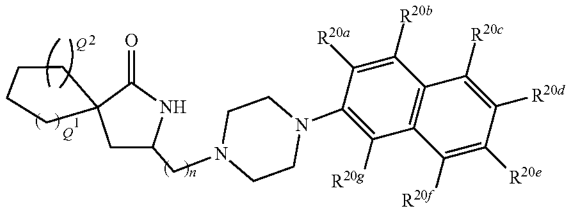

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIs):

(IIs)

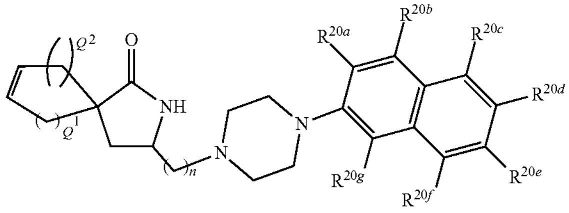

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIt):

(IIt)

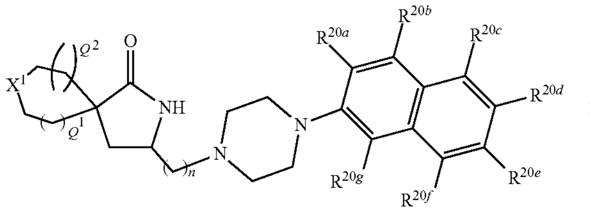

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIt-1):

(IIt-1)

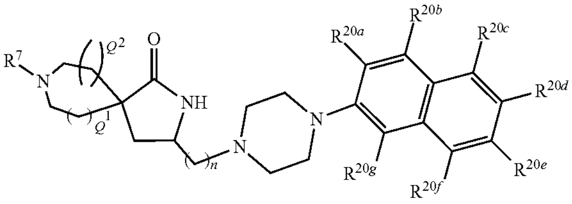

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIt-2):

(IIt-2)

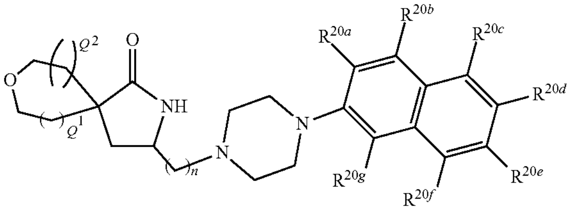

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIt-3):

(IIt-3)

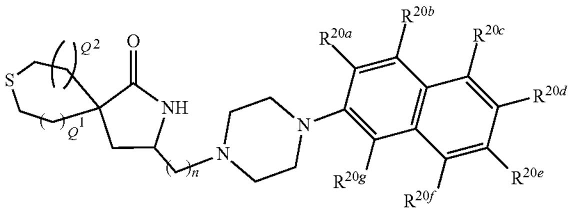

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIt-4):

(IIt-4)

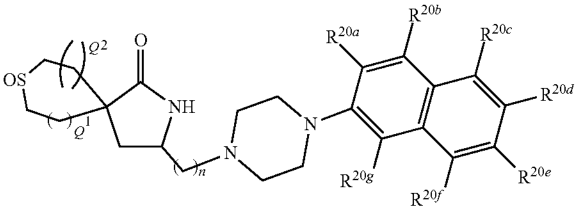

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIt-5):

(IIt-5)

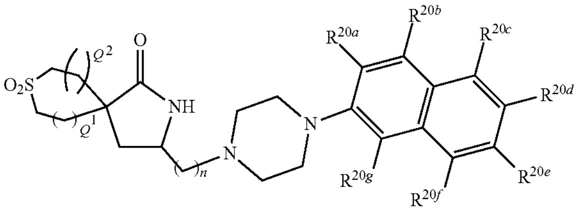

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIu):

(IIu)

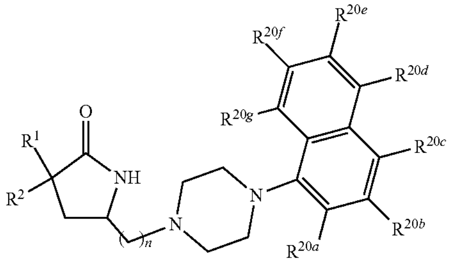

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7 cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

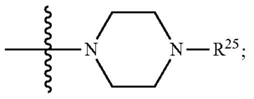;

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl; and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (IIv):

(IIv)

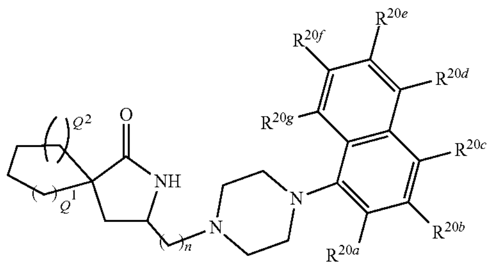

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIw):

(IIw)

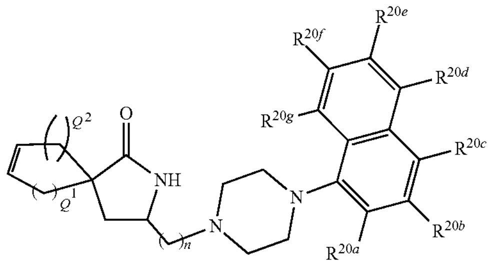

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIx):

(IIx)

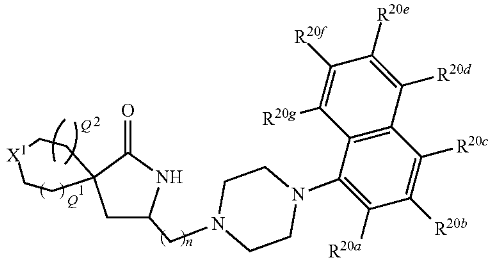

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIx-1):

(IIx-1)

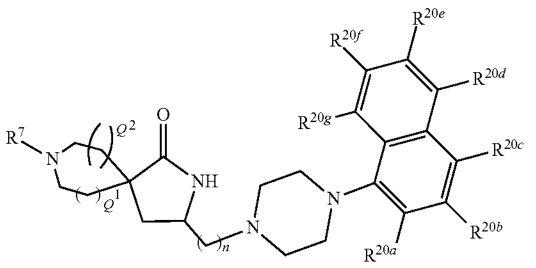

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIx-2):

(IIx-2)

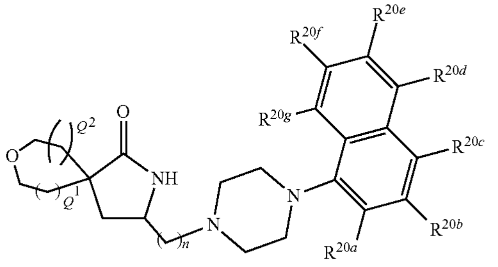

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIx-3):

(IIx-3)

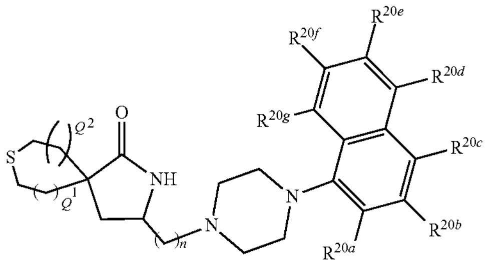

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIx-4):

(IIx-4)

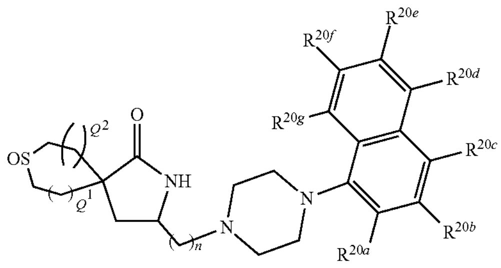

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIx-5):

(IIx-5)

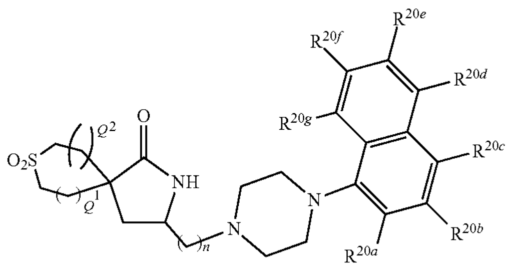

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (III):

(III)

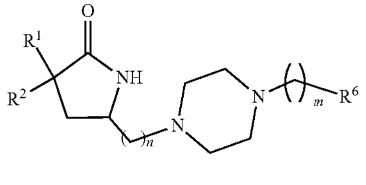

Including hydrates, solvates, enantiomers, diastereomers, pharmaceutically acceptable salts, and complexes thereof.

The embodiments of the present invention include compounds having formula (IIIa):

(IIIa)

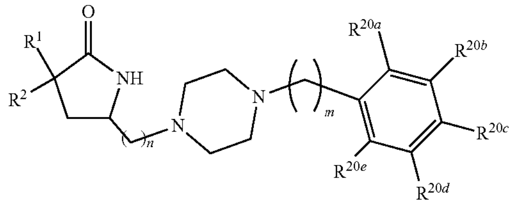

Including hydrates, solvates, enantiomers, diastereomers, pharmaceutically acceptable salts, and complexes thereof wherein $R^{20a}$, $R^{20b}$, $R^{20c}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

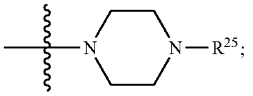

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl; and at least 3 of $R^{20a}$, $R^{20b}$, $R^{20c}$, $R^{20d}$, and $R^{20e}$ are hydrogen.

The embodiments of the present invention include compounds having formula (IIIb):

(IIIb)

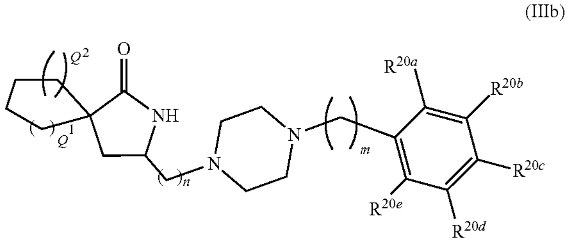

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIc):

(IIIc)

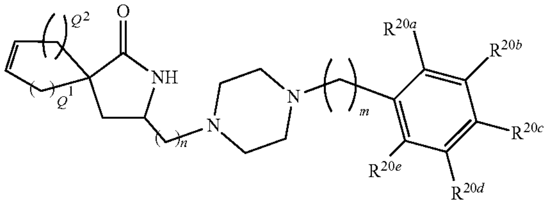

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIId):

(IIId)

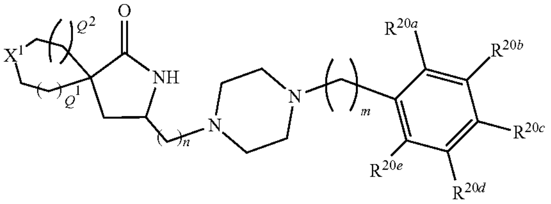

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIId-1):

(IIId-1)

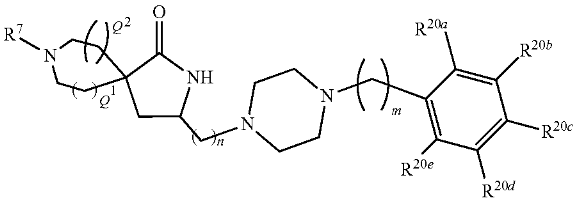

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIId-2):

(IIId-2)

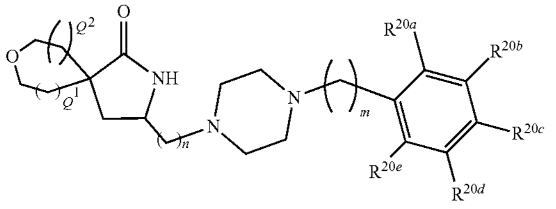

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIId-3):

(IIId-3)

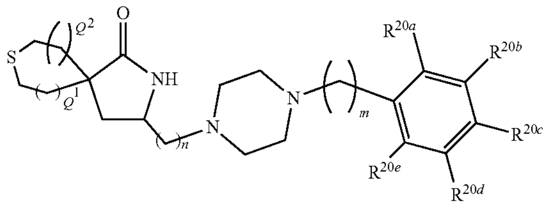

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIId-4):

(IIId-4)

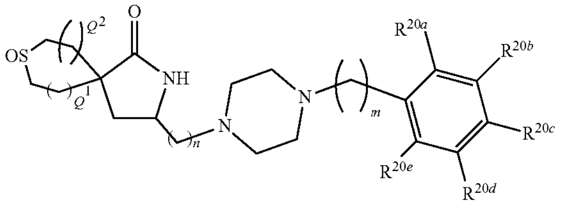

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIId-5):

(IIId-5)

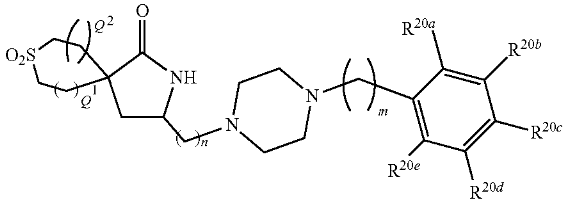

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIe):

(IIIe)

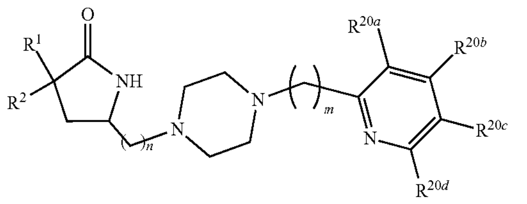

Including hydrates, solvates, enantiomers, diastereomers, pharmaceutically acceptable salts, and complexes thereof wherein $R^{20a}$, $R^{20b}$, $R^{20c}$, and $R^{20d}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

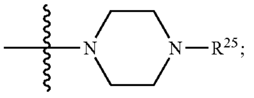

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl; and at least 2 of $R^{20a}$, $R^{20b}$, $R^{20c}$, and $R^{20d}$ are hydrogen.

The embodiments of the present invention include compounds having formula (IIIf):

(IIIf)

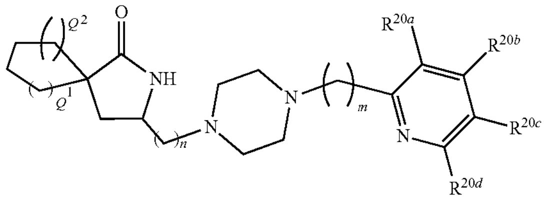

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIg):

(IIIg)

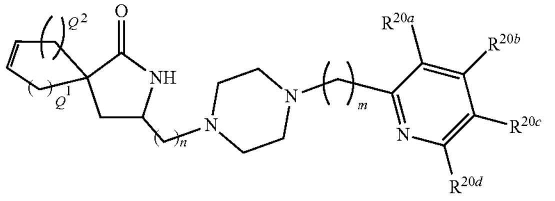

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIh):

(IIIh)

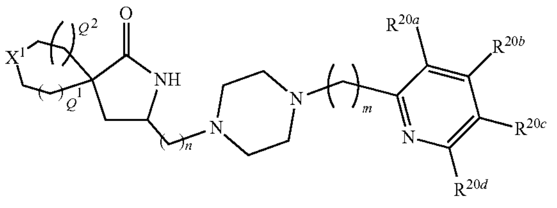

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIIh-1):

(IIIh-1)

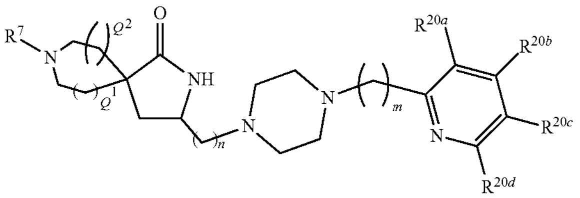

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIh-2):

(IIIh-2)

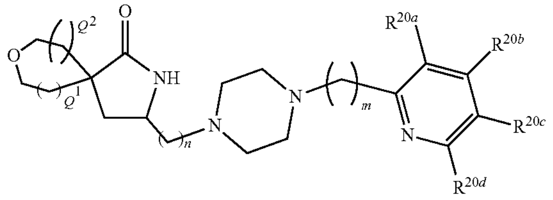

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIh-3):

(IIIh-3)

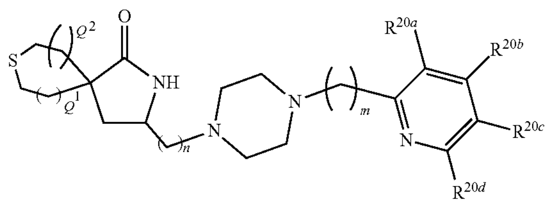

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIh-4):

(IIIh-4)

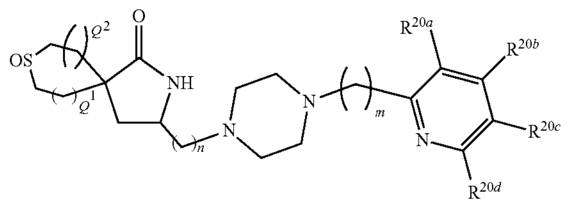

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIh-5):

(IIIh-5)

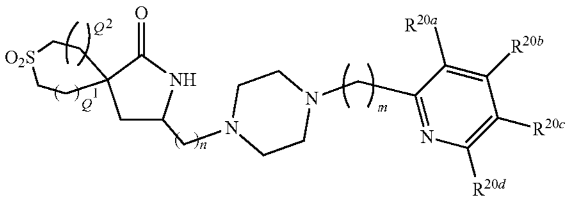

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIi):

(IIIi)

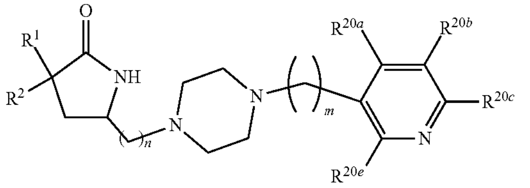

Including hydrates, solvates, enantiomers, diastereomers, pharmaceutically acceptable salts, and complexes thereof wherein $R^{20a}$, $R^{20b}$, $R^{20c}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

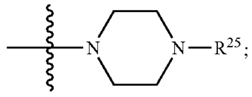

;

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl; and at least 2 of $R^{20a}$, $R^{20b}$, $R^{20c}$, and $R^{20e}$ are hydrogen.

The embodiments of the present invention include compounds having formula (IIIj):

(IIIj)

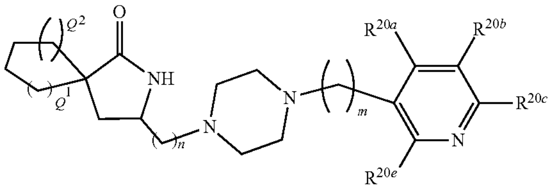

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIk):

(IIIk)

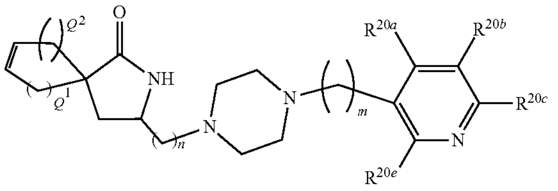

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIL):

(IIIL)

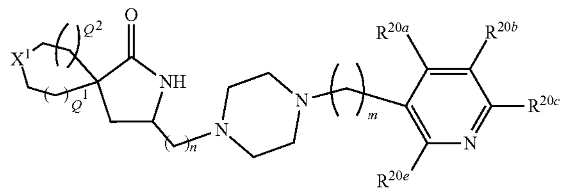

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIIL-1):

(IIIL-1)

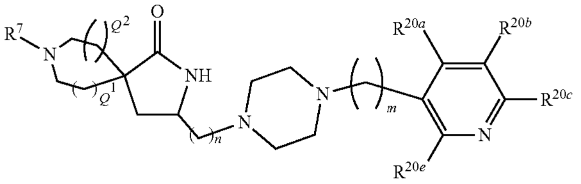

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIL-2):

(IIIL-2)

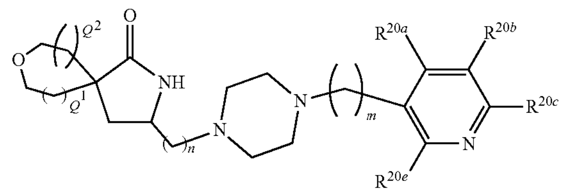

Including hydrates, solvates, enantiomers, diastereomers pharmaceutically acceptable salts, and complexes thereof wherein $Q^1$ is 1 or 2;

and $Q^2$ is 1 or 2.

The embodiments of the present invention include compounds having formula (IIIL-3):

(IIIL-3)

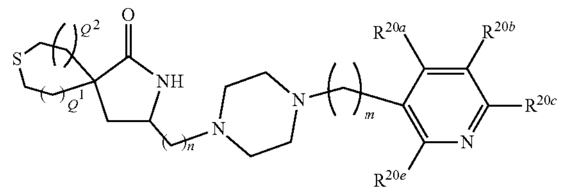

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIL-4):

(IIIL-4)

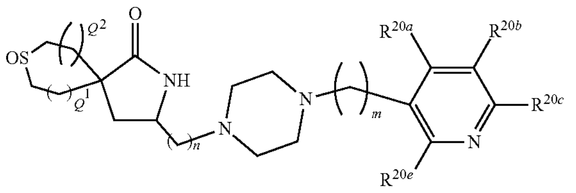

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIL-5):

(IIIL-5)

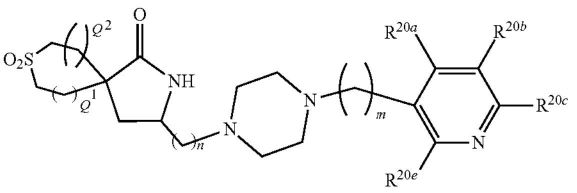

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIm):

(IIIm)

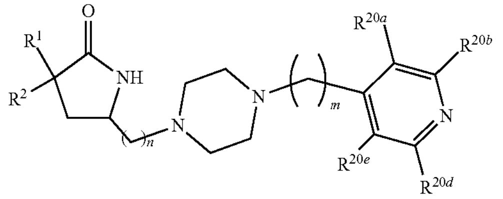

Including hydrates, solvates, enantiomers, diastereomers, pharmaceutically acceptable salts, and complexes thereof wherein $R^{20a}$, $R^{20b}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

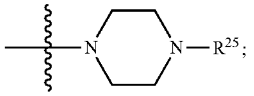

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (IIIn):

(IIIn)

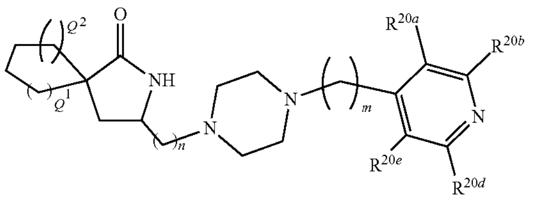

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIo):

(IIIo)

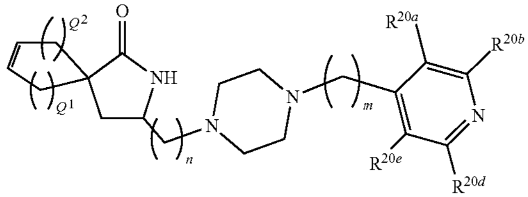

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIp):

(IIIp)

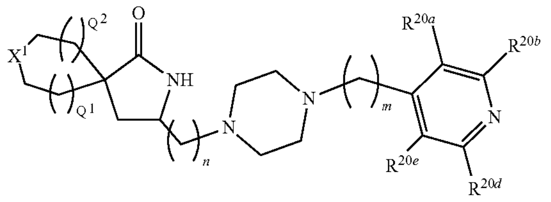

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIIp-1):

(IIIp)

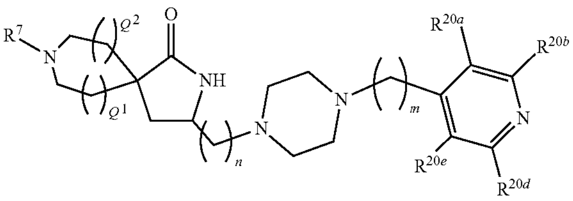

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIp-2):

(IIIp-2)

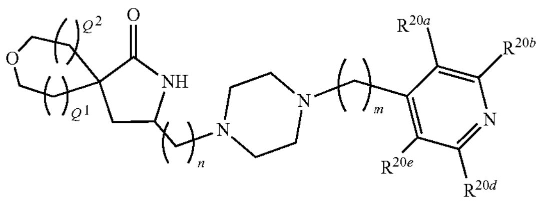

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIp-3):

(IIIp-3)

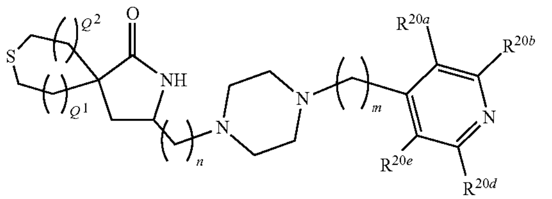

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIp-4):

(IIIp-4)

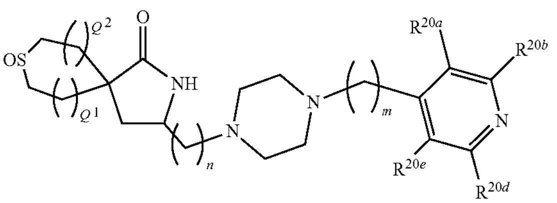

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIp-5):

(IIIp-5)

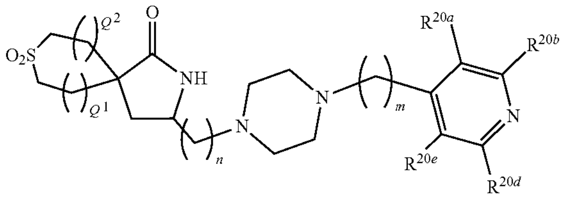

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIq):

(IIIq)

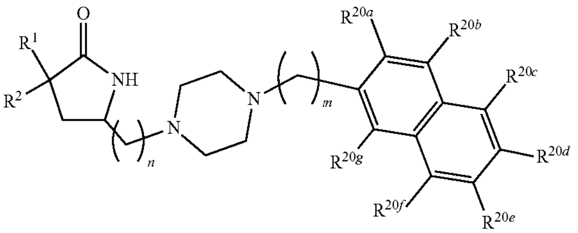

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

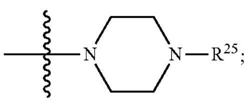

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (IIIr):

(IIIr)

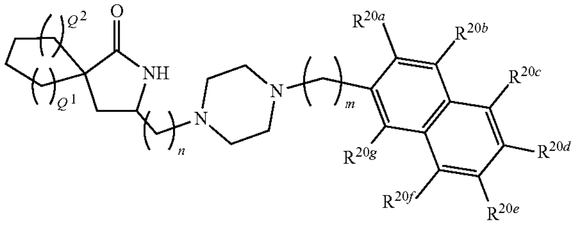

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIs):

(IIIs)

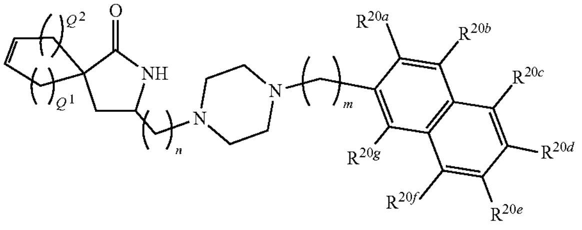

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIt):

(IIIt)

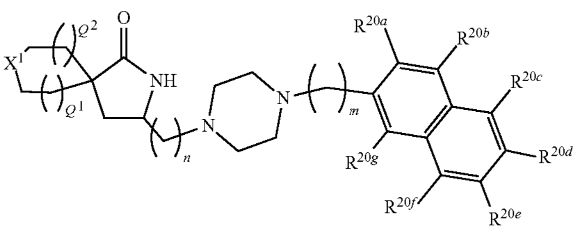

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIIt-1):

(IIIt-1)

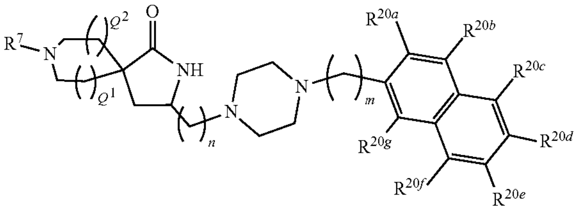

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIt-2):

(IIIt-2)

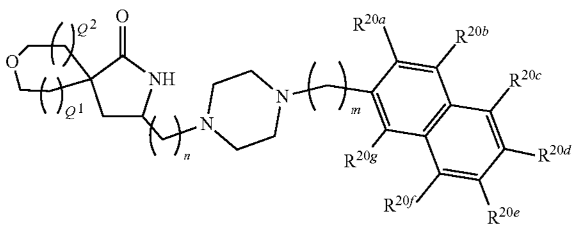

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIt-3):

(IIIt-3)

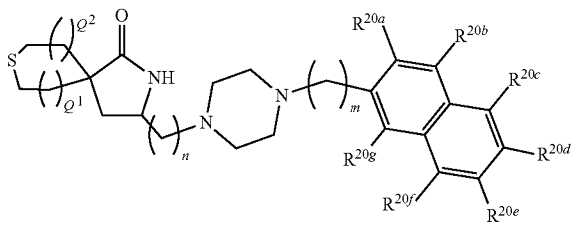

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIt-4):

(IIIt-4)

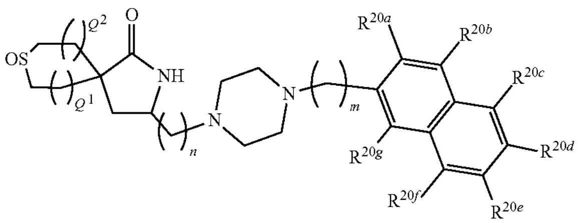

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIt-5):

(IIIt-5)

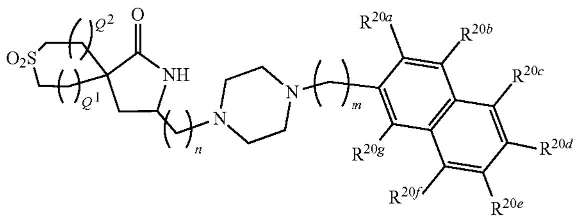

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIu):

(IIIu)

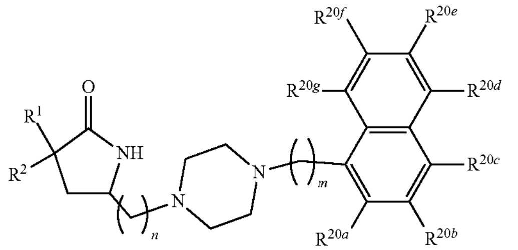

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

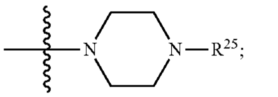

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (IIIv):

(IIIv)

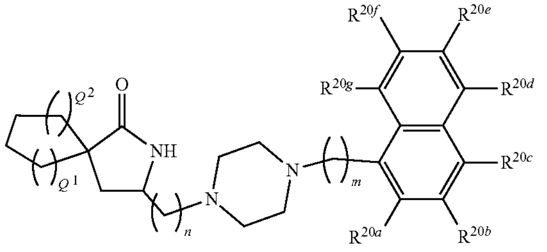

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIw):

(IIIw)

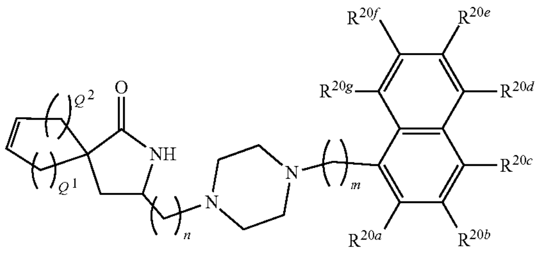

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIx):

(IIIx)

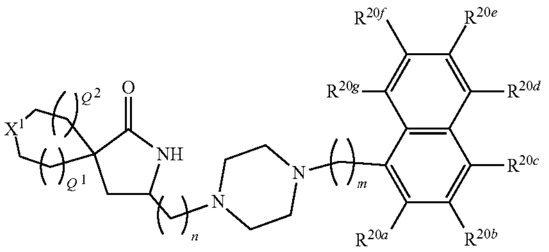

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IIIx-1):

(IIIx-1)

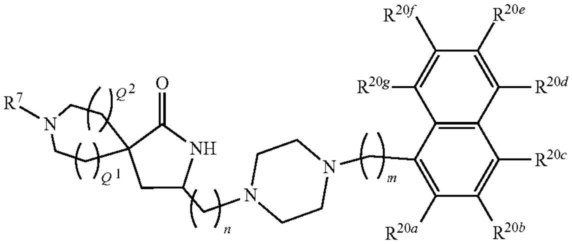

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIx-2):

(IIIx-2)

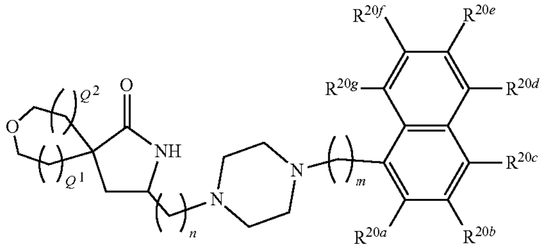

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIx-3):

(IIIx-3)

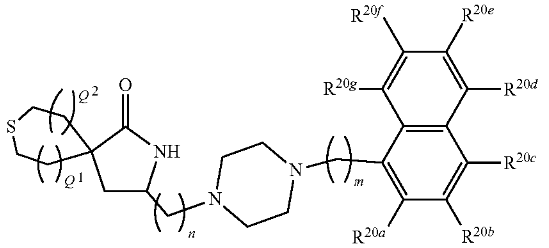

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIx-4):

(IIIx-4)

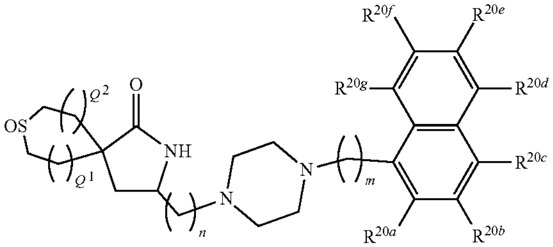

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IIIx-5):

(IIIx-5)

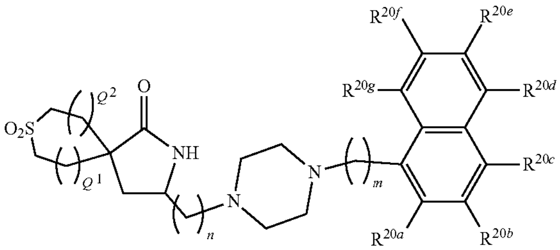

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IV):

(IV)

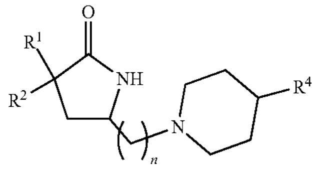

Including hydrates, solvates, enantiomers, diastereomers, pharmaceutically acceptable salts, and complexes thereof.

In embodiments, a compound has a structure according to Formula (XLVII), (XLVII)

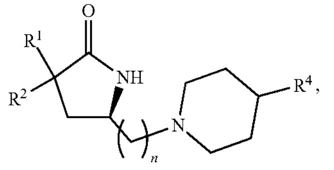

or a pharmaceutically acceptable salt thereof.

In embodiments, a compound has a structure according to Formula (XLVII), (XLVII)

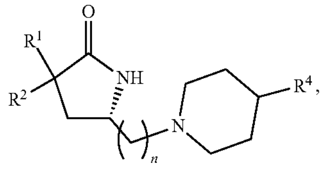

or a pharmaceutically acceptable salt thereof.

In embodiments, n is 1, 2, or 3. In embodiments, n is 1. In embodiments, n is 2. In embodiments, n is 1 or 2.

In embodiments, each of $R^1$ and $R^2$ is unsubstituted $C_{1-6}$ alkyl. In embodiments, each of $R^1$ and $R^2$ is ethyl. In embodiments, each of $R^1$ and $R^2$ is methyl.

In embodiments, $R^1$ and $R^2$ are taken together with the atoms to which they are bound to form a 5- to 8-membered ring, optionally containing one carbon-carbon double bonds and/or a ring atom selected from the group consisting of O, S, SO, $SO_2$, and $NR^7$.

In embodiments, $R^1$ and $R^2$ are taken together with the atoms to which they are bound to form a $C_3$-$C_8$ cycloalkyl or a $C_5$-$C_8$ cycloalkenyl.

In embodiments, $R^1$ and $R^2$ are taken together with the atoms to which they are bound to form a $C_3$-$C_8$ cycloalkyl or $C_5$-$C_8$ cycloalkenyl selected from the group consisting of cyclopropyl, cyclobutyl, cyclopentyl, cyclopentenyl, cyclohexyl, cyclohexenyl, cycloheptyl, cycloheptenyl, cyclooctyl, and cyclooctenyl. In embodiments, said $C_3$-$C_8$ cycloalkyl or $C_5$-$C_8$ cycloalkenyl is unsubstituted. In embodiments, said $C_3$-$C_8$ cycloalkyl or $C_5$-$C_8$ cycloalkenyl is substituted by 1, 2, 3, or 4 substituents (e.g., 1 or 2 substituents as described herein). In embodiments, said substituents are selected from oxo (═O), hydroxyl, halo, cyano, $C_{1-6}$ alkoxy, $C_{1-6}$ linear alkyl, $C_{3-7}$ branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

In embodiments, $R^1$ and $R^2$ are taken together with the atoms to which they are bound to form a 5- to 8-membered ring containing a ring atom that is $NR^7$. In embodiments, said 5- to 8-membered ring is not further substituted. In embodiments, said 5- to 8-membered ring further comprises 1, 2, 3, or 4 substituents (e.g., 1 or 2 substituents as described herein). In embodiments, said substituents are selected from oxo (═O), hydroxyl, halo, cyano, $C_{1-6}$ alkoxy, $C_{1-6}$ linear alkyl, $C_{3-7}$ branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

In embodiments, $R^1$ and $R^2$ are taken together to form a pyrrolidinyl or piperidinyl group where the nitrogen atom is $NR^7$. In embodiments, said pyrrolidinyl or piperidinyl group is not further substituted. In embodiments, said pyrrolidinyl or piperidinyl group further comprises 1, 2, 3, or 4 substituents as described herein.

In embodiments, $R^7$ is $COR^8$, and $R^8$ is $C_{1-6}$ linear alkyl.

In embodiments, $R^7$ is acetyl.

In embodiments, $R^7$ is $SO_2R^{10c}$, and $R^{10c}$ is $C_{1-6}$ linear alkyl.

In embodiments, $R^{10c}$ is methyl (i.e., $R^7$ is $SO_2Me$).

In embodiments, $R^4$ is phenyl.

In embodiments, $R^4$ is substituted phenyl. In embodiments, $R^4$ is phenyl substituted by 1, 2, 3, 4, or 5 substituents (e.g., phenyl substituted by 1 or 2 substituents as described herein). In embodiments, the substitutents are selected from the group consisting of hydroxyl, halo, cyano, $C_{1-6}$ alkoxy, $C_{1-6}$ linear alkyl, $C_{3-7}$ branched alkyl, $C_{1-6}$haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

In embodiments, $R^4$ is selected from the group consisting of hydroxylphenyl, fluorophenyl, chlorophenyl, bromophenyl, cyanophenyl, tolyl, methoxylphenyl, difluorophenyl, dichlorophenyl, chloro-fluorophenyl, dimethylphenyl, trifluoromethylphenyl, di(trifluoromethyl)phenyl, In embodiments, $R^4$ is selected from the group consisting of 4-hydroxyphenyl, 3-fluorophenyl, 4-fluorophenyl, 3-chlorophenyl, 4-chlorophenyl, 3,4-dichlorophenyl, 4-fluoro-3-chlorophenyl, 4-cyanophenyl, 2-methoxyphenyl, 2-methylphenyl, 3-methylphenyl, 4-methylphenyl, 2-isopropylphenyl, 4-trifluoromethylphenyl, 2-morpholinophenyl, and 4-methyl-2-morpholinophenyl.

In embodiments, $R^4$ is pyridyl. In embodiments, $R^4$ is 2-pyridyl. In embodiments, $R^4$ is 3-pyridyl. In embodiments, $R^4$ is 4-pyridyl. In embodiments, said pyridyl is unsubstituted. In embodiments, said pyridyl is substituted by 1, 2, 3, or 4 substituents (e.g., pyridyl substituted by 1 or 2 substituents as described herein). In embodiments, the substitutents are selected from the group consisting of hydroxyl, halo, cyano, $C_{1-6}$ alkoxy, $C_{1-6}$ linear alkyl, $C_3$-7 branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

The embodiments of the present invention include compounds having formula (IVa):

(IVa)

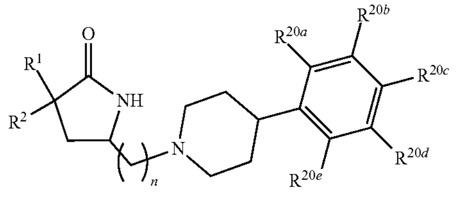

Including hydrates, solvates, enantiomers, diastereomers, pharmaceutically acceptable salts, and complexes thereof wherein $R^{20a}$, $R^{20b}$, $R^{20c}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

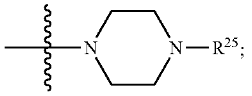

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 3 of $R^{20a}$, $R^{20b}$, $R^{20c}$, $R^{20d}$, and $R^{20e}$ are hydrogen.

The embodiments of the present invention include compounds having formula (IVb):

(IVb)

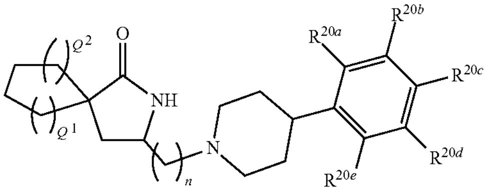

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVc):

(IVc)

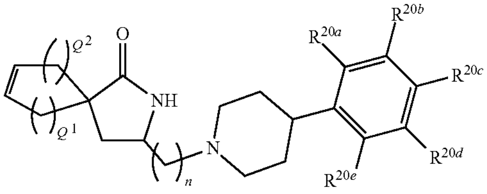

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVd):

(IVd)

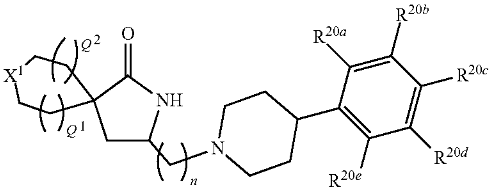

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IVd-1):

(IVd-1)

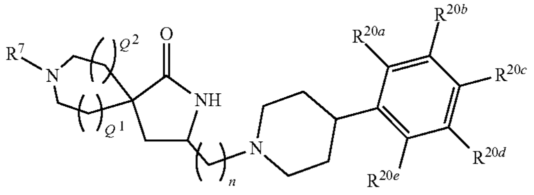

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVd-2):

(IVd-2)

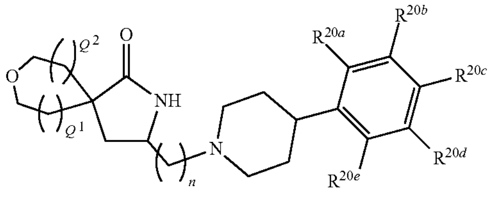

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVd-3):

(IVd-3)

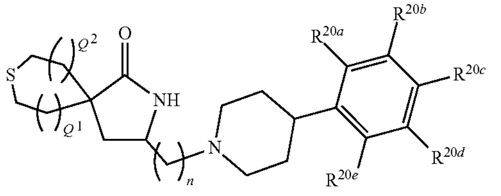

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVd-4):

(IVd-4)

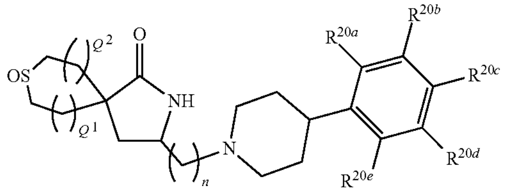

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVd-5):

(IVd-5)

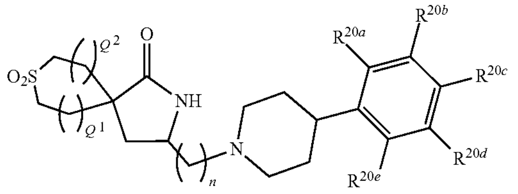

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVe):

(IVe)

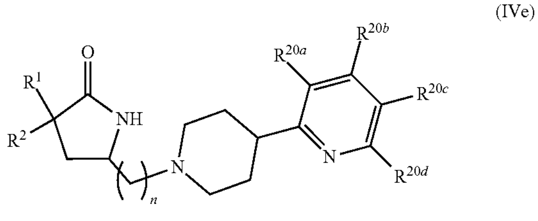

Including hydrates, solvates, enantiomers, diastereomers, pharmaceutically acceptable salts, and complexes thereof wherein $R^{20a}$, $R^{20b}$, $R^{20c}$, and $R^{20d}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

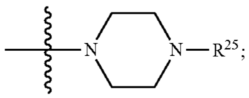

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (IVf):

(IVf)

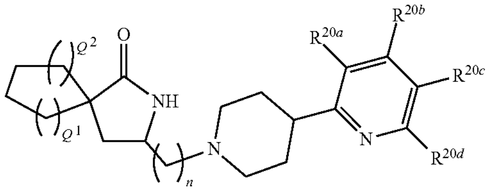

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVg):

(IVg)

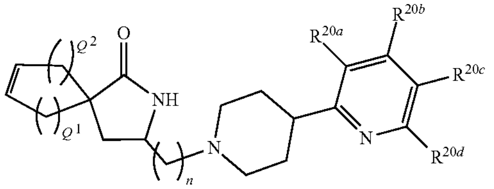

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVh):

(IVh)

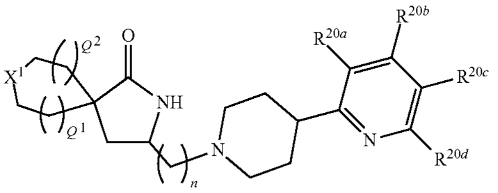

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IVh-1):

(IVh-1)

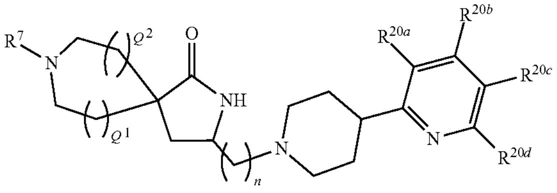

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVh-2):

(IVh-2)

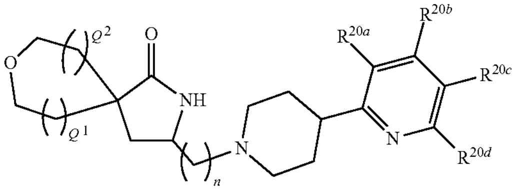

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVh-3):

(IVh-3)

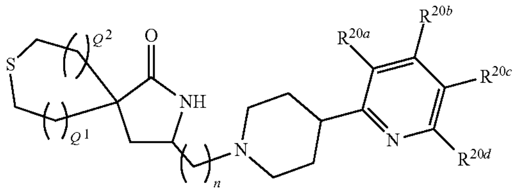

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVh-4):

(IVh-4)

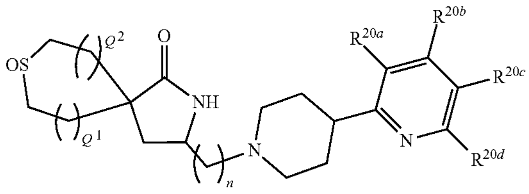

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVh-5):

(IVh-5)

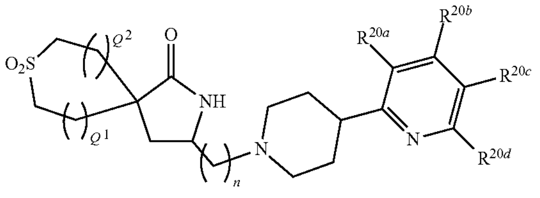

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVi):

(IVi)

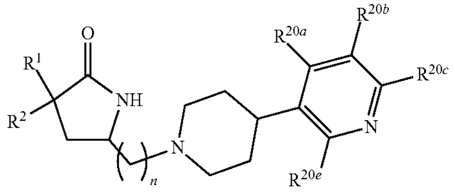

Including hydrates, solvates, enantiomers, diastereomers, pharmaceutically acceptable salts, and complexes thereof wherein $R^{20a}$, $R^{20b}$, $R^{20c}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

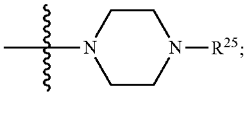

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20e}$ are hydrogen.

The embodiments of the present invention include compounds having formula (IVj):

(IVj)

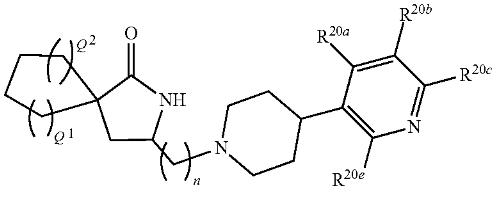

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVk):

(IVk)

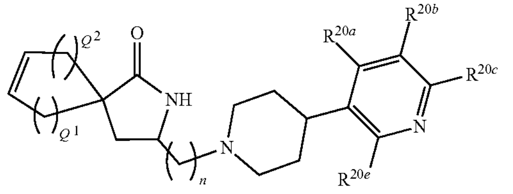

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVL):

(IVL)

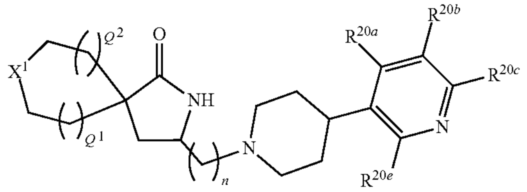

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IVL-1):

(IVL-1)

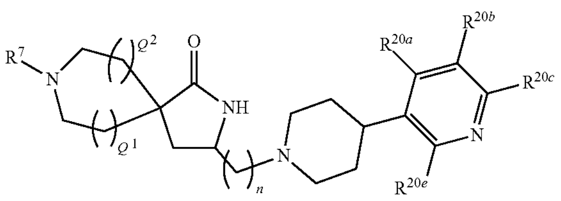

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVL-2):

(IVL-2)

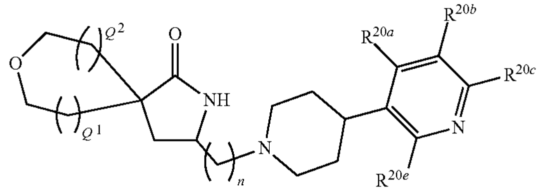

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVL-3):

(IVL-3)

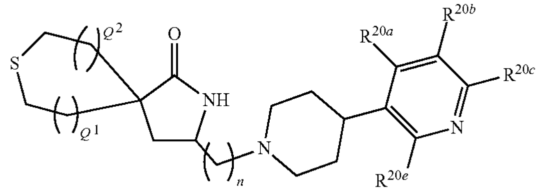

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVL-4):

(IVL-4)

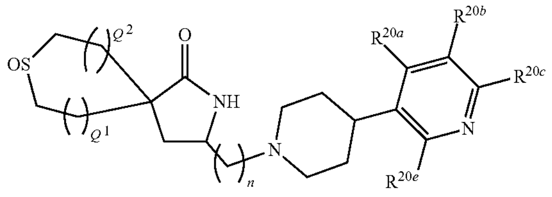

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVL-5):

(IVL-5)

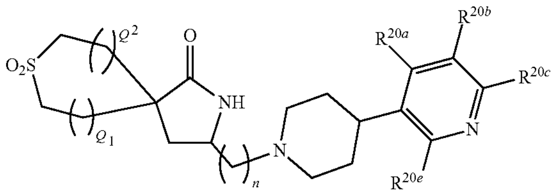

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVm):

(IVm)

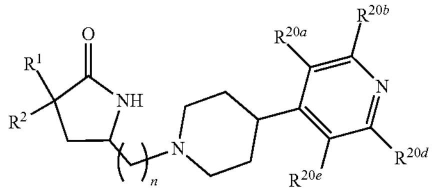

Including hydrates, solvates, enantiomers, diastereomers, pharmaceutically acceptable salts, and complexes thereof wherein $R^{20a}$, $R^{20b}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

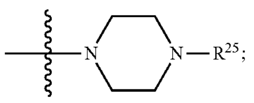

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (IVn):

(IVn)

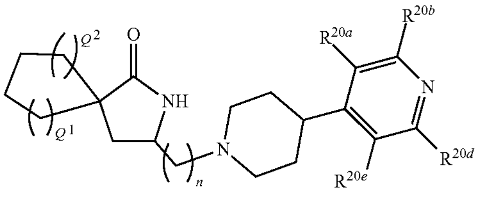

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVo):

(IVo)

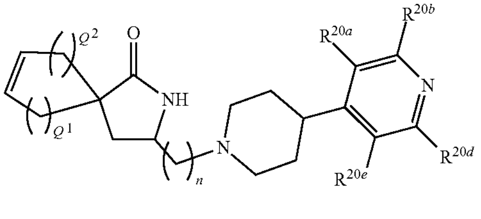

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVp):

(IVp)

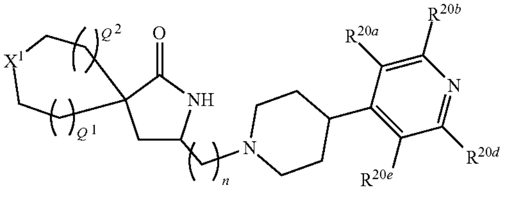

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IVp-1):

(IVp-1)

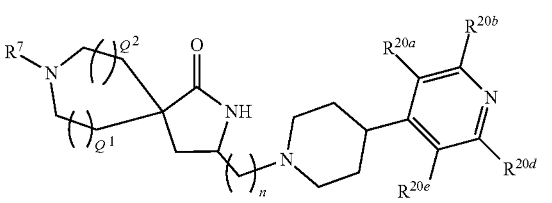

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVp-2):

(IVp-2)

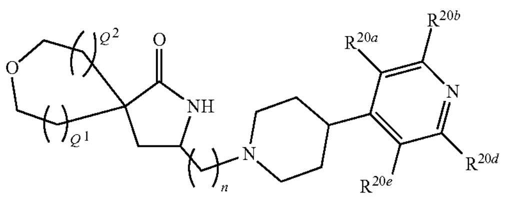

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVp-3):

(IVp-3)

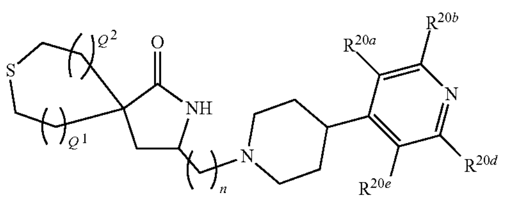

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVp-4):

(IVp-4)

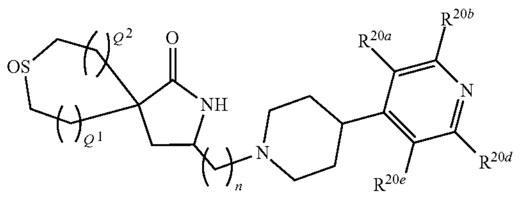

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVp-5):

(IVp-5)

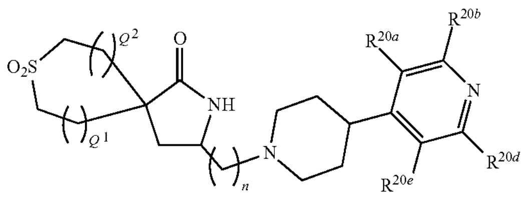

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVq):

(IVq)

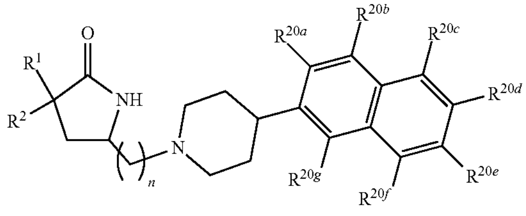

Including hydrates, solvates, enantiomers, diastereomers, pharmaceutically acceptable salts, and complexes thereof wherein $R^{20a}$, $R^{20b}$, $R^{20c}$, $R^{20a}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

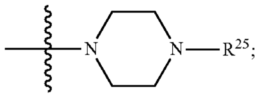

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (IVr):

(IVr)

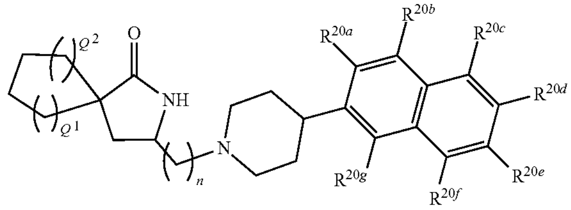

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVs):

(IVs)

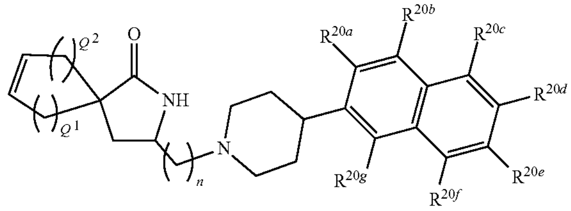

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVt):

(IVt)

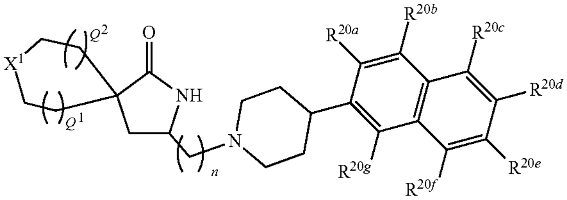

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IVt-1):

(IVt-1)

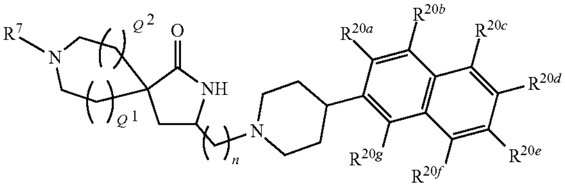

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVt-2):

(IVt-2)

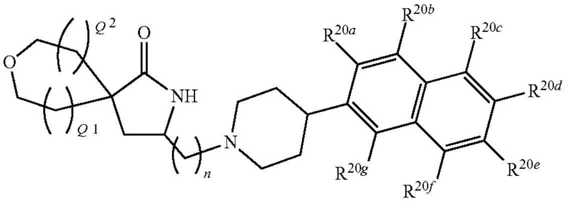

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVt-3):

(IVt-3)

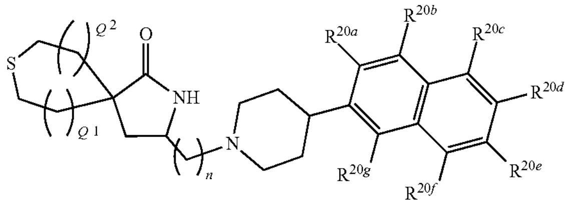

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVt-4):

(IVt-4)

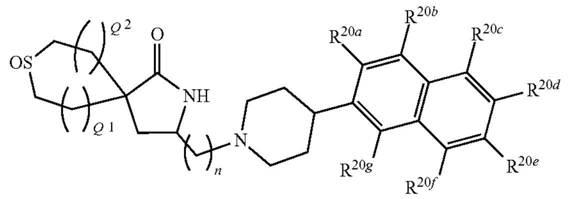

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVt-5):

(IVt-5)

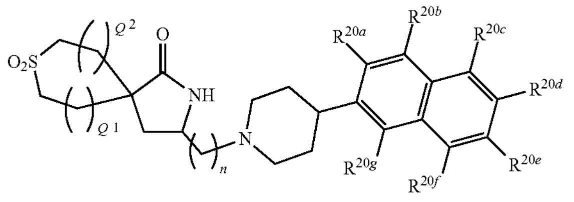

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVu):

(IVu)

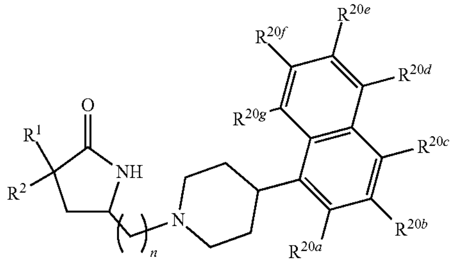

Including hydrates, solvates, enantiomers, diastereomers, pharmaceutically acceptable salts, and complexes thereof wherein $R^{20a}$, $R^{20b}$, $R^{20c}$, $R^{20a}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

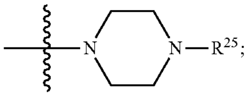

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (IVv):

(IVv)

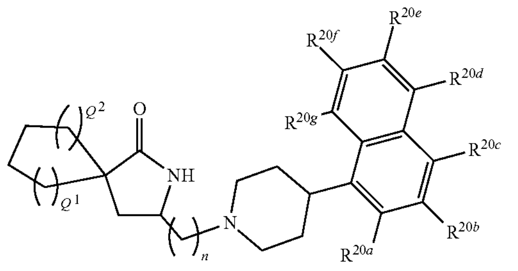

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVw):

(IVw)

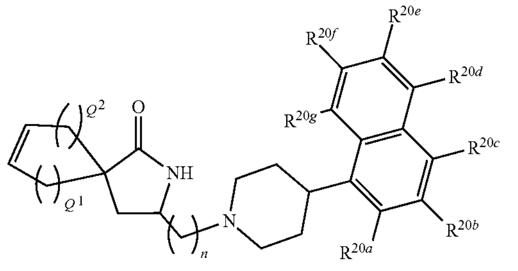

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVx):

(IVx)

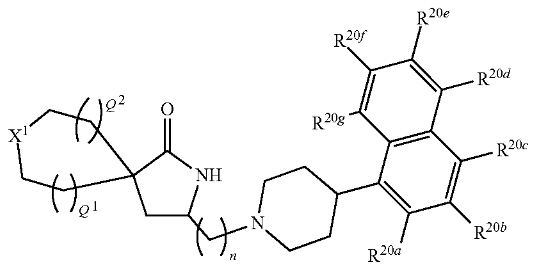

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (IVx-1):

(IVx-1)

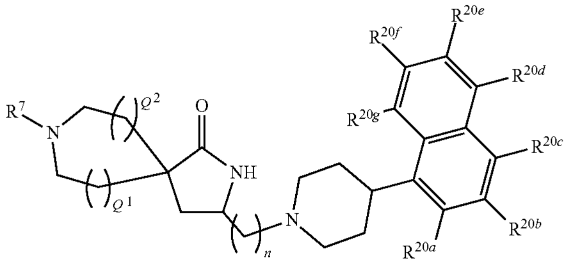

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVx-2):

(IVx-2)

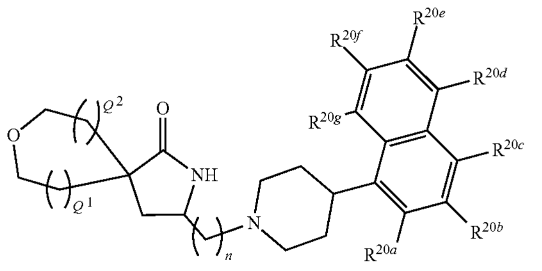

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVx-3):

(IVx-3)

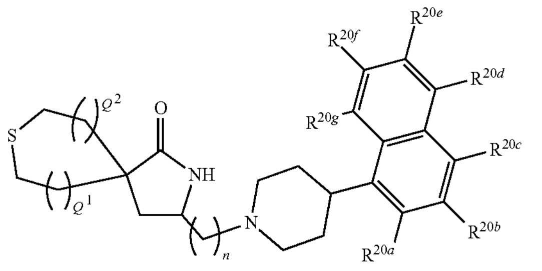

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVx-4):

(IVx-4)

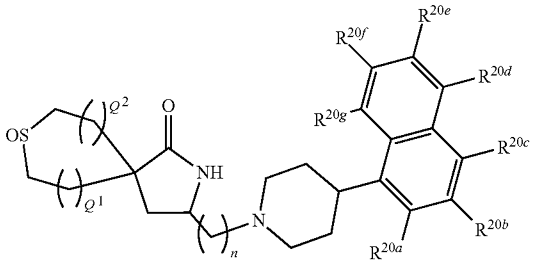

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (IVx-5):

(IVx-5)

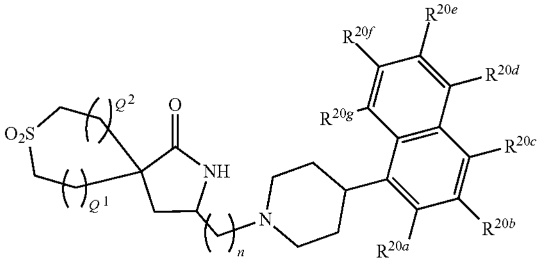

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (V):

(V)

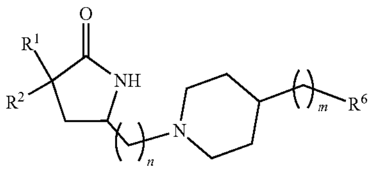

Including hydrates, solvates, enantiomers, diastereomers, pharmaceutically acceptable salts, and complexes thereof.

The embodiments of the present invention include compounds having formula (Va):

(Va)

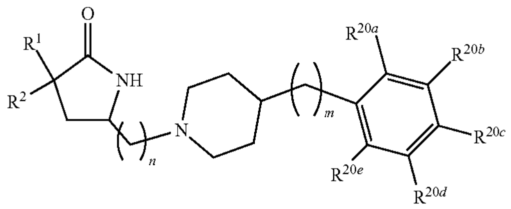

Including hydrates, solvates, enantiomers, diastereomers, pharmaceutically acceptable salts, and complexes thereof wherein $R^{20a}$, $R^{20b}$, $R^{20c}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

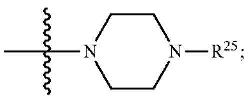

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 3 of $R^{20a}$, $R^{20b}$, $R^{20c}$, $R^{20d}$, and $R^{20e}$ are hydrogen.

The embodiments of the present invention include compounds having formula (Vb):

(Vb)

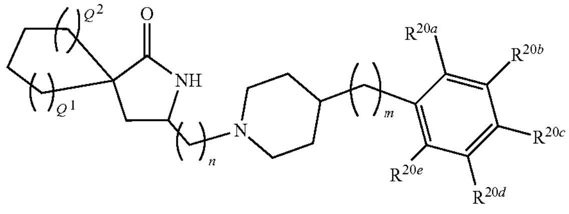

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vc):

(Vc)

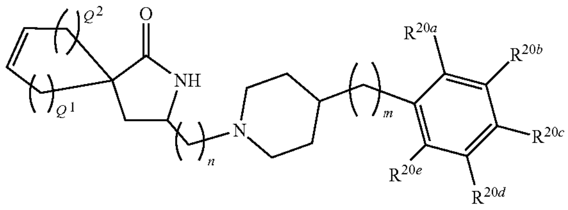

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vd):

(Vd)

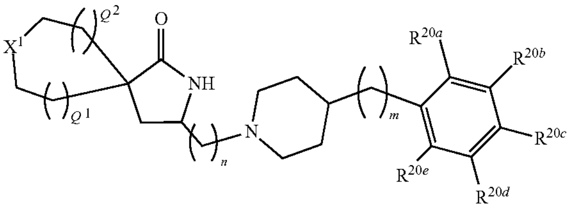

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (Vd-1):

(Vd-1)

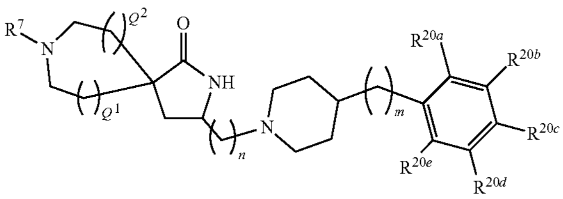

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vd-2):

(Vd-2)

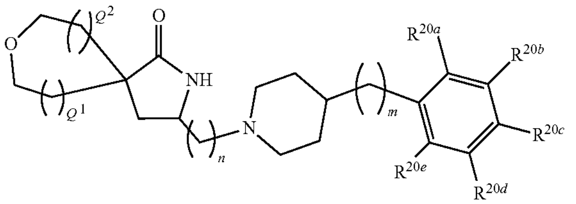

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vd-3):

(Vd-3)

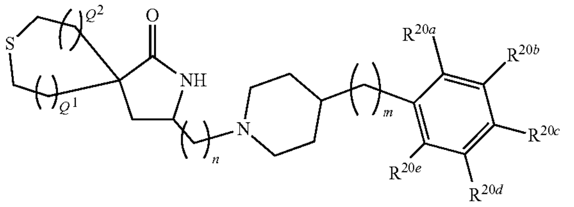

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vd-4):

(Vd-4)

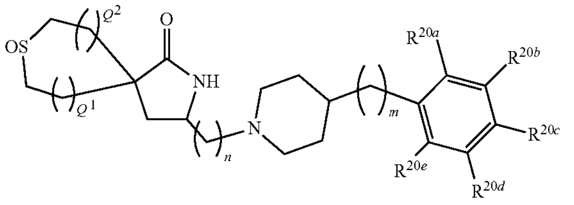

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vd-5):

(Vd-5)

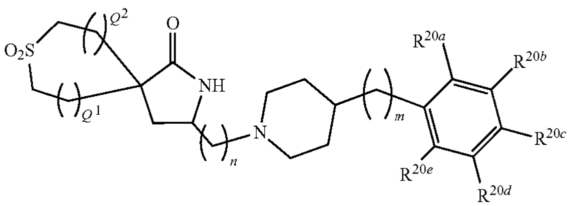

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Ve):

(Ve)

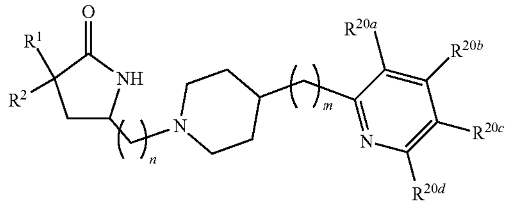

Including hydrates, solvates, enantiomers, diastereomers, pharmaceutically acceptable salts, and complexes thereof wherein $R^{20a}$, $R^{20b}$, $R^{20c}$, and $R^{20d}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

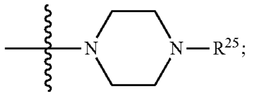

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (Vf):

(Vf)

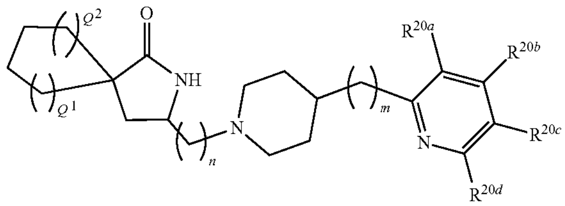

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vg):

(Vg)

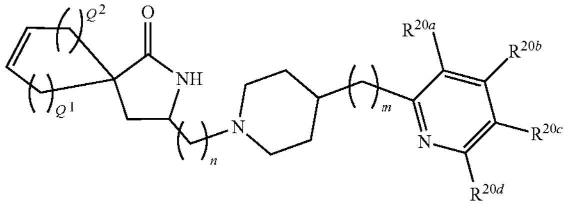

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vh):

(Vh)

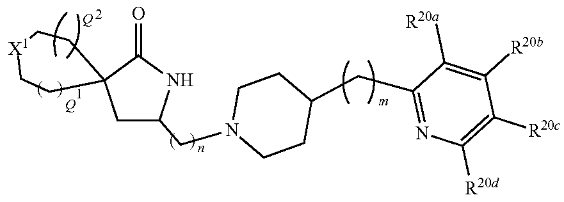

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (Vh-1):

(Vh-1)

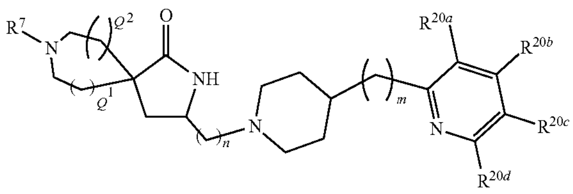

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vh-2):

(Vh-2)

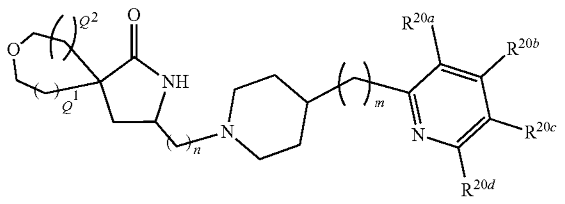

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vh-3):

(Vh-3)

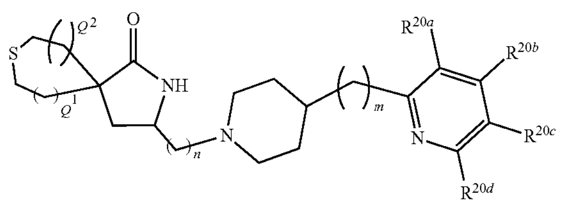

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vh-4):

(Vh-4)

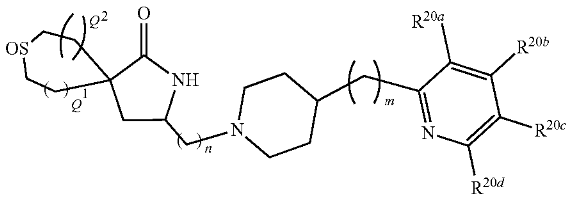

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vh-5):

(Vh-5)

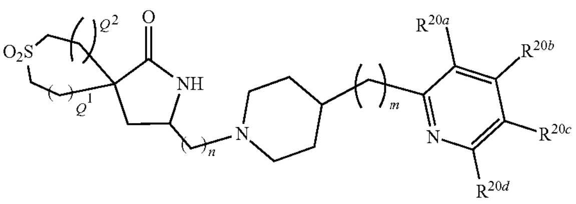

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vi):

(Vi)

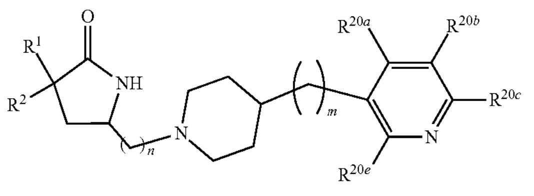

Including hydrates, solvates, enantiomers, diastereomers, pharmaceutically acceptable salts, and complexes thereof wherein $R^{20a}$, $R^{20b}$, $R^{20c}$, and $R^{20d}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

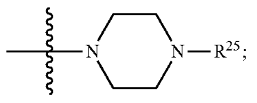

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20e}$ are hydrogen.

The embodiments of the present invention include compounds having formula (Vj):

(Vj)

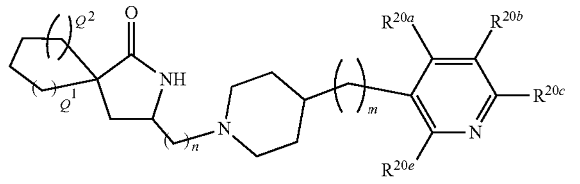

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vk):

(Vk)

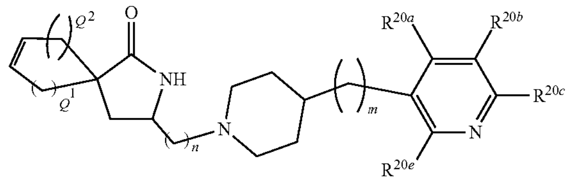

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VL):

(VL)

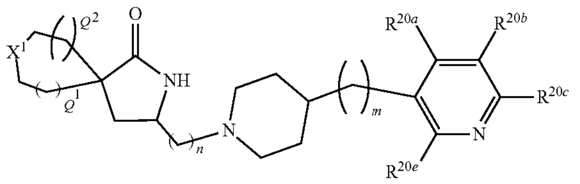

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VL-1):

(VL-1)

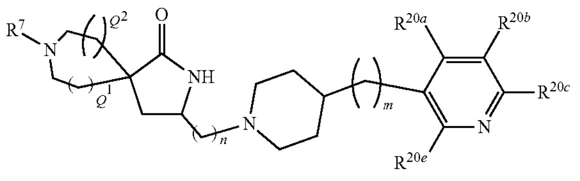

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VL-2):

(VL-2)

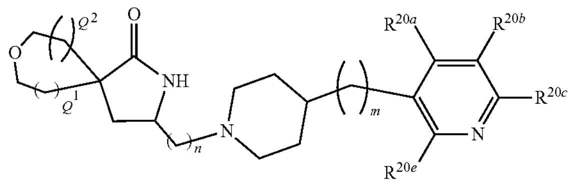

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VL-3):

(VL-3)

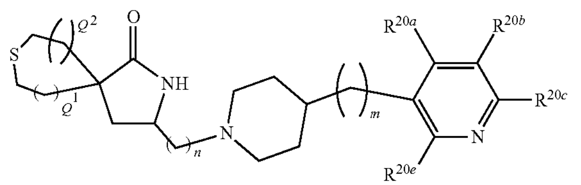

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VL-4):

(VL-4)

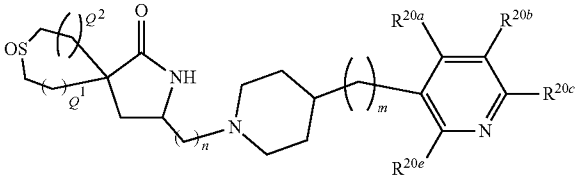

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VL-5):

(VL-5)

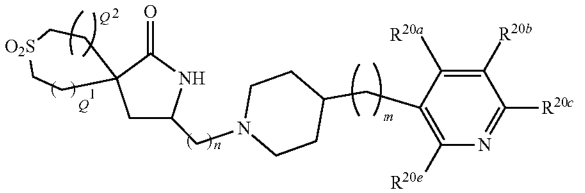

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vm):

(Vm)

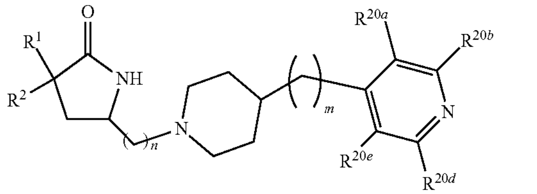

Including hydrates, solvates, enantiomers, diastereomers, pharmaceutically acceptable salts, and complexes thereof wherein $R^{20a}$, $R^{20b}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

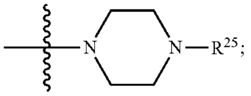

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (Vn):

(Vn)

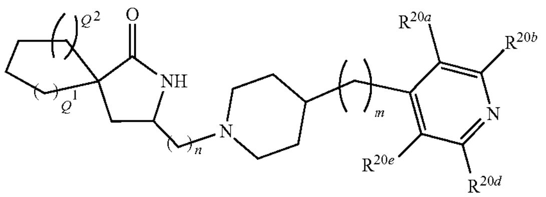

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vo):

(Vo)

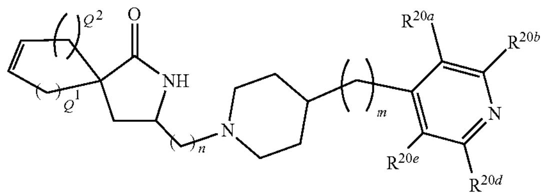

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vp):

(Vp)

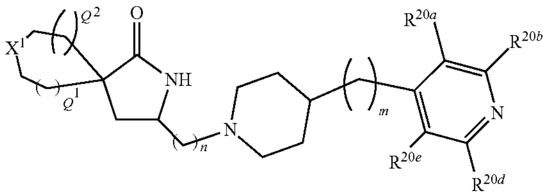

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (Vp-1):

(Vp-1)

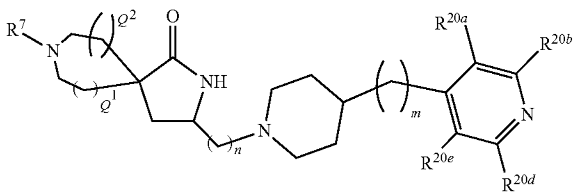

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vp-2):

(Vp-2)

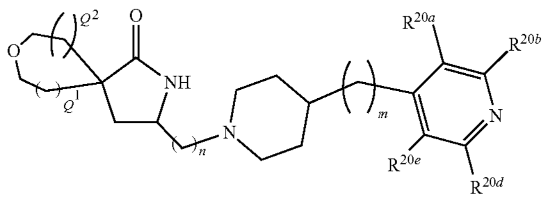

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vp-3):

(Vp-3)

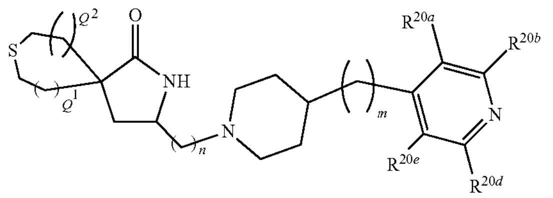

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vp-4):

(Vp-4)

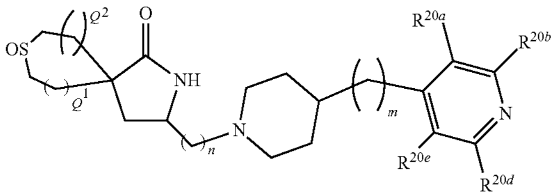

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vp-5):

(Vp-5)

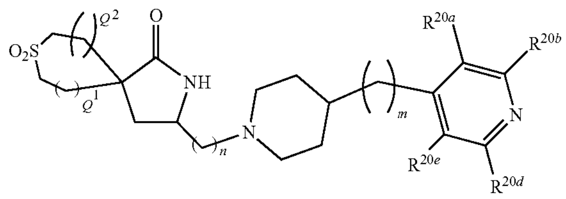

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vq):

(Vq)

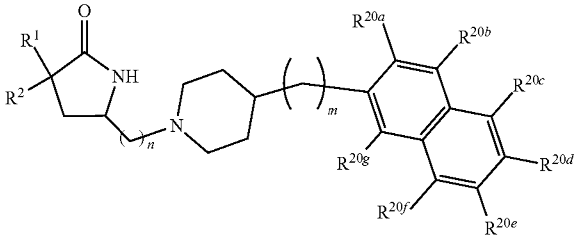

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

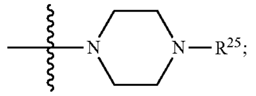

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (Vr):

(Vr)

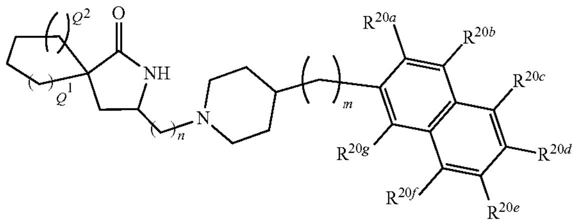

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vs):

(Vs)

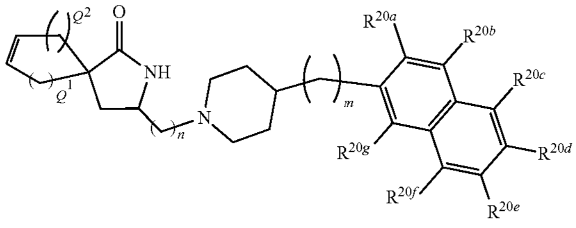

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vt):

(Vt)

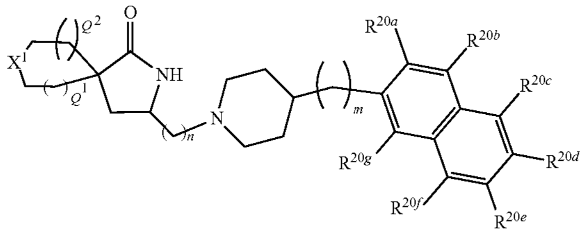

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (Vt-1):

(Vt-1)

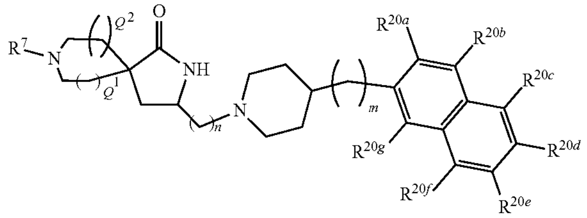

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vt-2):

(Vt-2)

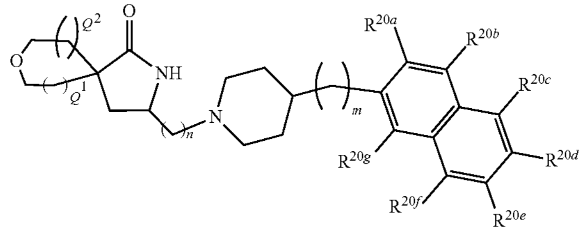

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vt-3):

(Vt-3)

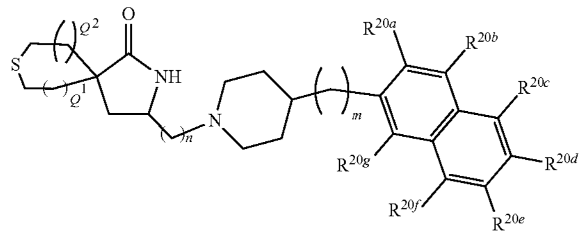

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vt-4):

(Vt-4)

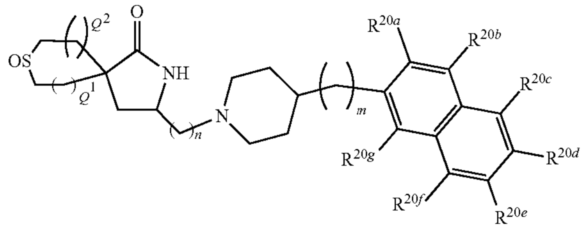

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vt-5):

(Vt-5)

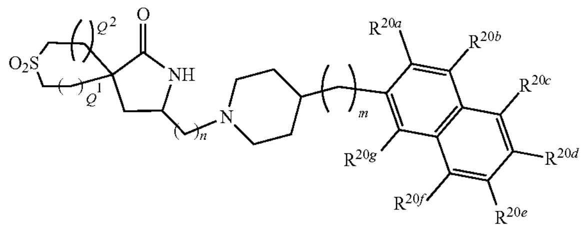

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vu):

(Vu)

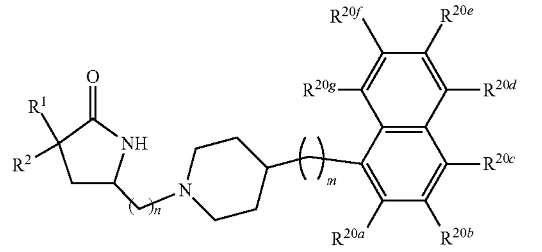

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, $—NR^{23a}R^{23b}$, $NHC(O)R^{24}$, $C(O)NHR^{24}$, $C(O)N(R^{24})_2$, morpholino, and

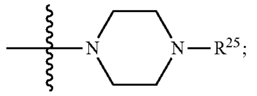

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (Vv):

(Vv)

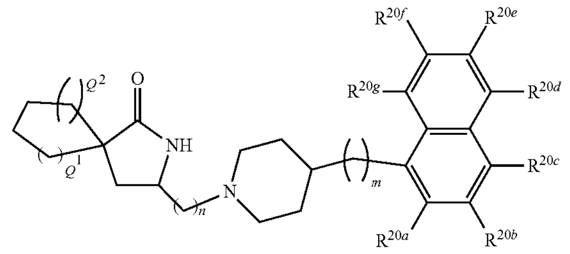

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vw):

(Vw)

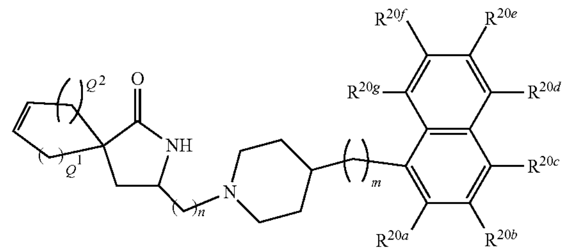

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vx):

(Vx)

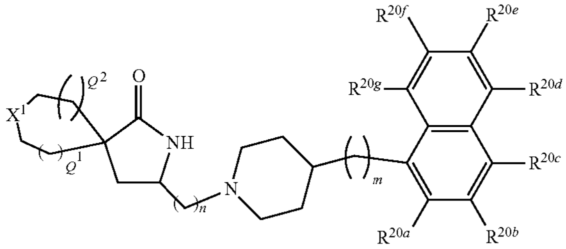

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (Vx-1):

(Vx-1)

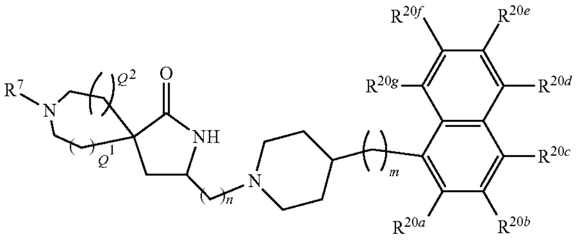

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vx-2):

(Vx-2)

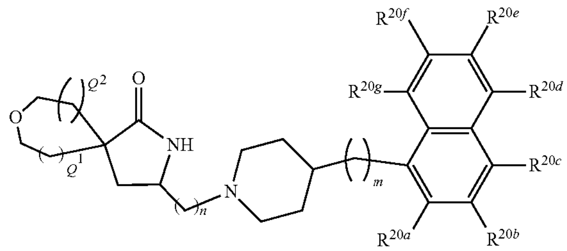

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vx-3):

(Vx-3)

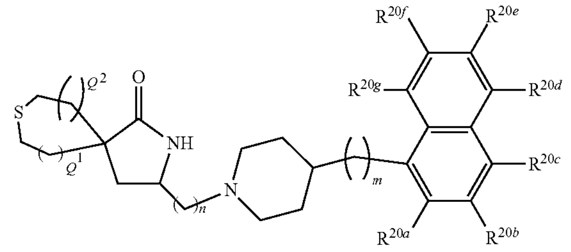

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vx-4):

(Vx-4)

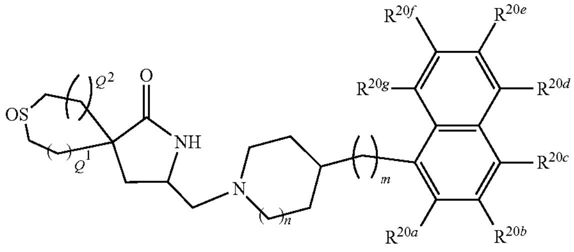

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vx-5):

(Vx-5)

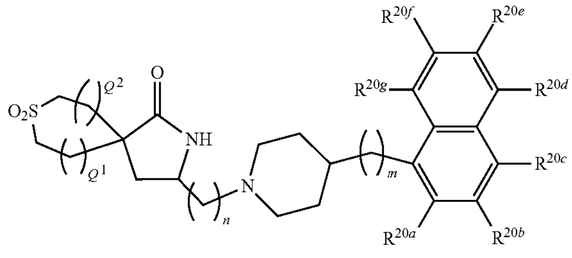

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VI):

(VI)

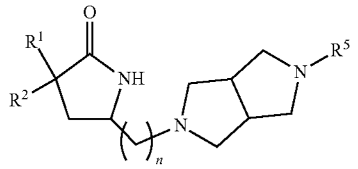

Including hydrates, solvates, enantiomers, diastereomers, pharmaceutically acceptable salts, and complexes thereof.

In embodiments, a compound has a structure according to Formula (XLVI)

(XLVI)

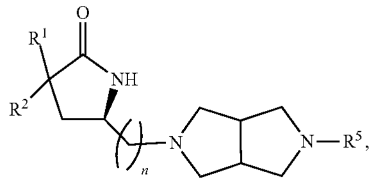

or a pharmaceutically acceptable salt thereof.

In embodiments, a compound has a structure according to Formula (XLVIa)

(XLVIa)

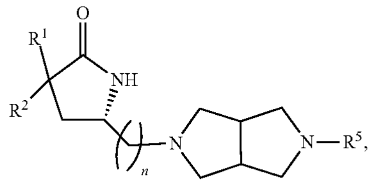

or a pharmaceutically acceptable salt thereof.

In embodiments, n is 1, 2, or 3. In embodiments, n is 1. In embodiments, n is 2. In embodiments, n is 1 or 2.

In embodiments, each of $R^1$ and $R^2$ is unsubstituted $C_{1-6}$ alkyl. In embodiments, each of $R^1$ and $R^2$ is ethyl. In embodiments, each of $R^1$ and $R^2$ is methyl.

In embodiments, $R^1$ and $R^2$ are taken together with the atoms to which they are bound to form a 5- to 8-membered ring, optionally containing one carbon-carbon double bonds and/or a ring atom selected from the group consisting of O, S, SO, $SO_2$, and $NR^7$.

In embodiments, $R^1$ and $R^2$ are taken together with the atoms to which they are bound to form a $C_3$-$C_8$ cycloalkyl or a $C_5$-$C_8$ cycloalkenyl.

In embodiments, $R^1$ and $R^2$ are taken together with the atoms to which they are bound to form a $C_3$-$C_8$ cycloalkyl or $C_5$-$C_8$ cycloalkenyl selected from the group consisting of cyclopropyl, cyclobutyl, cyclopentyl, cyclopentenyl, cyclohexyl, cyclohexenyl, cycloheptyl, cycloheptenyl, cyclooctyl, and cyclooctenyl. In embodiments, said $C_3$-$C_8$ cycloalkyl or $C_5$-$C_8$ cycloalkenyl is unsubstituted. In embodiments, said $C_3$-$C_8$ cycloalkyl or $C_5$-$C_8$ cycloalkenyl is substituted by 1, 2, 3, or 4 substituents (e.g., 1 or 2 substituents as described herein). In embodiments, said substituents are selected from oxo (═O), hydroxyl, halo, cyano, $C_{1-6}$ alkoxy, $C_{1-6}$ linear alkyl, $C_{3-7}$ branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

In embodiments, $R^1$ and $R^2$ are taken together with the atoms to which they are bound to form a 5- to 8-membered ring containing a ring atom that is $NR^7$. In embodiments, said 5- to 8-membered ring is not further substituted. In embodiments, said 5- to 8-membered ring further comprises 1, 2, 3, or 4 substituents (e.g., 1 or 2 substituents as described herein). In embodiments, said substituents are selected from oxo (═O), hydroxyl, halo, cyano, $C_{1-6}$ alkoxy, $C_{1-6}$ linear alkyl, $C_{3-7}$ branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

In embodiments, $R^1$ and $R^2$ are taken together to form a pyrrolidinyl or piperidinyl group where the nitrogen atom is $NR^7$. In embodiments, said pyrrolidinyl or piperidinyl group is not further substituted. In embodiments, said pyrrolidinyl or piperidinyl group further comprises 1, 2, 3, or 4 substituents as described herein.

In embodiments, $R^7$ is $COR^8$, and $R^8$ is $C_{1-6}$ linear alkyl.

In embodiments, $R^7$ is acetyl.

In embodiments, $R^7$ is $SO_2R^{10c}$, and $R^{10c}$ is $C_{1-6}$ linear alkyl.

In embodiments, $R^{10c}$ is methyl (i.e., $R^7$ is $SO_2Me$).

In embodiments, $R^5$ is phenyl.

In embodiments, $R^5$ is substituted phenyl. In embodiments, $R^5$ is phenyl substituted by 1, 2, 3, 4, or 5 substituents (e.g., phenyl substituted by 1 or 2 substituents as described herein). In embodiments, the substitutents are selected from the group consisting of hydroxyl, halo, cyano, $C_{1-6}$ alkoxy, $C_{1-6}$ linear alkyl, $C_{3-7}$ branched alkyl, $C_{1-6}$haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

In embodiments, $R^5$ is selected from the group consisting of hydroxylphenyl, fluorophenyl, chlorophenyl, bromophenyl, cyanophenyl, tolyl, methoxylphenyl, difluorophenyl, dichlorophenyl, chloro-fluorophenyl, dimethylphenyl, trifluoromethylphenyl, di(trifluoromethyl)phenyl, In embodiments, $R^5$ is selected from the group consisting of 4-hydroxyphenyl, 3-fluorophenyl, 4-fluorophenyl, 3-chlorophenyl, 4-chlorophenyl, 3,4-dichlorophenyl, 4-fluoro-3-chlorophenyl, 4-cyanophenyl, 2-methoxyphenyl, 2-methylphenyl, 3-methylphenyl, 4-methylphenyl, 2-isopropylphenyl, 4-trifluoromethylphenyl, 2-morpholinophenyl, and 4-methyl-2-morpholinophenyl.

In embodiments, $R^5$ is pyridyl. In embodiments, $R^5$ is 2-pyridyl. In embodiments, $R^5$ is 3-pyridyl. In embodiments, $R^5$ is 4-pyridyl. In embodiments, said pyridyl is unsubstituted. In embodiments, said pyridyl is substituted by 1, 2, 3, or 4 substituents (e.g., pyridyl substituted by 1 or 2 substituents as described herein). In embodiments, the substitutents are selected from the group consisting of hydroxyl, halo, cyano, $C_{1-6}$ alkoxy, $C_{1-6}$ linear alkyl, $C_{3-7}$ branched alkyl, $C_{1-6}$ haloalkyl, $C_{3-8}$ cycloalkyl, and 3- to 8-membered heterocylyl. In embodiments, the substituents are selected from the group consisting of —OH, —F, —Cl, —Br, —I, —CN, —OMe, —OEt, —O$^n$Pr, —O$^i$Pr, —OCF3, -Me, -Et, -$^n$Pr, -$^i$Pr, —$CF_3$, cyclopentyl, cyclohexyl, pyrrolidinyl, piperidinyl, and morpholino.

The embodiments of the present invention include compounds having formula (VIa):

(VIa)

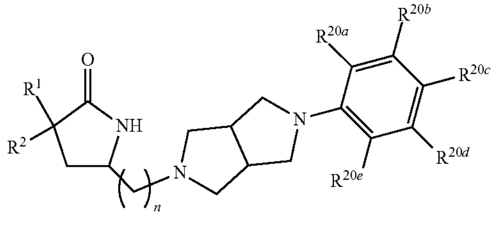

Including hydrates, solvates, enantiomers, diastereomers, pharmaceutically acceptable salts, and complexes thereof wherein $R^{20a}$, $R^{20b}$, $R^{20c}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

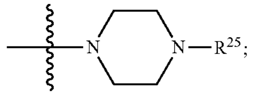

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 3 of $R^{20a}$, $R^{20b}$, $R^{20c}$, $R^{20d}$, and $R^{20e}$ are hydrogen.

The embodiments of the present invention include compounds having formula (VIb):

(VIb)

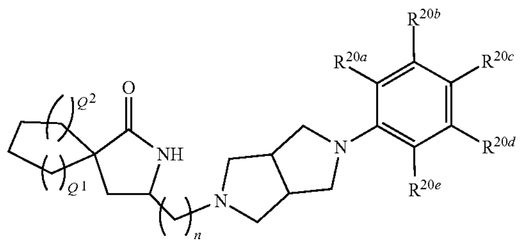

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIc):

(VIc)

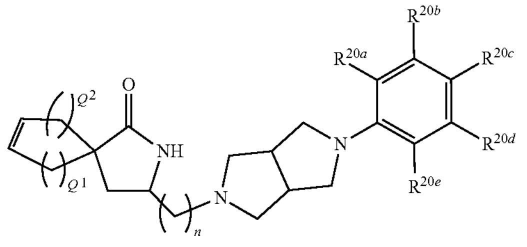

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VId):

(VId)

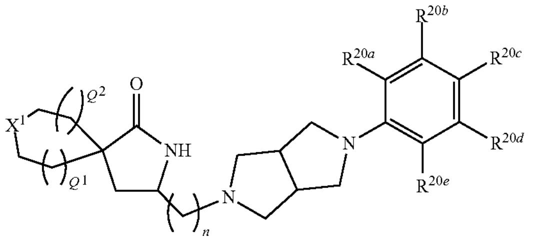

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (Vid-1):

(VId-1)

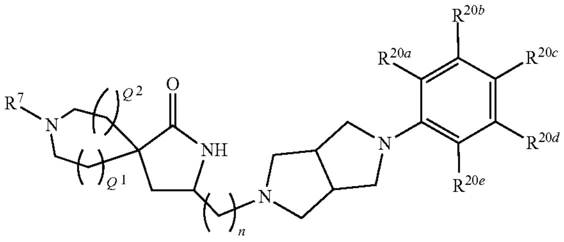

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vid-2):

(VId-2)

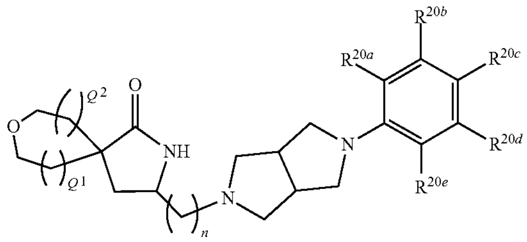

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vid-3):

(VId-3)

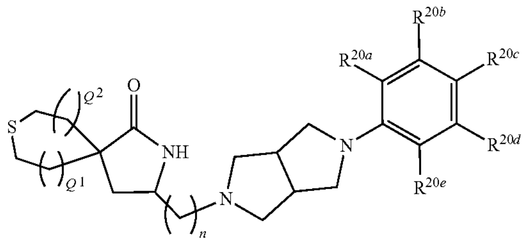

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vid-4):

(VId-4)

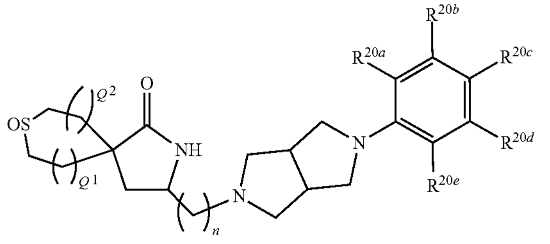

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (Vid-5):

(VId-5)

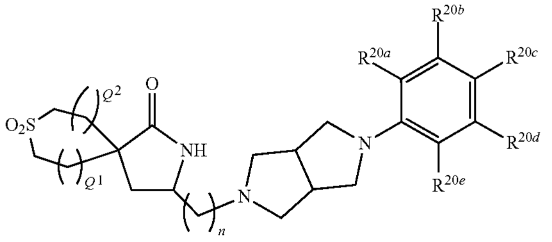

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIe):

(VIe)

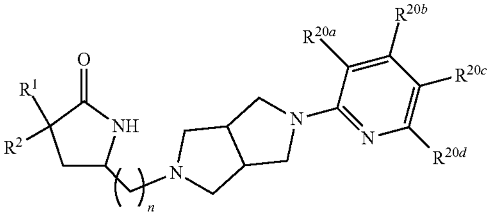

Including hydrates, solvates, enantiomers, diastereomers, pharmaceutically acceptable salts, and complexes thereof wherein $R^{20a}$, $R^{20b}$, $R^{20c}$, and $R^{20d}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

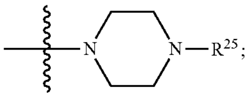

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (VIf):

(VIf)

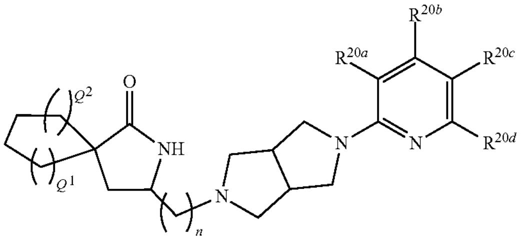

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIg):

(VIg)

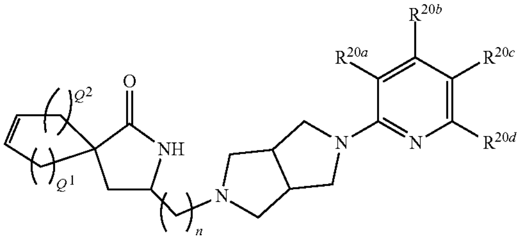

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIh):

(VIh)

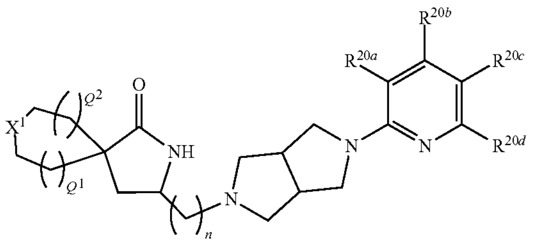

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIh-1):

(VIh-1)

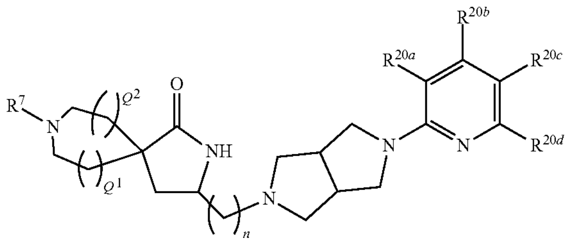

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIh-2):

(VIh-2)

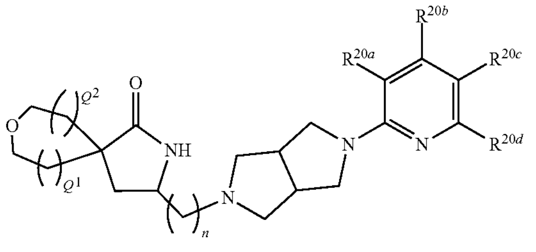

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIh-3):

(VIh-3)

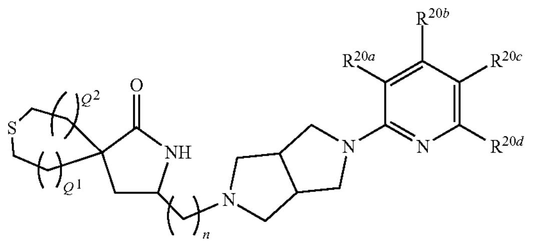

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIh-):

(VIh-4)

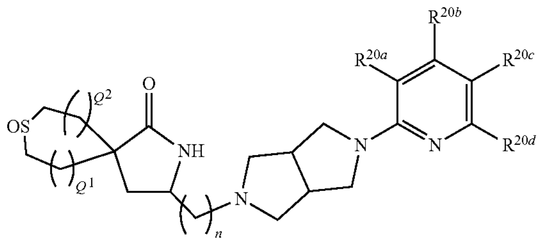

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIh-5):

(VIh-5)

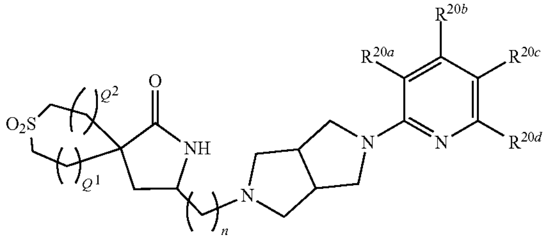

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIi):

(VIc)

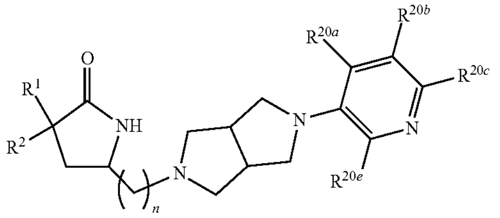

Including hydrates, solvates, enantiomers, diastereomers, pharmaceutically acceptable salts, and complexes thereof wherein $R^{20a}$, $R^{20b}$, $R^{20c}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

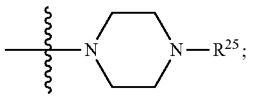

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20e}$ are hydrogen.

The embodiments of the present invention include compounds having formula (VIj):

(VIj)

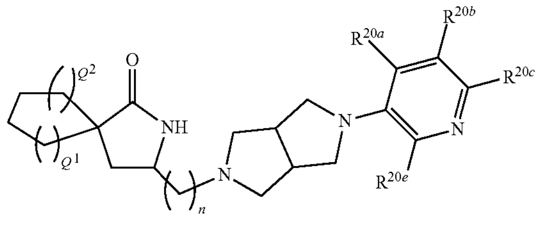

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIk):

(VIk)

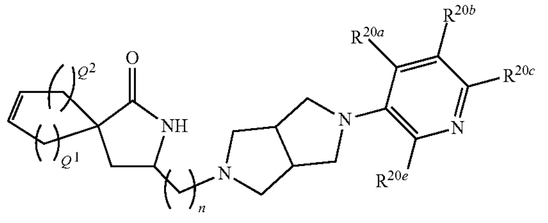

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIL):

(VIL)

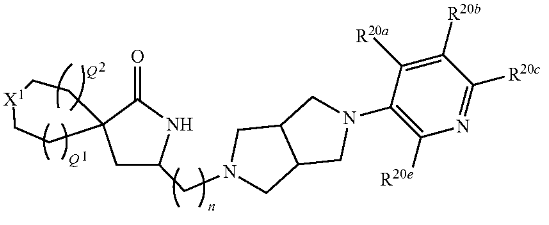

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIL-1):

(VIL-1)

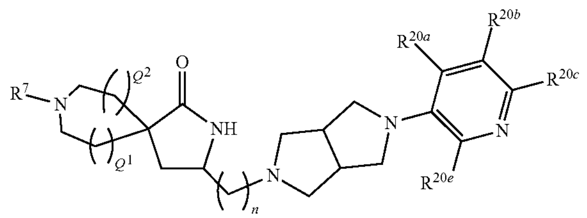

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIL-2):

(VIL-2)

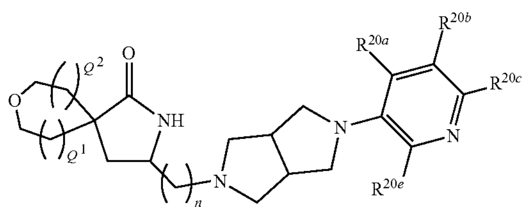

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIL-3):

(VIL-3)

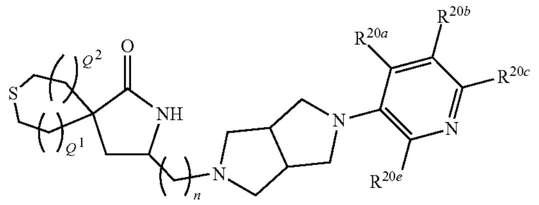

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIL-4):

(VIL-4)

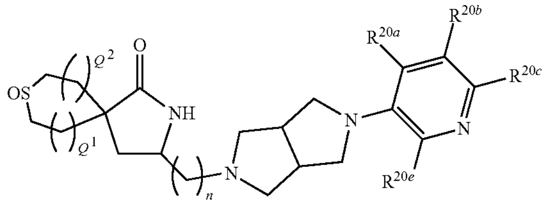

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIL-5):

(VIL-5)

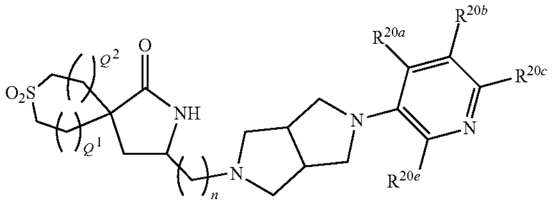

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIm):

(VIm)

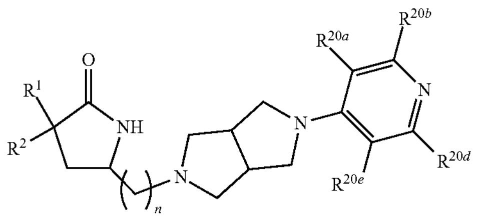

Including hydrates, solvates, enantiomers, diastereomers, pharmaceutically acceptable salts, and complexes thereof wherein $R^{20a}$, $R^{20b}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

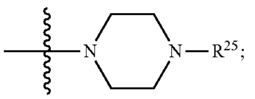

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (VIn):

(VIn)

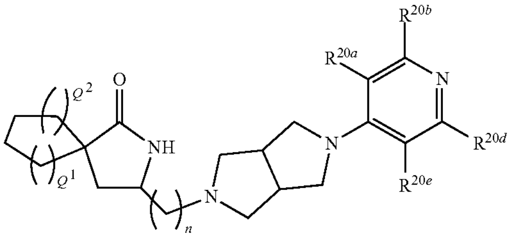

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIo):

(VIo)

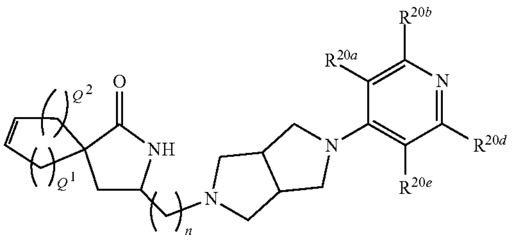

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIp):

(VIp)

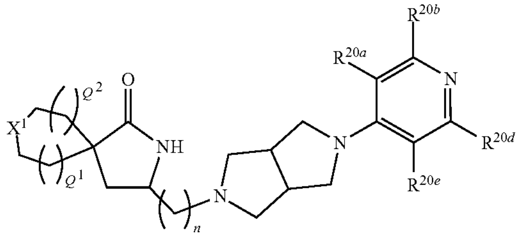

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIp-1):

(VIp-1)

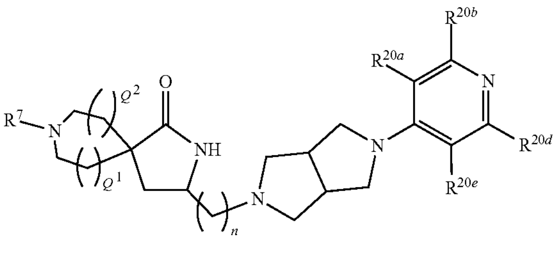

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIp-2):

(VIp-2)

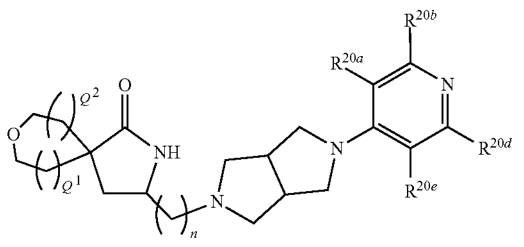

Including hydrates. solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIp-3):

(VIp-3)

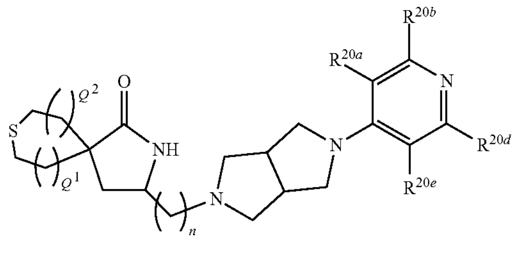

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIp-4):

(VIp-4)

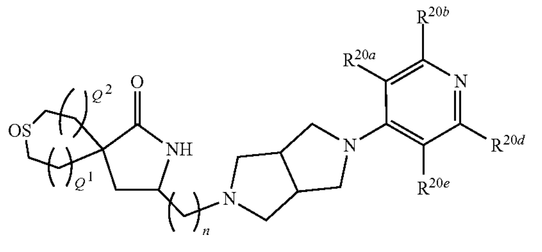

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIp-5):

(VIp-5)

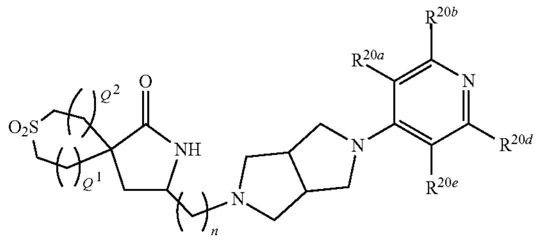

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIq):

(VIq)

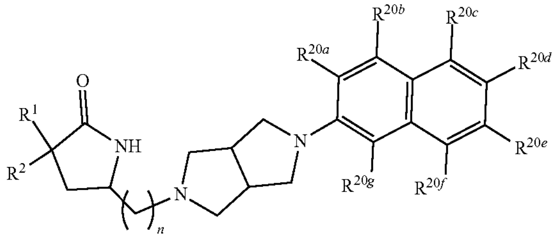

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

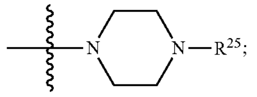

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (VIr):

(VIr)

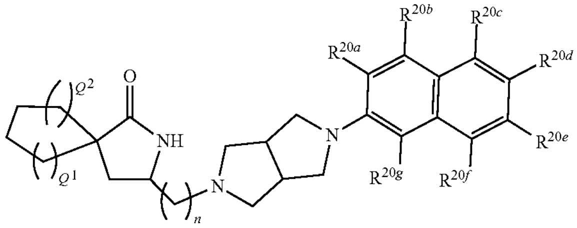

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIs):

(VIs)

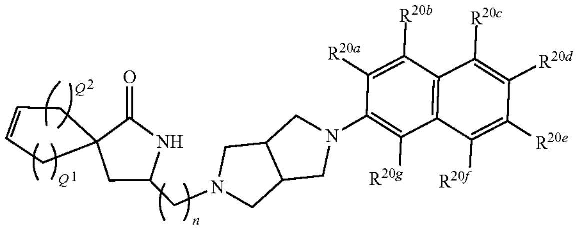

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIt):

(VIt)

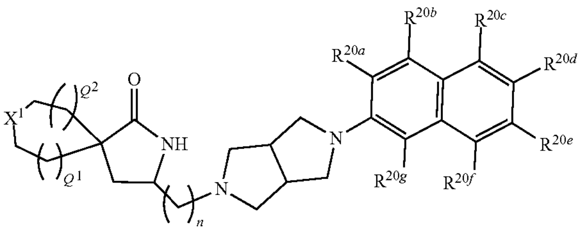

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIt-1):

(VIt-1)

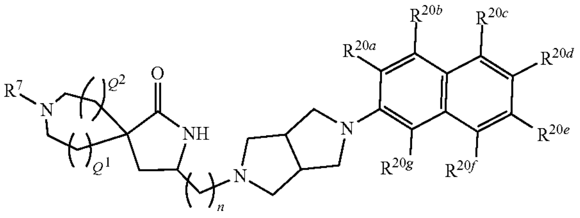

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIt-2):

(VIt-2)

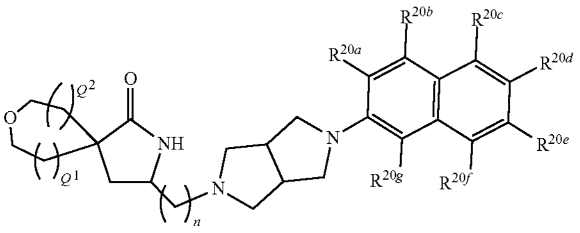

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIt-3):

(VIt-3)

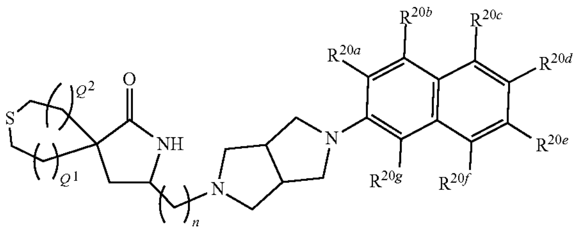

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIt-4):

(VIt-4)

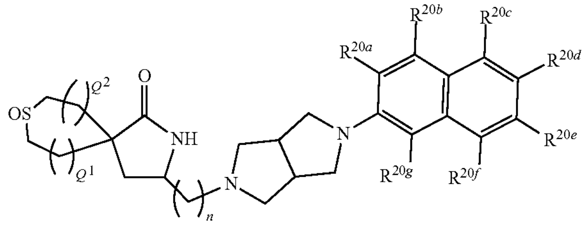

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIt-5):

(VIt-5)

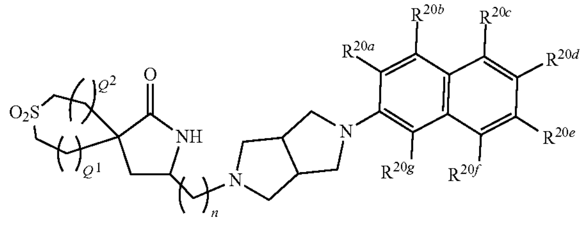

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIu):

(VIu)

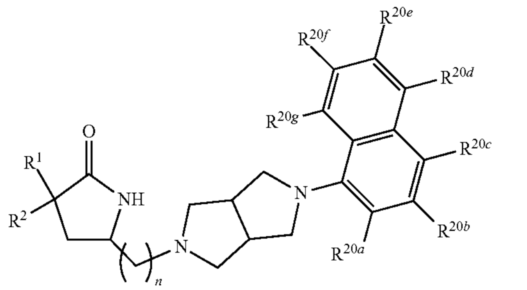

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

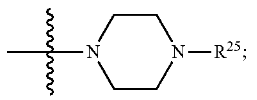

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (VIv):

(VIv)

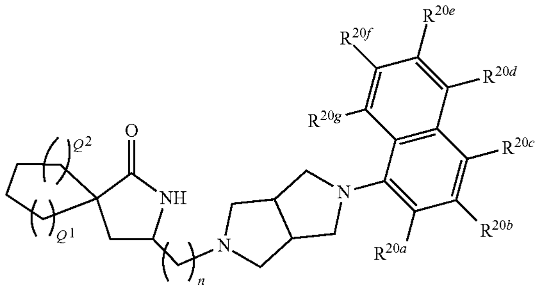

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIw):

(VIw)

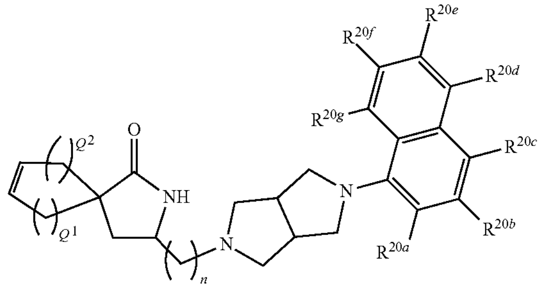

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIx):

(VIx)

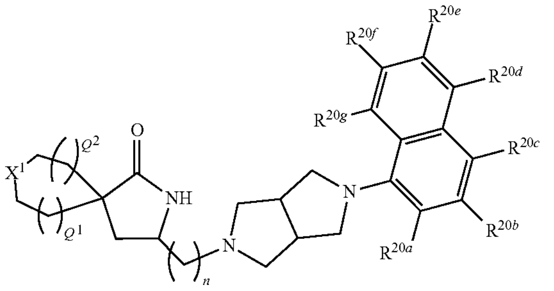

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIx-1):

(VIx-1)

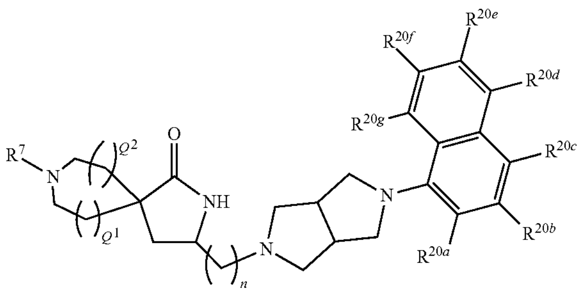

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIx-2):

(VIx-2)

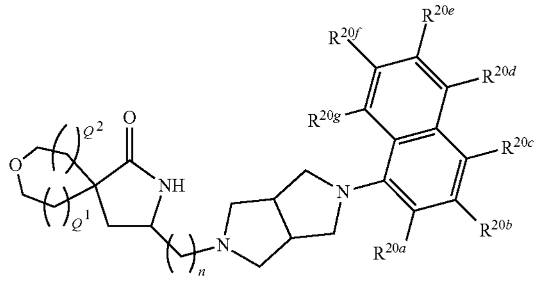

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIx-3):

(VIx-3)

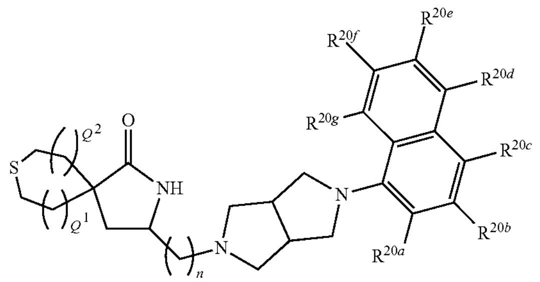

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIx-4):

(VIx-4)

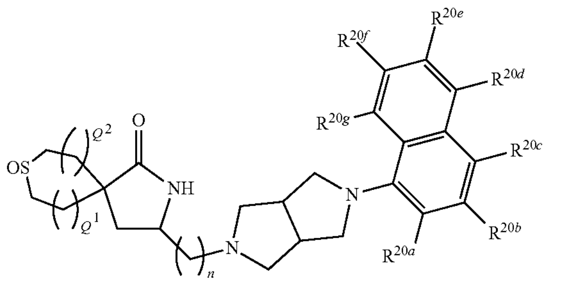

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIx-5):

(VIx-5)

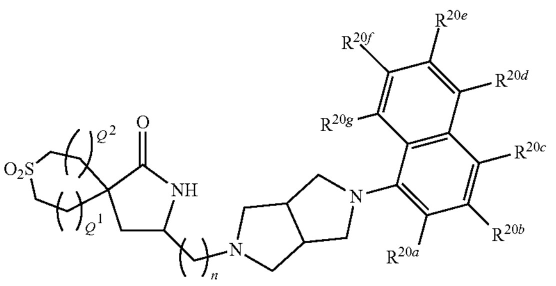

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VII):

(VII)

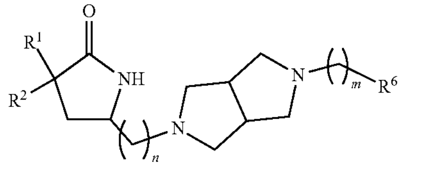

Including hydrates, solvates, enantiomers, diastereomers, pharmaceutically acceptable salts, and complexes thereof.

The embodiments of the present invention include compounds having formula (VIIa):

(VIIa)

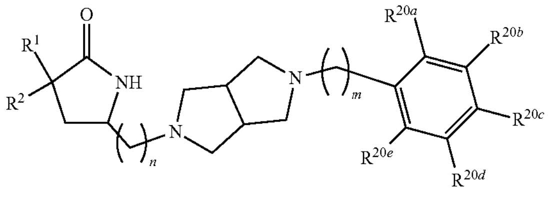

Including hydrates, solvates, enantiomers, diastereomers, pharmaceutically acceptable salts, and complexes thereof wherein $R^{20a}$, $R^{20b}$, $R^{20c}$, $R^{20d}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

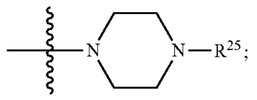

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 3 of $R^{20a}$, $R^{20b}$, $R^{20c}$, $R^{20d}$, and $R^{20e}$ are hydrogen.

The embodiments of the present invention include compounds having formula (VIIb):

(VIIb)

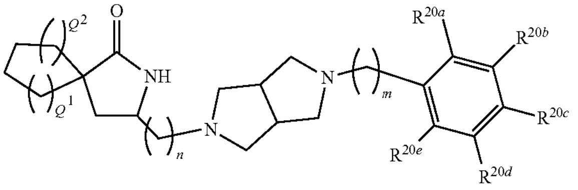

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIc):

(VIIc)

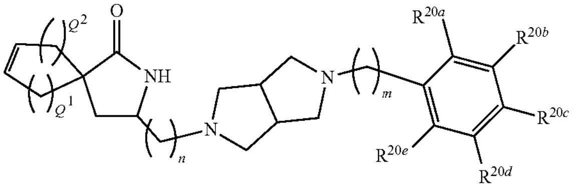

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIId):

(VIId)

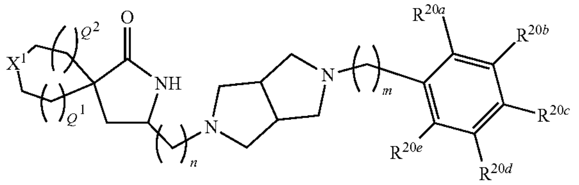

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIId-1):

(VIId-1)

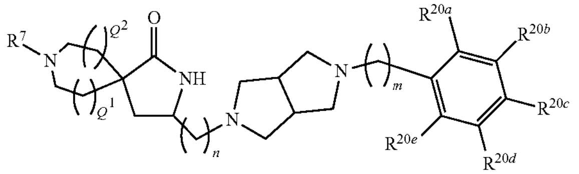

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIId-2):

(VIId-2)

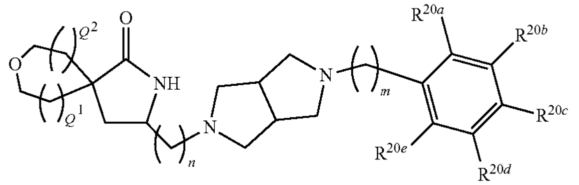

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIId-3):

(VIId-3)

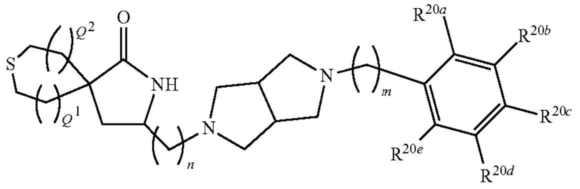

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIId-4):

(VIId-4)

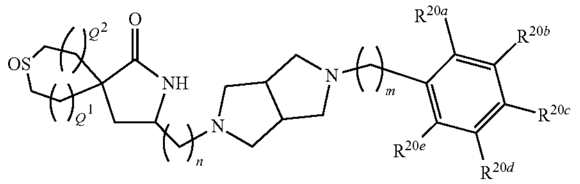

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIId-5):

(VIId-5)

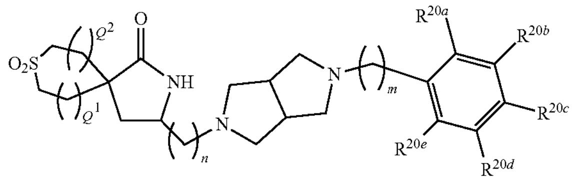

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIe):

(VIIb)

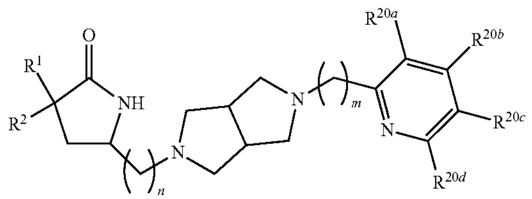

Including hydrates, solvates, enantiomers, diastereomers, pharmaceutically acceptable salts, and complexes thereof wherein $R^{20a}$, $R^{20b}$, $R^{20c}$, and $R^{20d}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

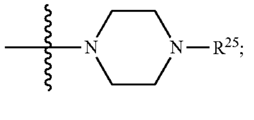

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (VIIf):

(VIIf)

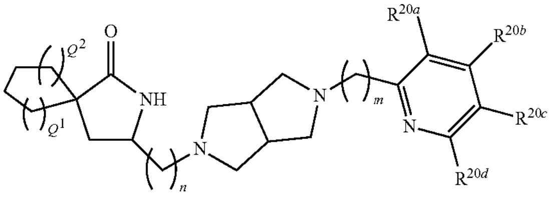

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIg):

(VIIg)

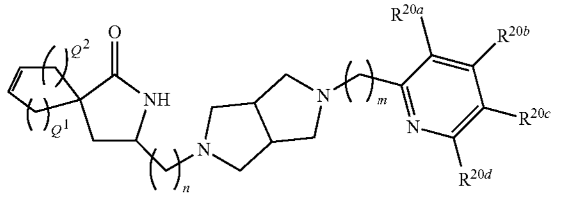

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIh):

(VIIh)

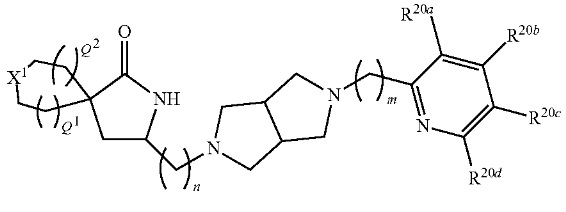

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIIh-1):

(VIIh-1)

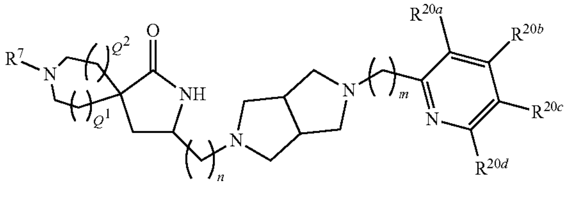

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIh-2):

(VIIh-2)

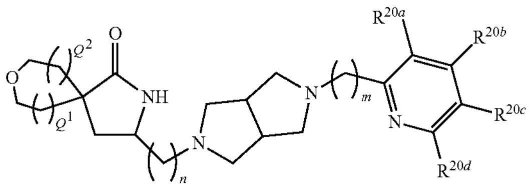

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIh-3):

(VIIh-3)

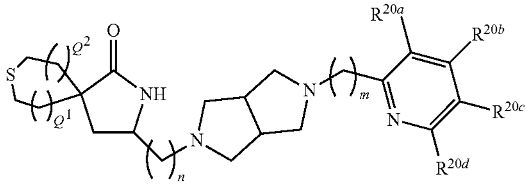

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIh-4):

(VIIh-4)

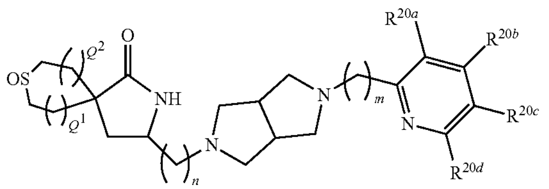

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIh-5):

(VIIh-5)

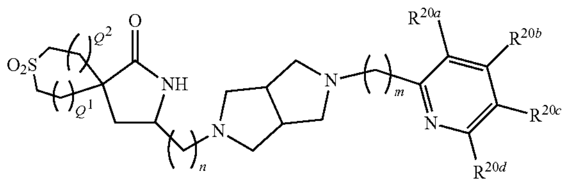

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIi):

(VIIc)

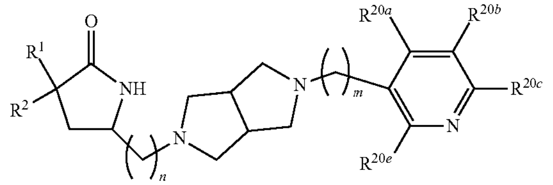

Including hydrates, solvates, enantiomers, diastereomers, pharmaceutically acceptable salts, and complexes thereof wherein $R^{20a}$, $R^{20b}$, $R^{20c}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

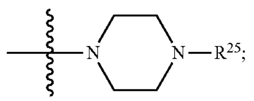

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20e}$ are hydrogen.

The embodiments of the present invention include compounds having formula (VIIj):

(VIIj)

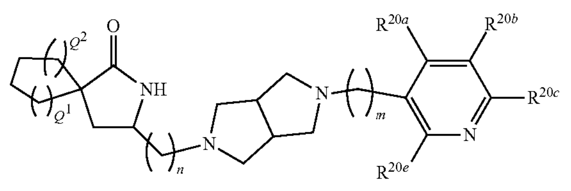

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIk):

(VIIk)

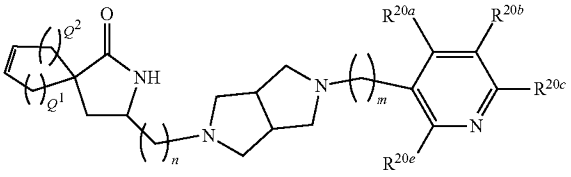

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIL):

(VIIL)

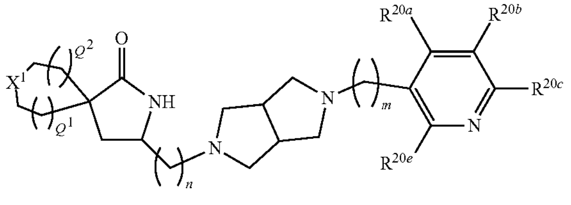

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIIL-1):

(VIIL-1)

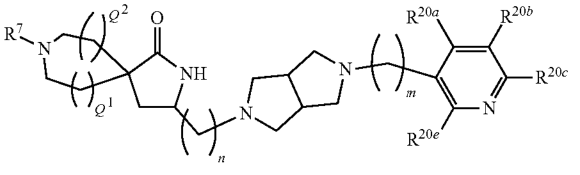

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIL-2):

(VIIL-2)

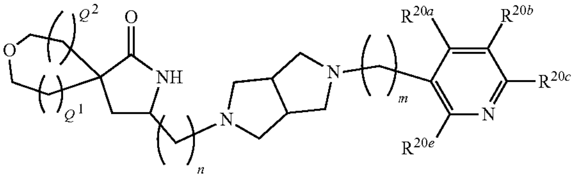

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIL-3):

(VIIL-3)

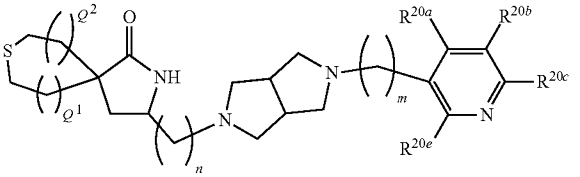

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIL-4):

(VIIL-4)

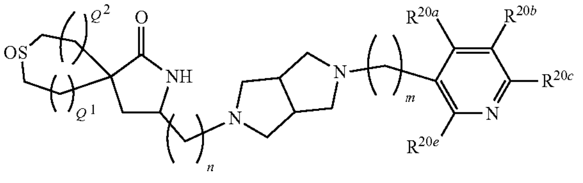

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIL-5):

(VIIL-5)

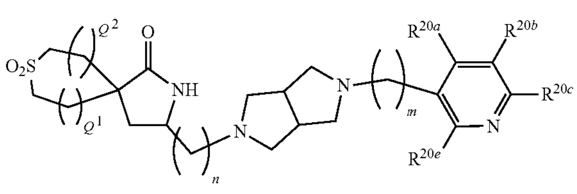

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIm):

(VIIm)

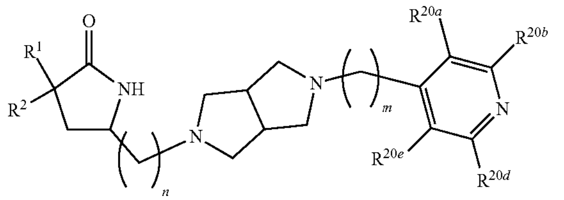

Including hydrates, solvates, enantiomers, diastereomers, pharmaceutically acceptable salts, and complexes thereof wherein $R^{20a}$, $R^{20b}$, $R^{20c}$, and $R^{20e}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_3$-7cycloalkyl, $SO_2C_{1-6}$ linear alkyl, $SO_2C_{3-7}$ branched alkyl, $SO_2C_{3-7}$cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

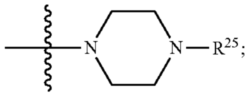

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 2 of $R^{20a}$, $R^{20b}$, $R^{20c}$, and $R^{20d}$ are hydrogen.

The embodiments of the present invention include compounds having formula (VIIn):

(VIIn)

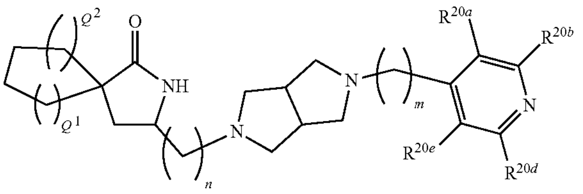

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIo):

(VIIo)

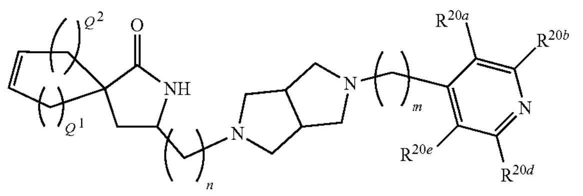

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIp):

(VIIp)

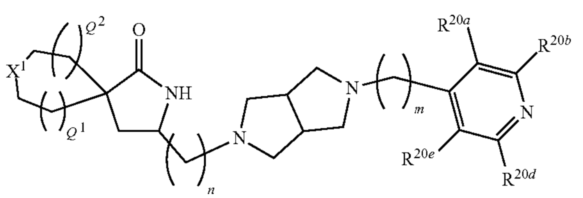

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIIp-1):

(VIIp-1)

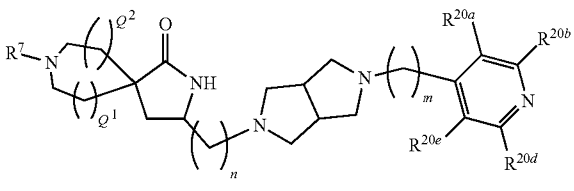

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIp-2):

(VIIp-2)

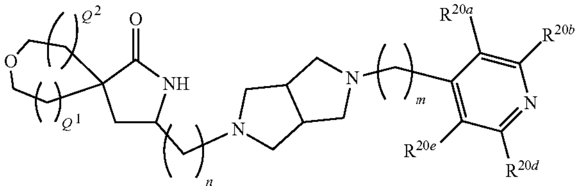

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIp-3):

(VIIp-3)

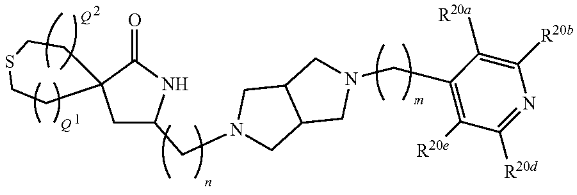

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIp-4):

(VIIp-4)

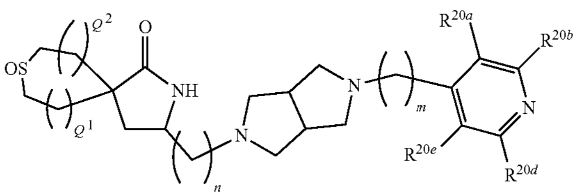

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIp-5):

(VIIp-5)

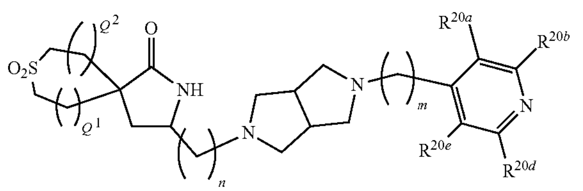

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIq):

(VIIq)

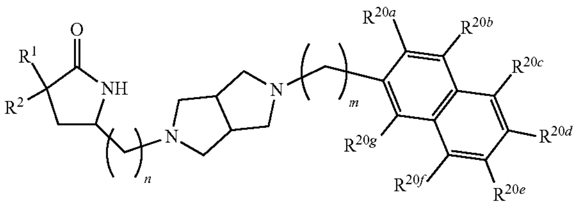

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

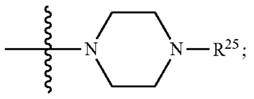

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (VIIr):

(VIIr)

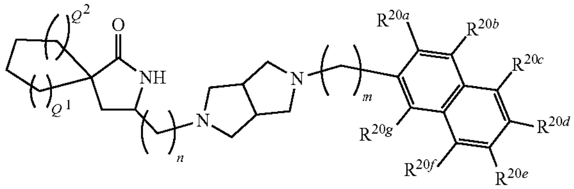

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIs):

(VIIs)

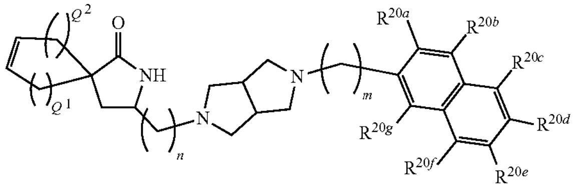

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIt):

(VIIt)

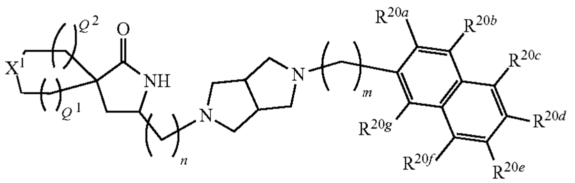

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIIt-1):

(VIIt-1)

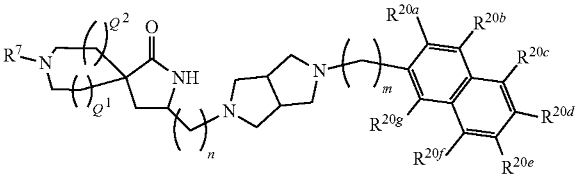

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIt-2):

(VIIt-2)

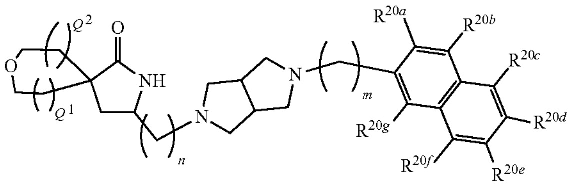

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIt-3):

(VIIt-3)

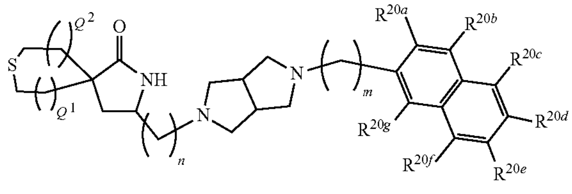

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIt-4):

(VIIt-4)

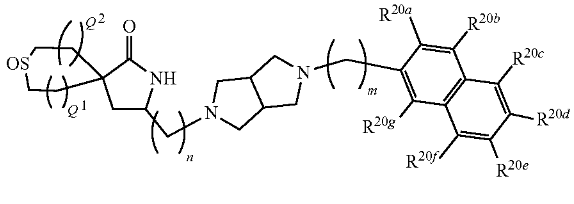

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIt-5):

(VIIt-5)

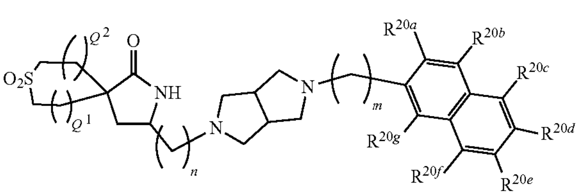

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIu):

(VIIu)

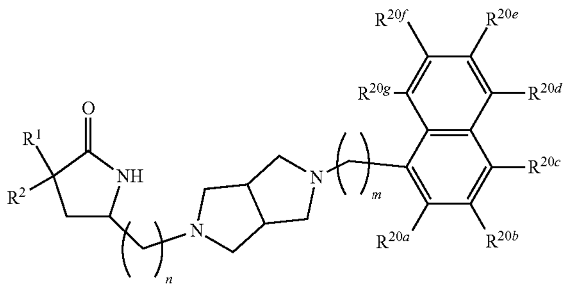

Including hydrates, solvates, enantiomers, diastereomers, pharmaceutically acceptable salts, and complexes thereof wherein $R^{20a}$, $R^{20b}$, $R^{20c}$, $R^{20d}$, $R^{20e}$, $R^{20f}$, and $R^{20g}$ are independently selected from the group consisting of hydrogen, —CN, —$NO_2$, —OH, halogen, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, $C_{3-7}$ branched haloalkoxy, SH, $SC_{1-6}$ linear alkyl, $SC_{3-7}$ branched alkyl, $SC_{3-7}$cycloalkyl, $SO_2C_{1-6}$ linear alkyl, $SO_2C_{3-7}$ branched alkyl, $SO_2C_3$-7cycloalkyl, $SO_2NH_2$, $SO_2NHR^{21}$, $NHSO_2R^{22}$, —$NR^{23a}R^{23b}$, $NHC(O)R^{24}$, $C(O)NHR^{24}$, $C(O)N(R^{24})_2$, morpholino, and

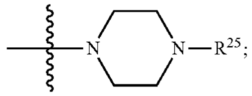

$R^{21}$ at each occurrence is independently selected from the group consisting of hydrogen, $C_{1-6}$ linear alkyl, $C_{3-7}$ branched alkyl, and $C_{3-7}$ cycloalkyl;

$R^{22}$ at each occurrence is independently selected from the group consisting of hydrogen, $C_{1-6}$ linear alkyl, $C_{3-7}$ branched alkyl, and $C_{3-7}$ cycloalkyl;

$R^{23a}$ at each occurrence is independently is selected from the group consisting of hydrogen, $C_{1-6}$ linear alkyl, $C_{3-7}$ branched alkyl, and $C_{3-7}$ cycloalkyl;

$R^{23b}$ at each occurrence is independently is selected from the group consisting of hydrogen, $C_{1-6}$ linear alkyl, $C_{3-7}$ branched alkyl, and $C_{3-7}$ cycloalkyl;

$R^{24}$ at each occurrence is independently is selected from the group consisting of hydrogen, $C_{1-6}$ linear alkyl, $C_{3-7}$ branched alkyl, and $C_{3-7}$ cycloalkyl;

$R^{25}$ at each occurrence is independently is selected from the group consisting of hydrogen, $C_{1-6}$ linear alkyl, $C_{3-7}$ branched alkyl, and $C_{3-7}$ cycloalkyl;

and at least 5 of $R^{20a}$, $R^{20b}$, $R^{20c}$, $R^{20d}$, $R^{20e}$, $R^{20f}$, and $R^{20g}$ are hydrogen.

The embodiments of the present invention include compounds having formula (VIIv):

(VIIv)

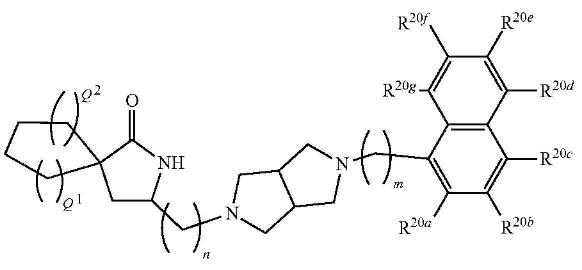

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIw):

(VIIw)

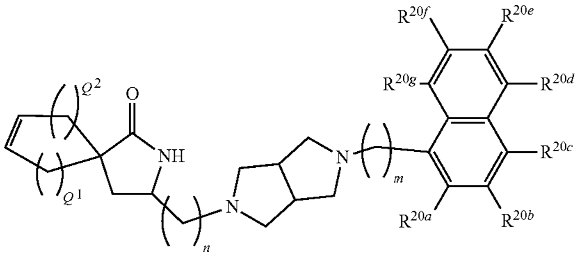

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIx):

(VIIx)

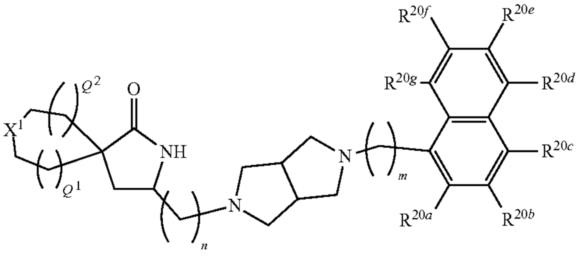

Including hydrates, solvates, enantiomers, diastereomers, pharmaceutically acceptable salts, and complexes thereof wherein $X^1$ is selected from the group consisting of O, S, SO, $SO_2$, and $NR^7$;

$Q^1$ is 1 or 2;

and $Q^2$ is 1 or 2.

The embodiments of the present invention include compounds having formula (VIIx-1):

(VIIx-1)

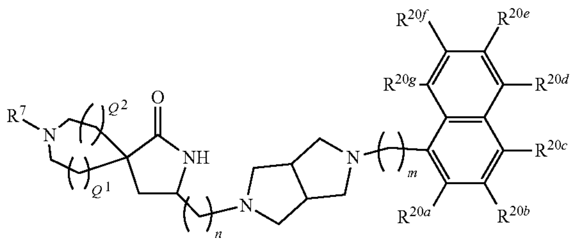

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIx-2):

(VIIx-2)

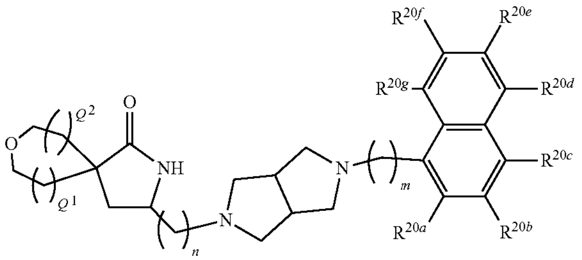

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIx-3):

(VIIx-3)

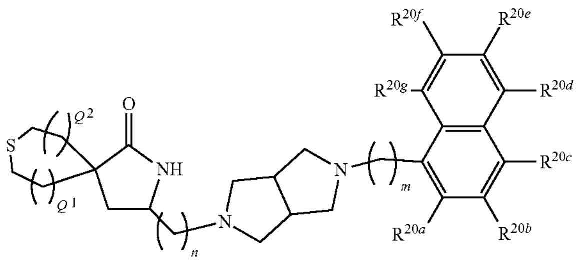

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIx-4):

(VIIx-4)

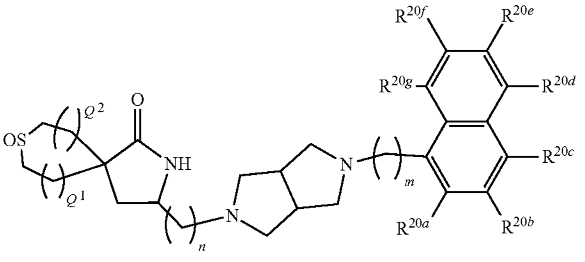

Including hydrates, solvates, enantiomers, diastereomers, pharmaceutically acceptable salts, and complexes thereof wherein $Q^1$ is 1 or 2;

and $Q^2$ is 1 or 2.

The embodiments of the present invention include compounds having formula (VIIx-5):

(VIIx-5)

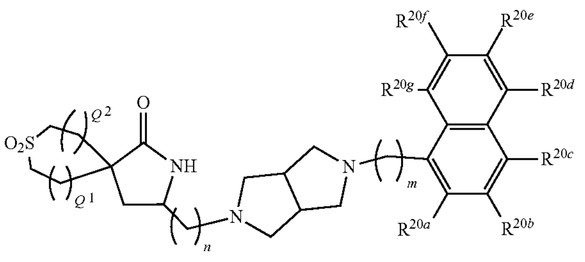

Including hydrates, solvates, enantiomers, diastereomers, pharmaceutically acceptable salts, and complexes thereof wherein $Q^1$ is 1 or 2;

and $Q^2$ is 1 or 2.

In some embodiments A is

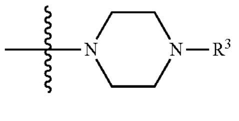

In some embodiments A is

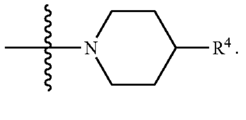

In some embodiments A is

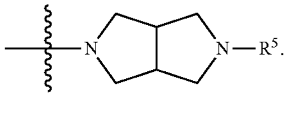

In some embodiments $R^1$ is hydrogen.

In some embodiments $R^1$ is $C_{1-6}$ linear alkyl.

In some embodiments $R^1$ is $C_{3-7}$ branched alkyl.

In some embodiments $R^2$ is hydrogen.

In some embodiments $R^2$ is $C_{1-6}$ linear alkyl.

In some embodiments $R^2$ is $C_{3-7}$ branched alkyl.

In some embodiments $R^1$ and $R^2$ are taken together with the atoms to which they are bound to form a ring having 5 ring atoms.

In some embodiments $R^1$ and $R^2$ are taken together with the atoms to which they are bound to form a ring having 5 ring atoms and containing a double bond.

In some embodiments $R^1$ and $R^2$ are taken together with the atoms to which they are bound to form a ring having 6 ring atoms.

In some embodiments $R^1$ and $R^2$ are taken together with the atoms to which they are bound to form a ring having 6 ring atoms and containing a double bond.

In some embodiments $R^1$ and $R^2$ are taken together with the atoms to which they are bound to form a ring having 7 ring atoms.

In some embodiments $R^1$ and $R^2$ are taken together with the atoms to which they are bound to form a ring having 7 ring atoms and containing a double bond.

In some embodiments $R^1$ and $R^2$ are taken together with the atoms to which they are bound to form a ring having 6 ring atoms containing one of which is O.

In some embodiments $R^1$ and $R^2$ are taken together with the atoms to which they are bound to form a ring having 7 ring atoms containing one of which is O.

In some embodiments $R^1$ and $R^2$ are taken together with the atoms to which they are bound to form a ring having 8 ring atoms containing one of which is O.

In some embodiments $R^1$ and $R^2$ are taken together with the atoms to which they are bound to form a ring having 6 ring atoms containing one of which is S.

In some embodiments $R^1$ and $R^2$ are taken together with the atoms to which they are bound to form a ring having 7 ring atoms containing one of which is S.

In some embodiments $R^1$ and $R^2$ are taken together with the atoms to which they are bound to form a ring having 8 ring atoms containing one of which is S.

In some embodiments $R^1$ and $R^2$ are taken together with the atoms to which they are bound to form a ring having 6 ring atoms containing one of which is SO.

In some embodiments $R^1$ and $R^2$ are taken together with the atoms to which they are bound to form a ring having 7 ring atoms containing one of which is SO.

In some embodiments $R^1$ and $R^2$ are taken together with the atoms to which they are bound to form a ring having 8 ring atoms containing one of which is SO.

In some embodiments $R^1$ and $R^2$ are taken together with the atoms to which they are bound to form a ring having 6 ring atoms containing one of which is $SO_2$.

In some embodiments $R^1$ and $R^2$ are taken together with the atoms to which they are bound to form a ring having 7 ring atoms containing one of which is $SO_2$.

In some embodiments $R^1$ and $R^2$ are taken together with the atoms to which they are bound to form a ring having 8 ring atoms containing one of which is $SO_2$.

In some embodiments $R^1$ and $R^2$ are taken together with the atoms to which they are bound to form a ring having 6 ring atoms containing one of which is $NR^7$.

In some embodiments $R^1$ and $R^2$ are taken together with the atoms to which they are bound to form a ring having 7 ring atoms containing one of which is $NR^7$.

In some embodiments $R^1$ and $R^2$ are taken together with the atoms to which they are bound to form a ring having 8 ring atoms containing one of which is $NR^7$.

In some embodiments $R^3$ is optionally substituted phenyl.

In some embodiments $R^3$ is optionally substituted naphthylen-1-yl.

In some embodiments $R^3$ is optionally substituted naphthylen-2-yl.

In some embodiments $R^3$ is optionally substituted 2-pyridyl

In some embodiments $R^3$ is optionally substituted 3-pyridyl.

In some embodiments $R^3$ is optionally substituted 4-pyridyl.

In some embodiments $R^3$ is

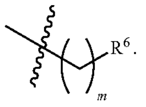

In some embodiments $R^4$ is optionally substituted phenyl.

In some embodiments $R^4$ is optionally substituted naphthylen-1-yl.

In some embodiments $R^4$ is optionally substituted naphthylen-2-yl.

In some embodiments $R^4$ is optionally substituted 2-pyridyl

In some embodiments $R^4$ is optionally substituted 3-pyridyl.

In some embodiments $R^4$ is optionally substituted 4-pyridyl.

In some embodiments $R^4$ is

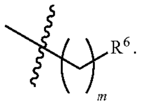

In some embodiments $R^5$ is optionally substituted phenyl.

In some embodiments $R^5$ is optionally substituted naphthylen-1-yl.

In some embodiments $R^5$ is optionally substituted naphthylen-2-yl.

In some embodiments $R^5$ is optionally substituted 2-pyridyl

In some embodiments $R^5$ is optionally substituted 3-pyridyl.

In some embodiments $R^5$ is optionally substituted 4-pyridyl.

In some embodiments $R^5$ is

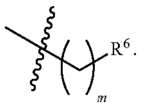

In some embodiments $R^6$ is optionally substituted phenyl.

In some embodiments $R^6$ is optionally substituted naphthylen-1-yl.

In some embodiments $R^6$ is optionally substituted naphthylen-2-yl.

In some embodiments $R^6$ is optionally substituted 2-pyridyl

In some embodiments $R^6$ is optionally substituted 3-pyridyl.

In some embodiments $R^6$ is optionally substituted 4-pyridyl.

In some embodiments $R^7$ is H.

In some embodiments $R^7$ is $C_{1-6}$ linear alkyl.

In some embodiments $R^7$ is $C_{3-7}$ branched alkyl.

In some embodiments $R^7$ is $C_{3-7}$ cycloalkyl.

In some embodiments $R^7$ is optionally substituted phenyl.

In some embodiments $R^7$ is optionally substituted benzyl.

In some embodiments $R^7$ is $COR^8$.

In some embodiments $R^7$ is $CO_2R^9$.

In some embodiments $R^7$ is $CONR^{10a}R^{10b}$.

In some embodiments $R^7$ is $SO_2NR^{10a}R^{10b}$.

In some embodiments $R^7$ is $SO_2R^{10c}$.

In some embodiments $R^8$ is selected H.

In some embodiments $R^8$ is $C_{1-6}$ linear alkyl.

In some embodiments $R^8$ is $C_{3-7}$ branched alkyl

In some embodiments $R^8$ is $C_{3-7}$ cycloalkyl.

In some embodiments $R^9$ is $C_{1-6}$ linear alkyl.

In some embodiments $R^9$ is $C_{3-7}$ branched alkyl.

In some embodiments $R^9$ is $C_{3-7}$ cycloalkyl.

In some embodiments $R^{10a}$ is H.

In some embodiments $R^{10a}$ is $C_{1-6}$ linear alkyl.

In some embodiments $R^{10a}$ is $C_{3-7}$ branched alkyl.

In some embodiments $R^{10a}$ is $C_{3-7}$ cycloalkyl.

In some embodiments $R^{10b}$ is H.

In some embodiments $R^{10b}$ is $C_{1-6}$ linear alkyl.

In some embodiments $R^{10b}$ is $C_{3-7}$ branched alkyl.

In some embodiments $R^{10b}$ is $C_{3-7}$ cycloalkyl.

In some embodiments $R^{10c}$ is $C_{1-6}$ linear alkyl.

In some embodiments $R^{10c}$ is $C_{3-7}$ branched alkyl.

In some embodiments $R^{10c}$ is $C_{3-7}$ cycloalkyl.

In some embodiments $R^{10c}$ is $C_{1-6}$ linear haloalkyl.

In some embodiments $R^{10c}$ is $C_{3-7}$ branched haloalkyl.

In some embodiments $R^{10c}$ is $—(CH_2)_qCN$.

In some embodiments $R^{10c}$ is $—(CH_2)_qSO_2R^{11}$.

In some embodiments $R^{10c}$ is $—(CH_2)_qOR^2$.

In some embodiments $R^{10c}$ is

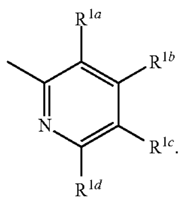

In some embodiments $R^{10c}$ is

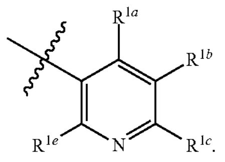

In some embodiments $R^{10c}$ is

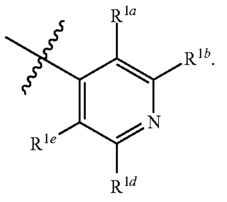

In some embodiments $R^{10c}$ is

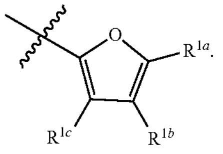

In some embodiments $R^{10c}$ is

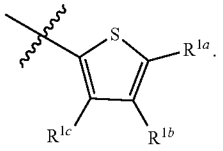

In some embodiments $R^{10c}$ is

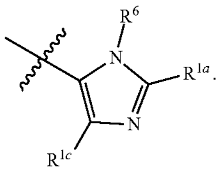

In some embodiments $R^{10c}$ is

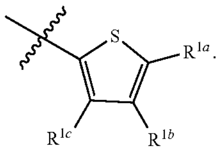

In some embodiments $R^{10c}$ is

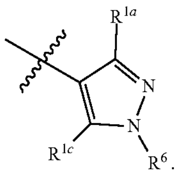

In some embodiments $R^{10c}$

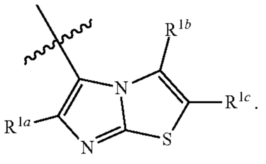

In some embodiments $R^{10c}$ is

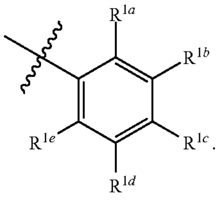

In some embodiments $R^{10c}$ is

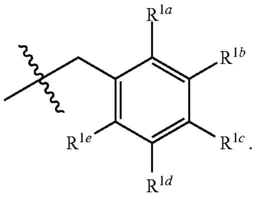

In some embodiments $R^{10c}$ is

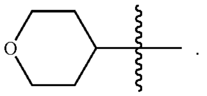

In some embodiments $R^{11}$ is $C_{1-6}$ linear alkyl.
In some embodiments $R^{11}$ is $C_{3-7}$ branched alkyl.
In some embodiments $R^{11}$ is $C_{3-7}$ cycloalkyl.
In some embodiments $R^{12}$ is $C_{1-6}$ linear alkyl.
In some embodiments $R^{12}$ is $C_{3-7}$ branched alkyl.
In some embodiments $R^{12}$ is $C_{3-7}$ cycloalkyl.
In some embodiments $R^{1a}$ is H.
In some embodiments $R^{1a}$ is OH
In some embodiments $R^{1a}$ is $NO_2$.
In some embodiments $R^{1a}$ is halogen.
In some embodiments $R^{1a}$ is CN.
In some embodiments $R^{1a}$ is $C_{1-6}$ linear alkyl.
In some embodiments $R^{1a}$ is $C_{3-7}$ branched alkyl.
In some embodiments $R^{1a}$ is $C_{3-7}$ cycloalkyl.
In some embodiments $R^{1a}$ is $C_{1-6}$ linear alkoxy.
In some embodiments $R^{1a}$ is $C_{3-7}$ branched alkoxy.
In some embodiments $R^{1a}$ is $C_{3-7}$ cycloalkoxy.
In some embodiments $R^{1a}$ is $C_{1-6}$ linear haloalkyl.
In some embodiments $R^{1a}$ is $C_{3-7}$ branched haloalkyl.
In some embodiments $R^{1a}$ is $C_{1-6}$ linear haloalkoxy.
In some embodiments $R^{1a}$ is —$S(C_{1-6}$ linear alkyl).
In some embodiments $R^{1a}$ is $S(C_{3-7}$ branched alkyl).
In some embodiments $R^{1a}$ is —$S(C_{3-7}$ cycloalkyl).
In some embodiments $R^{1a}$ is $COR^{13}$
In some embodiments $R^{1a}$ is $CO_2R^{14}$.
In some embodiments $R^{1a}$ is $CONR^{15a}R^{15b}$
In some embodiments $R^{1a}$ is $SO_2NR^{15a}R^{15b}$.

In some embodiments $R^{1a}$ is $NR^{16a}R^{16b}$.

In some embodiments $R^{1a}$ is $NR^{16a}COR^{17}$.

In some embodiments $R^{1a}$ is $NR^{16a}SO_2R^{18}$.

In some embodiments $R^{1a}$ is $NR^{16a}SO_2NR^{19a}R^{19b}$.

In some embodiments $R^{1b}$ is H.

In some embodiments $R^{1b}$ is OH

In some embodiments $R^{1b}$ is $NO_2$.

In some embodiments $R^{1b}$ is halogen.

In some embodiments $R^{1b}$ is CN.

In some embodiments $R^{1b}$ is $C_{1-6}$ linear alkyl.

In some embodiments $R^{1b}$ is $C_{3-7}$ branched alkyl.

In some embodiments $R^{1b}$ is $C_{3-7}$ cycloalkyl.

In some embodiments $R^{1b}$ is $C_{1-6}$ linear alkoxy.

In some embodiments $R^{1b}$ is $C_{3-7}$ branched alkoxy.

In some embodiments $R^{1b}$ is $C_{3-7}$ cycloalkoxy.

In some embodiments $R^{1b}$ is $C_{1-6}$ linear haloalkyl.

In some embodiments $R^{1b}$ is $C_{3-7}$ branched haloalkyl.

In some embodiments $R^{1b}$ is $C_{1-6}$ linear haloalkoxy.

In some embodiments $R^{1b}$ is —S($C_{1-6}$ linear alkyl).

In some embodiments $R^{1b}$ is S($C_{3-7}$ branched alkyl).

In some embodiments $R^{1b}$ is —S($C_{3-7}$ cycloalkyl).

In some embodiments $R^{1b}$ is $COR^{13}$.

In some embodiments $R^{1b}$ is $CO_2R^1$.

In some embodiments $R^{1b}$ is $CONR^{15a}R^{15b}$.

In some embodiments $R^{1b}$ is $SO_2NR^{15a}R^{15b}$.

In some embodiments $R^{1b}$ is $NR^{16a}R^{16b}$.

In some embodiments $R^{1b}$ is $NR^{16a}COR^{17}$.

In some embodiments $R^{1b}$ is $NR^{16a}SO_2R^{18}$.

In some embodiments $R^{1b}$ is $NR^{16a}SO_2NR^{19a}R^{19b}$.

In some embodiments $R^{1c}$ is H.

In some embodiments $R^{1c}$ is OH

In some embodiments $R^{1c}$ is $NO_2$.

In some embodiments $R^{1c}$ is halogen.

In some embodiments $R^{1c}$ is CN.

In some embodiments $R^{1c}$ is $C_{1-6}$ linear alkyl.

In some embodiments $R^{1c}$ is $C_{3-7}$ branched alkyl.

In some embodiments $R^{1c}$ is $C_{3-7}$ cycloalkyl.

In some embodiments $R^{1c}$ is $C_{1-6}$ linear alkoxy.

In some embodiments $R^{1c}$ is $C_{3-7}$ branched alkoxy.

In some embodiments $R^{1c}$ is $C_{3-7}$ cycloalkoxy.

In some embodiments $R^{1c}$ is $C_{1-6}$ linear haloalkyl.

In some embodiments $R^{1c}$ is $C_{3-7}$ branched haloalkyl.

In some embodiments $R^{1c}$ is $C_{1-6}$ linear haloalkoxy.

In some embodiments $R^{1c}$ is —S($C_{1-6}$ linear alkyl).

In some embodiments $R^{1c}$ is S($C_{3-7}$ branched alkyl).

In some embodiments $R^{1c}$ is —S($C_{3-7}$ cycloalkyl).

In some embodiments $R^{1c}$ is $COR^{13}$.

In some embodiments $R^{1c}$ is $CO_2R^{14}$.

In some embodiments $R^{1c}$ is $CONR^{15a}R^{15b}$.

In some embodiments $R^{1c}$ is $SO_2NR^{15a}R^{15b}$.

In some embodiments $R^{1c}$ is $NR^{16a}R^{16b}$.

In some embodiments $R^{1c}$ is $NR^{16a}COR^{17}$.

In some embodiments $R^{1c}$ is $NR^{16a}SO_2R^{18}$.

In some embodiments $R^{1c}$ is $NR^{16a}SO_2NR^{19a}R^{19b}$.

In some embodiments $R^{1d}$ is H.

In some embodiments $R^{1d}$ is OH

In some embodiments $R^{1d}$ is $NO_2$.

In some embodiments $R^{1d}$ is halogen.

In some embodiments $R^{1d}$ is CN.

In some embodiments $R^{1d}$ is $C_{1-6}$ linear alkyl.

In some embodiments $R^{1d}$ is $C_{3-7}$ branched alkyl.

In some embodiments $R^{1d}$ is $C_{3-7}$ cycloalkyl.

In some embodiments $R^{1d}$ is $C_{1-6}$ linear alkoxy.

In some embodiments $R^{1d}$ is $C_{3-7}$ branched alkoxy.

In some embodiments $R^{1d}$ is $C_{3-7}$ cycloalkoxy.

In some embodiments $R^{1d}$ is $C_{1-6}$ linear haloalkyl.

In some embodiments $R^{1d}$ is $C_{3-7}$ branched haloalkyl.

In some embodiments $R^{1d}$ is $C_{1-6}$ linear haloalkoxy.

In some embodiments $R^{1d}$ is —S($C_{1-6}$ linear alkyl).

In some embodiments $R^{1d}$ is S($C_{3-7}$ branched alkyl).

In some embodiments $R^{1d}$ is —S($C_{3-7}$ cycloalkyl).

In some embodiments $R^{1d}$ is $COR^{13}$.

In some embodiments $R^{1d}$ is $CO_2R^{14}$.

In some embodiments $R^{1d}$ is $CONR^{15a}R^{15b}$.

In some embodiments $R^{1d}$ is $SO_2NR^{15a}R^{15b}$.

In some embodiments $R^{1d}$ is $NR^{16a}R^{16b}$.

In some embodiments $R^{1d}$ is $NR^{16a}COR^{17}$.

In some embodiments $R^{1d}$ is $NR^{16a}SO_2R^{18}$.

In some embodiments $R^{1d}$ is $NR^{16a}SO_2NR^{19a}R^{19b}$.

In some embodiments $R^{1e}$ is H.

In some embodiments $R^{1e}$ is OH.

In some embodiments $R^{1e}$ is $NO_2$.

In some embodiments $R^{1e}$ is halogen.

In some embodiments $R^{1e}$ is CN.

In some embodiments $R^{1e}$ is $C_{1-6}$ linear alkyl.

In some embodiments $R^{1e}$ is $C_{3-7}$ branched alkyl.

In some embodiments $R^{1e}$ is $C_{3-7}$ cycloalkyl.

In some embodiments $R^{1e}$ is $C_{1-6}$ linear alkoxy.

In some embodiments $R^{1e}$ is $C_{3-7}$ branched alkoxy.

In some embodiments $R^{1e}$ is $C_{3-7}$ cycloalkoxy.

In some embodiments $R^{1e}$ is $C_{1-6}$ linear haloalkyl.

In some embodiments $R^{1e}$ is $C_{3-7}$ branched haloalkyl.

In some embodiments $R^{1e}$ is $C_{1-6}$ linear haloalkoxy.

In some embodiments $R^{1e}$ is —S($C_{1-6}$ linear alkyl).

In some embodiments $R^{1e}$ is S($C_{3-7}$ branched alkyl).

In some embodiments $R^{1e}$ is —S($C_{3-7}$ cycloalkyl).

In some embodiments $R^{1e}$ is $COR^{13}$.

In some embodiments $R^{1e}$ is $CO_2R^{14}$.

In some embodiments $R^{1e}$ is $CONR^{15a}R^{15b}$.

In some embodiments $R^{1e}$ is $SO_2NR^{15a}R^{15b}$.

In some embodiments $R^{1e}$ is $NR^{16a}R^{16b}$.

In some embodiments $R^{1e}$ is $NR^{16a}COR^{17}$.

In some embodiments $R^{1e}$ is $NR^{16a}SO_2R^{18}$.

In some embodiments $R^{1e}$ is $NR^{16a}SO_2NR^{19a}R^{19b}$.

In some embodiments $R^{13}$ is H.

In some embodiments $R^{13}$ is $C_{1-6}$ linear alkyl.

In some embodiments $R^{13}$ is $C_{3-7}$ branched alkyl.

In some embodiments $R^{13}$ is $C_{3-7}$ cycloalkyl.

In some embodiments $R^{14}$ is $C_{1-6}$ linear alkyl.

In some embodiments $R^{14}$ is $C_{3-7}$ branched alkyl.

In some embodiments $R^{14}$ is $C_{3-7}$ cycloalkyl.

In some embodiments $R^{15a}$ is H.

In some embodiments $R^{15a}$ is $C_{1-6}$ linear alkyl.

In some embodiments $R^{15a}$ is $C_{3-7}$ branched alkyl.

In some embodiments $R^{15a}$ is $C_{3-7}$ cycloalkyl.

In some embodiments $R^{15b}$ is H.

In some embodiments $R^{15b}$ is $C_{1-6}$ linear alkyl.

In some embodiments $R^{15b}$ is $C_{3-7}$ branched alkyl.

In some embodiments $R^{15b}$ is $C_{3-7}$ cycloalkyl.

In some embodiments $R^{16a}$ is H.

In some embodiments $R^{16a}$ is $C_{1-6}$ linear alkyl.

In some embodiments $R^{16a}$ is $C_{3-7}$ branched alkyl.

In some embodiments $R^{16a}$ is $C_{3-7}$ cycloalkyl.

In some embodiments $R^{16b}$ is H.

In some embodiments $R^{16b}$ is $C_{1-6}$ linear alkyl.

In some embodiments $R^{16b}$ is $C_{3-7}$ branched alkyl.

In some embodiments $R^{16b}$ is $C_{3-7}$ cycloalkyl.

In some embodiments $R^{17}$ is H.

In some embodiments $R^{17}$ is $C_{1-6}$ linear alkyl.

In some embodiments $R^{17}$ is $C_{3-7}$ branched alkyl.

In some embodiments $R^{17}$ is $C_{3-7}$ cycloalkyl.

In some embodiments $R^{18}$ is $C_{1-6}$ linear alkyl.

In some embodiments $R^{18}$ is $C_{3-7}$ branched alkyl.

In some embodiments $R^{18}$ is $C_{3-7}$ cycloalkyl.

In some embodiments $R^{19a}$ is $C_{1-6}$ linear alkyl.
In some embodiments $R^{19a}$ is $C_{3-7}$ branched alkyl.
In some embodiments $R^{19a}$ is $C_{3-7}$ cycloalkyl.
In some embodiments $R^{19b}$ is $C_{1-6}$ linear alkyl.
In some embodiments $R^{19b}$ is $C_{3-7}$ branched alkyl.
In some embodiments $R^{19b}$ is $C_{3-7}$ cycloalkyl.
In some embodiments n is 1.
In some embodiments n is 2.
In some embodiments n is 3.
In some embodiments n is 4.
In some embodiments m is 1.
In some embodiments m is 2.
In some embodiments m is 3.
In some embodiments $R^{20a}$ is hydrogen.
In some embodiments $R^{20a}$ is —CN.
In some embodiments $R^{20a}$ is —$NO_2$.
In some embodiments $R^{20a}$ is —OH.
In some embodiments $R^{20a}$ is halogen.
In some embodiments $R^{20a}$ is $C_{1-6}$ linear alkyl.
In some embodiments $R^{20a}$ is $C_{3-7}$ branched alkyl.
In some embodiments $R^{20a}$ is $C_{3-7}$ cycloalkyl.
In some embodiments $R^{20a}$ is $C_{1-6}$ linear alkoxy.
In some embodiments $R^{20a}$ is $C_{3-7}$ branched alkoxy.
In some embodiments $R^{20a}$ is $C_{3-7}$ cycloalkoxy.
In some embodiments $R^{20a}$ is $C_{1-6}$ linear haloalkyl.
In some embodiments $R^{20a}$ is $C_{3-7}$ branched haloalkyl.
In some embodiments $R^{20a}$ is $C_{1-6}$ linear haloalkoxy.
In some embodiments $R^{20a}$ is $C_{3-7}$ branched haloalkoxy.
In some embodiments $R^{20a}$ is SH.
In some embodiments $R^{20a}$ is $SC_{1-6}$ linear alkyl.
In some embodiments $R^{20a}$ is $SC_{3-7}$ branched alkyl.
In some embodiments $R^{20a}$ is $SC_{3-7}$cycloalkyl.
In some embodiments $R^{20a}$ is $SO_2C_{1-6}$ linear alkyl.
In some embodiments $R^{20a}$ is $SO_2C_{3-7}$ branched alkyl.
In some embodiments $R^{20a}$ is $SO_2C_{3-7}$cycloalkyl.
In some embodiments $R^{20a}$ is $SO_2NH_2$.
In some embodiments $R^{20a}$ is $SO_2NHR^{21}$.
In some embodiments $R^{20a}$ is $NHSO_2R^{22}$.
In some embodiments $R^{20a}$ is —$NR^{23a}R^{23b}$.
In some embodiments $R^{20a}$ is $NHC(O)R^{24}$.
In some embodiments $R^{20a}$ ais $C(O)NHR^{24}$.
In some embodiments $R^{20a}$ is $C(O)N(R^{24})_2$.
In some embodiments $R^{20a}$ is morpholino.
In some embodiments $R^{20a}$ is

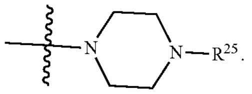

In some embodiments $R^{20b}$ is hydrogen.
In some embodiments $R^{20b}$ is —CN.
In some embodiments $R^{20b}$ is —$NO_2$.
In some embodiments $R^{20b}$ is —OH.
In some embodiments $R^{20b}$ is halogen.
In some embodiments $R^{20b}$ is $C_{1-6}$ linear alkyl.
In some embodiments $R^{20b}$ is $C_{3-7}$ branched alkyl.
In some embodiments $R^{20b}$ is $C_{3-7}$ cycloalkyl.
In some embodiments $R^{20b}$ is $C_{1-6}$ linear alkoxy.
In some embodiments $R^{20b}$ is $C_{3-7}$ branched alkoxy.
In some embodiments $R^{20b}$ is $C_{3-7}$ cycloalkoxy.
In some embodiments $R^{20b}$ is $C_{1-6}$ linear haloalkyl.
In some embodiments $R^{20b}$ is $C_{3-7}$ branched haloalkyl.
In some embodiments $R^{20b}$ is $C_{1-6}$ linear haloalkoxy.
In some embodiments $R^{20b}$ is $C_{3-7}$ branched haloalkoxy.
In some embodiments $R^{20b}$ is SH.
In some embodiments $R^{20b}$ is $SC_{1-6}$ linear alkyl.
In some embodiments $R^{20b}$ is $SC_{3-7}$ branched alkyl.
In some embodiments $R^{20b}$ is $SC_{3-7}$cycloalkyl.
In some embodiments $R^{20b}$ is $SO_2C_{1-6}$ linear alkyl.
In some embodiments $R^{20b}$ is $SO_2C_{3-7}$ branched alkyl.
In some embodiments $R^{20b}$ is $SO_2C_{3-7}$cycloalkyl.
In some embodiments $R^{20b}$ is $SO_2NH_2$.
In some embodiments $R^{20b}$ is $SO_2NHR^{21}$.
In some embodiments $R^{20b}$ is $NHSO_2R^{22}$.
In some embodiments $R^{20b}$ is —$NR^{23a}R^{23b}$
In some embodiments $R^{20b}$ is $NHC(O)R^{24}$.
In some embodiments $R^{20b}$ is $C(O)NHR^{24}$.
In some embodiments $R^{20b}$ is $C(O)N(R^{24})_2$.
In some embodiments $R^{20b}$ is morpholino.
In some embodiments $R^{20b}$ is

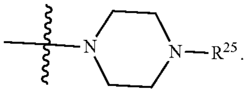

In some embodiments $R^{20c}$ is hydrogen.
In some embodiments $R^{20c}$ is —CN.
In some embodiments $R^{20c}$ is —$NO_2$.
In some embodiments $R^{20c}$ is —OH.
In some embodiments $R^{20c}$ is halogen.
In some embodiments $R^{20c}$ is $C_{1-6}$ linear alkyl.
In some embodiments $R^{20c}$ is $C_{3-7}$ branched alkyl.
In some embodiments $R^{20c}$ is $C_{3-7}$ cycloalkyl.
In some embodiments $R^{20c}$ is $C_{1-6}$ linear alkoxy.
In some embodiments $R^{20c}$ is $C_{3-7}$ branched alkoxy.
In some embodiments $R^{20c}$ is $C_{3-7}$ cycloalkoxy.
In some embodiments $R^{20c}$ is $C_{1-6}$ linear haloalkyl.
In some embodiments $R^{20c}$ is $C_{3-7}$ branched haloalkyl.
In some embodiments $R^{20c}$ is $C_{1-6}$ linear haloalkoxy.
In some embodiments $R^{20c}$ is $C_{3-7}$ branched haloalkoxy.
In some embodiments $R^{20c}$ is SH.
In some embodiments $R^{20c}$ is $SC_{1-6}$ linear alkyl.
In some embodiments $R^{20c}$ is $SC_{3-7}$ branched alkyl.
In some embodiments $R^{20c}$ is $SC_{3-7}$cycloalkyl.
In some embodiments $R^{20c}$ is $SO_2C_{1-6}$ linear alkyl.
In some embodiments $R^{20c}$ is $SO_2C_{3-7}$ branched alkyl.
In some embodiments $R^{20c}$ is $SO_2C_{3-7}$cycloalkyl.
In some embodiments $R^{20c}$ is $SO_2NH_2$.
In some embodiments $R^{20c}$ is $SO_2NHR^{21}$.
In some embodiments $R^{20c}$ is $NHSO_2R^{22}$.
In some embodiments $R^{20c}$ is —$NR^{23a}R^{23b}$.
In some embodiments $R^{20c}$ is $NHC(O)R^{24}$.
In some embodiments $R^{20c}$ is $C(O)NHR^{24}$.
In some embodiments $R^{20c}$ is $C(O)N(R^{24})_2$.
In some embodiments $R^{20c}$ is morpholino.
In some embodiments $R^{20c}$ is

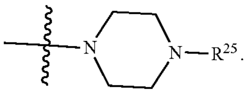

In some embodiments $R^{20d}$ is hydrogen.
In some embodiments $R^{20d}$ is —CN.
In some embodiments $R^{20d}$ is —$NO_2$.
In some embodiments $R^{20d}$ is —OH.
In some embodiments $R^{20d}$ is halogen.
In some embodiments $R^{20d}$ is $C_{1-6}$ linear alkyl.
In some embodiments $R^{20d}$ is $C_{3-7}$ branched alkyl.

In some embodiments $R^{20d}$ is $C_{3-7}$ cycloalkyl.
In some embodiments $R^{20d}$ is $C_{1-6}$ linear alkoxy.
In some embodiments $R^{20d}$ is $C_{3-7}$ branched alkoxy.
In some embodiments $R^{20d}$ is $C_{3-7}$ cycloalkoxy.
In some embodiments $R^{20d}$ is $C_{1-6}$ linear haloalkyl.
In some embodiments $R^{20d}$ is $C_{3-7}$ branched haloalkyl.
In some embodiments $R^{20d}$ is $C_{1-6}$ linear haloalkoxy.
In some embodiments $R^{20d}$ is $C_{3-7}$ branched haloalkoxy.
In some embodiments $R^{20d}$ is SH.
In some embodiments $R^{20d}$ is $SC_{1-6}$ linear alkyl.
In some embodiments $R^{20d}$ is $SC_{3-7}$ branched alkyl.
In some embodiments $R^{20d}$ is $SC_{3-7}$cycloalkyl.
In some embodiments $R^{20d}$ is $SO_2C_{1-6}$ linear alkyl.
In some embodiments $R^{20d}$ is $SO_2C_{3-7}$ branched alkyl.
In some embodiments $R^{20d}$ is $SO_2C_{3-7}$cycloalkyl.
In some embodiments $R^{20d}$ is $SO_2NH_2$.
In some embodiments $R^{20d}$ is $SO_2NHR^{21}$.
In some embodiments $R^{20d}$ is $NHSO_2R^{22}$.
In some embodiments $R^{20d}$ is $—NR^{23a}R^{23b}$
In some embodiments $R^{20d}$ is $NHC(O)R^{24}$.
In some embodiments $R^{20d}$ is $C(O)NHR^{24}$.
In some embodiments $R^{20d}$ is $C(O)N(R^{24})_2$.
In some embodiments $R^{20d}$ is morpholino.
In some embodiments $R^{20d}$ is

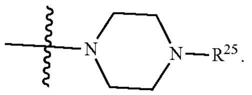

In some embodiments $R^{20e}$ is hydrogen.
In some embodiments $R^{20e}$ is —CN.
In some embodiments $R^{20e}$ is $—NO_2$.
In some embodiments $R^{20e}$ is —OH.
In some embodiments $R^{20e}$ is halogen.
In some embodiments $R^{20e}$ is $C_{1-6}$ linear alkyl.
In some embodiments $R^{20e}$ is $C_{3-7}$ branched alkyl.
In some embodiments $R^{20e}$ is $C_{3-7}$ cycloalkyl.
In some embodiments $R^{20e}$ is $C_{1-6}$ linear alkoxy.
In some embodiments $R^{20e}$ is $C_{3-7}$ branched alkoxy.
In some embodiments $R^{20e}$ is $C_{3-7}$ cycloalkoxy.
In some embodiments $R^{20e}$ is $C_{1-6}$ linear haloalkyl.
In some embodiments $R^{20e}$ is $C_{3-7}$ branched haloalkyl.
In some embodiments $R^{20e}$ is $C_{1-6}$ linear haloalkoxy.
In some embodiments $R^{20e}$ is $C_{3-7}$ branched haloalkoxy.
In some embodiments $R^{20e}$ is SH.
In some embodiments $R^{20e}$ is $SC_{1-6}$ linear alkyl.
In some embodiments $R^{20e}$ is $SC_{3-7}$ branched alkyl.
In some embodiments $R^{20e}$ is $SC_{3-7}$cycloalkyl.
In some embodiments $R^{20e}$ is $SO_2C_{1-6}$ linear alkyl.
In some embodiments $R^{20e}$ is $SO_2C_{3-7}$ branched alkyl.
In some embodiments $R^{20e}$ is $SO_2C_{3-7}$cycloalkyl.
In some embodiments $R^{20e}$ is $SO_2NH_2$.
In some embodiments $R^{20e}$ is $SO_2NHR^{21}$.
In some embodiments $R^{20e}$ is $NHSO_2R^{22}$.
In some embodiments $R^{20e}$ is $—NR^{23a}R^{23b}$
In some embodiments $R^{20e}$ is $NHC(O)R^{24}$.
In some embodiments $R^{20e}$ is $C(O)NHR^{24}$.
In some embodiments $R^{20e}$ is $C(O)N(R^{24})_2$.
In some embodiments $R^{20e}$ is morpholino.
In some embodiments $R^{20e}$ is

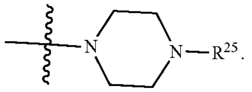

In some embodiments $R^{20f}$ is hydrogen.
In some embodiments $R^{20f}$ is —CN.
In some embodiments $R^{20f}$ is $—NO_2$.
In some embodiments $R^{20f}$ is —OH.
In some embodiments $R^{20f}$ is halogen.
In some embodiments $R^{20f}$ is $C_{1-6}$ linear alkyl.
In some embodiments $R^{20f}$ is $C_{3-7}$ branched alkyl.
In some embodiments $R^{20f}$ is $C_{3-7}$ cycloalkyl.
In some embodiments $R^{20f}$ is $C_{1-6}$ linear alkoxy.
In some embodiments $R^{20f}$ is $C_{3-7}$ branched alkoxy.
In some embodiments $R^{20f}$ is $C_{3-7}$ cycloalkoxy.
In some embodiments $R^{20f}$ is $C_{1-6}$ linear haloalkyl.
In some embodiments $R^{20f}$ is $C_{3-7}$ branched haloalkyl.
In some embodiments $R^{20f}$ is $C_{1-6}$ linear haloalkoxy.
In some embodiments $R^{20f}$ is $C_{3-7}$ branched haloalkoxy.
In some embodiments $R^{20f}$ is SH.
In some embodiments $R^{20f}$ is $SC_{1-6}$ linear alkyl.
In some embodiments $R^{20f}$ is $SC_{3-7}$ branched alkyl.
In some embodiments $R^{20f}$ is $SC_{3-7}$cycloalkyl.
In some embodiments $R^{20f}$ is $SO_2C_{1-6}$ linear alkyl.
In some embodiments $R^{20f}$ is $SO_2C_{3-7}$ branched alkyl.
In some embodiments $R^{20f}$ is $SO_2C_{3-7}$cycloalkyl.
In some embodiments $R^{20f}$ is $SO_2NH_2$.
In some embodiments $R^{20f}$ is $SO_2NHR^{21}$
In some embodiments $R^{20f}$ is $NHSO_2R^{22}$
In some embodiments $R^{20f}$ is $—NR^{23a}R^{23b}$
In some embodiments $R^{20f}$ is $NHC(O)R^{24}$.
In some embodiments $R^{20f}$ is $C(O)NHR^{24}$.
In some embodiments $R^{20f}$ is $C(O)N(R^{24})_2$.
In some embodiments $R^{20f}$ is morpholino.
In some embodiments $R^{20f}$ is

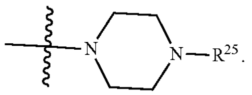

In some embodiments $R^{20g}$ is hydrogen.
In some embodiments $R^{20g}$ is —CN.
In some embodiments $R^{20g}$ is $—NO_2$.
In some embodiments $R^{20g}$ is —OH.
In some embodiments $R^{20g}$ is halogen.
In some embodiments $R^{20g}$ is $C_{1-6}$ linear alkyl.
In some embodiments $R^{20g}$ is $C_{3-7}$ branched alkyl.
In some embodiments $R^{20g}$ is $C_{3-7}$ cycloalkyl.
In some embodiments $R^{20g}$ is $C_{1-6}$ linear alkoxy.
In some embodiments $R^{20g}$ is $C_{3-7}$ branched alkoxy.
In some embodiments $R^{20g}$ is $C_{3-7}$ cycloalkoxy.
In some embodiments $R^{20g}$ is $C_{1-6}$ linear haloalkyl.
In some embodiments $R^{20g}$ is $C_{3-7}$ branched haloalkyl.
In some embodiments $R^{20g}$ is $C_{1-6}$ linear haloalkoxy.
In some embodiments $R^{20g}$ is $C_{3-7}$ branched haloalkoxy.
In some embodiments $R^{20g}$ is SH.
In some embodiments $R^{20g}$ is $SC_{1-6}$ linear alkyl.
In some embodiments $R^{20g}$ is $SC_{3-7}$ branched alkyl.
In some embodiments $R^{20g}$ is $SC_{3-7}$cycloalkyl.
In some embodiments $R^{20g}$ is $SO_2C_{1-6}$ linear alkyl.
In some embodiments $R^{20g}$ is $SO_2C_{3-7}$ branched alkyl.
In some embodiments $R^{20g}$ is $SO_2C_{3-7}$cycloalkyl.
In some embodiments $R^{20g}$ is $SO_2NH_2$.
In some embodiments $R^{20g}$ is $SO_2NHR^{21}$.
In some embodiments $R^{20g}$ is $NHSO_2R^{22}$.
In some embodiments $R^{20g}$ is $—NR^{23a}R^{23b}$
In some embodiments $R^{20g}$ is $NHC(O)R^{24}$.
In some embodiments $R^{20g}$ is $C(O)NHR^{24}$.
In some embodiments $R^{20g}$ is $C(O)N(R^{24})_2$.

In some embodiments $R^{20g}$ is morpholino.

In some embodiments $R^{20g}$ is

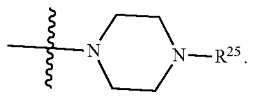

In some embodiments $R^{21}$ is hydrogen.

In some embodiments $R^{21}$ is $C_{1-6}$ linear alkyl.

In some embodiments $R^{21}$ is $C_{3-7}$ branched alkyl.

In some embodiments $R^{21}$ is $C_{3-7}$ cycloalkyl.

In some embodiments $R^{22}$ is hydrogen.

In some embodiments $R^{22}$ is $C_{1-6}$ linear alkyl.

In some embodiments $R^{22}$ is $C_{3-7}$ branched alkyl.

In some embodiments $R^{22}$ is $C_{3-7}$ cycloalkyl.

In some embodiments $R^{23a}$ is hydrogen.

In some embodiments $R^{23a}$ is $C_{1-6}$ linear alkyl.

In some embodiments $R^{23a}$ is $C_{3-7}$ branched alkyl.

In some embodiments $R^{23a}$ is $C_{3-7}$ cycloalkyl.

In some embodiments $R^{23b}$ is hydrogen.

In some embodiments $R^{23b}$ is $C_{1-6}$ linear alkyl.

In some embodiments $R^{23b}$ is $C_{3-7}$ branched alkyl.

In some embodiments $R^{23b}$ is $C_{3-7}$ cycloalkyl.

In some embodiments $R^{24}$ is hydrogen.

In some embodiments $R^{24}$ is $C_{1-6}$ linear alkyl.

In some embodiments $R^{24}$ is $C_{3-7}$ branched alkyl.

In some embodiments $R^{24}$ is $C_{3-7}$ cycloalkyl.

In some embodiments $R^{25}$ is hydrogen.

In some embodiments $R^{25}$ is $C_{1-6}$ linear alkyl.

In some embodiments $R^{25}$ is $C_{3-7}$ branched alkyl.

In some embodiments $R^{25}$ is $C_{3-7}$ cycloalkyl.

In some embodiments $Q^1$ is 1.

In some embodiments $Q^1$ is 2.

In some embodiments $Q^2$ is 1.

In some embodiments $Q^2$ is 2.

In some embodiments $X^1$ is O.

In some embodiments $X^1$ is S.

In some embodiments $X^1$ is SO.

In some embodiments $X^1$ is $SO_2$.

In some embodiments $X^1$ is $NR^7$.

Exemplary Compounds

Exemplary compounds include any of the compounds described herein. In embodiments where the compounds or formulas described herein do not specify the configuration of the lactam stereocenter (i.e., the carbon substituted by the nitrogen of the lactam) is not indicated, said lactam stereocenter can have the R-configuration. In other embodiments, said lactam stereocenter can have the S-configuration.

In embodiments, a compound is any compound described herein or a pharmaceutically acceptable salt thereof. In embodiments, a compound that is described in any one of Tables 1-39, or a pharmaceutically acceptable salt thereof. In embodiments, a compound is a compound described in any one of Tables 34-39, or a pharmaceutically acceptable salt thereof.

Exemplary embodiments include compounds having the formula (II)

(II)

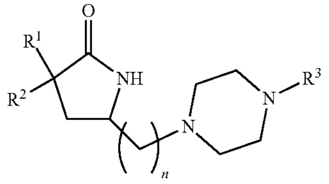

or a pharmaceutically acceptable salt form thereof defined herein below in Table 1.

TABLE 1

| Entry | $R^1$ | $R^2$ | n | $R^3$ |
|---|---|---|---|---|
| 1 | Methyl | Methyl | 1 | Phenyl |
| 2 | Methyl | Methyl | 2 | Phenyl |
| 3 | Methyl | Methyl | 3 | Phenyl |
| 4 | Methyl | Methyl | 4 | Phenyl |
| 5 | Methyl | Methyl | 1 | 4-OH-Phenyl |
| 6 | Methyl | Methyl | 2 | 4-OH-Phenyl |
| 7 | Methyl | Methyl | 3 | 4-OH-Phenyl |
| 8 | Methyl | Methyl | 4 | 4-OH-Phenyl |
| 9 | Methyl | Methyl | 1 | 3-OH-Phenyl |
| 10 | Methyl | Methyl | 2 | 3-OH-Phenyl |
| 11 | Methyl | Methyl | 3 | 3-OH-Phenyl |
| 12 | Methyl | Methyl | 4 | 3-OH-Phenyl |
| 13 | Methyl | Methyl | 1 | 2-OH-Phenyl |
| 14 | Methyl | Methyl | 2 | 2-OH-Phenyl |
| 15 | Methyl | Methyl | 3 | 2-OH-Phenyl |
| 16 | Methyl | Methyl | 4 | 2-OH-Phenyl |
| 17 | Methyl | Methyl | 1 | 4-OMe-Phenyl |
| 18 | Methyl | Methyl | 2 | 4-OMe-Phenyl |
| 19 | Methyl | Methyl | 3 | 4-OMe-Phenyl |
| 20 | Methyl | Methyl | 4 | 4-OMe-Phenyl |
| 21 | Methyl | Methyl | 1 | 3-OMe-Phenyl |
| 22 | Methyl | Methyl | 2 | 3-OMe-Phenyl |
| 23 | Methyl | Methyl | 3 | 3-OMe-Phenyl |
| 24 | Methyl | Methyl | 4 | 3-OMe-Phenyl |
| 25 | Methyl | Methyl | 1 | 2-OMe-Phenyl |
| 26 | Methyl | Methyl | 2 | 2-OMe-Phenyl |
| 27 | Methyl | Methyl | 3 | 2-OMe-Phenyl |
| 28 | Methyl | Methyl | 4 | 2-OMe-Phenyl |
| 29 | Methyl | Methyl | 1 | 4-CN-Phenyl |
| 30 | Methyl | Methyl | 2 | 4-CN-Phenyl |
| 31 | Methyl | Methyl | 3 | 4-CN-Phenyl |
| 32 | Methyl | Methyl | 4 | 4-CN-Phenyl |
| 33 | Methyl | Methyl | 1 | 3-CN-Phenyl |
| 34 | Methyl | Methyl | 2 | 3-CN-Phenyl |
| 35 | Methyl | Methyl | 3 | 3-CN-Phenyl |
| 36 | Methyl | Methyl | 4 | 3-CN-Phenyl |
| 37 | Methyl | Methyl | 1 | 2-CN-Phenyl |
| 38 | Methyl | Methyl | 2 | 2-CN-Phenyl |
| 39 | Methyl | Methyl | 3 | 2-CN-Phenyl |
| 40 | Methyl | Methyl | 4 | 2-CN-Phenyl |
| 41 | Methyl | Methyl | 1 | 4-Me-Phenyl |
| 42 | Methyl | Methyl | 2 | 4-Me-Phenyl |
| 43 | Methyl | Methyl | 3 | 4-Me-Phenyl |
| 44 | Methyl | Methyl | 4 | 4-Me-Phenyl |
| 45 | Methyl | Methyl | 1 | 3-Me-Phenyl |
| 46 | Methyl | Methyl | 2 | 3-Me-Phenyl |
| 47 | Methyl | Methyl | 3 | 3-Me-Phenyl |
| 48 | Methyl | Methyl | 4 | 3-Me-Phenyl |
| 49 | Methyl | Methyl | 1 | 2-Me-Phenyl |
| 50 | Methyl | Methyl | 2 | 2-Me-Phenyl |
| 51 | Methyl | Methyl | 3 | 2-Me-Phenyl |
| 52 | Methyl | Methyl | 4 | 2-Me-Phenyl |
| 53 | Methyl | Methyl | 1 | 4-F-Phenyl |
| 54 | Methyl | Methyl | 2 | 4-F-Phenyl |
| 55 | Methyl | Methyl | 3 | 4-F-Phenyl |
| 56 | Methyl | Methyl | 4 | 4-F-Phenyl |
| 57 | Methyl | Methyl | 1 | 3-F-Phenyl |
| 58 | Methyl | Methyl | 2 | 3-F-Phenyl |
| 59 | Methyl | Methyl | 3 | 3-F-Phenyl |
| 60 | Methyl | Methyl | 4 | 3-F-Phenyl |
| 61 | Methyl | Methyl | 1 | 2-F-Phenyl |

TABLE 1-continued

| Entry | $R^1$ | $R^2$ | n | $R^3$ |
|---|---|---|---|---|
| 62 | Methyl | Methyl | 2 | 2-F-Phenyl |
| 63 | Methyl | Methyl | 3 | 2-F-Phenyl |
| 64 | Methyl | Methyl | 4 | 2-F-Phenyl |
| 65 | Methyl | Methyl | 1 | 4-Cl-Phenyl |
| 66 | Methyl | Methyl | 2 | 4-Cl-Phenyl |
| 67 | Methyl | Methyl | 3 | 4-Cl-Phenyl |
| 68 | Methyl | Methyl | 4 | 4-Cl-Phenyl |
| 69 | Methyl | Methyl | 1 | 3-Cl-Phenyl |
| 70 | Methyl | Methyl | 2 | 3-Cl-Phenyl |
| 71 | Methyl | Methyl | 3 | 3-Cl-Phenyl |
| 72 | Methyl | Methyl | 4 | 3-Cl-Phenyl |
| 73 | Methyl | Methyl | 1 | 2-Cl-Phenyl |
| 74 | Methyl | Methyl | 2 | 2-Cl-Phenyl |
| 75 | Methyl | Methyl | 3 | 2-Cl-Phenyl |
| 76 | Methyl | Methyl | 4 | 2-Cl-Phenyl |
| 77 | Methyl | Methyl | 1 | 4-Br-Phenyl |
| 78 | Methyl | Methyl | 2 | 4-Br-Phenyl |
| 79 | Methyl | Methyl | 3 | 4-Br-Phenyl |
| 80 | Methyl | Methyl | 4 | 4-Br-Phenyl |
| 81 | Methyl | Methyl | 1 | 3-Br-Phenyl |
| 82 | Methyl | Methyl | 2 | 3-Br-Phenyl |
| 83 | Methyl | Methyl | 3 | 3-Br-Phenyl |
| 84 | Methyl | Methyl | 4 | 3-Br-Phenyl |
| 85 | Methyl | Methyl | 1 | 2-Br-Phenyl |
| 86 | Methyl | Methyl | 2 | 2-Br-Phenyl |
| 87 | Methyl | Methyl | 3 | 2-Br-Phenyl |
| 88 | Methyl | Methyl | 4 | 2-Br-Phenyl |
| 89 | Methyl | Methyl | 1 | 4-$CF_3$-Phenyl |
| 90 | Methyl | Methyl | 2 | 4-$CF_3$-Phenyl |
| 91 | Methyl | Methyl | 3 | 4-$CF_3$-Phenyl |
| 92 | Methyl | Methyl | 4 | 4-$CF_3$-Phenyl |
| 93 | Methyl | Methyl | 1 | 3-$CF_3$-Phenyl |
| 94 | Methyl | Methyl | 2 | 3-$CF_3$-Phenyl |
| 95 | Methyl | Methyl | 3 | 3-$CF_3$-Phenyl |
| 96 | Methyl | Methyl | 4 | 3-$CF_3$-Phenyl |
| 97 | Methyl | Methyl | 1 | 2-$CF_3$-Phenyl |
| 98 | Methyl | Methyl | 2 | 2-$CF_3$-Phenyl |
| 99 | Methyl | Methyl | 3 | 2-$CF_3$-Phenyl |
| 100 | Methyl | Methyl | 4 | 2-$CF_3$-Phenyl |
| 101 | Methyl | Methyl | 1 | 4-iPr-Phenyl |
| 102 | Methyl | Methyl | 2 | 4-iPr-Phenyl |
| 103 | Methyl | Methyl | 3 | 4-iPr-Phenyl |
| 104 | Methyl | Methyl | 4 | 4-iPr-Phenyl |
| 105 | Methyl | Methyl | 1 | 3-iPr-Phenyl |
| 106 | Methyl | Methyl | 2 | 3-iPr-Phenyl |
| 107 | Methyl | Methyl | 3 | 3-iPr-Phenyl |
| 108 | Methyl | Methyl | 4 | 3-iPr-Phenyl |
| 109 | Methyl | Methyl | 1 | 2-iPr-Phenyl |
| 110 | Methyl | Methyl | 2 | 2-iPr-Phenyl |
| 111 | Methyl | Methyl | 3 | 2-iPr-Phenyl |
| 112 | Methyl | Methyl | 4 | 2-iPr-Phenyl |
| 113 | Methyl | Methyl | 1 | 4-$NH_2$-Phenyl |
| 114 | Methyl | Methyl | 2 | 4-$NH_2$-Phenyl |
| 115 | Methyl | Methyl | 3 | 4-$NH_2$-Phenyl |
| 116 | Methyl | Methyl | 4 | 4-$NH_2$-Phenyl |
| 117 | Methyl | Methyl | 1 | 3-$NH_2$-Phenyl |
| 118 | Methyl | Methyl | 2 | 3-$NH_2$-Phenyl |
| 119 | Methyl | Methyl | 3 | 3-$NH_2$-Phenyl |
| 120 | Methyl | Methyl | 4 | 3-$NH_2$-Phenyl |
| 121 | Methyl | Methyl | 1 | 2-$NH_2$-Phenyl |
| 122 | Methyl | Methyl | 2 | 2-$NH_2$-Phenyl |
| 123 | Methyl | Methyl | 3 | 2-$NH_2$-Phenyl |
| 124 | Methyl | Methyl | 4 | 2-$NH_2$-Phenyl |
| 125 | Methyl | Methyl | 1 | 2,3-di-Me-Phenyl |
| 126 | Methyl | Methyl | 2 | 2,3-di-Me-Phenyl |
| 127 | Methyl | Methyl | 3 | 2,3-di-Me-Phenyl |
| 128 | Methyl | Methyl | 4 | 2,3-di-Me-Phenyl |
| 129 | Methyl | Methyl | 1 | 2,4-di-Me-Phenyl |
| 130 | Methyl | Methyl | 2 | 2,4-di-Me-Phenyl |
| 131 | Methyl | Methyl | 3 | 2,4-di-Me-Phenyl |
| 132 | Methyl | Methyl | 4 | 2,4-di-Me-Phenyl |
| 133 | Methyl | Methyl | 1 | 2,5-di-Me-Phenyl |
| 134 | Methyl | Methyl | 2 | 2,5-di-Me-Phenyl |
| 135 | Methyl | Methyl | 3 | 2,5-di-Me-Phenyl |
| 136 | Methyl | Methyl | 4 | 2,5-di-Me-Phenyl |
| 137 | Methyl | Methyl | 1 | 2,6-di-Me-Phenyl |
| 138 | Methyl | Methyl | 2 | 2,6-di-Me-Phenyl |
| 139 | Methyl | Methyl | 3 | 2,6-di-Me-Phenyl |

TABLE 1-continued

| Entry | $R^1$ | $R^2$ | n | $R^3$ |
|---|---|---|---|---|
| 140 | Methyl | Methyl | 4 | 2,6-di-Me-Phenyl |
| 141 | Methyl | Methyl | 1 | 2,6-di-iPr-Phenyl |
| 142 | Methyl | Methyl | 2 | 2,6-di-iPr-Phenyl |
| 143 | Methyl | Methyl | 3 | 2,6-di-iPr-Phenyl |
| 144 | Methyl | Methyl | 4 | 2,6-di-iPr-Phenyl |
| 145 | Methyl | Methyl | 1 | 2-morpholino-phenyl |
| 146 | Methyl | Methyl | 2 | 2-morpholino-phenyl |
| 147 | Methyl | Methyl | 3 | 2-morpholino-phenyl |
| 148 | Methyl | Methyl | 4 | 2-morpholino-phenyl |
| 149 | Methyl | Methyl | 1 | 3-morpholino-phenyl |
| 150 | Methyl | Methyl | 2 | 3-morpholino-phenyl |
| 151 | Methyl | Methyl | 3 | 3-morpholino-phenyl |
| 152 | Methyl | Methyl | 4 | 3-morpholino-phenyl |
| 153 | Methyl | Methyl | 1 | 4-morpholino-phenyl |
| 154 | Methyl | Methyl | 2 | 4-morpholino-phenyl |
| 155 | Methyl | Methyl | 3 | 4-morpholino-phenyl |
| 156 | Methyl | Methyl | 4 | 4-morpholino-phenyl |
| 157 | Methyl | Methyl | 1 | 4-CN-2-morpholino-phenyl |
| 158 | Methyl | Methyl | 2 | 4-CN-2-morpholino-phenyl |
| 159 | Methyl | Methyl | 3 | 4-CN-2-morpholino-phenyl |
| 160 | Methyl | Methyl | 4 | 4-CN-2-morpholino-phenyl |
| 161 | Methyl | Methyl | 1 | 4-$CH_3$-2-morpholino-phenyl |
| 162 | Methyl | Methyl | 2 | 4-$CH_3$-2-morpholino-phenyl |
| 163 | Methyl | Methyl | 3 | 4-$CH_3$-2-morpholino-phenyl |
| 164 | Methyl | Methyl | 4 | 4-$CH_3$-2-morpholino-phenyl |
| 165 | Methyl | Methyl | 1 | 4-OH-2-morpholino-phenyl |
| 166 | Methyl | Methyl | 2 | 4-OH-2-morpholino-phenyl |
| 167 | Methyl | Methyl | 3 | 4-OH-2-morpholino-phenyl |
| 168 | Methyl | Methyl | 4 | 4-OH-2-morpholino-phenyl |
| 169 | Methyl | Methyl | 1 | naphthylen-1-yl |
| 170 | Methyl | Methyl | 2 | naphthylen-1-yl |
| 171 | Methyl | Methyl | 3 | naphthylen-1-yl |
| 172 | Methyl | Methyl | 4 | naphthylen-1-yl |
| 173 | Methyl | Methyl | 1 | naphthylen-2-yl |
| 174 | Methyl | Methyl | 2 | naphthylen-2-yl |
| 175 | Methyl | Methyl | 3 | naphthylen-2-yl |
| 176 | Methyl | Methyl | 4 | naphthylen-2-yl |
| 177 | Ethyl | Ethyl | 1 | Phenyl |
| 178 | Ethyl | Ethyl | 2 | Phenyl |
| 179 | Ethyl | Ethyl | 3 | Phenyl |
| 180 | Ethyl | Ethyl | 4 | Phenyl |
| 181 | Ethyl | Ethyl | 1 | 4-OH-Phenyl |
| 182 | Ethyl | Ethyl | 2 | 4-OH-Phenyl |
| 183 | Ethyl | Ethyl | 3 | 4-OH-Phenyl |
| 184 | Ethyl | Ethyl | 4 | 4-OH-Phenyl |
| 185 | Ethyl | Ethyl | 1 | 3-OH-Phenyl |
| 186 | Ethyl | Ethyl | 2 | 3-OH-Phenyl |
| 187 | Ethyl | Ethyl | 3 | 3-OH-Phenyl |
| 188 | Ethyl | Ethyl | 4 | 3-OH-Phenyl |
| 189 | Ethyl | Ethyl | 1 | 2-OH-Phenyl |
| 190 | Ethyl | Ethyl | 2 | 2-OH-Phenyl |
| 191 | Ethyl | Ethyl | 3 | 2-OH-Phenyl |
| 192 | Ethyl | Ethyl | 4 | 2-OH-Phenyl |
| 193 | Ethyl | Ethyl | 1 | 4-OMe-Phenyl |
| 194 | Ethyl | Ethyl | 2 | 4-OMe-Phenyl |
| 195 | Ethyl | Ethyl | 3 | 4-OMe-Phenyl |
| 196 | Ethyl | Ethyl | 4 | 4-OMe-Phenyl |
| 197 | Ethyl | Ethyl | 1 | 3-OMe-Phenyl |
| 198 | Ethyl | Ethyl | 2 | 3-OMe-Phenyl |
| 199 | Ethyl | Ethyl | 3 | 3-OMe-Phenyl |
| 200 | Ethyl | Ethyl | 4 | 3-OMe-Phenyl |
| 201 | Ethyl | Ethyl | 1 | 2-OMe-Phenyl |
| 202 | Ethyl | Ethyl | 2 | 2-OMe-Phenyl |
| 203 | Ethyl | Ethyl | 3 | 2-OMe-Phenyl |
| 204 | Ethyl | Ethyl | 4 | 2-OMe-Phenyl |
| 205 | Ethyl | Ethyl | 1 | 4-CN-Phenyl |
| 206 | Ethyl | Ethyl | 2 | 4-CN-Phenyl |
| 207 | Ethyl | Ethyl | 3 | 4-CN-Phenyl |
| 208 | Ethyl | Ethyl | 4 | 4-CN-Phenyl |
| 209 | Ethyl | Ethyl | 1 | 3-CN-Phenyl |
| 210 | Ethyl | Ethyl | 2 | 3-CN-Phenyl |
| 211 | Ethyl | Ethyl | 3 | 3-CN-Phenyl |
| 212 | Ethyl | Ethyl | 4 | 3-CN-Phenyl |
| 213 | Ethyl | Ethyl | 1 | 2-CN-Phenyl |
| 214 | Ethyl | Ethyl | 2 | 2-CN-Phenyl |
| 215 | Ethyl | Ethyl | 3 | 2-CN-Phenyl |
| 216 | Ethyl | Ethyl | 4 | 2-CN-Phenyl |
| 217 | Ethyl | Ethyl | 1 | 4-Me-Phenyl |

TABLE 1-continued

| Entry | $R^1$ | $R^2$ | n | $R^3$ |
|---|---|---|---|---|
| 218 | Ethyl | Ethyl | 2 | 4-Me-Phenyl |
| 219 | Ethyl | Ethyl | 3 | 4-Me-Phenyl |
| 220 | Ethyl | Ethyl | 4 | 4-Me-Phenyl |
| 221 | Ethyl | Ethyl | 1 | 3-Me-Phenyl |
| 222 | Ethyl | Ethyl | 2 | 3-Me-Phenyl |
| 223 | Ethyl | Ethyl | 3 | 3-Me-Phenyl |
| 224 | Ethyl | Ethyl | 4 | 3-Me-Phenyl |
| 225 | Ethyl | Ethyl | 1 | 2-Me-Phenyl |
| 226 | Ethyl | Ethyl | 2 | 2-Me-Phenyl |
| 227 | Ethyl | Ethyl | 3 | 2-Me-Phenyl |
| 228 | Ethyl | Ethyl | 4 | 2-Me-Phenyl |
| 229 | Ethyl | Ethyl | 1 | 4-F-Phenyl |
| 230 | Ethyl | Ethyl | 2 | 4-F-Phenyl |
| 231 | Ethyl | Ethyl | 3 | 4-F-Phenyl |
| 232 | Ethyl | Ethyl | 4 | 4-F-Phenyl |
| 233 | Ethyl | Ethyl | 1 | 3-F-Phenyl |
| 234 | Ethyl | Ethyl | 2 | 3-F-Phenyl |
| 235 | Ethyl | Ethyl | 3 | 3-F-Phenyl |
| 236 | Ethyl | Ethyl | 4 | 3-F-Phenyl |
| 237 | Ethyl | Ethyl | 1 | 2-F-Phenyl |
| 238 | Ethyl | Ethyl | 2 | 2-F-Phenyl |
| 239 | Ethyl | Ethyl | 3 | 2-F-Phenyl |
| 240 | Ethyl | Ethyl | 4 | 2-F-Phenyl |
| 241 | Ethyl | Ethyl | 1 | 4-Cl-Phenyl |
| 242 | Ethyl | Ethyl | 2 | 4-Cl-Phenyl |
| 243 | Ethyl | Ethyl | 3 | 4-Cl-Phenyl |
| 244 | Ethyl | Ethyl | 4 | 4-Cl-Phenyl |
| 245 | Ethyl | Ethyl | 1 | 3-Cl-Phenyl |
| 246 | Ethyl | Ethyl | 2 | 3-Cl-Phenyl |
| 247 | Ethyl | Ethyl | 3 | 3-Cl-Phenyl |
| 248 | Ethyl | Ethyl | 4 | 3-Cl-Phenyl |
| 249 | Ethyl | Ethyl | 1 | 2-Cl-Phenyl |
| 250 | Ethyl | Ethyl | 2 | 2-Cl-Phenyl |
| 251 | Ethyl | Ethyl | 3 | 2-Cl-Phenyl |
| 252 | Ethyl | Ethyl | 4 | 2-Cl-Phenyl |
| 253 | Ethyl | Ethyl | 1 | 4-Br-Phenyl |
| 254 | Ethyl | Ethyl | 2 | 4-Br-Phenyl |
| 255 | Ethyl | Ethyl | 3 | 4-Br-Phenyl |
| 256 | Ethyl | Ethyl | 4 | 4-Br-Phenyl |
| 257 | Ethyl | Ethyl | 1 | 3-Br-Phenyl |
| 258 | Ethyl | Ethyl | 2 | 3-Br-Phenyl |
| 259 | Ethyl | Ethyl | 3 | 3-Br-Phenyl |
| 260 | Ethyl | Ethyl | 4 | 3-Br-Phenyl |
| 261 | Ethyl | Ethyl | 1 | 2-Br-Phenyl |
| 262 | Ethyl | Ethyl | 2 | 2-Br-Phenyl |
| 263 | Ethyl | Ethyl | 3 | 2-Br-Phenyl |
| 264 | Ethyl | Ethyl | 4 | 2-Br-Phenyl |
| 265 | Ethyl | Ethyl | 1 | 4-$CF_3$-Phenyl |
| 266 | Ethyl | Ethyl | 2 | 4-$CF_3$-Phenyl |
| 267 | Ethyl | Ethyl | 3 | 4-$CF_3$-Phenyl |
| 268 | Ethyl | Ethyl | 4 | 4-$CF_3$-Phenyl |
| 269 | Ethyl | Ethyl | 1 | 3-$CF_3$-Phenyl |
| 270 | Ethyl | Ethyl | 2 | 3-$CF_3$-Phenyl |
| 271 | Ethyl | Ethyl | 3 | 3-$CF_3$-Phenyl |
| 272 | Ethyl | Ethyl | 4 | 3-$CF_3$-Phenyl |
| 273 | Ethyl | Ethyl | 1 | 2-$CF_3$-Phenyl |
| 274 | Ethyl | Ethyl | 2 | 2-$CF_3$-Phenyl |
| 275 | Ethyl | Ethyl | 3 | 2-$CF_3$-Phenyl |
| 276 | Ethyl | Ethyl | 4 | 2-$CF_3$-Phenyl |
| 277 | Ethyl | Ethyl | 1 | 4-iPr-Phenyl |
| 278 | Ethyl | Ethyl | 2 | 4-iPr-Phenyl |
| 279 | Ethyl | Ethyl | 3 | 4-iPr-Phenyl |
| 280 | Ethyl | Ethyl | 4 | 4-iPr-Phenyl |
| 281 | Ethyl | Ethyl | 1 | 3-iPr-Phenyl |
| 282 | Ethyl | Ethyl | 2 | 3-iPr-Phenyl |
| 283 | Ethyl | Ethyl | 3 | 3-iPr-Phenyl |
| 284 | Ethyl | Ethyl | 4 | 3-iPr-Phenyl |
| 285 | Ethyl | Ethyl | 1 | 2-iPr-Phenyl |
| 286 | Ethyl | Ethyl | 2 | 2-iPr-Phenyl |
| 287 | Ethyl | Ethyl | 3 | 2-iPr-Phenyl |
| 288 | Ethyl | Ethyl | 4 | 2-iPr-Phenyl |
| 289 | Ethyl | Ethyl | 1 | 4-$NH_2$-Phenyl |
| 290 | Ethyl | Ethyl | 2 | 4-$NH_2$-Phenyl |
| 291 | Ethyl | Ethyl | 3 | 4-$NH_2$-Phenyl |
| 292 | Ethyl | Ethyl | 4 | 4-$NH_2$-Phenyl |
| 293 | Ethyl | Ethyl | 1 | 3-$NH_2$-Phenyl |
| 294 | Ethyl | Ethyl | 2 | 3-$NH_2$-Phenyl |
| 295 | Ethyl | Ethyl | 3 | 3-$NH_2$-Phenyl |
| 296 | Ethyl | Ethyl | 4 | 3-$NH_2$-Phenyl |
| 297 | Ethyl | Ethyl | 1 | 2-$NH_2$-Phenyl |
| 298 | Ethyl | Ethyl | 2 | 2-$NH_2$-Phenyl |
| 299 | Ethyl | Ethyl | 3 | 2-$NH_2$-Phenyl |
| 300 | Ethyl | Ethyl | 4 | 2-$NH_2$-Phenyl |
| 301 | Ethyl | Ethyl | 1 | 2,3-di-Me-Phenyl |
| 302 | Ethyl | Ethyl | 2 | 2,3-di-Me-Phenyl |
| 303 | Ethyl | Ethyl | 3 | 2,3-di-Me-Phenyl |
| 304 | Ethyl | Ethyl | 4 | 2,3-di-Me-Phenyl |
| 305 | Ethyl | Ethyl | 1 | 2,4-di-Me-Phenyl |
| 306 | Ethyl | Ethyl | 2 | 2,4-di-Me-Phenyl |
| 307 | Ethyl | Ethyl | 3 | 2,4-di-Me-Phenyl |
| 308 | Ethyl | Ethyl | 4 | 2,4-di-Me-Phenyl |
| 309 | Ethyl | Ethyl | 1 | 2,5-di-Me-Phenyl |
| 310 | Ethyl | Ethyl | 2 | 2,5-di-Me-Phenyl |
| 311 | Ethyl | Ethyl | 3 | 2,5-di-Me-Phenyl |
| 312 | Ethyl | Ethyl | 4 | 2,5-di-Me-Phenyl |
| 313 | Ethyl | Ethyl | 1 | 2,6-di-Me-Phenyl |
| 314 | Ethyl | Ethyl | 2 | 2,6-di-Me-Phenyl |
| 315 | Ethyl | Ethyl | 3 | 2,6-di-Me-Phenyl |
| 316 | Ethyl | Ethyl | 4 | 2,6-di-Me-Phenyl |
| 317 | Ethyl | Ethyl | 1 | 2,6-di-iPr-Phenyl |
| 318 | Ethyl | Ethyl | 2 | 2,6-di-iPr-Phenyl |
| 319 | Ethyl | Ethyl | 3 | 2,6-di-iPr-Phenyl |
| 320 | Ethyl | Ethyl | 4 | 2,6-di-iPr-Phenyl |
| 321 | Ethyl | Ethyl | 1 | 2-morpholino-phenyl |
| 322 | Ethyl | Ethyl | 2 | 2-morpholino-phenyl |
| 323 | Ethyl | Ethyl | 3 | 2-morpholino-phenyl |
| 324 | Ethyl | Ethyl | 4 | 2-morpholino-phenyl |
| 325 | Ethyl | Ethyl | 1 | 3-morpholino-phenyl |
| 326 | Ethyl | Ethyl | 2 | 3-morpholino-phenyl |
| 327 | Ethyl | Ethyl | 3 | 3-morpholino-phenyl |
| 328 | Ethyl | Ethyl | 4 | 3-morpholino-phenyl |
| 329 | Ethyl | Ethyl | 1 | 4-morpholino-phenyl |
| 330 | Ethyl | Ethyl | 2 | 4-morpholino-phenyl |
| 331 | Ethyl | Ethyl | 3 | 4-morpholino-phenyl |
| 332 | Ethyl | Ethyl | 4 | 4-morpholino-phenyl |
| 333 | Ethyl | Ethyl | 1 | 4-CN-2-morpholino-phenyl |
| 334 | Ethyl | Ethyl | 2 | 4-CN-2-morpholino-phenyl |
| 335 | Ethyl | Ethyl | 3 | 4-CN-2-morpholino-phenyl |
| 336 | Ethyl | Ethyl | 4 | 4-CN-2-morpholino-phenyl |
| 337 | Ethyl | Ethyl | 1 | 4-$CH_3$-2-morpholino-phenyl |
| 338 | Ethyl | Ethyl | 2 | 4-$CH_3$-2-morpholino-phenyl |
| 339 | Ethyl | Ethyl | 3 | 4-$CH_3$-2-morpholino-phenyl |
| 340 | Ethyl | Ethyl | 4 | 4-$CH_3$-2-morpholino-phenyl |
| 341 | Ethyl | Ethyl | 1 | 4-OH-2-morpholino-phenyl |
| 342 | Ethyl | Ethyl | 2 | 4-OH-2-morpholino-phenyl |
| 343 | Ethyl | Ethyl | 3 | 4-OH-2-morpholino-phenyl |
| 344 | Ethyl | Ethyl | 4 | 4-OH-2-morpholino-phenyl |
| 345 | Ethyl | Ethyl | 1 | naphthylen-1-yl |
| 346 | Ethyl | Ethyl | 2 | naphthylen-1-yl |
| 347 | Ethyl | Ethyl | 3 | naphthylen-1-yl |
| 348 | Ethyl | Ethyl | 4 | naphthylen-1-yl |
| 349 | Ethyl | Ethyl | 1 | naphthylen-2-yl |
| 350 | Ethyl | Ethyl | 2 | naphthylen-2-yl |
| 351 | Ethyl | Ethyl | 3 | naphthylen-2-yl |
| 352 | Ethyl | Ethyl | 4 | naphthylen-2-yl |

Exemplary embodiments include compounds having the formula (VIII)

(VIII)

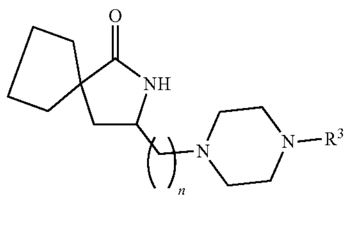

or a pharmaceutically acceptable salt form thereof defined herein below in Table 2.

TABLE 2

| Entry | n | $R^3$ |
|---|---|---|
| 1 | 1 | Phenyl |
| 2 | 2 | Phenyl |
| 3 | 3 | Phenyl |
| 4 | 4 | Phenyl |
| 5 | 1 | 4-OH-Phenyl |
| 6 | 2 | 4-OH-Phenyl |
| 7 | 3 | 4-OH-Phenyl |
| 8 | 4 | 4-OH-Phenyl |
| 9 | 1 | 3-OH-Phenyl |
| 10 | 2 | 3-OH-Phenyl |
| 11 | 3 | 3-OH-Phenyl |
| 12 | 4 | 3-OH-Phenyl |
| 13 | 1 | 2-OH-Phenyl |
| 14 | 2 | 2-OH-Phenyl |
| 15 | 3 | 2-OH-Phenyl |
| 16 | 4 | 2-OH-Phenyl |
| 17 | 1 | 4-OMe-Phenyl |
| 18 | 2 | 4-OMe-Phenyl |
| 19 | 3 | 4-OMe-Phenyl |
| 20 | 4 | 4-OMe-Phenyl |
| 21 | 1 | 3-OMe-Phenyl |
| 22 | 2 | 3-OMe-Phenyl |
| 23 | 3 | 3-OMe-Phenyl |
| 24 | 4 | 3-OMe-Phenyl |
| 25 | 1 | 2-OMe-Phenyl |
| 26 | 2 | 2-OMe-Phenyl |
| 27 | 3 | 2-OMe-Phenyl |
| 28 | 4 | 2-OMe-Phenyl |
| 29 | 1 | 4-CN-Phenyl |
| 30 | 2 | 4-CN-Phenyl |
| 31 | 3 | 4-CN-Phenyl |
| 32 | 4 | 4-CN-Phenyl |
| 33 | 1 | 3-CN-Phenyl |
| 34 | 2 | 3-CN-Phenyl |
| 35 | 3 | 3-CN-Phenyl |
| 36 | 4 | 3-CN-Phenyl |
| 37 | 1 | 2-CN-Phenyl |
| 38 | 2 | 2-CN-Phenyl |
| 39 | 3 | 2-CN-Phenyl |
| 40 | 4 | 2-CN-Phenyl |
| 41 | 1 | 4-Me-Phenyl |
| 42 | 2 | 4-Me-Phenyl |
| 43 | 3 | 4-Me-Phenyl |
| 44 | 4 | 4-Me-Phenyl |
| 45 | 1 | 3-Me-Phenyl |
| 46 | 2 | 3-Me-Phenyl |
| 47 | 3 | 3-Me-Phenyl |
| 48 | 4 | 3-Me-Phenyl |
| 49 | 1 | 2-Me-Phenyl |
| 50 | 2 | 2-Me-Phenyl |
| 51 | 3 | 2-Me-Phenyl |
| 52 | 4 | 2-Me-Phenyl |
| 53 | 1 | 4-F-Phenyl |
| 54 | 2 | 4-F-Phenyl |
| 55 | 3 | 4-F-Phenyl |
| 56 | 4 | 4-F-Phenyl |
| 57 | 1 | 3-F-Phenyl |
| 58 | 2 | 3-F-Phenyl |
| 59 | 3 | 3-F-Phenyl |
| 60 | 4 | 3-F-Phenyl |
| 61 | 1 | 2-F-Phenyl |
| 62 | 2 | 2-F-Phenyl |
| 63 | 3 | 2-F-Phenyl |
| 64 | 4 | 2-F-Phenyl |
| 65 | 1 | 4-Cl-Phenyl |
| 66 | 2 | 4-Cl-Phenyl |
| 67 | 3 | 4-Cl-Phenyl |
| 68 | 4 | 4-Cl-Phenyl |
| 69 | 1 | 3-Cl-Phenyl |
| 70 | 2 | 3-Cl-Phenyl |
| 71 | 3 | 3-Cl-Phenyl |
| 72 | 4 | 3-Cl-Phenyl |
| 73 | 1 | 2-Cl-Phenyl |
| 74 | 2 | 2-Cl-Phenyl |
| 75 | 3 | 2-Cl-Phenyl |
| 76 | 4 | 2-Cl-Phenyl |
| 77 | 1 | 4-Br-Phenyl |
| 78 | 2 | 4-Br-Phenyl |

TABLE 2-continued

| Entry | n | $R^3$ |
|---|---|---|
| 79 | 3 | 4-Br-Phenyl |
| 80 | 4 | 4-Br-Phenyl |
| 81 | 1 | 3-Br-Phenyl |
| 82 | 2 | 3-Br-Phenyl |
| 83 | 3 | 3-Br-Phenyl |
| 84 | 4 | 3-Br-Phenyl |
| 85 | 1 | naphthylen-1-yl |
| 86 | 2 | naphthylen-1-yl |
| 87 | 3 | naphthylen-1-yl |
| 88 | 4 | naphthylen-1-yl |
| 89 | 1 | 2-Br-Phenyl |
| 90 | 2 | 2-Br-Phenyl |
| 91 | 3 | 2-Br-Phenyl |
| 92 | 4 | 2-Br-Phenyl |
| 93 | 1 | 4-$CF_3$-Phenyl |
| 94 | 2 | 4-$CF_3$-Phenyl |
| 95 | 3 | 4-$CF_3$-Phenyl |
| 96 | 4 | 4-$CF_3$-Phenyl |
| 97 | 1 | 3-$CF_3$-Phenyl |
| 98 | 2 | 3-$CF_3$-Phenyl |
| 99 | 3 | 3-$CF_3$-Phenyl |
| 100 | 4 | 3-$CF_3$-Phenyl |
| 101 | 1 | 2-$CF_3$-Phenyl |
| 102 | 2 | 2-$CF_3$-Phenyl |
| 103 | 3 | 2-$CF_3$-Phenyl |
| 104 | 4 | 2-$CF_3$-Phenyl |
| 105 | 1 | 4-iPr-Phenyl |
| 106 | 2 | 4-iPr-Phenyl |
| 107 | 3 | 4-iPr-Phenyl |
| 108 | 4 | 4-iPr-Phenyl |
| 109 | 1 | 3-iPr-Phenyl |
| 110 | 2 | 3-iPr-Phenyl |
| 111 | 3 | 3-iPr-Phenyl |
| 112 | 4 | 3-iPr-Phenyl |
| 113 | 1 | 2-iPr-Phenyl |
| 114 | 2 | 2-iPr-Phenyl |
| 115 | 3 | 2-iPr-Phenyl |
| 116 | 4 | 2-iPr-Phenyl |
| 117 | 1 | 4-$NH_2$-Phenyl |
| 118 | 2 | 4-$NH_2$-Phenyl |
| 119 | 3 | 4-$NH_2$-Phenyl |
| 120 | 4 | 4-$NH_2$-Phenyl |
| 121 | 1 | 3-$NH_2$-Phenyl |
| 122 | 2 | 3-$NH_2$-Phenyl |
| 123 | 3 | 3-$NH_2$-Phenyl |
| 124 | 4 | 3-$NH_2$-Phenyl |
| 125 | 1 | 2-$NH_2$-Phenyl |
| 126 | 2 | 2-$NH_2$-Phenyl |
| 127 | 3 | 2-$NH_2$-Phenyl |
| 128 | 4 | 2-$NH_2$-Phenyl |
| 129 | 1 | 2,3-di-Me-Phenyl |
| 130 | 2 | 2,3-di-Me-Phenyl |
| 131 | 3 | 2,3-di-Me-Phenyl |
| 132 | 4 | 2,3-di-Me-Phenyl |
| 133 | 1 | 2,4-di-Me-Phenyl |
| 134 | 2 | 2,4-di-Me-Phenyl |
| 135 | 3 | 2,4-di-Me-Phenyl |
| 136 | 4 | 2,4-di-Me-Phenyl |
| 137 | 1 | 2,5-di-Me-Phenyl |
| 138 | 2 | 2,5-di-Me-Phenyl |
| 139 | 3 | 2,5-di-Me-Phenyl |
| 140 | 4 | 2,5-di-Me-Phenyl |
| 141 | 1 | 2,6-di-Me-Phenyl |
| 142 | 2 | 2,6-di-Me-Phenyl |
| 143 | 3 | 2,6-di-Me-Phenyl |
| 144 | 4 | 2,6-di-Me-Phenyl |
| 145 | 1 | 2,6-di-iPr-Phenyl |
| 146 | 2 | 2,6-di-iPr-Phenyl |
| 147 | 3 | 2,6-di-iPr-Phenyl |
| 148 | 4 | 2,6-di-iPr-Phenyl |
| 149 | 1 | 2-morpholino-phenyl |
| 150 | 2 | 2-morpholino-phenyl |
| 151 | 3 | 2-morpholino-phenyl |
| 152 | 4 | 2-morpholino-phenyl |
| 153 | 1 | 3-morpholino-phenyl |
| 154 | 2 | 3-morpholino-phenyl |
| 155 | 3 | 3-morpholino-phenyl |
| 156 | 4 | 3-morpholino-phenyl |

TABLE 2-continued

| Entry | n | $R^3$ |
|---|---|---|
| 157 | 1 | 4-morpholino-phenyl |
| 158 | 2 | 4-morpholino-phenyl |
| 159 | 3 | 4-morpholino-phenyl |
| 160 | 4 | 4-morpholino-phenyl |
| 161 | 1 | 4-CN-2-morpholino-phenyl |
| 162 | 2 | 4-CN-2-morpholino-phenyl |
| 163 | 3 | 4-CN-2-morpholino-phenyl |
| 164 | 4 | 4-CN-2-morpholino-phenyl |
| 165 | 1 | 4-$CH_3$-2-morpholino-phenyl |
| 166 | 2 | 4-$CH_3$-2-morpholino-phenyl |
| 167 | 3 | 4-$CH_3$-2-morpholino-phenyl |
| 168 | 4 | 4-$CH_3$-2-morpholino-phenyl |
| 169 | 1 | 4-OH-2-morpholino-phenyl |
| 170 | 2 | 4-OH-2-morpholino-phenyl |
| 171 | 3 | 4-OH-2-morpholino-phenyl |
| 172 | 4 | 4-OH-2-morpholino-phenyl |
| 173 | 1 | naphthylen-2-yl |
| 174 | 2 | naphthylen-2-yl |
| 175 | 3 | naphthylen-2-yl |
| 176 | 4 | naphthylen-2-yl |

Exemplary embodiments include compounds having the formula (IX)

(IX)

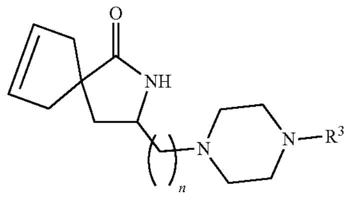

or a pharmaceutically acceptable salt form thereof defined herein below in Table 3.

TABLE 3

| Entry | n | $R^3$ |
|---|---|---|
| 1 | 1 | Phenyl |
| 2 | 2 | Phenyl |
| 3 | 3 | Phenyl |
| 4 | 4 | Phenyl |
| 5 | 1 | 4-OH-Phenyl |
| 6 | 2 | 4-OH-Phenyl |
| 7 | 3 | 4-OH-Phenyl |
| 8 | 4 | 4-OH-Phenyl |
| 9 | 1 | 3-OH-Phenyl |
| 10 | 2 | 3-OH-Phenyl |
| 11 | 3 | 3-OH-Phenyl |
| 12 | 4 | 3-OH-Phenyl |
| 13 | 1 | 2-OH-Phenyl |
| 14 | 2 | 2-OH-Phenyl |
| 15 | 3 | 2-OH-Phenyl |
| 16 | 4 | 2-OH-Phenyl |
| 17 | 1 | 4-OMe-Phenyl |
| 18 | 2 | 4-OMe-Phenyl |
| 19 | 3 | 4-OMe-Phenyl |
| 20 | 4 | 4-OMe-Phenyl |
| 21 | 1 | 3-OMe-Phenyl |
| 22 | 2 | 3-OMe-Phenyl |
| 23 | 3 | 3-OMe-Phenyl |
| 24 | 4 | 3-OMe-Phenyl |
| 25 | 1 | 2-OMe-Phenyl |
| 26 | 2 | 2-OMe-Phenyl |
| 27 | 3 | 2-OMe-Phenyl |
| 28 | 4 | 2-OMe-Phenyl |
| 29 | 1 | 4-CN-Phenyl |
| 30 | 2 | 4-CN-Phenyl |
| 31 | 3 | 4-CN-Phenyl |

TABLE 3-continued

| Entry | n | $R^3$ |
|---|---|---|
| 32 | 4 | 4-CN-Phenyl |
| 33 | 1 | 3-CN-Phenyl |
| 34 | 2 | 3-CN-Phenyl |
| 35 | 3 | 3-CN-Phenyl |
| 36 | 4 | 3-CN-Phenyl |
| 37 | 1 | 2-CN-Phenyl |
| 38 | 2 | 2-CN-Phenyl |
| 39 | 3 | 2-CN-Phenyl |
| 40 | 4 | 2-CN-Phenyl |
| 41 | 1 | 4-Me-Phenyl |
| 42 | 2 | 4-Me-Phenyl |
| 43 | 3 | 4-Me-Phenyl |
| 44 | 4 | 4-Me-Phenyl |
| 45 | 1 | 3-Me-Phenyl |
| 46 | 2 | 3-Me-Phenyl |
| 47 | 3 | 3-Me-Phenyl |
| 48 | 4 | 3-Me-Phenyl |
| 49 | 1 | 2-Me-Phenyl |
| 50 | 2 | 2-Me-Phenyl |
| 51 | 3 | 2-Me-Phenyl |
| 52 | 4 | 2-Me-Phenyl |
| 53 | 1 | 4-F-Phenyl |
| 54 | 2 | 4-F-Phenyl |
| 55 | 3 | 4-F-Phenyl |
| 56 | 4 | 4-F-Phenyl |
| 57 | 1 | 3-F-Phenyl |
| 58 | 2 | 3-F-Phenyl |
| 59 | 3 | 3-F-Phenyl |
| 60 | 4 | 3-F-Phenyl |
| 61 | 1 | 2-F-Phenyl |
| 62 | 2 | 2-F-Phenyl |
| 63 | 3 | 2-F-Phenyl |
| 64 | 4 | 2-F-Phenyl |
| 65 | 1 | 4-Cl-Phenyl |
| 66 | 2 | 4-Cl-Phenyl |
| 67 | 3 | 4-Cl-Phenyl |
| 68 | 4 | 4-Cl-Phenyl |
| 69 | 1 | 3-Cl-Phenyl |
| 70 | 2 | 3-Cl-Phenyl |
| 71 | 3 | 3-Cl-Phenyl |
| 72 | 4 | 3-Cl-Phenyl |
| 73 | 1 | 2-Cl-Phenyl |
| 74 | 2 | 2-Cl-Phenyl |
| 75 | 3 | 2-Cl-Phenyl |
| 76 | 4 | 2-Cl-Phenyl |
| 77 | 1 | 4-Br-Phenyl |
| 78 | 2 | 4-Br-Phenyl |
| 79 | 3 | 4-Br-Phenyl |
| 80 | 4 | 4-Br-Phenyl |
| 81 | 1 | 3-Br-Phenyl |
| 82 | 2 | 3-Br-Phenyl |
| 83 | 3 | 3-Br-Phenyl |
| 84 | 4 | 3-Br-Phenyl |
| 85 | 1 | naphthylen-1-yl |
| 86 | 2 | naphthylen-1-yl |
| 87 | 3 | naphthylen-1-yl |
| 88 | 4 | naphthylen-1-yl |
| 89 | 1 | 2-Br-Phenyl |
| 90 | 2 | 2-Br-Phenyl |
| 91 | 3 | 2-Br-Phenyl |
| 92 | 4 | 2-Br-Phenyl |
| 93 | 1 | 4-$CF_3$-Phenyl |
| 94 | 2 | 4-$CF_3$-Phenyl |
| 95 | 3 | 4-$CF_3$-Phenyl |
| 96 | 4 | 4-$CF_3$-Phenyl |
| 97 | 1 | 3-$CF_3$-Phenyl |
| 98 | 2 | 3-$CF_3$-Phenyl |
| 99 | 3 | 3-$CF_3$-Phenyl |
| 100 | 4 | 3-$CF_3$-Phenyl |
| 101 | 1 | 2-$CF_3$-Phenyl |
| 102 | 2 | 2-$CF_3$-Phenyl |
| 103 | 3 | 2-$CF_3$-Phenyl |
| 104 | 4 | 2-$CF_3$-Phenyl |
| 105 | 1 | 4-iPr-Phenyl |
| 106 | 2 | 4-iPr-Phenyl |
| 107 | 3 | 4-iPr-Phenyl |
| 108 | 4 | 4-iPr-Phenyl |
| 109 | 1 | 3-iPr-Phenyl |

TABLE 3-continued

| Entry | n | $R^3$ |
|---|---|---|
| 110 | 2 | 3-iPr-Phenyl |
| 111 | 3 | 3-iPr-Phenyl |
| 112 | 4 | 3-iPr-Phenyl |
| 113 | 1 | 2-iPr-Phenyl |
| 114 | 2 | 2-iPr-Phenyl |
| 115 | 3 | 2-iPr-Phenyl |
| 116 | 4 | 2-iPr-Phenyl |
| 117 | 1 | 4-$NH_2$-Phenyl |
| 118 | 2 | 4-$NH_2$-Phenyl |
| 119 | 3 | 4-$NH_2$-Phenyl |
| 120 | 4 | 4-$NH_2$-Phenyl |
| 121 | 1 | 3-$NH_2$-Phenyl |
| 122 | 2 | 3-$NH_2$-Phenyl |
| 123 | 3 | 3-$NH_2$-Phenyl |
| 124 | 4 | 3-$NH_2$-Phenyl |
| 125 | 1 | 2-$NH_2$-Phenyl |
| 126 | 2 | 2-$NH_2$-Phenyl |
| 127 | 3 | 2-$NH_2$-Phenyl |
| 128 | 4 | 2-$NH_2$-Phenyl |
| 129 | 1 | 2,3-di-Me-Phenyl |
| 130 | 2 | 2,3-di-Me-Phenyl |
| 131 | 3 | 2,3-di-Me-Phenyl |
| 132 | 4 | 2,3-di-Me-Phenyl |
| 133 | 1 | 2,4-di-Me-Phenyl |
| 134 | 2 | 2,4-di-Me-Phenyl |
| 135 | 3 | 2,4-di-Me-Phenyl |
| 136 | 4 | 2,4-di-Me-Phenyl |
| 137 | 1 | 2,5-di-Me-Phenyl |
| 138 | 2 | 2,5-di-Me-Phenyl |
| 139 | 3 | 2,5-di-Me-Phenyl |
| 140 | 4 | 2,5-di-Me-Phenyl |
| 141 | 1 | 2,6-di-Me-Phenyl |
| 142 | 2 | 2,6-di-Me-Phenyl |
| 143 | 3 | 2,6-di-Me-Phenyl |
| 144 | 4 | 2,6-di-Me-Phenyl |
| 145 | 1 | 2,6-di-iPr-Phenyl |
| 146 | 2 | 2,6-di-iPr-Phenyl |
| 147 | 3 | 2,6-di-iPr-Phenyl |
| 148 | 4 | 2,6-di-iPr-Phenyl |
| 149 | 1 | 2-morpholino-phenyl |
| 150 | 2 | 2-morpholino-phenyl |
| 151 | 3 | 2-morpholino-phenyl |
| 152 | 4 | 2-morpholino-phenyl |
| 153 | 1 | 3-morpholino-phenyl |
| 154 | 2 | 3-morpholino-phenyl |
| 155 | 3 | 3-morpholino-phenyl |
| 156 | 4 | 3-morpholino-phenyl |
| 157 | 1 | 4-morpholino-phenyl |
| 158 | 2 | 4-morpholino-phenyl |
| 159 | 3 | 4-morpholino-phenyl |
| 160 | 4 | 4-morpholino-phenyl |
| 161 | 1 | 4-CN-2-morpholino-phenyl |
| 162 | 2 | 4-CN-2-morpholino-phenyl |
| 163 | 3 | 4-CN-2-morpholino-phenyl |
| 164 | 4 | 4-CN-2-morpholino-phenyl |
| 165 | 1 | 4-$CH_3$-2-morpholino-phenyl |
| 166 | 2 | 4-$CH_3$-2-morpholino-phenyl |
| 167 | 3 | 4-$CH_3$-2-morpholino-phenyl |
| 168 | 4 | 4-$CH_3$-2-morpholino-phenyl |
| 169 | 1 | 4-OH-2-morpholino-phenyl |
| 170 | 2 | 4-OH-2-morpholino-phenyl |
| 171 | 3 | 4-OH-2-morpholino-phenyl |
| 172 | 4 | 4-OH-2-morpholino-phenyl |
| 173 | 1 | naphthylen-2-yl |
| 174 | 2 | naphthylen-2-yl |
| 175 | 3 | naphthylen-2-yl |
| 176 | 4 | naphthylen-2-yl |

Exemplary embodiments include compounds having the formula (X)

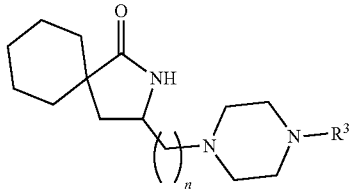

(X)

or a pharmaceutically acceptable salt form thereof defined herein below in Table 4.

TABLE 4

| Entry | n | $R^3$ |
|---|---|---|
| 1 | 1 | Phenyl |
| 2 | 2 | Phenyl |
| 3 | 3 | Phenyl |
| 4 | 4 | Phenyl |
| 5 | 1 | 4-OH-Phenyl |
| 6 | 2 | 4-OH-Phenyl |
| 7 | 3 | 4-OH-Phenyl |
| 8 | 4 | 4-OH-Phenyl |
| 9 | 1 | 3-OH-Phenyl |
| 10 | 2 | 3-OH-Phenyl |
| 11 | 3 | 3-OH-Phenyl |
| 12 | 4 | 3-OH-Phenyl |
| 13 | 1 | 2-OH-Phenyl |
| 14 | 2 | 2-OH-Phenyl |
| 15 | 3 | 2-OH-Phenyl |
| 16 | 4 | 2-OH-Phenyl |
| 17 | 1 | 4-OMe-Phenyl |
| 18 | 2 | 4-OMe-Phenyl |
| 19 | 3 | 4-OMe-Phenyl |
| 20 | 4 | 4-OMe-Phenyl |
| 21 | 1 | 3-OMe-Phenyl |
| 22 | 2 | 3-OMe-Phenyl |
| 23 | 3 | 3-OMe-Phenyl |
| 24 | 4 | 3-OMe-Phenyl |
| 25 | 1 | 2-OMe-Phenyl |
| 26 | 2 | 2-OMe-Phenyl |
| 27 | 3 | 2-OMe-Phenyl |
| 28 | 4 | 2-OMe-Phenyl |
| 29 | 1 | 4-CN-Phenyl |
| 30 | 2 | 4-CN-Phenyl |
| 31 | 3 | 4-CN-Phenyl |
| 32 | 4 | 4-CN-Phenyl |
| 33 | 1 | 3-CN-Phenyl |
| 34 | 2 | 3-CN-Phenyl |
| 35 | 3 | 3-CN-Phenyl |
| 36 | 4 | 3-CN-Phenyl |
| 37 | 1 | 2-CN-Phenyl |
| 38 | 2 | 2-CN-Phenyl |
| 39 | 3 | 2-CN-Phenyl |
| 40 | 4 | 2-CN-Phenyl |
| 41 | 1 | 4-Me-Phenyl |
| 42 | 2 | 4-Me-Phenyl |
| 43 | 3 | 4-Me-Phenyl |
| 44 | 4 | 4-Me-Phenyl |
| 45 | 1 | 3-Me-Phenyl |
| 46 | 2 | 3-Me-Phenyl |
| 47 | 3 | 3-Me-Phenyl |
| 48 | 4 | 3-Me-Phenyl |
| 49 | 1 | 2-Me-Phenyl |
| 50 | 2 | 2-Me-Phenyl |
| 51 | 3 | 2-Me-Phenyl |
| 52 | 4 | 2-Me-Phenyl |
| 53 | 1 | 4-F-Phenyl |
| 54 | 2 | 4-F-Phenyl |
| 55 | 3 | 4-F-Phenyl |
| 56 | 4 | 4-F-Phenyl |
| 57 | 1 | 3-F-Phenyl |
| 58 | 2 | 3-F-Phenyl |
| 59 | 3 | 3-F-Phenyl |
| 60 | 4 | 3-F-Phenyl |
| 61 | 1 | 2-F-Phenyl |

TABLE 4-continued

| Entry | n | $R^3$ |
|---|---|---|
| 62 | 2 | 2-F-Phenyl |
| 63 | 3 | 2-F-Phenyl |
| 64 | 4 | 2-F-Phenyl |
| 65 | 1 | 4-Cl-Phenyl |
| 66 | 2 | 4-Cl-Phenyl |
| 67 | 3 | 4-Cl-Phenyl |
| 68 | 4 | 4-Cl-Phenyl |
| 69 | 1 | 3-Cl-Phenyl |
| 70 | 2 | 3-Cl-Phenyl |
| 71 | 3 | 3-Cl-Phenyl |
| 72 | 4 | 3-Cl-Phenyl |
| 73 | 1 | 2-Cl-Phenyl |
| 74 | 2 | 2-Cl-Phenyl |
| 75 | 3 | 2-Cl-Phenyl |
| 76 | 4 | 2-Cl-Phenyl |
| 77 | 1 | 4-Br-Phenyl |
| 78 | 2 | 4-Br-Phenyl |
| 79 | 3 | 4-Br-Phenyl |
| 80 | 4 | 4-Br-Phenyl |
| 81 | 1 | 3-Br-Phenyl |
| 82 | 2 | 3-Br-Phenyl |
| 83 | 3 | 3-Br-Phenyl |
| 84 | 4 | 3-Br-Phenyl |
| 85 | 1 | naphthylen-1-yl |
| 86 | 2 | naphthylen-1-yl |
| 87 | 3 | naphthylen-1-yl |
| 88 | 4 | naphthylen-1-yl |
| 89 | 1 | 2-Br-Phenyl |
| 90 | 2 | 2-Br-Phenyl |
| 91 | 3 | 2-Br-Phenyl |
| 92 | 4 | 2-Br-Phenyl |
| 93 | 1 | 4-$CF_3$-Phenyl |
| 94 | 2 | 4-$CF_3$-Phenyl |
| 95 | 3 | 4-$CF_3$-Phenyl |
| 96 | 4 | 4-$CF_3$-Phenyl |
| 97 | 1 | 3-$CF_3$-Phenyl |
| 98 | 2 | 3-$CF_3$-Phenyl |
| 99 | 3 | 3-$CF_3$-Phenyl |
| 100 | 4 | 3-$CF_3$-Phenyl |
| 101 | 1 | 2-$CF_3$-Phenyl |
| 102 | 2 | 2-$CF_3$-Phenyl |
| 103 | 3 | 2-$CF_3$-Phenyl |
| 104 | 4 | 2-$CF_3$-Phenyl |
| 105 | 1 | 4-iPr-Phenyl |
| 106 | 2 | 4-iPr-Phenyl |
| 107 | 3 | 4-iPr-Phenyl |
| 108 | 4 | 4-iPr-Phenyl |
| 109 | 1 | 3-iPr-Phenyl |
| 110 | 2 | 3-iPr-Phenyl |
| 111 | 3 | 3-iPr-Phenyl |
| 112 | 4 | 3-iPr-Phenyl |
| 113 | 1 | 2-iPr-Phenyl |
| 114 | 2 | 2-iPr-Phenyl |
| 115 | 3 | 2-iPr-Phenyl |
| 116 | 4 | 2-iPr-Phenyl |
| 117 | 1 | 4-$NH_2$-Phenyl |
| 118 | 2 | 4-$NH_2$-Phenyl |
| 119 | 3 | 4-$NH_2$-Phenyl |
| 120 | 4 | 4-$NH_2$-Phenyl |
| 121 | 1 | 3-$NH_2$-Phenyl |
| 122 | 2 | 3-$NH_2$-Phenyl |
| 123 | 3 | 3-$NH_2$-Phenyl |
| 124 | 4 | 3-$NH_2$-Phenyl |
| 125 | 1 | 2-$NH_2$-Phenyl |
| 126 | 2 | 2-$NH_2$-Phenyl |
| 127 | 3 | 2-$NH_2$-Phenyl |
| 128 | 4 | 2-$NH_2$-Phenyl |
| 129 | 1 | 2,3-di-Me-Phenyl |
| 130 | 2 | 2,3-di-Me-Phenyl |
| 131 | 3 | 2,3-di-Me-Phenyl |
| 132 | 4 | 2,3-di-Me-Phenyl |
| 133 | 1 | 2,4-di-Me-Phenyl |
| 134 | 2 | 2,4-di-Me-Phenyl |
| 135 | 3 | 2,4-di-Me-Phenyl |
| 136 | 4 | 2,4-di-Me-Phenyl |
| 137 | 1 | 2,5-di-Me-Phenyl |
| 138 | 2 | 2,5-di-Me-Phenyl |
| 139 | 3 | 2,5-di-Me-Phenyl |

TABLE 4-continued

| Entry | n | $R^3$ |
|---|---|---|
| 140 | 4 | 2,5-di-Me-Phenyl |
| 141 | 1 | 2,6-di-Me-Phenyl |
| 142 | 2 | 2,6-di-Me-Phenyl |
| 143 | 3 | 2,6-di-Me-Phenyl |
| 144 | 4 | 2,6-di-Me-Phenyl |
| 145 | 1 | 2,6-di-iPr-Phenyl |
| 146 | 2 | 2,6-di-iPr-Phenyl |
| 147 | 3 | 2,6-di-iPr-Phenyl |
| 148 | 4 | 2,6-di-iPr-Phenyl |
| 149 | 1 | 2-morpholino-phenyl |
| 150 | 2 | 2-morpholino-phenyl |
| 151 | 3 | 2-morpholino-phenyl |
| 152 | 4 | 2-morpholino-phenyl |
| 153 | 1 | 3-morpholino-phenyl |
| 154 | 2 | 3-morpholino-phenyl |
| 155 | 3 | 3-morpholino-phenyl |
| 156 | 4 | 3-morpholino-phenyl |
| 157 | 1 | 4-morpholino-phenyl |
| 158 | 2 | 4-morpholino-phenyl |
| 159 | 3 | 4-morpholino-phenyl |
| 160 | 4 | 4-morpholino-phenyl |
| 161 | 1 | 4-CN-2-morpholino-phenyl |
| 162 | 2 | 4-CN-2-morpholino-phenyl |
| 163 | 3 | 4-CN-2-morpholino-phenyl |
| 164 | 4 | 4-CN-2-morpholino-phenyl |
| 165 | 1 | 4-$CH_3$-2-morpholino-phenyl |
| 166 | 2 | 4-$CH_3$-2-morpholino-phenyl |
| 167 | 3 | 4-$CH_3$-2-morpholino-phenyl |
| 168 | 4 | 4-$CH_3$-2-morpholino-phenyl |
| 169 | 1 | 4-OH-2-morpholino-phenyl |
| 170 | 2 | 4-OH-2-morpholino-phenyl |
| 171 | 3 | 4-OH-2-morpholino-phenyl |
| 172 | 4 | 4-OH-2-morpholino-phenyl |
| 173 | 1 | naphthylen-2-yl |
| 174 | 2 | naphthylen-2-yl |
| 175 | 3 | naphthylen-2-yl |
| 176 | 4 | naphthylen-2-yl |

Exemplary embodiments include compounds having the formula (XI)

(XI)

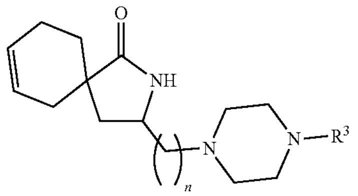

or a pharmaceutically acceptable salt form thereof defined herein below in Table 5.

TABLE 5

| Entry | n | $R^3$ |
|---|---|---|
| 1 | 1 | Phenyl |
| 2 | 2 | Phenyl |
| 3 | 3 | Phenyl |
| 4 | 4 | Phenyl |
| 5 | 1 | 4-OH-Phenyl |
| 6 | 2 | 4-OH-Phenyl |
| 7 | 3 | 4-OH-Phenyl |
| 8 | 4 | 4-OH-Phenyl |
| 9 | 1 | 3-OH-Phenyl |
| 10 | 2 | 3-OH-Phenyl |
| 11 | 3 | 3-OH-Phenyl |
| 12 | 4 | 3-OH-Phenyl |
| 13 | 1 | 2-OH-Phenyl |
| 14 | 2 | 2-OH-Phenyl |

TABLE 5-continued

| Entry | n | $R^3$ |
|---|---|---|
| 15 | 3 | 2-OH-Phenyl |
| 16 | 4 | 2-OH-Phenyl |
| 17 | 1 | 4-OMe-Phenyl |
| 18 | 2 | 4-OMe-Phenyl |
| 19 | 3 | 4-OMe-Phenyl |
| 20 | 4 | 4-OMe-Phenyl |
| 21 | 1 | 3-OMe-Phenyl |
| 22 | 2 | 3-OMe-Phenyl |
| 23 | 3 | 3-OMe-Phenyl |
| 24 | 4 | 3-OMe-Phenyl |
| 25 | 1 | 2-OMe-Phenyl |
| 26 | 2 | 2-OMe-Phenyl |
| 27 | 3 | 2-OMe-Phenyl |
| 28 | 4 | 2-OMe-Phenyl |
| 29 | 1 | 4-CN-Phenyl |
| 30 | 2 | 4-CN-Phenyl |
| 31 | 3 | 4-CN-Phenyl |
| 32 | 4 | 4-CN-Phenyl |
| 33 | 1 | 3-CN-Phenyl |
| 34 | 2 | 3-CN-Phenyl |
| 35 | 3 | 3-CN-Phenyl |
| 36 | 4 | 3-CN-Phenyl |
| 37 | 1 | 2-CN-Phenyl |
| 38 | 2 | 2-CN-Phenyl |
| 39 | 3 | 2-CN-Phenyl |
| 40 | 4 | 2-CN-Phenyl |
| 41 | 1 | 4-Me-Phenyl |
| 42 | 2 | 4-Me-Phenyl |
| 43 | 3 | 4-Me-Phenyl |
| 44 | 4 | 4-Me-Phenyl |
| 45 | 1 | 3-Me-Phenyl |
| 46 | 2 | 3-Me-Phenyl |
| 47 | 3 | 3-Me-Phenyl |
| 48 | 4 | 3-Me-Phenyl |
| 49 | 1 | 2-Me-Phenyl |
| 50 | 2 | 2-Me-Phenyl |
| 51 | 3 | 2-Me-Phenyl |
| 52 | 4 | 2-Me-Phenyl |
| 53 | 1 | 4-F-Phenyl |
| 54 | 2 | 4-F-Phenyl |
| 55 | 3 | 4-F-Phenyl |
| 56 | 4 | 4-F-Phenyl |
| 57 | 1 | 3-F-Phenyl |
| 58 | 2 | 3-F-Phenyl |
| 59 | 3 | 3-F-Phenyl |
| 60 | 4 | 3-F-Phenyl |
| 61 | 1 | 2-F-Phenyl |
| 62 | 2 | 2-F-Phenyl |
| 63 | 3 | 2-F-Phenyl |
| 64 | 4 | 2-F-Phenyl |
| 65 | 1 | 4-Cl-Phenyl |
| 66 | 2 | 4-Cl-Phenyl |
| 67 | 3 | 4-Cl-Phenyl |
| 68 | 4 | 4-Cl-Phenyl |
| 69 | 1 | 3-Cl-Phenyl |
| 70 | 2 | 3-Cl-Phenyl |
| 71 | 3 | 3-Cl-Phenyl |
| 72 | 4 | 3-Cl-Phenyl |
| 73 | 1 | 2-Cl-Phenyl |
| 74 | 2 | 2-Cl-Phenyl |
| 75 | 3 | 2-Cl-Phenyl |
| 76 | 4 | 2-Cl-Phenyl |
| 77 | 1 | 4-Br-Phenyl |
| 78 | 2 | 4-Br-Phenyl |
| 79 | 3 | 4-Br-Phenyl |
| 80 | 4 | 4-Br-Phenyl |
| 81 | 1 | 3-Br-Phenyl |
| 82 | 2 | 3-Br-Phenyl |
| 83 | 3 | 3-Br-Phenyl |
| 84 | 4 | 3-Br-Phenyl |
| 85 | 1 | naphthylen-1-yl |
| 86 | 2 | naphthylen-1-yl |
| 87 | 3 | naphthylen-1-yl |
| 88 | 4 | naphthylen-1-yl |
| 85 | 1 | 2-Br-Phenyl |
| 86 | 2 | 2-Br-Phenyl |
| 87 | 3 | 2-Br-Phenyl |
| 88 | 4 | 2-Br-Phenyl |

TABLE 5-continued

| Entry | n | $R^3$ |
|---|---|---|
| 89 | 1 | 4-$CF_3$-Phenyl |
| 90 | 2 | 4-$CF_3$-Phenyl |
| 91 | 3 | 4-$CF_3$-Phenyl |
| 92 | 4 | 4-$CF_3$-Phenyl |
| 93 | 1 | 3-$CF_3$-Phenyl |
| 94 | 2 | 3-$CF_3$-Phenyl |
| 95 | 3 | 3-$CF_3$-Phenyl |
| 96 | 4 | 3-$CF_3$-Phenyl |
| 97 | 1 | 2-$CF_3$-Phenyl |
| 98 | 2 | 2-$CF_3$-Phenyl |
| 99 | 3 | 2-$CF_3$-Phenyl |
| 100 | 4 | 2-$CF_3$-Phenyl |
| 101 | 1 | 4-iPr-Phenyl |
| 102 | 2 | 4-iPr-Phenyl |
| 103 | 3 | 4-iPr-Phenyl |
| 104 | 4 | 4-iPr-Phenyl |
| 105 | 1 | 3-iPr-Phenyl |
| 106 | 2 | 3-iPr-Phenyl |
| 107 | 3 | 3-iPr-Phenyl |
| 108 | 4 | 3-iPr-Phenyl |
| 109 | 1 | 2-iPr-Phenyl |
| 110 | 2 | 2-iPr-Phenyl |
| 111 | 3 | 2-iPr-Phenyl |
| 112 | 4 | 2-iPr-Phenyl |
| 113 | 1 | 4-$NH_2$-Phenyl |
| 114 | 2 | 4-$NH_2$-Phenyl |
| 115 | 3 | 4-$NH_2$-Phenyl |
| 116 | 4 | 4-$NH_2$-Phenyl |
| 117 | 1 | 3-$NH_2$-Phenyl |
| 118 | 2 | 3-$NH_2$-Phenyl |
| 119 | 3 | 3-$NH_2$-Phenyl |
| 120 | 4 | 3-$NH_2$-Phenyl |
| 121 | 1 | 2-$NH_2$-Phenyl |
| 122 | 2 | 2-$NH_2$-Phenyl |
| 123 | 3 | 2-$NH_2$-Phenyl |
| 124 | 4 | 2-$NH_2$-Phenyl |
| 125 | 1 | 2,3-di-Me-Phenyl |
| 126 | 2 | 2,3-di-Me-Phenyl |
| 127 | 3 | 2,3-di-Me-Phenyl |
| 128 | 4 | 2,3-di-Me-Phenyl |
| 129 | 1 | 2,4-di-Me-Phenyl |
| 130 | 2 | 2,4-di-Me-Phenyl |
| 131 | 3 | 2,4-di-Me-Phenyl |
| 132 | 4 | 2,4-di-Me-Phenyl |
| 133 | 1 | 2,5-di-Me-Phenyl |
| 134 | 2 | 2,5-di-Me-Phenyl |
| 135 | 3 | 2,5-di-Me-Phenyl |
| 136 | 4 | 2,5-di-Me-Phenyl |
| 137 | 1 | 2,6-di-Me-Phenyl |
| 138 | 2 | 2,6-di-Me-Phenyl |
| 139 | 3 | 2,6-di-Me-Phenyl |
| 140 | 4 | 2,6-di-Me-Phenyl |
| 141 | 1 | 2,6-di-iPr-Phenyl |
| 142 | 2 | 2,6-di-iPr-Phenyl |
| 143 | 3 | 2,6-di-iPr-Phenyl |
| 144 | 4 | 2,6-di-iPr-Phenyl |
| 145 | 1 | 2-morpholino-phenyl |
| 146 | 2 | 2-morpholino-phenyl |
| 147 | 3 | 2-morpholino-phenyl |
| 148 | 4 | 2-morpholino-phenyl |
| 149 | 1 | 3-morpholino-phenyl |
| 150 | 2 | 3-morpholino-phenyl |
| 151 | 3 | 3-morpholino-phenyl |
| 152 | 4 | 3-morpholino-phenyl |
| 153 | 1 | 4-morpholino-phenyl |
| 154 | 2 | 4-morpholino-phenyl |
| 155 | 3 | 4-morpholino-phenyl |
| 156 | 4 | 4-morpholino-phenyl |
| 157 | 1 | 4-CN-2-morpholino-phenyl |
| 158 | 2 | 4-CN-2-morpholino-phenyl |
| 159 | 3 | 4-CN-2-morpholino-phenyl |
| 160 | 4 | 4-CN-2-morpholino-phenyl |
| 161 | 1 | 4-$CH_3$-2-morpholino-phenyl |
| 162 | 2 | 4-$CH_3$-2-morpholino-phenyl |
| 163 | 3 | 4-$CH_3$-2-morpholino-phenyl |
| 164 | 4 | 4-$CH_3$-2-morpholino-phenyl |
| 165 | 1 | 4-OH-2-morpholino-phenyl |
| 166 | 2 | 4-OH-2-morpholino-phenyl |

TABLE 5-continued

| Entry | n | $R^3$ |
|---|---|---|
| 167 | 3 | 4-OH-2-morpholino-phenyl |
| 168 | 4 | 4-OH-2-morpholino-phenyl |
| 173 | 1 | naphthylen-2-yl |
| 174 | 2 | naphthylen-2-yl |
| 175 | 3 | naphthylen-2-yl |
| 176 | 4 | naphthylen-2-yl |

Exemplary embodiments include compounds having the formula (XII)

(XII)

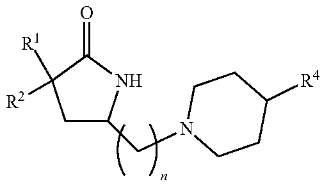

or a pharmaceutically acceptable salt form thereof defined herein below in Table 6.

TABLE 6

| Entry | $R^1$ | $R^2$ | n | $R^4$ |
|---|---|---|---|---|
| 1 | Methyl | Methyl | 1 | Phenyl |
| 2 | Methyl | Methyl | 2 | Phenyl |
| 3 | Methyl | Methyl | 3 | Phenyl |
| 4 | Methyl | Methyl | 4 | Phenyl |
| 5 | Methyl | Methyl | 1 | 4-OH-Phenyl |
| 6 | Methyl | Methyl | 2 | 4-OH-Phenyl |
| 7 | Methyl | Methyl | 3 | 4-OH-Phenyl |
| 8 | Methyl | Methyl | 4 | 4-OH-Phenyl |
| 9 | Methyl | Methyl | 1 | 3-OH-Phenyl |
| 10 | Methyl | Methyl | 2 | 3-OH-Phenyl |
| 11 | Methyl | Methyl | 3 | 3-OH-Phenyl |
| 12 | Methyl | Methyl | 4 | 3-OH-Phenyl |
| 13 | Methyl | Methyl | 1 | 2-OH-Phenyl |
| 14 | Methyl | Methyl | 2 | 2-OH-Phenyl |
| 15 | Methyl | Methyl | 3 | 2-OH-Phenyl |
| 16 | Methyl | Methyl | 4 | 2-OH-Phenyl |
| 17 | Methyl | Methyl | 1 | 4-OMe-Phenyl |
| 18 | Methyl | Methyl | 2 | 4-OMe-Phenyl |
| 19 | Methyl | Methyl | 3 | 4-OMe-Phenyl |
| 20 | Methyl | Methyl | 4 | 4-OMe-Phenyl |
| 21 | Methyl | Methyl | 1 | 3-OMe-Phenyl |
| 22 | Methyl | Methyl | 2 | 3-OMe-Phenyl |
| 23 | Methyl | Methyl | 3 | 3-OMe-Phenyl |
| 24 | Methyl | Methyl | 4 | 3-OMe-Phenyl |
| 25 | Methyl | Methyl | 1 | 2-OMe-Phenyl |
| 26 | Methyl | Methyl | 2 | 2-OMe-Phenyl |
| 27 | Methyl | Methyl | 3 | 2-OMe-Phenyl |
| 28 | Methyl | Methyl | 4 | 2-OMe-Phenyl |
| 29 | Methyl | Methyl | 1 | 4-CN-Phenyl |
| 30 | Methyl | Methyl | 2 | 4-CN-Phenyl |
| 31 | Methyl | Methyl | 3 | 4-CN-Phenyl |
| 32 | Methyl | Methyl | 4 | 4-CN-Phenyl |
| 33 | Methyl | Methyl | 1 | 3-CN-Phenyl |
| 34 | Methyl | Methyl | 2 | 3-CN-Phenyl |
| 35 | Methyl | Methyl | 3 | 3-CN-Phenyl |
| 36 | Methyl | Methyl | 4 | 3-CN-Phenyl |
| 37 | Methyl | Methyl | 1 | 2-CN-Phenyl |
| 38 | Methyl | Methyl | 2 | 2-CN-Phenyl |
| 39 | Methyl | Methyl | 3 | 2-CN-Phenyl |
| 40 | Methyl | Methyl | 4 | 2-CN-Phenyl |
| 41 | Methyl | Methyl | 1 | 4-Me-Phenyl |
| 42 | Methyl | Methyl | 2 | 4-Me-Phenyl |
| 43 | Methyl | Methyl | 3 | 4-Me-Phenyl |
| 44 | Methyl | Methyl | 4 | 4-Me-Phenyl |
| 45 | Methyl | Methyl | 1 | 3-Me-Phenyl |
| 46 | Methyl | Methyl | 2 | 3-Me-Phenyl |

TABLE 6-continued

| Entry | $R^1$ | $R^2$ | n | $R^4$ |
|---|---|---|---|---|
| 47 | Methyl | Methyl | 3 | 3-Me-Phenyl |
| 48 | Methyl | Methyl | 4 | 3-Me-Phenyl |
| 49 | Methyl | Methyl | 1 | 2-Me-Phenyl |
| 50 | Methyl | Methyl | 2 | 2-Me-Phenyl |
| 51 | Methyl | Methyl | 3 | 2-Me-Phenyl |
| 52 | Methyl | Methyl | 4 | 2-Me-Phenyl |
| 53 | Methyl | Methyl | 1 | 4-F-Phenyl |
| 54 | Methyl | Methyl | 2 | 4-F-Phenyl |
| 55 | Methyl | Methyl | 3 | 4-F-Phenyl |
| 56 | Methyl | Methyl | 4 | 4-F-Phenyl |
| 57 | Methyl | Methyl | 1 | 3-F-Phenyl |
| 58 | Methyl | Methyl | 2 | 3-F-Phenyl |
| 59 | Methyl | Methyl | 3 | 3-F-Phenyl |
| 60 | Methyl | Methyl | 4 | 3-F-Phenyl |
| 61 | Methyl | Methyl | 1 | 2-F-Phenyl |
| 62 | Methyl | Methyl | 2 | 2-F-Phenyl |
| 63 | Methyl | Methyl | 3 | 2-F-Phenyl |
| 64 | Methyl | Methyl | 4 | 2-F-Phenyl |
| 65 | Methyl | Methyl | 1 | 4-Cl-Phenyl |
| 66 | Methyl | Methyl | 2 | 4-Cl-Phenyl |
| 67 | Methyl | Methyl | 3 | 4-Cl-Phenyl |
| 68 | Methyl | Methyl | 4 | 4-Cl-Phenyl |
| 69 | Methyl | Methyl | 1 | 3-Cl-Phenyl |
| 70 | Methyl | Methyl | 2 | 3-Cl-Phenyl |
| 71 | Methyl | Methyl | 3 | 3-Cl-Phenyl |
| 72 | Methyl | Methyl | 4 | 3-Cl-Phenyl |
| 73 | Methyl | Methyl | 1 | 2-Cl-Phenyl |
| 74 | Methyl | Methyl | 2 | 2-Cl-Phenyl |
| 75 | Methyl | Methyl | 3 | 2-Cl-Phenyl |
| 76 | Methyl | Methyl | 4 | 2-Cl-Phenyl |
| 77 | Methyl | Methyl | 1 | 4-Br-Phenyl |
| 78 | Methyl | Methyl | 2 | 4-Br-Phenyl |
| 79 | Methyl | Methyl | 3 | 4-Br-Phenyl |
| 80 | Methyl | Methyl | 4 | 4-Br-Phenyl |
| 81 | Methyl | Methyl | 1 | 3-Br-Phenyl |
| 82 | Methyl | Methyl | 2 | 3-Br-Phenyl |
| 83 | Methyl | Methyl | 3 | 3-Br-Phenyl |
| 84 | Methyl | Methyl | 4 | 3-Br-Phenyl |
| 85 | Methyl | Methyl | 1 | 2-Br-Phenyl |
| 86 | Methyl | Methyl | 2 | 2-Br-Phenyl |
| 87 | Methyl | Methyl | 3 | 2-Br-Phenyl |
| 88 | Methyl | Methyl | 4 | 2-Br-Phenyl |
| 89 | Methyl | Methyl | 1 | 4-$CF_3$-Phenyl |
| 90 | Methyl | Methyl | 2 | 4-$CF_3$-Phenyl |
| 91 | Methyl | Methyl | 3 | 4-$CF_3$-Phenyl |
| 92 | Methyl | Methyl | 4 | 4-$CF_3$-Phenyl |
| 93 | Methyl | Methyl | 1 | 3-$CF_3$-Phenyl |
| 94 | Methyl | Methyl | 2 | 3-$CF_3$-Phenyl |
| 95 | Methyl | Methyl | 3 | 3-$CF_3$-Phenyl |
| 96 | Methyl | Methyl | 4 | 3-$CF_3$-Phenyl |
| 97 | Methyl | Methyl | 1 | 2-$CF_3$-Phenyl |
| 98 | Methyl | Methyl | 2 | 2-$CF_3$-Phenyl |
| 99 | Methyl | Methyl | 3 | 2-$CF_3$-Phenyl |
| 100 | Methyl | Methyl | 4 | 2-$CF_3$-Phenyl |
| 101 | Methyl | Methyl | 1 | 4-iPr-Phenyl |
| 102 | Methyl | Methyl | 2 | 4-iPr-Phenyl |
| 103 | Methyl | Methyl | 3 | 4-iPr-Phenyl |
| 104 | Methyl | Methyl | 4 | 4-iPr-Phenyl |
| 105 | Methyl | Methyl | 1 | 3-iPr-Phenyl |
| 106 | Methyl | Methyl | 2 | 3-iPr-Phenyl |
| 107 | Methyl | Methyl | 3 | 3-iPr-Phenyl |
| 108 | Methyl | Methyl | 4 | 3-iPr-Phenyl |
| 109 | Methyl | Methyl | 1 | 2-iPr-Phenyl |
| 110 | Methyl | Methyl | 2 | 2-iPr-Phenyl |
| 111 | Methyl | Methyl | 3 | 2-iPr-Phenyl |
| 112 | Methyl | Methyl | 4 | 2-iPr-Phenyl |
| 113 | Methyl | Methyl | 1 | 4-$NH_2$-Phenyl |
| 114 | Methyl | Methyl | 2 | 4-$NH_2$-Phenyl |
| 115 | Methyl | Methyl | 3 | 4-$NH_2$-Phenyl |
| 116 | Methyl | Methyl | 4 | 4-$NH_2$-Phenyl |
| 117 | Methyl | Methyl | 1 | 3-$NH_2$-Phenyl |
| 118 | Methyl | Methyl | 2 | 3-$NH_2$-Phenyl |
| 119 | Methyl | Methyl | 3 | 3-$NH_2$-Phenyl |
| 120 | Methyl | Methyl | 4 | 3-$NH_2$-Phenyl |
| 121 | Methyl | Methyl | 1 | 2-$NH_2$-Phenyl |
| 122 | Methyl | Methyl | 2 | 2-$NH_2$-Phenyl |
| 123 | Methyl | Methyl | 3 | 2-$NH_2$-Phenyl |
| 124 | Methyl | Methyl | 4 | 2-$NH_2$-Phenyl |

TABLE 6-continued

| Entry | $R^1$ | $R^2$ | n | $R^4$ |
|---|---|---|---|---|
| 125 | Methyl | Methyl | 1 | 2,3-di-Me-Phenyl |
| 126 | Methyl | Methyl | 2 | 2,3-di-Me-Phenyl |
| 127 | Methyl | Methyl | 3 | 2,3-di-Me-Phenyl |
| 128 | Methyl | Methyl | 4 | 2,3-di-Me-Phenyl |
| 129 | Methyl | Methyl | 1 | 2,4-di-Me-Phenyl |
| 130 | Methyl | Methyl | 2 | 2,4-di-Me-Phenyl |
| 131 | Methyl | Methyl | 3 | 2,4-di-Me-Phenyl |
| 132 | Methyl | Methyl | 4 | 2,4-di-Me-Phenyl |
| 133 | Methyl | Methyl | 1 | 2,5-di-Me-Phenyl |
| 134 | Methyl | Methyl | 2 | 2,5-di-Me-Phenyl |
| 135 | Methyl | Methyl | 3 | 2,5-di-Me-Phenyl |
| 136 | Methyl | Methyl | 4 | 2,5-di-Me-Phenyl |
| 137 | Methyl | Methyl | 1 | 2,6-di-Me-Phenyl |
| 138 | Methyl | Methyl | 2 | 2,6-di-Me-Phenyl |
| 139 | Methyl | Methyl | 3 | 2,6-di-Me-Phenyl |
| 140 | Methyl | Methyl | 4 | 2,6-di-Me-Phenyl |
| 141 | Methyl | Methyl | 1 | 2,6-di-iPr-Phenyl |
| 142 | Methyl | Methyl | 2 | 2,6-di-iPr-Phenyl |
| 143 | Methyl | Methyl | 3 | 2,6-di-iPr-Phenyl |
| 144 | Methyl | Methyl | 4 | 2,6-di-iPr-Phenyl |
| 145 | Methyl | Methyl | 1 | 2-morpholino-phenyl |
| 146 | Methyl | Methyl | 2 | 2-morpholino-phenyl |
| 147 | Methyl | Methyl | 3 | 2-morpholino-phenyl |
| 148 | Methyl | Methyl | 4 | 2-morpholino-phenyl |
| 149 | Methyl | Methyl | 1 | 3-morpholino-phenyl |
| 150 | Methyl | Methyl | 2 | 3-morpholino-phenyl |
| 151 | Methyl | Methyl | 3 | 3-morpholino-phenyl |
| 152 | Methyl | Methyl | 4 | 3-morpholino-phenyl |
| 153 | Methyl | Methyl | 1 | 4-morpholino-phenyl |
| 154 | Methyl | Methyl | 2 | 4-morpholino-phenyl |
| 155 | Methyl | Methyl | 3 | 4-morpholino-phenyl |
| 156 | Methyl | Methyl | 4 | 4-morpholino-phenyl |
| 157 | Methyl | Methyl | 1 | 4-CN-2-morpholino-phenyl |
| 158 | Methyl | Methyl | 2 | 4-CN-2-morpholino-phenyl |
| 159 | Methyl | Methyl | 3 | 4-CN-2-morpholino-phenyl |
| 160 | Methyl | Methyl | 4 | 4-CN-2-morpholino-phenyl |
| 161 | Methyl | Methyl | 1 | 4-$CH_3$-2-morpholino-phenyl |
| 162 | Methyl | Methyl | 2 | 4-$CH_3$-2-morpholino-phenyl |
| 163 | Methyl | Methyl | 3 | 4-$CH_3$-2-morpholino-phenyl |
| 164 | Methyl | Methyl | 4 | 4-$CH_3$-2-morpholino-phenyl |
| 165 | Methyl | Methyl | 1 | 4-OH-2-morpholino-phenyl |
| 166 | Methyl | Methyl | 2 | 4-OH-2-morpholino-phenyl |
| 167 | Methyl | Methyl | 3 | 4-OH-2-morpholino-phenyl |
| 168 | Methyl | Methyl | 4 | 4-OH-2-morpholino-phenyl |
| 169 | Methyl | Methyl | 1 | naphthylen-1-yl |
| 170 | Methyl | Methyl | 2 | naphthylen-1-yl |
| 171 | Methyl | Methyl | 3 | naphthylen-1-yl |
| 172 | Methyl | Methyl | 4 | naphthylen-1-yl |
| 173 | Methyl | Methyl | 1 | naphthylen-2-yl |
| 174 | Methyl | Methyl | 2 | naphthylen-2-yl |
| 175 | Methyl | Methyl | 3 | naphthylen-2-yl |
| 176 | Methyl | Methyl | 4 | naphthylen-2-yl |
| 177 | Ethyl | Ethyl | 1 | Phenyl |
| 178 | Ethyl | Ethyl | 2 | Phenyl |
| 179 | Ethyl | Ethyl | 3 | Phenyl |
| 180 | Ethyl | Ethyl | 4 | Phenyl |
| 181 | Ethyl | Ethyl | 1 | 4-OH-Phenyl |
| 182 | Ethyl | Ethyl | 2 | 4-OH-Phenyl |
| 183 | Ethyl | Ethyl | 3 | 4-OH-Phenyl |
| 184 | Ethyl | Ethyl | 4 | 4-OH-Phenyl |
| 185 | Ethyl | Ethyl | 1 | 3-OH-Phenyl |
| 186 | Ethyl | Ethyl | 2 | 3-OH-Phenyl |
| 187 | Ethyl | Ethyl | 3 | 3-OH-Phenyl |
| 188 | Ethyl | Ethyl | 4 | 3-OH-Phenyl |
| 189 | Ethyl | Ethyl | 1 | 2-OH-Phenyl |
| 190 | Ethyl | Ethyl | 2 | 2-OH-Phenyl |
| 191 | Ethyl | Ethyl | 3 | 2-OH-Phenyl |
| 192 | Ethyl | Ethyl | 4 | 2-OH-Phenyl |
| 193 | Ethyl | Ethyl | 1 | 4-OMe-Phenyl |
| 194 | Ethyl | Ethyl | 2 | 4-OMe-Phenyl |
| 195 | Ethyl | Ethyl | 3 | 4-OMe-Phenyl |
| 196 | Ethyl | Ethyl | 4 | 4-OMe-Phenyl |
| 197 | Ethyl | Ethyl | 1 | 3-OMe-Phenyl |
| 198 | Ethyl | Ethyl | 2 | 3-OMe-Phenyl |
| 199 | Ethyl | Ethyl | 3 | 3-OMe-Phenyl |
| 200 | Ethyl | Ethyl | 4 | 3-OMe-Phenyl |
| 201 | Ethyl | Ethyl | 1 | 2-OMe-Phenyl |
| 202 | Ethyl | Ethyl | 2 | 2-OMe-Phenyl |

TABLE 6-continued

| Entry | $R^1$ | $R^2$ | n | $R^4$ |
|---|---|---|---|---|
| 203 | Ethyl | Ethyl | 3 | 2-OMe-Phenyl |
| 204 | Ethyl | Ethyl | 4 | 2-OMe-Phenyl |
| 205 | Ethyl | Ethyl | 1 | 4-CN-Phenyl |
| 206 | Ethyl | Ethyl | 2 | 4-CN-Phenyl |
| 207 | Ethyl | Ethyl | 3 | 4-CN-Phenyl |
| 208 | Ethyl | Ethyl | 4 | 4-CN-Phenyl |
| 209 | Ethyl | Ethyl | 1 | 3-CN-Phenyl |
| 210 | Ethyl | Ethyl | 2 | 3-CN-Phenyl |
| 211 | Ethyl | Ethyl | 3 | 3-CN-Phenyl |
| 212 | Ethyl | Ethyl | 4 | 3-CN-Phenyl |
| 213 | Ethyl | Ethyl | 1 | 2-CN-Phenyl |
| 214 | Ethyl | Ethyl | 2 | 2-CN-Phenyl |
| 215 | Ethyl | Ethyl | 3 | 2-CN-Phenyl |
| 216 | Ethyl | Ethyl | 4 | 2-CN-Phenyl |
| 217 | Ethyl | Ethyl | 1 | 4-Me-Phenyl |
| 218 | Ethyl | Ethyl | 2 | 4-Me-Phenyl |
| 219 | Ethyl | Ethyl | 3 | 4-Me-Phenyl |
| 220 | Ethyl | Ethyl | 4 | 4-Me-Phenyl |
| 221 | Ethyl | Ethyl | 1 | 3-Me-Phenyl |
| 222 | Ethyl | Ethyl | 2 | 3-Me-Phenyl |
| 223 | Ethyl | Ethyl | 3 | 3-Me-Phenyl |
| 224 | Ethyl | Ethyl | 4 | 3-Me-Phenyl |
| 225 | Ethyl | Ethyl | 1 | 2-Me-Phenyl |
| 226 | Ethyl | Ethyl | 2 | 2-Me-Phenyl |
| 227 | Ethyl | Ethyl | 3 | 2-Me-Phenyl |
| 228 | Ethyl | Ethyl | 4 | 2-Me-Phenyl |
| 229 | Ethyl | Ethyl | 1 | 4-F-Phenyl |
| 230 | Ethyl | Ethyl | 2 | 4-F-Phenyl |
| 231 | Ethyl | Ethyl | 3 | 4-F-Phenyl |
| 232 | Ethyl | Ethyl | 4 | 4-F-Phenyl |
| 233 | Ethyl | Ethyl | 1 | 3-F-Phenyl |
| 234 | Ethyl | Ethyl | 2 | 3-F-Phenyl |
| 235 | Ethyl | Ethyl | 3 | 3-F-Phenyl |
| 236 | Ethyl | Ethyl | 4 | 3-F-Phenyl |
| 237 | Ethyl | Ethyl | 1 | 2-F-Phenyl |
| 238 | Ethyl | Ethyl | 2 | 2-F-Phenyl |
| 239 | Ethyl | Ethyl | 3 | 2-F-Phenyl |
| 240 | Ethyl | Ethyl | 4 | 2-F-Phenyl |
| 241 | Ethyl | Ethyl | 1 | 4-Cl-Phenyl |
| 242 | Ethyl | Ethyl | 2 | 4-Cl-Phenyl |
| 243 | Ethyl | Ethyl | 3 | 4-Cl-Phenyl |
| 244 | Ethyl | Ethyl | 4 | 4-Cl-Phenyl |
| 245 | Ethyl | Ethyl | 1 | 3-Cl-Phenyl |
| 246 | Ethyl | Ethyl | 2 | 3-Cl-Phenyl |
| 247 | Ethyl | Ethyl | 3 | 3-Cl-Phenyl |
| 248 | Ethyl | Ethyl | 4 | 3-Cl-Phenyl |
| 249 | Ethyl | Ethyl | 1 | 2-Cl-Phenyl |
| 250 | Ethyl | Ethyl | 2 | 2-Cl-Phenyl |
| 251 | Ethyl | Ethyl | 3 | 2-Cl-Phenyl |
| 252 | Ethyl | Ethyl | 4 | 2-Cl-Phenyl |
| 253 | Ethyl | Ethyl | 1 | 4-Br-Phenyl |
| 254 | Ethyl | Ethyl | 2 | 4-Br-Phenyl |
| 255 | Ethyl | Ethyl | 3 | 4-Br-Phenyl |
| 256 | Ethyl | Ethyl | 4 | 4-Br-Phenyl |
| 257 | Ethyl | Ethyl | 1 | 3-Br-Phenyl |
| 258 | Ethyl | Ethyl | 2 | 3-Br-Phenyl |
| 259 | Ethyl | Ethyl | 3 | 3-Br-Phenyl |
| 260 | Ethyl | Ethyl | 4 | 3-Br-Phenyl |
| 261 | Ethyl | Ethyl | 1 | 2-Br-Phenyl |
| 262 | Ethyl | Ethyl | 2 | 2-Br-Phenyl |
| 263 | Ethyl | Ethyl | 3 | 2-Br-Phenyl |
| 264 | Ethyl | Ethyl | 4 | 2-Br-Phenyl |
| 265 | Ethyl | Ethyl | 1 | 4-$CF_3$-Phenyl |
| 266 | Ethyl | Ethyl | 2 | 4-$CF_3$-Phenyl |
| 267 | Ethyl | Ethyl | 3 | 4-$CF_3$-Phenyl |
| 268 | Ethyl | Ethyl | 4 | 4-$CF_3$-Phenyl |
| 269 | Ethyl | Ethyl | 1 | 3-$CF_3$-Phenyl |
| 270 | Ethyl | Ethyl | 2 | 3-$CF_3$-Phenyl |
| 271 | Ethyl | Ethyl | 3 | 3-$CF_3$-Phenyl |
| 272 | Ethyl | Ethyl | 4 | 3-$CF_3$-Phenyl |
| 273 | Ethyl | Ethyl | 1 | 2-$CF_3$-Phenyl |
| 274 | Ethyl | Ethyl | 2 | 2-$CF_3$-Phenyl |
| 275 | Ethyl | Ethyl | 3 | 2-$CF_3$-Phenyl |
| 276 | Ethyl | Ethyl | 4 | 2-$CF_3$-Phenyl |
| 277 | Ethyl | Ethyl | 1 | 4-iPr-Phenyl |
| 278 | Ethyl | Ethyl | 2 | 4-iPr-Phenyl |
| 279 | Ethyl | Ethyl | 3 | 4-iPr-Phenyl |
| 280 | Ethyl | Ethyl | 4 | 4-iPr-Phenyl |

TABLE 6-continued

| Entry | $R^1$ | $R^2$ | n | $R^4$ |
|---|---|---|---|---|
| 281 | Ethyl | Ethyl | 1 | 3-iPr-Phenyl |
| 282 | Ethyl | Ethyl | 2 | 3-iPr-Phenyl |
| 283 | Ethyl | Ethyl | 3 | 3-iPr-Phenyl |
| 284 | Ethyl | Ethyl | 4 | 3-iPr-Phenyl |
| 285 | Ethyl | Ethyl | 1 | 2-iPr-Phenyl |
| 286 | Ethyl | Ethyl | 2 | 2-iPr-Phenyl |
| 287 | Ethyl | Ethyl | 3 | 2-iPr-Phenyl |
| 288 | Ethyl | Ethyl | 4 | 2-iPr-Phenyl |
| 289 | Ethyl | Ethyl | 1 | 4-$NH_2$-Phenyl |
| 290 | Ethyl | Ethyl | 2 | 4-$NH_2$-Phenyl |
| 291 | Ethyl | Ethyl | 3 | 4-$NH_2$-Phenyl |
| 292 | Ethyl | Ethyl | 4 | 4-$NH_2$-Phenyl |
| 293 | Ethyl | Ethyl | 1 | 3-$NH_2$-Phenyl |
| 294 | Ethyl | Ethyl | 2 | 3-$NH_2$-Phenyl |
| 295 | Ethyl | Ethyl | 3 | 3-$NH_2$-Phenyl |
| 296 | Ethyl | Ethyl | 4 | 3-$NH_2$-Phenyl |
| 297 | Ethyl | Ethyl | 1 | 2-$NH_2$-Phenyl |
| 298 | Ethyl | Ethyl | 2 | 2-$NH_2$-Phenyl |
| 299 | Ethyl | Ethyl | 3 | 2-$NH_2$-Phenyl |
| 300 | Ethyl | Ethyl | 4 | 2-$NH_2$-Phenyl |
| 301 | Ethyl | Ethyl | 1 | 2,3-di-Me-Phenyl |
| 302 | Ethyl | Ethyl | 2 | 2,3-di-Me-Phenyl |
| 303 | Ethyl | Ethyl | 3 | 2,3-di-Me-Phenyl |
| 304 | Ethyl | Ethyl | 4 | 2,3-di-Me-Phenyl |
| 305 | Ethyl | Ethyl | 1 | 2,4-di-Me-Phenyl |
| 306 | Ethyl | Ethyl | 2 | 2,4-di-Me-Phenyl |
| 307 | Ethyl | Ethyl | 3 | 2,4-di-Me-Phenyl |
| 308 | Ethyl | Ethyl | 4 | 2,4-di-Me-Phenyl |
| 309 | Ethyl | Ethyl | 1 | 2,5-di-Me-Phenyl |
| 310 | Ethyl | Ethyl | 2 | 2,5-di-Me-Phenyl |
| 311 | Ethyl | Ethyl | 3 | 2,5-di-Me-Phenyl |
| 312 | Ethyl | Ethyl | 4 | 2,5-di-Me-Phenyl |
| 313 | Ethyl | Ethyl | 1 | 2,6-di-Me-Phenyl |
| 314 | Ethyl | Ethyl | 2 | 2,6-di-Me-Phenyl |
| 315 | Ethyl | Ethyl | 3 | 2,6-di-Me-Phenyl |
| 316 | Ethyl | Ethyl | 4 | 2,6-di-Me-Phenyl |
| 317 | Ethyl | Ethyl | 1 | 2,6-di-iPr-Phenyl |
| 318 | Ethyl | Ethyl | 2 | 2,6-di-iPr-Phenyl |
| 319 | Ethyl | Ethyl | 3 | 2,6-di-iPr-Phenyl |
| 320 | Ethyl | Ethyl | 4 | 2,6-di-iPr-Phenyl |
| 321 | Ethyl | Ethyl | 1 | 2-morpholino-phenyl |
| 322 | Ethyl | Ethyl | 2 | 2-morpholino-phenyl |
| 323 | Ethyl | Ethyl | 3 | 2-morpholino-phenyl |
| 324 | Ethyl | Ethyl | 4 | 2-morpholino-phenyl |
| 325 | Ethyl | Ethyl | 1 | 3-morpholino-phenyl |
| 326 | Ethyl | Ethyl | 2 | 3-morpholino-phenyl |
| 327 | Ethyl | Ethyl | 3 | 3-morpholino-phenyl |
| 328 | Ethyl | Ethyl | 4 | 3-morpholino-phenyl |
| 329 | Ethyl | Ethyl | 1 | 4-morpholino-phenyl |
| 330 | Ethyl | Ethyl | 2 | 4-morpholino-phenyl |
| 331 | Ethyl | Ethyl | 3 | 4-morpholino-phenyl |
| 332 | Ethyl | Ethyl | 4 | 4-morpholino-phenyl |
| 333 | Ethyl | Ethyl | 1 | 4-CN-2-morpholino-phenyl |
| 334 | Ethyl | Ethyl | 2 | 4-CN-2-morpholino-phenyl |
| 335 | Ethyl | Ethyl | 3 | 4-CN-2-morpholino-phenyl |
| 336 | Ethyl | Ethyl | 4 | 4-CN-2-morpholino-phenyl |
| 337 | Ethyl | Ethyl | 1 | 4-$CH_3$-2-morpholino-phenyl |
| 338 | Ethyl | Ethyl | 2 | 4-$CH_3$-2-morpholino-phenyl |
| 339 | Ethyl | Ethyl | 3 | 4-$CH_3$-2-morpholino-phenyl |
| 340 | Ethyl | Ethyl | 4 | 4-$CH_3$-2-morpholino-phenyl |
| 341 | Ethyl | Ethyl | 1 | 4-OH-2-morpholino-phenyl |
| 342 | Ethyl | Ethyl | 2 | 4-OH-2-morpholino-phenyl |
| 343 | Ethyl | Ethyl | 3 | 4-OH-2-morpholino-phenyl |
| 344 | Ethyl | Ethyl | 4 | 4-OH-2-morpholino-phenyl |
| 345 | Ethyl | Ethyl | 1 | naphthylen-1-yl |
| 346 | Ethyl | Ethyl | 2 | naphthylen-1-yl |
| 347 | Ethyl | Ethyl | 3 | naphthylen-1-yl |
| 348 | Ethyl | Ethyl | 4 | naphthylen-2-yl |
| 349 | Ethyl | Ethyl | 1 | naphthylen-2-yl |
| 350 | Ethyl | Ethyl | 2 | naphthylen-2-yl |
| 351 | Ethyl | Ethyl | 3 | naphthylen-2-yl |
| 352 | Ethyl | Ethyl | 4 | naphthylen-2-yl |

Exemplary embodiments include compounds having the formula (XIII)

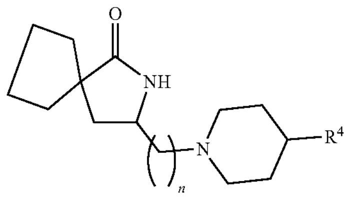

(XIII)

or a pharmaceutically acceptable salt form thereof defined herein below in Table 7

TABLE 7

| Entry | n | $R^4$ |
|---|---|---|
| 1 | 1 | Phenyl |
| 2 | 2 | Phenyl |
| 3 | 3 | Phenyl |
| 4 | 4 | Phenyl |
| 5 | 1 | 4-OH-Phenyl |
| 6 | 2 | 4-OH-Phenyl |
| 7 | 3 | 4-OH-Phenyl |
| 8 | 4 | 4-OH-Phenyl |
| 9 | 1 | 3-OH-Phenyl |
| 10 | 2 | 3-OH-Phenyl |
| 11 | 3 | 3-OH-Phenyl |
| 12 | 4 | 3-OH-Phenyl |
| 13 | 1 | 2-OH-Phenyl |
| 14 | 2 | 2-OH-Phenyl |
| 15 | 3 | 2-OH-Phenyl |
| 16 | 4 | 2-OH-Phenyl |
| 17 | 1 | 4-OMe-Phenyl |
| 18 | 2 | 4-OMe-Phenyl |
| 19 | 3 | 4-OMe-Phenyl |
| 20 | 4 | 4-OMe-Phenyl |
| 21 | 1 | 3-OMe-Phenyl |
| 22 | 2 | 3-OMe-Phenyl |
| 23 | 3 | 3-OMe-Phenyl |
| 24 | 4 | 3-OMe-Phenyl |
| 25 | 1 | 2-OMe-Phenyl |
| 26 | 2 | 2-OMe-Phenyl |
| 27 | 3 | 2-OMe-Phenyl |
| 28 | 4 | 2-OMe-Phenyl |
| 29 | 1 | 4-CN-Phenyl |
| 30 | 2 | 4-CN-Phenyl |
| 31 | 3 | 4-CN-Phenyl |
| 32 | 4 | 4-CN-Phenyl |
| 33 | 1 | 3-CN-Phenyl |
| 34 | 2 | 3-CN-Phenyl |
| 35 | 3 | 3-CN-Phenyl |
| 36 | 4 | 3-CN-Phenyl |
| 37 | 1 | 2-CN-Phenyl |
| 38 | 2 | 2-CN-Phenyl |
| 39 | 3 | 2-CN-Phenyl |
| 40 | 4 | 2-CN-Phenyl |
| 41 | 1 | 4-Me-Phenyl |
| 42 | 2 | 4-Me-Phenyl |
| 43 | 3 | 4-Me-Phenyl |
| 44 | 4 | 4-Me-Phenyl |
| 45 | 1 | 3-Me-Phenyl |
| 46 | 2 | 3-Me-Phenyl |
| 47 | 3 | 3-Me-Phenyl |
| 48 | 4 | 3-Me-Phenyl |
| 49 | 1 | 2-Me-Phenyl |
| 50 | 2 | 2-Me-Phenyl |
| 51 | 3 | 2-Me-Phenyl |
| 52 | 4 | 2-Me-Phenyl |
| 53 | 1 | 4-F-Phenyl |
| 54 | 2 | 4-F-Phenyl |
| 55 | 3 | 4-F-Phenyl |
| 56 | 4 | 4-F-Phenyl |
| 57 | 1 | 3-F-Phenyl |
| 58 | 2 | 3-F-Phenyl |
| 59 | 3 | 3-F-Phenyl |
| 60 | 4 | 3-F-Phenyl |
| 61 | 1 | 2-F-Phenyl |

TABLE 7-continued

| Entry | n | $R^4$ |
|---|---|---|
| 62 | 2 | 2-F-Phenyl |
| 63 | 3 | 2-F-Phenyl |
| 64 | 4 | 2-F-Phenyl |
| 65 | 1 | 4-Cl-Phenyl |
| 66 | 2 | 4-Cl-Phenyl |
| 67 | 3 | 4-Cl-Phenyl |
| 68 | 4 | 4-Cl-Phenyl |
| 69 | 1 | 3-Cl-Phenyl |
| 70 | 2 | 3-Cl-Phenyl |
| 71 | 3 | 3-Cl-Phenyl |
| 72 | 4 | 3-Cl-Phenyl |
| 73 | 1 | 2-Cl-Phenyl |
| 74 | 2 | 2-Cl-Phenyl |
| 75 | 3 | 2-Cl-Phenyl |
| 76 | 4 | 2-Cl-Phenyl |
| 77 | 1 | 4-Br-Phenyl |
| 78 | 2 | 4-Br-Phenyl |
| 79 | 3 | 4-Br-Phenyl |
| 80 | 4 | 4-Br-Phenyl |
| 81 | 1 | 3-Br-Phenyl |
| 82 | 2 | 3-Br-Phenyl |
| 83 | 3 | 3-Br-Phenyl |
| 84 | 4 | 3-Br-Phenyl |
| 85 | 1 | naphthylen-1-yl |
| 86 | 2 | naphthylen-1-yl |
| 87 | 3 | naphthylen-1-yl |
| 88 | 4 | naphthylen-1-yl |
| 85 | 1 | 2-Br-Phenyl |
| 86 | 2 | 2-Br-Phenyl |
| 87 | 3 | 2-Br-Phenyl |
| 88 | 4 | 2-Br-Phenyl |
| 89 | 1 | 4-$CF_3$-Phenyl |
| 90 | 2 | 4-$CF_3$-Phenyl |
| 91 | 3 | 4-$CF_3$-Phenyl |
| 92 | 4 | 4-$CF_3$-Phenyl |
| 93 | 1 | 3-$CF_3$-Phenyl |
| 94 | 2 | 3-$CF_3$-Phenyl |
| 95 | 3 | 3-$CF_3$-Phenyl |
| 96 | 4 | 3-$CF_3$-Phenyl |
| 97 | 1 | 2-$CF_3$-Phenyl |
| 98 | 2 | 2-$CF_3$-Phenyl |
| 99 | 3 | 2-$CF_3$-Phenyl |
| 100 | 4 | 2-$CF_3$-Phenyl |
| 101 | 1 | 4-iPr-Phenyl |
| 102 | 2 | 4-iPr-Phenyl |
| 103 | 3 | 4-iPr-Phenyl |
| 104 | 4 | 4-iPr-Phenyl |
| 105 | 1 | 3-iPr-Phenyl |
| 106 | 2 | 3-iPr-Phenyl |
| 107 | 3 | 3-iPr-Phenyl |
| 108 | 4 | 3-iPr-Phenyl |
| 109 | 1 | 2-iPr-Phenyl |
| 110 | 2 | 2-iPr-Phenyl |
| 111 | 3 | 2-iPr-Phenyl |
| 112 | 4 | 2-iPr-Phenyl |
| 113 | 1 | 4-$NH_2$-Phenyl |
| 114 | 2 | 4-$NH_2$-Phenyl |
| 115 | 3 | 4-$NH_2$-Phenyl |
| 116 | 4 | 4-$NH_2$-Phenyl |
| 117 | 1 | 3-$NH_2$-Phenyl |
| 118 | 2 | 3-$NH_2$-Phenyl |
| 119 | 3 | 3-$NH_2$-Phenyl |
| 120 | 4 | 3-$NH_2$-Phenyl |
| 121 | 1 | 2-$NH_2$-Phenyl |
| 122 | 2 | 2-$NH_2$-Phenyl |
| 123 | 3 | 2-$NH_2$-Phenyl |
| 124 | 4 | 2-$NH_2$-Phenyl |
| 125 | 1 | 2,3-di-Me-Phenyl |
| 126 | 2 | 2,3-di-Me-Phenyl |
| 127 | 3 | 2,3-di-Me-Phenyl |
| 128 | 4 | 2,3-di-Me-Phenyl |
| 129 | 1 | 2,4-di-Me-Phenyl |
| 130 | 2 | 2,4-di-Me-Phenyl |
| 131 | 3 | 2,4-di-Me-Phenyl |
| 132 | 4 | 2,4-di-Me-Phenyl |
| 133 | 1 | 2,5-di-Me-Phenyl |
| 134 | 2 | 2,5-di-Me-Phenyl |
| 135 | 3 | 2,5-di-Me-Phenyl |
| 136 | 4 | 2,5-di-Me-Phenyl |
| 137 | 1 | 2,6-di-Me-Phenyl |
| 138 | 2 | 2,6-di-Me-Phenyl |
| 139 | 3 | 2,6-di-Me-Phenyl |
| 140 | 4 | 2,6-di-Me-Phenyl |
| 141 | 1 | 2,6-di-iPr-Phenyl |
| 142 | 2 | 2,6-di-iPr-Phenyl |
| 143 | 3 | 2,6-di-iPr-Phenyl |
| 144 | 4 | 2,6-di-iPr-Phenyl |
| 145 | 1 | 2-morpholino-phenyl |
| 146 | 2 | 2-morpholino-phenyl |
| 147 | 3 | 2-morpholino-phenyl |
| 148 | 4 | 2-morpholino-phenyl |
| 149 | 1 | 3-morpholino-phenyl |
| 150 | 2 | 3-morpholino-phenyl |
| 151 | 3 | 3-morpholino-phenyl |
| 152 | 4 | 3-morpholino-phenyl |
| 153 | 1 | 4-morpholino-phenyl |
| 154 | 2 | 4-morpholino-phenyl |
| 155 | 3 | 4-morpholino-phenyl |
| 156 | 4 | 4-morpholino-phenyl |
| 157 | 1 | 4-CN-2-morpholino-phenyl |
| 158 | 2 | 4-CN-2-morpholino-phenyl |
| 159 | 3 | 4-CN-2-morpholino-phenyl |
| 160 | 4 | 4-CN-2-morpholino-phenyl |
| 161 | 1 | 4-$CH_3$-2-morpholino-phenyl |
| 162 | 2 | 4-$CH_3$-2-morpholino-phenyl |
| 163 | 3 | 4-$CH_3$-2-morpholino-phenyl |
| 164 | 4 | 4-$CH_3$-2-morpholino-phenyl |
| 165 | 1 | 4-OH-2-morpholino-phenyl |
| 166 | 2 | 4-OH-2-morpholino-phenyl |
| 167 | 3 | 4-OH-2-morpholino-phenyl |
| 168 | 4 | 4-OH-2-morpholino-phenyl |
| 173 | 1 | naphthylen-2-yl |
| 174 | 2 | naphthylen-2-yl |
| 175 | 3 | naphthylen-2-yl |
| 176 | 4 | naphthylen-2-yl |

Exemplary embodiments include compounds having the formula (XIV)

(XIV)

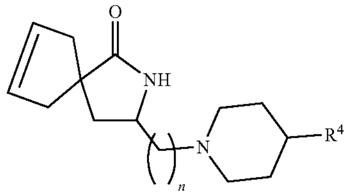

or a pharmaceutically acceptable salt form thereof defined herein below in Table 8.

TABLE 8

| Entry | n | $R^4$ |
|---|---|---|
| 1 | 1 | Phenyl |
| 2 | 2 | Phenyl |
| 3 | 3 | Phenyl |
| 4 | 4 | Phenyl |
| 5 | 1 | 4-OH-Phenyl |
| 6 | 2 | 4-OH-Phenyl |
| 7 | 3 | 4-OH-Phenyl |
| 8 | 4 | 4-OH-Phenyl |
| 9 | 1 | 3-OH-Phenyl |
| 10 | 2 | 3-OH-Phenyl |
| 11 | 3 | 3-OH-Phenyl |
| 12 | 4 | 3-OH-Phenyl |
| 13 | 1 | 2-OH-Phenyl |
| 14 | 2 | 2-OH-Phenyl |

TABLE 8-continued

| Entry | n | $R^4$ |
|---|---|---|
| 15 | 3 | 2-OH-Phenyl |
| 16 | 4 | 2-OH-Phenyl |
| 17 | 1 | 4-OMe-Phenyl |
| 18 | 2 | 4-OMe-Phenyl |
| 19 | 3 | 4-OMe-Phenyl |
| 20 | 4 | 4-OMe-Phenyl |
| 21 | 1 | 3-OMe-Phenyl |
| 22 | 2 | 3-OMe-Phenyl |
| 23 | 3 | 3-OMe-Phenyl |
| 24 | 4 | 3-OMe-Phenyl |
| 25 | 1 | 2-OMe-Phenyl |
| 26 | 2 | 2-OMe-Phenyl |
| 27 | 3 | 2-OMe-Phenyl |
| 28 | 4 | 2-OMe-Phenyl |
| 29 | 1 | 4-CN-Phenyl |
| 30 | 2 | 4-CN-Phenyl |
| 31 | 3 | 4-CN-Phenyl |
| 32 | 4 | 4-CN-Phenyl |
| 33 | 1 | 3-CN-Phenyl |
| 34 | 2 | 3-CN-Phenyl |
| 35 | 3 | 3-CN-Phenyl |
| 36 | 4 | 3-CN-Phenyl |
| 37 | 1 | 2-CN-Phenyl |
| 38 | 2 | 2-CN-Phenyl |
| 39 | 3 | 2-CN-Phenyl |
| 40 | 4 | 2-CN-Phenyl |
| 41 | 1 | 4-Me-Phenyl |
| 42 | 2 | 4-Me-Phenyl |
| 43 | 3 | 4-Me-Phenyl |
| 44 | 4 | 4-Me-Phenyl |
| 45 | 1 | 3-Me-Phenyl |
| 46 | 2 | 3-Me-Phenyl |
| 47 | 3 | 3-Me-Phenyl |
| 48 | 4 | 3-Me-Phenyl |
| 49 | 1 | 2-Me-Phenyl |
| 50 | 2 | 2-Me-Phenyl |
| 51 | 3 | 2-Me-Phenyl |
| 52 | 4 | 2-Me-Phenyl |
| 53 | 1 | 4-F-Phenyl |
| 54 | 2 | 4-F-Phenyl |
| 55 | 3 | 4-F-Phenyl |
| 56 | 4 | 4-F-Phenyl |
| 57 | 1 | 3-F-Phenyl |
| 58 | 2 | 3-F-Phenyl |
| 59 | 3 | 3-F-Phenyl |
| 60 | 4 | 3-F-Phenyl |
| 61 | 1 | 2-F-Phenyl |
| 62 | 2 | 2-F-Phenyl |
| 63 | 3 | 2-F-Phenyl |
| 64 | 4 | 2-F-Phenyl |
| 65 | 1 | 4-Cl-Phenyl |
| 66 | 2 | 4-Cl-Phenyl |
| 67 | 3 | 4-Cl-Phenyl |
| 68 | 4 | 4-Cl-Phenyl |
| 69 | 1 | 3-Cl-Phenyl |
| 70 | 2 | 3-Cl-Phenyl |
| 71 | 3 | 3-Cl-Phenyl |
| 72 | 4 | 3-Cl-Phenyl |
| 73 | 1 | 2-Cl-Phenyl |
| 74 | 2 | 2-Cl-Phenyl |
| 75 | 3 | 2-Cl-Phenyl |
| 76 | 4 | 2-Cl-Phenyl |
| 77 | 1 | 4-Br-Phenyl |
| 78 | 2 | 4-Br-Phenyl |
| 79 | 3 | 4-Br-Phenyl |
| 80 | 4 | 4-Br-Phenyl |
| 81 | 1 | 3-Br-Phenyl |
| 82 | 2 | 3-Br-Phenyl |
| 83 | 3 | 3-Br-Phenyl |
| 84 | 4 | 3-Br-Phenyl |
| 85 | 1 | naphthylen-1-yl |
| 86 | 2 | naphthylen-1-yl |
| 87 | 3 | naphthylen-1-yl |
| 88 | 4 | naphthylen-1-yl |
| 85 | 1 | 2-Br-Phenyl |
| 86 | 2 | 2-Br-Phenyl |
| 87 | 3 | 2-Br-Phenyl |
| 88 | 4 | 2-Br-Phenyl |

TABLE 8-continued

| Entry | n | $R^4$ |
|---|---|---|
| 89 | 1 | 4-$CF_3$-Phenyl |
| 90 | 2 | 4-$CF_3$-Phenyl |
| 91 | 3 | 4-$CF_3$-Phenyl |
| 92 | 4 | 4-$CF_3$-Phenyl |
| 93 | 1 | 3-$CF_3$-Phenyl |
| 94 | 2 | 3-$CF_3$-Phenyl |
| 95 | 3 | 3-$CF_3$-Phenyl |
| 96 | 4 | 3-$CF_3$-Phenyl |
| 97 | 1 | 2-$CF_3$-Phenyl |
| 98 | 2 | 2-$CF_3$-Phenyl |
| 99 | 3 | 2-$CF_3$-Phenyl |
| 100 | 4 | 2-$CF_3$-Phenyl |
| 101 | 1 | 4-iPr-Phenyl |
| 102 | 2 | 4-iPr-Phenyl |
| 103 | 3 | 4-iPr-Phenyl |
| 104 | 4 | 4-iPr-Phenyl |
| 105 | 1 | 3-iPr-Phenyl |
| 106 | 2 | 3-iPr-Phenyl |
| 107 | 3 | 3-iPr-Phenyl |
| 108 | 4 | 3-iPr-Phenyl |
| 109 | 1 | 2-iPr-Phenyl |
| 110 | 2 | 2-iPr-Phenyl |
| 111 | 3 | 2-iPr-Phenyl |
| 112 | 4 | 2-iPr-Phenyl |
| 113 | 1 | 4-$NH_2$-Phenyl |
| 114 | 2 | 4-$NH_2$-Phenyl |
| 115 | 3 | 4-$NH_2$-Phenyl |
| 116 | 4 | 4-$NH_2$-Phenyl |
| 117 | 1 | 3-$NH_2$-Phenyl |
| 118 | 2 | 3-$NH_2$-Phenyl |
| 119 | 3 | 3-$NH_2$-Phenyl |
| 120 | 4 | 3-$NH_2$-Phenyl |
| 121 | 1 | 2-$NH_2$-Phenyl |
| 122 | 2 | 2-$NH_2$-Phenyl |
| 123 | 3 | 2-$NH_2$-Phenyl |
| 124 | 4 | 2-$NH_2$-Phenyl |
| 125 | 1 | 2,3-di-Me-Phenyl |
| 126 | 2 | 2,3-di-Me-Phenyl |
| 127 | 3 | 2,3-di-Me-Phenyl |
| 128 | 4 | 2,3-di-Me-Phenyl |
| 129 | 1 | 2,4-di-Me-Phenyl |
| 130 | 2 | 2,4-di-Me-Phenyl |
| 131 | 3 | 2,4-di-Me-Phenyl |
| 132 | 4 | 2,4-di-Me-Phenyl |
| 133 | 1 | 2,5-di-Me-Phenyl |
| 134 | 2 | 2,5-di-Me-Phenyl |
| 135 | 3 | 2,5-di-Me-Phenyl |
| 136 | 4 | 2,5-di-Me-Phenyl |
| 137 | 1 | 2,6-di-Me-Phenyl |
| 138 | 2 | 2,6-di-Me-Phenyl |
| 139 | 3 | 2,6-di-Me-Phenyl |
| 140 | 4 | 2,6-di-Me-Phenyl |
| 141 | 1 | 2,6-di-iPr-Phenyl |
| 142 | 2 | 2,6-di-iPr-Phenyl |
| 143 | 3 | 2,6-di-iPr-Phenyl |
| 144 | 4 | 2,6-di-iPr-Phenyl |
| 145 | 1 | 2-morpholino-phenyl |
| 146 | 2 | 2-morpholino-phenyl |
| 147 | 3 | 2-morpholino-phenyl |
| 148 | 4 | 2-morpholino-phenyl |
| 149 | 1 | 3-morpholino-phenyl |
| 150 | 2 | 3-morpholino-phenyl |
| 151 | 3 | 3-morpholino-phenyl |
| 152 | 4 | 3-morpholino-phenyl |
| 153 | 1 | 4-morpholino-phenyl |
| 154 | 2 | 4-morpholino-phenyl |
| 155 | 3 | 4-morpholino-phenyl |
| 156 | 4 | 4-morpholino-phenyl |
| 157 | 1 | 4-CN-2-morpholino-phenyl |
| 158 | 2 | 4-CN-2-morpholino-phenyl |
| 159 | 3 | 4-CN-2-morpholino-phenyl |
| 160 | 4 | 4-CN-2-morpholino-phenyl |
| 161 | 1 | 4-$CH_3$-2-morpholino-phenyl |
| 162 | 2 | 4-$CH_3$-2-morpholino-phenyl |
| 163 | 3 | 4-$CH_3$-2-morpholino-phenyl |
| 164 | 4 | 4-$CH_3$-2-morpholino-phenyl |
| 165 | 1 | 4-OH-2-morpholino-phenyl |
| 166 | 2 | 4-OH-2-morpholino-phenyl |

TABLE 8-continued

| Entry | n | $R^4$ |
|---|---|---|
| 167 | 3 | 4-OH-2-morpholino-phenyl |
| 168 | 4 | 4-OH-2-morpholino-phenyl |
| 173 | 1 | naphthylen-2-yl |
| 174 | 2 | naphthylen-2-yl |
| 175 | 3 | naphthylen-2-yl |
| 176 | 4 | naphthylen-2-yl |

Exemplary embodiments include compounds having the formula (XV)

(XV)

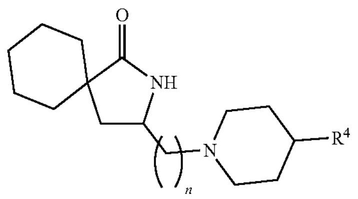

or a pharmaceutically acceptable salt form thereof defined herein below in Table 9.

TABLE 9

| Entry | n | $R^4$ |
|---|---|---|
| 1 | 1 | Phenyl |
| 2 | 2 | Phenyl |
| 3 | 3 | Phenyl |
| 4 | 4 | Phenyl |
| 5 | 1 | 4-OH-Phenyl |
| 6 | 2 | 4-OH-Phenyl |
| 7 | 3 | 4-OH-Phenyl |
| 8 | 4 | 4-OH-Phenyl |
| 9 | 1 | 3-OH-Phenyl |
| 10 | 2 | 3-OH-Phenyl |
| 11 | 3 | 3-OH-Phenyl |
| 12 | 4 | 3-OH-Phenyl |
| 13 | 1 | 2-OH-Phenyl |
| 14 | 2 | 2-OH-Phenyl |
| 15 | 3 | 2-OH-Phenyl |
| 16 | 4 | 2-OH-Phenyl |
| 17 | 1 | 4-OMe-Phenyl |
| 18 | 2 | 4-OMe-Phenyl |
| 19 | 3 | 4-OMe-Phenyl |
| 20 | 4 | 4-OMe-Phenyl |
| 21 | 1 | 3-OMe-Phenyl |
| 22 | 2 | 3-OMe-Phenyl |
| 23 | 3 | 3-OMe-Phenyl |
| 24 | 4 | 3-OMe-Phenyl |
| 25 | 1 | 2-OMe-Phenyl |
| 26 | 2 | 2-OMe-Phenyl |
| 27 | 3 | 2-OMe-Phenyl |
| 28 | 4 | 2-OMe-Phenyl |
| 29 | 1 | 4-CN-Phenyl |
| 30 | 2 | 4-CN-Phenyl |
| 31 | 3 | 4-CN-Phenyl |
| 32 | 4 | 4-CN-Phenyl |
| 33 | 1 | 3-CN-Phenyl |
| 34 | 2 | 3-CN-Phenyl |
| 35 | 3 | 3-CN-Phenyl |
| 36 | 4 | 3-CN-Phenyl |
| 37 | 1 | 2-CN-Phenyl |
| 38 | 2 | 2-CN-Phenyl |
| 39 | 3 | 2-CN-Phenyl |
| 40 | 4 | 2-CN-Phenyl |
| 41 | 1 | 4-Me-Phenyl |
| 42 | 2 | 4-Me-Phenyl |
| 43 | 3 | 4-Me-Phenyl |
| 44 | 4 | 4-Me-Phenyl |
| 45 | 1 | 3-Me-Phenyl |

TABLE 9-continued

| Entry | n | $R^4$ |
|---|---|---|
| 46 | 2 | 3-Me-Phenyl |
| 47 | 3 | 3-Me-Phenyl |
| 48 | 4 | 3-Me-Phenyl |
| 49 | 1 | 2-Me-Phenyl |
| 50 | 2 | 2-Me-Phenyl |
| 51 | 3 | 2-Me-Phenyl |
| 52 | 4 | 2-Me-Phenyl |
| 53 | 1 | 4-F-Phenyl |
| 54 | 2 | 4-F-Phenyl |
| 55 | 3 | 4-F-Phenyl |
| 56 | 4 | 4-F-Phenyl |
| 57 | 1 | 3-F-Phenyl |
| 58 | 2 | 3-F-Phenyl |
| 59 | 3 | 3-F-Phenyl |
| 60 | 4 | 3-F-Phenyl |
| 61 | 1 | 2-F-Phenyl |
| 62 | 2 | 2-F-Phenyl |
| 63 | 3 | 2-F-Phenyl |
| 64 | 4 | 2-F-Phenyl |
| 65 | 1 | 4-Cl-Phenyl |
| 66 | 2 | 4-Cl-Phenyl |
| 67 | 3 | 4-Cl-Phenyl |
| 68 | 4 | 4-Cl-Phenyl |
| 69 | 1 | 3-Cl-Phenyl |
| 70 | 2 | 3-Cl-Phenyl |
| 71 | 3 | 3-Cl-Phenyl |
| 72 | 4 | 3-Cl-Phenyl |
| 73 | 1 | 2-Cl-Phenyl |
| 74 | 2 | 2-Cl-Phenyl |
| 75 | 3 | 2-Cl-Phenyl |
| 76 | 4 | 2-Cl-Phenyl |
| 77 | 1 | 4-Br-Phenyl |
| 78 | 2 | 4-Br-Phenyl |
| 79 | 3 | 4-Br-Phenyl |
| 80 | 4 | 4-Br-Phenyl |
| 81 | 1 | 3-Br-Phenyl |
| 82 | 2 | 3-Br-Phenyl |
| 83 | 3 | 3-Br-Phenyl |
| 84 | 4 | 3-Br-Phenyl |
| 85 | 1 | naphthylen-1-yl |
| 86 | 2 | naphthylen-1-yl |
| 87 | 3 | naphthylen-1-yl |
| 88 | 4 | naphthylen-1-yl |
| 85 | 1 | 2-Br-Phenyl |
| 86 | 2 | 2-Br-Phenyl |
| 87 | 3 | 2-Br-Phenyl |
| 88 | 4 | 2-Br-Phenyl |
| 89 | 1 | 4-$CF_3$-Phenyl |
| 90 | 2 | 4-$CF_3$-Phenyl |
| 91 | 3 | 4-$CF_3$-Phenyl |
| 92 | 4 | 4-$CF_3$-Phenyl |
| 93 | 1 | 3-$CF_3$-Phenyl |
| 94 | 2 | 3-$CF_3$-Phenyl |
| 95 | 3 | 3-$CF_3$-Phenyl |
| 96 | 4 | 3-$CF_3$-Phenyl |
| 97 | 1 | 2-$CF_3$-Phenyl |
| 98 | 2 | 2-$CF_3$-Phenyl |
| 99 | 3 | 2-$CF_3$-Phenyl |
| 100 | 4 | 2-$CF_3$-Phenyl |
| 101 | 1 | 4-iPr-Phenyl |
| 102 | 2 | 4-iPr-Phenyl |
| 103 | 3 | 4-iPr-Phenyl |
| 104 | 4 | 4-iPr-Phenyl |
| 105 | 1 | 3-iPr-Phenyl |
| 106 | 2 | 3-iPr-Phenyl |
| 107 | 3 | 3-iPr-Phenyl |
| 108 | 4 | 3-iPr-Phenyl |
| 109 | 1 | 2-iPr-Phenyl |
| 110 | 2 | 2-iPr-Phenyl |
| 111 | 3 | 2-iPr-Phenyl |
| 112 | 4 | 2-iPr-Phenyl |
| 113 | 1 | 4-$NH_2$-Phenyl |
| 114 | 2 | 4-$NH_2$-Phenyl |
| 115 | 3 | 4-$NH_2$-Phenyl |
| 116 | 4 | 4-$NH_2$-Phenyl |
| 117 | 1 | 3-$NH_2$-Phenyl |
| 118 | 2 | 3-$NH_2$-Phenyl |
| 119 | 3 | 3-$NH_2$-Phenyl |

TABLE 9-continued

| Entry | n | $R^4$ |
|---|---|---|
| 120 | 4 | $3\text{-}NH_2$-Phenyl |
| 121 | 1 | $2\text{-}NH_2$-Phenyl |
| 122 | 2 | $2\text{-}NH_2$-Phenyl |
| 123 | 3 | $2\text{-}NH_2$-Phenyl |
| 124 | 4 | $2\text{-}NH_2$-Phenyl |
| 125 | 1 | 2,3-di-Me-Phenyl |
| 126 | 2 | 2,3-di-Me-Phenyl |
| 127 | 3 | 2,3-di-Me-Phenyl |
| 128 | 4 | 2,3-di-Me-Phenyl |
| 129 | 1 | 2,4-di-Me-Phenyl |
| 130 | 2 | 2,4-di-Me-Phenyl |
| 131 | 3 | 2,4-di-Me-Phenyl |
| 132 | 4 | 2,4-di-Me-Phenyl |
| 133 | 1 | 2,5-di-Me-Phenyl |
| 134 | 2 | 2,5-di-Me-Phenyl |
| 135 | 3 | 2,5-di-Me-Phenyl |
| 136 | 4 | 2,5-di-Me-Phenyl |
| 137 | 1 | 2,6-di-Me-Phenyl |
| 138 | 2 | 2,6-di-Me-Phenyl |
| 139 | 3 | 2,6-di-Me-Phenyl |
| 140 | 4 | 2,6-di-Me-Phenyl |
| 141 | 1 | 2,6-di-iPr-Phenyl |
| 142 | 2 | 2,6-di-iPr-Phenyl |
| 143 | 3 | 2,6-di-iPr-Phenyl |
| 144 | 4 | 2,6-di-iPr-Phenyl |
| 145 | 1 | 2-morpholino-phenyl |
| 146 | 2 | 2-morpholino-phenyl |
| 147 | 3 | 2-morpholino-phenyl |
| 148 | 4 | 2-morpholino-phenyl |
| 149 | 1 | 3-morpholino-phenyl |
| 150 | 2 | 3-morpholino-phenyl |
| 151 | 3 | 3-morpholino-phenyl |
| 152 | 4 | 3-morpholino-phenyl |
| 153 | 1 | 4-morpholino-phenyl |
| 154 | 2 | 4-morpholino-phenyl |
| 155 | 3 | 4-morpholino-phenyl |
| 156 | 4 | 4-morpholino-phenyl |
| 157 | 1 | 4-CN-2-morpholino-phenyl |
| 158 | 2 | 4-CN-2-morpholino-phenyl |
| 159 | 3 | 4-CN-2-morpholino-phenyl |
| 160 | 4 | 4-CN-2-morpholino-phenyl |
| 161 | 1 | $4\text{-}CH_3$-2-morpholino-phenyl |
| 162 | 2 | $4\text{-}CH_3$-2-morpholino-phenyl |
| 163 | 3 | $4\text{-}CH_3$-2-morpholino-phenyl |
| 164 | 4 | $4\text{-}CH_3$-2-morpholino-phenyl |
| 165 | 1 | 4-OH-2-morpholino-phenyl |
| 166 | 2 | 4-OH-2-morpholino-phenyl |
| 167 | 3 | 4-OH-2-morpholino-phenyl |
| 168 | 4 | 4-OH-2-morpholino-phenyl |
| 173 | 1 | naphthylen-2-yl |
| 174 | 2 | naphthylen-2-yl |
| 175 | 3 | naphthylen-2-yl |
| 176 | 4 | naphthylen-2-yl |

Exemplary embodiments include compounds having the formula (XVI)

(XVI)

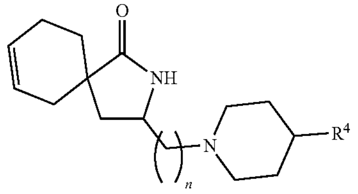

or a pharmaceutically acceptable salt form thereof defined herein below in Table 10.

TABLE 10

| Entry | n | $R^4$ | Entry | n | $R^4$ |
|---|---|---|---|---|---|
| 1 | 1 | Phenyl | 85 | 1 | 2-Br-Phenyl |
| 2 | 2 | Phenyl | 86 | 2 | 2-Br-Phenyl |
| 3 | 3 | Phenyl | 87 | 3 | 2-Br-Phenyl |
| 4 | 4 | Phenyl | 88 | 4 | 2-Br-Phenyl |
| 5 | 1 | 4-OH-Phenyl | 89 | 1 | $4\text{-}CF_3$-Phenyl |
| 6 | 2 | 4-OH-Phenyl | 90 | 2 | $4\text{-}CF_3$-Phenyl |
| 7 | 3 | 4-OH-Phenyl | 91 | 3 | $4\text{-}CF_3$-Phenyl |
| 8 | 4 | 4-OH-Phenyl | 92 | 4 | $4\text{-}CF_3$-Phenyl |
| 9 | 1 | 3-OH-Phenyl | 93 | 1 | $3\text{-}CF_3$-Phenyl |
| 10 | 2 | 3-OH-Phenyl | 94 | 2 | $3\text{-}CF_3$-Phenyl |
| 11 | 3 | 3-OH-Phenyl | 95 | 3 | $3\text{-}CF_3$-Phenyl |
| 12 | 4 | 3-OH-Phenyl | 96 | 4 | $3\text{-}CF_3$-Phenyl |
| 13 | 1 | 2-OH-Phenyl | 97 | 1 | $2\text{-}CF_3$-Phenyl |
| 14 | 2 | 2-OH-Phenyl | 98 | 2 | $2\text{-}CF_3$-Phenyl |
| 15 | 3 | 2-OH-Phenyl | 99 | 3 | $2\text{-}CF_3$-Phenyl |
| 16 | 4 | 2-OH-Phenyl | 100 | 4 | $2\text{-}CF_3$-Phenyl |
| 17 | 1 | 4-OMe-Phenyl | 101 | 1 | 4-iPr-Phenyl |
| 18 | 2 | 4-OMe-Phenyl | 102 | 2 | 4-iPr-Phenyl |
| 19 | 3 | 4-OMe-Phenyl | 103 | 3 | 4-iPr-Phenyl |
| 20 | 4 | 4-OMe-Phenyl | 104 | 4 | 4-iPr-Phenyl |
| 21 | 1 | 3-OMe-Phenyl | 105 | 1 | 3-iPr-Phenyl |
| 22 | 2 | 3-OMe-Phenyl | 106 | 2 | 3-iPr-Phenyl |
| 23 | 3 | 3-OMe-Phenyl | 107 | 3 | 3-iPr-Phenyl |
| 24 | 4 | 3-OMe-Phenyl | 108 | 4 | 3-iPr-Phenyl |
| 25 | 1 | 2-OMe-Phenyl | 109 | 1 | 2-iPr-Phenyl |
| 26 | 2 | 2-OMe-Phenyl | 110 | 2 | 2-iPr-Phenyl |
| 27 | 3 | 2-OMe-Phenyl | 111 | 3 | 2-iPr-Phenyl |
| 28 | 4 | 2-OMe-Phenyl | 112 | 4 | 2-iPr-Phenyl |
| 29 | 1 | 4-CN-Phenyl | 113 | 1 | $4\text{-}NH_2$-Phenyl |
| 30 | 2 | 4-CN-Phenyl | 114 | 2 | $4\text{-}NH_2$-Phenyl |
| 31 | 3 | 4-CN-Phenyl | 115 | 3 | $4\text{-}NH_2$-Phenyl |
| 32 | 4 | 4-CN-Phenyl | 116 | 4 | $4\text{-}NH_2$-Phenyl |
| 33 | 1 | 3-CN-Phenyl | 117 | 1 | $3\text{-}NH_2$-Phenyl |
| 34 | 2 | 3-CN-Phenyl | 118 | 2 | $3\text{-}NH_2$-Phenyl |
| 35 | 3 | 3-CN-Phenyl | 119 | 3 | $3\text{-}NH_2$-Phenyl |
| 36 | 4 | 3-CN-Phenyl | 120 | 4 | $3\text{-}NH_2$-Phenyl |
| 37 | 1 | 2-CN-Phenyl | 121 | 1 | $2\text{-}NH_2$-Phenyl |
| 38 | 2 | 2-CN-Phenyl | 122 | 2 | $2\text{-}NH_2$-Phenyl |
| 39 | 3 | 2-CN-Phenyl | 123 | 3 | $2\text{-}NH_2$-Phenyl |
| 40 | 4 | 2-CN-Phenyl | 124 | 4 | $2\text{-}NH_2$-Phenyl |
| 41 | 1 | 4-Me-Phenyl | 125 | 1 | 2,3-di-Me-Phenyl |
| 42 | 2 | 4-Me-Phenyl | 126 | 2 | 2,3-di-Me-Phenyl |
| 43 | 3 | 4-Me-Phenyl | 127 | 3 | 2,3-di-Me-Phenyl |
| 44 | 4 | 4-Me-Phenyl | 128 | 4 | 2,3-di-Me-Phenyl |
| 45 | 1 | 3-Me-Phenyl | 129 | 1 | 2,4-di-Me-Phenyl |
| 46 | 2 | 3-Me-Phenyl | 130 | 2 | 2,4-di-Me-Phenyl |
| 47 | 3 | 3-Me-Phenyl | 131 | 3 | 2,4-di-Me-Phenyl |
| 48 | 4 | 3-Me-Phenyl | 132 | 4 | 2,4-di-Me-Phenyl |
| 49 | 1 | 2-Me-Phenyl | 133 | 1 | 2,5-di-Me-Phenyl |
| 50 | 2 | 2-Me-Phenyl | 134 | 2 | 2,5-di-Me-Phenyl |
| 51 | 3 | 2-Me-Phenyl | 135 | 3 | 2,5-di-Me-Phenyl |
| 52 | 4 | 2-Me-Phenyl | 136 | 4 | 2,5-di-Me-Phenyl |
| 53 | 1 | 4-F-Phenyl | 137 | 1 | 2,6-di-Me-Phenyl |
| 54 | 2 | 4-F-Phenyl | 138 | 2 | 2,6-di-Me-Phenyl |
| 55 | 3 | 4-F-Phenyl | 139 | 3 | 2,6-di-Me-Phenyl |
| 56 | 4 | 4-F-Phenyl | 140 | 4 | 2,6-di-Me-Phenyl |
| 57 | 1 | 3-F-Phenyl | 141 | 1 | 2,6-di-iPr-Phenyl |
| 58 | 2 | 3-F-Phenyl | 142 | 2 | 2,6-di-iPr-Phenyl |
| 59 | 3 | 3-F-Phenyl | 143 | 3 | 2,6-di-iPr-Phenyl |
| 60 | 4 | 3-F-Phenyl | 144 | 4 | 2,6-di-iPr-Phenyl |
| 61 | 1 | 2-F-Phenyl | 145 | 1 | 2-morpholino-phenyl |
| 62 | 2 | 2-F-Phenyl | 146 | 2 | 2-morpholino-phenyl |
| 63 | 3 | 2-F-Phenyl | 147 | 3 | 2-morpholino-phenyl |
| 64 | 4 | 2-F-Phenyl | 148 | 4 | 2-morpholino-phenyl |
| 65 | 1 | 4-Cl-Phenyl | 149 | 1 | 3-morpholino-phenyl |
| 66 | 2 | 4-Cl-Phenyl | 150 | 2 | 3-morpholino-phenyl |
| 67 | 3 | 4-Cl-Phenyl | 151 | 3 | 3-morpholino-phenyl |
| 68 | 4 | 4-Cl-Phenyl | 152 | 4 | 3-morpholino-phenyl |
| 69 | 1 | 3-Cl-Phenyl | 153 | 1 | 4-morpholino-phenyl |
| 70 | 2 | 3-Cl-Phenyl | 154 | 2 | 4-morpholino-phenyl |
| 71 | 3 | 3-Cl-Phenyl | 155 | 3 | 4-morpholino-phenyl |
| 72 | 4 | 3-Cl-Phenyl | 156 | 4 | 4-morpholino-phenyl |
| 73 | 1 | 2-Cl-Phenyl | 157 | 1 | 4-CN-2-morpholino-phenyl |
| 74 | 2 | 2-Cl-Phenyl | 158 | 2 | 4-CN-2-morpholino-phenyl |
| 75 | 3 | 2-Cl-Phenyl | 159 | 3 | 4-CN-2-morpholino-phenyl |
| 76 | 4 | 2-Cl-Phenyl | 160 | 4 | 4-CN-2-morpholino-phenyl |
| 77 | 1 | 4-Br-Phenyl | 161 | 1 | $4\text{-}CH_3$-2-morpholino-phenyl |
| 78 | 2 | 4-Br-Phenyl | 162 | 2 | $4\text{-}CH_3$-2-morpholino-phenyl |

TABLE 10-continued

| Entry | n | $R^4$ | Entry | n | $R^4$ |
|---|---|---|---|---|---|
| 79 | 3 | 4-Br-Phenyl | 163 | 3 | 4-$CH_3$-2-morpholino-phenyl |
| 80 | 4 | 4-Br-Phenyl | 164 | 4 | 4-$CH_3$-2-morpholino-phenyl |
| 81 | 1 | 3-Br-Phenyl | 165 | 1 | 4-OH-2-morpholino-phenyl |
| 82 | 2 | 3-Br-Phenyl | 166 | 2 | 4-OH-2-morpholino-phenyl |
| 83 | 3 | 3-Br-Phenyl | 167 | 3 | 4-OH-2-morpholino-phenyl |
| 84 | 4 | 3-Br-Phenyl | 168 | 4 | 4-OH-2-morpholino-phenyl |
| 85 | 1 | naphthylen-1-yl | 173 | 1 | naphthylen-2-yl |
| 86 | 2 | naphthylen-1-yl | 174 | 2 | naphthylen-2-yl |
| 87 | 3 | naphthylen-1-yl | 175 | 3 | naphthylen-2-yl |
| 88 | 4 | naphthylen-1-yl | 176 | 4 | naphthylen-2-yl |

Exemplary embodiments include compounds having the formula (XVII)

(XVII)

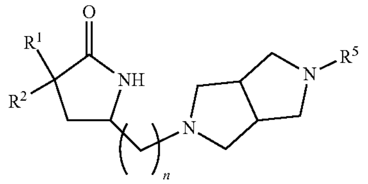

or a pharmaceutically acceptable salt form thereof defined herein below in Table 11.

TABLE 11

| Entry | $R^1$ | $R^2$ | n | $R^5$ |
|---|---|---|---|---|
| 1 | Methyl | Methyl | 1 | Phenyl |
| 2 | Methyl | Methyl | 2 | Phenyl |
| 3 | Methyl | Methyl | 3 | Phenyl |
| 4 | Methyl | Methyl | 4 | Phenyl |
| 5 | Methyl | Methyl | 1 | 4-OH-Phenyl |
| 6 | Methyl | Methyl | 2 | 4-OH-Phenyl |
| 7 | Methyl | Methyl | 3 | 4-OH-Phenyl |
| 8 | Methyl | Methyl | 4 | 4-OH-Phenyl |
| 9 | Methyl | Methyl | 1 | 3-OH-Phenyl |
| 10 | Methyl | Methyl | 2 | 3-OH-Phenyl |
| 11 | Methyl | Methyl | 3 | 3-OH-Phenyl |
| 12 | Methyl | Methyl | 4 | 3-OH-Phenyl |
| 13 | Methyl | Methyl | 1 | 2-OH-Phenyl |
| 14 | Methyl | Methyl | 2 | 2-OH-Phenyl |
| 15 | Methyl | Methyl | 3 | 2-OH-Phenyl |
| 16 | Methyl | Methyl | 4 | 2-OH-Phenyl |
| 17 | Methyl | Methyl | 1 | 4-OMe-Phenyl |
| 18 | Methyl | Methyl | 2 | 4-OMe-Phenyl |
| 19 | Methyl | Methyl | 3 | 4-OMe-Phenyl |
| 20 | Methyl | Methyl | 4 | 4-OMe-Phenyl |
| 21 | Methyl | Methyl | 1 | 3-OMe-Phenyl |
| 22 | Methyl | Methyl | 2 | 3-OMe-Phenyl |
| 23 | Methyl | Methyl | 3 | 3-OMe-Phenyl |
| 24 | Methyl | Methyl | 4 | 3-OMe-Phenyl |
| 25 | Methyl | Methyl | 1 | 2-OMe-Phenyl |
| 26 | Methyl | Methyl | 2 | 2-OMe-Phenyl |
| 27 | Methyl | Methyl | 3 | 2-OMe-Phenyl |
| 28 | Methyl | Methyl | 4 | 2-OMe-Phenyl |
| 29 | Methyl | Methyl | 1 | 4-CN-Phenyl |
| 30 | Methyl | Methyl | 2 | 4-CN-Phenyl |
| 31 | Methyl | Methyl | 3 | 4-CN-Phenyl |
| 32 | Methyl | Methyl | 4 | 4-CN-Phenyl |
| 33 | Methyl | Methyl | 1 | 3-CN-Phenyl |
| 34 | Methyl | Methyl | 2 | 3-CN-Phenyl |
| 35 | Methyl | Methyl | 3 | 3-CN-Phenyl |
| 36 | Methyl | Methyl | 4 | 3-CN-Phenyl |
| 37 | Methyl | Methyl | 1 | 2-CN-Phenyl |
| 38 | Methyl | Methyl | 2 | 2-CN-Phenyl |
| 39 | Methyl | Methyl | 3 | 2-CN-Phenyl |
| 40 | Methyl | Methyl | 4 | 2-CN-Phenyl |
| 41 | Methyl | Methyl | 1 | 4-Me-Phenyl |
| 42 | Methyl | Methyl | 2 | 4-Me-Phenyl |

TABLE 11-continued

| Entry | $R^1$ | $R^2$ | n | $R^5$ |
|---|---|---|---|---|
| 43 | Methyl | Methyl | 3 | 4-Me-Phenyl |
| 44 | Methyl | Methyl | 4 | 4-Me-Phenyl |
| 45 | Methyl | Methyl | 1 | 3-Me-Phenyl |
| 46 | Methyl | Methyl | 2 | 3-Me-Phenyl |
| 47 | Methyl | Methyl | 3 | 3-Me-Phenyl |
| 48 | Methyl | Methyl | 4 | 3-Me-Phenyl |
| 49 | Methyl | Methyl | 1 | 2-Me-Phenyl |
| 50 | Methyl | Methyl | 2 | 2-Me-Phenyl |
| 51 | Methyl | Methyl | 3 | 2-Me-Phenyl |
| 52 | Methyl | Methyl | 4 | 2-Me-Phenyl |
| 53 | Methyl | Methyl | 1 | 4-F-Phenyl |
| 54 | Methyl | Methyl | 2 | 4-F-Phenyl |
| 55 | Methyl | Methyl | 3 | 4-F-Phenyl |
| 56 | Methyl | Methyl | 4 | 4-F-Phenyl |
| 57 | Methyl | Methyl | 1 | 3-F-Phenyl |
| 58 | Methyl | Methyl | 2 | 3-F-Phenyl |
| 59 | Methyl | Methyl | 3 | 3-F-Phenyl |
| 60 | Methyl | Methyl | 4 | 3-F-Phenyl |
| 61 | Methyl | Methyl | 1 | 2-F-Phenyl |
| 62 | Methyl | Methyl | 2 | 2-F-Phenyl |
| 63 | Methyl | Methyl | 3 | 2-F-Phenyl |
| 64 | Methyl | Methyl | 4 | 2-F-Phenyl |
| 65 | Methyl | Methyl | 1 | 4-Cl-Phenyl |
| 66 | Methyl | Methyl | 2 | 4-Cl-Phenyl |
| 67 | Methyl | Methyl | 3 | 4-Cl-Phenyl |
| 68 | Methyl | Methyl | 4 | 4-Cl-Phenyl |
| 69 | Methyl | Methyl | 1 | 3-Cl-Phenyl |
| 70 | Methyl | Methyl | 2 | 3-Cl-Phenyl |
| 71 | Methyl | Methyl | 3 | 3-Cl-Phenyl |
| 72 | Methyl | Methyl | 4 | 3-Cl-Phenyl |
| 73 | Methyl | Methyl | 1 | 2-Cl-Phenyl |
| 74 | Methyl | Methyl | 2 | 2-Cl-Phenyl |
| 75 | Methyl | Methyl | 3 | 2-Cl-Phenyl |
| 76 | Methyl | Methyl | 4 | 2-Cl-Phenyl |
| 77 | Methyl | Methyl | 1 | 4-Br-Phenyl |
| 78 | Methyl | Methyl | 2 | 4-Br-Phenyl |
| 79 | Methyl | Methyl | 3 | 4-Br-Phenyl |
| 80 | Methyl | Methyl | 4 | 4-Br-Phenyl |
| 81 | Methyl | Methyl | 1 | 3-Br-Phenyl |
| 82 | Methyl | Methyl | 2 | 3-Br-Phenyl |
| 83 | Methyl | Methyl | 3 | 3-Br-Phenyl |
| 84 | Methyl | Methyl | 4 | 3-Br-Phenyl |
| 85 | Methyl | Methyl | 1 | 2-Br-Phenyl |
| 86 | Methyl | Methyl | 2 | 2-Br-Phenyl |
| 87 | Methyl | Methyl | 3 | 2-Br-Phenyl |
| 88 | Methyl | Methyl | 4 | 2-Br-Phenyl |
| 89 | Methyl | Methyl | 1 | 4-$CF_3$-Phenyl |
| 90 | Methyl | Methyl | 2 | 4-$CF_3$-Phenyl |
| 91 | Methyl | Methyl | 3 | 4-$CF_3$-Phenyl |
| 92 | Methyl | Methyl | 4 | 4-$CF_3$-Phenyl |
| 93 | Methyl | Methyl | 1 | 3-$CF_3$-Phenyl |
| 94 | Methyl | Methyl | 2 | 3-$CF_3$-Phenyl |
| 95 | Methyl | Methyl | 3 | 3-$CF_3$-Phenyl |
| 96 | Methyl | Methyl | 4 | 3-$CF_3$-Phenyl |
| 97 | Methyl | Methyl | 1 | 2-$CF_3$-Phenvl |
| 98 | Methyl | Methyl | 2 | 2-$CF_3$-Phenvl |
| 99 | Methyl | Methyl | 3 | 2-$CF_3$-Phenvl |
| 100 | Methyl | Methyl | 4 | 2-$CF_3$-Phenyl |
| 101 | Methyl | Methyl | 1 | 4-iPr-Phenyl |
| 102 | Methyl | Methyl | 2 | 4-iPr-Phenyl |
| 103 | Methyl | Methyl | 3 | 4-iPr-Phenyl |
| 104 | Methyl | Methyl | 4 | 4-iPr-Phenyl |
| 105 | Methyl | Methyl | 1 | 3-iPr-Phenyl |
| 106 | Methyl | Methyl | 2 | 3-iPr-Phenyl |
| 107 | Methyl | Methyl | 3 | 3-iPr-Phenyl |
| 108 | Methyl | Methyl | 4 | 3-iPr-Phenyl |
| 109 | Methyl | Methyl | 1 | 2-iPr-Phenyl |
| 110 | Methyl | Methyl | 2 | 2-iPr-Phenyl |
| 111 | Methyl | Methyl | 3 | 2-iPr-Phenyl |
| 112 | Methyl | Methyl | 4 | 2-iPr-Phenyl |
| 113 | Methyl | Methyl | 1 | 4-$NH_2$-Phenyl |
| 114 | Methyl | Methyl | 2 | 4-$NH_2$-Phenyl |
| 115 | Methyl | Methyl | 3 | 4-$NH_2$-Phenyl |
| 116 | Methyl | Methyl | 4 | 4-$NH_2$-Phenyl |
| 117 | Methyl | Methyl | 1 | 3-$NH_2$-Phenyl |
| 118 | Methyl | Methyl | 2 | 3-$NH_2$-Phenyl |
| 119 | Methyl | Methyl | 3 | 3-$NH_2$-Phenyl |
| 120 | Methyl | Methyl | 4 | 3-$NH_2$-Phenyl |

TABLE 11-continued

| Entry | $R^1$ | $R^2$ | n | $R^5$ |
|---|---|---|---|---|
| 121 | Methyl | Methyl | 1 | 2-$NH_2$-Phenyl |
| 122 | Methyl | Methyl | 2 | 2-$NH_2$-Phenyl |
| 123 | Methyl | Methyl | 3 | 2-$NH_2$-Phenyl |
| 124 | Methyl | Methyl | 4 | 2-$NH_2$-Phenyl |
| 125 | Methyl | Methyl | 1 | 2,3-di-Me-Phenyl |
| 126 | Methyl | Methyl | 2 | 2,3-di-Me-Phenyl |
| 127 | Methyl | Methyl | 3 | 2,3-di-Me-Phenyl |
| 128 | Methyl | Methyl | 4 | 2,3-di-Me-Phenyl |
| 129 | Methyl | Methyl | 1 | 2,4-di-Me-Phenyl |
| 130 | Methyl | Methyl | 2 | 2,4-di-Me-Phenyl |
| 131 | Methyl | Methyl | 3 | 2,4-di-Me-Phenyl |
| 132 | Methyl | Methyl | 4 | 2,4-di-Me-Phenyl |
| 133 | Methyl | Methyl | 1 | 2,5-di-Me-Phenyl |
| 134 | Methyl | Methyl | 2 | 2,5-di-Me-Phenyl |
| 135 | Methyl | Methyl | 3 | 2,5-di-Me-Phenyl |
| 136 | Methyl | Methyl | 4 | 2,5-di-Me-Phenyl |
| 137 | Methyl | Methyl | 1 | 2,6-di-Me-Phenyl |
| 138 | Methyl | Methyl | 2 | 2,6-di-Me-Phenyl |
| 139 | Methyl | Methyl | 3 | 2,6-di-Me-Phenyl |
| 140 | Methyl | Methyl | 4 | 2,6-di-Me-Phenyl |
| 141 | Methyl | Methyl | 1 | 2,6-di-iPr-Phenyl |
| 142 | Methyl | Methyl | 2 | 2,6-di-iPr-Phenyl |
| 143 | Methyl | Methyl | 3 | 2,6-di-iPr-Phenyl |
| 144 | Methyl | Methyl | 4 | 2,6-di-iPr-Phenyl |
| 145 | Methyl | Methyl | 1 | 2-morpholino-phenyl |
| 146 | Methyl | Methyl | 2 | 2-morpholino-phenyl |
| 147 | Methyl | Methyl | 3 | 2-morpholino-phenyl |
| 148 | Methyl | Methyl | 4 | 2-morpholino-phenyl |
| 149 | Methyl | Methyl | 1 | 3-morpholino-phenyl |
| 150 | Methyl | Methyl | 2 | 3-morpholino-phenyl |
| 151 | Methyl | Methyl | 3 | 3-morpholino-phenyl |
| 152 | Methyl | Methyl | 4 | 3-morpholino-phenyl |
| 153 | Methyl | Methyl | 1 | 4-morpholino-phenyl |
| 154 | Methyl | Methyl | 2 | 4-morpholino-phenyl |
| 155 | Methyl | Methyl | 3 | 4-morpholino-phenyl |
| 156 | Methyl | Methyl | 4 | 4-morpholino-phenyl |
| 157 | Methyl | Methyl | 1 | 4-CN-2-morpholino-phenyl |
| 158 | Methyl | Methyl | 2 | 4-CN-2-morpholino-phenyl |
| 159 | Methyl | Methyl | 3 | 4-CN-2-morpholino-phenyl |
| 160 | Methyl | Methyl | 4 | 4-CN-2-morpholino-phenyl |
| 161 | Methyl | Methyl | 1 | 4-$CH_3$-2-morpholino-phenyl |
| 162 | Methyl | Methyl | 2 | 4-$CH_3$-2-morpholino-phenyl |
| 163 | Methyl | Methyl | 3 | 4-$CH_3$-2-morpholino-phenyl |
| 164 | Methyl | Methyl | 4 | 4-$CH_3$-2-morpholino-phenyl |
| 165 | Methyl | Methyl | 1 | 4-OH-2-morpholino-phenyl |
| 166 | Methyl | Methyl | 2 | 4-OH-2-morpholino-phenyl |
| 167 | Methyl | Methyl | 3 | 4-OH-2-morpholino-phenyl |
| 168 | Methyl | Methyl | 4 | 4-OH-2-morpholino-phenyl |
| 169 | Methyl | Methyl | 1 | naphthylen-1-yl |
| 170 | Methyl | Methyl | 2 | naphthylen-1-yl |
| 171 | Methyl | Methyl | 3 | naphthylen-1-yl |
| 172 | Methyl | Methyl | 4 | naphthylen-1-yl |
| 173 | Methyl | Methyl | 1 | naphthylen-2-yl |
| 174 | Methyl | Methyl | 2 | naphthylen-2-yl |
| 175 | Methyl | Methyl | 3 | naphthylen-2-yl |
| 176 | Methyl | Methyl | 4 | naphthylen-2-yl |
| 177 | Ethyl | Ethyl | 1 | Phenyl |
| 178 | Ethyl | Ethyl | 2 | Phenyl |
| 179 | Ethyl | Ethyl | 3 | Phenyl |
| 180 | Ethyl | Ethyl | 4 | Phenyl |
| 181 | Ethyl | Ethyl | 1 | 4-OH-Phenyl |
| 182 | Ethyl | Ethyl | 2 | 4-OH-Phenyl |
| 183 | Ethyl | Ethyl | 3 | 4-OH-Phenyl |
| 184 | Ethyl | Ethyl | 4 | 4-OH-Phenyl |
| 185 | Ethyl | Ethyl | 1 | 3-OH-Phenyl |
| 186 | Ethyl | Ethyl | 2 | 3-OH-Phenyl |
| 187 | Ethyl | Ethyl | 3 | 3-OH-Phenyl |
| 188 | Ethyl | Ethyl | 4 | 3-OH-Phenyl |
| 189 | Ethyl | Ethyl | 1 | 2-OH-Phenyl |
| 190 | Ethyl | Ethyl | 2 | 2-OH-Phenyl |
| 191 | Ethyl | Ethyl | 3 | 2-OH-Phenyl |
| 192 | Ethyl | Ethyl | 4 | 2-OH-Phenyl |
| 193 | Ethyl | Ethyl | 1 | 4-OMe-Phenyl |
| 194 | Ethyl | Ethyl | 2 | 4-OMe-Phenyl |
| 195 | Ethyl | Ethyl | 3 | 4-OMe-Phenyl |
| 196 | Ethyl | Ethyl | 4 | 4-OMe-Phenyl |
| 197 | Ethyl | Ethyl | 1 | 3-OMe-Phenyl |
| 198 | Ethyl | Ethyl | 2 | 3-OMe-Phenyl |

TABLE 11-continued

| Entry | $R^1$ | $R^2$ | n | $R^5$ |
|---|---|---|---|---|
| 199 | Ethyl | Ethyl | 3 | 3-OMe-Phenyl |
| 200 | Ethyl | Ethyl | 4 | 3-OMe-Phenyl |
| 201 | Ethyl | Ethyl | 1 | 2-OMe-Phenyl |
| 202 | Ethyl | Ethyl | 2 | 2-OMe-Phenyl |
| 203 | Ethyl | Ethyl | 3 | 2-OMe-Phenyl |
| 204 | Ethyl | Ethyl | 4 | 2-OMe-Phenyl |
| 205 | Ethyl | Ethyl | 1 | 4-CN-Phenyl |
| 206 | Ethyl | Ethyl | 2 | 4-CN-Phenyl |
| 207 | Ethyl | Ethyl | 3 | 4-CN-Phenyl |
| 208 | Ethyl | Ethyl | 4 | 4-CN-Phenyl |
| 209 | Ethyl | Ethyl | 1 | 3-CN-Phenyl |
| 210 | Ethyl | Ethyl | 2 | 3-CN-Phenyl |
| 211 | Ethyl | Ethyl | 3 | 3-CN-Phenyl |
| 212 | Ethyl | Ethyl | 4 | 3-CN-Phenyl |
| 213 | Ethyl | Ethyl | 1 | 2-CN-Phenyl |
| 214 | Ethyl | Ethyl | 2 | 2-CN-Phenyl |
| 215 | Ethyl | Ethyl | 3 | 2-CN-Phenyl |
| 216 | Ethyl | Ethyl | 4 | 2-CN-Phenyl |
| 217 | Ethyl | Ethyl | 1 | 4-Me-Phenyl |
| 218 | Ethyl | Ethyl | 2 | 4-Me-Phenyl |
| 219 | Ethyl | Ethyl | 3 | 4-Me-Phenyl |
| 220 | Ethyl | Ethyl | 4 | 4-Me-Phenyl |
| 221 | Ethyl | Ethyl | 1 | 3-Me-Phenyl |
| 222 | Ethyl | Ethyl | 2 | 3-Me-Phenyl |
| 223 | Ethyl | Ethyl | 3 | 3-Me-Phenyl |
| 224 | Ethyl | Ethyl | 4 | 3-Me-Phenyl |
| 225 | Ethyl | Ethyl | 1 | 2-Me-Phenyl |
| 226 | Ethyl | Ethyl | 2 | 2-Me-Phenyl |
| 227 | Ethyl | Ethyl | 3 | 2-Me-Phenyl |
| 228 | Ethyl | Ethyl | 4 | 2-Me-Phenyl |
| 229 | Ethyl | Ethyl | 1 | 4-F-Phenyl |
| 230 | Ethyl | Ethyl | 2 | 4-F-Phenyl |
| 231 | Ethyl | Ethyl | 3 | 4-F-Phenyl |
| 232 | Ethyl | Ethyl | 4 | 4-F-Phenyl |
| 233 | Ethyl | Ethyl | 1 | 3-F-Phenyl |
| 234 | Ethyl | Ethyl | 2 | 3-F-Phenyl |
| 235 | Ethyl | Ethyl | 3 | 3-F-Phenyl |
| 236 | Ethyl | Ethyl | 4 | 3-F-Phenyl |
| 237 | Ethyl | Ethyl | 1 | 2-F-Phenyl |
| 238 | Ethyl | Ethyl | 2 | 2-F-Phenyl |
| 239 | Ethyl | Ethyl | 3 | 2-F-Phenyl |
| 240 | Ethyl | Ethyl | 4 | 2-F-Phenyl |
| 241 | Ethyl | Ethyl | 1 | 4-Cl-Phenyl |
| 242 | Ethyl | Ethyl | 2 | 4-Cl-Phenyl |
| 243 | Ethyl | Ethyl | 3 | 4-Cl-Phenyl |
| 244 | Ethyl | Ethyl | 4 | 4-Cl-Phenyl |
| 245 | Ethyl | Ethyl | 1 | 3-Cl-Phenyl |
| 246 | Ethyl | Ethyl | 2 | 3-Cl-Phenyl |
| 247 | Ethyl | Ethyl | 3 | 3-Cl-Phenyl |
| 248 | Ethyl | Ethyl | 4 | 3-Cl-Phenyl |
| 249 | Ethyl | Ethyl | 1 | 2-Cl-Phenyl |
| 250 | Ethyl | Ethyl | 2 | 2-Cl-Phenyl |
| 251 | Ethyl | Ethyl | 3 | 2-Cl-Phenyl |
| 252 | Ethyl | Ethyl | 4 | 2-Cl-Phenyl |
| 253 | Ethyl | Ethyl | 1 | 4-Br-Phenyl |
| 254 | Ethyl | Ethyl | 2 | 4-Br-Phenyl |
| 255 | Ethyl | Ethyl | 3 | 4-Br-Phenyl |
| 256 | Ethyl | Ethyl | 4 | 4-Br-Phenyl |
| 257 | Ethyl | Ethyl | 1 | 3-Br-Phenyl |
| 258 | Ethyl | Ethyl | 2 | 3-Br-Phenyl |
| 259 | Ethyl | Ethyl | 3 | 3-Br-Phenyl |
| 260 | Ethyl | Ethyl | 4 | 3-Br-Phenyl |
| 261 | Ethyl | Ethyl | 1 | 2-Br-Phenyl |
| 262 | Ethyl | Ethyl | 2 | 2-Br-Phenyl |
| 263 | Ethyl | Ethyl | 3 | 2-Br-Phenyl |
| 264 | Ethyl | Ethyl | 4 | 2-Br-Phenyl |
| 265 | Ethyl | Ethyl | 1 | 4-$CF_3$-Phenyl |
| 266 | Ethyl | Ethyl | 2 | 4-$CF_3$-Phenyl |
| 267 | Ethyl | Ethyl | 3 | 4-$CF_3$-Phenyl |
| 268 | Ethyl | Ethyl | 4 | 4-$CF_3$-Phenyl |
| 269 | Ethyl | Ethyl | 1 | 3-$CF_3$-Phenyl |
| 270 | Ethyl | Ethyl | 2 | 3-$CF_3$-Phenyl |
| 271 | Ethyl | Ethyl | 3 | 3-$CF_3$-Phenyl |
| 272 | Ethyl | Ethyl | 4 | 3-$CF_3$-Phenyl |
| 273 | Ethyl | Ethyl | 1 | 2-$CF_3$-Phenyl |
| 274 | Ethyl | Ethyl | 2 | 2-$CF_3$-Phenyl |
| 275 | Ethyl | Ethyl | 3 | 2-$CF_3$-Phenyl |
| 276 | Ethyl | Ethyl | 4 | 2-$CF_3$-Phenyl |

TABLE 11-continued

| Entry | $R^1$ | $R^2$ | n | $R^5$ |
|---|---|---|---|---|
| 277 | Ethyl | Ethyl | 1 | 4-iPr-Phenyl |
| 278 | Ethyl | Ethyl | 2 | 4-iPr-Phenyl |
| 279 | Ethyl | Ethyl | 3 | 4-iPr-Phenyl |
| 280 | Ethyl | Ethyl | 4 | 4-iPr-Phenyl |
| 281 | Ethyl | Ethyl | 1 | 3-iPr-Phenyl |
| 282 | Ethyl | Ethyl | 2 | 3-iPr-Phenyl |
| 283 | Ethyl | Ethyl | 3 | 3-iPr-Phenyl |
| 284 | Ethyl | Ethyl | 4 | 3-iPr-Phenyl |
| 285 | Ethyl | Ethyl | 1 | 2-iPr-Phenyl |
| 286 | Ethyl | Ethyl | 2 | 2-iPr-Phenyl |
| 287 | Ethyl | Ethyl | 3 | 2-iPr-Phenyl |
| 288 | Ethyl | Ethyl | 4 | 2-iPr-Phenyl |
| 289 | Ethyl | Ethyl | 1 | 4-$NH_2$-Phenyl |
| 290 | Ethyl | Ethyl | 2 | 4-$NH_2$-Phenyl |
| 291 | Ethyl | Ethyl | 3 | 4-$NH_2$-Phenyl |
| 292 | Ethyl | Ethyl | 4 | 4-$NH_2$-Phenyl |
| 293 | Ethyl | Ethyl | 1 | 3-$NH_2$-Phenyl |
| 294 | Ethyl | Ethyl | 2 | 3-$NH_2$-Phenyl |
| 295 | Ethyl | Ethyl | 3 | 3-$NH_2$-Phenyl |
| 296 | Ethyl | Ethyl | 4 | 3-$NH_2$-Phenyl |
| 297 | Ethyl | Ethyl | 1 | 2-$NH_2$-Phenyl |
| 298 | Ethyl | Ethyl | 2 | 2-$NH_2$-Phenyl |
| 299 | Ethyl | Ethyl | 3 | 2-$NH_2$-Phenyl |
| 300 | Ethyl | Ethyl | 4 | 2-$NH_2$-Phenyl |
| 301 | Ethyl | Ethyl | 1 | 2.3-di-Me-Phenvl |
| 302 | Ethyl | Ethyl | 2 | 2.3-di-Me-Phenyl |
| 303 | Ethyl | Ethyl | 3 | 2,3-di-Me-Phenyl |
| 304 | Ethyl | Ethyl | 4 | 2,3-di-Me-Phenyl |
| 305 | Ethyl | Ethyl | 1 | 2.4-di-Me-Phenyl |
| 306 | Ethyl | Ethyl | 2 | 2,4-di-Me-Phenyl |
| 307 | Ethyl | Ethyl | 3 | 2,4-di-Me-Phenyl |
| 308 | Ethyl | Ethyl | 4 | 2,4-di-Me-Phenyl |
| 309 | Ethyl | Ethyl | 1 | 2,5-di-Me-Phenyl |
| 310 | Ethyl | Ethyl | 2 | 2,5-di-Me-Phenyl |
| 311 | Ethyl | Ethyl | 3 | 2,5-di-Me-Phenyl |
| 312 | Ethyl | Ethyl | 4 | 2,5-di-Me-Phenyl |
| 313 | Ethyl | Ethyl | 1 | 2,6-di-Me-Phenyl |
| 314 | Ethyl | Ethyl | 2 | 2,6-di-Me-Phenyl |
| 315 | Ethyl | Ethyl | 3 | 2,6-di-Me-Phenyl |
| 316 | Ethyl | Ethyl | 4 | 2,6-di-Me-Phenyl |
| 317 | Ethyl | Ethyl | 1 | 2,6-di-iPr-Phenyl |
| 318 | Ethyl | Ethyl | 2 | 2,6-di-iPr-Phenyl |
| 319 | Ethyl | Ethyl | 3 | 2,6-di-iPr-Phenyl |
| 320 | Ethyl | Ethyl | 4 | 2,6-di-iPr-Phenyl |
| 321 | Ethyl | Ethyl | 1 | 2-morpholino-phenyl |
| 322 | Ethyl | Ethyl | 2 | 2-morpholino-phenyl |
| 323 | Ethyl | Ethyl | 3 | 2-morpholino-phenyl |
| 324 | Ethyl | Ethyl | 4 | 2-morpholino-phenyl |
| 325 | Ethyl | Ethyl | 1 | 3-morpholino-phenyl |
| 326 | Ethyl | Ethyl | 2 | 3-morpholino-phenyl |
| 327 | Ethyl | Ethyl | 3 | 3-morpholino-phenyl |
| 328 | Ethyl | Ethyl | 4 | 3-morpholino-phenyl |
| 329 | Ethyl | Ethyl | 1 | 4-morpholino-phenyl |
| 330 | Ethyl | Ethyl | 2 | 4-morpholino-phenyl |
| 331 | Ethyl | Ethyl | 3 | 4-morpholino-phenyl |
| 332 | Ethyl | Ethyl | 4 | 4-morpholino-phenyl |
| 333 | Ethyl | Ethyl | 1 | 4-CN-2-morpholino-phenyl |
| 334 | Ethyl | Ethyl | 2 | 4-CN-2-morpholino-phenyl |
| 335 | Ethyl | Ethyl | 3 | 4-CN-2-morpholino-phenyl |
| 336 | Ethyl | Ethyl | 4 | 4-CN-2-morpholino-phenyl |
| 337 | Ethyl | Ethyl | 1 | 4-$CH_3$-2-morpholino-phenyl |
| 338 | Ethyl | Ethyl | 2 | 4-$CH_3$-2-morpholino-phenyl |
| 339 | Ethyl | Ethyl | 3 | 4-$CH_3$-2-morpholino-phenyl |
| 340 | Ethyl | Ethyl | 4 | 4-$CH_3$-2-morpholino-phenyl |
| 341 | Ethyl | Ethyl | 1 | 4-OH-2-morpholino-phenyl |
| 342 | Ethyl | Ethyl | 2 | 4-OH-2-morpholino-phenyl |
| 343 | Ethyl | Ethyl | 3 | 4-OH-2-morpholino-phenyl |
| 344 | Ethyl | Ethyl | 4 | 4-OH-2-morpholino-phenyl |
| 345 | Ethyl | Ethyl | 1 | naphthylen-1-yl |
| 346 | Ethyl | Ethyl | 2 | naphthylen-1-yl |
| 347 | Ethyl | Ethyl | 3 | naphthylen-1-yl |
| 348 | Ethyl | Ethyl | 4 | naphthylen-1-yl |
| 349 | Ethyl | Ethyl | 1 | naphthylen-2-yl |
| 350 | Ethyl | Ethyl | 2 | naphthylen-2-yl |
| 351 | Ethyl | Ethyl | 3 | naphthylen-2-yl |
| 352 | Ethyl | Ethyl | 4 | naphthylen-2-yl |

Exemplary embodiments include compounds having the formula (XVIII)

(XVIII)

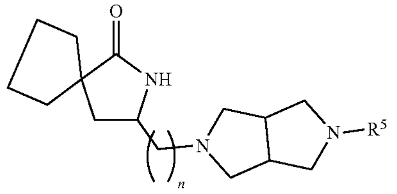

or a pharmaceutically acceptable salt form thereof defined herein below in Table 12

TABLE 12

| Entry | n | $R^5$ | Entry | n | $R^5$ |
|---|---|---|---|---|---|
| 1 | 1 | Phenyl | 85 | 1 | 2-Br-Phenyl |
| 2 | 2 | Phenyl | 86 | 2 | 2-Br-Phenyl |
| 3 | 3 | Phenyl | 87 | 3 | 2-Br-Phenyl |
| 4 | 4 | Phenyl | 88 | 4 | 2-Br-Phenyl |
| 5 | 1 | 4-OH-Phenyl | 89 | 1 | 4-$CF_3$-Phenyl |
| 6 | 2 | 4-OH-Phenyl | 90 | 2 | 4-$CF_3$-Phenyl |
| 7 | 3 | 4-OH-Phenyl | 91 | 3 | 4-$CF_3$-Phenyl |
| 8 | 4 | 4-OH-Phenyl | 92 | 4 | 4-$CF_3$-Phenyl |
| 9 | 1 | 3-OH-Phenyl | 93 | 1 | 3-$CF_3$-Phenyl |
| 10 | 2 | 3-OH-Phenyl | 94 | 2 | 3-$CF_3$-Phenyl |
| 11 | 3 | 3-OH-Phenyl | 95 | 3 | 3-$CF_3$-Phenyl |
| 12 | 4 | 3-OH-Phenyl | 96 | 4 | 3-$CF_3$-Phenyl |
| 13 | 1 | 2-OH-Phenyl | 97 | 1 | 2-$CF_3$-Phenyl |
| 14 | 2 | 2-OH-Phenyl | 98 | 2 | 2-$CF_3$-Phenyl |
| 15 | 3 | 2-OH-Phenyl | 99 | 3 | 2-$CF_3$-Phenyl |
| 16 | 4 | 2-OH-Phenyl | 100 | 4 | 2-$CF_3$-Phenyl |
| 17 | 1 | 4-OMe-Phenyl | 101 | 1 | 4-iPr-Phenyl |
| 18 | 2 | 4-OMe-Phenyl | 102 | 2 | 4-iPr-Phenyl |
| 19 | 3 | 4-OMe-Phenyl | 103 | 3 | 4-iPr-Phenyl |
| 20 | 4 | 4-OMe-Phenyl | 104 | 4 | 4-iPr-Phenyl |
| 21 | 1 | 3-OMe-Phenyl | 105 | 1 | 3-iPr-Phenyl |
| 22 | 2 | 3-OMe-Phenyl | 106 | 2 | 3-iPr-Phenyl |
| 23 | 3 | 3-OMe-Phenyl | 107 | 3 | 3-iPr-Phenyl |
| 24 | 4 | 3-OMe-Phenyl | 108 | 4 | 3-iPr-Phenyl |
| 25 | 1 | 2-OMe-Phenyl | 109 | 1 | 2-iPr-Phenyl |
| 26 | 2 | 2-OMe-Phenyl | 110 | 2 | 2-iPr-Phenyl |
| 27 | 3 | 2-OMe-Phenyl | 111 | 3 | 2-iPr-Phenyl |
| 28 | 4 | 2-OMe-Phenyl | 112 | 4 | 2-iPr-Phenyl |
| 29 | 1 | 4-CN-Phenyl | 113 | 1 | 4-$NH_2$-Phenyl |
| 30 | 2 | 4-CN-Phenyl | 114 | 2 | 4-$NH_2$-Phenyl |
| 31 | 3 | 4-CN-Phenyl | 115 | 3 | 4-$NH_2$-Phenyl |
| 32 | 4 | 4-CN-Phenyl | 116 | 4 | 4-$NH_2$-Phenyl |
| 33 | 1 | 3-CN-Phenyl | 117 | 1 | 3-$NH_2$-Phenyl |
| 34 | 2 | 3-CN-Phenyl | 118 | 2 | 3-$NH_2$-Phenyl |
| 35 | 3 | 3-CN-Phenyl | 119 | 3 | 3-$NH_2$-Phenyl |
| 36 | 4 | 3-CN-Phenyl | 120 | 4 | 3-$NH_2$-Phenyl |
| 37 | 1 | 2-CN-Phenyl | 121 | 1 | 2-$NH_2$-Phenyl |
| 38 | 2 | 2-CN-Phenyl | 122 | 2 | 2-$NH_2$-Phenyl |
| 39 | 3 | 2-CN-Phenyl | 123 | 3 | 2-$NH_2$-Phenyl |
| 40 | 4 | 2-CN-Phenyl | 124 | 4 | 2-$NH_2$-Phenyl |
| 41 | 1 | 4-Me-Phenyl | 125 | 1 | 2,3-di-Me-Phenyl |
| 42 | 2 | 4-Me-Phenyl | 126 | 2 | 2,3-di-Me-Phenyl |
| 43 | 3 | 4-Me-Phenyl | 127 | 3 | 2,3-di-Me-Phenyl |
| 44 | 4 | 4-Me-Phenyl | 128 | 4 | 2,3-di-Me-Phenyl |
| 45 | 1 | 3-Me-Phenyl | 129 | 1 | 2,4-di-Me-Phenyl |
| 46 | 2 | 3-Me-Phenyl | 130 | 2 | 2,4-di-Me-Phenyl |
| 47 | 3 | 3-Me-Phenyl | 131 | 3 | 2,4-di-Me-Phenyl |
| 48 | 4 | 3-Me-Phenyl | 132 | 4 | 2,4-di-Me-Phenyl |
| 49 | 1 | 2-Me-Phenyl | 133 | 1 | 2,5-di-Me-Phenyl |
| 50 | 2 | 2-Me-Phenyl | 134 | 2 | 2,5-di-Me-Phenyl |
| 51 | 3 | 2-Me-Phenyl | 135 | 3 | 2,5-di-Me-Phenyl |
| 52 | 4 | 2-Me-Phenyl | 136 | 4 | 2,5-di-Me-Phenyl |
| 53 | 1 | 4-F-Phenyl | 137 | 1 | 2,6-di-Me-Phenyl |
| 54 | 2 | 4-F-Phenyl | 138 | 2 | 2,6-di-Me-Phenyl |
| 55 | 3 | 4-F-Phenyl | 139 | 3 | 2,6-di-Me-Phenyl |
| 56 | 4 | 4-F-Phenyl | 140 | 4 | 2,6-di-Me-Phenyl |
| 57 | 1 | 3-F-Phenyl | 141 | 1 | 2,6-di-iPr-Phenyl |

TABLE 12-continued

| Entry | n | $R^5$ | Entry | n | $R^5$ |
|---|---|---|---|---|---|
| 58 | 2 | 3-F-Phenyl | 142 | 2 | 2,6-di-iPr-Phenyl |
| 59 | 3 | 3-F-Phenyl | 143 | 3 | 2,6-di-iPr-Phenyl |
| 60 | 4 | 3-F-Phenyl | 144 | 4 | 2,6-di-iPr-Phenyl |
| 61 | 1 | 2-F-Phenyl | 145 | 1 | 2-morpholino-phenyl |
| 62 | 2 | 2-F-Phenyl | 146 | 2 | 2-morpholino-phenyl |
| 63 | 3 | 2-F-Phenyl | 147 | 3 | 2-morpholino-phenyl |
| 64 | 4 | 2-F-Phenyl | 148 | 4 | 2-morpholino-phenyl |
| 65 | 1 | 4-Cl-Phenyl | 149 | 1 | 3-morpholino-phenyl |
| 66 | 2 | 4-Cl-Phenyl | 150 | 2 | 3-morpholino-phenyl |
| 67 | 3 | 4-Cl-Phenyl | 151 | 3 | 3-morpholino-phenyl |
| 68 | 4 | 4-Cl-Phenyl | 152 | 4 | 3-morpholino-phenyl |
| 69 | 1 | 3-Cl-Phenyl | 153 | 1 | 4-morpholino-phenyl |
| 70 | 2 | 3-Cl-Phenyl | 154 | 2 | 4-morpholino-phenyl |
| 71 | 3 | 3-Cl-Phenyl | 155 | 3 | 4-morpholino-phenyl |
| 72 | 4 | 3-Cl-Phenyl | 156 | 4 | 4-morpholino-phenyl |
| 73 | 1 | 2-Cl-Phenyl | 157 | 1 | 4-CN-2-morpholino-phenyl |
| 74 | 2 | 2-Cl-Phenyl | 158 | 2 | 4-CN-2-morpholino-phenyl |
| 75 | 3 | 2-Cl-Phenyl | 159 | 3 | 4-CN-2-morpholino-phenyl |
| 76 | 4 | 2-Cl-Phenyl | 160 | 4 | 4-CN-2-morpholino-phenyl |
| 77 | 1 | 4-Br-Phenyl | 161 | 1 | 4-$CH_3$-2-morpholino-phenyl |
| 78 | 2 | 4-Br-Phenyl | 162 | 2 | 4-$CH_3$-2-morpholino-phenyl |
| 79 | 3 | 4-Br-Phenyl | 163 | 3 | 4-$CH_3$-2-morpholino-phenyl |
| 80 | 4 | 4-Br-Phenyl | 164 | 4 | 4-$CH_3$-2-morpholino-phenyl |
| 81 | 1 | 3-Br-Phenyl | 165 | 1 | 4-OH-2-morpholino-phenyl |
| 82 | 2 | 3-Br-Phenyl | 166 | 2 | 4-OH-2-morpholino-phenyl |
| 83 | 3 | 3-Br-Phenyl | 167 | 3 | 4-OH-2-morpholino-phenyl |
| 84 | 4 | 3-Br-Phenyl | 168 | 4 | 4-OH-2-morpholino-phenyl |
| 85 | 1 | naphthylen-1-yl | 173 | 1 | naphthylen-2-yl |
| 86 | 2 | naphthylen-1-yl | 174 | 2 | naphthylen-2-yl |
| 87 | 3 | naphthylen-1-yl | 175 | 3 | naphthylen-2-yl |
| 88 | 4 | naphthylen-1-yl | 176 | 4 | naphthylen-2-yl |

Exemplary embodiments include compounds having the formula (XIX)

(XIX)

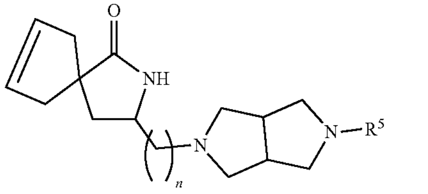

or a pharmaceutically acceptable salt form thereof defined herein below in Table 13.

TABLE 13

| Entry | n | $R^5$ | Entry | n | $R^5$ |
|---|---|---|---|---|---|
| 1 | 1 | Phenyl | 85 | 1 | 2-Br-Phenyl |
| 2 | 2 | Phenyl | 86 | 2 | 2-Br-Phenyl |
| 3 | 3 | Phenyl | 87 | 3 | 2-Br-Phenyl |
| 4 | 4 | Phenyl | 88 | 4 | 2-Br-Phenyl |
| 5 | 1 | 4-OH-Phenyl | 89 | 1 | 4-$CF_3$-Phenyl |
| 6 | 2 | 4-OH-Phenyl | 90 | 2 | 4-$CF_3$-Phenyl |
| 7 | 3 | 4-OH-Phenyl | 91 | 3 | 4-$CF_3$-Phenyl |
| 8 | 4 | 4-OH-Phenyl | 92 | 4 | 4-$CF_3$-Phenyl |
| 9 | 1 | 3-OH-Phenyl | 93 | 1 | 3-$CF_3$-Phenyl |
| 10 | 2 | 3-OH-Phenyl | 94 | 2 | 3-$CF_3$-Phenyl |
| 11 | 3 | 3-OH-Phenyl | 95 | 3 | 3-$CF_3$-Phenyl |
| 12 | 4 | 3-OH-Phenyl | 96 | 4 | 3-$CF_3$-Phenyl |
| 13 | 1 | 2-OH-Phenyl | 97 | 1 | 2-$CF_3$-Phenyl |
| 14 | 2 | 2-OH-Phenyl | 98 | 2 | 2-$CF_3$-Phenyl |
| 15 | 3 | 2-OH-Phenyl | 99 | 3 | 2-$CF_3$-Phenyl |
| 16 | 4 | 2-OH-Phenyl | 100 | 4 | 2-$CF_3$-Phenyl |
| 17 | 1 | 4-OMe-Phenyl | 101 | 1 | 4-iPr-Phenyl |
| 18 | 2 | 4-OMe-Phenyl | 102 | 2 | 4-iPr-Phenyl |
| 19 | 3 | 4-OMe-Phenyl | 103 | 3 | 4-iPr-Phenyl |
| 20 | 4 | 4-OMe-Phenyl | 104 | 4 | 4-iPr-Phenyl |

TABLE 13-continued

| Entry | n | $R^5$ | Entry | n | $R^5$ |
|---|---|---|---|---|---|
| 21 | 1 | 3-OMe-Phenyl | 105 | 1 | 3-iPr-Phenyl |
| 22 | 2 | 3-OMe-Phenyl | 106 | 2 | 3-iPr-Phenyl |
| 23 | 3 | 3-OMe-Phenyl | 107 | 3 | 3-iPr-Phenyl |
| 24 | 4 | 3-OMe-Phenyl | 108 | 4 | 3-iPr-Phenyl |
| 25 | 1 | 2-OMe-Phenyl | 109 | 1 | 2-iPr-Phenyl |
| 26 | 2 | 2-OMe-Phenyl | 110 | 2 | 2-iPr-Phenyl |
| 27 | 3 | 2-OMe-Phenyl | 111 | 3 | 2-iPr-Phenyl |
| 28 | 4 | 2-OMe-Phenyl | 112 | 4 | 2-iPr-Phenyl |
| 29 | 1 | 4-CN-Phenyl | 113 | 1 | 4-$NH_2$-Phenyl |
| 30 | 2 | 4-CN-Phenyl | 114 | 2 | 4-$NH_2$-Phenyl |
| 31 | 3 | 4-CN-Phenyl | 115 | 3 | 4-$NH_2$-Phenyl |
| 32 | 4 | 4-CN-Phenyl | 116 | 4 | 4-$NH_2$-Phenyl |
| 33 | 1 | 3-CN-Phenyl | 117 | 1 | 3-$NH_2$-Phenyl |
| 34 | 2 | 3-CN-Phenyl | 118 | 2 | 3-$NH_2$-Phenyl |
| 35 | 3 | 3-CN-Phenyl | 119 | 3 | 3-$NH_2$-Phenyl |
| 36 | 4 | 3-CN-Phenyl | 120 | 4 | 3-$NH_2$-Phenyl |
| 37 | 1 | 2-CN-Phenyl | 121 | 1 | 2-$NH_2$-Phenyl |
| 38 | 2 | 2-CN-Phenyl | 122 | 2 | 2-$NH_2$-Phenyl |
| 39 | 3 | 2-CN-Phenyl | 123 | 3 | 2-$NH_2$-Phenyl |
| 40 | 4 | 2-CN-Phenyl | 124 | 4 | 2-$NH_2$-Phenyl |
| 41 | 1 | 4-Me-Phenyl | 125 | 1 | 2,3-di-Me-Phenyl |
| 42 | 2 | 4-Me-Phenyl | 126 | 2 | 2,3-di-Me-Phenyl |
| 43 | 3 | 4-Me-Phenyl | 127 | 3 | 2,3-di-Me-Phenyl |
| 44 | 4 | 4-Me-Phenyl | 128 | 4 | 2,3-di-Me-Phenyl |
| 45 | 1 | 3-Me-Phenyl | 129 | 1 | 2,4-di-Me-Phenyl |
| 46 | 2 | 3-Me-Phenyl | 130 | 2 | 2,4-di-Me-Phenyl |
| 47 | 3 | 3-Me-Phenyl | 131 | 3 | 2,4-di-Me-Phenyl |
| 48 | 4 | 3-Me-Phenyl | 132 | 4 | 2,4-di-Me-Phenyl |
| 49 | 1 | 2-Me-Phenyl | 133 | 1 | 2,5-di-Me-Phenyl |
| 50 | 2 | 2-Me-Phenyl | 134 | 2 | 2,5-di-Me-Phenyl |
| 51 | 3 | 2-Me-Phenyl | 135 | 3 | 2,5-di-Me-Phenyl |
| 52 | 4 | 2-Me-Phenyl | 136 | 4 | 2,5-di-Me-Phenyl |
| 53 | 1 | 4-F-Phenyl | 137 | 1 | 2,6-di-Me-Phenyl |
| 54 | 2 | 4-F-Phenyl | 138 | 2 | 2,6-di-Me-Phenyl |
| 55 | 3 | 4-F-Phenyl | 139 | 3 | 2,6-di-Me-Phenyl |
| 56 | 4 | 4-F-Phenyl | 140 | 4 | 2,6-di-Me-Phenyl |
| 57 | 1 | 3-F-Phenyl | 141 | 1 | 2,6-di-iPr-Phenyl |
| 58 | 2 | 3-F-Phenyl | 142 | 2 | 2,6-di-iPr-Phenyl |
| 59 | 3 | 3-F-Phenyl | 143 | 3 | 2,6-di-iPr-Phenyl |
| 60 | 4 | 3-F-Phenyl | 144 | 4 | 2,6-di-iPr-Phenyl |
| 61 | 1 | 2-F-Phenyl | 145 | 1 | 2-morpholino-phenyl |
| 62 | 2 | 2-F-Phenyl | 146 | 2 | 2-morpholino-phenyl |
| 63 | 3 | 2-F-Phenyl | 147 | 3 | 2-morpholino-phenyl |
| 64 | 4 | 2-F-Phenyl | 148 | 4 | 2-morpholino-phenyl |
| 65 | 1 | 4-Cl-Phenyl | 149 | 1 | 3-morpholino-phenyl |
| 66 | 2 | 4-Cl-Phenyl | 150 | 2 | 3-morpholino-phenyl |
| 67 | 3 | 4-Cl-Phenyl | 151 | 3 | 3-morpholino-phenyl |
| 68 | 4 | 4-Cl-Phenyl | 152 | 4 | 3-morpholino-phenyl |
| 69 | 1 | 3-Cl-Phenyl | 153 | 1 | 4-morpholino-phenyl |
| 70 | 2 | 3-Cl-Phenyl | 154 | 2 | 4-morpholino-phenyl |
| 71 | 3 | 3-Cl-Phenyl | 155 | 3 | 4-morpholino-phenyl |
| 72 | 4 | 3-Cl-Phenyl | 156 | 4 | 4-morpholino-phenyl |
| 73 | 1 | 2-Cl-Phenyl | 157 | 1 | 4-CN-2-morpholino-phenyl |
| 74 | 2 | 2-Cl-Phenyl | 158 | 2 | 4-CN-2-morpholino-phenyl |
| 75 | 3 | 2-Cl-Phenyl | 159 | 3 | 4-CN-2-morpholino-phenyl |
| 76 | 4 | 2-Cl-Phenyl | 160 | 4 | 4-CN-2-morpholino-phenyl |
| 77 | 1 | 4-Br-Phenyl | 161 | 1 | 4-$CH_3$-2-morpholino-phenyl |
| 78 | 2 | 4-Br-Phenyl | 162 | 2 | 4-$CH_3$-2-morpholino-phenyl |
| 79 | 3 | 4-Br-Phenyl | 163 | 3 | 4-$CH_3$-2-morpholino-phenyl |
| 80 | 4 | 4-Br-Phenyl | 164 | 4 | 4-$CH_3$-2-morpholino-phenyl |
| 81 | 1 | 3-Br-Phenyl | 165 | 1 | 4-OH-2-morpholino-phenyl |
| 82 | 2 | 3-Br-Phenyl | 166 | 2 | 4-OH-2-morpholino-phenyl |
| 83 | 3 | 3-Br-Phenyl | 167 | 3 | 4-OH-2-morpholino-phenyl |
| 84 | 4 | 3-Br-Phenyl | 168 | 4 | 4-OH-2-morpholino-phenyl |
| 85 | 1 | naphthylen-1-yl | 173 | 1 | naphthylen-2-yl |
| 86 | 2 | naphthylen-1-yl | 174 | 2 | naphthylen-2-yl |
| 87 | 3 | naphthylen-1-yl | 175 | 3 | naphthylen-2-yl |
| 88 | 4 | naphthylen-1-yl | 176 | 4 | naphthylen-2-yl |

Exemplary embodiments include compounds having the formula (XX)

(XX)

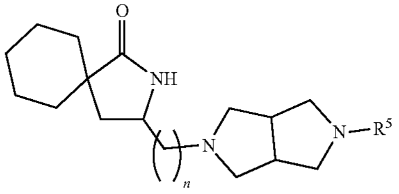

or a pharmaceutically acceptable salt form thereof defined herein below in Table 14.

TABLE 14

| Entry | n | $R^5$ | Entry | n | $R^5$ |
|---|---|---|---|---|---|
| 1 | 1 | Phenyl | 85 | 1 | 2-Br-Phenyl |
| 2 | 2 | Phenyl | 86 | 2 | 2-Br-Phenyl |
| 3 | 3 | Phenyl | 87 | 3 | 2-Br-Phenyl |
| 4 | 4 | Phenyl | 88 | 4 | 2-Br-Phenyl |
| 5 | 1 | 4-OH-Phenyl | 89 | 1 | 4-$CF_3$-Phenyl |
| 6 | 2 | 4-OH-Phenyl | 90 | 2 | 4-$CF_3$-Phenyl |
| 7 | 3 | 4-OH-Phenyl | 91 | 3 | 4-$CF_3$-Phenyl |
| 8 | 4 | 4-OH-Phenyl | 92 | 4 | 4-$CF_3$-Phenyl |
| 9 | 1 | 3-OH-Phenyl | 93 | 1 | 3-$CF_3$-Phenyl |
| 10 | 2 | 3-OH-Phenyl | 94 | 2 | 3-$CF_3$-Phenyl |
| 11 | 3 | 3-OH-Phenyl | 95 | 3 | 3-$CF_3$-Phenyl |
| 12 | 4 | 3-OH-Phenyl | 96 | 4 | 3-$CF_3$-Phenyl |
| 13 | 1 | 2-OH-Phenyl | 97 | 1 | 2-$CF_3$-Phenyl |
| 14 | 2 | 2-OH-Phenyl | 98 | 2 | 2-$CF_3$-Phenyl |
| 15 | 3 | 2-OH-Phenyl | 99 | 3 | 2-$CF_3$-Phenyl |
| 16 | 4 | 2-OH-Phenyl | 100 | 4 | 2-$CF_3$-Phenyl |
| 17 | 1 | 4-OMe-Phenyl | 101 | 1 | 4-iPr-Phenyl |
| 18 | 2 | 4-OMe-Phenyl | 102 | 2 | 4-iPr-Phenyl |
| 19 | 3 | 4-OMe-Phenyl | 103 | 3 | 4-iPr-Phenyl |
| 20 | 4 | 4-OMe-Phenyl | 104 | 4 | 4-iPr-Phenyl |
| 21 | 1 | 3-OMe-Phenyl | 105 | 1 | 3-iPr-Phenyl |
| 22 | 2 | 3-OMe-Phenyl | 106 | 2 | 3-iPr-Phenyl |
| 23 | 3 | 3-OMe-Phenyl | 107 | 3 | 3-iPr-Phenyl |
| 24 | 4 | 3-OMe-Phenyl | 108 | 4 | 3-iPr-Phenyl |
| 25 | 1 | 2-OMe-Phenyl | 109 | 1 | 2-iPr-Phenyl |
| 26 | 2 | 2-OMe-Phenyl | 110 | 2 | 2-iPr-Phenyl |
| 27 | 3 | 2-OMe-Phenyl | 111 | 3 | 2-iPr-Phenyl |
| 28 | 4 | 2-OMe-Phenyl | 112 | 4 | 2-iPr-Phenyl |
| 29 | 1 | 4-CN-Phenyl | 113 | 1 | 4-$NH_2$-Phenyl |
| 30 | 2 | 4-CN-Phenyl | 114 | 2 | 4-$NH_2$-Phenyl |
| 31 | 3 | 4-CN-Phenyl | 115 | 3 | 4-$NH_2$-Phenyl |
| 32 | 4 | 4-CN-Phenyl | 116 | 4 | 4-$NH_2$-Phenyl |
| 33 | 1 | 3-CN-Phenyl | 117 | 1 | 3-$NH_2$-Phenyl |
| 34 | 2 | 3-CN-Phenyl | 118 | 2 | 3-$NH_2$-Phenyl |
| 35 | 3 | 3-CN-Phenyl | 119 | 3 | 3-$NH_2$-Phenyl |
| 36 | 4 | 3-CN-Phenyl | 120 | 4 | 3-$NH_2$-Phenyl |
| 37 | 1 | 2-CN-Phenyl | 121 | 1 | 2-$NH_2$-Phenyl |
| 38 | 2 | 2-CN-Phenyl | 122 | 2 | 2-$NH_2$-Phenyl |
| 39 | 3 | 2-CN-Phenyl | 123 | 3 | 2-$NH_2$-Phenyl |
| 40 | 4 | 2-CN-Phenyl | 124 | 4 | 2-$NH_2$-Phenyl |
| 41 | 1 | 4-Me-Phenyl | 125 | 1 | 2,3-di-Me-Phenyl |
| 42 | 2 | 4-Me-Phenyl | 126 | 2 | 2,3-di-Me-Phenyl |
| 43 | 3 | 4-Me-Phenyl | 127 | 3 | 2,3-di-Me-Phenyl |
| 44 | 4 | 4-Me-Phenyl | 128 | 4 | 2,3-di-Me-Phenyl |
| 45 | 1 | 3-Me-Phenyl | 129 | 1 | 2,4-di-Me-Phenyl |
| 46 | 2 | 3-Me-Phenyl | 130 | 2 | 2,4-di-Me-Phenyl |
| 47 | 3 | 3-Me-Phenyl | 131 | 3 | 2,4-di-Me-Phenyl |
| 48 | 4 | 3-Me-Phenyl | 132 | 4 | 2,4-di-Me-Phenyl |
| 49 | 1 | 2-Me-Phenyl | 133 | 1 | 2,5-di-Me-Phenyl |
| 50 | 2 | 2-Me-Phenyl | 134 | 2 | 2,5-di-Me-Phenyl |
| 51 | 3 | 2-Me-Phenyl | 135 | 3 | 2,5-di-Me-Phenyl |
| 52 | 4 | 2-Me-Phenyl | 136 | 4 | 2,5-di-Me-Phenyl |
| 53 | 1 | 4-F-Phenyl | 137 | 1 | 2,6-di-Me-Phenyl |
| 54 | 2 | 4-F-Phenyl | 138 | 2 | 2,6-di-Me-Phenyl |
| 55 | 3 | 4-F-Phenyl | 139 | 3 | 2,6-di-Me-Phenyl |
| 56 | 4 | 4-F-Phenyl | 140 | 4 | 2,6-di-Me-Phenyl |
| 57 | 1 | 3-F-Phenyl | 141 | 1 | 2,6-di-iPr-Phenyl |
| 58 | 2 | 3-F-Phenyl | 142 | 2 | 2,6-di-iPr-Phenyl |
| 59 | 3 | 3-F-Phenyl | 143 | 3 | 2,6-di-iPr-Phenyl |
| 60 | 4 | 3-F-Phenyl | 144 | 4 | 2,6-di-iPr-Phenyl |
| 61 | 1 | 2-F-Phenyl | 145 | 1 | 2-morpholino-phenyl |

TABLE 14-continued

| Entry | n | $R^5$ | Entry | n | $R^5$ |
|---|---|---|---|---|---|
| 62 | 2 | 2-F-Phenyl | 146 | 2 | 2-morpholino-phenyl |
| 63 | 3 | 2-F-Phenyl | 147 | 3 | 2-morpholino-phenyl |
| 64 | 4 | 2-F-Phenyl | 148 | 4 | 2-morpholino-phenyl |
| 65 | 1 | 4-Cl-Phenyl | 149 | 1 | 3-morpholino-phenyl |
| 66 | 2 | 4-Cl-Phenyl | 150 | 2 | 3-morpholino-phenyl |
| 67 | 3 | 4-Cl-Phenyl | 151 | 3 | 3-morpholino-phenyl |
| 68 | 4 | 4-Cl-Phenyl | 152 | 4 | 3-morpholino-phenyl |
| 69 | 1 | 3-Cl-Phenyl | 153 | 1 | 4-morpholino-phenyl |
| 70 | 2 | 3-Cl-Phenyl | 154 | 2 | 4-morpholino-phenyl |
| 71 | 3 | 3-Cl-Phenyl | 155 | 3 | 4-morpholino-phenyl |
| 72 | 4 | 3-Cl-Phenyl | 156 | 4 | 4-morpholino-phenyl |
| 73 | 1 | 2-Cl-Phenyl | 157 | 1 | 4-CN-2-morpholino-phenyl |
| 74 | 2 | 2-Cl-Phenyl | 158 | 2 | 4-CN-2-morpholino-phenyl |
| 75 | 3 | 2-Cl-Phenyl | 159 | 3 | 4-CN-2-morpholino-phenyl |
| 76 | 4 | 2-Cl-Phenyl | 160 | 4 | 4-CN-2-morpholino-phenyl |
| 77 | 1 | 4-Br-Phenyl | 161 | 1 | 4-$CH_3$-2-morpholino-phenyl |
| 78 | 2 | 4-Br-Phenyl | 162 | 2 | 4-$CH_3$-2-morpholino-phenyl |
| 79 | 3 | 4-Br-Phenyl | 163 | 3 | 4-$CH_3$-2-morpholino-phenyl |
| 80 | 4 | 4-Br-Phenyl | 164 | 4 | 4-$CH_3$-2-morpholino-phenyl |
| 81 | 1 | 3-Br-Phenyl | 165 | 1 | 4-OH-2-morpholino-phenyl |
| 82 | 2 | 3-Br-Phenyl | 166 | 2 | 4-OH-2-morpholino-phenyl |
| 83 | 3 | 3-Br-Phenyl | 167 | 3 | 4-OH-2-morpholino-phenyl |
| 84 | 4 | 3-Br-Phenyl | 168 | 4 | 4-OH-2-morpholino-phenyl |
| 85 | 1 | naphthylen-1-yl | 173 | 1 | naphthylen-2-yl |
| 86 | 2 | naphthylen-1-yl | 174 | 2 | naphthylen-2-yl |
| 87 | 3 | naphthylen-1-yl | 175 | 3 | naphthylen-2-yl |
| 88 | 4 | naphthylen-1-yl | 176 | 4 | naphthylen-2-yl |

Exemplary embodiments include compounds having the formula (XXI)

(XXI)

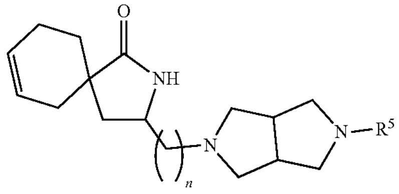

or a pharmaceutically acceptable salt form thereof defined herein below in Table 15.

TABLE 15

| Entry | n | $R^5$ | Entry | n | $R^5$ |
|---|---|---|---|---|---|
| 1 | 1 | Phenyl | 85 | 1 | 2-Br-Phenyl |
| 2 | 2 | Phenyl | 86 | 2 | 2-Br-Phenyl |
| 3 | 3 | Phenyl | 87 | 3 | 2-Br-Phenyl |
| 4 | 4 | Phenyl | 88 | 4 | 2-Br-Phenyl |
| 5 | 1 | 4-OH-Phenyl | 89 | 1 | 4-$CF_3$-Phenyl |
| 6 | 2 | 4-OH-Phenyl | 90 | 2 | 4-$CF_3$-Phenyl |
| 7 | 3 | 4-OH-Phenyl | 91 | 3 | 4-$CF_3$-Phenyl |
| 8 | 4 | 4-OH-Phenyl | 92 | 4 | 4-$CF_3$-Phenyl |
| 9 | 1 | 3-OH-Phenyl | 93 | 1 | 3-$CF_3$-Phenyl |
| 10 | 2 | 3-OH-Phenyl | 94 | 2 | 3-$CF_3$-Phenyl |
| 11 | 3 | 3-OH-Phenyl | 95 | 3 | 3-$CF_3$-Phenyl |
| 12 | 4 | 3-OH-Phenyl | 96 | 4 | 3-$CF_3$-Phenyl |
| 13 | 1 | 2-OH-Phenyl | 97 | 1 | 2-$CF_3$-Phenyl |
| 14 | 2 | 2-OH-Phenyl | 98 | 2 | 2-$CF_3$-Phenyl |
| 15 | 3 | 2-OH-Phenyl | 99 | 3 | 2-$CF_3$-Phenyl |
| 16 | 4 | 2-OH-Phenyl | 100 | 4 | 2-$CF_3$-Phenyl |
| 17 | 1 | 4-OMe-Phenyl | 101 | 1 | 4-iPr-Phenyl |
| 18 | 2 | 4-OMe-Phenyl | 102 | 2 | 4-iPr-Phenyl |
| 19 | 3 | 4-OMe-Phenyl | 103 | 3 | 4-iPr-Phenyl |
| 20 | 4 | 4-OMe-Phenyl | 104 | 4 | 4-iPr-Phenyl |
| 21 | 1 | 3-OMe-Phenyl | 105 | 1 | 3-iPr-Phenyl |
| 22 | 2 | 3-OMe-Phenyl | 106 | 2 | 3-iPr-Phenyl |
| 23 | 3 | 3-OMe-Phenyl | 107 | 3 | 3-iPr-Phenyl |
| 24 | 4 | 3-OMe-Phenyl | 108 | 4 | 3-iPr-Phenyl |

TABLE 15-continued

| Entry | n | $R^5$ | Entry | n | $R^5$ |
|---|---|---|---|---|---|
| 25 | 1 | 2-OMe-Phenyl | 109 | 1 | 2-iPr-Phenyl |
| 26 | 2 | 2-OMe-Phenyl | 110 | 2 | 2-iPr-Phenyl |
| 27 | 3 | 2-OMe-Phenyl | 111 | 3 | 2-iPr-Phenyl |
| 28 | 4 | 2-OMe-Phenyl | 112 | 4 | 2-iPr-Phenyl |
| 29 | 1 | 4-CN-Phenyl | 113 | 1 | 4-$NH_2$-Phenyl |
| 30 | 2 | 4-CN-Phenyl | 114 | 2 | 4-$NH_2$-Phenyl |
| 31 | 3 | 4-CN-Phenyl | 115 | 3 | 4-$NH_2$-Phenyl |
| 32 | 4 | 4-CN-Phenyl | 116 | 4 | 4-$NH_2$-Phenyl |
| 33 | 1 | 3-CN-Phenyl | 117 | 1 | 3-$NH_2$-Phenyl |
| 34 | 2 | 3-CN-Phenyl | 118 | 2 | 3-$NH_2$-Phenyl |
| 35 | 3 | 3-CN-Phenyl | 119 | 3 | 3-$NH_2$-Phenyl |
| 36 | 4 | 3-CN-Phenyl | 120 | 4 | 3-$NH_2$-Phenyl |
| 37 | 1 | 2-CN-Phenyl | 121 | 1 | 2-$NH_2$-Phenyl |
| 38 | 2 | 2-CN-Phenyl | 122 | 2 | 2-$NH_2$-Phenyl |
| 39 | 3 | 2-CN-Phenyl | 123 | 3 | 2-$NH_2$-Phenyl |
| 40 | 4 | 2-CN-Phenyl | 124 | 4 | 2-$NH_2$-Phenyl |
| 41 | 1 | 4-Me-Phenyl | 125 | 1 | 2,3-di-Me-Phenyl |
| 42 | 2 | 4-Me-Phenyl | 126 | 2 | 2,3-di-Me-Phenyl |
| 43 | 3 | 4-Me-Phenyl | 127 | 3 | 2,3-di-Me-Phenyl |
| 44 | 4 | 4-Me-Phenyl | 128 | 4 | 2,3-di-Me-Phenyl |
| 45 | 1 | 3-Me-Phenyl | 129 | 1 | 2,4-di-Me-Phenyl |
| 46 | 2 | 3-Me-Phenyl | 130 | 2 | 2,4-di-Me-Phenyl |
| 47 | 3 | 3-Me-Phenyl | 131 | 3 | 2,4-di-Me-Phenyl |
| 48 | 4 | 3-Me-Phenyl | 132 | 4 | 2,4-di-Me-Phenyl |
| 49 | 1 | 2-Me-Phenyl | 133 | 1 | 2,5-di-Me-Phenyl |
| 50 | 2 | 2-Me-Phenyl | 134 | 2 | 2,5-di-Me-Phenyl |
| 51 | 3 | 2-Me-Phenyl | 135 | 3 | 2,5-di-Me-Phenyl |
| 52 | 4 | 2-Me-Phenyl | 136 | 4 | 2,5-di-Me-Phenyl |
| 53 | 1 | 4-F-Phenyl | 137 | 1 | 2,6-di-Me-Phenyl |
| 54 | 2 | 4-F-Phenyl | 138 | 2 | 2,6-di-Me-Phenyl |
| 55 | 3 | 4-F-Phenyl | 139 | 3 | 2,6-di-Me-Phenyl |
| 56 | 4 | 4-F-Phenyl | 140 | 4 | 2,6-di-Me-Phenyl |
| 57 | 1 | 3-F-Phenyl | 141 | 1 | 2,6-di-iPr-Phenyl |
| 58 | 2 | 3-F-Phenyl | 142 | 2 | 2,6-di-iPr-Phenyl |
| 59 | 3 | 3-F-Phenyl | 143 | 3 | 2,6-di-iPr-Phenyl |
| 60 | 4 | 3-F-Phenyl | 144 | 4 | 2,6-di-iPr-Phenyl |
| 61 | 1 | 2-F-Phenyl | 145 | 1 | 2-morpholino-phenyl |
| 62 | 2 | 2-F-Phenyl | 146 | 2 | 2-morpholino-phenyl |
| 63 | 3 | 2-F-Phenyl | 147 | 3 | 2-morpholino-phenyl |
| 64 | 4 | 2-F-Phenyl | 148 | 4 | 2-morpholino-phenyl |
| 65 | 1 | 4-Cl-Phenyl | 149 | 1 | 3-morpholino-phenyl |
| 66 | 2 | 4-Cl-Phenyl | 150 | 2 | 3-morpholino-phenyl |
| 67 | 3 | 4-Cl-Phenyl | 151 | 3 | 3-morpholino-phenyl |
| 68 | 4 | 4-Cl-Phenyl | 152 | 4 | 3-morpholino-phenyl |
| 69 | 1 | 3-Cl-Phenyl | 153 | 1 | 4-morpholino-phenyl |
| 70 | 2 | 3-Cl-Phenyl | 154 | 2 | 4-morpholino-phenyl |
| 71 | 3 | 3-Cl-Phenyl | 155 | 3 | 4-morpholino-phenyl |
| 72 | 4 | 3-Cl-Phenyl | 156 | 4 | 4-morpholino-phenyl |
| 73 | 1 | 2-Cl-Phenyl | 157 | 1 | 4-CN-2-morpholino-phenyl |
| 74 | 2 | 2-Cl-Phenyl | 158 | 2 | 4-CN-2-morpholino-phenyl |
| 75 | 3 | 2-Cl-Phenyl | 159 | 3 | 4-CN-2-morpholino-phenyl |
| 76 | 4 | 2-Cl-Phenyl | 160 | 4 | 4-CN-2-morpholino-phenyl |
| 77 | 1 | 4-Br-Phenyl | 161 | 1 | 4-$CH_3$-2-morpholino-phenyl |
| 78 | 2 | 4-Br-Phenyl | 162 | 2 | 4-$CH_3$-2-morpholino-phenyl |
| 79 | 3 | 4-Br-Phenyl | 163 | 3 | 4-$CH_3$-2-morpholino-phenyl |
| 80 | 4 | 4-Br-Phenyl | 164 | 4 | 4-$CH_3$-2-morpholino-phenyl |
| 81 | 1 | 3-Br-Phenyl | 165 | 1 | 4-OH-2-morpholino-phenyl |
| 82 | 2 | 3-Br-Phenyl | 166 | 2 | 4-OH-2-morpholino-phenyl |
| 83 | 3 | 3-Br-Phenyl | 167 | 3 | 4-OH-2-morpholino-phenyl |
| 84 | 4 | 3-Br-Phenyl | 168 | 4 | 4-OH-2-morpholino-phenyl |
| 85 | 1 | naphthylen-1-yl | 173 | 1 | naphthylen-2-yl |
| 86 | 2 | naphthylen-1-yl | 174 | 2 | naphthylen-2-yl |
| 87 | 3 | naphthylen-1-yl | 175 | 3 | naphthylen-2-yl |
| 88 | 4 | naphthylen-1-yl | 176 | 4 | naphthylen-2-yl |

Exemplary embodiments include compounds having the formula (XXII)

(XXII)

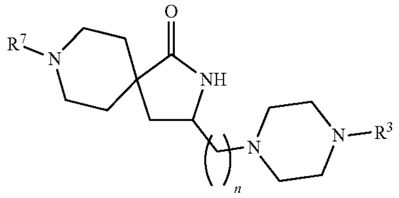

or a pharmaceutically acceptable salt form thereof defined herein below in Table 16.

TABLE 16

| Entry | n | $R^7$ | $R^3$ |
|---|---|---|---|
| 1 | 1 | H | Phenyl |
| 2 | 2 | H | Phenyl |
| 3 | 3 | H | Phenyl |
| 4 | 4 | H | Phenyl |
| 5 | 1 | Me | Phenyl |
| 6 | 2 | Me | Phenyl |
| 7 | 3 | Me | Phenyl |
| 8 | 4 | Me | Phenyl |
| 9 | 1 | $CH_2$Ph | Phenyl |
| 10 | 2 | $CH_2$Ph | Phenyl |
| 11 | 3 | $CH_2$Ph | Phenyl |
| 12 | 4 | $CH_2$Ph | Phenyl |
| 13 | 1 | COMe | Phenyl |
| 14 | 2 | COMe | Phenyl |
| 15 | 3 | COMe | Phenyl |
| 16 | 4 | COMe | Phenyl |
| 17 | 1 | $CO_2$Me | Phenyl |
| 18 | 2 | $CO_2$Me | Phenyl |
| 19 | 3 | $CO_2$Me | Phenyl |
| 20 | 4 | $CO_2$Me | Phenyl |
| 21 | 1 | $CO_2$tBu | Phenyl |
| 22 | 2 | $CO_2$tBu | Phenyl |
| 23 | 3 | $CO_2$tBu | Phenyl |
| 24 | 4 | $CO_2$tBu | Phenyl |
| 25 | 1 | CONHMe | Phenyl |
| 26 | 2 | CONHMe | Phenyl |
| 27 | 3 | CONHMe | Phenyl |
| 28 | 4 | CONHMe | Phenyl |
| 29 | 1 | $SO_2$Me | Phenyl |
| 30 | 2 | $SO_2$Me | Phenyl |
| 31 | 3 | $SO_2$Me | Phenyl |
| 32 | 4 | $SO_2$Me | Phenyl |
| 33 | 1 | $SO_2NH_2$ | Phenyl |
| 34 | 2 | $SO_2NH_2$ | Phenyl |
| 35 | 3 | $SO_2NH_2$ | Phenyl |
| 36 | 4 | $SO_2NH_2$ | Phenyl |
| 37 | 1 | H | 3-OH-Phenyl |
| 38 | 2 | H | 3-OH-Phenyl |
| 39 | 3 | H | 3-OH-Phenyl |
| 40 | 4 | H | 3-OH-Phenyl |
| 41 | 1 | Me | 3-OH-Phenyl |
| 42 | 2 | Me | 3-OH-Phenyl |
| 43 | 3 | Me | 3-OH-Phenyl |
| 44 | 4 | Me | 3-OH-Phenyl |
| 45 | 1 | $CH_2$Ph | 3-OH-Phenyl |
| 46 | 2 | $CH_2$Ph | 3-OH-Phenyl |
| 47 | 3 | $CH_2$Ph | 3-OH-Phenyl |
| 48 | 4 | $CH_2$Ph | 3-OH-Phenyl |
| 49 | 1 | COMe | 3-OH-Phenyl |
| 50 | 2 | COMe | 3-OH-Phenyl |
| 51 | 3 | COMe | 3-OH-Phenyl |
| 52 | 4 | COMe | 3-OH-Phenyl |
| 53 | 1 | $CO_2$Me | 3-OH-Phenyl |
| 54 | 2 | $CO_2$Me | 3-OH-Phenyl |
| 55 | 3 | $CO_2$Me | 3-OH-Phenyl |
| 56 | 4 | $CO_2$Me | 3-OH-Phenyl |
| 57 | 1 | $CO_2$tBu | 3-OH-Phenyl |
| 58 | 2 | $CO_2$tBu | 3-OH-Phenyl |
| 59 | 3 | $CO_2$tBu | 3-OH-Phenyl |
| 60 | 4 | $CO_2$tBu | 3-OH-Phenyl |
| 61 | 1 | CONHMe | 3-OH-Phenyl |

TABLE 16-continued

| Entry | n | $R^7$ | $R^3$ |
|---|---|---|---|
| 62 | 2 | CONHMe | 3-OH-Phenyl |
| 63 | 3 | CONHMe | 3-OH-Phenyl |
| 64 | 4 | CONHMe | 3-OH-Phenyl |
| 65 | 1 | $SO_2Me$ | 3-OH-Phenyl |
| 66 | 2 | $SO_2Me$ | 3-OH-Phenyl |
| 67 | 3 | $SO_2Me$ | 3-OH-Phenyl |
| 68 | 4 | $SO_2Me$ | 3-OH-Phenyl |
| 69 | 1 | $SO_2NH_2$ | 3-OH-Phenyl |
| 70 | 2 | $SO_2NH_2$ | 3-OH-Phenyl |
| 71 | 3 | $SO_2NH_2$ | 3-OH-Phenyl |
| 72 | 4 | $SO_2NH_2$ | 3-OH-Phenyl |
| 73 | 1 | H | 4-$NO_2$-Phenyl |
| 74 | 2 | H | 4-$NO_2$-Phenyl |
| 75 | 3 | H | 4-$NO_2$-Phenyl |
| 76 | 4 | H | 4-$NO_2$-Phenyl |
| 77 | 1 | Me | 4-$NO_2$-Phenyl |
| 78 | 2 | Me | 4-$NO_2$-Phenyl |
| 79 | 3 | Me | 4-$NO_2$-Phenyl |
| 80 | 4 | Me | 4-$NO_2$-Phenyl |
| 81 | 1 | $CH_2Ph$ | 4-$NO_2$-Phenyl |
| 82 | 2 | $CH_2Ph$ | 4-$NO_2$-Phenyl |
| 83 | 3 | $CH_2Ph$ | 4-$NO_2$-Phenyl |
| 84 | 4 | $CH_2Ph$ | 4-$NO_2$-Phenyl |
| 85 | 1 | COMe | 4-$NO_2$-Phenyl |
| 86 | 2 | COMe | 4-$NO_2$-Phenyl |
| 87 | 3 | COMe | 4-$NO_2$-Phenyl |
| 88 | 4 | COMe | 4-$NO_2$-Phenyl |
| 89 | 1 | $CO_2Me$ | 4-$NO_2$-Phenyl |
| 90 | 2 | $CO_2Me$ | 4-$NO_2$-Phenyl |
| 91 | 3 | $CO_2Me$ | 4-$NO_2$-Phenyl |
| 92 | 4 | $CO_2Me$ | 4-$NO_2$-Phenyl |
| 93 | 1 | $CO_2tBu$ | 4-$NO_2$-Phenyl |
| 94 | 2 | $CO_2tBu$ | 4-$NO_2$-Phenyl |
| 95 | 3 | $CO_2tBu$ | 4-$NO_2$-Phenyl |
| 96 | 4 | $CO_2tBu$ | 4-$NO_2$-Phenyl |
| 97 | 1 | CONHMe | 4-$NO_2$-Phenyl |
| 98 | 2 | CONHMe | 4-$NO_2$-Phenyl |
| 99 | 3 | CONHMe | 4-$NO_2$-Phenyl |
| 100 | 4 | CONHMe | 4-$NO_2$-Phenyl |
| 101 | 1 | $SO_2Me$ | 4-$NO_2$-Phenyl |
| 102 | 2 | $SO_2Me$ | 4-$NO_2$-Phenyl |
| 103 | 3 | $SO_2Me$ | 4-$NO_2$-Phenyl |
| 104 | 4 | $SO_2Me$ | 4-$NO_2$-Phenyl |
| 105 | 1 | $SO_2NH_2$ | 4-$NO_2$-Phenyl |
| 106 | 2 | $SO_2NH_2$ | 4-$NO_2$-Phenyl |
| 107 | 3 | $SO_2NH_2$ | 4-$NO_2$-Phenyl |
| 108 | 4 | $SO_2NH_2$ | 4-$NO_2$-Phenyl |
| 109 | 1 | H | 3-OMe-Phenyl |
| 110 | 2 | H | 3-OMe-Phenyl |
| 111 | 3 | H | 3-OMe-Phenyl |
| 112 | 4 | H | 3-OMe-Phenyl |
| 113 | 1 | Me | 3-OMe-Phenyl |
| 114 | 2 | Me | 3-OMe-Phenyl |
| 115 | 3 | Me | 3-OMe-Phenyl |
| 116 | 4 | Me | 3-OMe-Phenyl |
| 117 | 1 | $CH_2Ph$ | 3-OMe-Phenyl |
| 118 | 2 | $CH_2Ph$ | 3-OMe-Phenyl |
| 119 | 3 | $CH_2Ph$ | 3-OMe-Phenyl |
| 120 | 4 | $CH_2Ph$ | 3-OMe-Phenyl |
| 121 | 1 | COMe | 3-OMe-Phenyl |
| 122 | 2 | COMe | 3-OMe-Phenyl |
| 123 | 3 | COMe | 3-OMe-Phenyl |
| 124 | 4 | COMe | 3-OMe-Phenyl |
| 125 | 1 | $CO_2Me$ | 3-OMe-Phenyl |
| 126 | 2 | $CO_2Me$ | 3-OMe-Phenyl |
| 127 | 3 | $CO_2Me$ | 3-OMe-Phenyl |
| 128 | 4 | $CO_2Me$ | 3-OMe-Phenyl |
| 129 | 1 | $CO_2tBu$ | 3-OMe-Phenyl |
| 130 | 2 | $CO_2tBu$ | 3-OMe-Phenyl |
| 131 | 3 | $CO_2tBu$ | 3-OMe-Phenyl |
| 132 | 4 | $CO_2tBu$ | 3-OMe-Phenyl |
| 133 | 1 | CONHMe | 3-OMe-Phenyl |
| 134 | 2 | CONHMe | 3-OMe-Phenyl |
| 135 | 3 | CONHMe | 3-OMe-Phenyl |
| 136 | 4 | CONHMe | 3-OMe-Phenyl |
| 137 | 1 | $SO_2Me$ | 3-OMe-Phenyl |
| 138 | 2 | $SO_2Me$ | 3-OMe-Phenyl |
| 139 | 3 | $SO_2Me$ | 3-OMe-Phenyl |

TABLE 16-continued

| Entry | n | $R^7$ | $R^3$ |
|---|---|---|---|
| 140 | 4 | $SO_2Me$ | 3-OMe-Phenyl |
| 141 | 1 | $SO_2NH_2$ | 3-OMe-Phenyl |
| 142 | 2 | $SO_2NH_2$ | 3-OMe-Phenyl |
| 143 | 3 | $SO_2NH_2$ | 3-OMe-Phenyl |
| 144 | 4 | $SO_2NH_2$ | 3-OMe-Phenyl |
| 145 | 1 | H | 4-CN-Phenyl |
| 146 | 2 | H | 4-CN-Phenyl |
| 147 | 3 | H | 4-CN-Phenyl |
| 148 | 4 | H | 4-CN-Phenyl |
| 149 | 1 | Me | 4-CN-Phenyl |
| 150 | 2 | Me | 4-CN-Phenyl |
| 151 | 3 | Me | 4-CN-Phenyl |
| 152 | 4 | Me | 4-CN-Phenyl |
| 153 | 1 | $CH_2Ph$ | 4-CN-Phenyl |
| 154 | 2 | $CH_2Ph$ | 4-CN-Phenyl |
| 155 | 3 | $CH_2Ph$ | 4-CN-Phenyl |
| 156 | 4 | $CH_2Ph$ | 4-CN-Phenyl |
| 157 | 1 | COMe | 4-CN-Phenyl |
| 158 | 2 | COMe | 4-CN-Phenyl |
| 159 | 3 | COMe | 4-CN-Phenyl |
| 160 | 4 | COMe | 4-CN-Phenyl |
| 161 | 1 | $CO_2Me$ | 4-CN-Phenyl |
| 162 | 2 | $CO_2Me$ | 4-CN-Phenyl |
| 163 | 3 | $CO_2Me$ | 4-CN-Phenyl |
| 164 | 4 | $CO_2Me$ | 4-CN-Phenyl |
| 165 | 1 | $CO_2tBu$ | 4-CN-Phenyl |
| 166 | 2 | $CO_2tBu$ | 4-CN-Phenyl |
| 167 | 3 | $CO_2tBu$ | 4-CN-Phenyl |
| 168 | 4 | $CO_2tBu$ | 4-CN-Phenyl |
| 169 | 1 | CONHMe | 4-CN-Phenyl |
| 170 | 2 | CONHMe | 4-CN-Phenyl |
| 171 | 3 | CONHMe | 4-CN-Phenyl |
| 172 | 4 | CONHMe | 4-CN-Phenyl |
| 173 | 1 | $SO_2Me$ | 4-CN-Phenyl |
| 174 | 2 | $SO_2Me$ | 4-CN-Phenyl |
| 175 | 3 | $SO_2Me$ | 4-CN-Phenyl |
| 176 | 4 | $SO_2Me$ | 4-CN-Phenyl |
| 177 | 1 | $SO_2NH_2$ | 4-CN-Phenyl |
| 178 | 2 | $SO_2NH_2$ | 4-CN-Phenyl |
| 179 | 3 | $SO_2NH_2$ | 4-CN-Phenyl |
| 180 | 4 | $SO_2NH_2$ | 4-CN-Phenyl |
| 181 | 1 | H | 2-CN-Phenyl |
| 182 | 2 | H | 2-CN-Phenyl |
| 183 | 3 | H | 2-CN-Phenyl |
| 184 | 4 | H | 2-CN-Phenyl |
| 185 | 1 | Me | 2-CN-Phenyl |
| 186 | 2 | Me | 2-CN-Phenyl |
| 187 | 3 | Me | 2-CN-Phenyl |
| 188 | 4 | Me | 2-CN-Phenyl |
| 189 | 1 | $CH_2Ph$ | 2-CN-Phenyl |
| 190 | 2 | $CH_2Ph$ | 2-CN-Phenyl |
| 191 | 3 | $CH_2Ph$ | 2-CN-Phenyl |
| 192 | 4 | $CH_2Ph$ | 2-CN-Phenyl |
| 193 | 1 | COMe | 2-CN-Phenyl |
| 194 | 2 | COMe | 2-CN-Phenyl |
| 195 | 3 | COMe | 2-CN-Phenyl |
| 196 | 4 | COMe | 2-CN-Phenyl |
| 197 | 1 | $CO_2Me$ | 2-CN-Phenyl |
| 198 | 2 | $CO_2Me$ | 2-CN-Phenyl |
| 199 | 3 | $CO_2Me$ | 2-CN-Phenyl |
| 200 | 4 | $CO_2Me$ | 2-CN-Phenyl |
| 201 | 1 | $CO_2tBu$ | 2-CN-Phenyl |
| 202 | 2 | $CO_2tBu$ | 2-CN-Phenyl |
| 203 | 3 | $CO_2tBu$ | 2-CN-Phenyl |
| 204 | 4 | $CO_2tBu$ | 2-CN-Phenyl |
| 205 | 1 | CONHMe | 2-CN-Phenyl |
| 206 | 2 | CONHMe | 2-CN-Phenyl |
| 207 | 3 | CONHMe | 2-CN-Phenyl |
| 208 | 4 | CONHMe | 2-CN-Phenyl |
| 209 | 1 | $SO_2Me$ | 2-CN-Phenyl |
| 210 | 2 | $SO_2Me$ | 2-CN-Phenyl |
| 211 | 3 | $SO_2Me$ | 2-CN-Phenyl |
| 212 | 4 | $SO_2Me$ | 2-CN-Phenyl |
| 213 | 1 | $SO_2NH_2$ | 2-CN-Phenyl |
| 214 | 2 | $SO_2NH_2$ | 2-CN-Phenyl |
| 215 | 3 | $SO_2NH_2$ | 2-CN-Phenyl |
| 216 | 4 | $SO_2NH_2$ | 2-CN-Phenyl |
| 217 | 1 | H | 3-Me-Phenyl |

TABLE 16-continued

| Entry | n | $R^7$ | $R^3$ |
|---|---|---|---|
| 218 | 2 | H | 3-Me-Phenyl |
| 219 | 3 | H | 3-Me-Phenyl |
| 220 | 4 | H | 3-Me-Phenyl |
| 221 | 1 | Me | 3-Me-Phenyl |
| 222 | 2 | Me | 3-Me-Phenyl |
| 223 | 3 | Me | 3-Me-Phenyl |
| 224 | 4 | Me | 3-Me-Phenyl |
| 225 | 1 | $CH_2Ph$ | 3-Me-Phenyl |
| 226 | 2 | $CH_2Ph$ | 3-Me-Phenyl |
| 227 | 3 | $CH_2Ph$ | 3-Me-Phenyl |
| 228 | 4 | $CH_2Ph$ | 3-Me-Phenyl |
| 229 | 1 | COMe | 3-Me-Phenyl |
| 230 | 2 | COMe | 3-Me-Phenyl |
| 231 | 3 | COMe | 3-Me-Phenyl |
| 232 | 4 | COMe | 3-Me-Phenyl |
| 233 | 1 | $CO_2Me$ | 3-Me-Phenyl |
| 234 | 2 | $CO_2Me$ | 3-Me-Phenyl |
| 235 | 3 | $CO_2Me$ | 3-Me-Phenyl |
| 236 | 4 | $CO_2Me$ | 3-Me-Phenyl |
| 237 | 1 | $CO_2tBu$ | 3-Me-Phenyl |
| 238 | 2 | $CO_2tBu$ | 3-Me-Phenyl |
| 239 | 3 | $CO_2tBu$ | 3-Me-Phenyl |
| 240 | 4 | $CO_2tBu$ | 3-Me-Phenyl |
| 241 | 1 | CONHMe | 3-Me-Phenyl |
| 242 | 2 | CONHMe | 3-Me-Phenyl |
| 243 | 3 | CONHMe | 3-Me-Phenyl |
| 244 | 4 | CONHMe | 3-Me-Phenyl |
| 245 | 1 | $SO_2Me$ | 3-Me-Phenyl |
| 246 | 2 | $SO_2Me$ | 3-Me-Phenyl |
| 247 | 3 | $SO_2Me$ | 3-Me-Phenyl |
| 248 | 4 | $SO_2Me$ | 3-Me-Phenyl |
| 249 | 1 | $SO_2NH_2$ | 3-Me-Phenyl |
| 250 | 2 | $SO_2NH_2$ | 3-Me-Phenyl |
| 251 | 3 | $SO_2NH_2$ | 3-Me-Phenyl |
| 252 | 4 | $SO_2NH_2$ | 3-Me-Phenyl |
| 253 | 1 | H | 2-F-Phenyl |
| 254 | 2 | H | 2-F-Phenyl |
| 255 | 3 | H | 2-F-Phenyl |
| 256 | 4 | H | 2-F-Phenyl |
| 257 | 1 | Me | 2-F-Phenyl |
| 258 | 2 | Me | 2-F-Phenyl |
| 259 | 3 | Me | 2-F-Phenyl |
| 260 | 4 | Me | 2-F-Phenyl |
| 261 | 1 | $CH_2Ph$ | 2-F-Phenyl |
| 262 | 2 | $CH_2Ph$ | 2-F-Phenyl |
| 263 | 3 | $CH_2Ph$ | 2-F-Phenyl |
| 264 | 4 | $CH_2Ph$ | 2-F-Phenyl |
| 265 | 1 | COMe | 2-F-Phenyl |
| 266 | 2 | COMe | 2-F-Phenyl |
| 267 | 3 | COMe | 2-F-Phenyl |
| 268 | 4 | COMe | 2-F-Phenyl |
| 269 | 1 | $CO_2Me$ | 2-F-Phenyl |
| 270 | 2 | $CO_2Me$ | 2-F-Phenyl |
| 271 | 3 | $CO_2Me$ | 2-F-Phenyl |
| 272 | 4 | $CO_2Me$ | 2-F-Phenyl |
| 273 | 1 | $CO_2tBu$ | 2-F-Phenyl |
| 274 | 2 | $CO_2tBu$ | 2-F-Phenyl |
| 275 | 3 | $CO_2tBu$ | 2-F-Phenyl |
| 276 | 4 | $CO_2tBu$ | 2-F-Phenyl |
| 277 | 1 | CONHMe | 2-F-Phenyl |
| 278 | 2 | CONHMe | 2-F-Phenyl |
| 279 | 3 | CONHMe | 2-F-Phenyl |
| 280 | 4 | CONHMe | 2-F-Phenyl |
| 281 | 1 | $SO_2Me$ | 2-F-Phenyl |
| 282 | 2 | $SO_2Me$ | 2-F-Phenyl |
| 283 | 3 | $SO_2Me$ | 2-F-Phenyl |
| 284 | 4 | $SO_2Me$ | 2-F-Phenyl |
| 285 | 1 | $SO_2NH_2$ | 2-F-Phenyl |
| 286 | 2 | $SO_2NH_2$ | 2-F-Phenyl |
| 287 | 3 | $SO_2NH_2$ | 2-F-Phenyl |
| 288 | 4 | $SO_2NH_2$ | 2-F-Phenyl |
| 289 | 1 | H | 4-F-Phenyl |
| 290 | 2 | H | 4-F-Phenyl |
| 291 | 3 | H | 4-F-Phenyl |
| 292 | 4 | H | 4-F-Phenyl |
| 293 | 1 | Me | 4-F-Phenyl |
| 294 | 2 | Me | 4-F-Phenyl |
| 295 | 3 | Me | 4-F-Phenyl |
| 296 | 4 | Me | 4-F-Phenyl |
| 297 | 1 | $CH_2Ph$ | 4-F-Phenyl |
| 298 | 2 | $CH_2Ph$ | 4-F-Phenyl |
| 299 | 3 | $CH_2Ph$ | 4-F-Phenyl |
| 300 | 4 | $CH_2Ph$ | 4-F-Phenyl |
| 301 | 1 | COMe | 4-F-Phenyl |
| 302 | 2 | COMe | 4-F-Phenyl |
| 303 | 3 | COMe | 4-F-Phenyl |
| 304 | 4 | COMe | 4-F-Phenyl |
| 305 | 1 | $CO_2Me$ | 4-F-Phenyl |
| 306 | 2 | $CO_2Me$ | 4-F-Phenyl |
| 307 | 3 | $CO_2Me$ | 4-F-Phenyl |
| 308 | 4 | $CO_2Me$ | 4-F-Phenyl |
| 309 | 1 | $CO_2tBu$ | 4-F-Phenyl |
| 310 | 2 | $CO_2tBu$ | 4-F-Phenyl |
| 311 | 3 | $CO_2tBu$ | 4-F-Phenyl |
| 312 | 4 | $CO_2tBu$ | 4-F-Phenyl |
| 313 | 1 | CONHMe | 4-F-Phenyl |
| 314 | 2 | CONHMe | 4-F-Phenyl |
| 315 | 3 | CONHMe | 4-F-Phenyl |
| 316 | 4 | CONHMe | 4-F-Phenyl |
| 317 | 1 | $SO_2Me$ | 4-F-Phenyl |
| 318 | 2 | $SO_2Me$ | 4-F-Phenyl |
| 319 | 3 | $SO_2Me$ | 4-F-Phenyl |
| 320 | 4 | $SO_2Me$ | 4-F-Phenyl |
| 321 | 1 | $SO_2NH_2$ | 4-F-Phenyl |
| 322 | 2 | $SO_2NH_2$ | 4-F-Phenyl |
| 323 | 3 | $SO_2NH_2$ | 4-F-Phenyl |
| 324 | 4 | $SO_2NH_2$ | 4-F-Phenyl |
| 325 | 1 | H | 3-Cl-Phenyl |
| 326 | 2 | H | 3-Cl-Phenyl |
| 327 | 3 | H | 3-Cl-Phenyl |
| 328 | 4 | H | 3-Cl-Phenyl |
| 329 | 1 | Me | 3-Cl-Phenyl |
| 330 | 2 | Me | 3-Cl-Phenyl |
| 331 | 3 | Me | 3-Cl-Phenyl |
| 332 | 4 | Me | 3-Cl-Phenyl |
| 333 | 1 | $CH_2Ph$ | 3-Cl-Phenyl |
| 334 | 2 | $CH_2Ph$ | 3-Cl-Phenyl |
| 335 | 3 | $CH_2Ph$ | 3-Cl-Phenyl |
| 336 | 4 | $CH_2Ph$ | 3-Cl-Phenyl |
| 337 | 1 | COMe | 3-Cl-Phenyl |
| 338 | 2 | COMe | 3-Cl-Phenyl |
| 339 | 3 | COMe | 3-Cl-Phenyl |
| 340 | 4 | COMe | 3-Cl-Phenyl |
| 341 | 1 | $CO_2Me$ | 3-Cl-Phenyl |
| 342 | 2 | $CO_2Me$ | 3-Cl-Phenyl |
| 343 | 3 | $CO_2Me$ | 3-Cl-Phenyl |
| 344 | 4 | $CO_2Me$ | 3-Cl-Phenyl |
| 345 | 1 | $CO_2tBu$ | 3-Cl-Phenyl |
| 346 | 2 | $CO_2tBu$ | 3-Cl-Phenyl |
| 347 | 3 | $CO_2tBu$ | 3-Cl-Phenyl |
| 348 | 4 | $CO_2tBu$ | 3-Cl-Phenyl |
| 349 | 1 | CONHMe | 3-Cl-Phenyl |
| 350 | 2 | CONHMe | 3-Cl-Phenyl |
| 351 | 3 | CONHMe | 3-Cl-Phenyl |
| 352 | 4 | CONHMe | 3-Cl-Phenyl |
| 353 | 1 | $SO_2Me$ | 3-Cl-Phenyl |
| 354 | 2 | $SO_2Me$ | 3-Cl-Phenyl |
| 355 | 3 | $SO_2Me$ | 3-Cl-Phenyl |
| 356 | 4 | $SO_2Me$ | 3-Cl-Phenyl |
| 357 | 1 | $SO_2NH_2$ | 3-Cl-Phenyl |
| 358 | 2 | $SO_2NH_2$ | 3-Cl-Phenyl |
| 359 | 3 | $SO_2NH_2$ | 3-Cl-Phenyl |
| 360 | 4 | $SO_2NH_2$ | 3-Cl-Phenyl |
| 361 | 1 | H | 2-Br-Phenyl |
| 362 | 2 | H | 2-Br-Phenyl |
| 363 | 3 | H | 2-Br-Phenyl |
| 364 | 4 | H | 2-Br-Phenyl |
| 365 | 1 | Me | 2-Br-Phenyl |
| 366 | 2 | Me | 2-Br-Phenyl |
| 367 | 3 | Me | 2-Br-Phenyl |
| 368 | 4 | Me | 2-Br-Phenyl |
| 369 | 1 | $CH_2Ph$ | 2-Br-Phenyl |
| 370 | 2 | $CH_2Ph$ | 2-Br-Phenyl |
| 371 | 3 | $CH_2Ph$ | 2-Br-Phenyl |
| 372 | 4 | $CH_2Ph$ | 2-Br-Phenyl |
| 373 | 1 | COMe | 2-Br-Phenyl |

TABLE 16-continued

| Entry | n | $R^7$ | $R^3$ |
|---|---|---|---|
| 374 | 2 | COMe | 2-Br-Phenyl |
| 375 | 3 | COMe | 2-Br-Phenyl |
| 376 | 4 | COMe | 2-Br-Phenyl |
| 377 | 1 | $CO_2Me$ | 2-Br-Phenyl |
| 378 | 2 | $CO_2Me$ | 2-Br-Phenyl |
| 379 | 3 | $CO_2Me$ | 2-Br-Phenyl |
| 380 | 4 | $CO_2Me$ | 2-Br-Phenyl |
| 381 | 1 | $CO_2tBu$ | 2-Br-Phenyl |
| 382 | 2 | $CO_2tBu$ | 2-Br-Phenyl |
| 383 | 3 | $CO_2tBu$ | 2-Br-Phenyl |
| 384 | 4 | $CO_2tBu$ | 2-Br-Phenyl |
| 385 | 1 | CONHMe | 2-Br-Phenyl |
| 386 | 2 | CONHMe | 2-Br-Phenyl |
| 387 | 3 | CONHMe | 2-Br-Phenyl |
| 388 | 4 | CONHMe | 2-Br-Phenyl |
| 389 | 1 | $SO_2Me$ | 2-Br-Phenyl |
| 390 | 2 | $SO_2Me$ | 2-Br-Phenyl |
| 391 | 3 | $SO_2Me$ | 2-Br-Phenyl |
| 392 | 4 | $SO_2Me$ | 2-Br-Phenyl |
| 393 | 1 | $SO_2NH_2$ | 2-Br-Phenyl |
| 394 | 2 | $SO_2NH_2$ | 2-Br-Phenyl |
| 395 | 3 | $SO_2NH_2$ | 2-Br-Phenyl |
| 396 | 4 | $SO_2NH_2$ | 2-Br-Phenyl |
| 397 | 1 | H | 4-Br-Phenyl |
| 398 | 2 | H | 4-Br-Phenyl |
| 399 | 3 | H | 4-Br-Phenyl |
| 400 | 4 | H | 4-Br-Phenyl |
| 401 | 1 | Me | 4-Br-Phenyl |
| 402 | 2 | Me | 4-Br-Phenyl |
| 403 | 3 | Me | 4-Br-Phenyl |
| 404 | 4 | Me | 4-Br-Phenyl |
| 405 | 1 | $CH_2Ph$ | 4-Br-Phenyl |
| 406 | 2 | $CH_2Ph$ | 4-Br-Phenyl |
| 407 | 3 | $CH_2Ph$ | 4-Br-Phenyl |
| 408 | 4 | $CH_2Ph$ | 4-Br-Phenyl |
| 409 | 1 | COMe | 4-Br-Phenyl |
| 410 | 2 | COMe | 4-Br-Phenyl |
| 411 | 3 | COMe | 4-Br-Phenyl |
| 412 | 4 | COMe | 4-Br-Phenyl |
| 413 | 1 | $CO_2Me$ | 4-Br-Phenyl |
| 414 | 2 | $CO_2Me$ | 4-Br-Phenyl |
| 415 | 3 | $CO_2Me$ | 4-Br-Phenyl |
| 416 | 4 | $CO_2Me$ | 4-Br-Phenyl |
| 417 | 1 | $CO_2tBu$ | 4-Br-Phenyl |
| 418 | 2 | $CO_2tBu$ | 4-Br-Phenyl |
| 419 | 3 | $CO_2tBu$ | 4-Br-Phenyl |
| 420 | 4 | $CO_2tBu$ | 4-Br-Phenyl |
| 421 | 1 | CONHMe | 4-Br-Phenyl |
| 422 | 2 | CONHMe | 4-Br-Phenyl |
| 423 | 3 | CONHMe | 4-Br-Phenyl |
| 424 | 4 | CONHMe | 4-Br-Phenyl |
| 425 | 1 | $SO_2Me$ | 4-Br-Phenyl |
| 426 | 2 | $SO_2Me$ | 4-Br-Phenyl |
| 427 | 3 | $SO_2Me$ | 4-Br-Phenyl |
| 428 | 4 | $SO_2Me$ | 4-Br-Phenyl |
| 429 | 1 | $SO_2NH_2$ | 4-Br-Phenyl |
| 430 | 2 | $SO_2NH_2$ | 4-Br-Phenyl |
| 431 | 3 | $SO_2NH_2$ | 4-Br-Phenyl |
| 432 | 4 | $SO_2NH_2$ | 4-Br-Phenyl |
| 433 | 1 | H | $3-CF_3$-Phenyl |
| 434 | 2 | H | $3-CF_3$-Phenyl |
| 435 | 3 | H | $3-CF_3$-Phenyl |
| 436 | 4 | H | $3-CF_3$-Phenyl |
| 437 | 1 | Me | $3-CF_3$-Phenyl |
| 438 | 2 | Me | $3-CF_3$-Phenyl |
| 439 | 3 | Me | $3-CF_3$-Phenyl |
| 440 | 4 | Me | $3-CF_3$-Phenyl |
| 441 | 1 | $CH_2Ph$ | $3-CF_3$-Phenyl |
| 442 | 2 | $CH_2Ph$ | $3-CF_3$-Phenyl |
| 443 | 3 | $CH_2Ph$ | $3-CF_3$-Phenyl |
| 444 | 4 | $CH_2Ph$ | $3-CF_3$-Phenyl |
| 445 | 1 | COMe | $3-CF_3$-Phenyl |
| 446 | 2 | COMe | $3-CF_3$-Phenyl |
| 447 | 3 | COMe | $3-CF_3$-Phenyl |
| 448 | 4 | COMe | $3-CF_3$-Phenyl |
| 449 | 1 | $CO_2Me$ | $3-CF_3$-Phenyl |
| 450 | 2 | $CO_2Me$ | $3-CF_3$-Phenyl |
| 451 | 3 | $CO_2Me$ | $3-CF_3$-Phenyl |

TABLE 16-continued

| Entry | n | $R^7$ | $R^3$ |
|---|---|---|---|
| 452 | 4 | $CO_2Me$ | $3-CF_3$-Phenyl |
| 453 | 1 | $CO_2tBu$ | $3-CF_3$-Phenyl |
| 454 | 2 | $CO_2tBu$ | $3-CF_3$-Phenyl |
| 455 | 3 | $CO_2tBu$ | $3-CF_3$-Phenyl |
| 456 | 4 | $CO_2tBu$ | $3-CF_3$-Phenyl |
| 457 | 1 | CONHMe | $3-CF_3$-Phenyl |
| 458 | 2 | CONHMe | $3-CF_3$-Phenyl |
| 459 | 3 | CONHMe | $3-CF_3$-Phenyl |
| 460 | 4 | CONHMe | $3-CF_3$-Phenyl |
| 461 | 1 | $SO_2Me$ | $3-CF_3$-Phenyl |
| 462 | 2 | $SO_2Me$ | $3-CF_3$-Phenyl |
| 463 | 3 | $SO_2Me$ | $3-CF_3$-Phenyl |
| 464 | 4 | $SO_2Me$ | $3-CF_3$-Phenyl |
| 465 | 1 | $SO_2NH_2$ | $3-CF_3$-Phenyl |
| 466 | 2 | $SO_2NH_2$ | $3-CF_3$-Phenyl |
| 467 | 3 | $SO_2NH_2$ | $3-CF_3$-Phenyl |
| 468 | 4 | $SO_2NH_2$ | $3-CF_3$-Phenyl |
| 469 | 1 | H | 2-iPr-Phenyl |
| 470 | 2 | H | 2-iPr-Phenyl |
| 471 | 3 | H | 2-iPr-Phenyl |
| 472 | 4 | H | 2-iPr-Phenyl |
| 473 | 1 | Me | 2-iPr-Phenyl |
| 474 | 2 | Me | 2-iPr-Phenyl |
| 475 | 3 | Me | 2-iPr-Phenyl |
| 476 | 4 | Me | 2-iPr-Phenyl |
| 477 | 1 | $CH_2Ph$ | 2-iPr-Phenyl |
| 478 | 2 | $CH_2Ph$ | 2-iPr-Phenyl |
| 479 | 3 | $CH_2Ph$ | 2-iPr-Phenyl |
| 480 | 4 | $CH_2Ph$ | 2-iPr-Phenyl |
| 481 | 1 | COMe | 2-iPr-Phenyl |
| 482 | 2 | COMe | 2-iPr-Phenyl |
| 483 | 3 | COMe | 2-iPr-Phenyl |
| 484 | 4 | COMe | 2-iPr-Phenyl |
| 485 | 1 | $CO_2Me$ | 2-iPr-Phenyl |
| 486 | 2 | $CO_2Me$ | 2-iPr-Phenyl |
| 487 | 3 | $CO_2Me$ | 2-iPr-Phenyl |
| 488 | 4 | $CO_2Me$ | 2-iPr-Phenyl |
| 489 | 1 | $CO_2tBu$ | 2-iPr-Phenyl |
| 490 | 2 | $CO_2tBu$ | 2-iPr-Phenyl |
| 491 | 3 | $CO_2tBu$ | 2-iPr-Phenyl |
| 492 | 4 | $CO_2tBu$ | 2-iPr-Phenyl |
| 493 | 1 | CONHMe | 2-iPr-Phenyl |
| 494 | 2 | CONHMe | 2-iPr-Phenyl |
| 495 | 3 | CONHMe | 2-iPr-Phenyl |
| 496 | 4 | CONHMe | 2-iPr-Phenyl |
| 497 | 1 | $SO_2Me$ | 2-iPr-Phenyl |
| 498 | 2 | $SO_2Me$ | 2-iPr-Phenyl |
| 499 | 3 | $SO_2Me$ | 2-iPr-Phenyl |
| 500 | 4 | $SO_2Me$ | 2-iPr-Phenyl |
| 501 | 1 | $SO_2NH_2$ | 2-iPr-Phenyl |
| 502 | 2 | $SO_2NH_2$ | 2-iPr-Phenyl |
| 503 | 3 | $SO_2NH_2$ | 2-iPr-Phenyl |
| 504 | 4 | $SO_2NH_2$ | 2-iPr-Phenyl |
| 505 | 1 | H | 4-iPr-Phenyl |
| 506 | 2 | H | 4-iPr-Phenyl |
| 507 | 3 | H | 4-iPr-Phenyl |
| 508 | 4 | H | 4-iPr-Phenyl |
| 509 | 1 | Me | 4-iPr-Phenyl |
| 510 | 2 | Me | 4-iPr-Phenyl |
| 511 | 3 | Me | 4-iPr-Phenyl |
| 512 | 4 | Me | 4-iPr-Phenyl |
| 513 | 1 | $CH_2Ph$ | 4-iPr-Phenyl |
| 514 | 2 | $CH_2Ph$ | 4-iPr-Phenyl |
| 515 | 3 | $CH_2Ph$ | 4-iPr-Phenyl |
| 516 | 4 | $CH_2Ph$ | 4-iPr-Phenyl |
| 517 | 1 | COMe | 4-iPr-Phenyl |
| 518 | 2 | COMe | 4-iPr-Phenyl |
| 519 | 3 | COMe | 4-iPr-Phenyl |
| 520 | 4 | COMe | 4-iPr-Phenyl |
| 521 | 1 | $CO_2Me$ | 4-iPr-Phenyl |
| 522 | 2 | $CO_2Me$ | 4-iPr-Phenyl |
| 523 | 3 | $CO_2Me$ | 4-iPr-Phenyl |
| 524 | 4 | $CO_2Me$ | 4-iPr-Phenyl |
| 525 | 1 | $CO_2tBu$ | 4-iPr-Phenyl |
| 526 | 2 | $CO_2tBu$ | 4-iPr-Phenyl |
| 527 | 3 | $CO_2tBu$ | 4-iPr-Phenyl |
| 528 | 4 | $CO_2tBu$ | 4-iPr-Phenyl |
| 529 | 1 | CONHMe | 4-iPr-Phenyl |

TABLE 16-continued

| Entry | n | $R^7$ | $R^3$ |
|---|---|---|---|
| 530 | 2 | CONHMe | 4-iPr-Phenyl |
| 531 | 3 | CONHMe | 4-iPr-Phenyl |
| 532 | 4 | CONHMe | 4-iPr-Phenyl |
| 533 | 1 | $SO_2Me$ | 4-iPr-Phenyl |
| 534 | 2 | $SO_2Me$ | 4-iPr-Phenyl |
| 535 | 3 | $SO_2Me$ | 4-iPr-Phenyl |
| 536 | 4 | $SO_2Me$ | 4-iPr-Phenyl |
| 537 | 1 | $SO_2NH_2$ | 4-iPr-Phenyl |
| 538 | 2 | $SO_2NH_2$ | 4-iPr-Phenyl |
| 539 | 3 | $SO_2NH_2$ | 4-iPr-Phenyl |
| 540 | 4 | $SO_2NH_2$ | 4-iPr-Phenyl |
| 541 | 1 | H | 3-$NH_2$-Phenyl |
| 542 | 2 | H | 3-$NH_2$-Phenyl |
| 543 | 3 | H | 3-$NH_2$-Phenyl |
| 544 | 4 | H | 3-$NH_2$-Phenyl |
| 545 | 1 | Me | 3-$NH_2$-Phenyl |
| 546 | 2 | Me | 3-$NH_2$-Phenyl |
| 547 | 3 | Me | 3-$NH_2$-Phenyl |
| 548 | 4 | Me | 3-$NH_2$-Phenyl |
| 549 | 1 | $CH_2Ph$ | 3-$NH_2$-Phenyl |
| 550 | 2 | $CH_2Ph$ | 3-$NH_2$-Phenyl |
| 551 | 3 | $CH_2Ph$ | 3-$NH_2$-Phenyl |
| 552 | 4 | $CH_2Ph$ | 3-$NH_2$-Phenyl |
| 553 | 1 | COMe | 3-$NH_2$-Phenyl |
| 554 | 2 | COMe | 3-$NH_2$-Phenyl |
| 555 | 3 | COMe | 3-$NH_2$-Phenyl |
| 556 | 4 | COMe | 3-$NH_2$-Phenyl |
| 557 | 1 | $CO_2Me$ | 3-$NH_2$-Phenyl |
| 558 | 2 | $CO_2Me$ | 3-$NH_2$-Phenyl |
| 559 | 3 | $CO_2Me$ | 3-$NH_2$-Phenyl |
| 560 | 4 | $CO_2Me$ | 3-$NH_2$-Phenyl |
| 561 | 1 | $CO_2tBu$ | 3-$NH_2$-Phenyl |
| 562 | 2 | $CO_2tBu$ | 3-$NH_2$-Phenyl |
| 563 | 3 | $CO_2tBu$ | 3-$NH_2$-Phenyl |
| 564 | 4 | $CO_2tBu$ | 3-$NH_2$-Phenyl |
| 565 | 1 | CONHMe | 3-$NH_2$-Phenyl |
| 566 | 2 | CONHMe | 3-$NH_2$-Phenyl |
| 567 | 3 | CONHMe | 3-$NH_2$-Phenyl |
| 568 | 4 | CONHMe | 3-$NH_2$-Phenyl |
| 569 | 1 | $SO_2Me$ | 3-$NH_2$-Phenyl |
| 570 | 2 | $SO_2Me$ | 3-$NH_2$-Phenyl |
| 571 | 3 | $SO_2Me$ | 3-$NH_2$-Phenyl |
| 572 | 4 | $SO_2Me$ | 3-$NH_2$-Phenyl |
| 573 | 1 | $SO_2NH_2$ | 3-$NH_2$-Phenyl |
| 574 | 2 | $SO_2NH_2$ | 3-$NH_2$-Phenyl |
| 575 | 3 | $SO_2NH_2$ | 3-$NH_2$-Phenyl |
| 576 | 4 | $SO_2NH_2$ | 3-$NH_2$-Phenyl |
| 577 | 1 | H | 2,4-di-Me-Phenyl |
| 578 | 2 | H | 2,4-di-Me-Phenyl |
| 579 | 3 | H | 2,4-di-Me-Phenyl |
| 580 | 4 | H | 2,4-di-Me-Phenyl |
| 581 | 1 | Me | 2,4-di-Me-Phenyl |
| 582 | 2 | Me | 2,4-di-Me-Phenyl |
| 583 | 3 | Me | 2,4-di-Me-Phenyl |
| 584 | 4 | Me | 2,4-di-Me-Phenyl |
| 585 | 1 | $CH_2Ph$ | 2,4-di-Me-Phenyl |
| 586 | 2 | $CH_2Ph$ | 2,4-di-Me-Phenyl |
| 587 | 3 | $CH_2Ph$ | 2,4-di-Me-Phenyl |
| 588 | 4 | $CH_2Ph$ | 2,4-di-Me-Phenyl |
| 589 | 1 | COMe | 2,4-di-Me-Phenyl |
| 590 | 2 | COMe | 2,4-di-Me-Phenyl |
| 591 | 3 | COMe | 2,4-di-Me-Phenyl |
| 592 | 4 | COMe | 2,4-di-Me-Phenyl |
| 593 | 1 | $CO_2Me$ | 2,4-di-Me-Phenyl |
| 594 | 2 | $CO_2Me$ | 2,4-di-Me-Phenyl |
| 595 | 3 | $CO_2Me$ | 2,4-di-Me-Phenyl |
| 596 | 4 | $CO_2Me$ | 2,4-di-Me-Phenyl |
| 597 | 1 | $CO_2tBu$ | 2,4-di-Me-Phenyl |
| 598 | 2 | $CO_2tBu$ | 2,4-di-Me-Phenyl |
| 599 | 3 | $CO_2tBu$ | 2,4-di-Me-Phenyl |
| 600 | 4 | $CO_2tBu$ | 2,4-di-Me-Phenyl |
| 601 | 1 | CONHMe | 2,4-di-Me-Phenyl |
| 602 | 2 | CONHMe | 2,4-di-Me-Phenyl |
| 603 | 3 | CONHMe | 2,4-di-Me-Phenyl |
| 604 | 4 | CONHMe | 2,4-di-Me-Phenyl |
| 605 | 1 | $SO_2Me$ | 2,4-di-Me-Phenyl |
| 606 | 2 | $SO_2Me$ | 2,4-di-Me-Phenyl |
| 607 | 3 | $SO_2Me$ | 2,4-di-Me-Phenyl |
| 608 | 4 | $SO_2Me$ | 2,4-di-Me-Phenyl |
| 609 | 1 | $SO_2NH_2$ | 2,4-di-Me-Phenyl |
| 610 | 2 | $SO_2NH_2$ | 2,4-di-Me-Phenyl |
| 611 | 3 | $SO_2NH_2$ | 2,4-di-Me-Phenyl |
| 612 | 4 | $SO_2NH_2$ | 2,4-di-Me-Phenyl |
| 613 | 1 | H | 2,6-di-iPr-Phenyl |
| 614 | 2 | H | 2,6-di-iPr-Phenyl |
| 615 | 3 | H | 2,6-di-iPr-Phenyl |
| 616 | 4 | H | 2,6-di-iPr-Phenyl |
| 617 | 1 | Me | 2,6-di-iPr-Phenyl |
| 618 | 2 | Me | 2,6-di-iPr-Phenyl |
| 619 | 3 | Me | 2,6-di-iPr-Phenyl |
| 620 | 4 | Me | 2,6-di-iPr-Phenyl |
| 621 | 1 | $CH_2Ph$ | 2,6-di-iPr-Phenyl |
| 622 | 2 | $CH_2Ph$ | 2,6-di-iPr-Phenyl |
| 623 | 3 | $CH_2Ph$ | 2,6-di-iPr-Phenyl |
| 624 | 3 | $CH_2Ph$ | 2,6-di-iPr-Phenyl |
| 625 | 1 | COMe | 2,6-di-iPr-Phenyl |
| 626 | 2 | COMe | 2,6-di-iPr-Phenyl |
| 627 | 3 | COMe | 2,6-di-iPr-Phenyl |
| 628 | 4 | COMe | 2,6-di-iPr-Phenyl |
| 629 | 1 | $CO_2Me$ | 2,6-di-iPr-Phenyl |
| 630 | 2 | $CO_2Me$ | 2,6-di-iPr-Phenyl |
| 631 | 3 | $CO_2Me$ | 2,6-di-iPr-Phenyl |
| 632 | 4 | $CO_2Me$ | 2,6-di-iPr-Phenyl |
| 633 | 1 | $CO_2tBu$ | 2,6-di-iPr-Phenyl |
| 634 | 2 | $CO_2tBu$ | 2,6-di-iPr-Phenyl |
| 635 | 3 | $CO_2tBu$ | 2,6-di-iPr-Phenyl |
| 636 | 4 | $CO_2tBu$ | 2,6-di-iPr-Phenyl |
| 637 | 1 | CONHMe | 2,6-di-iPr-Phenyl |
| 638 | 2 | CONHMe | 2,6-di-iPr-Phenyl |
| 639 | 3 | CONHMe | 2,6-di-iPr-Phenyl |
| 640 | 4 | CONHMe | 2,6-di-iPr-Phenyl |
| 641 | 1 | $SO_2Me$ | 2,6-di-iPr-Phenyl |
| 642 | 2 | $SO_2Me$ | 2,6-di-iPr-Phenyl |
| 643 | 3 | $SO_2Me$ | 2,6-di-iPr-Phenyl |
| 644 | 4 | $SO_2Me$ | 2,6-di-iPr-Phenyl |
| 645 | 1 | $SO_2NH_2$ | 2,6-di-iPr-Phenyl |
| 646 | 2 | $SO_2NH_2$ | 2,6-di-iPr-Phenyl |
| 647 | 3 | $SO_2NH_2$ | 2,6-di-iPr-Phenyl |
| 648 | 4 | $SO_2NH_2$ | 2,6-di-iPr-Phenyl |
| 649 | 1 | H | 3-Ph-Phenyl |
| 650 | 2 | H | 3-Ph-Phenyl |
| 651 | 3 | H | 3-Ph-Phenyl |
| 652 | 4 | H | 3-Ph-Phenyl |
| 653 | 1 | Me | 3-Ph-Phenyl |
| 654 | 2 | Me | 3-Ph-Phenyl |
| 655 | 3 | Me | 3-Ph-Phenyl |
| 656 | 4 | Me | 3-Ph-Phenyl |
| 657 | 1 | $CH_2Ph$ | 3-Ph-Phenyl |
| 658 | 2 | $CH_2Ph$ | 3-Ph-Phenyl |
| 659 | 3 | $CH_2Ph$ | 3-Ph-Phenyl |
| 660 | 4 | $CH_2Ph$ | 3-Ph-Phenyl |
| 661 | 1 | COMe | 3-Ph-Phenyl |
| 662 | 2 | COMe | 3-Ph-Phenyl |
| 663 | 3 | COMe | 3-Ph-Phenyl |
| 664 | 4 | COMe | 3-Ph-Phenyl |
| 665 | 1 | $CO_2Me$ | 3-Ph-Phenyl |
| 666 | 2 | $CO_2Me$ | 3-Ph-Phenyl |
| 667 | 3 | $CO_2Me$ | 3-Ph-Phenyl |
| 668 | 4 | $CO_2Me$ | 3-Ph-Phenyl |
| 669 | 1 | $CO_2tBu$ | 3-Ph-Phenyl |
| 670 | 2 | $CO_2tBu$ | 3-Ph-Phenyl |
| 671 | 3 | $CO_2tBu$ | 3-Ph-Phenyl |
| 672 | 4 | $CO_2tBu$ | 3-Ph-Phenyl |
| 673 | 1 | CONHMe | 3-Ph-Phenyl |
| 674 | 2 | CONHMe | 3-Ph-Phenyl |
| 675 | 3 | CONHMe | 3-Ph-Phenyl |
| 676 | 4 | CONHMe | 3-Ph-Phenyl |
| 677 | 1 | $SO_2Me$ | 3-Ph-Phenyl |
| 678 | 2 | $SO_2Me$ | 3-Ph-Phenyl |
| 679 | 3 | $SO_2Me$ | 3-Ph-Phenyl |
| 680 | 4 | $SO_2Me$ | 3-Ph-Phenyl |
| 681 | 1 | $SO_2NH_2$ | 3-Ph-Phenyl |
| 682 | 2 | $SO_2NH_2$ | 3-Ph-Phenyl |
| 683 | 3 | $SO_2NH_2$ | 3-Ph-Phenyl |
| 684 | 4 | $SO_2NH_2$ | 3-Ph-Phenyl |
| 685 | 1 | H | 2-morpholino-phenyl |

TABLE 16-continued

| Entry | n | $R^7$ | $R^3$ |
|---|---|---|---|
| 686 | 2 | H | 2-morpholino-phenyl |
| 687 | 3 | H | 2-morpholino-phenyl |
| 688 | 4 | H | 2-morpholino-phenyl |
| 689 | 1 | Me | 2-morpholino-phenyl |
| 690 | 2 | Me | 2-morpholino-phenyl |
| 691 | 3 | Me | 2-morpholino-phenyl |
| 692 | 4 | Me | 2-morpholino-phenyl |
| 693 | 1 | $CH_2Ph$ | 2-morpholino-phenyl |
| 694 | 2 | $CH_2Ph$ | 2-morpholino-phenyl |
| 695 | 3 | $CH_2Ph$ | 2-morpholino-phenyl |
| 696 | 4 | $CH_2Ph$ | 2-morpholino-phenyl |
| 697 | 1 | COMe | 2-morpholino-phenyl |
| 698 | 2 | COMe | 2-morpholino-phenyl |
| 699 | 3 | COMe | 2-morpholino-phenyl |
| 700 | 4 | COMe | 2-morpholino-phenyl |
| 701 | 1 | $CO_2Me$ | 2-morpholino-phenyl |
| 702 | 2 | $CO_2Me$ | 2-morpholino-phenyl |
| 703 | 3 | $CO_2Me$ | 2-morpholino-phenyl |
| 704 | 4 | $CO_2Me$ | 2-morpholino-phenyl |
| 705 | 1 | $CO_2tBu$ | 2-morpholino-phenyl |
| 706 | 2 | $CO_2tBu$ | 2-morpholino-phenyl |
| 707 | 3 | $CO_2tBu$ | 2-morpholino-phenyl |
| 708 | 4 | $CO_2tBu$ | 2-morpholino-phenyl |
| 709 | 1 | CONHMe | 2-morpholino-phenyl |
| 710 | 2 | CONHMe | 2-morpholino-phenyl |
| 711 | 3 | CONHMe | 2-morpholino-phenyl |
| 712 | 4 | CONHMe | 2-morpholino-phenyl |
| 713 | 1 | $SO_2Me$ | 2-morpholino-phenyl |
| 714 | 2 | $SO_2Me$ | 2-morpholino-phenyl |
| 715 | 3 | $SO_2Me$ | 2-morpholino-phenyl |
| 716 | 4 | $SO_2Me$ | 2-morpholino-phenyl |
| 717 | 1 | $SO_2NH_2$ | 2-morpholino-phenyl |
| 718 | 2 | $SO_2NH_2$ | 2-morpholino-phenyl |
| 719 | 3 | $SO_2NH_2$ | 2-morpholino-phenyl |
| 720 | 4 | $SO_2NH_2$ | 2-morpholino-phenyl |
| 721 | 1 | H | 4-morpholino-phenyl |
| 722 | 2 | H | 4-morpholino-phenyl |
| 723 | 3 | H | 4-morpholino-phenyl |
| 724 | 4 | H | 4-morpholino-phenyl |
| 725 | 1 | $CH_2Ph$ | 4-morpholino-phenyl |
| 726 | 2 | $CH_2Ph$ | 4-morpholino-phenyl |
| 727 | 3 | $CH_2Ph$ | 4-morpholino-phenyl |
| 728 | 4 | $CH_2Ph$ | 4-morpholino-phenyl |
| 729 | 1 | COMe | 4-morpholino-phenyl |
| 730 | 2 | COMe | 4-morpholino-phenyl |
| 731 | 3 | COMe | 4-morpholino-phenyl |
| 732 | 4 | COMe | 4-morpholino-phenyl |
| 733 | 1 | $CO_2Me$ | 4-morpholino-phenyl |
| 734 | 2 | $CO_2Me$ | 4-morpholino-phenyl |
| 735 | 3 | $CO_2Me$ | 4-morpholino-phenyl |
| 736 | 4 | $CO_2Me$ | 4-morpholino-phenyl |
| 737 | 1 | $CO_2tBu$ | 4-morpholino-phenyl |
| 738 | 2 | $CO_2tBu$ | 4-morpholino-phenyl |
| 739 | 3 | $CO_2tBu$ | 4-morpholino-phenyl |
| 740 | 1 | H | naphthylen-1-yl |
| 741 | 2 | H | naphthylen-1-yl |
| 742 | 3 | H | naphthylen-1-yl |
| 743 | 4 | H | naphthylen-1-yl |
| 744 | 1 | Me | naphthylen-1-yl |
| 745 | 2 | Me | naphthylen-1-yl |
| 746 | 3 | Me | naphthylen-1-yl |
| 747 | 4 | Me | naphthylen-1-yl |
| 748 | 1 | $CH_2Ph$ | naphthylen-1-yl |
| 749 | 2 | $CH_2Ph$ | naphthylen-1-yl |
| 750 | 3 | $CH_2Ph$ | naphthylen-1-yl |
| 751 | 4 | $CH_2Ph$ | naphthylen-1-yl |
| 752 | 1 | COMe | naphthylen-1-yl |
| 753 | 2 | COMe | naphthylen-1-yl |
| 754 | 3 | COMe | naphthylen-1-yl |
| 755 | 4 | COMe | naphthylen-1-yl |
| 756 | 1 | $CO_2Me$ | naphthylen-1-yl |
| 757 | 2 | $CO_2Me$ | naphthylen-1-yl |
| 758 | 3 | $CO_2Me$ | naphthylen-1-yl |
| 759 | 4 | $CO_2Me$ | naphthylen-1-yl |
| 760 | 1 | $CO_2tBu$ | naphthylen-1-yl |
| 761 | 2 | $CO_2tBu$ | naphthylen-1-yl |
| 762 | 3 | $CO_2tBu$ | naphthylen-1-yl |
| 763 | 4 | $CO_2tBu$ | naphthylen-1-yl |

TABLE 16-continued

| Entry | n | $R^7$ | $R^3$ |
|---|---|---|---|
| 764 | 1 | CONHMe | naphthylen-1-yl |
| 765 | 2 | CONHMe | naphthylen-1-yl |
| 767 | 3 | CONHMe | naphthylen-1-yl |
| 768 | 4 | CONHMe | naphthylen-1-yl |
| 769 | 1 | $SO_2Me$ | naphthylen-1-yl |
| 770 | 2 | $SO_2Me$ | naphthylen-1-yl |
| 771 | 3 | $SO_2Me$ | naphthylen-1-yl |
| 772 | 4 | $SO_2Me$ | naphthylen-1-yl |
| 773 | 1 | $SO_2NH_2$ | naphthylen-1-yl |
| 774 | 2 | $SO_2NH_2$ | naphthylen-1-yl |
| 775 | 3 | $SO_2NH_2$ | naphthylen-1-yl |
| 778 | 4 | $SO_2NH_2$ | naphthylen-1-yl |
| 779 | 1 | H | 4-OH-Phenyl |
| 780 | 2 | H | 4-OH-Phenyl |
| 781 | 3 | H | 4-OH-Phenyl |
| 782 | 4 | H | 4-OH-Phenyl |
| 783 | 1 | Me | 4-OH-Phenyl |
| 784 | 2 | Me | 4-OH-Phenyl |
| 785 | 3 | Me | 4-OH-Phenyl |
| 786 | 4 | Me | 4-OH-Phenyl |
| 787 | 1 | $CH_2Ph$ | 4-OH-Phenyl |
| 788 | 2 | $CH_2Ph$ | 4-OH-Phenyl |
| 789 | 3 | $CH_2Ph$ | 4-OH-Phenyl |
| 790 | 4 | $CH_2Ph$ | 4-OH-Phenyl |
| 791 | 1 | COMe | 4-OH-Phenyl |
| 792 | 2 | COMe | 4-OH-Phenyl |
| 793 | 3 | COMe | 4-OH-Phenyl |
| 794 | 4 | COMe | 4-OH-Phenyl |
| 795 | 1 | $CO_2Me$ | 4-OH-Phenyl |
| 796 | 2 | $CO_2Me$ | 4-OH-Phenyl |
| 797 | 3 | $CO_2Me$ | 4-OH-Phenyl |
| 798 | 4 | $CO_2Me$ | 4-OH-Phenyl |
| 799 | 1 | $CO_2tBu$ | 4-OH-Phenyl |
| 800 | 2 | $CO_2tBu$ | 4-OH-Phenyl |
| 801 | 3 | $CO_2tBu$ | 4-OH-Phenyl |
| 802 | 4 | $CO_2tBu$ | 4-OH-Phenyl |
| 803 | 1 | CONHMe | 4-OH-Phenyl |
| 804 | 2 | CONHMe | 4-OH-Phenyl |
| 805 | 3 | CONHMe | 4-OH-Phenyl |
| 806 | 4 | CONHMe | 4-OH-Phenyl |
| 807 | 1 | $SO_2Me$ | 4-OH-Phenyl |
| 808 | 2 | $SO_2Me$ | 4-OH-Phenyl |
| 809 | 3 | $SO_2Me$ | 4-OH-Phenyl |
| 810 | 4 | $SO_2Me$ | 4-OH-Phenyl |
| 811 | 1 | $SO_2NH_2$ | 4-OH-Phenyl |
| 812 | 2 | $SO_2NH_2$ | 4-OH-Phenyl |
| 813 | 3 | $SO_2NH_2$ | 4-OH-Phenyl |
| 814 | 4 | $SO_2NH_2$ | 4-OH-Phenyl |
| 815 | 1 | H | 2-OH-Phenyl |
| 816 | 2 | H | 2-OH-Phenyl |
| 817 | 3 | H | 2-OH-Phenyl |
| 818 | 4 | H | 2-OH-Phenyl |
| 819 | 1 | Me | 2-OH-Phenyl |
| 820 | 2 | Me | 2-OH-Phenyl |
| 821 | 3 | Me | 2-OH-Phenyl |
| 822 | 4 | Me | 2-OH-Phenyl |
| 823 | 1 | $CH_2Ph$ | 2-OH-Phenyl |
| 824 | 2 | $CH_2Ph$ | 2-OH-Phenyl |
| 825 | 3 | $CH_2Ph$ | 2-OH-Phenyl |
| 826 | 4 | $CH_2Ph$ | 2-OH-Phenyl |
| 827 | 1 | COMe | 2-OH-Phenyl |
| 828 | 2 | COMe | 2-OH-Phenyl |
| 829 | 3 | COMe | 2-OH-Phenyl |
| 830 | 4 | COMe | 2-OH-Phenyl |
| 831 | 1 | $CO_2Me$ | 2-OH-Phenyl |
| 832 | 2 | $CO_2Me$ | 2-OH-Phenyl |
| 833 | 3 | $CO_2Me$ | 2-OH-Phenyl |
| 834 | 4 | $CO_2Me$ | 2-OH-Phenyl |
| 835 | 1 | $CO_2tBu$ | 2-OH-Phenyl |
| 836 | 2 | $CO_2tBu$ | 2-OH-Phenyl |
| 837 | 3 | $CO_2tBu$ | 2-OH-Phenyl |
| 838 | 4 | $CO_2tBu$ | 2-OH-Phenyl |
| 839 | 1 | CONHMe | 2-OH-Phenyl |
| 840 | 2 | CONHMe | 2-OH-Phenyl |
| 841 | 3 | CONHMe | 2-OH-Phenyl |
| 842 | 4 | CONHMe | 2-OH-Phenyl |
| 843 | 1 | $SO_2Me$ | 2-OH-Phenyl |
| 844 | 2 | $SO_2Me$ | 2-OH-Phenyl |

TABLE 16-continued

| Entry | n | $R^7$ | $R^3$ |
|---|---|---|---|
| 845 | 3 | $SO_2Me$ | 2-OH-Phenyl |
| 846 | 4 | $SO_2Me$ | 2-OH-Phenyl |
| 847 | 1 | $SO_2NH_2$ | 2-OH-Phenyl |
| 848 | 2 | $SO_2NH_2$ | 2-OH-Phenyl |
| 849 | 3 | $SO_2NH_2$ | 2-OH-Phenyl |
| 850 | 4 | $SO_2NH_2$ | 2-OH-Phenyl |
| 851 | 1 | H | 4-OMe-Phenyl |
| 852 | 2 | H | 4-OMe-Phenyl |
| 853 | 3 | H | 4-OMe-Phenyl |
| 854 | 4 | H | 4-OMe-Phenyl |
| 855 | 1 | Me | 4-OMe-Phenyl |
| 856 | 2 | Me | 4-OMe-Phenyl |
| 857 | 3 | Me | 4-OMe-Phenyl |
| 858 | 4 | Me | 4-OMe-Phenyl |
| 859 | 1 | $CH_2Ph$ | 4-OMe-Phenyl |
| 860 | 2 | $CH_2Ph$ | 4-OMe-Phenyl |
| 861 | 3 | $CH_2Ph$ | 4-OMe-Phenyl |
| 862 | 4 | $CH_2Ph$ | 4-OMe-Phenyl |
| 863 | 1 | COMe | 4-OMe-Phenyl |
| 864 | 2 | COMe | 4-OMe-Phenyl |
| 865 | 3 | COMe | 4-OMe-Phenyl |
| 866 | 4 | COMe | 4-OMe-Phenyl |
| 867 | 1 | $CO_2Me$ | 4-OMe-Phenyl |
| 868 | 2 | $CO_2Me$ | 4-OMe-Phenyl |
| 869 | 3 | $CO_2Me$ | 4-OMe-Phenyl |
| 870 | 4 | $CO_2Me$ | 4-OMe-Phenyl |
| 871 | 1 | $CO_2tBu$ | 4-OMe-Phenyl |
| 872 | 2 | $CO_2tBu$ | 4-OMe-Phenyl |
| 873 | 3 | $CO_2tBu$ | 4-OMe-Phenyl |
| 874 | 4 | $CO_2tBu$ | 4-OMe-Phenyl |
| 875 | 1 | CONHMe | 4-OMe-Phenyl |
| 876 | 2 | CONHMe | 4-OMe-Phenyl |
| 877 | 3 | CONHMe | 4-OMe-Phenyl |
| 878 | 4 | CONHMe | 4-OMe-Phenyl |
| 879 | 1 | $SO_2Me$ | 4-OMe-Phenyl |
| 880 | 2 | $SO_2Me$ | 4-OMe-Phenyl |
| 881 | 3 | $SO_2Me$ | 4-OMe-Phenyl |
| 882 | 4 | $SO_2Me$ | 4-OMe-Phenyl |
| 883 | 1 | $SO_2NH_2$ | 4-OMe-Phenyl |
| 884 | 2 | $SO_2NH_2$ | 4-OMe-Phenyl |
| 885 | 3 | $SO_2NH_2$ | 4-OMe-Phenyl |
| 886 | 4 | $SO_2NH_2$ | 4-OMe-Phenyl |
| 887 | 1 | H | 2-OMe-Phenyl |
| 888 | 2 | H | 2-OMe-Phenyl |
| 889 | 3 | H | 2-OMe-Phenyl |
| 890 | 4 | H | 2-OMe-Phenyl |
| 891 | 1 | Me | 2-OMe-Phenyl |
| 892 | 2 | Me | 2-OMe-Phenyl |
| 893 | 3 | Me | 2-OMe-Phenyl |
| 894 | 4 | Me | 2-OMe-Phenyl |
| 895 | 1 | $CH_2Ph$ | 2-OMe-Phenyl |
| 896 | 2 | $CH_2Ph$ | 2-OMe-Phenyl |
| 897 | 3 | $CH_2Ph$ | 2-OMe-Phenyl |
| 898 | 4 | $CH_2Ph$ | 2-OMe-Phenyl |
| 899 | 1 | COMe | 2-OMe-Phenyl |
| 900 | 2 | COMe | 2-OMe-Phenyl |
| 901 | 3 | COMe | 2-OMe-Phenyl |
| 902 | 4 | COMe | 2-OMe-Phenyl |
| 903 | 1 | $CO_2Me$ | 2-OMe-Phenyl |
| 904 | 2 | $CO_2Me$ | 2-OMe-Phenyl |
| 905 | 3 | $CO_2Me$ | 2-OMe-Phenyl |
| 906 | 4 | $CO_2Me$ | 2-OMe-Phenyl |
| 907 | 1 | $CO_2tBu$ | 2-OMe-Phenyl |
| 908 | 2 | $CO_2tBu$ | 2-OMe-Phenyl |
| 909 | 3 | $CO_2tBu$ | 2-OMe-Phenyl |
| 910 | 4 | $CO_2tBu$ | 2-OMe-Phenyl |
| 911 | 1 | CONHMe | 2-OMe-Phenyl |
| 912 | 2 | CONHMe | 2-OMe-Phenyl |
| 913 | 3 | CONHMe | 2-OMe-Phenyl |
| 914 | 4 | CONHMe | 2-OMe-Phenyl |
| 915 | 1 | $SO_2Me$ | 2-OMe-Phenyl |
| 916 | 2 | $SO_2Me$ | 2-OMe-Phenyl |
| 917 | 3 | $SO_2Me$ | 2-OMe-Phenyl |
| 918 | 4 | $SO_2Me$ | 2-OMe-Phenyl |
| 919 | 1 | $SO_2NH_2$ | 2-OMe-Phenyl |
| 920 | 2 | $SO_2NH_2$ | 2-OMe-Phenyl |
| 921 | 3 | $SO_2NH_2$ | 2-OMe-Phenyl |
| 922 | 4 | $SO_2NH_2$ | 2-OMe-Phenyl |

TABLE 16-continued

| Entry | n | $R^7$ | $R^3$ |
|---|---|---|---|
| 923 | 1 | H | 3-CN-Phenyl |
| 924 | 2 | H | 3-CN-Phenyl |
| 925 | 3 | H | 3-CN-Phenyl |
| 926 | 4 | H | 3-CN-Phenyl |
| 927 | 1 | Me | 3-CN-Phenyl |
| 928 | 2 | Me | 3-CN-Phenyl |
| 929 | 3 | Me | 3-CN-Phenyl |
| 930 | 4 | Me | 3-CN-Phenyl |
| 931 | 1 | $CH_2Ph$ | 3-CN-Phenyl |
| 932 | 2 | $CH_2Ph$ | 3-CN-Phenyl |
| 933 | 3 | $CH_2Ph$ | 3-CN-Phenyl |
| 934 | 4 | $CH_2Ph$ | 3-CN-Phenyl |
| 935 | 1 | COMe | 3-CN-Phenyl |
| 936 | 2 | COMe | 3-CN-Phenyl |
| 937 | 3 | COMe | 3-CN-Phenyl |
| 938 | 4 | COMe | 3-CN-Phenyl |
| 939 | 1 | $CO_2Me$ | 3-CN-Phenyl |
| 940 | 2 | $CO_2Me$ | 3-CN-Phenyl |
| 941 | 3 | $CO_2Me$ | 3-CN-Phenyl |
| 942 | 4 | $CO_2Me$ | 3-CN-Phenyl |
| 943 | 1 | $CO_2tBu$ | 3-CN-Phenyl |
| 944 | 2 | $CO_2tBu$ | 3-CN-Phenyl |
| 945 | 3 | $CO_2tBu$ | 3-CN-Phenyl |
| 946 | 4 | $CO_2tBu$ | 3-CN-Phenyl |
| 947 | 1 | CONHMe | 3-CN-Phenyl |
| 948 | 2 | CONHMe | 3-CN-Phenyl |
| 949 | 3 | CONHMe | 3-CN-Phenyl |
| 950 | 4 | CONHMe | 3-CN-Phenyl |
| 951 | 1 | $SO_2Me$ | 3-CN-Phenyl |
| 952 | 2 | $SO_2Me$ | 3-CN-Phenyl |
| 953 | 3 | $SO_2Me$ | 3-CN-Phenyl |
| 954 | 4 | $SO_2Me$ | 3-CN-Phenyl |
| 955 | 1 | $SO_2NH_2$ | 3-CN-Phenyl |
| 956 | 2 | $SO_2NH_2$ | 3-CN-Phenyl |
| 957 | 3 | $SO_2NH_2$ | 3-CN-Phenyl |
| 958 | 4 | $SO_2NH_2$ | 3-CN-Phenyl |
| 959 | 1 | H | 2-Me-Phenyl |
| 960 | 2 | H | 2-Me-Phenyl |
| 961 | 3 | H | 2-Me-Phenyl |
| 962 | 4 | H | 2-Me-Phenyl |
| 963 | 1 | Me | 2-Me-Phenyl |
| 964 | 2 | Me | 2-Me-Phenyl |
| 965 | 3 | Me | 2-Me-Phenyl |
| 966 | 4 | Me | 2-Me-Phenyl |
| 967 | 1 | $CH_2Ph$ | 2-Me-Phenyl |
| 968 | 2 | $CH_2Ph$ | 2-Me-Phenyl |
| 969 | 3 | $CH_2Ph$ | 2-Me-Phenyl |
| 970 | 4 | $CH_2Ph$ | 2-Me-Phenyl |
| 971 | 1 | COMe | 2-Me-Phenyl |
| 972 | 2 | COMe | 2-Me-Phenyl |
| 973 | 3 | COMe | 2-Me-Phenyl |
| 974 | 4 | COMe | 2-Me-Phenyl |
| 975 | 1 | $CO_2Me$ | 2-Me-Phenyl |
| 976 | 2 | $CO_2Me$ | 2-Me-Phenyl |
| 977 | 3 | $CO_2Me$ | 2-Me-Phenyl |
| 978 | 4 | $CO_2Me$ | 2-CN-Phenyl |
| 979 | 1 | $CO_2tBu$ | 2-Me-Phenyl |
| 980 | 2 | $CO_2tBu$ | 2-Me-Phenyl |
| 981 | 3 | $CO_2tBu$ | 2-Me-Phenyl |
| 982 | 4 | $CO_2tBu$ | 2-Me-Phenyl |
| 983 | 1 | CONHMe | 2-Me-Phenyl |
| 984 | 2 | CONHMe | 2-Me-Phenyl |
| 985 | 3 | CONHMe | 2-Me-Phenyl |
| 986 | 4 | CONHMe | 2-Me-Phenyl |
| 987 | 1 | $SO_2Me$ | 2-Me-Phenyl |
| 988 | 2 | $SO_2Me$ | 2-Me-Phenyl |
| 989 | 3 | $SO_2Me$ | 2-Me-Phenyl |
| 990 | 4 | $SO_2Me$ | 2-Me-Phenyl |
| 991 | 1 | $SO_2NH_2$ | 2-Me-Phenyl |
| 992 | 2 | $SO_2NH_2$ | 2-Me-Phenyl |
| 993 | 3 | $SO_2NH_2$ | 2-Me-Phenyl |
| 994 | 4 | $SO_2NH_2$ | 2-Me-Phenyl |
| 995 | 1 | H | 4-Me-Phenyl |
| 996 | 2 | H | 4-Me-Phenyl |
| 997 | 3 | H | 4-Me-Phenyl |
| 998 | 4 | H | 4-Me-Phenyl |
| 999 | 1 | Me | 4-Me-Phenyl |
| 1000 | 2 | Me | 4-Me-Phenyl |

TABLE 16-continued

| Entry | n | $R^7$ | $R^3$ |
|---|---|---|---|
| 1001 | 3 | Me | 4-Me-Phenyl |
| 1002 | 4 | Me | 4-Me-Phenyl |
| 1003 | 1 | $CH_2Ph$ | 4-Me-Phenyl |
| 1004 | 2 | $CH_2Ph$ | 4-Me-Phenyl |
| 1005 | 3 | $CH_2Ph$ | 4-Me-Phenyl |
| 1006 | 4 | $CH_2Ph$ | 4-Me-Phenyl |
| 1007 | 1 | COMe | 4-Me-Phenyl |
| 1008 | 2 | COMe | 4-Me-Phenyl |
| 1009 | 3 | COMe | 4-Me-Phenyl |
| 1010 | 4 | COMe | 4-Me-Phenyl |
| 1011 | 1 | $CO_2Me$ | 4-Me-Phenyl |
| 1012 | 2 | $CO_2Me$ | 4-Me-Phenyl |
| 1013 | 3 | $CO_2Me$ | 4-Me-Phenyl |
| 1014 | 4 | $CO_2Me$ | 4-Me-Phenyl |
| 1015 | 1 | $CO_2tBu$ | 4-Me-Phenyl |
| 1016 | 2 | $CO_2tBu$ | 4-Me-Phenyl |
| 1017 | 3 | $CO_2tBu$ | 4-Me-Phenyl |
| 1018 | 4 | $CO_2tBu$ | 4-Me-Phenyl |
| 1019 | 1 | CONHMe | 4-Me-Phenyl |
| 1020 | 2 | CONHMe | 4-Me-Phenyl |
| 1021 | 3 | CONHMe | 4-Me-Phenyl |
| 1022 | 4 | CONHMe | 4-Me-Phenyl |
| 1023 | 1 | $SO_2Me$ | 4-Me-Phenyl |
| 1024 | 2 | $SO_2Me$ | 4-Me-Phenyl |
| 1025 | 3 | $SO_2Me$ | 4-Me-Phenyl |
| 1026 | 4 | $SO_2Me$ | 4-Me-Phenyl |
| 1027 | 1 | $SO_2NH_2$ | 4-Me-Phenyl |
| 1028 | 2 | $SO_2NH_2$ | 4-Me-Phenyl |
| 1029 | 3 | $SO_2NH_2$ | 4-Me-Phenyl |
| 1030 | 4 | $SO_2NH_2$ | 4-Me-Phenyl |
| 1031 | 1 | H | 3-F-Phenyl |
| 1032 | 2 | H | 3-F-Phenyl |
| 1033 | 3 | H | 3-F-Phenyl |
| 1034 | 4 | H | 3-F-Phenyl |
| 1035 | 1 | Me | 3-F-Phenyl |
| 1036 | 2 | Me | 3-F-Phenyl |
| 1037 | 3 | Me | 3-F-Phenyl |
| 1038 | 4 | Me | 3-F-Phenyl |
| 1039 | 1 | $CH_2Ph$ | 3-F-Phenyl |
| 1040 | 2 | $CH_2Ph$ | 3-F-Phenyl |
| 1041 | 3 | $CH_2Ph$ | 3-F-Phenyl |
| 1042 | 4 | $CH_2Ph$ | 3-F-Phenyl |
| 1043 | 1 | COMe | 3-F-Phenyl |
| 1044 | 2 | COMe | 3-F-Phenyl |
| 1045 | 3 | COMe | 3-F-Phenyl |
| 1046 | 4 | COMe | 3-F-Phenyl |
| 1047 | 1 | $CO_2Me$ | 3-F-Phenyl |
| 1048 | 2 | $CO_2Me$ | 3-F-Phenyl |
| 1049 | 3 | $CO_2Me$ | 3-F-Phenyl |
| 1050 | 4 | $CO_2Me$ | 3-F-Phenyl |
| 1051 | 1 | $CO_2tBu$ | 3-F-Phenyl |
| 1052 | 2 | $CO_2tBu$ | 3-F-Phenyl |
| 1053 | 3 | $CO_2tBu$ | 3-F-Phenyl |
| 1054 | 4 | $CO_2tBu$ | 3-F-Phenyl |
| 1055 | 1 | CONHMe | 3-F-Phenyl |
| 1056 | 2 | CONHMe | 3-F-Phenyl |
| 1057 | 3 | CONHMe | 3-F-Phenyl |
| 1058 | 4 | CONHMe | 3-F-Phenyl |
| 1059 | 1 | $SO_2Me$ | 3-F-Phenyl |
| 1060 | 2 | $SO_2Me$ | 3-F-Phenyl |
| 1061 | 3 | $SO_2Me$ | 3-F-Phenyl |
| 1062 | 4 | $SO_2Me$ | 3-F-Phenyl |
| 1063 | 1 | $SO_2NH_2$ | 3-F-Phenyl |
| 1064 | 2 | $SO_2NH_2$ | 3-F-Phenyl |
| 1065 | 3 | $SO_2NH_2$ | 3-F-Phenyl |
| 1066 | 4 | $SO_2NH_2$ | 3-F-Phenyl |
| 1067 | 1 | H | 2-Cl-Phenyl |
| 1068 | 2 | H | 2-Cl-Phenyl |
| 1069 | 3 | H | 2-Cl-Phenyl |
| 1070 | 4 | H | 2-Cl-Phenyl |
| 1071 | 1 | Me | 2-Cl-Phenyl |
| 1072 | 2 | Me | 2-Cl-Phenyl |
| 1073 | 3 | Me | 2-Cl-Phenyl |
| 1074 | 4 | Me | 2-Cl-Phenyl |
| 1075 | 1 | $CH_2Ph$ | 2-Cl-Phenyl |
| 1076 | 2 | $CH_2Ph$ | 2-Cl-Phenyl |
| 1077 | 3 | $CH_2Ph$ | 2-Cl-Phenyl |
| 1078 | 4 | $CH_2Ph$ | 2-Cl-Phenyl |

TABLE 16-continued

| Entry | n | $R^7$ | $R^3$ |
|---|---|---|---|
| 1079 | 1 | COMe | 2-Cl-Phenyl |
| 1080 | 2 | COMe | 2-Cl-Phenyl |
| 1081 | 3 | COMe | 2-Cl-Phenyl |
| 1082 | 4 | COMe | 2-Cl-Phenyl |
| 1083 | 1 | $CO_2Me$ | 2-Cl-Phenyl |
| 1084 | 2 | $CO_2Me$ | 2-Cl-Phenyl |
| 1085 | 3 | $CO_2Me$ | 2-Cl-Phenyl |
| 1086 | 4 | $CO_2Me$ | 2-Cl-Phenyl |
| 1087 | 1 | $CO_2tBu$ | 2-Cl-Phenyl |
| 1088 | 2 | $CO_2tBu$ | 2-Cl-Phenyl |
| 1089 | 3 | $CO_2tBu$ | 2-Cl-Phenyl |
| 1090 | 4 | $CO_2tBu$ | 2-Cl-Phenyl |
| 1091 | 1 | CONHMe | 2-Cl-Phenyl |
| 1092 | 2 | CONHMe | 2-Cl-Phenyl |
| 1093 | 3 | CONHMe | 2-Cl-Phenyl |
| 1094 | 4 | CONHMe | 2-Cl-Phenyl |
| 1095 | 1 | $SO_2Me$ | 2-Cl-Phenyl |
| 1096 | 2 | $SO_2Me$ | 2-Cl-Phenyl |
| 1097 | 3 | $SO_2Me$ | 2-Cl-Phenyl |
| 1098 | 4 | $SO_2Me$ | 2-Cl-Phenyl |
| 1099 | 1 | $SO_2NH_2$ | 2-Cl-Phenyl |
| 1100 | 2 | $SO_2NH_2$ | 2-Cl-Phenyl |
| 1101 | 3 | $SO_2NH_2$ | 2-Cl-Phenyl |
| 1102 | 4 | $SO_2NH_2$ | 2-Cl-Phenyl |
| 1103 | 1 | H | 4-Cl-Phenyl |
| 1104 | 2 | H | 4-Cl-Phenyl |
| 1105 | 3 | H | 4-Cl-Phenyl |
| 1106 | 4 | H | 4-Cl-Phenyl |
| 1107 | 1 | Me | 4-Cl-Phenyl |
| 1108 | 2 | Me | 4-Cl-Phenyl |
| 1109 | 3 | Me | 4-Cl-Phenyl |
| 1110 | 4 | Me | 4-Cl-Phenyl |
| 1111 | 1 | $CH_2Ph$ | 4-Cl-Phenyl |
| 1112 | 2 | $CH_2Ph$ | 4-Cl-Phenyl |
| 1113 | 3 | $CH_2Ph$ | 4-Cl-Phenyl |
| 1114 | 4 | $CH_2Ph$ | 4-Cl-Phenyl |
| 1115 | 1 | COMe | 4-Cl-Phenyl |
| 1116 | 2 | COMe | 4-Cl-Phenyl |
| 1117 | 3 | COMe | 4-Cl-Phenyl |
| 1118 | 4 | COMe | 4-Cl-Phenyl |
| 1119 | 1 | $CO_2Me$ | 4-Cl-Phenyl |
| 1120 | 2 | $CO_2Me$ | 4-Cl-Phenyl |
| 1121 | 3 | $CO_2Me$ | 4-Cl-Phenyl |
| 1122 | 4 | $CO_2Me$ | 4-Cl-Phenyl |
| 1123 | 1 | $CO_2tBu$ | 4-Cl-Phenyl |
| 1124 | 2 | $CO_2tBu$ | 4-Cl-Phenyl |
| 1125 | 3 | $CO_2tBu$ | 4-Cl-Phenyl |
| 1126 | 4 | $CO_2tBu$ | 4-Cl-Phenyl |
| 1127 | 1 | CONHMe | 4-Cl-Phenyl |
| 1128 | 2 | CONHMe | 4-Cl-Phenyl |
| 1129 | 3 | CONHMe | 4-Cl-Phenyl |
| 1130 | 4 | CONHMe | 4-Cl-Phenyl |
| 1131 | 1 | $SO_2Me$ | 4-Cl-Phenyl |
| 1132 | 2 | $SO_2Me$ | 4-Cl-Phenyl |
| 1133 | 3 | $SO_2Me$ | 4-Cl-Phenyl |
| 1134 | 4 | $SO_2Me$ | 4-Cl-Phenyl |
| 1135 | 1 | $SO_2NH_2$ | 4-Cl-Phenyl |
| 1136 | 2 | $SO_2NH_2$ | 4-Cl-Phenyl |
| 1137 | 3 | $SO_2NH_2$ | 4-Cl-Phenyl |
| 1138 | 4 | $SO_2NH_2$ | 4-Cl-Phenyl |
| 1139 | 1 | H | 3-Br-Phenyl |
| 1140 | 2 | H | 3-Br-Phenyl |
| 1141 | 3 | H | 3-Br-Phenyl |
| 1142 | 4 | H | 3-Br-Phenyl |
| 1143 | 1 | Me | 3-Br-Phenyl |
| 1144 | 2 | Me | 3-Br-Phenyl |
| 1145 | 3 | Me | 3-Br-Phenyl |
| 1146 | 4 | Me | 3-Br-Phenyl |
| 1147 | 1 | $CH_2Ph$ | 3-Br-Phenyl |
| 1148 | 2 | $CH_2Ph$ | 3-Br-Phenyl |
| 1149 | 3 | $CH_2Ph$ | 3-Br-Phenyl |
| 1150 | 4 | $CH_2Ph$ | 3-Br-Phenyl |
| 1151 | 1 | COMe | 3-Br-Phenyl |
| 1152 | 2 | COMe | 3-Br-Phenyl |
| 1153 | 3 | COMe | 3-Br-Phenyl |
| 1154 | 4 | COMe | 3-Br-Phenyl |
| 1155 | 1 | $CO_2Me$ | 3-Br-Phenyl |
| 1156 | 2 | $CO_2Me$ | 3-Br-Phenyl |

TABLE 16-continued

| Entry | n | $R^7$ | $R^3$ |
|---|---|---|---|
| 1157 | 3 | $CO_2Me$ | 3-Br-Phenyl |
| 1158 | 4 | $CO_2Me$ | 3-Br-Phenyl |
| 1159 | 1 | $CO_2tBu$ | 3-Br-Phenyl |
| 1160 | 2 | $CO_2tBu$ | 3-Br-Phenyl |
| 1161 | 3 | $CO_2tBu$ | 3-Br-Phenyl |
| 1162 | 4 | $CO_2tBu$ | 3-Br-Phenyl |
| 1163 | 1 | CONHMe | 3-Br-Phenyl |
| 1164 | 2 | CONHMe | 3-Br-Phenyl |
| 1165 | 3 | CONHMe | 3-Br-Phenyl |
| 1166 | 4 | CONHMe | 3-Br-Phenyl |
| 1167 | 1 | $SO_2Me$ | 3-Br-Phenyl |
| 1168 | 2 | $SO_2Me$ | 3-Br-Phenyl |
| 1169 | 3 | $SO_2Me$ | 3-Br-Phenyl |
| 1170 | 4 | $SO_2Me$ | 3-Br-Phenyl |
| 1171 | 1 | $SO_2NH_2$ | 3-Br-Phenyl |
| 1172 | 2 | $SO_2NH_2$ | 3-Br-Phenyl |
| 1173 | 3 | $SO_2NH_2$ | 3-Br-Phenyl |
| 1174 | 4 | $SO_2NH_2$ | 3-Br-Phenyl |
| 1175 | 1 | H | 2-$CF_3$-Phenyl |
| 1176 | 2 | H | 2-$CF_3$-Phenyl |
| 1177 | 3 | H | 2-$CF_3$-Phenyl |
| 1178 | 4 | H | 2-$CF_3$-Phenyl |
| 1179 | 1 | Me | 2-$CF_3$-Phenyl |
| 1180 | 2 | Me | 2-$CF_3$-Phenyl |
| 1181 | 3 | Me | 2-$CF_3$-Phenyl |
| 1182 | 4 | Me | 2-$CF_3$-Phenyl |
| 1183 | 1 | $CH_2Ph$ | 2-$CF_3$-Phenyl |
| 1184 | 2 | $CH_2Ph$ | 2-$CF_3$-Phenyl |
| 1185 | 3 | $CH_2Ph$ | 2-$CF_3$-Phenyl |
| 1186 | 4 | $CH_2Ph$ | 2-$CF_3$-Phenyl |
| 1187 | 1 | COMe | 2-$CF_3$-Phenyl |
| 1188 | 2 | COMe | 2-$CF_3$-Phenyl |
| 1189 | 3 | COMe | 2-$CF_3$-Phenyl |
| 1190 | 4 | COMe | 2-$CF_3$-Phenyl |
| 1191 | 1 | $CO_2Me$ | 2-$CF_3$-Phenyl |
| 1192 | 2 | $CO_2Me$ | 2-$CF_3$-Phenyl |
| 1193 | 3 | $CO_2Me$ | 2-$CF_3$-Phenyl |
| 1194 | 4 | $CO_2Me$ | 2-$CF_3$-Phenyl |
| 1195 | 1 | $CO_2tBu$ | 2-$CF_3$-Phenyl |
| 1196 | 2 | $CO_2tBu$ | 2-$CF_3$-Phenyl |
| 1197 | 3 | $CO_2tBu$ | 2-$CF_3$-Phenyl |
| 1198 | 4 | $CO_2tBu$ | 2-$CF_3$-Phenyl |
| 1199 | 1 | CONHMe | 2-$CF_3$-Phenyl |
| 1200 | 2 | CONHMe | 2-$CF_3$-Phenyl |
| 1201 | 3 | CONHMe | 2-$CF_3$-Phenyl |
| 1202 | 4 | CONHMe | 2-$CF_3$-Phenyl |
| 1203 | 1 | $SO_2Me$ | 2-$CF_3$-Phenyl |
| 1204 | 2 | $SO_2Me$ | 2-$CF_3$-Phenyl |
| 1205 | 3 | $SO_2Me$ | 2-$CF_3$-Phenyl |
| 1206 | 4 | $SO_2Me$ | 2-$CF_3$-Phenyl |
| 1207 | 1 | $SO_2NH_2$ | 2-$CF_3$-Phenyl |
| 1208 | 2 | $SO_2NH_2$ | 2-$CF_3$-Phenyl |
| 1209 | 3 | $SO_2NH_2$ | 2-$CF_3$-Phenyl |
| 1210 | 4 | $SO_2NH_2$ | 2-$CF_3$-Phenyl |
| 1211 | 1 | H | 4-$CF_3$-Phenyl |
| 1212 | 2 | H | 4-$CF_3$-Phenyl |
| 1213 | 3 | H | 4-$CF_3$-Phenyl |
| 1214 | 4 | H | 4-$CF_3$-Phenyl |
| 1215 | 1 | Me | 4-$CF_3$-Phenyl |
| 1216 | 2 | Me | 4-$CF_3$-Phenyl |
| 1217 | 3 | Me | 4-$CF_3$-Phenyl |
| 1218 | 4 | Me | 4-$CF_3$-Phenyl |
| 1219 | 1 | $CH_2Ph$ | 4-$CF_3$-Phenyl |
| 1220 | 2 | $CH_2Ph$ | 4-$CF_3$-Phenyl |
| 1221 | 3 | $CH_2Ph$ | 4-$CF_3$-Phenyl |
| 1222 | 4 | $CH_2Ph$ | 4-$CF_3$-Phenyl |
| 1223 | 1 | COMe | 4-$CF_3$-Phenyl |
| 1224 | 2 | COMe | 4-$CF_3$-Phenyl |
| 1225 | 3 | COMe | 4-$CF_3$-Phenyl |
| 1226 | 4 | COMe | 4-$CF_3$-Phenyl |
| 1227 | 1 | $CO_2Me$ | 4-$CF_3$-Phenyl |
| 1228 | 2 | $CO_2Me$ | 4-$CF_3$-Phenyl |
| 1229 | 3 | $CO_2Me$ | 4-$CF_3$-Phenyl |
| 1230 | 4 | $CO_2Me$ | 4-$CF_3$-Phenyl |
| 1231 | 1 | $CO_2tBu$ | 4-$CF_3$-Phenyl |
| 1232 | 2 | $CO_2tBu$ | 4-$CF_3$-Phenyl |
| 1233 | 3 | $CO_2tBu$ | 4-$CF_3$-Phenyl |
| 1234 | 4 | $CO_2tBu$ | 4-$CF_3$-Phenyl |

TABLE 16-continued

| Entry | n | $R^7$ | $R^3$ |
|---|---|---|---|
| 1235 | 1 | CONHMe | 4-$CF_3$-Phenyl |
| 1236 | 2 | CONHMe | 4-$CF_3$-Phenyl |
| 1237 | 3 | CONHMe | 4-$CF_3$-Phenyl |
| 1238 | 4 | CONHMe | 4-$CF_3$-Phenyl |
| 1239 | 1 | $SO_2Me$ | 4-$CF_3$-Phenyl |
| 1240 | 2 | $SO_2Me$ | 4-$CF_3$-Phenyl |
| 1241 | 3 | $SO_2Me$ | 4-$CF_3$-Phenyl |
| 1242 | 4 | $SO_2Me$ | 4-$CF_3$-Phenyl |
| 1243 | 1 | $SO_2NH_2$ | 4-$CF_3$-Phenyl |
| 1244 | 2 | $SO_2NH_2$ | 4-$CF_3$-Phenyl |
| 1245 | 3 | $SO_2NH_2$ | 4-$CF_3$-Phenyl |
| 1246 | 4 | $SO_2NH_2$ | 4-$CF_3$-Phenyl |
| 1247 | 1 | H | 3-iPr-Phenyl |
| 1248 | 2 | H | 3-iPr-Phenyl |
| 1249 | 3 | H | 3-iPr-Phenyl |
| 1250 | 4 | H | 3-iPr-Phenyl |
| 1251 | 1 | Me | 3-iPr-Phenyl |
| 1252 | 2 | Me | 3-iPr-Phenyl |
| 1253 | 3 | Me | 3-iPr-Phenyl |
| 1254 | 4 | Me | 3-iPr-Phenyl |
| 1255 | 1 | $CH_2Ph$ | 3-iPr-Phenyl |
| 1256 | 2 | $CH_2Ph$ | 3-iPr-Phenyl |
| 1257 | 3 | $CH_2Ph$ | 3-iPr-Phenyl |
| 1258 | 4 | $CH_2Ph$ | 3-iPr-Phenyl |
| 1259 | 1 | COMe | 3-iPr-Phenyl |
| 1260 | 2 | COMe | 3-iPr-Phenyl |
| 1261 | 3 | COMe | 3-iPr-Phenyl |
| 1262 | 4 | COMe | 3-iPr-Phenyl |
| 1263 | 1 | $CO_2Me$ | 3-iPr-Phenyl |
| 1264 | 2 | $CO_2Me$ | 3-iPr-Phenyl |
| 1265 | 3 | $CO_2Me$ | 3-iPr-Phenyl |
| 1266 | 4 | $CO_2Me$ | 3-iPr-Phenyl |
| 1267 | 1 | $CO_2tBu$ | 3-iPr-Phenyl |
| 1268 | 2 | $CO_2tBu$ | 3-iPr-Phenyl |
| 1269 | 3 | $CO_2tBu$ | 3-iPr-Phenyl |
| 1270 | 4 | $CO_2tBu$ | 3-iPr-Phenyl |
| 1271 | 1 | CONHMe | 3-iPr-Phenyl |
| 1272 | 2 | CONHMe | 3-iPr-Phenyl |
| 1273 | 3 | CONHMe | 3-iPr-Phenyl |
| 1274 | 4 | CONHMe | 3-iPr-Phenyl |
| 1275 | 1 | $SO_2Me$ | 3-iPr-Phenyl |
| 1276 | 2 | $SO_2Me$ | 3-iPr-Phenyl |
| 1277 | 3 | $SO_2Me$ | 3-iPr-Phenyl |
| 1278 | 4 | $SO_2Me$ | 3-iPr-Phenyl |
| 1279 | 1 | $SO_2NH_2$ | 3-iPr-Phenyl |
| 1280 | 2 | $SO_2NH_2$ | 3-iPr-Phenyl |
| 1281 | 3 | $SO_2NH_2$ | 3-iPr-Phenyl |
| 1282 | 4 | $SO_2NH_2$ | 3-iPr-Phenyl |
| 1283 | 1 | H | 4-$NH_2$-Phenyl |
| 1284 | 2 | H | 4-$NH_2$-Phenyl |
| 1285 | 3 | H | 4-$NH_2$-Phenyl |
| 1286 | 4 | H | 4-$NH_2$-Phenyl |
| 1287 | 1 | Me | 4-$NH_2$-Phenyl |
| 1288 | 2 | Me | 4-$NH_2$-Phenyl |
| 1289 | 3 | Me | 4-$NH_2$-Phenyl |
| 1290 | 4 | Me | 4-$NH_2$-Phenyl |
| 1291 | 1 | $CH_2Ph$ | 4-$NH_2$-Phenyl |
| 1292 | 2 | $CH_2Ph$ | 4-$NH_2$-Phenyl |
| 1293 | 3 | $CH_2Ph$ | 4-$NH_2$-Phenyl |
| 1294 | 4 | $CH_2Ph$ | 4-$NH_2$-Phenyl |
| 1295 | 1 | COMe | 4-$NH_2$-Phenyl |
| 1296 | 2 | COMe | 4-$NH_2$-Phenyl |
| 1297 | 3 | COMe | 4-$NH_2$-Phenyl |
| 1298 | 4 | COMe | 4-$NH_2$-Phenyl |
| 1299 | 1 | $CO_2Me$ | 4-$NH_2$-Phenyl |
| 1300 | 2 | $CO_2Me$ | 4-$NH_2$-Phenyl |
| 1301 | 3 | $CO_2Me$ | 4-$NH_2$-Phenyl |
| 1302 | 4 | $CO_2Me$ | 4-$NH_2$-Phenyl |
| 1303 | 1 | $CO_2tBu$ | 4-$NH_2$-Phenyl |
| 1304 | 2 | $CO_2tBu$ | 4-$NH_2$-Phenyl |
| 1305 | 3 | $CO_2tBu$ | 4-$NH_2$-Phenyl |
| 1306 | 4 | $CO_2tBu$ | 4-$NH_2$-Phenyl |
| 1307 | 1 | CONHMe | 4-$NH_2$-Phenyl |
| 1308 | 2 | CONHMe | 4-$NH_2$-Phenyl |
| 1309 | 3 | CONHMe | 4-$NH_2$-Phenyl |
| 1310 | 4 | CONHMe | 4-$NH_2$-Phenyl |
| 1311 | 1 | $SO_2Me$ | 4-$NH_2$-Phenyl |
| 1312 | 2 | $SO_2Me$ | 4-$NH_2$-Phenyl |

TABLE 16-continued

| Entry | n | $R^7$ | $R^3$ |
|---|---|---|---|
| 1313 | 3 | $SO_2Me$ | 4-$NH_2$-Phenyl |
| 1314 | 4 | $SO_2Me$ | 4-$NH_2$-Phenyl |
| 1315 | 1 | $SO_2NH_2$ | 4-$NH_2$-Phenyl |
| 1316 | 2 | $SO_2NH_2$ | 4-$NH_2$-Phenyl |
| 1317 | 3 | $SO_2NH_2$ | 4-$NH_2$-Phenyl |
| 1318 | 4 | $SO_2NH_2$ | 4-$NH_2$-Phenyl |
| 1319 | 1 | H | 2-$NH_2$-Phenyl |
| 1320 | 2 | H | 2-$NH_2$-Phenyl |
| 1321 | 3 | H | 2-$NH_2$-Phenyl |
| 1322 | 4 | H | 2-$NH_2$-Phenyl |
| 1323 | 1 | Me | 2-$NH_2$-Phenyl |
| 1324 | 2 | Me | 2-$NH_2$-Phenyl |
| 1325 | 3 | Me | 2-$NH_2$-Phenyl |
| 1326 | 4 | Me | 2-$NH_2$-Phenyl |
| 1327 | 1 | $CH_2Ph$ | 2-$NH_2$-Phenyl |
| 1328 | 2 | $CH_2Ph$ | 2-$NH_2$-Phenyl |
| 1329 | 3 | $CH_2Ph$ | 2-$NH_2$-Phenyl |
| 1330 | 4 | $CH_2Ph$ | 2-$NH_2$-Phenyl |
| 1331 | 1 | COMe | 2-$NH_2$-Phenyl |
| 1332 | 2 | COMe | 2-$NH_2$-Phenyl |
| 1333 | 3 | COMe | 2-$NH_2$-Phenyl |
| 1334 | 4 | COMe | 2-$NH_2$-Phenyl |
| 1335 | 1 | $CO_2Me$ | 2-$NH_2$-Phenyl |
| 1336 | 2 | $CO_2Me$ | 2-$NH_2$-Phenyl |
| 1337 | 3 | $CO_2Me$ | 2-$NH_2$-Phenyl |
| 1338 | 4 | $CO_2Me$ | 2-$NH_2$-Phenyl |
| 1339 | 1 | $CO_2tBu$ | 2-$NH_2$-Phenyl |
| 1340 | 2 | $CO_2tBu$ | 2-$NH_2$-Phenyl |
| 1341 | 3 | $CO_2tBu$ | 2-$NH_2$-Phenyl |
| 1342 | 4 | $CO_2tBu$ | 2-$NH_2$-Phenyl |
| 1343 | 1 | CONHMe | 2-$NH_2$-Phenyl |
| 1344 | 2 | CONHMe | 2-$NH_2$-Phenyl |
| 1345 | 3 | CONHMe | 2-$NH_2$-Phenyl |
| 1346 | 4 | CONHMe | 2-$NH_2$-Phenyl |
| 1347 | 1 | $SO_2Me$ | 2-$NH_2$-Phenyl |
| 1348 | 2 | $SO_2Me$ | 2-$NH_2$-Phenyl |
| 1349 | 3 | $SO_2Me$ | 2-$NH_2$-Phenyl |
| 1350 | 4 | $SO_2Me$ | 2-$NH_2$-Phenyl |
| 1351 | 1 | $SO_2NH_2$ | 2-$NH_2$-Phenyl |
| 1352 | 2 | $SO_2NH_2$ | 2-$NH_2$-Phenyl |
| 1353 | 3 | $SO_2NH_2$ | 2-$NH_2$-Phenyl |
| 1354 | 4 | $SO_2NH_2$ | 2-$NH_2$-Phenyl |
| 1355 | 1 | H | 2,6-di-Me-Phenyl |
| 1356 | 2 | H | 2,6-di-Me-Phenyl |
| 1357 | 3 | H | 2,6-di-Me-Phenyl |
| 1358 | 4 | H | 2,6-di-Me-Phenyl |
| 1359 | 1 | Me | 2,6-di-Me-Phenyl |
| 1360 | 2 | Me | 2,6-di-Me-Phenyl |
| 1361 | 3 | Me | 2,6-di-Me-Phenyl |
| 1362 | 4 | Me | 2,6-di-Me-Phenyl |
| 1363 | 1 | $CH_2Ph$ | 2,6-di-Me-Phenyl |
| 1364 | 2 | $CH_2Ph$ | 2,6-di-Me-Phenyl |
| 1365 | 3 | $CH_2Ph$ | 2,6-di-Me-Phenyl |
| 1366 | 4 | $CH_2Ph$ | 2,6-di-Me-Phenyl |
| 1367 | 1 | COMe | 2,6-di-Me-Phenyl |
| 1368 | 2 | COMe | 2,6-di-Me-Phenyl |
| 1369 | 3 | COMe | 2,6-di-Me-Phenyl |
| 1370 | 4 | COMe | 2,6-di-Me-Phenyl |
| 1371 | 1 | $CO_2Me$ | 2,6-di-Me-Phenyl |
| 1372 | 2 | $CO_2Me$ | 2,6-di-Me-Phenyl |
| 1373 | 3 | $CO_2Me$ | 2,6-di-Me-Phenyl |
| 1374 | 4 | $CO_2Me$ | 2,6-di-Me-Phenyl |
| 1375 | 1 | $CO_2tBu$ | 2,6-di-Me-Phenyl |
| 1376 | 2 | $CO_2tBu$ | 2,6-di-Me-Phenyl |
| 1377 | 3 | $CO_2tBu$ | 2,6-di-Me-Phenyl |
| 1378 | 4 | $CO_2tBu$ | 2,6-di-Me-Phenyl |
| 1379 | 1 | CONHMe | 2,6-di-Me-Phenyl |
| 1380 | 2 | CONHMe | 2,6-di-Me-Phenyl |
| 1381 | 3 | CONHMe | 2,6-di-Me-Phenyl |
| 1382 | 4 | CONHMe | 2,6-di-Me-Phenyl |
| 1383 | 1 | $SO_2Me$ | 2,6-di-Me-Phenyl |
| 1384 | 2 | $SO_2Me$ | 2,6-di-Me-Phenyl |
| 1385 | 3 | $SO_2Me$ | 2,6-di-Me-Phenyl |
| 1386 | 4 | $SO_2Me$ | 2,6-di-Me-Phenyl |
| 1387 | 1 | $SO_2NH_2$ | 2,6-di-Me-Phenyl |
| 1388 | 2 | $SO_2NH_2$ | 2,6-di-Me-Phenyl |
| 1389 | 3 | $SO_2NH_2$ | 2,6-di-Me-Phenyl |
| 1390 | 4 | $SO_2NH_2$ | 2,6-di-Me-Phenyl |

TABLE 16-continued

| Entry | n | $R^7$ | $R^3$ |
|---|---|---|---|
| 1391 | 1 | H | 2-Ph-Phenyl |
| 1392 | 2 | H | 2-Ph-Phenyl |
| 1393 | 3 | H | 2-Ph-Phenyl |
| 1394 | 4 | H | 2-Ph-Phenyl |
| 1395 | 1 | Me | 2-Ph-Phenyl |
| 1396 | 2 | Me | 2-Ph-Phenyl |
| 1397 | 3 | Me | 2-Ph-Phenyl |
| 1398 | 4 | Me | 2-Ph-Phenyl |
| 1399 | 1 | $CH_2Ph$ | 2-Ph-Phenyl |
| 1400 | 2 | $CH_2Ph$ | 2-Ph-Phenyl |
| 1401 | 3 | $CH_2Ph$ | 2-Ph-Phenyl |
| 1402 | 4 | $CH_2Ph$ | 2-Ph-Phenyl |
| 1403 | 1 | COMe | 2-Ph-Phenyl |
| 1404 | 2 | COMe | 2-Ph-Phenyl |
| 1405 | 3 | COMe | 2-Ph-Phenyl |
| 1406 | 4 | COMe | 2-Ph-Phenyl |
| 1407 | 1 | $CO_2Me$ | 2-Ph-Phenyl |
| 1408 | 2 | $CO_2Me$ | 2-Ph-Phenyl |
| 1409 | 3 | $CO_2Me$ | 2-Ph-Phenyl |
| 1410 | 4 | $CO_2Me$ | 2-Ph-Phenyl |
| 1411 | 1 | $CO_2tBu$ | 2-Ph-Phenyl |
| 1412 | 2 | $CO_2tBu$ | 2-Ph-Phenyl |
| 1413 | 3 | $CO_2tBu$ | 2-Ph-Phenyl |
| 1414 | 4 | $CO_2tBu$ | 2-Ph-Phenyl |
| 1415 | 1 | CONHMe | 2-Ph-Phenyl |
| 1416 | 2 | CONHMe | 2-Ph-Phenyl |
| 1417 | 3 | CONHMe | 2-Ph-Phenyl |
| 1418 | 4 | CONHMe | 2-Ph-Phenyl |
| 1419 | 1 | $SO_2Me$ | 2-Ph-Phenyl |
| 1420 | 2 | $SO_2Me$ | 2-Ph-Phenyl |
| 1421 | 3 | $SO_2Me$ | 2-Ph-Phenyl |
| 1422 | 4 | $SO_2Me$ | 2-Ph-Phenyl |
| 1423 | 1 | $SO_2NH_2$ | 2-Ph-Phenyl |
| 1424 | 2 | $SO_2NH_2$ | 2-Ph-Phenyl |
| 1425 | 3 | $SO_2NH_2$ | 2-Ph-Phenyl |
| 1426 | 4 | $SO_2NH_2$ | 2-Ph-Phenyl |
| 1427 | 1 | H | 4-Ph-Phenyl |
| 1428 | 2 | H | 4-Ph-Phenyl |
| 1429 | 3 | H | 4-Ph-Phenyl |
| 1430 | 4 | H | 4-Ph-Phenyl |
| 1431 | 1 | Me | 4-Ph-Phenyl |
| 1432 | 2 | Me | 4-Ph-Phenyl |
| 1433 | 3 | Me | 4-Ph-Phenyl |
| 1434 | 4 | Me | 4-Ph-Phenyl |
| 1435 | 1 | $CH_2Ph$ | 4-Ph-Phenyl |
| 1436 | 2 | $CH_2Ph$ | 4-Ph-Phenyl |
| 1437 | 3 | $CH_2Ph$ | 4-Ph-Phenyl |
| 1438 | 4 | $CH_2Ph$ | 4-Ph-Phenyl |
| 1439 | 1 | COMe | 4-Ph-Phenyl |
| 1440 | 2 | COMe | 4-Ph-Phenyl |
| 1441 | 3 | COMe | 4-Ph-Phenyl |
| 1442 | 4 | COMe | 4-Ph-Phenyl |
| 1443 | 1 | $CO_2Me$ | 4-Ph-Phenyl |
| 1444 | 2 | $CO_2Me$ | 4-Ph-Phenyl |
| 1445 | 3 | $CO_2Me$ | 4-Ph-Phenyl |
| 1446 | 4 | $CO_2Me$ | 4-Ph-Phenyl |
| 1447 | 1 | $CO_2tBu$ | 4-Ph-Phenyl |
| 1448 | 2 | $CO_2tBu$ | 4-Ph-Phenyl |
| 1449 | 3 | $CO_2tBu$ | 4-Ph-Phenyl |
| 1450 | 4 | $CO_2tBu$ | 4-Ph-Phenyl |
| 1451 | 1 | CONHMe | 4-Ph-Phenyl |
| 1452 | 2 | CONHMe | 4-Ph-Phenyl |
| 1453 | 3 | CONHMe | 4-Ph-Phenyl |
| 1454 | 4 | CONHMe | 4-Ph-Phenyl |
| 1455 | 1 | $SO_2Me$ | 4-Ph-Phenyl |
| 1456 | 2 | $SO_2Me$ | 4-Ph-Phenyl |
| 1457 | 3 | $SO_2Me$ | 4-Ph-Phenyl |
| 1458 | 4 | $SO_2Me$ | 4-Ph-Phenyl |
| 1459 | 1 | $SO_2NH_2$ | 4-Ph-Phenyl |
| 1460 | 2 | $SO_2NH_2$ | 4-Ph-Phenyl |
| 1461 | 3 | $SO_2NH_2$ | 4-Ph-Phenyl |
| 1462 | 4 | $SO_2NH_2$ | 4-Ph-Phenyl |
| 1463 | 1 | H | 3-morpholino-phenyl |
| 1464 | 2 | H | 3-morpholino-phenyl |
| 1465 | 3 | H | 3-morpholino-phenyl |
| 1466 | 4 | H | 3-morpholino-phenyl |
| 1467 | 1 | Me | 3-morpholino-phenyl |
| 1468 | 2 | Me | 3-morpholino-phenyl |

TABLE 16-continued

| Entry | n | $R^7$ | $R^3$ |
|---|---|---|---|
| 1469 | 3 | Me | 3-morpholino-phenyl |
| 1470 | 4 | Me | 3-morpholino-phenyl |
| 1471 | 1 | $CH_2Ph$ | 3-morpholino-phenyl |
| 1472 | 2 | $CH_2Ph$ | 3-morpholino-phenyl |
| 1473 | 3 | $CH_2Ph$ | 3-morpholino-phenyl |
| 1474 | 4 | $CH_2Ph$ | 3-morpholino-phenyl |
| 1475 | 1 | COMe | 3-morpholino-phenyl |
| 1476 | 2 | COMe | 3-morpholino-phenyl |
| 1477 | 3 | COMe | 3-morpholino-phenyl |
| 1478 | 4 | COMe | 3-morpholino-phenyl |
| 1479 | 1 | $CO_2Me$ | 3-morpholino-phenyl |
| 1480 | 2 | $CO_2Me$ | 3-morpholino-phenyl |
| 1481 | 3 | $CO_2Me$ | 3-morpholino-phenyl |
| 1482 | 4 | $CO_2Me$ | 3-morpholino-phenyl |
| 1483 | 1 | $CO_2tBu$ | 3-morpholino-phenyl |
| 1484 | 2 | $CO_2tBu$ | 3-morpholino-phenyl |
| 1485 | 3 | $CO_2tBu$ | 3-morpholino-phenyl |
| 1486 | 4 | $CO_2tBu$ | 3-morpholino-phenyl |
| 1487 | 1 | CONHMe | 3-morpholino-phenyl |
| 1488 | 2 | CONHMe | 3-morpholino-phenyl |
| 1489 | 3 | CONHMe | 3-morpholino-phenyl |
| 1490 | 4 | CONHMe | 3-morpholino-phenyl |
| 1491 | 1 | $SO_2Me$ | 3-morpholino-phenyl |
| 1492 | 2 | $SO_2Me$ | 3-morpholino-phenyl |
| 1493 | 3 | $SO_2Me$ | 3-morpholino-phenyl |
| 1494 | 4 | $SO_2Me$ | 3-morpholino-phenyl |
| 1495 | 1 | $SO_2NH_2$ | 3-morpholino-phenyl |
| 1496 | 2 | $SO_2NH_2$ | 3-morpholino-phenyl |
| 1497 | 3 | $SO_2NH_2$ | 3-morpholino-phenyl |
| 1498 | 4 | $SO_2NH_2$ | 3-morpholino-phenyl |
| 1499 | 1 | Me | 4-morpholino-phenyl |
| 1500 | 2 | Me | 4-morpholino-phenyl |
| 1501 | 3 | Me | 4-morpholino-phenyl |
| 1502 | 4 | Me | 4-morpholino-phenyl |
| 103 | 1 | COMe | 4-morpholino-phenyl |
| 1504 | 2 | COMe | 4-morpholino-phenyl |
| 1505 | 3 | COMe | 4-morpholino-phenyl |
| 1506 | 4 | COMe | 4-morpholino-phenyl |
| 1507 | 1 | $CO_2tBu$ | 4-morpholino-phenyl |
| 1508 | 2 | $CO_2tBu$ | 4-morpholino-phenyl |
| 1509 | 3 | $CO_2tBu$ | 4-morpholino-phenyl |
| 1510 | 4 | $CO_2tBu$ | 4-morpholino-phenyl |
| 1511 | 1 | $SO_2Me$ | 4-morpholino-phenyl |
| 1512 | 2 | $SO_2Me$ | 4-morpholino-phenyl |
| 1513 | 3 | $SO_2Me$ | 4-morpholino-phenyl |
| 1514 | 4 | $SO_2Me$ | 4-morpholino-phenyl |
| 1516 | 1 | H | naphthylen-2-yl |
| 1517 | 2 | H | naphthylen-2-yl |
| 1518 | 3 | H | naphthylen-2-yl |
| 1519 | 4 | H | naphthylen-2-yl |
| 1520 | 1 | Me | naphthylen-2-yl |
| 1521 | 2 | Me | naphthylen-2-yl |
| 1522 | 3 | Me | naphthylen-2-yl |
| 1523 | 4 | Me | naphthylen-2-yl |
| 1524 | 1 | $CH_2Ph$ | naphthylen-2-yl |
| 1525 | 2 | $CH_2Ph$ | naphthylen-2-yl |
| 1526 | 3 | $CH_2Ph$ | naphthylen-2-yl |
| 1527 | 4 | $CH_2Ph$ | naphthylen-2-yl |
| 1528 | 1 | COMe | naphthylen-2-yl |
| 1529 | 2 | COMe | naphthylen-2-yl |
| 1530 | 3 | COMe | naphthylen-2-yl |
| 1531 | 4 | COMe | naphthylen-2-yl |
| 1532 | 1 | $CO_2Me$ | naphthylen-2-yl |
| 1533 | 2 | $CO_2Me$ | naphthylen-2-yl |
| 1534 | 3 | $CO_2Me$ | naphthylen-2-yl |
| 1535 | 4 | $CO_2Me$ | naphthylen-2-yl |
| 1536 | 1 | $CO_2tBu$ | naphthylen-2-yl |
| 1537 | 2 | $CO_2tBu$ | naphthylen-2-yl |
| 1538 | 3 | $CO_2tBu$ | naphthylen-2-yl |
| 1539 | 4 | $CO_2tBu$ | naphthylen-2-yl |
| 1540 | 1 | CONHMe | naphthylen-2-yl |
| 1541 | 2 | CONHMe | naphthylen-2-yl |
| 1542 | 3 | CONHMe | naphthylen-2-yl |
| 1543 | 4 | CONHMe | naphthylen-2-yl |
| 1544 | 1 | $SO_2Me$ | naphthylen-2-yl |
| 1545 | 2 | $SO_2Me$ | naphthylen-2-yl |
| 1546 | 3 | $SO_2Me$ | naphthylen-2-yl |
| 1547 | 4 | $SO_2Me$ | naphthylen-2-yl |
| 1548 | 1 | $SO_2NH_2$ | naphthylen-2-yl |
| 1549 | 2 | $SO_2NH_2$ | naphthylen-2-yl |
| 1550 | 3 | $SO_2NH_2$ | naphthylen-2-yl |
| 1551 | 4 | $SO_2NH_2$ | naphthylen-2-yl |

Exemplary embodiments include compounds having the formula (XXIII)

(XXIII)

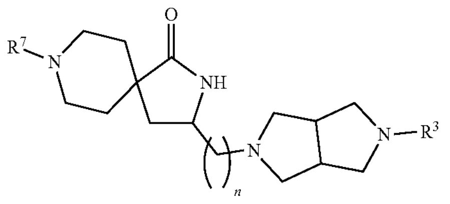

or a pharmaceutically acceptable salt form thereof defined herein below in Table 17.

TABLE 17

| Entry | n | $R^7$ | $R^3$ |
|---|---|---|---|
| 1 | 1 | H | Phenyl |
| 2 | 2 | H | Phenyl |
| 3 | 3 | H | Phenyl |
| 4 | 4 | H | Phenyl |
| 5 | 1 | Me | Phenyl |
| 6 | 2 | Me | Phenyl |
| 7 | 3 | Me | Phenyl |
| 8 | 4 | Me | Phenyl |
| 9 | 1 | $CH_2Ph$ | Phenyl |
| 10 | 2 | $CH_2Ph$ | Phenyl |
| 11 | 3 | $CH_2Ph$ | Phenyl |
| 12 | 4 | $CH_2Ph$ | Phenyl |
| 13 | 1 | COMe | Phenyl |
| 14 | 2 | COMe | Phenyl |
| 15 | 3 | COMe | Phenyl |
| 16 | 4 | COMe | Phenyl |
| 17 | 1 | $CO_2Me$ | Phenyl |
| 18 | 2 | $CO_2Me$ | Phenyl |
| 19 | 3 | $CO_2Me$ | Phenyl |
| 20 | 4 | $CO_2Me$ | Phenyl |
| 21 | 1 | $CO_2tBu$ | Phenyl |
| 22 | 2 | $CO_2tBu$ | Phenyl |
| 23 | 3 | $CO_2tBu$ | Phenyl |
| 24 | 4 | $CO_2tBu$ | Phenyl |
| 25 | 1 | CONHMe | Phenyl |
| 26 | 2 | CONHMe | Phenyl |
| 27 | 3 | CONHMe | Phenyl |
| 28 | 4 | CONHMe | Phenyl |
| 29 | 1 | $SO_2Me$ | Phenyl |
| 30 | 2 | $SO_2Me$ | Phenyl |
| 31 | 3 | $SO_2Me$ | Phenyl |
| 32 | 4 | $SO_2Me$ | Phenyl |
| 33 | 1 | $SO_2NH_2$ | Phenyl |
| 34 | 2 | $SO_2NH_2$ | Phenyl |
| 35 | 3 | $SO_2NH_2$ | Phenyl |
| 36 | 4 | $SO_2NH_2$ | Phenyl |
| 37 | 1 | H | 3-OH-Phenyl |
| 38 | 2 | H | 3-OH-Phenyl |
| 39 | 3 | H | 3-OH-Phenyl |
| 40 | 4 | H | 3-OH-Phenyl |
| 41 | 1 | Me | 3-OH-Phenyl |
| 42 | 2 | Me | 3-OH-Phenyl |
| 43 | 3 | Me | 3-OH-Phenyl |
| 44 | 4 | Me | 3-OH-Phenyl |
| 45 | 1 | $CH_2Ph$ | 3-OH-Phenyl |
| 46 | 2 | $CH_2Ph$ | 3-OH-Phenyl |
| 47 | 3 | $CH_2Ph$ | 3-OH-Phenyl |

TABLE 17-continued

| Entry | n | $R^7$ | $R^3$ |
|---|---|---|---|
| 48 | 4 | $CH_2Ph$ | 3-OH-Phenyl |
| 49 | 1 | COMe | 3-OH-Phenyl |
| 50 | 2 | COMe | 3-OH-Phenyl |
| 51 | 3 | COMe | 3-OH-Phenyl |
| 52 | 4 | COMe | 3-OH-Phenyl |
| 53 | 1 | $CO_2Me$ | 3-OH-Phenyl |
| 54 | 2 | $CO_2Me$ | 3-OH-Phenyl |
| 55 | 3 | $CO_2Me$ | 3-OH-Phenyl |
| 56 | 4 | $CO_2Me$ | 3-OH-Phenyl |
| 57 | 1 | $CO_2tBu$ | 3-OH-Phenyl |
| 58 | 2 | $CO_2tBu$ | 3-OH-Phenyl |
| 59 | 3 | $CO_2tBu$ | 3-OH-Phenyl |
| 60 | 4 | $CO_2tBu$ | 3-OH-Phenyl |
| 61 | 1 | CONHMe | 3-OH-Phenyl |
| 62 | 2 | CONHMe | 3-OH-Phenyl |
| 63 | 3 | CONHMe | 3-OH-Phenyl |
| 64 | 4 | CONHMe | 3-OH-Phenyl |
| 65 | 1 | $SO_2Me$ | 3-OH-Phenyl |
| 66 | 2 | $SO_2Me$ | 3-OH-Phenyl |
| 67 | 3 | $SO_2Me$ | 3-OH-Phenyl |
| 68 | 4 | $SO_2Me$ | 3-OH-Phenyl |
| 69 | 1 | $SO_2NH_2$ | 3-OH-Phenyl |
| 70 | 2 | $SO_2NH_2$ | 3-OH-Phenyl |
| 71 | 3 | $SO_2NH_2$ | 3-OH-Phenyl |
| 72 | 4 | $SO_2NH_2$ | 3-OH-Phenyl |
| 73 | 1 | H | 4-$NO_2$-Phenyl |
| 74 | 2 | H | 4-$NO_2$-Phenyl |
| 75 | 3 | H | 4-$NO_2$-Phenyl |
| 76 | 4 | H | 4-$NO_2$-Phenyl |
| 77 | 1 | Me | 4-$NO_2$-Phenyl |
| 78 | 2 | Me | 4-$NO_2$-Phenyl |
| 79 | 3 | Me | 4-$NO_2$-Phenyl |
| 80 | 4 | Me | 4-$NO_2$-Phenyl |
| 81 | 1 | $CH_2Ph$ | 4-$NO_2$-Phenyl |
| 82 | 2 | $CH_2Ph$ | 4-$NO_2$-Phenyl |
| 83 | 3 | $CH_2Ph$ | 4-$NO_2$-Phenyl |
| 84 | 4 | $CH_2Ph$ | 4-$NO_2$-Phenyl |
| 85 | 1 | COMe | 4-$NO_2$-Phenyl |
| 86 | 2 | COMe | 4-$NO_2$-Phenyl |
| 87 | 3 | COMe | 4-$NO_2$-Phenyl |
| 88 | 4 | COMe | 4-$NO_2$-Phenyl |
| 89 | 1 | $CO_2Me$ | 4-$NO_2$-Phenyl |
| 90 | 2 | $CO_2Me$ | 4-$NO_2$-Phenyl |
| 91 | 3 | $CO_2Me$ | 4-$NO_2$-Phenyl |
| 92 | 4 | $CO_2Me$ | 4-$NO_2$-Phenyl |
| 93 | 1 | $CO_2tBu$ | 4-$NO_2$-Phenyl |
| 94 | 2 | $CO_2tBu$ | 4-$NO_2$-Phenyl |
| 95 | 3 | $CO_2tBu$ | 4-$NO_2$-Phenyl |
| 96 | 4 | $CO_2tBu$ | 4-$NO_2$-Phenyl |
| 97 | 1 | CONHMe | 4-$NO_2$-Phenyl |
| 98 | 2 | CONHMe | 4-$NO_2$-Phenyl |
| 99 | 3 | CONHMe | 4-$NO_2$-Phenyl |
| 100 | 4 | CONHMe | 4-$NO_2$-Phenyl |
| 101 | 1 | $SO_2Me$ | 4-$NO_2$-Phenyl |
| 102 | 2 | $SO_2Me$ | 4-$NO_2$-Phenyl |
| 103 | 3 | $SO_2Me$ | 4-$NO_2$-Phenyl |
| 104 | 4 | $SO_2Me$ | 4-$NO_2$-Phenyl |
| 105 | 1 | $SO_2NH_2$ | 4-$NO_2$-Phenyl |
| 106 | 2 | $SO_2NH_2$ | 4-$NO_2$-Phenyl |
| 107 | 3 | $SO_2NH_2$ | 4-$NO_2$-Phenyl |
| 108 | 4 | $SO_2NH_2$ | 4-$NO_2$-Phenyl |
| 109 | 1 | H | 3-OMe-Phenyl |
| 110 | 2 | H | 3-OMe-Phenyl |
| 111 | 3 | H | 3-OMe-Phenyl |
| 112 | 4 | H | 3-OMe-Phenyl |
| 113 | 1 | Me | 3-OMe-Phenyl |
| 114 | 2 | Me | 3-OMe-Phenyl |
| 115 | 3 | Me | 3-OMe-Phenyl |
| 116 | 4 | Me | 3-OMe-Phenyl |
| 117 | 1 | $CH_2Ph$ | 3-OMe-Phenyl |
| 118 | 2 | $CH_2Ph$ | 3-OMe-Phenyl |
| 119 | 3 | $CH_2Ph$ | 3-OMe-Phenyl |
| 120 | 4 | $CH_2Ph$ | 3-OMe-Phenyl |
| 121 | 1 | COMe | 3-OMe-Phenyl |
| 122 | 2 | COMe | 3-OMe-Phenyl |
| 123 | 3 | COMe | 3-OMe-Phenyl |
| 124 | 4 | COMe | 3-OMe-Phenyl |
| 125 | 1 | $CO_2Me$ | 3-OMe-Phenyl |

TABLE 17-continued

| Entry | n | $R^7$ | $R^3$ |
|---|---|---|---|
| 126 | 2 | $CO_2Me$ | 3-OMe-Phenyl |
| 127 | 3 | $CO_2Me$ | 3-OMe-Phenyl |
| 128 | 4 | $CO_2Me$ | 3-OMe-Phenyl |
| 129 | 1 | $CO_2tBu$ | 3-OMe-Phenyl |
| 130 | 2 | $CO_2tBu$ | 3-OMe-Phenyl |
| 131 | 3 | $CO_2tBu$ | 3-OMe-Phenyl |
| 132 | 4 | $CO_2tBu$ | 3-OMe-Phenyl |
| 133 | 1 | CONHMe | 3-OMe-Phenyl |
| 134 | 2 | CONHMe | 3-OMe-Phenyl |
| 135 | 3 | CONHMe | 3-OMe-Phenyl |
| 136 | 4 | CONHMe | 3-OMe-Phenyl |
| 137 | 1 | $SO_2Me$ | 3-OMe-Phenyl |
| 138 | 2 | $SO_2Me$ | 3-OMe-Phenyl |
| 139 | 3 | $SO_2Me$ | 3-OMe-Phenyl |
| 140 | 4 | $SO_2Me$ | 3-OMe-Phenyl |
| 141 | 1 | $SO_2NH_2$ | 3-OMe-Phenyl |
| 142 | 2 | $SO_2NH_2$ | 3-OMe-Phenyl |
| 143 | 3 | $SO_2NH_2$ | 3-OMe-Phenyl |
| 144 | 4 | $SO_2NH_2$ | 3-OMe-Phenyl |
| 145 | 1 | H | 4-CN-Phenyl |
| 146 | 2 | H | 4-CN-Phenyl |
| 147 | 3 | H | 4-CN-Phenyl |
| 148 | 4 | H | 4-CN-Phenyl |
| 149 | 1 | Me | 4-CN-Phenyl |
| 150 | 2 | Me | 4-CN-Phenyl |
| 151 | 3 | Me | 4-CN-Phenyl |
| 152 | 4 | Me | 4-CN-Phenyl |
| 153 | 1 | $CH_2Ph$ | 4-CN-Phenyl |
| 154 | 2 | $CH_2Ph$ | 4-CN-Phenyl |
| 155 | 3 | $CH_2Ph$ | 4-CN-Phenyl |
| 156 | 4 | $CH_2Ph$ | 4-CN-Phenyl |
| 157 | 1 | COMe | 4-CN-Phenyl |
| 158 | 2 | COMe | 4-CN-Phenyl |
| 159 | 3 | COMe | 4-CN-Phenyl |
| 160 | 4 | COMe | 4-CN-Phenyl |
| 161 | 1 | $CO_2Me$ | 4-CN-Phenyl |
| 162 | 2 | $CO_2Me$ | 4-CN-Phenyl |
| 163 | 3 | $CO_2Me$ | 4-CN-Phenyl |
| 164 | 4 | $CO_2Me$ | 4-CN-Phenyl |
| 165 | 1 | $CO_2tBu$ | 4-CN-Phenyl |
| 166 | 2 | $CO_2tBu$ | 4-CN-Phenyl |
| 167 | 3 | $CO_2tBu$ | 4-CN-Phenyl |
| 168 | 4 | $CO_2tBu$ | 4-CN-Phenyl |
| 169 | 1 | CONHMe | 4-CN-Phenyl |
| 170 | 2 | CONHMe | 4-CN-Phenyl |
| 171 | 3 | CONHMe | 4-CN-Phenyl |
| 172 | 4 | CONHMe | 4-CN-Phenyl |
| 173 | 1 | $SO_2Me$ | 4-CN-Phenyl |
| 174 | 2 | $SO_2Me$ | 4-CN-Phenyl |
| 175 | 3 | $SO_2Me$ | 4-CN-Phenyl |
| 176 | 4 | $SO_2Me$ | 4-CN-Phenyl |
| 177 | 1 | $SO_2NH_2$ | 4-CN-Phenyl |
| 178 | 2 | $SO_2NH_2$ | 4-CN-Phenyl |
| 179 | 3 | $SO_2NH_2$ | 4-CN-Phenyl |
| 180 | 4 | $SO_2NH_2$ | 4-CN-Phenyl |
| 181 | 1 | H | 2-CN-Phenyl |
| 182 | 2 | H | 2-CN-Phenyl |
| 183 | 3 | H | 2-CN-Phenyl |
| 184 | 4 | H | 2-CN-Phenyl |
| 185 | 1 | Me | 2-CN-Phenyl |
| 186 | 2 | Me | 2-CN-Phenyl |
| 187 | 3 | Me | 2-CN-Phenyl |
| 188 | 4 | Me | 2-CN-Phenyl |
| 189 | 1 | $CH_2Ph$ | 2-CN-Phenyl |
| 190 | 2 | $CH_2Ph$ | 2-CN-Phenyl |
| 191 | 3 | $CH_2Ph$ | 2-CN-Phenyl |
| 192 | 4 | $CH_2Ph$ | 2-CN-Phenyl |
| 193 | 1 | COMe | 2-CN-Phenyl |
| 194 | 2 | COMe | 2-CN-Phenyl |
| 195 | 3 | COMe | 2-CN-Phenyl |
| 196 | 4 | COMe | 2-CN-Phenyl |
| 197 | 1 | $CO_2Me$ | 2-CN-Phenyl |
| 198 | 2 | $CO_2Me$ | 2-CN-Phenyl |
| 199 | 3 | $CO_2Me$ | 2-CN-Phenyl |
| 200 | 4 | $CO_2Me$ | 2-CN-Phenyl |
| 201 | 1 | $CO_2tBu$ | 2-CN-Phenyl |
| 202 | 2 | $CO_2tBu$ | 2-CN-Phenyl |
| 203 | 3 | $CO_2tBu$ | 2-CN-Phenyl |

TABLE 17-continued

| Entry | n | $R^7$ | $R^3$ |
|---|---|---|---|
| 204 | 4 | $CO_2tBu$ | 2-CN-Phenyl |
| 205 | 1 | CONHMe | 2-CN-Phenyl |
| 206 | 2 | CONHMe | 2-CN-Phenyl |
| 207 | 3 | CONHMe | 2-CN-Phenyl |
| 208 | 4 | CONHMe | 2-CN-Phenyl |
| 209 | 1 | $SO_2Me$ | 2-CN-Phenyl |
| 210 | 2 | $SO_2Me$ | 2-CN-Phenyl |
| 211 | 3 | $SO_2Me$ | 2-CN-Phenyl |
| 212 | 4 | $SO_2Me$ | 2-CN-Phenyl |
| 213 | 1 | $SO_2NH_2$ | 2-CN-Phenyl |
| 214 | 2 | $SO_2NH_2$ | 2-CN-Phenyl |
| 215 | 3 | $SO_2NH_2$ | 2-CN-Phenyl |
| 216 | 4 | $SO_2NH_2$ | 2-CN-Phenyl |
| 217 | 1 | H | 3-Me-Phenyl |
| 218 | 2 | H | 3-Me-Phenyl |
| 219 | 3 | H | 3-Me-Phenyl |
| 220 | 4 | H | 3-Me-Phenyl |
| 221 | 1 | Me | 3-Me-Phenyl |
| 222 | 2 | Me | 3-Me-Phenyl |
| 223 | 3 | Me | 3-Me-Phenyl |
| 224 | 4 | Me | 3-Me-Phenyl |
| 225 | 1 | $CH_2Ph$ | 3-Me-Phenyl |
| 226 | 2 | $CH_2Ph$ | 3-Me-Phenyl |
| 227 | 3 | $CH_2Ph$ | 3-Me-Phenyl |
| 228 | 4 | $CH_2Ph$ | 3-Me-Phenyl |
| 229 | 1 | COMe | 3-Me-Phenyl |
| 230 | 2 | COMe | 3-Me-Phenyl |
| 231 | 3 | COMe | 3-Me-Phenyl |
| 232 | 4 | COMe | 3-Me-Phenyl |
| 233 | 1 | $CO_2Me$ | 3-Me-Phenyl |
| 234 | 2 | $CO_2Me$ | 3-Me-Phenyl |
| 235 | 3 | $CO_2Me$ | 3-Me-Phenyl |
| 236 | 4 | $CO_2Me$ | 3-Me-Phenyl |
| 237 | 1 | $CO_2tBu$ | 3-Me-Phenyl |
| 238 | 2 | $CO_2tBu$ | 3-Me-Phenyl |
| 239 | 3 | $CO_2tBu$ | 3-Me-Phenyl |
| 240 | 4 | $CO_2tBu$ | 3-Me-Phenyl |
| 241 | 1 | CONHMe | 3-Me-Phenyl |
| 242 | 2 | CONHMe | 3-Me-Phenyl |
| 243 | 3 | CONHMe | 3-Me-Phenyl |
| 244 | 4 | CONHMe | 3-Me-Phenyl |
| 245 | 1 | $SO_2Me$ | 3-Me-Phenyl |
| 246 | 2 | $SO_2Me$ | 3-Me-Phenyl |
| 247 | 3 | $SO_2Me$ | 3-Me-Phenyl |
| 248 | 4 | $SO_2Me$ | 3-Me-Phenyl |
| 249 | 1 | $SO_2NH_2$ | 3-Me-Phenyl |
| 250 | 2 | $SO_2NH_2$ | 3-Me-Phenyl |
| 251 | 3 | $SO_2NH_2$ | 3-Me-Phenyl |
| 252 | 4 | $SO_2NH_2$ | 3-Me-Phenyl |
| 253 | 1 | H | 2-F-Phenyl |
| 254 | 2 | H | 2-F-Phenyl |
| 255 | 3 | H | 2-F-Phenyl |
| 256 | 4 | H | 2-F-Phenyl |
| 257 | 1 | Me | 2-F-Phenyl |
| 258 | 2 | Me | 2-F-Phenyl |
| 259 | 3 | Me | 2-F-Phenyl |
| 260 | 4 | Me | 2-F-Phenyl |
| 261 | 1 | $CH_2Ph$ | 2-F-Phenyl |
| 262 | 2 | $CH_2Ph$ | 2-F-Phenyl |
| 263 | 3 | $CH_2Ph$ | 2-F-Phenyl |
| 264 | 4 | $CH_2Ph$ | 2-F-Phenyl |
| 265 | 1 | COMe | 2-F-Phenyl |
| 266 | 2 | COMe | 2-F-Phenyl |
| 267 | 3 | COMe | 2-F-Phenyl |
| 268 | 4 | COMe | 2-F-Phenyl |
| 269 | 1 | $CO_2Me$ | 2-F-Phenyl |
| 270 | 2 | $CO_2Me$ | 2-F-Phenyl |
| 271 | 3 | $CO_2Me$ | 2-F-Phenyl |
| 272 | 4 | $CO_2Me$ | 2-F-Phenyl |
| 273 | 1 | $CO_2tBu$ | 2-F-Phenyl |
| 274 | 2 | $CO_2tBu$ | 2-F-Phenyl |
| 275 | 3 | $CO_2tBu$ | 2-F-Phenyl |
| 276 | 4 | $CO_2tBu$ | 2-F-Phenyl |
| 277 | 1 | CONHMe | 2-F-Phenyl |
| 278 | 2 | CONHMe | 2-F-Phenyl |
| 279 | 3 | CONHMe | 2-F-Phenyl |
| 280 | 4 | CONHMe | 2-F-Phenyl |
| 281 | 1 | $SO_2Me$ | 2-F-Phenyl |

TABLE 17-continued

| Entry | n | $R^7$ | $R^3$ |
|---|---|---|---|
| 282 | 2 | $SO_2Me$ | 2-F-Phenyl |
| 283 | 3 | $SO_2Me$ | 2-F-Phenyl |
| 284 | 4 | $SO_2Me$ | 2-F-Phenyl |
| 285 | 1 | $SO_2NH_2$ | 2-F-Phenyl |
| 286 | 2 | $SO_2NH_2$ | 2-F-Phenyl |
| 287 | 3 | $SO_2NH_2$ | 2-F-Phenyl |
| 288 | 4 | $SO_2NH_2$ | 2-F-Phenyl |
| 289 | 1 | H | 4-F-Phenyl |
| 290 | 2 | H | 4-F-Phenyl |
| 291 | 3 | H | 4-F-Phenyl |
| 292 | 4 | H | 4-F-Phenyl |
| 293 | 1 | Me | 4-F-Phenyl |
| 294 | 2 | Me | 4-F-Phenyl |
| 295 | 3 | Me | 4-F-Phenyl |
| 296 | 4 | Me | 4-F-Phenyl |
| 297 | 1 | $CH_2Ph$ | 4-F-Phenyl |
| 298 | 2 | $CH_2Ph$ | 4-F-Phenyl |
| 299 | 3 | $CH_2Ph$ | 4-F-Phenyl |
| 300 | 4 | $CH_2Ph$ | 4-F-Phenyl |
| 301 | 1 | COMe | 4-F-Phenyl |
| 302 | 2 | COMe | 4-F-Phenyl |
| 303 | 3 | COMe | 4-F-Phenyl |
| 304 | 4 | COMe | 4-F-Phenyl |
| 305 | 1 | $CO_2Me$ | 4-F-Phenyl |
| 306 | 2 | $CO_2Me$ | 4-F-Phenyl |
| 307 | 3 | $CO_2Me$ | 4-F-Phenyl |
| 308 | 4 | $CO_2Me$ | 4-F-Phenyl |
| 309 | 1 | $CO_2tBu$ | 4-F-Phenyl |
| 310 | 2 | $CO_2tBu$ | 4-F-Phenyl |
| 311 | 3 | $CO_2tBu$ | 4-F-Phenyl |
| 312 | 4 | $CO_2tBu$ | 4-F-Phenyl |
| 313 | 1 | CONHMe | 4-F-Phenyl |
| 314 | 2 | CONHMe | 4-F-Phenyl |
| 315 | 3 | CONHMe | 4-F-Phenyl |
| 316 | 4 | CONHMe | 4-F-Phenyl |
| 317 | 1 | $SO_2Me$ | 4-F-Phenyl |
| 318 | 2 | $SO_2Me$ | 4-F-Phenyl |
| 319 | 3 | $SO_2Me$ | 4-F-Phenyl |
| 320 | 4 | $SO_2Me$ | 4-F-Phenyl |
| 321 | 1 | $SO_2NH_2$ | 4-F-Phenyl |
| 322 | 2 | $SO_2NH_2$ | 4-F-Phenyl |
| 323 | 3 | $SO_2NH_2$ | 4-F-Phenyl |
| 324 | 4 | $SO_2NH_2$ | 4-F-Phenyl |
| 325 | 1 | H | 3-Cl-Phenyl |
| 326 | 2 | H | 3-Cl-Phenyl |
| 327 | 3 | H | 3-Cl-Phenyl |
| 328 | 4 | H | 3-Cl-Phenyl |
| 329 | 1 | Me | 3-Cl-Phenyl |
| 330 | 2 | Me | 3-Cl-Phenyl |
| 331 | 3 | Me | 3-Cl-Phenyl |
| 332 | 4 | Me | 3-Cl-Phenyl |
| 333 | 1 | $CH_2Ph$ | 3-Cl-Phenyl |
| 334 | 2 | $CH_2Ph$ | 3-Cl-Phenyl |
| 335 | 3 | $CH_2Ph$ | 3-Cl-Phenyl |
| 336 | 4 | $CH_2Ph$ | 3-Cl-Phenyl |
| 337 | 1 | COMe | 3-Cl-Phenyl |
| 338 | 2 | COMe | 3-Cl-Phenyl |
| 339 | 3 | COMe | 3-Cl-Phenyl |
| 340 | 4 | COMe | 3-Cl-Phenyl |
| 341 | 1 | $CO_2Me$ | 3-Cl-Phenyl |
| 342 | 2 | $CO_2Me$ | 3-Cl-Phenyl |
| 343 | 3 | $CO_2Me$ | 3-Cl-Phenyl |
| 344 | 4 | $CO_2Me$ | 3-Cl-Phenyl |
| 345 | 1 | $CO_2tBu$ | 3-Cl-Phenyl |
| 346 | 2 | $CO_2tBu$ | 3-Cl-Phenyl |
| 347 | 3 | $CO_2tBu$ | 3-Cl-Phenyl |
| 348 | 4 | $CO_2tBu$ | 3-Cl-Phenyl |
| 349 | 1 | CONHMe | 3-Cl-Phenyl |
| 350 | 2 | CONHMe | 3-Cl-Phenyl |
| 351 | 3 | CONHMe | 3-Cl-Phenyl |
| 352 | 4 | CONHMe | 3-Cl-Phenyl |
| 353 | 1 | $SO_2Me$ | 3-Cl-Phenyl |
| 354 | 2 | $SO_2Me$ | 3-Cl-Phenyl |
| 355 | 3 | $SO_2Me$ | 3-Cl-Phenyl |
| 356 | 4 | $SO_2Me$ | 3-Cl-Phenyl |
| 357 | 1 | $SO_2NH_2$ | 3-Cl-Phenyl |
| 358 | 2 | $SO_2NH_2$ | 3-Cl-Phenyl |
| 359 | 3 | $SO_2NH_2$ | 3-Cl-Phenyl |

TABLE 17-continued

| Entry | n | $R^7$ | $R^3$ |
|---|---|---|---|
| 360 | 4 | $SO_2NH_2$ | 3-Cl-Phenyl |
| 361 | 1 | H | 2-Br-Phenyl |
| 362 | 2 | H | 2-Br-Phenyl |
| 363 | 3 | H | 2-Br-Phenyl |
| 364 | 4 | H | 2-Br-Phenyl |
| 365 | 1 | Me | 2-Br-Phenyl |
| 366 | 2 | Me | 2-Br-Phenyl |
| 367 | 3 | Me | 2-Br-Phenyl |
| 368 | 4 | Me | 2-Br-Phenyl |
| 369 | 1 | $CH_2Ph$ | 2-Br-Phenyl |
| 370 | 2 | $CH_2Ph$ | 2-Br-Phenyl |
| 371 | 3 | $CH_2Ph$ | 2-Br-Phenyl |
| 372 | 4 | $CH_2Ph$ | 2-Br-Phenyl |
| 373 | 1 | COMe | 2-Br-Phenyl |
| 374 | 2 | COMe | 2-Br-Phenyl |
| 375 | 3 | COMe | 2-Br-Phenyl |
| 376 | 4 | COMe | 2-Br-Phenyl |
| 377 | 1 | $CO_2Me$ | 2-Br-Phenyl |
| 378 | 2 | $CO_2Me$ | 2-Br-Phenyl |
| 379 | 3 | $CO_2Me$ | 2-Br-Phenyl |
| 380 | 4 | $CO_2Me$ | 2-Br-Phenyl |
| 381 | 1 | $CO_2tBu$ | 2-Br-Phenyl |
| 382 | 2 | $CO_2tBu$ | 2-Br-Phenyl |
| 383 | 3 | $CO_2tBu$ | 2-Br-Phenyl |
| 384 | 4 | $CO_2tBu$ | 2-Br-Phenyl |
| 385 | 1 | CONHMe | 2-Br-Phenyl |
| 386 | 2 | CONHMe | 2-Br-Phenyl |
| 387 | 3 | CONHMe | 2-Br-Phenyl |
| 388 | 4 | CONHMe | 2-Br-Phenyl |
| 389 | 1 | $SO_2Me$ | 2-Br-Phenyl |
| 390 | 2 | $SO_2Me$ | 2-Br-Phenyl |
| 391 | 3 | $SO_2Me$ | 2-Br-Phenyl |
| 392 | 4 | $SO_2Me$ | 2-Br-Phenyl |
| 393 | 1 | $SO_2NH_2$ | 2-Br-Phenyl |
| 394 | 2 | $SO_2NH_2$ | 2-Br-Phenyl |
| 395 | 3 | $SO_2NH_2$ | 2-Br-Phenyl |
| 396 | 4 | $SO_2NH_2$ | 2-Br-Phenyl |
| 397 | 1 | H | 4-Br-Phenyl |
| 398 | 2 | H | 4-Br-Phenyl |
| 399 | 3 | H | 4-Br-Phenyl |
| 400 | 4 | H | 4-Br-Phenyl |
| 401 | 1 | Me | 4-Br-Phenyl |
| 402 | 2 | Me | 4-Br-Phenyl |
| 403 | 3 | Me | 4-Br-Phenyl |
| 404 | 4 | Me | 4-Br-Phenyl |
| 405 | 1 | $CH_2Ph$ | 4-Br-Phenyl |
| 406 | 2 | $CH_2Ph$ | 4-Br-Phenyl |
| 407 | 3 | $CH_2Ph$ | 4-Br-Phenyl |
| 408 | 4 | $CH_2Ph$ | 4-Br-Phenyl |
| 409 | 1 | COMe | 4-Br-Phenyl |
| 410 | 2 | COMe | 4-Br-Phenyl |
| 411 | 3 | COMe | 4-Br-Phenyl |
| 412 | 4 | COMe | 4-Br-Phenyl |
| 413 | 1 | $CO_2Me$ | 4-Br-Phenyl |
| 414 | 2 | $CO_2Me$ | 4-Br-Phenyl |
| 415 | 3 | $CO_2Me$ | 4-Br-Phenyl |
| 416 | 4 | $CO_2Me$ | 4-Br-Phenyl |
| 417 | 1 | $CO_2tBu$ | 4-Br-Phenyl |
| 418 | 2 | $CO_2tBu$ | 4-Br-Phenyl |
| 419 | 3 | $CO_2tBu$ | 4-Br-Phenyl |
| 420 | 4 | $CO_2tBu$ | 4-Br-Phenyl |
| 421 | 1 | CONHMe | 4-Br-Phenyl |
| 422 | 2 | CONHMe | 4-Br-Phenyl |
| 423 | 3 | CONHMe | 4-Br-Phenyl |
| 424 | 4 | CONHMe | 4-Br-Phenyl |
| 425 | 1 | $SO_2Me$ | 4-Br-Phenyl |
| 426 | 2 | $SO_2Me$ | 4-Br-Phenyl |
| 427 | 3 | $SO_2Me$ | 4-Br-Phenyl |
| 428 | 4 | $SO_2Me$ | 4-Br-Phenyl |
| 429 | 1 | $SO_2NH_2$ | 4-Br-Phenyl |
| 430 | 2 | $SO_2NH_2$ | 4-Br-Phenyl |
| 431 | 3 | $SO_2NH_2$ | 4-Br-Phenyl |
| 432 | 4 | $SO_2NH_2$ | 4-Br-Phenyl |
| 433 | 1 | H | 3-$CF_3$-Phenyl |
| 434 | 2 | H | 3-$CF_3$-Phenyl |
| 435 | 3 | H | 3-$CF_3$-Phenyl |
| 436 | 4 | H | 3-$CF_3$-Phenyl |
| 437 | 1 | Me | 3-$CF_3$-Phenyl |

TABLE 17-continued

| Entry | n | $R^7$ | $R^3$ |
|---|---|---|---|
| 438 | 2 | Me | 3-$CF_3$-Phenyl |
| 439 | 3 | Me | 3-$CF_3$-Phenyl |
| 440 | 4 | Me | 3-$CF_3$-Phenyl |
| 441 | 1 | $CH_2Ph$ | 3-$CF_3$-Phenyl |
| 442 | 2 | $CH_2Ph$ | 3-$CF_3$-Phenyl |
| 443 | 3 | $CH_2Ph$ | 3-$CF_3$-Phenyl |
| 444 | 4 | $CH_2Ph$ | 3-$CF_3$-Phenyl |
| 445 | 1 | COMe | 3-$CF_3$-Phenyl |
| 446 | 2 | COMe | 3-$CF_3$-Phenyl |
| 447 | 3 | COMe | 3-$CF_3$-Phenyl |
| 448 | 4 | COMe | 3-$CF_3$-Phenyl |
| 449 | 1 | $CO_2Me$ | 3-$CF_3$-Phenyl |
| 450 | 2 | $CO_2Me$ | 3-$CF_3$-Phenyl |
| 451 | 3 | $CO_2Me$ | 3-$CF_3$-Phenyl |
| 452 | 4 | $CO_2Me$ | 3-$CF_3$-Phenyl |
| 453 | 1 | $CO_2tBu$ | 3-$CF_3$-Phenyl |
| 454 | 2 | $CO_2tBu$ | 3-$CF_3$-Phenyl |
| 455 | 3 | $CO_2tBu$ | 3-$CF_3$-Phenyl |
| 456 | 4 | $CO_2tBu$ | 3-$CF_3$-Phenyl |
| 457 | 1 | CONHMe | 3-$CF_3$-Phenyl |
| 458 | 2 | CONHMe | 3-$CF_3$-Phenyl |
| 459 | 3 | CONHMe | 3-$CF_3$-Phenyl |
| 460 | 4 | CONHMe | 3-$CF_3$-Phenyl |
| 461 | 1 | $SO_2Me$ | 3-$CF_3$-Phenyl |
| 462 | 2 | $SO_2Me$ | 3-$CF_3$-Phenyl |
| 463 | 3 | $SO_2Me$ | 3-$CF_3$-Phenyl |
| 464 | 4 | $SO_2Me$ | 3-$CF_3$-Phenyl |
| 465 | 1 | $SO_2NH_2$ | 3-$CF_3$-Phenyl |
| 466 | 2 | $SO_2NH_2$ | 3-$CF_3$-Phenyl |
| 467 | 3 | $SO_2NH_2$ | 3-$CF_3$-Phenyl |
| 468 | 4 | $SO_2NH_2$ | 3-$CF_3$-Phenyl |
| 469 | 1 | H | 2-iPr-Phenyl |
| 470 | 2 | H | 2-iPr-Phenyl |
| 471 | 3 | H | 2-iPr-Phenyl |
| 472 | 4 | H | 2-iPr-Phenyl |
| 473 | 1 | Me | 2-iPr-Phenyl |
| 474 | 2 | Me | 2-iPr-Phenyl |
| 475 | 3 | Me | 2-iPr-Phenyl |
| 476 | 4 | Me | 2-iPr-Phenyl |
| 477 | 1 | $CH_2Ph$ | 2-iPr-Phenyl |
| 478 | 2 | $CH_2Ph$ | 2-iPr-Phenyl |
| 479 | 3 | $CH_2Ph$ | 2-iPr-Phenyl |
| 480 | 4 | $CH_2Ph$ | 2-iPr-Phenyl |
| 481 | 1 | COMe | 2-iPr-Phenyl |
| 482 | 2 | COMe | 2-iPr-Phenyl |
| 483 | 3 | COMe | 2-iPr-Phenyl |
| 484 | 4 | COMe | 2-iPr-Phenyl |
| 485 | 1 | $CO_2Me$ | 2-iPr-Phenyl |
| 486 | 2 | $CO_2Me$ | 2-iPr-Phenyl |
| 487 | 3 | $CO_2Me$ | 2-iPr-Phenyl |
| 488 | 4 | $CO_2Me$ | 2-iPr-Phenyl |
| 489 | 1 | $CO_2tBu$ | 2-iPr-Phenyl |
| 490 | 2 | $CO_2tBu$ | 2-iPr-Phenyl |
| 491 | 3 | $CO_2tBu$ | 2-iPr-Phenyl |
| 492 | 4 | $CO_2tBu$ | 2-iPr-Phenyl |
| 493 | 1 | CONHMe | 2-iPr-Phenyl |
| 494 | 2 | CONHMe | 2-iPr-Phenyl |
| 495 | 3 | CONHMe | 2-iPr-Phenyl |
| 496 | 4 | CONHMe | 2-iPr-Phenyl |
| 497 | 1 | $SO_2Me$ | 2-iPr-Phenyl |
| 498 | 2 | $SO_2Me$ | 2-iPr-Phenyl |
| 499 | 3 | $SO_2Me$ | 2-iPr-Phenyl |
| 500 | 4 | $SO_2Me$ | 2-iPr-Phenyl |
| 501 | 1 | $SO_2NH_2$ | 2-iPr-Phenyl |
| 502 | 2 | $SO_2NH_2$ | 2-iPr-Phenyl |
| 503 | 3 | $SO_2NH_2$ | 2-iPr-Phenyl |
| 504 | 4 | $SO_2NH_2$ | 2-iPr-Phenyl |
| 505 | 1 | H | 4-iPr-Phenyl |
| 506 | 2 | H | 4-iPr-Phenyl |
| 507 | 3 | H | 4-iPr-Phenyl |
| 508 | 4 | H | 4-iPr-Phenyl |
| 509 | 1 | Me | 4-iPr-Phenyl |
| 510 | 2 | Me | 4-iPr-Phenyl |
| 511 | 3 | Me | 4-iPr-Phenyl |
| 512 | 4 | Me | 4-iPr-Phenyl |
| 513 | 1 | $CH_2Ph$ | 4-iPr-Phenyl |
| 514 | 2 | $CH_2Ph$ | 4-iPr-Phenyl |
| 515 | 3 | $CH_2Ph$ | 4-iPr-Phenyl |

TABLE 17-continued

| Entry | n | $R^7$ | $R^3$ |
|---|---|---|---|
| 516 | 4 | $CH_2Ph$ | 4-iPr-Phenyl |
| 517 | 1 | COMe | 4-iPr-Phenyl |
| 518 | 2 | COMe | 4-iPr-Phenyl |
| 519 | 3 | COMe | 4-iPr-Phenyl |
| 520 | 4 | COMe | 4-iPr-Phenyl |
| 521 | 1 | $CO_2Me$ | 4-iPr-Phenyl |
| 522 | 2 | $CO_2Me$ | 4-iPr-Phenyl |
| 523 | 3 | $CO_2Me$ | 4-iPr-Phenyl |
| 524 | 4 | $CO_2Me$ | 4-iPr-Phenyl |
| 525 | 1 | $CO_2tBu$ | 4-iPr-Phenyl |
| 526 | 2 | $CO_2tBu$ | 4-iPr-Phenyl |
| 527 | 3 | $CO_2tBu$ | 4-iPr-Phenyl |
| 528 | 4 | $CO_2tBu$ | 4-iPr-Phenyl |
| 529 | 1 | CONHMe | 4-iPr-Phenyl |
| 530 | 2 | CONHMe | 4-iPr-Phenyl |
| 531 | 3 | CONHMe | 4-iPr-Phenyl |
| 532 | 4 | CONHMe | 4-iPr-Phenyl |
| 533 | 1 | $SO_2Me$ | 4-iPr-Phenyl |
| 534 | 2 | $SO_2Me$ | 4-iPr-Phenyl |
| 535 | 3 | $SO_2Me$ | 4-iPr-Phenyl |
| 536 | 4 | $SO_2Me$ | 4-iPr-Phenyl |
| 537 | 1 | $SO_2NH_2$ | 4-iPr-Phenyl |
| 538 | 2 | $SO_2NH_2$ | 4-iPr-Phenyl |
| 539 | 3 | $SO_2NH_2$ | 4-iPr-Phenyl |
| 540 | 4 | $SO_2NH_2$ | 4-iPr-Phenyl |
| 541 | 1 | H | 3-$NH_2$-Phenyl |
| 542 | 2 | H | 3-$NH_2$-Phenyl |
| 543 | 3 | H | 3-$NH_2$-Phenyl |
| 544 | 4 | H | 3-$NH_2$-Phenyl |
| 545 | 1 | Me | 3-$NH_2$-Phenyl |
| 546 | 2 | Me | 3-$NH_2$-Phenyl |
| 547 | 3 | Me | 3-$NH_2$-Phenyl |
| 548 | 4 | Me | 3-$NH_2$-Phenyl |
| 549 | 1 | $CH_2Ph$ | 3-$NH_2$-Phenyl |
| 550 | 2 | $CH_2Ph$ | 3-$NH_2$-Phenyl |
| 551 | 3 | $CH_2Ph$ | 3-$NH_2$-Phenyl |
| 552 | 4 | $CH_2Ph$ | 3-$NH_2$-Phenyl |
| 553 | 1 | COMe | 3-$NH_2$-Phenyl |
| 554 | 2 | COMe | 3-$NH_2$-Phenyl |
| 555 | 3 | COMe | 3-$NH_2$-Phenyl |
| 556 | 4 | COMe | 3-$NH_2$-Phenyl |
| 557 | 1 | $CO_2Me$ | 3-$NH_2$-Phenyl |
| 558 | 2 | $CO_2Me$ | 3-$NH_2$-Phenyl |
| 559 | 3 | $CO_2Me$ | 3-$NH_2$-Phenyl |
| 560 | 4 | $CO_2Me$ | 3-$NH_2$-Phenyl |
| 561 | 1 | $CO_2tBu$ | 3-$NH_2$-Phenyl |
| 562 | 2 | $CO_2tBu$ | 3-$NH_2$-Phenyl |
| 563 | 3 | $CO_2tBu$ | 3-$NH_2$-Phenyl |
| 564 | 4 | $CO_2tBu$ | 3-$NH_2$-Phenyl |
| 565 | 1 | CONHMe | 3-$NH_2$-Phenyl |
| 566 | 2 | CONHMe | 3-$NH_2$-Phenyl |
| 567 | 3 | CONHMe | 3-$NH_2$-Phenyl |
| 568 | 4 | CONHMe | 3-$NH_2$-Phenyl |
| 569 | 1 | $SO_2Me$ | 3-$NH_2$-Phenyl |
| 570 | 2 | $SO_2Me$ | 3-$NH_2$-Phenyl |
| 571 | 3 | $SO_2Me$ | 3-$NH_2$-Phenyl |
| 572 | 4 | $SO_2Me$ | 3-$NH_2$-Phenyl |
| 573 | 1 | $SO_2NH_2$ | 3-$NH_2$-Phenyl |
| 574 | 2 | $SO_2NH_2$ | 3-$NH_2$-Phenyl |
| 575 | 3 | $SO_2NH_2$ | 3-$NH_2$-Phenyl |
| 576 | 4 | $SO_2NH_2$ | 3-$NH_2$-Phenyl |
| 577 | 1 | H | 2,4-di-Me-Phenyl |
| 578 | 2 | H | 2,4-di-Me-Phenyl |
| 579 | 3 | H | 2,4-di-Me-Phenyl |
| 580 | 4 | H | 2,4-di-Me-Phenyl |
| 581 | 1 | Me | 2,4-di-Me-Phenyl |
| 582 | 2 | Me | 2,4-di-Me-Phenyl |
| 583 | 3 | Me | 2,4-di-Me-Phenyl |
| 584 | 4 | Me | 2,4-di-Me-Phenyl |
| 585 | 1 | $CH_2Ph$ | 2,4-di-Me-Phenyl |
| 586 | 2 | $CH_2Ph$ | 2,4-di-Me-Phenyl |
| 587 | 3 | $CH_2Ph$ | 2,4-di-Me-Phenyl |
| 588 | 4 | $CH_2Ph$ | 2,4-di-Me-Phenyl |
| 589 | 1 | COMe | 2,4-di-Me-Phenyl |
| 590 | 2 | COMe | 2,4-di-Me-Phenyl |
| 591 | 3 | COMe | 2,4-di-Me-Phenyl |
| 592 | 4 | COMe | 2,4-di-Me-Phenyl |
| 593 | 1 | $CO_2Me$ | 2,4-di-Me-Phenyl |

TABLE 17-continued

| Entry | n | $R^7$ | $R^3$ |
|---|---|---|---|
| 594 | 2 | $CO_2Me$ | 2,4-di-Me-Phenyl |
| 595 | 3 | $CO_2Me$ | 2,4-di-Me-Phenyl |
| 596 | 4 | $CO_2Me$ | 2,4-di-Me-Phenyl |
| 597 | 1 | $CO_2tBu$ | 2,4-di-Me-Phenyl |
| 598 | 2 | $CO_2tBu$ | 2,4-di-Me-Phenyl |
| 599 | 3 | $CO_2tBu$ | 2,4-di-Me-Phenyl |
| 600 | 4 | $CO_2tBu$ | 2,4-di-Me-Phenyl |
| 601 | 1 | CONHMe | 2,4-di-Me-Phenyl |
| 602 | 2 | CONHMe | 2,4-di-Me-Phenyl |
| 603 | 3 | CONHMe | 2,4-di-Me-Phenyl |
| 604 | 4 | CONHMe | 2,4-di-Me-Phenyl |
| 605 | 1 | $SO_2Me$ | 2,4-di-Me-Phenyl |
| 606 | 2 | $SO_2Me$ | 2,4-di-Me-Phenyl |
| 607 | 3 | $SO_2Me$ | 2,4-di-Me-Phenyl |
| 608 | 4 | $SO_2Me$ | 2,4-di-Me-Phenyl |
| 609 | 1 | $SO_2NH_2$ | 2,4-di-Me-Phenyl |
| 610 | 2 | $SO_2NH_2$ | 2,4-di-Me-Phenyl |
| 611 | 3 | $SO_2NH_2$ | 2,4-di-Me-Phenyl |
| 612 | 4 | $SO_2NH_2$ | 2,4-di-Me-Phenyl |
| 613 | 1 | H | 2,6-di-iPr-Phenyl |
| 614 | 2 | H | 2,6-di-iPr-Phenyl |
| 615 | 3 | H | 2,6-di-iPr-Phenyl |
| 616 | 4 | H | 2,6-di-iPr-Phenyl |
| 617 | 1 | Me | 2,6-di-iPr-Phenyl |
| 618 | 2 | Me | 2,6-di-iPr-Phenyl |
| 619 | 3 | Me | 2,6-di-iPr-Phenyl |
| 620 | 4 | Me | 2,6-di-iPr-Phenyl |
| 621 | 1 | $CH_2Ph$ | 2,6-di-iPr-Phenyl |
| 622 | 2 | $CH_2Ph$ | 2,6-di-iPr-Phenyl |
| 623 | 3 | $CH_2Ph$ | 2,6-di-iPr-Phenyl |
| 624 | 3 | $CH_2Ph$ | 2,6-di-iPr-Phenyl |
| 625 | 1 | COMe | 2,6-di-iPr-Phenyl |
| 626 | 2 | COMe | 2,6-di-iPr-Phenyl |
| 627 | 3 | COMe | 2,6-di-iPr-Phenyl |
| 628 | 4 | COMe | 2,6-di-iPr-Phenyl |
| 629 | 1 | $CO_2Me$ | 2,6-di-iPr-Phenyl |
| 630 | 2 | $CO_2Me$ | 2,6-di-iPr-Phenyl |
| 631 | 3 | $CO_2Me$ | 2,6-di-iPr-Phenyl |
| 632 | 4 | $CO_2Me$ | 2,6-di-iPr-Phenyl |
| 633 | 1 | $CO_2tBu$ | 2,6-di-iPr-Phenyl |
| 634 | 2 | $CO_2tBu$ | 2,6-di-iPr-Phenyl |
| 635 | 3 | $CO_2tBu$ | 2,6-di-iPr-Phenyl |
| 636 | 4 | $CO_2tBu$ | 2,6-di-iPr-Phenyl |
| 637 | 1 | CONHMe | 2,6-di-iPr-Phenyl |
| 638 | 2 | CONHMe | 2,6-di-iPr-Phenyl |
| 639 | 3 | CONHMe | 2,6-di-iPr-Phenyl |
| 640 | 4 | CONHMe | 2,6-di-iPr-Phenyl |
| 641 | 1 | $SO_2Me$ | 2,6-di-iPr-Phenyl |
| 642 | 2 | $SO_2Me$ | 2,6-di-iPr-Phenyl |
| 643 | 3 | $SO_2Me$ | 2,6-di-iPr-Phenyl |
| 644 | 4 | $SO_2Me$ | 2,6-di-iPr-Phenyl |
| 645 | 1 | $SO_2NH_2$ | 2,6-di-iPr-Phenyl |
| 646 | 2 | $SO_2NH_2$ | 2,6-di-iPr-Phenyl |
| 647 | 3 | $SO_2NH_2$ | 2,6-di-iPr-Phenyl |
| 648 | 4 | $SO_2NH_2$ | 2,6-di-iPr-Phenyl |
| 649 | 1 | H | 3-Ph-Phenyl |
| 650 | 2 | H | 3-Ph-Phenyl |
| 651 | 3 | H | 3-Ph-Phenyl |
| 652 | 4 | H | 3-Ph-Phenyl |
| 653 | 1 | Me | 3-Ph-Phenyl |
| 654 | 2 | Me | 3-Ph-Phenyl |
| 655 | 3 | Me | 3-Ph-Phenyl |
| 656 | 4 | Me | 3-Ph-Phenyl |
| 657 | 1 | $CH_2Ph$ | 3-Ph-Phenyl |
| 658 | 2 | $CH_2Ph$ | 3-Ph-Phenyl |
| 659 | 3 | $CH_2Ph$ | 3-Ph-Phenyl |
| 660 | 4 | $CH_2Ph$ | 3-Ph-Phenyl |
| 661 | 1 | COMe | 3-Ph-Phenyl |
| 662 | 2 | COMe | 3-Ph-Phenyl |
| 663 | 3 | COMe | 3-Ph-Phenyl |
| 664 | 4 | COMe | 3-Ph-Phenyl |
| 665 | 1 | $CO_2Me$ | 3-Ph-Phenyl |
| 666 | 2 | $CO_2Me$ | 3-Ph-Phenyl |
| 667 | 3 | $CO_2Me$ | 3-Ph-Phenyl |
| 668 | 4 | $CO_2Me$ | 3-Ph-Phenyl |
| 669 | 1 | $CO_2tBu$ | 3-Ph-Phenyl |
| 670 | 2 | $CO_2tBu$ | 3-Ph-Phenyl |
| 671 | 3 | $CO_2tBu$ | 3-Ph-Phenyl |

TABLE 17-continued

| Entry | n | $R^7$ | $R^3$ |
|---|---|---|---|
| 672 | 4 | $CO_2tBu$ | 3-Ph-Phenyl |
| 673 | 1 | CONHMe | 3-Ph-Phenyl |
| 674 | 2 | CONHMe | 3-Ph-Phenyl |
| 675 | 3 | CONHMe | 3-Ph-Phenyl |
| 676 | 4 | CONHMe | 3-Ph-Phenyl |
| 677 | 1 | $SO_2Me$ | 3-Ph-Phenyl |
| 678 | 2 | $SO_2Me$ | 3-Ph-Phenyl |
| 679 | 3 | $SO_2Me$ | 3-Ph-Phenyl |
| 680 | 4 | $SO_2Me$ | 3-Ph-Phenyl |
| 681 | 1 | $SO_2NH_2$ | 3-Ph-Phenyl |
| 682 | 2 | $SO_2NH_2$ | 3-Ph-Phenyl |
| 683 | 3 | $SO_2NH_2$ | 3-Ph-Phenyl |
| 684 | 4 | $SO_2NH_2$ | 3-Ph-Phenyl |
| 685 | 1 | H | 2-morpholino-phenyl |
| 686 | 2 | H | 2-morpholino-phenyl |
| 687 | 3 | H | 2-morpholino-phenyl |
| 688 | 4 | H | 2-morpholino-phenyl |
| 689 | 1 | Me | 2-morpholino-phenyl |
| 690 | 2 | Me | 2-morpholino-phenyl |
| 691 | 3 | Me | 2-morpholino-phenyl |
| 692 | 4 | Me | 2-morpholino-phenyl |
| 693 | 1 | $CH_2Ph$ | 2-morpholino-phenyl |
| 694 | 2 | $CH_2Ph$ | 2-morpholino-phenyl |
| 695 | 3 | $CH_2Ph$ | 2-morpholino-phenyl |
| 696 | 4 | $CH_2Ph$ | 2-morpholino-phenyl |
| 697 | 1 | COMe | 2-morpholino-phenyl |
| 698 | 2 | COMe | 2-morpholino-phenyl |
| 699 | 3 | COMe | 2-morpholino-phenyl |
| 700 | 4 | COMe | 2-morpholino-phenyl |
| 701 | 1 | $CO_2Me$ | 2-morpholino-phenyl |
| 702 | 2 | $CO_2Me$ | 2-morpholino-phenyl |
| 703 | 3 | $CO_2Me$ | 2-morpholino-phenyl |
| 704 | 4 | $CO_2Me$ | 2-morpholino-phenyl |
| 705 | 1 | $CO_2tBu$ | 2-morpholino-phenyl |
| 706 | 2 | $CO_2tBu$ | 2-morpholino-phenyl |
| 707 | 3 | $CO_2tBu$ | 2-morpholino-phenyl |
| 708 | 4 | $CO_2tBu$ | 2-morpholino-phenyl |
| 709 | 1 | CONHMe | 2-morpholino-phenyl |
| 710 | 2 | CONHMe | 2-morpholino-phenyl |
| 711 | 3 | CONHMe | 2-morpholino-phenyl |
| 712 | 4 | CONHMe | 2-morpholino-phenyl |
| 713 | 1 | $SO_2Me$ | 2-morpholino-phenyl |
| 714 | 2 | $SO_2Me$ | 2-morpholino-phenyl |
| 715 | 3 | $SO_2Me$ | 2-morpholino-phenyl |
| 716 | 4 | $SO_2Me$ | 2-morpholino-phenyl |
| 717 | 1 | $SO_2NH_2$ | 2-morpholino-phenyl |
| 718 | 2 | $SO_2NH_2$ | 2-morpholino-phenyl |
| 719 | 3 | $SO_2NH_2$ | 2-morpholino-phenyl |
| 720 | 4 | $SO_2NH_2$ | 2-morpholino-phenyl |
| 721 | 1 | H | 4-morpholino-phenyl |
| 722 | 2 | H | 4-morpholino-phenyl |
| 723 | 3 | H | 4-morpholino-phenyl |
| 724 | 4 | H | 4-morpholino-phenyl |
| 725 | 1 | $CH_2Ph$ | 4-morpholino-phenyl |
| 726 | 2 | $CH_2Ph$ | 4-morpholino-phenyl |
| 727 | 3 | $CH_2Ph$ | 4-morpholino-phenyl |
| 728 | 4 | $CH_2Ph$ | 4-morpholino-phenyl |
| 729 | 1 | $CO_2Me$ | 4-morpholino-phenyl |
| 730 | 2 | $CO_2Me$ | 4-morpholino-phenyl |
| 731 | 3 | $CO_2Me$ | 4-morpholino-phenyl |
| 732 | 4 | $CO_2Me$ | 4-morpholino-phenyl |
| 733 | 1 | CONHMe | 4-morpholino-phenyl |
| 734 | 2 | CONHMe | 4-morpholino-phenyl |
| 735 | 3 | CONHMe | 4-morpholino-phenyl |
| 736 | 4 | CONHMe | 4-morpholino-phenyl |
| 737 | 1 | $SO_2NH_2$ | 4-morpholino-phenyl |
| 738 | 2 | $SO_2NH_2$ | 4-morpholino-phenyl |
| 739 | 3 | $SO_2NH_2$ | 4-morpholino-phenyl |
| 740 | 1 | H | naphthylen-1-yl |
| 741 | 2 | H | naphthylen-1-yl |
| 742 | 3 | H | naphthylen-1-yl |
| 743 | 4 | H | naphthylen-1-yl |
| 744 | 1 | Me | naphthylen-1-yl |
| 745 | 2 | Me | naphthylen-1-yl |
| 746 | 3 | Me | naphthylen-1-yl |
| 747 | 4 | Me | naphthylen-1-yl |
| 748 | 1 | $CH_2Ph$ | naphthylen-1-yl |
| 749 | 2 | $CH_2Ph$ | naphthylen-1-yl |

TABLE 17-continued

| Entry | n | $R^7$ | $R^3$ |
|---|---|---|---|
| 750 | 3 | $CH_2Ph$ | naphthylen-1-yl |
| 751 | 4 | $CH_2Ph$ | naphthylen-1-yl |
| 752 | 1 | COMe | naphthylen-1-yl |
| 753 | 2 | COMe | naphthylen-1-yl |
| 754 | 3 | COMe | naphthylen-1-yl |
| 755 | 4 | COMe | naphthylen-1-yl |
| 756 | 1 | $CO_2Me$ | naphthylen-1-yl |
| 757 | 2 | $CO_2Me$ | naphthylen-1-yl |
| 758 | 3 | $CO_2Me$ | naphthylen-1-yl |
| 759 | 4 | $CO_2Me$ | naphthylen-1-yl |
| 760 | 1 | $CO_2tBu$ | naphthylen-1-yl |
| 761 | 2 | $CO_2tBu$ | naphthylen-1-yl |
| 762 | 3 | $CO_2tBu$ | naphthylen-1-yl |
| 763 | 4 | $CO_2tBu$ | naphthylen-1-yl |
| 764 | 1 | CONHMe | naphthylen-1-yl |
| 765 | 2 | CONHMe | naphthylen-1-yl |
| 767 | 3 | CONHMe | naphthylen-1-yl |
| 768 | 4 | CONHMe | naphthylen-1-yl |
| 769 | 1 | $SO_2Me$ | naphthylen-1-yl |
| 770 | 2 | $SO_2Me$ | naphthylen-1-yl |
| 771 | 3 | $SO_2Me$ | naphthylen-1-yl |
| 772 | 4 | $SO_2Me$ | naphthylen-1-yl |
| 773 | 1 | $SO_2NH_2$ | naphthylen-1-yl |
| 774 | 2 | $SO_2NH_2$ | naphthylen-1-yl |
| 775 | 3 | $SO_2NH_2$ | naphthylen-1-yl |
| 778 | 4 | $SO_2NH_2$ | naphthylen-1-yl |
| 779 | 1 | H | 4-OH-Phenyl |
| 780 | 2 | H | 4-OH-Phenyl |
| 781 | 3 | H | 4-OH-Phenyl |
| 782 | 4 | H | 4-OH-Phenyl |
| 783 | 1 | Me | 4-OH-Phenyl |
| 784 | 2 | Me | 4-OH-Phenyl |
| 785 | 3 | Me | 4-OH-Phenyl |
| 786 | 4 | Me | 4-OH-Phenyl |
| 787 | 1 | $CH_2Ph$ | 4-OH-Phenyl |
| 788 | 2 | $CH_2Ph$ | 4-OH-Phenyl |
| 789 | 3 | $CH_2Ph$ | 4-OH-Phenyl |
| 790 | 4 | $CH_2Ph$ | 4-OH-Phenyl |
| 791 | 1 | COMe | 4-OH-Phenyl |
| 792 | 2 | COMe | 4-OH-Phenyl |
| 793 | 3 | COMe | 4-OH-Phenyl |
| 794 | 4 | COMe | 4-OH-Phenyl |
| 795 | 1 | $CO_2Me$ | 4-OH-Phenyl |
| 796 | 2 | $CO_2Me$ | 4-OH-Phenyl |
| 797 | 3 | $CO_2Me$ | 4-OH-Phenyl |
| 798 | 4 | $CO_2Me$ | 4-OH-Phenyl |
| 799 | 1 | $CO_2tBu$ | 4-OH-Phenyl |
| 800 | 2 | $CO_2tBu$ | 4-OH-Phenyl |
| 801 | 3 | $CO_2tBu$ | 4-OH-Phenyl |
| 802 | 4 | $CO_2tBu$ | 4-OH-Phenyl |
| 803 | 1 | CONHMe | 4-OH-Phenyl |
| 804 | 2 | CONHMe | 4-OH-Phenyl |
| 805 | 3 | CONHMe | 4-OH-Phenyl |
| 806 | 4 | CONHMe | 4-OH-Phenyl |
| 807 | 1 | $SO_2Me$ | 4-OH-Phenyl |
| 808 | 2 | $SO_2Me$ | 4-OH-Phenyl |
| 809 | 3 | $SO_2Me$ | 4-OH-Phenyl |
| 810 | 4 | $SO_2Me$ | 4-OH-Phenyl |
| 811 | 1 | $SO_2NH_2$ | 4-OH-Phenyl |
| 812 | 2 | $SO_2NH_2$ | 4-OH-Phenyl |
| 813 | 3 | $SO_2NH_2$ | 4-OH-Phenyl |
| 814 | 4 | $SO_2NH_2$ | 4-OH-Phenyl |
| 815 | 1 | H | 2-OH-Phenyl |
| 816 | 2 | H | 2-OH-Phenyl |
| 817 | 3 | H | 2-OH-Phenyl |
| 818 | 4 | H | 2-OH-Phenyl |
| 819 | 1 | Me | 2-OH-Phenyl |
| 820 | 2 | Me | 2-OH-Phenyl |
| 821 | 3 | Me | 2-OH-Phenyl |
| 822 | 4 | Me | 2-OH-Phenyl |
| 823 | 1 | $CH_2Ph$ | 2-OH-Phenyl |
| 824 | 2 | $CH_2Ph$ | 2-OH-Phenyl |
| 825 | 3 | $CH_2Ph$ | 2-OH-Phenyl |
| 826 | 4 | $CH_2Ph$ | 2-OH-Phenyl |
| 827 | 1 | COMe | 2-OH-Phenyl |
| 828 | 2 | COMe | 2-OH-Phenyl |
| 829 | 3 | COMe | 2-OH-Phenyl |
| 830 | 4 | COMe | 2-OH-Phenyl |

TABLE 17-continued

| Entry | n | $R^7$ | $R^3$ |
|---|---|---|---|
| 831 | 1 | $CO_2Me$ | 2-OH-Phenyl |
| 832 | 2 | $CO_2Me$ | 2-OH-Phenyl |
| 833 | 3 | $CO_2Me$ | 2-OH-Phenyl |
| 834 | 4 | $CO_2Me$ | 2-OH-Phenyl |
| 835 | 1 | $CO_2tBu$ | 2-OH-Phenyl |
| 836 | 2 | $CO_2tBu$ | 2-OH-Phenyl |
| 837 | 3 | $CO_2tBu$ | 2-OH-Phenyl |
| 838 | 4 | $CO_2tBu$ | 2-OH-Phenyl |
| 839 | 1 | CONHMe | 2-OH-Phenyl |
| 840 | 2 | CONHMe | 2-OH-Phenyl |
| 841 | 3 | CONHMe | 2-OH-Phenyl |
| 842 | 4 | CONHMe | 2-OH-Phenyl |
| 843 | 1 | $SO_2Me$ | 2-OH-Phenyl |
| 844 | 2 | $SO_2Me$ | 2-OH-Phenyl |
| 845 | 3 | $SO_2Me$ | 2-OH-Phenyl |
| 846 | 4 | $SO_2Me$ | 2-OH-Phenyl |
| 847 | 1 | $SO_2NH_2$ | 2-OH-Phenyl |
| 848 | 2 | $SO_2NH_2$ | 2-OH-Phenyl |
| 849 | 3 | $SO_2NH_2$ | 2-OH-Phenyl |
| 850 | 4 | $SO_2NH_2$ | 2-OH-Phenyl |
| 851 | 1 | H | 4-OMe-Phenyl |
| 852 | 2 | H | 4-OMe-Phenyl |
| 853 | 3 | H | 4-OMe-Phenyl |
| 854 | 4 | H | 4-OMe-Phenyl |
| 855 | 1 | Me | 4-OMe-Phenyl |
| 856 | 2 | Me | 4-OMe-Phenyl |
| 857 | 3 | Me | 4-OMe-Phenyl |
| 858 | 4 | Me | 4-OMe-Phenyl |
| 859 | 1 | $CH_2Ph$ | 4-OMe-Phenyl |
| 860 | 2 | $CH_2Ph$ | 4-OMe-Phenyl |
| 861 | 3 | $CH_2Ph$ | 4-OMe-Phenyl |
| 862 | 4 | $CH_2Ph$ | 4-OMe-Phenyl |
| 863 | 1 | COMe | 4-OMe-Phenyl |
| 864 | 2 | COMe | 4-OMe-Phenyl |
| 865 | 3 | COMe | 4-OMe-Phenyl |
| 866 | 4 | COMe | 4-OMe-Phenyl |
| 867 | 1 | $CO_2Me$ | 4-OMe-Phenyl |
| 868 | 2 | $CO_2Me$ | 4-OMe-Phenyl |
| 869 | 3 | $CO_2Me$ | 4-OMe-Phenyl |
| 870 | 4 | $CO_2Me$ | 4-OMe-Phenyl |
| 871 | 1 | $CO_2tBu$ | 4-OMe-Phenyl |
| 872 | 2 | $CO_2tBu$ | 4-OMe-Phenyl |
| 873 | 3 | $CO_2tBu$ | 4-OMe-Phenyl |
| 874 | 4 | $CO_2tBu$ | 4-OMe-Phenyl |
| 875 | 1 | CONHMe | 4-OMe-Phenyl |
| 876 | 2 | CONHMe | 4-OMe-Phenyl |
| 877 | 3 | CONHMe | 4-OMe-Phenyl |
| 878 | 4 | CONHMe | 4-OMe-Phenyl |
| 879 | 1 | $SO_2Me$ | 4-OMe-Phenyl |
| 880 | 2 | $SO_2Me$ | 4-OMe-Phenyl |
| 881 | 3 | $SO_2Me$ | 4-OMe-Phenyl |
| 882 | 4 | $SO_2Me$ | 4-OMe-Phenyl |
| 883 | 1 | $SO_2NH_2$ | 4-OMe-Phenyl |
| 884 | 2 | $SO_2NH_2$ | 4-OMe-Phenyl |
| 885 | 3 | $SO_2NH_2$ | 4-OMe-Phenyl |
| 886 | 4 | $SO_2NH_2$ | 4-OMe-Phenyl |
| 887 | 1 | H | 2-OMe-Phenyl |
| 888 | 2 | H | 2-OMe-Phenyl |
| 889 | 3 | H | 2-OMe-Phenyl |
| 890 | 4 | H | 2-OMe-Phenyl |
| 891 | 1 | Me | 2-OMe-Phenyl |
| 892 | 2 | Me | 2-OMe-Phenyl |
| 893 | 3 | Me | 2-OMe-Phenyl |
| 894 | 4 | Me | 2-OMe-Phenyl |
| 895 | 1 | $CH_2Ph$ | 2-OMe-Phenyl |
| 896 | 2 | $CH_2Ph$ | 2-OMe-Phenyl |
| 897 | 3 | $CH_2Ph$ | 2-OMe-Phenyl |
| 898 | 4 | $CH_2Ph$ | 2-OMe-Phenyl |
| 899 | 1 | COMe | 2-OMe-Phenyl |
| 900 | 2 | COMe | 2-OMe-Phenyl |
| 901 | 3 | COMe | 2-OMe-Phenyl |
| 902 | 4 | COMe | 2-OMe-Phenyl |
| 903 | 1 | $CO_2Me$ | 2-OMe-Phenyl |
| 904 | 2 | $CO_2Me$ | 2-OMe-Phenyl |
| 905 | 3 | $CO_2Me$ | 2-OMe-Phenyl |
| 906 | 4 | $CO_2Me$ | 2-OMe-Phenyl |
| 907 | 1 | $CO_2tBu$ | 2-OMe-Phenyl |
| 908 | 2 | $CO_2tBu$ | 2-OMe-Phenyl |

TABLE 17-continued

| Entry | n | $R^7$ | $R^3$ |
|---|---|---|---|
| 909 | 3 | $CO_2tBu$ | 2-OMe-Phenyl |
| 910 | 4 | $CO_2tBu$ | 2-OMe-Phenyl |
| 911 | 1 | CONHMe | 2-OMe-Phenyl |
| 912 | 2 | CONHMe | 2-OMe-Phenyl |
| 913 | 3 | CONHMe | 2-OMe-Phenyl |
| 914 | 4 | CONHMe | 2-OMe-Phenyl |
| 915 | 1 | $SO_2Me$ | 2-OMe-Phenyl |
| 916 | 2 | $SO_2Me$ | 2-OMe-Phenyl |
| 917 | 3 | $SO_2Me$ | 2-OMe-Phenyl |
| 918 | 4 | $SO_2Me$ | 2-OMe-Phenyl |
| 919 | 1 | $SO_2NH_2$ | 2-OMe-Phenyl |
| 920 | 2 | $SO_2NH_2$ | 2-OMe-Phenyl |
| 921 | 3 | $SO_2NH_2$ | 2-OMe-Phenyl |
| 922 | 4 | $SO_2NH_2$ | 2-OMe-Phenyl |
| 923 | 1 | H | 3-CN-Phenyl |
| 924 | 2 | H | 3-CN-Phenyl |
| 925 | 3 | H | 3-CN-Phenyl |
| 926 | 4 | H | 3-CN-Phenyl |
| 927 | 1 | Me | 3-CN-Phenyl |
| 928 | 2 | Me | 3-CN-Phenyl |
| 929 | 3 | Me | 3-CN-Phenyl |
| 930 | 4 | Me | 3-CN-Phenyl |
| 931 | 1 | $CH_2Ph$ | 3-CN-Phenyl |
| 932 | 2 | $CH_2Ph$ | 3-CN-Phenyl |
| 933 | 3 | $CH_2Ph$ | 3-CN-Phenyl |
| 934 | 4 | $CH_2Ph$ | 3-CN-Phenyl |
| 935 | 1 | COMe | 3-CN-Phenyl |
| 936 | 2 | COMe | 3-CN-Phenyl |
| 937 | 3 | COMe | 3-CN-Phenyl |
| 938 | 4 | COMe | 3-CN-Phenyl |
| 939 | 1 | $CO_2Me$ | 3-CN-Phenyl |
| 940 | 2 | $CO_2Me$ | 3-CN-Phenyl |
| 941 | 3 | $CO_2Me$ | 3-CN-Phenyl |
| 942 | 4 | $CO_2Me$ | 3-CN-Phenyl |
| 943 | 1 | $CO_2tBu$ | 3-CN-Phenyl |
| 944 | 2 | $CO_2tBu$ | 3-CN-Phenyl |
| 945 | 3 | $CO_2tBu$ | 3-CN-Phenyl |
| 946 | 4 | $CO_2tBu$ | 3-CN-Phenyl |
| 947 | 1 | CONHMe | 3-CN-Phenyl |
| 948 | 2 | CONHMe | 3-CN-Phenyl |
| 949 | 3 | CONHMe | 3-CN-Phenyl |
| 950 | 4 | CONHMe | 3-CN-Phenyl |
| 951 | 1 | $SO_2Me$ | 3-CN-Phenyl |
| 952 | 2 | $SO_2Me$ | 3-CN-Phenyl |
| 953 | 3 | $SO_2Me$ | 3-CN-Phenyl |
| 954 | 4 | $SO_2Me$ | 3-CN-Phenyl |
| 955 | 1 | $SO_2NH_2$ | 3-CN-Phenyl |
| 956 | 2 | $SO_2NH_2$ | 3-CN-Phenyl |
| 957 | 3 | $SO_2NH_2$ | 3-CN-Phenyl |
| 958 | 4 | $SO_2NH_2$ | 3-CN-Phenyl |
| 959 | 1 | H | 2-Me-Phenyl |
| 960 | 2 | H | 2-Me-Phenyl |
| 961 | 3 | H | 2-Me-Phenyl |
| 962 | 4 | H | 2-Me-Phenyl |
| 963 | 1 | Me | 2-Me-Phenyl |
| 964 | 2 | Me | 2-Me-Phenyl |
| 965 | 3 | Me | 2-Me-Phenyl |
| 966 | 4 | Me | 2-Me-Phenyl |
| 967 | 1 | $CH_2Ph$ | 2-Me-Phenyl |
| 968 | 2 | $CH_2Ph$ | 2-Me-Phenyl |
| 969 | 3 | $CH_2Ph$ | 2-Me-Phenyl |
| 970 | 4 | $CH_2Ph$ | 2-Me-Phenyl |
| 971 | 1 | COMe | 2-Me-Phenyl |
| 972 | 2 | COMe | 2-Me-Phenyl |
| 973 | 3 | COMe | 2-Me-Phenyl |
| 974 | 4 | COMe | 2-Me-Phenyl |
| 975 | 1 | $CO_2Me$ | 2-Me-Phenyl |
| 976 | 2 | $CO_2Me$ | 2-Me-Phenyl |
| 977 | 3 | $CO_2Me$ | 2-Me-Phenyl |
| 978 | 4 | $CO_2Me$ | 2-CN-Phenyl |
| 979 | 1 | $CO_2tBu$ | 2-Me-Phenyl |
| 980 | 2 | $CO_2tBu$ | 2-Me-Phenyl |
| 981 | 3 | $CO_2tBu$ | 2-Me-Phenyl |
| 982 | 4 | $CO_2tBu$ | 2-Me-Phenyl |
| 983 | 1 | CONHMe | 2-Me-Phenyl |
| 984 | 2 | CONHMe | 2-Me-Phenyl |
| 985 | 3 | CONHMe | 2-Me-Phenyl |
| 986 | 4 | CONHMe | 2-Me-Phenyl |

TABLE 17-continued

| Entry | n | $R^7$ | $R^3$ |
|---|---|---|---|
| 987 | 1 | $SO_2Me$ | 2-Me-Phenyl |
| 988 | 2 | $SO_2Me$ | 2-Me-Phenyl |
| 989 | 3 | $SO_2Me$ | 2-Me-Phenyl |
| 990 | 4 | $SO_2Me$ | 2-Me-Phenyl |
| 991 | 1 | $SO_2NH_2$ | 2-Me-Phenyl |
| 992 | 2 | $SO_2NH_2$ | 2-Me-Phenyl |
| 993 | 3 | $SO_2NH_2$ | 2-Me-Phenyl |
| 994 | 4 | $SO_2NH_2$ | 2-Me-Phenyl |
| 995 | 1 | H | 4-Me-Phenyl |
| 996 | 2 | H | 4-Me-Phenyl |
| 997 | 3 | H | 4-Me-Phenyl |
| 998 | 4 | H | 4-Me-Phenyl |
| 999 | 1 | Me | 4-Me-Phenyl |
| 1000 | 2 | Me | 4-Me-Phenyl |
| 1001 | 3 | Me | 4-Me-Phenyl |
| 1002 | 4 | Me | 4-Me-Phenyl |
| 1003 | 1 | $CH_2Ph$ | 4-Me-Phenyl |
| 1004 | 2 | $CH_2Ph$ | 4-Me-Phenyl |
| 1005 | 3 | $CH_2Ph$ | 4-Me-Phenyl |
| 1006 | 4 | $CH_2Ph$ | 4-Me-Phenyl |
| 1007 | 1 | COMe | 4-Me-Phenyl |
| 1008 | 2 | COMe | 4-Me-Phenyl |
| 1009 | 3 | COMe | 4-Me-Phenyl |
| 1010 | 4 | COMe | 4-Me-Phenyl |
| 1011 | 1 | $CO_2Me$ | 4-Me-Phenyl |
| 1012 | 2 | $CO_2Me$ | 4-Me-Phenyl |
| 1013 | 3 | $CO_2Me$ | 4-Me-Phenyl |
| 1014 | 4 | $CO_2Me$ | 4-Me-Phenyl |
| 1015 | 1 | $CO_2tBu$ | 4-Me-Phenyl |
| 1016 | 2 | $CO_2tBu$ | 4-Me-Phenyl |
| 1017 | 3 | $CO_2tBu$ | 4-Me-Phenyl |
| 1018 | 4 | $CO_2tBu$ | 4-Me-Phenyl |
| 1019 | 1 | CONHMe | 4-Me-Phenyl |
| 1020 | 2 | CONHMe | 4-Me-Phenyl |
| 1021 | 3 | CONHMe | 4-Me-Phenyl |
| 1022 | 4 | CONHMe | 4-Me-Phenyl |
| 1023 | 1 | $SO_2Me$ | 4-Me-Phenyl |
| 1024 | 2 | $SO_2Me$ | 4-Me-Phenyl |
| 1025 | 3 | $SO_2Me$ | 4-Me-Phenyl |
| 1026 | 4 | $SO_2Me$ | 4-Me-Phenyl |
| 1027 | 1 | $SO_2NH_2$ | 4-Me-Phenyl |
| 1028 | 2 | $SO_2NH_2$ | 4-Me-Phenyl |
| 1029 | 3 | $SO_2NH_2$ | 4-Me-Phenyl |
| 1030 | 4 | $SO_2NH_2$ | 4-Me-Phenyl |
| 1031 | 1 | H | 3-F-Phenyl |
| 1032 | 2 | H | 3-F-Phenyl |
| 1033 | 3 | H | 3-F-Phenyl |
| 1034 | 4 | H | 3-F-Phenyl |
| 1035 | 1 | Me | 3-F-Phenyl |
| 1036 | 2 | Me | 3-F-Phenyl |
| 1037 | 3 | Me | 3-F-Phenyl |
| 1038 | 4 | Me | 3-F-Phenyl |
| 1039 | 1 | $CH_2Ph$ | 3-F-Phenyl |
| 1040 | 2 | $CH_2Ph$ | 3-F-Phenyl |
| 1041 | 3 | $CH_2Ph$ | 3-F-Phenyl |
| 1042 | 4 | $CH_2Ph$ | 3-F-Phenyl |
| 1043 | 1 | COMe | 3-F-Phenyl |
| 1044 | 2 | COMe | 3-F-Phenyl |
| 1045 | 3 | COMe | 3-F-Phenyl |
| 1046 | 4 | COMe | 3-F-Phenyl |
| 1047 | 1 | $CO_2Me$ | 3-F-Phenyl |
| 1048 | 2 | $CO_2Me$ | 3-F-Phenyl |
| 1049 | 3 | $CO_2Me$ | 3-F-Phenyl |
| 1050 | 4 | $CO_2Me$ | 3-F-Phenyl |
| 1051 | 1 | $CO_2tBu$ | 3-F-Phenyl |
| 1052 | 2 | $CO_2tBu$ | 3-F-Phenyl |
| 1053 | 3 | $CO_2tBu$ | 3-F-Phenyl |
| 1054 | 4 | $CO_2tBu$ | 3-F-Phenyl |
| 1055 | 1 | CONHMe | 3-F-Phenyl |
| 1056 | 2 | CONHMe | 3-F-Phenyl |
| 1057 | 3 | CONHMe | 3-F-Phenyl |
| 1058 | 4 | CONHMe | 3-F-Phenyl |
| 1059 | 1 | $SO_2Me$ | 3-F-Phenyl |
| 1060 | 2 | $SO_2Me$ | 3-F-Phenyl |
| 1061 | 3 | $SO_2Me$ | 3-F-Phenyl |
| 1062 | 4 | $SO_2Me$ | 3-F-Phenyl |
| 1063 | 1 | $SO_2NH_2$ | 3-F-Phenyl |
| 1064 | 2 | $SO_2NH_2$ | 3-F-Phenyl |

TABLE 17-continued

| Entry | n | $R^7$ | $R^3$ |
|---|---|---|---|
| 1065 | 3 | $SO_2NH_2$ | 3-F-Phenyl |
| 1066 | 4 | $SO_2NH_2$ | 3-F-Phenyl |
| 1067 | 1 | H | 2-Cl-Phenyl |
| 1068 | 2 | H | 2-Cl-Phenyl |
| 1069 | 3 | H | 2-Cl-Phenyl |
| 1070 | 4 | H | 2-Cl-Phenyl |
| 1071 | 1 | Me | 2-Cl-Phenyl |
| 1072 | 2 | Me | 2-Cl-Phenyl |
| 1073 | 3 | Me | 2-Cl-Phenyl |
| 1074 | 4 | Me | 2-Cl-Phenyl |
| 1075 | 1 | $CH_2Ph$ | 2-Cl-Phenyl |
| 1076 | 2 | $CH_2Ph$ | 2-Cl-Phenyl |
| 1077 | 3 | $CH_2Ph$ | 2-Cl-Phenyl |
| 1078 | 4 | $CH_2Ph$ | 2-Cl-Phenyl |
| 1079 | 1 | COMe | 2-Cl-Phenyl |
| 1080 | 2 | COMe | 2-Cl-Phenyl |
| 1081 | 3 | COMe | 2-Cl-Phenyl |
| 1082 | 4 | COMe | 2-Cl-Phenyl |
| 1083 | 1 | $CO_2Me$ | 2-Cl-Phenyl |
| 1084 | 2 | $CO_2Me$ | 2-Cl-Phenyl |
| 1085 | 3 | $CO_2Me$ | 2-Cl-Phenyl |
| 1086 | 4 | $CO_2Me$ | 2-Cl-Phenyl |
| 1087 | 1 | $CO_2tBu$ | 2-Cl-Phenyl |
| 1088 | 2 | $CO_2tBu$ | 2-Cl-Phenyl |
| 1089 | 3 | $CO_2tBu$ | 2-Cl-Phenyl |
| 1090 | 4 | $CO_2tBu$ | 2-Cl-Phenyl |
| 1091 | 1 | CONHMe | 2-Cl-Phenyl |
| 1092 | 2 | CONHMe | 2-Cl-Phenyl |
| 1093 | 3 | CONHMe | 2-Cl-Phenyl |
| 1094 | 4 | CONHMe | 2-Cl-Phenyl |
| 1095 | 1 | $SO_2Me$ | 2-Cl-Phenyl |
| 1096 | 2 | $SO_2Me$ | 2-Cl-Phenyl |
| 1097 | 3 | $SO_2Me$ | 2-Cl-Phenyl |
| 1098 | 4 | $SO_2Me$ | 2-Cl-Phenyl |
| 1099 | 1 | $SO_2NH_2$ | 2-Cl-Phenyl |
| 1100 | 2 | $SO_2NH_2$ | 2-Cl-Phenyl |
| 1101 | 3 | $SO_2NH_2$ | 2-Cl-Phenyl |
| 1102 | 4 | $SO_2NH_2$ | 2-Cl-Phenyl |
| 1103 | 1 | H | 4-Cl-Phenyl |
| 1104 | 2 | H | 4-Cl-Phenyl |
| 1105 | 3 | H | 4-Cl-Phenyl |
| 1106 | 4 | H | 4-Cl-Phenyl |
| 1107 | 1 | Me | 4-Cl-Phenyl |
| 1108 | 2 | Me | 4-Cl-Phenyl |
| 1109 | 3 | Me | 4-Cl-Phenyl |
| 1110 | 4 | Me | 4-Cl-Phenyl |
| 1111 | 1 | $CH_2Ph$ | 4-Cl-Phenyl |
| 1112 | 2 | $CH_2Ph$ | 4-Cl-Phenyl |
| 1113 | 3 | $CH_2Ph$ | 4-Cl-Phenyl |
| 1114 | 4 | $CH_2Ph$ | 4-Cl-Phenyl |
| 1115 | 1 | COMe | 4-Cl-Phenyl |
| 1116 | 2 | COMe | 4-Cl-Phenyl |
| 1117 | 3 | COMe | 4-Cl-Phenyl |
| 1118 | 4 | COMe | 4-Cl-Phenyl |
| 1119 | 1 | $CO_2Me$ | 4-Cl-Phenyl |
| 1120 | 2 | $CO_2Me$ | 4-Cl-Phenyl |
| 1121 | 3 | $CO_2Me$ | 4-Cl-Phenyl |
| 1122 | 4 | $CO_2Me$ | 4-Cl-Phenyl |
| 1123 | 1 | $CO_2tBu$ | 4-Cl-Phenyl |
| 1124 | 2 | $CO_2tBu$ | 4-Cl-Phenyl |
| 1125 | 3 | $CO_2tBu$ | 4-Cl-Phenyl |
| 1126 | 4 | $CO_2tBu$ | 4-Cl-Phenyl |
| 1127 | 1 | CONHMe | 4-Cl-Phenyl |
| 1128 | 2 | CONHMe | 4-Cl-Phenyl |
| 1129 | 3 | CONHMe | 4-Cl-Phenyl |
| 1130 | 4 | CONHMe | 4-Cl-Phenyl |
| 1131 | 1 | $SO_2Me$ | 4-Cl-Phenyl |
| 1132 | 2 | $SO_2Me$ | 4-Cl-Phenyl |
| 1133 | 3 | $SO_2Me$ | 4-Cl-Phenyl |
| 1134 | 4 | $SO_2Me$ | 4-Cl-Phenyl |
| 1135 | 1 | $SO_2NH_2$ | 4-Cl-Phenyl |
| 1136 | 2 | $SO_2NH_2$ | 4-Cl-Phenyl |
| 1137 | 3 | $SO_2NH_2$ | 4-Cl-Phenyl |
| 1138 | 4 | $SO_2NH_2$ | 4-Cl-Phenyl |
| 1139 | 1 | H | 3-Br-Phenyl |
| 1140 | 2 | H | 3-Br-Phenyl |
| 1141 | 3 | H | 3-Br-Phenyl |
| 1142 | 4 | H | 3-Br-Phenyl |

TABLE 17-continued

| Entry | n | $R^7$ | $R^3$ |
|---|---|---|---|
| 1143 | 1 | Me | 3-Br-Phenyl |
| 1144 | 2 | Me | 3-Br-Phenyl |
| 1145 | 3 | Me | 3-Br-Phenyl |
| 1146 | 4 | Me | 3-Br-Phenyl |
| 1147 | 1 | $CH_2Ph$ | 3-Br-Phenyl |
| 1148 | 2 | $CH_2Ph$ | 3-Br-Phenyl |
| 1149 | 3 | $CH_2Ph$ | 3-Br-Phenyl |
| 1150 | 4 | $CH_2Ph$ | 3-Br-Phenyl |
| 1151 | 1 | COMe | 3-Br-Phenyl |
| 1152 | 2 | COMe | 3-Br-Phenyl |
| 1153 | 3 | COMe | 3-Br-Phenyl |
| 1154 | 4 | COMe | 3-Br-Phenyl |
| 1155 | 1 | $CO_2Me$ | 3-Br-Phenyl |
| 1156 | 2 | $CO_2Me$ | 3-Br-Phenyl |
| 1157 | 3 | $CO_2Me$ | 3-Br-Phenyl |
| 1158 | 4 | $CO_2Me$ | 3-Br-Phenyl |
| 1159 | 1 | $CO_2tBu$ | 3-Br-Phenyl |
| 1160 | 2 | $CO_2tBu$ | 3-Br-Phenyl |
| 1161 | 3 | $CO_2tBu$ | 3-Br-Phenyl |
| 1162 | 4 | $CO_2tBu$ | 3-Br-Phenyl |
| 1163 | 1 | CONHMe | 3-Br-Phenyl |
| 1164 | 2 | CONHMe | 3-Br-Phenyl |
| 1165 | 3 | CONHMe | 3-Br-Phenyl |
| 1166 | 4 | CONHMe | 3-Br-Phenyl |
| 1167 | 1 | $SO_2Me$ | 3-Br-Phenyl |
| 1168 | 2 | $SO_2Me$ | 3-Br-Phenyl |
| 1169 | 3 | $SO_2Me$ | 3-Br-Phenyl |
| 1170 | 4 | $SO_2Me$ | 3-Br-Phenyl |
| 1171 | 1 | $SO_2NH_2$ | 3-Br-Phenyl |
| 1172 | 2 | $SO_2NH_2$ | 3-Br-Phenyl |
| 1173 | 3 | $SO_2NH_2$ | 3-Br-Phenyl |
| 1174 | 4 | $SO_2NH_2$ | 3-Br-Phenyl |
| 1175 | 1 | H | 2-$CF_3$-Phenyl |
| 1176 | 2 | H | 2-$CF_3$-Phenyl |
| 1177 | 3 | H | 2-$CF_3$-Phenyl |
| 1178 | 4 | H | 2-$CF_3$-Phenyl |
| 1179 | 1 | Me | 2-$CF_3$-Phenyl |
| 1180 | 2 | Me | 2-$CF_3$-Phenyl |
| 1181 | 3 | Me | 2-$CF_3$-Phenyl |
| 1182 | 4 | Me | 2-$CF_3$-Phenyl |
| 1183 | 1 | $CH_2Ph$ | 2-$CF_3$-Phenyl |
| 1184 | 2 | $CH_2Ph$ | 2-$CF_3$-Phenyl |
| 1185 | 3 | $CH_2Ph$ | 2-$CF_3$-Phenyl |
| 1186 | 4 | $CH_2Ph$ | 2-$CF_3$-Phenyl |
| 1187 | 1 | COMe | 2-$CF_3$-Phenyl |
| 1188 | 2 | COMe | 2-$CF_3$-Phenyl |
| 1189 | 3 | COMe | 2-$CF_3$-Phenyl |
| 1190 | 4 | COMe | 2-$CF_3$-Phenyl |
| 1191 | 1 | $CO_2Me$ | 2-$CF_3$-Phenyl |
| 1192 | 2 | $CO_2Me$ | 2-$CF_3$-Phenyl |
| 1193 | 3 | $CO_2Me$ | 2-$CF_3$-Phenyl |
| 1194 | 4 | $CO_2Me$ | 2-$CF_3$-Phenyl |
| 1195 | 1 | $CO_2tBu$ | 2-$CF_3$-Phenyl |
| 1196 | 2 | $CO_2tBu$ | 2-$CF_3$-Phenyl |
| 1197 | 3 | $CO_2tBu$ | 2-$CF_3$-Phenyl |
| 1198 | 4 | $CO_2tBu$ | 2-$CF_3$-Phenyl |
| 1199 | 1 | CONHMe | 2-$CF_3$-Phenyl |
| 1200 | 2 | CONHMe | 2-$CF_3$-Phenyl |
| 1201 | 3 | CONHMe | 2-$CF_3$-Phenyl |
| 1202 | 4 | CONHMe | 2-$CF_3$-Phenyl |
| 1203 | 1 | $SO_2Me$ | 2-$CF_3$-Phenyl |
| 1204 | 2 | $SO_2Me$ | 2-$CF_3$-Phenyl |
| 1205 | 3 | $SO_2Me$ | 2-$CF_3$-Phenyl |
| 1206 | 4 | $SO_2Me$ | 2-$CF_3$-Phenyl |
| 1207 | 1 | $SO_2NH_2$ | 2-$CF_3$-Phenyl |
| 1208 | 2 | $SO_2NH_2$ | 2-$CF_3$-Phenyl |
| 1209 | 3 | $SO_2NH_2$ | 2-$CF_3$-Phenyl |
| 1210 | 4 | $SO_2NH_2$ | 2-$CF_3$-Phenyl |
| 1211 | 1 | H | 4-$CF_3$-Phenyl |
| 1212 | 2 | H | 4-$CF_3$-Phenyl |
| 1213 | 3 | H | 4-$CF_3$-Phenyl |
| 1214 | 4 | H | 4-$CF_3$-Phenyl |
| 1215 | 1 | Me | 4-$CF_3$-Phenyl |
| 1216 | 2 | Me | 4-$CF_3$-Phenyl |
| 1217 | 3 | Me | 4-$CF_3$-Phenyl |
| 1218 | 4 | Me | 4-$CF_3$-Phenyl |
| 1219 | 1 | $CH_2Ph$ | 4-$CF_3$-Phenyl |
| 1220 | 2 | $CH_2Ph$ | 4-$CF_3$-Phenyl |

TABLE 17-continued

| Entry | n | $R^7$ | $R^3$ |
|---|---|---|---|
| 1221 | 3 | $CH_2Ph$ | 4-$CF_3$-Phenyl |
| 1222 | 4 | $CH_2Ph$ | 4-$CF_3$-Phenyl |
| 1223 | 1 | COMe | 4-$CF_3$-Phenyl |
| 1224 | 2 | COMe | 4-$CF_3$-Phenyl |
| 1225 | 3 | COMe | 4-$CF_3$-Phenyl |
| 1226 | 4 | COMe | 4-$CF_3$-Phenyl |
| 1227 | 1 | $CO_2Me$ | 4-$CF_3$-Phenyl |
| 1228 | 2 | $CO_2Me$ | 4-$CF_3$-Phenyl |
| 1229 | 3 | $CO_2Me$ | 4-$CF_3$-Phenyl |
| 1230 | 4 | $CO_2Me$ | 4-$CF_3$-Phenyl |
| 1231 | 1 | $CO_2tBu$ | 4-$CF_3$-Phenyl |
| 1232 | 2 | $CO_2tBu$ | 4-$CF_3$-Phenyl |
| 1233 | 3 | $CO_2tBu$ | 4-$CF_3$-Phenyl |
| 1234 | 4 | $CO_2tBu$ | 4-$CF_3$-Phenyl |
| 1235 | 1 | CONHMe | 4-$CF_3$-Phenyl |
| 1236 | 2 | CONHMe | 4-$CF_3$-Phenyl |
| 1237 | 3 | CONHMe | 4-$CF_3$-Phenyl |
| 1238 | 4 | CONHMe | 4-$CF_3$-Phenyl |
| 1239 | 1 | $SO_2Me$ | 4-$CF_3$-Phenyl |
| 1240 | 2 | $SO_2Me$ | 4-$CF_3$-Phenyl |
| 1241 | 3 | $SO_2Me$ | 4-$CF_3$-Phenyl |
| 1242 | 4 | $SO_2Me$ | 4-$CF_3$-Phenyl |
| 1243 | 1 | $SO_2NH_2$ | 4-$CF_3$-Phenyl |
| 1244 | 2 | $SO_2NH_2$ | 4-$CF_3$-Phenyl |
| 1245 | 3 | $SO_2NH_2$ | 4-$CF_3$-Phenyl |
| 1246 | 4 | $SO_2NH_2$ | 4-$CF_3$-Phenyl |
| 1247 | 1 | H | 3-iPr-Phenyl |
| 1248 | 2 | H | 3-iPr-Phenyl |
| 1249 | 3 | H | 3-iPr-Phenyl |
| 1250 | 4 | H | 3-iPr-Phenyl |
| 1251 | 1 | Me | 3-iPr-Phenyl |
| 1252 | 2 | Me | 3-iPr-Phenyl |
| 1253 | 3 | Me | 3-iPr-Phenyl |
| 1254 | 4 | Me | 3-iPr-Phenyl |
| 1255 | 1 | $CH_2Ph$ | 3-iPr-Phenyl |
| 1256 | 2 | $CH_2Ph$ | 3-iPr-Phenyl |
| 1257 | 3 | $CH_2Ph$ | 3-iPr-Phenyl |
| 1258 | 4 | $CH_2Ph$ | 3-iPr-Phenyl |
| 1259 | 1 | COMe | 3-iPr-Phenyl |
| 1260 | 2 | COMe | 3-iPr-Phenyl |
| 1261 | 3 | COMe | 3-iPr-Phenyl |
| 1262 | 4 | COMe | 3-iPr-Phenyl |
| 1263 | 1 | $CO_2Me$ | 3-iPr-Phenyl |
| 1264 | 2 | $CO_2Me$ | 3-iPr-Phenyl |
| 1265 | 3 | $CO_2Me$ | 3-iPr-Phenyl |
| 1266 | 4 | $CO_2Me$ | 3-iPr-Phenyl |
| 1267 | 1 | $CO_2tBu$ | 3-iPr-Phenyl |
| 1268 | 2 | $CO_2tBu$ | 3-iPr-Phenyl |
| 1269 | 3 | $CO_2tBu$ | 3-iPr-Phenyl |
| 1270 | 4 | $CO_2tBu$ | 3-iPr-Phenyl |
| 1271 | 1 | CONHMe | 3-iPr-Phenyl |
| 1272 | 2 | CONHMe | 3-iPr-Phenyl |
| 1273 | 3 | CONHMe | 3-iPr-Phenyl |
| 1274 | 4 | CONHMe | 3-iPr-Phenyl |
| 1275 | 1 | $SO_2Me$ | 3-iPr-Phenyl |
| 1276 | 2 | $SO_2Me$ | 3-iPr-Phenyl |
| 1277 | 3 | $SO_2Me$ | 3-iPr-Phenyl |
| 1278 | 4 | $SO_2Me$ | 3-iPr-Phenyl |
| 1279 | 1 | $SO_2NH_2$ | 3-iPr-Phenyl |
| 1280 | 2 | $SO_2NH_2$ | 3-iPr-Phenyl |
| 1281 | 3 | $SO_2NH_2$ | 3-iPr-Phenyl |
| 1282 | 4 | $SO_2NH_2$ | 3-iPr-Phenyl |
| 1283 | 1 | H | 4-$NH_2$-Phenyl |
| 1284 | 2 | H | 4-$NH_2$-Phenyl |
| 1285 | 3 | H | 4-$NH_2$-Phenyl |
| 1286 | 4 | H | 4-$NH_2$-Phenyl |
| 1287 | 1 | Me | 4-$NH_2$-Phenyl |
| 1288 | 2 | Me | 4-$NH_2$-Phenyl |
| 1289 | 3 | Me | 4-$NH_2$-Phenyl |
| 1290 | 4 | Me | 4-$NH_2$-Phenyl |
| 1291 | 1 | $CH_2Ph$ | 4-$NH_2$-Phenyl |
| 1292 | 2 | $CH_2Ph$ | 4-$NH_2$-Phenyl |
| 1293 | 3 | $CH_2Ph$ | 4-$NH_2$-Phenyl |
| 1294 | 4 | $CH_2Ph$ | 4-$NH_2$-Phenyl |
| 1295 | 1 | COMe | 4-$NH_2$-Phenyl |
| 1296 | 2 | COMe | 4-$NH_2$-Phenyl |
| 1297 | 3 | COMe | 4-$NH_2$-Phenyl |
| 1298 | 4 | COMe | 4-$NH_2$-Phenyl |

TABLE 17-continued

| Entry | n | $R^7$ | $R^3$ |
|---|---|---|---|
| 1299 | 1 | $CO_2Me$ | 4-$NH_2$-Phenyl |
| 1300 | 2 | $CO_2Me$ | 4-$NH_2$-Phenyl |
| 1301 | 3 | $CO_2Me$ | 4-$NH_2$-Phenyl |
| 1302 | 4 | $CO_2Me$ | 4-$NH_2$-Phenyl |
| 1303 | 1 | $CO_2tBu$ | 4-$NH_2$-Phenyl |
| 1304 | 2 | $CO_2tBu$ | 4-$NH_2$-Phenyl |
| 1305 | 3 | $CO_2tBu$ | 4-$NH_2$-Phenyl |
| 1306 | 4 | $CO_2tBu$ | 4-$NH_2$-Phenyl |
| 1307 | 1 | CONHMe | 4-$NH_2$-Phenyl |
| 1308 | 2 | CONHMe | 4-$NH_2$-Phenyl |
| 1309 | 3 | CONHMe | 4-$NH_2$-Phenyl |
| 1310 | 4 | CONHMe | 4-$NH_2$-Phenyl |
| 1311 | 1 | $SO_2Me$ | 4-$NH_2$-Phenyl |
| 1312 | 2 | $SO_2Me$ | 4-$NH_2$-Phenyl |
| 1313 | 3 | $SO_2Me$ | 4-$NH_2$-Phenyl |
| 1314 | 4 | $SO_2Me$ | 4-$NH_2$-Phenyl |
| 1315 | 1 | $SO_2NH_2$ | 4-$NH_2$-Phenyl |
| 1316 | 2 | $SO_2NH_2$ | 4-$NH_2$-Phenyl |
| 1317 | 3 | $SO_2NH_2$ | 4-$NH_2$-Phenyl |
| 1318 | 4 | $SO_2NH_2$ | 4-$NH_2$-Phenyl |
| 1319 | 1 | H | 2-$NH_2$-Phenyl |
| 1320 | 2 | H | 2-$NH_2$-Phenyl |
| 1321 | 3 | H | 2-$NH_2$-Phenyl |
| 1322 | 4 | H | 2-$NH_2$-Phenyl |
| 1323 | 1 | Me | 2-$NH_2$-Phenyl |
| 1324 | 2 | Me | 2-$NH_2$-Phenyl |
| 1325 | 3 | Me | 2-$NH_2$-Phenyl |
| 1326 | 4 | Me | 2-$NH_2$-Phenyl |
| 1327 | 1 | $CH_2Ph$ | 2-$NH_2$-Phenyl |
| 1328 | 2 | $CH_2Ph$ | 2-$NH_2$-Phenyl |
| 1329 | 3 | $CH_2Ph$ | 2-$NH_2$-Phenyl |
| 1330 | 4 | $CH_2Ph$ | 2-$NH_2$-Phenyl |
| 1331 | 1 | COMe | 2-$NH_2$-Phenyl |
| 1332 | 2 | COMe | 2-$NH_2$-Phenyl |
| 1333 | 3 | COMe | 2-$NH_2$-Phenyl |
| 1334 | 4 | COMe | 2-$NH_2$-Phenyl |
| 1335 | 1 | $CO_2Me$ | 2-$NH_2$-Phenyl |
| 1336 | 2 | $CO_2Me$ | 2-$NH_2$-Phenyl |
| 1337 | 3 | $CO_2Me$ | 2-$NH_2$-Phenyl |
| 1338 | 4 | $CO_2Me$ | 2-$NH_2$-Phenyl |
| 1339 | 1 | $CO_2tBu$ | 2-$NH_2$-Phenyl |
| 1340 | 2 | $CO_2tBu$ | 2-$NH_2$-Phenyl |
| 1341 | 3 | $CO_2tBu$ | 2-$NH_2$-Phenyl |
| 1342 | 4 | $CO_2tBu$ | 2-$NH_2$-Phenyl |
| 1343 | 1 | CONHMe | 2-$NH_2$-Phenyl |
| 1344 | 2 | CONHMe | 2-$NH_2$-Phenyl |
| 1345 | 3 | CONHMe | 2-$NH_2$-Phenyl |
| 1346 | 4 | CONHMe | 2-$NH_2$-Phenyl |
| 1347 | 1 | $SO_2Me$ | 2-$NH_2$-Phenyl |
| 1348 | 2 | $SO_2Me$ | 2-$NH_2$-Phenyl |
| 1349 | 3 | $SO_2Me$ | 2-$NH_2$-Phenyl |
| 1350 | 4 | $SO_2Me$ | 2-$NH_2$-Phenyl |
| 1351 | 1 | $SO_2NH_2$ | 2-$NH_2$-Phenyl |
| 1352 | 2 | $SO_2NH_2$ | 2-$NH_2$-Phenyl |
| 1353 | 3 | $SO_2NH_2$ | 2-$NH_2$-Phenyl |
| 1354 | 4 | $SO_2NH_2$ | 2-$NH_2$-Phenyl |
| 1355 | 1 | H | 2,6-di-Me-Phenyl |
| 1356 | 2 | H | 2,6-di-Me-Phenyl |
| 1357 | 3 | H | 2,6-di-Me-Phenyl |
| 1358 | 4 | H | 2,6-di-Me-Phenyl |
| 1359 | 1 | Me | 2,6-di-Me-Phenyl |
| 1360 | 2 | Me | 2,6-di-Me-Phenyl |
| 1361 | 3 | Me | 2,6-di-Me-Phenyl |
| 1362 | 4 | Me | 2,6-di-Me-Phenyl |
| 1363 | 1 | $CH_2Ph$ | 2,6-di-Me-Phenyl |
| 1364 | 2 | $CH_2Ph$ | 2,6-di-Me-Phenyl |
| 1365 | 3 | $CH_2Ph$ | 2,6-di-Me-Phenyl |
| 1366 | 4 | $CH_2Ph$ | 2,6-di-Me-Phenyl |
| 1367 | 1 | COMe | 2,6-di-Me-Phenyl |
| 1368 | 2 | COMe | 2,6-di-Me-Phenyl |
| 1369 | 3 | COMe | 2,6-di-Me-Phenyl |
| 1370 | 4 | COMe | 2,6-di-Me-Phenyl |
| 1371 | 1 | $CO_2Me$ | 2,6-di-Me-Phenyl |
| 1372 | 2 | $CO_2Me$ | 2,6-di-Me-Phenyl |
| 1373 | 3 | $CO_2Me$ | 2,6-di-Me-Phenyl |
| 1374 | 4 | $CO_2Me$ | 2,6-di-Me-Phenyl |
| 1375 | 1 | $CO_2tBu$ | 2,6-di-Me-Phenyl |
| 1376 | 2 | $CO_2tBu$ | 2,6-di-Me-Phenyl |

TABLE 17-continued

| Entry | n | $R^7$ | $R^3$ |
|---|---|---|---|
| 1377 | 3 | $CO_2tBu$ | 2,6-di-Me-Phenyl |
| 1378 | 4 | $CO_2tBu$ | 2,6-di-Me-Phenyl |
| 1379 | 1 | CONHMe | 2,6-di-Me-Phenyl |
| 1380 | 2 | CONHMe | 2,6-di-Me-Phenyl |
| 1381 | 3 | CONHMe | 2,6-di-Me-Phenyl |
| 1382 | 4 | CONHMe | 2,6-di-Me-Phenyl |
| 1383 | 1 | $SO_2Me$ | 2,6-di-Me-Phenyl |
| 1384 | 2 | $SO_2Me$ | 2,6-di-Me-Phenyl |
| 1385 | 3 | $SO_2Me$ | 2,6-di-Me-Phenyl |
| 1386 | 4 | $SO_2Me$ | 2,6-di-Me-Phenyl |
| 1387 | 1 | $SO_2NH_2$ | 2,6-di-Me-Phenyl |
| 1388 | 2 | $SO_2NH_2$ | 2,6-di-Me-Phenyl |
| 1389 | 3 | $SO_2NH_2$ | 2,6-di-Me-Phenyl |
| 1390 | 4 | $SO_2NH_2$ | 2,6-di-Me-Phenyl |
| 1391 | 1 | H | 2-Ph-Phenyl |
| 1392 | 2 | H | 2-Ph-Phenyl |
| 1393 | 3 | H | 2-Ph-Phenyl |
| 1394 | 4 | H | 2-Ph-Phenyl |
| 1395 | 1 | Me | 2-Ph-Phenyl |
| 1396 | 2 | Me | 2-Ph-Phenyl |
| 1397 | 3 | Me | 2-Ph-Phenyl |
| 1398 | 4 | Me | 2-Ph-Phenyl |
| 1399 | 1 | $CH_2Ph$ | 2-Ph-Phenyl |
| 1400 | 2 | $CH_2Ph$ | 2-Ph-Phenyl |
| 1401 | 3 | $CH_2Ph$ | 2-Ph-Phenyl |
| 1402 | 4 | $CH_2Ph$ | 2-Ph-Phenyl |
| 1403 | 1 | COMe | 2-Ph-Phenyl |
| 1404 | 2 | COMe | 2-Ph-Phenyl |
| 1405 | 3 | COMe | 2-Ph-Phenyl |
| 1406 | 4 | COMe | 2-Ph-Phenyl |
| 1407 | 1 | $CO_2Me$ | 2-Ph-Phenyl |
| 1408 | 2 | $CO_2Me$ | 2-Ph-Phenyl |
| 1409 | 3 | $CO_2Me$ | 2-Ph-Phenyl |
| 1410 | 4 | $CO_2Me$ | 2-Ph-Phenyl |
| 1411 | 1 | $CO_2tBu$ | 2-Ph-Phenyl |
| 1412 | 2 | $CO_2tBu$ | 2-Ph-Phenyl |
| 1413 | 3 | $CO_2tBu$ | 2-Ph-Phenyl |
| 1414 | 4 | $CO_2tBu$ | 2-Ph-Phenyl |
| 1415 | 1 | CONHMe | 2-Ph-Phenyl |
| 1416 | 2 | CONHMe | 2-Ph-Phenyl |
| 1417 | 3 | CONHMe | 2-Ph-Phenyl |
| 1418 | 4 | CONHMe | 2-Ph-Phenyl |
| 1419 | 1 | $SO_2Me$ | 2-Ph-Phenyl |
| 1420 | 2 | $SO_2Me$ | 2-Ph-Phenyl |
| 1421 | 3 | $SO_2Me$ | 2-Ph-Phenyl |
| 1422 | 4 | $SO_2Me$ | 2-Ph-Phenyl |
| 1423 | 1 | $SO_2NH_2$ | 2-Ph-Phenyl |
| 1424 | 2 | $SO_2NH_2$ | 2-Ph-Phenyl |
| 1425 | 3 | $SO_2NH_2$ | 2-Ph-Phenyl |
| 1426 | 4 | $SO_2NH_2$ | 2-Ph-Phenyl |
| 1427 | 1 | H | 4-Ph-Phenyl |
| 1428 | 2 | H | 4-Ph-Phenyl |
| 1429 | 3 | H | 4-Ph-Phenyl |
| 1430 | 4 | H | 4-Ph-Phenyl |
| 1431 | 1 | Me | 4-Ph-Phenyl |
| 1432 | 2 | Me | 4-Ph-Phenyl |
| 1433 | 3 | Me | 4-Ph-Phenyl |
| 1434 | 4 | Me | 4-Ph-Phenyl |
| 1435 | 1 | $CH_2Ph$ | 4-Ph-Phenyl |
| 1436 | 2 | $CH_2Ph$ | 4-Ph-Phenyl |
| 1437 | 3 | $CH_2Ph$ | 4-Ph-Phenyl |
| 1438 | 4 | $CH_2Ph$ | 4-Ph-Phenyl |
| 1439 | 1 | COMe | 4-Ph-Phenyl |
| 1440 | 2 | COMe | 4-Ph-Phenyl |
| 1441 | 3 | COMe | 4-Ph-Phenyl |
| 1442 | 4 | COMe | 4-Ph-Phenyl |
| 1443 | 1 | $CO_2Me$ | 4-Ph-Phenyl |
| 1444 | 2 | $CO_2Me$ | 4-Ph-Phenyl |
| 1445 | 3 | $CO_2Me$ | 4-Ph-Phenyl |
| 1446 | 4 | $CO_2Me$ | 4-Ph-Phenyl |
| 1447 | 1 | $CO_2tBu$ | 4-Ph-Phenyl |
| 1448 | 2 | $CO_2tBu$ | 4-Ph-Phenyl |
| 1449 | 3 | $CO_2tBu$ | 4-Ph-Phenyl |
| 1450 | 4 | $CO_2tBu$ | 4-Ph-Phenyl |
| 1451 | 1 | CONHMe | 4-Ph-Phenyl |
| 1452 | 2 | CONHMe | 4-Ph-Phenyl |
| 1453 | 3 | CONHMe | 4-Ph-Phenyl |
| 1454 | 4 | CONHMe | 4-Ph-Phenyl |

TABLE 17-continued

| Entry | n | $R^7$ | $R^3$ |
|---|---|---|---|
| 1455 | 1 | $SO_2Me$ | 4-Ph-Phenyl |
| 1456 | 2 | $SO_2Me$ | 4-Ph-Phenyl |
| 1457 | 3 | $SO_2Me$ | 4-Ph-Phenyl |
| 1458 | 4 | $SO_2Me$ | 4-Ph-Phenyl |
| 1459 | 1 | $SO_2NH_2$ | 4-Ph-Phenyl |
| 1460 | 2 | $SO_2NH_2$ | 4-Ph-Phenyl |
| 1461 | 3 | $SO_2NH_2$ | 4-Ph-Phenyl |
| 1462 | 4 | $SO_2NH_2$ | 4-Ph-Phenyl |
| 1463 | 1 | H | 3-morpholino-phenyl |
| 1464 | 2 | H | 3-morpholino-phenyl |
| 1465 | 3 | H | 3-morpholino-phenyl |
| 1466 | 4 | H | 3-morpholino-phenyl |
| 1467 | 1 | Me | 3-morpholino-phenyl |
| 1468 | 2 | Me | 3-morpholino-phenyl |
| 1469 | 3 | Me | 3-morpholino-phenyl |
| 1470 | 4 | Me | 3-morpholino-phenyl |
| 1471 | 1 | $CH_2Ph$ | 3-morpholino-phenyl |
| 1472 | 2 | $CH_2Ph$ | 3-morpholino-phenyl |
| 1473 | 3 | $CH_2Ph$ | 3-morpholino-phenyl |
| 1474 | 4 | $CH_2Ph$ | 3-morpholino-phenyl |
| 1475 | 1 | COMe | 3-morpholino-phenyl |
| 1476 | 2 | COMe | 3-morpholino-phenyl |
| 1477 | 3 | COMe | 3-morpholino-phenyl |
| 1478 | 4 | COMe | 3-morpholino-phenyl |
| 1479 | 1 | $CO_2Me$ | 3-morpholino-phenyl |
| 1480 | 2 | $CO_2Me$ | 3-morpholino-phenyl |
| 1481 | 3 | $CO_2Me$ | 3-morpholino-phenyl |
| 1482 | 4 | $CO_2Me$ | 3-morpholino-phenyl |
| 1483 | 1 | $CO_2tBu$ | 3-morpholino-phenyl |
| 1484 | 2 | $CO_2tBu$ | 3-morpholino-phenyl |
| 1485 | 3 | $CO_2tBu$ | 3-morpholino-phenyl |
| 1486 | 4 | $CO_2tBu$ | 3-morpholino-phenyl |
| 1487 | 1 | CONHMe | 3-morpholino-phenyl |
| 1488 | 2 | CONHMe | 3-morpholino-phenyl |
| 1489 | 3 | CONHMe | 3-morpholino-phenyl |
| 1490 | 4 | CONHMe | 3-morpholino-phenyl |
| 1491 | 1 | $SO_2Me$ | 3-morpholino-phenyl |
| 1492 | 2 | $SO_2Me$ | 3-morpholino-phenyl |
| 1493 | 3 | $SO_2Me$ | 3-morpholino-phenyl |
| 1494 | 4 | $SO_2Me$ | 3-morpholino-phenyl |
| 1495 | 1 | $SO_2NH_2$ | 3-morpholino-phenyl |
| 1496 | 2 | $SO_2NH_2$ | 3-morpholino-phenyl |
| 1497 | 3 | $SO_2NH_2$ | 3-morpholino-phenyl |
| 1498 | 4 | $SO_2NH_2$ | 3-morpholino-phenyl |
| 1499 | 1 | Me | 4-morpholino-phenyl |
| 1500 | 2 | Me | 4-morpholino-phenyl |
| 1501 | 3 | Me | 4-morpholino-phenyl |
| 1502 | 4 | Me | 4-morpholino-phenyl |
| 103 | 1 | COMe | 4-morpholino-phenyl |
| 1504 | 2 | COMe | 4-morpholino-phenyl |
| 1505 | 3 | COMe | 4-morpholino-phenyl |
| 1506 | 4 | COMe | 4-morpholino-phenyl |
| 1507 | 1 | $CO_2tBu$ | 4-morpholino-phenyl |
| 1508 | 2 | $CO_2tBu$ | 4-morpholino-phenyl |
| 1509 | 3 | $CO_2tBu$ | 4-morpholino-phenyl |
| 1510 | 4 | $CO_2tBu$ | 4-morpholino-phenyl |
| 1511 | 1 | $SO_2Me$ | 4-morpholino-phenyl |
| 1512 | 2 | $SO_2Me$ | 4-morpholino-phenyl |
| 1513 | 3 | $SO_2Me$ | 4-morpholino-phenyl |
| 1514 | 4 | $SO_2Me$ | 4-morpholino-phenyl |
| 1516 | 1 | H | naphthylen-2-yl |
| 1517 | 2 | H | naphthylen-2-yl |
| 1518 | 3 | H | naphthylen-2-yl |
| 1519 | 4 | H | naphthylen-2-yl |
| 1520 | 1 | Me | naphthylen-2-yl |
| 1521 | 2 | Me | naphthylen-2-yl |
| 1522 | 3 | Me | naphthylen-2-yl |
| 1523 | 4 | Me | naphthylen-2-yl |
| 1524 | 1 | $CH_2Ph$ | naphthylen-2-yl |
| 1525 | 2 | $CH_2Ph$ | naphthylen-2-yl |
| 1526 | 3 | $CH_2Ph$ | naphthylen-2-yl |
| 1527 | 4 | $CH_2Ph$ | naphthylen-2-yl |
| 1528 | 1 | COMe | naphthylen-2-yl |
| 1529 | 2 | COMe | naphthylen-2-yl |
| 1530 | 3 | COMe | naphthylen-2-yl |
| 1531 | 4 | COMe | naphthylen-2-yl |
| 1532 | 1 | $CO_2Me$ | naphthylen-2-yl |
| 1533 | 2 | $CO_2Me$ | naphthylen-2-yl |

TABLE 17-continued

| Entry | n | $R^7$ | $R^3$ |
|---|---|---|---|
| 1534 | 3 | $CO_2Me$ | naphthylen-2-yl |
| 1535 | 4 | $CO_2Me$ | naphthylen-2-yl |
| 1536 | 1 | $CO_2tBu$ | naphthylen-2-yl |
| 1537 | 2 | $CO_2tBu$ | naphthylen-2-yl |
| 1538 | 3 | $CO_2tBu$ | naphthylen-2-yl |
| 1539 | 4 | $CO_2tBu$ | naphthylen-2-yl |
| 1540 | 1 | CONHMe | naphthylen-2-yl |
| 1541 | 2 | CONHMe | naphthylen-2-yl |
| 1542 | 3 | CONHMe | naphthylen-2-yl |
| 1543 | 4 | CONHMe | naphthylen-2-yl |
| 1544 | 1 | $SO_2Me$ | naphthylen-2-yl |
| 1545 | 2 | $SO_2Me$ | naphthylen-2-yl |
| 1546 | 3 | $SO_2Me$ | naphthylen-2-yl |
| 1547 | 4 | $SO_2Me$ | naphthylen-2-yl |
| 1548 | 1 | $SO_2NH_2$ | naphthylen-2-yl |
| 1549 | 2 | $SO_2NH_2$ | naphthylen-2-yl |
| 1550 | 3 | $SO_2NH_2$ | naphthylen-2-yl |
| 1551 | 4 | $SO_2NH_2$ | naphthylen-2-yl |

Exemplary embodiments include compounds having the formula (XXIV)

(XXIV)

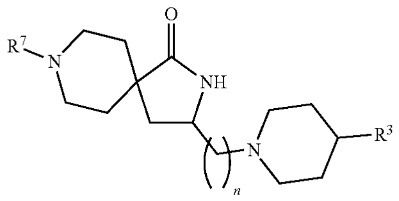

or a pharmaceutically acceptable salt form thereof defined herein below in Table 18. Table 18:

TABLE 18

| Entry | n | $R^7$ | $R^3$ |
|---|---|---|---|
| 1 | 1 | H | Phenyl |
| 2 | 2 | H | Phenyl |
| 3 | 3 | H | Phenyl |
| 4 | 4 | H | Phenyl |
| 5 | 1 | Me | Phenyl |
| 6 | 2 | Me | Phenyl |
| 7 | 3 | Me | Phenyl |
| 8 | 4 | Me | Phenyl |
| 9 | 1 | $CH_2Ph$ | Phenyl |
| 10 | 2 | $CH_2Ph$ | Phenyl |
| 11 | 3 | $CH_2Ph$ | Phenyl |
| 12 | 4 | $CH_2Ph$ | Phenyl |
| 13 | 1 | COMe | Phenyl |
| 14 | 2 | COMe | Phenyl |
| 15 | 3 | COMe | Phenyl |
| 16 | 4 | COMe | Phenyl |
| 17 | 1 | $CO_2Me$ | Phenyl |
| 18 | 2 | $CO_2Me$ | Phenyl |
| 19 | 3 | $CO_2Me$ | Phenyl |
| 20 | 4 | $CO_2Me$ | Phenyl |
| 21 | 1 | $CO_2tBu$ | Phenyl |
| 22 | 2 | $CO_2tBu$ | Phenyl |
| 23 | 3 | $CO_2tBu$ | Phenyl |
| 24 | 4 | $CO_2tBu$ | Phenyl |
| 25 | 1 | CONHMe | Phenyl |
| 26 | 2 | CONHMe | Phenyl |
| 27 | 3 | CONHMe | Phenyl |
| 28 | 4 | CONHMe | Phenyl |
| 29 | 1 | $SO_2Me$ | Phenyl |
| 30 | 2 | $SO_2Me$ | Phenyl |
| 31 | 3 | $SO_2Me$ | Phenyl |
| 32 | 4 | $SO_2Me$ | Phenyl |
| 33 | 1 | $SO_2NH_2$ | Phenyl |

TABLE 18-continued

| Entry | n | $R^7$ | $R^3$ |
|---|---|---|---|
| 34 | 2 | $SO_2NH_2$ | Phenyl |
| 35 | 3 | $SO_2NH_2$ | Phenyl |
| 36 | 4 | $SO_2NH_2$ | Phenyl |
| 37 | 1 | H | 3-OH-Phenyl |
| 38 | 2 | H | 3-OH-Phenyl |
| 39 | 3 | H | 3-OH-Phenyl |
| 40 | 4 | H | 3-OH-Phenyl |
| 41 | 1 | Me | 3-OH-Phenyl |
| 42 | 2 | Me | 3-OH-Phenyl |
| 43 | 3 | Me | 3-OH-Phenyl |
| 44 | 4 | Me | 3-OH-Phenyl |
| 45 | 1 | $CH_2Ph$ | 3-OH-Phenyl |
| 46 | 2 | $CH_2Ph$ | 3-OH-Phenyl |
| 47 | 3 | $CH_2Ph$ | 3-OH-Phenyl |
| 48 | 4 | $CH_2Ph$ | 3-OH-Phenyl |
| 49 | 1 | COMe | 3-OH-Phenyl |
| 50 | 2 | COMe | 3-OH-Phenyl |
| 51 | 3 | COMe | 3-OH-Phenyl |
| 52 | 4 | COMe | 3-OH-Phenyl |
| 53 | 1 | $CO_2Me$ | 3-OH-Phenyl |
| 54 | 2 | $CO_2Me$ | 3-OH-Phenyl |
| 55 | 3 | $CO_2Me$ | 3-OH-Phenyl |
| 56 | 4 | $CO_2Me$ | 3-OH-Phenyl |
| 57 | 1 | $CO_2tBu$ | 3-OH-Phenyl |
| 58 | 2 | $CO_2tBu$ | 3-OH-Phenyl |
| 59 | 3 | $CO_2tBu$ | 3-OH-Phenyl |
| 60 | 4 | $CO_2tBu$ | 3-OH-Phenyl |
| 61 | 1 | CONHMe | 3-OH-Phenyl |
| 62 | 2 | CONHMe | 3-OH-Phenyl |
| 63 | 3 | CONHMe | 3-OH-Phenyl |
| 64 | 4 | CONHMe | 3-OH-Phenyl |
| 65 | 1 | $SO_2Me$ | 3-OH-Phenyl |
| 66 | 2 | $SO_2Me$ | 3-OH-Phenyl |
| 67 | 3 | $SO_2Me$ | 3-OH-Phenyl |
| 68 | 4 | $SO_2Me$ | 3-OH-Phenyl |
| 69 | 1 | $SO_2NH_2$ | 3-OH-Phenyl |
| 70 | 2 | $SO_2NH_2$ | 3-OH-Phenyl |
| 71 | 3 | $SO_2NH_2$ | 3-OH-Phenyl |
| 72 | 4 | $SO_2NH_2$ | 3-OH-Phenyl |
| 73 | 1 | H | 4-$NO_2$-Phenyl |
| 74 | 2 | H | 4-$NO_2$-Phenyl |
| 75 | 3 | H | 4-$NO_2$-Phenyl |
| 76 | 4 | H | 4-$NO_2$-Phenyl |
| 77 | 1 | Me | 4-$NO_2$-Phenyl |
| 78 | 2 | Me | 4-$NO_2$-Phenyl |
| 79 | 3 | Me | 4-$NO_2$-Phenyl |
| 80 | 4 | Me | 4-$NO_2$-Phenyl |
| 81 | 1 | $CH_2Ph$ | 4-$NO_2$-Phenyl |
| 82 | 2 | $CH_2Ph$ | 4-$NO_2$-Phenyl |
| 83 | 3 | $CH_2Ph$ | 4-$NO_2$-Phenyl |
| 84 | 4 | $CH_2Ph$ | 4-$NO_2$-Phenyl |
| 85 | 1 | COMe | 4-$NO_2$-Phenyl |
| 86 | 2 | COMe | 4-$NO_2$-Phenyl |
| 87 | 3 | COMe | 4-$NO_2$-Phenyl |
| 88 | 4 | COMe | 4-$NO_2$-Phenyl |
| 89 | 1 | $CO_2Me$ | 4-$NO_2$-Phenyl |
| 90 | 2 | $CO_2Me$ | 4-$NO_2$-Phenyl |
| 91 | 3 | $CO_2Me$ | 4-$NO_2$-Phenyl |
| 92 | 4 | $CO_2Me$ | 4-$NO_2$-Phenyl |
| 93 | 1 | $CO_2tBu$ | 4-$NO_2$-Phenyl |
| 94 | 2 | $CO_2tBu$ | 4-$NO_2$-Phenyl |
| 95 | 3 | $CO_2tBu$ | 4-$NO_2$-Phenyl |
| 96 | 4 | $CO_2tBu$ | 4-$NO_2$-Phenyl |
| 97 | 1 | CONHMe | 4-$NO_2$-Phenyl |
| 98 | 2 | CONHMe | 4-$NO_2$-Phenyl |
| 99 | 3 | CONHMe | 4-$NO_2$-Phenyl |
| 100 | 4 | CONHMe | 4-$NO_2$-Phenyl |
| 101 | 1 | $SO_2Me$ | 4-$NO_2$-Phenyl |
| 102 | 2 | $SO_2Me$ | 4-$NO_2$-Phenyl |
| 103 | 3 | $SO_2Me$ | 4-$NO_2$-Phenyl |
| 104 | 4 | $SO_2Me$ | 4-$NO_2$-Phenyl |
| 105 | 1 | $SO_2NH_2$ | 4-$NO_2$-Phenyl |
| 106 | 2 | $SO_2NH_2$ | 4-$NO_2$-Phenyl |
| 107 | 3 | $SO_2NH_2$ | 4-$NO_2$-Phenyl |
| 108 | 4 | $SO_2NH_2$ | 4-$NO_2$-Phenyl |
| 109 | 1 | H | 3-OMe-Phenyl |
| 110 | 2 | H | 3-OMe-Phenyl |
| 111 | 3 | H | 3-OMe-Phenyl |

TABLE 18-continued

| Entry | n | $R^7$ | $R^3$ |
|---|---|---|---|
| 112 | 4 | H | 3-OMe-Phenyl |
| 113 | 1 | Me | 3-OMe-Phenyl |
| 114 | 2 | Me | 3-OMe-Phenyl |
| 115 | 3 | Me | 3-OMe-Phenyl |
| 116 | 4 | Me | 3-OMe-Phenyl |
| 117 | 1 | $CH_2Ph$ | 3-OMe-Phenyl |
| 118 | 2 | $CH_2Ph$ | 3-OMe-Phenyl |
| 119 | 3 | $CH_2Ph$ | 3-OMe-Phenyl |
| 120 | 4 | $CH_2Ph$ | 3-OMe-Phenyl |
| 121 | 1 | COMe | 3-OMe-Phenyl |
| 122 | 2 | COMe | 3-OMe-Phenyl |
| 123 | 3 | COMe | 3-OMe-Phenyl |
| 124 | 4 | COMe | 3-OMe-Phenyl |
| 125 | 1 | $CO_2Me$ | 3-OMe-Phenyl |
| 126 | 2 | $CO_2Me$ | 3-OMe-Phenyl |
| 127 | 3 | $CO_2Me$ | 3-OMe-Phenyl |
| 128 | 4 | $CO_2Me$ | 3-OMe-Phenyl |
| 129 | 1 | $CO_2tBu$ | 3-OMe-Phenyl |
| 130 | 2 | $CO_2tBu$ | 3-OMe-Phenyl |
| 131 | 3 | $CO_2tBu$ | 3-OMe-Phenyl |
| 132 | 4 | $CO_2tBu$ | 3-OMe-Phenyl |
| 133 | 1 | CONHMe | 3-OMe-Phenyl |
| 134 | 2 | CONHMe | 3-OMe-Phenyl |
| 135 | 3 | CONHMe | 3-OMe-Phenyl |
| 136 | 4 | CONHMe | 3-OMe-Phenyl |
| 137 | 1 | $SO_2Me$ | 3-OMe-Phenyl |
| 138 | 2 | $SO_2Me$ | 3-OMe-Phenyl |
| 139 | 3 | $SO_2Me$ | 3-OMe-Phenyl |
| 140 | 4 | $SO_2Me$ | 3-OMe-Phenyl |
| 141 | 1 | $SO_2NH_2$ | 3-OMe-Phenyl |
| 142 | 2 | $SO_2NH_2$ | 3-OMe-Phenyl |
| 143 | 3 | $SO_2NH_2$ | 3-OMe-Phenyl |
| 144 | 4 | $SO_2NH_2$ | 3-OMe-Phenyl |
| 145 | 1 | H | 4-CN-Phenyl |
| 146 | 2 | H | 4-CN-Phenyl |
| 147 | 3 | H | 4-CN-Phenyl |
| 148 | 4 | H | 4-CN-Phenyl |
| 149 | 1 | Me | 4-CN-Phenyl |
| 150 | 2 | Me | 4-CN-Phenyl |
| 151 | 3 | Me | 4-CN-Phenyl |
| 152 | 4 | Me | 4-CN-Phenyl |
| 153 | 1 | $CH_2Ph$ | 4-CN-Phenyl |
| 154 | 2 | $CH_2Ph$ | 4-CN-Phenyl |
| 155 | 3 | $CH_2Ph$ | 4-CN-Phenyl |
| 156 | 4 | $CH_2Ph$ | 4-CN-Phenyl |
| 157 | 1 | COMe | 4-CN-Phenyl |
| 158 | 2 | COMe | 4-CN-Phenyl |
| 159 | 3 | COMe | 4-CN-Phenyl |
| 160 | 4 | COMe | 4-CN-Phenyl |
| 161 | 1 | $CO_2Me$ | 4-CN-Phenyl |
| 162 | 2 | $CO_2Me$ | 4-CN-Phenyl |
| 163 | 3 | $CO_2Me$ | 4-CN-Phenyl |
| 164 | 4 | $CO_2Me$ | 4-CN-Phenyl |
| 165 | 1 | $CO_2tBu$ | 4-CN-Phenyl |
| 166 | 2 | $CO_2tBu$ | 4-CN-Phenyl |
| 167 | 3 | $CO_2tBu$ | 4-CN-Phenyl |
| 168 | 4 | $CO_2tBu$ | 4-CN-Phenyl |
| 169 | 1 | CONHMe | 4-CN-Phenyl |
| 170 | 2 | CONHMe | 4-CN-Phenyl |
| 171 | 3 | CONHMe | 4-CN-Phenyl |
| 172 | 4 | CONHMe | 4-CN-Phenyl |
| 173 | 1 | $SO_2Me$ | 4-CN-Phenyl |
| 174 | 2 | $SO_2Me$ | 4-CN-Phenyl |
| 175 | 3 | $SO_2Me$ | 4-CN-Phenyl |
| 176 | 4 | $SO_2Me$ | 4-CN-Phenyl |
| 177 | 1 | $SO_2NH_2$ | 4-CN-Phenyl |
| 178 | 2 | $SO_2NH_2$ | 4-CN-Phenyl |
| 179 | 3 | $SO_2NH_2$ | 4-CN-Phenyl |
| 180 | 4 | $SO_2NH_2$ | 4-CN-Phenyl |
| 181 | 1 | H | 2-CN-Phenyl |
| 182 | 2 | H | 2-CN-Phenyl |
| 183 | 3 | H | 2-CN-Phenyl |
| 184 | 4 | H | 2-CN-Phenyl |
| 185 | 1 | Me | 2-CN-Phenyl |
| 186 | 2 | Me | 2-CN-Phenyl |
| 187 | 3 | Me | 2-CN-Phenyl |
| 188 | 4 | Me | 2-CN-Phenyl |
| 189 | 1 | $CH_2Ph$ | 2-CN-Phenyl |

TABLE 18-continued

| Entry | n | $R^7$ | $R^3$ |
|---|---|---|---|
| 190 | 2 | $CH_2Ph$ | 2-CN-Phenyl |
| 191 | 3 | $CH_2Ph$ | 2-CN-Phenyl |
| 192 | 4 | $CH_2Ph$ | 2-CN-Phenyl |
| 193 | 1 | COMe | 2-CN-Phenyl |
| 194 | 2 | COMe | 2-CN-Phenyl |
| 195 | 3 | COMe | 2-CN-Phenyl |
| 196 | 4 | COMe | 2-CN-Phenyl |
| 197 | 1 | $CO_2Me$ | 2-CN-Phenyl |
| 198 | 2 | $CO_2Me$ | 2-CN-Phenyl |
| 199 | 3 | $CO_2Me$ | 2-CN-Phenyl |
| 200 | 4 | $CO_2Me$ | 2-CN-Phenyl |
| 201 | 1 | $CO_2tBu$ | 2-CN-Phenyl |
| 202 | 2 | $CO_2tBu$ | 2-CN-Phenyl |
| 203 | 3 | $CO_2tBu$ | 2-CN-Phenyl |
| 204 | 4 | $CO_2tBu$ | 2-CN-Phenyl |
| 205 | 1 | CONHMe | 2-CN-Phenyl |
| 206 | 2 | CONHMe | 2-CN-Phenyl |
| 207 | 3 | CONHMe | 2-CN-Phenyl |
| 208 | 4 | CONHMe | 2-CN-Phenyl |
| 209 | 1 | $SO_2Me$ | 2-CN-Phenyl |
| 210 | 2 | $SO_2Me$ | 2-CN-Phenyl |
| 211 | 3 | $SO_2Me$ | 2-CN-Phenyl |
| 212 | 4 | $SO_2Me$ | 2-CN-Phenyl |
| 213 | 1 | $SO_2NH_2$ | 2-CN-Phenyl |
| 214 | 2 | $SO_2NH_2$ | 2-CN-Phenyl |
| 215 | 3 | $SO_2NH_2$ | 2-CN-Phenyl |
| 216 | 4 | $SO_2NH_2$ | 2-CN-Phenyl |
| 217 | 1 | H | 3-Me-Phenyl |
| 218 | 2 | H | 3-Me-Phenyl |
| 219 | 3 | H | 3-Me-Phenyl |
| 220 | 4 | H | 3-Me-Phenyl |
| 221 | 1 | Me | 3-Me-Phenyl |
| 222 | 2 | Me | 3-Me-Phenyl |
| 223 | 3 | Me | 3-Me-Phenyl |
| 224 | 4 | Me | 3-Me-Phenyl |
| 225 | 1 | $CH_2Ph$ | 3-Me-Phenyl |
| 226 | 2 | $CH_2Ph$ | 3-Me-Phenyl |
| 227 | 3 | $CH_2Ph$ | 3-Me-Phenyl |
| 228 | 4 | $CH_2Ph$ | 3-Me-Phenyl |
| 229 | 1 | COMe | 3-Me-Phenyl |
| 230 | 2 | COMe | 3-Me-Phenyl |
| 231 | 3 | COMe | 3-Me-Phenyl |
| 232 | 4 | COMe | 3-Me-Phenyl |
| 233 | 1 | $CO_2Me$ | 3-Me-Phenyl |
| 234 | 2 | $CO_2Me$ | 3-Me-Phenyl |
| 235 | 3 | $CO_2Me$ | 3-Me-Phenyl |
| 236 | 4 | $CO_2Me$ | 3-Me-Phenyl |
| 237 | 1 | $CO_2tBu$ | 3-Me-Phenyl |
| 238 | 2 | $CO_2tBu$ | 3-Me-Phenyl |
| 239 | 3 | $CO_2tBu$ | 3-Me-Phenyl |
| 240 | 4 | $CO_2tBu$ | 3-Me-Phenyl |
| 241 | 1 | CONHMe | 3-Me-Phenyl |
| 242 | 2 | CONHMe | 3-Me-Phenyl |
| 243 | 3 | CONHMe | 3-Me-Phenyl |
| 244 | 4 | CONHMe | 3-Me-Phenyl |
| 245 | 1 | $SO_2Me$ | 3-Me-Phenyl |
| 246 | 2 | $SO_2Me$ | 3-Me-Phenyl |
| 247 | 3 | $SO_2Me$ | 3-Me-Phenyl |
| 248 | 4 | $SO_2Me$ | 3-Me-Phenyl |
| 249 | 1 | $SO_2NH_2$ | 3-Me-Phenyl |
| 250 | 2 | $SO_2NH_2$ | 3-Me-Phenyl |
| 251 | 3 | $SO_2NH_2$ | 3-Me-Phenyl |
| 252 | 4 | $SO_2NH_2$ | 3-Me-Phenyl |
| 253 | 1 | H | 2-F-Phenyl |
| 254 | 2 | H | 2-F-Phenyl |
| 255 | 3 | H | 2-F-Phenyl |
| 256 | 4 | H | 2-F-Phenyl |
| 257 | 1 | Me | 2-F-Phenyl |
| 258 | 2 | Me | 2-F-Phenyl |
| 259 | 3 | Me | 2-F-Phenyl |
| 260 | 4 | Me | 2-F-Phenyl |
| 261 | 1 | $CH_2Ph$ | 2-F-Phenyl |
| 262 | 2 | $CH_2Ph$ | 2-F-Phenyl |
| 263 | 3 | $CH_2Ph$ | 2-F-Phenyl |
| 264 | 4 | $CH_2Ph$ | 2-F-Phenyl |
| 265 | 1 | COMe | 2-F-Phenyl |
| 266 | 2 | COMe | 2-F-Phenyl |
| 267 | 3 | COMe | 2-F-Phenyl |

TABLE 18-continued

| Entry | n | $R^7$ | $R^3$ |
|---|---|---|---|
| 268 | 4 | COMe | 2-F-Phenyl |
| 269 | 1 | $CO_2Me$ | 2-F-Phenyl |
| 270 | 2 | $CO_2Me$ | 2-F-Phenyl |
| 271 | 3 | $CO_2Me$ | 2-F-Phenyl |
| 272 | 4 | $CO_2Me$ | 2-F-Phenyl |
| 273 | 1 | $CO_2tBu$ | 2-F-Phenyl |
| 274 | 2 | $CO_2tBu$ | 2-F-Phenyl |
| 275 | 3 | $CO_2tBu$ | 2-F-Phenyl |
| 276 | 4 | $CO_2tBu$ | 2-F-Phenyl |
| 277 | 1 | CONHMe | 2-F-Phenyl |
| 278 | 2 | CONHMe | 2-F-Phenyl |
| 279 | 3 | CONHMe | 2-F-Phenyl |
| 280 | 4 | CONHMe | 2-F-Phenyl |
| 281 | 1 | $SO_2Me$ | 2-F-Phenyl |
| 282 | 2 | $SO_2Me$ | 2-F-Phenyl |
| 283 | 3 | $SO_2Me$ | 2-F-Phenyl |
| 284 | 4 | $SO_2Me$ | 2-F-Phenyl |
| 285 | 1 | $SO_2NH_2$ | 2-F-Phenyl |
| 286 | 2 | $SO_2NH_2$ | 2-F-Phenyl |
| 287 | 3 | $SO_2NH_2$ | 2-F-Phenyl |
| 288 | 4 | $SO_2NH_2$ | 2-F-Phenyl |
| 289 | 1 | H | 4-F-Phenyl |
| 290 | 2 | H | 4-F-Phenyl |
| 291 | 3 | H | 4-F-Phenyl |
| 292 | 4 | H | 4-F-Phenyl |
| 293 | 1 | Me | 4-F-Phenyl |
| 294 | 2 | Me | 4-F-Phenyl |
| 295 | 3 | Me | 4-F-Phenyl |
| 296 | 4 | Me | 4-F-Phenyl |
| 297 | 1 | $CH_2Ph$ | 4-F-Phenyl |
| 298 | 2 | $CH_2Ph$ | 4-F-Phenyl |
| 299 | 3 | $CH_2Ph$ | 4-F-Phenyl |
| 300 | 4 | $CH_2Ph$ | 4-F-Phenyl |
| 301 | 1 | COMe | 4-F-Phenyl |
| 302 | 2 | COMe | 4-F-Phenyl |
| 303 | 3 | COMe | 4-F-Phenyl |
| 304 | 4 | COMe | 4-F-Phenyl |
| 305 | 1 | $CO_2Me$ | 4-F-Phenyl |
| 306 | 2 | $CO_2Me$ | 4-F-Phenyl |
| 307 | 3 | $CO_2Me$ | 4-F-Phenyl |
| 308 | 4 | $CO_2Me$ | 4-F-Phenyl |
| 309 | 1 | $CO_2tBu$ | 4-F-Phenyl |
| 310 | 2 | $CO_2tBu$ | 4-F-Phenyl |
| 311 | 3 | $CO_2tBu$ | 4-F-Phenyl |
| 312 | 4 | $CO_2tBu$ | 4-F-Phenyl |
| 313 | 1 | CONHMe | 4-F-Phenyl |
| 314 | 2 | CONHMe | 4-F-Phenyl |
| 315 | 3 | CONHMe | 4-F-Phenyl |
| 316 | 4 | CONHMe | 4-F-Phenyl |
| 317 | 1 | $SO_2Me$ | 4-F-Phenyl |
| 318 | 2 | $SO_2Me$ | 4-F-Phenyl |
| 319 | 3 | $SO_2Me$ | 4-F-Phenyl |
| 320 | 4 | $SO_2Me$ | 4-F-Phenyl |
| 321 | 1 | $SO_2NH_2$ | 4-F-Phenyl |
| 322 | 2 | $SO_2NH_2$ | 4-F-Phenyl |
| 323 | 3 | $SO_2NH_2$ | 4-F-Phenyl |
| 324 | 4 | $SO_2NH_2$ | 4-F-Phenyl |
| 325 | 1 | H | 3-Cl-Phenyl |
| 326 | 2 | H | 3-Cl-Phenyl |
| 327 | 3 | H | 3-Cl-Phenyl |
| 328 | 4 | H | 3-Cl-Phenyl |
| 329 | 1 | Me | 3-Cl-Phenyl |
| 330 | 2 | Me | 3-Cl-Phenyl |
| 331 | 3 | Me | 3-Cl-Phenyl |
| 332 | 4 | Me | 3-Cl-Phenyl |
| 333 | 1 | $CH_2Ph$ | 3-Cl-Phenyl |
| 334 | 2 | $CH_2Ph$ | 3-Cl-Phenyl |
| 335 | 3 | $CH_2Ph$ | 3-Cl-Phenyl |
| 336 | 4 | $CH_2Ph$ | 3-Cl-Phenyl |
| 337 | 1 | COMe | 3-Cl-Phenyl |
| 338 | 2 | COMe | 3-Cl-Phenyl |
| 339 | 3 | COMe | 3-Cl-Phenyl |
| 340 | 4 | COMe | 3-Cl-Phenyl |
| 341 | 1 | $CO_2Me$ | 3-Cl-Phenyl |
| 342 | 2 | $CO_2Me$ | 3-Cl-Phenyl |
| 343 | 3 | $CO_2Me$ | 3-Cl-Phenyl |
| 344 | 4 | $CO_2Me$ | 3-Cl-Phenyl |
| 345 | 1 | $CO_2tBu$ | 3-Cl-Phenyl |

TABLE 18-continued

| Entry | n | $R^7$ | $R^3$ |
|---|---|---|---|
| 346 | 2 | $CO_2tBu$ | 3-Cl-Phenyl |
| 347 | 3 | $CO_2tBu$ | 3-Cl-Phenyl |
| 348 | 4 | $CO_2tBu$ | 3-Cl-Phenyl |
| 349 | 1 | CONHMe | 3-Cl-Phenyl |
| 350 | 2 | CONHMe | 3-Cl-Phenyl |
| 351 | 3 | CONHMe | 3-Cl-Phenyl |
| 352 | 4 | CONHMe | 3-Cl-Phenyl |
| 353 | 1 | $SO_2Me$ | 3-Cl-Phenyl |
| 354 | 2 | $SO_2Me$ | 3-Cl-Phenyl |
| 355 | 3 | $SO_2Me$ | 3-Cl-Phenyl |
| 356 | 4 | $SO_2Me$ | 3-Cl-Phenyl |
| 357 | 1 | $SO_2NH_2$ | 3-Cl-Phenyl |
| 358 | 2 | $SO_2NH_2$ | 3-Cl-Phenyl |
| 359 | 3 | $SO_2NH_2$ | 3-Cl-Phenyl |
| 360 | 4 | $SO_2NH_2$ | 3-Cl-Phenyl |
| 361 | 1 | H | 2-Br-Phenyl |
| 362 | 2 | H | 2-Br-Phenyl |
| 363 | 3 | H | 2-Br-Phenyl |
| 364 | 4 | H | 2-Br-Phenyl |
| 365 | 1 | Me | 2-Br-Phenyl |
| 366 | 2 | Me | 2-Br-Phenyl |
| 367 | 3 | Me | 2-Br-Phenyl |
| 368 | 4 | Me | 2-Br-Phenyl |
| 369 | 1 | $CH_2Ph$ | 2-Br-Phenyl |
| 370 | 2 | $CH_2Ph$ | 2-Br-Phenyl |
| 371 | 3 | $CH_2Ph$ | 2-Br-Phenyl |
| 372 | 4 | $CH_2Ph$ | 2-Br-Phenyl |
| 373 | 1 | COMe | 2-Br-Phenyl |
| 374 | 2 | COMe | 2-Br-Phenyl |
| 375 | 3 | COMe | 2-Br-Phenyl |
| 376 | 4 | COMe | 2-Br-Phenyl |
| 377 | 1 | $CO_2Me$ | 2-Br-Phenyl |
| 378 | 2 | $CO_2Me$ | 2-Br-Phenyl |
| 379 | 3 | $CO_2Me$ | 2-Br-Phenyl |
| 380 | 4 | $CO_2Me$ | 2-Br-Phenyl |
| 381 | 1 | $CO_2tBu$ | 2-Br-Phenyl |
| 382 | 2 | $CO_2tBu$ | 2-Br-Phenyl |
| 383 | 3 | $CO_2tBu$ | 2-Br-Phenyl |
| 384 | 4 | $CO_2tBu$ | 2-Br-Phenyl |
| 385 | 1 | CONHMe | 2-Br-Phenyl |
| 386 | 2 | CONHMe | 2-Br-Phenyl |
| 387 | 3 | CONHMe | 2-Br-Phenyl |
| 388 | 4 | CONHMe | 2-Br-Phenyl |
| 389 | 1 | $SO_2Me$ | 2-Br-Phenyl |
| 390 | 2 | $SO_2Me$ | 2-Br-Phenyl |
| 391 | 3 | $SO_2Me$ | 2-Br-Phenyl |
| 392 | 4 | $SO_2Me$ | 2-Br-Phenyl |
| 393 | 1 | $SO_2NH_2$ | 2-Br-Phenyl |
| 394 | 2 | $SO_2NH_2$ | 2-Br-Phenyl |
| 395 | 3 | $SO_2NH_2$ | 2-Br-Phenyl |
| 396 | 4 | $SO_2NH_2$ | 2-Br-Phenyl |
| 397 | 1 | H | 4-Br-Phenyl |
| 398 | 2 | H | 4-Br-Phenyl |
| 399 | 3 | H | 4-Br-Phenyl |
| 400 | 4 | H | 4-Br-Phenyl |
| 401 | 1 | Me | 4-Br-Phenyl |
| 402 | 2 | Me | 4-Br-Phenyl |
| 403 | 3 | Me | 4-Br-Phenyl |
| 404 | 4 | Me | 4-Br-Phenyl |
| 405 | 1 | $CH_2Ph$ | 4-Br-Phenyl |
| 406 | 2 | $CH_2Ph$ | 4-Br-Phenyl |
| 407 | 3 | $CH_2Ph$ | 4-Br-Phenyl |
| 408 | 4 | $CH_2Ph$ | 4-Br-Phenyl |
| 409 | 1 | COMe | 4-Br-Phenyl |
| 410 | 2 | COMe | 4-Br-Phenyl |
| 411 | 3 | COMe | 4-Br-Phenyl |
| 412 | 4 | COMe | 4-Br-Phenyl |
| 413 | 1 | $CO_2Me$ | 4-Br-Phenyl |
| 414 | 2 | $CO_2Me$ | 4-Br-Phenyl |
| 415 | 3 | $CO_2Me$ | 4-Br-Phenyl |
| 416 | 4 | $CO_2Me$ | 4-Br-Phenyl |
| 417 | 1 | $CO_2tBu$ | 4-Br-Phenyl |
| 418 | 2 | $CO_2tBu$ | 4-Br-Phenyl |
| 419 | 3 | $CO_2tBu$ | 4-Br-Phenyl |
| 420 | 4 | $CO_2tBu$ | 4-Br-Phenyl |
| 421 | 1 | CONHMe | 4-Br-Phenyl |
| 422 | 2 | CONHMe | 4-Br-Phenyl |
| 423 | 3 | CONHMe | 4-Br-Phenyl |
| 424 | 4 | CONHMe | 4-Br-Phenyl |
| 425 | 1 | $SO_2Me$ | 4-Br-Phenyl |
| 426 | 2 | $SO_2Me$ | 4-Br-Phenyl |
| 427 | 3 | $SO_2Me$ | 4-Br-Phenyl |
| 428 | 4 | $SO_2Me$ | 4-Br-Phenyl |
| 429 | 1 | $SO_2NH_2$ | 4-Br-Phenyl |
| 430 | 2 | $SO_2NH_2$ | 4-Br-Phenyl |
| 431 | 3 | $SO_2NH_2$ | 4-Br-Phenyl |
| 432 | 4 | $SO_2NH_2$ | 4-Br-Phenyl |
| 433 | 1 | H | 3-$CF_3$-Phenyl |
| 434 | 2 | H | 3-$CF_3$-Phenyl |
| 435 | 3 | H | 3-$CF_3$-Phenyl |
| 436 | 4 | H | 3-$CF_3$-Phenyl |
| 437 | 1 | Me | 3-$CF_3$-Phenyl |
| 438 | 2 | Me | 3-$CF_3$-Phenyl |
| 439 | 3 | Me | 3-$CF_3$-Phenyl |
| 440 | 4 | Me | 3-$CF_3$-Phenyl |
| 441 | 1 | $CH_2Ph$ | 3-$CF_3$-Phenyl |
| 442 | 2 | $CH_2Ph$ | 3-$CF_3$-Phenyl |
| 443 | 3 | $CH_2Ph$ | 3-$CF_3$-Phenyl |
| 444 | 4 | $CH_2Ph$ | 3-$CF_3$-Phenyl |
| 445 | 1 | COMe | 3-$CF_3$-Phenyl |
| 446 | 2 | COMe | 3-$CF_3$-Phenyl |
| 447 | 3 | COMe | 3-$CF_3$-Phenyl |
| 448 | 4 | COMe | 3-$CF_3$-Phenyl |
| 449 | 1 | $CO_2Me$ | 3-$CF_3$-Phenyl |
| 450 | 2 | $CO_2Me$ | 3-$CF_3$-Phenyl |
| 451 | 3 | $CO_2Me$ | 3-$CF_3$-Phenyl |
| 452 | 4 | $CO_2Me$ | 3-$CF_3$-Phenyl |
| 453 | 1 | $CO_2tBu$ | 3-$CF_3$-Phenyl |
| 454 | 2 | $CO_2tBu$ | 3-$CF_3$-Phenyl |
| 455 | 3 | $CO_2tBu$ | 3-$CF_3$-Phenyl |
| 456 | 4 | $CO_2tBu$ | 3-$CF_3$-Phenyl |
| 457 | 1 | CONHMe | 3-$CF_3$-Phenyl |
| 458 | 2 | CONHMe | 3-$CF_3$-Phenyl |
| 459 | 3 | CONHMe | 3-$CF_3$-Phenyl |
| 460 | 4 | CONHMe | 3-$CF_3$-Phenyl |
| 461 | 1 | $SO_2Me$ | 3-$CF_3$-Phenyl |
| 462 | 2 | $SO_2Me$ | 3-$CF_3$-Phenyl |
| 463 | 3 | $SO_2Me$ | 3-$CF_3$-Phenyl |
| 464 | 4 | $SO_2Me$ | 3-$CF_3$-Phenyl |
| 465 | 1 | $SO_2NH_2$ | 3-$CF_3$-Phenyl |
| 466 | 2 | $SO_2NH_2$ | 3-$CF_3$-Phenyl |
| 467 | 3 | $SO_2NH_2$ | 3-$CF_3$-Phenyl |
| 468 | 4 | $SO_2NH_2$ | 3-$CF_3$-Phenyl |
| 469 | 1 | H | 2-iPr-Phenyl |
| 470 | 2 | H | 2-iPr-Phenyl |
| 471 | 3 | H | 2-iPr-Phenyl |
| 472 | 4 | H | 2-iPr-Phenyl |
| 473 | 1 | Me | 2-iPr-Phenyl |
| 474 | 2 | Me | 2-iPr-Phenyl |
| 475 | 3 | Me | 2-iPr-Phenyl |
| 476 | 4 | Me | 2-iPr-Phenyl |
| 477 | 1 | $CH_2Ph$ | 2-iPr-Phenyl |
| 478 | 2 | $CH_2Ph$ | 2-iPr-Phenyl |
| 479 | 3 | $CH_2Ph$ | 2-iPr-Phenyl |
| 480 | 4 | $CH_2Ph$ | 2-iPr-Phenyl |
| 481 | 1 | COMe | 2-iPr-Phenyl |
| 482 | 2 | COMe | 2-iPr-Phenyl |
| 483 | 3 | COMe | 2-iPr-Phenyl |
| 484 | 4 | COMe | 2-iPr-Phenyl |
| 485 | 1 | $CO_2Me$ | 2-iPr-Phenyl |
| 486 | 2 | $CO_2Me$ | 2-iPr-Phenyl |
| 487 | 3 | $CO_2Me$ | 2-iPr-Phenyl |
| 488 | 4 | $CO_2Me$ | 2-iPr-Phenyl |
| 489 | 1 | $CO_2tBu$ | 2-iPr-Phenyl |
| 490 | 2 | $CO_2tBu$ | 2-iPr-Phenyl |
| 491 | 3 | $CO_2tBu$ | 2-iPr-Phenyl |
| 492 | 4 | $CO_2tBu$ | 2-iPr-Phenyl |
| 493 | 1 | CONHMe | 2-iPr-Phenyl |
| 494 | 2 | CONHMe | 2-iPr-Phenyl |
| 495 | 3 | CONHMe | 2-iPr-Phenyl |
| 496 | 4 | CONHMe | 2-iPr-Phenyl |
| 497 | 1 | $SO_2Me$ | 2-iPr-Phenyl |
| 498 | 2 | $SO_2Me$ | 2-iPr-Phenyl |
| 499 | 3 | $SO_2Me$ | 2-iPr-Phenyl |
| 500 | 4 | $SO_2Me$ | 2-iPr-Phenyl |
| 501 | 1 | $SO_2NH_2$ | 2-iPr-Phenyl |

TABLE 18-continued

| Entry | n | $R^7$ | $R^3$ |
|---|---|---|---|
| 502 | 2 | $SO_2NH_2$ | 2-iPr-Phenyl |
| 503 | 3 | $SO_2NH_2$ | 2-iPr-Phenyl |
| 504 | 4 | $SO_2NH_2$ | 2-iPr-Phenyl |
| 505 | 1 | H | 4-iPr-Phenyl |
| 506 | 2 | H | 4-iPr-Phenyl |
| 507 | 3 | H | 4-iPr-Phenyl |
| 508 | 4 | H | 4-iPr-Phenyl |
| 509 | 1 | Me | 4-iPr-Phenyl |
| 510 | 2 | Me | 4-iPr-Phenyl |
| 511 | 3 | Me | 4-iPr-Phenyl |
| 512 | 4 | Me | 4-iPr-Phenyl |
| 513 | 1 | $CH_2Ph$ | 4-iPr-Phenyl |
| 514 | 2 | $CH_2Ph$ | 4-iPr-Phenyl |
| 515 | 3 | $CH_2Ph$ | 4-iPr-Phenyl |
| 516 | 4 | $CH_2Ph$ | 4-iPr-Phenyl |
| 517 | 1 | COMe | 4-iPr-Phenyl |
| 518 | 2 | COMe | 4-iPr-Phenyl |
| 519 | 3 | COMe | 4-iPr-Phenyl |
| 520 | 4 | COMe | 4-iPr-Phenyl |
| 521 | 1 | $CO_2Me$ | 4-iPr-Phenyl |
| 522 | 2 | $CO_2Me$ | 4-iPr-Phenyl |
| 523 | 3 | $CO_2Me$ | 4-iPr-Phenyl |
| 524 | 4 | $CO_2Me$ | 4-iPr-Phenyl |
| 525 | 1 | $CO_2tBu$ | 4-iPr-Phenyl |
| 526 | 2 | $CO_2tBu$ | 4-iPr-Phenyl |
| 527 | 3 | $CO_2tBu$ | 4-iPr-Phenyl |
| 528 | 4 | $CO_2tBu$ | 4-iPr-Phenyl |
| 529 | 1 | CONHMe | 4-iPr-Phenyl |
| 530 | 2 | CONHMe | 4-iPr-Phenyl |
| 531 | 3 | CONHMe | 4-iPr-Phenyl |
| 532 | 4 | CONHMe | 4-iPr-Phenyl |
| 533 | 1 | $SO_2Me$ | 4-iPr-Phenyl |
| 534 | 2 | $SO_2Me$ | 4-iPr-Phenyl |
| 535 | 3 | $SO_2Me$ | 4-iPr-Phenyl |
| 536 | 4 | $SO_2Me$ | 4-iPr-Phenyl |
| 537 | 1 | $SO_2NH_2$ | 4-iPr-Phenyl |
| 538 | 2 | $SO_2NH_2$ | 4-iPr-Phenyl |
| 539 | 3 | $SO_2NH_2$ | 4-iPr-Phenyl |
| 540 | 4 | $SO_2NH_2$ | 4-iPr-Phenyl |
| 541 | 1 | H | 3-$NH_2$-Phenyl |
| 542 | 2 | H | 3-$NH_2$-Phenyl |
| 543 | 3 | H | 3-$NH_2$-Phenyl |
| 544 | 4 | H | 3-$NH_2$-Phenyl |
| 545 | 1 | Me | 3-$NH_2$-Phenyl |
| 546 | 2 | Me | 3-$NH_2$-Phenyl |
| 547 | 3 | Me | 3-$NH_2$-Phenyl |
| 548 | 4 | Me | 3-$NH_2$-Phenyl |
| 549 | 1 | $CH_2Ph$ | 3-$NH_2$-Phenyl |
| 550 | 2 | $CH_2Ph$ | 3-$NH_2$-Phenyl |
| 551 | 3 | $CH_2Ph$ | 3-$NH_2$-Phenyl |
| 552 | 4 | $CH_2Ph$ | 3-$NH_2$-Phenyl |
| 553 | 1 | COMe | 3-$NH_2$-Phenyl |
| 554 | 2 | COMe | 3-$NH_2$-Phenyl |
| 555 | 3 | COMe | 3-$NH_2$-Phenyl |
| 556 | 4 | COMe | 3-$NH_2$-Phenyl |
| 557 | 1 | $CO_2Me$ | 3-$NH_2$-Phenyl |
| 558 | 2 | $CO_2Me$ | 3-$NH_2$-Phenyl |
| 559 | 3 | $CO_2Me$ | 3-$NH_2$-Phenyl |
| 560 | 4 | $CO_2Me$ | 3-$NH_2$-Phenyl |
| 561 | 1 | $CO_2tBu$ | 3-$NH_2$-Phenyl |
| 562 | 2 | $CO_2tBu$ | 3-$NH_2$-Phenyl |
| 563 | 3 | $CO_2tBu$ | 3-$NH_2$-Phenyl |
| 564 | 4 | $CO_2tBu$ | 3-$NH_2$-Phenyl |
| 565 | 1 | CONHMe | 3-$NH_2$-Phenyl |
| 566 | 2 | CONHMe | 3-$NH_2$-Phenyl |
| 567 | 3 | CONHMe | 3-$NH_2$-Phenyl |
| 568 | 4 | CONHMe | 3-$NH_2$-Phenyl |
| 569 | 1 | $SO_2Me$ | 3-$NH_2$-Phenyl |
| 570 | 2 | $SO_2Me$ | 3-$NH_2$-Phenyl |
| 571 | 3 | $SO_2Me$ | 3-$NH_2$-Phenyl |
| 572 | 4 | $SO_2Me$ | 3-$NH_2$-Phenyl |
| 573 | 1 | $SO_2NH_2$ | 3-$NH_2$-Phenyl |
| 574 | 2 | $SO_2NH_2$ | 3-$NH_2$-Phenyl |
| 575 | 3 | $SO_2NH_2$ | 3-$NH_2$-Phenyl |
| 576 | 4 | $SO_2NH_2$ | 3-$NH_2$-Phenyl |
| 577 | 1 | H | 2,4-di-Me-Phenyl |
| 578 | 2 | H | 2,4-di-Me-Phenyl |
| 579 | 3 | H | 2,4-di-Me-Phenyl |

TABLE 18-continued

| Entry | n | $R^7$ | $R^3$ |
|---|---|---|---|
| 580 | 4 | H | 2,4-di-Me-Phenyl |
| 581 | 1 | Me | 2,4-di-Me-Phenyl |
| 582 | 2 | Me | 2,4-di-Me-Phenyl |
| 583 | 3 | Me | 2,4-di-Me-Phenyl |
| 584 | 4 | Me | 2,4-di-Me-Phenyl |
| 585 | 1 | $CH_2Ph$ | 2,4-di-Me-Phenyl |
| 586 | 2 | $CH_2Ph$ | 2,4-di-Me-Phenyl |
| 587 | 3 | $CH_2Ph$ | 2,4-di-Me-Phenyl |
| 588 | 4 | $CH_2Ph$ | 2,4-di-Me-Phenyl |
| 589 | 1 | COMe | 2,4-di-Me-Phenyl |
| 590 | 2 | COMe | 2,4-di-Me-Phenyl |
| 591 | 3 | COMe | 2,4-di-Me-Phenyl |
| 592 | 4 | COMe | 2,4-di-Me-Phenyl |
| 593 | 1 | $CO_2Me$ | 2,4-di-Me-Phenyl |
| 594 | 2 | $CO_2Me$ | 2,4-di-Me-Phenyl |
| 595 | 3 | $CO_2Me$ | 2,4-di-Me-Phenyl |
| 596 | 4 | $CO_2Me$ | 2,4-di-Me-Phenyl |
| 597 | 1 | $CO_2tBu$ | 2,4-di-Me-Phenyl |
| 598 | 2 | $CO_2tBu$ | 2,4-di-Me-Phenyl |
| 599 | 3 | $CO_2tBu$ | 2,4-di-Me-Phenyl |
| 600 | 4 | $CO_2tBu$ | 2,4-di-Me-Phenyl |
| 601 | 1 | CONHMe | 2,4-di-Me-Phenyl |
| 602 | 2 | CONHMe | 2,4-di-Me-Phenyl |
| 603 | 3 | CONHMe | 2,4-di-Me-Phenyl |
| 604 | 4 | CONHMe | 2,4-di-Me-Phenyl |
| 605 | 1 | $SO_2Me$ | 2,4-di-Me-Phenyl |
| 606 | 2 | $SO_2Me$ | 2,4-di-Me-Phenyl |
| 607 | 3 | $SO_2Me$ | 2,4-di-Me-Phenyl |
| 608 | 4 | $SO_2Me$ | 2,4-di-Me-Phenyl |
| 609 | 1 | $SO_2NH_2$ | 2,4-di-Me-Phenyl |
| 610 | 2 | $SO_2NH_2$ | 2,4-di-Me-Phenyl |
| 611 | 3 | $SO_2NH_2$ | 2,4-di-Me-Phenyl |
| 612 | 4 | $SO_2NH_2$ | 2,4-di-Me-Phenyl |
| 613 | 1 | H | 2,6-di-iPr-Phenyl |
| 614 | 2 | H | 2,6-di-iPr-Phenyl |
| 615 | 3 | H | 2,6-di-iPr-Phenyl |
| 616 | 4 | H | 2,6-di-iPr-Phenyl |
| 617 | 1 | Me | 2,6-di-iPr-Phenyl |
| 618 | 2 | Me | 2,6-di-iPr-Phenyl |
| 619 | 3 | Me | 2,6-di-iPr-Phenyl |
| 620 | 4 | Me | 2,6-di-iPr-Phenyl |
| 621 | 1 | $CH_2Ph$ | 2,6-di-iPr-Phenyl |
| 622 | 2 | $CH_2Ph$ | 2,6-di-iPr-Phenyl |
| 623 | 3 | $CH_2Ph$ | 2,6-di-iPr-Phenyl |
| 624 | 3 | $CH_2Ph$ | 2,6-di-iPr-Phenyl |
| 625 | 1 | COMe | 2,6-di-iPr-Phenyl |
| 626 | 2 | COMe | 2,6-di-iPr-Phenyl |
| 627 | 3 | COMe | 2,6-di-iPr-Phenyl |
| 628 | 4 | COMe | 2,6-di-iPr-Phenyl |
| 629 | 1 | $CO_2Me$ | 2,6-di-iPr-Phenyl |
| 630 | 2 | $CO_2Me$ | 2,6-di-iPr-Phenyl |
| 631 | 3 | $CO_2Me$ | 2,6-di-iPr-Phenyl |
| 632 | 4 | $CO_2Me$ | 2,6-di-iPr-Phenyl |
| 633 | 1 | $CO_2tBu$ | 2,6-di-iPr-Phenyl |
| 634 | 2 | $CO_2tBu$ | 2,6-di-iPr-Phenyl |
| 635 | 3 | $CO_2tBu$ | 2,6-di-iPr-Phenyl |
| 636 | 4 | $CO_2tBu$ | 2,6-di-iPr-Phenyl |
| 637 | 1 | CONHMe | 2,6-di-iPr-Phenyl |
| 638 | 2 | CONHMe | 2,6-di-iPr-Phenyl |
| 639 | 3 | CONHMe | 2,6-di-iPr-Phenyl |
| 640 | 4 | CONHMe | 2,6-di-iPr-Phenyl |
| 641 | 1 | $SO_2Me$ | 2,6-di-iPr-Phenyl |
| 642 | 2 | $SO_2Me$ | 2,6-di-iPr-Phenyl |
| 643 | 3 | $SO_2Me$ | 2,6-di-iPr-Phenyl |
| 644 | 4 | $SO_2Me$ | 2,6-di-iPr-Phenyl |
| 645 | 1 | $SO_2NH_2$ | 2,6-di-iPr-Phenyl |
| 646 | 2 | $SO_2NH_2$ | 2,6-di-iPr-Phenyl |
| 647 | 3 | $SO_2NH_2$ | 2,6-di-iPr-Phenyl |
| 648 | 4 | $SO_2NH_2$ | 2,6-di-iPr-Phenyl |
| 649 | 1 | H | 3-Ph-Phenyl |
| 650 | 2 | H | 3-Ph-Phenyl |
| 651 | 3 | H | 3-Ph-Phenyl |
| 652 | 4 | H | 3-Ph-Phenyl |
| 653 | 1 | Me | 3-Ph-Phenyl |
| 654 | 2 | Me | 3-Ph-Phenyl |
| 655 | 3 | Me | 3-Ph-Phenyl |
| 656 | 4 | Me | 3-Ph-Phenyl |
| 657 | 1 | $CH_2Ph$ | 3-Ph-Phenyl |

TABLE 18-continued

| Entry | n | $R^7$ | $R^3$ |
|---|---|---|---|
| 658 | 2 | $CH_2Ph$ | 3-Ph-Phenyl |
| 659 | 3 | $CH_2Ph$ | 3-Ph-Phenyl |
| 660 | 4 | $CH_2Ph$ | 3-Ph-Phenyl |
| 661 | 1 | COMe | 3-Ph-Phenyl |
| 662 | 2 | COMe | 3-Ph-Phenyl |
| 663 | 3 | COMe | 3-Ph-Phenyl |
| 664 | 4 | COMe | 3-Ph-Phenyl |
| 665 | 1 | $CO_2Me$ | 3-Ph-Phenyl |
| 666 | 2 | $CO_2Me$ | 3-Ph-Phenyl |
| 667 | 3 | $CO_2Me$ | 3-Ph-Phenyl |
| 668 | 4 | $CO_2Me$ | 3-Ph-Phenyl |
| 669 | 1 | $CO_2tBu$ | 3-Ph-Phenyl |
| 670 | 2 | $CO_2tBu$ | 3-Ph-Phenyl |
| 671 | 3 | $CO_2tBu$ | 3-Ph-Phenyl |
| 672 | 4 | $CO_2tBu$ | 3-Ph-Phenyl |
| 673 | 1 | CONHMe | 3-Ph-Phenyl |
| 674 | 2 | CONHMe | 3-Ph-Phenyl |
| 675 | 3 | CONHMe | 3-Ph-Phenyl |
| 676 | 4 | CONHMe | 3-Ph-Phenyl |
| 677 | 1 | $SO_2Me$ | 3-Ph-Phenyl |
| 678 | 2 | $SO_2Me$ | 3-Ph-Phenyl |
| 679 | 3 | $SO_2Me$ | 3-Ph-Phenyl |
| 680 | 4 | $SO_2Me$ | 3-Ph-Phenyl |
| 681 | 1 | $SO_2NH_2$ | 3-Ph-Phenyl |
| 682 | 2 | $SO_2NH_2$ | 3-Ph-Phenyl |
| 683 | 3 | $SO_2NH_2$ | 3-Ph-Phenyl |
| 684 | 4 | $SO_2NH_2$ | 3-Ph-Phenyl |
| 685 | 1 | H | 2-morpholino-phenyl |
| 686 | 2 | H | 2-morpholino-phenyl |
| 687 | 3 | H | 2-morpholino-phenyl |
| 688 | 4 | H | 2-morpholino-phenyl |
| 689 | 1 | Me | 2-morpholino-phenyl |
| 690 | 2 | Me | 2-morpholino-phenyl |
| 691 | 3 | Me | 2-morpholino-phenyl |
| 692 | 4 | Me | 2-morpholino-phenyl |
| 693 | 1 | $CH_2Ph$ | 2-morpholino-phenyl |
| 694 | 2 | $CH_2Ph$ | 2-morpholino-phenyl |
| 695 | 3 | $CH_2Ph$ | 2-morpholino-phenyl |
| 696 | 4 | $CH_2Ph$ | 2-morpholino-phenyl |
| 697 | 1 | COMe | 2-morpholino-phenyl |
| 698 | 2 | COMe | 2-morpholino-phenyl |
| 699 | 3 | COMe | 2-morpholino-phenyl |
| 700 | 4 | COMe | 2-morpholino-phenyl |
| 701 | 1 | $CO_2Me$ | 2-morpholino-phenyl |
| 702 | 2 | $CO_2Me$ | 2-morpholino-phenyl |
| 703 | 3 | $CO_2Me$ | 2-morpholino-phenyl |
| 704 | 4 | $CO_2Me$ | 2-morpholino-phenyl |
| 705 | 1 | $CO_2tBu$ | 2-morpholino-phenyl |
| 706 | 2 | $CO_2tBu$ | 2-morpholino-phenyl |
| 707 | 3 | $CO_2tBu$ | 2-morpholino-phenyl |
| 708 | 4 | $CO_2tBu$ | 2-morpholino-phenyl |
| 709 | 1 | CONHMe | 2-morpholino-phenyl |

TABLE 18-continued

| Entry | n | $R^7$ | $R^3$ |
|---|---|---|---|
| 710 | 2 | CONHMe | 2-morpholino-phenyl |
| 711 | 3 | CONHMe | 2-morpholino-phenyl |
| 712 | 4 | CONHMe | 2-morpholino-phenyl |
| 713 | 1 | $SO_2Me$ | 2-morpholino-phenyl |
| 714 | 2 | $SO_2Me$ | 2-morpholino-phenyl |
| 715 | 3 | $SO_2Me$ | 2-morpholino-phenyl |
| 716 | 4 | $SO_2Me$ | 2-morpholino-phenyl |
| 717 | 1 | $SO_2NH_2$ | 2-morpholino-phenyl |
| 718 | 2 | $SO_2NH_2$ | 2-morpholino-phenyl |
| 719 | 3 | $SO_2NH_2$ | 2-morpholino-phenyl |
| 720 | 4 | $SO_2NH_2$ | 2-morpholino-phenyl |
| 721 | 1 | H | 4-morpholino-phenyl |
| 722 | 2 | H | 4-morpholino-phenyl |
| 723 | 3 | H | 4-morpholino-phenyl |
| 724 | 4 | H | 4-morpholino-phenyl |
| 725 | 1 | $CH_2Ph$ | 4-morpholino-phenyl |
| 726 | 2 | $CH_2Ph$ | 4-morpholino-phenyl |
| 727 | 3 | $CH_2Ph$ | 4-morpholino-phenyl |
| 728 | 4 | $CH_2Ph$ | 4-morpholino-phenyl |
| 729 | 1 | $CO_2Me$ | 4-morpholino-phenyl |
| 730 | 2 | $CO_2Me$ | 4-morpholino-phenyl |
| 731 | 3 | $CO_2Me$ | 4-morpholino-phenyl |
| 732 | 4 | $CO_2Me$ | 4-morpholino-phenyl |
| 733 | 1 | CONHMe | 4-morpholino-phenyl |
| 734 | 2 | CONHMe | 4-morpholino-phenyl |
| 735 | 3 | CONHMe | 4-morpholino-phenyl |
| 736 | 4 | CONHMe | 4-morpholino-phenyl |
| 737 | 1 | $SO_2NH_2$ | 4-morpholino-phenyl |
| 738 | 2 | $SO_2NH_2$ | 4-morpholino-phenyl |
| 739 | 3 | $SO_2NH_2$ | 4-morpholino-phenyl |
| 740 | 1 | H | naphthylen-1-yl |
| 741 | 2 | H | naphthylen-1-yl |
| 742 | 3 | H | naphthylen-1-yl |
| 743 | 4 | H | naphthylen-1-yl |
| 744 | 1 | Me | naphthylen-1-yl |
| 745 | 2 | Me | naphthylen-1-yl |
| 746 | 3 | Me | naphthylen-1-yl |
| 747 | 4 | Me | naphthylen-1-yl |
| 748 | 1 | $CH_2Ph$ | naphthylen-1-yl |
| 749 | 2 | $CH_2Ph$ | naphthylen-1-yl |
| 750 | 3 | $CH_2Ph$ | naphthylen-1-yl |
| 751 | 4 | $CH_2Ph$ | naphthylen-1-yl |
| 752 | 1 | COMe | naphthylen-1-yl |
| 753 | 2 | COMe | naphthylen-1-yl |
| 754 | 3 | COMe | naphthylen-1-yl |
| 755 | 4 | COMe | naphthylen-1-yl |
| 756 | 1 | $CO_2Me$ | naphthylen-1-yl |
| 757 | 2 | $CO_2Me$ | naphthylen-1-yl |

TABLE 18-continued

| Entry | n | $R^7$ | $R^3$ |
|---|---|---|---|
| 758 | 3 | $CO_2Me$ | naphthylen-1-yl |
| 759 | 4 | $CO_2Me$ | naphthylen-1-yl |
| 760 | 1 | $CO_2tBu$ | naphthylen-1-yl |
| 761 | 2 | $CO_2tBu$ | naphthylen-1-yl |
| 762 | 3 | $CO_2tBu$ | naphthylen-1-yl |
| 763 | 4 | $CO_2tBu$ | naphthylen-1-yl |
| 764 | 1 | CONHMe | naphthylen-1-yl |
| 765 | 2 | CONHMe | naphthylen-1-yl |
| 767 | 3 | CONHMe | naphthylen-1-yl |
| 768 | 4 | CONHMe | naphthylen-1-yl |
| 769 | 1 | $SO_2Me$ | naphthylen-1-yl |
| 770 | 2 | $SO_2Me$ | naphthylen-1-yl |
| 771 | 3 | $SO_2Me$ | naphthylen-1-yl |
| 772 | 4 | $SO_2Me$ | naphthylen-1-yl |
| 773 | 1 | $SO_2NH_2$ | naphthylen-1-yl |
| 774 | 2 | $SO_2NH_2$ | naphthylen-1-yl |
| 775 | 3 | $SO_2NH_2$ | naphthylen-1-yl |
| 778 | 4 | $SO_2NH_2$ | naphthylen-1-yl |
| 779 | 1 | H | 4-OH-Phenyl |
| 780 | 2 | H | 4-OH-Phenyl |
| 781 | 3 | H | 4-OH-Phenyl |
| 782 | 4 | H | 4-OH-Phenyl |
| 783 | 1 | Me | 4-OH-Phenyl |
| 784 | 2 | Me | 4-OH-Phenyl |
| 785 | 3 | Me | 4-OH-Phenyl |
| 786 | 4 | Me | 4-OH-Phenyl |
| 787 | 1 | $CH_2Ph$ | 4-OH-Phenyl |
| 788 | 2 | $CH_2Ph$ | 4-OH-Phenyl |
| 789 | 3 | $CH_2Ph$ | 4-OH-Phenyl |
| 790 | 4 | $CH_2Ph$ | 4-OH-Phenyl |
| 791 | 1 | COMe | 4-OH-Phenyl |
| 792 | 2 | COMe | 4-OH-Phenyl |
| 793 | 3 | COMe | 4-OH-Phenyl |
| 794 | 4 | COMe | 4-OH-Phenyl |
| 795 | 1 | $CO_2Me$ | 4-OH-Phenyl |
| 796 | 2 | $CO_2Me$ | 4-OH-Phenyl |
| 797 | 3 | $CO_2Me$ | 4-OH-Phenyl |
| 798 | 4 | $CO_2Me$ | 4-OH-Phenyl |
| 799 | 1 | $CO_2tBu$ | 4-OH-Phenyl |
| 800 | 2 | $CO_2tBu$ | 4-OH-Phenyl |
| 801 | 3 | $CO_2tBu$ | 4-OH-Phenyl |
| 802 | 4 | $CO_2tBu$ | 4-OH-Phenyl |
| 803 | 1 | CONHMe | 4-OH-Phenyl |
| 804 | 2 | CONHMe | 4-OH-Phenyl |
| 805 | 3 | CONHMe | 4-OH-Phenyl |
| 806 | 4 | CONHMe | 4-OH-Phenyl |
| 807 | 1 | $SO_2Me$ | 4-OH-Phenyl |
| 808 | 2 | $SO_2Me$ | 4-OH-Phenyl |
| 809 | 3 | $SO_2Me$ | 4-OH-Phenyl |
| 810 | 4 | $SO_2Me$ | 4-OH-Phenyl |
| 811 | 1 | $SO_2NH_2$ | 4-OH-Phenyl |
| 812 | 2 | $SO_2NH_2$ | 4-OH-Phenyl |
| 813 | 3 | $SO_2NH_2$ | 4-OH-Phenyl |
| 814 | 4 | $SO_2NH_2$ | 4-OH-Phenyl |
| 815 | 1 | H | 2-OH-Phenyl |
| 816 | 2 | H | 2-OH-Phenyl |
| 817 | 3 | H | 2-OH-Phenyl |
| 818 | 4 | H | 2-OH-Phenyl |
| 819 | 1 | Me | 2-OH-Phenyl |
| 820 | 2 | Me | 2-OH-Phenyl |
| 821 | 3 | Me | 2-OH-Phenyl |
| 822 | 4 | Me | 2-OH-Phenyl |
| 823 | 1 | $CH_2Ph$ | 2-OH-Phenyl |
| 824 | 2 | $CH_2Ph$ | 2-OH-Phenyl |
| 825 | 3 | $CH_2Ph$ | 2-OH-Phenyl |
| 826 | 4 | $CH_2Ph$ | 2-OH-Phenyl |
| 827 | 1 | COMe | 2-OH-Phenyl |
| 828 | 2 | COMe | 2-OH-Phenyl |
| 829 | 3 | COMe | 2-OH-Phenyl |
| 830 | 4 | COMe | 2-OH-Phenyl |
| 831 | 1 | $CO_2Me$ | 2-OH-Phenyl |
| 832 | 2 | $CO_2Me$ | 2-OH-Phenyl |
| 833 | 3 | $CO_2Me$ | 2-OH-Phenyl |
| 834 | 4 | $CO_2Me$ | 2-OH-Phenyl |
| 835 | 1 | $CO_2tBu$ | 2-OH-Phenyl |
| 836 | 2 | $CO_2tBu$ | 2-OH-Phenyl |
| 837 | 3 | $CO_2tBu$ | 2-OH-Phenyl |
| 838 | 4 | $CO_2tBu$ | 2-OH-Phenyl |

TABLE 18-continued

| Entry | n | $R^7$ | $R^3$ |
|---|---|---|---|
| 839 | 1 | CONHMe | 2-OH-Phenyl |
| 840 | 2 | CONHMe | 2-OH-Phenyl |
| 841 | 3 | CONHMe | 2-OH-Phenyl |
| 842 | 4 | CONHMe | 2-OH-Phenyl |
| 843 | 1 | $SO_2Me$ | 2-OH-Phenyl |
| 844 | 2 | $SO_2Me$ | 2-OH-Phenyl |
| 845 | 3 | $SO_2Me$ | 2-OH-Phenyl |
| 846 | 4 | $SO_2Me$ | 2-OH-Phenyl |
| 847 | 1 | $SO_2NH_2$ | 2-OH-Phenyl |
| 848 | 2 | $SO_2NH_2$ | 2-OH-Phenyl |
| 849 | 3 | $SO_2NH_2$ | 2-OH-Phenyl |
| 850 | 4 | $SO_2NH_2$ | 2-OH-Phenyl |
| 851 | 1 | H | 4-OMe-Phenyl |
| 852 | 2 | H | 4-OMe-Phenyl |
| 853 | 3 | H | 4-OMe-Phenyl |
| 854 | 4 | H | 4-OMe-Phenyl |
| 855 | 1 | Me | 4-OMe-Phenyl |
| 856 | 2 | Me | 4-OMe-Phenyl |
| 857 | 3 | Me | 4-OMe-Phenyl |
| 858 | 4 | Me | 4-OMe-Phenyl |
| 859 | 1 | $CH_2Ph$ | 4-OMe-Phenyl |
| 860 | 2 | $CH_2Ph$ | 4-OMe-Phenyl |
| 861 | 3 | $CH_2Ph$ | 4-OMe-Phenyl |
| 862 | 4 | $CH_2Ph$ | 4-OMe-Phenyl |
| 863 | 1 | COMe | 4-OMe-Phenyl |
| 864 | 2 | COMe | 4-OMe-Phenyl |
| 865 | 3 | COMe | 4-OMe-Phenyl |
| 866 | 4 | COMe | 4-OMe-Phenyl |
| 867 | 1 | $CO_2Me$ | 4-OMe-Phenyl |
| 868 | 2 | $CO_2Me$ | 4-OMe-Phenyl |
| 869 | 3 | $CO_2Me$ | 4-OMe-Phenyl |
| 870 | 4 | $CO_2Me$ | 4-OMe-Phenyl |
| 871 | 1 | $CO_2tBu$ | 4-OMe-Phenyl |
| 872 | 2 | $CO_2tBu$ | 4-OMe-Phenyl |
| 873 | 3 | $CO_2tBu$ | 4-OMe-Phenyl |
| 874 | 4 | $CO_2tBu$ | 4-OMe-Phenyl |
| 875 | 1 | CONHMe | 4-OMe-Phenyl |
| 876 | 2 | CONHMe | 4-OMe-Phenyl |
| 877 | 3 | CONHMe | 4-OMe-Phenyl |
| 878 | 4 | CONHMe | 4-OMe-Phenyl |
| 879 | 1 | $SO_2Me$ | 4-OMe-Phenyl |
| 880 | 2 | $SO_2Me$ | 4-OMe-Phenyl |
| 881 | 3 | $SO_2Me$ | 4-OMe-Phenyl |
| 882 | 4 | $SO_2Me$ | 4-OMe-Phenyl |
| 883 | 1 | $SO_2NH_2$ | 4-OMe-Phenyl |
| 884 | 2 | $SO_2NH_2$ | 4-OMe-Phenyl |
| 885 | 3 | $SO_2NH_2$ | 4-OMe-Phenyl |
| 886 | 4 | $SO_2NH_2$ | 4-OMe-Phenyl |
| 887 | 1 | H | 2-OMe-Phenyl |
| 888 | 2 | H | 2-OMe-Phenyl |
| 889 | 3 | H | 2-OMe-Phenyl |
| 890 | 4 | H | 2-OMe-Phenyl |
| 891 | 1 | Me | 2-OMe-Phenyl |
| 892 | 2 | Me | 2-OMe-Phenyl |
| 893 | 3 | Me | 2-OMe-Phenyl |
| 894 | 4 | Me | 2-OMe-Phenyl |
| 895 | 1 | $CH_2Ph$ | 2-OMe-Phenyl |
| 896 | 2 | $CH_2Ph$ | 2-OMe-Phenyl |
| 897 | 3 | $CH_2Ph$ | 2-OMe-Phenyl |
| 898 | 4 | $CH_2Ph$ | 2-OMe-Phenyl |
| 899 | 1 | COMe | 2-OMe-Phenyl |
| 900 | 2 | COMe | 2-OMe-Phenyl |
| 901 | 3 | COMe | 2-OMe-Phenyl |
| 902 | 4 | COMe | 2-OMe-Phenyl |
| 903 | 1 | $CO_2Me$ | 2-OMe-Phenyl |
| 904 | 2 | $CO_2Me$ | 2-OMe-Phenyl |
| 905 | 3 | $CO_2Me$ | 2-OMe-Phenyl |
| 906 | 4 | $CO_2Me$ | 2-OMe-Phenyl |
| 907 | 1 | $CO_2tBu$ | 2-OMe-Phenyl |
| 908 | 2 | $CO_2tBu$ | 2-OMe-Phenyl |
| 909 | 3 | $CO_2tBu$ | 2-OMe-Phenyl |
| 910 | 4 | $CO_2tBu$ | 2-OMe-Phenyl |
| 911 | 1 | CONHMe | 2-OMe-Phenyl |
| 912 | 2 | CONHMe | 2-OMe-Phenyl |
| 913 | 3 | CONHMe | 2-OMe-Phenyl |
| 914 | 4 | CONHMe | 2-OMe-Phenyl |
| 915 | 1 | $SO_2Me$ | 2-OMe-Phenyl |
| 916 | 2 | $SO_2Me$ | 2-OMe-Phenyl |

TABLE 18-continued

| Entry | n | $R^7$ | $R^3$ |
|---|---|---|---|
| 917 | 3 | $SO_2Me$ | 2-OMe-Phenyl |
| 918 | 4 | $SO_2Me$ | 2-OMe-Phenyl |
| 919 | 1 | $SO_2NH_2$ | 2-OMe-Phenyl |
| 920 | 2 | $SO_2NH_2$ | 2-OMe-Phenyl |
| 921 | 3 | $SO_2NH_2$ | 2-OMe-Phenyl |
| 922 | 4 | $SO_2NH_2$ | 2-OMe-Phenyl |
| 923 | 1 | H | 3-CN-Phenyl |
| 924 | 2 | H | 3-CN-Phenyl |
| 925 | 3 | H | 3-CN-Phenyl |
| 926 | 4 | H | 3-CN-Phenyl |
| 927 | 1 | Me | 3-CN-Phenyl |
| 928 | 2 | Me | 3-CN-Phenyl |
| 929 | 3 | Me | 3-CN-Phenyl |
| 930 | 4 | Me | 3-CN-Phenyl |
| 931 | 1 | $CH_2Ph$ | 3-CN-Phenyl |
| 932 | 2 | $CH_2Ph$ | 3-CN-Phenyl |
| 933 | 3 | $CH_2Ph$ | 3-CN-Phenyl |
| 934 | 4 | $CH_2Ph$ | 3-CN-Phenyl |
| 935 | 1 | COMe | 3-CN-Phenyl |
| 936 | 2 | COMe | 3-CN-Phenyl |
| 937 | 3 | COMe | 3-CN-Phenyl |
| 938 | 4 | COMe | 3-CN-Phenyl |
| 939 | 1 | $CO_2Me$ | 3-CN-Phenyl |
| 940 | 2 | $CO_2Me$ | 3-CN-Phenyl |
| 941 | 3 | $CO_2Me$ | 3-CN-Phenyl |
| 942 | 4 | $CO_2Me$ | 3-CN-Phenyl |
| 943 | 1 | $CO_2tBu$ | 3-CN-Phenyl |
| 944 | 2 | $CO_2tBu$ | 3-CN-Phenyl |
| 945 | 3 | $CO_2tBu$ | 3-CN-Phenyl |
| 946 | 4 | $CO_2tBu$ | 3-CN-Phenyl |
| 947 | 1 | CONHMe | 3-CN-Phenyl |
| 948 | 2 | CONHMe | 3-CN-Phenyl |
| 949 | 3 | CONHMe | 3-CN-Phenyl |
| 950 | 4 | CONHMe | 3-CN-Phenyl |
| 951 | 1 | $SO_2Me$ | 3-CN-Phenyl |
| 952 | 2 | $SO_2Me$ | 3-CN-Phenyl |
| 953 | 3 | $SO_2Me$ | 3-CN-Phenyl |
| 954 | 4 | $SO_2Me$ | 3-CN-Phenyl |
| 955 | 1 | $SO_2NH_2$ | 3-CN-Phenyl |
| 956 | 2 | $SO_2NH_2$ | 3-CN-Phenyl |
| 957 | 3 | $SO_2NH_2$ | 3-CN-Phenyl |
| 958 | 4 | $SO_2NH_2$ | 3-CN-Phenyl |
| 959 | 1 | H | 2-Me-Phenyl |
| 960 | 2 | H | 2-Me-Phenyl |
| 961 | 3 | H | 2-Me-Phenyl |
| 962 | 4 | H | 2-Me-Phenyl |
| 963 | 1 | Me | 2-Me-Phenyl |
| 964 | 2 | Me | 2-Me-Phenyl |
| 965 | 3 | Me | 2-Me-Phenyl |
| 966 | 4 | Me | 2-Me-Phenyl |
| 967 | 1 | $CH_2Ph$ | 2-Me-Phenyl |
| 968 | 2 | $CH_2Ph$ | 2-Me-Phenyl |
| 969 | 3 | $CH_2Ph$ | 2-Me-Phenyl |
| 970 | 4 | $CH_2Ph$ | 2-Me-Phenyl |
| 971 | 1 | COMe | 2-Me-Phenyl |
| 972 | 2 | COMe | 2-Me-Phenyl |
| 973 | 3 | COMe | 2-Me-Phenyl |
| 974 | 4 | COMe | 2-Me-Phenyl |
| 975 | 1 | $CO_2Me$ | 2-Me-Phenyl |
| 976 | 2 | $CO_2Me$ | 2-Me-Phenyl |
| 977 | 3 | $CO_2Me$ | 2-Me-Phenyl |
| 978 | 4 | $CO_2Me$ | 2-CN-Phenyl |
| 979 | 1 | $CO_2tBu$ | 2-Me-Phenyl |
| 980 | 2 | $CO_2tBu$ | 2-Me-Phenyl |
| 981 | 3 | $CO_2tBu$ | 2-Me-Phenyl |
| 982 | 4 | $CO_2tBu$ | 2-Me-Phenyl |
| 983 | 1 | CONHMe | 2-Me-Phenyl |
| 984 | 2 | CONHMe | 2-Me-Phenyl |
| 985 | 3 | CONHMe | 2-Me-Phenyl |
| 986 | 4 | CONHMe | 2-Me-Phenyl |
| 987 | 1 | $SO_2Me$ | 2-Me-Phenyl |
| 988 | 2 | $SO_2Me$ | 2-Me-Phenyl |
| 989 | 3 | $SO_2Me$ | 2-Me-Phenyl |
| 990 | 4 | $SO_2Me$ | 2-Me-Phenyl |
| 991 | 1 | $SO_2NH_2$ | 2-Me-Phenyl |
| 992 | 2 | $SO_2NH_2$ | 2-Me-Phenyl |
| 993 | 3 | $SO_2NH_2$ | 2-Me-Phenyl |
| 994 | 4 | $SO_2NH_2$ | 2-Me-Phenyl |

TABLE 18-continued

| Entry | n | $R^7$ | $R^3$ |
|---|---|---|---|
| 995 | 1 | H | 4-Me-Phenyl |
| 996 | 2 | H | 4-Me-Phenyl |
| 997 | 3 | H | 4-Me-Phenyl |
| 998 | 4 | H | 4-Me-Phenyl |
| 999 | 1 | Me | 4-Me-Phenyl |
| 1000 | 2 | Me | 4-Me-Phenyl |
| 1001 | 3 | Me | 4-Me-Phenyl |
| 1002 | 4 | Me | 4-Me-Phenyl |
| 1003 | 1 | $CH_2Ph$ | 4-Me-Phenyl |
| 1004 | 2 | $CH_2Ph$ | 4-Me-Phenyl |
| 1005 | 3 | $CH_2Ph$ | 4-Me-Phenyl |
| 1006 | 4 | $CH_2Ph$ | 4-Me-Phenyl |
| 1007 | 1 | COMe | 4-Me-Phenyl |
| 1008 | 2 | COMe | 4-Me-Phenyl |
| 1009 | 3 | COMe | 4-Me-Phenyl |
| 1010 | 4 | COMe | 4-Me-Phenyl |
| 1011 | 1 | $CO_2Me$ | 4-Me-Phenyl |
| 1012 | 2 | $CO_2Me$ | 4-Me-Phenyl |
| 1013 | 3 | $CO_2Me$ | 4-Me-Phenyl |
| 1014 | 4 | $CO_2Me$ | 4-Me-Phenyl |
| 1015 | 1 | $CO_2tBu$ | 4-Me-Phenyl |
| 1016 | 2 | $CO_2tBu$ | 4-Me-Phenyl |
| 1017 | 3 | $CO_2tBu$ | 4-Me-Phenyl |
| 1018 | 4 | $CO_2tBu$ | 4-Me-Phenyl |
| 1019 | 1 | CONHMe | 4-Me-Phenyl |
| 1020 | 2 | CONHMe | 4-Me-Phenyl |
| 1021 | 3 | CONHMe | 4-Me-Phenyl |
| 1022 | 4 | CONHMe | 4-Me-Phenyl |
| 1023 | 1 | $SO_2Me$ | 4-Me-Phenyl |
| 1024 | 2 | $SO_2Me$ | 4-Me-Phenyl |
| 1025 | 3 | $SO_2Me$ | 4-Me-Phenyl |
| 1026 | 4 | $SO_2Me$ | 4-Me-Phenyl |
| 1027 | 1 | $SO_2NH_2$ | 4-Me-Phenyl |
| 1028 | 2 | $SO_2NH_2$ | 4-Me-Phenyl |
| 1029 | 3 | $SO_2NH_2$ | 4-Me-Phenyl |
| 1030 | 4 | $SO_2NH_2$ | 4-Me-Phenyl |
| 1031 | 1 | H | 3-F-Phenyl |
| 1032 | 2 | H | 3-F-Phenyl |
| 1033 | 3 | H | 3-F-Phenyl |
| 1034 | 4 | H | 3-F-Phenyl |
| 1035 | 1 | Me | 3-F-Phenyl |
| 1036 | 2 | Me | 3-F-Phenyl |
| 1037 | 3 | Me | 3-F-Phenyl |
| 1038 | 4 | Me | 3-F-Phenyl |
| 1039 | 1 | $CH_2Ph$ | 3-F-Phenyl |
| 1040 | 2 | $CH_2Ph$ | 3-F-Phenyl |
| 1041 | 3 | $CH_2Ph$ | 3-F-Phenyl |
| 1042 | 4 | $CH_2Ph$ | 3-F-Phenyl |
| 1043 | 1 | COMe | 3-F-Phenyl |
| 1044 | 2 | COMe | 3-F-Phenyl |
| 1045 | 3 | COMe | 3-F-Phenyl |
| 1046 | 4 | COMe | 3-F-Phenyl |
| 1047 | 1 | $CO_2Me$ | 3-F-Phenyl |
| 1048 | 2 | $CO_2Me$ | 3-F-Phenyl |
| 1049 | 3 | $CO_2Me$ | 3-F-Phenyl |
| 1050 | 4 | $CO_2Me$ | 3-F-Phenyl |
| 1051 | 1 | $CO_2tBu$ | 3-F-Phenyl |
| 1052 | 2 | $CO_2tBu$ | 3-F-Phenyl |
| 1053 | 3 | $CO_2tBu$ | 3-F-Phenyl |
| 1054 | 4 | $CO_2tBu$ | 3-F-Phenyl |
| 1055 | 1 | CONHMe | 3-F-Phenyl |
| 1056 | 2 | CONHMe | 3-F-Phenyl |
| 1057 | 3 | CONHMe | 3-F-Phenyl |
| 1058 | 4 | CONHMe | 3-F-Phenyl |
| 1059 | 1 | $SO_2Me$ | 3-F-Phenyl |
| 1060 | 2 | $SO_2Me$ | 3-F-Phenyl |
| 1061 | 3 | $SO_2Me$ | 3-F-Phenyl |
| 1062 | 4 | $SO_2Me$ | 3-F-Phenyl |
| 1063 | 1 | $SO_2NH_2$ | 3-F-Phenyl |
| 1064 | 2 | $SO_2NH_2$ | 3-F-Phenyl |
| 1065 | 3 | $SO_2NH_2$ | 3-F-Phenyl |
| 1066 | 4 | $SO_2NH_2$ | 3-F-Phenyl |
| 1067 | 1 | H | 2-Cl-Phenyl |
| 1068 | 2 | H | 2-Cl-Phenyl |
| 1069 | 3 | H | 2-Cl-Phenyl |
| 1070 | 4 | H | 2-Cl-Phenyl |
| 1071 | 1 | Me | 2-Cl-Phenyl |
| 1072 | 2 | Me | 2-Cl-Phenyl |

TABLE 18-continued

| Entry | n | $R^7$ | $R^3$ |
|---|---|---|---|
| 1073 | 3 | Me | 2-Cl-Phenyl |
| 1074 | 4 | Me | 2-Cl-Phenyl |
| 1075 | 1 | $CH_2Ph$ | 2-Cl-Phenyl |
| 1076 | 2 | $CH_2Ph$ | 2-Cl-Phenyl |
| 1077 | 3 | $CH_2Ph$ | 2-Cl-Phenyl |
| 1078 | 4 | $CH_2Ph$ | 2-Cl-Phenyl |
| 1079 | 1 | COMe | 2-Cl-Phenyl |
| 1080 | 2 | COMe | 2-Cl-Phenyl |
| 1081 | 3 | COMe | 2-Cl-Phenyl |
| 1082 | 4 | COMe | 2-Cl-Phenyl |
| 1083 | 1 | $CO_2Me$ | 2-Cl-Phenyl |
| 1084 | 2 | $CO_2Me$ | 2-Cl-Phenyl |
| 1085 | 3 | $CO_2Me$ | 2-Cl-Phenyl |
| 1086 | 4 | $CO_2Me$ | 2-Cl-Phenyl |
| 1087 | 1 | $CO_2tBu$ | 2-Cl-Phenyl |
| 1088 | 2 | $CO_2tBu$ | 2-Cl-Phenyl |
| 1089 | 3 | $CO_2tBu$ | 2-Cl-Phenyl |
| 1090 | 4 | $CO_2tBu$ | 2-Cl-Phenyl |
| 1091 | 1 | CONHMe | 2-Cl-Phenyl |
| 1092 | 2 | CONHMe | 2-Cl-Phenyl |
| 1093 | 3 | CONHMe | 2-Cl-Phenyl |
| 1094 | 4 | CONHMe | 2-Cl-Phenyl |
| 1095 | 1 | $SO_2Me$ | 2-Cl-Phenyl |
| 1096 | 2 | $SO_2Me$ | 2-Cl-Phenyl |
| 1097 | 3 | $SO_2Me$ | 2-Cl-Phenyl |
| 1098 | 4 | $SO_2Me$ | 2-Cl-Phenyl |
| 1099 | 1 | $SO_2NH_2$ | 2-Cl-Phenyl |
| 1100 | 2 | $SO_2NH_2$ | 2-Cl-Phenyl |
| 1101 | 3 | $SO_2NH_2$ | 2-Cl-Phenyl |
| 1102 | 4 | $SO_2NH_2$ | 2-Cl-Phenyl |
| 1103 | 1 | H | 4-Cl-Phenyl |
| 1104 | 2 | H | 4-Cl-Phenyl |
| 1105 | 3 | H | 4-Cl-Phenyl |
| 1106 | 4 | H | 4-Cl-Phenyl |
| 1107 | 1 | Me | 4-Cl-Phenyl |
| 1108 | 2 | Me | 4-Cl-Phenyl |
| 1109 | 3 | Me | 4-Cl-Phenyl |
| 1110 | 4 | Me | 4-Cl-Phenyl |
| 1111 | 1 | $CH_2Ph$ | 4-Cl-Phenyl |
| 1112 | 2 | $CH_2Ph$ | 4-Cl-Phenyl |
| 1113 | 3 | $CH_2Ph$ | 4-Cl-Phenyl |
| 1114 | 4 | $CH_2Ph$ | 4-Cl-Phenyl |
| 1115 | 1 | COMe | 4-Cl-Phenyl |
| 1116 | 2 | COMe | 4-Cl-Phenyl |
| 1117 | 3 | COMe | 4-Cl-Phenyl |
| 1118 | 4 | COMe | 4-Cl-Phenyl |
| 1119 | 1 | $CO_2Me$ | 4-Cl-Phenyl |
| 1120 | 2 | $CO_2Me$ | 4-Cl-Phenyl |
| 1121 | 3 | $CO_2Me$ | 4-Cl-Phenyl |
| 1122 | 4 | $CO_2Me$ | 4-Cl-Phenyl |
| 1123 | 1 | $CO_2tBu$ | 4-Cl-Phenyl |
| 1124 | 2 | $CO_2tBu$ | 4-Cl-Phenyl |
| 1125 | 3 | $CO_2tBu$ | 4-Cl-Phenyl |
| 1126 | 4 | $CO_2tBu$ | 4-Cl-Phenyl |
| 1127 | 1 | CONHMe | 4-Cl-Phenyl |
| 1128 | 2 | CONHMe | 4-Cl-Phenyl |
| 1129 | 3 | CONHMe | 4-Cl-Phenyl |
| 1130 | 4 | CONHMe | 4-Cl-Phenyl |
| 1131 | 1 | $SO_2Me$ | 4-Cl-Phenyl |
| 1132 | 2 | $SO_2Me$ | 4-Cl-Phenyl |
| 1133 | 3 | $SO_2Me$ | 4-Cl-Phenyl |
| 1134 | 4 | $SO_2Me$ | 4-Cl-Phenyl |
| 1135 | 1 | $SO_2NH_2$ | 4-Cl-Phenyl |
| 1136 | 2 | $SO_2NH_2$ | 4-Cl-Phenyl |
| 1137 | 3 | $SO_2NH_2$ | 4-Cl-Phenyl |
| 1138 | 4 | $SO_2NH_2$ | 4-Cl-Phenyl |
| 1139 | 1 | H | 3-Br-Phenyl |
| 1140 | 2 | H | 3-Br-Phenyl |
| 1141 | 3 | H | 3-Br-Phenyl |
| 1142 | 4 | H | 3-Br-Phenyl |
| 1143 | 1 | Me | 3-Br-Phenyl |
| 1144 | 2 | Me | 3-Br-Phenyl |
| 1145 | 3 | Me | 3-Br-Phenyl |
| 1146 | 4 | Me | 3-Br-Phenyl |
| 1147 | 1 | $CH_2Ph$ | 3-Br-Phenyl |
| 1148 | 2 | $CH_2Ph$ | 3-Br-Phenyl |
| 1149 | 3 | $CH_2Ph$ | 3-Br-Phenyl |
| 1150 | 4 | $CH_2Ph$ | 3-Br-Phenyl |

TABLE 18-continued

| Entry | n | $R^7$ | $R^3$ |
|---|---|---|---|
| 1151 | 1 | COMe | 3-Br-Phenyl |
| 1152 | 2 | COMe | 3-Br-Phenyl |
| 1153 | 3 | COMe | 3-Br-Phenyl |
| 1154 | 4 | COMe | 3-Br-Phenyl |
| 1155 | 1 | $CO_2Me$ | 3-Br-Phenyl |
| 1156 | 2 | $CO_2Me$ | 3-Br-Phenyl |
| 1157 | 3 | $CO_2Me$ | 3-Br-Phenyl |
| 1158 | 4 | $CO_2Me$ | 3-Br-Phenyl |
| 1159 | 1 | $CO_2tBu$ | 3-Br-Phenyl |
| 1160 | 2 | $CO_2tBu$ | 3-Br-Phenyl |
| 1161 | 3 | $CO_2tBu$ | 3-Br-Phenyl |
| 1162 | 4 | $CO_2tBu$ | 3-Br-Phenyl |
| 1163 | 1 | CONHMe | 3-Br-Phenyl |
| 1164 | 2 | CONHMe | 3-Br-Phenyl |
| 1165 | 3 | CONHMe | 3-Br-Phenyl |
| 1166 | 4 | CONHMe | 3-Br-Phenyl |
| 1167 | 1 | $SO_2Me$ | 3-Br-Phenyl |
| 1168 | 2 | $SO_2Me$ | 3-Br-Phenyl |
| 1169 | 3 | $SO_2Me$ | 3-Br-Phenyl |
| 1170 | 4 | $SO_2Me$ | 3-Br-Phenyl |
| 1171 | 1 | $SO_2NH_2$ | 3-Br-Phenyl |
| 1172 | 2 | $SO_2NH_2$ | 3-Br-Phenyl |
| 1173 | 3 | $SO_2NH_2$ | 3-Br-Phenyl |
| 1174 | 4 | $SO_2NH_2$ | 3-Br-Phenyl |
| 1175 | 1 | H | 2-$CF_3$-Phenyl |
| 1176 | 2 | H | 2-$CF_3$-Phenyl |
| 1177 | 3 | H | 2-$CF_3$-Phenyl |
| 1178 | 4 | H | 2-$CF_3$-Phenyl |
| 1179 | 1 | Me | 2-$CF_3$-Phenyl |
| 1180 | 2 | Me | 2-$CF_3$-Phenyl |
| 1181 | 3 | Me | 2-$CF_3$-Phenyl |
| 1182 | 4 | Me | 2-$CF_3$-Phenyl |
| 1183 | 1 | $CH_2Ph$ | 2-$CF_3$-Phenyl |
| 1184 | 2 | $CH_2Ph$ | 2-$CF_3$-Phenyl |
| 1185 | 3 | $CH_2Ph$ | 2-$CF_3$-Phenyl |
| 1186 | 4 | $CH_2Ph$ | 2-$CF_3$-Phenyl |
| 1187 | 1 | COMe | 2-$CF_3$-Phenyl |
| 1188 | 2 | COMe | 2-$CF_3$-Phenyl |
| 1189 | 3 | COMe | 2-$CF_3$-Phenyl |
| 1190 | 4 | COMe | 2-$CF_3$-Phenyl |
| 1191 | 1 | $CO_2Me$ | 2-$CF_3$-Phenyl |
| 1192 | 2 | $CO_2Me$ | 2-$CF_3$-Phenyl |
| 1193 | 3 | $CO_2Me$ | 2-$CF_3$-Phenyl |
| 1194 | 4 | $CO_2Me$ | 2-$CF_3$-Phenyl |
| 1195 | 1 | $CO_2tBu$ | 2-$CF_3$-Phenyl |
| 1196 | 2 | $CO_2tBu$ | 2-$CF_3$-Phenyl |
| 1197 | 3 | $CO_2tBu$ | 2-$CF_3$-Phenyl |
| 1198 | 4 | $CO_2tBu$ | 2-$CF_3$-Phenyl |
| 1199 | 1 | CONHMe | 2-$CF_3$-Phenyl |
| 1200 | 2 | CONHMe | 2-$CF_3$-Phenyl |
| 1201 | 3 | CONHMe | 2-$CF_3$-Phenyl |
| 1202 | 4 | CONHMe | 2-$CF_3$-Phenyl |
| 1203 | 1 | $SO_2Me$ | 2-$CF_3$-Phenyl |
| 1204 | 2 | $SO_2Me$ | 2-$CF_3$-Phenyl |
| 1205 | 3 | $SO_2Me$ | 2-$CF_3$-Phenyl |
| 1206 | 4 | $SO_2Me$ | 2-$CF_3$-Phenyl |
| 1207 | 1 | $SO_2NH_2$ | 2-$CF_3$-Phenyl |
| 1208 | 2 | $SO_2NH_2$ | 2-$CF_3$-Phenyl |
| 1209 | 3 | $SO_2NH_2$ | 2-$CF_3$-Phenyl |
| 1210 | 4 | $SO_2NH_2$ | 2-$CF_3$-Phenyl |
| 1211 | 1 | H | 4-$CF_3$-Phenyl |
| 1212 | 2 | H | 4-$CF_3$-Phenyl |
| 1213 | 3 | H | 4-$CF_3$-Phenyl |
| 1214 | 4 | H | 4-$CF_3$-Phenyl |
| 1215 | 1 | Me | 4-$CF_3$-Phenyl |
| 1216 | 2 | Me | 4-$CF_3$-Phenyl |
| 1217 | 3 | Me | 4-$CF_3$-Phenyl |
| 1218 | 4 | Me | 4-$CF_3$-Phenyl |
| 1219 | 1 | $CH_2Ph$ | 4-$CF_3$-Phenyl |
| 1220 | 2 | $CH_2Ph$ | 4-$CF_3$-Phenyl |
| 1221 | 3 | $CH_2Ph$ | 4-$CF_3$-Phenyl |
| 1222 | 4 | $CH_2Ph$ | 4-$CF_3$-Phenyl |
| 1223 | 1 | COMe | 4-$CF_3$-Phenyl |
| 1224 | 2 | COMe | 4-$CF_3$-Phenyl |
| 1225 | 3 | COMe | 4-$CF_3$-Phenyl |
| 1226 | 4 | COMe | 4-$CF_3$-Phenyl |
| 1227 | 1 | $CO_2Me$ | 4-$CF_3$-Phenyl |
| 1228 | 2 | $CO_2Me$ | 4-$CF_3$-Phenyl |

TABLE 18-continued

| Entry | n | $R^7$ | $R^3$ |
|---|---|---|---|
| 1229 | 3 | $CO_2Me$ | 4-$CF_3$-Phenyl |
| 1230 | 4 | $CO_2Me$ | 4-$CF_3$-Phenyl |
| 1231 | 1 | $CO_2tBu$ | 4-$CF_3$-Phenyl |
| 1232 | 2 | $CO_2tBu$ | 4-$CF_3$-Phenyl |
| 1233 | 3 | $CO_2tBu$ | 4-$CF_3$-Phenyl |
| 1234 | 4 | $CO_2tBu$ | 4-$CF_3$-Phenyl |
| 1235 | 1 | CONHMe | 4-$CF_3$-Phenyl |
| 1236 | 2 | CONHMe | 4-$CF_3$-Phenyl |
| 1237 | 3 | CONHMe | 4-$CF_3$-Phenyl |
| 1238 | 4 | CONHMe | 4-$CF_3$-Phenyl |
| 1239 | 1 | $SO_2Me$ | 4-$CF_3$-Phenyl |
| 1240 | 2 | $SO_2Me$ | 4-$CF_3$-Phenyl |
| 1241 | 3 | $SO_2Me$ | 4-$CF_3$-Phenyl |
| 1242 | 4 | $SO_2Me$ | 4-$CF_3$-Phenyl |
| 1243 | 1 | $SO_2NH_2$ | 4-$CF_3$-Phenyl |
| 1244 | 2 | $SO_2NH_2$ | 4-$CF_3$-Phenyl |
| 1245 | 3 | $SO_2NH_2$ | 4-$CF_3$-Phenyl |
| 1246 | 4 | $SO_2NH_2$ | 4-$CF_3$-Phenyl |
| 1247 | 1 | H | 3-iPr-Phenyl |
| 1248 | 2 | H | 3-iPr-Phenyl |
| 1249 | 3 | H | 3-iPr-Phenyl |
| 1250 | 4 | H | 3-iPr-Phenyl |
| 1251 | 1 | Me | 3-iPr-Phenyl |
| 1252 | 2 | Me | 3-iPr-Phenyl |
| 1253 | 3 | Me | 3-iPr-Phenyl |
| 1254 | 4 | Me | 3-iPr-Phenyl |
| 1255 | 1 | $CH_2Ph$ | 3-iPr-Phenyl |
| 1256 | 2 | $CH_2Ph$ | 3-iPr-Phenyl |
| 1257 | 3 | $CH_2Ph$ | 3-iPr-Phenyl |
| 1258 | 4 | $CH_2Ph$ | 3-iPr-Phenyl |
| 1259 | 1 | COMe | 3-iPr-Phenyl |
| 1260 | 2 | COMe | 3-iPr-Phenyl |
| 1261 | 3 | COMe | 3-iPr-Phenyl |
| 1262 | 4 | COMe | 3-iPr-Phenyl |
| 1263 | 1 | $CO_2Me$ | 3-iPr-Phenyl |
| 1264 | 2 | $CO_2Me$ | 3-iPr-Phenyl |
| 1265 | 3 | $CO_2Me$ | 3-iPr-Phenyl |
| 1266 | 4 | $CO_2Me$ | 3-iPr-Phenyl |
| 1267 | 1 | $CO_2tBu$ | 3-iPr-Phenyl |
| 1268 | 2 | $CO_2tBu$ | 3-iPr-Phenyl |
| 1269 | 3 | $CO_2tBu$ | 3-iPr-Phenyl |
| 1270 | 4 | $CO_2tBu$ | 3-iPr-Phenyl |
| 1271 | 1 | CONHMe | 3-iPr-Phenyl |
| 1272 | 2 | CONHMe | 3-iPr-Phenyl |
| 1273 | 3 | CONHMe | 3-iPr-Phenyl |
| 1274 | 4 | CONHMe | 3-iPr-Phenyl |
| 1275 | 1 | $SO_2Me$ | 3-iPr-Phenyl |
| 1276 | 2 | $SO_2Me$ | 3-iPr-Phenyl |
| 1277 | 3 | $SO_2Me$ | 3-iPr-Phenyl |
| 1278 | 4 | $SO_2Me$ | 3-iPr-Phenyl |
| 1279 | 1 | $SO_2NH_2$ | 3-iPr-Phenyl |
| 1280 | 2 | $SO_2NH_2$ | 3-iPr-Phenyl |
| 1281 | 3 | $SO_2NH_2$ | 3-iPr-Phenyl |
| 1282 | 4 | $SO_2NH_2$ | 3-iPr-Phenyl |
| 1283 | 1 | H | 4-$NH_2$-Phenyl |
| 1284 | 2 | H | 4-$NH_2$-Phenyl |
| 1285 | 3 | H | 4-$NH_2$-Phenyl |
| 1286 | 4 | H | 4-$NH_2$-Phenyl |
| 1287 | 1 | Me | 4-$NH_2$-Phenyl |
| 1288 | 2 | Me | 4-$NH_2$-Phenyl |
| 1289 | 3 | Me | 4-$NH_2$-Phenyl |
| 1290 | 4 | Me | 4-$NH_2$-Phenyl |
| 1291 | 1 | $CH_2Ph$ | 4-$NH_2$-Phenyl |
| 1292 | 2 | $CH_2Ph$ | 4-$NH_2$-Phenyl |
| 1293 | 3 | $CH_2Ph$ | 4-$NH_2$-Phenyl |
| 1294 | 4 | $CH_2Ph$ | 4-$NH_2$-Phenyl |
| 1295 | 1 | COMe | 4-$NH_2$-Phenyl |
| 1296 | 2 | COMe | 4-$NH_2$-Phenyl |
| 1297 | 3 | COMe | 4-$NH_2$-Phenyl |
| 1298 | 4 | COMe | 4-$NH_2$-Phenyl |
| 1299 | 1 | $CO_2Me$ | 4-$NH_2$-Phenyl |
| 1300 | 2 | $CO_2Me$ | 4-$NH_2$-Phenyl |
| 1301 | 3 | $CO_2Me$ | 4-$NH_2$-Phenyl |
| 1302 | 4 | $CO_2Me$ | 4-$NH_2$-Phenyl |
| 1303 | 1 | $CO_2tBu$ | 4-$NH_2$-Phenyl |
| 1304 | 2 | $CO_2tBu$ | 4-$NH_2$-Phenyl |
| 1305 | 3 | $CO_2tBu$ | 4-$NH_2$-Phenyl |
| 1306 | 4 | $CO_2tBu$ | 4-$NH_2$-Phenyl |

TABLE 18-continued

| Entry | n | $R^7$ | $R^3$ |
|---|---|---|---|
| 1307 | 1 | CONHMe | 4-$NH_2$-Phenyl |
| 1308 | 2 | CONHMe | 4-$NH_2$-Phenyl |
| 1309 | 3 | CONHMe | 4-$NH_2$-Phenyl |
| 1310 | 4 | CONHMe | 4-$NH_2$-Phenyl |
| 1311 | 1 | $SO_2Me$ | 4-$NH_2$-Phenyl |
| 1312 | 2 | $SO_2Me$ | 4-$NH_2$-Phenyl |
| 1313 | 3 | $SO_2Me$ | 4-$NH_2$-Phenyl |
| 1314 | 4 | $SO_2Me$ | 4-$NH_2$-Phenyl |
| 1315 | 1 | $SO_2NH_2$ | 4-$NH_2$-Phenyl |
| 1316 | 2 | $SO_2NH_2$ | 4-$NH_2$-Phenyl |
| 1317 | 3 | $SO_2NH_2$ | 4-$NH_2$-Phenyl |
| 1318 | 4 | $SO_2NH_2$ | 4-$NH_2$-Phenyl |
| 1319 | 1 | H | 2-$NH_2$-Phenyl |
| 1320 | 2 | H | 2-$NH_2$-Phenyl |
| 1321 | 3 | H | 2-$NH_2$-Phenyl |
| 1322 | 4 | H | 2-$NH_2$-Phenyl |
| 1323 | 1 | Me | 2-$NH_2$-Phenyl |
| 1324 | 2 | Me | 2-$NH_2$-Phenyl |
| 1325 | 3 | Me | 2-$NH_2$-Phenyl |
| 1326 | 4 | Me | 2-$NH_2$-Phenyl |
| 1327 | 1 | $CH_2Ph$ | 2-$NH_2$-Phenyl |
| 1328 | 2 | $CH_2Ph$ | 2-$NH_2$-Phenyl |
| 1329 | 3 | $CH_2Ph$ | 2-$NH_2$-Phenyl |
| 1330 | 4 | $CH_2Ph$ | 2-$NH_2$-Phenyl |
| 1331 | 1 | COMe | 2-$NH_2$-Phenyl |
| 1332 | 2 | COMe | 2-$NH_2$-Phenyl |
| 1333 | 3 | COMe | 2-$NH_2$-Phenyl |
| 1334 | 4 | COMe | 2-$NH_2$-Phenyl |
| 1335 | 1 | $CO_2Me$ | 2-$NH_2$-Phenyl |
| 1336 | 2 | $CO_2Me$ | 2-$NH_2$-Phenyl |
| 1337 | 3 | $CO_2Me$ | 2-$NH_2$-Phenyl |
| 1338 | 4 | $CO_2Me$ | 2-$NH_2$-Phenyl |
| 1339 | 1 | $CO_2tBu$ | 2-$NH_2$-Phenyl |
| 1340 | 2 | $CO_2tBu$ | 2-$NH_2$-Phenyl |
| 1341 | 3 | $CO_2tBu$ | 2-$NH_2$-Phenyl |
| 1342 | 4 | $CO_2tBu$ | 2-$NH_2$-Phenyl |
| 1343 | 1 | CONHMe | 2-$NH_2$-Phenyl |
| 1344 | 2 | CONHMe | 2-$NH_2$-Phenyl |
| 1345 | 3 | CONHMe | 2-$NH_2$-Phenyl |
| 1346 | 4 | CONHMe | 2-$NH_2$-Phenyl |
| 1347 | 1 | $SO_2Me$ | 2-$NH_2$-Phenyl |
| 1348 | 2 | $SO_2Me$ | 2-$NH_2$-Phenyl |
| 1349 | 3 | $SO_2Me$ | 2-$NH_2$-Phenyl |
| 1350 | 4 | $SO_2Me$ | 2-$NH_2$-Phenyl |
| 1351 | 1 | SO2NH2 | 2-$NH_2$-Phenyl |
| 1352 | 2 | $SO_2NH_2$ | 2-$NH_2$-Phenyl |
| 1353 | 3 | $SO_2NH_2$ | 2-$NH_2$-Phenyl |
| 1354 | 4 | $SO_2NH_2$ | 2-$NH_2$-Phenyl |
| 1355 | 1 | H | 2,6-di-Me-Phenyl |
| 1356 | 2 | H | 2,6-di-Me-Phenyl |
| 1357 | 3 | H | 2,6-di-Me-Phenyl |
| 1358 | 4 | H | 2,6-di-Me-Phenyl |
| 1359 | 1 | Me | 2,6-di-Me-Phenyl |
| 1360 | 2 | Me | 2,6-di-Me-Phenyl |
| 1361 | 3 | Me | 2,6-di-Me-Phenyl |
| 1362 | 4 | Me | 2,6-di-Me-Phenyl |
| 1363 | 1 | $CH_2Ph$ | 2,6-di-Me-Phenyl |
| 1364 | 2 | $CH_2Ph$ | 2,6-di-Me-Phenyl |
| 1365 | 3 | $CH_2Ph$ | 2,6-di-Me-Phenyl |
| 1366 | 4 | $CH_2Ph$ | 2,6-di-Me-Phenyl |
| 1367 | 1 | COMe | 2,6-di-Me-Phenyl |
| 1368 | 2 | COMe | 2,6-di-Me-Phenyl |
| 1369 | 3 | COMe | 2,6-di-Me-Phenyl |
| 1370 | 4 | COMe | 2,6-di-Me-Phenyl |
| 1371 | 1 | $CO_2Me$ | 2,6-di-Me-Phenyl |
| 1372 | 2 | $CO_2Me$ | 2,6-di-Me-Phenyl |
| 1373 | 3 | $CO_2Me$ | 2,6-di-Me-Phenyl |
| 1374 | 4 | $CO_2Me$ | 2,6-di-Me-Phenyl |
| 1375 | 1 | $CO_2tBu$ | 2,6-di-Me-Phenyl |
| 1376 | 2 | $CO_2tBu$ | 2,6-di-Me-Phenyl |
| 1377 | 3 | $CO_2tBu$ | 2,6-di-Me-Phenyl |
| 1378 | 4 | $CO_2tBu$ | 2,6-di-Me-Phenyl |
| 1379 | 1 | CONHMe | 2,6-di-Me-Phenyl |
| 1380 | 2 | CONHMe | 2,6-di-Me-Phenyl |
| 1381 | 3 | CONHMe | 2,6-di-Me-Phenyl |
| 1382 | 4 | CONHMe | 2,6-di-Me-Phenyl |
| 1383 | 1 | $SO_2Me$ | 2,6-di-Me-Phenyl |
| 1384 | 2 | $SO_2Me$ | 2,6-di-Me-Phenyl |

TABLE 18-continued

| Entry | n | $R^7$ | $R^3$ |
|---|---|---|---|
| 1385 | 3 | $SO_2Me$ | 2,6-di-Me-Phenyl |
| 1386 | 4 | $SO_2Me$ | 2,6-di-Me-Phenyl |
| 1387 | 1 | $SO_2NH_2$ | 2,6-di-Me-Phenyl |
| 1388 | 2 | $SO_2NH_2$ | 2,6-di-Me-Phenyl |
| 1389 | 3 | $SO_2NH_2$ | 2,6-di-Me-Phenyl |
| 1390 | 4 | $SO_2NH_2$ | 2,6-di-Me-Phenyl |
| 1391 | 1 | H | 2-Ph-Phenyl |
| 1392 | 2 | H | 2-Ph-Phenyl |
| 1393 | 3 | H | 2-Ph-Phenyl |
| 1394 | 4 | H | 2-Ph-Phenyl |
| 1395 | 1 | Me | 2-Ph-Phenyl |
| 1396 | 2 | Me | 2-Ph-Phenyl |
| 1397 | 3 | Me | 2-Ph-Phenyl |
| 1398 | 4 | Me | 2-Ph-Phenyl |
| 1399 | 1 | $CH_2Ph$ | 2-Ph-Phenyl |
| 1400 | 2 | $CH_2Ph$ | 2-Ph-Phenyl |
| 1401 | 3 | $CH_2Ph$ | 2-Ph-Phenyl |
| 1402 | 4 | $CH_2Ph$ | 2-Ph-Phenyl |
| 1403 | 1 | COMe | 2-Ph-Phenyl |
| 1404 | 2 | COMe | 2-Ph-Phenyl |
| 1405 | 3 | COMe | 2-Ph-Phenyl |
| 1406 | 4 | COMe | 2-Ph-Phenyl |
| 1407 | 1 | $CO_2Me$ | 2-Ph-Phenyl |
| 1408 | 2 | $CO_2Me$ | 2-Ph-Phenyl |
| 1409 | 3 | $CO_2Me$ | 2-Ph-Phenyl |
| 1410 | 4 | $CO_2Me$ | 2-Ph-Phenyl |
| 1411 | 1 | $CO_2tBu$ | 2-Ph-Phenyl |
| 1412 | 2 | $CO_2tBu$ | 2-Ph-Phenyl |
| 1413 | 3 | $CO_2tBu$ | 2-Ph-Phenyl |
| 1414 | 4 | $CO_2tBu$ | 2-Ph-Phenyl |
| 1415 | 1 | CONHMe | 2-Ph-Phenyl |
| 1416 | 2 | CONHMe | 2-Ph-Phenyl |
| 1417 | 3 | CONHMe | 2-Ph-Phenyl |
| 1418 | 4 | CONHMe | 2-Ph-Phenyl |
| 1419 | 1 | $SO_2Me$ | 2-Ph-Phenyl |
| 1420 | 2 | $SO_2Me$ | 2-Ph-Phenyl |
| 1421 | 3 | $SO_2Me$ | 2-Ph-Phenyl |
| 1422 | 4 | $SO_2Me$ | 2-Ph-Phenyl |
| 1423 | 1 | $SO_2NH_2$ | 2-Ph-Phenyl |
| 1424 | 2 | $SO_2NH_2$ | 2-Ph-Phenyl |
| 1425 | 3 | $SO_2NH_2$ | 2-Ph-Phenyl |
| 1426 | 4 | $SO_2NH_2$ | 2-Ph-Phenyl |
| 1427 | 1 | H | 4-Ph-Phenyl |
| 1428 | 2 | H | 4-Ph-Phenyl |
| 1429 | 3 | H | 4-Ph-Phenyl |
| 1430 | 4 | H | 4-Ph-Phenyl |
| 1431 | 1 | Me | 4-Ph-Phenyl |
| 1432 | 2 | Me | 4-Ph-Phenyl |
| 1433 | 3 | Me | 4-Ph-Phenyl |
| 1434 | 4 | Me | 4-Ph-Phenyl |
| 1435 | 1 | $CH_2Ph$ | 4-Ph-Phenyl |
| 1436 | 2 | $CH_2Ph$ | 4-Ph-Phenyl |
| 1437 | 3 | $CH_2Ph$ | 4-Ph-Phenyl |
| 1438 | 4 | $CH_2Ph$ | 4-Ph-Phenyl |
| 1439 | 1 | COMe | 4-Ph-Phenyl |
| 1440 | 2 | COMe | 4-Ph-Phenyl |
| 1441 | 3 | COMe | 4-Ph-Phenyl |
| 1442 | 4 | COMe | 4-Ph-Phenyl |
| 1443 | 1 | $CO_2Me$ | 4-Ph-Phenyl |
| 1444 | 2 | $CO_2Me$ | 4-Ph-Phenyl |
| 1445 | 3 | $CO_2Me$ | 4-Ph-Phenyl |
| 1446 | 4 | $CO_2Me$ | 4-Ph-Phenyl |
| 1447 | 1 | $CO_2tBu$ | 4-Ph-Phenyl |
| 1448 | 2 | $CO_2tBu$ | 4-Ph-Phenyl |
| 1449 | 3 | $CO_2tBu$ | 4-Ph-Phenyl |
| 1450 | 4 | $CO_2tBu$ | 4-Ph-Phenyl |
| 1451 | 1 | CONHMe | 4-Ph-Phenyl |
| 1452 | 2 | CONHMe | 4-Ph-Phenyl |
| 1453 | 3 | CONHMe | 4-Ph-Phenyl |
| 1454 | 4 | CONHMe | 4-Ph-Phenyl |
| 1455 | 1 | $SO_2Me$ | 4-Ph-Phenyl |
| 1456 | 2 | $SO_2Me$ | 4-Ph-Phenyl |
| 1457 | 3 | $SO_2Me$ | 4-Ph-Phenyl |
| 1458 | 4 | $SO_2Me$ | 4-Ph-Phenyl |
| 1459 | 1 | $SO_2NH_2$ | 4-Ph-Phenyl |
| 1460 | 2 | $SO_2NH_2$ | 4-Ph-Phenyl |
| 1461 | 3 | $SO_2NH_2$ | 4-Ph-Phenyl |
| 1462 | 4 | $SO_2NH_2$ | 4-Ph-Phenyl |

TABLE 18-continued

| Entry | n | $R^7$ | $R^3$ |
|---|---|---|---|
| 1463 | 1 | H | 3-morpholino-phenyl |
| 1464 | 2 | H | 3-morpholino-phenyl |
| 1465 | 3 | H | 3-morpholino-phenyl |
| 1466 | 4 | H | 3-morpholino-phenyl |
| 1467 | 1 | Me | 3-morpholino-phenyl |
| 1468 | 2 | Me | 3-morpholino-phenyl |
| 1469 | 3 | Me | 3-morpholino-phenyl |
| 1470 | 4 | Me | 3-morpholino-phenyl |
| 1471 | 1 | $CH_2Ph$ | 3-morpholino-phenyl |
| 1472 | 2 | $CH_2Ph$ | 3-morpholino-phenyl |
| 1473 | 3 | $CH_2Ph$ | 3-morpholino-phenyl |
| 1474 | 4 | $CH_2Ph$ | 3-morpholino-phenyl |
| 1475 | 1 | COMe | 3-morpholino-phenyl |
| 1476 | 2 | COMe | 3-morpholino-phenyl |
| 1477 | 3 | COMe | 3-morpholino-phenyl |
| 1478 | 4 | COMe | 3-morpholino-phenyl |
| 1479 | 1 | $CO_2Me$ | 3-morpholino-phenyl |
| 1480 | 2 | $CO_2Me$ | 3-morpholino-phenyl |
| 1481 | 3 | $CO_2Me$ | 3-morpholino-phenyl |
| 1482 | 4 | $CO_2Me$ | 3-morpholino-phenyl |
| 1483 | 1 | $CO_2tBu$ | 3-morpholino-phenyl |
| 1484 | 2 | $CO_2tBu$ | 3-morpholino-phenyl |
| 1485 | 3 | $CO_2tBu$ | 3-morpholino-phenyl |
| 1486 | 4 | $CO_2tBu$ | 3-morpholino-phenyl |
| 1487 | 1 | CONHMe | 3-morpholino-phenyl |
| 1488 | 2 | CONHMe | 3-morpholino-phenyl |
| 1489 | 3 | CONHMe | 3-morpholino-phenyl |
| 1490 | 4 | CONHMe | 3-morpholino-phenyl |
| 1491 | 1 | $SO_2Me$ | 3-morpholino-phenyl |
| 1492 | 2 | $SO_2Me$ | 3-morpholino-phenyl |
| 1493 | 3 | $SO_2Me$ | 3-morpholino-phenyl |
| 1494 | 4 | $SO_2Me$ | 3-morpholino-phenyl |
| 1495 | 1 | $SO_2NH_2$ | 3-morpholino-phenyl |
| 1496 | 2 | $SO_2NH_2$ | 3-morpholino-phenyl |
| 1497 | 3 | $SO_2NH_2$ | 3-morpholino-phenyl |
| 1498 | 4 | $SO_2NH_2$ | 3-morpholino-phenyl |
| 1499 | 1 | Me | 4-morpholino-phenyl |
| 1500 | 2 | Me | 4-morpholino-phenyl |
| 1501 | 3 | Me | 4-morpholino-phenyl |

TABLE 18-continued

| Entry | n | $R^7$ | $R^3$ |
|---|---|---|---|
| 1502 | 4 | Me | 4-morpholino-phenyl |
| 103 | 1 | COMe | 4-morpholino-phenyl |
| 1504 | 2 | COMe | 4-morpholino-phenyl |
| 1505 | 3 | COMe | 4-morpholino-phenyl |
| 1506 | 4 | COMe | 4-morpholino-phenyl |
| 1507 | 1 | $CO_2tBu$ | 4-morpholino-phenyl |
| 1508 | 2 | $CO_2tBu$ | 4-morpholino-phenyl |
| 1509 | 3 | $CO_2tBu$ | 4-morpholino-phenyl |
| 1510 | 4 | $CO_2tBu$ | 4-morpholino-phenyl |
| 1511 | 1 | $SO_2Me$ | 4-morpholino-phenyl |
| 1512 | 2 | $SO_2Me$ | 4-morpholino-phenyl |
| 1513 | 3 | $SO_2Me$ | 4-morpholino-phenyl |
| 1514 | 4 | $SO_2Me$ | 4-morpholino-phenyl |
| 1516 | 1 | H | naphthylen-2-yl |
| 1517 | 2 | H | naphthylen-2-yl |
| 1518 | 3 | H | naphthylen-2-yl |
| 1519 | 4 | H | naphthylen-2-yl |
| 1520 | 1 | Me | naphthylen-2-yl |
| 1521 | 2 | Me | naphthylen-2-yl |
| 1522 | 3 | Me | naphthylen-2-yl |
| 1523 | 4 | Me | naphthylen-2-yl |
| 1524 | 1 | $CH_2Ph$ | naphthylen-2-yl |
| 1525 | 2 | $CH_2Ph$ | naphthylen-2-yl |
| 1526 | 3 | $CH_2Ph$ | naphthylen-2-yl |
| 1527 | 4 | $CH_2Ph$ | naphthylen-2-yl |
| 1528 | 1 | COMe | naphthylen-2-yl |
| 1529 | 2 | COMe | naphthylen-2-yl |
| 1530 | 3 | COMe | naphthylen-2-yl |
| 1531 | 4 | COMe | naphthylen-2-yl |
| 1532 | 1 | $CO_2Me$ | naphthylen-2-yl |
| 1533 | 2 | $CO_2Me$ | naphthylen-2-yl |
| 1534 | 3 | $CO_2Me$ | naphthylen-2-yl |
| 1535 | 4 | $CO_2Me$ | naphthylen-2-yl |
| 1536 | 1 | $CO_2tBu$ | naphthylen-2-yl |
| 1537 | 2 | $CO_2tBu$ | naphthylen-2-yl |
| 1538 | 3 | $CO_2tBu$ | naphthylen-2-yl |
| 1539 | 4 | $CO_2tBu$ | naphthylen-2-yl |
| 1540 | 1 | CONHMe | naphthylen-2-yl |
| 1541 | 2 | CONHMe | naphthylen-2-yl |
| 1542 | 3 | CONHMe | naphthylen-2-yl |
| 1543 | 4 | CONHMe | naphthylen-2-yl |
| 1544 | 1 | $SO_2Me$ | naphthylen-2-yl |
| 1545 | 2 | $SO_2Me$ | naphthylen-2-yl |
| 1546 | 3 | $SO_2Me$ | naphthylen-2-yl |
| 1547 | 4 | $SO_2Me$ | naphthylen-2-yl |
| 1548 | 1 | $SO_2NH_2$ | naphthylen-2-yl |
| 1549 | 2 | $SO_2NH_2$ | naphthylen-2-yl |
| 1550 | 3 | $SO_2NH_2$ | naphthylen-2-yl |
| 1551 | 4 | $SO_2NH_2$ | naphthylen-2-yl |

Exemplary embodiments include compounds having the formula (XXV)

(XXV)

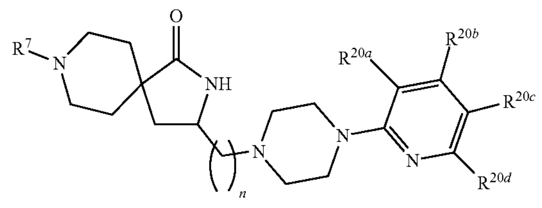

or a pharmaceutically acceptable salt form thereof defined herein below in Table 19.

TABLE 19

| Entry | n | $R^7$ | $R^{20a}$ | $R^{20b}$ | $R^{20c}$ | $R^{20d}$ |
|---|---|---|---|---|---|---|
| 1 | 1 | H | H | H | H | H |
| 2 | 2 | H | H | H | H | H |
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |
| 60 | 4 | $CO_2tBu$ | H | H | OH | H |

TABLE 19-continued

| Entry | n | $R^7$ | $R^{20a}$ | $R^{20b}$ | $R^{20c}$ | $R^{20d}$ |
|---|---|---|---|---|---|---|
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |
| 79 | 3 | Me | H | H | OMe | H |
| 80 | 4 | Me | H | H | OMe | H |
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |
| 138 | 2 | $SO_2Me$ | H | H | Me | H |

TABLE 19-continued

| Entry | n | $R^7$ | $R^{20a}$ | $R^{20b}$ | $R^{20c}$ | $R^{20d}$ |
|---|---|---|---|---|---|---|
| 139 | 3 | SO2Me | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |
| 157 | 1 | COMe | H | H | $CF_3$ | H |
| 158 | 2 | COMe | H | H | $CF_3$ | H |
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | $CO_2tBu$ | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |
| 216 | 4 | $SO_2NH_2$ | H | H | F | H |

TABLE 19-continued

| Entry | n | $R^7$ | $R^{20a}$ | $R^{20b}$ | $R^{20c}$ | $R^{20d}$ |
|---|---|---|---|---|---|---|
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |
| 235 | 3 | $CO_2Me$ | H | H | Cl | H |
| 236 | 4 | $CO_2Me$ | H | H | Cl | H |
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | v | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | $CH_2Ph$ | H | H | CN | H |
| 266 | 2 | COMe | H | H | CN | H |
| 267 | 3 | COMe | H | H | CN | H |
| 268 | 4 | COMe | H | H | CN | H |
| 269 | 1 | COMe | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2Me$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |
| 277 | 1 | $CO_2tBu$ | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | CONHMe | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2Me$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | $SO_2NH_2$ | H | OH | H | H |
| 290 | 2 | H | H | OH | H | H |
| 291 | 3 | H | H | OH | H | H |
| 292 | 4 | H | H | OH | H | H |
| 293 | 1 | Me | H | OH | H | H |
| 294 | 2 | Me | H | OH | H | H |

TABLE 19-continued

| Entry | n | $R^7$ | $R^{20a}$ | $R^{20b}$ | $R^{20c}$ | $R^{20d}$ |
|---|---|---|---|---|---|---|
| 295 | 3 | Me | H | OH | H | H |
| 296 | 4 | Me | H | OH | H | H |
| 297 | 1 | $CH_2Ph$ | H | OH | H | H |
| 298 | 2 | $CH_2Ph$ | H | OH | H | H |
| 299 | 3 | $CH_2Ph$ | H | OH | H | H |
| 300 | 4 | $CH_2Ph$ | H | OH | H | H |
| 301 | 1 | COMe | H | OH | H | H |
| 302 | 2 | COMe | H | OH | H | H |
| 303 | 3 | COMe | H | OH | H | H |
| 304 | 4 | COMe | H | OH | H | H |
| 305 | 1 | $CO_2Me$ | H | OH | H | H |
| 306 | 2 | $CO_2Me$ | H | OH | H | H |
| 307 | 3 | $CO_2Me$ | H | OH | H | H |
| 308 | 4 | $CO_2Me$ | H | OH | H | H |
| 309 | 1 | $CO_2tBu$ | H | OH | H | H |
| 310 | 2 | $CO_2tBu$ | H | OH | H | H |
| 311 | 3 | $CO_2tBu$ | H | OH | H | H |
| 312 | 4 | $CO_2tBu$ | H | OH | H | H |
| 313 | 1 | CONHMe | H | OH | H | H |
| 314 | 2 | CONHMe | H | OH | H | H |
| 315 | 3 | CONHMe | H | OH | H | H |
| 316 | 4 | CONHMe | H | OH | H | H |
| 317 | 1 | $SO_2Me$ | H | OH | H | H |
| 318 | 2 | $SO_2Me$ | H | OH | H | H |
| 319 | 3 | $SO_2Me$ | H | OH | H | H |
| 320 | 4 | $SO_2Me$ | H | OH | H | H |
| 321 | 1 | $SO_2NH_2$ | H | OH | H | H |
| 322 | 2 | $SO_2NH_2$ | H | OH | H | H |
| 323 | 3 | $SO_2NH_2$ | H | OH | H | H |
| 324 | 4 | $SO_2NH_2$ | H | OH | H | H |
| 325 | 1 | H | H | OMe | H | H |
| 326 | 2 | H | H | OMe | H | H |
| 327 | 3 | H | H | OMe | H | H |
| 328 | 4 | H | H | OMe | H | H |
| 329 | 1 | Me | H | OMe | H | H |
| 330 | 2 | Me | H | OMe | H | H |
| 331 | 3 | Me | H | OMe | H | H |
| 332 | 4 | Me | H | OMe | H | H |
| 333 | 1 | $CH_2Ph$ | H | OMe | H | H |
| 334 | 2 | $CH_2Ph$ | H | OMe | H | H |
| 335 | 3 | $CH_2Ph$ | H | OMe | H | H |
| 336 | 4 | $CH_2Ph$ | H | OMe | H | H |
| 337 | 1 | COMe | H | OMe | H | H |
| 338 | 2 | COMe | H | OMe | H | H |
| 339 | 3 | COMe | H | OMe | H | H |
| 340 | 4 | COMe | H | OMe | H | H |
| 341 | 1 | $CO_2Me$ | H | OMe | H | H |
| 342 | 2 | $CO_2Me$ | H | OMe | H | H |
| 343 | 3 | $CO_2Me$ | H | OMe | H | H |
| 344 | 4 | $CO_2Me$ | H | OMe | H | H |
| 345 | 1 | $CO_2tBu$ | H | OMe | H | H |
| 346 | 2 | $CO_2tBu$ | H | OMe | H | H |
| 347 | 3 | $CO_2tBu$ | H | OMe | H | H |
| 348 | 4 | $CO_2tBu$ | H | OMe | H | H |
| 349 | 1 | CONHMe | H | OMe | H | H |
| 350 | 2 | CONHMe | H | OMe | H | H |
| 351 | 3 | CONHMe | H | OMe | H | H |
| 352 | 4 | CONHMe | H | OMe | H | H |
| 353 | 1 | $SO_2Me$ | H | OMe | H | H |
| 354 | 2 | $SO_2Me$ | H | OMe | H | H |
| 355 | 3 | $SO_2Me$ | H | OMe | H | H |
| 356 | 4 | $SO_2Me$ | H | OMe | H | H |
| 357 | 1 | $SO_2NH_2$ | H | OMe | H | H |
| 358 | 2 | $SO_2NH_2$ | H | OMe | H | H |
| 359 | 3 | $SO_2NH_2$ | H | OMe | H | H |
| 360 | 4 | $SO_2NH_2$ | H | OMe | H | H |
| 361 | 1 | H | H | Me | H | H |
| 362 | 2 | H | H | Me | H | H |
| 363 | 3 | H | H | Me | H | H |
| 364 | 4 | H | H | Me | H | H |
| 365 | 1 | Me | H | Me | H | H |
| 366 | 2 | Me | H | Me | H | H |
| 367 | 3 | Me | H | Me | H | H |
| 368 | 4 | Me | H | Me | H | H |
| 369 | 1 | $CH_2Ph$ | H | Me | H | H |
| 370 | 2 | $CH_2Ph$ | H | Me | H | H |
| 371 | 3 | $CH_2Ph$ | H | Me | H | H |
| 372 | 4 | $CH_2Ph$ | H | Me | H | H |

TABLE 19-continued

| Entry | n | $R^7$ | $R^{20a}$ | $R^{20b}$ | $R^{20c}$ | $R^{20d}$ |
|---|---|---|---|---|---|---|
| 373 | 1 | COMe | H | Me | H | H |
| 374 | 2 | COMe | H | Me | H | H |
| 375 | 3 | COMe | H | Me | H | H |
| 376 | 4 | COMe | H | Me | H | H |
| 377 | 1 | $CO_2Me$ | H | Me | H | H |
| 378 | 2 | $CO_2Me$ | H | Me | H | H |
| 379 | 3 | $CO_2Me$ | H | Me | H | H |
| 380 | 4 | $CO_2Me$ | H | Me | H | H |
| 381 | 1 | $CO_2tBu$ | H | Me | H | H |
| 382 | 2 | $CO_2tBu$ | H | Me | H | H |
| 383 | 3 | $CO_2tBu$ | H | Me | H | H |
| 384 | 4 | $CO_2tBu$ | H | Me | H | H |
| 385 | 1 | CONHMe | H | Me | H | H |
| 386 | 2 | CONHMe | H | Me | H | H |
| 387 | 3 | CONHMe | H | Me | H | H |
| 388 | 4 | CONHMe | H | Me | H | H |
| 389 | 1 | $SO_2Me$ | H | Me | H | H |
| 390 | 2 | $SO_2Me$ | H | Me | H | H |
| 391 | 3 | $SO_2Me$ | H | Me | H | H |
| 392 | 4 | $SO_2Me$ | H | Me | H | H |
| 393 | 1 | $SO_2NH_2$ | H | Me | H | H |
| 394 | 2 | $SO_2NH_2$ | H | Me | H | H |
| 395 | 3 | $SO_2NH_2$ | H | Me | H | H |
| 396 | 4 | $SO_2NH_2$ | H | Me | H | H |
| 397 | 1 | H | H | $CF_3$ | H | H |
| 398 | 2 | H | H | $CF_3$ | H | H |
| 399 | 3 | H | H | $CF_3$ | H | H |
| 400 | 4 | H | H | $CF_3$ | H | H |
| 401 | 1 | Me | H | $CF_3$ | H | H |
| 402 | 2 | Me | H | $CF_3$ | H | H |
| 403 | 3 | Me | H | $CF_3$ | H | H |
| 404 | 4 | Me | H | $CF_3$ | H | H |
| 405 | 1 | $CH_2Ph$ | H | $CF_3$ | H | H |
| 406 | 2 | $CH_2Ph$ | H | $CF_3$ | H | H |
| 407 | 3 | $CH_2Ph$ | H | $CF_3$ | H | H |
| 408 | 4 | $CH_2Ph$ | H | $CF_3$ | H | H |
| 409 | 1 | COMe | H | $CF_3$ | H | H |
| 410 | 2 | COMe | H | $CF_3$ | H | H |
| 411 | 3 | COMe | H | $CF_3$ | H | H |
| 412 | 4 | COMe | H | $CF_3$ | H | H |
| 413 | 1 | $CO_2Me$ | H | $CF_3$ | H | H |
| 414 | 2 | $CO_2Me$ | H | $CF_3$ | H | H |
| 415 | 3 | $CO_2Me$ | H | $CF_3$ | H | H |
| 416 | 4 | $CO_2Me$ | H | $CF_3$ | H | H |
| 417 | 1 | $CO_2tBu$ | H | $CF_3$ | H | H |
| 418 | 2 | $CO_2tBu$ | H | $CF_3$ | H | H |
| 419 | 3 | $CO_2tBu$ | H | $CF_3$ | H | H |
| 420 | 4 | $CO_2tBu$ | H | $CF_3$ | H | H |
| 421 | 1 | CONHMe | H | $CF_3$ | H | H |
| 422 | 2 | CONHMe | H | $CF_3$ | H | H |
| 423 | 3 | CONHMe | H | $CF_3$ | H | H |
| 424 | 4 | CONHMe | H | $CF_3$ | H | H |
| 425 | 1 | $SO_2Me$ | H | $CF_3$ | H | H |
| 426 | 2 | $SO_2Me$ | H | $CF_3$ | H | H |
| 427 | 3 | $SO_2Me$ | H | $CF_3$ | H | H |
| 428 | 4 | $SO_2Me$ | H | $CF_3$ | H | H |
| 429 | 1 | $SO_2NH_2$ | H | $CF_3$ | H | H |
| 430 | 2 | $SO_2NH_2$ | H | $CF_3$ | H | H |
| 431 | 3 | $SO_2NH_2$ | H | $CF_3$ | H | H |
| 432 | 4 | $SO_2NH_2$ | H | $CF_3$ | H | H |
| 433 | 1 | H | H | F | H | H |
| 434 | 2 | H | H | F | H | H |
| 435 | 3 | H | H | F | H | H |
| 436 | 3 | H | H | F | H | H |
| 437 | 1 | Me | H | F | H | H |
| 438 | 2 | Me | H | F | H | H |
| 439 | 3 | Me | H | F | H | H |
| 440 | 4 | Me | H | F | H | H |
| 441 | 1 | $CH_2Ph$ | H | F | H | H |
| 442 | 2 | $CH_2Ph$ | H | F | H | H |
| 443 | 3 | $CH_2Ph$ | H | F | H | H |
| 444 | 4 | $CH_2Ph$ | H | F | H | H |
| 445 | 1 | COMe | H | F | H | H |
| 446 | 2 | COMe | H | F | H | H |
| 447 | 3 | COMe | H | F | H | H |
| 448 | 4 | COMe | H | F | H | H |
| 449 | 1 | $CO_2Me$ | H | F | H | H |
| 450 | 2 | $CO_2Me$ | H | F | H | H |

TABLE 19-continued

| Entry | n | $R^7$ | $R^{20a}$ | $R^{20b}$ | $R^{20c}$ | $R^{20d}$ |
|---|---|---|---|---|---|---|
| 451 | 3 | $CO_2Me$ | H | F | H | H |
| 452 | 4 | $CO_2Me$ | H | F | H | H |
| 453 | 1 | $CO_2tBu$ | H | F | H | H |
| 454 | 2 | $CO_2tBu$ | H | F | H | H |
| 455 | 3 | $CO_2tBu$ | H | F | H | H |
| 456 | 4 | $CO_2tBu$ | H | F | H | H |
| 457 | 1 | CONHMe | H | F | H | H |
| 458 | 2 | CONHMe | H | F | H | H |
| 459 | 3 | CONHMe | H | F | H | H |
| 460 | 4 | CONHMe | H | F | H | H |
| 461 | 1 | $SO_2Me$ | H | F | H | H |
| 462 | 2 | $SO_2Me$ | H | F | H | H |
| 463 | 3 | $SO_2Me$ | H | F | H | H |
| 464 | 4 | $SO_2Me$ | H | F | H | H |
| 465 | 1 | $SO_2NH_2$ | H | F | H | H |
| 466 | 2 | $SO_2NH_2$ | H | F | H | H |
| 467 | 3 | $SO_2NH_2$ | H | F | H | H |
| 468 | 4 | $SO_2NH_2$ | H | F | H | H |
| 469 | 1 | H | H | Cl | H | H |
| 470 | 2 | H | H | Cl | H | H |
| 471 | 3 | H | H | Cl | H | H |
| 472 | 4 | H | H | Cl | H | H |
| 473 | 1 | Me | H | Cl | H | H |
| 474 | 2 | Me | H | Cl | H | H |
| 475 | 3 | Me | H | Cl | H | H |
| 476 | 4 | Me | H | Cl | H | H |
| 477 | 1 | $CH_2Ph$ | H | Cl | H | H |
| 478 | 2 | $CH_2Ph$ | H | Cl | H | H |
| 479 | 3 | $CH_2Ph$ | H | Cl | H | H |
| 480 | 4 | $CH_2Ph$ | H | Cl | H | H |
| 481 | 1 | COMe | H | Cl | H | H |
| 482 | 2 | COMe | H | Cl | H | H |
| 483 | 3 | COMe | H | Cl | H | H |
| 484 | 4 | COMe | H | Cl | H | H |
| 485 | 1 | $CO_2Me$ | H | Cl | H | H |
| 486 | 2 | $CO_2Me$ | H | Cl | H | H |
| 487 | 3 | $CO_2Me$ | H | Cl | H | H |
| 488 | 4 | $CO_2Me$ | H | Cl | H | H |
| 489 | 1 | $CO_2tBu$ | H | Cl | H | H |
| 490 | 2 | $CO_2tBu$ | H | Cl | H | H |
| 491 | 3 | $CO_2tBu$ | H | Cl | H | H |
| 492 | 4 | $CO_2tBu$ | H | Cl | H | H |
| 493 | 1 | CONHMe | H | Cl | H | H |
| 494 | 2 | CONHMe | H | Cl | H | H |
| 495 | 3 | CONHMe | H | Cl | H | H |
| 496 | 4 | CONHMe | H | Cl | H | H |
| 497 | 1 | $SO_2Me$ | H | Cl | H | H |
| 498 | 2 | $SO_2Me$ | H | Cl | H | H |
| 499 | 3 | $SO_2Me$ | H | Cl | H | H |
| 500 | 4 | $SO_2Me$ | H | Cl | H | H |
| 501 | 1 | $SO_2NH_2$ | H | Cl | H | H |
| 502 | 2 | $SO_2NH_2$ | H | Cl | H | H |
| 503 | 3 | $SO_2NH_2$ | H | Cl | H | H |
| 504 | 4 | $SO_2NH_2$ | H | Cl | H | H |
| 505 | 1 | H | H | CN | H | H |
| 506 | 2 | H | H | CN | H | H |
| 507 | 3 | H | H | CN | H | H |
| 508 | 4 | H | H | CN | H | H |
| 509 | 1 | Me | H | CN | H | H |
| 510 | 2 | Me | H | CN | H | H |
| 511 | 3 | Me | H | CN | H | H |
| 512 | 4 | Me | H | CN | H | H |
| 513 | 1 | $CH_2Ph$ | H | CN | H | H |
| 514 | 2 | $CH_2Ph$ | H | CN | H | H |
| 515 | 3 | $CH_2Ph$ | H | CN | H | H |
| 516 | 4 | $CH_2Ph$ | H | CN | H | H |
| 517 | 1 | COMe | H | CN | H | H |
| 518 | 2 | COMe | H | CN | H | H |
| 519 | 3 | COMe | H | CN | H | H |
| 520 | 4 | COMe | H | CN | H | H |
| 521 | 1 | $CO_2Me$ | H | CN | H | H |
| 522 | 2 | $CO_2Me$ | H | CN | H | H |
| 523 | 3 | $CO_2Me$ | H | CN | H | H |
| 524 | 4 | $CO_2Me$ | H | CN | H | H |
| 525 | 1 | $CO_2tBu$ | H | CN | H | H |
| 526 | 2 | $CO_2tBu$ | H | CN | H | H |
| 527 | 3 | $CO_2tBu$ | H | CN | H | H |
| 528 | 4 | $CO_2tBu$ | H | CN | H | H |

TABLE 19-continued

| Entry | n | $R^7$ | $R^{20a}$ | $R^{20b}$ | $R^{20c}$ | $R^{20d}$ |
|---|---|---|---|---|---|---|
| 529 | 1 | CONHMe | H | CN | H | H |
| 530 | 2 | CONHMe | H | CN | H | H |
| 531 | 3 | CONHMe | H | CN | H | H |
| 532 | 4 | CONHMe | H | CN | H | H |
| 533 | 1 | $SO_2Me$ | H | CN | H | H |
| 534 | 2 | $SO_2Me$ | H | CN | H | H |
| 535 | 3 | $SO_2Me$ | H | CN | H | H |
| 536 | 4 | $SO_2Me$ | H | CN | H | H |
| 537 | 1 | $SO_2NH_2$ | H | CN | H | H |
| 538 | 2 | $SO_2NH_2$ | H | CN | H | H |
| 539 | 3 | $SO_2NH_2$ | H | CN | H | H |
| 540 | 4 | $SO_2NH_2$ | H | CN | H | H |
| 541 | 1 | H | OH | H | H | H |
| 542 | 2 | H | OH | H | H | H |
| 543 | 3 | H | OH | H | H | H |
| 544 | 4 | H | OH | H | H | H |
| 545 | 1 | Me | OH | H | H | H |
| 546 | 2 | Me | OH | H | H | H |
| 547 | 3 | Me | OH | H | H | H |
| 548 | 4 | Me | OH | H | H | H |
| 549 | 1 | $CH_2Ph$ | OH | H | H | H |
| 550 | 2 | $CH_2Ph$ | OH | H | H | H |
| 551 | 3 | $CH_2Ph$ | OH | H | H | H |
| 552 | 4 | $CH_2Ph$ | OH | H | H | H |
| 553 | 1 | COMe | OH | H | H | H |
| 554 | 2 | COMe | OH | H | H | H |
| 555 | 3 | COMe | OH | H | H | H |
| 556 | 4 | COMe | OH | H | H | H |
| 557 | 1 | $CO_2Me$ | OH | H | H | H |
| 558 | 2 | $CO_2Me$ | OH | H | H | H |
| 559 | 3 | $CO_2Me$ | OH | H | H | H |
| 560 | 4 | $CO_2Me$ | OH | H | H | H |
| 561 | 1 | $CO_2tBu$ | OH | H | H | H |
| 562 | 2 | $CO_2tBu$ | OH | H | H | H |
| 563 | 3 | $CO_2tBu$ | OH | H | H | H |
| 564 | 4 | $CO_2tBu$ | OH | H | H | H |
| 565 | 1 | CONHMe | OH | H | H | H |
| 566 | 2 | CONHMe | OH | H | H | H |
| 567 | 3 | CONHMe | OH | H | H | H |
| 568 | 4 | CONHMe | OH | H | H | H |
| 569 | 1 | $SO_2Me$ | OH | H | H | H |
| 570 | 2 | $SO_2Me$ | OH | H | H | H |
| 571 | 3 | $SO_2Me$ | OH | H | H | H |
| 572 | 4 | $SO_2Me$ | OH | H | H | H |
| 573 | 1 | $SO_2NH_2$ | OH | H | H | H |
| 574 | 2 | $SO_2NH_2$ | OH | H | H | H |
| 575 | 3 | $SO_2NH_2$ | OH | H | H | H |
| 576 | 4 | $SO_2NH_2$ | OH | H | H | H |
| 577 | 1 | H | OMe | H | H | H |
| 578 | 2 | H | OMe | H | H | H |
| 579 | 3 | H | OMe | H | H | H |
| 580 | 4 | H | OMe | H | H | H |
| 581 | 1 | Me | OMe | H | H | H |
| 582 | 2 | Me | OMe | H | H | H |
| 583 | 3 | Me | OMe | H | H | H |
| 584 | 4 | Me | OMe | H | H | H |
| 585 | 1 | $CH_2Ph$ | OMe | H | H | H |
| 586 | 2 | $CH_2Ph$ | OMe | H | H | H |
| 587 | 3 | $CH_2Ph$ | OMe | H | H | H |
| 588 | 4 | $CH_2Ph$ | OMe | H | H | H |
| 589 | 1 | COMe | OMe | H | H | H |
| 590 | 2 | COMe | OMe | H | H | H |
| 591 | 3 | COMe | OMe | H | H | H |
| 592 | 4 | COMe | OMe | H | H | H |
| 593 | 1 | $CO_2Me$ | OMe | H | H | H |
| 594 | 2 | $CO_2Me$ | OMe | H | H | H |
| 595 | 3 | $CO_2Me$ | OMe | H | H | H |
| 596 | 4 | $CO_2Me$ | OMe | H | H | H |
| 597 | 1 | $CO_2tBu$ | OMe | H | H | H |
| 598 | 2 | $CO_2tBu$ | OMe | H | H | H |
| 599 | 3 | $CO_2tBu$ | OMe | H | H | H |
| 600 | 4 | $CO_2tBu$ | OMe | H | H | H |
| 601 | 1 | CONHMe | OMe | H | H | H |
| 602 | 2 | CONHMe | OMe | H | H | H |
| 603 | 3 | CONHMe | OMe | H | H | H |
| 604 | 4 | CONHMe | OMe | H | H | H |
| 605 | 1 | $SO_2Me$ | OMe | H | H | H |
| 606 | 2 | $SO_2Me$ | OMe | H | H | H |

TABLE 19-continued

| Entry | n | $R^7$ | $R^{20a}$ | $R^{20b}$ | $R^{20c}$ | $R^{20d}$ |
|---|---|---|---|---|---|---|
| 607 | 3 | $SO_2Me$ | OMe | H | H | H |
| 608 | 4 | $SO_2Me$ | OMe | H | H | H |
| 609 | 1 | $SO_2NH_2$ | OMe | H | H | H |
| 610 | 2 | $SO_2NH_2$ | OMe | H | H | H |
| 611 | 3 | $SO_2NH_2$ | OMe | H | H | H |
| 612 | 4 | $SO_2NH_2$ | OMe | H | H | H |
| 613 | 1 | H | Me | H | H | H |
| 614 | 2 | H | Me | H | H | H |
| 615 | 3 | H | Me | H | H | H |
| 616 | 4 | H | Me | H | H | H |
| 617 | 1 | Me | Me | H | H | H |
| 618 | 2 | Me | Me | H | H | H |
| 619 | 3 | Me | Me | H | H | H |
| 620 | 4 | Me | Me | H | H | H |
| 621 | 1 | $CH_2Ph$ | Me | H | H | H |
| 622 | 2 | $CH_2Ph$ | Me | H | H | H |
| 623 | 3 | $CH_2Ph$ | Me | H | H | H |
| 624 | 4 | $CH_2Ph$ | Me | H | H | H |
| 625 | 1 | COMe | Me | H | H | H |
| 626 | 2 | COMe | Me | H | H | H |
| 627 | 3 | COMe | Me | H | H | H |
| 628 | 4 | COMe | Me | H | H | H |
| 629 | 1 | $CO_2Me$ | Me | H | H | H |
| 630 | 2 | $CO_2Me$ | Me | H | H | H |
| 631 | 3 | $CO_2Me$ | Me | H | H | H |
| 632 | 4 | $CO_2Me$ | Me | H | H | H |
| 633 | 1 | $CO_2tBu$ | Me | H | H | H |
| 634 | 2 | $CO_2tBu$ | Me | H | H | H |
| 635 | 3 | $CO_2tBu$ | Me | H | H | H |
| 636 | 4 | $CO_2tBu$ | Me | H | H | H |
| 637 | 1 | CONHMe | Me | H | H | H |
| 638 | 2 | CONHMe | Me | H | H | H |
| 639 | 3 | CONHMe | Me | H | H | H |
| 640 | 4 | CONHMe | Me | H | H | H |
| 641 | 1 | $SO_2Me$ | Me | H | H | H |
| 642 | 2 | $SO_2Me$ | Me | H | H | H |
| 643 | 3 | $SO_2Me$ | Me | H | H | H |
| 644 | 4 | $SO_2Me$ | Me | H | H | H |
| 645 | 1 | $SO_2NH_2$ | Me | H | H | H |
| 646 | 2 | $SO_2NH_2$ | Me | H | H | H |
| 647 | 3 | $SO_2NH_2$ | Me | H | H | H |
| 648 | 4 | $SO_2NH_2$ | Me | H | H | H |
| 649 | 1 | H | $CF_3$ | H | H | H |
| 650 | 2 | H | $CF_3$ | H | H | H |
| 651 | 3 | H | $CF_3$ | H | H | H |
| 652 | 4 | H | $CF_3$ | H | H | H |
| 653 | 1 | Me | $CF_3$ | H | H | H |
| 654 | 2 | Me | $CF_3$ | H | H | H |
| 655 | 3 | Me | $CF_3$ | H | H | H |
| 656 | 4 | Me | $CF_3$ | H | H | H |
| 657 | 1 | $CH_2Ph$ | $CF_3$ | H | H | H |
| 658 | 2 | $CH_2Ph$ | $CF_3$ | H | H | H |
| 659 | 3 | $CH_2Ph$ | $CF_3$ | H | H | H |
| 660 | 4 | $CH_2Ph$ | $CF_3$ | H | H | H |
| 661 | 1 | COMe | $CF_3$ | H | H | H |
| 662 | 2 | COMe | $CF_3$ | H | H | H |
| 663 | 3 | COMe | $CF_3$ | H | H | H |
| 664 | 4 | COMe | $CF_3$ | H | H | H |
| 665 | 1 | $CO_2Me$ | $CF_3$ | H | H | H |
| 666 | 2 | $CO_2Me$ | $CF_3$ | H | H | H |
| 667 | 3 | $CO_2Me$ | $CF_3$ | H | H | H |
| 668 | 4 | $CO_2Me$ | $CF_3$ | H | H | H |
| 669 | 1 | $CO_2tBu$ | $CF_3$ | H | H | H |
| 670 | 2 | $CO_2tBu$ | $CF_3$ | H | H | H |
| 671 | 3 | $CO_2tBu$ | $CF_3$ | H | H | H |
| 672 | 4 | $CO_2tBu$ | $CF_3$ | H | H | H |
| 673 | 1 | CONHMe | $CF_3$ | H | H | H |
| 674 | 2 | CONHMe | $CF_3$ | H | H | H |
| 675 | 3 | CONHMe | $CF_3$ | H | H | H |
| 676 | 4 | CONHMe | $CF_3$ | H | H | H |
| 677 | 1 | $SO_2Me$ | $CF_3$ | H | H | H |
| 678 | 2 | $SO_2Me$ | $CF_3$ | H | H | H |
| 679 | 3 | $SO_2Me$ | $CF_3$ | H | H | H |
| 680 | 4 | $SO_2Me$ | $CF_3$ | H | H | H |
| 681 | 1 | $SO_2NH_2$ | $CF_3$ | H | H | H |
| 682 | 2 | $SO_2NH_2$ | $CF_3$ | H | H | H |
| 683 | 3 | $SO_2NH_2$ | $CF_3$ | H | H | H |
| 684 | 4 | $SO_2NH_2$ | $CF_3$ | H | H | H |

TABLE 19-continued

| Entry | n | $R^7$ | $R^{20a}$ | $R^{20b}$ | $R^{20c}$ | $R^{20d}$ |
|---|---|---|---|---|---|---|
| 685 | 1 | H | F | H | H | H |
| 686 | 2 | H | F | H | H | H |
| 687 | 3 | H | F | H | H | H |
| 688 | 3 | H | F | H | H | H |
| 689 | 1 | Me | F | H | H | H |
| 690 | 2 | Me | F | H | H | H |
| 691 | 3 | Me | F | H | H | H |
| 692 | 4 | Me | F | H | H | H |
| 693 | 1 | $CH_2Ph$ | F | H | H | H |
| 694 | 2 | $CH_2Ph$ | F | H | H | H |
| 695 | 3 | $CH_2Ph$ | F | H | H | H |
| 696 | 4 | $CH_2Ph$ | F | H | H | H |
| 697 | 1 | COMe | F | H | H | H |
| 698 | 2 | COMe | F | H | H | H |
| 699 | 3 | COMe | F | H | H | H |
| 700 | 4 | COMe | F | H | H | H |
| 701 | 1 | $CO_2Me$ | F | H | H | H |
| 702 | 2 | $CO_2Me$ | F | H | H | H |
| 703 | 3 | $CO_2Me$ | F | H | H | H |
| 704 | 4 | $CO_2Me$ | F | H | H | H |
| 705 | 1 | $CO_2tBu$ | F | H | H | H |
| 706 | 2 | $CO_2tBu$ | F | H | H | H |
| 707 | 3 | $CO_2tBu$ | F | H | H | H |
| 708 | 4 | $CO_2tBu$ | F | H | H | H |
| 709 | 1 | CONHMe | F | H | H | H |
| 710 | 2 | CONHMe | F | H | H | H |
| 711 | 3 | CONHMe | F | H | H | H |
| 712 | 4 | CONHMe | F | H | H | H |
| 713 | 1 | $SO_2Me$ | F | H | H | H |
| 714 | 2 | $SO_2Me$ | F | H | H | H |
| 715 | 3 | $SO_2Me$ | F | H | H | H |
| 716 | 4 | $SO_2Me$ | F | H | H | H |
| 717 | 1 | $SO_2NH_2$ | F | H | H | H |
| 718 | 2 | $SO_2NH_2$ | F | H | H | H |
| 719 | 3 | $SO_2NH_2$ | F | H | H | H |
| 720 | 4 | $SO_2NH_2$ | F | H | H | H |
| 721 | 1 | H | Cl | H | H | H |
| 722 | 2 | H | Cl | H | H | H |
| 723 | 3 | H | Cl | H | H | H |
| 724 | 4 | H | Cl | H | H | H |
| 725 | 1 | Me | Cl | H | H | H |
| 726 | 2 | Me | Cl | H | H | H |
| 727 | 3 | Me | Cl | H | H | H |
| 728 | 4 | Me | Cl | H | H | H |
| 729 | 1 | $CH_2Ph$ | Cl | H | H | H |
| 730 | 2 | $CH_2Ph$ | Cl | H | H | H |
| 731 | 3 | $CH_2Ph$ | Cl | H | H | H |
| 732 | 4 | $CH_2Ph$ | Cl | H | H | H |
| 733 | 1 | COMe | Cl | H | H | H |
| 734 | 2 | COMe | Cl | H | H | H |
| 735 | 3 | COMe | Cl | H | H | H |
| 736 | 4 | COMe | Cl | H | H | H |
| 737 | 1 | $CO_2Me$ | Cl | H | H | H |
| 738 | 2 | $CO_2Me$ | Cl | H | H | H |
| 739 | 3 | $CO_2Me$ | Cl | H | H | H |
| 740 | 4 | $CO_2Me$ | Cl | H | H | H |
| 741 | 1 | $CO_2tBu$ | Cl | H | H | H |
| 742 | 2 | $CO_2tBu$ | Cl | H | H | H |
| 743 | 3 | $CO_2tBu$ | Cl | H | H | H |
| 744 | 4 | $CO_2tBu$ | Cl | H | H | H |
| 745 | 1 | CONHMe | Cl | H | H | H |
| 746 | 2 | CONHMe | Cl | H | H | H |
| 747 | 3 | CONHMe | Cl | H | H | H |
| 748 | 4 | CONHMe | Cl | H | H | H |
| 749 | 1 | $SO_2Me$ | Cl | H | H | H |
| 750 | 2 | $SO_2Me$ | Cl | H | H | H |
| 751 | 3 | $SO_2Me$ | Cl | H | H | H |
| 752 | 4 | $SO_2Me$ | Cl | H | H | H |
| 753 | 1 | $SO_2NH_2$ | Cl | H | H | H |
| 754 | 2 | $SO_2NH_2$ | Cl | H | H | H |
| 755 | 3 | $SO_2NH_2$ | Cl | H | H | H |
| 756 | 4 | $SO_2NH_2$ | Cl | H | H | H |
| 757 | 1 | H | CN | H | H | H |
| 758 | 2 | H | CN | H | H | H |
| 759 | 3 | H | CN | H | H | H |
| 760 | 4 | H | CN | H | H | H |
| 761 | 1 | Me | CN | H | H | H |
| 762 | 2 | Me | CN | H | H | H |

TABLE 19-continued

| Entry | n | $R^7$ | $R^{20a}$ | $R^{20b}$ | $R^{20c}$ | $R^{20d}$ |
|---|---|---|---|---|---|---|
| 763 | 3 | Me | CN | H | H | H |
| 764 | 4 | Me | CN | H | H | H |
| 765 | 1 | $CH_2Ph$ | CN | H | H | H |
| 766 | 2 | $CH_2Ph$ | CN | H | H | H |
| 767 | 3 | $CH_2Ph$ | CN | H | H | H |
| 768 | 4 | $CH_2Ph$ | CN | H | H | H |
| 769 | 1 | COMe | CN | H | H | H |
| 770 | 2 | COMe | CN | H | H | H |
| 771 | 3 | COMe | CN | H | H | H |
| 772 | 4 | COMe | CN | H | H | H |
| 773 | 1 | $CO_2Me$ | CN | H | H | H |
| 774 | 2 | $CO_2Me$ | CN | H | H | H |
| 775 | 3 | $CO_2Me$ | CN | H | H | H |
| 776 | 4 | $CO_2Me$ | CN | H | H | H |
| 777 | 1 | $CO_2tBu$ | CN | H | H | H |
| 778 | 2 | $CO_2tBu$ | CN | H | H | H |
| 779 | 3 | $CO_2tBu$ | CN | H | H | H |
| 780 | 4 | $CO_2tBu$ | CN | H | H | H |
| 781 | 1 | CONHMe | CN | H | H | H |
| 782 | 2 | CONHMe | CN | H | H | H |
| 783 | 3 | CONHMe | CN | H | H | H |
| 784 | 4 | CONHMe | CN | H | H | H |
| 785 | 1 | $SO_2Me$ | CN | H | H | H |
| 786 | 2 | $SO_2Me$ | CN | H | H | H |
| 787 | 3 | $SO_2Me$ | CN | H | H | H |
| 788 | 4 | $SO_2Me$ | CN | H | H | H |
| 789 | 1 | $SO_2NH_2$ | CN | H | H | H |
| 790 | 2 | $SO_2NH_2$ | CN | H | H | H |
| 791 | 3 | $SO_2NH_2$ | CN | H | H | H |
| 792 | 4 | $SO_2NH_2$ | CN | H | H | H |
| 793 | 1 | H | H | H | H | OH |
| 794 | 2 | H | H | H | H | OH |
| 795 | 3 | H | H | H | H | OH |
| 796 | 4 | H | H | H | H | OH |
| 797 | 1 | Me | H | H | H | OH |
| 798 | 2 | Me | H | H | H | OH |
| 799 | 3 | Me | H | H | H | OH |
| 800 | 4 | Me | H | H | H | OH |
| 801 | 1 | $CH_2Ph$ | H | H | H | OH |
| 802 | 2 | $CH_2Ph$ | H | H | H | OH |
| 803 | 3 | $CH_2Ph$ | H | H | H | OH |
| 804 | 4 | $CH_2Ph$ | H | H | H | OH |
| 805 | 1 | COMe | H | H | H | OH |
| 806 | 2 | COMe | H | H | H | OH |
| 807 | 3 | COMe | H | H | H | OH |
| 808 | 4 | COMe | H | H | H | OH |
| 809 | 1 | $CO_2Me$ | H | H | H | OH |
| 810 | 2 | $CO_2Me$ | H | H | H | OH |
| 811 | 3 | $CO_2Me$ | H | H | H | OH |
| 812 | 4 | $CO_2Me$ | H | H | H | OH |
| 813 | 1 | $CO_2tBu$ | H | H | H | OH |
| 814 | 2 | $CO_2tBu$ | H | H | H | OH |
| 815 | 3 | $CO_2tBu$ | H | H | H | OH |
| 816 | 4 | $CO_2tBu$ | H | H | H | OH |
| 817 | 1 | CONHMe | H | H | H | OH |
| 818 | 2 | CONHMe | H | H | H | OH |
| 819 | 3 | CONHMe | H | H | H | OH |
| 820 | 4 | CONHMe | H | H | H | OH |
| 821 | 1 | $SO_2Me$ | H | H | H | OH |
| 822 | 2 | $SO_2Me$ | H | H | H | OH |
| 823 | 3 | $SO_2Me$ | H | H | H | OH |
| 824 | 4 | $SO_2Me$ | H | H | H | OH |
| 825 | 1 | $SO_2NH_2$ | H | H | H | OH |
| 826 | 2 | $SO_2NH_2$ | H | H | H | OH |
| 827 | 3 | $SO_2NH_2$ | H | H | H | OH |
| 828 | 4 | $SO_2NH_2$ | H | H | H | OH |
| 829 | 1 | H | H | H | H | OMe |
| 830 | 2 | H | H | H | H | OMe |
| 831 | 3 | H | H | H | H | OMe |
| 832 | 4 | H | H | H | H | OMe |
| 833 | 1 | Me | H | H | H | OMe |
| 834 | 2 | Me | H | H | H | OMe |
| 835 | 3 | Me | H | H | H | OMe |
| 836 | 4 | Me | H | H | H | OMe |
| 837 | 1 | $CH_2Ph$ | H | H | H | OMe |
| 838 | 2 | $CH_2Ph$ | H | H | H | OMe |
| 839 | 3 | $CH_2Ph$ | H | H | H | OMe |
| 840 | 4 | $CH_2Ph$ | H | H | H | OMe |

TABLE 19-continued

| Entry | n | $R^7$ | $R^{20a}$ | $R^{20b}$ | $R^{20c}$ | $R^{20d}$ |
|---|---|---|---|---|---|---|
| 841 | 1 | COMe | H | H | H | OMe |
| 842 | 2 | COMe | H | H | H | OMe |
| 843 | 3 | COMe | H | H | H | OMe |
| 844 | 4 | COMe | H | H | H | OMe |
| 845 | 1 | $CO_2Me$ | H | H | H | OMe |
| 846 | 2 | $CO_2Me$ | H | H | H | OMe |
| 847 | 3 | $CO_2Me$ | H | H | H | OMe |
| 848 | 4 | $CO_2Me$ | H | H | H | OMe |
| 849 | 1 | $CO_2tBu$ | H | H | H | OMe |
| 850 | 2 | $CO_2tBu$ | H | H | H | OMe |
| 851 | 3 | $CO_2tBu$ | H | H | H | OMe |
| 852 | 4 | $CO_2tBu$ | H | H | H | OMe |
| 853 | 1 | CONHMe | H | H | H | OMe |
| 854 | 2 | CONHMe | H | H | H | OMe |
| 855 | 3 | CONHMe | H | H | H | OMe |
| 856 | 4 | CONHMe | H | H | H | OMe |
| 857 | 1 | $SO_2Me$ | H | H | H | OMe |
| 858 | 2 | $SO_2Me$ | H | H | H | OMe |
| 859 | 3 | $SO_2Me$ | H | H | H | OMe |
| 860 | 4 | $SO_2Me$ | H | H | H | OMe |
| 861 | 1 | $SO_2NH_2$ | H | H | H | OMe |
| 862 | 2 | $SO_2NH_2$ | H | H | H | OMe |
| 863 | 3 | $SO_2NH_2$ | H | H | H | OMe |
| 864 | 4 | $SO_2NH_2$ | H | H | H | OMe |
| 865 | 1 | H | H | H | H | Me |
| 866 | 2 | H | H | H | H | Me |
| 867 | 3 | H | H | H | H | Me |
| 868 | 4 | H | H | H | H | Me |
| 869 | 1 | Me | H | H | H | Me |
| 870 | 2 | Me | H | H | H | Me |
| 871 | 3 | Me | H | H | H | Me |
| 872 | 4 | Me | H | H | H | Me |
| 873 | 1 | $CH_2Ph$ | H | H | H | Me |
| 874 | 2 | $CH_2Ph$ | H | H | H | Me |
| 875 | 3 | $CH_2Ph$ | H | H | H | Me |
| 876 | 4 | $CH_2Ph$ | H | H | H | Me |
| 877 | 1 | COMe | H | H | H | Me |
| 878 | 2 | COMe | H | H | H | Me |
| 879 | 3 | COMe | H | H | H | Me |
| 880 | 4 | COMe | H | H | H | Me |
| 881 | 1 | $CO_2Me$ | H | H | H | Me |
| 882 | 2 | $CO_2Me$ | H | H | H | Me |
| 883 | 3 | $CO_2Me$ | H | H | H | Me |
| 884 | 4 | $CO_2Me$ | H | H | H | Me |
| 885 | 1 | $CO_2tBu$ | H | H | H | Me |
| 886 | 2 | $CO_2tBu$ | H | H | H | Me |
| 887 | 3 | $CO_2tBu$ | H | H | H | Me |
| 888 | 4 | $CO_2tBu$ | H | H | H | Me |
| 889 | 1 | CONHMe | H | H | H | Me |
| 890 | 2 | CONHMe | H | H | H | Me |
| 891 | 3 | CONHMe | H | H | H | Me |
| 892 | 4 | CONHMe | H | H | H | Me |
| 893 | 1 | $SO_2Me$ | H | H | H | Me |
| 894 | 2 | $SO_2Me$ | H | H | H | Me |
| 895 | 3 | $SO_2Me$ | H | H | H | Me |
| 896 | 4 | $SO_2Me$ | H | H | H | Me |
| 897 | 1 | $SO_2NH_2$ | H | H | H | Me |
| 898 | 2 | $SO_2NH_2$ | H | H | H | Me |
| 899 | 3 | $SO_2NH_2$ | H | H | H | Me |
| 900 | 4 | $SO_2NH_2$ | H | H | H | Me |
| 901 | 1 | H | H | H | H | $CF_3$ |
| 902 | 2 | H | H | H | H | $CF_3$ |
| 903 | 3 | H | H | H | H | $CF_3$ |
| 904 | 4 | H | H | H | H | $CF_3$ |
| 905 | 1 | Me | H | H | H | $CF_3$ |
| 906 | 2 | Me | H | H | H | $CF_3$ |
| 907 | 3 | Me | H | H | H | $CF_3$ |
| 908 | 4 | Me | H | H | H | $CF_3$ |
| 909 | 1 | $CH_2Ph$ | H | H | H | $CF_3$ |
| 910 | 2 | $CH_2Ph$ | H | H | H | $CF_3$ |
| 911 | 3 | $CH_2Ph$ | H | H | H | $CF_3$ |
| 912 | 4 | $CH_2Ph$ | H | H | H | $CF_3$ |
| 913 | 1 | COMe | H | H | H | $CF_3$ |
| 914 | 2 | COMe | H | H | H | $CF_3$ |
| 915 | 3 | COMe | H | H | H | $CF_3$ |
| 916 | 4 | COMe | H | H | H | $CF_3$ |
| 917 | 1 | $CO_2Me$ | H | H | H | $CF_3$ |
| 918 | 2 | $CO_2Me$ | H | H | H | $CF_3$ |
| 919 | 3 | $CO_2Me$ | H | H | H | $CF_3$ |
| 920 | 4 | $CO_2Me$ | H | H | H | $CF_3$ |
| 921 | 1 | $CO_2tBu$ | H | H | H | $CF_3$ |
| 922 | 2 | $CO_2tBu$ | H | H | H | $CF_3$ |
| 923 | 3 | $CO_2tBu$ | H | H | H | $CF_3$ |
| 924 | 4 | $CO_2tBu$ | H | H | H | $CF_3$ |
| 925 | 1 | CONHMe | H | H | H | $CF_3$ |
| 926 | 2 | CONHMe | H | H | H | $CF_3$ |
| 927 | 3 | CONHMe | H | H | H | $CF_3$ |
| 928 | 4 | CONHMe | H | H | H | $CF_3$ |
| 929 | 1 | $SO_2Me$ | H | H | H | $CF_3$ |
| 930 | 2 | $SO_2Me$ | H | H | H | $CF_3$ |
| 931 | 3 | $SO_2Me$ | H | H | H | $CF_3$ |
| 932 | 4 | $SO_2Me$ | H | H | H | $CF_3$ |
| 933 | 1 | $SO_2NH_2$ | H | H | H | $CF_3$ |
| 934 | 2 | $SO_2NH_2$ | H | H | H | $CF_3$ |
| 935 | 3 | $SO_2NH_2$ | H | H | H | $CF_3$ |
| 936 | 4 | $SO_2NH_2$ | H | H | H | $CF_3$ |
| 937 | 1 | H | H | H | H | F |
| 938 | 2 | H | H | H | H | F |
| 939 | 3 | H | H | H | H | F |
| 940 | 3 | H | H | H | H | F |
| 941 | 1 | Me | H | H | H | F |
| 942 | 2 | Me | H | H | H | F |
| 943 | 3 | Me | H | H | H | F |
| 944 | 4 | Me | H | H | H | F |
| 945 | 1 | $CH_2Ph$ | H | H | H | F |
| 946 | 2 | $CH_2Ph$ | H | H | H | F |
| 947 | 3 | $CH_2Ph$ | H | H | H | F |
| 948 | 4 | $CH_2Ph$ | H | H | H | F |
| 949 | 1 | COMe | H | H | H | F |
| 950 | 2 | COMe | H | H | H | F |
| 951 | 3 | COMe | H | H | H | F |
| 952 | 4 | COMe | H | H | H | F |
| 953 | 1 | $CO_2Me$ | H | H | H | F |
| 954 | 2 | $CO_2Me$ | H | H | H | F |
| 955 | 3 | $CO_2Me$ | H | H | H | F |
| 956 | 4 | $CO_2Me$ | H | H | H | F |
| 957 | 1 | $CO_2tBu$ | H | H | H | F |
| 958 | 2 | $CO_2tBu$ | H | H | H | F |
| 959 | 3 | $CO_2tBu$ | H | H | H | F |
| 960 | 4 | $CO_2tBu$ | H | H | H | F |
| 961 | 1 | CONHMe | H | H | H | F |
| 962 | 2 | CONHMe | H | H | H | F |
| 963 | 3 | CONHMe | H | H | H | F |
| 964 | 4 | CONHMe | H | H | H | F |
| 965 | 1 | $SO_2Me$ | H | H | H | F |
| 966 | 2 | $SO_2Me$ | H | H | H | F |
| 967 | 3 | $SO_2Me$ | H | H | H | F |
| 968 | 4 | $SO_2Me$ | H | H | H | F |
| 969 | 1 | $SO_2NH_2$ | H | H | H | F |
| 970 | 2 | $SO_2NH_2$ | H | H | H | F |
| 971 | 3 | $SO_2NH_2$ | H | H | H | F |
| 972 | 4 | $SO_2NH_2$ | H | H | H | F |
| 973 | 1 | H | H | H | H | Cl |
| 974 | 2 | H | H | H | H | Cl |
| 975 | 3 | H | H | H | H | Cl |
| 976 | 4 | H | H | H | H | Cl |
| 977 | 1 | Me | H | H | H | Cl |
| 978 | 2 | Me | H | H | H | Cl |
| 979 | 3 | Me | H | H | H | Cl |
| 980 | 4 | Me | H | H | H | Cl |
| 981 | 1 | $CH_2Ph$ | H | H | H | Cl |
| 982 | 2 | $CH_2Ph$ | H | H | H | Cl |
| 983 | 3 | $CH_2Ph$ | H | H | H | Cl |
| 984 | 4 | $CH_2Ph$ | H | H | H | Cl |
| 985 | 1 | COMe | H | H | H | Cl |
| 986 | 2 | COMe | H | H | H | Cl |
| 987 | 3 | COMe | H | H | H | Cl |
| 988 | 4 | COMe | H | H | H | Cl |
| 989 | 1 | $CO_2Me$ | H | H | H | Cl |
| 990 | 2 | $CO_2Me$ | H | H | H | Cl |
| 991 | 3 | $CO_2Me$ | H | H | H | Cl |
| 992 | 4 | $CO_2Me$ | H | H | H | Cl |
| 993 | 1 | $CO_2tBu$ | H | H | H | Cl |
| 994 | 2 | $CO_2tBu$ | H | H | H | Cl |
| 995 | 3 | $CO_2tBu$ | H | H | H | Cl |
| 996 | 4 | $CO_2tBu$ | H | H | H | Cl |

TABLE 19-continued

| Entry | n | $R^7$ | $R^{20a}$ | $R^{20b}$ | $R^{20c}$ | $R^{20d}$ |
|---|---|---|---|---|---|---|
| 997 | 1 | CONHMe | H | H | H | Cl |
| 998 | 2 | CONHMe | H | H | H | Cl |
| 999 | 3 | CONHMe | H | H | H | Cl |
| 1000 | 4 | CONHMe | H | H | H | Cl |
| 1001 | 1 | $SO_2Me$ | H | H | H | Cl |
| 1002 | 2 | $SO_2Me$ | H | H | H | Cl |
| 1003 | 3 | $SO_2Me$ | H | H | H | Cl |
| 1004 | 4 | $SO_2Me$ | H | H | H | Cl |
| 1005 | 1 | $SO_2NH_2$ | H | H | H | Cl |
| 1006 | 2 | $SO_2NH_2$ | H | H | H | Cl |
| 1007 | 3 | $SO_2NH_2$ | H | H | H | Cl |
| 1008 | 4 | $SO_2NH_2$ | H | H | H | Cl |
| 1009 | 1 | H | H | H | H | CN |
| 1010 | 2 | H | H | H | H | CN |
| 1011 | 3 | H | H | H | H | CN |
| 1012 | 4 | H | H | H | H | CN |
| 1013 | 1 | Me | H | H | H | CN |
| 1014 | 2 | Me | H | H | H | CN |
| 1015 | 3 | Me | H | H | H | CN |
| 1016 | 4 | Me | H | H | H | CN |
| 1017 | 1 | $CH_2Ph$ | H | H | H | CN |
| 1018 | 2 | $CH_2Ph$ | H | H | H | CN |
| 1019 | 3 | $CH_2Ph$ | H | H | H | CN |
| 1020 | 4 | $CH_2Ph$ | H | H | H | CN |
| 1021 | 1 | COMe | H | H | H | CN |
| 1022 | 2 | COMe | H | H | H | CN |
| 1023 | 3 | COMe | H | H | H | CN |
| 1024 | 4 | COMe | H | H | H | CN |
| 1025 | 1 | $CO_2Me$ | H | H | H | CN |
| 1026 | 2 | $CO_2Me$ | H | H | H | CN |
| 1027 | 3 | $CO_2Me$ | H | H | H | CN |
| 1028 | 4 | $CO_2Me$ | H | H | H | CN |
| 1029 | 1 | $CO_2tBu$ | H | H | H | CN |
| 1030 | 2 | $CO_2tBu$ | H | H | H | CN |
| 1031 | 3 | $CO_2tBu$ | H | H | H | CN |
| 1032 | 4 | $CO_2tBu$ | H | H | H | CN |
| 1033 | 1 | CONHMe | H | H | H | CN |
| 1034 | 2 | CONHMe | H | H | H | CN |
| 1035 | 3 | CONHMe | H | H | H | CN |
| 1036 | 4 | CONHMe | H | H | H | CN |
| 1037 | 1 | $SO_2Me$ | H | H | H | CN |
| 1038 | 2 | $SO_2Me$ | H | H | H | CN |
| 1039 | 3 | $SO_2Me$ | H | H | H | CN |
| 1040 | 4 | $SO_2Me$ | H | H | H | CN |
| 1041 | 1 | $SO_2NH_2$ | H | H | H | CN |
| 1042 | 2 | $SO_2NH_2$ | H | H | H | CN |
| 1043 | 3 | $SO_2NH_2$ | H | H | H | CN |
| 1044 | 4 | $SO_2NH_2$ | H | H | H | CN |

Exemplary embodiments include compounds having the formula (XXVI)

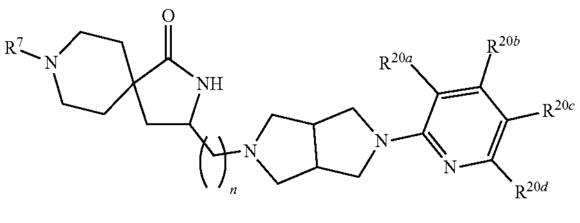

or a pharmaceutically acceptable salt form thereof defined herein below in Table 20.

TABLE 20

| Entry | n | $R^7$ | $R^{20a}$ | $R^{20b}$ | $R^{20c}$ | $R^{20d}$ |
|---|---|---|---|---|---|---|
| 1 | 1 | H | H | H | H | H |
| 2 | 2 | H | H | H | H | H |
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |
| 60 | 4 | $CO_2tBu$ | H | H | OH | H |
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |
| 79 | 3 | Me | H | H | OMe | H |
| 80 | 4 | Me | H | H | OMe | H |

TABLE 20-continued

| Entry | n | $R^7$ | $R^{20a}$ | $R^{20b}$ | $R^{20c}$ | $R^{20d}$ |
|---|---|---|---|---|---|---|
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |
| 138 | 2 | $SO_2Me$ | H | H | Me | H |
| 139 | 3 | $SO_2Me$ | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |
| 157 | 1 | COMe | H | H | $CF_3$ | H |
| 158 | 2 | COMe | H | H | $CF_3$ | H |

TABLE 20-continued

| Entry | n | $R^7$ | $R^{20a}$ | $R^{20b}$ | $R^{20c}$ | $R^{20d}$ |
|---|---|---|---|---|---|---|
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | $CO_2tBu$ | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |
| 216 | 4 | $SO_2NH_2$ | H | H | F | H |
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |
| 235 | 3 | $CO_2Me$ | H | H | Cl | H |
| 236 | 4 | $CO_2Me$ | H | H | Cl | H |

TABLE 20-continued

| Entry | n | $R^7$ | $R^{20a}$ | $R^{20b}$ | $R^{20c}$ | $R^{20d}$ |
|---|---|---|---|---|---|---|
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | $CH_2Ph$ | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | COMe | H | H | CN | H |
| 266 | 2 | COMe | H | H | CN | H |
| 267 | 3 | COMe | H | H | CN | H |
| 268 | 4 | COMe | H | H | CN | H |
| 269 | 1 | $CO_2Me$ | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2tBu$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |
| 277 | 1 | CONHMe | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | $SO_2Me$ | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2NH_2$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | H | H | OH | H | H |
| 290 | 2 | H | H | OH | H | H |
| 291 | 3 | H | H | OH | H | H |
| 292 | 4 | H | H | OH | H | H |
| 293 | 1 | Me | H | OH | H | H |
| 294 | 2 | Me | H | OH | H | H |
| 295 | 3 | Me | H | OH | H | H |
| 296 | 4 | Me | H | OH | H | H |
| 297 | 1 | $CH_2Ph$ | H | OH | H | H |
| 298 | 2 | $CH_2Ph$ | H | OH | H | H |
| 299 | 3 | $CH_2Ph$ | H | OH | H | H |
| 300 | 4 | $CH_2Ph$ | H | OH | H | H |
| 301 | 1 | COMe | H | OH | H | H |
| 302 | 2 | COMe | H | OH | H | H |
| 303 | 3 | COMe | H | OH | H | H |
| 304 | 4 | COMe | H | OH | H | H |
| 305 | 1 | $CO_2Me$ | H | OH | H | H |
| 306 | 2 | $CO_2Me$ | H | OH | H | H |
| 307 | 3 | $CO_2Me$ | H | OH | H | H |
| 308 | 4 | $CO_2Me$ | H | OH | H | H |
| 309 | 1 | $CO_2tBu$ | H | OH | H | H |
| 310 | 2 | $CO_2tBu$ | H | OH | H | H |
| 311 | 3 | $CO_2tBu$ | H | OH | H | H |
| 312 | 4 | $CO_2tBu$ | H | OH | H | H |
| 313 | 1 | CONHMe | H | OH | H | H |
| 314 | 2 | CONHMe | H | OH | H | H |

TABLE 20-continued

| Entry | n | $R^7$ | $R^{20a}$ | $R^{20b}$ | $R^{20c}$ | $R^{20d}$ |
|---|---|---|---|---|---|---|
| 315 | 3 | CONHMe | H | OH | H | H |
| 316 | 4 | CONHMe | H | OH | H | H |
| 317 | 1 | $SO_2Me$ | H | OH | H | H |
| 318 | 2 | $SO_2Me$ | H | OH | H | H |
| 319 | 3 | $SO_2Me$ | H | OH | H | H |
| 320 | 4 | $SO_2Me$ | H | OH | H | H |
| 321 | 1 | $SO_2NH_2$ | H | OH | H | H |
| 322 | 2 | $SO_2NH_2$ | H | OH | H | H |
| 323 | 3 | $SO_2NH_2$ | H | OH | H | H |
| 324 | 4 | $SO_2NH_2$ | H | OH | H | H |
| 325 | 1 | H | H | OMe | H | H |
| 326 | 2 | H | H | OMe | H | H |
| 327 | 3 | H | H | OMe | H | H |
| 328 | 4 | H | H | OMe | H | H |
| 329 | 1 | Me | H | OMe | H | H |
| 330 | 2 | Me | H | OMe | H | H |
| 331 | 3 | Me | H | OMe | H | H |
| 332 | 4 | Me | H | OMe | H | H |
| 333 | 1 | $CH_2Ph$ | H | OMe | H | H |
| 334 | 2 | $CH_2Ph$ | H | OMe | H | H |
| 335 | 3 | $CH_2Ph$ | H | OMe | H | H |
| 336 | 4 | $CH_2Ph$ | H | OMe | H | H |
| 337 | 1 | COMe | H | OMe | H | H |
| 338 | 2 | COMe | H | OMe | H | H |
| 339 | 3 | COMe | H | OMe | H | H |
| 340 | 4 | COMe | H | OMe | H | H |
| 341 | 1 | $CO_2Me$ | H | OMe | H | H |
| 342 | 2 | $CO_2Me$ | H | OMe | H | H |
| 343 | 3 | $CO_2Me$ | H | OMe | H | H |
| 344 | 4 | $CO_2Me$ | H | OMe | H | H |
| 345 | 1 | $CO_2tBu$ | H | OMe | H | H |
| 346 | 2 | $CO_2tBu$ | H | OMe | H | H |
| 347 | 3 | $CO_2tBu$ | H | OMe | H | H |
| 348 | 4 | $CO_2tBu$ | H | OMe | H | H |
| 349 | 1 | CONHMe | H | OMe | H | H |
| 350 | 2 | CONHMe | H | OMe | H | H |
| 351 | 3 | CONHMe | H | OMe | H | H |
| 352 | 4 | CONHMe | H | OMe | H | H |
| 353 | 1 | $SO_2Me$ | H | OMe | H | H |
| 354 | 2 | $SO_2Me$ | H | OMe | H | H |
| 355 | 3 | $SO_2Me$ | H | OMe | H | H |
| 356 | 4 | $SO_2Me$ | H | OMe | H | H |
| 357 | 1 | $SO_2NH_2$ | H | OMe | H | H |
| 358 | 2 | $SO_2NH_2$ | H | OMe | H | H |
| 359 | 3 | $SO_2NH_2$ | H | OMe | H | H |
| 360 | 4 | $SO_2NH_2$ | H | OMe | H | H |
| 361 | 1 | H | H | Me | H | H |
| 362 | 2 | H | H | Me | H | H |
| 363 | 3 | H | H | Me | H | H |
| 364 | 4 | H | H | Me | H | H |
| 365 | 1 | Me | H | Me | H | H |
| 366 | 2 | Me | H | Me | H | H |
| 367 | 3 | Me | H | Me | H | H |
| 368 | 4 | Me | H | Me | H | H |
| 369 | 1 | $CH_2Ph$ | H | Me | H | H |
| 370 | 2 | $CH_2Ph$ | H | Me | H | H |
| 371 | 3 | $CH_2Ph$ | H | Me | H | H |
| 372 | 4 | $CH_2Ph$ | H | Me | H | H |
| 373 | 1 | COMe | H | Me | H | H |
| 374 | 2 | COMe | H | Me | H | H |
| 375 | 3 | COMe | H | Me | H | H |
| 376 | 4 | COMe | H | Me | H | H |
| 377 | 1 | $CO_2Me$ | H | Me | H | H |
| 378 | 2 | $CO_2Me$ | H | Me | H | H |
| 379 | 3 | $CO_2Me$ | H | Me | H | H |
| 380 | 4 | $CO_2Me$ | H | Me | H | H |
| 381 | 1 | $CO_2tBu$ | H | Me | H | H |
| 382 | 2 | $CO_2tBu$ | H | Me | H | H |
| 383 | 3 | $CO_2tBu$ | H | Me | H | H |
| 384 | 4 | $CO_2tBu$ | H | Me | H | H |
| 385 | 1 | CONHMe | H | Me | H | H |
| 386 | 2 | CONHMe | H | Me | H | H |
| 387 | 3 | CONHMe | H | Me | H | H |
| 388 | 4 | CONHMe | H | Me | H | H |
| 389 | 1 | $SO_2Me$ | H | Me | H | H |
| 390 | 2 | $SO_2Me$ | H | Me | H | H |
| 391 | 3 | $SO_2Me$ | H | Me | H | H |
| 392 | 4 | $SO_2Me$ | H | Me | H | H |

TABLE 20-continued

| Entry | n | $R^7$ | $R^{20a}$ | $R^{20b}$ | $R^{20c}$ | $R^{20d}$ |
|---|---|---|---|---|---|---|
| 393 | 1 | $SO_2NH_2$ | H | Me | H | H |
| 394 | 2 | $SO_2NH_2$ | H | Me | H | H |
| 395 | 3 | $SO_2NH_2$ | H | Me | H | H |
| 396 | 4 | $SO_2NH_2$ | H | Me | H | H |
| 397 | 1 | H | H | $CF_3$ | H | H |
| 398 | 2 | H | H | $CF_3$ | H | H |
| 399 | 3 | H | H | $CF_3$ | H | H |
| 400 | 4 | H | H | $CF_3$ | H | H |
| 401 | 1 | Me | H | $CF_3$ | H | H |
| 402 | 2 | Me | H | $CF_3$ | H | H |
| 403 | 3 | Me | H | $CF_3$ | H | H |
| 404 | 4 | Me | H | $CF_3$ | H | H |
| 405 | 1 | $CH_2Ph$ | H | $CF_3$ | H | H |
| 406 | 2 | $CH_2Ph$ | H | $CF_3$ | H | H |
| 407 | 3 | $CH_2Ph$ | H | $CF_3$ | H | H |
| 408 | 4 | $CH_2Ph$ | H | $CF_3$ | H | H |
| 409 | 1 | COMe | H | $CF_3$ | H | H |
| 410 | 2 | COMe | H | $CF_3$ | H | H |
| 411 | 3 | COMe | H | $CF_3$ | H | H |
| 412 | 4 | COMe | H | $CF_3$ | H | H |
| 413 | 1 | $CO_2Me$ | H | $CF_3$ | H | H |
| 414 | 2 | $CO_2Me$ | H | $CF_3$ | H | H |
| 415 | 3 | $CO_2Me$ | H | $CF_3$ | H | H |
| 416 | 4 | $CO_2Me$ | H | $CF_3$ | H | H |
| 417 | 1 | $CO_2tBu$ | H | $CF_3$ | H | H |
| 418 | 2 | $CO_2tBu$ | H | $CF_3$ | H | H |
| 419 | 3 | $CO_2tBu$ | H | $CF_3$ | H | H |
| 420 | 4 | $CO_2tBu$ | H | $CF_3$ | H | H |
| 421 | 1 | CONHMe | H | $CF_3$ | H | H |
| 422 | 2 | CONHMe | H | $CF_3$ | H | H |
| 423 | 3 | CONHMe | H | $CF_3$ | H | H |
| 424 | 4 | CONHMe | H | $CF_3$ | H | H |
| 425 | 1 | $SO_2Me$ | H | $CF_3$ | H | H |
| 426 | 2 | $SO_2Me$ | H | $CF_3$ | H | H |
| 427 | 3 | $SO_2Me$ | H | $CF_3$ | H | H |
| 428 | 4 | $SO_2Me$ | H | $CF_3$ | H | H |
| 429 | 1 | $SO_2NH_2$ | H | $CF_3$ | H | H |
| 430 | 2 | $SO_2NH_2$ | H | $CF_3$ | H | H |
| 431 | 3 | $SO_2NH_2$ | H | $CF_3$ | H | H |
| 432 | 4 | $SO_2NH_2$ | H | $CF_3$ | H | H |
| 433 | 1 | H | H | F | H | H |
| 434 | 2 | H | H | F | H | H |
| 435 | 3 | H | H | F | H | H |
| 436 | 3 | H | H | F | H | H |
| 437 | 1 | Me | H | F | H | H |
| 438 | 2 | Me | H | F | H | H |
| 439 | 3 | Me | H | F | H | H |
| 440 | 4 | Me | H | F | H | H |
| 441 | 1 | $CH_2Ph$ | H | F | H | H |
| 442 | 2 | $CH_2Ph$ | H | F | H | H |
| 443 | 3 | $CH_2Ph$ | H | F | H | H |
| 444 | 4 | $CH_2Ph$ | H | F | H | H |
| 445 | 1 | COMe | H | F | H | H |
| 446 | 2 | COMe | H | F | H | H |
| 447 | 3 | COMe | H | F | H | H |
| 448 | 4 | COMe | H | F | H | H |
| 449 | 1 | $CO_2Me$ | H | F | H | H |
| 450 | 2 | $CO_2Me$ | H | F | H | H |
| 451 | 3 | $CO_2Me$ | H | F | H | H |
| 452 | 4 | $CO_2Me$ | H | F | H | H |
| 453 | 1 | $CO_2tBu$ | H | F | H | H |
| 454 | 2 | $CO_2tBu$ | H | F | H | H |
| 455 | 3 | $CO_2tBu$ | H | F | H | H |
| 456 | 4 | $CO_2tBu$ | H | F | H | H |
| 457 | 1 | CONHMe | H | F | H | H |
| 458 | 2 | CONHMe | H | F | H | H |
| 459 | 3 | CONHMe | H | F | H | H |
| 460 | 4 | CONHMe | H | F | H | H |
| 461 | 1 | $SO_2Me$ | H | F | H | H |
| 462 | 2 | $SO_2Me$ | H | F | H | H |
| 463 | 3 | $SO_2Me$ | H | F | H | H |
| 464 | 4 | $SO_2Me$ | H | F | H | H |
| 465 | 1 | $SO_2NH_2$ | H | F | H | H |
| 466 | 2 | $SO_2NH_2$ | H | F | H | H |
| 467 | 3 | $SO_2NH_2$ | H | F | H | H |
| 468 | 4 | $SO_2NH_2$ | H | F | H | H |
| 469 | 1 | H | H | Cl | H | H |
| 470 | 2 | H | H | Cl | H | H |

TABLE 20-continued

| Entry | n | $R^7$ | $R^{20a}$ | $R^{20b}$ | $R^{20c}$ | $R^{20d}$ |
|---|---|---|---|---|---|---|
| 471 | 3 | H | H | Cl | H | H |
| 472 | 4 | H | H | Cl | H | H |
| 473 | 1 | Me | H | Cl | H | H |
| 474 | 2 | Me | H | Cl | H | H |
| 475 | 3 | Me | H | Cl | H | H |
| 476 | 4 | Me | H | Cl | H | H |
| 477 | 1 | $CH_2Ph$ | H | Cl | H | H |
| 478 | 2 | $CH_2Ph$ | H | Cl | H | H |
| 479 | 3 | $CH_2Ph$ | H | Cl | H | H |
| 480 | 4 | $CH_2Ph$ | H | Cl | H | H |
| 481 | 1 | COMe | H | Cl | H | H |
| 482 | 2 | COMe | H | Cl | H | H |
| 483 | 3 | COMe | H | Cl | H | H |
| 484 | 4 | COMe | H | Cl | H | H |
| 485 | 1 | $CO_2Me$ | H | Cl | H | H |
| 486 | 2 | $CO_2Me$ | H | Cl | H | H |
| 487 | 3 | $CO_2Me$ | H | Cl | H | H |
| 488 | 4 | $CO_2Me$ | H | Cl | H | H |
| 489 | 1 | $CO_2tBu$ | H | Cl | H | H |
| 490 | 2 | $CO_2tBu$ | H | Cl | H | H |
| 491 | 3 | $CO_2tBu$ | H | Cl | H | H |
| 492 | 4 | $CO_2tBu$ | H | Cl | H | H |
| 493 | 1 | CONHMe | H | Cl | H | H |
| 494 | 2 | CONHMe | H | Cl | H | H |
| 495 | 3 | CONHMe | H | Cl | H | H |
| 496 | 4 | CONHMe | H | Cl | H | H |
| 497 | 1 | $SO_2Me$ | H | Cl | H | H |
| 498 | 2 | $SO_2Me$ | H | Cl | H | H |
| 499 | 3 | $SO_2Me$ | H | Cl | H | H |
| 500 | 4 | $SO_2Me$ | H | Cl | H | H |
| 501 | 1 | $SO_2NH_2$ | H | Cl | H | H |
| 502 | 2 | $SO_2NH_2$ | H | Cl | H | H |
| 503 | 3 | $SO_2NH_2$ | H | Cl | H | H |
| 504 | 4 | $SO_2NH_2$ | H | Cl | H | H |
| 505 | 1 | H | H | CN | H | H |
| 506 | 2 | H | H | CN | H | H |
| 507 | 3 | H | H | CN | H | H |
| 508 | 4 | H | H | CN | H | H |
| 509 | 1 | Me | H | CN | H | H |
| 510 | 2 | Me | H | CN | H | H |
| 511 | 3 | Me | H | CN | H | H |
| 512 | 4 | Me | H | CN | H | H |
| 513 | 1 | $CH_2Ph$ | H | CN | H | H |
| 514 | 2 | $CH_2Ph$ | H | CN | H | H |
| 515 | 3 | $CH_2Ph$ | H | CN | H | H |
| 516 | 4 | $CH_2Ph$ | H | CN | H | H |
| 517 | 1 | COMe | H | CN | H | H |
| 518 | 2 | COMe | H | CN | H | H |
| 519 | 3 | COMe | H | CN | H | H |
| 520 | 4 | COMe | H | CN | H | H |
| 521 | 1 | $CO_2Me$ | H | CN | H | H |
| 522 | 2 | $CO_2Me$ | H | CN | H | H |
| 523 | 3 | $CO_2Me$ | H | CN | H | H |
| 524 | 4 | $CO_2Me$ | H | CN | H | H |
| 525 | 1 | $CO_2tBu$ | H | CN | H | H |
| 526 | 2 | $CO_2tBu$ | H | CN | H | H |
| 527 | 3 | $CO_2tBu$ | H | CN | H | H |
| 528 | 4 | $CO_2tBu$ | H | CN | H | H |
| 529 | 1 | CONHMe | H | CN | H | H |
| 530 | 2 | CONHMe | H | CN | H | H |
| 531 | 3 | CONHMe | H | CN | H | H |
| 532 | 4 | CONHMe | H | CN | H | H |
| 533 | 1 | $SO_2Me$ | H | CN | H | H |
| 534 | 2 | $SO_2Me$ | H | CN | H | H |
| 535 | 3 | $SO_2Me$ | H | CN | H | H |
| 536 | 4 | $SO_2Me$ | H | CN | H | H |
| 537 | 1 | $SO_2NH_2$ | H | CN | H | H |
| 538 | 2 | $SO_2NH_2$ | H | CN | H | H |
| 539 | 3 | $SO_2NH_2$ | H | CN | H | H |
| 540 | 4 | $SO_2NH_2$ | H | CN | H | H |
| 541 | 1 | H | OH | H | H | H |
| 542 | 2 | H | OH | H | H | H |
| 543 | 3 | H | OH | H | H | H |
| 544 | 4 | H | OH | H | H | H |
| 545 | 1 | Me | OH | H | H | H |
| 546 | 2 | Me | OH | H | H | H |
| 547 | 3 | Me | OH | H | H | H |
| 548 | 4 | Me | OH | H | H | H |

TABLE 20-continued

| Entry | n | $R^7$ | $R^{20a}$ | $R^{20b}$ | $R^{20c}$ | $R^{20d}$ |
|---|---|---|---|---|---|---|
| 549 | 1 | $CH_2Ph$ | OH | H | H | H |
| 550 | 2 | $CH_2Ph$ | OH | H | H | H |
| 551 | 3 | $CH_2Ph$ | OH | H | H | H |
| 552 | 4 | $CH_2Ph$ | OH | H | H | H |
| 553 | 1 | COMe | OH | H | H | H |
| 554 | 2 | COMe | OH | H | H | H |
| 555 | 3 | COMe | OH | H | H | H |
| 556 | 4 | COMe | OH | H | H | H |
| 557 | 1 | $CO_2Me$ | OH | H | H | H |
| 558 | 2 | $CO_2Me$ | OH | H | H | H |
| 559 | 3 | $CO_2Me$ | OH | H | H | H |
| 560 | 4 | $CO_2Me$ | OH | H | H | H |
| 561 | 1 | $CO_2tBu$ | OH | H | H | H |
| 562 | 2 | $CO_2tBu$ | OH | H | H | H |
| 563 | 3 | $CO_2tBu$ | OH | H | H | H |
| 564 | 4 | $CO_2tBu$ | OH | H | H | H |
| 565 | 1 | CONHMe | OH | H | H | H |
| 566 | 2 | CONHMe | OH | H | H | H |
| 567 | 3 | CONHMe | OH | H | H | H |
| 568 | 4 | CONHMe | OH | H | H | H |
| 569 | 1 | $SO_2Me$ | OH | H | H | H |
| 570 | 2 | $SO_2Me$ | OH | H | H | H |
| 571 | 3 | $SO_2Me$ | OH | H | H | H |
| 572 | 4 | $SO_2Me$ | OH | H | H | H |
| 573 | 1 | $SO_2NH_2$ | OH | H | H | H |
| 574 | 2 | $SO_2NH_2$ | OH | H | H | H |
| 575 | 3 | $SO_2NH_2$ | OH | H | H | H |
| 576 | 4 | $SO_2NH_2$ | OH | H | H | H |
| 577 | 1 | H | OMe | H | H | H |
| 578 | 2 | H | OMe | H | H | H |
| 579 | 3 | H | OMe | H | H | H |
| 580 | 4 | H | OMe | H | H | H |
| 581 | 1 | Me | OMe | H | H | H |
| 582 | 2 | Me | OMe | H | H | H |
| 583 | 3 | Me | OMe | H | H | H |
| 584 | 4 | Me | OMe | H | H | H |
| 585 | 1 | $CH_2Ph$ | OMe | H | H | H |
| 586 | 2 | $CH_2Ph$ | OMe | H | H | H |
| 587 | 3 | $CH_2Ph$ | OMe | H | H | H |
| 588 | 4 | $CH_2Ph$ | OMe | H | H | H |
| 589 | 1 | COMe | OMe | H | H | H |
| 590 | 2 | COMe | OMe | H | H | H |
| 591 | 3 | COMe | OMe | H | H | H |
| 592 | 4 | COMe | OMe | H | H | H |
| 593 | 1 | $CO_2Me$ | OMe | H | H | H |
| 594 | 2 | $CO_2Me$ | OMe | H | H | H |
| 595 | 3 | $CO_2Me$ | OMe | H | H | H |
| 596 | 4 | $CO_2Me$ | OMe | H | H | H |
| 597 | 1 | $CO_2tBu$ | OMe | H | H | H |
| 598 | 2 | $CO_2tBu$ | OMe | H | H | H |
| 599 | 3 | $CO_2tBu$ | OMe | H | H | H |
| 600 | 4 | $CO_2tBu$ | OMe | H | H | H |
| 601 | 1 | CONHMe | OMe | H | H | H |
| 602 | 2 | CONHMe | OMe | H | H | H |
| 603 | 3 | CONHMe | OMe | H | H | H |
| 604 | 4 | CONHMe | OMe | H | H | H |
| 605 | 1 | $SO_2Me$ | OMe | H | H | H |
| 606 | 2 | $SO_2Me$ | OMe | H | H | H |
| 607 | 3 | $SO_2Me$ | OMe | H | H | H |
| 608 | 4 | $SO_2Me$ | OMe | H | H | H |
| 609 | 1 | $SO_2NH_2$ | OMe | H | H | H |
| 610 | 2 | $SO_2NH_2$ | OMe | H | H | H |
| 611 | 3 | $SO_2NH_2$ | OMe | H | H | H |
| 612 | 4 | $SO_2NH_2$ | OMe | H | H | H |
| 613 | 1 | H | Me | H | H | H |
| 614 | 2 | H | Me | H | H | H |
| 615 | 3 | H | Me | H | H | H |
| 616 | 4 | H | Me | H | H | H |
| 617 | 1 | Me | Me | H | H | H |
| 618 | 2 | Me | Me | H | H | H |
| 619 | 3 | Me | Me | H | H | H |
| 620 | 4 | Me | Me | H | H | H |
| 621 | 1 | $CH_2Ph$ | Me | H | H | H |
| 622 | 2 | $CH_2Ph$ | Me | H | H | H |
| 623 | 3 | $CH_2Ph$ | Me | H | H | H |
| 624 | 4 | $CH_2Ph$ | Me | H | H | H |
| 625 | 1 | COMe | Me | H | H | H |
| 626 | 2 | COMe | Me | H | H | H |
| 627 | 3 | COMe | Me | H | H | H |
| 628 | 4 | COMe | Me | H | H | H |
| 629 | 1 | $CO_2Me$ | Me | H | H | H |
| 630 | 2 | $CO_2Me$ | Me | H | H | H |
| 631 | 3 | $CO_2Me$ | Me | H | H | H |
| 632 | 4 | $CO_2Me$ | Me | H | H | H |
| 633 | 1 | $CO_2tBu$ | Me | H | H | H |
| 634 | 2 | $CO_2tBu$ | Me | H | H | H |
| 635 | 3 | $CO_2tBu$ | Me | H | H | H |
| 636 | 4 | $CO_2tBu$ | Me | H | H | H |
| 637 | 1 | CONHMe | Me | H | H | H |
| 638 | 2 | CONHMe | Me | H | H | H |
| 639 | 3 | CONHMe | Me | H | H | H |
| 640 | 4 | CONHMe | Me | H | H | H |
| 641 | 1 | $SO_2Me$ | Me | H | H | H |
| 642 | 2 | $SO_2Me$ | Me | H | H | H |
| 643 | 3 | $SO_2Me$ | Me | H | H | H |
| 644 | 4 | $SO_2Me$ | Me | H | H | H |
| 645 | 1 | $SO_2NH_2$ | Me | H | H | H |
| 646 | 2 | $SO_2NH_2$ | Me | H | H | H |
| 647 | 3 | $SO_2NH_2$ | Me | H | H | H |
| 648 | 4 | $SO_2NH_2$ | Me | H | H | H |
| 649 | 1 | H | $CF_3$ | H | H | H |
| 650 | 2 | H | $CF_3$ | H | H | H |
| 651 | 3 | H | $CF_3$ | H | H | H |
| 652 | 4 | H | $CF_3$ | H | H | H |
| 653 | 1 | Me | $CF_3$ | H | H | H |
| 654 | 2 | Me | $CF_3$ | H | H | H |
| 655 | 3 | Me | $CF_3$ | H | H | H |
| 656 | 4 | Me | $CF_3$ | H | H | H |
| 657 | 1 | $CH_2Ph$ | $CF_3$ | H | H | H |
| 658 | 2 | $CH_2Ph$ | $CF_3$ | H | H | H |
| 659 | 3 | $CH_2Ph$ | $CF_3$ | H | H | H |
| 660 | 4 | $CH_2Ph$ | $CF_3$ | H | H | H |
| 661 | 1 | COMe | $CF_3$ | H | H | H |
| 662 | 2 | COMe | $CF_3$ | H | H | H |
| 663 | 3 | COMe | $CF_3$ | H | H | H |
| 664 | 4 | COMe | $CF_3$ | H | H | H |
| 665 | 1 | $CO_2Me$ | $CF_3$ | H | H | H |
| 666 | 2 | $CO_2Me$ | $CF_3$ | H | H | H |
| 667 | 3 | $CO_2Me$ | $CF_3$ | H | H | H |
| 668 | 4 | $CO_2Me$ | $CF_3$ | H | H | H |
| 669 | 1 | $CO_2tBu$ | $CF_3$ | H | H | H |
| 670 | 2 | $CO_2tBu$ | $CF_3$ | H | H | H |
| 671 | 3 | $CO_2tBu$ | $CF_3$ | H | H | H |
| 672 | 4 | $CO_2tBu$ | $CF_3$ | H | H | H |
| 673 | 1 | CONHMe | $CF_3$ | H | H | H |
| 674 | 2 | CONHMe | $CF_3$ | H | H | H |
| 675 | 3 | CONHMe | $CF_3$ | H | H | H |
| 676 | 4 | CONHMe | $CF_3$ | H | H | H |
| 677 | 1 | $SO_2Me$ | $CF_3$ | H | H | H |
| 678 | 2 | $SO_2Me$ | $CF_3$ | H | H | H |
| 679 | 3 | $SO_2Me$ | $CF_3$ | H | H | H |
| 680 | 4 | $SO_2Me$ | $CF_3$ | H | H | H |
| 681 | 1 | $SO_2NH_2$ | $CF_3$ | H | H | H |
| 682 | 2 | $SO_2NH_2$ | $CF_3$ | H | H | H |
| 683 | 3 | $SO_2NH_2$ | $CF_3$ | H | H | H |
| 684 | 4 | $SO_2NH_2$ | $CF_3$ | H | H | H |
| 685 | 1 | H | F | H | H | H |
| 686 | 2 | H | F | H | H | H |
| 687 | 3 | H | F | H | H | H |
| 688 | 3 | H | F | H | H | H |
| 689 | 1 | Me | F | H | H | H |
| 690 | 2 | Me | F | H | H | H |
| 691 | 3 | Me | F | H | H | H |
| 692 | 4 | Me | F | H | H | H |
| 693 | 1 | $CH_2Ph$ | F | H | H | H |
| 694 | 2 | $CH_2Ph$ | F | H | H | H |
| 695 | 3 | $CH_2Ph$ | F | H | H | H |
| 696 | 4 | $CH_2Ph$ | F | H | H | H |
| 697 | 1 | COMe | F | H | H | H |
| 698 | 2 | COMe | F | H | H | H |
| 699 | 3 | COMe | F | H | H | H |
| 700 | 4 | COMe | F | H | H | H |
| 701 | 1 | $CO_2Me$ | F | H | H | H |
| 702 | 2 | $CO_2Me$ | F | H | H | H |
| 703 | 3 | $CO_2Me$ | F | H | H | H |
| 704 | 4 | $CO_2Me$ | F | H | H | H |

TABLE 20-continued

| Entry | n | $R^7$ | $R^{20a}$ | $R^{20b}$ | $R^{20c}$ | $R^{20d}$ |
|---|---|---|---|---|---|---|
| 705 | 1 | $CO_2tBu$ | F | H | H | H |
| 706 | 2 | $CO_2tBu$ | F | H | H | H |
| 707 | 3 | $CO_2tBu$ | F | H | H | H |
| 708 | 4 | $CO_2tBu$ | F | H | H | H |
| 709 | 1 | CONHMe | F | H | H | H |
| 710 | 2 | CONHMe | F | H | H | H |
| 711 | 3 | CONHMe | F | H | H | H |
| 712 | 4 | CONHMe | F | H | H | H |
| 713 | 1 | $SO_2Me$ | F | H | H | H |
| 714 | 2 | $SO_2Me$ | F | H | H | H |
| 715 | 3 | $SO_2Me$ | F | H | H | H |
| 716 | 4 | $SO_2Me$ | F | H | H | H |
| 717 | 1 | $SO_2NH_2$ | F | H | H | H |
| 718 | 2 | $SO_2NH_2$ | F | H | H | H |
| 719 | 3 | $SO_2NH_2$ | F | H | H | H |
| 720 | 4 | $SO_2NH_2$ | F | H | H | H |
| 721 | 1 | H | Cl | H | H | H |
| 722 | 2 | H | Cl | H | H | H |
| 723 | 3 | H | Cl | H | H | H |
| 724 | 4 | H | Cl | H | H | H |
| 725 | 1 | Me | Cl | H | H | H |
| 726 | 2 | Me | Cl | H | H | H |
| 727 | 3 | Me | Cl | H | H | H |
| 728 | 4 | Me | Cl | H | H | H |
| 729 | 1 | $CH_2Ph$ | Cl | H | H | H |
| 730 | 2 | $CH_2Ph$ | Cl | H | H | H |
| 731 | 3 | $CH_2Ph$ | Cl | H | H | H |
| 732 | 4 | $CH_2Ph$ | Cl | H | H | H |
| 733 | 1 | COMe | Cl | H | H | H |
| 734 | 2 | COMe | Cl | H | H | H |
| 735 | 3 | COMe | Cl | H | H | H |
| 736 | 4 | COMe | Cl | H | H | H |
| 737 | 1 | $CO_2Me$ | Cl | H | H | H |
| 738 | 2 | $CO_2Me$ | Cl | H | H | H |
| 739 | 3 | $CO_2Me$ | Cl | H | H | H |
| 740 | 4 | $CO_2Me$ | Cl | H | H | H |
| 741 | 1 | $CO_2tBu$ | Cl | H | H | H |
| 742 | 2 | $CO_2tBu$ | Cl | H | H | H |
| 743 | 3 | $CO_2tBu$ | Cl | H | H | H |
| 744 | 4 | $CO_2tBu$ | Cl | H | H | H |
| 745 | 1 | CONHMe | Cl | H | H | H |
| 746 | 2 | CONHMe | Cl | H | H | H |
| 747 | 3 | CONHMe | Cl | H | H | H |
| 748 | 4 | CONHMe | Cl | H | H | H |
| 749 | 1 | $SO_2Me$ | Cl | H | H | H |
| 750 | 2 | $SO_2Me$ | Cl | H | H | H |
| 751 | 3 | $SO_2Me$ | Cl | H | H | H |
| 752 | 4 | $SO_2Me$ | Cl | H | H | H |
| 753 | 1 | $SO_2NH_2$ | Cl | H | H | H |
| 754 | 2 | $SO_2NH_2$ | Cl | H | H | H |
| 755 | 3 | $SO_2NH_2$ | Cl | H | H | H |
| 756 | 4 | $SO_2NH_2$ | Cl | H | H | H |
| 757 | 1 | H | CN | H | H | H |
| 758 | 2 | H | CN | H | H | H |
| 759 | 3 | H | CN | H | H | H |
| 760 | 4 | H | CN | H | H | H |
| 761 | 1 | Me | CN | H | H | H |
| 762 | 2 | Me | CN | H | H | H |
| 763 | 3 | Me | CN | H | H | H |
| 764 | 4 | Me | CN | H | H | H |
| 765 | 1 | $CH_2Ph$ | CN | H | H | H |
| 766 | 2 | $CH_2Ph$ | CN | H | H | H |
| 767 | 3 | $CH_2Ph$ | CN | H | H | H |
| 768 | 4 | $CH_2Ph$ | CN | H | H | H |
| 769 | 1 | COMe | CN | H | H | H |
| 770 | 2 | COMe | CN | H | H | H |
| 771 | 3 | COMe | CN | H | H | H |
| 772 | 4 | COMe | CN | H | H | H |
| 773 | 1 | $CO_2Me$ | CN | H | H | H |
| 774 | 2 | $CO_2Me$ | CN | H | H | H |
| 775 | 3 | $CO_2Me$ | CN | H | H | H |
| 776 | 4 | $CO_2Me$ | CN | H | H | H |
| 777 | 1 | $CO_2tBu$ | CN | H | H | H |
| 778 | 2 | $CO_2tBu$ | CN | H | H | H |
| 779 | 3 | $CO_2tBu$ | CN | H | H | H |
| 780 | 4 | $CO_2tBu$ | CN | H | H | H |
| 781 | 1 | CONHMe | CN | H | H | H |
| 782 | 2 | CONHMe | CN | H | H | H |

TABLE 20-continued

| Entry | n | $R^7$ | $R^{20a}$ | $R^{20b}$ | $R^{20c}$ | $R^{20d}$ |
|---|---|---|---|---|---|---|
| 783 | 3 | CONHMe | CN | H | H | H |
| 784 | 4 | CONHMe | CN | H | H | H |
| 785 | 1 | $SO_2Me$ | CN | H | H | H |
| 786 | 2 | $SO_2Me$ | CN | H | H | H |
| 787 | 3 | $SO_2Me$ | CN | H | H | H |
| 788 | 4 | $SO_2Me$ | CN | H | H | H |
| 789 | 1 | $SO_2NH_2$ | CN | H | H | H |
| 790 | 2 | $SO_2NH_2$ | CN | H | H | H |
| 791 | 3 | $SO_2NH_2$ | CN | H | H | H |
| 792 | 4 | $SO_2NH_2$ | CN | H | H | H |
| 793 | 1 | H | H | H | H | OH |
| 794 | 2 | H | H | H | H | OH |
| 795 | 3 | H | H | H | H | OH |
| 796 | 4 | H | H | H | H | OH |
| 797 | 1 | Me | H | H | H | OH |
| 798 | 2 | Me | H | H | H | OH |
| 799 | 3 | Me | H | H | H | OH |
| 800 | 4 | Me | H | H | H | OH |
| 801 | 1 | $CH_2Ph$ | H | H | H | OH |
| 802 | 2 | $CH_2Ph$ | H | H | H | OH |
| 803 | 3 | $CH_2Ph$ | H | H | H | OH |
| 804 | 4 | $CH_2Ph$ | H | H | H | OH |
| 805 | 1 | COMe | H | H | H | OH |
| 806 | 2 | COMe | H | H | H | OH |
| 807 | 3 | COMe | H | H | H | OH |
| 808 | 4 | COMe | H | H | H | OH |
| 809 | 1 | $CO_2Me$ | H | H | H | OH |
| 810 | 2 | $CO_2Me$ | H | H | H | OH |
| 811 | 3 | $CO_2Me$ | H | H | H | OH |
| 812 | 4 | $CO_2Me$ | H | H | H | OH |
| 813 | 1 | $CO_2tBu$ | H | H | H | OH |
| 814 | 2 | $CO_2tBu$ | H | H | H | OH |
| 815 | 3 | $CO_2tBu$ | H | H | H | OH |
| 816 | 4 | $CO_2tBu$ | H | H | H | OH |
| 817 | 1 | CONHMe | H | H | H | OH |
| 818 | 2 | CONHMe | H | H | H | OH |
| 819 | 3 | CONHMe | H | H | H | OH |
| 820 | 4 | CONHMe | H | H | H | OH |
| 821 | 1 | $SO_2Me$ | H | H | H | OH |
| 822 | 2 | $SO_2Me$ | H | H | H | OH |
| 823 | 3 | $SO_2Me$ | H | H | H | OH |
| 824 | 4 | $SO_2Me$ | H | H | H | OH |
| 825 | 1 | $SO_2NH_2$ | H | H | H | OH |
| 826 | 2 | $SO_2NH_2$ | H | H | H | OH |
| 827 | 3 | $SO_2NH_2$ | H | H | H | OH |
| 828 | 4 | $SO_2NH_2$ | H | H | H | OH |
| 829 | 1 | H | H | H | H | OMe |
| 830 | 2 | H | H | H | H | OMe |
| 831 | 3 | H | H | H | H | OMe |
| 832 | 4 | H | H | H | H | OMe |
| 833 | 1 | Me | H | H | H | OMe |
| 834 | 2 | Me | H | H | H | OMe |
| 835 | 3 | Me | H | H | H | OMe |
| 836 | 4 | Me | H | H | H | OMe |
| 837 | 1 | $CH_2Ph$ | H | H | H | OMe |
| 838 | 2 | $CH_2Ph$ | H | H | H | OMe |
| 839 | 3 | $CH_2Ph$ | H | H | H | OMe |
| 840 | 4 | $CH_2Ph$ | H | H | H | OMe |
| 841 | 1 | COMe | H | H | H | OMe |
| 842 | 2 | COMe | H | H | H | OMe |
| 843 | 3 | COMe | H | H | H | OMe |
| 844 | 4 | COMe | H | H | H | OMe |
| 845 | 1 | $CO_2Me$ | H | H | H | OMe |
| 846 | 2 | $CO_2Me$ | H | H | H | OMe |
| 847 | 3 | $CO_2Me$ | H | H | H | OMe |
| 848 | 4 | $CO_2Me$ | H | H | H | OMe |
| 849 | 1 | $CO_2tBu$ | H | H | H | OMe |
| 850 | 2 | $CO_2tBu$ | H | H | H | OMe |
| 851 | 3 | $CO_2tBu$ | H | H | H | OMe |
| 852 | 4 | $CO_2tBu$ | H | H | H | OMe |
| 853 | 1 | CONHMe | H | H | H | OMe |
| 854 | 2 | CONHMe | H | H | H | OMe |
| 855 | 3 | CONHMe | H | H | H | OMe |
| 856 | 4 | CONHMe | H | H | H | OMe |
| 857 | 1 | $SO_2Me$ | H | H | H | OMe |
| 858 | 2 | $SO_2Me$ | H | H | H | OMe |
| 859 | 3 | $SO_2Me$ | H | H | H | OMe |
| 860 | 4 | $SO_2Me$ | H | H | H | OMe |

TABLE 20-continued

| Entry | n | $R^7$ | $R^{20a}$ | $R^{20b}$ | $R^{20c}$ | $R^{20d}$ |
|---|---|---|---|---|---|---|
| 861 | 1 | $SO_2NH_2$ | H | H | H | OMe |
| 862 | 2 | $SO_2NH_2$ | H | H | H | OMe |
| 863 | 3 | $SO_2NH_2$ | H | H | H | OMe |
| 864 | 4 | $SO_2NH_2$ | H | H | H | OMe |
| 865 | 1 | H | H | H | H | Me |
| 866 | 2 | H | H | H | H | Me |
| 867 | 3 | H | H | H | H | Me |
| 868 | 4 | H | H | H | H | Me |
| 869 | 1 | Me | H | H | H | Me |
| 870 | 2 | Me | H | H | H | Me |
| 871 | 3 | Me | H | H | H | Me |
| 872 | 4 | Me | H | H | H | Me |
| 873 | 1 | $CH_2Ph$ | H | H | H | Me |
| 874 | 2 | $CH_2Ph$ | H | H | H | Me |
| 875 | 3 | $CH_2Ph$ | H | H | H | Me |
| 876 | 4 | $CH_2Ph$ | H | H | H | Me |
| 877 | 1 | COMe | H | H | H | Me |
| 878 | 2 | COMe | H | H | H | Me |
| 879 | 3 | COMe | H | H | H | Me |
| 880 | 4 | COMe | H | H | H | Me |
| 881 | 1 | $CO_2Me$ | H | H | H | Me |
| 882 | 2 | $CO_2Me$ | H | H | H | Me |
| 883 | 3 | $CO_2Me$ | H | H | H | Me |
| 884 | 4 | $CO_2Me$ | H | H | H | Me |
| 885 | 1 | $CO_2tBu$ | H | H | H | Me |
| 886 | 2 | $CO_2tBu$ | H | H | H | Me |
| 887 | 3 | $CO_2tBu$ | H | H | H | Me |
| 888 | 4 | $CO_2tBu$ | H | H | H | Me |
| 889 | 1 | CONHMe | H | H | H | Me |
| 890 | 2 | CONHMe | H | H | H | Me |
| 891 | 3 | CONHMe | H | H | H | Me |
| 892 | 4 | CONHMe | H | H | H | Me |
| 893 | 1 | $SO_2Me$ | H | H | H | Me |
| 894 | 2 | $SO_2Me$ | H | H | H | Me |
| 895 | 3 | $SO_2Me$ | H | H | H | Me |
| 896 | 4 | $SO_2Me$ | H | H | H | Me |
| 897 | 1 | $SO_2NH_2$ | H | H | H | Me |
| 898 | 2 | $SO_2NH_2$ | H | H | H | Me |
| 899 | 3 | $SO_2NH_2$ | H | H | H | Me |
| 900 | 4 | $SO_2NH_2$ | H | H | H | Me |
| 901 | 1 | H | H | H | H | $CF_3$ |
| 902 | 2 | H | H | H | H | $CF_3$ |
| 903 | 3 | H | H | H | H | $CF_3$ |
| 904 | 4 | H | H | H | H | $CF_3$ |
| 905 | 1 | Me | H | H | H | $CF_3$ |
| 906 | 2 | Me | H | H | H | $CF_3$ |
| 907 | 3 | Me | H | H | H | $CF_3$ |
| 908 | 4 | Me | H | H | H | $CF_3$ |
| 909 | 1 | $CH_2Ph$ | H | H | H | $CF_3$ |
| 910 | 2 | $CH_2Ph$ | H | H | H | $CF_3$ |
| 911 | 3 | $CH_2Ph$ | H | H | H | $CF_3$ |
| 912 | 4 | $CH_2Ph$ | H | H | H | $CF_3$ |
| 913 | 1 | COMe | H | H | H | $CF_3$ |
| 914 | 2 | COMe | H | H | H | $CF_3$ |
| 915 | 3 | COMe | H | H | H | $CF_3$ |
| 916 | 4 | COMe | H | H | H | $CF_3$ |
| 917 | 1 | $CO_2Me$ | H | H | H | $CF_3$ |
| 918 | 2 | $CO_2Me$ | H | H | H | $CF_3$ |
| 919 | 3 | $CO_2Me$ | H | H | H | $CF_3$ |
| 920 | 4 | $CO_2Me$ | H | H | H | $CF_3$ |
| 921 | 1 | $CO_2tBu$ | H | H | H | $CF_3$ |
| 922 | 2 | $CO_2tBu$ | H | H | H | $CF_3$ |
| 923 | 3 | $CO_2tBu$ | H | H | H | $CF_3$ |
| 924 | 4 | $CO_2tBu$ | H | H | H | $CF_3$ |
| 925 | 1 | CONHMe | H | H | H | $CF_3$ |
| 926 | 2 | CONHMe | H | H | H | $CF_3$ |
| 927 | 3 | CONHMe | H | H | H | $CF_3$ |
| 928 | 4 | CONHMe | H | H | H | $CF_3$ |
| 929 | 1 | $SO_2Me$ | H | H | H | $CF_3$ |
| 930 | 2 | $SO_2Me$ | H | H | H | $CF_3$ |
| 931 | 3 | $SO_2Me$ | H | H | H | $CF_3$ |
| 932 | 4 | $SO_2Me$ | H | H | H | $CF_3$ |
| 933 | 1 | $SO_2NH_2$ | H | H | H | $CF_3$ |
| 934 | 2 | $SO_2NH_2$ | H | H | H | $CF_3$ |
| 935 | 3 | $SO_2NH_2$ | H | H | H | $CF_3$ |
| 936 | 4 | $SO_2NH_2$ | H | H | H | $CF_3$ |
| 937 | 1 | H | H | H | H | F |
| 938 | 2 | H | H | H | H | F |

TABLE 20-continued

| Entry | n | $R^7$ | $R^{20a}$ | $R^{20b}$ | $R^{20c}$ | $R^{20d}$ |
|---|---|---|---|---|---|---|
| 939 | 3 | H | H | H | H | F |
| 940 | 3 | H | H | H | H | F |
| 941 | 1 | Me | H | H | H | F |
| 942 | 2 | Me | H | H | H | F |
| 943 | 3 | Me | H | H | H | F |
| 944 | 4 | Me | H | H | H | F |
| 945 | 1 | $CH_2Ph$ | H | H | H | F |
| 946 | 2 | $CH_2Ph$ | H | H | H | F |
| 947 | 3 | $CH_2Ph$ | H | H | H | F |
| 948 | 4 | $CH_2Ph$ | H | H | H | F |
| 949 | 1 | COMe | H | H | H | F |
| 950 | 2 | COMe | H | H | H | F |
| 951 | 3 | COMe | H | H | H | F |
| 952 | 4 | COMe | H | H | H | F |
| 953 | 1 | $CO_2Me$ | H | H | H | F |
| 954 | 2 | $CO_2Me$ | H | H | H | F |
| 955 | 3 | $CO_2Me$ | H | H | H | F |
| 956 | 4 | $CO_2Me$ | H | H | H | F |
| 957 | 1 | $CO_2tBu$ | H | H | H | F |
| 958 | 2 | $CO_2tBu$ | H | H | H | F |
| 959 | 3 | $CO_2tBu$ | H | H | H | F |
| 960 | 4 | $CO_2tBu$ | H | H | H | F |
| 961 | 1 | CONHMe | H | H | H | F |
| 962 | 2 | CONHMe | H | H | H | F |
| 963 | 3 | CONHMe | H | H | H | F |
| 964 | 4 | CONHMe | H | H | H | F |
| 965 | 1 | $SO_2Me$ | H | H | H | F |
| 966 | 2 | $SO_2Me$ | H | H | H | F |
| 967 | 3 | $SO_2Me$ | H | H | H | F |
| 968 | 4 | $SO_2Me$ | H | H | H | F |
| 969 | 1 | $SO_2NH_2$ | H | H | H | F |
| 970 | 2 | $SO_2NH_2$ | H | H | H | F |
| 971 | 3 | $SO_2NH_2$ | H | H | H | F |
| 972 | 4 | $SO_2NH_2$ | H | H | H | F |
| 973 | 1 | H | H | H | H | Cl |
| 974 | 2 | H | H | H | H | Cl |
| 975 | 3 | H | H | H | H | Cl |
| 976 | 4 | H | H | H | H | Cl |
| 977 | 1 | Me | H | H | H | Cl |
| 978 | 2 | Me | H | H | H | Cl |
| 979 | 3 | Me | H | H | H | Cl |
| 980 | 4 | Me | H | H | H | Cl |
| 981 | 1 | $CH_2Ph$ | H | H | H | Cl |
| 982 | 2 | $CH_2Ph$ | H | H | H | Cl |
| 983 | 3 | $CH_2Ph$ | H | H | H | Cl |
| 984 | 4 | $CH_2Ph$ | H | H | H | Cl |
| 985 | 1 | COMe | H | H | H | Cl |
| 986 | 2 | COMe | H | H | H | Cl |
| 987 | 3 | COMe | H | H | H | Cl |
| 988 | 4 | COMe | H | H | H | Cl |
| 989 | 1 | $CO_2Me$ | H | H | H | Cl |
| 990 | 2 | $CO_2Me$ | H | H | H | Cl |
| 991 | 3 | $CO_2Me$ | H | H | H | Cl |
| 992 | 4 | $CO_2Me$ | H | H | H | Cl |
| 993 | 1 | $CO_2tBu$ | H | H | H | Cl |
| 994 | 2 | $CO_2tBu$ | H | H | H | Cl |
| 995 | 3 | $CO_2tBu$ | H | H | H | Cl |
| 996 | 4 | $CO_2tBu$ | H | H | H | Cl |
| 997 | 1 | CONHMe | H | H | H | Cl |
| 998 | 2 | CONHMe | H | H | H | Cl |
| 999 | 3 | CONHMe | H | H | H | Cl |
| 1000 | 4 | CONHMe | H | H | H | Cl |
| 1001 | 1 | $SO_2Me$ | H | H | H | Cl |
| 1002 | 2 | $SO_2Me$ | H | H | H | Cl |
| 1003 | 3 | $SO_2Me$ | H | H | H | Cl |
| 1004 | 4 | $SO_2Me$ | H | H | H | Cl |
| 1005 | 1 | $SO_2NH_2$ | H | H | H | Cl |
| 1006 | 2 | $SO_2NH_2$ | H | H | H | Cl |
| 1007 | 3 | $SO_2NH_2$ | H | H | H | Cl |
| 1008 | 4 | $SO_2NH_2$ | H | H | H | Cl |
| 1009 | 1 | H | H | H | H | CN |
| 1010 | 2 | H | H | H | H | CN |
| 1011 | 3 | H | H | H | H | CN |
| 1012 | 4 | H | H | H | H | CN |
| 1013 | 1 | Me | H | H | H | CN |
| 1014 | 2 | Me | H | H | H | CN |
| 1015 | 3 | Me | H | H | H | CN |
| 1016 | 4 | Me | H | H | H | CN |

TABLE 20-continued

| Entry | n | $R^7$ | $R^{20a}$ | $R^{20b}$ | $R^{20c}$ | $R^{20d}$ |
|---|---|---|---|---|---|---|
| 1017 | 1 | $CH_2Ph$ | H | H | H | CN |
| 1018 | 2 | $CH_2Ph$ | H | H | H | CN |
| 1019 | 3 | $CH_2Ph$ | H | H | H | CN |
| 1020 | 4 | $CH_2Ph$ | H | H | H | CN |
| 1021 | 1 | COMe | H | H | H | CN |
| 1022 | 2 | COMe | H | H | H | CN |
| 1023 | 3 | COMe | H | H | H | CN |
| 1024 | 4 | COMe | H | H | H | CN |
| 1025 | 1 | $CO_2Me$ | H | H | H | CN |
| 1026 | 2 | $CO_2Me$ | H | H | H | CN |
| 1027 | 3 | $CO_2Me$ | H | H | H | CN |
| 1028 | 4 | $CO_2Me$ | H | H | H | CN |
| 1029 | 1 | $CO_2tBu$ | H | H | H | CN |
| 1030 | 2 | $CO_2tBu$ | H | H | H | CN |
| 1031 | 3 | $CO_2tBu$ | H | H | H | CN |
| 1032 | 4 | $CO_2tBu$ | H | H | H | CN |
| 1033 | 1 | CONHMe | H | H | H | CN |
| 1034 | 2 | CONHMe | H | H | H | CN |
| 1035 | 3 | CONHMe | H | H | H | CN |
| 1036 | 4 | CONHMe | H | H | H | CN |
| 1037 | 1 | $SO_2Me$ | H | H | H | CN |
| 1038 | 2 | $SO_2Me$ | H | H | H | CN |
| 1039 | 3 | $SO_2Me$ | H | H | H | CN |
| 1040 | 4 | $SO_2Me$ | H | H | H | CN |
| 1041 | 1 | $SO_2NH_2$ | H | H | H | CN |
| 1042 | 2 | $SO_2NH_2$ | H | H | H | CN |
| 1043 | 3 | $SO_2NH_2$ | H | H | H | CN |
| 1044 | 4 | $SO_2NH_2$ | H | H | H | CN |

Exemplary embodiments include compounds having the formula (XXVII)

(XXVII)

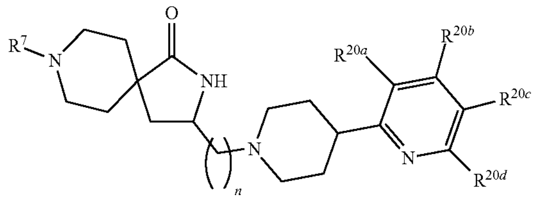

or a pharmaceutically acceptable salt form thereof defined herein below in Table 21.

TABLE 21

| Entry | n | $R^7$ | $R^{20a}$ | $R^{20b}$ | $R^{20c}$ | $R^{20d}$ |
|---|---|---|---|---|---|---|
| 1 | 1 | H | H | H | H | H |
| 2 | 2 | H | H | H | H | H |
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |

TABLE 21-continued

| Entry | n | $R^7$ | $R^{20a}$ | $R^{20b}$ | $R^{20c}$ | $R^{20d}$ |
|---|---|---|---|---|---|---|
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |
| 60 | 4 | $CO_2tBu$ | H | H | OH | H |
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |
| 79 | 3 | Me | H | H | OMe | H |
| 80 | 4 | Me | H | H | OMe | H |
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |

TABLE 21-continued

| Entry | n | $R^7$ | $R^{20a}$ | $R^{20b}$ | $R^{20c}$ | $R^{20d}$ |
|---|---|---|---|---|---|---|
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |
| 138 | 2 | $SO_2Me$ | H | H | Me | H |
| 139 | 3 | $SO_2Me$ | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |
| 157 | 1 | COMe | H | H | $CF_3$ | H |
| 158 | 2 | COMe | H | H | $CF_3$ | H |
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | $CO_2tBu$ | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |
| 216 | 4 | $SO_2NH_2$ | H | H | F | H |
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |
| 235 | 3 | $CO_2Me$ | H | H | Cl | H |
| 236 | 4 | $CO_2Me$ | H | H | Cl | H |
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |

TABLE 21-continued

| Entry | n | $R^7$ | $R^{20a}$ | $R^{20b}$ | $R^{20c}$ | $R^{20d}$ |
|---|---|---|---|---|---|---|
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | $CH_2Ph$ | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | COMe | H | H | CN | H |
| 266 | 2 | COMe | H | H | CN | H |
| 267 | 3 | COMe | H | H | CN | H |
| 268 | 4 | COMe | H | H | CN | H |
| 269 | 1 | $CO_2Me$ | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2tBu$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |
| 277 | 1 | CONHMe | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | $SO_2Me$ | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2NH_2$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | H | H | OH | H | H |
| 290 | 2 | H | H | OH | H | H |
| 291 | 3 | H | H | OH | H | H |
| 292 | 4 | H | H | OH | H | H |
| 293 | 1 | Me | H | OH | H | H |
| 294 | 2 | Me | H | OH | H | H |
| 295 | 3 | Me | H | OH | H | H |
| 296 | 4 | Me | H | OH | H | H |
| 297 | 1 | $CH_2Ph$ | H | OH | H | H |
| 298 | 2 | $CH_2Ph$ | H | OH | H | H |
| 299 | 3 | $CH_2Ph$ | H | OH | H | H |
| 300 | 4 | $CH_2Ph$ | H | OH | H | H |
| 301 | 1 | COMe | H | OH | H | H |
| 302 | 2 | COMe | H | OH | H | H |
| 303 | 3 | COMe | H | OH | H | H |
| 304 | 4 | COMe | H | OH | H | H |
| 305 | 1 | $CO_2Me$ | H | OH | H | H |
| 306 | 2 | $CO_2Me$ | H | OH | H | H |
| 307 | 3 | $CO_2Me$ | H | OH | H | H |
| 308 | 4 | $CO_2Me$ | H | OH | H | H |
| 309 | 1 | $CO_2tBu$ | H | OH | H | H |
| 310 | 2 | $CO_2tBu$ | H | OH | H | H |
| 311 | 3 | $CO_2tBu$ | H | OH | H | H |
| 312 | 4 | $CO_2tBu$ | H | OH | H | H |
| 313 | 1 | CONHMe | H | OH | H | H |
| 314 | 2 | CONHMe | H | OH | H | H |
| 315 | 3 | CONHMe | H | OH | H | H |
| 316 | 4 | CONHMe | H | OH | H | H |
| 317 | 1 | $SO_2Me$ | H | OH | H | H |
| 318 | 2 | $SO_2Me$ | H | OH | H | H |
| 319 | 3 | $SO_2Me$ | H | OH | H | H |
| 320 | 4 | $SO_2Me$ | H | OH | H | H |
| 321 | 1 | $SO_2NH_2$ | H | OH | H | H |
| 322 | 2 | $SO_2NH_2$ | H | OH | H | H |
| 323 | 3 | $SO_2NH_2$ | H | OH | H | H |
| 324 | 4 | $SO_2NH_2$ | H | OH | H | H |
| 325 | 1 | H | H | OMe | H | H |
| 326 | 2 | H | H | OMe | H | H |
| 327 | 3 | H | H | OMe | H | H |
| 328 | 4 | H | H | OMe | H | H |
| 329 | 1 | Me | H | OMe | H | H |
| 330 | 2 | Me | H | OMe | H | H |
| 331 | 3 | Me | H | OMe | H | H |
| 332 | 4 | Me | H | OMe | H | H |
| 333 | 1 | $CH_2Ph$ | H | OMe | H | H |
| 334 | 2 | $CH_2Ph$ | H | OMe | H | H |

TABLE 21-continued

| Entry | n | $R^7$ | $R^{20a}$ | $R^{20b}$ | $R^{20c}$ | $R^{20d}$ |
|---|---|---|---|---|---|---|
| 335 | 3 | $CH_2Ph$ | H | OMe | H | H |
| 336 | 4 | $CH_2Ph$ | H | OMe | H | H |
| 337 | 1 | COMe | H | OMe | H | H |
| 338 | 2 | COMe | H | OMe | H | H |
| 339 | 3 | COMe | H | OMe | H | H |
| 340 | 4 | COMe | H | OMe | H | H |
| 341 | 1 | $CO_2Me$ | H | OMe | H | H |
| 342 | 2 | $CO_2Me$ | H | OMe | H | H |
| 343 | 3 | $CO_2Me$ | H | OMe | H | H |
| 344 | 4 | $CO_2Me$ | H | OMe | H | H |
| 345 | 1 | $CO_2tBu$ | H | OMe | H | H |
| 346 | 2 | $CO_2tBu$ | H | OMe | H | H |
| 347 | 3 | $CO_2tBu$ | H | OMe | H | H |
| 348 | 4 | $CO_2tBu$ | H | OMe | H | H |
| 349 | 1 | CONHMe | H | OMe | H | H |
| 350 | 2 | CONHMe | H | OMe | H | H |
| 351 | 3 | CONHMe | H | OMe | H | H |
| 352 | 4 | CONHMe | H | OMe | H | H |
| 353 | 1 | $SO_2Me$ | H | OMe | H | H |
| 354 | 2 | $SO_2Me$ | H | OMe | H | H |
| 355 | 3 | $SO_2Me$ | H | OMe | H | H |
| 356 | 4 | $SO_2Me$ | H | OMe | H | H |
| 357 | 1 | $SO_2NH_2$ | H | OMe | H | H |
| 358 | 2 | $SO_2NH_2$ | H | OMe | H | H |
| 359 | 3 | $SO_2NH_2$ | H | OMe | H | H |
| 360 | 4 | $SO_2NH_2$ | H | OMe | H | H |
| 361 | 1 | H | H | Me | H | H |
| 362 | 2 | H | H | Me | H | H |
| 363 | 3 | H | H | Me | H | H |
| 364 | 4 | H | H | Me | H | H |
| 365 | 1 | Me | H | Me | H | H |
| 366 | 2 | Me | H | Me | H | H |
| 367 | 3 | Me | H | Me | H | H |
| 368 | 4 | Me | H | Me | H | H |
| 369 | 1 | $CH_2Ph$ | H | Me | H | H |
| 370 | 2 | $CH_2Ph$ | H | Me | H | H |
| 371 | 3 | $CH_2Ph$ | H | Me | H | H |
| 372 | 4 | $CH_2Ph$ | H | Me | H | H |
| 373 | 1 | COMe | H | Me | H | H |
| 374 | 2 | COMe | H | Me | H | H |
| 375 | 3 | COMe | H | Me | H | H |
| 376 | 4 | COMe | H | Me | H | H |
| 377 | 1 | $CO_2Me$ | H | Me | H | H |
| 378 | 2 | $CO_2Me$ | H | Me | H | H |
| 379 | 3 | $CO_2Me$ | H | Me | H | H |
| 380 | 4 | $CO_2Me$ | H | Me | H | H |
| 381 | 1 | $CO_2tBu$ | H | Me | H | H |
| 382 | 2 | $CO_2tBu$ | H | Me | H | H |
| 383 | 3 | $CO_2tBu$ | H | Me | H | H |
| 384 | 4 | $CO_2tBu$ | H | Me | H | H |
| 385 | 1 | CONHMe | H | Me | H | H |
| 386 | 2 | CONHMe | H | Me | H | H |
| 387 | 3 | CONHMe | H | Me | H | H |
| 388 | 4 | CONHMe | H | Me | H | H |
| 389 | 1 | $SO_2Me$ | H | Me | H | H |
| 390 | 2 | $SO_2Me$ | H | Me | H | H |
| 391 | 3 | $SO_2Me$ | H | Me | H | H |
| 392 | 4 | $SO_2Me$ | H | Me | H | H |
| 393 | 1 | $SO_2NH_2$ | H | Me | H | H |
| 394 | 2 | $SO_2NH_2$ | H | Me | H | H |
| 395 | 3 | $SO_2NH_2$ | H | Me | H | H |
| 396 | 4 | $SO_2NH_2$ | H | Me | H | H |
| 397 | 1 | H | H | $CF_3$ | H | H |
| 398 | 2 | H | H | $CF_3$ | H | H |
| 399 | 3 | H | H | $CF_3$ | H | H |
| 400 | 4 | H | H | $CF_3$ | H | H |
| 401 | 1 | Me | H | $CF_3$ | H | H |
| 402 | 2 | Me | H | $CF_3$ | H | H |
| 403 | 3 | Me | H | $CF_3$ | H | H |
| 404 | 4 | Me | H | $CF_3$ | H | H |
| 405 | 1 | $CH_2Ph$ | H | $CF_3$ | H | H |
| 406 | 2 | $CH_2Ph$ | H | $CF_3$ | H | H |
| 407 | 3 | $CH_2Ph$ | H | $CF_3$ | H | H |
| 408 | 4 | $CH_2Ph$ | H | $CF_3$ | H | H |
| 409 | 1 | COMe | H | $CF_3$ | H | H |
| 410 | 2 | COMe | H | $CF_3$ | H | H |
| 411 | 3 | COMe | H | $CF_3$ | H | H |
| 412 | 4 | COMe | H | $CF_3$ | H | H |

TABLE 21-continued

| Entry | n | $R^7$ | $R^{20a}$ | $R^{20b}$ | $R^{20c}$ | $R^{20d}$ |
|---|---|---|---|---|---|---|
| 413 | 1 | $CO_2Me$ | H | $CF_3$ | H | H |
| 414 | 2 | $CO_2Me$ | H | $CF_3$ | H | H |
| 415 | 3 | $CO_2Me$ | H | $CF_3$ | H | H |
| 416 | 4 | $CO_2Me$ | H | $CF_3$ | H | H |
| 417 | 1 | $CO_2tBu$ | H | $CF_3$ | H | H |
| 418 | 2 | $CO_2tBu$ | H | $CF_3$ | H | H |
| 419 | 3 | $CO_2tBu$ | H | $CF_3$ | H | H |
| 420 | 4 | $CO_2tBu$ | H | $CF_3$ | H | H |
| 421 | 1 | CONHMe | H | $CF_3$ | H | H |
| 422 | 2 | CONHMe | H | $CF_3$ | H | H |
| 423 | 3 | CONHMe | H | $CF_3$ | H | H |
| 424 | 4 | CONHMe | H | $CF_3$ | H | H |
| 425 | 1 | $SO_2Me$ | H | $CF_3$ | H | H |
| 426 | 2 | $SO_2Me$ | H | $CF_3$ | H | H |
| 427 | 3 | $SO_2Me$ | H | $CF_3$ | H | H |
| 428 | 4 | $SO_2Me$ | H | $CF_3$ | H | H |
| 429 | 1 | $SO_2NH_2$ | H | $CF_3$ | H | H |
| 430 | 2 | $SO_2NH_2$ | H | $CF_3$ | H | H |
| 431 | 3 | $SO_2NH_2$ | H | $CF_3$ | H | H |
| 432 | 4 | $SO_2NH_2$ | H | $CF_3$ | H | H |
| 433 | 1 | H | H | F | H | H |
| 434 | 2 | H | H | F | H | H |
| 435 | 3 | H | H | F | H | H |
| 436 | 3 | H | H | F | H | H |
| 437 | 1 | Me | H | F | H | H |
| 438 | 2 | Me | H | F | H | H |
| 439 | 3 | Me | H | F | H | H |
| 440 | 4 | Me | H | F | H | H |
| 441 | 1 | $CH_2Ph$ | H | F | H | H |
| 442 | 2 | $CH_2Ph$ | H | F | H | H |
| 443 | 3 | $CH_2Ph$ | H | F | H | H |
| 444 | 4 | $CH_2Ph$ | H | F | H | H |
| 445 | 1 | COMe | H | F | H | H |
| 446 | 2 | COMe | H | F | H | H |
| 447 | 3 | COMe | H | F | H | H |
| 448 | 4 | COMe | H | F | H | H |
| 449 | 1 | $CO_2Me$ | H | F | H | H |
| 450 | 2 | $CO_2Me$ | H | F | H | H |
| 451 | 3 | $CO_2Me$ | H | F | H | H |
| 452 | 4 | $CO_2Me$ | H | F | H | H |
| 453 | 1 | $CO_2tBu$ | H | F | H | H |
| 454 | 2 | $CO_2tBu$ | H | F | H | H |
| 455 | 3 | $CO_2tBu$ | H | F | H | H |
| 456 | 4 | $CO_2tBu$ | H | F | H | H |
| 457 | 1 | CONHMe | H | F | H | H |
| 458 | 2 | CONHMe | H | F | H | H |
| 459 | 3 | CONHMe | H | F | H | H |
| 460 | 4 | CONHMe | H | F | H | H |
| 461 | 1 | $SO_2Me$ | H | F | H | H |
| 462 | 2 | $SO_2Me$ | H | F | H | H |
| 463 | 3 | $SO_2Me$ | H | F | H | H |
| 464 | 4 | $SO_2Me$ | H | F | H | H |
| 465 | 1 | $SO_2NH_2$ | H | F | H | H |
| 466 | 2 | $SO_2NH_2$ | H | F | H | H |
| 467 | 3 | $SO_2NH_2$ | H | F | H | H |
| 468 | 4 | $SO_2NH_2$ | H | F | H | H |
| 469 | 1 | H | H | Cl | H | H |
| 470 | 2 | H | H | Cl | H | H |
| 471 | 3 | H | H | Cl | H | H |
| 472 | 4 | H | H | Cl | H | H |
| 473 | 1 | Me | H | Cl | H | H |
| 474 | 2 | Me | H | Cl | H | H |
| 475 | 3 | Me | H | Cl | H | H |
| 476 | 4 | Me | H | Cl | H | H |
| 477 | 1 | $CH_2Ph$ | H | Cl | H | H |
| 478 | 2 | $CH_2Ph$ | H | Cl | H | H |
| 479 | 3 | $CH_2Ph$ | H | Cl | H | H |
| 480 | 4 | $CH_2Ph$ | H | Cl | H | H |
| 481 | 1 | COMe | H | Cl | H | H |
| 482 | 2 | COMe | H | Cl | H | H |
| 483 | 3 | COMe | H | Cl | H | H |
| 484 | 4 | COMe | H | Cl | H | H |
| 485 | 1 | $CO_2Me$ | H | Cl | H | H |
| 486 | 2 | $CO_2Me$ | H | Cl | H | H |
| 487 | 3 | $CO_2Me$ | H | Cl | H | H |
| 488 | 4 | $CO_2Me$ | H | Cl | H | H |
| 489 | 1 | $CO_2tBu$ | H | Cl | H | H |
| 490 | 2 | $CO_2tBu$ | H | Cl | H | H |
| 491 | 3 | $CO_2tBu$ | H | Cl | H | H |
| 492 | 4 | $CO_2tBu$ | H | Cl | H | H |
| 493 | 1 | CONHMe | H | Cl | H | H |
| 494 | 2 | CONHMe | H | Cl | H | H |
| 495 | 3 | CONHMe | H | Cl | H | H |
| 496 | 4 | CONHMe | H | Cl | H | H |
| 497 | 1 | $SO_2Me$ | H | Cl | H | H |
| 498 | 2 | $SO_2Me$ | H | Cl | H | H |
| 499 | 3 | $SO_2Me$ | H | Cl | H | H |
| 500 | 4 | $SO_2Me$ | H | Cl | H | H |
| 501 | 1 | $SO_2NH_2$ | H | Cl | H | H |
| 502 | 2 | $SO_2NH_2$ | H | Cl | H | H |
| 503 | 3 | $SO_2NH_2$ | H | Cl | H | H |
| 504 | 4 | $SO_2NH_2$ | H | Cl | H | H |
| 505 | 1 | H | H | CN | H | H |
| 506 | 2 | H | H | CN | H | H |
| 507 | 3 | H | H | CN | H | H |
| 508 | 4 | H | H | CN | H | H |
| 509 | 1 | Me | H | CN | H | H |
| 510 | 2 | Me | H | CN | H | H |
| 511 | 3 | Me | H | CN | H | H |
| 512 | 4 | Me | H | CN | H | H |
| 513 | 1 | $CH_2Ph$ | H | CN | H | H |
| 514 | 2 | $CH_2Ph$ | H | CN | H | H |
| 515 | 3 | $CH_2Ph$ | H | CN | H | H |
| 516 | 4 | $CH_2Ph$ | H | CN | H | H |
| 517 | 1 | COMe | H | CN | H | H |
| 518 | 2 | COMe | H | CN | H | H |
| 519 | 3 | COMe | H | CN | H | H |
| 520 | 4 | COMe | H | CN | H | H |
| 521 | 1 | $CO_2Me$ | H | CN | H | H |
| 522 | 2 | $CO_2Me$ | H | CN | H | H |
| 523 | 3 | $CO_2Me$ | H | CN | H | H |
| 524 | 4 | $CO_2Me$ | H | CN | H | H |
| 525 | 1 | $CO_2tBu$ | H | CN | H | H |
| 526 | 2 | $CO_2tBu$ | H | CN | H | H |
| 527 | 3 | $CO_2tBu$ | H | CN | H | H |
| 528 | 4 | $CO_2tBu$ | H | CN | H | H |
| 529 | 1 | CONHMe | H | CN | H | H |
| 530 | 2 | CONHMe | H | CN | H | H |
| 531 | 3 | CONHMe | H | CN | H | H |
| 532 | 4 | CONHMe | H | CN | H | H |
| 533 | 1 | $SO_2Me$ | H | CN | H | H |
| 534 | 2 | $SO_2Me$ | H | CN | H | H |
| 535 | 3 | $SO_2Me$ | H | CN | H | H |
| 536 | 4 | $SO_2Me$ | H | CN | H | H |
| 537 | 1 | $SO_2NH_2$ | H | CN | H | H |
| 538 | 2 | $SO_2NH_2$ | H | CN | H | H |
| 539 | 3 | $SO_2NH_2$ | H | CN | H | H |
| 540 | 4 | $SO_2NH_2$ | H | CN | H | H |
| 541 | 1 | H | OH | H | H | H |
| 542 | 2 | H | OH | H | H | H |
| 543 | 3 | H | OH | H | H | H |
| 544 | 4 | H | OH | H | H | H |
| 545 | 1 | Me | OH | H | H | H |
| 546 | 2 | Me | OH | H | H | H |
| 547 | 3 | Me | OH | H | H | H |
| 548 | 4 | Me | OH | H | H | H |
| 549 | 1 | $CH_2Ph$ | OH | H | H | H |
| 550 | 2 | $CH_2Ph$ | OH | H | H | H |
| 551 | 3 | $CH_2Ph$ | OH | H | H | H |
| 552 | 4 | $CH_2Ph$ | OH | H | H | H |
| 553 | 1 | COMe | OH | H | H | H |
| 554 | 2 | COMe | OH | H | H | H |
| 555 | 3 | COMe | OH | H | H | H |
| 556 | 4 | COMe | OH | H | H | H |
| 557 | 1 | $CO_2Me$ | OH | H | H | H |
| 558 | 2 | $CO_2Me$ | OH | H | H | H |
| 559 | 3 | $CO_2Me$ | OH | H | H | H |
| 560 | 4 | $CO_2Me$ | OH | H | H | H |
| 561 | 1 | $CO_2tBu$ | OH | H | H | H |
| 562 | 2 | $CO_2tBu$ | OH | H | H | H |
| 563 | 3 | $CO_2tBu$ | OH | H | H | H |
| 564 | 4 | $CO_2tBu$ | OH | H | H | H |
| 565 | 1 | CONHMe | OH | H | H | H |
| 566 | 2 | CONHMe | OH | H | H | H |
| 567 | 3 | CONHMe | OH | H | H | H |
| 568 | 4 | CONHMe | OH | H | H | H |

TABLE 21-continued

| Entry | n | $R^7$ | $R^{20a}$ | $R^{20b}$ | $R^{20c}$ | $R^{20d}$ |
|---|---|---|---|---|---|---|
| 569 | 1 | $SO_2Me$ | OH | H | H | H |
| 570 | 2 | $SO_2Me$ | OH | H | H | H |
| 571 | 3 | $SO_2Me$ | OH | H | H | H |
| 572 | 4 | $SO_2Me$ | OH | H | H | H |
| 573 | 1 | $SO_2NH_2$ | OH | H | H | H |
| 574 | 2 | $SO_2NH_2$ | OH | H | H | H |
| 575 | 3 | $SO_2NH_2$ | OH | H | H | H |
| 576 | 4 | $SO_2NH_2$ | OH | H | H | H |
| 577 | 1 | H | OMe | H | H | H |
| 578 | 2 | H | OMe | H | H | H |
| 579 | 3 | H | OMe | H | H | H |
| 580 | 4 | H | OMe | H | H | H |
| 581 | 1 | Me | OMe | H | H | H |
| 582 | 2 | Me | OMe | H | H | H |
| 583 | 3 | Me | OMe | H | H | H |
| 584 | 4 | Me | OMe | H | H | H |
| 585 | 1 | $CH_2Ph$ | OMe | H | H | H |
| 586 | 2 | $CH_2Ph$ | OMe | H | H | H |
| 587 | 3 | $CH_2Ph$ | OMe | H | H | H |
| 588 | 4 | $CH_2Ph$ | OMe | H | H | H |
| 589 | 1 | COMe | OMe | H | H | H |
| 590 | 2 | COMe | OMe | H | H | H |
| 591 | 3 | COMe | OMe | H | H | H |
| 592 | 4 | COMe | OMe | H | H | H |
| 593 | 1 | $CO_2Me$ | OMe | H | H | H |
| 594 | 2 | $CO_2Me$ | OMe | H | H | H |
| 595 | 3 | $CO_2Me$ | OMe | H | H | H |
| 596 | 4 | $CO_2Me$ | OMe | H | H | H |
| 597 | 1 | $CO_2tBu$ | OMe | H | H | H |
| 598 | 2 | $CO_2tBu$ | OMe | H | H | H |
| 599 | 3 | $CO_2tBu$ | OMe | H | H | H |
| 600 | 4 | $CO_2tBu$ | OMe | H | H | H |
| 601 | 1 | CONHMe | OMe | H | H | H |
| 602 | 2 | CONHMe | OMe | H | H | H |
| 603 | 3 | CONHMe | OMe | H | H | H |
| 604 | 4 | CONHMe | OMe | H | H | H |
| 605 | 1 | $SO_2Me$ | OMe | H | H | H |
| 606 | 2 | $SO_2Me$ | OMe | H | H | H |
| 607 | 3 | $SO_2Me$ | OMe | H | H | H |
| 608 | 4 | $SO_2Me$ | OMe | H | H | H |
| 609 | 1 | $SO_2NH_2$ | OMe | H | H | H |
| 610 | 2 | $SO_2NH_2$ | OMe | H | H | H |
| 611 | 3 | $SO_2NH_2$ | OMe | H | H | H |
| 612 | 4 | $SO_2NH_2$ | OMe | H | H | H |
| 613 | 1 | H | Me | H | H | H |
| 614 | 2 | H | Me | H | H | H |
| 615 | 3 | H | Me | H | H | H |
| 616 | 4 | H | Me | H | H | H |
| 617 | 1 | Me | Me | H | H | H |
| 618 | 2 | Me | Me | H | H | H |
| 619 | 3 | Me | Me | H | H | H |
| 620 | 4 | Me | Me | H | H | H |
| 621 | 1 | $CH_2Ph$ | Me | H | H | H |
| 622 | 2 | $CH_2Ph$ | Me | H | H | H |
| 623 | 3 | $CH_2Ph$ | Me | H | H | H |
| 624 | 4 | $CH_2Ph$ | Me | H | H | H |
| 625 | 1 | COMe | Me | H | H | H |
| 626 | 2 | COMe | Me | H | H | H |
| 627 | 3 | COMe | Me | H | H | H |
| 628 | 4 | COMe | Me | H | H | H |
| 629 | 1 | $CO_2Me$ | Me | H | H | H |
| 630 | 2 | $CO_2Me$ | Me | H | H | H |
| 631 | 3 | $CO_2Me$ | Me | H | H | H |
| 632 | 4 | $CO_2Me$ | Me | H | H | H |
| 633 | 1 | $CO_2tBu$ | Me | H | H | H |
| 634 | 2 | $CO_2tBu$ | Me | H | H | H |
| 635 | 3 | $CO_2tBu$ | Me | H | H | H |
| 636 | 4 | $CO_2tBu$ | Me | H | H | H |
| 637 | 1 | CONHMe | Me | H | H | H |
| 638 | 2 | CONHMe | Me | H | H | H |
| 639 | 3 | CONHMe | Me | H | H | H |
| 640 | 4 | CONHMe | Me | H | H | H |
| 641 | 1 | $SO_2Me$ | Me | H | H | H |
| 642 | 2 | $SO_2Me$ | Me | H | H | H |
| 643 | 3 | $SO_2Me$ | Me | H | H | H |
| 644 | 4 | $SO_2Me$ | Me | H | H | H |
| 645 | 1 | $SO_2NH_2$ | Me | H | H | H |
| 646 | 2 | $SO_2NH_2$ | Me | H | H | H |

TABLE 21-continued

| Entry | n | $R^7$ | $R^{20a}$ | $R^{20b}$ | $R^{20c}$ | $R^{20d}$ |
|---|---|---|---|---|---|---|
| 647 | 3 | $SO_2NH_2$ | Me | H | H | H |
| 648 | 4 | $SO_2NH_2$ | Me | H | H | H |
| 649 | 1 | H | $CF_3$ | H | H | H |
| 650 | 2 | H | $CF_3$ | H | H | H |
| 651 | 3 | H | $CF_3$ | H | H | H |
| 652 | 4 | H | $CF_3$ | H | H | H |
| 653 | 1 | Me | $CF_3$ | H | H | H |
| 654 | 2 | Me | $CF_3$ | H | H | H |
| 655 | 3 | Me | $CF_3$ | H | H | H |
| 656 | 4 | Me | $CF_3$ | H | H | H |
| 657 | 1 | $CH_2Ph$ | $CF_3$ | H | H | H |
| 658 | 2 | $CH_2Ph$ | $CF_3$ | H | H | H |
| 659 | 3 | $CH_2Ph$ | $CF_3$ | H | H | H |
| 660 | 4 | $CH_2Ph$ | $CF_3$ | H | H | H |
| 661 | 1 | COMe | $CF_3$ | H | H | H |
| 662 | 2 | COMe | $CF_3$ | H | H | H |
| 663 | 3 | COMe | $CF_3$ | H | H | H |
| 664 | 4 | COMe | $CF_3$ | H | H | H |
| 665 | 1 | $CO_2Me$ | $CF_3$ | H | H | H |
| 666 | 2 | $CO_2Me$ | $CF_3$ | H | H | H |
| 667 | 3 | $CO_2Me$ | $CF_3$ | H | H | H |
| 668 | 4 | $CO_2Me$ | $CF_3$ | H | H | H |
| 669 | 1 | $CO_2tBu$ | $CF_3$ | H | H | H |
| 670 | 2 | $CO_2tBu$ | $CF_3$ | H | H | H |
| 671 | 3 | $CO_2tBu$ | $CF_3$ | H | H | H |
| 672 | 4 | $CO_2tBu$ | $CF_3$ | H | H | H |
| 673 | 1 | CONHMe | $CF_3$ | H | H | H |
| 674 | 2 | CONHMe | $CF_3$ | H | H | H |
| 675 | 3 | CONHMe | $CF_3$ | H | H | H |
| 676 | 4 | CONHMe | $CF_3$ | H | H | H |
| 677 | 1 | $SO_2Me$ | $CF_3$ | H | H | H |
| 678 | 2 | $SO_2Me$ | $CF_3$ | H | H | H |
| 679 | 3 | $SO_2Me$ | $CF_3$ | H | H | H |
| 680 | 4 | $SO_2Me$ | $CF_3$ | H | H | H |
| 681 | 1 | $SO_2NH_2$ | $CF_3$ | H | H | H |
| 682 | 2 | $SO_2NH_2$ | $CF_3$ | H | H | H |
| 683 | 3 | $SO_2NH_2$ | $CF_3$ | H | H | H |
| 684 | 4 | $SO_2NH_2$ | $CF_3$ | H | H | H |
| 685 | 1 | H | F | H | H | H |
| 686 | 2 | H | F | H | H | H |
| 687 | 3 | H | F | H | H | H |
| 688 | 3 | H | F | H | H | H |
| 689 | 1 | Me | F | H | H | H |
| 690 | 2 | Me | F | H | H | H |
| 691 | 3 | Me | F | H | H | H |
| 692 | 4 | Me | F | H | H | H |
| 693 | 1 | $CH_2Ph$ | F | H | H | H |
| 694 | 2 | $CH_2Ph$ | F | H | H | H |
| 695 | 3 | $CH_2Ph$ | F | H | H | H |
| 696 | 4 | $CH_2Ph$ | F | H | H | H |
| 697 | 1 | COMe | F | H | H | H |
| 698 | 2 | COMe | F | H | H | H |
| 699 | 3 | COMe | F | H | H | H |
| 700 | 4 | COMe | F | H | H | H |
| 701 | 1 | $CO_2Me$ | F | H | H | H |
| 702 | 2 | $CO_2Me$ | F | H | H | H |
| 703 | 3 | $CO_2Me$ | F | H | H | H |
| 704 | 4 | $CO_2Me$ | F | H | H | H |
| 705 | 1 | $CO_2tBu$ | F | H | H | H |
| 706 | 2 | $CO_2tBu$ | F | H | H | H |
| 707 | 3 | $CO_2tBu$ | F | H | H | H |
| 708 | 4 | $CO_2tBu$ | F | H | H | H |
| 709 | 1 | CONHMe | F | H | H | H |
| 710 | 2 | CONHMe | F | H | H | H |
| 711 | 3 | CONHMe | F | H | H | H |
| 712 | 4 | CONHMe | F | H | H | H |
| 713 | 1 | $SO_2Me$ | F | H | H | H |
| 714 | 2 | $SO_2Me$ | F | H | H | H |
| 715 | 3 | $SO_2Me$ | F | H | H | H |
| 716 | 4 | $SO_2Me$ | F | H | H | H |
| 717 | 1 | $SO_2NH_2$ | F | H | H | H |
| 718 | 2 | $SO_2NH_2$ | F | H | H | H |
| 719 | 3 | $SO_2NH_2$ | F | H | H | H |
| 720 | 4 | $SO_2NH_2$ | F | H | H | H |
| 721 | 1 | H | Cl | H | H | H |
| 722 | 2 | H | Cl | H | H | H |
| 723 | 3 | H | Cl | H | H | H |
| 724 | 4 | H | Cl | H | H | H |

TABLE 21-continued

| Entry | n | $R^7$ | $R^{20a}$ | $R^{20b}$ | $R^{20c}$ | $R^{20d}$ |
|---|---|---|---|---|---|---|
| 725 | 1 | Me | Cl | H | H | H |
| 726 | 2 | Me | Cl | H | H | H |
| 727 | 3 | Me | Cl | H | H | H |
| 728 | 4 | Me | Cl | H | H | H |
| 729 | 1 | $CH_2Ph$ | Cl | H | H | H |
| 730 | 2 | $CH_2Ph$ | Cl | H | H | H |
| 731 | 3 | $CH_2Ph$ | Cl | H | H | H |
| 732 | 4 | $CH_2Ph$ | Cl | H | H | H |
| 733 | 1 | COMe | Cl | H | H | H |
| 734 | 2 | COMe | Cl | H | H | H |
| 735 | 3 | COMe | Cl | H | H | H |
| 736 | 4 | COMe | Cl | H | H | H |
| 737 | 1 | $CO_2Me$ | Cl | H | H | H |
| 738 | 2 | $CO_2Me$ | Cl | H | H | H |
| 739 | 3 | $CO_2Me$ | Cl | H | H | H |
| 740 | 4 | $CO_2Me$ | Cl | H | H | H |
| 741 | 1 | $CO_2tBu$ | Cl | H | H | H |
| 742 | 2 | $CO_2tBu$ | Cl | H | H | H |
| 743 | 3 | $CO_2tBu$ | Cl | H | H | H |
| 744 | 4 | $CO_2tBu$ | Cl | H | H | H |
| 745 | 1 | CONHMe | Cl | H | H | H |
| 746 | 2 | CONHMe | Cl | H | H | H |
| 747 | 3 | CONHMe | Cl | H | H | H |
| 748 | 4 | CONHMe | Cl | H | H | H |
| 749 | 1 | $SO_2Me$ | Cl | H | H | H |
| 750 | 2 | $SO_2Me$ | Cl | H | H | H |
| 751 | 3 | $SO_2Me$ | Cl | H | H | H |
| 752 | 4 | $SO_2Me$ | Cl | H | H | H |
| 753 | 1 | $SO_2NH_2$ | Cl | H | H | H |
| 754 | 2 | $SO_2NH_2$ | Cl | H | H | H |
| 755 | 3 | $SO_2NH_2$ | Cl | H | H | H |
| 756 | 4 | $SO_2NH_2$ | Cl | H | H | H |
| 757 | 1 | H | CN | H | H | H |
| 758 | 2 | H | CN | H | H | H |
| 759 | 3 | H | CN | H | H | H |
| 760 | 4 | H | CN | H | H | H |
| 761 | 1 | Me | CN | H | H | H |
| 762 | 2 | Me | CN | H | H | H |
| 763 | 3 | Me | CN | H | H | H |
| 764 | 4 | Me | CN | H | H | H |
| 765 | 1 | $CH_2Ph$ | CN | H | H | H |
| 766 | 2 | $CH_2Ph$ | CN | H | H | H |
| 767 | 3 | $CH_2Ph$ | CN | H | H | H |
| 768 | 4 | $CH_2Ph$ | CN | H | H | H |
| 769 | 1 | COMe | CN | H | H | H |
| 770 | 2 | COMe | CN | H | H | H |
| 771 | 3 | COMe | CN | H | H | H |
| 772 | 4 | COMe | CN | H | H | H |
| 773 | 1 | $CO_2Me$ | CN | H | H | H |
| 774 | 2 | $CO_2Me$ | CN | H | H | H |
| 775 | 3 | $CO_2Me$ | CN | H | H | H |
| 776 | 4 | $CO_2Me$ | CN | H | H | H |
| 777 | 1 | $CO_2tBu$ | CN | H | H | H |
| 778 | 2 | $CO_2tBu$ | CN | H | H | H |
| 779 | 3 | $CO_2tBu$ | CN | H | H | H |
| 780 | 4 | $CO_2tBu$ | CN | H | H | H |
| 781 | 1 | CONHMe | CN | H | H | H |
| 782 | 2 | CONHMe | CN | H | H | H |
| 783 | 3 | CONHMe | CN | H | H | H |
| 784 | 4 | CONHMe | CN | H | H | H |
| 785 | 1 | $SO_2Me$ | CN | H | H | H |
| 786 | 2 | $SO_2Me$ | CN | H | H | H |
| 787 | 3 | $SO_2Me$ | CN | H | H | H |
| 788 | 4 | $SO_2Me$ | CN | H | H | H |
| 789 | 1 | $SO_2NH_2$ | CN | H | H | H |
| 790 | 2 | $SO_2NH_2$ | CN | H | H | H |
| 791 | 3 | $SO_2NH_2$ | CN | H | H | H |
| 792 | 4 | $SO_2NH_2$ | CN | H | H | H |
| 793 | 1 | H | H | H | H | OH |
| 794 | 2 | H | H | H | H | OH |
| 795 | 3 | H | H | H | H | OH |
| 796 | 4 | H | H | H | H | OH |
| 797 | 1 | Me | H | H | H | OH |
| 798 | 2 | Me | H | H | H | OH |
| 799 | 3 | Me | H | H | H | OH |
| 800 | 4 | Me | H | H | H | OH |
| 801 | 1 | $CH_2Ph$ | H | H | H | OH |
| 802 | 2 | $CH_2Ph$ | H | H | H | OH |

TABLE 21-continued

| Entry | n | $R^7$ | $R^{20a}$ | $R^{20b}$ | $R^{20c}$ | $R^{20d}$ |
|---|---|---|---|---|---|---|
| 803 | 3 | $CH_2Ph$ | H | H | H | OH |
| 804 | 4 | $CH_2Ph$ | H | H | H | OH |
| 805 | 1 | COMe | H | H | H | OH |
| 806 | 2 | COMe | H | H | H | OH |
| 807 | 3 | COMe | H | H | H | OH |
| 808 | 4 | COMe | H | H | H | OH |
| 809 | 1 | $CO_2Me$ | H | H | H | OH |
| 810 | 2 | $CO_2Me$ | H | H | H | OH |
| 811 | 3 | $CO_2Me$ | H | H | H | OH |
| 812 | 4 | $CO_2Me$ | H | H | H | OH |
| 813 | 1 | $CO_2tBu$ | H | H | H | OH |
| 814 | 2 | $CO_2tBu$ | H | H | H | OH |
| 815 | 3 | $CO_2tBu$ | H | H | H | OH |
| 816 | 4 | $CO_2tBu$ | H | H | H | OH |
| 817 | 1 | CONHMe | H | H | H | OH |
| 818 | 2 | CONHMe | H | H | H | OH |
| 819 | 3 | CONHMe | H | H | H | OH |
| 820 | 4 | CONHMe | H | H | H | OH |
| 821 | 1 | $SO_2Me$ | H | H | H | OH |
| 822 | 2 | $SO_2Me$ | H | H | H | OH |
| 823 | 3 | $SO_2Me$ | H | H | H | OH |
| 824 | 4 | $SO_2Me$ | H | H | H | OH |
| 825 | 1 | $SO_2NH_2$ | H | H | H | OH |
| 826 | 2 | $SO_2NH_2$ | H | H | H | OH |
| 827 | 3 | $SO_2NH_2$ | H | H | H | OH |
| 828 | 4 | $SO_2NH_2$ | H | H | H | OH |
| 829 | 1 | H | H | H | H | OMe |
| 830 | 2 | H | H | H | H | OMe |
| 831 | 3 | H | H | H | H | OMe |
| 832 | 4 | H | H | H | H | OMe |
| 833 | 1 | Me | H | H | H | OMe |
| 834 | 2 | Me | H | H | H | OMe |
| 835 | 3 | Me | H | H | H | OMe |
| 836 | 4 | Me | H | H | H | OMe |
| 837 | 1 | $CH_2Ph$ | H | H | H | OMe |
| 838 | 2 | $CH_2Ph$ | H | H | H | OMe |
| 839 | 3 | $CH_2Ph$ | H | H | H | OMe |
| 840 | 4 | $CH_2Ph$ | H | H | H | OMe |
| 841 | 1 | COMe | H | H | H | OMe |
| 842 | 2 | COMe | H | H | H | OMe |
| 843 | 3 | COMe | H | H | H | OMe |
| 844 | 4 | COMe | H | H | H | OMe |
| 845 | 1 | $CO_2Me$ | H | H | H | OMe |
| 846 | 2 | $CO_2Me$ | H | H | H | OMe |
| 847 | 3 | $CO_2Me$ | H | H | H | OMe |
| 848 | 4 | $CO_2Me$ | H | H | H | OMe |
| 849 | 1 | $CO_2tBu$ | H | H | H | OMe |
| 850 | 2 | $CO_2tBu$ | H | H | H | OMe |
| 851 | 3 | $CO_2tBu$ | H | H | H | OMe |
| 852 | 4 | $CO_2tBu$ | H | H | H | OMe |
| 853 | 1 | CONHMe | H | H | H | OMe |
| 854 | 2 | CONHMe | H | H | H | OMe |
| 855 | 3 | CONHMe | H | H | H | OMe |
| 856 | 4 | CONHMe | H | H | H | OMe |
| 857 | 1 | $SO_2Me$ | H | H | H | OMe |
| 858 | 2 | $SO_2Me$ | H | H | H | OMe |
| 859 | 3 | $SO_2Me$ | H | H | H | OMe |
| 860 | 4 | $SO_2Me$ | H | H | H | OMe |
| 861 | 1 | $SO_2NH_2$ | H | H | H | OMe |
| 862 | 2 | $SO_2NH_2$ | H | H | H | OMe |
| 863 | 3 | $SO_2NH_2$ | H | H | H | OMe |
| 864 | 4 | $SO_2NH_2$ | H | H | H | OMe |
| 865 | 1 | H | H | H | H | Me |
| 866 | 2 | H | H | H | H | Me |
| 867 | 3 | H | H | H | H | Me |
| 868 | 4 | H | H | H | H | Me |
| 869 | 1 | Me | H | H | H | Me |
| 870 | 2 | Me | H | H | H | Me |
| 871 | 3 | Me | H | H | H | Me |
| 872 | 4 | Me | H | H | H | Me |
| 873 | 1 | $CH_2Ph$ | H | H | H | Me |
| 874 | 2 | $CH_2Ph$ | H | H | H | Me |
| 875 | 3 | $CH_2Ph$ | H | H | H | Me |
| 876 | 4 | $CH_2Ph$ | H | H | H | Me |
| 877 | 1 | COMe | H | H | H | Me |
| 878 | 2 | COMe | H | H | H | Me |
| 879 | 3 | COMe | H | H | H | Me |
| 880 | 4 | COMe | H | H | H | Me |

TABLE 21-continued

| Entry | n | $R^7$ | $R^{20a}$ | $R^{20b}$ | $R^{20c}$ | $R^{20d}$ |
|---|---|---|---|---|---|---|
| 881 | 1 | $CO_2Me$ | H | H | H | Me |
| 882 | 2 | $CO_2Me$ | H | H | H | Me |
| 883 | 3 | $CO_2Me$ | H | H | H | Me |
| 884 | 4 | $CO_2Me$ | H | H | H | Me |
| 885 | 1 | $CO_2tBu$ | H | H | H | Me |
| 886 | 2 | $CO_2tBu$ | H | H | H | Me |
| 887 | 3 | $CO_2tBu$ | H | H | H | Me |
| 888 | 4 | $CO_2tBu$ | H | H | H | Me |
| 889 | 1 | CONHMe | H | H | H | Me |
| 890 | 2 | CONHMe | H | H | H | Me |
| 891 | 3 | CONHMe | H | H | H | Me |
| 892 | 4 | CONHMe | H | H | H | Me |
| 893 | 1 | $SO_2Me$ | H | H | H | Me |
| 894 | 2 | $SO_2Me$ | H | H | H | Me |
| 895 | 3 | $SO_2Me$ | H | H | H | Me |
| 896 | 4 | $SO_2Me$ | H | H | H | Me |
| 897 | 1 | $SO_2NH_2$ | H | H | H | Me |
| 898 | 2 | $SO_2NH_2$ | H | H | H | Me |
| 899 | 3 | $SO_2NH_2$ | H | H | H | Me |
| 900 | 4 | $SO_2NH_2$ | H | H | H | Me |
| 901 | 1 | H | H | H | H | $CF_3$ |
| 902 | 2 | H | H | H | H | $CF_3$ |
| 903 | 3 | H | H | H | H | $CF_3$ |
| 904 | 4 | H | H | H | H | $CF_3$ |
| 905 | 1 | Me | H | H | H | $CF_3$ |
| 906 | 2 | Me | H | H | H | $CF_3$ |
| 907 | 3 | Me | H | H | H | $CF_3$ |
| 908 | 4 | Me | H | H | H | $CF_3$ |
| 909 | 1 | $CH_2Ph$ | H | H | H | $CF_3$ |
| 910 | 2 | $CH_2Ph$ | H | H | H | $CF_3$ |
| 911 | 3 | $CH_2Ph$ | H | H | H | $CF_3$ |
| 912 | 4 | $CH_2Ph$ | H | H | H | $CF_3$ |
| 913 | 1 | COMe | H | H | H | $CF_3$ |
| 914 | 2 | COMe | H | H | H | $CF_3$ |
| 915 | 3 | COMe | H | H | H | $CF_3$ |
| 916 | 4 | COMe | H | H | H | $CF_3$ |
| 917 | 1 | $CO_2Me$ | H | H | H | $CF_3$ |
| 918 | 2 | $CO_2Me$ | H | H | H | $CF_3$ |
| 919 | 3 | $CO_2Me$ | H | H | H | $CF_3$ |
| 920 | 4 | $CO_2Me$ | H | H | H | $CF_3$ |
| 921 | 1 | $CO_2tBu$ | H | H | H | $CF_3$ |
| 922 | 2 | $CO_2tBu$ | H | H | H | $CF_3$ |
| 923 | 3 | $CO_2tBu$ | H | H | H | $CF_3$ |
| 924 | 4 | $CO_2tBu$ | H | H | H | $CF_3$ |
| 925 | 1 | CONHMe | H | H | H | $CF_3$ |
| 926 | 2 | CONHMe | H | H | H | $CF_3$ |
| 927 | 3 | CONHMe | H | H | H | $CF_3$ |
| 928 | 4 | CONHMe | H | H | H | $CF_3$ |
| 929 | 1 | $SO_2Me$ | H | H | H | $CF_3$ |
| 930 | 2 | $SO_2Me$ | H | H | H | $CF_3$ |
| 931 | 3 | $SO_2Me$ | H | H | H | $CF_3$ |
| 932 | 4 | $SO_2Me$ | H | H | H | $CF_3$ |
| 933 | 1 | $SO_2NH_2$ | H | H | H | $CF_3$ |
| 934 | 2 | $SO_2NH_2$ | H | H | H | $CF_3$ |
| 935 | 3 | $SO_2NH_2$ | H | H | H | $CF_3$ |
| 936 | 4 | $SO_2NH_2$ | H | H | H | $CF_3$ |
| 937 | 1 | H | H | H | H | F |
| 938 | 2 | H | H | H | H | F |
| 939 | 3 | H | H | H | H | F |
| 940 | 3 | H | H | H | H | F |
| 941 | 1 | Me | H | H | H | F |
| 942 | 2 | Me | H | H | H | F |
| 943 | 3 | Me | H | H | H | F |
| 944 | 4 | Me | H | H | H | F |
| 945 | 1 | $CH_2Ph$ | H | H | H | F |
| 946 | 2 | $CH_2Ph$ | H | H | H | F |
| 947 | 3 | $CH_2Ph$ | H | H | H | F |
| 948 | 4 | $CH_2Ph$ | H | H | H | F |
| 949 | 1 | COMe | H | H | H | F |
| 950 | 2 | COMe | H | H | H | F |
| 951 | 3 | COMe | H | H | H | F |
| 952 | 4 | COMe | H | H | H | F |
| 953 | 1 | $CO_2Me$ | H | H | H | F |
| 954 | 2 | $CO_2Me$ | H | H | H | F |
| 955 | 3 | $CO_2Me$ | H | H | H | F |
| 956 | 4 | $CO_2Me$ | H | H | H | F |
| 957 | 1 | $CO_2tBu$ | H | H | H | F |
| 958 | 2 | $CO_2tBu$ | H | H | H | F |

TABLE 21-continued

| Entry | n | $R^7$ | $R^{20a}$ | $R^{20b}$ | $R^{20c}$ | $R^{20d}$ |
|---|---|---|---|---|---|---|
| 959 | 3 | $CO_2tBu$ | H | H | H | F |
| 960 | 4 | $CO_2tBu$ | H | H | H | F |
| 961 | 1 | CONHMe | H | H | H | F |
| 962 | 2 | CONHMe | H | H | H | F |
| 963 | 3 | CONHMe | H | H | H | F |
| 964 | 4 | CONHMe | H | H | H | F |
| 965 | 1 | $SO_2Me$ | H | H | H | F |
| 966 | 2 | $SO_2Me$ | H | H | H | F |
| 967 | 3 | $SO_2Me$ | H | H | H | F |
| 968 | 4 | $SO_2Me$ | H | H | H | F |
| 969 | 1 | $SO_2NH_2$ | H | H | H | F |
| 970 | 2 | $SO_2NH_2$ | H | H | H | F |
| 971 | 3 | $SO_2NH_2$ | H | H | H | F |
| 972 | 4 | $SO_2NH_2$ | H | H | H | F |
| 973 | 1 | H | H | H | H | Cl |
| 974 | 2 | H | H | H | H | Cl |
| 975 | 3 | H | H | H | H | Cl |
| 976 | 4 | H | H | H | H | Cl |
| 977 | 1 | Me | H | H | H | Cl |
| 978 | 2 | Me | H | H | H | Cl |
| 979 | 3 | Me | H | H | H | Cl |
| 980 | 4 | Me | H | H | H | Cl |
| 981 | 1 | $CH_2Ph$ | H | H | H | Cl |
| 982 | 2 | $CH_2Ph$ | H | H | H | Cl |
| 983 | 3 | $CH_2Ph$ | H | H | H | Cl |
| 984 | 4 | $CH_2Ph$ | H | H | H | Cl |
| 985 | 1 | COMe | H | H | H | Cl |
| 986 | 2 | COMe | H | H | H | Cl |
| 987 | 3 | COMe | H | H | H | Cl |
| 988 | 4 | COMe | H | H | H | Cl |
| 989 | 1 | $CO_2Me$ | H | H | H | Cl |
| 990 | 2 | $CO_2Me$ | H | H | H | Cl |
| 991 | 3 | $CO_2Me$ | H | H | H | Cl |
| 992 | 4 | $CO_2Me$ | H | H | H | Cl |
| 993 | 1 | $CO_2tBu$ | H | H | H | Cl |
| 994 | 2 | $CO_2tBu$ | H | H | H | Cl |
| 995 | 3 | $CO_2tBu$ | H | H | H | Cl |
| 996 | 4 | $CO_2tBu$ | H | H | H | Cl |
| 997 | 1 | CONHMe | H | H | H | Cl |
| 998 | 2 | CONHMe | H | H | H | Cl |
| 999 | 3 | CONHMe | H | H | H | Cl |
| 1000 | 4 | CONHMe | H | H | H | Cl |
| 1001 | 1 | $SO_2Me$ | H | H | H | Cl |
| 1002 | 2 | $SO_2Me$ | H | H | H | Cl |
| 1003 | 3 | $SO_2Me$ | H | H | H | Cl |
| 1004 | 4 | $SO_2Me$ | H | H | H | Cl |
| 1005 | 1 | $SO_2NH_2$ | H | H | H | Cl |
| 1006 | 2 | $SO_2NH_2$ | H | H | H | Cl |
| 1007 | 3 | $SO_2NH_2$ | H | H | H | Cl |
| 1008 | 4 | $SO_2NH_2$ | H | H | H | Cl |
| 1009 | 1 | H | H | H | H | CN |
| 1010 | 2 | H | H | H | H | CN |
| 1011 | 3 | H | H | H | H | CN |
| 1012 | 4 | H | H | H | H | CN |
| 1013 | 1 | Me | H | H | H | CN |
| 1014 | 2 | Me | H | H | H | CN |
| 1015 | 3 | Me | H | H | H | CN |
| 1016 | 4 | Me | H | H | H | CN |
| 1017 | 1 | $CH_2Ph$ | H | H | H | CN |
| 1018 | 2 | $CH_2Ph$ | H | H | H | CN |
| 1019 | 3 | $CH_2Ph$ | H | H | H | CN |
| 1020 | 4 | $CH_2Ph$ | H | H | H | CN |
| 1021 | 1 | COMe | H | H | H | CN |
| 1022 | 2 | COMe | H | H | H | CN |
| 1023 | 3 | COMe | H | H | H | CN |
| 1024 | 4 | COMe | H | H | H | CN |
| 1025 | 1 | $CO_2Me$ | H | H | H | CN |
| 1026 | 2 | $CO_2Me$ | H | H | H | CN |
| 1027 | 3 | $CO_2Me$ | H | H | H | CN |
| 1028 | 4 | $CO_2Me$ | H | H | H | CN |
| 1029 | 1 | $CO_2tBu$ | H | H | H | CN |
| 1030 | 2 | $CO_2tBu$ | H | H | H | CN |
| 1031 | 3 | $CO_2tBu$ | H | H | H | CN |
| 1032 | 4 | $CO_2tBu$ | H | H | H | CN |
| 1033 | 1 | CONHMe | H | H | H | CN |
| 1034 | 2 | CONHMe | H | H | H | CN |
| 1035 | 3 | CONHMe | H | H | H | CN |
| 1036 | 4 | CONHMe | H | H | H | CN |

TABLE 21-continued

| Entry | n | $R^7$ | $R^{20a}$ | $R^{20b}$ | $R^{20c}$ | $R^{20d}$ |
|---|---|---|---|---|---|---|
| 1037 | 1 | $SO_2Me$ | H | H | H | CN |
| 1038 | 2 | $SO_2Me$ | H | H | H | CN |
| 1039 | 3 | $SO_2Me$ | H | H | H | CN |
| 1040 | 4 | $SO_2Me$ | H | H | H | CN |
| 1041 | 1 | $SO_2NH_2$ | H | H | H | CN |
| 1042 | 2 | $SO_2NH_2$ | H | H | H | CN |
| 1043 | 3 | $SO_2NH_2$ | H | H | H | CN |
| 1044 | 4 | $SO_2NH_2$ | H | H | H | CN |

Exemplary embodiments include compounds having the formula (XXVIII)

(XXVIII)

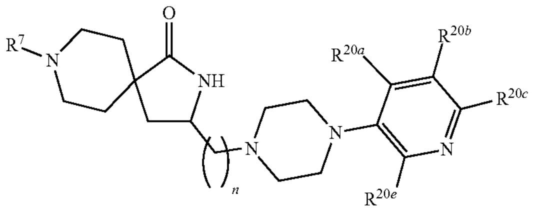

or a pharmaceutically acceptable salt form thereof defined herein below in Table 22.

TABLE 22

| Entry | n | $R^7$ | $R^{20a}$ | $R^{20b}$ | $R^{20c}$ | $R^{20e}$ |
|---|---|---|---|---|---|---|
| 1 | 1 | H | H | H | H | H |
| 2 | 2 | H | H | H | H | H |
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |

TABLE 22-continued

| Entry | n | $R^7$ | $R^{20a}$ | $R^{20b}$ | $R^{20c}$ | $R^{20e}$ |
|---|---|---|---|---|---|---|
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |
| 60 | 4 | $CO_2tBu$ | H | H | OH | H |
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |
| 79 | 3 | Me | H | H | OMe | H |
| 80 | 4 | Me | H | H | OMe | H |
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |

TABLE 22-continued

| Entry | n | $R^7$ | $R^{20a}$ | $R^{20b}$ | $R^{20c}$ | $R^{20e}$ |
|---|---|---|---|---|---|---|
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |
| 138 | 2 | $SO_2Me$ | H | H | Me | H |
| 139 | 3 | $SO_2Me$ | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |
| 157 | 1 | COMe | H | H | $CF_3$ | H |
| 158 | 2 | COMe | H | H | $CF_3$ | H |
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |

TABLE 22-continued

| Entry | n | $R^7$ | $R^{20a}$ | $R^{20b}$ | $R^{20c}$ | $R^{20e}$ |
|---|---|---|---|---|---|---|
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | $CO_2tBu$ | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |
| 216 | 4 | $SO_2NH_2$ | H | H | F | H |
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |
| 235 | 3 | $CO_2Me$ | H | H | Cl | H |
| 236 | 4 | $CO_2Me$ | H | H | Cl | H |
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | $CH_2Ph$ | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | COMe | H | H | CN | H |
| 266 | 2 | COMe | H | H | CN | H |
| 267 | 3 | COMe | H | H | CN | H |
| 268 | 4 | COMe | H | H | CN | H |
| 269 | 1 | $CO_2Me$ | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2tBu$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |

TABLE 22-continued

| Entry | n | $R^7$ | $R^{20a}$ | $R^{20b}$ | $R^{20c}$ | $R^{20e}$ |
|---|---|---|---|---|---|---|
| 277 | 1 | CONHMe | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | $SO_2Me$ | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2NH_2$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | H | H | OH | H | H |
| 290 | 2 | H | H | OH | H | H |
| 291 | 3 | H | H | OH | H | H |
| 292 | 4 | H | H | OH | H | H |
| 293 | 1 | Me | H | OH | H | H |
| 294 | 2 | Me | H | OH | H | H |
| 295 | 3 | Me | H | OH | H | H |
| 296 | 4 | Me | H | OH | H | H |
| 297 | 1 | $CH_2Ph$ | H | OH | H | H |
| 298 | 2 | $CH_2Ph$ | H | OH | H | H |
| 299 | 3 | $CH_2Ph$ | H | OH | H | H |
| 300 | 4 | $CH_2Ph$ | H | OH | H | H |
| 301 | 1 | COMe | H | OH | H | H |
| 302 | 2 | COMe | H | OH | H | H |
| 303 | 3 | COMe | H | OH | H | H |
| 304 | 4 | COMe | H | OH | H | H |
| 305 | 1 | $CO_2Me$ | H | OH | H | H |
| 306 | 2 | $CO_2Me$ | H | OH | H | H |
| 307 | 3 | $CO_2Me$ | H | OH | H | H |
| 308 | 4 | $CO_2Me$ | H | OH | H | H |
| 309 | 1 | $CO_2tBu$ | H | OH | H | H |
| 310 | 2 | $CO_2tBu$ | H | OH | H | H |
| 311 | 3 | $CO_2tBu$ | H | OH | H | H |
| 312 | 4 | $CO_2tBu$ | H | OH | H | H |
| 313 | 1 | CONHMe | H | OH | H | H |
| 314 | 2 | CONHMe | H | OH | H | H |
| 315 | 3 | CONHMe | H | OH | H | H |
| 316 | 4 | CONHMe | H | OH | H | H |
| 317 | 1 | $SO_2Me$ | H | OH | H | H |
| 318 | 2 | $SO_2Me$ | H | OH | H | H |
| 319 | 3 | $SO_2Me$ | H | OH | H | H |
| 320 | 4 | $SO_2Me$ | H | OH | H | H |
| 321 | 1 | $SO_2NH_2$ | H | OH | H | H |
| 322 | 2 | $SO_2NH_2$ | H | OH | H | H |
| 323 | 3 | $SO_2NH_2$ | H | OH | H | H |
| 324 | 4 | $SO_2NH_2$ | H | OH | H | H |
| 325 | 1 | H | H | OMe | H | H |
| 326 | 2 | H | H | OMe | H | H |
| 327 | 3 | H | H | OMe | H | H |
| 328 | 4 | H | H | OMe | H | H |
| 329 | 1 | Me | H | OMe | H | H |
| 330 | 2 | Me | H | OMe | H | H |
| 331 | 3 | Me | H | OMe | H | H |
| 332 | 4 | Me | H | OMe | H | H |
| 333 | 1 | $CH_2Ph$ | H | OMe | H | H |
| 334 | 2 | $CH_2Ph$ | H | OMe | H | H |
| 335 | 3 | $CH_2Ph$ | H | OMe | H | H |
| 336 | 4 | $CH_2Ph$ | H | OMe | H | H |
| 337 | 1 | COMe | H | OMe | H | H |
| 338 | 2 | COMe | H | OMe | H | H |
| 339 | 3 | COMe | H | OMe | H | H |
| 340 | 4 | COMe | H | OMe | H | H |
| 341 | 1 | $CO_2Me$ | H | OMe | H | H |
| 342 | 2 | $CO_2Me$ | H | OMe | H | H |
| 343 | 3 | $CO_2Me$ | H | OMe | H | H |
| 344 | 4 | $CO_2Me$ | H | OMe | H | H |
| 345 | 1 | $CO_2tBu$ | H | OMe | H | H |
| 346 | 2 | $CO_2tBu$ | H | OMe | H | H |
| 347 | 3 | $CO_2tBu$ | H | OMe | H | H |
| 348 | 4 | $CO_2tBu$ | H | OMe | H | H |
| 349 | 1 | CONHMe | H | OMe | H | H |
| 350 | 2 | CONHMe | H | OMe | H | H |
| 351 | 3 | CONHMe | H | OMe | H | H |
| 352 | 4 | CONHMe | H | OMe | H | H |
| 353 | 1 | $SO_2Me$ | H | OMe | H | H |
| 354 | 2 | $SO_2Me$ | H | OMe | H | H |

TABLE 22-continued

| Entry | n | $R^7$ | $R^{20a}$ | $R^{20b}$ | $R^{20c}$ | $R^{20e}$ |
|---|---|---|---|---|---|---|
| 355 | 3 | $SO_2Me$ | H | OMe | H | H |
| 356 | 4 | $SO_2Me$ | H | OMe | H | H |
| 357 | 1 | $SO_2NH_2$ | H | OMe | H | H |
| 358 | 2 | $SO_2NH_2$ | H | OMe | H | H |
| 359 | 3 | $SO_2NH_2$ | H | OMe | H | H |
| 360 | 4 | $SO_2NH_2$ | H | OMe | H | H |
| 361 | 1 | H | H | Me | H | H |
| 362 | 2 | H | H | Me | H | H |
| 363 | 3 | H | H | Me | H | H |
| 364 | 4 | H | H | Me | H | H |
| 365 | 1 | Me | H | Me | H | H |
| 366 | 2 | Me | H | Me | H | H |
| 367 | 3 | Me | H | Me | H | H |
| 368 | 4 | Me | H | Me | H | H |
| 369 | 1 | $CH_2Ph$ | H | Me | H | H |
| 370 | 2 | $CH_2Ph$ | H | Me | H | H |
| 371 | 3 | $CH_2Ph$ | H | Me | H | H |
| 372 | 4 | $CH_2Ph$ | H | Me | H | H |
| 373 | 1 | COMe | H | Me | H | H |
| 374 | 2 | COMe | H | Me | H | H |
| 375 | 3 | COMe | H | Me | H | H |
| 376 | 4 | COMe | H | Me | H | H |
| 377 | 1 | $CO_2Me$ | H | Me | H | H |
| 378 | 2 | $CO_2Me$ | H | Me | H | H |
| 379 | 3 | $CO_2Me$ | H | Me | H | H |
| 380 | 4 | $CO_2Me$ | H | Me | H | H |
| 381 | 1 | $CO_2tBu$ | H | Me | H | H |
| 382 | 2 | $CO_2tBu$ | H | Me | H | H |
| 383 | 3 | $CO_2tBu$ | H | Me | H | H |
| 384 | 4 | $CO_2tBu$ | H | Me | H | H |
| 385 | 1 | CONHMe | H | Me | H | H |
| 386 | 2 | CONHMe | H | Me | H | H |
| 387 | 3 | CONHMe | H | Me | H | H |
| 388 | 4 | CONHMe | H | Me | H | H |
| 389 | 1 | $SO_2Me$ | H | Me | H | H |
| 390 | 2 | $SO_2Me$ | H | Me | H | H |
| 391 | 3 | $SO_2Me$ | H | Me | H | H |
| 392 | 4 | $SO_2Me$ | H | Me | H | H |
| 393 | 1 | $SO_2NH_2$ | H | Me | H | H |
| 394 | 2 | $SO_2NH_2$ | H | Me | H | H |
| 395 | 3 | $SO_2NH_2$ | H | Me | H | H |
| 396 | 4 | $SO_2NH_2$ | H | Me | H | H |
| 397 | 1 | H | H | $CF_3$ | H | H |
| 398 | 2 | H | H | $CF_3$ | H | H |
| 399 | 3 | H | H | $CF_3$ | H | H |
| 400 | 4 | H | H | $CF_3$ | H | H |
| 401 | 1 | Me | H | $CF_3$ | H | H |
| 402 | 2 | Me | H | $CF_3$ | H | H |
| 403 | 3 | Me | H | $CF_3$ | H | H |
| 404 | 4 | Me | H | $CF_3$ | H | H |
| 405 | 1 | $CH_2Ph$ | H | $CF_3$ | H | H |
| 406 | 2 | $CH_2Ph$ | H | $CF_3$ | H | H |
| 407 | 3 | $CH_2Ph$ | H | $CF_3$ | H | H |
| 408 | 4 | $CH_2Ph_2$ | H | $CF_3$ | H | H |
| 409 | 1 | COMe | H | $CF_3$ | H | H |
| 410 | 2 | COMe | H | $CF_3$ | H | H |
| 411 | 3 | COMe | H | $CF_3$ | H | H |
| 412 | 4 | COMe | H | $CF_3$ | H | H |
| 413 | 1 | $CO_2Me$ | H | $CF_3$ | H | H |
| 414 | 2 | $CO_2Me$ | H | $CF_3$ | H | H |
| 415 | 3 | $CO_2Me$ | H | $CF_3$ | H | H |
| 416 | 4 | $CO_2Me$ | H | $CF_3$ | H | H |
| 417 | 1 | $CO_2tBu$ | H | $CF_3$ | H | H |
| 418 | 2 | $CO_2tBu$ | H | $CF_3$ | H | H |
| 419 | 3 | $CO_2tBu$ | H | $CF_3$ | H | H |
| 420 | 4 | $CO_2tBu$ | H | $CF_3$ | H | H |
| 421 | 1 | CONHMe | H | $CF_3$ | H | H |
| 422 | 2 | CONHMe | H | $CF_3$ | H | H |
| 423 | 3 | CONHMe | H | $CF_3$ | H | H |
| 424 | 4 | CONHMe | H | $CF_3$ | H | H |
| 425 | 1 | $SO_2Me$ | H | $CF_3$ | H | H |
| 426 | 2 | $SO_2Me$ | H | $CF_3$ | H | H |
| 427 | 3 | $SO_2Me$ | H | $CF_3$ | H | H |
| 428 | 4 | $SO_2Me$ | H | $CF_3$ | H | H |
| 429 | 1 | $SO_2NH_2$ | H | $CF_3$ | H | H |
| 430 | 2 | $SO_2NH_2$ | H | $CF_3$ | H | H |
| 431 | 3 | $SO_2NH_2$ | H | $CF_3$ | H | H |
| 432 | 4 | $SO_2NH_2$ | H | $CF_3$ | H | H |

TABLE 22-continued

| Entry | n | $R^7$ | $R^{20a}$ | $R^{20b}$ | $R^{20c}$ | $R^{20e}$ |
|---|---|---|---|---|---|---|
| 433 | 1 | H | H | F | H | H |
| 434 | 2 | H | H | F | H | H |
| 435 | 3 | H | H | F | H | H |
| 436 | 3 | H | H | F | H | H |
| 437 | 1 | Me | H | F | H | H |
| 438 | 2 | Me | H | F | H | H |
| 439 | 3 | Me | H | F | H | H |
| 440 | 4 | Me | H | F | H | H |
| 441 | 1 | $CH_2Ph$ | H | F | H | H |
| 442 | 2 | $CH_2Ph$ | H | F | H | H |
| 443 | 3 | $CH_2Ph$ | H | F | H | H |
| 444 | 4 | $CH_2Ph$ | H | F | H | H |
| 445 | 1 | COMe | H | F | H | H |
| 446 | 2 | COMe | H | F | H | H |
| 447 | 3 | COMe | H | F | H | H |
| 448 | 4 | COMe | H | F | H | H |
| 449 | 1 | $CO_2Me$ | H | F | H | H |
| 450 | 2 | $CO_2Me$ | H | F | H | H |
| 451 | 3 | $CO_2Me$ | H | F | H | H |
| 452 | 4 | $CO_2Me$ | H | F | H | H |
| 453 | 1 | $CO_2tBu$ | H | F | H | H |
| 454 | 2 | $CO_2tBu$ | H | F | H | H |
| 455 | 3 | $CO_2tBu$ | H | F | H | H |
| 456 | 4 | $CO_2tBu$ | H | F | H | H |
| 457 | 1 | CONHMe | H | F | H | H |
| 458 | 2 | CONHMe | H | F | H | H |
| 459 | 3 | CONHMe | H | F | H | H |
| 460 | 4 | CONHMe | H | F | H | H |
| 461 | 1 | $SO_2Me$ | H | F | H | H |
| 462 | 2 | $SO_2Me$ | H | F | H | H |
| 463 | 3 | $SO_2Me$ | H | F | H | H |
| 464 | 4 | $SO_2Me$ | H | F | H | H |
| 465 | 1 | $SO_2NH_2$ | H | F | H | H |
| 466 | 2 | $SO_2NH_2$ | H | F | H | H |
| 467 | 3 | $SO_2NH_2$ | H | F | H | H |
| 468 | 4 | $SO_2NH_2$ | H | F | H | H |
| 469 | 1 | H | H | Cl | H | H |
| 470 | 2 | H | H | Cl | H | H |
| 471 | 3 | H | H | Cl | H | H |
| 472 | 4 | H | H | Cl | H | H |
| 473 | 1 | Me | H | Cl | H | H |
| 474 | 2 | Me | H | Cl | H | H |
| 475 | 3 | Me | H | Cl | H | H |
| 476 | 4 | Me | H | Cl | H | H |
| 477 | 1 | $CH_2Ph$ | H | Cl | H | H |
| 478 | 2 | $CH_2Ph$ | H | Cl | H | H |
| 479 | 3 | $CH_2Ph$ | H | Cl | H | H |
| 480 | 4 | $CH_2Ph$ | H | Cl | H | H |
| 481 | 1 | COMe | H | Cl | H | H |
| 482 | 2 | COMe | H | Cl | H | H |
| 483 | 3 | COMe | H | Cl | H | H |
| 484 | 4 | COMe | H | Cl | H | H |
| 485 | 1 | $CO_2Me$ | H | Cl | H | H |
| 486 | 2 | $CO_2Me$ | H | Cl | H | H |
| 487 | 3 | $CO_2Me$ | H | Cl | H | H |
| 488 | 4 | $CO_2Me$ | H | Cl | H | H |
| 489 | 1 | $CO_2tBu$ | H | Cl | H | H |
| 490 | 2 | $CO_2tBu$ | H | Cl | H | H |
| 491 | 3 | $CO_2tBu$ | H | Cl | H | H |
| 492 | 4 | $CO_2tBu$ | H | Cl | H | H |
| 493 | 1 | CONHMe | H | Cl | H | H |
| 494 | 2 | CONHMe | H | Cl | H | H |
| 495 | 3 | CONHMe | H | Cl | H | H |
| 496 | 4 | CONHMe | H | Cl | H | H |
| 497 | 1 | $SO_2Me$ | H | Cl | H | H |
| 498 | 2 | $SO_2Me$ | H | Cl | H | H |
| 499 | 3 | $SO_2Me$ | H | Cl | H | H |
| 500 | 4 | $SO_2Me$ | H | Cl | H | H |
| 501 | 1 | $SO_2NH_2$ | H | Cl | H | H |
| 502 | 2 | $SO_2NH_2$ | H | Cl | H | H |
| 503 | 3 | $SO_2NH_2$ | H | Cl | H | H |
| 504 | 4 | $SO_2NH_2$ | H | Cl | H | H |
| 505 | 1 | H | H | CN | H | H |
| 506 | 2 | H | H | CN | H | H |
| 507 | 3 | H | H | CN | H | H |
| 508 | 4 | H | H | CN | H | H |
| 509 | 1 | Me | H | CN | H | H |
| 510 | 2 | Me | H | CN | H | H |

TABLE 22-continued

| Entry | n | $R^7$ | $R^{20a}$ | $R^{20b}$ | $R^{20c}$ | $R^{20e}$ |
|---|---|---|---|---|---|---|
| 511 | 3 | Me | H | CN | H | H |
| 512 | 4 | Me | H | CN | H | H |
| 513 | 1 | $CH_2Ph$ | H | CN | H | H |
| 514 | 2 | $CH_2Ph$ | H | CN | H | H |
| 515 | 3 | $CH_2Ph$ | H | CN | H | H |
| 516 | 4 | $CH_2Ph$ | H | CN | H | H |
| 517 | 1 | COMe | H | CN | H | H |
| 518 | 2 | COMe | H | CN | H | H |
| 519 | 3 | COMe | H | CN | H | H |
| 520 | 4 | COMe | H | CN | H | H |
| 521 | 1 | $CO_2Me$ | H | CN | H | H |
| 522 | 2 | $CO_2Me$ | H | CN | H | H |
| 523 | 3 | $CO_2Me$ | H | CN | H | H |
| 524 | 4 | $CO_2Me$ | H | CN | H | H |
| 525 | 1 | $CO_2tBu$ | H | CN | H | H |
| 526 | 2 | $CO_2tBu$ | H | CN | H | H |
| 527 | 3 | $CO_2tBu$ | H | CN | H | H |
| 528 | 4 | $CO_2tBu$ | H | CN | H | H |
| 529 | 1 | CONHMe | H | CN | H | H |
| 530 | 2 | CONHMe | H | CN | H | H |
| 531 | 3 | CONHMe | H | CN | H | H |
| 532 | 4 | CONHMe | H | CN | H | H |
| 533 | 1 | $SO_2Me$ | H | CN | H | H |
| 534 | 2 | $SO_2Me$ | H | CN | H | H |
| 535 | 3 | $SO_2Me$ | H | CN | H | H |
| 536 | 4 | $SO_2Me$ | H | CN | H | H |
| 537 | 1 | $SO_2NH_2$ | H | CN | H | H |
| 538 | 2 | $SO_2NH_2$ | H | CN | H | H |
| 539 | 3 | $SO_2NH_2$ | H | CN | H | H |
| 540 | 4 | $SO_2NH_2$ | H | CN | H | H |
| 541 | 1 | H | OH | H | H | H |
| 542 | 2 | H | OH | H | H | H |
| 543 | 3 | H | OH | H | H | H |
| 544 | 4 | H | OH | H | H | H |
| 545 | 1 | Me | OH | H | H | H |
| 546 | 2 | Me | OH | H | H | H |
| 547 | 3 | Me | OH | H | H | H |
| 548 | 4 | Me | OH | H | H | H |
| 549 | 1 | $CH_2Ph$ | OH | H | H | H |
| 550 | 2 | $CH_2Ph$ | OH | H | H | H |
| 551 | 3 | $CH_2Ph$ | OH | H | H | H |
| 552 | 4 | $CH_2Ph$ | OH | H | H | H |
| 553 | 1 | COMe | OH | H | H | H |
| 554 | 2 | COMe | OH | H | H | H |
| 555 | 3 | COMe | OH | H | H | H |
| 556 | 4 | COMe | OH | H | H | H |
| 557 | 1 | $CO_2Me$ | OH | H | H | H |
| 558 | 2 | $CO_2Me$ | OH | H | H | H |
| 559 | 3 | $CO_2Me$ | OH | H | H | H |
| 560 | 4 | $CO_2Me$ | OH | H | H | H |
| 561 | 1 | $CO_2tBu$ | OH | H | H | H |
| 562 | 2 | $CO_2tBu$ | OH | H | H | H |
| 563 | 3 | $CO_2tBu$ | OH | H | H | H |
| 564 | 4 | $CO_2tBu$ | OH | H | H | H |
| 565 | 1 | CONHMe | OH | H | H | H |
| 566 | 2 | CONHMe | OH | H | H | H |
| 567 | 3 | CONHMe | OH | H | H | H |
| 568 | 4 | CONHMe | OH | H | H | H |
| 569 | 1 | $SO_2Me$ | OH | H | H | H |
| 570 | 2 | $SO_2Me$ | OH | H | H | H |
| 571 | 3 | $SO_2Me$ | OH | H | H | H |
| 572 | 4 | $SO_2Me$ | OH | H | H | H |
| 573 | 1 | $SO_2NH_2$ | OH | H | H | H |
| 574 | 2 | $SO_2NH_2$ | OH | H | H | H |
| 575 | 3 | $SO_2NH_2$ | OH | H | H | H |
| 576 | 4 | $SO_2NH_2$ | OH | H | H | H |
| 577 | 1 | H | OMe | H | H | H |
| 578 | 2 | H | OMe | H | H | H |
| 579 | 3 | H | OMe | H | H | H |
| 580 | 4 | H | OMe | H | H | H |
| 581 | 1 | Me | OMe | H | H | H |
| 582 | 2 | Me | OMe | H | H | H |
| 583 | 3 | Me | OMe | H | H | H |
| 584 | 4 | Me | OMe | H | H | H |
| 585 | 1 | $CH_2Ph$ | OMe | H | H | H |
| 586 | 2 | $CH_2Ph$ | OMe | H | H | H |
| 587 | 3 | $CH_2Ph$ | OMe | H | H | H |
| 588 | 4 | $CH_2Ph$ | OMe | H | H | H |

TABLE 22-continued

| Entry | n | $R^7$ | $R^{20a}$ | $R^{20b}$ | $R^{20c}$ | $R^{20e}$ |
|---|---|---|---|---|---|---|
| 589 | 1 | COMe | OMe | H | H | H |
| 590 | 2 | COMe | OMe | H | H | H |
| 591 | 3 | COMe | OMe | H | H | H |
| 592 | 4 | COMe | OMe | H | H | H |
| 593 | 1 | $CO_2Me$ | OMe | H | H | H |
| 594 | 2 | $CO_2Me$ | OMe | H | H | H |
| 595 | 3 | $CO_2Me$ | OMe | H | H | H |
| 596 | 4 | $CO_2Me$ | OMe | H | H | H |
| 597 | 1 | $CO_2tBu$ | OMe | H | H | H |
| 598 | 2 | $CO_2tBu$ | OMe | H | H | H |
| 599 | 3 | $CO_2tBu$ | OMe | H | H | H |
| 600 | 4 | $CO_2tBu$ | OMe | H | H | H |
| 601 | 1 | CONHMe | OMe | H | H | H |
| 602 | 2 | CONHMe | OMe | H | H | H |
| 603 | 3 | CONHMe | OMe | H | H | H |
| 604 | 4 | CONHMe | OMe | H | H | H |
| 605 | 1 | $SO_2Me$ | OMe | H | H | H |
| 606 | 2 | $SO_2Me$ | OMe | H | H | H |
| 607 | 3 | $SO_2Me$ | OMe | H | H | H |
| 608 | 4 | $SO_2Me$ | OMe | H | H | H |
| 609 | 1 | $SO_2NH_2$ | OMe | H | H | H |
| 610 | 2 | $SO_2NH_2$ | OMe | H | H | H |
| 611 | 3 | $SO_2NH_2$ | OMe | H | H | H |
| 612 | 4 | $SO_2NH_2$ | OMe | H | H | H |
| 613 | 1 | H | Me | H | H | H |
| 614 | 2 | H | Me | H | H | H |
| 615 | 3 | H | Me | H | H | H |
| 616 | 4 | H | Me | H | H | H |
| 617 | 1 | Me | Me | H | H | H |
| 618 | 2 | Me | Me | H | H | H |
| 619 | 3 | Me | Me | H | H | H |
| 620 | 4 | Me | Me | H | H | H |
| 621 | 1 | $CH_2Ph$ | Me | H | H | H |
| 622 | 2 | $CH_2Ph$ | Me | H | H | H |
| 623 | 3 | $CH_2Ph$ | Me | H | H | H |
| 624 | 4 | $CH_2Ph$ | Me | H | H | H |
| 625 | 1 | COMe | Me | H | H | H |
| 626 | 2 | COMe | Me | H | H | H |
| 627 | 3 | COMe | Me | H | H | H |
| 628 | 4 | COMe | Me | H | H | H |
| 629 | 1 | $CO_2Me$ | Me | H | H | H |
| 630 | 2 | $CO_2Me$ | Me | H | H | H |
| 631 | 3 | $CO_2Me$ | Me | H | H | H |
| 632 | 4 | $CO_2Me$ | Me | H | H | H |
| 633 | 1 | $CO_2tBu$ | Me | H | H | H |
| 634 | 2 | $CO_2tBu$ | Me | H | H | H |
| 635 | 3 | $CO_2tBu$ | Me | H | H | H |
| 636 | 4 | $CO_2tBu$ | Me | H | H | H |
| 637 | 1 | CONHMe | Me | H | H | H |
| 638 | 2 | CONHMe | Me | H | H | H |
| 639 | 3 | CONHMe | Me | H | H | H |
| 640 | 4 | CONHMe | Me | H | H | H |
| 641 | 1 | $SO_2Me$ | Me | H | H | H |
| 642 | 2 | $SO_2Me$ | Me | H | H | H |
| 643 | 3 | $SO_2Me$ | Me | H | H | H |
| 644 | 4 | $SO_2Me$ | Me | H | H | H |
| 645 | 1 | $SO_2NH_2$ | Me | H | H | H |
| 646 | 2 | $SO_2NH_2$ | Me | H | H | H |
| 647 | 3 | $SO_2NH_2$ | Me | H | H | H |
| 648 | 4 | $SO_2NH_2$ | Me | H | H | H |
| 649 | 1 | H | $CF_3$ | H | H | H |
| 650 | 2 | H | $CF_3$ | H | H | H |
| 651 | 3 | H | $CF_3$ | H | H | H |
| 652 | 4 | H | $CF_3$ | H | H | H |
| 653 | 1 | Me | $CF_3$ | H | H | H |
| 654 | 2 | Me | $CF_3$ | H | H | H |
| 655 | 3 | Me | $CF_3$ | H | H | H |
| 656 | 4 | Me | $CF_3$ | H | H | H |
| 657 | 1 | $CH_2Ph$ | $CF_3$ | H | H | H |
| 658 | 2 | $CH_2Ph$ | $CF_3$ | H | H | H |
| 659 | 3 | $CH_2Ph$ | $CF_3$ | H | H | H |
| 660 | 4 | $CH_2Ph$ | $CF_3$ | H | H | H |
| 661 | 1 | COMe | $CF_3$ | H | H | H |
| 662 | 2 | COMe | $CF_3$ | H | H | H |
| 663 | 3 | COMe | $CF_3$ | H | H | H |
| 664 | 4 | COMe | $CF_3$ | H | H | H |
| 665 | 1 | $CO_2Me$ | $CF_3$ | H | H | H |
| 666 | 2 | $CO_2Me$ | $CF_3$ | H | H | H |

TABLE 22-continued

| Entry | n | $R^7$ | $R^{20a}$ | $R^{20b}$ | $R^{20c}$ | $R^{20e}$ |
|---|---|---|---|---|---|---|
| 667 | 3 | $CO_2Me$ | $CF_3$ | H | H | H |
| 668 | 4 | $CO_2Me$ | $CF_3$ | H | H | H |
| 669 | 1 | $CO_2tBu$ | $CF_3$ | H | H | H |
| 670 | 2 | $CO_2tBu$ | $CF_3$ | H | H | H |
| 671 | 3 | $CO_2tBu$ | $CF_3$ | H | H | H |
| 672 | 4 | $CO_2tBu$ | $CF_3$ | H | H | H |
| 673 | 1 | CONHMe | $CF_3$ | H | H | H |
| 674 | 2 | CONHMe | $CF_3$ | H | H | H |
| 675 | 3 | CONHMe | $CF_3$ | H | H | H |
| 676 | 4 | CONHMe | $CF_3$ | H | H | H |
| 677 | 1 | $SO_2Me$ | $CF_3$ | H | H | H |
| 678 | 2 | $SO_2Me$ | $CF_3$ | H | H | H |
| 679 | 3 | $SO_2Me$ | $CF_3$ | H | H | H |
| 680 | 4 | $SO_2Me$ | $CF_3$ | H | H | H |
| 681 | 1 | $SO_2NH_2$ | $CF_3$ | H | H | H |
| 682 | 2 | $SO_2NH_2$ | $CF_3$ | H | H | H |
| 683 | 3 | $SO_2NH_2$ | $CF_3$ | H | H | H |
| 684 | 4 | $SO_2NH_2$ | $CF_3$ | H | H | H |
| 685 | 1 | H | F | H | H | H |
| 686 | 2 | H | F | H | H | H |
| 687 | 3 | H | F | H | H | H |
| 688 | 3 | H | F | H | H | H |
| 689 | 1 | Me | F | H | H | H |
| 690 | 2 | Me | F | H | H | H |
| 691 | 3 | Me | F | H | H | H |
| 692 | 4 | Me | F | H | H | H |
| 693 | 1 | $CH_2Ph$ | F | H | H | H |
| 694 | 2 | $CH_2Ph$ | F | H | H | H |
| 695 | 3 | $CH_2Ph$ | F | H | H | H |
| 696 | 4 | $CH_2Ph$ | F | H | H | H |
| 697 | 1 | COMe | F | H | H | H |
| 698 | 2 | COMe | F | H | H | H |
| 699 | 3 | COMe | F | H | H | H |
| 700 | 4 | COMe | F | H | H | H |
| 701 | 1 | $CO_2Me$ | F | H | H | H |
| 702 | 2 | $CO_2Me$ | F | H | H | H |
| 703 | 3 | $CO_2Me$ | F | H | H | H |
| 704 | 4 | $CO_2Me$ | F | H | H | H |
| 705 | 1 | $CO_2tBu$ | F | H | H | H |
| 706 | 2 | $CO_2tBu$ | F | H | H | H |
| 707 | 3 | $CO_2tBu$ | F | H | H | H |
| 708 | 4 | $CO_2tBu$ | F | H | H | H |
| 709 | 1 | CONHMe | F | H | H | H |
| 710 | 2 | CONHMe | F | H | H | H |
| 711 | 3 | CONHMe | F | H | H | H |
| 712 | 4 | CONHMe | F | H | H | H |
| 713 | 1 | $SO_2Me$ | F | H | H | H |
| 714 | 2 | $SO_2Me$ | F | H | H | H |
| 715 | 3 | $SO_2Me$ | F | H | H | H |
| 716 | 4 | $SO_2Me$ | F | H | H | H |
| 717 | 1 | $SO_2NH_2$ | F | H | H | H |
| 718 | 2 | $SO_2NH_2$ | F | H | H | H |
| 719 | 3 | $SO_2NH_2$ | F | H | H | H |
| 720 | 4 | $SO_2NH_2$ | F | H | H | H |
| 721 | 1 | H | Cl | H | H | H |
| 722 | 2 | H | Cl | H | H | H |
| 723 | 3 | H | Cl | H | H | H |
| 724 | 4 | H | Cl | H | H | H |
| 725 | 1 | Me | Cl | H | H | H |
| 726 | 2 | Me | Cl | H | H | H |
| 727 | 3 | Me | Cl | H | H | H |
| 728 | 4 | Me | Cl | H | H | H |
| 729 | 1 | $CH_2Ph$ | Cl | H | H | H |
| 730 | 2 | $CH_2Ph$ | Cl | H | H | H |
| 731 | 3 | $CH_2Ph$ | Cl | H | H | H |
| 732 | 4 | $CH_2Ph$ | Cl | H | H | H |
| 733 | 1 | COMe | Cl | H | H | H |
| 734 | 2 | COMe | Cl | H | H | H |
| 735 | 3 | COMe | Cl | H | H | H |
| 736 | 4 | COMe | Cl | H | H | H |
| 737 | 1 | $CO_2Me$ | Cl | H | H | H |
| 738 | 2 | $CO_2Me$ | Cl | H | H | H |
| 739 | 3 | $CO_2Me$ | Cl | H | H | H |
| 740 | 4 | $CO_2Me$ | Cl | H | H | H |
| 741 | 1 | $CO_2tBu$ | Cl | H | H | H |
| 742 | 2 | $CO_2tBu$ | Cl | H | H | H |
| 743 | 3 | $CO_2tBu$ | Cl | H | H | H |
| 744 | 4 | $CO_2tBu$ | Cl | H | H | H |

TABLE 22-continued

| Entry | n | $R^7$ | $R^{20a}$ | $R^{20b}$ | $R^{20c}$ | $R^{20e}$ |
|---|---|---|---|---|---|---|
| 745 | 1 | CONHMe | Cl | H | H | H |
| 746 | 2 | CONHMe | Cl | H | H | H |
| 747 | 3 | CONHMe | Cl | H | H | H |
| 748 | 4 | CONHMe | Cl | H | H | H |
| 749 | 1 | $SO_2Me$ | Cl | H | H | H |
| 750 | 2 | $SO_2Me$ | Cl | H | H | H |
| 751 | 3 | $SO_2Me$ | Cl | H | H | H |
| 752 | 4 | $SO_2Me$ | Cl | H | H | H |
| 753 | 1 | $SO_2NH_2$ | Cl | H | H | H |
| 754 | 2 | $SO_2NH_2$ | Cl | H | H | H |
| 755 | 3 | $SO_2NH_2$ | Cl | H | H | H |
| 756 | 4 | $SO_2NH_2$ | Cl | H | H | H |
| 757 | 1 | H | CN | H | H | H |
| 758 | 2 | H | CN | H | H | H |
| 759 | 3 | H | CN | H | H | H |
| 760 | 4 | H | CN | H | H | H |
| 761 | 1 | Me | CN | H | H | H |
| 762 | 2 | Me | CN | H | H | H |
| 763 | 3 | Me | CN | H | H | H |
| 764 | 4 | Me | CN | H | H | H |
| 765 | 1 | $CH_2Ph$ | CN | H | H | H |
| 766 | 2 | $CH_2Ph$ | CN | H | H | H |
| 767 | 3 | $CH_2Ph$ | CN | H | H | H |
| 768 | 4 | $CH_2Ph$ | CN | H | H | H |
| 769 | 1 | COMe | CN | H | H | H |
| 770 | 2 | COMe | CN | H | H | H |
| 771 | 3 | COMe | CN | H | H | H |
| 772 | 4 | COMe | CN | H | H | H |
| 773 | 1 | $CO_2Me$ | CN | H | H | H |
| 774 | 2 | $CO_2Me$ | CN | H | H | H |
| 775 | 3 | $CO_2Me$ | CN | H | H | H |
| 776 | 4 | $CO_2Me$ | CN | H | H | H |
| 777 | 1 | $CO_2tBu$ | CN | H | H | H |
| 778 | 2 | $CO_2tBu$ | CN | H | H | H |
| 779 | 3 | $CO_2tBu$ | CN | H | H | H |
| 780 | 4 | $CO_2tBu$ | CN | H | H | H |
| 781 | 1 | CONHMe | CN | H | H | H |
| 782 | 2 | CONHMe | CN | H | H | H |
| 783 | 3 | CONHMe | CN | H | H | H |
| 784 | 4 | CONHMe | CN | H | H | H |
| 785 | 1 | $SO_2Me$ | CN | H | H | H |
| 786 | 2 | $SO_2Me$ | CN | H | H | H |
| 787 | 3 | $SO_2Me$ | CN | H | H | H |
| 788 | 4 | $SO_2Me$ | CN | H | H | H |
| 789 | 1 | $SO_2NH_2$ | CN | H | H | H |
| 790 | 2 | $SO_2NH_2$ | CN | H | H | H |
| 791 | 3 | $SO_2NH_2$ | CN | H | H | H |
| 792 | 4 | $SO_2NH_2$ | CN | H | H | H |
| 793 | 1 | H | H | H | H | OH |
| 794 | 2 | H | H | H | H | OH |
| 795 | 3 | H | H | H | H | OH |
| 796 | 4 | H | H | H | H | OH |
| 797 | 1 | Me | H | H | H | OH |
| 798 | 2 | Me | H | H | H | OH |
| 799 | 3 | Me | H | H | H | OH |
| 800 | 4 | Me | H | H | H | OH |
| 801 | 1 | $CH_2Ph$ | H | H | H | OH |
| 802 | 2 | $CH_2Ph$ | H | H | H | OH |
| 803 | 3 | $CH_2Ph$ | H | H | H | OH |
| 804 | 4 | $CH_2Ph$ | H | H | H | OH |
| 805 | 1 | COMe | H | H | H | OH |
| 806 | 2 | COMe | H | H | H | OH |
| 807 | 3 | COMe | H | H | H | OH |
| 808 | 4 | COMe | H | H | H | OH |
| 809 | 1 | $CO_2Me$ | H | H | H | OH |
| 810 | 2 | $CO_2Me$ | H | H | H | OH |
| 811 | 3 | $CO_2Me$ | H | H | H | OH |
| 812 | 4 | $CO_2Me$ | H | H | H | OH |
| 813 | 1 | $CO_2tBu$ | H | H | H | OH |
| 814 | 2 | $CO_2tBu$ | H | H | H | OH |
| 815 | 3 | $CO_2tBu$ | H | H | H | OH |
| 816 | 4 | $CO_2tBu$ | H | H | H | OH |
| 817 | 1 | CONHMe | H | H | H | OH |
| 818 | 2 | CONHMe | H | H | H | OH |
| 819 | 3 | CONHMe | H | H | H | OH |
| 820 | 4 | CONHMe | H | H | H | OH |
| 821 | 1 | $SO_2Me$ | H | H | H | OH |
| 822 | 2 | $SO_2Me$ | H | H | H | OH |

TABLE 22-continued

| Entry | n | $R^7$ | $R^{20a}$ | $R^{20b}$ | $R^{20c}$ | $R^{20e}$ |
|---|---|---|---|---|---|---|
| 823 | 3 | $SO_2Me$ | H | H | H | OH |
| 824 | 4 | $SO_2Me$ | H | H | H | OH |
| 825 | 1 | $SO_2NH_2$ | H | H | H | OH |
| 826 | 2 | $SO_2NH_2$ | H | H | H | OH |
| 827 | 3 | $SO_2NH_2$ | H | H | H | OH |
| 828 | 4 | $SO_2NH_2$ | H | H | H | OH |
| 829 | 1 | H | H | H | H | OMe |
| 830 | 2 | H | H | H | H | OMe |
| 831 | 3 | H | H | H | H | OMe |
| 832 | 4 | H | H | H | H | OMe |
| 833 | 1 | Me | H | H | H | OMe |
| 834 | 2 | Me | H | H | H | OMe |
| 835 | 3 | Me | H | H | H | OMe |
| 836 | 4 | Me | H | H | H | OMe |
| 837 | 1 | $CH_2Ph$ | H | H | H | OMe |
| 838 | 2 | $CH_2Ph$ | H | H | H | OMe |
| 839 | 3 | $CH_2Ph$ | H | H | H | OMe |
| 840 | 4 | $CH_2Ph$ | H | H | H | OMe |
| 841 | 1 | COMe | H | H | H | OMe |
| 842 | 2 | COMe | H | H | H | OMe |
| 843 | 3 | COMe | H | H | H | OMe |
| 844 | 4 | COMe | H | H | H | OMe |
| 845 | 1 | $CO_2Me$ | H | H | H | OMe |
| 846 | 2 | $CO_2Me$ | H | H | H | OMe |
| 847 | 3 | $CO_2Me$ | H | H | H | OMe |
| 848 | 4 | $CO_2Me$ | H | H | H | OMe |
| 849 | 1 | $CO_2tBu$ | H | H | H | OMe |
| 850 | 2 | $CO_2tBu$ | H | H | H | OMe |
| 851 | 3 | $CO_2tBu$ | H | H | H | OMe |
| 852 | 4 | $CO_2tBu$ | H | H | H | OMe |
| 853 | 1 | CONHMe | H | H | H | OMe |
| 854 | 2 | CONHMe | H | H | H | OMe |
| 855 | 3 | CONHMe | H | H | H | OMe |
| 856 | 4 | CONHMe | H | H | H | OMe |
| 857 | 1 | $SO_2Me$ | H | H | H | OMe |
| 858 | 2 | $SO_2Me$ | H | H | H | OMe |
| 859 | 3 | $SO_2Me$ | H | H | H | OMe |
| 860 | 4 | $SO_2Me$ | H | H | H | OMe |
| 861 | 1 | $SO_2NH_2$ | H | H | H | OMe |
| 862 | 2 | $SO_2NH_2$ | H | H | H | OMe |
| 863 | 3 | $SO_2NH_2$ | H | H | H | OMe |
| 864 | 4 | $SO_2NH_2$ | H | H | H | OMe |
| 865 | 1 | H | H | H | H | Me |
| 866 | 2 | H | H | H | H | Me |
| 867 | 3 | H | H | H | H | Me |
| 868 | 4 | H | H | H | H | Me |
| 869 | 1 | Me | H | H | H | Me |
| 870 | 2 | Me | H | H | H | Me |
| 871 | 3 | Me | H | H | H | Me |
| 872 | 4 | Me | H | H | H | Me |
| 873 | 1 | $CH_2Ph$ | H | H | H | Me |
| 874 | 2 | $CH_2Ph$ | H | H | H | Me |
| 875 | 3 | $CH_2Ph$ | H | H | H | Me |
| 876 | 4 | $CH_2Ph$ | H | H | H | Me |
| 877 | 1 | COMe | H | H | H | Me |
| 878 | 2 | COMe | H | H | H | Me |
| 879 | 3 | COMe | H | H | H | Me |
| 880 | 4 | COMe | H | H | H | Me |
| 881 | 1 | $CO_2Me$ | H | H | H | Me |
| 882 | 2 | $CO_2Me$ | H | H | H | Me |
| 883 | 3 | $CO_2Me$ | H | H | H | Me |
| 884 | 4 | $CO_2Me$ | H | H | H | Me |
| 885 | 1 | $CO_2tBu$ | H | H | H | Me |
| 886 | 2 | $CO_2tBu$ | H | H | H | Me |
| 887 | 3 | $CO_2tBu$ | H | H | H | Me |
| 888 | 4 | $CO_2tBu$ | H | H | H | Me |
| 889 | 1 | CONHMe | H | H | H | Me |
| 890 | 2 | CONHMe | H | H | H | Me |
| 891 | 3 | CONHMe | H | H | H | Me |
| 892 | 4 | CONHMe | H | H | H | Me |
| 893 | 1 | $SO_2Me$ | H | H | H | Me |
| 894 | 2 | $SO_2Me$ | H | H | H | Me |
| 895 | 3 | $SO_2Me$ | H | H | H | Me |
| 896 | 4 | $SO_2Me$ | H | H | H | Me |
| 897 | 1 | $SO_2NH_2$ | H | H | H | Me |
| 898 | 2 | $SO_2NH_2$ | H | H | H | Me |
| 899 | 3 | $SO_2NH_2$ | H | H | H | Me |
| 900 | 4 | $SO_2NH_2$ | H | H | H | Me |

TABLE 22-continued

| Entry | n | $R^7$ | $R^{20a}$ | $R^{20b}$ | $R^{20c}$ | $R^{20e}$ |
|---|---|---|---|---|---|---|
| 901 | 1 | H | H | H | H | $CF_3$ |
| 902 | 2 | H | H | H | H | $CF_3$ |
| 903 | 3 | H | H | H | H | $CF_3$ |
| 904 | 4 | H | H | H | H | $CF_3$ |
| 905 | 1 | Me | H | H | H | $CF_3$ |
| 906 | 2 | Me | H | H | H | $CF_3$ |
| 907 | 3 | Me | H | H | H | $CF_3$ |
| 908 | 4 | Me | H | H | H | $CF_3$ |
| 909 | 1 | $CH_2Ph$ | H | H | H | $CF_3$ |
| 910 | 2 | $CH_2Ph$ | H | H | H | $CF_3$ |
| 911 | 3 | $CH_2Ph$ | H | H | H | $CF_3$ |
| 912 | 4 | $CH_2Ph$ | H | H | H | $CF_3$ |
| 913 | 1 | COMe | H | H | H | $CF_3$ |
| 914 | 2 | COMe | H | H | H | $CF_3$ |
| 915 | 3 | COMe | H | H | H | $CF_3$ |
| 916 | 4 | COMe | H | H | H | $CF_3$ |
| 917 | 1 | $CO_2Me$ | H | H | H | $CF_3$ |
| 918 | 2 | $CO_2Me$ | H | H | H | $CF_3$ |
| 919 | 3 | $CO_2Me$ | H | H | H | $CF_3$ |
| 920 | 4 | $CO_2Me$ | H | H | H | $CF_3$ |
| 921 | 1 | $CO_2tBu$ | H | H | H | $CF_3$ |
| 922 | 2 | $CO_2tBu$ | H | H | H | $CF_3$ |
| 923 | 3 | $CO_2tBu$ | H | H | H | $CF_3$ |
| 924 | 4 | $CO_2tBu$ | H | H | H | $CF_3$ |
| 925 | 1 | CONHMe | H | H | H | $CF_3$ |
| 926 | 2 | CONHMe | H | H | H | $CF_3$ |
| 927 | 3 | CONHMe | H | H | H | $CF_3$ |
| 928 | 4 | CONHMe | H | H | H | $CF_3$ |
| 929 | 1 | $SO_2Me$ | H | H | H | $CF_3$ |
| 930 | 2 | $SO_2Me$ | H | H | H | $CF_3$ |
| 931 | 3 | $SO_2Me$ | H | H | H | $CF_3$ |
| 932 | 4 | $SO_2Me$ | H | H | H | $CF_3$ |
| 933 | 1 | $SO_2NH_2$ | H | H | H | $CF_3$ |
| 934 | 2 | $SO_2NH_2$ | H | H | H | $CF_3$ |
| 935 | 3 | $SO_2NH_2$ | H | H | H | $CF_3$ |
| 936 | 4 | $SO_2NH_2$ | H | H | H | $CF_3$ |
| 937 | 1 | H | H | H | H | F |
| 938 | 2 | H | H | H | H | F |
| 939 | 3 | H | H | H | H | F |
| 940 | 3 | H | H | H | H | F |
| 941 | 1 | Me | H | H | H | F |
| 942 | 2 | Me | H | H | H | F |
| 943 | 3 | Me | H | H | H | F |
| 944 | 4 | Me | H | H | H | F |
| 945 | 1 | $CH_2Ph$ | H | H | H | F |
| 946 | 2 | $CH_2Ph$ | H | H | H | F |
| 947 | 3 | $CH_2Ph$ | H | H | H | F |
| 948 | 4 | $CH_2Ph$ | H | H | H | F |
| 949 | 1 | COMe | H | H | H | F |
| 950 | 2 | COMe | H | H | H | F |
| 951 | 3 | COMe | H | H | H | F |
| 952 | 4 | COMe | H | H | H | F |
| 953 | 1 | $CO_2Me$ | H | H | H | F |
| 954 | 2 | $CO_2Me$ | H | H | H | F |
| 955 | 3 | $CO_2Me$ | H | H | H | F |
| 956 | 4 | $CO_2Me$ | H | H | H | F |
| 957 | 1 | $CO_2tBu$ | H | H | H | F |
| 958 | 2 | $CO_2tBu$ | H | H | H | F |
| 959 | 3 | $CO_2tBu$ | H | H | H | F |
| 960 | 4 | $CO_2tBu$ | H | H | H | F |
| 961 | 1 | CONHMe | H | H | H | F |
| 962 | 2 | CONHMe | H | H | H | F |
| 963 | 3 | CONHMe | H | H | H | F |
| 964 | 4 | CONHMe | H | H | H | F |
| 965 | 1 | $SO_2Me$ | H | H | H | F |
| 966 | 2 | $SO_2Me$ | H | H | H | F |
| 967 | 3 | $SO_2Me$ | H | H | H | F |
| 968 | 4 | $SO_2Me$ | H | H | H | F |
| 969 | 1 | $SO_2NH_2$ | H | H | H | F |
| 970 | 2 | $SO_2NH_2$ | H | H | H | F |
| 971 | 3 | $SO_2NH_2$ | H | H | H | F |
| 972 | 4 | $SO_2NH_2$ | H | H | H | F |
| 973 | 1 | H | H | H | H | Cl |
| 974 | 2 | H | H | H | H | Cl |
| 975 | 3 | H | H | H | H | Cl |
| 976 | 4 | H | H | H | H | Cl |
| 977 | 1 | Me | H | H | H | Cl |
| 978 | 2 | Me | H | H | H | Cl |
| 979 | 3 | Me | H | H | H | Cl |
| 980 | 4 | Me | H | H | H | Cl |
| 981 | 1 | $CH_2Ph$ | H | H | H | Cl |
| 982 | 2 | $CH_2Ph$ | H | H | H | Cl |
| 983 | 3 | $CH_2Ph$ | H | H | H | Cl |
| 984 | 4 | $CH_2Ph$ | H | H | H | Cl |
| 985 | 1 | COMe | H | H | H | Cl |
| 986 | 2 | COMe | H | H | H | Cl |
| 987 | 3 | COMe | H | H | H | Cl |
| 988 | 4 | COMe | H | H | H | Cl |
| 989 | 1 | $CO_2Me$ | H | H | H | Cl |
| 990 | 2 | $CO_2Me$ | H | H | H | Cl |
| 991 | 3 | $CO_2Me$ | H | H | H | Cl |
| 992 | 4 | $CO_2Me$ | H | H | H | Cl |
| 993 | 1 | $CO_2tBu$ | H | H | H | Cl |
| 994 | 2 | $CO_2tBu$ | H | H | H | Cl |
| 995 | 3 | $CO_2tBu$ | H | H | H | Cl |
| 996 | 4 | $CO_2tBu$ | H | H | H | Cl |
| 997 | 1 | CONHMe | H | H | H | Cl |
| 998 | 2 | CONHMe | H | H | H | Cl |
| 999 | 3 | CONHMe | H | H | H | Cl |
| 1000 | 4 | CONHMe | H | H | H | Cl |
| 1001 | 1 | $SO_2Me$ | H | H | H | Cl |
| 1002 | 2 | $SO_2Me$ | H | H | H | Cl |
| 1003 | 3 | $SO_2Me$ | H | H | H | Cl |
| 1004 | 4 | $SO_2Me$ | H | H | H | Cl |
| 1005 | 1 | $SO_2NH_2$ | H | H | H | Cl |
| 1006 | 2 | $SO_2NH_2$ | H | H | H | Cl |
| 1007 | 3 | $SO_2NH_2$ | H | H | H | Cl |
| 1008 | 4 | $SO_2NH_2$ | H | H | H | Cl |
| 1009 | 1 | H | H | H | H | CN |
| 1010 | 2 | H | H | H | H | CN |
| 1011 | 3 | H | H | H | H | CN |
| 1012 | 4 | H | H | H | H | CN |
| 1013 | 1 | Me | H | H | H | CN |
| 1014 | 2 | Me | H | H | H | CN |
| 1015 | 3 | Me | H | H | H | CN |
| 1016 | 4 | Me | H | H | H | CN |
| 1017 | 1 | $CH_2Ph$ | H | H | H | CN |
| 1018 | 2 | $CH_2Ph$ | H | H | H | CN |
| 1019 | 3 | $CH_2Ph$ | H | H | H | CN |
| 1020 | 4 | $CH_2Ph$ | H | H | H | CN |
| 1021 | 1 | COMe | H | H | H | CN |
| 1022 | 2 | COMe | H | H | H | CN |
| 1023 | 3 | COMe | H | H | H | CN |
| 1024 | 4 | COMe | H | H | H | CN |
| 1025 | 1 | $CO_2Me$ | H | H | H | CN |
| 1026 | 2 | $CO_2Me$ | H | H | H | CN |
| 1027 | 3 | $CO_2Me$ | H | H | H | CN |
| 1028 | 4 | $CO_2Me$ | H | H | H | CN |
| 1029 | 1 | $CO_2tBu$ | H | H | H | CN |
| 1030 | 2 | $CO_2tBu$ | H | H | H | CN |
| 1031 | 3 | $CO_2tBu$ | H | H | H | CN |
| 1032 | 4 | $CO_2tBu$ | H | H | H | CN |
| 1033 | 1 | CONHMe | H | H | H | CN |
| 1034 | 2 | CONHMe | H | H | H | CN |
| 1035 | 3 | CONHMe | H | H | H | CN |
| 1036 | 4 | CONHMe | H | H | H | CN |
| 1037 | 1 | $SO_2Me$ | H | H | H | CN |
| 1038 | 2 | $SO_2Me$ | H | H | H | CN |
| 1039 | 3 | $SO_2Me$ | H | H | H | CN |
| 1040 | 4 | $SO_2Me$ | H | H | H | CN |
| 1041 | 1 | $SO_2NH_2$ | H | H | H | CN |
| 1042 | 2 | $SO_2NH_2$ | H | H | H | CN |
| 1043 | 3 | $SO_2NH_2$ | H | H | H | CN |
| 1044 | 4 | $SO_2NH_2$ | H | H | H | CN |

Exemplary embodiments include compounds having the formula (XXIX)

(XXIX)

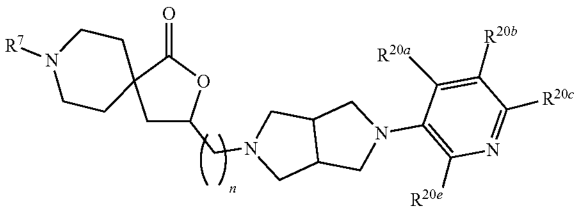

or a pharmaceutically acceptable salt form thereof defined herein below in Table 23.

TABLE 23

| Entry | n | $R^7$ | $R^{20a}$ | $R^{20b}$ | $R^{20c}$ | $R^{20e}$ |
|---|---|---|---|---|---|---|
| 1 | 1 | H | H | H | H | H |
| 2 | 2 | H | H | H | H | H |
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |

TABLE 23-continued

| Entry | n | $R^7$ | $R^{20a}$ | $R^{20b}$ | $R^{20c}$ | $R^{20e}$ |
|---|---|---|---|---|---|---|
| 60 | 4 | $CO_2tBu$ | H | H | OH | H |
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |
| 79 | 3 | Me | H | H | OMe | H |
| 80 | 4 | Me | H | H | OMe | H |
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |

TABLE 23-continued

| Entry | n | $R^7$ | $R^{20a}$ | $R^{20b}$ | $R^{20c}$ | $R^{20e}$ |
|---|---|---|---|---|---|---|
| 138 | 2 | $SO_2Me$ | H | H | Me | H |
| 139 | 3 | $SO_2Me$ | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |
| 157 | 1 | COMe | H | H | $CF_3$ | H |
| 158 | 2 | COMe | H | H | $CF_3$ | H |
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | $CO_2tBu$ | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |

TABLE 23-continued

| Entry | n | $R^7$ | $R^{20a}$ | $R^{20b}$ | $R^{20c}$ | $R^{20e}$ |
|---|---|---|---|---|---|---|
| 216 | 4 | $SO_2NH_2$ | H | H | F | H |
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |
| 235 | 3 | $CO_2Me$ | H | H | Cl | H |
| 236 | 4 | $CO_2Me$ | H | H | Cl | H |
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | $CH_2Ph$ | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | COMe | H | H | CN | H |
| 266 | 2 | COMe | H | H | CN | H |
| 267 | 3 | COMe | H | H | CN | H |
| 268 | 4 | COMe | H | H | CN | H |
| 269 | 1 | $CO_2Me$ | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2tBu$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |
| 277 | 1 | CONHMe | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | $SO_2Me$ | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2NH_2$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | H | H | OH | H | H |
| 290 | 2 | H | H | OH | H | H |
| 291 | 3 | H | H | OH | H | H |
| 292 | 4 | H | H | OH | H | H |
| 293 | 1 | Me | H | OH | H | H |

TABLE 23-continued

| Entry | n | $R^7$ | $R^{20a}$ | $R^{20b}$ | $R^{20c}$ | $R^{20e}$ |
|---|---|---|---|---|---|---|
| 294 | 2 | Me | H | OH | H | H |
| 295 | 3 | Me | H | OH | H | H |
| 296 | 4 | Me | H | OH | H | H |
| 297 | 1 | $CH_2Ph$ | H | OH | H | H |
| 298 | 2 | $CH_2Ph$ | H | OH | H | H |
| 299 | 3 | $CH_2Ph$ | H | OH | H | H |
| 300 | 4 | $CH_2Ph$ | H | OH | H | H |
| 301 | 1 | COMe | H | OH | H | H |
| 302 | 2 | COMe | H | OH | H | H |
| 303 | 3 | COMe | H | OH | H | H |
| 304 | 4 | COMe | H | OH | H | H |
| 305 | 1 | $CO_2Me$ | H | OH | H | H |
| 306 | 2 | $CO_2Me$ | H | OH | H | H |
| 307 | 3 | $CO_2Me$ | H | OH | H | H |
| 308 | 4 | $CO_2Me$ | H | OH | H | H |
| 309 | 1 | $CO_2tBu$ | H | OH | H | H |
| 310 | 2 | $CO_2tBu$ | H | OH | H | H |
| 311 | 3 | $CO_2tBu$ | H | OH | H | H |
| 312 | 4 | $CO_2tBu$ | H | OH | H | H |
| 313 | 1 | CONHMe | H | OH | H | H |
| 314 | 2 | CONHMe | H | OH | H | H |
| 315 | 3 | CONHMe | H | OH | H | H |
| 316 | 4 | CONHMe | H | OH | H | H |
| 317 | 1 | $SO_2Me$ | H | OH | H | H |
| 318 | 2 | $SO_2Me$ | H | OH | H | H |
| 319 | 3 | $SO_2Me$ | H | OH | H | H |
| 320 | 4 | $SO_2Me$ | H | OH | H | H |
| 321 | 1 | $SO_2NH_2$ | H | OH | H | H |
| 322 | 2 | $SO_2NH_2$ | H | OH | H | H |
| 323 | 3 | $SO_2NH_2$ | H | OH | H | H |
| 324 | 4 | $SO_2NH_2$ | H | OH | H | H |
| 325 | 1 | H | H | OMe | H | H |
| 326 | 2 | H | H | OMe | H | H |
| 327 | 3 | H | H | OMe | H | H |
| 328 | 4 | H | H | OMe | H | H |
| 329 | 1 | Me | H | OMe | H | H |
| 330 | 2 | Me | H | OMe | H | H |
| 331 | 3 | Me | H | OMe | H | H |
| 332 | 4 | Me | H | OMe | H | H |
| 333 | 1 | $CH_2Ph$ | H | OMe | H | H |
| 334 | 2 | $CH_2Ph$ | H | OMe | H | H |
| 335 | 3 | $CH_2Ph$ | H | OMe | H | H |
| 336 | 4 | $CH_2Ph$ | H | OMe | H | H |
| 337 | 1 | COMe | H | OMe | H | H |
| 338 | 2 | COMe | H | OMe | H | H |
| 339 | 3 | COMe | H | OMe | H | H |
| 340 | 4 | COMe | H | OMe | H | H |
| 341 | 1 | $CO_2Me$ | H | OMe | H | H |
| 342 | 2 | $CO_2Me$ | H | OMe | H | H |
| 343 | 3 | $CO_2Me$ | H | OMe | H | H |
| 344 | 4 | $CO_2Me$ | H | OMe | H | H |
| 345 | 1 | $CO_2tBu$ | H | OMe | H | H |
| 346 | 2 | $CO_2tBu$ | H | OMe | H | H |
| 347 | 3 | $CO_2tBu$ | H | OMe | H | H |
| 348 | 4 | $CO_2tBu$ | H | OMe | H | H |
| 349 | 1 | CONHMe | H | OMe | H | H |
| 350 | 2 | CONHMe | H | OMe | H | H |
| 351 | 3 | CONHMe | H | OMe | H | H |
| 352 | 4 | CONHMe | H | OMe | H | H |
| 353 | 1 | $SO_2Me$ | H | OMe | H | H |
| 354 | 2 | $SO_2Me$ | H | OMe | H | H |
| 355 | 3 | $SO_2Me$ | H | OMe | H | H |
| 356 | 4 | $SO_2Me$ | H | OMe | H | H |
| 357 | 1 | $SO_2NH_2$ | H | OMe | H | H |
| 358 | 2 | $SO_2NH_2$ | H | OMe | H | H |
| 359 | 3 | $SO_2NH_2$ | H | OMe | H | H |
| 360 | 4 | $SO_2NH_2$ | H | OMe | H | H |
| 361 | 1 | H | H | Me | H | H |
| 362 | 2 | H | H | Me | H | H |
| 363 | 3 | H | H | Me | H | H |
| 364 | 4 | H | H | Me | H | H |
| 365 | 1 | Me | H | Me | H | H |
| 366 | 2 | Me | H | Me | H | H |
| 367 | 3 | Me | H | Me | H | H |
| 368 | 4 | Me | H | Me | H | H |
| 369 | 1 | $CH_2Ph$ | H | Me | H | H |
| 370 | 2 | $CH_2Ph$ | H | Me | H | H |
| 371 | 3 | $CH_2Ph$ | H | Me | H | H |

TABLE 23-continued

| Entry | n | $R^7$ | $R^{20a}$ | $R^{20b}$ | $R^{20c}$ | $R^{20e}$ |
|---|---|---|---|---|---|---|
| 372 | 4 | $CH_2Ph$ | H | Me | H | H |
| 373 | 1 | COMe | H | Me | H | H |
| 374 | 2 | COMe | H | Me | H | H |
| 375 | 3 | COMe | H | Me | H | H |
| 376 | 4 | COMe | H | Me | H | H |
| 377 | 1 | $CO_2Me$ | H | Me | H | H |
| 378 | 2 | $CO_2Me$ | H | Me | H | H |
| 379 | 3 | $CO_2Me$ | H | Me | H | H |
| 380 | 4 | $CO_2Me$ | H | Me | H | H |
| 381 | 1 | $CO_2tBu$ | H | Me | H | H |
| 382 | 2 | $CO_2tBu$ | H | Me | H | H |
| 383 | 3 | $CO_2tBu$ | H | Me | H | H |
| 384 | 4 | $CO_2tBu$ | H | Me | H | H |
| 385 | 1 | CONHMe | H | Me | H | H |
| 386 | 2 | CONHMe | H | Me | H | H |
| 387 | 3 | CONHMe | H | Me | H | H |
| 388 | 4 | CONHMe | H | Me | H | H |
| 389 | 1 | $SO_2Me$ | H | Me | H | H |
| 390 | 2 | $SO_2Me$ | H | Me | H | H |
| 391 | 3 | $SO_2Me$ | H | Me | H | H |
| 392 | 4 | $SO_2Me$ | H | Me | H | H |
| 393 | 1 | $SO_2NH_2$ | H | Me | H | H |
| 394 | 2 | $SO_2NH_2$ | H | Me | H | H |
| 395 | 3 | $SO_2NH_2$ | H | Me | H | H |
| 396 | 4 | $SO_2NH_2$ | H | Me | H | H |
| 397 | 1 | H | H | $CF_3$ | H | H |
| 398 | 2 | H | H | $CF_3$ | H | H |
| 399 | 3 | H | H | $CF_3$ | H | H |
| 400 | 4 | H | H | $CF_3$ | H | H |
| 401 | 1 | Me | H | $CF_3$ | H | H |
| 402 | 2 | Me | H | $CF_3$ | H | H |
| 403 | 3 | Me | H | $CF_3$ | H | H |
| 404 | 4 | Me | H | $CF_3$ | H | H |
| 405 | 1 | $CH_2Ph$ | H | $CF_3$ | H | H |
| 406 | 2 | $CH_2Ph$ | H | $CF_3$ | H | H |
| 407 | 3 | $CH_2Ph$ | H | $CF_3$ | H | H |
| 408 | 4 | $CH_2Ph$ | H | $CF_3$ | H | H |
| 409 | 1 | COMe | H | $CF_3$ | H | H |
| 410 | 2 | COMe | H | $CF_3$ | H | H |
| 411 | 3 | COMe | H | $CF_3$ | H | H |
| 412 | 4 | COMe | H | $CF_3$ | H | H |
| 413 | 1 | $CO_2Me$ | H | $CF_3$ | H | H |
| 414 | 2 | $CO_2Me$ | H | $CF_3$ | H | H |
| 415 | 3 | $CO_2Me$ | H | $CF_3$ | H | H |
| 416 | 4 | $CO_2Me$ | H | $CF_3$ | H | H |
| 417 | 1 | $CO_2tBu$ | H | $CF_3$ | H | H |
| 418 | 2 | $CO_2tBu$ | H | $CF_3$ | H | H |
| 419 | 3 | $CO_2tBu$ | H | $CF_3$ | H | H |
| 420 | 4 | $CO_2tBu$ | H | $CF_3$ | H | H |
| 421 | 1 | CONHMe | H | $CF_3$ | H | H |
| 422 | 2 | CONHMe | H | $CF_3$ | H | H |
| 423 | 3 | CONHMe | H | $CF_3$ | H | H |
| 424 | 4 | CONHMe | H | $CF_3$ | H | H |
| 425 | 1 | $SO_2Me$ | H | $CF_3$ | H | H |
| 426 | 2 | $SO_2Me$ | H | $CF_3$ | H | H |
| 427 | 3 | $SO_2Me$ | H | $CF_3$ | H | H |
| 428 | 4 | $SO_2Me$ | H | $CF_3$ | H | H |
| 429 | 1 | $SO_2NH_2$ | H | $CF_3$ | H | H |
| 430 | 2 | $SO_2NH_2$ | H | $CF_3$ | H | H |
| 431 | 3 | $SO_2NH_2$ | H | $CF_3$ | H | H |
| 432 | 4 | $SO_2NH_2$ | H | $CF_3$ | H | H |
| 433 | 1 | H | H | F | H | H |
| 434 | 2 | H | H | F | H | H |
| 435 | 3 | H | H | F | H | H |
| 436 | 3 | H | H | F | H | H |
| 437 | 1 | Me | H | F | H | H |
| 438 | 2 | Me | H | F | H | H |
| 439 | 3 | Me | H | F | H | H |
| 440 | 4 | Me | H | F | H | H |
| 441 | 1 | $CH_2Ph$ | H | F | H | H |
| 442 | 2 | $CH_2Ph$ | H | F | H | H |
| 443 | 3 | $CH_2Ph$ | H | F | H | H |
| 444 | 4 | $CH_2Ph$ | H | F | H | H |
| 445 | 1 | COMe | H | F | H | H |
| 446 | 2 | COMe | H | F | H | H |
| 447 | 3 | COMe | H | F | H | H |
| 448 | 4 | COMe | H | F | H | H |
| 449 | 1 | $CO_2Me$ | H | F | H | H |

TABLE 23-continued

| Entry | n | $R^7$ | $R^{20a}$ | $R^{20b}$ | $R^{20c}$ | $R^{20e}$ |
|---|---|---|---|---|---|---|
| 450 | 2 | $CO_2Me$ | H | F | H | H |
| 451 | 3 | $CO_2Me$ | H | F | H | H |
| 452 | 4 | $CO_2Me$ | H | F | H | H |
| 453 | 1 | $CO_2tBu$ | H | F | H | H |
| 454 | 2 | $CO_2tBu$ | H | F | H | H |
| 455 | 3 | $CO_2tBu$ | H | F | H | H |
| 456 | 4 | $CO_2tBu$ | H | F | H | H |
| 457 | 1 | CONHMe | H | F | H | H |
| 458 | 2 | CONHMe | H | F | H | H |
| 459 | 3 | CONHMe | H | F | H | H |
| 460 | 4 | CONHMe | H | F | H | H |
| 461 | 1 | $SO_2Me$ | H | F | H | H |
| 462 | 2 | $SO_2Me$ | H | F | H | H |
| 463 | 3 | $SO_2Me$ | H | F | H | H |
| 464 | 4 | $SO_2Me$ | H | F | H | H |
| 465 | 1 | $SO_2NH_2$ | H | F | H | H |
| 466 | 2 | $SO_2NH_2$ | H | F | H | H |
| 467 | 3 | $SO_2NH_2$ | H | F | H | H |
| 468 | 4 | $SO_2NH_2$ | H | F | H | H |
| 469 | 1 | H | H | Cl | H | H |
| 470 | 2 | H | H | Cl | H | H |
| 471 | 3 | H | H | Cl | H | H |
| 472 | 4 | H | H | Cl | H | H |
| 473 | 1 | Me | H | Cl | H | H |
| 474 | 2 | Me | H | Cl | H | H |
| 475 | 3 | Me | H | Cl | H | H |
| 476 | 4 | Me | H | Cl | H | H |
| 477 | 1 | $CH_2Ph$ | H | Cl | H | H |
| 478 | 2 | $CH_2Ph$ | H | Cl | H | H |
| 479 | 3 | $CH_2Ph$ | H | Cl | H | H |
| 480 | 4 | $CH_2Ph$ | H | Cl | H | H |
| 481 | 1 | COMe | H | Cl | H | H |
| 482 | 2 | COMe | H | Cl | H | H |
| 483 | 3 | COMe | H | Cl | H | H |
| 484 | 4 | COMe | H | Cl | H | H |
| 485 | 1 | $CO_2Me$ | H | Cl | H | H |
| 486 | 2 | $CO_2Me$ | H | Cl | H | H |
| 487 | 3 | $CO_2Me$ | H | Cl | H | H |
| 488 | 4 | $CO_2Me$ | H | Cl | H | H |
| 489 | 1 | $CO_2tBu$ | H | Cl | H | H |
| 490 | 2 | $CO_2tBu$ | H | Cl | H | H |
| 491 | 3 | $CO_2tBu$ | H | Cl | H | H |
| 492 | 4 | $CO_2tBu$ | H | Cl | H | H |
| 493 | 1 | CONHMe | H | Cl | H | H |
| 494 | 2 | CONHMe | H | Cl | H | H |
| 495 | 3 | CONHMe | H | Cl | H | H |
| 496 | 4 | CONHMe | H | Cl | H | H |
| 497 | 1 | $SO_2Me$ | H | Cl | H | H |
| 498 | 2 | $SO_2Me$ | H | Cl | H | H |
| 499 | 3 | $SO_2Me$ | H | Cl | H | H |
| 500 | 4 | $SO_2Me$ | H | Cl | H | H |
| 501 | 1 | $SO_2NH_2$ | H | Cl | H | H |
| 502 | 2 | $SO_2NH_2$ | H | Cl | H | H |
| 503 | 3 | $SO_2NH_2$ | H | Cl | H | H |
| 504 | 4 | $SO_2NH_2$ | H | Cl | H | H |
| 505 | 1 | H | H | CN | H | H |
| 506 | 2 | H | H | CN | H | H |
| 507 | 3 | H | H | CN | H | H |
| 508 | 4 | H | H | CN | H | H |
| 509 | 1 | Me | H | CN | H | H |
| 510 | 2 | Me | H | CN | H | H |
| 511 | 3 | Me | H | CN | H | H |
| 512 | 4 | Me | H | CN | H | H |
| 513 | 1 | $CH_2Ph$ | H | CN | H | H |
| 514 | 2 | $CH_2Ph$ | H | CN | H | H |
| 515 | 3 | $CH_2Ph$ | H | CN | H | H |
| 516 | 4 | $CH_2Ph$ | H | CN | H | H |
| 517 | 1 | COMe | H | CN | H | H |
| 518 | 2 | COMe | H | CN | H | H |
| 519 | 3 | COMe | H | CN | H | H |
| 520 | 4 | COMe | H | CN | H | H |
| 521 | 1 | $CO_2Me$ | H | CN | H | H |
| 522 | 2 | $CO_2Me$ | H | CN | H | H |
| 523 | 3 | $CO_2Me$ | H | CN | H | H |
| 524 | 4 | $CO_2Me$ | H | CN | H | H |
| 525 | 1 | $CO_2tBu$ | H | CN | H | H |
| 526 | 2 | $CO_2tBu$ | H | CN | H | H |
| 527 | 3 | $CO_2tBu$ | H | CN | H | H |
| 528 | 4 | $CO_2tBu$ | H | CN | H | H |
| 529 | 1 | CONHMe | H | CN | H | H |
| 530 | 2 | CONHMe | H | CN | H | H |
| 531 | 3 | CONHMe | H | CN | H | H |
| 532 | 4 | CONHMe | H | CN | H | H |
| 533 | 1 | $SO_2Me$ | H | CN | H | H |
| 534 | 2 | $SO_2Me$ | H | CN | H | H |
| 535 | 3 | $SO_2Me$ | H | CN | H | H |
| 536 | 4 | $SO_2Me$ | H | CN | H | H |
| 537 | 1 | $SO_2NH_2$ | H | CN | H | H |
| 538 | 2 | $SO_2NH_2$ | H | CN | H | H |
| 539 | 3 | $SO_2NH_2$ | H | CN | H | H |
| 540 | 4 | $SO_2NH_2$ | H | CN | H | H |
| 541 | 1 | H | OH | H | H | H |
| 542 | 2 | H | OH | H | H | H |
| 543 | 3 | H | OH | H | H | H |
| 544 | 4 | H | OH | H | H | H |
| 545 | 1 | Me | OH | H | H | H |
| 546 | 2 | Me | OH | H | H | H |
| 547 | 3 | Me | OH | H | H | H |
| 548 | 4 | Me | OH | H | H | H |
| 549 | 1 | $CH_2Ph$ | OH | H | H | H |
| 550 | 2 | $CH_2Ph$ | OH | H | H | H |
| 551 | 3 | $CH_2Ph$ | OH | H | H | H |
| 552 | 4 | $CH_2Ph$ | OH | H | H | H |
| 553 | 1 | COMe | OH | H | H | H |
| 554 | 2 | COMe | OH | H | H | H |
| 555 | 3 | COMe | OH | H | H | H |
| 556 | 4 | COMe | OH | H | H | H |
| 557 | 1 | $CO_2Me$ | OH | H | H | H |
| 558 | 2 | $CO_2Me$ | OH | H | H | H |
| 559 | 3 | $CO_2Me$ | OH | H | H | H |
| 560 | 4 | $CO_2Me$ | OH | H | H | H |
| 561 | 1 | $CO_2tBu$ | OH | H | H | H |
| 562 | 2 | $CO_2tBu$ | OH | H | H | H |
| 563 | 3 | $CO_2tBu$ | OH | H | H | H |
| 564 | 4 | $CO_2tBu$ | OH | H | H | H |
| 565 | 1 | CONHMe | OH | H | H | H |
| 566 | 2 | CONHMe | OH | H | H | H |
| 567 | 3 | CONHMe | OH | H | H | H |
| 568 | 4 | CONHMe | OH | H | H | H |
| 569 | 1 | $SO_2Me$ | OH | H | H | H |
| 570 | 2 | $SO_2Me$ | OH | H | H | H |
| 571 | 3 | $SO_2Me$ | OH | H | H | H |
| 572 | 4 | $SO_2Me$ | OH | H | H | H |
| 573 | 1 | $SO_2NH_2$ | OH | H | H | H |
| 574 | 2 | $SO_2NH_2$ | OH | H | H | H |
| 575 | 3 | $SO_2NH_2$ | OH | H | H | H |
| 576 | 4 | $SO_2NH_2$ | OH | H | H | H |
| 577 | 1 | H | OMe | H | H | H |
| 578 | 2 | H | OMe | H | H | H |
| 579 | 3 | H | OMe | H | H | H |
| 580 | 4 | H | OMe | H | H | H |
| 581 | 1 | Me | OMe | H | H | H |
| 582 | 2 | Me | OMe | H | H | H |
| 583 | 3 | Me | OMe | H | H | H |
| 584 | 4 | Me | OMe | H | H | H |
| 585 | 1 | $CH_2Ph$ | OMe | H | H | H |
| 586 | 2 | $CH_2Ph$ | OMe | H | H | H |
| 587 | 3 | $CH_2Ph$ | OMe | H | H | H |
| 588 | 4 | $CH_2Ph$ | OMe | H | H | H |
| 589 | 1 | COMe | OMe | H | H | H |
| 590 | 2 | COMe | OMe | H | H | H |
| 591 | 3 | COMe | OMe | H | H | H |
| 592 | 4 | COMe | OMe | H | H | H |
| 593 | 1 | $CO_2Me$ | OMe | H | H | H |
| 594 | 2 | $CO_2Me$ | OMe | H | H | H |
| 595 | 3 | $CO_2Me$ | OMe | H | H | H |
| 596 | 4 | $CO_2Me$ | OMe | H | H | H |
| 597 | 1 | $CO_2tBu$ | OMe | H | H | H |
| 598 | 2 | $CO_2tBu$ | OMe | H | H | H |
| 599 | 3 | $CO_2tBu$ | OMe | H | H | H |
| 600 | 4 | $CO_2tBu$ | OMe | H | H | H |
| 601 | 1 | CONHMe | OMe | H | H | H |
| 602 | 2 | CONHMe | OMe | H | H | H |
| 603 | 3 | CONHMe | OMe | H | H | H |
| 604 | 4 | CONHMe | OMe | H | H | H |
| 605 | 1 | $SO_2Me$ | OMe | H | H | H |

TABLE 23-continued

| Entry | n | $R^7$ | $R^{20a}$ | $R^{20b}$ | $R^{20c}$ | $R^{20e}$ |
|---|---|---|---|---|---|---|
| 606 | 2 | $SO_2Me$ | OMe | H | H | H |
| 607 | 3 | $SO_2Me$ | OMe | H | H | H |
| 608 | 4 | $SO_2Me$ | OMe | H | H | H |
| 609 | 1 | $SO_2NH_2$ | OMe | H | H | H |
| 610 | 2 | $SO_2NH_2$ | OMe | H | H | H |
| 611 | 3 | $SO_2NH_2$ | OMe | H | H | H |
| 612 | 4 | $SO_2NH_2$ | OMe | H | H | H |
| 613 | 1 | H | Me | H | H | H |
| 614 | 2 | H | Me | H | H | H |
| 615 | 3 | H | Me | H | H | H |
| 616 | 4 | H | Me | H | H | H |
| 617 | 1 | Me | Me | H | H | H |
| 618 | 2 | Me | Me | H | H | H |
| 619 | 3 | Me | Me | H | H | H |
| 620 | 4 | Me | Me | H | H | H |
| 621 | 1 | $CH_2Ph$ | Me | H | H | H |
| 622 | 2 | $CH_2Ph$ | Me | H | H | H |
| 623 | 3 | $CH_2Ph$ | Me | H | H | H |
| 624 | 4 | $CH_2Ph$ | Me | H | H | H |
| 625 | 1 | COMe | Me | H | H | H |
| 626 | 2 | COMe | Me | H | H | H |
| 627 | 3 | COMe | Me | H | H | H |
| 628 | 4 | COMe | Me | H | H | H |
| 629 | 1 | $CO_2Me$ | Me | H | H | H |
| 630 | 2 | $CO_2Me$ | Me | H | H | H |
| 631 | 3 | $CO_2Me$ | Me | H | H | H |
| 632 | 4 | $CO_2Me$ | Me | H | H | H |
| 633 | 1 | $CO_2tBu$ | Me | H | H | H |
| 634 | 2 | $CO_2tBu$ | Me | H | H | H |
| 635 | 3 | $CO_2tBu$ | Me | H | H | H |
| 636 | 4 | $CO_2tBu$ | Me | H | H | H |
| 637 | 1 | CONHMe | Me | H | H | H |
| 638 | 2 | CONHMe | Me | H | H | H |
| 639 | 3 | CONHMe | Me | H | H | H |
| 640 | 4 | CONHMe | Me | H | H | H |
| 641 | 1 | $SO_2Me$ | Me | H | H | H |
| 642 | 2 | $SO_2Me$ | Me | H | H | H |
| 643 | 3 | $SO_2Me$ | Me | H | H | H |
| 644 | 4 | $SO_2Me$ | Me | H | H | H |
| 645 | 1 | $SO_2NH_2$ | Me | H | H | H |
| 646 | 2 | $SO_2NH_2$ | Me | H | H | H |
| 647 | 3 | $SO_2NH_2$ | Me | H | H | H |
| 648 | 4 | $SO_2NH_2$ | Me | H | H | H |
| 649 | 1 | H | $CF_3$ | H | H | H |
| 650 | 2 | H | $CF_3$ | H | H | H |
| 651 | 3 | H | $CF_3$ | H | H | H |
| 652 | 4 | H | $CF_3$ | H | H | H |
| 653 | 1 | Me | $CF_3$ | H | H | H |
| 654 | 2 | Me | $CF_3$ | H | H | H |
| 655 | 3 | Me | $CF_3$ | H | H | H |
| 656 | 4 | Me | $CF_3$ | H | H | H |
| 657 | 1 | $CH_2Ph$ | $CF_3$ | H | H | H |
| 658 | 2 | $CH_2Ph$ | $CF_3$ | H | H | H |
| 659 | 3 | $CH_2Ph$ | $CF_3$ | H | H | H |
| 660 | 4 | $CH_2Ph$ | $CF_3$ | H | H | H |
| 661 | 1 | COMe | $CF_3$ | H | H | H |
| 662 | 2 | COMe | $CF_3$ | H | H | H |
| 663 | 3 | COMe | $CF_3$ | H | H | H |
| 664 | 4 | COMe | $CF_3$ | H | H | H |
| 665 | 1 | $CO_2Me$ | $CF_3$ | H | H | H |
| 666 | 2 | $CO_2Me$ | $CF_3$ | H | H | H |
| 667 | 3 | $CO_2Me$ | $CF_3$ | H | H | H |
| 668 | 4 | $CO_2Me$ | $CF_3$ | H | H | H |
| 669 | 1 | $CO_2tBu$ | $CF_3$ | H | H | H |
| 670 | 2 | $CO_2tBu$ | $CF_3$ | H | H | H |
| 671 | 3 | $CO_2tBu$ | $CF_3$ | H | H | H |
| 672 | 4 | $CO_2tBu$ | $CF_3$ | H | H | H |
| 673 | 1 | CONHMe | $CF_3$ | H | H | H |
| 674 | 2 | CONHMe | $CF_3$ | H | H | H |
| 675 | 3 | CONHMe | $CF_3$ | H | H | H |
| 676 | 4 | CONHMe | $CF_3$ | H | H | H |
| 677 | 1 | $SO_2Me$ | $CF_3$ | H | H | H |
| 678 | 2 | $SO_2Me$ | $CF_3$ | H | H | H |
| 679 | 3 | $SO_2Me$ | $CF_3$ | H | H | H |
| 680 | 4 | $SO_2Me$ | $CF_3$ | H | H | H |
| 681 | 1 | $SO_2NH_2$ | $CF_3$ | H | H | H |
| 682 | 2 | $SO_2NH_2$ | $CF_3$ | H | H | H |
| 683 | 3 | $SO_2NH_2$ | $CF_3$ | H | H | H |

TABLE 23-continued

| Entry | n | $R^7$ | $R^{20a}$ | $R^{20b}$ | $R^{20c}$ | $R^{20e}$ |
|---|---|---|---|---|---|---|
| 684 | 4 | $SO_2NH_2$ | $CF_3$ | H | H | H |
| 685 | 1 | H | F | H | H | H |
| 686 | 2 | H | F | H | H | H |
| 687 | 3 | H | F | H | H | H |
| 688 | 3 | H | F | H | H | H |
| 689 | 1 | Me | F | H | H | H |
| 690 | 2 | Me | F | H | H | H |
| 691 | 3 | Me | F | H | H | H |
| 692 | 4 | Me | F | H | H | H |
| 693 | 1 | $CH_2Ph$ | F | H | H | H |
| 694 | 2 | $CH_2Ph$ | F | H | H | H |
| 695 | 3 | $CH_2Ph$ | F | H | H | H |
| 696 | 4 | $CH_2Ph$ | F | H | H | H |
| 697 | 1 | COMe | F | H | H | H |
| 698 | 2 | COMe | F | H | H | H |
| 699 | 3 | COMe | F | H | H | H |
| 700 | 4 | COMe | F | H | H | H |
| 701 | 1 | $CO_2Me$ | F | H | H | H |
| 702 | 2 | $CO_2Me$ | F | H | H | H |
| 703 | 3 | $CO_2Me$ | F | H | H | H |
| 704 | 4 | $CO_2Me$ | F | H | H | H |
| 705 | 1 | $CO_2tBu$ | F | H | H | H |
| 706 | 2 | $CO_2tBu$ | F | H | H | H |
| 707 | 3 | $CO_2tBu$ | F | H | H | H |
| 708 | 4 | $CO_2tBu$ | F | H | H | H |
| 709 | 1 | CONHMe | F | H | H | H |
| 710 | 2 | CONHMe | F | H | H | H |
| 711 | 3 | CONHMe | F | H | H | H |
| 712 | 4 | CONHMe | F | H | H | H |
| 713 | 1 | $SO_2Me$ | F | H | H | H |
| 714 | 2 | $SO_2Me$ | F | H | H | H |
| 715 | 3 | $SO_2Me$ | F | H | H | H |
| 716 | 4 | $SO_2Me$ | F | H | H | H |
| 717 | 1 | $SO_2NH_2$ | F | H | H | H |
| 718 | 2 | $SO_2NH_2$ | F | H | H | H |
| 719 | 3 | $SO_2NH_2$ | F | H | H | H |
| 720 | 4 | $SO_2NH_2$ | F | H | H | H |
| 721 | 1 | H | Cl | H | H | H |
| 722 | 2 | H | Cl | H | H | H |
| 723 | 3 | H | Cl | H | H | H |
| 724 | 4 | H | Cl | H | H | H |
| 725 | 1 | Me | Cl | H | H | H |
| 726 | 2 | Me | Cl | H | H | H |
| 727 | 3 | Me | Cl | H | H | H |
| 728 | 4 | Me | Cl | H | H | H |
| 729 | 1 | $CH_2Ph$ | Cl | H | H | H |
| 730 | 2 | $CH_2Ph$ | Cl | H | H | H |
| 731 | 3 | $CH_2Ph$ | Cl | H | H | H |
| 732 | 4 | $CH_2Ph$ | Cl | H | H | H |
| 733 | 1 | COMe | Cl | H | H | H |
| 734 | 2 | COMe | Cl | H | H | H |
| 735 | 3 | COMe | Cl | H | H | H |
| 736 | 4 | COMe | Cl | H | H | H |
| 737 | 1 | $CO_2Me$ | Cl | H | H | H |
| 738 | 2 | $CO_2Me$ | Cl | H | H | H |
| 739 | 3 | $CO_2Me$ | Cl | H | H | H |
| 740 | 4 | $CO_2Me$ | Cl | H | H | H |
| 741 | 1 | $CO_2tBu$ | Cl | H | H | H |
| 742 | 2 | $CO_2tBu$ | Cl | H | H | H |
| 743 | 3 | $CO_2tBu$ | Cl | H | H | H |
| 744 | 4 | $CO_2tBu$ | Cl | H | H | H |
| 745 | 1 | CONHMe | Cl | H | H | H |
| 746 | 2 | CONHMe | Cl | H | H | H |
| 747 | 3 | CONHMe | Cl | H | H | H |
| 748 | 4 | CONHMe | Cl | H | H | H |
| 749 | 1 | $SO_2Me$ | Cl | H | H | H |
| 750 | 2 | $SO_2Me$ | Cl | H | H | H |
| 751 | 3 | $SO_2Me$ | Cl | H | H | H |
| 752 | 4 | $SO_2Me$ | Cl | H | H | H |
| 753 | 1 | $SO_2NH_2$ | Cl | H | H | H |
| 754 | 2 | $SO_2NH_2$ | Cl | H | H | H |
| 755 | 3 | $SO_2NH_2$ | Cl | H | H | H |
| 756 | 4 | $SO_2NH_2$ | Cl | H | H | H |
| 757 | 1 | H | CN | H | H | H |
| 758 | 2 | H | CN | H | H | H |
| 759 | 3 | H | CN | H | H | H |
| 760 | 4 | H | CN | H | H | H |
| 761 | 1 | Me | CN | H | H | H |

TABLE 23-continued

| Entry | n | $R^7$ | $R^{20a}$ | $R^{20b}$ | $R^{20c}$ | $R^{20e}$ |
|---|---|---|---|---|---|---|
| 762 | 2 | Me | CN | H | H | H |
| 763 | 3 | Me | CN | H | H | H |
| 764 | 4 | Me | CN | H | H | H |
| 765 | 1 | $CH_2Ph$ | CN | H | H | H |
| 766 | 2 | $CH_2Ph$ | CN | H | H | H |
| 767 | 3 | $CH_2Ph$ | CN | H | H | H |
| 768 | 4 | $CH_2Ph$ | CN | H | H | H |
| 769 | 1 | COMe | CN | H | H | H |
| 770 | 2 | COMe | CN | H | H | H |
| 771 | 3 | COMe | CN | H | H | H |
| 772 | 4 | COMe | CN | H | H | H |
| 773 | 1 | $CO_2Me$ | CN | H | H | H |
| 774 | 2 | $CO_2Me$ | CN | H | H | H |
| 775 | 3 | $CO_2Me$ | CN | H | H | H |
| 776 | 4 | $CO_2Me$ | CN | H | H | H |
| 777 | 1 | $CO_2tBu$ | CN | H | H | H |
| 778 | 2 | $CO_2tBu$ | CN | H | H | H |
| 779 | 3 | $CO_2tBu$ | CN | H | H | H |
| 780 | 4 | $CO_2tBu$ | CN | H | H | H |
| 781 | 1 | CONHMe | CN | H | H | H |
| 782 | 2 | CONHMe | CN | H | H | H |
| 783 | 3 | CONHMe | CN | H | H | H |
| 784 | 4 | CONHMe | CN | H | H | H |
| 785 | 1 | $SO_2Me$ | CN | H | H | H |
| 786 | 2 | $SO_2Me$ | CN | H | H | H |
| 787 | 3 | $SO_2Me$ | CN | H | H | H |
| 788 | 4 | $SO_2Me$ | CN | H | H | H |
| 789 | 1 | $SO_2NH_2$ | CN | H | H | H |
| 790 | 2 | $SO_2NH_2$ | CN | H | H | H |
| 791 | 3 | $SO_2NH_2$ | CN | H | H | H |
| 792 | 4 | $SO_2NH_2$ | CN | H | H | H |
| 793 | 1 | H | H | H | H | OH |
| 794 | 2 | H | H | H | H | OH |
| 795 | 3 | H | H | H | H | OH |
| 796 | 4 | H | H | H | H | OH |
| 797 | 1 | Me | H | H | H | OH |
| 798 | 2 | Me | H | H | H | OH |
| 799 | 3 | Me | H | H | H | OH |
| 800 | 4 | Me | H | H | H | OH |
| 801 | 1 | $CH_2Ph$ | H | H | H | OH |
| 802 | 2 | $CH_2Ph$ | H | H | H | OH |
| 803 | 3 | $CH_2Ph$ | H | H | H | OH |
| 804 | 4 | $CH_2Ph$ | H | H | H | OH |
| 805 | 1 | COMe | H | H | H | OH |
| 806 | 2 | COMe | H | H | H | OH |
| 807 | 3 | COMe | H | H | H | OH |
| 808 | 4 | COMe | H | H | H | OH |
| 809 | 1 | $CO_2Me$ | H | H | H | OH |
| 810 | 2 | $CO_2Me$ | H | H | H | OH |
| 811 | 3 | $CO_2Me$ | H | H | H | OH |
| 812 | 4 | $CO_2Me$ | H | H | H | OH |
| 813 | 1 | $CO_2tBu$ | H | H | H | OH |
| 814 | 2 | $CO_2tBu$ | H | H | H | OH |
| 815 | 3 | $CO_2tBu$ | H | H | H | OH |
| 816 | 4 | $CO_2tBu$ | H | H | H | OH |
| 817 | 1 | CONHMe | H | H | H | OH |
| 818 | 2 | CONHMe | H | H | H | OH |
| 819 | 3 | CONHMe | H | H | H | OH |
| 820 | 4 | CONHMe | H | H | H | OH |
| 821 | 1 | $SO_2Me$ | H | H | H | OH |
| 822 | 2 | $SO_2Me$ | H | H | H | OH |
| 823 | 3 | $SO_2Me$ | H | H | H | OH |
| 824 | 4 | $SO_2Me$ | H | H | H | OH |
| 825 | 1 | $SO_2NH_2$ | H | H | H | OH |
| 826 | 2 | $SO_2NH_2$ | H | H | H | OH |
| 827 | 3 | $SO_2NH_2$ | H | H | H | OH |
| 828 | 4 | $SO_2NH_2$ | H | H | H | OH |
| 829 | 1 | H | H | H | H | OMe |
| 830 | 2 | H | H | H | H | OMe |
| 831 | 3 | H | H | H | H | OMe |
| 832 | 4 | H | H | H | H | OMe |
| 833 | 1 | Me | H | H | H | OMe |
| 834 | 2 | Me | H | H | H | OMe |
| 835 | 3 | Me | H | H | H | OMe |
| 836 | 4 | Me | H | H | H | OMe |
| 837 | 1 | $CH_2Ph$ | H | H | H | OMe |
| 838 | 2 | $CH_2Ph$ | H | H | H | OMe |
| 839 | 3 | $CH_2Ph$ | H | H | H | OMe |

TABLE 23-continued

| Entry | n | $R^7$ | $R^{20a}$ | $R^{20b}$ | $R^{20c}$ | $R^{20e}$ |
|---|---|---|---|---|---|---|
| 840 | 4 | $CH_2Ph$ | H | H | H | OMe |
| 841 | 1 | COMe | H | H | H | OMe |
| 842 | 2 | COMe | H | H | H | OMe |
| 843 | 3 | COMe | H | H | H | OMe |
| 844 | 4 | COMe | H | H | H | OMe |
| 845 | 1 | $CO_2Me$ | H | H | H | OMe |
| 846 | 2 | $CO_2Me$ | H | H | H | OMe |
| 847 | 3 | $CO_2Me$ | H | H | H | OMe |
| 848 | 4 | $CO_2Me$ | H | H | H | OMe |
| 849 | 1 | $CO_2tBu$ | H | H | H | OMe |
| 850 | 2 | $CO_2tBu$ | H | H | H | OMe |
| 851 | 3 | $CO_2tBu$ | H | H | H | OMe |
| 852 | 4 | $CO_2tBu$ | H | H | H | OMe |
| 853 | 1 | CONHMe | H | H | H | OMe |
| 854 | 2 | CONHMe | H | H | H | OMe |
| 855 | 3 | CONHMe | H | H | H | OMe |
| 856 | 4 | CONHMe | H | H | H | OMe |
| 857 | 1 | $SO_2Me$ | H | H | H | OMe |
| 858 | 2 | $SO_2Me$ | H | H | H | OMe |
| 859 | 3 | $SO_2Me$ | H | H | H | OMe |
| 860 | 4 | $SO_2Me$ | H | H | H | OMe |
| 861 | 1 | $SO_2NH_2$ | H | H | H | OMe |
| 862 | 2 | $SO_2NH_2$ | H | H | H | OMe |
| 863 | 3 | $SO_2NH_2$ | H | H | H | OMe |
| 864 | 4 | $SO_2NH_2$ | H | H | H | OMe |
| 865 | 1 | H | H | H | H | Me |
| 866 | 2 | H | H | H | H | Me |
| 867 | 3 | H | H | H | H | Me |
| 868 | 4 | H | H | H | H | Me |
| 869 | 1 | Me | H | H | H | Me |
| 870 | 2 | Me | H | H | H | Me |
| 871 | 3 | Me | H | H | H | Me |
| 872 | 4 | Me | H | H | H | Me |
| 873 | 1 | $CH_2Ph$ | H | H | H | Me |
| 874 | 2 | $CH_2Ph$ | H | H | H | Me |
| 875 | 3 | $CH_2Ph$ | H | H | H | Me |
| 876 | 4 | $CH_2Ph$ | H | H | H | Me |
| 877 | 1 | COMe | H | H | H | Me |
| 878 | 2 | COMe | H | H | H | Me |
| 879 | 3 | COMe | H | H | H | Me |
| 880 | 4 | COMe | H | H | H | Me |
| 881 | 1 | $CO_2Me$ | H | H | H | Me |
| 882 | 2 | $CO_2Me$ | H | H | H | Me |
| 883 | 3 | $CO_2Me$ | H | H | H | Me |
| 884 | 4 | $CO_2Me$ | H | H | H | Me |
| 885 | 1 | $CO_2tBu$ | H | H | H | Me |
| 886 | 2 | $CO_2tBu$ | H | H | H | Me |
| 887 | 3 | $CO_2tBu$ | H | H | H | Me |
| 888 | 4 | $CO_2tBu$ | H | H | H | Me |
| 889 | 1 | CONHMe | H | H | H | Me |
| 890 | 2 | CONHMe | H | H | H | Me |
| 891 | 3 | CONHMe | H | H | H | Me |
| 892 | 4 | CONHMe | H | H | H | Me |
| 893 | 1 | $SO_2Me$ | H | H | H | Me |
| 894 | 2 | $SO_2Me$ | H | H | H | Me |
| 895 | 3 | $SO_2Me$ | H | H | H | Me |
| 896 | 4 | $SO_2Me$ | H | H | H | Me |
| 897 | 1 | $SO_2NH_2$ | H | H | H | Me |
| 898 | 2 | $SO_2NH_2$ | H | H | H | Me |
| 899 | 3 | $SO_2NH_2$ | H | H | H | Me |
| 900 | 4 | $SO_2NH_2$ | H | H | H | Me |
| 901 | 1 | H | H | H | H | $CF_3$ |
| 902 | 2 | H | H | H | H | $CF_3$ |
| 903 | 3 | H | H | H | H | $CF_3$ |
| 904 | 4 | H | H | H | H | $CF_3$ |
| 905 | 1 | Me | H | H | H | $CF_3$ |
| 906 | 2 | Me | H | H | H | $CF_3$ |
| 907 | 3 | Me | H | H | H | $CF_3$ |
| 908 | 4 | Me | H | H | H | $CF_3$ |
| 909 | 1 | $CH_2Ph$ | H | H | H | $CF_3$ |
| 910 | 2 | $CH_2Ph$ | H | H | H | $CF_3$ |
| 911 | 3 | $CH_2Ph$ | H | H | H | $CF_3$ |
| 912 | 4 | $CH_2Ph$ | H | H | H | $CF_3$ |
| 913 | 1 | COMe | H | H | H | $CF_3$ |
| 914 | 2 | COMe | H | H | H | $CF_3$ |
| 915 | 3 | COMe | H | H | H | $CF_3$ |
| 916 | 4 | COMe | H | H | H | $CF_3$ |
| 917 | 1 | $CO_2Me$ | H | H | H | $CF_3$ |

TABLE 23-continued

| Entry | n | $R^7$ | $R^{20a}$ | $R^{20b}$ | $R^{20c}$ | $R^{20e}$ |
|---|---|---|---|---|---|---|
| 918 | 2 | $CO_2Me$ | H | H | H | $CF_3$ |
| 919 | 3 | $CO_2Me$ | H | H | H | $CF_3$ |
| 920 | 4 | $CO_2Me$ | H | H | H | $CF_3$ |
| 921 | 1 | $CO_2tBu$ | H | H | H | $CF_3$ |
| 922 | 2 | $CO_2tBu$ | H | H | H | $CF_3$ |
| 923 | 3 | $CO_2tBu$ | H | H | H | $CF_3$ |
| 924 | 4 | $CO_2tBu$ | H | H | H | $CF_3$ |
| 925 | 1 | CONHMe | H | H | H | $CF_3$ |
| 926 | 2 | CONHMe | H | H | H | $CF_3$ |
| 927 | 3 | CONHMe | H | H | H | $CF_3$ |
| 928 | 4 | CONHMe | H | H | H | $CF_3$ |
| 929 | 1 | $SO_2Me$ | H | H | H | $CF_3$ |
| 930 | 2 | $SO_2Me$ | H | H | H | $CF_3$ |
| 931 | 3 | $SO_2Me$ | H | H | H | $CF_3$ |
| 932 | 4 | $SO_2Me$ | H | H | H | $CF_3$ |
| 933 | 1 | $SO_2NH_2$ | H | H | H | $CF_3$ |
| 934 | 2 | $SO_2NH_2$ | H | H | H | $CF_3$ |
| 935 | 3 | $SO_2NH_2$ | H | H | H | $CF_3$ |
| 936 | 4 | $SO_2NH_2$ | H | H | H | $CF_3$ |
| 937 | 1 | H | H | H | H | F |
| 938 | 2 | H | H | H | H | F |
| 939 | 3 | H | H | H | H | F |
| 940 | 3 | H | H | H | H | F |
| 941 | 1 | Me | H | H | H | F |
| 942 | 2 | Me | H | H | H | F |
| 943 | 3 | Me | H | H | H | F |
| 944 | 4 | Me | H | H | H | F |
| 945 | 1 | $CH_2Ph$ | H | H | H | F |
| 946 | 2 | $CH_2Ph$ | H | H | H | F |
| 947 | 3 | $CH_2Ph$ | H | H | H | F |
| 948 | 4 | $CH_2Ph$ | H | H | H | F |
| 949 | 1 | COMe | H | H | H | F |
| 950 | 2 | COMe | H | H | H | F |
| 951 | 3 | COMe | H | H | H | F |
| 952 | 4 | COMe | H | H | H | F |
| 953 | 1 | $CO_2Me$ | H | H | H | F |
| 954 | 2 | $CO_2Me$ | H | H | H | F |
| 955 | 3 | $CO_2Me$ | H | H | H | F |
| 956 | 4 | $CO_2Me$ | H | H | H | F |
| 957 | 1 | $CO_2tBu$ | H | H | H | F |
| 958 | 2 | $CO_2tBu$ | H | H | H | F |
| 959 | 3 | $CO_2tBu$ | H | H | H | F |
| 960 | 4 | $CO_2tBu$ | H | H | H | F |
| 961 | 1 | CONHMe | H | H | H | F |
| 962 | 2 | CONHMe | H | H | H | F |
| 963 | 3 | CONHMe | H | H | H | F |
| 964 | 4 | CONHMe | H | H | H | F |
| 965 | 1 | $SO_2Me$ | H | H | H | F |
| 966 | 2 | $SO_2Me$ | H | H | H | F |
| 967 | 3 | $SO_2Me$ | H | H | H | F |
| 968 | 4 | $SO_2Me$ | H | H | H | F |
| 969 | 1 | $SO_2NH_2$ | H | H | H | F |
| 970 | 2 | $SO_2NH_2$ | H | H | H | F |
| 971 | 3 | $SO_2NH_2$ | H | H | H | F |
| 972 | 4 | $SO_2NH_2$ | H | H | H | F |
| 973 | 1 | H | H | H | H | Cl |
| 974 | 2 | H | H | H | H | Cl |
| 975 | 3 | H | H | H | H | Cl |
| 976 | 4 | H | H | H | H | Cl |
| 977 | 1 | Me | H | H | H | Cl |
| 978 | 2 | Me | H | H | H | Cl |
| 979 | 3 | Me | H | H | H | Cl |
| 980 | 4 | Me | H | H | H | Cl |
| 981 | 1 | $CH_2Ph$ | H | H | H | Cl |
| 982 | 2 | $CH_2Ph$ | H | H | H | Cl |
| 983 | 3 | $CH_2Ph$ | H | H | H | Cl |
| 984 | 4 | $CH_2Ph$ | H | H | H | Cl |
| 985 | 1 | COMe | H | H | H | Cl |
| 986 | 2 | COMe | H | H | H | Cl |
| 987 | 3 | COMe | H | H | H | Cl |
| 988 | 4 | COMe | H | H | H | Cl |
| 989 | 1 | $CO_2Me$ | H | H | H | Cl |
| 990 | 2 | $CO_2Me$ | H | H | H | Cl |
| 991 | 3 | $CO_2Me$ | H | H | H | Cl |
| 992 | 4 | $CO_2Me$ | H | H | H | Cl |
| 993 | 1 | $CO_2tBu$ | H | H | H | Cl |
| 994 | 2 | $CO_2tBu$ | H | H | H | Cl |
| 995 | 3 | $CO_2tBu$ | H | H | H | Cl |
| 996 | 4 | $CO_2tBu$ | H | H | H | Cl |
| 997 | 1 | CONHMe | H | H | H | Cl |
| 998 | 2 | CONHMe | H | H | H | Cl |
| 999 | 3 | CONHMe | H | H | H | Cl |
| 1000 | 4 | CONHMe | H | H | H | Cl |
| 1001 | 1 | $SO_2Me$ | H | H | H | Cl |
| 1002 | 2 | $SO_2Me$ | H | H | H | Cl |
| 1003 | 3 | $SO_2Me$ | H | H | H | Cl |
| 1004 | 4 | $SO_2Me$ | H | H | H | Cl |
| 1005 | 1 | $SO_2NH_2$ | H | H | H | Cl |
| 1006 | 2 | $SO_2NH_2$ | H | H | H | Cl |
| 1007 | 3 | $SO_2NH_2$ | H | H | H | Cl |
| 1008 | 4 | $SO_2NH_2$ | H | H | H | Cl |
| 1009 | 1 | H | H | H | H | CN |
| 1010 | 2 | H | H | H | H | CN |
| 1011 | 3 | H | H | H | H | CN |
| 1012 | 4 | H | H | H | H | CN |
| 1013 | 1 | Me | H | H | H | CN |
| 1014 | 2 | Me | H | H | H | CN |
| 1015 | 3 | Me | H | H | H | CN |
| 1016 | 4 | Me | H | H | H | CN |
| 1017 | 1 | $CH_2Ph$ | H | H | H | CN |
| 1018 | 2 | $CH_2Ph$ | H | H | H | CN |
| 1019 | 3 | $CH_2Ph$ | H | H | H | CN |
| 1020 | 4 | $CH_2Ph$ | H | H | H | CN |
| 1021 | 1 | COMe | H | H | H | CN |
| 1022 | 2 | COMe | H | H | H | CN |
| 1023 | 3 | COMe | H | H | H | CN |
| 1024 | 4 | COMe | H | H | H | CN |
| 1025 | 1 | $CO_2Me$ | H | H | H | CN |
| 1026 | 2 | $CO_2Me$ | H | H | H | CN |
| 1027 | 3 | $CO_2Me$ | H | H | H | CN |
| 1028 | 4 | $CO_2Me$ | H | H | H | CN |
| 1029 | 1 | $CO_2tBu$ | H | H | H | CN |
| 1030 | 2 | $CO_2tBu$ | H | H | H | CN |
| 1031 | 3 | $CO_2tBu$ | H | H | H | CN |
| 1032 | 4 | $CO_2tBu$ | H | H | H | CN |
| 1033 | 1 | CONHMe | H | H | H | CN |
| 1034 | 2 | CONHMe | H | H | H | CN |
| 1035 | 3 | CONHMe | H | H | H | CN |
| 1036 | 4 | CONHMe | H | H | H | CN |
| 1037 | 1 | $SO_2Me$ | H | H | H | CN |
| 1038 | 2 | $SO_2Me$ | H | H | H | CN |
| 1039 | 3 | $SO_2Me$ | H | H | H | CN |
| 1040 | 4 | $SO_2Me$ | H | H | H | CN |
| 1041 | 1 | $SO_2NH_2$ | H | H | H | CN |
| 1042 | 2 | $SO_2NH_2$ | H | H | H | CN |
| 1043 | 3 | $SO_2NH_2$ | H | H | H | CN |
| 1044 | 4 | $SO_2NH_2$ | H | H | H | CN |

Exemplary embodiments include compounds having the formula (XXX)

(XXX)

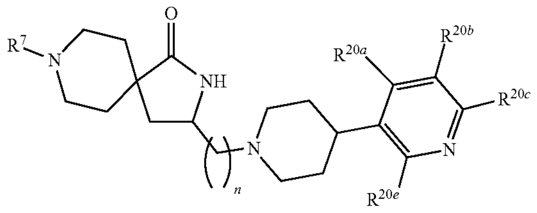

or a pharmaceutically acceptable salt form thereof defined herein below in Table 24.

TABLE 24

| Entry | n | $R^7$ | $R^{20a}$ | $R^{20b}$ | $R^{20c}$ | $R^{20e}$ |
|---|---|---|---|---|---|---|
| 1 | 1 | H | H | H | H | H |
| 2 | 2 | H | H | H | H | H |

TABLE 24-continued

| Entry | n | $R^7$ | $R^{20a}$ | $R^{20b}$ | $R^{20c}$ | $R^{20e}$ |
|---|---|---|---|---|---|---|
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |
| 60 | 4 | $CO_2tBu$ | H | H | OH | H |
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |
| 79 | 3 | Me | H | H | OMe | H |
| 80 | 4 | Me | H | H | OMe | H |
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |
| 138 | 2 | $SO_2Me$ | H | H | Me | H |
| 139 | 3 | $SO_2Me$ | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |
| 157 | 1 | COMe | H | H | $CF_3$ | H |
| 158 | 2 | COMe | H | H | $CF_3$ | H |

TABLE 24-continued

| Entry | n | $R^7$ | $R^{20a}$ | $R^{20b}$ | $R^{20c}$ | $R^{20e}$ |
|---|---|---|---|---|---|---|
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | $CO_2tBu$ | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |
| 216 | 4 | $SO_2NH_2$ | H | H | F | H |
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |
| 235 | 3 | $CO_2Me$ | H | H | Cl | H |
| 236 | 4 | $CO_2Me$ | H | H | Cl | H |

TABLE 24-continued

| Entry | n | $R^7$ | $R^{20a}$ | $R^{20b}$ | $R^{20c}$ | $R^{20e}$ |
|---|---|---|---|---|---|---|
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | $CH_2Ph$ | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | COMe | H | H | CN | H |
| 266 | 2 | COMe | H | H | CN | H |
| 267 | 3 | COMe | H | H | CN | H |
| 268 | 4 | COMe | H | H | CN | H |
| 269 | 1 | $CO_2Me$ | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2tBu$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |
| 277 | 1 | CONHMe | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | $SO_2Me$ | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2NH_2$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | H | H | OH | H | H |
| 290 | 2 | H | H | OH | H | H |
| 291 | 3 | H | H | OH | H | H |
| 292 | 4 | H | H | OH | H | H |
| 293 | 1 | Me | H | OH | H | H |
| 294 | 2 | Me | H | OH | H | H |
| 295 | 3 | Me | H | OH | H | H |
| 296 | 4 | Me | H | OH | H | H |
| 297 | 1 | $CH_2Ph$ | H | OH | H | H |
| 298 | 2 | $CH_2Ph$ | H | OH | H | H |
| 299 | 3 | $CH_2Ph$ | H | OH | H | H |
| 300 | 4 | $CH_2Ph$ | H | OH | H | H |
| 301 | 1 | COMe | H | OH | H | H |
| 302 | 2 | COMe | H | OH | H | H |
| 303 | 3 | COMe | H | OH | H | H |
| 304 | 4 | COMe | H | OH | H | H |
| 305 | 1 | $CO_2Me$ | H | OH | H | H |
| 306 | 2 | $CO_2Me$ | H | OH | H | H |
| 307 | 3 | $CO_2Me$ | H | OH | H | H |
| 308 | 4 | $CO_2Me$ | H | OH | H | H |
| 309 | 1 | $CO_2tBu$ | H | OH | H | H |
| 310 | 2 | $CO_2tBu$ | H | OH | H | H |
| 311 | 3 | $CO_2tBu$ | H | OH | H | H |
| 312 | 4 | $CO_2tBu$ | H | OH | H | H |
| 313 | 1 | CONHMe | H | OH | H | H |
| 314 | 2 | CONHMe | H | OH | H | H |

TABLE 24-continued

| Entry | n | $R^7$ | $R^{20a}$ | $R^{20b}$ | $R^{20c}$ | $R^{20e}$ |
|---|---|---|---|---|---|---|
| 315 | 3 | CONHMe | H | OH | H | H |
| 316 | 4 | CONHMe | H | OH | H | H |
| 317 | 1 | $SO_2Me$ | H | OH | H | H |
| 318 | 2 | $SO_2Me$ | H | OH | H | H |
| 319 | 3 | $SO_2Me$ | H | OH | H | H |
| 320 | 4 | $SO_2Me$ | H | OH | H | H |
| 321 | 1 | $SO_2NH_2$ | H | OH | H | H |
| 322 | 2 | $SO_2NH_2$ | H | OH | H | H |
| 323 | 3 | $SO_2NH_2$ | H | OH | H | H |
| 324 | 4 | $SO_2NH_2$ | H | OH | H | H |
| 325 | 1 | H | H | OMe | H | H |
| 326 | 2 | H | H | OMe | H | H |
| 327 | 3 | H | H | OMe | H | H |
| 328 | 4 | H | H | OMe | H | H |
| 329 | 1 | Me | H | OMe | H | H |
| 330 | 2 | Me | H | OMe | H | H |
| 331 | 3 | Me | H | OMe | H | H |
| 332 | 4 | Me | H | OMe | H | H |
| 333 | 1 | $CH_2Ph$ | H | OMe | H | H |
| 334 | 2 | $CH_2Ph$ | H | OMe | H | H |
| 335 | 3 | $CH_2Ph$ | H | OMe | H | H |
| 336 | 4 | $CH_2Ph$ | H | OMe | H | H |
| 337 | 1 | COMe | H | OMe | H | H |
| 338 | 2 | COMe | H | OMe | H | H |
| 339 | 3 | COMe | H | OMe | H | H |
| 340 | 4 | COMe | H | OMe | H | H |
| 341 | 1 | $CO_2Me$ | H | OMe | H | H |
| 342 | 2 | $CO_2Me$ | H | OMe | H | H |
| 343 | 3 | $CO_2Me$ | H | OMe | H | H |
| 344 | 4 | $CO_2Me$ | H | OMe | H | H |
| 345 | 1 | $CO_2tBu$ | H | OMe | H | H |
| 346 | 2 | $CO_2tBu$ | H | OMe | H | H |
| 347 | 3 | $CO_2tBu$ | H | OMe | H | H |
| 348 | 4 | $CO_2tBu$ | H | OMe | H | H |
| 349 | 1 | CONHMe | H | OMe | H | H |
| 350 | 2 | CONHMe | H | OMe | H | H |
| 351 | 3 | CONHMe | H | OMe | H | H |
| 352 | 4 | CONHMe | H | OMe | H | H |
| 353 | 1 | $SO_2Me$ | H | OMe | H | H |
| 354 | 2 | $SO_2Me$ | H | OMe | H | H |
| 355 | 3 | $SO_2Me$ | H | OMe | H | H |
| 356 | 4 | $SO_2Me$ | H | OMe | H | H |
| 357 | 1 | $SO_2NH_2$ | H | OMe | H | H |
| 358 | 2 | $SO_2NH_2$ | H | OMe | H | H |
| 359 | 3 | $SO_2NH_2$ | H | OMe | H | H |
| 360 | 4 | $SO_2NH_2$ | H | OMe | H | H |
| 361 | 1 | H | H | Me | H | H |
| 362 | 2 | H | H | Me | H | H |
| 363 | 3 | H | H | Me | H | H |
| 364 | 4 | H | H | Me | H | H |
| 365 | 1 | Me | H | Me | H | H |
| 366 | 2 | Me | H | Me | H | H |
| 367 | 3 | Me | H | Me | H | H |
| 368 | 4 | Me | H | Me | H | H |
| 369 | 1 | $CH_2Ph$ | H | Me | H | H |
| 370 | 2 | $CH_2Ph$ | H | Me | H | H |
| 371 | 3 | $CH_2Ph$ | H | Me | H | H |
| 372 | 4 | $CH_2Ph$ | H | Me | H | H |
| 373 | 1 | COMe | H | Me | H | H |
| 374 | 2 | COMe | H | Me | H | H |
| 375 | 3 | COMe | H | Me | H | H |
| 376 | 4 | COMe | H | Me | H | H |
| 377 | 1 | $CO_2Me$ | H | Me | H | H |
| 378 | 2 | $CO_2Me$ | H | Me | H | H |
| 379 | 3 | $CO_2Me$ | H | Me | H | H |
| 380 | 4 | $CO_2Me$ | H | Me | H | H |
| 381 | 1 | $CO_2tBu$ | H | Me | H | H |
| 382 | 2 | $CO_2tBu$ | H | Me | H | H |
| 383 | 3 | $CO_2tBu$ | H | Me | H | H |
| 384 | 4 | $CO_2tBu$ | H | Me | H | H |
| 385 | 1 | CONHMe | H | Me | H | H |
| 386 | 2 | CONHMe | H | Me | H | H |
| 387 | 3 | CONHMe | H | Me | H | H |
| 388 | 4 | CONHMe | H | Me | H | H |
| 389 | 1 | $SO_2Me$ | H | Me | H | H |
| 390 | 2 | $SO_2Me$ | H | Me | H | H |
| 391 | 3 | $SO_2Me$ | H | Me | H | H |
| 392 | 4 | $SO_2Me$ | H | Me | H | H |

TABLE 24-continued

| Entry | n | $R^7$ | $R^{20a}$ | $R^{20b}$ | $R^{20c}$ | $R^{20e}$ |
|---|---|---|---|---|---|---|
| 393 | 1 | $SO_2NH_2$ | H | Me | H | H |
| 394 | 2 | $SO_2NH_2$ | H | Me | H | H |
| 395 | 3 | $SO_2NH_2$ | H | Me | H | H |
| 396 | 4 | $SO_2NH_2$ | H | Me | H | H |
| 397 | 1 | H | H | $CF_3$ | H | H |
| 398 | 2 | H | H | $CF_3$ | H | H |
| 399 | 3 | H | H | $CF_3$ | H | H |
| 400 | 4 | H | H | $CF_3$ | H | H |
| 401 | 1 | Me | H | $CF_3$ | H | H |
| 402 | 2 | Me | H | $CF_3$ | H | H |
| 403 | 3 | Me | H | $CF_3$ | H | H |
| 404 | 4 | Me | H | $CF_3$ | H | H |
| 405 | 1 | $CH_2Ph$ | H | $CF_3$ | H | H |
| 406 | 2 | $CH_2Ph$ | H | $CF_3$ | H | H |
| 407 | 3 | $CH_2Ph$ | H | $CF_3$ | H | H |
| 408 | 4 | $CH_2Ph$ | H | $CF_3$ | H | H |
| 409 | 1 | COMe | H | $CF_3$ | H | H |
| 410 | 2 | COMe | H | $CF_3$ | H | H |
| 411 | 3 | COMe | H | $CF_3$ | H | H |
| 412 | 4 | COMe | H | $CF_3$ | H | H |
| 413 | 1 | $CO_2Me$ | H | $CF_3$ | H | H |
| 414 | 2 | $CO_2Me$ | H | $CF_3$ | H | H |
| 415 | 3 | $CO_2Me$ | H | $CF_3$ | H | H |
| 416 | 4 | $CO_2Me$ | H | $CF_3$ | H | H |
| 417 | 1 | $CO_2tBu$ | H | $CF_3$ | H | H |
| 418 | 2 | $CO_2tBu$ | H | $CF_3$ | H | H |
| 419 | 3 | $CO_2tBu$ | H | $CF_3$ | H | H |
| 420 | 4 | $CO_2tBu$ | H | $CF_3$ | H | H |
| 421 | 1 | CONHMe | H | $CF_3$ | H | H |
| 422 | 2 | CONHMe | H | $CF_3$ | H | H |
| 423 | 3 | CONHMe | H | $CF_3$ | H | H |
| 424 | 4 | CONHMe | H | $CF_3$ | H | H |
| 425 | 1 | $SO_2Me$ | H | $CF_3$ | H | H |
| 426 | 2 | $SO_2Me$ | H | $CF_3$ | H | H |
| 427 | 3 | $SO_2Me$ | H | $CF_3$ | H | H |
| 428 | 4 | $SO_2Me$ | H | $CF_3$ | H | H |
| 429 | 1 | $SO_2NH_2$ | H | $CF_3$ | H | H |
| 430 | 2 | $SO_2NH_2$ | H | $CF_3$ | H | H |
| 431 | 3 | $SO_2NH_2$ | H | $CF_3$ | H | H |
| 432 | 4 | $SO_2NH_2$ | H | $CF_3$ | H | H |
| 433 | 1 | H | H | F | H | H |
| 434 | 2 | H | H | F | H | H |
| 435 | 3 | H | H | F | H | H |
| 436 | 3 | H | H | F | H | H |
| 437 | 1 | Me | H | F | H | H |
| 438 | 2 | Me | H | F | H | H |
| 439 | 3 | Me | H | F | H | H |
| 440 | 4 | Me | H | F | H | H |
| 441 | 1 | $CH_2Ph$ | H | F | H | H |
| 442 | 2 | $CH_2Ph$ | H | F | H | H |
| 443 | 3 | $CH_2Ph$ | H | F | H | H |
| 444 | 4 | $CH_2Ph$ | H | F | H | H |
| 445 | 1 | COMe | H | F | H | H |
| 446 | 2 | COMe | H | F | H | H |
| 447 | 3 | COMe | H | F | H | H |
| 448 | 4 | COMe | H | F | H | H |
| 449 | 1 | $CO_2Me$ | H | F | H | H |
| 450 | 2 | $CO_2Me$ | H | F | H | H |
| 451 | 3 | $CO_2Me$ | H | F | H | H |
| 452 | 4 | $CO_2Me$ | H | F | H | H |
| 453 | 1 | $CO_2tBu$ | H | F | H | H |
| 454 | 2 | $CO_2tBu$ | H | F | H | H |
| 455 | 3 | $CO_2tBu$ | H | F | H | H |
| 456 | 4 | $CO_2tBu$ | H | F | H | H |
| 457 | 1 | CONHMe | H | F | H | H |
| 458 | 2 | CONHMe | H | F | H | H |
| 459 | 3 | CONHMe | H | F | H | H |
| 460 | 4 | CONHMe | H | F | H | H |
| 461 | 1 | $SO_2Me$ | H | F | H | H |
| 462 | 2 | $SO_2Me$ | H | F | H | H |
| 463 | 3 | $SO_2Me$ | H | F | H | H |
| 464 | 4 | $SO_2Me$ | H | F | H | H |
| 465 | 1 | $SO_2NH_2$ | H | F | H | H |
| 466 | 2 | $SO_2NH_2$ | H | F | H | H |
| 467 | 3 | $SO_2NH_2$ | H | F | H | H |
| 468 | 4 | $SO_2NH_2$ | H | F | H | H |
| 469 | 1 | H | H | Cl | H | H |
| 470 | 2 | H | H | Cl | H | H |

TABLE 24-continued

| Entry | n | $R^7$ | $R^{20a}$ | $R^{20b}$ | $R^{20c}$ | $R^{20e}$ |
|---|---|---|---|---|---|---|
| 471 | 3 | H | H | Cl | H | H |
| 472 | 4 | H | H | Cl | H | H |
| 473 | 1 | Me | H | Cl | H | H |
| 474 | 2 | Me | H | Cl | H | H |
| 475 | 3 | Me | H | Cl | H | H |
| 476 | 4 | Me | H | Cl | H | H |
| 477 | 1 | $CH_2Ph$ | H | Cl | H | H |
| 478 | 2 | $CH_2Ph$ | H | Cl | H | H |
| 479 | 3 | $CH_2Ph$ | H | Cl | H | H |
| 480 | 4 | $CH_2Ph$ | H | Cl | H | H |
| 481 | 1 | COMe | H | Cl | H | H |
| 482 | 2 | COMe | H | Cl | H | H |
| 483 | 3 | COMe | H | Cl | H | H |
| 484 | 4 | COMe | H | Cl | H | H |
| 485 | 1 | $CO_2Me$ | H | Cl | H | H |
| 486 | 2 | $CO_2Me$ | H | Cl | H | H |
| 487 | 3 | $CO_2Me$ | H | Cl | H | H |
| 488 | 4 | $CO_2Me$ | H | Cl | H | H |
| 489 | 1 | $CO_2tBu$ | H | Cl | H | H |
| 490 | 2 | $CO_2tBu$ | H | Cl | H | H |
| 491 | 3 | $CO_2tBu$ | H | Cl | H | H |
| 492 | 4 | $CO_2tBu$ | H | Cl | H | H |
| 493 | 1 | CONHMe | H | Cl | H | H |
| 494 | 2 | CONHMe | H | Cl | H | H |
| 495 | 3 | CONHMe | H | Cl | H | H |
| 496 | 4 | CONHMe | H | Cl | H | H |
| 497 | 1 | $SO_2Me$ | H | Cl | H | H |
| 498 | 2 | $SO_2Me$ | H | Cl | H | H |
| 499 | 3 | $SO_2Me$ | H | Cl | H | H |
| 500 | 4 | $SO_2Me$ | H | Cl | H | H |
| 501 | 1 | $SO_2NH_2$ | H | Cl | H | H |
| 502 | 2 | $SO_2NH_2$ | H | Cl | H | H |
| 503 | 3 | $SO_2NH_2$ | H | Cl | H | H |
| 504 | 4 | $SO_2NH_2$ | H | Cl | H | H |
| 505 | 1 | H | H | CN | H | H |
| 506 | 2 | H | H | CN | H | H |
| 507 | 3 | H | H | CN | H | H |
| 508 | 4 | H | H | CN | H | H |
| 509 | 1 | Me | H | CN | H | H |
| 510 | 2 | Me | H | CN | H | H |
| 511 | 3 | Me | H | CN | H | H |
| 512 | 4 | Me | H | CN | H | H |
| 513 | 1 | $CH_2Ph$ | H | CN | H | H |
| 514 | 2 | $CH_2Ph$ | H | CN | H | H |
| 515 | 3 | $CH_2Ph$ | H | CN | H | H |
| 516 | 4 | $CH_2Ph$ | H | CN | H | H |
| 517 | 1 | COMe | H | CN | H | H |
| 518 | 2 | COMe | H | CN | H | H |
| 519 | 3 | COMe | H | CN | H | H |
| 520 | 4 | COMe | H | CN | H | H |
| 521 | 1 | $CO_2Me$ | H | CN | H | H |
| 522 | 2 | $CO_2Me$ | H | CN | H | H |
| 523 | 3 | $CO_2Me$ | H | CN | H | H |
| 524 | 4 | $CO_2Me$ | H | CN | H | H |
| 525 | 1 | $CO_2tBu$ | H | CN | H | H |
| 526 | 2 | $CO_2tBu$ | H | CN | H | H |
| 527 | 3 | $CO_2tBu$ | H | CN | H | H |
| 528 | 4 | $CO_2tBu$ | H | CN | H | H |
| 529 | 1 | CONHMe | H | CN | H | H |
| 530 | 2 | CONHMe | H | CN | H | H |
| 531 | 3 | CONHMe | H | CN | H | H |
| 532 | 4 | CONHMe | H | CN | H | H |
| 533 | 1 | $SO_2Me$ | H | CN | H | H |
| 534 | 2 | $SO_2Me$ | H | CN | H | H |
| 535 | 3 | $SO_2Me$ | H | CN | H | H |
| 536 | 4 | $SO_2Me$ | H | CN | H | H |
| 537 | 1 | $SO_2NH_2$ | H | CN | H | H |
| 538 | 2 | $SO_2NH_2$ | H | CN | H | H |
| 539 | 3 | $SO_2NH_2$ | H | CN | H | H |
| 540 | 4 | $SO_2NH_2$ | H | CN | H | H |
| 541 | 1 | H | OH | H | H | H |
| 542 | 2 | H | OH | H | H | H |
| 543 | 3 | H | OH | H | H | H |
| 544 | 4 | H | OH | H | H | H |
| 545 | 1 | Me | OH | H | H | H |
| 546 | 2 | Me | OH | H | H | H |
| 547 | 3 | Me | OH | H | H | H |
| 548 | 4 | Me | OH | H | H | H |

TABLE 24-continued

| Entry | n | $R^7$ | $R^{20a}$ | $R^{20b}$ | $R^{20c}$ | $R^{20e}$ |
|---|---|---|---|---|---|---|
| 549 | 1 | $CH_2Ph$ | OH | H | H | H |
| 550 | 2 | $CH_2Ph$ | OH | H | H | H |
| 551 | 3 | $CH_2Ph$ | OH | H | H | H |
| 552 | 4 | $CH_2Ph$ | OH | H | H | H |
| 553 | 1 | COMe | OH | H | H | H |
| 554 | 2 | COMe | OH | H | H | H |
| 555 | 3 | COMe | OH | H | H | H |
| 556 | 4 | COMe | OH | H | H | H |
| 557 | 1 | $CO_2Me$ | OH | H | H | H |
| 558 | 2 | $CO_2Me$ | OH | H | H | H |
| 559 | 3 | $CO_2Me$ | OH | H | H | H |
| 560 | 4 | $CO_2Me$ | OH | H | H | H |
| 561 | 1 | $CO_2tBu$ | OH | H | H | H |
| 562 | 2 | $CO_2tBu$ | OH | H | H | H |
| 563 | 3 | $CO_2tBu$ | OH | H | H | H |
| 564 | 4 | $CO_2tBu$ | OH | H | H | H |
| 565 | 1 | CONHMe | OH | H | H | H |
| 566 | 2 | CONHMe | OH | H | H | H |
| 567 | 3 | CONHMe | OH | H | H | H |
| 568 | 4 | CONHMe | OH | H | H | H |
| 569 | 1 | $SO_2Me$ | OH | H | H | H |
| 570 | 2 | $SO_2Me$ | OH | H | H | H |
| 571 | 3 | $SO_2Me$ | OH | H | H | H |
| 572 | 4 | $SO_2Me$ | OH | H | H | H |
| 573 | 1 | $SO_2NH_2$ | OH | H | H | H |
| 574 | 2 | $SO_2NH_2$ | OH | H | H | H |
| 575 | 3 | $SO_2NH_2$ | OH | H | H | H |
| 576 | 4 | $SO_2NH_2$ | OH | H | H | H |
| 577 | 1 | H | OMe | H | H | H |
| 578 | 2 | H | OMe | H | H | H |
| 579 | 3 | H | OMe | H | H | H |
| 580 | 4 | H | OMe | H | H | H |
| 581 | 1 | Me | OMe | H | H | H |
| 582 | 2 | Me | OMe | H | H | H |
| 583 | 3 | Me | OMe | H | H | H |
| 584 | 4 | Me | OMe | H | H | H |
| 585 | 1 | $CH_2Ph$ | OMe | H | H | H |
| 586 | 2 | $CH_2Ph$ | OMe | H | H | H |
| 587 | 3 | $CH_2Ph$ | OMe | H | H | H |
| 588 | 4 | $CH_2Ph$ | OMe | H | H | H |
| 589 | 1 | COMe | OMe | H | H | H |
| 590 | 2 | COMe | OMe | H | H | H |
| 591 | 3 | COMe | OMe | H | H | H |
| 592 | 4 | COMe | OMe | H | H | H |
| 593 | 1 | $CO_2Me$ | OMe | H | H | H |
| 594 | 2 | $CO_2Me$ | OMe | H | H | H |
| 595 | 3 | $CO_2Me$ | OMe | H | H | H |
| 596 | 4 | $CO_2Me$ | OMe | H | H | H |
| 597 | 1 | $CO_2tBu$ | OMe | H | H | H |
| 598 | 2 | $CO_2tBu$ | OMe | H | H | H |
| 599 | 3 | $CO_2tBu$ | OMe | H | H | H |
| 600 | 4 | $CO_2tBu$ | OMe | H | H | H |
| 601 | 1 | CONHMe | OMe | H | H | H |
| 602 | 2 | CONHMe | OMe | H | H | H |
| 603 | 3 | CONHMe | OMe | H | H | H |
| 604 | 4 | CONHMe | OMe | H | H | H |
| 605 | 1 | $SO_2Me$ | OMe | H | H | H |
| 606 | 2 | $SO_2Me$ | OMe | H | H | H |
| 607 | 3 | $SO_2Me$ | OMe | H | H | H |
| 608 | 4 | $SO_2Me$ | OMe | H | H | H |
| 609 | 1 | $SO_2NH_2$ | OMe | H | H | H |
| 610 | 2 | $SO_2NH_2$ | OMe | H | H | H |
| 611 | 3 | $SO_2NH_2$ | OMe | H | H | H |
| 612 | 4 | $SO_2NH_2$ | OMe | H | H | H |
| 613 | 1 | H | Me | H | H | H |
| 614 | 2 | H | Me | H | H | H |
| 615 | 3 | H | Me | H | H | H |
| 616 | 4 | H | Me | H | H | H |
| 617 | 1 | Me | Me | H | H | H |
| 618 | 2 | Me | Me | H | H | H |
| 619 | 3 | Me | Me | H | H | H |
| 620 | 4 | Me | Me | H | H | H |
| 621 | 1 | $CH_2Ph$ | Me | H | H | H |
| 622 | 2 | $CH_2Ph$ | Me | H | H | H |
| 623 | 3 | $CH_2Ph$ | Me | H | H | H |
| 624 | 4 | $CH_2Ph$ | Me | H | H | H |
| 625 | 1 | COMe | Me | H | H | H |
| 626 | 2 | COMe | Me | H | H | H |

TABLE 24-continued

| Entry | n | $R^7$ | $R^{20a}$ | $R^{20b}$ | $R^{20c}$ | $R^{20e}$ |
|---|---|---|---|---|---|---|
| 627 | 3 | COMe | Me | H | H | H |
| 628 | 4 | COMe | Me | H | H | H |
| 629 | 1 | $CO_2Me$ | Me | H | H | H |
| 630 | 2 | $CO_2Me$ | Me | H | H | H |
| 631 | 3 | $CO_2Me$ | Me | H | H | H |
| 632 | 4 | $CO_2Me$ | Me | H | H | H |
| 633 | 1 | $CO_2tBu$ | Me | H | H | H |
| 634 | 2 | $CO_2tBu$ | Me | H | H | H |
| 635 | 3 | $CO_2tBu$ | Me | H | H | H |
| 636 | 4 | $CO_2tBu$ | Me | H | H | H |
| 637 | 1 | CONHMe | Me | H | H | H |
| 638 | 2 | CONHMe | Me | H | H | H |
| 639 | 3 | CONHMe | Me | H | H | H |
| 640 | 4 | CONHMe | Me | H | H | H |
| 641 | 1 | $SO_2Me$ | Me | H | H | H |
| 642 | 2 | $SO_2Me$ | Me | H | H | H |
| 643 | 3 | $SO_2Me$ | Me | H | H | H |
| 644 | 4 | $SO_2Me$ | Me | H | H | H |
| 645 | 1 | $SO_2NH_2$ | Me | H | H | H |
| 646 | 2 | $SO_2NH_2$ | Me | H | H | H |
| 647 | 3 | $SO_2NH_2$ | Me | H | H | H |
| 648 | 4 | $SO_2NH_2$ | Me | H | H | H |
| 649 | 1 | H | $CF_3$ | H | H | H |
| 650 | 2 | H | $CF_3$ | H | H | H |
| 651 | 3 | H | $CF_3$ | H | H | H |
| 652 | 4 | H | $CF_3$ | H | H | H |
| 653 | 1 | Me | $CF_3$ | H | H | H |
| 654 | 2 | Me | $CF_3$ | H | H | H |
| 655 | 3 | Me | $CF_3$ | H | H | H |
| 656 | 4 | Me | $CF_3$ | H | H | H |
| 657 | 1 | $CH_2Ph$ | $CF_3$ | H | H | H |
| 658 | 2 | $CH_2Ph$ | $CF_3$ | H | H | H |
| 659 | 3 | $CH_2Ph$ | $CF_3$ | H | H | H |
| 660 | 4 | $CH_2Ph$ | $CF_3$ | H | H | H |
| 661 | 1 | COMe | $CF_3$ | H | H | H |
| 662 | 2 | COMe | $CF_3$ | H | H | H |
| 663 | 3 | COMe | $CF_3$ | H | H | H |
| 664 | 4 | COMe | $CF_3$ | H | H | H |
| 665 | 1 | $CO_2Me$ | $CF_3$ | H | H | H |
| 666 | 2 | $CO_2Me$ | $CF_3$ | H | H | H |
| 667 | 3 | $CO_2Me$ | $CF_3$ | H | H | H |
| 668 | 4 | $CO_2Me$ | $CF_3$ | H | H | H |
| 669 | 1 | $CO_2tBu$ | $CF_3$ | H | H | H |
| 670 | 2 | $CO_2tBu$ | $CF_3$ | H | H | H |
| 671 | 3 | $CO_2tBu$ | $CF_3$ | H | H | H |
| 672 | 4 | $CO_2tBu$ | $CF_3$ | H | H | H |
| 673 | 1 | CONHMe | $CF_3$ | H | H | H |
| 674 | 2 | CONHMe | $CF_3$ | H | H | H |
| 675 | 3 | CONHMe | $CF_3$ | H | H | H |
| 676 | 4 | CONHMe | $CF_3$ | H | H | H |
| 677 | 1 | $SO_2Me$ | $CF_3$ | H | H | H |
| 678 | 2 | $SO_2Me$ | $CF_3$ | H | H | H |
| 679 | 3 | $SO_2Me$ | $CF_3$ | H | H | H |
| 680 | 4 | $SO_2Me$ | $CF_3$ | H | H | H |
| 681 | 1 | $SO_2NH_2$ | $CF_3$ | H | H | H |
| 682 | 2 | $SO_2NH_2$ | $CF_3$ | H | H | H |
| 683 | 3 | $SO_2NH_2$ | $CF_3$ | H | H | H |
| 684 | 4 | $SO_2NH_2$ | $CF_3$ | H | H | H |
| 685 | 1 | H | F | H | H | H |
| 686 | 2 | H | F | H | H | H |
| 687 | 3 | H | F | H | H | H |
| 688 | 3 | H | F | H | H | H |
| 689 | 1 | Me | F | H | H | H |
| 690 | 2 | Me | F | H | H | H |
| 691 | 3 | Me | F | H | H | H |
| 692 | 4 | Me | F | H | H | H |
| 693 | 1 | $CH_2Ph$ | F | H | H | H |
| 694 | 2 | $CH_2Ph$ | F | H | H | H |
| 695 | 3 | $CH_2Ph$ | F | H | H | H |
| 696 | 4 | $CH_2Ph$ | F | H | H | H |
| 697 | 1 | COMe | F | H | H | H |
| 698 | 2 | COMe | F | H | H | H |
| 699 | 3 | COMe | F | H | H | H |
| 700 | 4 | COMe | F | H | H | H |
| 701 | 1 | $CO_2Me$ | F | H | H | H |
| 702 | 2 | $CO_2Me$ | F | H | H | H |
| 703 | 3 | $CO_2Me$ | F | H | H | H |
| 704 | 4 | $CO_2Me$ | F | H | H | H |
| 705 | 1 | $CO_2tBu$ | F | H | H | H |
| 706 | 2 | $CO_2tBu$ | F | H | H | H |
| 707 | 3 | $CO_2tBu$ | F | H | H | H |
| 708 | 4 | $CO_2tBu$ | F | H | H | H |
| 709 | 1 | CONHMe | F | H | H | H |
| 710 | 2 | CONHMe | F | H | H | H |
| 711 | 3 | CONHMe | F | H | H | H |
| 712 | 4 | CONHMe | F | H | H | H |
| 713 | 1 | $SO_2Me$ | F | H | H | H |
| 714 | 2 | $SO_2Me$ | F | H | H | H |
| 715 | 3 | $SO_2Me$ | F | H | H | H |
| 716 | 4 | $SO_2Me$ | F | H | H | H |
| 717 | 1 | $SO_2NH_2$ | F | H | H | H |
| 718 | 2 | $SO_2NH_2$ | F | H | H | H |
| 719 | 3 | $SO_2NH_2$ | F | H | H | H |
| 720 | 4 | $SO_2NH_2$ | F | H | H | H |
| 721 | 1 | H | Cl | H | H | H |
| 722 | 2 | H | Cl | H | H | H |
| 723 | 3 | H | Cl | H | H | H |
| 724 | 4 | H | Cl | H | H | H |
| 725 | 1 | Me | Cl | H | H | H |
| 726 | 2 | Me | Cl | H | H | H |
| 727 | 3 | Me | Cl | H | H | H |
| 728 | 4 | Me | Cl | H | H | H |
| 729 | 1 | $CH_2Ph$ | Cl | H | H | H |
| 730 | 2 | $CH_2Ph$ | Cl | H | H | H |
| 731 | 3 | $CH_2Ph$ | Cl | H | H | H |
| 732 | 4 | $CH_2Ph$ | Cl | H | H | H |
| 733 | 1 | COMe | Cl | H | H | H |
| 734 | 2 | COMe | Cl | H | H | H |
| 735 | 3 | COMe | Cl | H | H | H |
| 736 | 4 | COMe | Cl | H | H | H |
| 737 | 1 | $CO_2Me$ | Cl | H | H | H |
| 738 | 2 | $CO_2Me$ | Cl | H | H | H |
| 739 | 3 | $CO_2Me$ | Cl | H | H | H |
| 740 | 4 | $CO_2Me$ | Cl | H | H | H |
| 741 | 1 | $CO_2tBu$ | Cl | H | H | H |
| 742 | 2 | $CO_2tBu$ | Cl | H | H | H |
| 743 | 3 | $CO_2tBu$ | Cl | H | H | H |
| 744 | 4 | $CO_2tBu$ | Cl | H | H | H |
| 745 | 1 | CONHMe | Cl | H | H | H |
| 746 | 2 | CONHMe | Cl | H | H | H |
| 747 | 3 | CONHMe | Cl | H | H | H |
| 748 | 4 | CONHMe | Cl | H | H | H |
| 749 | 1 | $SO_2Me$ | Cl | H | H | H |
| 750 | 2 | $SO_2Me$ | Cl | H | H | H |
| 751 | 3 | $SO_2Me$ | Cl | H | H | H |
| 752 | 4 | $SO_2Me$ | Cl | H | H | H |
| 753 | 1 | $SO_2NH_2$ | Cl | H | H | H |
| 754 | 2 | $SO_2NH_2$ | Cl | H | H | H |
| 755 | 3 | $SO_2NH_2$ | Cl | H | H | H |
| 756 | 4 | $SO_2NH_2$ | Cl | H | H | H |
| 757 | 1 | H | CN | H | H | H |
| 758 | 2 | H | CN | H | H | H |
| 759 | 3 | H | CN | H | H | H |
| 760 | 4 | H | CN | H | H | H |
| 761 | 1 | Me | CN | H | H | H |
| 762 | 2 | Me | CN | H | H | H |
| 763 | 3 | Me | CN | H | H | H |
| 764 | 4 | Me | CN | H | H | H |
| 765 | 1 | $CH_2Ph$ | CN | H | H | H |
| 766 | 2 | $CH_2Ph$ | CN | H | H | H |
| 767 | 3 | $CH_2Ph$ | CN | H | H | H |
| 768 | 4 | $CH_2Ph$ | CN | H | H | H |
| 769 | 1 | COMe | CN | H | H | H |
| 770 | 2 | COMe | CN | H | H | H |
| 771 | 3 | COMe | CN | H | H | H |
| 772 | 4 | COMe | CN | H | H | H |
| 773 | 1 | $CO_2Me$ | CN | H | H | H |
| 774 | 2 | $CO_2Me$ | CN | H | H | H |
| 775 | 3 | $CO_2Me$ | CN | H | H | H |
| 776 | 4 | $CO_2Me$ | CN | H | H | H |
| 777 | 1 | $CO_2tBu$ | CN | H | H | H |
| 778 | 2 | $CO_2tBu$ | CN | H | H | H |
| 779 | 3 | $CO_2tBu$ | CN | H | H | H |
| 780 | 4 | $CO_2tBu$ | CN | H | H | H |
| 781 | 1 | CONHMe | CN | H | H | H |
| 782 | 2 | CONHMe | CN | H | H | H |

TABLE 24-continued

| Entry | n | $R^7$ | $R^{20a}$ | $R^{20b}$ | $R^{20c}$ | $R^{20e}$ |
|---|---|---|---|---|---|---|
| 783 | 3 | CONHMe | CN | H | H | H |
| 784 | 4 | CONHMe | CN | H | H | H |
| 785 | 1 | $SO_2Me$ | CN | H | H | H |
| 786 | 2 | $SO_2Me$ | CN | H | H | H |
| 787 | 3 | $SO_2Me$ | CN | H | H | H |
| 788 | 4 | $SO_2Me$ | CN | H | H | H |
| 789 | 1 | $SO_2NH_2$ | CN | H | H | H |
| 790 | 2 | $SO_2NH_2$ | CN | H | H | H |
| 791 | 3 | $SO_2NH_2$ | CN | H | H | H |
| 792 | 4 | $SO_2NH_2$ | CN | H | H | H |
| 793 | 1 | H | H | H | H | OH |
| 794 | 2 | H | H | H | H | OH |
| 795 | 3 | H | H | H | H | OH |
| 796 | 4 | H | H | H | H | OH |
| 797 | 1 | Me | H | H | H | OH |
| 798 | 2 | Me | H | H | H | OH |
| 799 | 3 | Me | H | H | H | OH |
| 800 | 4 | Me | H | H | H | OH |
| 801 | 1 | $CH_2Ph$ | H | H | H | OH |
| 802 | 2 | $CH_2Ph$ | H | H | H | OH |
| 803 | 3 | $CH_2Ph$ | H | H | H | OH |
| 804 | 4 | $CH_2Ph$ | H | H | H | OH |
| 805 | 1 | COMe | H | H | H | OH |
| 806 | 2 | COMe | H | H | H | OH |
| 807 | 3 | COMe | H | H | H | OH |
| 808 | 4 | COMe | H | H | H | OH |
| 809 | 1 | $CO_2Me$ | H | H | H | OH |
| 810 | 2 | $CO_2Me$ | H | H | H | OH |
| 811 | 3 | $CO_2Me$ | H | H | H | OH |
| 812 | 4 | $CO_2Me$ | H | H | H | OH |
| 813 | 1 | $CO_2tBu$ | H | H | H | OH |
| 814 | 2 | $CO_2tBu$ | H | H | H | OH |
| 815 | 3 | $CO_2tBu$ | H | H | H | OH |
| 816 | 4 | $CO_2tBu$ | H | H | H | OH |
| 817 | 1 | CONHMe | H | H | H | OH |
| 818 | 2 | CONHMe | H | H | H | OH |
| 819 | 3 | CONHMe | H | H | H | OH |
| 820 | 4 | CONHMe | H | H | H | OH |
| 821 | 1 | $SO_2Me$ | H | H | H | OH |
| 822 | 2 | $SO_2Me$ | H | H | H | OH |
| 823 | 3 | $SO_2Me$ | H | H | H | OH |
| 824 | 4 | $SO_2Me$ | H | H | H | OH |
| 825 | 1 | $SO_2NH_2$ | H | H | H | OH |
| 826 | 2 | $SO_2NH_2$ | H | H | H | OH |
| 827 | 3 | $SO_2NH_2$ | H | H | H | OH |
| 828 | 4 | $SO_2NH_2$ | H | H | H | OH |
| 829 | 1 | H | H | H | H | OMe |
| 830 | 2 | H | H | H | H | OMe |
| 831 | 3 | H | H | H | H | OMe |
| 832 | 4 | H | H | H | H | OMe |
| 833 | 1 | Me | H | H | H | OMe |
| 834 | 2 | Me | H | H | H | OMe |
| 835 | 3 | Me | H | H | H | OMe |
| 836 | 4 | Me | H | H | H | OMe |
| 837 | 1 | $CH_2Ph$ | H | H | H | OMe |
| 838 | 2 | $CH_2Ph$ | H | H | H | OMe |
| 839 | 3 | $CH_2Ph$ | H | H | H | OMe |
| 840 | 4 | $CH_2Ph$ | H | H | H | OMe |
| 841 | 1 | COMe | H | H | H | OMe |
| 842 | 2 | COMe | H | H | H | OMe |
| 843 | 3 | COMe | H | H | H | OMe |
| 844 | 4 | COMe | H | H | H | OMe |
| 845 | 1 | $CO_2Me$ | H | H | H | OMe |
| 846 | 2 | $CO_2Me$ | H | H | H | OMe |
| 847 | 3 | $CO_2Me$ | H | H | H | OMe |
| 848 | 4 | $CO_2Me$ | H | H | H | OMe |
| 849 | 1 | $CO_2tBu$ | H | H | H | OMe |
| 850 | 2 | $CO_2tBu$ | H | H | H | OMe |
| 851 | 3 | $CO_2tBu$ | H | H | H | OMe |
| 852 | 4 | $CO_2tBu$ | H | H | H | OMe |
| 853 | 1 | CONHMe | H | H | H | OMe |
| 854 | 2 | CONHMe | H | H | H | OMe |
| 855 | 3 | CONHMe | H | H | H | OMe |
| 856 | 4 | CONHMe | H | H | H | OMe |
| 857 | 1 | $SO_2Me$ | H | H | H | OMe |
| 858 | 2 | $SO_2Me$ | H | H | H | OMe |
| 859 | 3 | $SO_2Me$ | H | H | H | OMe |
| 860 | 4 | $SO_2Me$ | H | H | H | OMe |

TABLE 24-continued

| Entry | n | $R^7$ | $R^{20a}$ | $R^{20b}$ | $R^{20c}$ | $R^{20e}$ |
|---|---|---|---|---|---|---|
| 861 | 1 | $SO_2NH_2$ | H | H | H | OMe |
| 862 | 2 | $SO_2NH_2$ | H | H | H | OMe |
| 863 | 3 | $SO_2NH_2$ | H | H | H | OMe |
| 864 | 4 | $SO_2NH_2$ | H | H | H | OMe |
| 865 | 1 | H | H | H | H | Me |
| 866 | 2 | H | H | H | H | Me |
| 867 | 3 | H | H | H | H | Me |
| 868 | 4 | H | H | H | H | Me |
| 869 | 1 | Me | H | H | H | Me |
| 870 | 2 | Me | H | H | H | Me |
| 871 | 3 | Me | H | H | H | Me |
| 872 | 4 | Me | H | H | H | Me |
| 873 | 1 | $CH_2Ph$ | H | H | H | Me |
| 874 | 2 | $CH_2Ph$ | H | H | H | Me |
| 875 | 3 | $CH_2Ph$ | H | H | H | Me |
| 876 | 4 | $CH_2Ph$ | H | H | H | Me |
| 877 | 1 | COMe | H | H | H | Me |
| 878 | 2 | COMe | H | H | H | Me |
| 879 | 3 | COMe | H | H | H | Me |
| 880 | 4 | COMe | H | H | H | Me |
| 881 | 1 | $CO_2Me$ | H | H | H | Me |
| 882 | 2 | $CO_2Me$ | H | H | H | Me |
| 883 | 3 | $CO_2Me$ | H | H | H | Me |
| 884 | 4 | $CO_2Me$ | H | H | H | Me |
| 885 | 1 | $CO_2tBu$ | H | H | H | Me |
| 886 | 2 | $CO_2tBu$ | H | H | H | Me |
| 887 | 3 | $CO_2tBu$ | H | H | H | Me |
| 888 | 4 | $CO_2tBu$ | H | H | H | Me |
| 889 | 1 | CONHMe | H | H | H | Me |
| 890 | 2 | CONHMe | H | H | H | Me |
| 891 | 3 | CONHMe | H | H | H | Me |
| 892 | 4 | CONHMe | H | H | H | Me |
| 893 | 1 | $SO_2Me$ | H | H | H | Me |
| 894 | 2 | $SO_2Me$ | H | H | H | Me |
| 895 | 3 | $SO_2Me$ | H | H | H | Me |
| 896 | 4 | $SO_2Me$ | H | H | H | Me |
| 897 | 1 | $SO_2NH_2$ | H | H | H | Me |
| 898 | 2 | $SO_2NH_2$ | H | H | H | Me |
| 899 | 3 | $SO_2NH_2$ | H | H | H | Me |
| 900 | 4 | $SO_2NH_2$ | H | H | H | Me |
| 901 | 1 | H | H | H | H | $CF_3$ |
| 902 | 2 | H | H | H | H | $CF_3$ |
| 903 | 3 | H | H | H | H | $CF_3$ |
| 904 | 4 | H | H | H | H | $CF_3$ |
| 905 | 1 | Me | H | H | H | $CF_3$ |
| 906 | 2 | Me | H | H | H | $CF_3$ |
| 907 | 3 | Me | H | H | H | $CF_3$ |
| 908 | 4 | Me | H | H | H | $CF_3$ |
| 909 | 1 | $CH_2Ph$ | H | H | H | $CF_3$ |
| 910 | 2 | $CH_2Ph$ | H | H | H | $CF_3$ |
| 911 | 3 | $CH_2Ph$ | H | H | H | $CF_3$ |
| 912 | 4 | $CH_2Ph$ | H | H | H | $CF_3$ |
| 913 | 1 | COMe | H | H | H | $CF_3$ |
| 914 | 2 | COMe | H | H | H | $CF_3$ |
| 915 | 3 | COMe | H | H | H | $CF_3$ |
| 916 | 4 | COMe | H | H | H | $CF_3$ |
| 917 | 1 | $CO_2Me$ | H | H | H | $CF_3$ |
| 918 | 2 | $CO_2Me$ | H | H | H | $CF_3$ |
| 919 | 3 | $CO_2Me$ | H | H | H | $CF_3$ |
| 920 | 4 | $CO_2Me$ | H | H | H | $CF_3$ |
| 921 | 1 | $CO_2tBu$ | H | H | H | $CF_3$ |
| 922 | 2 | $CO_2tBu$ | H | H | H | $CF_3$ |
| 923 | 3 | $CO_2tBu$ | H | H | H | $CF_3$ |
| 924 | 4 | $CO_2tBu$ | H | H | H | $CF_3$ |
| 925 | 1 | CONHMe | H | H | H | $CF_3$ |
| 926 | 2 | CONHMe | H | H | H | $CF_3$ |
| 927 | 3 | CONHMe | H | H | H | $CF_3$ |
| 928 | 4 | CONHMe | H | H | H | $CF_3$ |
| 929 | 1 | $SO_2Me$ | H | H | H | $CF_3$ |
| 930 | 2 | $SO_2Me$ | H | H | H | $CF_3$ |
| 931 | 3 | $SO_2Me$ | H | H | H | $CF_3$ |
| 932 | 4 | $SO_2Me$ | H | H | H | $CF_3$ |
| 933 | 1 | $SO_2NH_2$ | H | H | H | $CF_3$ |
| 934 | 2 | $SO_2NH_2$ | H | H | H | $CF_3$ |
| 935 | 3 | $SO_2NH_2$ | H | H | H | $CF_3$ |
| 936 | 4 | $SO_2NH_2$ | H | H | H | $CF_3$ |
| 937 | 1 | H | H | H | H | F |
| 938 | 2 | H | H | H | H | F |

TABLE 24-continued

| Entry | n | $R^7$ | $R^{20a}$ | $R^{20b}$ | $R^{20c}$ | $R^{20e}$ |
|---|---|---|---|---|---|---|
| 939 | 3 | H | H | H | H | F |
| 940 | 3 | H | H | H | H | F |
| 941 | 1 | Me | H | H | H | F |
| 942 | 2 | Me | H | H | H | F |
| 943 | 3 | Me | H | H | H | F |
| 944 | 4 | Me | H | H | H | F |
| 945 | 1 | $CH_2Ph$ | H | H | H | F |
| 946 | 2 | $CH_2Ph$ | H | H | H | F |
| 947 | 3 | $CH_2Ph$ | H | H | H | F |
| 948 | 4 | $CH_2Ph$ | H | H | H | F |
| 949 | 1 | COMe | H | H | H | F |
| 950 | 2 | COMe | H | H | H | F |
| 951 | 3 | COMe | H | H | H | F |
| 952 | 4 | COMe | H | H | H | F |
| 953 | 1 | $CO_2Me$ | H | H | H | F |
| 954 | 2 | $CO_2Me$ | H | H | H | F |
| 955 | 3 | $CO_2Me$ | H | H | H | F |
| 956 | 4 | $CO_2Me$ | H | H | H | F |
| 957 | 1 | $CO_2tBu$ | H | H | H | F |
| 958 | 2 | $CO_2tBu$ | H | H | H | F |
| 959 | 3 | $CO_2tBu$ | H | H | H | F |
| 960 | 4 | $CO_2tBu$ | H | H | H | F |
| 961 | 1 | CONHMe | H | H | H | F |
| 962 | 2 | CONHMe | H | H | H | F |
| 963 | 3 | CONHMe | H | H | H | F |
| 964 | 4 | CONHMe | H | H | H | F |
| 965 | 1 | $SO_2Me$ | H | H | H | F |
| 966 | 2 | $SO_2Me$ | H | H | H | F |
| 967 | 3 | $SO_2Me$ | H | H | H | F |
| 968 | 4 | $SO_2Me$ | H | H | H | F |
| 969 | 1 | $SO_2NH_2$ | H | H | H | F |
| 970 | 2 | $SO_2NH_2$ | H | H | H | F |
| 971 | 3 | $SO_2NH_2$ | H | H | H | F |
| 972 | 4 | $SO_2NH_2$ | H | H | H | F |
| 973 | 1 | H | H | H | H | Cl |
| 974 | 2 | H | H | H | H | Cl |
| 975 | 3 | H | H | H | H | Cl |
| 976 | 4 | H | H | H | H | Cl |
| 977 | 1 | Me | H | H | H | Cl |
| 978 | 2 | Me | H | H | H | Cl |
| 979 | 3 | Me | H | H | H | Cl |
| 980 | 4 | Me | H | H | H | Cl |
| 981 | 1 | $CH_2Ph$ | H | H | H | Cl |
| 982 | 2 | $CH_2Ph$ | H | H | H | Cl |
| 983 | 3 | $CH_2Ph$ | H | H | H | Cl |
| 984 | 4 | $CH_2Ph$ | H | H | H | Cl |
| 985 | 1 | COMe | H | H | H | Cl |
| 986 | 2 | COMe | H | H | H | Cl |
| 987 | 3 | COMe | H | H | H | Cl |
| 988 | 4 | COMe | H | H | H | Cl |
| 989 | 1 | $CO_2Me$ | H | H | H | Cl |
| 990 | 2 | $CO_2Me$ | H | H | H | Cl |
| 991 | 3 | $CO_2Me$ | H | H | H | Cl |
| 992 | 4 | $CO_2Me$ | H | H | H | Cl |
| 993 | 1 | $CO_2tBu$ | H | H | H | Cl |
| 994 | 2 | $CO_2tBu$ | H | H | H | Cl |
| 995 | 3 | $CO_2tBu$ | H | H | H | Cl |
| 996 | 4 | $CO_2tBu$ | H | H | H | Cl |
| 997 | 1 | CONHMe | H | H | H | Cl |
| 998 | 2 | CONHMe | H | H | H | Cl |
| 999 | 3 | CONHMe | H | H | H | Cl |
| 1000 | 4 | CONHMe | H | H | H | Cl |
| 1001 | 1 | $SO_2Me$ | H | H | H | Cl |
| 1002 | 2 | $SO_2Me$ | H | H | H | Cl |
| 1003 | 3 | $SO_2Me$ | H | H | H | Cl |
| 1004 | 4 | $SO_2Me$ | H | H | H | Cl |
| 1005 | 1 | $SO_2NH_2$ | H | H | H | Cl |
| 1006 | 2 | $SO_2NH_2$ | H | H | H | Cl |
| 1007 | 3 | $SO_2NH_2$ | H | H | H | Cl |
| 1008 | 4 | $SO_2NH_2$ | H | H | H | Cl |
| 1009 | 1 | H | H | H | H | CN |
| 1010 | 2 | H | H | H | H | CN |
| 1011 | 3 | H | H | H | H | CN |
| 1012 | 4 | H | H | H | H | CN |
| 1013 | 1 | Me | H | H | H | CN |
| 1014 | 2 | Me | H | H | H | CN |
| 1015 | 3 | Me | H | H | H | CN |
| 1016 | 4 | Me | H | H | H | CN |
| 1017 | 1 | $CH_2Ph$ | H | H | H | CN |
| 1018 | 2 | $CH_2Ph$ | H | H | H | CN |
| 1019 | 3 | $CH_2Ph$ | H | H | H | CN |
| 1020 | 4 | $CH_2Ph$ | H | H | H | CN |
| 1021 | 1 | COMe | H | H | H | CN |
| 1022 | 2 | COMe | H | H | H | CN |
| 1023 | 3 | COMe | H | H | H | CN |
| 1024 | 4 | COMe | H | H | H | CN |
| 1025 | 1 | $CO_2Me$ | H | H | H | CN |
| 1026 | 2 | $CO_2Me$ | H | H | H | CN |
| 1027 | 3 | $CO_2Me$ | H | H | H | CN |
| 1028 | 4 | $CO_2Me$ | H | H | H | CN |
| 1029 | 1 | $CO_2tBu$ | H | H | H | CN |
| 1030 | 2 | $CO_2tBu$ | H | H | H | CN |
| 1031 | 3 | $CO_2tBu$ | H | H | H | CN |
| 1032 | 4 | $CO_2tBu$ | H | H | H | CN |
| 1033 | 1 | CONHMe | H | H | H | CN |
| 1034 | 2 | CONHMe | H | H | H | CN |
| 1035 | 3 | CONHMe | H | H | H | CN |
| 1036 | 4 | CONHMe | H | H | H | CN |
| 1037 | 1 | $SO_2Me$ | H | H | H | CN |
| 1038 | 2 | $SO_2Me$ | H | H | H | CN |
| 1039 | 3 | $SO_2Me$ | H | H | H | CN |
| 1040 | 4 | $SO_2Me$ | H | H | H | CN |
| 1041 | 1 | $SO_2NH_2$ | H | H | H | CN |
| 1042 | 2 | $SO_2NH_2$ | H | H | H | CN |
| 1043 | 3 | $SO_2NH_2$ | H | H | H | CN |
| 1044 | 4 | $SO_2NH_2$ | H | H | H | CN |

Exemplary embodiments include compounds having the formula (XXXI)

(XXXI)

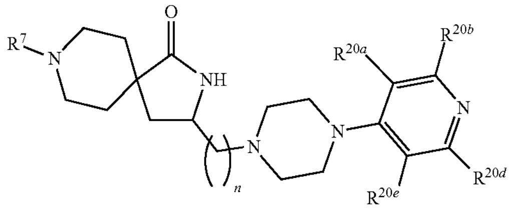

or a pharmaceutically acceptable salt form thereof defined herein below in Table 25.

TABLE 25

| Entry | n | $R^7$ | $R^{20a}$ | $R^{20b}$ | $R^{20d}$ | $R^{20e}$ |
|---|---|---|---|---|---|---|
| 1 | 1 | H | H | H | H | H |
| 2 | 2 | H | H | H | H | H |
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |

TABLE 25-continued

| Entry | n | $R^7$ | $R^{20a}$ | $R^{20b}$ | $R^{20d}$ | $R^{20e}$ |
|---|---|---|---|---|---|---|
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |
| 60 | 4 | $CO_2tBu$ | H | H | OH | H |
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |
| 79 | 3 | Me | H | H | OMe | H |
| 80 | 4 | Me | H | H | OMe | H |
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |
| 138 | 2 | $SO_2Me$ | H | H | Me | H |
| 139 | 3 | $SO_2Me$ | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |
| 157 | 1 | COMe | H | H | $CF_3$ | H |
| 158 | 2 | COMe | H | H | $CF_3$ | H |
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |

TABLE 25-continued

| Entry | n | $R^7$ | $R^{20a}$ | $R^{20b}$ | $R^{20d}$ | $R^{20e}$ |
|---|---|---|---|---|---|---|
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | $CO_2tBu$ | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |
| 216 | 4 | $SO_2NH_2$ | H | H | F | H |
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |
| 235 | 3 | $CO_2Me$ | H | H | Cl | H |
| 236 | 4 | $CO_2Me$ | H | H | Cl | H |
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | $CH_2Ph$ | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | COMe | H | H | CN | H |
| 266 | 2 | COMe | H | H | CN | H |
| 267 | 3 | COMe | H | H | CN | H |
| 268 | 4 | COMe | H | H | CN | H |
| 269 | 1 | $CO_2Me$ | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2tBu$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |
| 277 | 1 | CONHMe | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | $SO_2Me$ | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2NH_2$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | H | H | H | H | OH |
| 290 | 2 | H | H | H | H | OH |
| 291 | 3 | H | H | H | H | OH |
| 292 | 4 | H | H | H | H | OH |
| 293 | 1 | Me | H | H | H | OH |
| 294 | 2 | Me | H | H | H | OH |
| 295 | 3 | Me | H | H | H | OH |
| 296 | 4 | Me | H | H | H | OH |
| 297 | 1 | $CH_2Ph$ | H | H | H | OH |
| 298 | 2 | $CH_2Ph$ | H | H | H | OH |
| 299 | 3 | $CH_2Ph$ | H | H | H | OH |
| 300 | 4 | $CH_2Ph$ | H | H | H | OH |
| 301 | 1 | COMe | H | H | H | OH |
| 302 | 2 | COMe | H | H | H | OH |
| 303 | 3 | COMe | H | H | H | OH |
| 304 | 4 | COMe | H | H | H | OH |
| 305 | 1 | $CO_2Me$ | H | H | H | OH |
| 306 | 2 | $CO_2Me$ | H | H | H | OH |
| 307 | 3 | $CO_2Me$ | H | H | H | OH |
| 308 | 4 | $CO_2Me$ | H | H | H | OH |
| 309 | 1 | $CO_2tBu$ | H | H | H | OH |
| 310 | 2 | $CO_2tBu$ | H | H | H | OH |
| 311 | 3 | $CO_2tBu$ | H | H | H | OH |
| 312 | 4 | $CO_2tBu$ | H | H | H | OH |
| 313 | 1 | CONHMe | H | H | H | OH |
| 314 | 2 | CONHMe | H | H | H | OH |
| 315 | 3 | CONHMe | H | H | H | OH |
| 316 | 4 | CONHMe | H | H | H | OH |
| 317 | 1 | $SO_2Me$ | H | H | H | OH |
| 318 | 2 | $SO_2Me$ | H | H | H | OH |
| 319 | 3 | $SO_2Me$ | H | H | H | OH |
| 320 | 4 | $SO_2Me$ | H | H | H | OH |
| 321 | 1 | $SO_2NH_2$ | H | H | H | OH |
| 322 | 2 | $SO_2NH_2$ | H | H | H | OH |
| 323 | 3 | $SO_2NH_2$ | H | H | H | OH |
| 324 | 4 | $SO_2NH_2$ | H | H | H | OH |
| 325 | 1 | H | H | H | H | OMe |
| 326 | 2 | H | H | H | H | OMe |
| 327 | 3 | H | H | H | H | OMe |
| 328 | 4 | H | H | H | H | OMe |
| 329 | 1 | Me | H | H | H | OMe |
| 330 | 2 | Me | H | H | H | OMe |
| 331 | 3 | Me | H | H | H | OMe |
| 332 | 4 | Me | H | H | H | OMe |
| 333 | 1 | $CH_2Ph$ | H | H | H | OMe |
| 334 | 2 | $CH_2Ph$ | H | H | H | OMe |

TABLE 25-continued

| Entry | n | $R^7$ | $R^{20a}$ | $R^{20b}$ | $R^{20d}$ | $R^{20e}$ |
|---|---|---|---|---|---|---|
| 335 | 3 | $CH_2Ph$ | H | H | H | OMe |
| 336 | 4 | $CH_2Ph$ | H | H | H | OMe |
| 337 | 1 | COMe | H | H | H | OMe |
| 338 | 2 | COMe | H | H | H | OMe |
| 339 | 3 | COMe | H | H | H | OMe |
| 340 | 4 | COMe | H | H | H | OMe |
| 341 | 1 | $CO_2Me$ | H | H | H | OMe |
| 342 | 2 | $CO_2Me$ | H | H | H | OMe |
| 343 | 3 | $CO_2Me$ | H | H | H | OMe |
| 344 | 4 | $CO_2Me$ | H | H | H | OMe |
| 345 | 1 | $CO_2tBu$ | H | H | H | OMe |
| 346 | 2 | $CO_2tBu$ | H | H | H | OMe |
| 347 | 3 | $CO_2tBu$ | H | H | H | OMe |
| 348 | 4 | $CO_2tBu$ | H | H | H | OMe |
| 349 | 1 | CONHMe | H | H | H | OMe |
| 350 | 2 | CONHMe | H | H | H | OMe |
| 351 | 3 | CONHMe | H | H | H | OMe |
| 352 | 4 | CONHMe | H | H | H | OMe |
| 353 | 1 | $SO_2Me$ | H | H | H | OMe |
| 354 | 2 | $SO_2Me$ | H | H | H | OMe |
| 355 | 3 | $SO_2Me$ | H | H | H | OMe |
| 356 | 4 | $SO_2Me$ | H | H | H | OMe |
| 357 | 1 | $SO_2NH_2$ | H | H | H | OMe |
| 358 | 2 | $SO_2NH_2$ | H | H | H | OMe |
| 359 | 3 | $SO_2NH_2$ | H | H | H | OMe |
| 360 | 4 | $SO_2NH_2$ | H | H | H | OMe |
| 361 | 1 | H | H | H | H | Me |
| 362 | 2 | H | H | H | H | Me |
| 363 | 3 | H | H | H | H | Me |
| 364 | 4 | H | H | H | H | Me |
| 365 | 1 | Me | H | H | H | Me |
| 366 | 2 | Me | H | H | H | Me |
| 367 | 3 | Me | H | H | H | Me |
| 368 | 4 | Me | H | H | H | Me |
| 369 | 1 | $CH_2Ph$ | H | H | H | Me |
| 370 | 2 | $CH_2Ph$ | H | H | H | Me |
| 371 | 3 | $CH_2Ph$ | H | H | H | Me |
| 372 | 4 | $CH_2Ph$ | H | H | H | Me |
| 373 | 1 | COMe | H | H | H | Me |
| 374 | 2 | COMe | H | H | H | Me |
| 375 | 3 | COMe | H | H | H | Me |
| 376 | 4 | COMe | H | H | H | Me |
| 377 | 1 | $CO_2Me$ | H | H | H | Me |
| 378 | 2 | $CO_2Me$ | H | H | H | Me |
| 379 | 3 | $CO_2Me$ | H | H | H | Me |
| 380 | 4 | $CO_2Me$ | H | H | H | Me |
| 381 | 1 | $CO_2tBu$ | H | H | H | Me |
| 382 | 2 | $CO_2tBu$ | H | H | H | Me |
| 383 | 3 | $CO_2tBu$ | H | H | H | Me |
| 384 | 4 | $CO_2tBu$ | H | H | H | Me |
| 385 | 1 | CONHMe | H | H | H | Me |
| 386 | 2 | CONHMe | H | H | H | Me |
| 387 | 3 | CONHMe | H | H | H | Me |
| 388 | 4 | CONHMe | H | H | H | Me |
| 389 | 1 | $SO_2Me$ | H | H | H | Me |
| 390 | 2 | $SO_2Me$ | H | H | H | Me |
| 391 | 3 | $SO_2Me$ | H | H | H | Me |
| 392 | 4 | $SO_2Me$ | H | H | H | Me |
| 393 | 1 | $SO_2NH_2$ | H | H | H | Me |
| 394 | 2 | $SO_2NH_2$ | H | H | H | Me |
| 395 | 3 | $SO_2NH_2$ | H | H | H | Me |
| 396 | 4 | $SO_2NH_2$ | H | H | H | Me |
| 397 | 1 | H | H | H | H | $CF_3$ |
| 398 | 2 | H | H | H | H | $CF_3$ |
| 399 | 3 | H | H | H | H | $CF_3$ |
| 400 | 4 | H | H | H | H | $CF_3$ |
| 401 | 1 | Me | H | H | H | $CF_3$ |
| 402 | 2 | Me | H | H | H | $CF_3$ |
| 403 | 3 | Me | H | H | H | $CF_3$ |
| 404 | 4 | Me | H | H | H | $CF_3$ |
| 405 | 1 | $CH_2Ph$ | H | H | H | $CF_3$ |
| 406 | 2 | $CH_2Ph$ | H | H | H | $CF_3$ |
| 407 | 3 | $CH_2Ph$ | H | H | H | $CF_3$ |
| 408 | 4 | $CH_2Ph$ | H | H | H | $CF_3$ |
| 409 | 1 | COMe | H | H | H | $CF_3$ |
| 410 | 2 | COMe | H | H | H | $CF_3$ |
| 411 | 3 | COMe | H | H | H | $CF_3$ |
| 412 | 4 | COMe | H | H | H | $CF_3$ |

TABLE 25-continued

| Entry | n | $R^7$ | $R^{20a}$ | $R^{20b}$ | $R^{20d}$ | $R^{20e}$ |
|---|---|---|---|---|---|---|
| 413 | 1 | $CO_2Me$ | H | H | H | $CF_3$ |
| 414 | 2 | $CO_2Me$ | H | H | H | $CF_3$ |
| 415 | 3 | $CO_2Me$ | H | H | H | $CF_3$ |
| 416 | 4 | $CO_2Me$ | H | H | H | $CF_3$ |
| 417 | 1 | $CO_2tBu$ | H | H | H | $CF_3$ |
| 418 | 2 | $CO_2tBu$ | H | H | H | $CF_3$ |
| 419 | 3 | $CO_2tBu$ | H | H | H | $CF_3$ |
| 420 | 4 | $CO_2tBu$ | H | H | H | $CF_3$ |
| 421 | 1 | CONHMe | H | H | H | $CF_3$ |
| 422 | 2 | CONHMe | H | H | H | $CF_3$ |
| 423 | 3 | CONHMe | H | H | H | $CF_3$ |
| 424 | 4 | CONHMe | H | H | H | $CF_3$ |
| 425 | 1 | $SO_2Me$ | H | H | H | $CF_3$ |
| 426 | 2 | $SO_2Me$ | H | H | H | $CF_3$ |
| 427 | 3 | $SO_2Me$ | H | H | H | $CF_3$ |
| 428 | 4 | $SO_2Me$ | H | H | H | $CF_3$ |
| 429 | 1 | $SO_2NH_2$ | H | H | H | $CF_3$ |
| 430 | 2 | $SO_2NH_2$ | H | H | H | $CF_3$ |
| 431 | 3 | $SO_2NH_2$ | H | H | H | $CF_3$ |
| 432 | 4 | $SO_2NH_2$ | H | H | H | $CF_3$ |
| 433 | 1 | H | H | H | H | F |
| 434 | 2 | H | H | H | H | F |
| 435 | 3 | H | H | H | H | F |
| 436 | 3 | H | H | H | H | F |
| 437 | 1 | Me | H | H | H | F |
| 438 | 2 | Me | H | H | H | F |
| 439 | 3 | Me | H | H | H | F |
| 440 | 4 | Me | H | H | H | F |
| 441 | 1 | $CH_2Ph$ | H | H | H | F |
| 442 | 2 | $CH_2Ph$ | H | H | H | F |
| 443 | 3 | $CH_2Ph$ | H | H | H | F |
| 444 | 4 | $CH_2Ph$ | H | H | H | F |
| 445 | 1 | COMe | H | H | H | F |
| 446 | 2 | COMe | H | H | H | F |
| 447 | 3 | COMe | H | H | H | F |
| 448 | 4 | COMe | H | H | H | F |
| 449 | 1 | $CO_2Me$ | H | H | H | F |
| 450 | 2 | $CO_2Me$ | H | H | H | F |
| 451 | 3 | $CO_2Me$ | H | H | H | F |
| 452 | 4 | $CO_2Me$ | H | H | H | F |
| 453 | 1 | $CO_2tBu$ | H | H | H | F |
| 454 | 2 | $CO_2tBu$ | H | H | H | F |
| 455 | 3 | $CO_2tBu$ | H | H | H | F |
| 456 | 4 | $CO_2tBu$ | H | H | H | F |
| 457 | 1 | CONHMe | H | H | H | F |
| 458 | 2 | CONHMe | H | H | H | F |
| 459 | 3 | CONHMe | H | H | H | F |
| 460 | 4 | CONHMe | H | H | H | F |
| 461 | 1 | $SO_2Me$ | H | H | H | F |
| 462 | 2 | $SO_2Me$ | H | H | H | F |
| 463 | 3 | $SO_2Me$ | H | H | H | F |
| 464 | 4 | $SO_2Me$ | H | H | H | F |
| 465 | 1 | $SO_2NH_2$ | H | H | H | F |
| 466 | 2 | $SO_2NH_2$ | H | H | H | F |
| 467 | 3 | $SO_2NH_2$ | H | H | H | F |
| 468 | 4 | $SO_2NH_2$ | H | H | H | F |
| 469 | 1 | H | H | H | H | Cl |
| 470 | 2 | H | H | H | H | Cl |
| 471 | 3 | H | H | H | H | Cl |
| 472 | 4 | H | H | H | H | Cl |
| 473 | 1 | Me | H | H | H | Cl |
| 474 | 2 | Me | H | H | H | Cl |
| 475 | 3 | Me | H | H | H | Cl |
| 476 | 4 | Me | H | H | H | Cl |
| 477 | 1 | $CH_2Ph$ | H | H | H | Cl |
| 478 | 2 | $CH_2Ph$ | H | H | H | Cl |
| 479 | 3 | $CH_2Ph$ | H | H | H | Cl |
| 480 | 4 | $CH_2Ph$ | H | H | H | Cl |
| 481 | 1 | COMe | H | H | H | Cl |
| 482 | 2 | COMe | H | H | H | Cl |
| 483 | 3 | COMe | H | H | H | Cl |
| 484 | 4 | COMe | H | H | H | Cl |
| 485 | 1 | $CO_2Me$ | H | H | H | Cl |
| 486 | 2 | $CO_2Me$ | H | H | H | Cl |
| 487 | 3 | $CO_2Me$ | H | H | H | Cl |
| 488 | 4 | $CO_2Me$ | H | H | H | Cl |
| 489 | 1 | $CO_2tBu$ | H | H | H | Cl |
| 490 | 2 | $CO_2tBu$ | H | H | H | Cl |

TABLE 25-continued

| Entry | n | $R^7$ | $R^{20a}$ | $R^{20b}$ | $R^{20d}$ | $R^{20e}$ |
|---|---|---|---|---|---|---|
| 491 | 3 | $CO_2tBu$ | H | H | H | Cl |
| 492 | 4 | $CO_2tBu$ | H | H | H | Cl |
| 493 | 1 | CONHMe | H | H | H | Cl |
| 494 | 2 | CONHMe | H | H | H | Cl |
| 495 | 3 | CONHMe | H | H | H | Cl |
| 496 | 4 | CONHMe | H | H | H | Cl |
| 497 | 1 | $SO_2Me$ | H | H | H | Cl |
| 498 | 2 | $SO_2Me$ | H | H | H | Cl |
| 499 | 3 | $SO_2Me$ | H | H | H | Cl |
| 500 | 4 | $SO_2Me$ | H | H | H | Cl |
| 501 | 1 | $SO_2NH_2$ | H | H | H | Cl |
| 502 | 2 | $SO_2NH_2$ | H | H | H | Cl |
| 503 | 3 | $SO_2NH_2$ | H | H | H | Cl |
| 504 | 4 | $SO_2NH_2$ | H | H | H | Cl |
| 505 | 1 | H | H | H | H | CN |
| 506 | 2 | H | H | H | H | CN |
| 507 | 3 | H | H | H | H | CN |
| 508 | 4 | H | H | H | H | CN |
| 509 | 1 | Me | H | H | H | CN |
| 510 | 2 | Me | H | H | H | CN |
| 511 | 3 | Me | H | H | H | CN |
| 512 | 4 | Me | H | H | H | CN |
| 513 | 1 | $CH_2Ph$ | H | H | H | CN |
| 514 | 2 | $CH_2Ph$ | H | H | H | CN |
| 515 | 3 | $CH_2Ph$ | H | H | H | CN |
| 516 | 4 | $CH_2Ph$ | H | H | H | CN |
| 517 | 1 | COMe | H | H | H | CN |
| 518 | 2 | COMe | H | H | H | CN |
| 519 | 3 | COMe | H | H | H | CN |
| 520 | 4 | COMe | H | H | H | CN |
| 521 | 1 | $CO_2Me$ | H | H | H | CN |
| 522 | 2 | $CO_2Me$ | H | H | H | CN |
| 523 | 3 | $CO_2Me$ | H | H | H | CN |
| 524 | 4 | $CO_2Me$ | H | H | H | CN |
| 525 | 1 | $CO_2tBu$ | H | H | H | CN |
| 526 | 2 | $CO_2tBu$ | H | H | H | CN |
| 527 | 3 | $CO_2tBu$ | H | H | H | CN |
| 528 | 4 | $CO_2tBu$ | H | H | H | CN |
| 529 | 1 | CONHMe | H | H | H | CN |
| 530 | 2 | CONHMe | H | H | H | CN |
| 531 | 3 | CONHMe | H | H | H | CN |
| 532 | 4 | CONHMe | H | H | H | CN |
| 533 | 1 | $SO_2Me$ | H | H | H | CN |
| 534 | 2 | $SO_2Me$ | H | H | H | CN |
| 535 | 3 | $SO_2Me$ | H | H | H | CN |
| 536 | 4 | $SO_2Me$ | H | H | H | CN |
| 537 | 1 | $SO_2NH_2$ | H | H | H | CN |
| 538 | 2 | $SO_2NH_2$ | H | H | H | CN |
| 539 | 3 | $SO_2NH_2$ | H | H | H | CN |
| 540 | 4 | $SO_2NH_2$ | H | H | H | CN |

Exemplary embodiments include compounds having the formula (XXXII)

(XXXII)

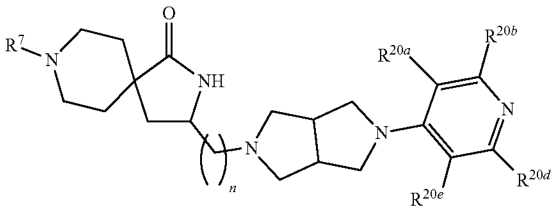

or a pharmaceutically acceptable salt form thereof defined herein below in Table 26.

TABLE 26

| Entry | n | $R^7$ | $R^{20a}$ | $R^{20b}$ | $R^{20d}$ | $R^{20e}$ |
|---|---|---|---|---|---|---|
| 1 | 1 | H | H | H | H | H |
| 2 | 2 | H | H | H | H | H |
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |
| 60 | 4 | $CO_2tBu$ | H | H | OH | H |
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |

TABLE 26-continued

| Entry | n | $R^7$ | $R^{20a}$ | $R^{20b}$ | $R^{20d}$ | $R^{20e}$ |
|---|---|---|---|---|---|---|
| 79 | 3 | Me | H | H | OMe | H |
| 80 | 4 | Me | H | H | OMe | H |
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |
| 138 | 2 | $SO_2Me$ | H | H | Me | H |
| 139 | 3 | $SO_2Me$ | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |

TABLE 26-continued

| Entry | n | $R^7$ | $R^{20a}$ | $R^{20b}$ | $R^{20d}$ | $R^{20e}$ |
|---|---|---|---|---|---|---|
| 157 | 1 | COMe | H | H | $CF_3$ | H |
| 158 | 2 | COMe | H | H | $CF_3$ | H |
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | CO2tBu | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |
| 216 | 4 | $SO_2NH_2$ | H | H | F | H |
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |

TABLE 26-continued

| Entry | n | $R^7$ | $R^{20a}$ | $R^{20b}$ | $R^{20d}$ | $R^{20e}$ |
|---|---|---|---|---|---|---|
| 235 | 3 | $CO_2Me$ | H | H | Cl | H |
| 236 | 4 | $CO_2Me$ | H | H | Cl | H |
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | $CH_2Ph$ | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | COMe | H | H | CN | H |
| 266 | 2 | COMe | H | H | CN | H |
| 267 | 3 | COMe | H | H | CN | H |
| 268 | 4 | COMe | H | H | CN | H |
| 269 | 1 | $CO_2Me$ | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2tBu$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |
| 277 | 1 | CONHMe | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | $SO_2Me$ | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2NH_2$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | H | H | H | H | OH |
| 290 | 2 | H | H | H | H | OH |
| 291 | 3 | H | H | H | H | OH |
| 292 | 4 | H | H | H | H | OH |
| 293 | 1 | Me | H | H | H | OH |
| 294 | 2 | Me | H | H | H | OH |
| 295 | 3 | Me | H | H | H | OH |
| 296 | 4 | Me | H | H | H | OH |
| 297 | 1 | $CH_2Ph$ | H | H | H | OH |
| 298 | 2 | $CH_2Ph$ | H | H | H | OH |
| 299 | 3 | $CH_2Ph$ | H | H | H | OH |
| 300 | 4 | $CH_2Ph$ | H | H | H | OH |
| 301 | 1 | COMe | H | H | H | OH |
| 302 | 2 | COMe | H | H | H | OH |
| 303 | 3 | COMe | H | H | H | OH |
| 304 | 4 | COMe | H | H | H | OH |
| 305 | 1 | $CO_2Me$ | H | H | H | OH |
| 306 | 2 | $CO_2Me$ | H | H | H | OH |
| 307 | 3 | $CO_2Me$ | H | H | H | OH |
| 308 | 4 | $CO_2Me$ | H | H | H | OH |
| 309 | 1 | $CO_2tBu$ | H | H | H | OH |
| 310 | 2 | $CO_2tBu$ | H | H | H | OH |
| 311 | 3 | $CO_2tBu$ | H | H | H | OH |
| 312 | 4 | $CO_2tBu$ | H | H | H | OH |

TABLE 26-continued

| Entry | n | $R^7$ | $R^{20a}$ | $R^{20b}$ | $R^{20d}$ | $R^{20e}$ |
|---|---|---|---|---|---|---|
| 313 | 1 | CONHMe | H | H | H | OH |
| 314 | 2 | CONHMe | H | H | H | OH |
| 315 | 3 | CONHMe | H | H | H | OH |
| 316 | 4 | CONHMe | H | H | H | OH |
| 317 | 1 | $SO_2Me$ | H | H | H | OH |
| 318 | 2 | $SO_2Me$ | H | H | H | OH |
| 319 | 3 | $SO_2Me$ | H | H | H | OH |
| 320 | 4 | $SO_2Me$ | H | H | H | OH |
| 321 | 1 | $SO_2NH_2$ | H | H | H | OH |
| 322 | 2 | $SO_2NH_2$ | H | H | H | OH |
| 323 | 3 | $SO_2NH_2$ | H | H | H | OH |
| 324 | 4 | $SO_2NH_2$ | H | H | H | OH |
| 325 | 1 | H | H | H | H | OMe |
| 326 | 2 | H | H | H | H | OMe |
| 327 | 3 | H | H | H | H | OMe |
| 328 | 4 | H | H | H | H | OMe |
| 329 | 1 | Me | H | H | H | OMe |
| 330 | 2 | Me | H | H | H | OMe |
| 331 | 3 | Me | H | H | H | OMe |
| 332 | 4 | Me | H | H | H | OMe |
| 333 | 1 | $CH_2Ph$ | H | H | H | OMe |
| 334 | 2 | $CH_2Ph$ | H | H | H | OMe |
| 335 | 3 | $CH_2Ph$ | H | H | H | OMe |
| 336 | 4 | $CH_2Ph$ | H | H | H | OMe |
| 337 | 1 | COMe | H | H | H | OMe |
| 338 | 2 | COMe | H | H | H | OMe |
| 339 | 3 | COMe | H | H | H | OMe |
| 340 | 4 | COMe | H | H | H | OMe |
| 341 | 1 | $CO_2Me$ | H | H | H | OMe |
| 342 | 2 | $CO_2Me$ | H | H | H | OMe |
| 343 | 3 | $CO_2Me$ | H | H | H | OMe |
| 344 | 4 | $CO_2Me$ | H | H | H | OMe |
| 345 | 1 | $CO_2tBu$ | H | H | H | OMe |
| 346 | 2 | $CO_2tBu$ | H | H | H | OMe |
| 347 | 3 | $CO_2tBu$ | H | H | H | OMe |
| 348 | 4 | $CO_2tBu$ | H | H | H | OMe |
| 349 | 1 | CONHMe | H | H | H | OMe |
| 350 | 2 | CONHMe | H | H | H | OMe |
| 351 | 3 | CONHMe | H | H | H | OMe |
| 352 | 4 | CONHMe | H | H | H | OMe |
| 353 | 1 | $SO_2Me$ | H | H | H | OMe |
| 354 | 2 | $SO_2Me$ | H | H | H | OMe |
| 355 | 3 | $SO_2Me$ | H | H | H | OMe |
| 356 | 4 | $SO_2Me$ | H | H | H | OMe |
| 357 | 1 | $SO_2NH_2$ | H | H | H | OMe |
| 358 | 2 | $SO_2NH_2$ | H | H | H | OMe |
| 359 | 3 | $SO_2NH_2$ | H | H | H | OMe |
| 360 | 4 | $SO_2NH_2$ | H | H | H | OMe |
| 361 | 1 | H | H | H | H | Me |
| 362 | 2 | H | H | H | H | Me |
| 363 | 3 | H | H | H | H | Me |
| 364 | 4 | H | H | H | H | Me |
| 365 | 1 | Me | H | H | H | Me |
| 366 | 2 | Me | H | H | H | Me |
| 367 | 3 | Me | H | H | H | Me |
| 368 | 4 | Me | H | H | H | Me |
| 369 | 1 | $CH_2Ph$ | H | H | H | Me |
| 370 | 2 | $CH_2Ph$ | H | H | H | Me |
| 371 | 3 | $CH_2Ph$ | H | H | H | Me |
| 372 | 4 | $CH_2Ph$ | H | H | H | Me |
| 373 | 1 | COMe | H | H | H | Me |
| 374 | 2 | COMe | H | H | H | Me |
| 375 | 3 | COMe | H | H | H | Me |
| 376 | 4 | COMe | H | H | H | Me |
| 377 | 1 | $CO_2Me$ | H | H | H | Me |
| 378 | 2 | $CO_2Me$ | H | H | H | Me |
| 379 | 3 | $CO_2Me$ | H | H | H | Me |
| 380 | 4 | $CO_2Me$ | H | H | H | Me |
| 381 | 1 | $CO_2tBu$ | H | H | H | Me |
| 382 | 2 | $CO_2tBu$ | H | H | H | Me |
| 383 | 3 | $CO_2tBu$ | H | H | H | Me |
| 384 | 4 | $CO_2tBu$ | H | H | H | Me |
| 385 | 1 | CONHMe | H | H | H | Me |
| 386 | 2 | CONHMe | H | H | H | Me |
| 387 | 3 | CONHMe | H | H | H | Me |
| 388 | 4 | CONHMe | H | H | H | Me |
| 389 | 1 | $SO_2Me$ | H | H | H | Me |
| 390 | 2 | $SO_2Me$ | H | H | H | Me |

TABLE 26-continued

| Entry | n | $R^7$ | $R^{20a}$ | $R^{20b}$ | $R^{20d}$ | $R^{20e}$ |
|---|---|---|---|---|---|---|
| 391 | 3 | $SO_2Me$ | H | H | H | Me |
| 392 | 4 | $SO_2Me$ | H | H | H | Me |
| 393 | 1 | $SO_2NH_2$ | H | H | H | Me |
| 394 | 2 | $SO_2NH_2$ | H | H | H | Me |
| 395 | 3 | $SO_2NH_2$ | H | H | H | Me |
| 396 | 4 | $SO_2NH_2$ | H | H | H | Me |
| 397 | 1 | H | H | H | H | $CF_3$ |
| 398 | 2 | H | H | H | H | $CF_3$ |
| 399 | 3 | H | H | H | H | $CF_3$ |
| 400 | 4 | H | H | H | H | $CF_3$ |
| 401 | 1 | Me | H | H | H | $CF_3$ |
| 402 | 2 | Me | H | H | H | $CF_3$ |
| 403 | 3 | Me | H | H | H | $CF_3$ |
| 404 | 4 | Me | H | H | H | $CF_3$ |
| 405 | 1 | $CH_2Ph$ | H | H | H | $CF_3$ |
| 406 | 2 | $CH_2Ph$ | H | H | H | $CF_3$ |
| 407 | 3 | $CH_2Ph$ | H | H | H | $CF_3$ |
| 408 | 4 | $CH_2Ph$ | H | H | H | $CF_3$ |
| 409 | 1 | COMe | H | H | H | $CF_3$ |
| 410 | 2 | COMe | H | H | H | $CF_3$ |
| 411 | 3 | COMe | H | H | H | $CF_3$ |
| 412 | 4 | COMe | H | H | H | $CF_3$ |
| 413 | 1 | $CO_2Me$ | H | H | H | $CF_3$ |
| 414 | 2 | $CO_2Me$ | H | H | H | $CF_3$ |
| 415 | 3 | $CO_2Me$ | H | H | H | $CF_3$ |
| 416 | 4 | $CO_2Me$ | H | H | H | $CF_3$ |
| 417 | 1 | $CO_2tBu$ | H | H | H | $CF_3$ |
| 418 | 2 | $CO_2tBu$ | H | H | H | $CF_3$ |
| 419 | 3 | $CO_2tBu$ | H | H | H | $CF_3$ |
| 420 | 4 | $CO_2tBu$ | H | H | H | $CF_3$ |
| 421 | 1 | CONHMe | H | H | H | $CF_3$ |
| 422 | 2 | CONHMe | H | H | H | $CF_3$ |
| 423 | 3 | CONHMe | H | H | H | $CF_3$ |
| 424 | 4 | CONHMe | H | H | H | $CF_3$ |
| 425 | 1 | $SO_2Me$ | H | H | H | $CF_3$ |
| 426 | 2 | $SO_2Me$ | H | H | H | $CF_3$ |
| 427 | 3 | $SO_2Me$ | H | H | H | $CF_3$ |
| 428 | 4 | $SO_2Me$ | H | H | H | $CF_3$ |
| 429 | 1 | $SO_2NH_2$ | H | H | H | $CF_3$ |
| 430 | 2 | $SO_2NH_2$ | H | H | H | $CF_3$ |
| 431 | 3 | $SO_2NH_2$ | H | H | H | $CF_3$ |
| 432 | 4 | $SO_2NH_2$ | H | H | H | $CF_3$ |
| 433 | 1 | H | H | H | H | F |
| 434 | 2 | H | H | H | H | F |
| 435 | 3 | H | H | H | H | F |
| 436 | 3 | H | H | H | H | F |
| 437 | 1 | Me | H | H | H | F |
| 438 | 2 | Me | H | H | H | F |
| 439 | 3 | Me | H | H | H | F |
| 440 | 4 | Me | H | H | H | F |
| 441 | 1 | $CH_2Ph$ | H | H | H | F |
| 442 | 2 | $CH_2Ph$ | H | H | H | F |
| 443 | 3 | $CH_2Ph$ | H | H | H | F |
| 444 | 4 | $CH_2Ph$ | H | H | H | F |
| 445 | 1 | COMe | H | H | H | F |
| 446 | 2 | COMe | H | H | H | F |
| 447 | 3 | COMe | H | H | H | F |
| 448 | 4 | COMe | H | H | H | F |
| 449 | 1 | $CO_2Me$ | H | H | H | F |
| 450 | 2 | $CO_2Me$ | H | H | H | F |
| 451 | 3 | $CO_2Me$ | H | H | H | F |
| 452 | 4 | $CO_2Me$ | H | H | H | F |
| 453 | 1 | $CO_2tBu$ | H | H | H | F |
| 454 | 2 | $CO_2tBu$ | H | H | H | F |
| 455 | 3 | $CO_2tBu$ | H | H | H | F |
| 456 | 4 | $CO_2tBu$ | H | H | H | F |
| 457 | 1 | CONHMe | H | H | H | F |
| 458 | 2 | CONHMe | H | H | H | F |
| 459 | 3 | CONHMe | H | H | H | F |
| 460 | 4 | CONHMe | H | H | H | F |
| 461 | 1 | $SO_2Me$ | H | H | H | F |
| 462 | 2 | $SO_2Me$ | H | H | H | F |
| 463 | 3 | $SO_2Me$ | H | H | H | F |
| 464 | 4 | $SO_2Me$ | H | H | H | F |
| 465 | 1 | $SO_2NH_2$ | H | H | H | F |
| 466 | 2 | $SO_2NH_2$ | H | H | H | F |
| 467 | 3 | $SO_2NH_2$ | H | H | H | F |
| 468 | 4 | $SO_2NH_2$ | H | H | H | F |

TABLE 26-continued

| Entry | n | $R^7$ | $R^{20a}$ | $R^{20b}$ | $R^{20d}$ | $R^{20e}$ |
|---|---|---|---|---|---|---|
| 469 | 1 | H | H | H | H | Cl |
| 470 | 2 | H | H | H | H | Cl |
| 471 | 3 | H | H | H | H | Cl |
| 472 | 4 | H | H | H | H | Cl |
| 473 | 1 | Me | H | H | H | Cl |
| 474 | 2 | Me | H | H | H | Cl |
| 475 | 3 | Me | H | H | H | Cl |
| 476 | 4 | Me | H | H | H | Cl |
| 477 | 1 | $CH_2Ph$ | H | H | H | Cl |
| 478 | 2 | $CH_2Ph$ | H | H | H | Cl |
| 479 | 3 | $CH_2Ph$ | H | H | H | Cl |
| 480 | 4 | $CH_2Ph$ | H | H | H | Cl |
| 481 | 1 | COMe | H | H | H | Cl |
| 482 | 2 | COMe | H | H | H | Cl |
| 483 | 3 | COMe | H | H | H | Cl |
| 484 | 4 | COMe | H | H | H | Cl |
| 485 | 1 | $CO_2Me$ | H | H | H | Cl |
| 486 | 2 | $CO_2Me$ | H | H | H | Cl |
| 487 | 3 | $CO_2Me$ | H | H | H | Cl |
| 488 | 4 | $CO_2Me$ | H | H | H | Cl |
| 489 | 1 | $CO_2tBu$ | H | H | H | Cl |
| 490 | 2 | $CO_2tBu$ | H | H | H | Cl |
| 491 | 3 | $CO_2tBu$ | H | H | H | Cl |
| 492 | 4 | $CO_2tBu$ | H | H | H | Cl |
| 493 | 1 | CONHMe | H | H | H | Cl |
| 494 | 2 | CONHMe | H | H | H | Cl |
| 495 | 3 | CONHMe | H | H | H | Cl |
| 496 | 4 | CONHMe | H | H | H | Cl |
| 497 | 1 | $SO_2Me$ | H | H | H | Cl |
| 498 | 2 | $SO_2Me$ | H | H | H | Cl |
| 499 | 3 | $SO_2Me$ | H | H | H | Cl |
| 500 | 4 | $SO_2Me$ | H | H | H | Cl |
| 501 | 1 | $SO_2NH_2$ | H | H | H | Cl |
| 502 | 2 | $SO_2NH_2$ | H | H | H | Cl |
| 503 | 3 | $SO_2NH_2$ | H | H | H | Cl |
| 504 | 4 | $SO_2NH_2$ | H | H | H | Cl |
| 505 | 1 | H | H | H | H | CN |
| 506 | 2 | H | H | H | H | CN |
| 507 | 3 | H | H | H | H | CN |
| 508 | 4 | H | H | H | H | CN |
| 509 | 1 | Me | H | H | H | CN |
| 510 | 2 | Me | H | H | H | CN |
| 511 | 3 | Me | H | H | H | CN |
| 512 | 4 | Me | H | H | H | CN |
| 513 | 1 | $CH_2Ph$ | H | H | H | CN |
| 514 | 2 | $CH_2Ph$ | H | H | H | CN |
| 515 | 3 | $CH_2Ph$ | H | H | H | CN |
| 516 | 4 | $CH_2Ph$ | H | H | H | CN |
| 517 | 1 | COMe | H | H | H | CN |
| 518 | 2 | COMe | H | H | H | CN |
| 519 | 3 | COMe | H | H | H | CN |
| 520 | 4 | COMe | H | H | H | CN |
| 521 | 1 | $CO_2Me$ | H | H | H | CN |
| 522 | 2 | $CO_2Me$ | H | H | H | CN |
| 523 | 3 | $CO_2Me$ | H | H | H | CN |
| 524 | 4 | $CO_2Me$ | H | H | H | CN |
| 525 | 1 | $CO_2tBu$ | H | H | H | CN |
| 526 | 2 | $CO_2tBu$ | H | H | H | CN |
| 527 | 3 | $CO_2tBu$ | H | H | H | CN |
| 528 | 4 | $CO_2tBu$ | H | H | H | CN |
| 529 | 1 | CONHMe | H | H | H | CN |
| 530 | 2 | CONHMe | H | H | H | CN |
| 531 | 3 | CONHMe | H | H | H | CN |
| 532 | 4 | CONHMe | H | H | H | CN |
| 533 | 1 | $SO_2Me$ | H | H | H | CN |
| 534 | 2 | $SO_2Me$ | H | H | H | CN |
| 535 | 3 | $SO_2Me$ | H | H | H | CN |
| 536 | 4 | $SO_2Me$ | H | H | H | CN |
| 537 | 1 | $SO_2NH_2$ | H | H | H | CN |
| 538 | 2 | $SO_2NH_2$ | H | H | H | CN |
| 539 | 3 | $SO_2NH_2$ | H | H | H | CN |
| 540 | 4 | $SO_2NH_2$ | H | H | H | CN |

Exemplary embodiments include compounds having the formula (XXXIV)

(XXXIV)

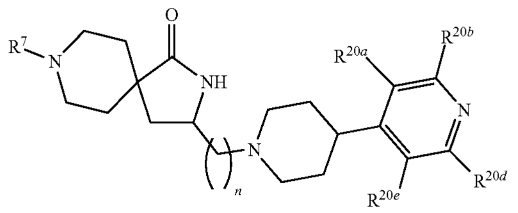

or a pharmaceutically acceptable salt form thereof defined herein below in Table 27.

TABLE 27

| Entry | n | $R^7$ | $R^{20a}$ | $R^{20b}$ | $R^{20d}$ | $R^{20e}$ |
|---|---|---|---|---|---|---|
| 1 | 1 | H | H | H | H | H |
| 2 | 2 | H | H | H | H | H |
| 3 | 3 | H | H | H | H | H |
| 4 | 4 | H | H | H | H | H |
| 5 | 1 | Me | H | H | H | H |
| 6 | 2 | Me | H | H | H | H |
| 7 | 3 | Me | H | H | H | H |
| 8 | 4 | Me | H | H | H | H |
| 9 | 1 | $CH_2Ph$ | H | H | H | H |
| 10 | 2 | $CH_2Ph$ | H | H | H | H |
| 11 | 3 | $CH_2Ph$ | H | H | H | H |
| 12 | 4 | $CH_2Ph$ | H | H | H | H |
| 13 | 1 | COMe | H | H | H | H |
| 14 | 2 | COMe | H | H | H | H |
| 15 | 3 | COMe | H | H | H | H |
| 16 | 4 | COMe | H | H | H | H |
| 17 | 1 | $CO_2Me$ | H | H | H | H |
| 18 | 2 | $CO_2Me$ | H | H | H | H |
| 19 | 3 | $CO_2Me$ | H | H | H | H |
| 20 | 4 | $CO_2Me$ | H | H | H | H |
| 21 | 1 | $CO_2tBu$ | H | H | H | H |
| 22 | 2 | $CO_2tBu$ | H | H | H | H |
| 23 | 3 | $CO_2tBu$ | H | H | H | H |
| 24 | 4 | $CO_2tBu$ | H | H | H | H |
| 25 | 1 | CONHMe | H | H | H | H |
| 26 | 2 | CONHMe | H | H | H | H |
| 27 | 3 | CONHMe | H | H | H | H |
| 28 | 4 | CONHMe | H | H | H | H |
| 29 | 1 | $SO_2Me$ | H | H | H | H |
| 30 | 2 | $SO_2Me$ | H | H | H | H |
| 31 | 3 | $SO_2Me$ | H | H | H | H |
| 32 | 4 | $SO_2Me$ | H | H | H | H |
| 33 | 1 | $SO_2NH_2$ | H | H | H | H |
| 34 | 2 | $SO_2NH_2$ | H | H | H | H |
| 35 | 3 | $SO_2NH_2$ | H | H | H | H |
| 36 | 4 | $SO_2NH_2$ | H | H | H | H |
| 37 | 1 | H | H | H | OH | H |
| 38 | 2 | H | H | H | OH | H |
| 39 | 3 | H | H | H | OH | H |
| 40 | 4 | H | H | H | OH | H |
| 41 | 1 | Me | H | H | OH | H |
| 42 | 2 | Me | H | H | OH | H |
| 43 | 3 | Me | H | H | OH | H |
| 44 | 4 | Me | H | H | OH | H |
| 45 | 1 | $CH_2Ph$ | H | H | OH | H |
| 46 | 2 | $CH_2Ph$ | H | H | OH | H |
| 47 | 3 | $CH_2Ph$ | H | H | OH | H |
| 48 | 4 | $CH_2Ph$ | H | H | OH | H |
| 49 | 1 | COMe | H | H | OH | H |
| 50 | 2 | COMe | H | H | OH | H |
| 51 | 3 | COMe | H | H | OH | H |
| 52 | 4 | COMe | H | H | OH | H |
| 53 | 1 | $CO_2Me$ | H | H | OH | H |
| 54 | 2 | $CO_2Me$ | H | H | OH | H |
| 55 | 3 | $CO_2Me$ | H | H | OH | H |
| 56 | 4 | $CO_2Me$ | H | H | OH | H |
| 57 | 1 | $CO_2tBu$ | H | H | OH | H |
| 58 | 2 | $CO_2tBu$ | H | H | OH | H |
| 59 | 3 | $CO_2tBu$ | H | H | OH | H |

TABLE 27-continued

| Entry | n | $R^7$ | $R^{20a}$ | $R^{20b}$ | $R^{20d}$ | $R^{20e}$ |
|---|---|---|---|---|---|---|
| 60 | 4 | $CO_2tBu$ | H | H | OH | H |
| 61 | 1 | CONHMe | H | H | OH | H |
| 62 | 2 | CONHMe | H | H | OH | H |
| 63 | 3 | CONHMe | H | H | OH | H |
| 64 | 4 | CONHMe | H | H | OH | H |
| 65 | 1 | $SO_2Me$ | H | H | OH | H |
| 66 | 2 | $SO_2Me$ | H | H | OH | H |
| 67 | 3 | $SO_2Me$ | H | H | OH | H |
| 68 | 4 | $SO_2Me$ | H | H | OH | H |
| 69 | 1 | $SO_2NH_2$ | H | H | OH | H |
| 70 | 2 | $SO_2NH_2$ | H | H | OH | H |
| 71 | 3 | $SO_2NH_2$ | H | H | OH | H |
| 72 | 4 | $SO_2NH_2$ | H | H | OH | H |
| 73 | 1 | H | H | H | OMe | H |
| 74 | 2 | H | H | H | OMe | H |
| 75 | 3 | H | H | H | OMe | H |
| 76 | 4 | H | H | H | OMe | H |
| 77 | 1 | Me | H | H | OMe | H |
| 78 | 2 | Me | H | H | OMe | H |
| 79 | 3 | Me | H | H | OMe | H |
| 80 | 4 | Me | H | H | OMe | H |
| 81 | 1 | $CH_2Ph$ | H | H | OMe | H |
| 82 | 2 | $CH_2Ph$ | H | H | OMe | H |
| 83 | 3 | $CH_2Ph$ | H | H | OMe | H |
| 84 | 4 | $CH_2Ph$ | H | H | OMe | H |
| 85 | 1 | COMe | H | H | OMe | H |
| 86 | 2 | COMe | H | H | OMe | H |
| 87 | 3 | COMe | H | H | OMe | H |
| 88 | 4 | COMe | H | H | OMe | H |
| 89 | 1 | $CO_2Me$ | H | H | OMe | H |
| 90 | 2 | $CO_2Me$ | H | H | OMe | H |
| 91 | 3 | $CO_2Me$ | H | H | OMe | H |
| 92 | 4 | $CO_2Me$ | H | H | OMe | H |
| 93 | 1 | $CO_2tBu$ | H | H | OMe | H |
| 94 | 2 | $CO_2tBu$ | H | H | OMe | H |
| 95 | 3 | $CO_2tBu$ | H | H | OMe | H |
| 96 | 1 | $CO_2tBu$ | H | H | OMe | H |
| 97 | 1 | CONHMe | H | H | OMe | H |
| 98 | 2 | CONHMe | H | H | OMe | H |
| 99 | 3 | CONHMe | H | H | OMe | H |
| 100 | 4 | CONHMe | H | H | OMe | H |
| 101 | 1 | $SO_2Me$ | H | H | OMe | H |
| 102 | 2 | $SO_2Me$ | H | H | OMe | H |
| 103 | 3 | $SO_2Me$ | H | H | OMe | H |
| 104 | 4 | $SO_2Me$ | H | H | OMe | H |
| 105 | 1 | $SO_2NH_2$ | H | H | OMe | H |
| 106 | 2 | $SO_2NH_2$ | H | H | OMe | H |
| 107 | 3 | $SO_2NH_2$ | H | H | OMe | H |
| 108 | 4 | $SO_2NH_2$ | H | H | OMe | H |
| 109 | 1 | H | H | H | Me | H |
| 110 | 2 | H | H | H | Me | H |
| 111 | 3 | H | H | H | Me | H |
| 112 | 4 | H | H | H | Me | H |
| 113 | 1 | Me | H | H | Me | H |
| 114 | 2 | Me | H | H | Me | H |
| 115 | 3 | Me | H | H | Me | H |
| 116 | 4 | Me | H | H | Me | H |
| 117 | 1 | $CH_2Ph$ | H | H | Me | H |
| 118 | 2 | $CH_2Ph$ | H | H | Me | H |
| 119 | 3 | $CH_2Ph$ | H | H | Me | H |
| 120 | 4 | $CH_2Ph$ | H | H | Me | H |
| 121 | 1 | COMe | H | H | Me | H |
| 122 | 2 | COMe | H | H | Me | H |
| 123 | 3 | COMe | H | H | Me | H |
| 124 | 4 | COMe | H | H | Me | H |
| 125 | 1 | $CO_2Me$ | H | H | Me | H |
| 126 | 2 | $CO_2Me$ | H | H | Me | H |
| 127 | 3 | $CO_2Me$ | H | H | Me | H |
| 128 | 4 | $CO_2Me$ | H | H | Me | H |
| 129 | 1 | $CO_2tBu$ | H | H | Me | H |
| 130 | 2 | $CO_2tBu$ | H | H | Me | H |
| 131 | 3 | $CO_2tBu$ | H | H | Me | H |
| 132 | 4 | $CO_2tBu$ | H | H | Me | H |
| 133 | 1 | CONHMe | H | H | Me | H |
| 134 | 2 | CONHMe | H | H | Me | H |
| 135 | 3 | CONHMe | H | H | Me | H |
| 136 | 4 | CONHMe | H | H | Me | H |
| 137 | 1 | $SO_2Me$ | H | H | Me | H |

TABLE 27-continued

| Entry | n | $R^7$ | $R^{20a}$ | $R^{20b}$ | $R^{20d}$ | $R^{20e}$ |
|---|---|---|---|---|---|---|
| 138 | 2 | $SO_2Me$ | H | H | Me | H |
| 139 | 3 | $SO_2Me$ | H | H | Me | H |
| 140 | 4 | $SO_2Me$ | H | H | Me | H |
| 141 | 1 | $SO_2NH_2$ | H | H | Me | H |
| 142 | 2 | $SO_2NH_2$ | H | H | Me | H |
| 143 | 3 | $SO_2NH_2$ | H | H | Me | H |
| 144 | 4 | $SO_2NH_2$ | H | H | Me | H |
| 145 | 1 | H | H | H | $CF_3$ | H |
| 146 | 2 | H | H | H | $CF_3$ | H |
| 147 | 3 | H | H | H | $CF_3$ | H |
| 148 | 4 | H | H | H | $CF_3$ | H |
| 149 | 1 | Me | H | H | $CF_3$ | H |
| 150 | 2 | Me | H | H | $CF_3$ | H |
| 151 | 3 | Me | H | H | $CF_3$ | H |
| 152 | 4 | Me | H | H | $CF_3$ | H |
| 153 | 1 | $CH_2Ph$ | H | H | $CF_3$ | H |
| 154 | 2 | $CH_2Ph$ | H | H | $CF_3$ | H |
| 155 | 3 | $CH_2Ph$ | H | H | $CF_3$ | H |
| 156 | 4 | $CH_2Ph$ | H | H | $CF_3$ | H |
| 157 | 1 | COMe | H | H | $CF_3$ | H |
| 158 | 2 | COMe | H | H | $CF_3$ | H |
| 159 | 3 | COMe | H | H | $CF_3$ | H |
| 160 | 4 | COMe | H | H | $CF_3$ | H |
| 161 | 1 | $CO_2Me$ | H | H | $CF_3$ | H |
| 162 | 2 | $CO_2Me$ | H | H | $CF_3$ | H |
| 163 | 3 | $CO_2Me$ | H | H | $CF_3$ | H |
| 164 | 4 | $CO_2Me$ | H | H | $CF_3$ | H |
| 165 | 1 | $CO_2tBu$ | H | H | $CF_3$ | H |
| 166 | 2 | $CO_2tBu$ | H | H | $CF_3$ | H |
| 167 | 3 | $CO_2tBu$ | H | H | $CF_3$ | H |
| 168 | 4 | $CO_2tBu$ | H | H | $CF_3$ | H |
| 169 | 1 | CONHMe | H | H | $CF_3$ | H |
| 170 | 2 | CONHMe | H | H | $CF_3$ | H |
| 171 | 3 | CONHMe | H | H | $CF_3$ | H |
| 172 | 4 | CONHMe | H | H | $CF_3$ | H |
| 173 | 1 | $SO_2Me$ | H | H | $CF_3$ | H |
| 174 | 2 | $SO_2Me$ | H | H | $CF_3$ | H |
| 175 | 3 | $SO_2Me$ | H | H | $CF_3$ | H |
| 176 | 4 | $SO_2Me$ | H | H | $CF_3$ | H |
| 177 | 1 | $SO_2NH_2$ | H | H | $CF_3$ | H |
| 178 | 2 | $SO_2NH_2$ | H | H | $CF_3$ | H |
| 179 | 3 | $SO_2NH_2$ | H | H | $CF_3$ | H |
| 180 | 4 | $SO_2NH_2$ | H | H | $CF_3$ | H |
| 181 | 1 | H | H | H | F | H |
| 182 | 2 | H | H | H | F | H |
| 183 | 3 | H | H | H | F | H |
| 184 | 4 | H | H | H | F | H |
| 185 | 1 | Me | H | H | F | H |
| 186 | 2 | Me | H | H | F | H |
| 187 | 3 | Me | H | H | F | H |
| 188 | 4 | Me | H | H | F | H |
| 189 | 1 | $CH_2Ph$ | H | H | F | H |
| 190 | 2 | $CH_2Ph$ | H | H | F | H |
| 191 | 3 | $CH_2Ph$ | H | H | F | H |
| 192 | 4 | $CH_2Ph$ | H | H | F | H |
| 193 | 1 | COMe | H | H | F | H |
| 194 | 2 | COMe | H | H | F | H |
| 195 | 3 | COMe | H | H | F | H |
| 196 | 4 | COMe | H | H | F | H |
| 197 | 1 | $CO_2Me$ | H | H | F | H |
| 198 | 2 | $CO_2Me$ | H | H | F | H |
| 199 | 3 | $CO_2Me$ | H | H | F | H |
| 200 | 4 | $CO_2Me$ | H | H | F | H |
| 201 | 1 | $CO_2tBu$ | H | H | F | H |
| 202 | 2 | $CO_2tBu$ | H | H | F | H |
| 203 | 3 | $CO_2tBu$ | H | H | F | H |
| 204 | 4 | $CO_2tBu$ | H | H | F | H |
| 205 | 1 | CONHMe | H | H | F | H |
| 206 | 2 | CONHMe | H | H | F | H |
| 207 | 3 | CONHMe | H | H | F | H |
| 208 | 4 | CONHMe | H | H | F | H |
| 209 | 1 | $SO_2Me$ | H | H | F | H |
| 210 | 2 | $SO_2Me$ | H | H | F | H |
| 211 | 3 | $SO_2Me$ | H | H | F | H |
| 212 | 4 | $SO_2Me$ | H | H | F | H |
| 213 | 1 | $SO_2NH_2$ | H | H | F | H |
| 214 | 2 | $SO_2NH_2$ | H | H | F | H |
| 215 | 3 | $SO_2NH_2$ | H | H | F | H |

TABLE 27-continued

| Entry | n | $R^7$ | $R^{20a}$ | $R^{20b}$ | $R^{20d}$ | $R^{20e}$ |
|---|---|---|---|---|---|---|
| 216 | 4 | $SO_2NH_2$ | H | H | F | H |
| 217 | 1 | H | H | H | Cl | H |
| 218 | 2 | H | H | H | Cl | H |
| 219 | 3 | H | H | H | Cl | H |
| 220 | 4 | H | H | H | Cl | H |
| 221 | 1 | Me | H | H | Cl | H |
| 222 | 2 | Me | H | H | Cl | H |
| 223 | 3 | Me | H | H | Cl | H |
| 224 | 4 | Me | H | H | Cl | H |
| 225 | 1 | $CH_2Ph$ | H | H | Cl | H |
| 226 | 2 | $CH_2Ph$ | H | H | Cl | H |
| 227 | 3 | $CH_2Ph$ | H | H | Cl | H |
| 228 | 4 | $CH_2Ph$ | H | H | Cl | H |
| 229 | 1 | COMe | H | H | Cl | H |
| 230 | 2 | COMe | H | H | Cl | H |
| 231 | 3 | COMe | H | H | Cl | H |
| 232 | 4 | COMe | H | H | Cl | H |
| 233 | 1 | $CO_2Me$ | H | H | Cl | H |
| 234 | 2 | $CO_2Me$ | H | H | Cl | H |
| 235 | 3 | $CO_2Me$ | H | H | Cl | H |
| 236 | 4 | $CO_2Me$ | H | H | Cl | H |
| 237 | 1 | $CO_2tBu$ | H | H | Cl | H |
| 238 | 2 | $CO_2tBu$ | H | H | Cl | H |
| 239 | 3 | $CO_2tBu$ | H | H | Cl | H |
| 240 | 4 | $CO_2tBu$ | H | H | Cl | H |
| 241 | 1 | CONHMe | H | H | Cl | H |
| 242 | 2 | CONHMe | H | H | Cl | H |
| 243 | 3 | CONHMe | H | H | Cl | H |
| 244 | 4 | CONHMe | H | H | Cl | H |
| 245 | 1 | $SO_2Me$ | H | H | Cl | H |
| 246 | 2 | $SO_2Me$ | H | H | Cl | H |
| 247 | 3 | $SO_2Me$ | H | H | Cl | H |
| 248 | 4 | $SO_2Me$ | H | H | Cl | H |
| 249 | 1 | $SO_2NH_2$ | H | H | Cl | H |
| 250 | 2 | $SO_2NH_2$ | H | H | Cl | H |
| 251 | 3 | $SO_2NH_2$ | H | H | Cl | H |
| 252 | 4 | $SO_2NH_2$ | H | H | Cl | H |
| 253 | 1 | H | H | H | CN | H |
| 254 | 2 | H | H | H | CN | H |
| 255 | 3 | H | H | H | CN | H |
| 256 | 4 | H | H | H | CN | H |
| 257 | 1 | Me | H | H | CN | H |
| 258 | 2 | Me | H | H | CN | H |
| 259 | 3 | Me | H | H | CN | H |
| 260 | 4 | Me | H | H | CN | H |
| 261 | 1 | $CH_2Ph$ | H | H | CN | H |
| 262 | 2 | $CH_2Ph$ | H | H | CN | H |
| 263 | 3 | $CH_2Ph$ | H | H | CN | H |
| 264 | 4 | $CH_2Ph$ | H | H | CN | H |
| 265 | 1 | COMe | H | H | CN | H |
| 266 | 2 | COMe | H | H | CN | H |
| 267 | 3 | COMe | H | H | CN | H |
| 268 | 4 | COMe | H | H | CN | H |
| 269 | 1 | $CO_2Me$ | H | H | CN | H |
| 270 | 2 | $CO_2Me$ | H | H | CN | H |
| 271 | 3 | $CO_2Me$ | H | H | CN | H |
| 272 | 4 | $CO_2Me$ | H | H | CN | H |
| 273 | 1 | $CO_2tBu$ | H | H | CN | H |
| 274 | 2 | $CO_2tBu$ | H | H | CN | H |
| 275 | 3 | $CO_2tBu$ | H | H | CN | H |
| 276 | 4 | $CO_2tBu$ | H | H | CN | H |
| 277 | 1 | CONHMe | H | H | CN | H |
| 278 | 2 | CONHMe | H | H | CN | H |
| 279 | 3 | CONHMe | H | H | CN | H |
| 280 | 4 | CONHMe | H | H | CN | H |
| 281 | 1 | $SO_2Me$ | H | H | CN | H |
| 282 | 2 | $SO_2Me$ | H | H | CN | H |
| 283 | 3 | $SO_2Me$ | H | H | CN | H |
| 284 | 4 | $SO_2Me$ | H | H | CN | H |
| 285 | 1 | $SO_2NH_2$ | H | H | CN | H |
| 286 | 2 | $SO_2NH_2$ | H | H | CN | H |
| 287 | 3 | $SO_2NH_2$ | H | H | CN | H |
| 288 | 4 | $SO_2NH_2$ | H | H | CN | H |
| 289 | 1 | H | H | H | H | OH |
| 290 | 2 | H | H | H | H | OH |
| 291 | 3 | H | H | H | H | OH |
| 292 | 4 | H | H | H | H | OH |
| 293 | 1 | Me | H | H | H | OH |

TABLE 27-continued

| Entry | n | $R^7$ | $R^{20a}$ | $R^{20b}$ | $R^{20d}$ | $R^{20e}$ |
|---|---|---|---|---|---|---|
| 294 | 2 | Me | H | H | H | OH |
| 295 | 3 | Me | H | H | H | OH |
| 296 | 4 | Me | H | H | H | OH |
| 297 | 1 | $CH_2Ph$ | H | H | H | OH |
| 298 | 2 | $CH_2Ph$ | H | H | H | OH |
| 299 | 3 | $CH_2Ph$ | H | H | H | OH |
| 300 | 4 | $CH_2Ph$ | H | H | H | OH |
| 301 | 1 | COMe | H | H | H | OH |
| 302 | 2 | COMe | H | H | H | OH |
| 303 | 3 | COMe | H | H | H | OH |
| 304 | 4 | COMe | H | H | H | OH |
| 305 | 1 | $CO_2Me$ | H | H | H | OH |
| 306 | 2 | $CO_2Me$ | H | H | H | OH |
| 307 | 3 | $CO_2Me$ | H | H | H | OH |
| 308 | 4 | $CO_2Me$ | H | H | H | OH |
| 309 | 1 | $CO_2tBu$ | H | H | H | OH |
| 310 | 2 | $CO_2tBu$ | H | H | H | OH |
| 311 | 3 | $CO_2tBu$ | H | H | H | OH |
| 312 | 4 | $CO_2tBu$ | H | H | H | OH |
| 313 | 1 | CONHMe | H | H | H | OH |
| 314 | 2 | CONHMe | H | H | H | OH |
| 315 | 3 | CONHMe | H | H | H | OH |
| 316 | 4 | CONHMe | H | H | H | OH |
| 317 | 1 | $SO_2Me$ | H | H | H | OH |
| 318 | 2 | $SO_2Me$ | H | H | H | OH |
| 319 | 3 | $SO_2Me$ | H | H | H | OH |
| 320 | 4 | $SO_2Me$ | H | H | H | OH |
| 321 | 1 | $SO_2NH_2$ | H | H | H | OH |
| 322 | 2 | $SO_2NH_2$ | H | H | H | OH |
| 323 | 3 | $SO_2NH_2$ | H | H | H | OH |
| 324 | 4 | $SO_2NH_2$ | H | H | H | OH |
| 325 | 1 | H | H | H | H | OMe |
| 326 | 2 | H | H | H | H | OMe |
| 327 | 3 | H | H | H | H | OMe |
| 328 | 4 | H | H | H | H | OMe |
| 329 | 1 | Me | H | H | H | OMe |
| 330 | 2 | Me | H | H | H | OMe |
| 331 | 3 | Me | H | H | H | OMe |
| 332 | 4 | Me | H | H | H | OMe |
| 333 | 1 | $CH_2Ph$ | H | H | H | OMe |
| 334 | 2 | $CH_2Ph$ | H | H | H | OMe |
| 335 | 3 | $CH_2Ph$ | H | H | H | OMe |
| 336 | 4 | $CH_2Ph$ | H | H | H | OMe |
| 337 | 1 | COMe | H | H | H | OMe |
| 338 | 2 | COMe | H | H | H | OMe |
| 339 | 3 | COMe | H | H | H | OMe |
| 340 | 4 | COMe | H | H | H | OMe |
| 341 | 1 | $CO_2Me$ | H | H | H | OMe |
| 342 | 2 | $CO_2Me$ | H | H | H | OMe |
| 343 | 3 | $CO_2Me$ | H | H | H | OMe |
| 344 | 4 | $CO_2Me$ | H | H | H | OMe |
| 345 | 1 | $CO_2tBu$ | H | H | H | OMe |
| 346 | 2 | $CO_2tBu$ | H | H | H | OMe |
| 347 | 3 | $CO_2tBu$ | H | H | H | OMe |
| 348 | 4 | $CO_2tBu$ | H | H | H | OMe |
| 349 | 1 | CONHMe | H | H | H | OMe |
| 350 | 2 | CONHMe | H | H | H | OMe |
| 351 | 3 | CONHMe | H | H | H | OMe |
| 352 | 4 | CONHMe | H | H | H | OMe |
| 353 | 1 | $SO_2Me$ | H | H | H | OMe |
| 354 | 2 | $SO_2Me$ | H | H | H | OMe |
| 355 | 3 | $SO_2Me$ | H | H | H | OMe |
| 356 | 4 | $SO_2Me$ | H | H | H | OMe |
| 357 | 1 | $SO_2NH_2$ | H | H | H | OMe |
| 358 | 2 | $SO_2NH_2$ | H | H | H | OMe |
| 359 | 3 | $SO_2NH_2$ | H | H | H | OMe |
| 360 | 4 | $SO_2NH_2$ | H | H | H | OMe |
| 361 | 1 | H | H | H | H | Me |
| 362 | 2 | H | H | H | H | Me |
| 363 | 3 | H | H | H | H | Me |
| 364 | 4 | H | H | H | H | Me |
| 365 | 1 | Me | H | H | H | Me |
| 366 | 2 | Me | H | H | H | Me |
| 367 | 3 | Me | H | H | H | Me |
| 368 | 4 | Me | H | H | H | Me |
| 369 | 1 | $CH_2Ph$ | H | H | H | Me |
| 370 | 2 | $CH_2Ph$ | H | H | H | Me |
| 371 | 3 | $CH_2Ph$ | H | H | H | Me |
| 372 | 4 | $CH_2Ph$ | H | H | H | Me |
| 373 | 1 | COMe | H | H | H | Me |
| 374 | 2 | COMe | H | H | H | Me |
| 375 | 3 | COMe | H | H | H | Me |
| 376 | 4 | COMe | H | H | H | Me |
| 377 | 1 | $CO_2Me$ | H | H | H | Me |
| 378 | 2 | $CO_2Me$ | H | H | H | Me |
| 379 | 3 | $CO_2Me$ | H | H | H | Me |
| 380 | 4 | $CO_2Me$ | H | H | H | Me |
| 381 | 1 | $CO_2tBu$ | H | H | H | Me |
| 382 | 2 | $CO_2tBu$ | H | H | H | Me |
| 383 | 3 | $CO_2tBu$ | H | H | H | Me |
| 384 | 4 | $CO_2tBu$ | H | H | H | Me |
| 385 | 1 | CONHMe | H | H | H | Me |
| 386 | 2 | CONHMe | H | H | H | Me |
| 387 | 3 | CONHMe | H | H | H | Me |
| 388 | 4 | CONHMe | H | H | H | Me |
| 389 | 1 | $SO_2Me$ | H | H | H | Me |
| 390 | 2 | $SO_2Me$ | H | H | H | Me |
| 391 | 3 | $SO_2Me$ | H | H | H | Me |
| 392 | 4 | $SO_2Me$ | H | H | H | Me |
| 393 | 1 | $SO_2NH_2$ | H | H | H | Me |
| 394 | 2 | $SO_2NH_2$ | H | H | H | Me |
| 395 | 3 | $SO_2NH_2$ | H | H | H | Me |
| 396 | 4 | $SO_2NH_2$ | H | H | H | Me |
| 397 | 1 | H | H | H | H | $CF_3$ |
| 398 | 2 | H | H | H | H | $CF_3$ |
| 399 | 3 | H | H | H | H | $CF_3$ |
| 400 | 4 | H | H | H | H | $CF_3$ |
| 401 | 1 | Me | H | H | H | $CF_3$ |
| 402 | 2 | Me | H | H | H | $CF_3$ |
| 403 | 3 | Me | H | H | H | $CF_3$ |
| 404 | 4 | Me | H | H | H | $CF_3$ |
| 405 | 1 | $CH_2Ph$ | H | H | H | $CF_3$ |
| 406 | 2 | $CH_2Ph$ | H | H | H | $CF_3$ |
| 407 | 3 | $CH_2Ph$ | H | H | H | $CF_3$ |
| 408 | 4 | $CH_2Ph$ | H | H | H | $CF_3$ |
| 409 | 1 | COMe | H | H | H | $CF_3$ |
| 410 | 2 | COMe | H | H | H | $CF_3$ |
| 411 | 3 | COMe | H | H | H | $CF_3$ |
| 412 | 4 | COMe | H | H | H | $CF_3$ |
| 413 | 1 | $CO_2Me$ | H | H | H | $CF_3$ |
| 414 | 2 | $CO_2Me$ | H | H | H | $CF_3$ |
| 415 | 3 | $CO_2Me$ | H | H | H | $CF_3$ |
| 416 | 4 | $CO_2Me$ | H | H | H | $CF_3$ |
| 417 | 1 | $CO_2tBu$ | H | H | H | $CF_3$ |
| 418 | 2 | $CO_2tBu$ | H | H | H | $CF_3$ |
| 419 | 3 | $CO_2tBu$ | H | H | H | $CF_3$ |
| 420 | 4 | $CO_2tBu$ | H | H | H | $CF_3$ |
| 421 | 1 | CONHMe | H | H | H | $CF_3$ |
| 422 | 2 | CONHMe | H | H | H | $CF_3$ |
| 423 | 3 | CONHMe | H | H | H | $CF_3$ |
| 424 | 4 | CONHMe | H | H | H | $CF_3$ |
| 425 | 1 | $SO_2Me$ | H | H | H | $CF_3$ |
| 426 | 2 | $SO_2Me$ | H | H | H | $CF_3$ |
| 427 | 3 | $SO_2Me$ | H | H | H | $CF_3$ |
| 428 | 4 | $SO_2Me$ | H | H | H | $CF_3$ |
| 429 | 1 | $SO_2NH_2$ | H | H | H | $CF_3$ |
| 430 | 2 | $SO_2NH_2$ | H | H | H | $CF_3$ |
| 431 | 3 | $SO_2NH_2$ | H | H | H | $CF_3$ |
| 432 | 4 | $SO_2NH_2$ | H | H | H | $CF_3$ |
| 433 | 1 | H | H | H | H | F |
| 434 | 2 | H | H | H | H | F |
| 435 | 3 | H | H | H | H | F |
| 436 | 3 | H | H | H | H | F |
| 437 | 1 | Me | H | H | H | F |
| 438 | 2 | Me | H | H | H | F |
| 439 | 3 | Me | H | H | H | F |
| 440 | 4 | Me | H | H | H | F |
| 441 | 1 | $CH_2Ph$ | H | H | H | F |
| 442 | 2 | $CH_2Ph$ | H | H | H | F |
| 443 | 3 | $CH_2Ph$ | H | H | H | F |
| 444 | 4 | $CH_2Ph$ | H | H | H | F |
| 445 | 1 | COMe | H | H | H | F |
| 446 | 2 | COMe | H | H | H | F |
| 447 | 3 | COMe | H | H | H | F |
| 448 | 4 | COMe | H | H | H | F |
| 449 | 1 | $CO_2Me$ | H | H | H | F |

TABLE 27-continued

| Entry | n | $R^7$ | $R^{20a}$ | $R^{20b}$ | $R^{20d}$ | $R^{20e}$ |
|---|---|---|---|---|---|---|
| 450 | 2 | $CO_2Me$ | H | H | H | F |
| 451 | 3 | $CO_2Me$ | H | H | H | F |
| 452 | 4 | $CO_2Me$ | H | H | H | F |
| 453 | 1 | $CO_2tBu$ | H | H | H | F |
| 454 | 2 | $CO_2tBu$ | H | H | H | F |
| 455 | 3 | $CO_2tBu$ | H | H | H | F |
| 456 | 4 | $CO_2tBu$ | H | H | H | F |
| 457 | 1 | CONHMe | H | H | H | F |
| 458 | 2 | CONHMe | H | H | H | F |
| 459 | 3 | CONHMe | H | H | H | F |
| 460 | 4 | CONHMe | H | H | H | F |
| 461 | 1 | $SO_2Me$ | H | H | H | F |
| 462 | 2 | $SO_2Me$ | H | H | H | F |
| 463 | 3 | $SO_2Me$ | H | H | H | F |
| 464 | 4 | $SO_2Me$ | H | H | H | F |
| 465 | 1 | $SO_2NH_2$ | H | H | H | F |
| 466 | 2 | $SO_2NH_2$ | H | H | H | F |
| 467 | 3 | $SO_2NH_2$ | H | H | H | F |
| 468 | 4 | $SO_2NH_2$ | H | H | H | F |
| 469 | 1 | H | H | H | H | Cl |
| 470 | 2 | H | H | H | H | Cl |
| 471 | 3 | H | H | H | H | Cl |
| 472 | 4 | H | H | H | H | Cl |
| 473 | 1 | Me | H | H | H | Cl |
| 474 | 2 | Me | H | H | H | Cl |
| 475 | 3 | Me | H | H | H | Cl |
| 476 | 4 | Me | H | H | H | Cl |
| 477 | 1 | $CH_2Ph$ | H | H | H | Cl |
| 478 | 2 | $CH_2Ph$ | H | H | H | Cl |
| 479 | 3 | $CH_2Ph$ | H | H | H | Cl |
| 480 | 4 | $CH_2Ph$ | H | H | H | Cl |
| 481 | 1 | COMe | H | H | H | Cl |
| 482 | 2 | COMe | H | H | H | Cl |
| 483 | 3 | COMe | H | H | H | Cl |
| 484 | 4 | COMe | H | H | H | Cl |
| 485 | 1 | $CO_2Me$ | H | H | H | Cl |
| 486 | 2 | $CO_2Me$ | H | H | H | Cl |
| 487 | 3 | $CO_2Me$ | H | H | H | Cl |
| 488 | 4 | $CO_2Me$ | H | H | H | Cl |
| 489 | 1 | $CO_2tBu$ | H | H | H | Cl |
| 490 | 2 | $CO_2tBu$ | H | H | H | Cl |
| 491 | 3 | $CO_2tBu$ | H | H | H | Cl |
| 492 | 4 | $CO_2tBu$ | H | H | H | Cl |
| 493 | 1 | CONHMe | H | H | H | Cl |
| 494 | 2 | CONHMe | H | H | H | Cl |
| 495 | 3 | CONHMe | H | H | H | Cl |
| 496 | 4 | CONHMe | H | H | H | Cl |
| 497 | 1 | $SO_2Me$ | H | H | H | Cl |
| 498 | 2 | $SO_2Me$ | H | H | H | Cl |
| 499 | 3 | $SO_2Me$ | H | H | H | Cl |
| 500 | 4 | $SO_2Me$ | H | H | H | Cl |
| 501 | 1 | $SO_2NH_2$ | H | H | H | Cl |
| 502 | 2 | $SO_2NH_2$ | H | H | H | Cl |
| 503 | 3 | $SO_2NH_2$ | H | H | H | Cl |
| 504 | 4 | $SO_2NH_2$ | H | H | H | Cl |
| 505 | 1 | H | H | H | H | CN |
| 506 | 2 | H | H | H | H | CN |
| 507 | 3 | H | H | H | H | CN |
| 508 | 4 | H | H | H | H | CN |
| 509 | 1 | Me | H | H | H | CN |
| 510 | 2 | Me | H | H | H | CN |
| 511 | 3 | Me | H | H | H | CN |
| 512 | 4 | Me | H | H | H | CN |
| 513 | 1 | $CH_2Ph$ | H | H | H | CN |
| 514 | 2 | $CH_2Ph$ | H | H | H | CN |
| 515 | 3 | $CH_2Ph$ | H | H | H | CN |
| 516 | 4 | $CH_2Ph$ | H | H | H | CN |
| 517 | 1 | COMe | H | H | H | CN |
| 518 | 2 | COMe | H | H | H | CN |
| 519 | 3 | COMe | H | H | H | CN |
| 520 | 4 | COMe | H | H | H | CN |
| 521 | 1 | $CO_2Me$ | H | H | H | CN |
| 522 | 2 | $CO_2Me$ | H | H | H | CN |
| 523 | 3 | $CO_2Me$ | H | H | H | CN |
| 524 | 4 | $CO_2Me$ | H | H | H | CN |
| 525 | 1 | $CO_2tBu$ | H | H | H | CN |
| 526 | 2 | $CO_2tBu$ | H | H | H | CN |
| 527 | 3 | $CO_2tBu$ | H | H | H | CN |

TABLE 27-continued

| Entry | n | $R^7$ | $R^{20a}$ | $R^{20b}$ | $R^{20d}$ | $R^{20e}$ |
|---|---|---|---|---|---|---|
| 528 | 4 | $CO_2tBu$ | H | H | H | CN |
| 529 | 1 | CONHMe | H | H | H | CN |
| 530 | 2 | CONHMe | H | H | H | CN |
| 531 | 3 | CONHMe | H | H | H | CN |
| 532 | 4 | CONHMe | H | H | H | CN |
| 533 | 1 | $SO_2Me$ | H | H | H | CN |
| 534 | 2 | $SO_2Me$ | H | H | H | CN |
| 535 | 3 | $SO_2Me$ | H | H | H | CN |
| 536 | 4 | $SO_2Me$ | H | H | H | CN |
| 537 | 1 | $SO_2NH_2$ | H | H | H | CN |
| 538 | 2 | $SO_2NH_2$ | H | H | H | CN |
| 539 | 3 | $SO_2NH_2$ | H | H | H | CN |
| 540 | 4 | $SO_2NH_2$ | H | H | H | CN |

Exemplary embodiments include compounds having the formula (XXXV)

(XXXV)

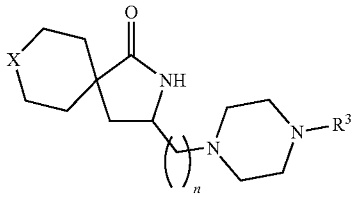

or a pharmaceutically acceptable salt form thereof defined herein below in Table 28.

TABLE 28

| Entry | n | X | $R^3$ |
|---|---|---|---|
| 1 | 1 | O | Phenyl |
| 2 | 2 | O | Phenyl |
| 3 | 3 | O | Phenyl |
| 4 | 4 | O | Phenyl |
| 5 | 1 | S | Phenyl |
| 6 | 2 | S | Phenyl |
| 7 | 3 | S | Phenyl |
| 8 | 4 | S | Phenyl |
| 9 | 1 | SO | Phenyl |
| 10 | 2 | SO | Phenyl |
| 11 | 3 | SO | Phenyl |
| 12 | 4 | SO | Phenyl |
| 13 | 1 | $SO_2$ | Phenyl |
| 14 | 2 | $SO_2$ | Phenyl |
| 15 | 3 | $SO_2$ | Phenyl |
| 16 | 4 | $SO_2$ | Phenyl |
| 17 | 1 | O | 3-OH-Phenyl |
| 18 | 2 | O | 3-OH-Phenyl |
| 19 | 3 | O | 3-OH-Phenyl |
| 20 | 4 | O | 3-OH-Phenyl |
| 21 | 1 | S | 3-OH-Phenyl |
| 22 | 2 | S | 3-OH-Phenyl |
| 23 | 3 | S | 3-OH-Phenyl |
| 24 | 4 | S | 3-OH-Phenyl |
| 25 | 1 | SO | 3-OH-Phenyl |
| 26 | 2 | SO | 3-OH-Phenyl |
| 27 | 3 | SO | 3-OH-Phenyl |
| 28 | 4 | SO | 3-OH-Phenyl |
| 29 | 1 | $SO_2$ | 3-OH-Phenyl |
| 30 | 2 | $SO_2$ | 3-OH-Phenyl |
| 31 | 3 | $SO_2$ | 3-OH-Phenyl |
| 32 | 4 | $SO_2$ | 3-OH-Phenyl |
| 33 | 1 | O | 4-$NO_2$-Phenyl |
| 34 | 2 | O | 4-$NO_2$-Phenyl |
| 35 | 3 | O | 4-$NO_2$-Phenyl |
| 36 | 4 | O | 4-$NO_2$-Phenyl |
| 37 | 1 | S | 4-$NO_2$-Phenyl |
| 38 | 2 | S | 4-$NO_2$-Phenyl |

TABLE 28-continued

| Entry | n | X | $R^3$ |
|---|---|---|---|
| 39 | 3 | S | 4-$NO_2$-Phenyl |
| 40 | 4 | S | 4-$NO_2$-Phenyl |
| 41 | 1 | SO | 4-$NO_2$-Phenyl |
| 42 | 2 | SO | 4-$NO_2$-Phenyl |
| 43 | 3 | SO | 4-$NO_2$-Phenyl |
| 44 | 4 | SO | 4-$NO_2$-Phenyl |
| 45 | 1 | $SO_2$ | 4-$NO_2$-Phenyl |
| 46 | 2 | $SO_2$ | 4-$NO_2$-Phenyl |
| 47 | 3 | $SO_2$ | 4-$NO_2$-Phenyl |
| 48 | 4 | $SO_2$ | 4-$NO_2$-Phenyl |
| 49 | 1 | O | 3-OMe-Phenyl |
| 50 | 2 | O | 3-OMe-Phenyl |
| 51 | 3 | O | 3-OMe-Phenyl |
| 52 | 4 | O | 3-OMe-Phenyl |
| 53 | 1 | S | 3-OMe-Phenyl |
| 54 | 2 | S | 3-OMe-Phenyl |
| 55 | 3 | S | 3-OMe-Phenyl |
| 56 | 4 | S | 3-OMe-Phenyl |
| 57 | 1 | SO | 3-OMe-Phenyl |
| 58 | 2 | SO | 3-OMe-Phenyl |
| 59 | 3 | SO | 3-OMe-Phenyl |
| 60 | 4 | SO | 3-OMe-Phenyl |
| 61 | 1 | $SO_2$ | 3-OMe-Phenyl |
| 62 | 2 | $SO_2$ | 3-OMe-Phenyl |
| 63 | 3 | $SO_2$ | 3-OMe-Phenyl |
| 64 | 4 | $SO_2$ | 3-OMe-Phenyl |
| 65 | 1 | O | 4-CN-Phenyl |
| 66 | 2 | O | 4-CN-Phenyl |
| 67 | 3 | O | 4-CN-Phenyl |
| 68 | 4 | O | 4-CN-Phenyl |
| 69 | 1 | S | 4-CN-Phenyl |
| 70 | 2 | S | 4-CN-Phenyl |
| 71 | 3 | S | 4-CN-Phenyl |
| 72 | 4 | S | 4-CN-Phenyl |
| 73 | 1 | SO | 4-CN-Phenyl |
| 74 | 2 | SO | 4-CN-Phenyl |
| 75 | 3 | SO | 4-CN-Phenyl |
| 76 | 4 | SO | 4-CN-Phenyl |
| 77 | 1 | $SO_2$ | 4-CN-Phenyl |
| 78 | 2 | $SO_2$ | 4-CN-Phenyl |
| 79 | 3 | $SO_2$ | 4-CN-Phenyl |
| 80 | 4 | $SO_2$ | 4-CN-Phenyl |
| 81 | 1 | O | 2-CN-Phenyl |
| 82 | 2 | O | 2-CN-Phenyl |
| 83 | 3 | O | 2-CN-Phenyl |
| 84 | 4 | O | 2-CN-Phenyl |
| 85 | 1 | S | 2-CN-Phenyl |
| 86 | 2 | S | 2-CN-Phenyl |
| 87 | 3 | S | 2-CN-Phenyl |
| 88 | 4 | S | 2-CN-Phenyl |
| 89 | 1 | SO | 2-CN-Phenyl |
| 90 | 2 | SO | 2-CN-Phenyl |
| 91 | 3 | SO | 2-CN-Phenyl |
| 92 | 4 | SO | 2-CN-Phenyl |
| 93 | 1 | $SO_2$ | 2-CN-Phenyl |
| 94 | 2 | $SO_2$ | 2-CN-Phenyl |
| 95 | 3 | $SO_2$ | 2-CN-Phenyl |
| 96 | 4 | $SO_2$ | 2-CN-Phenyl |
| 97 | 1 | O | 3-Me-Phenyl |
| 98 | 2 | O | 3-Me-Phenyl |
| 99 | 3 | O | 3-Me-Phenyl |
| 100 | 4 | O | 3-Me-Phenyl |
| 101 | 1 | S | 3-Me-Phenyl |
| 102 | 2 | S | 3-Me-Phenyl |
| 103 | 3 | S | 3-Me-Phenyl |
| 104 | 4 | S | 3-Me-Phenyl |
| 105 | 1 | SO | 3-Me-Phenyl |
| 106 | 2 | SO | 3-Me-Phenyl |
| 107 | 3 | SO | 3-Me-Phenyl |
| 108 | 4 | SO | 3-Me-Phenyl |
| 109 | 1 | $SO_2$ | 3-Me-Phenyl |
| 110 | 2 | $SO_2$ | 3-Me-Phenyl |
| 111 | 3 | $SO_2$ | 3-Me-Phenyl |
| 112 | 4 | $SO_2$ | 3-Me-Phenyl |
| 113 | 1 | O | 2-F-Phenyl |
| 114 | 2 | O | 2-F-Phenyl |
| 115 | 3 | O | 2-F-Phenyl |
| 116 | 4 | O | 2-F-Phenyl |

TABLE 28-continued

| Entry | n | X | $R^3$ |
|---|---|---|---|
| 117 | 1 | S | 2-F-Phenyl |
| 118 | 2 | S | 2-F-Phenyl |
| 119 | 3 | S | 2-F-Phenyl |
| 120 | 4 | S | 2-F-Phenyl |
| 121 | 1 | SO | 2-F-Phenyl |
| 122 | 2 | SO | 2-F-Phenyl |
| 123 | 3 | SO | 2-F-Phenyl |
| 124 | 4 | SO | 2-F-Phenyl |
| 125 | 1 | $SO_2$ | 2-F-Phenyl |
| 126 | 2 | $SO_2$ | 2-F-Phenyl |
| 127 | 3 | $SO_2$ | 2-F-Phenyl |
| 128 | 4 | $SO_2$ | 2-F-Phenyl |
| 129 | 1 | O | 4-F-Phenyl |
| 130 | 2 | O | 4-F-Phenyl |
| 131 | 3 | O | 4-F-Phenyl |
| 132 | 4 | O | 4-F-Phenyl |
| 133 | 1 | S | 4-F-Phenyl |
| 134 | 2 | S | 4-F-Phenyl |
| 135 | 3 | S | 4-F-Phenyl |
| 136 | 4 | S | 4-F-Phenyl |
| 137 | 1 | SO | 4-F-Phenyl |
| 138 | 2 | SO | 4-F-Phenyl |
| 139 | 3 | SO | 4-F-Phenyl |
| 140 | 4 | SO | 4-F-Phenyl |
| 141 | 1 | $SO_2$ | 4-F-Phenyl |
| 142 | 2 | $SO_2$ | 4-F-Phenyl |
| 143 | 3 | $SO_2$ | 4-F-Phenyl |
| 144 | 4 | $SO_2$ | 4-F-Phenyl |
| 145 | 1 | O | 3-Cl-Phenyl |
| 146 | 2 | O | 3-Cl-Phenyl |
| 147 | 3 | O | 3-Cl-Phenyl |
| 148 | 4 | O | 3-Cl-Phenyl |
| 149 | 1 | S | 3-Cl-Phenyl |
| 150 | 2 | S | 3-Cl-Phenyl |
| 151 | 3 | S | 3-Cl-Phenyl |
| 152 | 4 | S | 3-Cl-Phenyl |
| 153 | 1 | SO | 3-Cl-Phenyl |
| 154 | 2 | SO | 3-Cl-Phenyl |
| 155 | 3 | SO | 3-Cl-Phenyl |
| 156 | 4 | SO | 3-Cl-Phenyl |
| 157 | 1 | $SO_2$ | 3-Cl-Phenyl |
| 158 | 2 | $SO_2$ | 3-Cl-Phenyl |
| 159 | 3 | $SO_2$ | 3-Cl-Phenyl |
| 160 | 4 | $SO_2$ | 3-Cl-Phenyl |
| 161 | 1 | O | 2-Br-Phenyl |
| 162 | 2 | O | 2-Br-Phenyl |
| 163 | 3 | O | 2-Br-Phenyl |
| 164 | 4 | O | 2-Br-Phenyl |
| 165 | 1 | S | 2-Br-Phenyl |
| 166 | 2 | S | 2-Br-Phenyl |
| 167 | 3 | S | 2-Br-Phenyl |
| 168 | 4 | S | 2-Br-Phenyl |
| 169 | 1 | SO | 2-Br-Phenyl |
| 170 | 2 | SO | 2-Br-Phenyl |
| 171 | 3 | SO | 2-Br-Phenyl |
| 172 | 4 | SO | 2-Br-Phenyl |
| 173 | 1 | $SO_2$ | 2-Br-Phenyl |
| 174 | 2 | $SO_2$ | 2-Br-Phenyl |
| 175 | 3 | $SO_2$ | 2-Br-Phenyl |
| 176 | 4 | $SO_2$ | 2-Br-Phenyl |
| 177 | 1 | O | 4-Br-Phenyl |
| 178 | 2 | O | 4-Br-Phenyl |
| 179 | 3 | O | 4-Br-Phenyl |
| 180 | 4 | O | 4-Br-Phenyl |
| 181 | 1 | S | 4-Br-Phenyl |
| 182 | 2 | S | 4-Br-Phenyl |
| 183 | 3 | S | 4-Br-Phenyl |
| 184 | 4 | S | 4-Br-Phenyl |
| 185 | 1 | SO | 4-Br-Phenyl |
| 186 | 2 | SO | 4-Br-Phenyl |
| 187 | 3 | SO | 4-Br-Phenyl |
| 188 | 4 | SO | 4-Br-Phenyl |
| 189 | 1 | $SO_2$ | 4-Br-Phenyl |
| 190 | 2 | $SO_2$ | 4-Br-Phenyl |
| 191 | 3 | $SO_2$ | 4-Br-Phenyl |
| 192 | 4 | $SO_2$ | 4-Br-Phenyl |
| 193 | 1 | O | 3-$CF_3$-Phenyl |
| 194 | 2 | O | 3-$CF_3$-Phenyl |

TABLE 28-continued

| Entry | n | X | $R^3$ |
|---|---|---|---|
| 195 | 3 | O | 3-$CF_3$-Phenyl |
| 196 | 4 | O | 3-$CF_3$-Phenyl |
| 197 | 1 | S | 3-$CF_3$-Phenyl |
| 198 | 2 | S | 3-$CF_3$-Phenyl |
| 199 | 3 | S | 3-$CF_3$-Phenyl |
| 200 | 4 | S | 3-$CF_3$-Phenyl |
| 201 | 1 | SO | 3-$CF_3$-Phenyl |
| 202 | 2 | SO | 3-$CF_3$-Phenyl |
| 203 | 3 | SO | 3-$CF_3$-Phenyl |
| 204 | 4 | SO | 3-$CF_3$-Phenyl |
| 205 | 1 | $SO_2$ | 3-$CF_3$-Phenyl |
| 206 | 2 | $SO_2$ | 3-$CF_3$-Phenyl |
| 207 | 3 | $SO_2$ | 3-$CF_3$-Phenyl |
| 208 | 4 | $SO_2$ | 3-$CF_3$-Phenyl |
| 209 | 1 | O | 2-iPr-Phenyl |
| 210 | 2 | O | 2-iPr-Phenyl |
| 211 | 3 | O | 2-iPr-Phenyl |
| 212 | 4 | O | 2-iPr-Phenyl |
| 213 | 1 | S | 2-iPr-Phenyl |
| 214 | 2 | S | 2-iPr-Phenyl |
| 215 | 3 | S | 2-iPr-Phenyl |
| 216 | 4 | S | 2-iPr-Phenyl |
| 217 | 1 | SO | 2-iPr-Phenyl |
| 218 | 2 | SO | 2-iPr-Phenyl |
| 219 | 3 | SO | 2-iPr-Phenyl |
| 220 | 4 | SO | 2-iPr-Phenyl |
| 221 | 1 | $SO_2$ | 2-iPr-Phenyl |
| 222 | 2 | $SO_2$ | 2-iPr-Phenyl |
| 223 | 3 | $SO_2$ | 2-iPr-Phenyl |
| 224 | 4 | $SO_2$ | 2-iPr-Phenyl |
| 225 | 1 | O | 4-iPr-Phenyl |
| 226 | 2 | O | 4-iPr-Phenyl |
| 227 | 3 | O | 4-iPr-Phenyl |
| 228 | 4 | O | 4-iPr-Phenyl |
| 229 | 1 | S | 4-iPr-Phenyl |
| 230 | 2 | S | 4-iPr-Phenyl |
| 231 | 3 | S | 4-iPr-Phenyl |
| 232 | 4 | S | 4-iPr-Phenyl |
| 233 | 1 | SO | 4-iPr-Phenyl |
| 234 | 2 | SO | 4-iPr-Phenyl |
| 235 | 3 | SO | 4-iPr-Phenyl |
| 236 | 4 | SO | 4-iPr-Phenyl |
| 237 | 1 | $SO_2$ | 4-iPr-Phenyl |
| 238 | 2 | $SO_2$ | 4-iPr-Phenyl |
| 239 | 3 | $SO_2$ | 4-iPr-Phenyl |
| 240 | 4 | $SO_2$ | 4-iPr-Phenyl |
| 241 | 1 | O | 3-$NH_2$-Phenyl |
| 242 | 2 | O | 3-$NH_2$-Phenyl |
| 243 | 3 | O | 3-$NH_2$-Phenyl |
| 244 | 4 | O | 3-$NH_2$-Phenyl |
| 245 | 1 | S | 3-$NH_2$-Phenyl |
| 246 | 2 | S | 3-$NH_2$-Phenyl |
| 247 | 3 | S | 3-$NH_2$-Phenyl |
| 248 | 1 | S | 3-$NH_2$-Phenyl |
| 249 | 2 | SO | 3-$NH_2$-Phenyl |
| 250 | 3 | SO | 3-$NH_2$-Phenyl |
| 251 | 4 | SO | 3-$NH_2$-Phenyl |
| 252 | 1 | SO | 3-$NH_2$-Phenyl |
| 253 | 2 | $SO_2$ | 3-$NH_2$-Phenyl |
| 254 | 3 | $SO_2$ | 3-$NH_2$-Phenyl |
| 255 | 4 | $SO_2$ | 3-$NH_2$-Phenyl |
| 256 | 1 | O | 2,4-di-Me-Phenyl |
| 257 | 2 | O | 2,4-di-Me-Phenyl |
| 258 | 3 | O | 2,4-di-Me-Phenyl |
| 259 | 4 | O | 2,4-di-Me-Phenyl |
| 260 | 1 | S | 2,4-di-Me-Phenyl |
| 261 | 2 | S | 2,4-di-Me-Phenyl |
| 262 | 3 | S | 2,4-di-Me-Phenyl |
| 263 | 4 | S | 2,4-di-Me-Phenyl |
| 264 | 1 | SO | 2,4-di-Me-Phenyl |
| 265 | 2 | SO | 2,4-di-Me-Phenyl |
| 266 | 3 | SO | 2,4-di-Me-Phenyl |
| 267 | 4 | SO | 2,4-di-Me-Phenyl |
| 268 | 1 | $SO_2$ | 2,4-di-Me-Phenyl |
| 269 | 2 | $SO_2$ | 2,4-di-Me-Phenyl |
| 270 | 3 | $SO_2$ | 2,4-di-Me-Phenyl |
| 271 | 4 | $SO_2$ | 2,4-di-Me-Phenyl |
| 272 | 1 | O | 2,6-di-iPr-Phenyl |

TABLE 28-continued

| Entry | n | X | $R^3$ |
|---|---|---|---|
| 273 | 2 | O | 2,6-di-iPr-Phenyl |
| 274 | 3 | O | 2,6-di-iPr-Phenyl |
| 275 | 4 | O | 2,6-di-iPr-Phenyl |
| 276 | 1 | S | 2,6-di-iPr-Phenyl |
| 277 | 2 | S | 2,6-di-iPr-Phenyl |
| 278 | 3 | S | 2,6-di-iPr-Phenyl |
| 279 | 4 | S | 2,6-di-iPr-Phenyl |
| 280 | 1 | SO | 2,6-di-iPr-Phenyl |
| 281 | 2 | SO | 2,6-di-iPr-Phenyl |
| 282 | 3 | SO | 2,6-di-iPr-Phenyl |
| 283 | 4 | SO | 2,6-di-iPr-Phenyl |
| 284 | 1 | $SO_2$ | 2,6-di-iPr-Phenyl |
| 285 | 2 | $SO_2$ | 2,6-di-iPr-Phenyl |
| 286 | 3 | $SO_2$ | 2,6-di-iPr-Phenyl |
| 287 | 4 | $SO_2$ | 2,6-di-iPr-Phenyl |
| 288 | 1 | O | 3-Ph-Phenyl |
| 289 | 2 | O | 3-Ph-Phenyl |
| 290 | 3 | O | 3-Ph-Phenyl |
| 291 | 4 | O | 3-Ph-Phenyl |
| 292 | 1 | S | 3-Ph-Phenyl |
| 293 | 2 | S | 3-Ph-Phenyl |
| 294 | 3 | S | 3-Ph-Phenyl |
| 295 | 4 | S | 3-Ph-Phenyl |
| 296 | 1 | SO | 3-Ph-Phenyl |
| 297 | 2 | SO | 3-Ph-Phenyl |
| 298 | 3 | SO | 3-Ph-Phenyl |
| 299 | 4 | SO | 3-Ph-Phenyl |
| 300 | 1 | $SO_2$ | 3-Ph-Phenyl |
| 301 | 2 | $SO_2$ | 3-Ph-Phenyl |
| 302 | 3 | $SO_2$ | 3-Ph-Phenyl |
| 303 | 4 | $SO_2$ | 3-Ph-Phenyl |
| 304 | 1 | O | 2-morpholino-phenyl |
| 305 | 2 | O | 2-morpholino-phenyl |
| 306 | 3 | O | 2-morpholino-phenyl |
| 307 | 4 | O | 2-morpholino-phenyl |
| 308 | 1 | S | 2-morpholino-phenyl |
| 309 | 2 | S | 2-morpholino-phenyl |
| 310 | 3 | S | 2-morpholino-phenyl |
| 311 | 4 | S | 2-morpholino-phenyl |
| 312 | 1 | SO | 2-morpholino-phenyl |
| 313 | 2 | SO | 2-morpholino-phenyl |
| 314 | 3 | SO | 2-morpholino-phenyl |
| 315 | 4 | SO | 2-morpholino-phenyl |
| 316 | 1 | $SO_2$ | 2-morpholino-phenyl |
| 317 | 2 | $SO_2$ | 2-morpholino-phenyl |
| 318 | 3 | $SO_2$ | 2-morpholino-phenyl |
| 319 | 4 | $SO_2$ | 2-morpholino-phenyl |
| 320 | 1 | O | 4-morpholino-phenyl |
| 321 | 2 | O | 4-morpholino-phenyl |
| 322 | 3 | O | 4-morpholino-phenyl |
| 323 | 4 | O | 4-morpholino-phenyl |
| 324 | 1 | SO | 4-morpholino-phenyl |
| 325 | 2 | SO | 4-morpholino-phenyl |
| 326 | 3 | SO | 4-morpholino-phenyl |
| 327 | 4 | SO | 4-morpholino-phenyl |
| 328 | 1 | O | naphthylen-1-yl |
| 329 | 2 | O | naphthylen-1-yl |
| 330 | 3 | O | naphthylen-1-yl |
| 331 | 4 | O | naphthylen-1-yl |
| 332 | 1 | S | naphthylen-1-yl |
| 333 | 2 | S | naphthylen-1-yl |
| 334 | 3 | S | naphthylen-1-yl |
| 335 | 4 | S | naphthylen-1-yl |
| 336 | 1 | SO | naphthylen-1-yl |
| 337 | 2 | SO | naphthylen-1-yl |
| 338 | 3 | SO | naphthylen-1-yl |
| 339 | 4 | SO | naphthylen-1-yl |
| 340 | 1 | $SO_2$ | naphthylen-1-yl |
| 341 | 2 | $SO_2$ | naphthylen-1-yl |
| 342 | 3 | $SO_2$ | naphthylen-1-yl |
| 343 | 4 | $SO_2$ | naphthylen-1-yl |
| 344 | 1 | O | 4-OH-Phenyl |
| 345 | 2 | O | 4-OH-Phenyl |
| 346 | 3 | O | 4-OH-Phenyl |
| 347 | 4 | O | 4-OH-Phenyl |
| 348 | 1 | S | 4-OH-Phenyl |
| 349 | 2 | S | 4-OH-Phenyl |
| 350 | 3 | S | 4-OH-Phenyl |

TABLE 28-continued

| Entry | n | X | $R^3$ |
|---|---|---|---|
| 351 | 4 | S | 4-OH-Phenyl |
| 352 | 1 | SO | 4-OH-Phenyl |
| 353 | 2 | SO | 4-OH-Phenyl |
| 354 | 3 | SO | 4-OH-Phenyl |
| 355 | 4 | SO | 4-OH-Phenyl |
| 356 | 1 | $SO_2$ | 4-OH-Phenyl |
| 357 | 2 | $SO_2$ | 4-OH-Phenyl |
| 358 | 3 | $SO_2$ | 4-OH-Phenyl |
| 359 | 4 | $SO_2$ | 4-OH-Phenyl |
| 360 | 1 | O | 2-OH-Phenyl |
| 361 | 2 | O | 2-OH-Phenyl |
| 362 | 3 | O | 2-OH-Phenyl |
| 363 | 4 | O | 2-OH-Phenyl |
| 364 | 1 | S | 2-OH-Phenyl |
| 365 | 2 | S | 2-OH-Phenyl |
| 366 | 3 | S | 2-OH-Phenyl |
| 367 | 4 | S | 2-OH-Phenyl |
| 368 | 1 | SO | 2-OH-Phenyl |
| 369 | 2 | SO | 2-OH-Phenyl |
| 370 | 3 | SO | 2-OH-Phenyl |
| 371 | 4 | SO | 2-OH-Phenyl |
| 372 | 1 | $SO_2$ | 2-OH-Phenyl |
| 373 | 2 | $SO_2$ | 2-OH-Phenyl |
| 374 | 3 | $SO_2$ | 2-OH-Phenyl |
| 375 | 4 | $SO_2$ | 2-OH-Phenyl |
| 376 | 1 | O | 4-OMe-Phenyl |
| 377 | 2 | O | 4-OMe-Phenyl |
| 378 | 3 | O | 4-OMe-Phenyl |
| 379 | 4 | O | 4-OMe-Phenyl |
| 380 | 1 | S | 4-OMe-Phenyl |
| 381 | 2 | S | 4-OMe-Phenyl |
| 382 | 3 | S | 4-OMe-Phenyl |
| 383 | 4 | S | 4-OMe-Phenyl |
| 384 | 1 | SO | 4-OMe-Phenyl |
| 385 | 2 | SO | 4-OMe-Phenyl |
| 386 | 3 | SO | 4-OMe-Phenyl |
| 387 | 4 | SO | 4-OMe-Phenyl |
| 388 | 1 | $SO_2$ | 4-OMe-Phenyl |
| 389 | 2 | $SO_2$ | 4-OMe-Phenyl |
| 390 | 3 | $SO_2$ | 4-OMe-Phenyl |
| 391 | 4 | $SO_2$ | 4-OMe-Phenyl |
| 392 | 1 | O | 2-OMe-Phenyl |
| 393 | 2 | O | 2-OMe-Phenyl |
| 394 | 3 | O | 2-OMe-Phenyl |
| 395 | 4 | O | 2-OMe-Phenyl |
| 396 | 1 | S | 2-OMe-Phenyl |
| 397 | 2 | S | 2-OMe-Phenyl |
| 398 | 3 | S | 2-OMe-Phenyl |
| 399 | 4 | S | 2-OMe-Phenyl |
| 400 | 1 | SO | 2-OMe-Phenyl |
| 401 | 2 | SO | 2-OMe-Phenyl |
| 402 | 3 | SO | 2-OMe-Phenyl |
| 403 | 4 | SO | 2-OMe-Phenyl |
| 404 | 1 | $SO_2$ | 2-OMe-Phenyl |
| 405 | 2 | $SO_2$ | 2-OMe-Phenyl |
| 406 | 3 | $SO_2$ | 2-OMe-Phenyl |
| 407 | 4 | $SO_2$ | 2-OMe-Phenyl |
| 408 | 1 | O | 3-CN-Phenyl |
| 409 | 2 | O | 3-CN-Phenyl |
| 410 | 3 | O | 3-CN-Phenyl |
| 411 | 4 | O | 3-CN-Phenyl |
| 412 | 1 | S | 3-CN-Phenyl |
| 413 | 2 | S | 3-CN-Phenyl |
| 414 | 3 | S | 3-CN-Phenyl |
| 415 | 4 | S | 3-CN-Phenyl |
| 416 | 1 | SO | 3-CN-Phenyl |
| 417 | 2 | SO | 3-CN-Phenyl |
| 418 | 3 | SO | 3-CN-Phenyl |
| 419 | 4 | SO | 3-CN-Phenyl |
| 420 | 1 | $SO_2$ | 3-CN-Phenyl |
| 421 | 2 | $SO_2$ | 3-CN-Phenyl |
| 422 | 3 | $SO_2$ | 3-CN-Phenyl |
| 423 | 4 | $SO_2$ | 3-CN-Phenyl |
| 424 | 1 | O | 2-Me-Phenyl |
| 425 | 2 | O | 2-Me-Phenyl |
| 426 | 3 | O | 2-Me-Phenyl |
| 427 | 4 | O | 2-Me-Phenyl |
| 428 | 1 | S | 2-Me-Phenyl |
| 429 | 2 | S | 2-Me-Phenyl |
| 430 | 3 | S | 2-Me-Phenyl |
| 431 | 4 | S | 2-Me-Phenyl |
| 432 | 1 | SO | 2-Me-Phenyl |
| 433 | 2 | SO | 2-Me-Phenyl |
| 434 | 3 | SO | 2-Me-Phenyl |
| 435 | 4 | SO | 2-Me-Phenyl |
| 436 | 1 | $SO_2$ | 2-Me-Phenyl |
| 437 | 2 | $SO_2$ | 2-Me-Phenyl |
| 438 | 3 | $SO_2$ | 2-Me-Phenyl |
| 439 | 4 | $SO_2$ | 2-Me-Phenyl |
| 440 | 1 | O | 4-Me-Phenyl |
| 441 | 2 | O | 4-Me-Phenyl |
| 442 | 3 | O | 4-Me-Phenyl |
| 443 | 4 | O | 4-Me-Phenyl |
| 444 | 1 | S | 4-Me-Phenyl |
| 445 | 2 | S | 4-Me-Phenyl |
| 446 | 3 | S | 4-Me-Phenyl |
| 447 | 4 | S | 4-Me-Phenyl |
| 448 | 1 | SO | 4-Me-Phenyl |
| 449 | 2 | SO | 4-Me-Phenyl |
| 450 | 3 | SO | 4-Me-Phenyl |
| 451 | 4 | SO | 4-Me-Phenyl |
| 452 | 1 | $SO_2$ | 4-Me-Phenyl |
| 453 | 2 | $SO_2$ | 4-Me-Phenyl |
| 454 | 3 | $SO_2$ | 4-Me-Phenyl |
| 455 | 4 | $SO_2$ | 4-Me-Phenyl |
| 456 | 1 | O | 3-F-Phenyl |
| 457 | 2 | O | 3-F-Phenyl |
| 458 | 3 | O | 3-F-Phenyl |
| 459 | 4 | O | 3-F-Phenyl |
| 460 | 1 | S | 3-F-Phenyl |
| 461 | 2 | S | 3-F-Phenyl |
| 462 | 3 | S | 3-F-Phenyl |
| 463 | 4 | S | 3-F-Phenyl |
| 464 | 1 | SO | 3-F-Phenyl |
| 465 | 2 | SO | 3-F-Phenyl |
| 466 | 3 | SO | 3-F-Phenyl |
| 467 | 4 | SO | 3-F-Phenyl |
| 468 | 1 | $SO_2$ | 3-F-Phenyl |
| 469 | 2 | $SO_2$ | 3-F-Phenyl |
| 470 | 3 | $SO_2$ | 3-F-Phenyl |
| 471 | 4 | $SO_2$ | 3-F-Phenyl |
| 472 | 1 | O | 2-Cl-Phenyl |
| 473 | 2 | O | 2-Cl-Phenyl |
| 474 | 3 | O | 2-Cl-Phenyl |
| 475 | 4 | O | 2-Cl-Phenyl |
| 476 | 1 | S | 2-Cl-Phenyl |
| 477 | 2 | S | 2-Cl-Phenyl |
| 478 | 3 | S | 2-Cl-Phenyl |
| 479 | 4 | S | 2-Cl-Phenyl |
| 480 | 1 | SO | 2-Cl-Phenyl |
| 481 | 2 | SO | 2-Cl-Phenyl |
| 482 | 3 | SO | 2-Cl-Phenyl |
| 483 | 4 | SO | 2-Cl-Phenyl |
| 484 | 1 | $SO_2$ | 2-Cl-Phenyl |
| 485 | 2 | $SO_2$ | 2-Cl-Phenyl |
| 486 | 3 | $SO_2$ | 2-Cl-Phenyl |
| 487 | 4 | $SO_2$ | 2-Cl-Phenyl |
| 488 | 1 | O | 4-Cl-Phenyl |
| 489 | 2 | O | 4-Cl-Phenyl |
| 490 | 3 | O | 4-Cl-Phenyl |
| 491 | 4 | O | 4-Cl-Phenyl |
| 492 | 1 | S | 4-Cl-Phenyl |
| 493 | 2 | S | 4-Cl-Phenyl |
| 494 | 3 | S | 4-Cl-Phenyl |
| 495 | 4 | S | 4-Cl-Phenyl |
| 496 | 1 | SO | 4-Cl-Phenyl |
| 497 | 2 | SO | 4-Cl-Phenyl |
| 498 | 3 | SO | 4-Cl-Phenyl |
| 499 | 4 | SO | 4-Cl-Phenyl |
| 500 | 1 | $SO_2$ | 4-Cl-Phenyl |
| 501 | 2 | $SO_2$ | 4-Cl-Phenyl |
| 502 | 3 | $SO_2$ | 4-Cl-Phenyl |
| 503 | 4 | $SO_2$ | 4-Cl-Phenyl |
| 504 | 1 | O | 3-Br-Phenyl |
| 505 | 2 | O | 3-Br-Phenyl |
| 506 | 3 | O | 3-Br-Phenyl |

TABLE 28-continued

| Entry | n | X | $R^3$ |
|---|---|---|---|
| 507 | 4 | O | 3-Br-Phenyl |
| 508 | 1 | S | 3-Br-Phenyl |
| 509 | 2 | S | 3-Br-Phenyl |
| 510 | 3 | S | 3-Br-Phenyl |
| 511 | 4 | S | 3-Br-Phenyl |
| 512 | 1 | SO | 3-Br-Phenyl |
| 513 | 2 | SO | 3-Br-Phenyl |
| 514 | 3 | SO | 3-Br-Phenyl |
| 515 | 4 | SO | 3-Br-Phenyl |
| 516 | 1 | $SO_2$ | 3-Br-Phenyl |
| 517 | 2 | $SO_2$ | 3-Br-Phenyl |
| 518 | 3 | $SO_2$ | 3-Br-Phenyl |
| 519 | 4 | $SO_2$ | 3-Br-Phenyl |
| 520 | 1 | O | 2-$CF_3$-Phenyl |
| 521 | 2 | O | 2-$CF_3$-Phenyl |
| 522 | 3 | O | 2-$CF_3$-Phenyl |
| 523 | 4 | O | 2-$CF_3$-Phenyl |
| 524 | 1 | S | 2-$CF_3$-Phenyl |
| 525 | 2 | S | 2-$CF_3$-Phenyl |
| 526 | 3 | S | 2-$CF_3$-Phenyl |
| 527 | 4 | S | 2-$CF_3$-Phenyl |
| 528 | 1 | SO | 2-$CF_3$-Phenyl |
| 529 | 2 | SO | 2-$CF_3$-Phenyl |
| 530 | 3 | SO | 2-$CF_3$-Phenyl |
| 531 | 4 | SO | 2-$CF_3$-Phenyl |
| 532 | 1 | $SO_2$ | 2-$CF_3$-Phenyl |
| 533 | 2 | $SO_2$ | 2-$CF_3$-Phenyl |
| 534 | 3 | $SO_2$ | 2-$CF_3$-Phenyl |
| 535 | 4 | $SO_2$ | 2-$CF_3$-Phenyl |
| 536 | 1 | O | 4-$CF_3$-Phenyl |
| 537 | 2 | O | 4-$CF_3$-Phenyl |
| 538 | 3 | O | 4-$CF_3$-Phenyl |
| 539 | 4 | O | 4-$CF_3$-Phenyl |
| 540 | 1 | S | 4-$CF_3$-Phenyl |
| 541 | 2 | S | 4-$CF_3$-Phenyl |
| 542 | 3 | S | 4-$CF_3$-Phenyl |
| 543 | 4 | S | 4-$CF_3$-Phenyl |
| 544 | 1 | SO | 4-$CF_3$-Phenyl |
| 545 | 2 | SO | 4-$CF_3$-Phenyl |
| 546 | 3 | SO | 4-$CF_3$-Phenyl |
| 547 | 4 | SO | 4-$CF_3$-Phenyl |
| 548 | 1 | $SO_2$ | 4-$CF_3$-Phenyl |
| 549 | 2 | $SO_2$ | 4-$CF_3$-Phenyl |
| 550 | 3 | $SO_2$ | 4-$CF_3$-Phenyl |
| 551 | 4 | $SO_2$ | 4-$CF_3$-Phenyl |
| 552 | 1 | O | 3-iPr-Phenyl |
| 553 | 2 | O | 3-iPr-Phenyl |
| 554 | 3 | O | 3-iPr-Phenyl |
| 555 | 4 | O | 3-iPr-Phenyl |
| 556 | 1 | S | 3-iPr-Phenyl |
| 557 | 2 | S | 3-iPr-Phenyl |
| 558 | 3 | S | 3-iPr-Phenyl |
| 559 | 4 | S | 3-iPr-Phenyl |
| 560 | 1 | SO | 3-iPr-Phenyl |
| 561 | 2 | SO | 3-iPr-Phenyl |
| 562 | 3 | SO | 3-iPr-Phenyl |
| 563 | 4 | SO | 3-iPr-Phenyl |
| 564 | 1 | $SO_2$ | 3-iPr-Phenyl |
| 565 | 2 | $SO_2$ | 3-iPr-Phenyl |
| 566 | 3 | $SO_2$ | 3-iPr-Phenyl |
| 567 | 4 | $SO_2$ | 3-iPr-Phenyl |
| 568 | 1 | O | 4-$NH_2$-Phenyl |
| 569 | 2 | O | 4-$NH_2$-Phenyl |
| 570 | 3 | O | 4-$NH_2$-Phenyl |
| 571 | 4 | O | 4-$NH_2$-Phenyl |
| 572 | 1 | S | 4-$NH_2$-Phenyl |
| 573 | 2 | S | 4-$NH_2$-Phenyl |
| 574 | 3 | S | 4-$NH_2$-Phenyl |
| 575 | 4 | S | 4-$NH_2$-Phenyl |
| 576 | 1 | SO | 4-$NH_2$-Phenyl |
| 577 | 2 | SO | 4-$NH_2$-Phenyl |
| 578 | 3 | SO | 4-$NH_2$-Phenyl |
| 579 | 4 | SO | 4-$NH_2$-Phenyl |
| 580 | 1 | $SO_2$ | 4-$NH_2$-Phenyl |
| 581 | 2 | $SO_2$ | 4-$NH_2$-Phenyl |
| 582 | 3 | $SO_2$ | 4-$NH_2$-Phenyl |
| 583 | 4 | $SO_2$ | 4-$NH_2$-Phenyl |
| 584 | 1 | O | 2-$NH_2$-Phenyl |
| 585 | 2 | O | 2-$NH_2$-Phenyl |
| 586 | 3 | O | 2-$NH_2$-Phenyl |
| 587 | 4 | O | 2-$NH_2$-Phenyl |
| 588 | 1 | S | 2-$NH_2$-Phenyl |
| 589 | 2 | S | 2-$NH_2$-Phenyl |
| 590 | 3 | S | 2-$NH_2$-Phenyl |
| 591 | 1 | S | 2-$NH_2$-Phenyl |
| 592 | 2 | SO | 2-$NH_2$-Phenyl |
| 593 | 3 | SO | 2-$NH_2$-Phenyl |
| 594 | 4 | SO | 2-$NH_2$-Phenyl |
| 595 | 1 | SO | 2-$NH_2$-Phenyl |
| 596 | 2 | $SO_2$ | 2-$NH_2$-Phenyl |
| 597 | 3 | $SO_2$ | 2-$NH_2$-Phenyl |
| 598 | 4 | $SO_2$ | 2-$NH_2$-Phenyl |
| 599 | 1 | O | 2,6-di-Me-Phenyl |
| 600 | 2 | O | 2,6-di-Me-Phenyl |
| 601 | 3 | O | 2,6-di-Me-Phenyl |
| 602 | 4 | O | 2,6-di-Me-Phenyl |
| 603 | 1 | S | 2,6-di-Me-Phenyl |
| 604 | 2 | S | 2,6-di-Me-Phenyl |
| 605 | 3 | S | 2,6-di-Me-Phenyl |
| 606 | 4 | S | 2,6-di-Me-Phenyl |
| 607 | 1 | SO | 2,6-di-Me-Phenyl |
| 608 | 2 | SO | 2,6-di-Me-Phenyl |
| 609 | 3 | SO | 2,6-di-Me-Phenyl |
| 610 | 4 | SO | 2,6-di-Me-Phenyl |
| 611 | 1 | $SO_2$ | 2,6-di-Me-Phenyl |
| 612 | 2 | $SO_2$ | 2,6-di-Me-Phenyl |
| 613 | 3 | $SO_2$ | 2,6-di-Me-Phenyl |
| 614 | 4 | $SO_2$ | 2,6-di-Me-Phenyl |
| 615 | 1 | O | 2-Ph-Phenyl |
| 616 | 2 | O | 2-Ph-Phenyl |
| 617 | 3 | O | 2-Ph-Phenyl |
| 618 | 4 | O | 2-Ph-Phenyl |
| 619 | 1 | S | 2-Ph-Phenyl |
| 620 | 2 | S | 2-Ph-Phenyl |
| 621 | 3 | S | 2-Ph-Phenyl |
| 622 | 4 | S | 2-Ph-Phenyl |
| 623 | 1 | SO | 2-Ph-Phenyl |
| 624 | 2 | SO | 2-Ph-Phenyl |
| 625 | 3 | SO | 2-Ph-Phenyl |
| 626 | 4 | SO | 2-Ph-Phenyl |
| 627 | 1 | $SO_2$ | 2-Ph-Phenyl |
| 628 | 2 | $SO_2$ | 2-Ph-Phenyl |
| 629 | 3 | $SO_2$ | 2-Ph-Phenyl |
| 630 | 4 | $SO_2$ | 2-Ph-Phenyl |
| 631 | 1 | O | 4-Ph-Phenyl |
| 632 | 2 | O | 4-Ph-Phenyl |
| 633 | 3 | O | 4-Ph-Phenyl |
| 634 | 4 | O | 4-Ph-Phenyl |
| 635 | 1 | S | 4-Ph-Phenyl |
| 636 | 2 | S | 4-Ph-Phenyl |
| 637 | 3 | S | 4-Ph-Phenyl |
| 638 | 4 | S | 4-Ph-Phenyl |
| 639 | 1 | SO | 4-Ph-Phenyl |
| 640 | 2 | SO | 4-Ph-Phenyl |
| 641 | 3 | SO | 4-Ph-Phenyl |
| 642 | 4 | SO | 4-Ph-Phenyl |
| 643 | 1 | $SO_2$ | 4-Ph-Phenyl |
| 644 | 2 | $SO_2$ | 4-Ph-Phenyl |
| 645 | 3 | $SO_2$ | 4-Ph-Phenyl |
| 646 | 4 | $SO_2$ | 4-Ph-Phenyl |
| 647 | 1 | O | 3-morpholino-phenyl |
| 648 | 2 | O | 3-morpholino-phenyl |
| 649 | 3 | O | 3-morpholino-phenyl |
| 650 | 4 | O | 3-morpholino-phenyl |
| 651 | 1 | S | 3-morpholino-phenyl |
| 652 | 2 | S | 3-morpholino-phenyl |
| 653 | 3 | S | 3-morpholino-phenyl |
| 654 | 4 | S | 3-morpholino-phenyl |
| 655 | 1 | SO | 3-morpholino-phenyl |
| 656 | 2 | SO | 3-morpholino-phenyl |
| 657 | 3 | SO | 3-morpholino-phenyl |
| 658 | 4 | SO | 3-morpholino-phenyl |
| 659 | 1 | $SO_2$ | 3-morpholino-phenyl |
| 660 | 2 | $SO_2$ | 3-morpholino-phenyl |
| 661 | 3 | $SO_2$ | 3-morpholino-phenyl |
| 662 | 4 | $SO_2$ | 3-morpholino-phenyl |

TABLE 28-continued

| Entry | n | X | $R^3$ |
|---|---|---|---|
| 663 | 1 | S | 4-morpholino-phenyl |
| 664 | 2 | S | 4-morpholino-phenyl |
| 665 | 3 | S | 4-morpholino-phenyl |
| 667 | 4 | S | 4-morpholino-phenyl |
| 668 | 1 | $SO_2$ | 4-morpholino-phenyl |
| 669 | 2 | $SO_2$ | 4-morpholino-phenyl |
| 670 | 3 | $SO_2$ | 4-morpholino-phenyl |
| 671 | 4 | $SO_2$ | 4-morpholino-phenyl |
| 672 | 1 | O | naphthylen-2-yl |
| 673 | 2 | O | naphthylen-2-yl |
| 674 | 3 | O | naphthylen-2-yl |
| 675 | 4 | O | naphthylen-2-yl |
| 676 | 1 | S | naphthylen-2-yl |
| 678 | 2 | S | naphthylen-2-yl |
| 679 | 3 | S | naphthylen-2-yl |
| 680 | 4 | S | naphthylen-2-yl |
| 681 | 1 | SO | naphthylen-2-yl |
| 682 | 2 | SO | naphthylen-2-yl |
| 683 | 3 | SO | naphthylen-2-yl |
| 684 | 4 | SO | naphthylen-2-yl |
| 685 | 1 | $SO_2$ | naphthylen-2-yl |
| 686 | 2 | $SO_2$ | naphthylen-2-yl |
| 687 | 3 | $SO_2$ | naphthylen-2-yl |
| 688 | 4 | $SO_2$ | naphthylen-2-yl |

Exemplary embodiments include compounds having the formula (XXXVI)

(XXXVI)

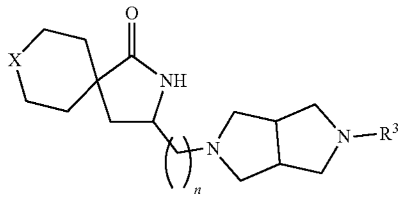

or a pharmaceutically acceptable salt form thereof defined herein below in Table 29.

TABLE 29

| Entry | n | X | $R^3$ |
|---|---|---|---|
| 1 | 1 | O | Phenyl |
| 2 | 2 | O | Phenyl |
| 3 | 3 | O | Phenyl |
| 4 | 4 | O | Phenyl |
| 5 | 1 | S | Phenyl |
| 6 | 2 | S | Phenyl |
| 7 | 3 | S | Phenyl |
| 8 | 4 | S | Phenyl |
| 9 | 1 | SO | Phenyl |
| 10 | 2 | SO | Phenyl |
| 11 | 3 | SO | Phenyl |
| 12 | 4 | SO | Phenyl |
| 13 | 1 | $SO_2$ | Phenyl |
| 14 | 2 | $SO_2$ | Phenyl |
| 15 | 3 | $SO_2$ | Phenyl |
| 16 | 4 | $SO_2$ | Phenyl |
| 17 | 1 | O | 3-OH-Phenyl |
| 18 | 2 | O | 3-OH-Phenyl |
| 19 | 3 | O | 3-OH-Phenyl |
| 20 | 4 | O | 3-OH-Phenyl |
| 21 | 1 | S | 3-OH-Phenyl |
| 22 | 2 | S | 3-OH-Phenyl |
| 23 | 3 | S | 3-OH-Phenyl |
| 24 | 4 | S | 3-OH-Phenyl |
| 25 | 1 | SO | 3-OH-Phenyl |
| 26 | 2 | SO | 3-OH-Phenyl |
| 27 | 3 | SO | 3-OH-Phenyl |

TABLE 29-continued

| Entry | n | X | $R^3$ |
|---|---|---|---|
| 28 | 4 | SO | 3-OH-Phenyl |
| 29 | 1 | $SO_2$ | 3-OH-Phenyl |
| 30 | 2 | $SO_2$ | 3-OH-Phenyl |
| 31 | 3 | $SO_2$ | 3-OH-Phenyl |
| 32 | 4 | $SO_2$ | 3-OH-Phenyl |
| 33 | 1 | O | 4-$NO_2$-Phenyl |
| 34 | 2 | O | 4-$NO_2$-Phenyl |
| 35 | 3 | O | 4-$NO_2$-Phenyl |
| 36 | 4 | O | 4-$NO_2$-Phenyl |
| 37 | 1 | S | 4-$NO_2$-Phenyl |
| 38 | 2 | S | 4-$NO_2$-Phenyl |
| 39 | 3 | S | 4-$NO_2$-Phenyl |
| 40 | 4 | S | 4-$NO_2$-Phenyl |
| 41 | 1 | SO | 4-$NO_2$-Phenyl |
| 42 | 2 | SO | 4-$NO_2$-Phenyl |
| 43 | 3 | SO | 4-$NO_2$-Phenyl |
| 44 | 4 | SO | 4-$NO_2$-Phenyl |
| 45 | 1 | $SO_2$ | 4-$NO_2$-Phenyl |
| 46 | 2 | $SO_2$ | 4-$NO_2$-Phenyl |
| 47 | 3 | $SO_2$ | 4-$NO_2$-Phenyl |
| 48 | 4 | $SO_2$ | 4-$NO_2$-Phenyl |
| 49 | 1 | O | 3-OMe-Phenyl |
| 50 | 2 | O | 3-OMe-Phenyl |
| 51 | 3 | O | 3-OMe-Phenyl |
| 52 | 4 | O | 3-OMe-Phenyl |
| 53 | 1 | S | 3-OMe-Phenyl |
| 54 | 2 | S | 3-OMe-Phenyl |
| 55 | 3 | S | 3-OMe-Phenyl |
| 56 | 4 | S | 3-OMe-Phenyl |
| 57 | 1 | SO | 3-OMe-Phenyl |
| 58 | 2 | SO | 3-OMe-Phenyl |
| 59 | 3 | SO | 3-OMe-Phenyl |
| 60 | 4 | SO | 3-OMe-Phenyl |
| 61 | 1 | $SO_2$ | 3-OMe-Phenyl |
| 62 | 2 | $SO_2$ | 3-OMe-Phenyl |
| 63 | 3 | $SO_2$ | 3-OMe-Phenyl |
| 64 | 4 | $SO_2$ | 3-OMe-Phenyl |
| 65 | 1 | O | 4-CN-Phenyl |
| 66 | 2 | O | 4-CN-Phenyl |
| 67 | 3 | O | 4-CN-Phenyl |
| 68 | 4 | O | 4-CN-Phenyl |
| 69 | 1 | S | 4-CN-Phenyl |
| 70 | 2 | S | 4-CN-Phenyl |
| 71 | 3 | S | 4-CN-Phenyl |
| 72 | 4 | S | 4-CN-Phenyl |
| 73 | 1 | SO | 4-CN-Phenyl |
| 74 | 2 | SO | 4-CN-Phenyl |
| 75 | 3 | SO | 4-CN-Phenyl |
| 76 | 4 | SO | 4-CN-Phenyl |
| 77 | 1 | $SO_2$ | 4-CN-Phenyl |
| 78 | 2 | $SO_2$ | 4-CN-Phenyl |
| 79 | 3 | $SO_2$ | 4-CN-Phenyl |
| 80 | 4 | $SO_2$ | 4-CN-Phenyl |
| 81 | 1 | O | 2-CN-Phenyl |
| 82 | 2 | O | 2-CN-Phenyl |
| 83 | 3 | O | 2-CN-Phenyl |
| 84 | 4 | O | 2-CN-Phenyl |
| 85 | 1 | S | 2-CN-Phenyl |
| 86 | 2 | S | 2-CN-Phenyl |
| 87 | 3 | S | 2-CN-Phenyl |
| 88 | 4 | S | 2-CN-Phenyl |
| 89 | 1 | SO | 2-CN-Phenyl |
| 90 | 2 | SO | 2-CN-Phenyl |
| 91 | 3 | SO | 2-CN-Phenyl |
| 92 | 4 | SO | 2-CN-Phenyl |
| 93 | 1 | $SO_2$ | 2-CN-Phenyl |
| 94 | 2 | $SO_2$ | 2-CN-Phenyl |
| 95 | 3 | $SO_2$ | 2-CN-Phenyl |
| 96 | 4 | $SO_2$ | 2-CN-Phenyl |
| 97 | 1 | O | 3-Me-Phenyl |
| 98 | 2 | O | 3-Me-Phenyl |
| 99 | 3 | O | 3-Me-Phenyl |
| 100 | 4 | O | 3-Me-Phenyl |
| 101 | 1 | S | 3-Me-Phenyl |
| 102 | 2 | S | 3-Me-Phenyl |
| 103 | 3 | S | 3-Me-Phenyl |
| 104 | 4 | S | 3-Me-Phenyl |
| 105 | 1 | SO | 3-Me-Phenyl |

TABLE 29-continued

| Entry | n | X | $R^3$ |
|---|---|---|---|
| 106 | 2 | SO | 3-Me-Phenyl |
| 107 | 3 | SO | 3-Me-Phenyl |
| 108 | 4 | SO | 3-Me-Phenyl |
| 109 | 1 | $SO_2$ | 3-Me-Phenyl |
| 110 | 2 | $SO_2$ | 3-Me-Phenyl |
| 111 | 3 | $SO_2$ | 3-Me-Phenyl |
| 112 | 4 | $SO_2$ | 3-Me-Phenyl |
| 113 | 1 | O | 2-F-Phenyl |
| 114 | 2 | O | 2-F-Phenyl |
| 115 | 3 | O | 2-F-Phenyl |
| 116 | 4 | O | 2-F-Phenyl |
| 117 | 1 | S | 2-F-Phenyl |
| 118 | 2 | S | 2-F-Phenyl |
| 119 | 3 | S | 2-F-Phenyl |
| 120 | 4 | S | 2-F-Phenyl |
| 121 | 1 | SO | 2-F-Phenyl |
| 122 | 2 | SO | 2-F-Phenyl |
| 123 | 3 | SO | 2-F-Phenyl |
| 124 | 4 | SO | 2-F-Phenyl |
| 125 | 1 | $SO_2$ | 2-F-Phenyl |
| 126 | 2 | $SO_2$ | 2-F-Phenyl |
| 127 | 3 | $SO_2$ | 2-F-Phenyl |
| 128 | 4 | $SO_2$ | 2-F-Phenyl |
| 129 | 1 | O | 4-F-Phenyl |
| 130 | 2 | O | 4-F-Phenyl |
| 131 | 3 | O | 4-F-Phenyl |
| 132 | 4 | O | 4-F-Phenyl |
| 133 | 1 | S | 4-F-Phenyl |
| 134 | 2 | S | 4-F-Phenyl |
| 135 | 3 | S | 4-F-Phenyl |
| 136 | 4 | S | 4-F-Phenyl |
| 137 | 1 | SO | 4-F-Phenyl |
| 138 | 2 | SO | 4-F-Phenyl |
| 139 | 3 | SO | 4-F-Phenyl |
| 140 | 4 | SO | 4-F-Phenyl |
| 141 | 1 | $SO_2$ | 4-F-Phenyl |
| 142 | 2 | $SO_2$ | 4-F-Phenyl |
| 143 | 3 | $SO_2$ | 4-F-Phenyl |
| 144 | 4 | $SO_2$ | 4-F-Phenyl |
| 145 | 1 | O | 3-Cl-Phenyl |
| 146 | 2 | O | 3-Cl-Phenyl |
| 147 | 3 | O | 3-Cl-Phenyl |
| 148 | 4 | O | 3-Cl-Phenyl |
| 149 | 1 | S | 3-Cl-Phenyl |
| 150 | 2 | S | 3-Cl-Phenyl |
| 151 | 3 | S | 3-Cl-Phenyl |
| 152 | 4 | S | 3-Cl-Phenyl |
| 153 | 1 | SO | 3-Cl-Phenyl |
| 154 | 2 | SO | 3-Cl-Phenyl |
| 155 | 3 | SO | 3-Cl-Phenyl |
| 156 | 4 | SO | 3-Cl-Phenyl |
| 157 | 1 | $SO_2$ | 3-Cl-Phenyl |
| 158 | 2 | $SO_2$ | 3-Cl-Phenyl |
| 159 | 3 | $SO_2$ | 3-Cl-Phenyl |
| 160 | 4 | $SO_2$ | 3-Cl-Phenyl |
| 161 | 1 | O | 2-Br-Phenyl |
| 162 | 2 | O | 2-Br-Phenyl |
| 163 | 3 | O | 2-Br-Phenyl |
| 164 | 4 | O | 2-Br-Phenyl |
| 165 | 1 | S | 2-Br-Phenyl |
| 166 | 2 | S | 2-Br-Phenyl |
| 167 | 3 | S | 2-Br-Phenyl |
| 168 | 4 | S | 2-Br-Phenyl |
| 169 | 1 | SO | 2-Br-Phenyl |
| 170 | 2 | SO | 2-Br-Phenyl |
| 171 | 3 | SO | 2-Br-Phenyl |
| 172 | 4 | SO | 2-Br-Phenyl |
| 173 | 1 | $SO_2$ | 2-Br-Phenyl |
| 174 | 2 | $SO_2$ | 2-Br-Phenyl |
| 175 | 3 | $SO_2$ | 2-Br-Phenyl |
| 176 | 4 | $SO_2$ | 2-Br-Phenyl |
| 177 | 1 | O | 4-Br-Phenyl |
| 178 | 2 | O | 4-Br-Phenyl |
| 179 | 3 | O | 4-Br-Phenyl |
| 180 | 4 | O | 4-Br-Phenyl |
| 181 | 1 | S | 4-Br-Phenyl |
| 182 | 2 | S | 4-Br-Phenyl |
| 183 | 3 | S | 4-Br-Phenyl |
| 184 | 4 | S | 4-Br-Phenyl |
| 185 | 1 | SO | 4-Br-Phenyl |
| 186 | 2 | SO | 4-Br-Phenyl |
| 187 | 3 | SO | 4-Br-Phenyl |
| 188 | 4 | SO | 4-Br-Phenyl |
| 189 | 1 | $SO_2$ | 4-Br-Phenyl |
| 190 | 2 | $SO_2$ | 4-Br-Phenyl |
| 191 | 3 | $SO_2$ | 4-Br-Phenyl |
| 192 | 4 | $SO_2$ | 4-Br-Phenyl |
| 193 | 1 | O | 3-$CF_3$-Phenyl |
| 194 | 2 | O | 3-$CF_3$-Phenyl |
| 195 | 3 | O | 3-$CF_3$-Phenyl |
| 196 | 4 | O | 3-$CF_3$-Phenyl |
| 197 | 1 | S | 3-$CF_3$-Phenyl |
| 198 | 2 | S | 3-$CF_3$-Phenyl |
| 199 | 3 | S | 3-$CF_3$-Phenyl |
| 200 | 4 | S | 3-$CF_3$-Phenyl |
| 201 | 1 | SO | 3-$CF_3$-Phenyl |
| 202 | 2 | SO | 3-$CF_3$-Phenyl |
| 203 | 3 | SO | 3-$CF_3$-Phenyl |
| 204 | 4 | SO | 3-$CF_3$-Phenyl |
| 205 | 1 | $SO_2$ | 3-$CF_3$-Phenyl |
| 206 | 2 | $SO_2$ | 3-$CF_3$-Phenyl |
| 207 | 3 | $SO_2$ | 3-$CF_3$-Phenyl |
| 208 | 4 | $SO_2$ | 3-$CF_3$-Phenyl |
| 209 | 1 | O | 2-iPr-Phenyl |
| 210 | 2 | O | 2-iPr-Phenyl |
| 211 | 3 | O | 2-iPr-Phenyl |
| 212 | 4 | O | 2-iPr-Phenyl |
| 213 | 1 | S | 2-iPr-Phenyl |
| 214 | 2 | S | 2-iPr-Phenyl |
| 215 | 3 | S | 2-iPr-Phenyl |
| 216 | 4 | S | 2-iPr-Phenyl |
| 217 | 1 | SO | 2-iPr-Phenyl |
| 218 | 2 | SO | 2-iPr-Phenyl |
| 219 | 3 | SO | 2-iPr-Phenyl |
| 220 | 4 | SO | 2-iPr-Phenyl |
| 221 | 1 | $SO_2$ | 2-iPr-Phenyl |
| 222 | 2 | $SO_2$ | 2-iPr-Phenyl |
| 223 | 3 | $SO_2$ | 2-iPr-Phenyl |
| 224 | 4 | $SO_2$ | 2-iPr-Phenyl |
| 225 | 1 | O | 4-iPr-Phenyl |
| 226 | 2 | O | 4-iPr-Phenyl |
| 227 | 3 | O | 4-iPr-Phenyl |
| 228 | 4 | O | 4-iPr-Phenyl |
| 229 | 1 | S | 4-iPr-Phenyl |
| 230 | 2 | S | 4-iPr-Phenyl |
| 231 | 3 | S | 4-iPr-Phenyl |
| 232 | 4 | S | 4-iPr-Phenyl |
| 233 | 1 | SO | 4-iPr-Phenyl |
| 234 | 2 | SO | 4-iPr-Phenyl |
| 235 | 3 | SO | 4-iPr-Phenyl |
| 236 | 4 | SO | 4-iPr-Phenyl |
| 237 | 1 | $SO_2$ | 4-iPr-Phenyl |
| 238 | 2 | $SO_2$ | 4-iPr-Phenyl |
| 239 | 3 | $SO_2$ | 4-iPr-Phenyl |
| 240 | 4 | $SO_2$ | 4-iPr-Phenyl |
| 241 | 1 | O | 3-$NH_2$-Phenyl |
| 242 | 2 | O | 3-$NH_2$-Phenyl |
| 243 | 3 | O | 3-$NH_2$-Phenyl |
| 244 | 4 | O | 3-$NH_2$-Phenyl |
| 245 | 1 | S | 3-$NH_2$-Phenyl |
| 246 | 2 | S | 3-$NH_2$-Phenyl |
| 247 | 3 | S | 3-$NH_2$-Phenyl |
| 248 | 1 | S | 3-$NH_2$-Phenyl |
| 249 | 2 | SO | 3-$NH_2$-Phenyl |
| 250 | 3 | SO | 3-$NH_2$-Phenyl |
| 251 | 4 | SO | 3-$NH_2$-Phenyl |
| 252 | 1 | SO | 3-$NH_2$-Phenyl |
| 253 | 2 | $SO_2$ | 3-$NH_2$-Phenyl |
| 254 | 3 | $SO_2$ | 3-$NH_2$-Phenyl |
| 255 | 4 | $SO_2$ | 3-$NH_2$-Phenyl |
| 256 | 1 | O | 2,4-di-Me-Phenyl |
| 257 | 2 | O | 2,4-di-Me-Phenyl |
| 258 | 3 | O | 2,4-di-Me-Phenyl |
| 259 | 4 | O | 2,4-di-Me-Phenyl |
| 260 | 1 | S | 2,4-di-Me-Phenyl |
| 261 | 2 | S | 2,4-di-Me-Phenyl |

TABLE 29-continued

| Entry | n | X | $R^3$ |
|---|---|---|---|
| 262 | 3 | S | 2,4-di-Me-Phenyl |
| 263 | 4 | S | 2,4-di-Me-Phenyl |
| 264 | 1 | SO | 2,4-di-Me-Phenyl |
| 265 | 2 | SO | 2,4-di-Me-Phenyl |
| 266 | 3 | SO | 2,4-di-Me-Phenyl |
| 267 | 4 | SO | 2,4-di-Me-Phenyl |
| 268 | 1 | $SO_2$ | 2,4-di-Me-Phenyl |
| 269 | 2 | $SO_2$ | 2,4-di-Me-Phenyl |
| 270 | 3 | $SO_2$ | 2,4-di-Me-Phenyl |
| 271 | 4 | $SO_2$ | 2,4-di-Me-Phenyl |
| 272 | 1 | O | 2,6-di-iPr-Phenyl |
| 273 | 2 | O | 2,6-di-iPr-Phenyl |
| 274 | 3 | O | 2,6-di-iPr-Phenyl |
| 275 | 4 | O | 2,6-di-iPr-Phenyl |
| 276 | 1 | S | 2,6-di-iPr-Phenyl |
| 277 | 2 | S | 2,6-di-iPr-Phenyl |
| 278 | 3 | S | 2,6-di-iPr-Phenyl |
| 279 | 4 | S | 2,6-di-iPr-Phenyl |
| 280 | 1 | SO | 2,6-di-iPr-Phenyl |
| 281 | 2 | SO | 2,6-di-iPr-Phenyl |
| 282 | 3 | SO | 2,6-di-iPr-Phenyl |
| 283 | 4 | SO | 2,6-di-iPr-Phenyl |
| 284 | 1 | $SO_2$ | 2,6-di-iPr-Phenyl |
| 285 | 2 | $SO_2$ | 2,6-di-iPr-Phenyl |
| 286 | 3 | $SO_2$ | 2,6-di-iPr-Phenyl |
| 287 | 4 | $SO_2$ | 2,6-di-iPr-Phenyl |
| 288 | 1 | O | 3-Ph-Phenyl |
| 289 | 2 | O | 3-Ph-Phenyl |
| 290 | 3 | O | 3-Ph-Phenyl |
| 291 | 4 | O | 3-Ph-Phenyl |
| 292 | 1 | S | 3-Ph-Phenyl |
| 293 | 2 | S | 3-Ph-Phenyl |
| 294 | 3 | S | 3-Ph-Phenyl |
| 295 | 4 | S | 3-Ph-Phenyl |
| 296 | 1 | SO | 3-Ph-Phenyl |
| 297 | 2 | SO | 3-Ph-Phenyl |
| 298 | 3 | SO | 3-Ph-Phenyl |
| 299 | 4 | SO | 3-Ph-Phenyl |
| 300 | 1 | $SO_2$ | 3-Ph-Phenyl |
| 301 | 2 | $SO_2$ | 3-Ph-Phenyl |
| 302 | 3 | $SO_2$ | 3-Ph-Phenyl |
| 303 | 4 | $SO_2$ | 3-Ph-Phenyl |
| 304 | 1 | O | 2-morpholino-phenyl |
| 305 | 2 | O | 2-morpholino-phenyl |
| 306 | 3 | O | 2-morpholino-phenyl |
| 307 | 4 | O | 2-morpholino-phenyl |
| 308 | 1 | S | 2-morpholino-phenyl |
| 309 | 2 | S | 2-morpholino-phenyl |
| 310 | 3 | S | 2-morpholino-phenyl |
| 311 | 4 | S | 2-morpholino-phenyl |
| 312 | 1 | SO | 2-morpholino-phenyl |
| 313 | 2 | SO | 2-morpholino-phenyl |
| 314 | 3 | SO | 2-morpholino-phenyl |
| 315 | 4 | SO | 2-morpholino-phenyl |
| 316 | 1 | $SO_2$ | 2-morpholino-phenyl |
| 317 | 2 | $SO_2$ | 2-morpholino-phenyl |
| 318 | 3 | $SO_2$ | 2-morpholino-phenyl |
| 319 | 4 | $SO_2$ | 2-morpholino-phenyl |
| 320 | 1 | O | 4-morpholino-phenyl |
| 321 | 2 | O | 4-morpholino-phenyl |
| 322 | 3 | O | 4-morpholino-phenyl |
| 323 | 4 | O | 4-morpholino-phenyl |
| 324 | 1 | SO | 4-morpholino-phenyl |
| 325 | 2 | SO | 4-morpholino-phenyl |
| 326 | 3 | SO | 4-morpholino-phenyl |
| 327 | 4 | SO | 4-morpholino-phenyl |
| 328 | 1 | O | naphthylen-1-yl |
| 329 | 2 | O | naphthylen-1-yl |
| 330 | 3 | O | naphthylen-1-yl |
| 331 | 4 | O | naphthylen-1-yl |
| 332 | 1 | S | naphthylen-1-yl |
| 333 | 2 | S | naphthylen-1-yl |
| 334 | 3 | S | naphthylen-1-yl |
| 335 | 4 | S | naphthylen-1-yl |
| 336 | 1 | SO | naphthylen-1-yl |
| 337 | 2 | SO | naphthylen-1-yl |
| 338 | 3 | SO | naphthylen-1-yl |
| 339 | 4 | SO | naphthylen-1-yl |

TABLE 29-continued

| Entry | n | X | $R^3$ |
|---|---|---|---|
| 340 | 1 | $SO_2$ | naphthylen-1-yl |
| 341 | 2 | $SO_2$ | naphthylen-1-yl |
| 342 | 3 | $SO_2$ | naphthylen-1-yl |
| 343 | 4 | $SO_2$ | naphthylen-1-yl |
| 344 | 1 | O | 4-OH-Phenyl |
| 345 | 2 | O | 4-OH-Phenyl |
| 346 | 3 | O | 4-OH-Phenyl |
| 347 | 4 | O | 4-OH-Phenyl |
| 348 | 1 | S | 4-OH-Phenyl |
| 349 | 2 | S | 4-OH-Phenyl |
| 350 | 3 | S | 4-OH-Phenyl |
| 351 | 4 | S | 4-OH-Phenyl |
| 352 | 1 | SO | 4-OH-Phenyl |
| 353 | 2 | SO | 4-OH-Phenyl |
| 354 | 3 | SO | 4-OH-Phenyl |
| 355 | 4 | SO | 4-OH-Phenyl |
| 356 | 1 | $SO_2$ | 4-OH-Phenyl |
| 357 | 2 | $SO_2$ | 4-OH-Phenyl |
| 358 | 3 | $SO_2$ | 4-OH-Phenyl |
| 359 | 4 | $SO_2$ | 4-OH-Phenyl |
| 360 | 1 | O | 2-OH-Phenyl |
| 361 | 2 | O | 2-OH-Phenyl |
| 362 | 3 | O | 2-OH-Phenyl |
| 363 | 4 | O | 2-OH-Phenyl |
| 364 | 1 | S | 2-OH-Phenyl |
| 365 | 2 | S | 2-OH-Phenyl |
| 366 | 3 | S | 2-OH-Phenyl |
| 367 | 4 | S | 2-OH-Phenyl |
| 368 | 1 | SO | 2-OH-Phenyl |
| 369 | 2 | SO | 2-OH-Phenyl |
| 370 | 3 | SO | 2-OH-Phenyl |
| 371 | 4 | SO | 2-OH-Phenyl |
| 372 | 1 | $SO_2$ | 2-OH-Phenyl |
| 373 | 2 | $SO_2$ | 2-OH-Phenyl |
| 374 | 3 | $SO_2$ | 2-OH-Phenyl |
| 375 | 4 | $SO_2$ | 2-OH-Phenyl |
| 376 | 1 | O | 4-OMe-Phenyl |
| 377 | 2 | O | 4-OMe-Phenyl |
| 378 | 3 | O | 4-OMe-Phenyl |
| 379 | 4 | O | 4-OMe-Phenyl |
| 380 | 1 | S | 4-OMe-Phenyl |
| 381 | 2 | S | 4-OMe-Phenyl |
| 382 | 3 | S | 4-OMe-Phenyl |
| 383 | 4 | S | 4-OMe-Phenyl |
| 384 | 1 | SO | 4-OMe-Phenyl |
| 385 | 2 | SO | 4-OMe-Phenyl |
| 386 | 3 | SO | 4-OMe-Phenyl |
| 387 | 4 | SO | 4-OMe-Phenyl |
| 388 | 1 | $SO_2$ | 4-OMe-Phenyl |
| 389 | 2 | $SO_2$ | 4-OMe-Phenyl |
| 390 | 3 | $SO_2$ | 4-OMe-Phenyl |
| 391 | 4 | $SO_2$ | 4-OMe-Phenyl |
| 392 | 1 | O | 2-OMe-Phenyl |
| 393 | 2 | O | 2-OMe-Phenyl |
| 394 | 3 | O | 2-OMe-Phenyl |
| 395 | 4 | O | 2-OMe-Phenyl |
| 396 | 1 | S | 2-OMe-Phenyl |
| 397 | 2 | S | 2-OMe-Phenyl |
| 398 | 3 | S | 2-OMe-Phenyl |
| 399 | 4 | S | 2-OMe-Phenyl |
| 400 | 1 | SO | 2-OMe-Phenyl |
| 401 | 2 | SO | 2-OMe-Phenyl |
| 402 | 3 | SO | 2-OMe-Phenyl |
| 403 | 4 | SO | 2-OMe-Phenyl |
| 404 | 1 | $SO_2$ | 2-OMe-Phenyl |
| 405 | 2 | $SO_2$ | 2-OMe-Phenyl |
| 406 | 3 | $SO_2$ | 2-OMe-Phenyl |
| 407 | 4 | $SO_2$ | 2-OMe-Phenyl |
| 408 | 1 | O | 3-CN-Phenyl |
| 409 | 2 | O | 3-CN-Phenyl |
| 410 | 3 | O | 3-CN-Phenyl |
| 411 | 4 | O | 3-CN-Phenyl |
| 412 | 1 | S | 3-CN-Phenyl |
| 413 | 2 | S | 3-CN-Phenyl |
| 414 | 3 | S | 3-CN-Phenyl |
| 415 | 4 | S | 3-CN-Phenyl |
| 416 | 1 | SO | 3-CN-Phenyl |
| 417 | 2 | SO | 3-CN-Phenyl |

TABLE 29-continued

| Entry | n | X | $R^3$ |
|---|---|---|---|
| 418 | 3 | SO | 3-CN-Phenyl |
| 419 | 4 | SO | 3-CN-Phenyl |
| 420 | 1 | $SO_2$ | 3-CN-Phenyl |
| 421 | 2 | $SO_2$ | 3-CN-Phenyl |
| 422 | 3 | $SO_2$ | 3-CN-Phenyl |
| 423 | 4 | $SO_2$ | 3-CN-Phenyl |
| 424 | 1 | O | 2-Me-Phenyl |
| 425 | 2 | O | 2-Me-Phenyl |
| 426 | 3 | O | 2-Me-Phenyl |
| 427 | 4 | O | 2-Me-Phenyl |
| 428 | 1 | S | 2-Me-Phenyl |
| 429 | 2 | S | 2-Me-Phenyl |
| 430 | 3 | S | 2-Me-Phenyl |
| 431 | 4 | S | 2-Me-Phenyl |
| 432 | 1 | SO | 2-Me-Phenyl |
| 433 | 2 | SO | 2-Me-Phenyl |
| 434 | 3 | SO | 2-Me-Phenyl |
| 435 | 4 | SO | 2-Me-Phenyl |
| 436 | 1 | $SO_2$ | 2-Me-Phenyl |
| 437 | 2 | $SO_2$ | 2-Me-Phenyl |
| 438 | 3 | $SO_2$ | 2-Me-Phenyl |
| 439 | 4 | $SO_2$ | 2-Me-Phenyl |
| 440 | 1 | O | 4-Me-Phenyl |
| 441 | 2 | O | 4-Me-Phenyl |
| 442 | 3 | O | 4-Me-Phenyl |
| 443 | 4 | O | 4-Me-Phenyl |
| 444 | 1 | S | 4-Me-Phenyl |
| 445 | 2 | S | 4-Me-Phenyl |
| 446 | 3 | S | 4-Me-Phenyl |
| 447 | 4 | S | 4-Me-Phenyl |
| 448 | 1 | SO | 4-Me-Phenyl |
| 449 | 2 | SO | 4-Me-Phenyl |
| 450 | 3 | SO | 4-Me-Phenyl |
| 451 | 4 | SO | 4-Me-Phenyl |
| 452 | 1 | $SO_2$ | 4-Me-Phenyl |
| 453 | 2 | $SO_2$ | 4-Me-Phenyl |
| 454 | 3 | $SO_2$ | 4-Me-Phenyl |
| 455 | 4 | $SO_2$ | 4-Me-Phenyl |
| 456 | 1 | O | 3-F-Phenyl |
| 457 | 2 | O | 3-F-Phenyl |
| 458 | 3 | O | 3-F-Phenyl |
| 459 | 4 | O | 3-F-Phenyl |
| 460 | 1 | S | 3-F-Phenyl |
| 461 | 2 | S | 3-F-Phenyl |
| 462 | 3 | S | 3-F-Phenyl |
| 463 | 4 | S | 3-F-Phenyl |
| 464 | 1 | SO | 3-F-Phenyl |
| 465 | 2 | SO | 3-F-Phenyl |
| 466 | 3 | SO | 3-F-Phenyl |
| 467 | 4 | SO | 3-F-Phenyl |
| 468 | 1 | $SO_2$ | 3-F-Phenyl |
| 469 | 2 | $SO_2$ | 3-F-Phenyl |
| 470 | 3 | $SO_2$ | 3-F-Phenyl |
| 471 | 4 | $SO_2$ | 3-F-Phenyl |
| 472 | 1 | O | 2-Cl-Phenyl |
| 473 | 2 | O | 2-Cl-Phenyl |
| 474 | 3 | O | 2-Cl-Phenyl |
| 475 | 4 | O | 2-Cl-Phenyl |
| 476 | 1 | S | 2-Cl-Phenyl |
| 477 | 2 | S | 2-Cl-Phenyl |
| 478 | 3 | S | 2-Cl-Phenyl |
| 479 | 4 | S | 2-Cl-Phenyl |
| 480 | 1 | SO | 2-Cl-Phenyl |
| 481 | 2 | SO | 2-Cl-Phenyl |
| 482 | 3 | SO | 2-Cl-Phenyl |
| 483 | 4 | SO | 2-Cl-Phenyl |
| 484 | 1 | $SO_2$ | 2-Cl-Phenyl |
| 485 | 2 | $SO_2$ | 2-Cl-Phenyl |
| 486 | 3 | $SO_2$ | 2-Cl-Phenyl |
| 487 | 4 | $SO_2$ | 2-Cl-Phenyl |
| 488 | 1 | O | 4-Cl-Phenyl |
| 489 | 2 | O | 4-Cl-Phenyl |
| 490 | 3 | O | 4-Cl-Phenyl |
| 491 | 4 | O | 4-Cl-Phenyl |
| 492 | 1 | S | 4-Cl-Phenyl |
| 493 | 2 | S | 4-Cl-Phenyl |
| 494 | 3 | S | 4-Cl-Phenyl |
| 495 | 4 | S | 4-Cl-Phenyl |

TABLE 29-continued

| Entry | n | X | $R^3$ |
|---|---|---|---|
| 496 | 1 | SO | 4-Cl-Phenyl |
| 497 | 2 | SO | 4-Cl-Phenyl |
| 498 | 3 | SO | 4-Cl-Phenyl |
| 499 | 4 | SO | 4-Cl-Phenyl |
| 500 | 1 | $SO_2$ | 4-Cl-Phenyl |
| 501 | 2 | $SO_2$ | 4-Cl-Phenyl |
| 502 | 3 | $SO_2$ | 4-Cl-Phenyl |
| 503 | 4 | $SO_2$ | 4-Cl-Phenyl |
| 504 | 1 | O | 3-Br-Phenyl |
| 505 | 2 | O | 3-Br-Phenyl |
| 506 | 3 | O | 3-Br-Phenyl |
| 507 | 4 | O | 3-Br-Phenyl |
| 508 | 1 | S | 3-Br-Phenyl |
| 509 | 2 | S | 3-Br-Phenyl |
| 510 | 3 | S | 3-Br-Phenyl |
| 511 | 4 | S | 3-Br-Phenyl |
| 512 | 1 | SO | 3-Br-Phenyl |
| 513 | 2 | SO | 3-Br-Phenyl |
| 514 | 3 | SO | 3-Br-Phenyl |
| 515 | 4 | SO | 3-Br-Phenyl |
| 516 | 1 | $SO_2$ | 3-Br-Phenyl |
| 517 | 2 | $SO_2$ | 3-Br-Phenyl |
| 518 | 3 | $SO_2$ | 3-Br-Phenyl |
| 519 | 4 | $SO_2$ | 3-Br-Phenyl |
| 520 | 1 | O | 2-$CF_3$-Phenyl |
| 521 | 2 | O | 2-$CF_3$-Phenyl |
| 522 | 3 | O | 2-$CF_3$-Phenyl |
| 523 | 4 | O | 2-$CF_3$-Phenyl |
| 524 | 1 | S | 2-$CF_3$-Phenyl |
| 525 | 2 | S | 2-$CF_3$-Phenyl |
| 526 | 3 | S | 2-$CF_3$-Phenyl |
| 527 | 4 | S | 2-$CF_3$-Phenyl |
| 528 | 1 | SO | 2-$CF_3$-Phenyl |
| 529 | 2 | SO | 2-$CF_3$-Phenyl |
| 530 | 3 | SO | 2-$CF_3$-Phenyl |
| 531 | 4 | SO | 2-$CF_3$-Phenyl |
| 532 | 1 | $SO_2$ | 2-$CF_3$-Phenyl |
| 533 | 2 | $SO_2$ | 2-$CF_3$-Phenyl |
| 534 | 3 | $SO_2$ | 2-$CF_3$-Phenyl |
| 535 | 4 | $SO_2$ | 2-$CF_3$-Phenyl |
| 536 | 1 | O | 4-$CF_3$-Phenyl |
| 537 | 2 | O | 4-$CF_3$-Phenyl |
| 538 | 3 | O | 4-$CF_3$-Phenyl |
| 539 | 4 | O | 4-$CF_3$-Phenyl |
| 540 | 1 | S | 4-$CF_3$-Phenyl |
| 541 | 2 | S | 4-$CF_3$-Phenyl |
| 542 | 3 | S | 4-$CF_3$-Phenyl |
| 543 | 4 | S | 4-$CF_3$-Phenyl |
| 544 | 1 | SO | 4-$CF_3$-Phenyl |
| 545 | 2 | SO | 4-$CF_3$-Phenyl |
| 546 | 3 | SO | 4-$CF_3$-Phenyl |
| 547 | 4 | SO | 3-$CF_3$-Phenyl |
| 548 | 1 | $SO_2$ | 4-$CF_3$-Phenyl |
| 549 | 2 | $SO_2$ | 4-$CF_3$-Phenyl |
| 550 | 3 | $SO_2$ | 4-$CF_3$-Phenyl |
| 551 | 4 | $SO_2$ | 4-$CF_3$-Phenyl |
| 552 | 1 | O | 3-iPr-Phenyl |
| 553 | 2 | O | 3-iPr-Phenyl |
| 554 | 3 | O | 3-iPr-Phenyl |
| 555 | 4 | O | 3-iPr-Phenyl |
| 556 | 1 | S | 3-iPr-Phenyl |
| 557 | 2 | S | 3-iPr-Phenyl |
| 558 | 3 | S | 3-iPr-Phenyl |
| 559 | 4 | S | 3-iPr-Phenyl |
| 560 | 1 | SO | 3-iPr-Phenyl |
| 561 | 2 | SO | 3-iPr-Phenyl |
| 562 | 3 | SO | 3-iPr-Phenyl |
| 563 | 4 | SO | 3-iPr-Phenyl |
| 564 | 1 | $SO_2$ | 3-iPr-Phenyl |
| 565 | 2 | $SO_2$ | 3-iPr-Phenyl |
| 566 | 3 | $SO_2$ | 3-iPr-Phenyl |
| 567 | 4 | $SO_2$ | 3-iPr-Phenyl |
| 568 | 1 | O | 4-$NH_2$-Phenyl |
| 569 | 2 | O | 4-$NH_2$-Phenyl |
| 570 | 3 | O | 4-$NH_2$-Phenyl |
| 571 | 4 | O | 4-$NH_2$-Phenyl |
| 572 | 1 | S | 4-$NH_2$-Phenyl |
| 573 | 2 | S | 4-$NH_2$-Phenyl |

TABLE 29-continued

| Entry | n | X | $R^3$ |
|---|---|---|---|
| 574 | 3 | S | 4-$NH_2$-Phenyl |
| 575 | 4 | S | 4-$NH_2$-Phenyl |
| 576 | 1 | SO | 4-$NH_2$-Phenyl |
| 577 | 2 | SO | 4-$NH_2$-Phenyl |
| 578 | 3 | SO | 4-$NH_2$-Phenyl |
| 579 | 4 | SO | 4-$NH_2$-Phenyl |
| 580 | 1 | $SO_2$ | 4-$NH_2$-Phenyl |
| 581 | 2 | $SO_2$ | 4-$NH_2$-Phenyl |
| 582 | 3 | $SO_2$ | 4-$NH_2$-Phenyl |
| 583 | 4 | $SO_2$ | 4-$NH_2$-Phenyl |
| 584 | 1 | O | 2-$NH_2$-Phenyl |
| 585 | 2 | O | 2-$NH_2$-Phenyl |
| 586 | 3 | O | 2-$NH_2$-Phenyl |
| 587 | 4 | O | 2-$NH_2$-Phenyl |
| 588 | 1 | S | 2-$NH_2$-Phenyl |
| 589 | 2 | S | 2-$NH_2$-Phenyl |
| 590 | 3 | S | 2-$NH_2$-Phenyl |
| 591 | 1 | S | 2-$NH_2$-Phenyl |
| 592 | 2 | SO | 2-$NH_2$-Phenyl |
| 593 | 3 | SO | 2-$NH_2$-Phenyl |
| 594 | 4 | SO | 2-$NH_2$-Phenyl |
| 595 | 1 | SO | 2-$NH_2$-Phenyl |
| 596 | 2 | $SO_2$ | 2-$NH_2$-Phenyl |
| 597 | 3 | $SO_2$ | 2-$NH_2$-Phenyl |
| 598 | 4 | $SO_2$ | 2-$NH_2$-Phenyl |
| 599 | 1 | O | 2,6-di-Me-Phenyl |
| 600 | 2 | O | 2,6-di-Me-Phenyl |
| 601 | 3 | O | 2,6-di-Me-Phenyl |
| 602 | 4 | O | 2,6-di-Me-Phenyl |
| 603 | 1 | S | 2,6-di-Me-Phenyl |
| 604 | 2 | S | 2,6-di-Me-Phenyl |
| 605 | 3 | S | 2,6-di-Me-Phenyl |
| 606 | 4 | S | 2,6-di-Me-Phenyl |
| 607 | 1 | SO | 2,6-di-Me-Phenyl |
| 608 | 2 | SO | 2,6-di-Me-Phenyl |
| 609 | 3 | SO | 2,6-di-Me-Phenyl |
| 610 | 4 | SO | 2,6-di-Me-Phenyl |
| 611 | 1 | $SO_2$ | 2,6-di-Me-Phenyl |
| 612 | 2 | $SO_2$ | 2,6-di-Me-Phenyl |
| 613 | 3 | $SO_2$ | 2,6-di-Me-Phenyl |
| 614 | 4 | $SO_2$ | 2,6-di-Me-Phenyl |
| 615 | 1 | O | 2-Ph-Phenyl |
| 616 | 2 | O | 2-Ph-Phenyl |
| 617 | 3 | O | 2-Ph-Phenyl |
| 618 | 4 | O | 2-Ph-Phenyl |
| 619 | 1 | S | 2-Ph-Phenyl |
| 620 | 2 | S | 2-Ph-Phenyl |
| 621 | 3 | S | 2-Ph-Phenyl |
| 622 | 4 | S | 2-Ph-Phenyl |
| 623 | 1 | SO | 2-Ph-Phenyl |
| 624 | 2 | SO | 2-Ph-Phenyl |
| 625 | 3 | SO | 2-Ph-Phenyl |
| 626 | 4 | SO | 2-Ph-Phenyl |
| 627 | 1 | $SO_2$ | 2-Ph-Phenyl |
| 628 | 2 | $SO_2$ | 2-Ph-Phenyl |
| 629 | 3 | $SO_2$ | 2-Ph-Phenyl |
| 630 | 4 | $SO_2$ | 2-Ph-Phenyl |
| 631 | 1 | O | 4-Ph-Phenyl |
| 632 | 2 | O | 4-Ph-Phenyl |
| 633 | 3 | O | 4-Ph-Phenyl |
| 634 | 4 | O | 4-Ph-Phenyl |
| 635 | 1 | S | 4-Ph-Phenyl |
| 636 | 2 | S | 4-Ph-Phenyl |
| 637 | 3 | S | 4-Ph-Phenyl |
| 638 | 4 | S | 4-Ph-Phenyl |
| 639 | 1 | SO | 4-Ph-Phenyl |
| 640 | 2 | SO | 4-Ph-Phenyl |
| 641 | 3 | SO | 4-Ph-Phenyl |
| 642 | 4 | SO | 4-Ph-Phenyl |
| 643 | 1 | $SO_2$ | 4-Ph-Phenyl |
| 644 | 2 | $SO_2$ | 4-Ph-Phenyl |
| 645 | 3 | $SO_2$ | 4-Ph-Phenyl |
| 646 | 4 | $SO_2$ | 4-Ph-Phenyl |
| 647 | 1 | O | 3-morpholino-phenyl |
| 648 | 2 | O | 3-morpholino-phenyl |
| 649 | 3 | O | 3-morpholino-phenyl |
| 650 | 4 | O | 3-morpholino-phenyl |
| 651 | 1 | S | 3-morpholino-phenyl |
| 652 | 2 | S | 3-morpholino-phenyl |
| 653 | 3 | S | 3-morpholino-phenyl |
| 654 | 4 | S | 3-morpholino-phenyl |
| 655 | 1 | SO | 3-morpholino-phenyl |
| 656 | 2 | SO | 3-morpholino-phenyl |
| 657 | 3 | SO | 3-morpholino-phenyl |
| 658 | 4 | SO | 3-morpholino-phenyl |
| 659 | 1 | $SO_2$ | 3-morpholino-phenyl |
| 660 | 2 | $SO_2$ | 3-morpholino-phenyl |
| 661 | 3 | $SO_2$ | 3-morpholino-phenyl |
| 662 | 4 | $SO_2$ | 3-morpholino-phenyl |
| 663 | 1 | S | 4-morpholino-phenyl |
| 664 | 2 | S | 4-morpholino-phenyl |
| 665 | 3 | S | 4-morpholino-phenyl |
| 667 | 4 | S | 4-morpholino-phenyl |
| 668 | 1 | $SO_2$ | 4-morpholino-phenyl |
| 669 | 2 | $SO_2$ | 4-morpholino-phenyl |
| 670 | 3 | $SO_2$ | 4-morpholino-phenyl |
| 671 | 4 | $SO_2$ | 4-morpholino-phenyl |
| 672 | 1 | O | naphthylen-2-yl |
| 673 | 2 | O | naphthylen-2-yl |
| 674 | 3 | O | naphthylen-2-yl |
| 675 | 4 | O | naphthylen-2-yl |
| 676 | 1 | S | naphthylen-2-yl |
| 678 | 2 | S | naphthylen-2-yl |
| 679 | 3 | S | naphthylen-2-yl |
| 680 | 4 | S | naphthylen-2-yl |
| 681 | 1 | SO | naphthylen-2-yl |
| 682 | 2 | SO | naphthylen-2-yl |
| 683 | 3 | SO | naphthylen-2-yl |
| 684 | 4 | SO | naphthylen-2-yl |
| 685 | 1 | $SO_2$ | naphthylen-2-yl |
| 686 | 2 | $SO_2$ | naphthylen-2-yl |
| 687 | 3 | $SO_2$ | naphthylen-2-yl |
| 688 | 4 | $SO_2$ | naphthylen-2-yl |

Exemplary embodiments include compounds having the formula (XXXVII)

(XXXVII)

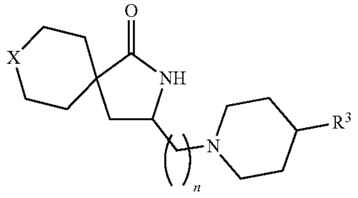

or a pharmaceutically acceptable salt form thereof defined herein below in Table 30.

TABLE 30

| Entry | n | X | $R^3$ |
|---|---|---|---|
| 1 | 1 | O | Phenyl |
| 2 | 2 | O | Phenyl |
| 3 | 3 | O | Phenyl |
| 4 | 4 | O | Phenyl |
| 5 | 1 | S | Phenyl |
| 6 | 2 | S | Phenyl |
| 7 | 3 | S | Phenyl |
| 8 | 4 | S | Phenyl |
| 9 | 1 | SO | Phenyl |
| 10 | 2 | SO | Phenyl |
| 11 | 3 | SO | Phenyl |
| 12 | 4 | SO | Phenyl |
| 13 | 1 | $SO_2$ | Phenyl |
| 14 | 2 | $SO_2$ | Phenyl |
| 15 | 3 | $SO_2$ | Phenyl |
| 16 | 4 | $SO_2$ | Phenyl |

TABLE 30-continued

| Entry | n | X | $R^3$ |
|---|---|---|---|
| 17 | 1 | O | 3-OH-Phenyl |
| 18 | 2 | O | 3-OH-Phenyl |
| 19 | 3 | O | 3-OH-Phenyl |
| 20 | 4 | O | 3-OH-Phenyl |
| 21 | 1 | S | 3-OH-Phenyl |
| 22 | 2 | S | 3-OH-Phenyl |
| 23 | 3 | S | 3-OH-Phenyl |
| 24 | 4 | S | 3-OH-Phenyl |
| 25 | 1 | SO | 3-OH-Phenyl |
| 26 | 2 | SO | 3-OH-Phenyl |
| 27 | 3 | SO | 3-OH-Phenyl |
| 28 | 4 | SO | 3-OH-Phenyl |
| 29 | 1 | $SO_2$ | 3-OH-Phenyl |
| 30 | 2 | $SO_2$ | 3-OH-Phenyl |
| 31 | 3 | $SO_2$ | 3-OH-Phenyl |
| 32 | 4 | $SO_2$ | 3-OH-Phenyl |
| 33 | 1 | O | 4-$NO_2$-Phenyl |
| 34 | 2 | O | 4-$NO_2$-Phenyl |
| 35 | 3 | O | 4-$NO_2$-Phenyl |
| 36 | 4 | O | 4-$NO_2$-Phenyl |
| 37 | 1 | S | 4-$NO_2$-Phenyl |
| 38 | 2 | S | 4-$NO_2$-Phenyl |
| 39 | 3 | S | 4-$NO_2$-Phenyl |
| 40 | 4 | S | 4-$NO_2$-Phenyl |
| 41 | 1 | SO | 4-$NO_2$-Phenyl |
| 42 | 2 | SO | 4-$NO_2$-Phenyl |
| 43 | 3 | SO | 4-$NO_2$-Phenyl |
| 44 | 4 | SO | 4-$NO_2$-Phenyl |
| 45 | 1 | $SO_2$ | 4-$NO_2$-Phenyl |
| 46 | 2 | $SO_2$ | 4-$NO_2$-Phenyl |
| 47 | 3 | $SO_2$ | 4-$NO_2$-Phenyl |
| 48 | 4 | $SO_2$ | 4-$NO_2$-Phenyl |
| 49 | 1 | O | 3-OMe-Phenyl |
| 50 | 2 | O | 3-OMe-Phenyl |
| 51 | 3 | O | 3-OMe-Phenyl |
| 52 | 4 | O | 3-OMe-Phenyl |
| 53 | 1 | S | 3-OMe-Phenyl |
| 54 | 2 | S | 3-OMe-Phenyl |
| 55 | 3 | S | 3-OMe-Phenyl |
| 56 | 4 | S | 3-OMe-Phenyl |
| 57 | 1 | SO | 3-OMe-Phenyl |
| 58 | 2 | SO | 3-OMe-Phenyl |
| 59 | 3 | SO | 3-OMe-Phenyl |
| 60 | 4 | SO | 3-OMe-Phenyl |
| 61 | 1 | $SO_2$ | 3-OMe-Phenyl |
| 62 | 2 | $SO_2$ | 3-OMe-Phenyl |
| 63 | 3 | $SO_2$ | 3-OMe-Phenyl |
| 64 | 4 | $SO_2$ | 3-OMe-Phenyl |
| 65 | 1 | O | 4-CN-Phenyl |
| 66 | 2 | O | 4-CN-Phenyl |
| 67 | 3 | O | 4-CN-Phenyl |
| 68 | 4 | O | 4-CN-Phenyl |
| 69 | 1 | S | 4-CN-Phenyl |
| 70 | 2 | S | 4-CN-Phenyl |
| 71 | 3 | S | 4-CN-Phenyl |
| 72 | 4 | S | 4-CN-Phenyl |
| 73 | 1 | SO | 4-CN-Phenyl |
| 74 | 2 | SO | 4-CN-Phenyl |
| 75 | 3 | SO | 4-CN-Phenyl |
| 76 | 4 | SO | 4-CN-Phenyl |
| 77 | 1 | $SO_2$ | 4-CN-Phenyl |
| 78 | 2 | $SO_2$ | 4-CN-Phenyl |
| 79 | 3 | $SO_2$ | 4-CN-Phenyl |
| 80 | 4 | $SO_2$ | 4-CN-Phenyl |
| 81 | 1 | O | 2-CN-Phenyl |
| 82 | 2 | O | 2-CN-Phenyl |
| 83 | 3 | O | 2-CN-Phenyl |
| 84 | 4 | O | 2-CN-Phenyl |
| 85 | 1 | S | 2-CN-Phenyl |
| 86 | 2 | S | 2-CN-Phenyl |
| 87 | 3 | S | 2-CN-Phenyl |
| 88 | 4 | S | 2-CN-Phenyl |
| 89 | 1 | SO | 2-CN-Phenyl |
| 90 | 2 | SO | 2-CN-Phenyl |
| 91 | 3 | SO | 2-CN-Phenyl |
| 92 | 4 | SO | 2-CN-Phenyl |
| 93 | 1 | $SO_2$ | 2-CN-Phenyl |
| 94 | 2 | $SO_2$ | 2-CN-Phenyl |

TABLE 30-continued

| Entry | n | X | $R^3$ |
|---|---|---|---|
| 95 | 3 | $SO_2$ | 2-CN-Phenyl |
| 96 | 4 | $SO_2$ | 2-CN-Phenyl |
| 97 | 1 | O | 3-Me-Phenyl |
| 98 | 2 | O | 3-Me-Phenyl |
| 99 | 3 | O | 3-Me-Phenyl |
| 100 | 4 | O | 3-Me-Phenyl |
| 101 | 1 | S | 3-Me-Phenyl |
| 102 | 2 | S | 3-Me-Phenyl |
| 103 | 3 | S | 3-Me-Phenyl |
| 104 | 4 | S | 3-Me-Phenyl |
| 105 | 1 | SO | 3-Me-Phenyl |
| 106 | 2 | SO | 3-Me-Phenyl |
| 107 | 3 | SO | 3-Me-Phenyl |
| 108 | 4 | SO | 3-Me-Phenyl |
| 109 | 1 | $SO_2$ | 3-Me-Phenyl |
| 110 | 2 | $SO_2$ | 3-Me-Phenyl |
| 111 | 3 | $SO_2$ | 3-Me-Phenyl |
| 112 | 4 | $SO_2$ | 3-Me-Phenyl |
| 113 | 1 | O | 2-F-Phenyl |
| 114 | 2 | O | 2-F-Phenyl |
| 115 | 3 | O | 2-F-Phenyl |
| 116 | 4 | O | 2-F-Phenyl |
| 117 | 1 | S | 2-F-Phenyl |
| 118 | 2 | S | 2-F-Phenyl |
| 119 | 3 | S | 2-F-Phenyl |
| 120 | 4 | S | 2-F-Phenyl |
| 121 | 1 | SO | 2-F-Phenyl |
| 122 | 2 | SO | 2-F-Phenyl |
| 123 | 3 | SO | 2-F-Phenyl |
| 124 | 4 | SO | 2-F-Phenyl |
| 125 | 1 | $SO_2$ | 2-F-Phenyl |
| 126 | 2 | $SO_2$ | 2-F-Phenyl |
| 127 | 3 | $SO_2$ | 2-F-Phenyl |
| 128 | 4 | $SO_2$ | 2-F-Phenyl |
| 129 | 1 | O | 4-F-Phenyl |
| 130 | 2 | O | 4-F-Phenyl |
| 131 | 3 | O | 4-F-Phenyl |
| 132 | 4 | O | 4-F-Phenyl |
| 133 | 1 | O | 4-F-Phenyl |
| 134 | 2 | S | 4-F-Phenyl |
| 135 | 3 | S | 4-F-Phenyl |
| 136 | 4 | S | 4-F-Phenyl |
| 137 | 1 | S | 4-F-Phenyl |
| 138 | 2 | SO | 4-F-Phenyl |
| 139 | 3 | SO | 4-F-Phenyl |
| 140 | 4 | SO | 4-F-Phenyl |
| 141 | 1 | SO | 4-F-Phenyl |
| 142 | 2 | $SO_2$ | 4-F-Phenyl |
| 143 | 3 | $SO_2$ | 4-F-Phenyl |
| 144 | 4 | $SO_2$ | 4-F-Phenyl |
| 145 | 1 | O | 3-Cl-Phenyl |
| 146 | 2 | O | 3-Cl-Phenyl |
| 147 | 3 | O | 3-Cl-Phenyl |
| 148 | 4 | O | 3-Cl-Phenyl |
| 149 | 1 | S | 3-Cl-Phenyl |
| 150 | 2 | S | 3-Cl-Phenyl |
| 151 | 3 | S | 3-Cl-Phenyl |
| 152 | 4 | S | 3-Cl-Phenyl |
| 153 | 1 | SO | 3-Cl-Phenyl |
| 154 | 2 | SO | 3-Cl-Phenyl |
| 155 | 3 | SO | 3-Cl-Phenyl |
| 156 | 4 | SO | 3-Cl-Phenyl |
| 157 | 1 | $SO_2$ | 3-Cl-Phenyl |
| 158 | 2 | $SO_2$ | 3-Cl-Phenyl |
| 159 | 3 | $SO_2$ | 3-Cl-Phenyl |
| 160 | 4 | $SO_2$ | 3-Cl-Phenyl |
| 161 | 1 | O | 2-Br-Phenyl |
| 162 | 2 | O | 2-Br-Phenyl |
| 163 | 3 | O | 2-Br-Phenyl |
| 164 | 4 | O | 2-Br-Phenyl |
| 165 | 1 | S | 2-Br-Phenyl |
| 166 | 2 | S | 2-Br-Phenyl |
| 167 | 3 | S | 2-Br-Phenyl |
| 168 | 4 | S | 2-Br-Phenyl |
| 169 | 1 | SO | 2-Br-Phenyl |
| 170 | 2 | SO | 2-Br-Phenyl |
| 171 | 3 | SO | 2-Br-Phenyl |
| 172 | 4 | SO | 2-Br-Phenyl |

TABLE 30-continued

| Entry | n | X | $R^3$ |
|---|---|---|---|
| 173 | 1 | $SO_2$ | 2-Br-Phenyl |
| 174 | 2 | $SO_2$ | 2-Br-Phenyl |
| 175 | 3 | $SO_2$ | 2-Br-Phenyl |
| 176 | 4 | $SO_2$ | 2-Br-Phenyl |
| 177 | 1 | O | 4-Br-Phenyl |
| 178 | 2 | O | 4-Br-Phenyl |
| 179 | 3 | O | 4-Br-Phenyl |
| 180 | 4 | O | 4-Br-Phenyl |
| 181 | 1 | S | 4-Br-Phenyl |
| 182 | 2 | S | 4-Br-Phenyl |
| 183 | 3 | S | 4-Br-Phenyl |
| 184 | 4 | S | 4-Br-Phenyl |
| 185 | 1 | SO | 4-Br-Phenyl |
| 186 | 2 | SO | 4-Br-Phenyl |
| 187 | 3 | SO | 4-Br-Phenyl |
| 188 | 4 | SO | 4-Br-Phenyl |
| 189 | 1 | $SO_2$ | 4-Br-Phenyl |
| 190 | 2 | $SO_2$ | 4-Br-Phenyl |
| 191 | 3 | $SO_2$ | 4-Br-Phenyl |
| 192 | 4 | $SO_2$ | 4-Br-Phenyl |
| 193 | 1 | O | 3-$CF_3$-Phenyl |
| 194 | 2 | O | 3-$CF_3$-Phenyl |
| 195 | 3 | O | 3-$CF_3$-Phenyl |
| 196 | 4 | O | 3-$CF_3$-Phenyl |
| 197 | 1 | S | 3-$CF_3$-Phenyl |
| 198 | 2 | S | 3-$CF_3$-Phenyl |
| 199 | 3 | S | 3-$CF_3$-Phenyl |
| 200 | 4 | S | 3-$CF_3$-Phenyl |
| 201 | 1 | SO | 3-$CF_3$-Phenyl |
| 202 | 2 | SO | 3-$CF_3$-Phenyl |
| 203 | 3 | SO | 3-$CF_3$-Phenyl |
| 204 | 4 | SO | 3-$CF_3$-Phenyl |
| 205 | 1 | $SO_2$ | 3-$CF_3$-Phenyl |
| 206 | 2 | $SO_2$ | 3-$CF_3$-Phenyl |
| 207 | 3 | $SO_2$ | 3-$CF_3$-Phenyl |
| 208 | 4 | $SO_2$ | 3-$CF_3$-Phenyl |
| 209 | 1 | O | 2-iPr-Phenyl |
| 210 | 2 | O | 2-iPr-Phenyl |
| 211 | 3 | O | 2-iPr-Phenyl |
| 212 | 4 | O | 2-iPr-Phenyl |
| 213 | 1 | S | 2-iPr-Phenyl |
| 214 | 2 | S | 2-iPr-Phenyl |
| 215 | 3 | S | 2-iPr-Phenyl |
| 216 | 4 | S | 2-iPr-Phenyl |
| 217 | 1 | SO | 2-iPr-Phenyl |
| 218 | 2 | SO | 2-iPr-Phenyl |
| 219 | 3 | SO | 2-iPr-Phenyl |
| 220 | 4 | SO | 2-iPr-Phenyl |
| 221 | 1 | $SO_2$ | 2-iPr-Phenyl |
| 222 | 2 | $SO_2$ | 2-iPr-Phenyl |
| 223 | 3 | $SO_2$ | 2-iPr-Phenyl |
| 224 | 4 | $SO_2$ | 2-iPr-Phenyl |
| 225 | 1 | O | 4-iPr-Phenyl |
| 226 | 2 | O | 4-iPr-Phenyl |
| 227 | 3 | O | 4-iPr-Phenyl |
| 228 | 4 | O | 4-iPr-Phenyl |
| 229 | 1 | S | 4-iPr-Phenyl |
| 230 | 2 | S | 4-iPr-Phenyl |
| 231 | 3 | S | 4-iPr-Phenyl |
| 232 | 4 | S | 4-iPr-Phenyl |
| 233 | 1 | SO | 4-iPr-Phenyl |
| 234 | 2 | SO | 4-iPr-Phenyl |
| 235 | 3 | SO | 4-iPr-Phenyl |
| 236 | 4 | SO | 4-iPr-Phenyl |
| 237 | 1 | $SO_2$ | 4-iPr-Phenyl |
| 238 | 2 | $SO_2$ | 4-iPr-Phenyl |
| 239 | 3 | $SO_2$ | 4-iPr-Phenyl |
| 240 | 4 | $SO_2$ | 4-iPr-Phenyl |
| 241 | 1 | O | 3-$NH_2$-Phenyl |
| 242 | 2 | O | 3-$NH_2$-Phenyl |
| 243 | 3 | O | 3-$NH_2$-Phenyl |
| 244 | 4 | O | 3-$NH_2$-Phenyl |
| 245 | 1 | S | 3-$NH_2$-Phenyl |
| 246 | 2 | S | 3-$NH_2$-Phenyl |
| 247 | 3 | S | 3-$NH_2$-Phenyl |
| 248 | 1 | S | 3-$NH_2$-Phenyl |
| 249 | 2 | SO | 3-$NH_2$-Phenyl |
| 250 | 3 | SO | 3-$NH_2$-Phenyl |

TABLE 30-continued

| Entry | n | X | $R^3$ |
|---|---|---|---|
| 251 | 4 | SO | 3-$NH_2$-Phenyl |
| 252 | 1 | SO | 3-$NH_2$-Phenyl |
| 253 | 2 | $SO_2$ | 3-$NH_2$-Phenyl |
| 254 | 3 | $SO_2$ | 3-$NH_2$-Phenyl |
| 255 | 4 | $SO_2$ | 3-$NH_2$-Phenyl |
| 256 | 1 | O | 2,4-di-Me-Phenyl |
| 257 | 2 | O | 2,4-di-Me-Phenyl |
| 258 | 3 | O | 2,4-di-Me-Phenyl |
| 259 | 4 | O | 2,4-di-Me-Phenyl |
| 260 | 1 | S | 2,4-di-Me-Phenyl |
| 261 | 2 | S | 2,4-di-Me-Phenyl |
| 262 | 3 | S | 2,4-di-Me-Phenyl |
| 263 | 4 | S | 2,4-di-Me-Phenyl |
| 264 | 1 | SO | 2,4-di-Me-Phenyl |
| 265 | 2 | SO | 2,4-di-Me-Phenyl |
| 266 | 3 | SO | 2,4-di-Me-Phenyl |
| 267 | 4 | SO | 2,4-di-Me-Phenyl |
| 268 | 1 | $SO_2$ | 2,4-di-Me-Phenyl |
| 269 | 2 | $SO_2$ | 2,4-di-Me-Phenyl |
| 270 | 3 | $SO_2$ | 2,4-di-Me-Phenyl |
| 271 | 4 | $SO_2$ | 2,4-di-Me-Phenyl |
| 272 | 1 | O | 2,6-di-iPr-Phenyl |
| 273 | 2 | O | 2,6-di-iPr-Phenyl |
| 274 | 3 | O | 2,6-di-iPr-Phenyl |
| 275 | 4 | O | 2,6-di-iPr-Phenyl |
| 276 | 1 | S | 2,6-di-iPr-Phenyl |
| 277 | 2 | S | 2,6-di-iPr-Phenyl |
| 278 | 3 | S | 2,6-di-iPr-Phenyl |
| 279 | 4 | S | 2,6-di-iPr-Phenyl |
| 280 | 1 | SO | 2,6-di-iPr-Phenyl |
| 281 | 2 | SO | 2,6-di-iPr-Phenyl |
| 282 | 3 | SO | 2,6-di-iPr-Phenyl |
| 283 | 4 | SO | 2,6-di-iPr-Phenyl |
| 284 | 1 | $SO_2$ | 2,6-di-iPr-Phenyl |
| 285 | 2 | $SO_2$ | 2,6-di-iPr-Phenyl |
| 286 | 3 | $SO_2$ | 2,6-di-iPr-Phenyl |
| 287 | 4 | $SO_2$ | 2,6-di-iPr-Phenyl |
| 288 | 1 | O | 3-Ph-Phenyl |
| 289 | 2 | O | 3-Ph-Phenyl |
| 290 | 3 | O | 3-Ph-Phenyl |
| 291 | 4 | O | 3-Ph-Phenyl |
| 292 | 1 | S | 3-Ph-Phenyl |
| 293 | 2 | S | 3-Ph-Phenyl |
| 294 | 3 | S | 3-Ph-Phenyl |
| 295 | 4 | S | 3-Ph-Phenyl |
| 296 | 1 | SO | 3-Ph-Phenyl |
| 297 | 2 | SO | 3-Ph-Phenyl |
| 298 | 3 | SO | 3-Ph-Phenyl |
| 299 | 4 | SO | 3-Ph-Phenyl |
| 300 | 1 | $SO_2$ | 3-Ph-Phenyl |
| 301 | 2 | $SO_2$ | 3-Ph-Phenyl |
| 302 | 3 | $SO_2$ | 3-Ph-Phenyl |
| 303 | 4 | $SO_2$ | 3-Ph-Phenyl |
| 304 | 1 | O | 2-morpholino-phenyl |
| 305 | 2 | O | 2-morpholino-phenyl |
| 306 | 3 | O | 2-morpholino-phenyl |
| 307 | 4 | O | 2-morpholino-phenyl |
| 308 | 1 | S | 2-morpholino-phenyl |
| 309 | 2 | S | 2-morpholino-phenyl |
| 310 | 3 | S | 2-morpholino-phenyl |
| 311 | 4 | S | 2-morpholino-phenyl |
| 312 | 1 | SO | 2-morpholino-phenyl |
| 313 | 2 | SO | 2-morpholino-phenyl |
| 314 | 3 | SO | 2-morpholino-phenyl |
| 315 | 4 | SO | 2-morpholino-phenyl |
| 316 | 1 | $SO_2$ | 2-morpholino-phenyl |
| 317 | 2 | $SO_2$ | 2-morpholino-phenyl |
| 318 | 3 | $SO_2$ | 2-morpholino-phenyl |
| 319 | 4 | $SO_2$ | 2-morpholino-phenyl |
| 320 | 1 | O | 4-morpholino-phenyl |
| 321 | 2 | O | 4-morpholino-phenyl |
| 322 | 3 | O | 4-morpholino-phenyl |
| 323 | 4 | O | 4-morpholino-phenyl |
| 324 | 1 | SO | 4-morpholino-phenyl |
| 325 | 2 | SO | 4-morpholino-phenyl |
| 326 | 3 | SO | 4-morpholino-phenyl |
| 327 | 4 | SO | 4-morpholino-phenyl |
| 328 | 1 | O | naphthylen-1-yl |

TABLE 30-continued

| Entry | n | X | $R^3$ |
|---|---|---|---|
| 329 | 2 | O | naphthylen-1-yl |
| 330 | 3 | O | naphthylen-1-yl |
| 331 | 4 | O | naphthylen-1-yl |
| 332 | 1 | S | naphthylen-1-yl |
| 333 | 2 | S | naphthylen-1-yl |
| 334 | 3 | S | naphthylen-1-yl |
| 335 | 4 | S | naphthylen-1-yl |
| 336 | 1 | SO | naphthylen-1-yl |
| 337 | 2 | SO | naphthylen-1-yl |
| 338 | 3 | SO | naphthylen-1-yl |
| 339 | 4 | SO | naphthylen-1-yl |
| 340 | 1 | $SO_2$ | naphthylen-1-yl |
| 341 | 2 | $SO_2$ | naphthylen-1-yl |
| 342 | 3 | $SO_2$ | naphthylen-1-yl |
| 343 | 4 | $SO_2$ | naphthylen-1-yl |
| 344 | 1 | O | 4-OH-Phenyl |
| 345 | 2 | O | 4-OH-Phenyl |
| 346 | 3 | O | 4-OH-Phenyl |
| 347 | 4 | O | 4-OH-Phenyl |
| 348 | 1 | S | 4-OH-Phenyl |
| 349 | 2 | S | 4-OH-Phenyl |
| 350 | 3 | S | 4-OH-Phenyl |
| 351 | 4 | S | 4-OH-Phenyl |
| 352 | 1 | SO | 4-OH-Phenyl |
| 353 | 2 | SO | 4-OH-Phenyl |
| 354 | 3 | SO | 4-OH-Phenyl |
| 355 | 4 | SO | 4-OH-Phenyl |
| 356 | 1 | $SO_2$ | 4-OH-Phenyl |
| 357 | 2 | $SO_2$ | 4-OH-Phenyl |
| 358 | 3 | $SO_2$ | 4-OH-Phenyl |
| 359 | 4 | $SO_2$ | 4-OH-Phenyl |
| 360 | 1 | O | 2-OH-Phenyl |
| 361 | 2 | O | 2-OH-Phenyl |
| 362 | 3 | O | 2-OH-Phenyl |
| 363 | 4 | O | 2-OH-Phenyl |
| 364 | 1 | S | 2-OH-Phenyl |
| 365 | 2 | S | 2-OH-Phenyl |
| 366 | 3 | S | 2-OH-Phenyl |
| 367 | 4 | S | 2-OH-Phenyl |
| 368 | 1 | SO | 2-OH-Phenyl |
| 369 | 2 | SO | 2-OH-Phenyl |
| 370 | 3 | SO | 2-OH-Phenyl |
| 371 | 4 | SO | 2-OH-Phenyl |
| 372 | 1 | $SO_2$ | 2-OH-Phenyl |
| 373 | 2 | $SO_2$ | 2-OH-Phenyl |
| 374 | 3 | $SO_2$ | 2-OH-Phenyl |
| 375 | 4 | $SO_2$ | 2-OH-Phenyl |
| 376 | 1 | O | 4-OMe-Phenyl |
| 377 | 2 | O | 4-OMe-Phenyl |
| 378 | 3 | O | 4-OMe-Phenyl |
| 379 | 4 | O | 4-OMe-Phenyl |
| 380 | 1 | S | 4-OMe-Phenyl |
| 381 | 2 | S | 4-OMe-Phenyl |
| 382 | 3 | S | 4-OMe-Phenyl |
| 383 | 4 | S | 4-OMe-Phenyl |
| 384 | 1 | SO | 4-OMe-Phenyl |
| 385 | 2 | SO | 4-OMe-Phenyl |
| 386 | 3 | SO | 4-OMe-Phenyl |
| 387 | 4 | SO | 4-OMe-Phenyl |
| 388 | 1 | $SO_2$ | 4-OMe-Phenyl |
| 389 | 2 | $SO_2$ | 4-OMe-Phenyl |
| 390 | 3 | $SO_2$ | 4-OMe-Phenyl |
| 391 | 4 | $SO_2$ | 4-OMe-Phenyl |
| 392 | 1 | O | 2-OMe-Phenyl |
| 393 | 2 | O | 2-OMe-Phenyl |
| 394 | 3 | O | 2-OMe-Phenyl |
| 395 | 4 | O | 2-OMe-Phenyl |
| 396 | 1 | S | 2-OMe-Phenyl |
| 397 | 2 | S | 2-OMe-Phenyl |
| 398 | 3 | S | 2-OMe-Phenyl |
| 399 | 4 | S | 2-OMe-Phenyl |
| 400 | 1 | SO | 2-OMe-Phenyl |
| 401 | 2 | SO | 2-OMe-Phenyl |
| 402 | 3 | SO | 2-OMe-Phenyl |
| 403 | 4 | SO | 2-OMe-Phenyl |
| 404 | 1 | $SO_2$ | 2-OMe-Phenyl |
| 405 | 2 | $SO_2$ | 2-OMe-Phenyl |
| 406 | 3 | $SO_2$ | 2-OMe-Phenyl |

TABLE 30-continued

| Entry | n | X | $R^3$ |
|---|---|---|---|
| 407 | 4 | $SO_2$ | 2-OMe-Phenyl |
| 408 | 1 | O | 3-CN-Phenyl |
| 409 | 2 | O | 3-CN-Phenyl |
| 410 | 3 | O | 3-CN-Phenyl |
| 411 | 4 | O | 3-CN-Phenyl |
| 412 | 1 | S | 3-CN-Phenyl |
| 413 | 2 | S | 3-CN-Phenyl |
| 414 | 3 | S | 3-CN-Phenyl |
| 415 | 4 | S | 3-CN-Phenyl |
| 416 | 1 | SO | 3-CN-Phenyl |
| 417 | 2 | SO | 3-CN-Phenyl |
| 418 | 3 | SO | 3-CN-Phenyl |
| 419 | 4 | SO | 3-CN-Phenyl |
| 420 | 1 | $SO_2$ | 3-CN-Phenyl |
| 421 | 2 | $SO_2$ | 3-CN-Phenyl |
| 422 | 3 | $SO_2$ | 3-CN-Phenyl |
| 423 | 4 | $SO_2$ | 3-CN-Phenyl |
| 424 | 1 | O | 2-Me-Phenyl |
| 425 | 2 | O | 2-Me-Phenyl |
| 426 | 3 | O | 2-Me-Phenyl |
| 427 | 4 | O | 2-Me-Phenyl |
| 428 | 1 | S | 2-Me-Phenyl |
| 429 | 2 | S | 2-Me-Phenyl |
| 430 | 3 | S | 2-Me-Phenyl |
| 431 | 4 | S | 2-Me-Phenyl |
| 432 | 1 | SO | 2-Me-Phenyl |
| 433 | 2 | SO | 2-Me-Phenyl |
| 434 | 3 | SO | 2-Me-Phenyl |
| 435 | 4 | SO | 2-Me-Phenyl |
| 436 | 1 | $SO_2$ | 2-Me-Phenyl |
| 437 | 2 | $SO_2$ | 2-Me-Phenyl |
| 438 | 3 | $SO_2$ | 2-Me-Phenyl |
| 439 | 4 | $SO_2$ | 2-Me-Phenyl |
| 440 | 1 | O | 4-Me-Phenyl |
| 441 | 2 | O | 4-Me-Phenyl |
| 442 | 3 | O | 4-Me-Phenyl |
| 443 | 4 | O | 4-Me-Phenyl |
| 444 | 1 | S | 4-Me-Phenyl |
| 445 | 2 | S | 4-Me-Phenyl |
| 446 | 3 | S | 4-Me-Phenyl |
| 447 | 4 | S | 4-Me-Phenyl |
| 448 | 1 | SO | 4-Me-Phenyl |
| 449 | 2 | SO | 4-Me-Phenyl |
| 450 | 3 | SO | 4-Me-Phenyl |
| 451 | 4 | SO | 4-Me-Phenyl |
| 452 | 1 | $SO_2$ | 4-Me-Phenyl |
| 453 | 2 | $SO_2$ | 4-Me-Phenyl |
| 454 | 3 | $SO_2$ | 4-Me-Phenyl |
| 455 | 4 | $SO_2$ | 4-Me-Phenyl |
| 456 | 1 | O | 3-F-Phenyl |
| 457 | 2 | O | 3-F-Phenyl |
| 458 | 3 | O | 3-F-Phenyl |
| 459 | 4 | O | 3-F-Phenyl |
| 460 | 1 | S | 3-F-Phenyl |
| 461 | 2 | S | 3-F-Phenyl |
| 462 | 3 | S | 3-F-Phenyl |
| 463 | 4 | S | 3-F-Phenyl |
| 464 | 1 | SO | 3-F-Phenyl |
| 465 | 2 | SO | 3-F-Phenyl |
| 466 | 3 | SO | 3-F-Phenyl |
| 467 | 4 | SO | 3-F-Phenyl |
| 468 | 1 | $SO_2$ | 3-F-Phenyl |
| 469 | 2 | $SO_2$ | 3-F-Phenyl |
| 470 | 3 | $SO_2$ | 3-F-Phenyl |
| 471 | 4 | $SO_2$ | 3-F-Phenyl |
| 472 | 1 | O | 2-Cl-Phenyl |
| 473 | 2 | O | 2-Cl-Phenyl |
| 474 | 3 | O | 2-Cl-Phenyl |
| 475 | 4 | O | 2-Cl-Phenyl |
| 476 | 1 | S | 2-Cl-Phenyl |
| 477 | 2 | S | 2-Cl-Phenyl |
| 478 | 3 | S | 2-Cl-Phenyl |
| 479 | 4 | S | 2-Cl-Phenyl |
| 480 | 1 | SO | 2-Cl-Phenyl |
| 481 | 2 | SO | 2-Cl-Phenyl |
| 482 | 3 | SO | 2-Cl-Phenyl |
| 483 | 4 | SO | 2-Cl-Phenyl |
| 484 | 1 | $SO_2$ | 2-Cl-Phenyl |

TABLE 30-continued

| Entry | n | X | $R^3$ |
|---|---|---|---|
| 485 | 2 | $SO_2$ | 2-Cl-Phenyl |
| 486 | 3 | $SO_2$ | 2-Cl-Phenyl |
| 487 | 4 | $SO_2$ | 2-Cl-Phenyl |
| 488 | 1 | O | 4-Cl-Phenyl |
| 489 | 2 | O | 4-Cl-Phenyl |
| 490 | 3 | O | 4-Cl-Phenyl |
| 491 | 4 | O | 4-Cl-Phenyl |
| 492 | 1 | S | 4-Cl-Phenyl |
| 493 | 2 | S | 4-Cl-Phenyl |
| 494 | 3 | S | 4-Cl-Phenyl |
| 495 | 4 | S | 4-Cl-Phenyl |
| 496 | 1 | SO | 4-Cl-Phenyl |
| 497 | 2 | SO | 4-Cl-Phenyl |
| 498 | 3 | SO | 4-Cl-Phenyl |
| 499 | 4 | SO | 4-Cl-Phenyl |
| 500 | 1 | $SO_2$ | 4-Cl-Phenyl |
| 501 | 2 | $SO_2$ | 4-Cl-Phenyl |
| 502 | 3 | $SO_2$ | 4-Cl-Phenyl |
| 503 | 4 | $SO_2$ | 4-Cl-Phenyl |
| 504 | 1 | O | 3-Br-Phenyl |
| 505 | 2 | O | 3-Br-Phenyl |
| 506 | 3 | O | 3-Br-Phenyl |
| 507 | 4 | O | 3-Br-Phenyl |
| 508 | 1 | S | 3-Br-Phenyl |
| 509 | 2 | S | 3-Br-Phenyl |
| 510 | 3 | S | 3-Br-Phenyl |
| 511 | 4 | S | 3-Br-Phenyl |
| 512 | 1 | SO | 3-Br-Phenyl |
| 513 | 2 | SO | 3-Br-Phenyl |
| 514 | 3 | SO | 3-Br-Phenyl |
| 515 | 4 | SO | 3-Br-Phenyl |
| 516 | 1 | $SO_2$ | 3-Br-Phenyl |
| 517 | 2 | $SO_2$ | 3-Br-Phenyl |
| 518 | 3 | $SO_2$ | 3-Br-Phenyl |
| 519 | 4 | $SO_2$ | 3-Br-Phenyl |
| 520 | 1 | O | 2-$CF_3$-Phenyl |
| 521 | 2 | O | 2-$CF_3$-Phenyl |
| 522 | 3 | O | 2-$CF_3$-Phenyl |
| 523 | 4 | O | 2-$CF_3$-Phenyl |
| 524 | 1 | S | 2-$CF_3$-Phenyl |
| 525 | 2 | S | 2-$CF_3$-Phenyl |
| 526 | 3 | S | 2-$CF_3$-Phenyl |
| 527 | 4 | S | 2-$CF_3$-Phenyl |
| 528 | 1 | SO | 2-$CF_3$-Phenyl |
| 529 | 2 | SO | 2-$CF_3$-Phenyl |
| 530 | 3 | SO | 2-$CF_3$-Phenyl |
| 531 | 4 | SO | 2-$CF_3$-Phenyl |
| 532 | 1 | $SO_2$ | 2-$CF_3$-Phenyl |
| 533 | 2 | $SO_2$ | 2-$CF_3$-Phenyl |
| 534 | 3 | $SO_2$ | 2-$CF_3$-Phenyl |
| 535 | 4 | $SO_2$ | 2-$CF_3$-Phenyl |
| 536 | 1 | O | 4-$CF_3$-Phenyl |
| 537 | 2 | O | 4-$CF_3$-Phenyl |
| 538 | 3 | O | 4-$CF_3$-Phenyl |
| 539 | 4 | O | 4-$CF_3$-Phenyl |
| 540 | 1 | S | 4-$CF_3$-Phenyl |
| 541 | 2 | S | 4-$CF_3$-Phenyl |
| 542 | 3 | S | 4-$CF_3$-Phenyl |
| 543 | 4 | S | 4-$CF_3$-Phenyl |
| 544 | 1 | SO | 4-$CF_3$-Phenyl |
| 545 | 2 | SO | 4-$CF_3$-Phenyl |
| 546 | 3 | SO | 4-$CF_3$-Phenyl |
| 547 | 4 | SO | 3-$CF_3$-Phenyl |
| 548 | 1 | $SO_2$ | 4-$CF_3$-Phenyl |
| 549 | 2 | $SO_2$ | 4-$CF_3$-Phenyl |
| 550 | 3 | $SO_2$ | 4-$CF_3$-Phenyl |
| 551 | 4 | $SO_2$ | 4-$CF_3$-Phenyl |
| 552 | 1 | O | 3-iPr-Phenyl |
| 553 | 2 | O | 3-iPr-Phenyl |
| 554 | 3 | O | 3-iPr-Phenyl |
| 555 | 4 | O | 3-iPr-Phenyl |
| 556 | 1 | S | 3-iPr-Phenyl |
| 557 | 2 | S | 3-iPr-Phenyl |
| 558 | 3 | S | 3-iPr-Phenyl |
| 559 | 4 | S | 3-iPr-Phenyl |
| 560 | 1 | SO | 3-iPr-Phenyl |
| 561 | 2 | SO | 3-iPr-Phenyl |
| 562 | 3 | SO | 3-iPr-Phenyl |

TABLE 30-continued

| Entry | n | X | $R^3$ |
|---|---|---|---|
| 563 | 4 | SO | 3-iPr-Phenyl |
| 564 | 1 | $SO_2$ | 3-iPr-Phenyl |
| 565 | 2 | $SO_2$ | 3-iPr-Phenyl |
| 566 | 3 | $SO_2$ | 3-iPr-Phenyl |
| 567 | 4 | $SO_2$ | 3-iPr-Phenyl |
| 568 | 1 | O | 4-$NH_2$-Phenyl |
| 569 | 2 | O | 4-$NH_2$-Phenyl |
| 570 | 3 | O | 4-$NH_2$-Phenyl |
| 571 | 4 | O | 4-$NH_2$-Phenyl |
| 572 | 1 | S | 4-$NH_2$-Phenyl |
| 573 | 2 | S | 4-$NH_2$-Phenyl |
| 574 | 3 | S | 4-$NH_2$-Phenyl |
| 575 | 4 | S | 4-$NH_2$-Phenyl |
| 576 | 1 | SO | 4-$NH_2$-Phenyl |
| 577 | 2 | SO | 4-$NH_2$-Phenyl |
| 578 | 3 | SO | 4-$NH_2$-Phenyl |
| 579 | 4 | SO | 4-$NH_2$-Phenyl |
| 580 | 1 | $SO_2$ | 4-$NH_2$-Phenyl |
| 581 | 2 | $SO_2$ | 4-$NH_2$-Phenyl |
| 582 | 3 | $SO_2$ | 4-$NH_2$-Phenyl |
| 583 | 4 | $SO_2$ | 4-$NH_2$-Phenyl |
| 584 | 1 | O | 2-$NH_2$-Phenyl |
| 585 | 2 | O | 2-$NH_2$-Phenyl |
| 586 | 3 | O | 2-$NH_2$-Phenyl |
| 587 | 4 | O | 2-$NH_2$-Phenyl |
| 588 | 1 | S | 2-$NH_2$-Phenyl |
| 589 | 2 | S | 2-$NH_2$-Phenyl |
| 590 | 3 | S | 2-$NH_2$-Phenyl |
| 591 | 1 | S | 2-$NH_2$-Phenyl |
| 592 | 2 | SO | 2-$NH_2$-Phenyl |
| 593 | 3 | SO | 2-$NH_2$-Phenyl |
| 594 | 4 | SO | 2-$NH_2$-Phenyl |
| 595 | 1 | SO | 2-$NH_2$-Phenyl |
| 596 | 2 | $SO_2$ | 2-$NH_2$-Phenyl |
| 597 | 3 | $SO_2$ | 2-$NH_2$-Phenyl |
| 598 | 4 | $SO_2$ | 2-$NH_2$-Phenyl |
| 599 | 1 | O | 2,6-di-Me-Phenyl |
| 600 | 2 | O | 2,6-di-Me-Phenyl |
| 601 | 3 | O | 2,6-di-Me-Phenyl |
| 602 | 4 | O | 2,6-di-Me-Phenyl |
| 603 | 1 | S | 2,6-di-Me-Phenyl |
| 604 | 2 | S | 2,6-di-Me-Phenyl |
| 605 | 3 | S | 2,6-di-Me-Phenyl |
| 606 | 4 | S | 2,6-di-Me-Phenyl |
| 607 | 1 | SO | 2,6-di-Me-Phenyl |
| 608 | 2 | SO | 2,6-di-Me-Phenyl |
| 609 | 3 | SO | 2,6-di-Me-Phenyl |
| 610 | 4 | SO | 2,6-di-Me-Phenyl |
| 611 | 1 | $SO_2$ | 2,6-di-Me-Phenyl |
| 612 | 2 | $SO_2$ | 2,6-di-Me-Phenyl |
| 613 | 3 | $SO_2$ | 2,6-di-Me-Phenyl |
| 614 | 4 | $SO_2$ | 2,6-di-Me-Phenyl |
| 615 | 1 | O | 2-Ph-Phenyl |
| 616 | 2 | O | 2-Ph-Phenyl |
| 617 | 3 | O | 2-Ph-Phenyl |
| 618 | 4 | O | 2-Ph-Phenyl |
| 619 | 1 | S | 2-Ph-Phenyl |
| 620 | 2 | S | 2-Ph-Phenyl |
| 621 | 3 | S | 2-Ph-Phenyl |
| 622 | 4 | S | 2-Ph-Phenyl |
| 623 | 1 | SO | 2-Ph-Phenyl |
| 624 | 2 | SO | 2-Ph-Phenyl |
| 625 | 3 | SO | 2-Ph-Phenyl |
| 626 | 4 | SO | 2-Ph-Phenyl |
| 627 | 1 | $SO_2$ | 2-Ph-Phenyl |
| 628 | 2 | $SO_2$ | 2-Ph-Phenyl |
| 629 | 3 | $SO_2$ | 2-Ph-Phenyl |
| 630 | 4 | $SO_2$ | 2-Ph-Phenyl |
| 631 | 1 | O | 4-Ph-Phenyl |
| 632 | 2 | O | 4-Ph-Phenyl |
| 633 | 3 | O | 4-Ph-Phenyl |
| 634 | 4 | O | 4-Ph-Phenyl |
| 635 | 1 | S | 4-Ph-Phenyl |
| 636 | 2 | S | 4-Ph-Phenyl |
| 637 | 3 | S | 4-Ph-Phenyl |
| 638 | 4 | S | 4-Ph-Phenyl |
| 639 | 1 | SO | 4-Ph-Phenyl |
| 640 | 2 | SO | 4-Ph-Phenyl |

TABLE 30-continued

| Entry | n | X | $R^3$ |
|---|---|---|---|
| 641 | 3 | SO | 4-Ph-Phenyl |
| 642 | 4 | SO | 4-Ph-Phenyl |
| 643 | 1 | $SO_2$ | 4-Ph-Phenyl |
| 644 | 2 | $SO_2$ | 4-Ph-Phenyl |
| 645 | 3 | $SO_2$ | 4-Ph-Phenyl |
| 646 | 4 | $SO_2$ | 4-Ph-Phenyl |
| 647 | 1 | O | 3-morpholino-phenyl |
| 648 | 2 | O | 3-morpholino-phenyl |
| 649 | 3 | O | 3-morpholino-phenyl |
| 650 | 4 | O | 3-morpholino-phenyl |
| 651 | 1 | S | 3-morpholino-phenyl |
| 652 | 2 | S | 3-morpholino-phenyl |
| 653 | 3 | S | 3-morpholino-phenyl |
| 654 | 4 | S | 3-morpholino-phenyl |
| 655 | 1 | SO | 3-morpholino-phenyl |
| 656 | 2 | SO | 3-morpholino-phenyl |
| 657 | 3 | SO | 3-morpholino-phenyl |
| 658 | 4 | SO | 3-morpholino-phenyl |
| 659 | 1 | $SO_2$ | 3-morpholino-phenyl |
| 660 | 2 | $SO_2$ | 3-morpholino-phenyl |
| 661 | 3 | $SO_2$ | 3-morpholino-phenyl |
| 662 | 4 | $SO_2$ | 3-morpholino-phenyl |
| 663 | 1 | S | 4-morpholino-phenyl |
| 664 | 2 | S | 4-morpholino-phenyl |
| 665 | 3 | S | 4-morpholino-phenyl |
| 667 | 4 | S | 4-morpholino-phenyl |
| 668 | 1 | $SO_2$ | 4-morpholino-phenyl |
| 669 | 2 | $SO_2$ | 4-morpholino-phenyl |
| 670 | 3 | $SO_2$ | 4-morpholino-phenyl |
| 671 | 4 | $SO_2$ | 4-morpholino-phenyl |
| 672 | 1 | O | naphthylen-2-yl |
| 673 | 2 | O | naphthylen-2-yl |
| 674 | 3 | O | naphthylen-2-yl |
| 675 | 4 | O | naphthylen-2-yl |
| 676 | 1 | S | naphthylen-2-yl |
| 678 | 2 | S | naphthylen-2-yl |
| 679 | 3 | S | naphthylen-2-yl |
| 680 | 4 | S | naphthylen-2-yl |
| 681 | 1 | SO | naphthylen-2-yl |
| 682 | 2 | SO | naphthylen-2-yl |
| 683 | 3 | SO | naphthylen-2-yl |
| 684 | 4 | SO | naphthylen-2-yl |
| 685 | 1 | $SO_2$ | naphthylen-2-yl |
| 686 | 2 | $SO_2$ | naphthylen-2-yl |
| 687 | 3 | $SO_2$ | naphthylen-2-yl |
| 688 | 4 | $SO_2$ | naphthylen-2-yl |

Exemplary embodiments include compounds having the formula (XXXVIII)

(XXXVIII)

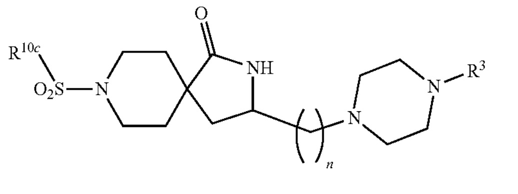

or a pharmaceutically acceptable salt form thereof defined herein below in Table 31

TABLE 31

| Entry | n | $R^3$ | $R^{10c}$ |
|---|---|---|---|
| 1 | 1 | 4-$CH_3$-phenyl | Ethyl |
| 2 | 1 | 4-$CH_3$-phenyl | n-propyl |
| 3 | 1 | 4-$CH_3$-phenyl | Isopropyl |
| 4 | 1 | 4-$CH_3$-phenyl | —$CH_2CH(CH_3)_2$ |
| 5 | 1 | 4-$CH_3$-phenyl | $CF_3$ |
| 6 | 1 | 4-$CH_3$-phenyl | —$CH_2CF_3$ |
| 7 | 1 | 4-$CH_3$-phenyl | —$CH_2CH_2CF_3$ |
| 8 | 1 | 4-$CH_3$-phenyl | Cyclopropyl |
| 9 | 1 | 4-$CH_3$-phenyl | Cyclobutyl |
| 10 | 1 | 4-$CH_3$-phenyl | Cyclopentyl |
| 11 | 1 | 4-$CH_3$-phenyl | Cyclohexyl |
| 12 | 1 | 4-$CH_3$-phenyl | 3-pyridyl |
| 13 | 1 | 4-$CH_3$-phenyl | 1-methyl-1H-pyrazol-4-yl |
| 14 | 1 | 4-$CH_3$-phenyl | 1H-imidazol-4-yl |
| 15 | 1 | 4-$CH_3$-phenyl | 2-furanyl |
| 16 | 1 | 4-$CH_3$-phenyl | Ethyl |
| 17 | 1 | 4-$CH_3$-phenyl | n-propyl |
| 18 | 1 | 4-$CH_3$-phenyl | Isopropyl |
| 19 | 1 | 4-$CH_3$-phenyl | —$CH_2CH(CH_3)_2$ |
| 20 | 1 | 4-$CH_3$-phenyl | $CF_3$ |
| 21 | 1 | 4-$CH_3$-phenyl | —$CH_2CF_3$ |
| 22 | 1 | 4-$CH_3$-phenyl | —$CH_2CH_2CF_3$ |
| 23 | 1 | 4-$CH_3$-phenyl | Cyclopropyl |
| 24 | 1 | 4-$CH_3$-phenyl | Cyclobutyl |
| 25 | 1 | 4-$CH_3$-phenyl | Cyclopentyl |
| 26 | 1 | 4-$CH_3$-phenyl | Cyclohexyl |
| 27 | 1 | 4-$CH_3$-phenyl | 3-pyridyl |
| 28 | 1 | 4-$CH_3$-phenyl | 1-methyl-1H-pyrazol-4-yl |
| 29 | 1 | 4-$CH_3$-phenyl | 1H-imidazol-4-yl |
| 30 | 1 | 4-$CH_3$-phenyl | 2-furanyl |
| 31 | 1 | 3-OH-Phenyl | Ethyl |
| 32 | 1 | 3-OH-Phenyl | n-propyl |
| 33 | 1 | 3-OH-Phenyl | Isopropyl |
| 34 | 1 | 3-OH-Phenyl | —$CH_2CH(CH_3)_2$ |
| 35 | 1 | 3-OH-Phenyl | $CF_3$ |
| 36 | 1 | 3-OH-Phenyl | —$CH_2CF_3$ |
| 37 | 1 | 3-OH-Phenyl | —$CH_2CH_2CF_3$ |
| 38 | 1 | 3-OH-Phenyl | Cyclopropyl |
| 39 | 1 | 3-OH-Phenyl | Cyclobutyl |
| 40 | 1 | 3-OH-Phenyl | Cyclopentyl |
| 41 | 1 | 3-OH-Phenyl | Cyclohexyl |
| 42 | 1 | 3-OH-Phenyl | 3-pyridyl |
| 43 | 1 | 3-OH-Phenyl | 1-methyl-1H-pyrazol-4-yl |
| 44 | 1 | 3-OH-Phenyl | 1H-imidazol-4-yl |
| 45 | 1 | 3-OH-Phenyl | 2-furanyl |
| 46 | 1 | 4-OMe-Phenyl | Ethyl |
| 47 | 1 | 4-OMe-Phenyl | n-propyl |
| 48 | 1 | 4-OMe-Phenyl | Isopropyl |
| 49 | 1 | 4-OMe-Phenyl | —$CH_2CH(CH_3)_2$ |
| 50 | 1 | 4-OMe-Phenyl | $CF_3$ |
| 51 | 1 | 4-OMe-Phenyl | —$CH_2CF_3$ |
| 52 | 1 | 4-OMe-Phenyl | —$CH_2CH_2CF_3$ |
| 53 | 1 | 4-OMe-Phenyl | Cyclopropyl |
| 54 | 1 | 4-OMe-Phenyl | Cyclobutyl |
| 55 | 1 | 4-OMe-Phenyl | Cyclopentyl |
| 56 | 1 | 4-OMe-Phenyl | Cyclohexyl |
| 57 | 1 | 4-OMe-Phenyl | 3-pyridyl |
| 58 | 1 | 4-OMe-Phenyl | 1-methyl-1H-pyrazol-4-yl |
| 59 | 1 | 4-OMe-Phenyl | 1H-imidazol-4-yl |
| 60 | 1 | 4-OMe-Phenyl | 2-furanyl |
| 61 | 1 | 2-OMe-Phenyl | Ethyl |
| 62 | 1 | 2-OMe-Phenyl | n-propyl |
| 63 | 1 | 2-OMe-Phenyl | Isopropyl |
| 64 | 1 | 2-OMe-Phenyl | —$CH_2CH(CH_3)_2$ |
| 65 | 1 | 2-OMe-Phenyl | $CF_3$ |
| 66 | 1 | 2-OMe-Phenyl | —$CH_2CF_3$ |
| 67 | 1 | 2-OMe-Phenyl | —$CH_2CH_2CF_3$ |
| 68 | 1 | 2-OMe-Phenyl | Cyclopropyl |
| 69 | 1 | 2-OMe-Phenyl | Cyclobutyl |
| 70 | 1 | 2-OMe-Phenyl | Cyclopentyl |
| 71 | 1 | 2-OMe-Phenyl | Cyclohexyl |
| 72 | 1 | 2-OMe-Phenyl | 3-pyridyl |
| 73 | 1 | 2-OMe-Phenyl | 1-methyl-1H-pyrazol-4-yl |
| 74 | 1 | 2-OMe-Phenyl | 1H-imidazol-4-yl |
| 75 | 1 | 2-OMe-Phenyl | 2-furanyl |
| 76 | 1 | 3-CN-Phenyl | Ethyl |
| 77 | 1 | 3-CN-Phenyl | n-propyl |
| 78 | 1 | 3-CN-Phenyl | Isopropyl |
| 79 | 1 | 3-CN-Phenyl | —$CH_2CH(CH_3)_2$ |
| 80 | 1 | 3-CN-Phenyl | $CF_3$ |
| 81 | 1 | 3-CN-Phenyl | —$CH_2CF_3$ |
| 82 | 1 | 3-CN-Phenyl | —$CH_2CH_2CF_3$ |
| 83 | 1 | 3-CN-Phenyl | Cyclopropyl |

TABLE 31-continued

| Entry | n | $R^3$ | $R^{10c}$ |
|---|---|---|---|
| 84 | 1 | 3-CN-Phenyl | Cyclobutyl |
| 85 | 1 | 3-CN-Phenyl | Cyclopentyl |
| 86 | 1 | 3-CN-Phenyl | Cyclohexyl |
| 87 | 1 | 3-CN-Phenyl | 3-pyridyl |
| 88 | 1 | 3-CN-Phenyl | 1-methyl-1H-pyrazol-4-yl |
| 89 | 1 | 3-CN-Phenyl | 1H-imidazol-4-yl |
| 90 | 1 | 3-CN-Phenyl | 2-furanyl |
| 91 | 1 | 2-F-Phenyl | Ethyl |
| 92 | 1 | 2-F-Phenyl | n-propyl |
| 93 | 1 | 2-F-Phenyl | Isopropyl |
| 94 | 1 | 2-F-Phenyl | $—CH_2CH(CH_3)_2$ |
| 95 | 1 | 2-F-Phenyl | $CF_3$ |
| 96 | 1 | 2-F-Phenyl | $—CH_2CF_3$ |
| 97 | 1 | 2-F-Phenyl | $—CH_2CH_2CF_3$ |
| 98 | 1 | 2-F-Phenyl | Cyclopropyl |
| 99 | 1 | 2-F-Phenyl | Cyclobutyl |
| 100 | 1 | 2-F-Phenyl | Cyclopentyl |
| 101 | 1 | 2-F-Phenyl | Cyclohexyl |
| 102 | 1 | 2-F-Phenyl | 3-pyridyl |
| 103 | 1 | 2-F-Phenyl | 1-methyl-1H-pyrazol-4-yl |
| 104 | 1 | 2-F-Phenyl | 1H-imidazol-4-yl |
| 105 | 1 | 2-F-Phenyl | 2-furanyl |
| 106 | 1 | 4-F-Phenyl | Ethyl |
| 107 | 1 | 4-F-Phenyl | n-propyl |
| 108 | 1 | 4-F-Phenyl | Isopropyl |
| 109 | 1 | 4-F-Phenyl | $—CH_2CH(CH_3)_2$ |
| 110 | 1 | 4-F-Phenyl | $CF_3$ |
| 111 | 1 | 4-F-Phenyl | $—CH_2CF_3$ |
| 112 | 1 | 4-F-Phenyl | $—CH_2CH_2CF_3$ |
| 113 | 1 | 4-F-Phenyl | Cyclopropyl |
| 114 | 1 | 4-F-Phenyl | Cyclobutyl |
| 115 | 1 | 4-F-Phenyl | Cyclopentyl |
| 116 | 1 | 4-F-Phenyl | Cyclohexyl |
| 117 | 1 | 4-F-Phenyl | 3-pyridyl |
| 118 | 1 | 4-F-Phenyl | 1-methyl-1H-pyrazol-4-yl |
| 119 | 1 | 4-F-Phenyl | 1H-imidazol-4-yl |
| 120 | 1 | 4-F-Phenyl | 2-furanyl |
| 121 | 1 | 3-Cl-Phenyl | Ethyl |
| 122 | 1 | 3-Cl-Phenyl | n-propyl |
| 123 | 1 | 3-Cl-Phenyl | Isopropyl |
| 124 | 1 | 3-Cl-Phenyl | $—CH_2CH(CH_3)_2$ |
| 125 | 1 | 3-Cl-Phenyl | $CF_3$ |
| 126 | 1 | 3-Cl-Phenyl | $—CH_2CF_3$ |
| 127 | 1 | 3-Cl-Phenyl | $—CH_2CH_2CF_3$ |
| 128 | 1 | 3-Cl-Phenyl | Cyclopropyl |
| 129 | 1 | 3-Cl-Phenyl | Cyclobutyl |
| 130 | 1 | 3-Cl-Phenyl | Cyclopentyl |
| 131 | 1 | 3-Cl-Phenyl | Cyclohexyl |
| 132 | 1 | 3-Cl-Phenyl | 3-pyridyl |
| 133 | 1 | 3-Cl-Phenyl | 1-methyl-1H-pyrazol-4-yl |
| 134 | 1 | 3-Cl-Phenyl | 1H-imidazol-4-yl |
| 135 | 1 | 3-Cl-Phenyl | 2-furanyl |
| 136 | 1 | 2-Br-Phenyl | ethyl |
| 137 | 1 | 2-Br-Phenyl | n-propyl |
| 138 | 1 | 2-Br-Phenyl | isopropyl |
| 139 | 1 | 2-Br-Phenyl | $—CH_2CH(CH_3)_2$ |
| 140 | 1 | 2-Br-Phenyl | $CF_3$ |
| 141 | 1 | 2-Br-Phenyl | $—CH_2CF_3$ |
| 142 | 1 | 2-Br-Phenyl | $—CH_2CH_2CF_3$ |
| 143 | 1 | 2-Br-Phenyl | cyclopropyl |
| 144 | 1 | 2-Br-Phenyl | Cyclobutyl |
| 145 | 1 | 2-Br-Phenyl | cyclopentyl |
| 146 | 1 | 2-Br-Phenyl | cyclohexyl |
| 147 | 1 | 2-Br-Phenyl | 3-pyridyl |
| 148 | 1 | 2-Br-Phenyl | 1-methyl-1H-pyrazol-4-yl |
| 149 | 1 | 2-Br-Phenyl | 1H-imidazol-4-yl |
| 150 | 1 | 2-Br-Phenyl | 2-furanyl |
| 151 | 1 | 4-Br-Phenyl | ethyl |
| 152 | 1 | 4-Br-Phenyl | n-propyl |
| 153 | 1 | 4-Br-Phenyl | isopropyl |
| 154 | 1 | 4-Br-Phenyl | $—CH_2CH(CH_3)_2$ |
| 155 | 1 | 4-Br-Phenyl | $CF_3$ |
| 156 | 1 | 4-Br-Phenyl | $—CH_2CF_3$ |
| 157 | 1 | 4-Br-Phenyl | $—CH_2CH_2CF_3$ |
| 158 | 1 | 4-Br-Phenyl | cyclopropyl |
| 159 | 1 | 4-Br-Phenyl | Cyclobutyl |
| 160 | 1 | 4-Br-Phenyl | cyclopentyl |
| 161 | 1 | 4-Br-Phenyl | cyclohexyl |

TABLE 31-continued

| Entry | n | $R^3$ | $R^{10c}$ |
|---|---|---|---|
| 162 | 1 | 4-Br-Phenyl | 3-pyridyl |
| 163 | 1 | 4-Br-Phenyl | 1-methyl-1H-pyrazol-4-yl |
| 164 | 1 | 4-Br-Phenyl | 1H-imidazol-4-yl |
| 165 | 1 | 4-Br-Phenyl | 2-furanyl |
| 166 | 1 | $3-CF_3$-Phenyl | ethyl |
| 167 | 1 | $3-CF_3$-Phenyl | n-propyl |
| 168 | 1 | $3-CF_3$-Phenyl | isopropyl |
| 169 | 1 | $3-CF_3$-Phenyl | $—CH_2CH(CH_3)_2$ |
| 170 | 1 | $3-CF_3$-Phenyl | $CF_3$ |
| 171 | 1 | $3-CF_3$-Phenyl | $—CH_2CF_3$ |
| 172 | 1 | $3-CF_3$-Phenyl | $—CH_2CH_2CF_3$ |
| 173 | 1 | $3-CF_3$-Phenyl | cyclopropyl |
| 174 | 1 | $3-CF_3$-Phenyl | Cyclobutyl |
| 175 | 1 | $3-CF_3$-Phenyl | cyclopentyl |
| 176 | 1 | $3-CF_3$-Phenyl | cyclohexyl |
| 177 | 1 | $3-CF_3$-Phenyl | 3-pyridyl |
| 178 | 1 | $3-CF_3$-Phenyl | 1-methyl-1H-pyrazol-4-yl |
| 179 | 1 | $3-CF_3$-Phenyl | 1H-imidazol-4-yl |
| 180 | 1 | $3-CF_3$-Phenyl | 2-furanyl |
| 181 | 1 | 2-iPr-Phenyl | ethyl |
| 182 | 1 | 2-iPr-Phenyl | n-propyl |
| 183 | 1 | 2-iPr-Phenyl | isopropyl |
| 184 | 1 | 2-iPr-Phenyl | $—CH_2CH(CH_3)_2$ |
| 185 | 1 | 2-iPr-Phenyl | $CF_3$ |
| 186 | 1 | 2-iPr-Phenyl | $—CH_2CF_3$ |
| 187 | 1 | 2-iPr-Phenyl | $—CH_2CH_2CF_3$ |
| 188 | 1 | 2-iPr-Phenyl | cyclopropyl |
| 189 | 1 | 2-iPr-Phenyl | Cyclobutyl |
| 190 | 1 | 2-iPr-Phenyl | cyclopentyl |
| 191 | 1 | 2-iPr-Phenyl | cyclohexyl |
| 192 | 1 | 2-iPr-Phenyl | 3-pyridyl |
| 193 | 1 | 2-iPr-Phenyl | 1-methyl-1H-pyrazol-4-yl |
| 194 | 1 | 2-iPr-Phenyl | 1H-imidazol-4-yl |
| 195 | 1 | 2-iPr-Phenyl | 2-furanyl |
| 196 | 1 | 4-iPr-Phenyl | ethyl |
| 197 | 1 | 4-iPr-Phenyl | n-propyl |
| 198 | 1 | 4-iPr-Phenyl | isopropyl |
| 199 | 1 | 4-iPr-Phenyl | $—CH_2CH(CH_3)_2$ |
| 200 | 1 | 4-iPr-Phenyl | $CF_3$ |
| 201 | 1 | 4-iPr-Phenyl | $—CH_2CF_3$ |
| 202 | 1 | 4-iPr-Phenyl | $—CH_2CH_2CF_3$ |
| 203 | 1 | 4-iPr-Phenyl | cyclopropyl |
| 204 | 1 | 4-iPr-Phenyl | Cyclobutyl |
| 205 | 1 | 4-iPr-Phenyl | cyclopentyl |
| 206 | 1 | 4-iPr-Phenyl | cyclohexyl |
| 207 | 1 | 4-iPr-Phenyl | 3-pyridyl |
| 208 | 1 | 4-iPr-Phenyl | 1-methyl-1H-pyrazol-4-yl |
| 209 | 1 | 4-iPr-Phenyl | 1H-imidazol-4-yl |
| 210 | 1 | 4-iPr-Phenyl | 2-furanyl |
| 211 | 1 | 3-morpholino-phenyl | ethyl |
| 212 | 1 | 3-morpholino-phenyl | n-propyl |
| 213 | 1 | 3-morpholino-phenyl | isopropyl |
| 214 | 1 | 3-morpholino-phenyl | $—CH_2CH(CH_3)_2$ |
| 215 | 1 | 3-morpholino-phenyl | $CF_3$ |
| 216 | 1 | 3-morpholino-phenyl | $—CH_2CF_3$ |
| 217 | 1 | 3-morpholino-phenyl | $—CH_2CH_2CF_3$ |
| 218 | 1 | 3-morpholino-phenyl | cyclopropyl |
| 219 | 1 | 3-morpholino-phenyl | Cyclobutyl |
| 220 | 1 | 3-morpholino-phenyl | cyclopentyl |
| 221 | 1 | 3-morpholino-phenyl | cyclohexyl |
| 222 | 1 | 3-morpholino-phenyl | 3-pyridyl |
| 223 | 1 | 3-morpholino-phenyl | 1-methyl-1H-pyrazol-4-yl |
| 224 | 1 | 3-morpholino-phenyl | 1H-imidazol-4-yl |
| 225 | 1 | 3-morpholino-phenyl | 2-furanyl |
| 226 | 1 | 4-cyano-2-morpholino-phenyl | ethyl |
| 227 | 1 | 4-cyano-2-morpholino-phenyl | n-propyl |
| 228 | 1 | 4-cyano-2-morpholino-phenyl | isopropyl |
| 229 | 1 | 4-cyano-2-morpholino-phenyl | $—CH_2CH(CH_3)_2$ |
| 230 | 1 | 4-cyano-2-morpholino-phenyl | $CF_3$ |
| 231 | 1 | 4-cyano-2-morpholino-phenyl | $—CH_2CF_3$ |
| 232 | 1 | 4-cyano-2-morpholino-phenyl | $—CH_2CH_2CF_3$ |
| 233 | 1 | 4-cyano-2-morpholino-phenyl | cyclopropyl |
| 234 | 1 | 4-cyano-2-morpholino-phenyl | Cyclobutyl |
| 235 | 1 | 4-cyano-2-morpholino-phenyl | cyclopentyl |
| 236 | 1 | 4-cyano-2-morpholino-phenyl | cyclohexyl |
| 237 | 1 | 4-cyano-2-morpholino-phenyl | 3-pyridyl |
| 238 | 1 | 4-cyano-2-morpholino-phenyl | 1-methyl-1H-pyrazol-4-yl |
| 239 | 1 | 4-cyano-2-morpholino-phenyl | 1H-imidazol-4-yl |

TABLE 31-continued

| Entry | n | $R^3$ | $R^{10c}$ |
|---|---|---|---|
| 240 | 1 | 4-cyano-2-morpholino-phenyl | 2-furanyl |
| 241 | 1 | 4-hydroxy-2-morpholino-phenyl | ethyl |
| 242 | 1 | 4-hydroxy-2-morpholino-phenyl | n-propyl |
| 243 | 1 | 4-hydroxy-2-morpholino-phenyl | isopropyl |
| 244 | 1 | 4-hydroxy-2-morpholino-phenyl | $—CH_2CH(CH_3)_2$ |
| 245 | 1 | 4-hydroxy-2-morpholino-phenyl | $CF_3$ |
| 246 | 1 | 4-hydroxy-2-morpholino-phenyl | $—CH_2CF_3$ |
| 247 | 1 | 4-hydroxy-2-morpholino-phenyl | $—CH_2CH_2CF_3$ |
| 248 | 1 | 4-hydroxy-2-morpholino-phenyl | cyclopropyl |
| 249 | 1 | 4-hydroxy-2-morpholino-phenyl | Cyclobutyl |
| 250 | 1 | 4-hydroxy-2-morpholino-phenyl | cyclopentyl |
| 251 | 1 | 4-hydroxy-2-morpholino-phenyl | cyclohexyl |
| 252 | 1 | 4-hydroxy-2-morpholino-phenyl | 3-pyridyl |
| 253 | 1 | 4-hydroxy-2-morpholino-phenyl | 1-methyl-1H-pyrazol-4-yl |
| 254 | 1 | 4-hydroxy-2-morpholino-phenyl | 1H-imidazol-4-yl |
| 255 | 1 | 4-hydroxy-2-morpholino-phenyl | 2-furanyl |
| 256 | 1 | $2-CH_3$-phenyl | Ethyl |
| 257 | 1 | $2-CH_3$-phenyl | n-propyl |
| 258 | 1 | $2-CH_3$-phenyl | Isopropyl |
| 259 | 1 | $2-CH_3$-phenyl | $—CH_2CH(CH_3)_2$ |
| 260 | 1 | $2-CH_3$-phenyl | $CF_3$ |
| 261 | 1 | $2-CH_3$-phenyl | $—CH_2CF_3$ |
| 262 | 1 | $2-CH_3$-phenyl | $—CH_2CH_2CF_3$ |
| 263 | 1 | $2-CH_3$-phenyl | cyclopropyl |
| 264 | 1 | $2-CH_3$-phenyl | Cyclobutyl |
| 265 | 1 | $2-CH_3$-phenyl | cyclopentyl |
| 266 | 1 | $2-CH_3$-phenyl | cyclohexyl |
| 267 | 1 | $2-CH_3$-phenyl | 3-pyridyl |
| 268 | 1 | $2-CH_3$-phenyl | 1-methyl-1H-pyrazol-4-yl |
| 269 | 1 | $2-CH_3$-phenyl | 1H-imidazol-4-yl |
| 270 | 1 | $2-CH_3$-phenyl | 2-furanyl |
| 271 | 1 | 4-OH-Phenyl | Ethyl |
| 272 | 1 | 4-OH-Phenyl | n-propyl |
| 273 | 1 | 4-OH-Phenyl | Isopropyl |
| 274 | 1 | 4-OH-Phenyl | $—CH_2CH(CH_3)_2$ |
| 275 | 1 | 4-OH-Phenyl | $CF_3$ |
| 276 | 1 | 4-OH-Phenyl | $—CH_2CF_3$ |
| 277 | 1 | 4-OH-Phenyl | $—CH_2CH_2CF_3$ |
| 278 | 1 | 4-OH-Phenyl | cyclopropyl |
| 279 | 1 | 4-OH-Phenyl | Cyclobutyl |
| 280 | 1 | 4-OH-Phenyl | cyclopentyl |
| 281 | 1 | 4-OH-Phenyl | cyclohexyl |
| 282 | 1 | 4-OH-Phenyl | 3-pyridyl |
| 283 | 1 | 4-OH-Phenyl | 1-methyl-1H-pyrazol-4-yl |
| 284 | 1 | 4-OH-Phenyl | 1H-imidazol-4-yl |
| 285 | 1 | 4-OH-Phenyl | 2-furanyl |
| 286 | 1 | 2-OH-Phenyl | Ethyl |
| 287 | 1 | 2-OH-Phenyl | n-propyl |
| 288 | 1 | 2-OH-Phenyl | Isopropyl |
| 289 | 1 | 2-OH-Phenyl | $—CH_2CH(CH_3)_2$ |
| 290 | 1 | 2-OH-Phenyl | $CF_3$ |
| 291 | 1 | 2-OH-Phenyl | $—CH_2CF_3$ |
| 292 | 1 | 2-OH-Phenyl | $—CH_2CH_2CF_3$ |
| 293 | 1 | 2-OH-Phenyl | cyclopropyl |
| 294 | 1 | 2-OH-Phenyl | Cyclobutyl |
| 295 | 1 | 2-OH-Phenyl | cyclopentyl |
| 296 | 1 | 2-OH-Phenyl | cyclohexyl |
| 297 | 1 | 2-OH-Phenyl | 3-pyridyl |
| 298 | 1 | 2-OH-Phenyl | 1-methyl-1H-pyrazol-4-yl |
| 299 | 1 | 2-OH-Phenyl | 1H-imidazol-4-yl |
| 300 | 1 | 2-OH-Phenyl | 2-furanyl |
| 301 | 1 | 3-OMe-Phenyl | Ethyl |
| 302 | 1 | 3-OMe-Phenyl | n-propyl |
| 303 | 1 | 3-OMe-Phenyl | Isopropyl |
| 304 | 1 | 3-OMe-Phenyl | $—CH_2CH(CH_3)_2$ |
| 305 | 1 | 3-OMe-Phenyl | $CF_3$ |
| 306 | 1 | 3-OMe-Phenyl | $—CH_2CF_3$ |
| 307 | 1 | 3-OMe-Phenyl | $—CH_2CH_2CF_3$ |
| 308 | 1 | 3-OMe-Phenyl | cyclopropyl |
| 309 | 1 | 3-OMe-Phenyl | Cyclobutyl |
| 310 | 1 | 3-OMe-Phenyl | cyclopentyl |
| 311 | 1 | 3-OMe-Phenyl | cyclohexyl |
| 312 | 1 | 3-OMe-Phenyl | 3-pyridyl |
| 313 | 1 | 3-OMe-Phenyl | 1-methyl-1H-pyrazol-4-yl |
| 314 | 1 | 3-OMe-Phenyl | 1H-imidazol-4-yl |
| 315 | 1 | 3-OMe-Phenyl | 2-furanyl |
| 316 | 1 | 4-CN-Phenyl | Ethyl |
| 317 | 1 | 4-CN-Phenyl | n-propyl |
| 318 | 1 | 4-CN-Phenyl | Isopropyl |
| 319 | 1 | 4-CN-Phenyl | $—CH_2CH(CH_3)_2$ |
| 320 | 1 | 4-CN-Phenyl | $CF_3$ |
| 321 | 1 | 4-CN-Phenyl | $—CH_2CF_3$ |
| 322 | 1 | 4-CN-Phenyl | $—CH_2CH_2CF_3$ |
| 323 | 1 | 4-CN-Phenyl | cyclopropyl |
| 324 | 1 | 4-CN-Phenyl | Cyclobutyl |
| 325 | 1 | 4-CN-Phenyl | cyclopentyl |
| 326 | 1 | 4-CN-Phenyl | cyclohexyl |
| 327 | 1 | 4-CN-Phenyl | 3-pyridyl |
| 328 | 1 | 4-CN-Phenyl | 1-methyl-1H-pyrazol-4-yl |
| 329 | 1 | 4-CN-Phenyl | 1H-imidazol-4-yl |
| 330 | 1 | 4-CN-Phenyl | 2-furanyl |
| 331 | 1 | 2-CN-Phenyl | Ethyl |
| 332 | 1 | 2-CN-Phenyl | n-propyl |
| 333 | 1 | 2-CN-Phenyl | Isopropyl |
| 334 | 1 | 2-CN-Phenyl | $—CH_2CH(CH_3)_2$ |
| 335 | 1 | 2-CN-Phenyl | $CF_3$ |
| 336 | 1 | 2-CN-Phenyl | $—CH_2CF_3$ |
| 337 | 1 | 2-CN-Phenyl | $—CH_2CH_2CF_3$ |
| 338 | 1 | 2-CN-Phenyl | cyclopropyl |
| 339 | 1 | 2-CN-Phenyl | Cyclobutyl |
| 340 | 1 | 2-CN-Phenyl | cyclopentyl |
| 341 | 1 | 2-CN-Phenyl | cyclohexyl |
| 342 | 1 | 2-CN-Phenyl | 3-pyridyl |
| 343 | 1 | 2-CN-Phenyl | 1-methyl-1H-pyrazol-4-yl |
| 344 | 1 | 2-CN-Phenyl | 1H-imidazol-4-yl |
| 345 | 1 | 2-CN-Phenyl | 2-furanyl |
| 346 | 1 | 3-F-Phenyl | Ethyl |
| 347 | 1 | 3-F-Phenyl | n-propyl |
| 348 | 1 | 3-F-Phenyl | Isopropyl |
| 349 | 1 | 3-F-Phenyl | $—CH_2CH(CH_3)_2$ |
| 350 | 1 | 3-F-Phenyl | $CF_3$ |
| 351 | 1 | 3-F-Phenyl | $—CH_2CF_3$ |
| 352 | 1 | 3-F-Phenyl | $—CH_2CH_2CF_3$ |
| 353 | 1 | 3-F-Phenyl | cyclopropyl |
| 354 | 1 | 3-F-Phenyl | Cyclobutyl |
| 355 | 1 | 3-F-Phenyl | cyclopentyl |
| 356 | 1 | 3-F-Phenyl | cyclohexyl |
| 357 | 1 | 3-F-Phenyl | 3-pyridyl |
| 358 | 1 | 3-F-Phenyl | 1-methyl-1H-pyrazol-4-yl |
| 359 | 1 | 3-F-Phenyl | 1H-imidazol-4-yl |
| 360 | 1 | 3-F-Phenyl | 2-furanyl |
| 361 | 1 | 2-Cl-Phenyl | Ethyl |
| 362 | 1 | 2-Cl-Phenyl | n-propyl |
| 363 | 1 | 2-Cl-Phenyl | Isopropyl |
| 364 | 1 | 2-Cl-Phenyl | $—CH_2CH(CH_3)_2$ |
| 365 | 1 | 2-Cl-Phenyl | $CF_3$ |
| 366 | 1 | 2-Cl-Phenyl | $—CH_2CF_3$ |
| 367 | 1 | 2-Cl-Phenyl | $—CH_2CH_2CF_3$ |
| 368 | 1 | 2-Cl-Phenyl | cyclopropyl |
| 369 | 1 | 2-Cl-Phenyl | Cyclobutyl |
| 370 | 1 | 2-Cl-Phenyl | cyclopentyl |
| 371 | 1 | 2-Cl-Phenyl | cyclohexyl |
| 372 | 1 | 2-Cl-Phenyl | 3-pyridyl |
| 373 | 1 | 2-Cl-Phenyl | 1-methyl-1H-pyrazol-4-yl |
| 374 | 1 | 2-Cl-Phenyl | 1H-imidazol-4-yl |
| 375 | 1 | 2-Cl-Phenyl | 2-furanyl |
| 376 | 1 | 4-Cl-Phenyl | Ethyl |
| 377 | 1 | 4-Cl-Phenyl | n-propyl |
| 378 | 1 | 4-Cl-Phenyl | Isopropyl |
| 379 | 1 | 4-Cl-Phenyl | $—CH_2CH(CH_3)_2$ |
| 380 | 1 | 4-Cl-Phenyl | $CF_3$ |
| 381 | 1 | 4-Cl-Phenyl | $—CH_2CF_3$ |
| 382 | 1 | 4-Cl-Phenyl | $—CH_2CH_2CF_3$ |
| 383 | 1 | 4-Cl-Phenyl | cyclopropyl |
| 384 | 1 | 4-Cl-Phenyl | Cyclobutyl |
| 385 | 1 | 4-Cl-Phenyl | cyclopentyl |
| 386 | 1 | 4-Cl-Phenyl | cyclohexyl |
| 387 | 1 | 4-Cl-Phenyl | 3-pyridyl |
| 388 | 1 | 4-Cl-Phenyl | 1-methyl-1H-pyrazol-4-yl |
| 389 | 1 | 4-Cl-Phenyl | 1H-imidazol-4-yl |
| 390 | 1 | 4-Cl-Phenyl | 2-furanyl |
| 391 | 1 | 3-Br-Phenyl | Ethyl |
| 392 | 1 | 3-Br-Phenyl | n-propyl |
| 393 | 1 | 3-Br-Phenyl | Isopropyl |
| 394 | 1 | 3-Br-Phenyl | $—CH_2CH(CH_3)_2$ |
| 395 | 1 | 3-Br-Phenyl | $CF_3$ |

TABLE 31-continued

| Entry | n | $R^3$ | $R^{10c}$ |
|---|---|---|---|
| 396 | 1 | 3-Br-Phenyl | —$CH_2CF_3$ |
| 397 | 1 | 3-Br-Phenyl | —$CH_2CH_2CF_3$ |
| 398 | 1 | 3-Br-Phenyl | cyclopropyl |
| 399 | 1 | 3-Br-Phenyl | Cyclobutyl |
| 400 | 1 | 3-Br-Phenyl | cyclopentyl |
| 401 | 1 | 3-Br-Phenyl | cyclohexyl |
| 402 | 1 | 3-Br-Phenyl | 3-pyridyl |
| 403 | 1 | 3-Br-Phenyl | 1-methyl-1H-pyrazol-4-yl |
| 404 | 1 | 3-Br-Phenyl | 1H-imidazol-4-yl |
| 405 | 1 | 3-Br-Phenyl | 2-furanyl |
| 406 | 1 | 2-$CF_3$-Phenyl | Ethyl |
| 407 | 1 | 2-$CF_3$-Phenyl | n-propyl |
| 408 | 1 | 2-$CF_3$-Phenyl | Isopropyl |
| 409 | 1 | 2-$CF_3$-Phenyl | —$CH_2CH(CH_3)_2$ |
| 410 | 1 | 2-$CF_3$-Phenyl | $CF_3$ |
| 411 | 1 | 2-$CF_3$-Phenyl | —$CH_2CF_3$ |
| 412 | 1 | 2-$CF_3$-Phenyl | —$CH_2CH_2CF_3$ |
| 413 | 1 | 2-$CF_3$-Phenyl | cyclopropyl |
| 414 | 1 | 2-$CF_3$-Phenyl | Cyclobutyl |
| 415 | 1 | 2-$CF_3$-Phenyl | cyclopentyl |
| 416 | 1 | 2-$CF_3$-Phenyl | cyclohexyl |
| 417 | 1 | 2-$CF_3$-Phenyl | 3-pyridyl |
| 418 | 1 | 2-$CF_3$-Phenyl | 1-methyl-1H-pyrazol-4-yl |
| 419 | 1 | 2-$CF_3$-Phenyl | 1H-imidazol-4-yl |
| 420 | 1 | 2-$CF_3$-Phenyl | 2-furanyl |
| 421 | 1 | 4-$CF_3$-Phenyl | Ethyl |
| 422 | 1 | 4-$CF_3$-Phenyl | n-propyl |
| 423 | 1 | 4-$CF_3$-Phenyl | Isopropyl |
| 424 | 1 | 4-$CF_3$-Phenyl | —$CH_2CH(CH_3)_2$ |
| 425 | 1 | 4-$CF_3$-Phenyl | $CF_3$ |
| 426 | 1 | 4-$CF_3$-Phenyl | —$CH_2CF_3$ |
| 427 | 1 | 4-$CF_3$-Phenyl | —$CH_2CH_2CF_3$ |
| 428 | 1 | 4-$CF_3$-Phenyl | cyclopropyl |
| 429 | 1 | 4-$CF_3$-Phenyl | Cyclobutyl |
| 430 | 1 | 4-$CF_3$-Phenyl | cyclopentyl |
| 431 | 1 | 4-$CF_3$-Phenyl | cyclohexyl |
| 432 | 1 | 4-$CF_3$-Phenyl | 3-pyridyl |
| 433 | 1 | 4-$CF_3$-Phenyl | 1-methyl-1H-pyrazol-4-yl |
| 434 | 1 | 4-$CF_3$-Phenyl | 1H-imidazol-4-yl |
| 435 | 1 | 4-$CF_3$-Phenyl | 2-furanyl |
| 436 | 1 | 3-iPr-Phenyl | Ethyl |
| 437 | 1 | 3-iPr-Phenyl | n-propyl |
| 438 | 1 | 3-iPr-Phenyl | Isopropyl |
| 439 | 1 | 3-iPr-Phenyl | —$CH_2CH(CH_3)_2$ |
| 440 | 1 | 3-iPr-Phenyl | $CF_3$ |
| 441 | 1 | 3-iPr-Phenyl | —$CH_2CF_3$ |
| 442 | 1 | 3-iPr-Phenyl | —$CH_2CH_2CF_3$ |
| 443 | 1 | 3-iPr-Phenyl | cyclopropyl |
| 444 | 1 | 3-iPr-Phenyl | Cyclobutyl |
| 445 | 1 | 3-iPr-Phenyl | cyclopentyl |
| 446 | 1 | 3-iPr-Phenyl | cyclohexyl |
| 447 | 1 | 3-iPr-Phenyl | 3-pyridyl |
| 448 | 1 | 3-iPr-Phenyl | 1-methyl-1H-pyrazol-4-yl |
| 449 | 1 | 3-iPr-Phenyl | 1H-imidazol-4-yl |
| 450 | 1 | 3-iPr-Phenyl | 2-furanyl |
| 451 | 1 | 2-morpholino-phenyl | Ethyl |
| 452 | 1 | 2-morpholino-phenyl | n-propyl |
| 453 | 1 | 2-morpholino-phenyl | isopropyl |
| 454 | 1 | 2-morpholino-phenyl | —$CH_2CH(CH_3)_2$ |
| 455 | 1 | 2-morpholino-phenyl | $CF_3$ |
| 456 | 1 | 2-morpholino-phenyl | —$CH_2CF_3$ |
| 457 | 1 | 2-morpholino-phenyl | —$CH_2CH_2CF_3$ |
| 458 | 1 | 2-morpholino-phenyl | cyclopropyl |
| 459 | 1 | 2-morpholino-phenyl | Cyclobutyl |
| 460 | 1 | 2-morpholino-phenyl | cyclopentyl |
| 461 | 1 | 2-morpholino-phenyl | cyclohexyl |
| 462 | 1 | 2-morpholino-phenyl | 3-pyridyl |
| 463 | 1 | 2-morpholino-phenyl | 1-methyl-1H-pyrazol-4-yl |
| 464 | 1 | 2-morpholino-phenyl | 1H-imidazol-4-yl |
| 465 | 1 | 2-morpholino-phenyl | 2-furanyl |
| 466 | 1 | 4-morpholino-phenyl | ethyl |
| 467 | 1 | 4-morpholino-phenyl | n-propyl |
| 468 | 1 | 4-morpholino-phenyl | isopropyl |
| 469 | 1 | 4-morpholino-phenyl | —$CH_2CH(CH_3)_2$ |
| 470 | 1 | 4-morpholino-phenyl | $CF_3$ |
| 471 | 1 | 4-morpholino-phenyl | —$CH_2CF_3$ |
| 472 | 1 | 4-morpholino-phenyl | —$CH_2CH_2CF_3$ |
| 473 | 1 | 4-morpholino-phenyl | cyclopropyl |

TABLE 31-continued

| Entry | n | $R^3$ | $R^{10c}$ |
|---|---|---|---|
| 474 | 1 | 4-morpholino-phenyl | Cyclobutyl |
| 475 | 1 | 4-morpholino-phenyl | cyclopentyl |
| 476 | 1 | 4-morpholino-phenyl | cyclohexyl |
| 477 | 1 | 4-morpholino-phenyl | 3-pyridyl |
| 478 | 1 | 4-morpholino-phenyl | 1-methyl-1H-pyrazol-4-yl |
| 479 | 1 | 4-morpholino-phenyl | 1H-imidazol-4-yl |
| 480 | 1 | 4-morpholino-phenyl | 2-furanyl |
| 481 | 1 | 4-methyl-2-morpholino-phenyl | ethyl |
| 482 | 1 | 4-methyl-2-morpholino-phenyl | n-propyl |
| 483 | 1 | 4-methyl-2-morpholino-phenyl | isopropyl |
| 484 | 1 | 4-methyl-2-morpholino-phenyl | —$CH_2CH(CH_3)_2$ |
| 485 | 1 | 4-methyl-2-morpholino-phenyl | $CF_3$ |
| 486 | 1 | 4-methyl-2-morpholino-phenyl | —$CH_2CF_3$ |
| 487 | 1 | 4-methyl-2-morpholino-phenyl | —$CH_2CH_2CF_3$ |
| 488 | 1 | 4-methyl-2-morpholino-phenyl | cyclopropyl |
| 489 | 1 | 4-methyl-2-morpholino-phenyl | Cyclobutyl |
| 490 | 1 | 4-methyl-2-morpholino-phenyl | cyclopentyl |
| 491 | 1 | 4-methyl-2-morpholino-phenyl | cyclohexyl |
| 492 | 1 | 4-methyl-2-morpholino-phenyl | 3-pyridyl |
| 493 | 1 | 4-methyl-2-morpholino-phenyl | 1-methyl-1H-pyrazol-4-yl |
| 494 | 1 | 4-methyl-2-morpholino-phenyl | 1H-imidazol-4-yl |
| 495 | 1 | 4-methyl-2-morpholino-phenyl | 2-furanyl |
| 496 | 2 | 4-$CH_3$-phenyl | ethyl |
| 497 | 2 | 4-$CH_3$-phenyl | n-propyl |
| 498 | 2 | 4-$CH_3$-phenyl | isopropyl |
| 499 | 2 | 4-$CH_3$-phenyl | —$CH_2CH(CH_3)_2$ |
| 500 | 2 | 4-$CH_3$-phenyl | $CF_3$ |
| 501 | 2 | 4-$CH_3$-phenyl | —$CH_2CF_3$ |
| 502 | 2 | 4-$CH_3$-phenyl | —$CH_2CH_2CF_3$ |
| 503 | 2 | 4-$CH_3$-phenyl | cyclopropyl |
| 504 | 2 | 4-$CH_3$-phenyl | Cyclobutyl |
| 505 | 2 | 4-$CH_3$-phenyl | cyclopentyl |
| 506 | 2 | 4-$CH_3$-phenyl | cyclohexyl |
| 507 | 2 | 4-$CH_3$-phenyl | 3-pyridyl |
| 508 | 2 | 4-$CH_3$-phenyl | 1-methyl-1H-pyrazol-4-yl |
| 509 | 2 | 4-$CH_3$-phenyl | 1H-imidazol-4-yl |
| 510 | 2 | 4-$CH_3$-phenyl | 2-furanyl |
| 511 | 2 | 3-$CH_3$-phenyl | ethyl |
| 512 | 2 | 3-$CH_3$-phenyl | n-propyl |
| 513 | 2 | 3-$CH_3$-phenyl | isopropyl |
| 514 | 2 | 3-$CH_3$-phenyl | —$CH_2CH(CH_3)_2$ |
| 515 | 2 | 3-$CH_3$-phenyl | $CF_3$ |
| 516 | 2 | 3-$CH_3$-phenyl | —$CH_2CF_3$ |
| 517 | 2 | 3-$CH_3$-phenyl | —$CH_2CH_2CF_3$ |
| 518 | 2 | 3-CHs-phenyl | cyclopropyl |
| 519 | 2 | 3-$CH_3$-phenyl | Cyclobutyl |
| 520 | 2 | 3-$CH_3$-phenyl | cyclopentyl |
| 521 | 2 | 3-$CH_3$-phenyl | cyclohexyl |
| 522 | 2 | 3-$CH_3$-phenyl | 3-pyridyl |
| 523 | 2 | 3-$CH_3$-phenyl | 1-methyl-1H-pyrazol-4-yl |
| 524 | 2 | 3-$CH_3$-phenyl | 1H-imidazol-4-yl |
| 525 | 2 | 3-$CH_3$-phenyl | 2-furanyl |
| 526 | 2 | 3-OH-Phenyl | ethyl |
| 527 | 2 | 3-OH-Phenyl | n-propyl |
| 528 | 2 | 3-OH-Phenyl | isopropyl |
| 529 | 2 | 3-OH-Phenyl | —$CH_2CH(CH_3)_2$ |
| 530 | 2 | 3-OH-Phenyl | $CF_3$ |
| 531 | 2 | 3-OH-Phenyl | —$CH_2CF_3$ |
| 532 | 2 | 3-OH-Phenyl | —$CH_2CH_2CF_3$ |
| 533 | 2 | 3-OH-Phenyl | cyclopropyl |
| 534 | 2 | 3-OH-Phenyl | Cyclobutyl |
| 535 | 2 | 3-OH-Phenyl | cyclopentyl |
| 536 | 2 | 3-OH-Phenyl | cyclohexyl |
| 537 | 2 | 3-OH-Phenyl | 3-pyridyl |
| 538 | 2 | 3-OH-Phenyl | 1-methyl-1H-pyrazol-4-yl |
| 539 | 2 | 3-OH-Phenyl | 1H-imidazol-4-yl |
| 540 | 2 | 3-OH-Phenyl | 2-furanyl |
| 541 | 2 | 4-OMe-Phenyl | ethyl |
| 542 | 2 | 4-OMe-Phenyl | n-propyl |
| 543 | 2 | 4-OMe-Phenyl | isopropyl |
| 544 | 2 | 4-OMe-Phenyl | —$CH_2CH(CH_3)_2$ |
| 545 | 2 | 4-OMe-Phenyl | $CF_3$ |
| 546 | 2 | 4-OMe-Phenyl | —$CH_2CF_3$ |
| 547 | 2 | 4-OMe-Phenyl | —$CH_2CH_2CF_3$ |
| 548 | 2 | 4-OMe-Phenyl | cyclopropyl |
| 549 | 2 | 4-OMe-Phenyl | Cyclobutyl |
| 550 | 2 | 4-OMe-Phenyl | cyclopentyl |
| 551 | 2 | 4-OMe-Phenyl | cyclohexyl |

TABLE 31-continued

| Entry | n | $R^3$ | $R^{10c}$ |
|---|---|---|---|
| 552 | 2 | 4-OMe-Phenyl | 3-pyridyl |
| 553 | 2 | 4-OMe-Phenyl | 1-methyl-1H-pyrazol-4-yl |
| 554 | 2 | 4-OMe-Phenyl | 1H-imidazol-4-yl |
| 555 | 2 | 4-OMe-Phenyl | 2-furanyl |
| 556 | 2 | 2-OMe-Phenyl | ethyl |
| 557 | 2 | 2-OMe-Phenyl | n-propyl |
| 558 | 2 | 2-OMe-Phenyl | isopropyl |
| 559 | 2 | 2-OMe-Phenyl | $-CH_2CH(CH_3)_2$ |
| 560 | 2 | 2-OMe-Phenyl | $CF_3$ |
| 561 | 2 | 2-OMe-Phenyl | $-CH_2CF_3$ |
| 562 | 2 | 2-OMe-Phenyl | $-CH_2CH_2CF_3$ |
| 563 | 2 | 2-OMe-Phenyl | cyclopropyl |
| 564 | 2 | 2-OMe-Phenyl | Cyclobutyl |
| 565 | 2 | 2-OMe-Phenyl | cyclopentyl |
| 566 | 2 | 2-OMe-Phenyl | cyclohexyl |
| 567 | 2 | 2-OMe-Phenyl | 3-pyridyl |
| 568 | 2 | 2-OMe-Phenyl | 1-methyl-1H-pyrazol-4-yl |
| 569 | 2 | 2-OMe-Phenyl | 1H-imidazol-4-yl |
| 570 | 2 | 2-OMe-Phenyl | 2-furanyl |
| 571 | 2 | 3-CN-Phenyl | ethyl |
| 572 | 2 | 3-CN-Phenyl | n-propyl |
| 573 | 2 | 3-CN-Phenyl | isopropyl |
| 574 | 2 | 3-CN-Phenyl | $-CH_2CH(CH_3)_2$ |
| 575 | 2 | 3-CN-Phenyl | $CF_3$ |
| 576 | 2 | 3-CN-Phenyl | $-CH_2CF_3$ |
| 577 | 2 | 3-CN-Phenyl | $-CH_2CH_2CF_3$ |
| 578 | 2 | 3-CN-Phenyl | cyclopropyl |
| 579 | 2 | 3-CN-Phenyl | Cyclobutyl |
| 580 | 2 | 3-CN-Phenyl | cyclopentyl |
| 581 | 2 | 3-CN-Phenyl | cyclohexyl |
| 582 | 2 | 3-CN-Phenyl | 3-pyridyl |
| 583 | 2 | 3-CN-Phenyl | 1-methyl-1H-pyrazol-4-yl |
| 584 | 2 | 3-CN-Phenyl | 1H-imidazol-4-yl |
| 585 | 2 | 3-CN-Phenyl | 2-furanyl |
| 586 | 2 | 2-F-Phenyl | ethyl |
| 587 | 2 | 2-F-Phenyl | n-propyl |
| 588 | 2 | 2-F-Phenyl | isopropyl |
| 589 | 2 | 2-F-Phenyl | $-CH_2CH(CH_3)_2$ |
| 590 | 2 | 2-F-Phenyl | $CF_3$ |
| 591 | 2 | 2-F-Phenyl | $-CH_2CF_3$ |
| 592 | 2 | 2-F-Phenyl | $-CH_2CH_2CF_3$ |
| 593 | 2 | 2-F-Phenyl | cyclopropyl |
| 594 | 2 | 2-F-Phenyl | Cyclobutyl |
| 595 | 2 | 2-F-Phenyl | cyclopentyl |
| 596 | 2 | 2-F-Phenyl | cyclohexyl |
| 597 | 2 | 2-F-Phenyl | 3-pyridyl |
| 598 | 2 | 2-F-Phenyl | 1-methyl-1H-pyrazol-4-yl |
| 599 | 2 | 2-F-Phenyl | 1H-imidazol-4-yl |
| 600 | 2 | 2-F-Phenyl | 2-furanyl |
| 601 | 2 | 4-F-Phenyl | ethyl |
| 602 | 2 | 4-F-Phenyl | n-propyl |
| 603 | 2 | 4-F-Phenyl | isopropyl |
| 604 | 2 | 4-F-Phenyl | $-CH_2CH(CH_3)_2$ |
| 605 | 2 | 4-F-Phenyl | $CF_3$ |
| 606 | 2 | 4-F-Phenyl | $-CH_2CF_3$ |
| 607 | 2 | 4-F-Phenyl | $-CH_2CH_2CF_3$ |
| 608 | 2 | 4-F-Phenyl | cyclopropyl |
| 609 | 2 | 4-F-Phenyl | Cyclobutyl |
| 610 | 2 | 4-F-Phenyl | cyclopentyl |
| 611 | 2 | 4-F-Phenyl | cyclohexyl |
| 612 | 2 | 4-F-Phenyl | 3-pyridyl |
| 613 | 2 | 4-F-Phenyl | 1-methyl-1H-pyrazol-4-yl |
| 614 | 2 | 4-F-Phenyl | 1H-imidazol-4-yl |
| 615 | 2 | 4-F-Phenyl | 2-furanyl |
| 616 | 2 | 3-Cl-Phenyl | ethyl |
| 617 | 2 | 3-Cl-Phenyl | n-propyl |
| 618 | 2 | 3-Cl-Phenyl | isopropyl |
| 619 | 2 | 3-Cl-Phenyl | $-CH_2CH(CH_3)_2$ |
| 620 | 2 | 3-Cl-Phenyl | $CF_3$ |
| 621 | 2 | 3-Cl-Phenyl | $-CH_2CF_3$ |
| 622 | 2 | 3-Cl-Phenyl | $-CH_2CH_2CF_3$ |
| 623 | 2 | 3-Cl-Phenyl | cyclopropyl |
| 624 | 2 | 3-Cl-Phenyl | Cyclobutyl |
| 625 | 2 | 3-Cl-Phenyl | cyclopentyl |
| 626 | 2 | 3-Cl-Phenyl | cyclohexyl |
| 627 | 2 | 3-Cl-Phenyl | 3-pyridyl |
| 628 | 2 | 3-Cl-Phenyl | 1-methyl-1H-pyrazol-4-yl |
| 629 | 2 | 3-Cl-Phenyl | 1H-imidazol-4-yl |

TABLE 31-continued

| Entry | n | $R^3$ | $R^{10c}$ |
|---|---|---|---|
| 630 | 2 | 3-Cl-Phenyl | 2-furanyl |
| 631 | 2 | 2-Br-Phenyl | ethyl |
| 632 | 2 | 2-Br-Phenyl | n-propyl |
| 633 | 2 | 2-Br-Phenyl | isopropyl |
| 634 | 2 | 2-Br-Phenyl | $-CH_2CH(CH_3)_2$ |
| 635 | 2 | 2-Br-Phenyl | $CF_3$ |
| 636 | 2 | 2-Br-Phenyl | $-CH_2CF_3$ |
| 637 | 2 | 2-Br-Phenyl | $-CH_2CH_2CF_3$ |
| 638 | 2 | 2-Br-Phenyl | cyclopropyl |
| 639 | 2 | 2-Br-Phenyl | Cyclobutyl |
| 640 | 2 | 2-Br-Phenyl | cyclopentyl |
| 641 | 2 | 2-Br-Phenyl | cyclohexyl |
| 642 | 2 | 2-Br-Phenyl | 3-pyridyl |
| 643 | 2 | 2-Br-Phenyl | 1-methyl-1H-pyrazol-4-yl |
| 644 | 2 | 2-Br-Phenyl | 1H-imidazol-4-yl |
| 645 | 2 | 2-Br-Phenyl | 2-furanyl |
| 646 | 2 | 4-Br-Phenyl | ethyl |
| 647 | 2 | 4-Br-Phenyl | n-propyl |
| 648 | 2 | 4-Br-Phenyl | isopropyl |
| 649 | 2 | 4-Br-Phenyl | $-CH_2CH(CH_3)_2$ |
| 650 | 2 | 4-Br-Phenyl | $CF_3$ |
| 651 | 2 | 4-Br-Phenyl | $-CH_2CF_3$ |
| 652 | 2 | 4-Br-Phenyl | $-CH_2CH_2CF_3$ |
| 653 | 2 | 4-Br-Phenyl | cyclopropyl |
| 654 | 2 | 4-Br-Phenyl | Cyclobutyl |
| 655 | 2 | 4-Br-Phenyl | cyclopentyl |
| 656 | 2 | 4-Br-Phenyl | cyclohexyl |
| 657 | 2 | 4-Br-Phenyl | 3-pyridyl |
| 658 | 2 | 4-Br-Phenyl | 1-methyl-1H-pyrazol-4-yl |
| 659 | 2 | 4-Br-Phenyl | 1H-imidazol-4-yl |
| 660 | 2 | 4-Br-Phenyl | 2-furanyl |
| 661 | 2 | $3-CF_3$-Phenyl | ethyl |
| 662 | 2 | $3-CF_3$-Phenyl | n-propyl |
| 663 | 2 | $3-CF_3$-Phenyl | isopropyl |
| 664 | 2 | $3-CF_3$-Phenyl | $-CH_2CH(CH_3)_2$ |
| 665 | 2 | $3-CF_3$-Phenyl | $CF_3$ |
| 666 | 2 | $3-CF_3$-Phenyl | $-CH_2CF_3$ |
| 667 | 2 | $3-CF_3$-Phenyl | $-CH_2CH_2CF_3$ |
| 668 | 2 | $3-CF_3$-Phenyl | cyclopropyl |
| 669 | 2 | $3-CF_3$-Phenyl | Cyclobutyl |
| 670 | 2 | $3-CF_3$-Phenyl | cyclopentyl |
| 671 | 2 | $3-CF_3$-Phenyl | cyclohexyl |
| 672 | 2 | $3-CF_3$-Phenyl | 3-pyridyl |
| 673 | 2 | $3-CF_3$-Phenyl | 1-methyl-1H-pyrazol-4-yl |
| 674 | 2 | $3-CF_3$-Phenyl | 1H-imidazol-4-yl |
| 675 | 2 | $3-CF_3$-Phenyl | 2-furanyl |
| 676 | 2 | 2-iPr-Phenyl | ethyl |
| 677 | 2 | 2-iPr-Phenyl | n-propyl |
| 678 | 2 | 2-iPr-Phenyl | isopropyl |
| 679 | 2 | 2-iPr-Phenyl | $-CH_2CH(CH_3)_2$ |
| 680 | 2 | 2-iPr-Phenyl | $CF_3$ |
| 681 | 2 | 2-iPr-Phenyl | $-CH_2CF_3$ |
| 682 | 2 | 2-iPr-Phenyl | $-CH_2CH_2CF_3$ |
| 683 | 2 | 2-iPr-Phenyl | cyclopropyl |
| 684 | 2 | 2-iPr-Phenyl | Cyclobutyl |
| 685 | 2 | 2-iPr-Phenyl | cyclopentyl |
| 686 | 2 | 2-iPr-Phenyl | cyclohexyl |
| 687 | 2 | 2-iPr-Phenyl | 3-pyridyl |
| 688 | 2 | 2-iPr-Phenyl | 1-methyl-1H-pyrazol-4-yl |
| 689 | 2 | 2-iPr-Phenyl | 1H-imidazol-4-yl |
| 690 | 2 | 2-iPr-Phenyl | 2-furanyl |
| 691 | 2 | 4-iPr-Phenyl | ethyl |
| 692 | 2 | 4-iPr-Phenyl | n-propyl |
| 693 | 2 | 4-iPr-Phenyl | isopropyl |
| 694 | 2 | 4-iPr-Phenyl | $-CH_2CH(CH_3)_2$ |
| 695 | 2 | 4-iPr-Phenyl | $CF_3$ |
| 696 | 2 | 4-iPr-Phenyl | $-CH_2CF_3$ |
| 697 | 2 | 4-iPr-Phenyl | $-CH_2CH_2CF_3$ |
| 698 | 2 | 4-iPr-Phenyl | cyclopropyl |
| 699 | 2 | 4-iPr-Phenyl | Cyclobutyl |
| 700 | 2 | 4-iPr-Phenyl | cyclopentyl |
| 701 | 2 | 4-iPr-Phenyl | cyclohexyl |
| 702 | 2 | 4-iPr-Phenyl | 3-pyridyl |
| 703 | 2 | 4-iPr-Phenyl | 1-methyl-1H-pyrazol-4-yl |
| 704 | 2 | 4-iPr-Phenyl | 1H-imidazol-4-yl |
| 705 | 2 | 4-iPr-Phenyl | 2-furanyl |
| 706 | 2 | 3-morpholino-phenyl | ethyl |
| 707 | 2 | 3-morpholino-phenyl | n-propyl |

TABLE 31-continued

| Entry | n | $R^3$ | $R^{10c}$ |
|---|---|---|---|
| 708 | 2 | 3-morpholino-phenyl | isopropyl |
| 709 | 2 | 3-morpholino-phenyl | $-CH_2CH(CH_3)_2$ |
| 710 | 2 | 3-morpholino-phenyl | $CF_3$ |
| 711 | 2 | 3-morpholino-phenyl | $-CH_2CF_3$ |
| 712 | 2 | 3-morpholino-phenyl | $-CH_2CH_2CF_3$ |
| 713 | 2 | 3-morpholino-phenyl | cyclopropyl |
| 714 | 2 | 3-morpholino-phenyl | Cyclobutyl |
| 715 | 2 | 3-morpholino-phenyl | cyclopentyl |
| 716 | 2 | 3-morpholino-phenyl | cyclohexyl |
| 717 | 2 | 3-morpholino-phenyl | 3-pyridyl |
| 718 | 2 | 3-morpholino-phenyl | 1-methyl-1H-pyrazol-4-yl |
| 719 | 2 | 3-morpholino-phenyl | 1H-imidazol-4-yl |
| 720 | 2 | 3-morpholino-phenyl | 2-furanyl |
| 721 | 2 | 4-cyano-2-morpholino-phenyl | ethyl |
| 722 | 2 | 4-cyano-2-morpholino-phenyl | n-propyl |
| 723 | 2 | 4-cyano-2-morpholino-phenyl | isopropyl |
| 724 | 2 | 4-cyano-2-morpholino-phenyl | $-CH_2CH(CH_3)_2$ |
| 725 | 2 | 4-cyano-2-morpholino-phenyl | $CF_3$ |
| 726 | 2 | 4-cyano-2-morpholino-phenyl | $-CH_2CF_3$ |
| 727 | 2 | 4-cyano-2-morpholino-phenyl | $-CH_2CH_2CF_3$ |
| 728 | 2 | 4-cyano-2-morpholino-phenyl | cyclopropyl |
| 729 | 2 | 4-cyano-2-morpholino-phenyl | Cyclobutyl |
| 730 | 2 | 4-cyano-2-morpholino-phenyl | cyclopentyl |
| 731 | 2 | 4-cyano-2-morpholino-phenyl | cyclohexyl |
| 732 | 2 | 4-cyano-2-morpholino-phenyl | 3-pyridyl |
| 733 | 2 | 4-cyano-2-morpholino-phenyl | 1-methyl-1H-pyrazol-4-yl |
| 734 | 2 | 4-cyano-2-morpholino-phenyl | 1H-imidazol-4-yl |
| 735 | 2 | 4-cyano-2-morpholino-phenyl | 2-furanyl |
| 736 | 2 | 4-hydroxy-2-morpholino-phenyl | ethyl |
| 737 | 2 | 4-hydroxy-2-morpholino-phenyl | n-propyl |
| 738 | 2 | 4-hydroxy-2-morpholino-phenyl | isopropyl |
| 739 | 2 | 4-hydroxy-2-morpholino-phenyl | $-CH_2CH(CH_3)_2$ |
| 740 | 2 | 4-hydroxy-2-morpholino-phenyl | $CF_3$ |
| 741 | 2 | 4-hydroxy-2-morpholino-phenyl | $-CH_2CF_3$ |
| 742 | 2 | 4-hydroxy-2-morpholino-phenyl | $-CH_2CH_2CF_3$ |
| 743 | 2 | 4-hydroxy-2-morpholino-phenyl | cyclopropyl |
| 744 | 2 | 4-hydroxy-2-morpholino-phenyl | Cyclobutyl |
| 745 | 2 | 4-hydroxy-2-morpholino-phenyl | cyclopentyl |
| 746 | 2 | 4-hydroxy-2-morpholino-phenyl | cyclohexyl |
| 747 | 2 | 4-hydroxy-2-morpholino-phenyl | 3-pyridyl |
| 748 | 2 | 4-hydroxy-2-morpholino-phenyl | 1-methyl-1H-pyrazol-4-yl |
| 749 | 2 | 4-hydroxy-2-morpholino-phenyl | 1H-imidazol-4-yl |
| 750 | 2 | 4-hydroxy-2-morpholino-phenyl | 2-furanyl |
| 751 | 2 | $2-CH_3$-phenyl | Ethyl |
| 752 | 2 | $2-CH_3$-phenyl | n-propyl |
| 753 | 2 | $2-CH_3$-phenyl | Isopropyl |
| 754 | 2 | $2-CH_3$-phenyl | $-CH_2CH(CH_3)_2$ |
| 755 | 2 | $2-CH_3$-phenyl | $CF_3$ |
| 756 | 2 | $2-CH_3$-phenyl | $-CH_2CF_3$ |
| 757 | 2 | $2-CH_3$-phenyl | $-CH_2CH_2CF_3$ |
| 758 | 2 | $2-CH_3$-phenyl | cyclopropyl |
| 759 | 2 | $2-CH_3$-phenyl | Cyclobutyl |
| 760 | 2 | $2-CH_3$-phenyl | cyclopentyl |
| 761 | 2 | $2-CH_3$-phenyl | cyclohexyl |
| 762 | 2 | $2-CH_3$-phenyl | 3-pyridyl |
| 763 | 2 | $2-CH_3$-phenyl | 1-methyl-1H-pyrazol-4-yl |
| 764 | 2 | $2-CH_3$-phenyl | 1H-imidazol-4-yl |
| 765 | 2 | $2-CH_3$-phenyl | 2-furanyl |
| 766 | 2 | 4-OH-Phenyl | Ethyl |
| 767 | 2 | 4-OH-Phenyl | n-propyl |
| 768 | 2 | 4-OH-Phenyl | Isopropyl |
| 769 | 2 | 4-OH-Phenyl | $-CH_2CH(CH_3)_2$ |
| 770 | 2 | 4-OH-Phenyl | $CF_3$ |
| 771 | 2 | 4-OH-Phenyl | $-CH_2CF_3$ |
| 772 | 2 | 4-OH-Phenyl | $-CH_2CH_2CF_3$ |
| 773 | 2 | 4-OH-Phenyl | cyclopropyl |
| 774 | 2 | 4-OH-Phenyl | Cyclobutyl |
| 775 | 2 | 4-OH-Phenyl | cyclopentyl |
| 776 | 2 | 4-OH-Phenyl | cyclohexyl |
| 777 | 2 | 4-OH-Phenyl | 3-pyridyl |
| 778 | 2 | 4-OH-Phenyl | 1-methyl-1H-pyrazol-4-yl |
| 779 | 2 | 4-OH-Phenyl | 1H-imidazol-4-yl |
| 780 | 2 | 4-OH-Phenyl | 2-furanyl |
| 781 | 2 | 2-OH-Phenyl | Ethyl |
| 782 | 2 | 2-OH-Phenyl | n-propyl |
| 783 | 2 | 2-OH-Phenyl | Isopropyl |
| 784 | 2 | 2-OH-Phenyl | $-CH_2CH(CH_3)_2$ |
| 785 | 2 | 2-OH-Phenyl | $CF_3$ |

TABLE 31-continued

| Entry | n | $R^3$ | $R^{10c}$ |
|---|---|---|---|
| 786 | 2 | 2-OH-Phenyl | $-CH_2CF_3$ |
| 787 | 2 | 2-OH-Phenyl | $-CH_2CH_2CF_3$ |
| 788 | 2 | 2-OH-Phenyl | cyclopropyl |
| 789 | 2 | 2-OH-Phenyl | Cyclobutyl |
| 790 | 2 | 2-OH-Phenyl | cyclopentyl |
| 791 | 2 | 2-OH-Phenyl | cyclohexyl |
| 792 | 2 | 2-OH-Phenyl | 3-pyridyl |
| 793 | 2 | 2-OH-Phenyl | 1-methyl-1H-pyrazol-4-yl |
| 794 | 2 | 2-OH-Phenyl | 1H-imidazol-4-yl |
| 795 | 2 | 2-OH-Phenyl | 2-furanyl |
| 796 | 2 | 3-OMe-Phenyl | Ethyl |
| 797 | 2 | 3-OMe-Phenyl | n-propyl |
| 798 | 2 | 3-OMe-Phenyl | Isopropyl |
| 799 | 2 | 3-OMe-Phenyl | $-CH_2CH(CH_3)_2$ |
| 800 | 2 | 3-OMe-Phenyl | $CF_3$ |
| 801 | 2 | 3-OMe-Phenyl | $-CH_2CF_3$ |
| 802 | 2 | 3-OMe-Phenyl | $-CH_2CH_2CF_3$ |
| 803 | 2 | 3-OMe-Phenyl | cyclopropyl |
| 804 | 2 | 3-OMe-Phenyl | Cyclobutyl |
| 805 | 2 | 3-OMe-Phenyl | cyclopentyl |
| 806 | 2 | 3-OMe-Phenyl | cyclohexyl |
| 807 | 2 | 3-OMe-Phenyl | 3-pyridyl |
| 808 | 2 | 3-OMe-Phenyl | 1-methyl-1H-pyrazol-4-yl |
| 809 | 2 | 3-OMe-Phenyl | 1H-imidazol-4-yl |
| 810 | 2 | 3-OMe-Phenyl | 2-furanyl |
| 811 | 2 | 4-CN-Phenyl | Ethyl |
| 812 | 2 | 4-CN-Phenyl | n-propyl |
| 813 | 2 | 4-CN-Phenyl | Isopropyl |
| 814 | 2 | 4-CN-Phenyl | $-CH_2CH(CH_3)_2$ |
| 815 | 2 | 4-CN-Phenyl | $CF_3$ |
| 816 | 2 | 4-CN-Phenyl | $-CH_2CF_3$ |
| 817 | 2 | 4-CN-Phenyl | $-CH_2CH_2CF_3$ |
| 818 | 2 | 4-CN-Phenyl | cyclopropyl |
| 819 | 2 | 4-CN-Phenyl | Cyclobutyl |
| 820 | 2 | 4-CN-Phenyl | cyclopentyl |
| 821 | 2 | 4-CN-Phenyl | cyclohexyl |
| 822 | 2 | 4-CN-Phenyl | 3-pyridyl |
| 823 | 2 | 4-CN-Phenyl | 1-methyl-1H-pyrazol-4-yl |
| 824 | 2 | 4-CN-Phenyl | 1H-imidazol-4-yl |
| 825 | 2 | 4-CN-Phenyl | 2-furanyl |
| 826 | 2 | 2-CN-Phenyl | Ethyl |
| 827 | 2 | 2-CN-Phenyl | n-propyl |
| 828 | 2 | 2-CN-Phenyl | Isopropyl |
| 829 | 2 | 2-CN-Phenyl | $-CH_2CH(CH_3)_2$ |
| 830 | 2 | 2-CN-Phenyl | $CF_3$ |
| 831 | 2 | 2-CN-Phenyl | $-CH_2CF_3$ |
| 832 | 2 | 2-CN-Phenyl | $-CH_2CH_2CF_3$ |
| 833 | 2 | 2-CN-Phenyl | cyclopropyl |
| 834 | 2 | 2-CN-Phenyl | Cyclobutyl |
| 835 | 2 | 2-CN-Phenyl | cyclopentyl |
| 836 | 2 | 2-CN-Phenyl | cyclohexyl |
| 837 | 2 | 2-CN-Phenyl | 3-pyridyl |
| 838 | 2 | 2-CN-Phenyl | 1-methyl-1H-pyrazol-4-yl |
| 839 | 2 | 2-CN-Phenyl | 1H-imidazol-4-yl |
| 840 | 2 | 2-CN-Phenyl | 2-furanyl |
| 841 | 2 | 3-F-Phenyl | Ethyl |
| 842 | 2 | 3-F-Phenyl | n-propyl |
| 843 | 2 | 3-F-Phenyl | Isopropyl |
| 844 | 2 | 3-F-Phenyl | $-CH_2CH(CH_3)_2$ |
| 845 | 2 | 3-F-Phenyl | $CF_3$ |
| 846 | 2 | 3-F-Phenyl | $-CH_2CF_3$ |
| 847 | 2 | 3-F-Phenyl | $-CH_2CH_2CF_3$ |
| 848 | 2 | 3-F-Phenyl | cyclopropyl |
| 849 | 2 | 3-F-Phenyl | Cyclobutyl |
| 850 | 2 | 3-F-Phenyl | cyclopentyl |
| 851 | 2 | 3-F-Phenyl | cyclohexyl |
| 852 | 2 | 3-F-Phenyl | 3-pyridyl |
| 853 | 2 | 3-F-Phenyl | 1-methyl-1H-pyrazol-4-yl |
| 854 | 2 | 3-F-Phenyl | 1H-imidazol-4-yl |
| 855 | 2 | 3-F-Phenyl | 2-furanyl |
| 856 | 2 | 2-Cl-Phenyl | Ethyl |
| 857 | 2 | 2-Cl-Phenyl | n-propyl |
| 858 | 2 | 2-Cl-Phenyl | Isopropyl |
| 859 | 2 | 2-Cl-Phenyl | $-CH_2CH(CH_3)_2$ |
| 860 | 2 | 2-Cl-Phenyl | $CF_3$ |
| 861 | 2 | 2-Cl-Phenyl | $-CH_2CF_3$ |
| 862 | 2 | 2-Cl-Phenyl | $-CH_2CH_2CF_3$ |
| 863 | 2 | 2-Cl-Phenyl | cyclopropyl |

TABLE 31-continued

| Entry | n | $R^3$ | $R^{10c}$ |
|---|---|---|---|
| 864 | 2 | 2-Cl-Phenyl | Cyclobutyl |
| 865 | 2 | 2-Cl-Phenyl | cyclopentyl |
| 866 | 2 | 2-Cl-Phenyl | cyclohexyl |
| 867 | 2 | 2-Cl-Phenyl | 3-pyridyl |
| 868 | 2 | 2-Cl-Phenyl | 1-methyl-1H-pyrazol-4-yl |
| 869 | 2 | 2-Cl-Phenyl | 1H-imidazol-4-yl |
| 870 | 2 | 2-Cl-Phenyl | 2-furanyl |
| 871 | 2 | 4-Cl-Phenyl | Ethyl |
| 872 | 2 | 4-Cl-Phenyl | n-propyl |
| 873 | 2 | 4-Cl-Phenyl | Isopropyl |
| 874 | 2 | 4-Cl-Phenyl | $—CH_2CH(CH_3)_2$ |
| 875 | 2 | 4-Cl-Phenyl | $CF_3$ |
| 876 | 2 | 4-Cl-Phenyl | $—CH_2CF_3$ |
| 877 | 2 | 4-Cl-Phenyl | $—CH_2CH_2CF_3$ |
| 878 | 2 | 4-Cl-Phenyl | cyclopropyl |
| 879 | 2 | 4-Cl-Phenyl | Cyclobutyl |
| 880 | 2 | 4-Cl-Phenyl | cyclopentyl |
| 881 | 2 | 4-Cl-Phenyl | cyclohexyl |
| 882 | 2 | 4-Cl-Phenyl | 3-pyridyl |
| 883 | 2 | 4-Cl-Phenyl | 1-methyl-1H-pyrazol-4-yl |
| 884 | 2 | 4-Cl-Phenyl | 1H-imidazol-4-yl |
| 885 | 2 | 4-Cl-Phenyl | 2-furanyl |
| 886 | 2 | 3-Br-Phenyl | Ethyl |
| 887 | 2 | 3-Br-Phenyl | n-propyl |
| 888 | 2 | 3-Br-Phenyl | Isopropyl |
| 889 | 2 | 3-Br-Phenyl | $—CH_2CH(CH_3)_2$ |
| 890 | 2 | 3-Br-Phenyl | $CF_3$ |
| 891 | 2 | 3-Br-Phenyl | $—CH_2CF_3$ |
| 892 | 2 | 3-Br-Phenyl | $—CH_2CH_2CF_3$ |
| 893 | 2 | 3-Br-Phenyl | cyclopropyl |
| 894 | 2 | 3-Br-Phenyl | Cyclobutyl |
| 895 | 2 | 3-Br-Phenyl | cyclopentyl |
| 896 | 2 | 3-Br-Phenyl | cyclohexyl |
| 897 | 2 | 3-Br-Phenyl | 3-pyridyl |
| 898 | 2 | 3-Br-Phenyl | 1-methyl-1H-pyrazol-4-yl |
| 899 | 2 | 3-Br-Phenyl | 1H-imidazol-4-yl |
| 900 | 2 | 3-Br-Phenyl | 2-furanyl |
| 901 | 2 | $2-CF_3$-Phenyl | Ethyl |
| 902 | 2 | $2-CF_3$-Phenyl | n-propyl |
| 903 | 2 | $2-CF_3$-Phenyl | Isopropyl |
| 904 | 2 | $2-CF_3$-Phenyl | $—CH_2CH(CH_3)_2$ |
| 905 | 2 | $2-CF_3$-Phenyl | $CF_3$ |
| 906 | 2 | $2-CF_3$-Phenyl | $—CH_2CF_3$ |
| 907 | 2 | $2-CF_3$-Phenyl | $—CH_2CH_2CF_3$ |
| 908 | 2 | $2-CF_3$-Phenyl | cyclopropyl |
| 909 | 2 | $2-CF_3$-Phenyl | Cyclobutyl |
| 910 | 2 | $2-CF_3$-Phenyl | cyclopentyl |
| 911 | 2 | $2-CF_3$-Phenyl | cyclohexyl |
| 912 | 2 | $2-CF_3$-Phenyl | 3-pyridyl |
| 913 | 2 | $2-CF_3$-Phenyl | 1-methyl-1H-pyrazol-4-yl |
| 914 | 2 | $2-CF_3$-Phenyl | 1H-imidazol-4-yl |
| 915 | 2 | $2-CF_3$-Phenyl | 2-furanyl |
| 916 | 2 | $4-CF_3$-Phenyl | Ethyl |
| 917 | 2 | $4-CF_3$-Phenyl | n-propyl |
| 918 | 2 | $4-CF_3$-Phenyl | Isopropyl |
| 919 | 2 | $4-CF_3$-Phenyl | $—CH_2CH(CH_3)_2$ |
| 920 | 2 | $4-CF_3$-Phenyl | $CF_3$ |
| 921 | 2 | $4-CF_3$-Phenyl | $—CH_2CF_3$ |
| 922 | 2 | $4-CF_3$-Phenyl | $—CH_2CH_2CF_3$ |
| 923 | 2 | $4-CF_3$-Phenyl | cyclopropyl |
| 924 | 2 | $4-CF_3$-Phenyl | Cyclobutyl |
| 925 | 2 | $4-CF_3$-Phenyl | cyclopentyl |
| 926 | 2 | $4-CF_3$-Phenyl | cyclohexyl |
| 927 | 2 | $4-CF_3$-Phenyl | 3-pyridyl |
| 928 | 2 | $4-CF_3$-Phenyl | 1-methyl-1H-pyrazol-4-yl |
| 929 | 2 | $4-CF_3$-Phenyl | 1H-imidazol-4-yl |
| 930 | 2 | $4-CF_3$-Phenyl | 2-furanyl |
| 931 | 2 | 3-iPr-Phenyl | Ethyl |
| 932 | 2 | 3-iPr-Phenyl | n-propyl |
| 933 | 2 | 3-iPr-Phenyl | Isopropyl |
| 934 | 2 | 3-iPr-Phenyl | $—CH_2CH(CH_3)_2$ |
| 935 | 2 | 3-iPr-Phenyl | $CF_3$ |
| 936 | 2 | 3-iPr-Phenyl | $—CH_2CF_3$ |
| 937 | 2 | 3-iPr-Phenyl | $—CH_2CH_2CF_3$ |
| 938 | 2 | 3-iPr-Phenyl | cyclopropyl |
| 939 | 2 | 3-iPr-Phenyl | Cyclobutyl |
| 940 | 2 | 3-iPr-Phenyl | cyclopentyl |
| 941 | 2 | 3-iPr-Phenyl | cyclohexyl |
| 942 | 2 | 3-iPr-Phenyl | 3-pyridyl |
| 943 | 2 | 3-iPr-Phenyl | 1-methyl-1H-pyrazol-4-yl |
| 944 | 2 | 3-iPr-Phenyl | 1H-imidazol-4-yl |
| 945 | 2 | 3-iPr-Phenyl | 2-furanyl |
| 946 | 2 | 2-morpholino-phenyl | Ethyl |
| 947 | 2 | 2-morpholino-phenyl | n-propyl |
| 948 | 2 | 2-morpholino-phenyl | isopropyl |
| 949 | 2 | 2-morpholino-phenyl | $—CH_2CH(CH_3)_2$ |
| 950 | 2 | 2-morpholino-phenyl | $CF_3$ |
| 951 | 2 | 2-morpholino-phenyl | $—CH_2CF_3$ |
| 952 | 2 | 2-morpholino-phenyl | $—CH_2CH_2CF_3$ |
| 953 | 2 | 2-morpholino-phenyl | cyclopropyl |
| 954 | 2 | 2-morpholino-phenyl | Cyclobutyl |
| 955 | 2 | 2-morpholino-phenyl | cyclopentyl |
| 956 | 2 | 2-morpholino-phenyl | cyclohexyl |
| 957 | 2 | 2-morpholino-phenyl | 3-pyridyl |
| 958 | 2 | 2-morpholino-phenyl | 1-methyl-1H-pyrazol-4-yl |
| 959 | 2 | 2-morpholino-phenyl | 1H-imidazol-4-yl |
| 960 | 2 | 2-morpholino-phenyl | 2-furanyl |
| 961 | 2 | 4-morpholino-phenyl | ethyl |
| 962 | 2 | 4-morpholino-phenyl | n-propyl |
| 963 | 2 | 4-morpholino-phenyl | isopropyl |
| 964 | 2 | 4-morpholino-phenyl | $—CH_2CH(CH_3)_2$ |
| 965 | 2 | 4-morpholino-phenyl | $CF_3$ |
| 966 | 2 | 4-morpholino-phenyl | $—CH_2CF_3$ |
| 967 | 2 | 4-morpholino-phenyl | $—CH_2CH_2CF_3$ |
| 968 | 2 | 4-morpholino-phenyl | cyclopropyl |
| 969 | 2 | 4-morpholino-phenyl | Cyclobutyl |
| 970 | 2 | 4-morpholino-phenyl | cyclopentyl |
| 971 | 2 | 4-morpholino-phenyl | cyclohexyl |
| 972 | 2 | 4-morpholino-phenyl | 3-pyridyl |
| 973 | 2 | 4-morpholino-phenyl | 1-methyl-1H-pyrazol-4-yl |
| 974 | 2 | 4-morpholino-phenyl | 1H-imidazol-4-yl |
| 975 | 2 | 4-morpholino-phenyl | 2-furanyl |
| 976 | 2 | 4-methyl-2-morpholino-phenyl | ethyl |
| 977 | 2 | 4-methyl-2-morpholino-phenyl | n-propyl |
| 978 | 2 | 4-methyl-2-morpholino-phenyl | isopropyl |
| 979 | 2 | 4-methyl-2-morpholino-phenyl | $—CH_2CH(CH_3)_2$ |
| 980 | 2 | 4-methyl-2-morpholino-phenyl | $CF_3$ |
| 981 | 2 | 4-methyl-2-morpholino-phenyl | $—CH_2CF_3$ |
| 982 | 2 | 4-methyl-2-morpholino-phenyl | $—CH_2CH_2CF_3$ |
| 983 | 2 | 4-methyl-2-morpholino-phenyl | cyclopropyl |
| 984 | 2 | 4-methyl-2-morpholino-phenyl | Cyclobutyl |
| 985 | 2 | 4-methyl-2-morpholino-phenyl | cyclopentyl |
| 986 | 2 | 4-methyl-2-morpholino-phenyl | cyclohexyl |
| 987 | 2 | 4-methyl-2-morpholino-phenyl | 3-pyridyl |
| 988 | 2 | 4-methyl-2-morpholino-phenyl | 1-methyl-1H-pyrazol-4-yl |
| 989 | 2 | 4-methyl-2-morpholino-phenyl | 1H-imidazol-4-yl |
| 990 | 2 | 4-methyl-2-morpholino-phenyl | 2-furanyl |
| 991 | 3 | $4-CH_3$-phenyl | ethyl |
| 992 | 3 | $4-CH_3$-phenyl | n-propyl |
| 993 | 3 | $4-CH_3$-phenyl | isopropyl |
| 994 | 3 | $4-CH_3$-phenyl | $—CH_2CH(CH_3)_2$ |
| 995 | 3 | $4-CH_3$-phenyl | $CF_3$ |
| 996 | 3 | $4-CH_3$-phenyl | $—CH_2CF_3$ |
| 997 | 3 | $4-CH_3$-phenyl | $—CH_2CH_2CF_3$ |
| 998 | 3 | $4-CH_3$-phenyl | cyclopropyl |
| 999 | 3 | $4-CH_3$-phenyl | Cyclobutyl |
| 1000 | 3 | $4-CH_3$-phenyl | cyclopentyl |
| 1001 | 3 | $4-CH_3$-phenyl | cyclohexyl |
| 1002 | 3 | $4-CH_3$-phenyl | 3-pyridyl |
| 1003 | 3 | $4-CH_3$-phenyl | 1-methyl-1H-pyrazol-4-yl |
| 1004 | 3 | $4-CH_3$-phenyl | 1H-imidazol-4-yl |
| 1005 | 3 | $4-CH_3$-phenyl | 2-furanyl |
| 1006 | 3 | $3-CH_3$-phenyl | ethyl |
| 1007 | 3 | $3-CH_3$-phenyl | n-propyl |
| 1008 | 3 | $3-CH_3$-phenyl | isopropyl |
| 1009 | 3 | $3-CH_3$-phenyl | $—CH_2CH(CH_3)_2$ |
| 1010 | 3 | $3-CH_3$-phenyl | $CF_3$ |
| 1011 | 3 | $3-CH_3$-phenyl | $—CH_2CF_3$ |
| 1012 | 3 | $3-CH_3$-phenyl | $—CH_2CH_2CF_3$ |
| 1013 | 3 | $3-CH_3$-phenyl | cyclopropyl |
| 1014 | 3 | 3-CHs-phenyl | Cyclobutyl |
| 1015 | 3 | $3-CH_3$-phenyl | cyclopentyl |
| 1016 | 3 | $3-CH_3$-phenyl | cyclohexyl |
| 1017 | 3 | $3-CH_3$-phenyl | 3-pyridyl |
| 1018 | 3 | $3-CH_3$-phenyl | 1-methyl-1H-pyrazol-4-yl |
| 1019 | 3 | $3-CH_3$-phenyl | 1H-imidazol-4-yl |

TABLE 31-continued

| Entry | n | $R^3$ | $R^{10c}$ |
|---|---|---|---|
| 1020 | 3 | 3-$CH_3$-phenyl | 2-furanyl |
| 1021 | 3 | 3-OH-Phenyl | ethyl |
| 1022 | 3 | 3-OH-Phenyl | n-propyl |
| 1023 | 3 | 3-OH-Phenyl | isopropyl |
| 1024 | 3 | 3-OH-Phenyl | —$CH_2CH(CH_3)_2$ |
| 1025 | 3 | 3-OH-Phenyl | $CF_3$ |
| 1026 | 3 | 3-OH-Phenyl | —$CH_2CF_3$ |
| 1027 | 3 | 3-OH-Phenyl | —$CH_2CH_2CF_3$ |
| 1028 | 3 | 3-OH-Phenyl | cyclopropyl |
| 1029 | 3 | 3-OH-Phenyl | Cyclobutyl |
| 1030 | 3 | 3-OH-Phenyl | cyclopentyl |
| 1031 | 3 | 3-OH-Phenyl | cyclohexyl |
| 1032 | 3 | 3-OH-Phenyl | 3-pyridyl |
| 1033 | 3 | 3-OH-Phenyl | 1-methyl-1H-pyrazol-4-yl |
| 1034 | 3 | 3-OH-Phenyl | 1H-imidazol-4-yl |
| 1035 | 3 | 3-OH-Phenyl | 2-furanyl |
| 1036 | 3 | 4-OMe-Phenyl | ethyl |
| 1037 | 3 | 4-OMe-Phenyl | n-propyl |
| 1038 | 3 | 4-OMe-Phenyl | isopropyl |
| 1039 | 3 | 4-OMe-Phenyl | —$CH_2CH(CH_3)_2$ |
| 1040 | 3 | 4-OMe-Phenyl | $CF_3$ |
| 1041 | 3 | 4-OMe-Phenyl | —$CH_2CF_3$ |
| 1042 | 3 | 4-OMe-Phenyl | —$CH_2CH_2CF_3$ |
| 1043 | 3 | 4-OMe-Phenyl | cyclopropyl |
| 1044 | 3 | 4-OMe-Phenyl | Cyclobutyl |
| 1045 | 3 | 4-OMe-Phenyl | cyclopentyl |
| 1046 | 3 | 4-OMe-Phenyl | cyclohexyl |
| 1047 | 3 | 4-OMe-Phenyl | 3-pyridyl |
| 1048 | 3 | 4-OMe-Phenyl | 1-methyl-1H-pyrazol-4-yl |
| 1049 | 3 | 4-OMe-Phenyl | 1H-imidazol-4-yl |
| 1050 | 3 | 4-OMe-Phenyl | 2-furanyl |
| 1051 | 3 | 2-OMe-Phenyl | ethyl |
| 1052 | 3 | 2-OMe-Phenyl | n-propyl |
| 1053 | 3 | 2-OMe-Phenyl | isopropyl |
| 1054 | 3 | 2-OMe-Phenyl | —$CH_2CH(CH_3)_2$ |
| 1055 | 3 | 2-OMe-Phenyl | $CF_3$ |
| 1056 | 3 | 2-OMe-Phenyl | —$CH_2CF_3$ |
| 1057 | 3 | 2-OMe-Phenyl | —$CH_2CH_2CF_3$ |
| 1058 | 3 | 2-OMe-Phenyl | cyclopropyl |
| 1059 | 3 | 2-OMe-Phenyl | Cyclobutyl |
| 1060 | 3 | 2-OMe-Phenyl | cyclopentyl |
| 1061 | 3 | 2-OMe-Phenyl | cyclohexyl |
| 1062 | 3 | 2-OMe-Phenyl | 3-pyridyl |
| 1063 | 3 | 2-OMe-Phenyl | 1-methyl-1H-pyrazol-4-yl |
| 1064 | 3 | 2-OMe-Phenyl | 1H-imidazol-4-yl |
| 1065 | 3 | 2-OMe-Phenyl | 2-furanyl |
| 1066 | 3 | 3-CN-Phenyl | ethyl |
| 1067 | 3 | 3-CN-Phenyl | n-propyl |
| 1068 | 3 | 3-CN-Phenyl | isopropyl |
| 1069 | 3 | 3-CN-Phenyl | —$CH_2CH(CH_3)_2$ |
| 1070 | 3 | 3-CN-Phenyl | $CF_3$ |
| 1071 | 3 | 3-CN-Phenyl | —$CH_2CF_3$ |
| 1072 | 3 | 3-CN-Phenyl | —$CH_2CH_2CF_3$ |
| 1073 | 3 | 3-CN-Phenyl | cyclopropyl |
| 1074 | 3 | 3-CN-Phenyl | Cyclobutyl |
| 1075 | 3 | 3-CN-Phenyl | cyclopentyl |
| 1076 | 3 | 3-CN-Phenyl | cyclohexyl |
| 1077 | 3 | 3-CN-Phenyl | 3-pyridyl |
| 1078 | 3 | 3-CN-Phenyl | 1-methyl-1H-pyrazol-4-yl |
| 1079 | 3 | 3-CN-Phenyl | 1H-imidazol-4-yl |
| 1080 | 3 | 3-CN-Phenyl | 2-furanyl |
| 1081 | 3 | 2-F-Phenyl | ethyl |
| 1082 | 3 | 2-F-Phenyl | n-propyl |
| 1083 | 3 | 2-F-Phenyl | isopropyl |
| 1084 | 3 | 2-F-Phenyl | —$CH_2CH(CH_3)_2$ |
| 1085 | 3 | 2-F-Phenyl | $CF_3$ |
| 1086 | 3 | 2-F-Phenyl | —$CH_2CF_3$ |
| 1087 | 3 | 2-F-Phenyl | —$CH_2CH_2CF_3$ |
| 1088 | 3 | 2-F-Phenyl | cyclopropyl |
| 1089 | 3 | 2-F-Phenyl | Cyclobutyl |
| 1090 | 3 | 2-F-Phenyl | cyclopentyl |
| 1091 | 3 | 2-F-Phenyl | cyclohexyl |
| 1092 | 3 | 2-F-Phenyl | 3-pyridyl |
| 1093 | 3 | 2-F-Phenyl | 1-methyl-1H-pyrazol-4-yl |
| 1094 | 3 | 2-F-Phenyl | 1H-imidazol-4-yl |
| 1095 | 3 | 2-F-Phenyl | 2-furanyl |
| 1096 | 3 | 4-F-Phenyl | ethyl |
| 1097 | 3 | 4-F-Phenyl | n-propyl |
| 1098 | 3 | 4-F-Phenyl | isopropyl |
| 1099 | 3 | 4-F-Phenyl | —$CH_2CH(CH_3)_2$ |
| 1100 | 3 | 4-F-Phenyl | $CF_3$ |
| 1101 | 3 | 4-F-Phenyl | —$CH_2CF_3$ |
| 1102 | 3 | 4-F-Phenyl | —$CH_2CH_2CF_3$ |
| 1103 | 3 | 4-F-Phenyl | cyclopropyl |
| 1104 | 3 | 4-F-Phenyl | Cyclobutyl |
| 1105 | 3 | 4-F-Phenyl | cyclopentyl |
| 1106 | 3 | 4-F-Phenyl | cyclohexyl |
| 1107 | 3 | 4-F-Phenyl | 3-pyridyl |
| 1108 | 3 | 4-F-Phenyl | 1-methyl-1H-pyrazol-4-yl |
| 1109 | 3 | 4-F-Phenyl | 1H-imidazol-4-yl |
| 1110 | 3 | 4-F-Phenyl | 2-furanyl |
| 1111 | 3 | 3-Cl-Phenyl | ethyl |
| 1112 | 3 | 3-Cl-Phenyl | n-propyl |
| 1113 | 3 | 3-Cl-Phenyl | isopropyl |
| 1114 | 3 | 3-Cl-Phenyl | —$CH_2CH(CH_3)_2$ |
| 1115 | 3 | 3-Cl-Phenyl | $CF_3$ |
| 1116 | 3 | 3-Cl-Phenyl | —$CH_2CF_3$ |
| 1117 | 3 | 3-Cl-Phenyl | —$CH_2CH_2CF_3$ |
| 1118 | 3 | 3-Cl-Phenyl | cyclopropyl |
| 1119 | 3 | 3-Cl-Phenyl | Cyclobutyl |
| 1120 | 3 | 3-Cl-Phenyl | cyclopentyl |
| 1121 | 3 | 3-Cl-Phenyl | cyclohexyl |
| 1122 | 3 | 3-Cl-Phenyl | 3-pyridyl |
| 1123 | 3 | 3-Cl-Phenyl | 1-methyl-1H-pyrazol-4-yl |
| 1124 | 3 | 3-Cl-Phenyl | 1H-imidazol-4-yl |
| 1125 | 3 | 3-Cl-Phenyl | 2-furanyl |
| 1126 | 3 | 2-Br-Phenyl | ethyl |
| 1127 | 3 | 2-Br-Phenyl | n-propyl |
| 1128 | 3 | 2-Br-Phenyl | isopropyl |
| 1129 | 3 | 2-Br-Phenyl | —$CH_2CH(CH_3)_2$ |
| 1130 | 3 | 2-Br-Phenyl | $CF_3$ |
| 1131 | 3 | 2-Br-Phenyl | —$CH_2CF_3$ |
| 1132 | 3 | 2-Br-Phenyl | —$CH_2CH_2CF_3$ |
| 1133 | 3 | 2-Br-Phenyl | cyclopropyl |
| 1134 | 3 | 2-Br-Phenyl | Cyclobutyl |
| 1135 | 3 | 2-Br-Phenyl | cyclopentyl |
| 1136 | 3 | 2-Br-Phenyl | cyclohexyl |
| 1137 | 3 | 2-Br-Phenyl | 3-pyridyl |
| 1138 | 3 | 2-Br-Phenyl | 1-methyl-1H-pyrazol-4-yl |
| 1139 | 3 | 2-Br-Phenyl | 1H-imidazol-4-yl |
| 1140 | 3 | 2-Br-Phenyl | 2-furanyl |
| 1141 | 3 | 4-Br-Phenyl | ethyl |
| 1142 | 3 | 4-Br-Phenyl | n-propyl |
| 1143 | 3 | 4-Br-Phenyl | isopropyl |
| 1144 | 3 | 4-Br-Phenyl | —$CH_2CH(CH_3)_2$ |
| 1145 | 3 | 4-Br-Phenyl | $CF_3$ |
| 1146 | 3 | 4-Br-Phenyl | —$CH_2CF_3$ |
| 1147 | 3 | 4-Br-Phenyl | —$CH_2CH_2CF_3$ |
| 1148 | 3 | 4-Br-Phenyl | cyclopropyl |
| 1149 | 3 | 4-Br-Phenyl | Cyclobutyl |
| 1150 | 3 | 4-Br-Phenyl | cyclopentyl |
| 1151 | 3 | 4-Br-Phenyl | cyclohexyl |
| 1152 | 3 | 4-Br-Phenyl | 3-pyridyl |
| 1153 | 3 | 4-Br-Phenyl | 1-methyl-1H-pyrazol-4-yl |
| 1154 | 3 | 4-Br-Phenyl | 1H-imidazol-4-yl |
| 1155 | 3 | 4-Br-Phenyl | 2-furanyl |
| 1156 | 3 | 3-$CF_3$-Phenyl | ethyl |
| 1157 | 3 | 3-$CF_3$-Phenyl | n-propyl |
| 1158 | 3 | 3-$CF_3$-Phenyl | isopropyl |
| 1159 | 3 | 3-$CF_3$-Phenyl | —$CH_2CH(CH_3)_2$ |
| 1160 | 3 | 3-$CF_3$-Phenyl | $CF_3$ |
| 1161 | 3 | 3-$CF_3$-Phenyl | —$CH_2CF_3$ |
| 1162 | 3 | 3-$CF_3$-Phenyl | —$CH_2CH_2CF_3$ |
| 1163 | 3 | 3-$CF_3$-Phenyl | cyclopropyl |
| 1164 | 3 | 3-$CF_3$-Phenyl | Cyclobutyl |
| 1165 | 3 | 3-$CF_3$-Phenyl | cyclopentyl |
| 1166 | 3 | 3-$CF_3$-Phenyl | cyclohexyl |
| 1167 | 3 | 3-$CF_3$-Phenyl | 3-pyridyl |
| 1168 | 3 | 3-$CF_3$-Phenyl | 1-methyl-1H-pyrazol-4-yl |
| 1169 | 3 | 3-$CF_3$-Phenyl | 1H-imidazol-4-yl |
| 1170 | 3 | 3-$CF_3$-Phenyl | 2-furanyl |
| 1171 | 3 | 2-iPr-Phenyl | ethyl |
| 1172 | 3 | 2-iPr-Phenyl | n-propyl |
| 1173 | 3 | 2-iPr-Phenyl | isopropyl |
| 1174 | 3 | 2-iPr-Phenyl | —$CH_2CH(CH_3)_2$ |
| 1175 | 3 | 2-iPr-Phenyl | $CF_3$ |

TABLE 31-continued

| Entry | n | $R^3$ | $R^{10c}$ |
|---|---|---|---|
| 1176 | 3 | 2-iPr-Phenyl | $—CH_2CF_3$ |
| 1177 | 3 | 2-iPr-Phenyl | $—CH_2CH_2CF_3$ |
| 1178 | 3 | 2-iPr-Phenyl | cyclopropyl |
| 1179 | 3 | 2-iPr-Phenyl | Cyclobutyl |
| 1180 | 3 | 2-iPr-Phenyl | cyclopentyl |
| 1181 | 3 | 2-iPr-Phenyl | cyclohexyl |
| 1182 | 3 | 2-iPr-Phenyl | 3-pyridyl |
| 1183 | 3 | 2-iPr-Phenyl | 1-methyl-1H-pyrazol-4-yl |
| 1184 | 3 | 2-iPr-Phenyl | 1H-imidazol-4-yl |
| 1185 | 3 | 2-iPr-Phenyl | 2-furanyl |
| 1186 | 3 | 4-iPr-Phenyl | ethyl |
| 1187 | 3 | 4-iPr-Phenyl | n-propyl |
| 1188 | 3 | 4-iPr-Phenyl | isopropyl |
| 1189 | 3 | 4-iPr-Phenyl | $—CH_2CH(CH_3)_2$ |
| 1190 | 3 | 4-iPr-Phenyl | $CF_3$ |
| 1191 | 3 | 4-iPr-Phenyl | $—CH_2CF_3$ |
| 1192 | 3 | 4-iPr-Phenyl | $—CH_{2CH_2}CF_3$ |
| 1193 | 3 | 4-iPr-Phenyl | cyclopropyl |
| 1194 | 3 | 4-iPr-Phenyl | Cyclobutyl |
| 1195 | 3 | 4-iPr-Phenyl | cyclopentyl |
| 1196 | 3 | 4-iPr-Phenyl | cyclohexyl |
| 1197 | 3 | 4-iPr-Phenyl | 3-pyridyl |
| 1198 | 3 | 4-iPr-Phenyl | 1-methyl-1H-pyrazol-4-yl |
| 1199 | 3 | 4-iPr-Phenyl | 1H-imidazol-4-yl |
| 1200 | 3 | 4-iPr-Phenyl | 2-furanyl |
| 1201 | 3 | 3-morpholino-phenyl | ethyl |
| 1202 | 3 | 3-morpholino-phenyl | n-propyl |
| 1203 | 3 | 3-morpholino-phenyl | isopropyl |
| 1204 | 3 | 3-morpholino-phenyl | $—CH_2CH(CH_3)_2$ |
| 1205 | 3 | 3-morpholino-phenyl | $CF_3$ |
| 1206 | 3 | 3-morpholino-phenyl | $—CH_2CF_3$ |
| 1207 | 3 | 3-morpholino-phenyl | $—CH_2CH_2CF_3$ |
| 1208 | 3 | 3-morpholino-phenyl | cyclopropyl |
| 1209 | 3 | 3-morpholino-phenyl | Cyclobutyl |
| 1210 | 3 | 3-morpholino-phenyl | cyclopentyl |
| 1211 | 3 | 3-morpholino-phenyl | cyclohexyl |
| 1212 | 3 | 3-morpholino-phenyl | 3-pyridyl |
| 1213 | 3 | 3-morpholino-phenyl | 1-methyl-1H-pyrazol-4-yl |
| 1214 | 3 | 3-morpholino-phenyl | 1H-imidazol-4-yl |
| 1215 | 3 | 3-morpholino-phenyl | 2-furanyl |
| 1216 | 3 | 4-cyano-2-morpholino-phenyl | ethyl |
| 1217 | 3 | 4-cyano-2-morpholino-phenyl | n-propyl |
| 1218 | 3 | 4-cyano-2-morpholino-phenyl | isopropyl |
| 1219 | 3 | 4-cyano-2-morpholino-phenyl | $—CH_2CH(CH_3)_2$ |
| 1220 | 3 | 4-cyano-2-morpholino-phenyl | $CF_3$ |
| 1221 | 3 | 4-cyano-2-morpholino-phenyl | $—CH_2CF_3$ |
| 1222 | 3 | 4-cyano-2-morpholino-phenyl | $—CH_2CH_2CF_3$ |
| 1223 | 3 | 4-cyano-2-morpholino-phenyl | cyclopropyl |
| 1224 | 3 | 4-cyano-2-morpholino-phenyl | Cyclobutyl |
| 1225 | 3 | 4-cyano-2-morpholino-phenyl | cyclopentyl |
| 1226 | 3 | 4-cyano-2-morpholino-phenyl | cyclohexyl |
| 1227 | 3 | 4-cyano-2-morpholino-phenyl | 3-pyridyl |
| 1228 | 3 | 4-cyano-2-morpholino-phenyl | 1-methyl-1H-pyrazol-4-yl |
| 1229 | 3 | 4-cyano-2-morpholino-phenyl | 1H-imidazol-4-yl |
| 1230 | 3 | 4-cyano-2-morpholino-phenyl | 2-furanyl |
| 1231 | 3 | 4-hydroxy-2-morpholino-phenyl | ethyl |
| 1232 | 3 | 4-hydroxy-2-morpholino-phenyl | n-propyl |
| 1233 | 3 | 4-hydroxy-2-morpholino-phenyl | isopropyl |
| 1234 | 3 | 4-hydroxy-2-morpholino-phenyl | $—CH_2CH(CH_3)_2$ |
| 1235 | 3 | 4-hydroxy-2-morpholino-phenyl | $CF_3$ |
| 1236 | 3 | 4-hydroxy-2-morpholino-phenyl | $—CH_2CF_3$ |
| 1237 | 3 | 4-hydroxy-2-morpholino-phenyl | $—CH_2CH_2CF_3$ |
| 1238 | 3 | 4-hydroxy-2-morpholino-phenyl | cyclopropyl |
| 1239 | 3 | 4-hydroxy-2-morpholino-phenyl | Cyclobutyl |
| 1240 | 3 | 4-hydroxy-2-morpholino-phenyl | cyclopentyl |
| 1241 | 3 | 4-hydroxy-2-morpholino-phenyl | cyclohexyl |
| 1242 | 3 | 4-hydroxy-2-morpholino-phenyl | 3-pyridyl |
| 1243 | 3 | 4-hydroxy-2-morpholino-phenyl | 1-methyl-1H-pyrazol-4-yl |
| 1244 | 3 | 4-hydroxy-2-morpholino-phenyl | 1H-imidazol-4-yl |
| 1245 | 3 | 4-hydroxy-2-morpholino-phenyl | 2-furanyl |
| 1246 | 3 | $2-CH_3$-phenyl | Ethyl |
| 1247 | 3 | $2-CH_3$-phenyl | n-propyl |
| 1248 | 3 | $2-CH_3$-phenyl | Isopropyl |
| 1249 | 3 | $2-CH_3$-phenyl | $—CH_2CH(CH_3)_2$ |
| 1250 | 3 | $2-CH_3$-phenyl | $CF_3$ |
| 1251 | 3 | $2-CH_3$-phenyl | $—CH_2CF_3$ |
| 1252 | 3 | $2-CH_3$-phenyl | $—CH_2CH_2CF_3$ |
| 1253 | 3 | $2-CH_3$-phenyl | cyclopropyl |
| 1254 | 3 | $2-CH_3$-phenyl | Cyclobutyl |
| 1255 | 3 | $2-CH_3$-phenyl | cyclopentyl |
| 1256 | 3 | $2-CH_3$-phenyl | cyclohexyl |
| 1257 | 3 | $2-CH_3$-phenyl | 3-pyridyl |
| 1258 | 3 | $2-CH_3$-phenyl | 1-methyl-1H-pyrazol-4-yl |
| 1259 | 3 | $2-CH_3$-phenyl | 1H-imidazol-4-yl |
| 1260 | 3 | $2-CH_3$-phenyl | 2-furanyl |
| 1261 | 3 | 4-OH-Phenyl | Ethyl |
| 1262 | 3 | 4-OH-Phenyl | n-propyl |
| 1263 | 3 | 4-OH-Phenyl | Isopropyl |
| 1264 | 3 | 4-OH-Phenyl | $—CH_2CH(CH_3)_2$ |
| 1265 | 3 | 4-OH-Phenyl | $CF_3$ |
| 1266 | 3 | 4-OH-Phenyl | $—CH_2CF_3$ |
| 1267 | 3 | 4-OH-Phenyl | $—CH_2CH_2CF_3$ |
| 1268 | 3 | 4-OH-Phenyl | cyclopropyl |
| 1269 | 3 | 4-OH-Phenyl | Cyclobutyl |
| 1270 | 3 | 4-OH-Phenyl | cyclopentyl |
| 1271 | 3 | 4-OH-Phenyl | cyclohexyl |
| 1272 | 3 | 4-OH-Phenyl | 3-pyridyl |
| 1273 | 3 | 4-OH-Phenyl | 1-methyl-1H-pyrazol-4-yl |
| 1274 | 3 | 4-OH-Phenyl | 1H-imidazol-4-yl |
| 1275 | 3 | 4-OH-Phenyl | 2-furanyl |
| 1276 | 3 | 2-OH-Phenyl | Ethyl |
| 1277 | 3 | 2-OH-Phenyl | n-propyl |
| 1278 | 3 | 2-OH-Phenyl | Isopropyl |
| 1279 | 3 | 2-OH-Phenyl | $—CH_2CH(CH_3)_2$ |
| 1280 | 3 | 2-OH-Phenyl | $CF_3$ |
| 1281 | 3 | 2-OH-Phenyl | $—CH_2CF_3$ |
| 1282 | 3 | 2-OH-Phenyl | $—CH_2CH_2CF_3$ |
| 1283 | 3 | 2-OH-Phenyl | cyclopropyl |
| 1284 | 3 | 2-OH-Phenyl | Cyclobutyl |
| 1285 | 3 | 2-OH-Phenyl | cyclopentyl |
| 1286 | 3 | 2-OH-Phenyl | cyclohexyl |
| 1287 | 3 | 2-OH-Phenyl | 3-pyridyl |
| 1288 | 3 | 2-OH-Phenyl | 1-methyl-1H-pyrazol-4-yl |
| 1289 | 3 | 2-OH-Phenyl | 1H-imidazol-4-yl |
| 1290 | 3 | 2-OH-Phenyl | 2-furanyl |
| 1291 | 3 | 3-OMe-Phenyl | Ethyl |
| 1292 | 3 | 3-OMe-Phenyl | n-propyl |
| 1293 | 3 | 3-OMe-Phenyl | Isopropyl |
| 1294 | 3 | 3-OMe-Phenyl | $—CH_2CH(CH_3)_2$ |
| 1295 | 3 | 3-OMe-Phenyl | $CF_3$ |
| 1296 | 3 | 3-OMe-Phenyl | $—CH_2CF_3$ |
| 1297 | 3 | 3-OMe-Phenyl | $—CH_2CH_2CF_3$ |
| 1298 | 3 | 3-OMe-Phenyl | cyclopropyl |
| 1299 | 3 | 3-OMe-Phenyl | Cyclobutyl |
| 1300 | 3 | 3-OMe-Phenyl | cyclopentyl |
| 1301 | 3 | 3-OMe-Phenyl | cyclohexyl |
| 1302 | 3 | 3-OMe-Phenyl | 3-pyridyl |
| 1303 | 3 | 3-OMe-Phenyl | 1-methyl-1H-pyrazol-4-yl |
| 1304 | 3 | 3-OMe-Phenyl | 1H-imidazol-4-yl |
| 1305 | 3 | 3-OMe-Phenyl | 2-furanyl |
| 1306 | 3 | 4-CN-Phenyl | Ethyl |
| 1307 | 3 | 4-CN-Phenyl | n-propyl |
| 1308 | 3 | 4-CN-Phenyl | Isopropyl |
| 1309 | 3 | 4-CN-Phenyl | $—CH_2CH(CH_3)_2$ |
| 1310 | 3 | 4-CN-Phenyl | $CF_3$ |
| 1311 | 3 | 4-CN-Phenyl | $—CH_2CF_3$ |
| 1312 | 3 | 4-CN-Phenyl | $—CH_2CH_2CF_3$ |
| 1313 | 3 | 4-CN-Phenyl | cyclopropyl |
| 1314 | 3 | 4-CN-Phenyl | Cyclobutyl |
| 1315 | 3 | 4-CN-Phenyl | cyclopentyl |
| 1316 | 3 | 4-CN-Phenyl | cyclohexyl |
| 1317 | 3 | 4-CN-Phenyl | 3-pyridyl |
| 1318 | 3 | 4-CN-Phenyl | 1-methyl-1H-pyrazol-4-yl |
| 1319 | 3 | 4-CN-Phenyl | 1H-imidazol-4-yl |
| 1320 | 3 | 4-CN-Phenyl | 2-furanyl |
| 1321 | 3 | 2-CN-Phenyl | Ethyl |
| 1322 | 3 | 2-CN-Phenyl | n-propyl |
| 1323 | 3 | 2-CN-Phenyl | Isopropyl |
| 1324 | 3 | 2-CN-Phenyl | $—CH_2CH(CH_3)_2$ |
| 1325 | 3 | 2-CN-Phenyl | $CF_3$ |
| 1326 | 3 | 2-CN-Phenyl | $—CH_2CF_3$ |
| 1327 | 3 | 2-CN-Phenyl | $—CH_2CH_2CF_3$ |
| 1328 | 3 | 2-CN-Phenyl | cyclopropyl |
| 1329 | 3 | 2-CN-Phenyl | Cyclobutyl |
| 1330 | 3 | 2-CN-Phenyl | cyclopentyl |
| 1331 | 3 | 2-CN-Phenyl | cyclohexyl |

TABLE 31-continued

| Entry | n | $R^3$ | $R^{10c}$ |
|---|---|---|---|
| 1332 | 3 | 2-CN-Phenyl | 3-pyridyl |
| 1333 | 3 | 2-CN-Phenyl | 1-methyl-1H-pyrazol-4-yl |
| 1334 | 3 | 2-CN-Phenyl | 1H-imidazol-4-yl |
| 1335 | 3 | 2-CN-Phenyl | 2-furanyl |
| 1336 | 3 | 3-F-Phenyl | Ethyl |
| 1337 | 3 | 3-F-Phenyl | n-propyl |
| 1338 | 3 | 3-F-Phenyl | Isopropyl |
| 1339 | 3 | 3-F-Phenyl | $—CH_2CH(CH_3)_2$ |
| 1340 | 3 | 3-F-Phenyl | $CF_3$ |
| 1341 | 3 | 3-F-Phenyl | $—CH_2CF_3$ |
| 1342 | 3 | 3-F-Phenyl | $—CH_2CH_2CF_3$ |
| 1343 | 3 | 3-F-Phenyl | cyclopropyl |
| 1344 | 3 | 3-F-Phenyl | Cyclobutyl |
| 1345 | 3 | 3-F-Phenyl | cyclopentyl |
| 1346 | 3 | 3-F-Phenyl | cyclohexyl |
| 1347 | 3 | 3-F-Phenyl | 3-pyridyl |
| 1348 | 3 | 3-F-Phenyl | 1-methyl-1H-pyrazol-4-yl |
| 1349 | 3 | 3-F-Phenyl | 1H-imidazol-4-yl |
| 1350 | 3 | 3-F-Phenyl | 2-furanyl |
| 1351 | 3 | 2-Cl-Phenyl | Ethyl |
| 1352 | 3 | 2-Cl-Phenyl | n-propyl |
| 1353 | 3 | 2-Cl-Phenyl | Isopropyl |
| 1354 | 3 | 2-Cl-Phenyl | $—CH_2CH(CH_3)_2$ |
| 1355 | 3 | 2-Cl-Phenyl | $CF_3$ |
| 1356 | 3 | 2-Cl-Phenyl | $—CH_2CF_3$ |
| 1357 | 3 | 2-Cl-Phenyl | $—CH_2CH_2CF_3$ |
| 1358 | 3 | 2-Cl-Phenyl | cyclopropyl |
| 1359 | 3 | 2-Cl-Phenyl | Cyclobutyl |
| 1360 | 3 | 2-Cl-Phenyl | cyclopentyl |
| 1361 | 3 | 2-Cl-Phenyl | cyclohexyl |
| 1362 | 3 | 2-Cl-Phenyl | 3-pyridyl |
| 1363 | 3 | 2-Cl-Phenyl | 1-methyl-1H-pyrazol-4-yl |
| 1364 | 3 | 2-Cl-Phenyl | 1H-imidazol-4-yl |
| 1365 | 3 | 2-Cl-Phenyl | 2-furanyl |
| 1366 | 3 | 4-Cl-Phenyl | Ethyl |
| 1367 | 3 | 4-Cl-Phenyl | n-propyl |
| 1368 | 3 | 4-Cl-Phenyl | Isopropyl |
| 1369 | 3 | 4-Cl-Phenyl | $—CH_2CH(CH_3)_2$ |
| 1370 | 3 | 4-Cl-Phenyl | $CF_3$ |
| 1371 | 3 | 4-Cl-Phenyl | $—CH_2CF_3$ |
| 1372 | 3 | 4-Cl-Phenyl | $—CH_2CH_2CF_3$ |
| 1373 | 3 | 4-Cl-Phenyl | cyclopropyl |
| 1374 | 3 | 4-Cl-Phenyl | Cyclobutyl |
| 1375 | 3 | 4-Cl-Phenyl | cyclopentyl |
| 1376 | 3 | 4-Cl-Phenyl | cyclohexyl |
| 1377 | 3 | 4-Cl-Phenyl | 3-pyridyl |
| 1378 | 3 | 4-Cl-Phenyl | 1-methyl-1H-pyrazol-4-yl |
| 1379 | 3 | 4-Cl-Phenyl | 1H-imidazol-4-yl |
| 1380 | 3 | 4-Cl-Phenyl | 2-furanyl |
| 1381 | 3 | 3-Br-Phenyl | Ethyl |
| 1382 | 3 | 3-Br-Phenyl | n-propyl |
| 1383 | 3 | 3-Br-Phenyl | Isopropyl |
| 1384 | 3 | 3-Br-Phenyl | $—CH_2CH(CH_3)_2$ |
| 1385 | 3 | 3-Br-Phenyl | $CF_3$ |
| 1386 | 3 | 3-Br-Phenyl | $—CH_2CF_3$ |
| 1387 | 3 | 3-Br-Phenyl | $—CH_2CH_2CF_3$ |
| 1388 | 3 | 3-Br-Phenyl | cyclopropyl |
| 1389 | 3 | 3-Br-Phenyl | Cyclobutyl |
| 1390 | 3 | 3-Br-Phenyl | cyclopentyl |
| 1391 | 3 | 3-Br-Phenyl | cyclohexyl |
| 1392 | 3 | 3-Br-Phenyl | 3-pyridyl |
| 1393 | 3 | 3-Br-Phenyl | 1-methyl-1H-pyrazol-4-yl |
| 1394 | 3 | 3-Br-Phenyl | 1H-imidazol-4-yl |
| 1395 | 3 | 3-Br-Phenyl | 2-furanyl |
| 1396 | 3 | $2-CF_3$-Phenyl | Ethyl |
| 1397 | 3 | $2-CF_3$-Phenyl | n-propyl |
| 1398 | 3 | $2-CF_3$-Phenyl | Isopropyl |
| 1399 | 3 | $2-CF_3$-Phenyl | $—CH_2CH(CH_3)_2$ |
| 1400 | 3 | $2-CF_3$-Phenyl | $CF_3$ |
| 1401 | 3 | $2-CF_3$-Phenyl | $—CH_2CF_3$ |
| 1402 | 3 | $2-CF_3$-Phenyl | $—CH_2CH_2CF_3$ |
| 1403 | 3 | $2-CF_3$-Phenyl | cyclopropyl |
| 1404 | 3 | $2-CF_3$-Phenyl | Cyclobutyl |
| 1405 | 3 | $2-CF_3$-Phenyl | cyclopentyl |
| 1406 | 3 | $2-CF_3$-Phenyl | cyclohexyl |
| 1407 | 3 | $2-CF_3$-Phenyl | 3-pyridyl |
| 1408 | 3 | $2-CF_3$-Phenyl | 1-methyl-1H-pyrazol-4-yl |
| 1409 | 3 | $2-CF_3$-Phenyl | 1H-imidazol-4-yl |
| 1410 | 3 | $2-CF_3$-Phenyl | 2-furanyl |
| 1411 | 3 | $4-CF_3$-Phenyl | Ethyl |
| 1412 | 3 | $4-CF_3$-Phenyl | n-propyl |
| 1413 | 3 | $4-CF_3$-Phenyl | Isopropyl |
| 1414 | 3 | $4-CF_3$-Phenyl | $—CH_2CH(CH_3)_2$ |
| 1415 | 3 | $4-CF_3$-Phenyl | $CF_3$ |
| 1416 | 3 | $4-CF_3$-Phenyl | $—CH_2CF_3$ |
| 1417 | 3 | $4-CF_3$-Phenyl | $—CH_2CH_2CF_3$ |
| 1418 | 3 | $4-CF_3$-Phenyl | cyclopropyl |
| 1419 | 3 | $4-CF_3$-Phenyl | Cyclobutyl |
| 1420 | 3 | $4-CF_3$-Phenyl | cyclopentyl |
| 1421 | 3 | $4-CF_3$-Phenyl | cyclohexyl |
| 1422 | 3 | $4-CF_3$-Phenyl | 3-pyridyl |
| 1423 | 3 | $4-CF_3$-Phenyl | 1-methyl-1H-pyrazol-4-yl |
| 1424 | 3 | $4-CF_3$-Phenyl | 1H-imidazol-4-yl |
| 1425 | 3 | $4-CF_3$-Phenyl | 2-furanyl |
| 1426 | 3 | 3-iPr-Phenyl | Ethyl |
| 1427 | 3 | 3-iPr-Phenyl | n-propyl |
| 1428 | 3 | 3-iPr-Phenyl | Isopropyl |
| 1429 | 3 | 3-iPr-Phenyl | $—CH_2CH(CH_3)_2$ |
| 1430 | 3 | 3-iPr-Phenyl | $CF_3$ |
| 1431 | 3 | 3-iPr-Phenyl | $—CH_2CF_3$ |
| 1432 | 3 | 3-iPr-Phenyl | $—CH_2CH_2CF_3$ |
| 1433 | 3 | 3-iPr-Phenyl | cyclopropyl |
| 1434 | 3 | 3-iPr-Phenyl | Cyclobutyl |
| 1435 | 3 | 3-iPr-Phenyl | cyclopentyl |
| 1436 | 3 | 3-iPr-Phenyl | cyclohexyl |
| 1437 | 3 | 3-iPr-Phenyl | 3-pyridyl |
| 1438 | 3 | 3-iPr-Phenyl | 1-methyl-1H-pyrazol-4-yl |
| 1439 | 3 | 3-iPr-Phenyl | 1H-imidazol-4-yl |
| 1440 | 3 | 3-iPr-Phenyl | 2-furanyl |
| 1441 | 3 | 2-morpholino-phenyl | Ethyl |
| 1442 | 3 | 2-morpholino-phenyl | n-propyl |
| 1443 | 3 | 2-morpholino-phenyl | isopropyl |
| 1444 | 3 | 2-morpholino-phenyl | $—CH_2CH(CH_3)_2$ |
| 1445 | 3 | 2-morpholino-phenyl | $CF_3$ |
| 1446 | 3 | 2-morpholino-phenyl | $—CH_2CF_3$ |
| 1447 | 3 | 2-morpholino-phenyl | $—CH_2CH_2CF_3$ |
| 1448 | 3 | 2-morpholino-phenyl | cyclopropyl |
| 1449 | 3 | 2-morpholino-phenyl | Cyclobutyl |
| 1450 | 3 | 2-morpholino-phenyl | cyclopentyl |
| 1451 | 3 | 2-morpholino-phenyl | cyclohexyl |
| 1452 | 3 | 2-morpholino-phenyl | 3-pyridyl |
| 1453 | 3 | 2-morpholino-phenyl | 1-methyl-1H-pyrazol-4-yl |
| 1454 | 3 | 2-morpholino-phenyl | 1H-imidazol-4-yl |
| 1455 | 3 | 2-morpholino-phenyl | 2-furanyl |
| 1456 | 3 | 4-morpholino-phenyl | ethyl |
| 1457 | 3 | 4-morpholino-phenyl | n-propyl |
| 1458 | 3 | 4-morpholino-phenyl | isopropyl |
| 1459 | 3 | 4-morpholino-phenyl | $—CH_2CH(CH_3)_2$ |
| 1460 | 3 | 4-morpholino-phenyl | $CF_3$ |
| 1461 | 3 | 4-morpholino-phenyl | $—CH_2CF_3$ |
| 1462 | 3 | 4-morpholino-phenyl | $—CH_2CH_2CF_3$ |
| 1463 | 3 | 4-morpholino-phenyl | cyclopropyl |
| 1464 | 3 | 4-morpholino-phenyl | Cyclobutyl |
| 1465 | 3 | 4-morpholino-phenyl | cyclopentyl |
| 1466 | 3 | 4-morpholino-phenyl | cyclohexyl |
| 1467 | 3 | 4-morpholino-phenyl | 3-pyridyl |
| 1468 | 3 | 4-morpholino-phenyl | 1-methyl-1H-pyrazol-4-yl |
| 1469 | 3 | 4-morpholino-phenyl | 1H-imidazol-4-yl |
| 1470 | 3 | 4-morpholino-phenyl | 2-furanyl |
| 1471 | 3 | 4-methyl-2-morpholino-phenyl | ethyl |
| 1472 | 3 | 4-methyl-2-morpholino-phenyl | n-propyl |
| 1473 | 3 | 4-methyl-2-morpholino-phenyl | isopropyl |
| 1474 | 3 | 4-methyl-2-morpholino-phenyl | $—CH_2CH(CH_3)_2$ |
| 1475 | 3 | 4-methyl-2-morpholino-phenyl | $CF_3$ |
| 1476 | 3 | 4-methyl-2-morpholino-phenyl | $—CH_2CF_3$ |
| 1477 | 3 | 4-methyl-2-morpholino-phenyl | $—CH_2CH_2CF_3$ |
| 1478 | 3 | 4-methyl-2-morpholino-phenyl | cyclopropyl |
| 1479 | 3 | 4-methyl-2-morpholino-phenyl | Cyclobutyl |
| 1480 | 3 | 4-methyl-2-morpholino-phenyl | cyclopentyl |
| 1481 | 3 | 4-methyl-2-morpholino-phenyl | cyclohexyl |
| 1482 | 3 | 4-methyl-2-morpholino-phenyl | 3-pyridyl |
| 1483 | 3 | 4-methyl-2-morpholino-phenyl | 1-methyl-1H-pyrazol-4-yl |
| 1484 | 3 | 4-methyl-2-morpholino-phenyl | 1H-imidazol-4-yl |
| 1485 | 3 | 4-methyl-2-morpholino-phenyl | 2-furanyl |
| 1486 | 4 | $4-CH_3$-phenyl | ethyl |
| 1487 | 4 | $4-CH_3$-phenyl | n-propyl |

TABLE 31-continued

| Entry | n | $R^3$ | $R^{10c}$ |
|---|---|---|---|
| 1488 | 4 | 4-$CH_3$-phenyl | isopropyl |
| 1489 | 4 | 4-$CH_3$-phenyl | —$CH_2CH(CH_3)_2$ |
| 1490 | 4 | 4-$CH_3$-phenyl | $CF_3$ |
| 1491 | 4 | 4-$CH_3$-phenyl | —$CH_2CF_3$ |
| 1492 | 4 | 4-$CH_3$-phenyl | —$CH_2CH_2CF_3$ |
| 1493 | 4 | 4-$CH_3$-phenyl | cyclopropyl |
| 1494 | 4 | 4-$CH_3$-phenyl | Cyclobutyl |
| 1495 | 4 | 4-$CH_3$-phenyl | cyclopentyl |
| 1496 | 4 | 4-$CH_3$-phenyl | cyclohexyl |
| 1497 | 4 | 4-$CH_3$-phenyl | 3-pyridyl |
| 1498 | 4 | 4-$CH_3$-phenyl | 1-methyl-1H-pyrazol-4-yl |
| 1499 | 4 | 4-$CH_3$-phenyl | 1H-imidazol-4-yl |
| 1500 | 4 | 4-$CH_3$-phenyl | 2-furanyl |
| 1501 | 4 | 3-$CH_3$-phenyl | ethyl |
| 1502 | 4 | 3-$CH_3$-phenyl | n-propyl |
| 1503 | 4 | 3-$CH_3$-phenyl | isopropyl |
| 1504 | 4 | 3-$CH_3$-phenyl | —$CH_2CH(CH_3)_2$ |
| 1505 | 4 | 3-$CH_3$-phenyl | $CF_3$ |
| 1506 | 4 | 3-$CH_3$-phenyl | —$CH_2CF_3$ |
| 1507 | 4 | 3-$CH_3$-phenyl | —$CH_2CH_2CF_3$ |
| 1508 | 4 | 3-$CH_3$-phenyl | cyclopropyl |
| 1509 | 4 | 3-$CH_3$-phenyl | Cyclobutyl |
| 1510 | 4 | 3-CHs-phenyl | cyclopentyl |
| 1511 | 4 | 3-$CH_3$-phenyl | cyclohexyl |
| 1512 | 4 | 3-$CH_3$-phenyl | 3-pyridyl |
| 1513 | 4 | 3-$CH_3$-phenyl | 1-methyl-1H-pyrazol-4-yl |
| 1514 | 4 | 3-$CH_3$-phenyl | 1H-imidazol-4-yl |
| 1515 | 4 | 3-$CH_3$-phenyl | 2-furanyl |
| 1516 | 4 | 3-OH-Phenyl | ethyl |
| 1517 | 4 | 3-OH-Phenyl | n-propyl |
| 1518 | 4 | 3-OH-Phenyl | isopropyl |
| 1519 | 4 | 3-OH-Phenyl | —$CH_2CH(CH_3)_2$ |
| 1520 | 4 | 3-OH-Phenyl | $CF_3$ |
| 1521 | 4 | 3-OH-Phenyl | —$CH_2CF_3$ |
| 1522 | 4 | 3-OH-Phenyl | —$CH_2CH_2CF_3$ |
| 1523 | 4 | 3-OH-Phenyl | cyclopropyl |
| 1524 | 4 | 3-OH-Phenyl | Cyclobutyl |
| 1525 | 4 | 3-OH-Phenyl | cyclopentyl |
| 1526 | 4 | 3-OH-Phenyl | cyclohexyl |
| 1527 | 4 | 3-OH-Phenyl | 3-pyridyl |
| 1528 | 4 | 3-OH-Phenyl | 1-methyl-1H-pyrazol-4-yl |
| 1529 | 4 | 3-OH-Phenyl | 1H-imidazol-4-yl |
| 1530 | 4 | 3-OH-Phenyl | 2-furanyl |
| 1531 | 4 | 4-OMe-Phenyl | ethyl |
| 1532 | 4 | 4-OMe-Phenyl | n-propyl |
| 1533 | 4 | 4-OMe-Phenyl | isopropyl |
| 1534 | 4 | 4-OMe-Phenyl | —$CH_2CH(CH_3)_2$ |
| 1535 | 4 | 4-OMe-Phenyl | $CF_3$ |
| 1536 | 4 | 4-OMe-Phenyl | —$CH_2CF_3$ |
| 1537 | 4 | 4-OMe-Phenyl | —$CH_2CH_2CF_3$ |
| 1538 | 4 | 4-OMe-Phenyl | cyclopropyl |
| 1539 | 4 | 4-OMe-Phenyl | Cyclobutyl |
| 1540 | 4 | 4-OMe-Phenyl | cyclopentyl |
| 1541 | 4 | 4-OMe-Phenyl | cyclohexyl |
| 1542 | 4 | 4-OMe-Phenyl | 3-pyridyl |
| 1543 | 4 | 4-OMe-Phenyl | 1-methyl-1H-pyrazol-4-yl |
| 1544 | 4 | 4-OMe-Phenyl | 1H-imidazol-4-yl |
| 1545 | 4 | 4-OMe-Phenyl | 2-furanyl |
| 1546 | 4 | 2-OMe-Phenyl | ethyl |
| 1547 | 4 | 2-OMe-Phenyl | n-propyl |
| 1548 | 4 | 2-OMe-Phenyl | isopropyl |
| 1549 | 4 | 2-OMe-Phenyl | —$CH_2CH(CH_3)_2$ |
| 1550 | 4 | 2-OMe-Phenyl | $CF_3$ |
| 1551 | 4 | 2-OMe-Phenyl | —$CH_2CF_3$ |
| 1552 | 4 | 2-OMe-Phenyl | —$CH_2CH_2CF_3$ |
| 1553 | 4 | 2-OMe-Phenyl | cyclopropyl |
| 1554 | 4 | 2-OMe-Phenyl | Cyclobutyl |
| 1555 | 4 | 2-OMe-Phenyl | cyclopentyl |
| 1556 | 4 | 2-OMe-Phenyl | cyclohexyl |
| 1557 | 4 | 2-OMe-Phenyl | 3-pyridyl |
| 1558 | 4 | 2-OMe-Phenyl | 1-methyl-1H-pyrazol-4-yl |
| 1559 | 4 | 2-OMe-Phenyl | 1H-imidazol-4-yl |
| 1560 | 4 | 2-OMe-Phenyl | 2-furanyl |
| 1561 | 4 | 3-CN-Phenyl | ethyl |
| 1562 | 4 | 3-CN-Phenyl | n-propyl |
| 1563 | 4 | 3-CN-Phenyl | isopropyl |
| 1564 | 4 | 3-CN-Phenyl | —$CH_2CH(CH_3)_2$ |
| 1565 | 4 | 3-CN-Phenyl | $CF_3$ |
| 1566 | 4 | 3-CN-Phenyl | —$CH_2CF_3$ |
| 1567 | 4 | 3-CN-Phenyl | —$CH_2CH_2CF_3$ |
| 1568 | 4 | 3-CN-Phenyl | cyclopropyl |
| 1569 | 4 | 3-CN-Phenyl | Cyclobutyl |
| 1570 | 4 | 3-CN-Phenyl | cyclopentyl |
| 1571 | 4 | 3-CN-Phenyl | cyclohexyl |
| 1572 | 4 | 3-CN-Phenyl | 3-pyridyl |
| 1573 | 4 | 3-CN-Phenyl | 1-methyl-1H-pyrazol-4-yl |
| 1574 | 4 | 3-CN-Phenyl | 1H-imidazol-4-yl |
| 1575 | 4 | 3-CN-Phenyl | 2-furanyl |
| 1576 | 4 | 2-F-Phenyl | ethyl |
| 1577 | 4 | 2-F-Phenyl | n-propyl |
| 1578 | 4 | 2-F-Phenyl | isopropyl |
| 1579 | 4 | 2-F-Phenyl | —$CH_2CH(CH_3)_2$ |
| 1580 | 4 | 2-F-Phenyl | $CF_3$ |
| 1581 | 4 | 2-F-Phenyl | —$CH_2CF_3$ |
| 1582 | 4 | 2-F-Phenyl | —$CH_2CH_2CF_3$ |
| 1583 | 4 | 2-F-Phenyl | cyclopropyl |
| 1584 | 4 | 2-F-Phenyl | Cyclobutyl |
| 1585 | 4 | 2-F-Phenyl | cyclopentyl |
| 1586 | 4 | 2-F-Phenyl | cyclohexyl |
| 1587 | 4 | 2-F-Phenyl | 3-pyridyl |
| 1588 | 4 | 2-F-Phenyl | 1-methyl-1H-pyrazol-4-yl |
| 1589 | 4 | 2-F-Phenyl | 1H-imidazol-4-yl |
| 1590 | 4 | 2-F-Phenyl | 2-furanyl |
| 1591 | 4 | 4-F-Phenyl | ethyl |
| 1592 | 4 | 4-F-Phenyl | n-propyl |
| 1593 | 4 | 4-F-Phenyl | isopropyl |
| 1594 | 4 | 4-F-Phenyl | —$CH_2CH(CH_3)_2$ |
| 1595 | 4 | 4-F-Phenyl | $CF_3$ |
| 1596 | 4 | 4-F-Phenyl | —$CH_2CF_3$ |
| 1597 | 4 | 4-F-Phenyl | —$CH_2CH_2CF_3$ |
| 1598 | 4 | 4-F-Phenyl | cyclopropyl |
| 1599 | 4 | 4-F-Phenyl | Cyclobutyl |
| 1600 | 4 | 4-F-Phenyl | cyclopentyl |
| 1601 | 4 | 4-F-Phenyl | cyclohexyl |
| 1602 | 4 | 4-F-Phenyl | 3-pyridyl |
| 1603 | 4 | 4-F-Phenyl | 1-methyl-1H-pyrazol-4-yl |
| 1604 | 4 | 4-F-Phenyl | 1H-imidazol-4-yl |
| 1605 | 4 | 4-F-Phenyl | 2-furanyl |
| 1606 | 4 | 3-Cl-Phenyl | ethyl |
| 1607 | 4 | 3-Cl-Phenyl | n-propyl |
| 1608 | 4 | 3-Cl-Phenyl | isopropyl |
| 1609 | 4 | 3-Cl-Phenyl | —$CH_2CH(CH_3)_2$ |
| 1610 | 4 | 3-Cl-Phenyl | $CF_3$ |
| 1611 | 4 | 3-Cl-Phenyl | —$CH_2CF_3$ |
| 1612 | 4 | 3-Cl-Phenyl | —$CH_2CH_2CF_3$ |
| 1613 | 4 | 3-Cl-Phenyl | cyclopropyl |
| 1614 | 4 | 3-Cl-Phenyl | Cyclobutyl |
| 1615 | 4 | 3-Cl-Phenyl | cyclopentyl |
| 1616 | 4 | 3-Cl-Phenyl | cyclohexyl |
| 1617 | 4 | 3-Cl-Phenyl | 3-pyridyl |
| 1618 | 4 | 3-Cl-Phenyl | 1-methyl-1H-pyrazol-4-yl |
| 1619 | 4 | 3-Cl-Phenyl | 1H-imidazol-4-yl |
| 1620 | 4 | 3-Cl-Phenyl | 2-furanyl |
| 1621 | 4 | 2-Br-Phenyl | ethyl |
| 1622 | 4 | 2-Br-Phenyl | n-propyl |
| 1623 | 4 | 2-Br-Phenyl | isopropyl |
| 1624 | 4 | 2-Br-Phenyl | —$CH_2CH(CH_3)_2$ |
| 1625 | 4 | 2-Br-Phenyl | $CF_3$ |
| 1626 | 4 | 2-Br-Phenyl | —$CH_2CF_3$ |
| 1627 | 4 | 2-Br-Phenyl | —$CH_2CH_2CF_3$ |
| 1628 | 4 | 2-Br-Phenyl | cyclopropyl |
| 1629 | 4 | 2-Br-Phenyl | Cyclobutyl |
| 1630 | 4 | 2-Br-Phenyl | cyclopentyl |
| 1631 | 4 | 2-Br-Phenyl | cyclohexyl |
| 1632 | 4 | 2-Br-Phenyl | 3-pyridyl |
| 1633 | 4 | 2-Br-Phenyl | 1-methyl-1H-pyrazol-4-yl |
| 1634 | 4 | 2-Br-Phenyl | 1H-imidazol-4-yl |
| 1635 | 4 | 2-Br-Phenyl | 2-furanyl |
| 1636 | 4 | 4-Br-Phenyl | ethyl |
| 1637 | 4 | 4-Br-Phenyl | n-propyl |
| 1638 | 4 | 4-Br-Phenyl | isopropyl |
| 1639 | 4 | 4-Br-Phenyl | —$CH_2CH(CH_3)_2$ |
| 1640 | 4 | 4-Br-Phenyl | $CF_3$ |
| 1641 | 4 | 4-Br-Phenyl | —$CH_2CF_3$ |
| 1642 | 4 | 4-Br-Phenyl | —$CH_2CH_2CF_3$ |
| 1643 | 4 | 4-Br-Phenyl | cyclopropyl |

TABLE 31-continued

| Entry | n | $R^3$ | $R^{10c}$ |
|---|---|---|---|
| 1644 | 4 | 4-Br-Phenyl | Cyclobutyl |
| 1645 | 4 | 4-Br-Phenyl | cyclopentyl |
| 1646 | 4 | 4-Br-Phenyl | cyclohexyl |
| 1647 | 4 | 4-Br-Phenyl | 3-pyridyl |
| 1648 | 4 | 4-Br-Phenyl | 1-methyl-1H-pyrazol-4-yl |
| 1649 | 4 | 4-Br-Phenyl | 1H-imidazol-4-yl |
| 1650 | 4 | 4-Br-Phenyl | 2-furanyl |
| 1651 | 4 | 3-$CF_3$-Phenyl | ethyl |
| 1652 | 4 | 3-$CF_3$-Phenyl | n-propyl |
| 1653 | 4 | 3-$CF_3$-Phenyl | isopropyl |
| 1654 | 4 | 3-$CF_3$-Phenyl | —$CH_2CH(CH_3)_2$ |
| 1655 | 4 | 3-$CF_3$-Phenyl | $CF_3$ |
| 1656 | 4 | 3-$CF_3$-Phenyl | —$CH_2CF_3$ |
| 1657 | 4 | 3-$CF_3$-Phenyl | —$CH_2CH_2CF_3$ |
| 1658 | 4 | 3-$CF_3$-Phenyl | cyclopropyl |
| 1659 | 4 | 3-$CF_3$-Phenyl | Cyclobutyl |
| 1660 | 4 | 3-$CF_3$-Phenyl | cyclopentyl |
| 1661 | 4 | 3-$CF_3$-Phenyl | cyclohexyl |
| 1662 | 4 | 3-$CF_3$-Phenyl | 3-pyridyl |
| 1663 | 4 | 3-$CF_3$-Phenyl | 1-methyl-1H-pyrazol-4-yl |
| 1664 | 4 | 3-$CF_3$-Phenyl | 1H-imidazol-4-yl |
| 1665 | 4 | 3-$CF_3$-Phenyl | 2-furanyl |
| 1666 | 4 | 2-iPr-Phenyl | ethyl |
| 1667 | 4 | 2-iPr-Phenyl | n-propyl |
| 1668 | 4 | 2-iPr-Phenyl | isopropyl |
| 1669 | 4 | 2-iPr-Phenyl | —$CH_2CH(CH_3)_2$ |
| 1670 | 4 | 2-iPr-Phenyl | $CF_3$ |
| 1671 | 4 | 2-iPr-Phenyl | —$CH_2CF_3$ |
| 1672 | 4 | 2-iPr-Phenyl | —$CH_2CH_2CF_3$ |
| 1673 | 4 | 2-iPr-Phenyl | cyclopropyl |
| 1674 | 4 | 2-iPr-Phenyl | Cyclobutyl |
| 1675 | 4 | 2-iPr-Phenyl | cyclopentyl |
| 1676 | 4 | 2-iPr-Phenyl | cyclohexyl |
| 1677 | 4 | 2-iPr-Phenyl | 3-pyridyl |
| 1678 | 4 | 2-iPr-Phenyl | 1-methyl-1H-pyrazol-4-yl |
| 1679 | 4 | 2-iPr-Phenyl | 1H-imidazol-4-yl |
| 1680 | 4 | 2-iPr-Phenyl | 2-furanyl |
| 1681 | 4 | 4-iPr-Phenyl | ethyl |
| 1682 | 4 | 4-iPr-Phenyl | n-propyl |
| 1683 | 4 | 4-iPr-Phenyl | isopropyl |
| 1684 | 4 | 4-iPr-Phenyl | —$CH_2CH(CH_3)_2$ |
| 1685 | 4 | 4-iPr-Phenyl | $CF_3$ |
| 1686 | 4 | 4-iPr-Phenyl | —$CH_2CF_3$ |
| 1687 | 4 | 4-iPr-Phenyl | —$CH_2CH_2CF_3$ |
| 1688 | 4 | 4-iPr-Phenyl | cyclopropyl |
| 1689 | 4 | 4-iPr-Phenyl | Cyclobutyl |
| 1690 | 4 | 4-iPr-Phenyl | cyclopentyl |
| 1691 | 4 | 4-iPr-Phenyl | cyclohexyl |
| 1692 | 4 | 4-iPr-Phenyl | 3-pyridyl |
| 1693 | 4 | 4-iPr-Phenyl | 1-methyl-1H-pyrazol-4-yl |
| 1694 | 4 | 4-iPr-Phenyl | 1H-imidazol-4-yl |
| 1695 | 4 | 4-iPr-Phenyl | 2-furanyl |
| 1696 | 4 | 3-morpholino-phenyl | ethyl |
| 1697 | 4 | 3-morpholino-phenyl | n-propyl |
| 1698 | 4 | 3-morpholino-phenyl | isopropyl |
| 1699 | 4 | 3-morpholino-phenyl | —$CH_2CH(CH_3)_2$ |
| 1700 | 4 | 3-morpholino-phenyl | $CF_3$ |
| 1701 | 4 | 3-morpholino-phenyl | —$CH_2CF_3$ |
| 1702 | 4 | 3-morpholino-phenyl | —$CH_2CH_2CF_3$ |
| 1703 | 4 | 3-morpholino-phenyl | cyclopropyl |
| 1704 | 4 | 3-morpholino-phenyl | Cyclobutyl |
| 1705 | 4 | 3-morpholino-phenyl | cyclopentyl |
| 1706 | 4 | 3-morpholino-phenyl | cyclohexyl |
| 1707 | 4 | 3-morpholino-phenyl | 3-pyridyl |
| 1708 | 4 | 3-morpholino-phenyl | 1-methyl-1H-pyrazol-4-yl |
| 1709 | 4 | 3-morpholino-phenyl | 1H-imidazol-4-yl |
| 1710 | 4 | 3-morpholino-phenyl | 2-furanyl |
| 1711 | 4 | 4-cyano-2-morpholino-phenyl | ethyl |
| 1712 | 4 | 4-cyano-2-morpholino-phenyl | n-propyl |
| 1713 | 4 | 4-cyano-2-morpholino-phenyl | isopropyl |
| 1714 | 4 | 4-cyano-2-morpholino-phenyl | —$CH_2CH(CH_3)_2$ |
| 1715 | 4 | 4-cyano-2-morpholino-phenyl | $CF_3$ |
| 1716 | 4 | 4-cyano-2-morpholino-phenyl | —$CH_2CF_3$ |
| 1717 | 4 | 4-cyano-2-morpholino-phenyl | —$CH_2CH_2CF_3$ |
| 1718 | 4 | 4-cyano-2-morpholino-phenyl | cyclopropyl |
| 1719 | 4 | 4-cyano-2-morpholino-phenyl | Cyclobutyl |
| 1720 | 4 | 4-cyano-2-morpholino-phenyl | cyclopentyl |
| 1721 | 4 | 4-cyano-2-morpholino-phenyl | cyclohexyl |

TABLE 31-continued

| Entry | n | $R^3$ | $R^{10c}$ |
|---|---|---|---|
| 1722 | 4 | 4-cyano-2-morpholino-phenyl | 3-pyridyl |
| 1723 | 4 | 4-cyano-2-morpholino-phenyl | 1-methyl-1H-pyrazol-4-yl |
| 1724 | 4 | 4-cyano-2-morpholino-phenyl | 1H-imidazol-4-yl |
| 1725 | 4 | 4-cyano-2-morpholino-phenyl | 2-furanyl |
| 1726 | 4 | 4-hydroxy-2-morpholino-phenyl | ethyl |
| 1727 | 4 | 4-hydroxy-2-morpholino-phenyl | n-propyl |
| 1728 | 4 | 4-hydroxy-2-morpholino-phenyl | isopropyl |
| 1729 | 4 | 4-hydroxy-2-morpholino-phenyl | —$CH_2CH(CH_3)_2$ |
| 1730 | 4 | 4-hydroxy-2-morpholino-phenyl | $CF_3$ |
| 1731 | 4 | 4-hydroxy-2-morpholino-phenyl | —$CH_2CF_3$ |
| 1732 | 4 | 4-hydroxy-2-morpholino-phenyl | —$CH_2CH_2CF_3$ |
| 1733 | 4 | 4-hydroxy-2-morpholino-phenyl | cyclopropyl |
| 1734 | 4 | 4-hydroxy-2-morpholino-phenyl | Cyclobutyl |
| 1735 | 4 | 4-hydroxy-2-morpholino-phenyl | cyclopentyl |
| 1736 | 4 | 4-hydroxy-2-morpholino-phenyl | cyclohexyl |
| 1737 | 4 | 4-hydroxy-2-morpholino-phenyl | 3-pyridyl |
| 1738 | 4 | 4-hydroxy-2-morpholino-phenyl | 1-methyl-1H-pyrazol-4-yl |
| 1739 | 4 | 4-hydroxy-2-morpholino-phenyl | 1H-imidazol-4-yl |
| 1740 | 4 | 4-hydroxy-2-morpholino-phenyl | 2-furanyl |
| 1741 | 4 | 2-$CH_3$-phenyl | Ethyl |
| 1742 | 4 | 2-$CH_3$-phenyl | n-propyl |
| 1743 | 4 | 2-$CH_3$-phenyl | Isopropyl |
| 1744 | 4 | 2-$CH_3$-phenyl | —$CH_2CH(CH_3)_2$ |
| 1745 | 4 | 2-$CH_3$-phenyl | $CF_3$ |
| 1746 | 4 | 2-$CH_3$-phenyl | —$CH_2CF_3$ |
| 1747 | 4 | 2-$CH_3$-phenyl | —$CH_2CH_2CF_3$ |
| 1748 | 4 | 2-$CH_3$-phenyl | cyclopropyl |
| 1749 | 4 | 2-$CH_3$-phenyl | Cyclobutyl |
| 1750 | 4 | 2-$CH_3$-phenyl | cyclopentyl |
| 1751 | 4 | 2-$CH_3$-phenyl | cyclohexyl |
| 1752 | 4 | 2-$CH_3$-phenyl | 3-pyridyl |
| 1753 | 4 | 2-$CH_3$-phenyl | 1-methyl-1H-pyrazol-4-yl |
| 1754 | 4 | 2-$CH_3$-phenyl | 1H-imidazol-4-yl |
| 1755 | 4 | 2-$CH_3$-phenyl | 2-furanyl |
| 1756 | 4 | 4-OH-Phenyl | Ethyl |
| 1757 | 4 | 4-OH-Phenyl | n-propyl |
| 1758 | 4 | 4-OH-Phenyl | Isopropyl |
| 1759 | 4 | 4-OH-Phenyl | —$CH_2CH(CH_3)_2$ |
| 1760 | 4 | 4-OH-Phenyl | $CF_3$ |
| 1761 | 4 | 4-OH-Phenyl | —$CH_2CF_3$ |
| 1762 | 4 | 4-OH-Phenyl | —$CH_2CH_2CF_3$ |
| 1763 | 4 | 4-OH-Phenyl | cyclopropyl |
| 1764 | 4 | 4-OH-Phenyl | Cyclobutyl |
| 1765 | 4 | 4-OH-Phenyl | cyclopentyl |
| 1766 | 4 | 4-OH-Phenyl | cyclohexyl |
| 1767 | 4 | 4-OH-Phenyl | 3-pyridyl |
| 1768 | 4 | 4-OH-Phenyl | 1-methyl-1H-pyrazol-4-yl |
| 1769 | 4 | 4-OH-Phenyl | 1H-imidazol-4-yl |
| 1770 | 4 | 4-OH-Phenyl | 2-furanyl |
| 1771 | 4 | 2-OH-Phenyl | Ethyl |
| 1772 | 4 | 2-OH-Phenyl | n-propyl |
| 1773 | 4 | 2-OH-Phenyl | Isopropyl |
| 1774 | 4 | 2-OH-Phenyl | —$CH_2CH(CH_3)_2$ |
| 1775 | 4 | 2-OH-Phenyl | $CF_3$ |
| 1776 | 4 | 2-OH-Phenyl | —$CH_2CF_3$ |
| 1777 | 4 | 2-OH-Phenyl | —$CH_2CH_2CF_3$ |
| 1778 | 4 | 2-OH-Phenyl | cyclopropyl |
| 1779 | 4 | 2-OH-Phenyl | Cyclobutyl |
| 1780 | 4 | 2-OH-Phenyl | cyclopentyl |
| 1781 | 4 | 2-OH-Phenyl | cyclohexyl |
| 1782 | 4 | 2-OH-Phenyl | 3-pyridyl |
| 1783 | 4 | 2-OH-Phenyl | 1-methyl-1H-pyrazol-4-yl |
| 1784 | 4 | 2-OH-Phenyl | 1H-imidazol-4-yl |
| 1785 | 4 | 2-OH-Phenyl | 2-furanyl |
| 1786 | 4 | 3-OMe-Phenyl | Ethyl |
| 1787 | 4 | 3-OMe-Phenyl | n-propyl |
| 1788 | 4 | 3-OMe-Phenyl | Isopropyl |
| 1789 | 4 | 3-OMe-Phenyl | —$CH_2CH(CH_3)_2$ |
| 1790 | 4 | 3-OMe-Phenyl | $CF_3$ |
| 1791 | 4 | 3-OMe-Phenyl | —$CH_2CF_3$ |
| 1792 | 4 | 3-OMe-Phenyl | —$CH_2CH_2CF_3$ |
| 1793 | 4 | 3-OMe-Phenyl | cyclopropyl |
| 1794 | 4 | 3-OMe-Phenyl | Cyclobutyl |
| 1795 | 4 | 3-OMe-Phenyl | cyclopentyl |
| 1796 | 4 | 3-OMe-Phenyl | cyclohexyl |
| 1797 | 4 | 3-OMe-Phenyl | 3-pyridyl |
| 1798 | 4 | 3-OMe-Phenyl | 1-methyl-1H-pyrazol-4-yl |
| 1799 | 4 | 3-OMe-Phenyl | 1H-imidazol-4-yl |

TABLE 31-continued

| Entry | n | $R^3$ | $R^{10c}$ |
|---|---|---|---|
| 1800 | 4 | 3-OMe-Phenyl | 2-furanyl |
| 1801 | 4 | 4-CN-Phenyl | Ethyl |
| 1802 | 4 | 4-CN-Phenyl | n-propyl |
| 1803 | 4 | 4-CN-Phenyl | Isopropyl |
| 1804 | 4 | 4-CN-Phenyl | $—CH_2CH(CH_3)_2$ |
| 1805 | 4 | 4-CN-Phenyl | $CF_3$ |
| 1806 | 4 | 4-CN-Phenyl | $—CH_2CF_3$ |
| 1807 | 4 | 4-CN-Phenyl | $—CH_2CH_2CF_3$ |
| 1808 | 4 | 4-CN-Phenyl | cyclopropyl |
| 1809 | 4 | 4-CN-Phenyl | Cyclobutyl |
| 1810 | 4 | 4-CN-Phenyl | cyclopentyl |
| 1811 | 4 | 4-CN-Phenyl | cyclohexyl |
| 1812 | 4 | 4-CN-Phenyl | 3-pyridyl |
| 1813 | 4 | 4-CN-Phenyl | 1-methyl-1H-pyrazol-4-yl |
| 1814 | 4 | 4-CN-Phenyl | 1H-imidazol-4-yl |
| 1815 | 4 | 4-CN-Phenyl | 2-furanyl |
| 1816 | 4 | 2-CN-Phenyl | Ethyl |
| 1817 | 4 | 2-CN-Phenyl | n-propyl |
| 1818 | 4 | 2-CN-Phenyl | Isopropyl |
| 1819 | 4 | 2-CN-Phenyl | $—CH_2CH(CH_3)_2$ |
| 1820 | 4 | 2-CN-Phenyl | $CF_3$ |
| 1821 | 4 | 2-CN-Phenyl | $—CH_2CF_3$ |
| 1822 | 4 | 2-CN-Phenyl | $—CH_2CH_2CF_3$ |
| 1823 | 4 | 2-CN-Phenyl | cyclopropyl |
| 1824 | 4 | 2-CN-Phenyl | Cyclobutyl |
| 1825 | 4 | 2-CN-Phenyl | cyclopentyl |
| 1826 | 4 | 2-CN-Phenyl | cyclohexyl |
| 1827 | 4 | 2-CN-Phenyl | 3-pyridyl |
| 1828 | 4 | 2-CN-Phenyl | 1-methyl-1H-pyrazol-4-yl |
| 1829 | 4 | 2-CN-Phenyl | 1H-imidazol-4-yl |
| 1830 | 4 | 2-CN-Phenyl | 2-furanyl |
| 1831 | 4 | 3-F-Phenyl | Ethyl |
| 1832 | 4 | 3-F-Phenyl | n-propyl |
| 1833 | 4 | 3-F-Phenyl | Isopropyl |
| 1834 | 4 | 3-F-Phenyl | $—CH_2CH(CH_3)_2$ |
| 1835 | 4 | 3-F-Phenyl | $CF_3$ |
| 1836 | 4 | 3-F-Phenyl | $—CH_2CF_3$ |
| 1837 | 4 | 3-F-Phenyl | $—CH_2CH_2CF_3$ |
| 1838 | 4 | 3-F-Phenyl | cyclopropyl |
| 1839 | 4 | 3-F-Phenyl | Cyclobutyl |
| 1840 | 4 | 3-F-Phenyl | cyclopentyl |
| 1841 | 4 | 3-F-Phenyl | cyclohexyl |
| 1842 | 4 | 3-F-Phenyl | 3-pyridyl |
| 1843 | 4 | 3-F-Phenyl | 1-methyl-1H-pyrazol-4-yl |
| 1844 | 4 | 3-F-Phenyl | 1H-imidazol-4-yl |
| 1845 | 4 | 3-F-Phenyl | 2-furanyl |
| 1846 | 4 | 2-Cl-Phenyl | Ethyl |
| 1847 | 4 | 2-Cl-Phenyl | n-propyl |
| 1848 | 4 | 2-Cl-Phenyl | Isopropyl |
| 1849 | 4 | 2-Cl-Phenyl | $—CH_2CH(CH_3)_2$ |
| 1850 | 4 | 2-Cl-Phenyl | $CF_3$ |
| 1851 | 4 | 2-Cl-Phenyl | $—CH_2CF_3$ |
| 1852 | 4 | 2-Cl-Phenyl | $—CH_2CH_2CF_3$ |
| 1853 | 4 | 2-Cl-Phenyl | cyclopropyl |
| 1854 | 4 | 2-Cl-Phenyl | Cyclobutyl |
| 1855 | 4 | 2-Cl-Phenyl | cyclopentyl |
| 1856 | 4 | 2-Cl-Phenyl | cyclohexyl |
| 1857 | 4 | 2-Cl-Phenyl | 3-pyridyl |
| 1858 | 4 | 2-Cl-Phenyl | 1-methyl-1H-pyrazol-4-yl |
| 1859 | 4 | 2-Cl-Phenyl | 1H-imidazol-4-yl |
| 1860 | 4 | 2-Cl-Phenyl | 2-furanyl |
| 1861 | 4 | 4-Cl-Phenyl | Ethyl |
| 1862 | 4 | 4-Cl-Phenyl | n-propyl |
| 1863 | 4 | 4-Cl-Phenyl | Isopropyl |
| 1864 | 4 | 4-Cl-Phenyl | $—CH_2CH(CH_3)_2$ |
| 1865 | 4 | 4-Cl-Phenyl | $CF_3$ |
| 1866 | 4 | 4-Cl-Phenyl | $—CH_2CF_3$ |
| 1867 | 4 | 4-Cl-Phenyl | $—CH_2CH_2CF_3$ |
| 1868 | 4 | 4-Cl-Phenyl | cyclopropyl |
| 1869 | 4 | 4-Cl-Phenyl | Cyclobutyl |
| 1870 | 4 | 4-Cl-Phenyl | cyclopentyl |
| 1871 | 4 | 4-Cl-Phenyl | cyclohexyl |
| 1872 | 4 | 4-Cl-Phenyl | 3-pyridyl |
| 1873 | 4 | 4-Cl-Phenyl | 1-methyl-1H-pyrazol-4-yl |
| 1874 | 4 | 4-Cl-Phenyl | 1H-imidazol-4-yl |
| 1875 | 4 | 4-Cl-Phenyl | 2-furanyl |
| 1876 | 4 | 3-Br-Phenyl | Ethyl |
| 1877 | 4 | 3-Br-Phenyl | n-propyl |
| 1878 | 4 | 3-Br-Phenyl | Isopropyl |
| 1879 | 4 | 3-Br-Phenyl | $—CH_2CH(CH_3)_2$ |
| 1880 | 4 | 3-Br-Phenyl | $CF_3$ |
| 1881 | 4 | 3-Br-Phenyl | $—CH_2CF_3$ |
| 1882 | 4 | 3-Br-Phenyl | $—CH_2CH_2CF_3$ |
| 1883 | 4 | 3-Br-Phenyl | cyclopropyl |
| 1884 | 4 | 3-Br-Phenyl | Cyclobutyl |
| 1885 | 4 | 3-Br-Phenyl | cyclopentyl |
| 1886 | 4 | 3-Br-Phenyl | cyclohexyl |
| 1887 | 4 | 3-Br-Phenyl | 3-pyridyl |
| 1888 | 4 | 3-Br-Phenyl | 1-methyl-1H-pyrazol-4-yl |
| 1889 | 4 | 3-Br-Phenyl | 1H-imidazol-4-yl |
| 1890 | 4 | 3-Br-Phenyl | 2-furanyl |
| 1891 | 4 | $2-CF_3$-Phenyl | Ethyl |
| 1892 | 4 | $2-CF_3$-Phenyl | n-propyl |
| 1893 | 4 | $2-CF_3$-Phenyl | Isopropyl |
| 1894 | 4 | $2-CF_3$-Phenyl | $—CH_2CH(CH_3)_2$ |
| 1895 | 4 | $2-CF_3$-Phenyl | $CF_3$ |
| 1896 | 4 | $2-CF_3$-Phenyl | $—CH_2CF_3$ |
| 1897 | 4 | $2-CF_3$-Phenyl | $—CH_2CH_2CF_3$ |
| 1898 | 4 | $2-CF_3$-Phenyl | cyclopropyl |
| 1899 | 4 | $2-CF_3$-Phenyl | Cyclobutyl |
| 1900 | 4 | $2-CF_3$-Phenyl | cyclopentyl |
| 1901 | 4 | $2-CF_3$-Phenyl | cyclohexyl |
| 1902 | 4 | $2-CF_3$-Phenyl | 3-pyridyl |
| 1903 | 4 | $2-CF_3$-Phenyl | 1-methyl-1H-pyrazol-4-yl |
| 1904 | 4 | $2-CF_3$-Phenyl | 1H-imidazol-4-yl |
| 1905 | 4 | $2-CF_3$-Phenyl | 2-furanyl |
| 1906 | 4 | $4-CF_3$-Phenyl | Ethyl |
| 1907 | 4 | $4-CF_3$-Phenyl | n-propyl |
| 1908 | 4 | $4-CF_3$-Phenyl | Isopropyl |
| 1909 | 4 | $4-CF_3$-Phenyl | $—CH_2CH(CH_3)_2$ |
| 1910 | 4 | $4-CF_3$-Phenyl | $CF_3$ |
| 1911 | 4 | $4-CF_3$-Phenyl | $—CH_2CF_3$ |
| 1912 | 4 | $4-CF_3$-Phenyl | $—CH_2CH_2CF_3$ |
| 1913 | 4 | $4-CF_3$-Phenyl | cyclopropyl |
| 1914 | 4 | $4-CF_3$-Phenyl | Cyclobutyl |
| 1915 | 4 | $4-CF_3$-Phenyl | cyclopentyl |
| 1916 | 4 | $4-CF_3$-Phenyl | cyclohexyl |
| 1917 | 4 | $4-CF_3$-Phenyl | 3-pyridyl |
| 1918 | 4 | $4-CF_3$-Phenyl | 1-methyl-1H-pyrazol-4-yl |
| 1919 | 4 | $4-CF_3$-Phenyl | 1H-imidazol-4-yl |
| 1920 | 4 | $4-CF_3$-Phenyl | 2-furanyl |
| 1921 | 4 | 3-iPr-Phenyl | Ethyl |
| 1922 | 4 | 3-iPr-Phenyl | n-propyl |
| 1923 | 4 | 3-iPr-Phenyl | Isopropyl |
| 1924 | 4 | 3-iPr-Phenyl | $—CH_2CH(CH_3)_2$ |
| 1925 | 4 | 3-iPr-Phenyl | $CF_3$ |
| 1926 | 4 | 3-iPr-Phenyl | $—CH_2CF_3$ |
| 1927 | 4 | 3-iPr-Phenyl | $—CH_2CH_2CF_3$ |
| 1928 | 4 | 3-iPr-Phenyl | cyclopropyl |
| 1929 | 4 | 3-iPr-Phenyl | Cyclobutyl |
| 1930 | 4 | 3-iPr-Phenyl | cyclopentyl |
| 1931 | 4 | 3-iPr-Phenyl | cyclohexyl |
| 1932 | 4 | 3-iPr-Phenyl | 3-pyridyl |
| 1933 | 4 | 3-iPr-Phenyl | 1-methyl-1H-pyrazol-4-yl |
| 1934 | 4 | 3-iPr-Phenyl | 1H-imidazol-4-yl |
| 1935 | 4 | 3-iPr-Phenyl | 2-furanyl |
| 1936 | 4 | 2-morpholino-phenyl | Ethyl |
| 1937 | 4 | 2-morpholino-phenyl | n-propyl |
| 1938 | 4 | 2-morpholino-phenyl | isopropyl |
| 1939 | 4 | 2-morpholino-phenyl | $—CH_2CH(CH_3)_2$ |
| 1940 | 4 | 2-morpholino-phenyl | $CF_3$ |
| 1941 | 4 | 2-morpholino-phenyl | $—CH_2CF_3$ |
| 1942 | 4 | 2-morpholino-phenyl | $—CH_2CH_2CF_3$ |
| 1943 | 4 | 2-morpholino-phenyl | cyclopropyl |
| 1944 | 4 | 2-morpholino-phenyl | Cyclobutyl |
| 1945 | 4 | 2-morpholino-phenyl | cyclopentyl |
| 1946 | 4 | 2-morpholino-phenyl | cyclohexyl |
| 1947 | 4 | 2-morpholino-phenyl | 3-pyridyl |
| 1948 | 4 | 2-morpholino-phenyl | 1-methyl-1H-pyrazol-4-yl |
| 1949 | 4 | 2-morpholino-phenyl | 1H-imidazol-4-yl |
| 1950 | 4 | 2-morpholino-phenyl | 2-furanyl |
| 1951 | 4 | 4-morpholino-phenyl | ethyl |
| 1952 | 4 | 4-morpholino-phenyl | n-propyl |
| 1953 | 4 | 4-morpholino-phenyl | isopropyl |
| 1954 | 4 | 4-morpholino-phenyl | $—CH_2CH(CH_3)_2$ |
| 1955 | 4 | 4-morpholino-phenyl | $CF_3$ |

TABLE 31-continued

| Entry | n | $R^3$ | $R^{10c}$ |
|---|---|---|---|
| 1956 | 4 | 4-morpholino-phenyl | $—CH_2CF_3$ |
| 1957 | 4 | 4-morpholino-phenyl | $—CH_2CH_2CF_3$ |
| 1958 | 4 | 4-morpholino-phenyl | cyclopropyl |
| 1959 | 4 | 4-morpholino-phenyl | Cyclobutyl |
| 1960 | 4 | 4-morpholino-phenyl | cyclopentyl |
| 1961 | 4 | 4-morpholino-phenyl | cyclohexyl |
| 1962 | 4 | 4-morpholino-phenyl | 3-pyridyl |
| 1963 | 4 | 4-morpholino-phenyl | 1-methyl-1H-pyrazol-4-yl |
| 1964 | 4 | 4-morpholino-phenyl | 1H-imidazol-4-yl |
| 1965 | 4 | 4-morpholino-phenyl | 2-furanyl |
| 1966 | 4 | 4-methyl-2-morpholino-phenyl | ethyl |
| 1967 | 4 | 4-methyl-2-morpholino-phenyl | n-propyl |
| 1968 | 4 | 4-methyl-2-morpholino-phenyl | isopropyl |
| 1969 | 4 | 4-methyl-2-morpholino-phenyl | $—CH_2CH(CH_3)_2$ |
| 1970 | 4 | 4-methyl-2-morpholino-phenyl | $CF_3$ |
| 1971 | 4 | 4-methyl-2-morpholino-phenyl | $—CH_2CF_3$ |
| 1972 | 4 | 4-methyl-2-morpholino-phenyl | $—CH_2CH_2CF_3$ |
| 1973 | 4 | 4-methyl-2-morpholino-phenyl | cyclopropyl |
| 1974 | 4 | 4-methyl-2-morpholino-phenyl | Cyclobutyl |
| 1975 | 4 | 4-methyl-2-morpholino-phenyl | cyclopentyl |
| 1976 | 4 | 4-methyl-2-morpholino-phenyl | cyclohexyl |
| 1977 | 4 | 4-methyl-2-morpholino-phenyl | 3-pyridyl |
| 1978 | 4 | 4-methyl-2-morpholino-phenyl | 1-methyl-1H-pyrazol-4-yl |
| 1979 | 4 | 4-methyl-2-morpholino-phenyl | 1H-imidazol-4-yl |
| 1980 | 4 | 4-methyl-2-morpholino-phenyl | 2-furanyl |
| 1981 | 1 | naphthylen-1-yl | Ethyl |
| 1982 | 1 | naphthylen-1-yl | n-propyl |
| 1983 | 1 | naphthylen-1-yl | Isopropyl |
| 1984 | 1 | naphthylen-1-yl | $—CH_2CH(CH_3)_2$ |
| 1985 | 1 | naphthylen-1-yl | $CF_3$ |
| 1986 | 1 | naphthylen-1-yl | $—CH_2CF_3$ |
| 1987 | 1 | naphthylen-1-yl | $—CH_2CH_2CF_3$ |
| 1988 | 1 | naphthylen-1-yl | Cyclopropyl |
| 1989 | 1 | naphthylen-1-yl | Cyclobutyl |
| 1990 | 1 | naphthylen-1-yl | Cyclopentyl |
| 1991 | 1 | naphthylen-1-yl | Cyclohexyl |
| 1992 | 1 | naphthylen-1-yl | 3-pyridyl |
| 1993 | 1 | naphthylen-1-yl | 1-methyl-1H-pyrazol-4-yl |
| 1994 | 1 | naphthylen-1-yl | 1H-imidazol-4-yl |
| 1995 | 1 | naphthylen-1-yl | 2-furanyl |
| 1996 | 1 | naphthylen-2-yl | Ethyl |
| 1997 | 1 | naphthylen-2-yl | n-propyl |
| 1998 | 1 | naphthylen-2-yl | Isopropyl |
| 1999 | 1 | naphthylen-2-yl | $—CH_2CH(CH_3)_2$ |
| 2000 | 1 | naphthylen-2-yl | $CF_3$ |
| 2001 | 1 | naphthylen-2-yl | $—CH_2CF_3$ |
| 2002 | 1 | naphthylen-2-yl | $—CH_2CH_2CF_3$ |
| 2003 | 1 | naphthylen-2-yl | Cyclopropyl |
| 2004 | 1 | naphthylen-2-yl | Cyclobutyl |
| 2005 | 1 | naphthylen-2-yl | Cyclopentyl |
| 2006 | 1 | naphthylen-2-yl | Cyclohexyl |
| 2007 | 1 | naphthylen-2-yl | 3-pyridyl |
| 2008 | 1 | naphthylen-2-yl | 1-methyl-1H-pyrazol-4-yl |
| 2009 | 1 | naphthylen-2-yl | 1H-imidazol-4-yl |
| 2010 | 1 | naphthylen-2-yl | 2-furanyl |
| 2011 | 2 | naphthylen-1-yl | Ethyl |
| 2012 | 2 | naphthylen-1-yl | n-propyl |
| 2013 | 2 | naphthylen-1-yl | Isopropyl |
| 2014 | 2 | naphthylen-1-yl | $—CH_2CH(CH_3)_2$ |
| 2015 | 2 | naphthylen-1-yl | $CF_3$ |
| 2016 | 2 | naphthylen-1-yl | $—CH_2CF_3$ |
| 2017 | 2 | naphthylen-1-yl | $—CH_2CH_2CF_3$ |
| 2018 | 2 | naphthylen-1-yl | Cyclopropyl |
| 2019 | 2 | naphthylen-1-yl | Cyclobutyl |
| 2020 | 2 | naphthylen-1-yl | Cyclopentyl |
| 2021 | 2 | naphthylen-1-yl | Cyclohexyl |
| 2022 | 2 | naphthylen-1-yl | 3-pyridyl |
| 2023 | 2 | naphthylen-1-yl | 1-methyl-1H-pyrazol-4-yl |
| 2024 | 2 | naphthylen-1-yl | 1H-imidazol-4-yl |
| 2025 | 2 | naphthylen-1-yl | 2-furanyl |
| 2026 | 2 | naphthylen-2-yl | Ethyl |
| 2027 | 2 | naphthylen-2-yl | n-propyl |
| 2028 | 2 | naphthylen-2-yl | Isopropyl |
| 2029 | 2 | naphthylen-2-yl | $—CH_2CH(CH_3)_2$ |
| 2030 | 2 | naphthylen-2-yl | $CF_3$ |
| 2031 | 2 | naphthylen-2-yl | $—CH_2CF_3$ |
| 2032 | 2 | naphthylen-2-yl | $—CH_2CH_2CF_3$ |
| 2033 | 2 | naphthylen-2-yl | Cyclopropyl |

TABLE 31-continued

| Entry | n | $R^3$ | $R^{10c}$ |
|---|---|---|---|
| 2034 | 2 | naphthylen-2-yl | Cyclobutyl |
| 2035 | 2 | naphthylen-2-yl | Cyclopentyl |
| 2036 | 2 | naphthylen-2-yl | Cyclohexyl |
| 2037 | 2 | naphthylen-2-yl | 3-pyridyl |
| 2038 | 2 | naphthylen-2-yl | 1-methyl-1H-pyrazol-4-yl |
| 2039 | 2 | naphthylen-2-yl | 1H-imidazol-4-yl |
| 2040 | 2 | naphthylen-2-yl | 2-furanyl |
| 2041 | 3 | naphthylen-1-yl | Ethyl |
| 2042 | 3 | naphthylen-1-yl | n-propyl |
| 2043 | 3 | naphthylen-1-yl | Isopropyl |
| 2044 | 3 | naphthylen-1-yl | $—CH_2CH(CH_3)_2$ |
| 2045 | 3 | naphthylen-1-yl | $CF_3$ |
| 2046 | 3 | naphthylen-1-yl | $—CH_2CF_3$ |
| 2047 | 3 | naphthylen-1-yl | $—CH_2CH_2CF_3$ |
| 2048 | 3 | naphthylen-1-yl | Cyclopropyl |
| 2049 | 3 | naphthylen-1-yl | Cyclobutyl |
| 2050 | 3 | naphthylen-1-yl | Cyclopentyl |
| 2051 | 3 | naphthylen-1-yl | Cyclohexyl |
| 2052 | 3 | naphthylen-1-yl | 3-pyridyl |
| 2053 | 3 | naphthylen-1-yl | 1-methyl-1H-pyrazol-4-yl |
| 2054 | 3 | naphthylen-1-yl | 1H-imidazol-4-yl |
| 2055 | 3 | naphthylen-1-yl | 2-furanyl |
| 2056 | 3 | naphthylen-2-yl | Ethyl |
| 2057 | 3 | naphthylen-2-yl | n-propyl |
| 2058 | 3 | naphthylen-2-yl | Isopropyl |
| 2059 | 3 | naphthylen-2-yl | $—CH_2CH(CH_3)_2$ |
| 2060 | 3 | naphthylen-2-yl | $CF_3$ |
| 2061 | 3 | naphthylen-2-yl | $—CH_2CF_3$ |
| 2062 | 3 | naphthylen-2-yl | $—CH_2CH_2CF_3$ |
| 2063 | 3 | naphthylen-2-yl | Cyclopropyl |
| 2064 | 3 | naphthylen-2-yl | Cyclobutyl |
| 2065 | 3 | naphthylen-2-yl | Cyclopentyl |
| 2066 | 3 | naphthylen-2-yl | Cyclohexyl |
| 2067 | 3 | naphthylen-2-yl | 3-pyridyl |
| 2068 | 3 | naphthylen-2-yl | 1-methyl-1H-pyrazol-4-yl |
| 2069 | 3 | naphthylen-2-yl | 1H-imidazol-4-yl |
| 2070 | 3 | naphthylen-2-yl | 2-furanyl |
| 2071 | 4 | naphthylen-1-yl | Ethyl |
| 2072 | 4 | naphthylen-1-yl | n-propyl |
| 2073 | 4 | naphthylen-1-yl | Isopropyl |
| 2074 | 4 | naphthylen-1-yl | $—CH_2CH(CH_3)_2$ |
| 2075 | 4 | naphthylen-1-yl | $CF_3$ |
| 2076 | 4 | naphthylen-1-yl | $—CH_2CF_3$ |
| 2077 | 4 | naphthylen-1-yl | $—CH_2CH_2CF_3$ |
| 2078 | 4 | naphthylen-1-yl | Cyclopropyl |
| 2079 | 4 | naphthylen-1-yl | Cyclobutyl |
| 2080 | 4 | naphthylen-1-yl | Cyclopentyl |
| 2081 | 4 | naphthylen-1-yl | Cyclohexyl |
| 2082 | 4 | naphthylen-1-yl | 3-pyridyl |
| 2083 | 4 | naphthylen-1-yl | 1-methyl-1H-pyrazol-4-yl |
| 2084 | 4 | naphthylen-1-yl | 1H-imidazol-4-yl |
| 2085 | 4 | naphthylen-1-yl | 2-furanyl |
| 2086 | 4 | naphthylen-2-yl | Ethyl |
| 2087 | 4 | naphthylen-2-yl | n-propyl |
| 2088 | 4 | naphthylen-2-yl | Isopropyl |
| 2089 | 4 | naphthylen-2-yl | $—CH_2CH(CH_3)_2$ |
| 2090 | 4 | naphthylen-2-yl | $CF_3$ |
| 2091 | 4 | naphthylen-2-yl | $—CH_2CF_3$ |
| 2092 | 4 | naphthylen-2-yl | $—CH_2CH_2CF_3$ |
| 2093 | 4 | naphthylen-2-yl | Cyclopropyl |
| 2094 | 4 | naphthylen-2-yl | Cyclobutyl |
| 2095 | 4 | naphthylen-2-yl | Cyclopentyl |
| 2096 | 4 | naphthylen-2-yl | Cyclohexyl |
| 2097 | 4 | naphthylen-2-yl | 3-pyridyl |
| 2098 | 4 | naphthylen-2-yl | 1-methyl-1H-pyrazol-4-yl |
| 2099 | 4 | naphthylen-2-yl | 1H-imidazol-4-yl |
| 2100 | 4 | naphthylen-2-yl | 2-furanyl |

Exemplary embodiments include compounds having the formula (XXXIX)

(XXXIX)

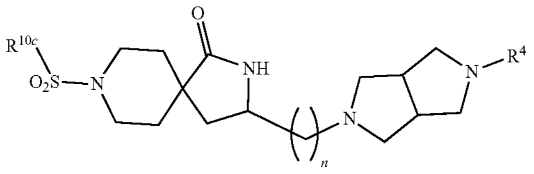

or a pharmaceutically acceptable salt form thereof defined herein below in Table 32.

TABLE 32

| Entry | n | $R^4$ | $R^{10c}$ |
|---|---|---|---|
| 1 | 1 | 4-$CH_3$-phenyl | Ethyl |
| 2 | 1 | 4-$CH_3$-phenyl | n-propyl |
| 3 | 1 | 4-$CH_3$-phenyl | Isopropyl |
| 4 | 1 | 4-$CH_3$-phenyl | —$CH_2CH(CH_3)_2$ |
| 5 | 1 | 4-$CH_3$-phenyl | $CF_3$ |
| 6 | 1 | 4-$CH_3$-phenyl | —$CH_2CF_3$ |
| 7 | 1 | 4-$CH_3$-phenyl | —$CH_2CH_2CF_3$ |
| 8 | 1 | 4-$CH_3$-phenyl | Cyclopropyl |
| 9 | 1 | 4-$CH_3$-phenyl | Cyclobutyl |
| 10 | 1 | 4-$CH_3$-phenyl | Cyclopentyl |
| 11 | 1 | 4-$CH_3$-phenyl | cyclohexyl |
| 12 | 1 | 4-$CH_3$-phenyl | 3-pyridyl |
| 13 | 1 | 4-$CH_3$-phenyl | 1-methyl-1H-pyrazol-4-yl |
| 14 | 1 | 4-$CH_3$-phenyl | 1H-imidazol-4-yl |
| 15 | 1 | 4-$CH_3$-phenyl | 2-furanyl |
| 16 | 1 | 3-$CH_3$-phenyl | ethyl |
| 17 | 1 | 3-$CH_3$-phenyl | n-propyl |
| 18 | 1 | 3-$CH_3$-phenyl | isopropyl |
| 19 | 1 | 3-$CH_3$-phenyl | —$CH_2CH(CH_3)_2$ |
| 20 | 1 | 3-$CH_3$-phenyl | $CF_3$ |
| 21 | 1 | 3-$CH_3$-phenyl | —$CH_2CF_3$ |
| 22 | 1 | 3-$CH_3$-phenyl | —$CH_2CH_2CF_3$ |
| 23 | 1 | 3-$CH_3$-phenyl | cyclopropyl |
| 24 | 1 | 3-$CH_3$-phenyl | Cyclobutyl |
| 25 | 1 | 3-$CH_3$-phenyl | cyclopentyl |
| 26 | 1 | 3-$CH_3$-phenyl | cyclohexyl |
| 27 | 1 | 3-$CH_3$-phenyl | 3-pyridyl |
| 28 | 1 | 3-$CH_3$-phenyl | 1-methyl-1H-pyrazol-4-yl |
| 29 | 1 | 3-$CH_3$-phenyl | 1H-imidazol-4-yl |
| 30 | 1 | 3-$CH_3$-phenyl | 2-furanyl |
| 31 | 1 | 3-OH-Phenyl | ethyl |
| 32 | 1 | 3-OH-Phenyl | n-propyl |
| 33 | 1 | 3-OH-Phenyl | isopropyl |
| 34 | 1 | 3-OH-Phenyl | —$CH_2CH(CH_3)_2$ |
| 35 | 1 | 3-OH-Phenyl | $CF_3$ |
| 36 | 1 | 3-OH-Phenyl | —$CH_2CF_3$ |
| 37 | 1 | 3-OH-Phenyl | —$CH_2CH_2CF_3$ |
| 38 | 1 | 3-OH-Phenyl | cyclopropyl |
| 39 | 1 | 3-OH-Phenyl | Cyclobutyl |
| 40 | 1 | 3-OH-Phenyl | cyclopentyl |
| 41 | 1 | 3-OH-Phenyl | cyclohexyl |
| 42 | 1 | 3-OH-Phenyl | 3-pyridyl |
| 43 | 1 | 3-OH-Phenyl | 1-methyl-1H-pyrazol-4-yl |
| 44 | 1 | 3-OH-Phenyl | 1H-imidazol-4-yl |
| 45 | 1 | 3-OH-Phenyl | 2-furanyl |
| 46 | 1 | 4-OMe-Phenyl | ethyl |
| 47 | 1 | 4-OMe-Phenyl | n-propyl |
| 48 | 1 | 4-OMe-Phenyl | isopropyl |
| 49 | 1 | 4-OMe-Phenyl | —$CH_2CH(CH_3)_2$ |
| 50 | 1 | 4-OMe-Phenyl | $CF_3$ |
| 51 | 1 | 4-OMe-Phenyl | —$CH_2CF_3$ |
| 52 | 1 | 4-OMe-Phenyl | —$CH_2CH_2CF_3$ |
| 53 | 1 | 4-OMe-Phenyl | cyclopropyl |
| 54 | 1 | 4-OMe-Phenyl | Cyclobutyl |
| 55 | 1 | 4-OMe-Phenyl | cyclopentyl |
| 56 | 1 | 4-OMe-Phenyl | cyclohexyl |
| 57 | 1 | 4-OMe-Phenyl | 3-pyridyl |
| 58 | 1 | 4-OMe-Phenyl | 1-methyl-1H-pyrazol-4-yl |
| 59 | 1 | 4-OMe-Phenyl | 1H-imidazol-4-yl |
| 60 | 1 | 4-OMe-Phenyl | 2-furanyl |
| 61 | 1 | 2-OMe-Phenyl | ethyl |

TABLE 32-continued

| Entry | n | $R^4$ | $R^{10c}$ |
|---|---|---|---|
| 62 | 1 | 2-OMe-Phenyl | n-propyl |
| 63 | 1 | 2-OMe-Phenyl | isopropyl |
| 64 | 1 | 2-OMe-Phenyl | —$CH_2CH(CH_3)_2$ |
| 65 | 1 | 2-OMe-Phenyl | $CF_3$ |
| 66 | 1 | 2-OMe-Phenyl | —$CH_2CF_3$ |
| 67 | 1 | 2-OMe-Phenyl | —$CH_2CH_2CF_3$ |
| 68 | 1 | 2-OMe-Phenyl | cyclopropyl |
| 69 | 1 | 2-OMe-Phenyl | Cyclobutyl |
| 70 | 1 | 2-OMe-Phenyl | cyclopentyl |
| 71 | 1 | 2-OMe-Phenyl | cyclohexyl |
| 72 | 1 | 2-OMe-Phenyl | 3-pyridyl |
| 73 | 1 | 2-OMe-Phenyl | 1-methyl-1H-pyrazol-4-yl |
| 74 | 1 | 2-OMe-Phenyl | 1H-imidazol-4-yl |
| 75 | 1 | 2-OMe-Phenyl | 2-furanyl |
| 76 | 1 | 3-CN-Phenyl | ethyl |
| 77 | 1 | 3-CN-Phenyl | n-propyl |
| 78 | 1 | 3-CN-Phenyl | isopropyl |
| 79 | 1 | 3-CN-Phenyl | —$CH_2CH(CH_3)_2$ |
| 80 | 1 | 3-CN-Phenyl | $CF_3$ |
| 81 | 1 | 3-CN-Phenyl | —$CH_2CF_3$ |
| 82 | 1 | 3-CN-Phenyl | —$CH_2CH_2CF_3$ |
| 83 | 1 | 3-CN-Phenyl | cyclopropyl |
| 84 | 1 | 3-CN-Phenyl | Cyclobutyl |
| 85 | 1 | 3-CN-Phenyl | cyclopentyl |
| 86 | 1 | 3-CN-Phenyl | cyclohexyl |
| 87 | 1 | 3-CN-Phenyl | 3-pyridyl |
| 88 | 1 | 3-CN-Phenyl | 1-methyl-1H-pyrazol-4-yl |
| 89 | 1 | 3-CN-Phenyl | 1H-imidazol-4-yl |
| 90 | 1 | 3-CN-Phenyl | 2-furanyl |
| 91 | 1 | 2-F-Phenyl | ethyl |
| 92 | 1 | 2-F-Phenyl | n-propyl |
| 93 | 1 | 2-F-Phenyl | isopropyl |
| 94 | 1 | 2-F-Phenyl | —$CH_2CH(CH_3)_2$ |
| 95 | 1 | 2-F-Phenyl | $CF_3$ |
| 96 | 1 | 2-F-Phenyl | —$CH_2CF_3$ |
| 97 | 1 | 2-F-Phenyl | —$CH_2CH_2CF_3$ |
| 98 | 1 | 2-F-Phenyl | cyclopropyl |
| 99 | 1 | 2-F-Phenyl | Cyclobutyl |
| 100 | 1 | 2-F-Phenyl | cyclopentyl |
| 101 | 1 | 2-F-Phenyl | cyclohexyl |
| 102 | 1 | 2-F-Phenyl | 3-pyridyl |
| 103 | 1 | 2-F-Phenyl | 1-methyl-1H-pyrazol-4-yl |
| 104 | 1 | 2-F-Phenyl | 1H-imidazol-4-yl |
| 105 | 1 | 2-F-Phenyl | 2-furanyl |
| 106 | 1 | 4-F-Phenyl | ethyl |
| 107 | 1 | 4-F-Phenyl | n-propyl |
| 108 | 1 | 4-F-Phenyl | isopropyl |
| 109 | 1 | 4-F-Phenyl | —$CH_2CH(CH_3)_2$ |
| 110 | 1 | 4-F-Phenyl | $CF_3$ |
| 111 | 1 | 4-F-Phenyl | —$CH_2CF_3$ |
| 112 | 1 | 4-F-Phenyl | —$CH_2CH_2CF_3$ |
| 113 | 1 | 4-F-Phenyl | cyclopropyl |
| 114 | 1 | 4-F-Phenyl | Cyclobutyl |
| 115 | 1 | 4-F-Phenyl | cyclopentyl |
| 116 | 1 | 4-F-Phenyl | cyclohexyl |
| 117 | 1 | 4-F-Phenyl | 3-pyridyl |
| 118 | 1 | 4-F-Phenyl | 1-methyl-1H-pyrazol-4-yl |
| 119 | 1 | 4-F-Phenyl | 1H-imidazol-4-yl |
| 120 | 1 | 4-F-Phenyl | 2-furanyl |
| 121 | 1 | 3-Cl-Phenyl | ethyl |
| 122 | 1 | 3-Cl-Phenyl | n-propyl |
| 123 | 1 | 3-Cl-Phenyl | isopropyl |
| 124 | 1 | 3-Cl-Phenyl | —$CH_2CH(CH_3)_2$ |
| 125 | 1 | 3-Cl-Phenyl | $CF_3$ |
| 126 | 1 | 3-Cl-Phenyl | —$CH_2CF_3$ |
| 127 | 1 | 3-Cl-Phenyl | —$CH_2CH_2CF_3$ |
| 128 | 1 | 3-Cl-Phenyl | cyclopropyl |
| 129 | 1 | 3-Cl-Phenyl | Cyclobutyl |
| 130 | 1 | 3-Cl-Phenyl | cyclopentyl |
| 131 | 1 | 3-Cl-Phenyl | cyclohexyl |
| 132 | 1 | 3-Cl-Phenyl | 3-pyridyl |
| 133 | 1 | 3-Cl-Phenyl | 1-methyl-1H-pyrazol-4-yl |
| 134 | 1 | 3-Cl-Phenyl | 1H-imidazol-4-yl |
| 135 | 1 | 3-Cl-Phenyl | 2-furanyl |
| 136 | 1 | 2-Br-Phenyl | ethyl |
| 137 | 1 | 2-Br-Phenyl | n-propyl |
| 138 | 1 | 2-Br-Phenyl | isopropyl |
| 139 | 1 | 2-Br-Phenyl | —$CH_2CH(CH_3)_2$ |

TABLE 32-continued

| Entry | n | $R^4$ | $R^{10c}$ |
|---|---|---|---|
| 140 | 1 | 2-Br-Phenyl | $CF_3$ |
| 141 | 1 | 2-Br-Phenyl | $—CH_2CF_3$ |
| 142 | 1 | 2-Br-Phenyl | $—CH_2CH_2CF_3$ |
| 143 | 1 | 2-Br-Phenyl | cyclopropyl |
| 144 | 1 | 2-Br-Phenyl | Cyclobutyl |
| 145 | 1 | 2-Br-Phenyl | cyclopentyl |
| 146 | 1 | 2-Br-Phenyl | cyclohexyl |
| 147 | 1 | 2-Br-Phenyl | 3-pyridyl |
| 148 | 1 | 2-Br-Phenyl | 1-methyl-1H-pyrazol-4-yl |
| 149 | 1 | 2-Br-Phenyl | 1H-imidazol-4-yl |
| 150 | 1 | 2-Br-Phenyl | 2-furanyl |
| 151 | 1 | 4-Br-Phenyl | ethyl |
| 152 | 1 | 4-Br-Phenyl | n-propyl |
| 153 | 1 | 4-Br-Phenyl | isopropyl |
| 154 | 1 | 4-Br-Phenyl | $—CH_2CH(CH_3)_2$ |
| 155 | 1 | 4-Br-Phenyl | $CF_3$ |
| 156 | 1 | 4-Br-Phenyl | $—CH_2CF_3$ |
| 157 | 1 | 4-Br-Phenyl | $—CH_2CH_2CF_3$ |
| 158 | 1 | 4-Br-Phenyl | cyclopropyl |
| 159 | 1 | 4-Br-Phenyl | Cyclobutyl |
| 160 | 1 | 4-Br-Phenyl | cyclopentyl |
| 161 | 1 | 4-Br-Phenyl | cyclohexyl |
| 162 | 1 | 4-Br-Phenyl | 3-pyridyl |
| 163 | 1 | 4-Br-Phenyl | 1-methyl-1H-pyrazol-4-yl |
| 164 | 1 | 4-Br-Phenyl | 1H-imidazol-4-yl |
| 165 | 1 | 4-Br-Phenyl | 2-furanyl |
| 166 | 1 | $3-CF_3$-Phenyl | ethyl |
| 167 | 1 | $3-CF_3$-Phenyl | n-propyl |
| 168 | 1 | $3-CF_3$-Phenyl | isopropyl |
| 169 | 1 | $3-CF_3$-Phenyl | $—CH_2CH(CH_3)_2$ |
| 170 | 1 | $3-CF_3$-Phenyl | $CF_3$ |
| 171 | 1 | $3-CF_3$-Phenyl | $—CH_2CF_3$ |
| 172 | 1 | $3-CF_3$-Phenyl | $—CH_2CH_2CF_3$ |
| 173 | 1 | $3-CF_3$-Phenyl | cyclopropyl |
| 174 | 1 | $3-CF_3$-Phenyl | Cyclobutyl |
| 175 | 1 | $3-CF_3$-Phenyl | cyclopentyl |
| 176 | 1 | $3-CF_3$-Phenyl | cyclohexyl |
| 177 | 1 | $3-CF_3$-Phenyl | 3-pyridyl |
| 178 | 1 | $3-CF_3$-Phenyl | 1-methyl-1H-pyrazol-4-yl |
| 179 | 1 | $3-CF_3$-Phenyl | 1H-imidazol-4-yl |
| 180 | 1 | $3-CF_3$-Phenyl | 2-furanyl |
| 181 | 1 | 2-iPr-Phenyl | ethyl |
| 182 | 1 | 2-iPr-Phenyl | n-propyl |
| 183 | 1 | 2-iPr-Phenyl | isopropyl |
| 184 | 1 | 2-iPr-Phenyl | $—CH_2CH(CH_3)_2$ |
| 185 | 1 | 2-iPr-Phenyl | $CF_3$ |
| 186 | 1 | 2-iPr-Phenyl | $—CH_2CF_3$ |
| 187 | 1 | 2-iPr-Phenyl | $—CH_2CH_2CF_3$ |
| 188 | 1 | 2-iPr-Phenyl | cyclopropyl |
| 189 | 1 | 2-iPr-Phenyl | Cyclobutyl |
| 190 | 1 | 2-iPr-Phenyl | cyclopentyl |
| 191 | 1 | 2-iPr-Phenyl | cyclohexyl |
| 192 | 1 | 2-iPr-Phenyl | 3-pyridyl |
| 193 | 1 | 2-iPr-Phenyl | 1-methyl-1H-pyrazol-4-yl |
| 194 | 1 | 2-iPr-Phenyl | 1H-imidazol-4-yl |
| 195 | 1 | 2-iPr-Phenyl | 2-furanyl |
| 196 | 1 | 4-iPr-Phenyl | ethyl |
| 197 | 1 | 4-iPr-Phenyl | n-propyl |
| 198 | 1 | 4-iPr-Phenyl | isopropyl |
| 199 | 1 | 4-iPr-Phenyl | $—CH_2CH(CH_3)_2$ |
| 200 | 1 | 4-iPr-Phenyl | $CF_3$ |
| 201 | 1 | 4-iPr-Phenyl | $—CH_2CF_3$ |
| 202 | 1 | 4-iPr-Phenyl | $—CH_2CH_2CF_3$ |
| 203 | 1 | 4-iPr-Phenyl | cyclopropyl |
| 204 | 1 | 4-iPr-Phenyl | Cyclobutyl |
| 205 | 1 | 4-iPr-Phenyl | cyclopentyl |
| 206 | 1 | 4-iPr-Phenyl | cyclohexyl |
| 207 | 1 | 4-iPr-Phenyl | 3-pyridyl |
| 208 | 1 | 4-iPr-Phenyl | 1-methyl-1H-pyrazol-4-yl |
| 209 | 1 | 4-iPr-Phenyl | 1H-imidazol-4-yl |
| 210 | 1 | 4-iPr-Phenyl | 2-furanyl |
| 211 | 1 | 3-morpholino-phenyl | ethyl |
| 212 | 1 | 3-morpholino-phenyl | n-propyl |
| 213 | 1 | 3-morpholino-phenyl | isopropyl |
| 214 | 1 | 3-morpholino-phenyl | $—CH_2CH(CH_3)_2$ |
| 215 | 1 | 3-morpholino-phenyl | $CF_3$ |
| 216 | 1 | 3-morpholino-phenyl | $—CH_2CF_3$ |
| 217 | 1 | 3-morpholino-phenyl | $—CH_2CH_2CF_3$ |
| 218 | 1 | 3-morpholino-phenyl | cyclopropyl |
| 219 | 1 | 3-morpholino-phenyl | Cyclobutyl |
| 220 | 1 | 3-morpholino-phenyl | cyclopentyl |
| 221 | 1 | 3-morpholino-phenyl | cyclohexyl |
| 222 | 1 | 3-morpholino-phenyl | 3-pyridyl |
| 223 | 1 | 3-morpholino-phenyl | 1-methyl-1H-pyrazol-4-yl |
| 224 | 1 | 3-morpholino-phenyl | 1H-imidazol-4-yl |
| 225 | 1 | 3-morpholino-phenyl | 2-furanyl |
| 226 | 1 | 4-cyano-2-morpholino-phenyl | ethyl |
| 227 | 1 | 4-cyano-2-morpholino-phenyl | n-propyl |
| 228 | 1 | 4-cyano-2-morpholino-phenyl | isopropyl |
| 229 | 1 | 4-cyano-2-morpholino-phenyl | $—CH_2CH(CH_3)_2$ |
| 230 | 1 | 4-cyano-2-morpholino-phenyl | $CF_3$ |
| 231 | 1 | 4-cyano-2-morpholino-phenyl | $—CH_2CF_3$ |
| 232 | 1 | 4-cyano-2-morpholino-phenyl | $—CH_2CH_2CF_3$ |
| 233 | 1 | 4-cyano-2-morpholino-phenyl | cyclopropyl |
| 234 | 1 | 4-cyano-2-morpholino-phenyl | Cyclobutyl |
| 235 | 1 | 4-cyano-2-morpholino-phenyl | cyclopentyl |
| 236 | 1 | 4-cyano-2-morpholino-phenyl | cyclohexyl |
| 237 | 1 | 4-cyano-2-morpholino-phenyl | 3-pyridyl |
| 238 | 1 | 4-cyano-2-morpholino-phenyl | 1-methyl-1H-pyrazol-4-yl |
| 239 | 1 | 4-cyano-2-morpholino-phenyl | 1H-imidazol-4-yl |
| 240 | 1 | 4-cyano-2-morpholino-phenyl | 2-furanyl |
| 241 | 1 | 4-hydroxy-2-morpholino-phenyl | ethyl |
| 242 | 1 | 4-hydroxy-2-morpholino-phenyl | n-propyl |
| 243 | 1 | 4-hydroxy-2-morpholino-phenyl | isopropyl |
| 244 | 1 | 4-hydroxy-2-morpholino-phenyl | $—CH_2CH(CH_3)_2$ |
| 245 | 1 | 4-hydroxy-2-morpholino-phenyl | $CF_3$ |
| 246 | 1 | 4-hydroxy-2-morpholino-phenyl | $—CH_2CF_3$ |
| 247 | 1 | 4-hydroxy-2-morpholino-phenyl | $—CH_2CH_2CF_3$ |
| 248 | 1 | 4-hydroxy-2-morpholino-phenyl | cyclopropyl |
| 249 | 1 | 4-hydroxy-2-morpholino-phenyl | Cyclobutyl |
| 250 | 1 | 4-hydroxy-2-morpholino-phenyl | cyclopentyl |
| 251 | 1 | 4-hydroxy-2-morpholino-phenyl | cyclohexyl |
| 252 | 1 | 4-hydroxy-2-morpholino-phenyl | 3-pyridyl |
| 253 | 1 | 4-hydroxy-2-morpholino-phenyl | 1-methyl-1H-pyrazol-4-yl |
| 254 | 1 | 4-hydroxy-2-morpholino-phenyl | 1H-imidazol-4-yl |
| 255 | 1 | 4-hydroxy-2-morpholino-phenyl | 2-furanyl |
| 256 | 1 | $2-CH_3$-phenyl | Ethyl |
| 257 | 1 | $2-CH_3$-phenyl | n-propyl |
| 258 | 1 | $2-CH_3$-phenyl | Isopropyl |
| 259 | 1 | $2-CH_3$-phenyl | $—CH_2CH(CH_3)_2$ |
| 260 | 1 | $2-CH_3$-phenyl | $CF_3$ |
| 261 | 1 | $2-CH_3$-phenyl | $—CH_2CF_3$ |
| 262 | 1 | $2-CH_3$-phenyl | $—CH_2CH_2CF_3$ |
| 263 | 1 | $2-CH_3$-phenyl | cyclopropyl |
| 264 | 1 | $2-CH_3$-phenyl | Cyclobutyl |
| 265 | 1 | $2-CH_3$-phenyl | cyclopentyl |
| 266 | 1 | $2-CH_3$-phenyl | cyclohexyl |
| 267 | 1 | $2-CH_3$-phenyl | 3-pyridyl |
| 268 | 1 | $2-CH_3$-phenyl | 1-methyl-1H-pyrazol-4-yl |
| 269 | 1 | $2-CH_3$-phenyl | 1H-imidazol-4-yl |
| 270 | 1 | $2-CH_3$-phenyl | 2-furanyl |
| 271 | 1 | 4-OH-Phenyl | Ethyl |
| 272 | 1 | 4-OH-Phenyl | n-propyl |
| 273 | 1 | 4-OH-Phenyl | Isopropyl |
| 274 | 1 | 4-OH-Phenyl | $—CH_2CH(CH_3)_2$ |
| 275 | 1 | 4-OH-Phenyl | $CF_3$ |
| 276 | 1 | 4-OH-Phenyl | $—CH_2CF_3$ |
| 277 | 1 | 4-OH-Phenyl | $—CH_2CH_2CF_3$ |
| 278 | 1 | 4-OH-Phenyl | cyclopropyl |
| 279 | 1 | 4-OH-Phenyl | Cyclobutyl |
| 280 | 1 | 4-OH-Phenyl | cyclopentyl |
| 281 | 1 | 4-OH-Phenyl | cyclohexyl |
| 282 | 1 | 4-OH-Phenyl | 3-pyridyl |
| 283 | 1 | 4-OH-Phenyl | 1-methyl-1H-pyrazol-4-yl |
| 284 | 1 | 4-OH-Phenyl | 1H-imidazol-4-yl |
| 285 | 1 | 4-OH-Phenyl | 2-furanyl |
| 286 | 1 | 2-OH-Phenyl | Ethyl |
| 287 | 1 | 2-OH-Phenyl | n-propyl |
| 288 | 1 | 2-OH-Phenyl | Isopropyl |
| 289 | 1 | 2-OH-Phenyl | $—CH_2CH(CH_3)_2$ |
| 290 | 1 | 2-OH-Phenyl | $CF_3$ |
| 291 | 1 | 2-OH-Phenyl | $—CH_2CF_3$ |
| 292 | 1 | 2-OH-Phenyl | $—CH_2CH_2CF_3$ |
| 293 | 1 | 2-OH-Phenyl | cyclopropyl |
| 294 | 1 | 2-OH-Phenyl | Cyclobutyl |
| 295 | 1 | 2-OH-Phenyl | cyclopentyl |

TABLE 32-continued

| Entry | n | $R^4$ | $R^{10c}$ |
|---|---|---|---|
| 296 | 1 | 2-OH-Phenyl | cyclohexyl |
| 297 | 1 | 2-OH-Phenyl | 3-pyridyl |
| 298 | 1 | 2-OH-Phenyl | 1-methyl-1H-pyrazol-4-yl |
| 299 | 1 | 2-OH-Phenyl | 1H-imidazol-4-yl |
| 300 | 1 | 2-OH-Phenyl | 2-furanyl |
| 301 | 1 | 3-OMe-Phenyl | Ethyl |
| 302 | 1 | 3-OMe-Phenyl | n-propyl |
| 303 | 1 | 3-OMe-Phenyl | Isopropyl |
| 304 | 1 | 3-OMe-Phenyl | $—CH_2CH(CH_3)_2$ |
| 305 | 1 | 3-OMe-Phenyl | $CF_3$ |
| 306 | 1 | 3-OMe-Phenyl | $—CH_2CF_3$ |
| 307 | 1 | 3-OMe-Phenyl | $—CH_2CH_2CF_3$ |
| 308 | 1 | 3-OMe-Phenyl | cyclopropyl |
| 309 | 1 | 3-OMe-Phenyl | Cyclobutyl |
| 310 | 1 | 3-OMe-Phenyl | cyclopentyl |
| 311 | 1 | 3-OMe-Phenyl | cyclohexyl |
| 312 | 1 | 3-OMe-Phenyl | 3-pyridyl |
| 313 | 1 | 3-OMe-Phenyl | 1-methyl-1H-pyrazol-4-yl |
| 314 | 1 | 3-OMe-Phenyl | 1H-imidazol-4-yl |
| 315 | 1 | 3-OMe-Phenyl | 2-furanyl |
| 316 | 1 | 4-CN-Phenyl | Ethyl |
| 317 | 1 | 4-CN-Phenyl | n-propyl |
| 318 | 1 | 4-CN-Phenyl | Isopropyl |
| 319 | 1 | 4-CN-Phenyl | $—CH_2CH(CH_3)_2$ |
| 320 | 1 | 4-CN-Phenyl | $CF_3$ |
| 321 | 1 | 4-CN-Phenyl | $—CH_2CF_3$ |
| 322 | 1 | 4-CN-Phenyl | $—CH_2CH_2CF_3$ |
| 323 | 1 | 4-CN-Phenyl | cyclopropyl |
| 324 | 1 | 4-CN-Phenyl | Cyclobutyl |
| 325 | 1 | 4-CN-Phenyl | cyclopentyl |
| 326 | 1 | 4-CN-Phenyl | cyclohexyl |
| 327 | 1 | 4-CN-Phenyl | 3-pyridyl |
| 328 | 1 | 4-CN-Phenyl | 1-methyl-1H-pyrazol-4-yl |
| 329 | 1 | 4-CN-Phenyl | 1H-imidazol-4-yl |
| 330 | 1 | 4-CN-Phenyl | 2-furanyl |
| 331 | 1 | 2-CN-Phenyl | Ethyl |
| 332 | 1 | 2-CN-Phenyl | n-propyl |
| 333 | 1 | 2-CN-Phenyl | Isopropyl |
| 334 | 1 | 2-CN-Phenyl | $—CH_2CH(CH_3)_2$ |
| 335 | 1 | 2-CN-Phenyl | $CF_3$ |
| 336 | 1 | 2-CN-Phenyl | $—CH_2CF_3$ |
| 337 | 1 | 2-CN-Phenyl | $—CH_2CH_2CF_3$ |
| 338 | 1 | 2-CN-Phenyl | cyclopropyl |
| 339 | 1 | 2-CN-Phenyl | Cyclobutyl |
| 340 | 1 | 2-CN-Phenyl | cyclopentyl |
| 341 | 1 | 2-CN-Phenyl | cyclohexyl |
| 342 | 1 | 2-CN-Phenyl | 3-pyridyl |
| 343 | 1 | 2-CN-Phenyl | 1-methyl-1H-pyrazol-4-yl |
| 344 | 1 | 2-CN-Phenyl | 1H-imidazol-4-yl |
| 345 | 1 | 2-CN-Phenyl | 2-furanyl |
| 346 | 1 | 3-F-Phenyl | Ethyl |
| 347 | 1 | 3-F-Phenyl | n-propyl |
| 348 | 1 | 3-F-Phenyl | Isopropyl |
| 349 | 1 | 3-F-Phenyl | $—CH_2CH(CH_3)_2$ |
| 350 | 1 | 3-F-Phenyl | $CF_3$ |
| 351 | 1 | 3-F-Phenyl | $—CH_2CF_3$ |
| 352 | 1 | 3-F-Phenyl | $—CH_2CH_2CF_3$ |
| 353 | 1 | 3-F-Phenyl | cyclopropyl |
| 354 | 1 | 3-F-Phenyl | Cyclobutyl |
| 355 | 1 | 3-F-Phenyl | cyclopentyl |
| 356 | 1 | 3-F-Phenyl | cyclohexyl |
| 357 | 1 | 3-F-Phenyl | 3-pyridyl |
| 358 | 1 | 3-F-Phenyl | 1-methyl-1H-pyrazol-4-yl |
| 359 | 1 | 3-F-Phenyl | 1H-imidazol-4-yl |
| 360 | 1 | 3-F-Phenyl | 2-furanyl |
| 361 | 1 | 2-Cl-Phenyl | Ethyl |
| 362 | 1 | 2-Cl-Phenyl | n-propyl |
| 363 | 1 | 2-Cl-Phenyl | Isopropyl |
| 364 | 1 | 2-Cl-Phenyl | $—CH_2CH(CH_3)_2$ |
| 365 | 1 | 2-Cl-Phenyl | $CF_3$ |
| 366 | 1 | 2-Cl-Phenyl | $—CH_2CF_3$ |
| 367 | 1 | 2-Cl-Phenyl | $—CH_2CH_2CF_3$ |
| 368 | 1 | 2-Cl-Phenyl | cyclopropyl |
| 369 | 1 | 2-Cl-Phenyl | Cyclobutyl |
| 370 | 1 | 2-Cl-Phenyl | cyclopentyl |
| 371 | 1 | 2-Cl-Phenyl | cyclohexyl |
| 372 | 1 | 2-Cl-Phenyl | 3-pyridyl |
| 373 | 1 | 2-Cl-Phenyl | 1-methyl-1H-pyrazol-4-yl |

TABLE 32-continued

| Entry | n | $R^4$ | $R^{10c}$ |
|---|---|---|---|
| 374 | 1 | 2-Cl-Phenyl | 1H-imidazol-4-yl |
| 375 | 1 | 2-Cl-Phenyl | 2-furanyl |
| 376 | 1 | 4-Cl-Phenyl | Ethyl |
| 377 | 1 | 4-Cl-Phenyl | n-propyl |
| 378 | 1 | 4-Cl-Phenyl | Isopropyl |
| 379 | 1 | 4-Cl-Phenyl | $—CH_2CH(CH_3)_2$ |
| 380 | 1 | 4-Cl-Phenyl | $CF_3$ |
| 381 | 1 | 4-Cl-Phenyl | $—CH_2CF_3$ |
| 382 | 1 | 4-Cl-Phenyl | $—CH_2CH_2CF_3$ |
| 383 | 1 | 4-Cl-Phenyl | cyclopropyl |
| 384 | 1 | 4-Cl-Phenyl | Cyclobutyl |
| 385 | 1 | 4-Cl-Phenyl | cyclopentyl |
| 386 | 1 | 4-Cl-Phenyl | cyclohexyl |
| 387 | 1 | 4-Cl-Phenyl | 3-pyridyl |
| 388 | 1 | 4-Cl-Phenyl | 1-methyl-1H-pyrazol-4-yl |
| 389 | 1 | 4-Cl-Phenyl | 1H-imidazol-4-yl |
| 390 | 1 | 4-Cl-Phenyl | 2-furanyl |
| 391 | 1 | 3-Br-Phenyl | Ethyl |
| 392 | 1 | 3-Br-Phenyl | n-propyl |
| 393 | 1 | 3-Br-Phenyl | Isopropyl |
| 394 | 1 | 3-Br-Phenyl | $—CH_2CH(CH_3)_2$ |
| 395 | 1 | 3-Br-Phenyl | $CF_3$ |
| 396 | 1 | 3-Br-Phenyl | $—CH_2CF_3$ |
| 397 | 1 | 3-Br-Phenyl | $—CH_2CH_2CF_3$ |
| 398 | 1 | 3-Br-Phenyl | cyclopropyl |
| 399 | 1 | 3-Br-Phenyl | Cyclobutyl |
| 400 | 1 | 3-Br-Phenyl | cyclopentyl |
| 401 | 1 | 3-Br-Phenyl | cyclohexyl |
| 402 | 1 | 3-Br-Phenyl | 3-pyridyl |
| 403 | 1 | 3-Br-Phenyl | 1-methyl-1H-pyrazol-4-yl |
| 404 | 1 | 3-Br-Phenyl | 1H-imidazol-4-yl |
| 405 | 1 | 3-Br-Phenyl | 2-furanyl |
| 406 | 1 | $2-CF_3$-Phenyl | Ethyl |
| 407 | 1 | $2-CF_3$-Phenyl | n-propyl |
| 408 | 1 | $2-CF_3$-Phenyl | Isopropyl |
| 409 | 1 | $2-CF_3$-Phenyl | $—CH_2CH(CH_3)_2$ |
| 410 | 1 | $2-CF_3$-Phenyl | $CF_3$ |
| 411 | 1 | $2-CF_3$-Phenyl | $—CH_2CF_3$ |
| 412 | 1 | $2-CF_3$-Phenyl | $—CH_2CH_2CF_3$ |
| 413 | 1 | $2-CF_3$-Phenyl | cyclopropyl |
| 414 | 1 | $2-CF_3$-Phenyl | Cyclobutyl |
| 415 | 1 | $2-CF_3$-Phenyl | cyclopentyl |
| 416 | 1 | $2-CF_3$-Phenyl | cyclohexyl |
| 417 | 1 | $2-CF_3$-Phenyl | 3-pyridyl |
| 418 | 1 | $2-CF_3$-Phenyl | 1-methyl-1H-pyrazol-4-yl |
| 419 | 1 | $2-CF_3$-Phenyl | 1H-imidazol-4-yl |
| 420 | 1 | $2-CF_3$-Phenyl | 2-furanyl |
| 421 | 1 | $4-CF_3$-Phenyl | Ethyl |
| 422 | 1 | $4-CF_3$-Phenyl | n-propyl |
| 423 | 1 | $4-CF_3$-Phenyl | Isopropyl |
| 424 | 1 | $4-CF_3$-Phenyl | $—CH_2CH(CH_3)_2$ |
| 425 | 1 | $4-CF_3$-Phenyl | $CF_3$ |
| 426 | 1 | $4-CF_3$-Phenyl | $—CH_2CF_3$ |
| 427 | 1 | $4-CF_3$-Phenyl | $—CH_2CH_2CF_3$ |
| 428 | 1 | $4-CF_3$-Phenyl | cyclopropyl |
| 429 | 1 | $4-CF_3$-Phenyl | Cyclobutyl |
| 430 | 1 | $4-CF_3$-Phenyl | cyclopentyl |
| 431 | 1 | $4-CF_3$-Phenyl | cyclohexyl |
| 432 | 1 | $4-CF_3$-Phenyl | 3-pyridyl |
| 433 | 1 | $4-CF_3$-Phenyl | 1-methyl-1H-pyrazol-4-yl |
| 434 | 1 | $4-CF_3$-Phenyl | 1H-imidazol-4-yl |
| 435 | 1 | $4-CF_3$-Phenyl | 2-furanyl |
| 436 | 1 | 3-iPr-Phenyl | Ethyl |
| 437 | 1 | 3-iPr-Phenyl | n-propyl |
| 438 | 1 | 3-iPr-Phenyl | Isopropyl |
| 439 | 1 | 3-iPr-Phenyl | $—CH_2CH(CH_3)_2$ |
| 440 | 1 | 3-iPr-Phenyl | $CF_3$ |
| 441 | 1 | 3-iPr-Phenyl | $—CH_2CF_3$ |
| 442 | 1 | 3-iPr-Phenyl | $—CH_2CH_2CF_3$ |
| 443 | 1 | 3-iPr-Phenyl | cyclopropyl |
| 444 | 1 | 3-iPr-Phenyl | Cyclobutyl |
| 445 | 1 | 3-iPr-Phenyl | cyclopentyl |
| 446 | 1 | 3-iPr-Phenyl | cyclohexyl |
| 447 | 1 | 3-iPr-Phenyl | 3-pyridyl |
| 448 | 1 | 3-iPr-Phenyl | 1-methyl-1H-pyrazol-4-yl |
| 449 | 1 | 3-iPr-Phenyl | 1H-imidazol-4-yl |
| 450 | 1 | 3-iPr-Phenyl | 2-furanyl |
| 451 | 1 | 2-morpholino-phenyl | Ethyl |

TABLE 32-continued

| Entry | n | $R^4$ | $R^{10c}$ |
|---|---|---|---|
| 452 | 1 | 2-morpholino-phenyl | n-propyl |
| 453 | 1 | 2-morpholino-phenyl | isopropyl |
| 454 | 1 | 2-morpholino-phenyl | $—CH_2CH(CH_3)_2$ |
| 455 | 1 | 2-morpholino-phenyl | $CF_3$ |
| 456 | 1 | 2-morpholino-phenyl | $—CH_2CF_3$ |
| 457 | 1 | 2-morpholino-phenyl | $—CH_2CH_2CF_3$ |
| 458 | 1 | 2-morpholino-phenyl | cyclopropyl |
| 459 | 1 | 2-morpholino-phenyl | Cyclobutyl |
| 460 | 1 | 2-morpholino-phenyl | cyclopentyl |
| 461 | 1 | 2-morpholino-phenyl | cyclohexyl |
| 462 | 1 | 2-morpholino-phenyl | 3-pyridyl |
| 463 | 1 | 2-morpholino-phenyl | 1-methyl-1H-pyrazol-4-yl |
| 464 | 1 | 2-morpholino-phenyl | 1H-imidazol-4-yl |
| 465 | 1 | 2-morpholino-phenyl | 2-furanyl |
| 466 | 1 | 4-morpholino-phenyl | ethyl |
| 467 | 1 | 4-morpholino-phenyl | n-propyl |
| 468 | 1 | 4-morpholino-phenyl | isopropyl |
| 469 | 1 | 4-morpholino-phenyl | $—CH_2CH(CH_3)_2$ |
| 470 | 1 | 4-morpholino-phenyl | $CF_3$ |
| 471 | 1 | 4-morpholino-phenyl | $—CH_2CF_3$ |
| 472 | 1 | 4-morpholino-phenyl | $—CH_2CH_2CF_3$ |
| 473 | 1 | 4-morpholino-phenyl | cyclopropyl |
| 474 | 1 | 4-morpholino-phenyl | Cyclobutyl |
| 475 | 1 | 4-morpholino-phenyl | cyclopentyl |
| 476 | 1 | 4-morpholino-phenyl | cyclohexyl |
| 477 | 1 | 4-morpholino-phenyl | 3-pyridyl |
| 478 | 1 | 4-morpholino-phenyl | 1-methyl-1H-pyrazol-4-yl |
| 479 | 1 | 4-morpholino-phenyl | 1H-imidazol-4-yl |
| 480 | 1 | 4-morpholino-phenyl | 2-furanyl |
| 481 | 1 | 4-methyl-2-morpholino-phenyl | ethyl |
| 482 | 1 | 4-methyl-2-morpholino-phenyl | n-propyl |
| 483 | 1 | 4-methyl-2-morpholino-phenyl | isopropyl |
| 484 | 1 | 4-methyl-2-morpholino-phenyl | $—CH_2CH(CH_3)_2$ |
| 485 | 1 | 4-methyl-2-morpholino-phenyl | $CF_3$ |
| 486 | 1 | 4-methyl-2-morpholino-phenyl | $—CH_2CF_3$ |
| 487 | 1 | 4-methyl-2-morpholino-phenyl | $—CH_2CH_2CF_3$ |
| 488 | 1 | 4-methyl-2-morpholino-phenyl | cyclopropyl |
| 489 | 1 | 4-methyl-2-morpholino-phenyl | Cyclobutyl |
| 490 | 1 | 4-methyl-2-morpholino-phenyl | cyclopentyl |
| 491 | 1 | 4-methyl-2-morpholino-phenyl | cyclohexyl |
| 492 | 1 | 4-methyl-2-morpholino-phenyl | 3-pyridyl |
| 493 | 1 | 4-methyl-2-morpholino-phenyl | 1-methyl-1H-pyrazol-4-yl |
| 494 | 1 | 4-methyl-2-morpholino-phenyl | 1H-imidazol-4-yl |
| 495 | 1 | 4-methyl-2-morpholino-phenyl | 2-furanyl |
| 496 | 2 | $4-CH_3$-phenyl | ethyl |
| 497 | 2 | $4-CH_3$-phenyl | n-propyl |
| 498 | 2 | $4-CH_3$-phenyl | isopropyl |
| 499 | 2 | $4-CH_3$-phenyl | $—CH_2CH(CH_3)_2$ |
| 500 | 2 | $4-CH_3$-phenyl | $CF_3$ |
| 501 | 2 | $4-CH_3$-phenyl | $—CH_2CF_3$ |
| 502 | 2 | $4-CH_3$-phenyl | $—CH_2CH_2CF_3$ |
| 503 | 2 | $4-CH_3$-phenyl | cyclopropyl |
| 504 | 2 | $4-CH_3$-phenyl | Cyclobutyl |
| 505 | 2 | $4-CH_3$-phenyl | cyclopentyl |
| 506 | 2 | $4-CH_3$-phenyl | cyclohexyl |
| 507 | 2 | $4-CH_3$-phenyl | 3-pyridyl |
| 508 | 2 | $4-CH_3$-phenyl | 1-methyl-1H-pyrazol-4-yl |
| 509 | 2 | $4-CH_3$-phenyl | 1H-imidazol-4-yl |
| 510 | 2 | $4-CH_3$-phenyl | 2-furanyl |
| 511 | 2 | $3-CH_3$-phenyl | ethyl |
| 512 | 2 | $3-CH_3$-phenyl | n-propyl |
| 513 | 2 | $3-CH_3$-phenyl | isopropyl |
| 514 | 2 | $3-CH_3$-phenyl | $—CH_2CH(CH_3)_2$ |
| 515 | 2 | $3-CH_3$-phenyl | $CF_3$ |
| 516 | 2 | $3-CH_3$-phenyl | $—CH_2CF_3$ |
| 517 | 2 | $3-CH_3$-phenyl | $—CH_2CH_2CF_3$ |
| 518 | 2 | $3-CH_3$-phenyl | cyclopropyl |
| 519 | 2 | $3-CH_3$-phenyl | Cyclobutyl |
| 520 | 2 | $3-CH_3$-phenyl | cyclopentyl |
| 521 | 2 | $3-CH_3$-phenyl | cyclohexyl |
| 522 | 2 | $3-CH_3$-phenyl | 3-pyridyl |
| 523 | 2 | $3-CH_3$-phenyl | 1-methyl-1H-pyrazol-4-yl |
| 524 | 2 | $3-CH_3$-phenyl | 1H-imidazol-4-yl |
| 525 | 2 | $3-CH_3$-phenyl | 2-furanyl |
| 526 | 2 | 3-OH-Phenyl | ethyl |
| 527 | 2 | 3-OH-Phenyl | n-propyl |
| 528 | 2 | 3-OH-Phenyl | isopropyl |
| 529 | 2 | 3-OH-Phenyl | $—CH_2CH(CH_3)_2$ |

TABLE 32-continued

| Entry | n | $R^4$ | $R^{10c}$ |
|---|---|---|---|
| 530 | 2 | 3-OH-Phenyl | $CF_3$ |
| 531 | 2 | 3-OH-Phenyl | $—CH_2CF_3$ |
| 532 | 2 | 3-OH-Phenyl | $—CH_2CH_2CF_3$ |
| 533 | 2 | 3-OH-Phenyl | cyclopropyl |
| 534 | 2 | 3-OH-Phenyl | Cyclobutyl |
| 535 | 2 | 3-OH-Phenyl | cyclopentyl |
| 536 | 2 | 3-OH-Phenyl | cyclohexyl |
| 537 | 2 | 3-OH-Phenyl | 3-pyridyl |
| 538 | 2 | 3-OH-Phenyl | 1-methyl-1H-pyrazol-4-yl |
| 539 | 2 | 3-OH-Phenyl | 1H-imidazol-4-yl |
| 540 | 2 | 3-OH-Phenyl | 2-furanyl |
| 541 | 2 | 4-OMe-Phenyl | ethyl |
| 542 | 2 | 4-OMe-Phenyl | n-propyl |
| 543 | 2 | 4-OMe-Phenyl | isopropyl |
| 544 | 2 | 4-OMe-Phenyl | $—CH_2CH(CH_3)_2$ |
| 545 | 2 | 4-OMe-Phenyl | $CF_3$ |
| 546 | 2 | 4-OMe-Phenyl | $—CH_2CF_3$ |
| 547 | 2 | 4-OMe-Phenyl | $—CH_2CH_2CF_3$ |
| 548 | 2 | 4-OMe-Phenyl | cyclopropyl |
| 549 | 2 | 4-OMe-Phenyl | Cyclobutyl |
| 550 | 2 | 4-OMe-Phenyl | cyclopentyl |
| 551 | 2 | 4-OMe-Phenyl | cyclohexyl |
| 552 | 2 | 4-OMe-Phenyl | 3-pyridyl |
| 553 | 2 | 4-OMe-Phenyl | 1-methyl-1H-pyrazol-4-yl |
| 554 | 2 | 4-OMe-Phenyl | 1H-imidazol-4-yl |
| 555 | 2 | 4-OMe-Phenyl | 2-furanyl |
| 556 | 2 | 2-OMe-Phenyl | ethyl |
| 557 | 2 | 2-OMe-Phenyl | n-propyl |
| 558 | 2 | 2-OMe-Phenyl | isopropyl |
| 559 | 2 | 2-OMe-Phenyl | $—CH_2CH(CH_3)_2$ |
| 560 | 2 | 2-OMe-Phenyl | $CF_3$ |
| 561 | 2 | 2-OMe-Phenyl | $—CH_2CF_3$ |
| 562 | 2 | 2-OMe-Phenyl | $—CH_2CH_2CF_3$ |
| 563 | 2 | 2-OMe-Phenyl | cyclopropyl |
| 564 | 2 | 2-OMe-Phenyl | Cyclobutyl |
| 565 | 2 | 2-OMe-Phenyl | cyclopentyl |
| 566 | 2 | 2-OMe-Phenyl | cyclohexyl |
| 567 | 2 | 2-OMe-Phenyl | 3-pyridyl |
| 568 | 2 | 2-OMe-Phenyl | 1-methyl-1H-pyrazol-4-yl |
| 569 | 2 | 2-OMe-Phenyl | 1H-imidazol-4-yl |
| 570 | 2 | 2-OMe-Phenyl | 2-furanyl |
| 571 | 2 | 3-CN-Phenyl | ethyl |
| 572 | 2 | 3-CN-Phenyl | n-propyl |
| 573 | 2 | 3-CN-Phenyl | isopropyl |
| 574 | 2 | 3-CN-Phenyl | $—CH_2CH(CH_3)_2$ |
| 575 | 2 | 3-CN-Phenyl | $CF_3$ |
| 576 | 2 | 3-CN-Phenyl | $—CH_2CF_3$ |
| 577 | 2 | 3-CN-Phenyl | $—CH_2CH_2CF_3$ |
| 578 | 2 | 3-CN-Phenyl | cyclopropyl |
| 579 | 2 | 3-CN-Phenyl | Cyclobutyl |
| 580 | 2 | 3-CN-Phenyl | cyclopentyl |
| 581 | 2 | 3-CN-Phenyl | cyclohexyl |
| 582 | 2 | 3-CN-Phenyl | 3-pyridyl |
| 583 | 2 | 3-CN-Phenyl | 1-methyl-1H-pyrazol-4-yl |
| 584 | 2 | 3-CN-Phenyl | 1H-imidazol-4-yl |
| 585 | 2 | 3-CN-Phenyl | 2-furanyl |
| 586 | 2 | 2-F-Phenyl | ethyl |
| 587 | 2 | 2-F-Phenyl | n-propyl |
| 588 | 2 | 2-F-Phenyl | isopropyl |
| 589 | 2 | 2-F-Phenyl | $—CH_2CH(CH_3)_2$ |
| 590 | 2 | 2-F-Phenyl | $CF_3$ |
| 591 | 2 | 2-F-Phenyl | $—CH_2CF_3$ |
| 592 | 2 | 2-F-Phenyl | $—CH_2CH_2CF_3$ |
| 593 | 2 | 2-F-Phenyl | cyclopropyl |
| 594 | 2 | 2-F-Phenyl | Cyclobutyl |
| 595 | 2 | 2-F-Phenyl | cyclopentyl |
| 596 | 2 | 2-F-Phenyl | cyclohexyl |
| 597 | 2 | 2-F-Phenyl | 3-pyridyl |
| 598 | 2 | 2-F-Phenyl | 1-methyl-1H-pyrazol-4-yl |
| 599 | 2 | 2-F-Phenyl | 1H-imidazol-4-yl |
| 600 | 2 | 2-F-Phenyl | 2-furanyl |
| 601 | 2 | 4-F-Phenyl | ethyl |
| 602 | 2 | 4-F-Phenyl | n-propyl |
| 603 | 2 | 4-F-Phenyl | isopropyl |
| 604 | 2 | 4-F-Phenyl | $—CH_2CH(CH_3)_2$ |
| 605 | 2 | 4-F-Phenyl | $CF_3$ |
| 606 | 2 | 4-F-Phenyl | $—CH_2CF_3$ |
| 607 | 2 | 4-F-Phenyl | $—CH_2CH_2CF_3$ |

TABLE 32-continued

| Entry | n | $R^4$ | $R^{10c}$ |
|---|---|---|---|
| 608 | 2 | 4-F-Phenyl | cyclopropyl |
| 609 | 2 | 4-F-Phenyl | Cyclobutyl |
| 610 | 2 | 4-F-Phenyl | cyclopentyl |
| 611 | 2 | 4-F-Phenyl | cyclohexyl |
| 612 | 2 | 4-F-Phenyl | 3-pyridyl |
| 613 | 2 | 4-F-Phenyl | 1-methyl-1H-pyrazol-4-yl |
| 614 | 2 | 4-F-Phenyl | 1H-imidazol-4-yl |
| 615 | 2 | 4-F-Phenyl | 2-furanyl |
| 616 | 2 | 3-Cl-Phenyl | ethyl |
| 617 | 2 | 3-Cl-Phenyl | n-propyl |
| 618 | 2 | 3-Cl-Phenyl | isopropyl |
| 619 | 2 | 3-Cl-Phenyl | $—CH_2CH(CH_3)_2$ |
| 620 | 2 | 3-Cl-Phenyl | $CF_3$ |
| 621 | 2 | 3-Cl-Phenyl | $—CH_2CF_3$ |
| 622 | 2 | 3-Cl-Phenyl | $—CH_2CH_2CF_3$ |
| 623 | 2 | 3-Cl-Phenyl | cyclopropyl |
| 624 | 2 | 3-Cl-Phenyl | Cyclobutyl |
| 625 | 2 | 3-Cl-Phenyl | cyclopentyl |
| 626 | 2 | 3-Cl-Phenyl | cyclohexyl |
| 627 | 2 | 3-Cl-Phenyl | 3-pyridyl |
| 628 | 2 | 3-Cl-Phenyl | 1-methyl-1H-pyrazol-4-yl |
| 629 | 2 | 3-Cl-Phenyl | 1H-imidazol-4-yl |
| 630 | 2 | 3-Cl-Phenyl | 2-furanyl |
| 631 | 2 | 2-Br-Phenyl | ethyl |
| 632 | 2 | 2-Br-Phenyl | n-propyl |
| 633 | 2 | 2-Br-Phenyl | isopropyl |
| 634 | 2 | 2-Br-Phenyl | $—CH_2CH(CH_3)_2$ |
| 635 | 2 | 2-Br-Phenyl | $CF_3$ |
| 636 | 2 | 2-Br-Phenyl | $—CH_2CF_3$ |
| 637 | 2 | 2-Br-Phenyl | $—CH_2CH_2CF_3$ |
| 638 | 2 | 2-Br-Phenyl | cyclopropyl |
| 639 | 2 | 2-Br-Phenyl | Cyclobutyl |
| 640 | 2 | 2-Br-Phenyl | cyclopentyl |
| 641 | 2 | 2-Br-Phenyl | cyclohexyl |
| 642 | 2 | 2-Br-Phenyl | 3-pyridyl |
| 643 | 2 | 2-Br-Phenyl | 1-methyl-1H-pyrazol-4-yl |
| 644 | 2 | 2-Br-Phenyl | 1H-imidazol-4-yl |
| 645 | 2 | 2-Br-Phenyl | 2-furanyl |
| 646 | 2 | 4-Br-Phenyl | ethyl |
| 647 | 2 | 4-Br-Phenyl | n-propyl |
| 648 | 2 | 4-Br-Phenyl | isopropyl |
| 649 | 2 | 4-Br-Phenyl | $—CH_2CH(CH_3)_2$ |
| 650 | 2 | 4-Br-Phenyl | $CF_3$ |
| 651 | 2 | 4-Br-Phenyl | $—CH_2CF_3$ |
| 652 | 2 | 4-Br-Phenyl | $—CH_2CH_2CF_3$ |
| 653 | 2 | 4-Br-Phenyl | cyclopropyl |
| 654 | 2 | 4-Br-Phenyl | Cyclobutyl |
| 655 | 2 | 4-Br-Phenyl | cyclopentyl |
| 656 | 2 | 4-Br-Phenyl | cyclohexyl |
| 657 | 2 | 4-Br-Phenyl | 3-pyridyl |
| 658 | 2 | 4-Br-Phenyl | 1-methyl-1H-pyrazol-4-yl |
| 659 | 2 | 4-Br-Phenyl | 1H-imidazol-4-yl |
| 660 | 2 | 4-Br-Phenyl | 2-furanyl |
| 661 | 2 | $3-CF_3$-Phenyl | ethyl |
| 662 | 2 | $3-CF_3$-Phenyl | n-propyl |
| 663 | 2 | $3-CF_3$-Phenyl | isopropyl |
| 664 | 2 | $3-CF_3$-Phenyl | $—CH_2CH(CH_3)_2$ |
| 665 | 2 | $3-CF_3$-Phenyl | $CF_3$ |
| 666 | 2 | $3-CF_3$-Phenyl | $—CH_2CF_3$ |
| 667 | 2 | $3-CF_3$-Phenyl | $—CH_2CH_2CF_3$ |
| 668 | 2 | $3-CF_3$-Phenyl | cyclopropyl |
| 669 | 2 | $3-CF_3$-Phenyl | Cyclobutyl |
| 670 | 2 | $3-CF_3$-Phenyl | cyclopentyl |
| 671 | 2 | $3-CF_3$-Phenyl | cyclohexyl |
| 672 | 2 | $3-CF_3$-Phenyl | 3-pyridyl |
| 673 | 2 | $3-CF_3$-Phenyl | 1-methyl-1H-pyrazol-4-yl |
| 674 | 2 | $3-CF_3$-Phenyl | 1H-imidazol-4-yl |
| 675 | 2 | $3-CF_3$-Phenyl | 2-furanyl |
| 676 | 2 | 2-iPr-Phenyl | ethyl |
| 677 | 2 | 2-iPr-Phenyl | n-propyl |
| 678 | 2 | 2-iPr-Phenyl | isopropyl |
| 679 | 2 | 2-iPr-Phenyl | $—CH_2CH(CH_3)_2$ |
| 680 | 2 | 2-iPr-Phenyl | $CF_3$ |
| 681 | 2 | 2-iPr-Phenyl | $—CH_2CF_3$ |
| 682 | 2 | 2-iPr-Phenyl | $—CH_2CH_2CF_3$ |
| 683 | 2 | 2-iPr-Phenyl | cyclopropyl |
| 684 | 2 | 2-iPr-Phenyl | Cyclobutyl |
| 685 | 2 | 2-iPr-Phenyl | cyclopentyl |
| 686 | 2 | 2-iPr-Phenyl | cyclohexyl |
| 687 | 2 | 2-iPr-Phenyl | 3-pyridyl |
| 688 | 2 | 2-iPr-Phenyl | 1-methyl-1H-pyrazol-4-yl |
| 689 | 2 | 2-iPr-Phenyl | 1H-imidazol-4-yl |
| 690 | 2 | 2-iPr-Phenyl | 2-furanyl |
| 691 | 2 | 4-iPr-Phenyl | ethyl |
| 692 | 2 | 4-iPr-Phenyl | n-propyl |
| 693 | 2 | 4-iPr-Phenyl | isopropyl |
| 694 | 2 | 4-iPr-Phenyl | $—CH_2CH(CH_3)_2$ |
| 695 | 2 | 4-iPr-Phenyl | $CF_3$ |
| 696 | 2 | 4-iPr-Phenyl | $—CH_2CF_3$ |
| 697 | 2 | 4-iPr-Phenyl | $—CH_2CH_2CF_3$ |
| 698 | 2 | 4-iPr-Phenyl | cyclopropyl |
| 699 | 2 | 4-iPr-Phenyl | Cyclobutyl |
| 700 | 2 | 4-iPr-Phenyl | cyclopentyl |
| 701 | 2 | 4-iPr-Phenyl | cyclohexyl |
| 702 | 2 | 4-iPr-Phenyl | 3-pyridyl |
| 703 | 2 | 4-iPr-Phenyl | 1-methyl-1H-pyrazol-4-yl |
| 704 | 2 | 4-iPr-Phenyl | 1H-imidazol-4-yl |
| 705 | 2 | 4-iPr-Phenyl | 2-furanyl |
| 706 | 2 | 3-morpholino-phenyl | ethyl |
| 707 | 2 | 3-morpholino-phenyl | n-propyl |
| 708 | 2 | 3-morpholino-phenyl | isopropyl |
| 709 | 2 | 3-morpholino-phenyl | $—CH_2CH(CH_3)_2$ |
| 710 | 2 | 3-morpholino-phenyl | $CF_3$ |
| 711 | 2 | 3-morpholino-phenyl | $—CH_2CF_3$ |
| 712 | 2 | 3-morpholino-phenyl | $—CH_2CH_2CF_3$ |
| 713 | 2 | 3-morpholino-phenyl | cyclopropyl |
| 714 | 2 | 3-morpholino-phenyl | Cyclobutyl |
| 715 | 2 | 3-morpholino-phenyl | cyclopentyl |
| 716 | 2 | 3-morpholino-phenyl | cyclohexyl |
| 717 | 2 | 3-morpholino-phenyl | 3-pyridyl |
| 718 | 2 | 3-morpholino-phenyl | 1-methyl-1H-pyrazol-4-yl |
| 719 | 2 | 3-morpholino-phenyl | 1H-imidazol-4-yl |
| 720 | 2 | 3-morpholino-phenyl | 2-furanyl |
| 721 | 2 | 4-cyano-2-morpholino-phenyl | ethyl |
| 722 | 2 | 4-cyano-2-morpholino-phenyl | n-propyl |
| 723 | 2 | 4-cyano-2-morpholino-phenyl | isopropyl |
| 724 | 2 | 4-cyano-2-morpholino-phenyl | $—CH_2CH(CH_3)_2$ |
| 725 | 2 | 4-cyano-2-morpholino-phenyl | $CF_3$ |
| 726 | 2 | 4-cyano-2-morpholino-phenyl | $—CH_2CF_3$ |
| 727 | 2 | 4-cyano-2-morpholino-phenyl | $—CH_2CH_2CF_3$ |
| 728 | 2 | 4-cyano-2-morpholino-phenyl | cyclopropyl |
| 729 | 2 | 4-cyano-2-morpholino-phenyl | Cyclobutyl |
| 730 | 2 | 4-cyano-2-morpholino-phenyl | cyclopentyl |
| 731 | 2 | 4-cyano-2-morpholino-phenyl | cyclohexyl |
| 732 | 2 | 4-cyano-2-morpholino-phenyl | 3-pyridyl |
| 733 | 2 | 4-cyano-2-morpholino-phenyl | 1-methyl-1H-pyrazol-4-yl |
| 734 | 2 | 4-cyano-2-morpholino-phenyl | 1H-imidazol-4-yl |
| 735 | 2 | 4-cyano-2-morpholino-phenyl | 2-furanyl |
| 736 | 2 | 4-hydroxy-2-morpholino-phenyl | ethyl |
| 737 | 2 | 4-hydroxy-2-morpholino-phenyl | n-propyl |
| 738 | 2 | 4-hydroxy-2-morpholino-phenyl | isopropyl |
| 739 | 2 | 4-hydroxy-2-morpholino-phenyl | $—CH_2CH(CH_3)_2$ |
| 740 | 2 | 4-hydroxy-2-morpholino-phenyl | $CF_3$ |
| 741 | 2 | 4-hydroxy-2-morpholino-phenyl | $—CH_2CF_3$ |
| 742 | 2 | 4-hydroxy-2-morpholino-phenyl | $—CH_2CH_2CF_3$ |
| 743 | 2 | 4-hydroxy-2-morpholino-phenyl | cyclopropyl |
| 744 | 2 | 4-hydroxy-2-morpholino-phenyl | Cyclobutyl |
| 745 | 2 | 4-hydroxy-2-morpholino-phenyl | cyclopentyl |
| 746 | 2 | 4-hydroxy-2-morpholino-phenyl | cyclohexyl |
| 747 | 2 | 4-hydroxy-2-morpholino-phenyl | 3-pyridyl |
| 748 | 2 | 4-hydroxy-2-morpholino-phenyl | 1-methyl-1H-pyrazol-4-yl |
| 749 | 2 | 4-hydroxy-2-morpholino-phenyl | 1H-imidazol-4-yl |
| 750 | 2 | 4-hydroxy-2-morpholino-phenyl | 2-furanyl |
| 751 | 2 | $2-CH_3$-phenyl | Ethyl |
| 752 | 2 | $2-CH_3$-phenyl | n-propyl |
| 753 | 2 | $2-CH_3$-phenyl | Isopropyl |
| 754 | 2 | $2-CH_3$-phenyl | $—CH_2CH(CH_3)_2$ |
| 755 | 2 | $2-CH_3$-phenyl | $CF_3$ |
| 756 | 2 | $2-CH_3$-phenyl | $—CH_2CF_3$ |
| 757 | 2 | $2-CH_3$-phenyl | $—CH_2CH_2CF_3$ |
| 758 | 2 | $2-CH_3$-phenyl | cyclopropyl |
| 759 | 2 | $2-CH_3$-phenyl | Cyclobutyl |
| 760 | 2 | $2-CH_3$-phenyl | cyclopentyl |
| 761 | 2 | $2-CH_3$-phenyl | cyclohexyl |
| 762 | 2 | $2-CH_3$-phenyl | 3-pyridyl |
| 763 | 2 | $2-CH_3$-phenyl | 1-methyl-1H-pyrazol-4-yl |

TABLE 32-continued

| Entry | n | $R^4$ | $R^{10c}$ |
|---|---|---|---|
| 764 | 2 | 2-$CH_3$-phenyl | 1H-imidazol-4-yl |
| 765 | 2 | 2-$CH_3$-phenyl | 2-furanyl |
| 766 | 2 | 4-OH-Phenyl | Ethyl |
| 767 | 2 | 4-OH-Phenyl | n-propyl |
| 768 | 2 | 4-OH-Phenyl | Isopropyl |
| 769 | 2 | 4-OH-Phenyl | —$CH_2CH(CH_3)_2$ |
| 770 | 2 | 4-OH-Phenyl | $CF_3$ |
| 771 | 2 | 4-OH-Phenyl | —$CH_2CF_3$ |
| 772 | 2 | 4-OH-Phenyl | —$CH_2CH_2CF_3$ |
| 773 | 2 | 4-OH-Phenyl | cyclopropyl |
| 774 | 2 | 4-OH-Phenyl | Cyclobutyl |
| 775 | 2 | 4-OH-Phenyl | cyclopentyl |
| 776 | 2 | 4-OH-Phenyl | cyclohexyl |
| 777 | 2 | 4-OH-Phenyl | 3-pyridyl |
| 778 | 2 | 4-OH-Phenyl | 1-methyl-1H-pyrazol-4-yl |
| 779 | 2 | 4-OH-Phenyl | 1H-imidazol-4-yl |
| 780 | 2 | 4-OH-Phenyl | 2-furanyl |
| 781 | 2 | 2-OH-Phenyl | Ethyl |
| 782 | 2 | 2-OH-Phenyl | n-propyl |
| 783 | 2 | 2-OH-Phenyl | Isopropyl |
| 784 | 2 | 2-OH-Phenyl | —$CH_2CH(CH_3)_2$ |
| 785 | 2 | 2-OH-Phenyl | $CF_3$ |
| 786 | 2 | 2-OH-Phenyl | —$CH_2CF_3$ |
| 787 | 2 | 2-OH-Phenyl | —$CH_2CH_2CF_3$ |
| 788 | 2 | 2-OH-Phenyl | cyclopropyl |
| 789 | 2 | 2-OH-Phenyl | Cyclobutyl |
| 790 | 2 | 2-OH-Phenyl | cyclopentyl |
| 791 | 2 | 2-OH-Phenyl | cyclohexyl |
| 792 | 2 | 2-OH-Phenyl | 3-pyridyl |
| 793 | 2 | 2-OH-Phenyl | 1-methyl-1H-pyrazol-4-yl |
| 794 | 2 | 2-OH-Phenyl | 1H-imidazol-4-yl |
| 795 | 2 | 2-OH-Phenyl | 2-furanyl |
| 796 | 2 | 3-OMe-Phenyl | Ethyl |
| 797 | 2 | 3-OMe-Phenyl | n-propyl |
| 798 | 2 | 3-OMe-Phenyl | Isopropyl |
| 799 | 2 | 3-OMe-Phenyl | —$CH_2CH(CH_3)_2$ |
| 800 | 2 | 3-OMe-Phenyl | $CF_3$ |
| 801 | 2 | 3-OMe-Phenyl | —$CH_2CF_3$ |
| 802 | 2 | 3-OMe-Phenyl | —$CH_2CH_2CF_3$ |
| 803 | 2 | 3-OMe-Phenyl | cyclopropyl |
| 804 | 2 | 3-OMe-Phenyl | Cyclobutyl |
| 805 | 2 | 3-OMe-Phenyl | cyclopentyl |
| 806 | 2 | 3-OMe-Phenyl | cyclohexyl |
| 807 | 2 | 3-OMe-Phenyl | 3-pyridyl |
| 808 | 2 | 3-OMe-Phenyl | 1-methyl-1H-pyrazol-4-yl |
| 809 | 2 | 3-OMe-Phenyl | 1H-imidazol-4-yl |
| 810 | 2 | 3-OMe-Phenyl | 2-furanyl |
| 811 | 2 | 4-CN-Phenyl | Ethyl |
| 812 | 2 | 4-CN-Phenyl | n-propyl |
| 813 | 2 | 4-CN-Phenyl | Isopropyl |
| 814 | 2 | 4-CN-Phenyl | —$CH_2CH(CH_3)_2$ |
| 815 | 2 | 4-CN-Phenyl | $CF_3$ |
| 816 | 2 | 4-CN-Phenyl | —$CH_2CF_3$ |
| 817 | 2 | 4-CN-Phenyl | —$CH_2CH_2CF_3$ |
| 818 | 2 | 4-CN-Phenyl | cyclopropyl |
| 819 | 2 | 4-CN-Phenyl | Cyclobutyl |
| 820 | 2 | 4-CN-Phenyl | cyclopentyl |
| 821 | 2 | 4-CN-Phenyl | cyclohexyl |
| 822 | 2 | 4-CN-Phenyl | 3-pyridyl |
| 823 | 2 | 4-CN-Phenyl | 1-methyl-1H-pyrazol-4-yl |
| 824 | 2 | 4-CN-Phenyl | 1H-imidazol-4-yl |
| 825 | 2 | 4-CN-Phenyl | 2-furanyl |
| 826 | 2 | 2-CN-Phenyl | Ethyl |
| 827 | 2 | 2-CN-Phenyl | n-propyl |
| 828 | 2 | 2-CN-Phenyl | Isopropyl |
| 829 | 2 | 2-CN-Phenyl | —$CH_2CH(CH_3)_2$ |
| 830 | 2 | 2-CN-Phenyl | $CF_3$ |
| 831 | 2 | 2-CN-Phenyl | —$CH_2CF_3$ |
| 832 | 2 | 2-CN-Phenyl | —$CH_2CH_2CF_3$ |
| 833 | 2 | 2-CN-Phenyl | cyclopropyl |
| 834 | 2 | 2-CN-Phenyl | Cyclobutyl |
| 835 | 2 | 2-CN-Phenyl | cyclopentyl |
| 836 | 2 | 2-CN-Phenyl | cyclohexyl |
| 837 | 2 | 2-CN-Phenyl | 3-pyridyl |
| 838 | 2 | 2-CN-Phenyl | 1-methyl-1H-pyrazol-4-yl |
| 839 | 2 | 2-CN-Phenyl | 1H-imidazol-4-yl |
| 840 | 2 | 2-CN-Phenyl | 2-furanyl |
| 841 | 2 | 3-F-Phenyl | Ethyl |

TABLE 32-continued

| Entry | n | $R^4$ | $R^{10c}$ |
|---|---|---|---|
| 842 | 2 | 3-F-Phenyl | n-propyl |
| 843 | 2 | 3-F-Phenyl | Isopropyl |
| 844 | 2 | 3-F-Phenyl | —$CH_2CH(CH_3)_2$ |
| 845 | 2 | 3-F-Phenyl | $CF_3$ |
| 846 | 2 | 3-F-Phenyl | —$CH_2CF_3$ |
| 847 | 2 | 3-F-Phenyl | —$CH_2CH_2CF_3$ |
| 848 | 2 | 3-F-Phenyl | cyclopropyl |
| 849 | 2 | 3-F-Phenyl | Cyclobutyl |
| 850 | 2 | 3-F-Phenyl | cyclopentyl |
| 851 | 2 | 3-F-Phenyl | cyclohexyl |
| 852 | 2 | 3-F-Phenyl | 3-pyridyl |
| 853 | 2 | 3-F-Phenyl | 1-methyl-1H-pyrazol-4-yl |
| 854 | 2 | 3-F-Phenyl | 1H-imidazol-4-yl |
| 855 | 2 | 3-F-Phenyl | 2-furanyl |
| 856 | 2 | 2-Cl-Phenyl | Ethyl |
| 857 | 2 | 2-Cl-Phenyl | n-propyl |
| 858 | 2 | 2-Cl-Phenyl | Isopropyl |
| 859 | 2 | 2-Cl-Phenyl | —$CH_2CH(CH_3)_2$ |
| 860 | 2 | 2-Cl-Phenyl | $CF_3$ |
| 861 | 2 | 2-Cl-Phenyl | —$CH_2CF_3$ |
| 862 | 2 | 2-Cl-Phenyl | —$CH_2CH_2CF_3$ |
| 863 | 2 | 2-Cl-Phenyl | cyclopropyl |
| 864 | 2 | 2-Cl-Phenyl | Cyclobutyl |
| 865 | 2 | 2-Cl-Phenyl | cyclopentyl |
| 866 | 2 | 2-Cl-Phenyl | cyclohexyl |
| 867 | 2 | 2-Cl-Phenyl | 3-pyridyl |
| 868 | 2 | 2-Cl-Phenyl | 1-methyl-1H-pyrazol-4-yl |
| 869 | 2 | 2-Cl-Phenyl | 1H-imidazol-4-yl |
| 870 | 2 | 2-Cl-Phenyl | 2-furanyl |
| 871 | 2 | 4-Cl-Phenyl | Ethyl |
| 872 | 2 | 4-Cl-Phenyl | n-propyl |
| 873 | 2 | 4-Cl-Phenyl | Isopropyl |
| 874 | 2 | 4-Cl-Phenyl | —$CH_2CH(CH_3)_2$ |
| 875 | 2 | 4-Cl-Phenyl | $CF_3$ |
| 876 | 2 | 4-Cl-Phenyl | —$CH_2CF_3$ |
| 877 | 2 | 4-Cl-Phenyl | —$CH_2CH_2CF_3$ |
| 878 | 2 | 4-Cl-Phenyl | cyclopropyl |
| 879 | 2 | 4-Cl-Phenyl | Cyclobutyl |
| 880 | 2 | 4-Cl-Phenyl | cyclopentyl |
| 881 | 2 | 4-Cl-Phenyl | cyclohexyl |
| 882 | 2 | 4-Cl-Phenyl | 3-pyridyl |
| 883 | 2 | 4-Cl-Phenyl | 1-methyl-1H-pyrazol-4-yl |
| 884 | 2 | 4-Cl-Phenyl | 1H-imidazol-4-yl |
| 885 | 2 | 4-Cl-Phenyl | 2-furanyl |
| 886 | 2 | 3-Br-Phenyl | Ethyl |
| 887 | 2 | 3-Br-Phenyl | n-propyl |
| 888 | 2 | 3-Br-Phenyl | Isopropyl |
| 889 | 2 | 3-Br-Phenyl | —$CH_2CH(CH_3)_2$ |
| 890 | 2 | 3-Br-Phenyl | $CF_3$ |
| 891 | 2 | 3-Br-Phenyl | —$CH_2CF_3$ |
| 892 | 2 | 3-Br-Phenyl | —$CH_2CH_2CF_3$ |
| 893 | 2 | 3-Br-Phenyl | cyclopropyl |
| 894 | 2 | 3-Br-Phenyl | Cyclobutyl |
| 895 | 2 | 3-Br-Phenyl | cyclopentyl |
| 896 | 2 | 3-Br-Phenyl | cyclohexyl |
| 897 | 2 | 3-Br-Phenyl | 3-pyridyl |
| 898 | 2 | 3-Br-Phenyl | 1-methyl-1H-pyrazol-4-yl |
| 899 | 2 | 3-Br-Phenyl | 1H-imidazol-4-yl |
| 900 | 2 | 3-Br-Phenyl | 2-furanyl |
| 901 | 2 | 2-$CF_3$-Phenyl | Ethyl |
| 902 | 2 | 2-$CF_3$-Phenyl | n-propyl |
| 903 | 2 | 2-$CF_3$-Phenyl | Isopropyl |
| 904 | 2 | 2-$CF_3$-Phenyl | —$CH_2CH(CH_3)_2$ |
| 905 | 2 | 2-$CF_3$-Phenyl | $CF_3$ |
| 906 | 2 | 2-$CF_3$-Phenyl | —$CH_2CF_3$ |
| 907 | 2 | 2-$CF_3$-Phenyl | —$CH_2CH_2CF_3$ |
| 908 | 2 | 2-$CF_3$-Phenyl | cyclopropyl |
| 909 | 2 | 2-$CF_3$-Phenyl | Cyclobutyl |
| 910 | 2 | 2-$CF_3$-Phenyl | cyclopentyl |
| 911 | 2 | 2-$CF_3$-Phenyl | cyclohexyl |
| 912 | 2 | 2-$CF_3$-Phenyl | 3-pyridyl |
| 913 | 2 | 2-$CF_3$-Phenyl | 1-methyl-1H-pyrazol-4-yl |
| 914 | 2 | 2-$CF_3$-Phenyl | 1H-imidazol-4-yl |
| 915 | 2 | 2-$CF_3$-Phenyl | 2-furanyl |
| 916 | 2 | 4-$CF_3$-Phenyl | Ethyl |
| 917 | 2 | 4-$CF_3$-Phenyl | n-propyl |
| 918 | 2 | 4-$CF_3$-Phenyl | Isopropyl |
| 919 | 2 | 4-$CF_3$-Phenyl | —$CH_2CH(CH_3)_2$ |

TABLE 32-continued

| Entry | n | $R^4$ | $R^{10c}$ |
|---|---|---|---|
| 920 | 2 | 4-$CF_3$-Phenyl | $CF_3$ |
| 921 | 2 | 4-$CF_3$-Phenyl | —$CH_2CF_3$ |
| 922 | 2 | 4-$CF_3$-Phenyl | —$CH_2CH_2CF_3$ |
| 923 | 2 | 4-$CF_3$-Phenyl | cyclopropyl |
| 924 | 2 | 4-$CF_3$-Phenyl | Cyclobutyl |
| 925 | 2 | 4-$CF_3$-Phenyl | cyclopentyl |
| 926 | 2 | 4-$CF_3$-Phenyl | cyclohexyl |
| 927 | 2 | 4-$CF_3$-Phenyl | 3-pyridyl |
| 928 | 2 | 4-$CF_3$-Phenyl | 1-methyl-1H-pyrazol-4-yl |
| 929 | 2 | 4-$CF_3$-Phenyl | 1H-imidazol-4-yl |
| 930 | 2 | 4-$CF_3$-Phenyl | 2-furanyl |
| 931 | 2 | 3-iPr-Phenyl | Ethyl |
| 932 | 2 | 3-iPr-Phenyl | n-propyl |
| 933 | 2 | 3-iPr-Phenyl | Isopropyl |
| 934 | 2 | 3-iPr-Phenyl | —$CH_2CH(CH_3)_2$ |
| 935 | 2 | 3-iPr-Phenyl | $CF_3$ |
| 936 | 2 | 3-iPr-Phenyl | —$CH_2CF_3$ |
| 937 | 2 | 3-iPr-Phenyl | —$CH_2CH_2CF_3$ |
| 938 | 2 | 3-iPr-Phenyl | cyclopropyl |
| 939 | 2 | 3-iPr-Phenyl | Cyclobutyl |
| 940 | 2 | 3-iPr-Phenyl | cyclopentyl |
| 941 | 2 | 3-iPr-Phenyl | cyclohexyl |
| 942 | 2 | 3-iPr-Phenyl | 3-pyridyl |
| 943 | 2 | 3-iPr-Phenyl | 1-methyl-1H-pyrazol-4-yl |
| 944 | 2 | 3-iPr-Phenyl | 1H-imidazol-4-yl |
| 945 | 2 | 3-iPr-Phenyl | 2-furanyl |
| 946 | 2 | 2-morpholino-phenyl | Ethyl |
| 947 | 2 | 2-morpholino-phenyl | n-propyl |
| 948 | 2 | 2-morpholino-phenyl | isopropyl |
| 949 | 2 | 2-morpholino-phenyl | —$CH_2CH(CH_3)_2$ |
| 950 | 2 | 2-morpholino-phenyl | $CF_3$ |
| 951 | 2 | 2-morpholino-phenyl | —$CH_2CF_3$ |
| 952 | 2 | 2-morpholino-phenyl | —$CH_2CH_2CF_3$ |
| 953 | 2 | 2-morpholino-phenyl | cyclopropyl |
| 954 | 2 | 2-morpholino-phenyl | Cyclobutyl |
| 955 | 2 | 2-morpholino-phenyl | cyclopentyl |
| 956 | 2 | 2-morpholino-phenyl | cyclohexyl |
| 957 | 2 | 2-morpholino-phenyl | 3-pyridyl |
| 958 | 2 | 2-morpholino-phenyl | 1-methyl-1H-pyrazol-4-yl |
| 959 | 2 | 2-morpholino-phenyl | 1H-imidazol-4-yl |
| 960 | 2 | 2-morpholino-phenyl | 2-furanyl |
| 961 | 2 | 4-morpholino-phenyl | ethyl |
| 962 | 2 | 4-morpholino-phenyl | n-propyl |
| 963 | 2 | 4-morpholino-phenyl | isopropyl |
| 964 | 2 | 4-morpholino-phenyl | —$CH_2CH(CH_3)_2$ |
| 965 | 2 | 4-morpholino-phenyl | $CF_3$ |
| 966 | 2 | 4-morpholino-phenyl | —$CH_2CF_3$ |
| 967 | 2 | 4-morpholino-phenyl | —$CH_2CH_2CF_3$ |
| 968 | 2 | 4-morpholino-phenyl | cyclopropyl |
| 969 | 2 | 4-morpholino-phenyl | Cyclobutyl |
| 970 | 2 | 4-morpholino-phenyl | cyclopentyl |
| 971 | 2 | 4-morpholino-phenyl | cyclohexyl |
| 972 | 2 | 4-morpholino-phenyl | 3-pyridyl |
| 973 | 2 | 4-morpholino-phenyl | 1-methyl-1H-pyrazol-4-yl |
| 974 | 2 | 4-morpholino-phenyl | 1H-imidazol-4-yl |
| 975 | 2 | 4-morpholino-phenyl | 2-furanyl |
| 976 | 2 | 4-methyl-2-morpholino-phenyl | ethyl |
| 977 | 2 | 4-methyl-2-morpholino-phenyl | n-propyl |
| 978 | 2 | 4-methyl-2-morpholino-phenyl | isopropyl |
| 979 | 2 | 4-methyl-2-morpholino-phenyl | —$CH_2CH(CH_3)_2$ |
| 980 | 2 | 4-methyl-2-morpholino-phenyl | $CF_3$ |
| 981 | 2 | 4-methyl-2-morpholino-phenyl | —$CH_2CF_3$ |
| 982 | 2 | 4-methyl-2-morpholino-phenyl | —$CH_2CH_2CF_3$ |
| 983 | 2 | 4-methyl-2-morpholino-phenyl | cyclopropyl |
| 984 | 2 | 4-methyl-2-morpholino-phenyl | Cyclobutyl |
| 985 | 2 | 4-methyl-2-morpholino-phenyl | cyclopentyl |
| 986 | 2 | 4-methyl-2-morpholino-phenyl | cyclohexyl |
| 987 | 2 | 4-methyl-2-morpholino-phenyl | 3-pyridyl |
| 988 | 2 | 4-methyl-2-morpholino-phenyl | 1-methyl-1H-pyrazol-4-yl |
| 989 | 2 | 4-methyl-2-morpholino-phenyl | 1H-imidazol-4-yl |
| 990 | 2 | 4-methyl-2-morpholino-phenyl | 2-furanyl |
| 991 | 3 | 4-$CH_3$-phenyl | ethyl |
| 992 | 3 | 4-$CH_3$-phenyl | n-propyl |
| 993 | 3 | 4-$CH_3$-phenyl | isopropyl |
| 994 | 3 | 4-$CH_3$-phenyl | —$CH_2CH(CH_3)_2$ |
| 995 | 3 | 4-$CH_3$-phenyl | $CF_3$ |
| 996 | 3 | 4-$CH_3$-phenyl | —$CH_2CF_3$ |
| 997 | 3 | 4-$CH_3$-phenyl | —$CH_2CH_2CF_3$ |

TABLE 32-continued

| Entry | n | $R^4$ | $R^{10c}$ |
|---|---|---|---|
| 998 | 3 | 4-$CH_3$-phenyl | cyclopropyl |
| 999 | 3 | 4-$CH_3$-phenyl | Cyclobutyl |
| 1000 | 3 | 4-$CH_3$-phenyl | cyclopentyl |
| 1001 | 3 | 4-$CH_3$-phenyl | cyclohexyl |
| 1002 | 3 | 4-$CH_3$-phenyl | 3-pyridyl |
| 1003 | 3 | 4-$CH_3$-phenyl | 1-methyl-1H-pyrazol-4-yl |
| 1004 | 3 | 4-$CH_3$-phenyl | 1H-imidazol-4-yl |
| 1005 | 3 | 4-$CH_3$-phenyl | 2-furanyl |
| 1006 | 3 | 3-$CH_3$-phenyl | ethyl |
| 1007 | 3 | 3-$CH_3$-phenyl | n-propyl |
| 1008 | 3 | 3-$CH_3$-phenyl | isopropyl |
| 1009 | 3 | 3-$CH_3$-phenyl | —$CH_2CH(CH_3)_2$ |
| 1010 | 3 | 3-$CH_3$-phenyl | $CF_3$ |
| 1011 | 3 | 3-$CH_3$-phenyl | —$CH_2CF_3$ |
| 1012 | 3 | 3-$CH_3$-phenyl | —$CH_2CH_2CF_3$ |
| 1013 | 3 | 3-$CH_3$-phenyl | cyclopropyl |
| 1014 | 3 | 3-$CH_3$-phenyl | Cyclobutyl |
| 1015 | 3 | 3-$CH_3$-phenyl | cyclopentyl |
| 1016 | 3 | 3-$CH_3$-phenyl | cyclohexyl |
| 1017 | 3 | 3-$CH_3$-phenyl | 3-pyridyl |
| 1018 | 3 | 3-$CH_3$-phenyl | 1-methyl-1H-pyrazol-4-yl |
| 1019 | 3 | 3-$CH_3$-phenyl | 1H-imidazol-4-yl |
| 1020 | 3 | 3-$CH_3$-phenyl | 2-furanyl |
| 1021 | 3 | 3-OH-Phenyl | ethyl |
| 1022 | 3 | 3-OH-Phenyl | n-propyl |
| 1023 | 3 | 3-OH-Phenyl | isopropyl |
| 1024 | 3 | 3-OH-Phenyl | —$CH_2CH(CH_3)_2$ |
| 1025 | 3 | 3-OH-Phenyl | $CF_3$ |
| 1026 | 3 | 3-OH-Phenyl | —$CH_2CF_3$ |
| 1027 | 3 | 3-OH-Phenyl | —$CH_2CH_2CF_3$ |
| 1028 | 3 | 3-OH-Phenyl | cyclopropyl |
| 1029 | 3 | 3-OH-Phenyl | Cyclobutyl |
| 1030 | 3 | 3-OH-Phenyl | cyclopentyl |
| 1031 | 3 | 3-OH-Phenyl | cyclohexyl |
| 1032 | 3 | 3-OH-Phenyl | 3-pyridyl |
| 1033 | 3 | 3-OH-Phenyl | 1-methyl-1H-pyrazol-4-yl |
| 1034 | 3 | 3-OH-Phenyl | 1H-imidazol-4-yl |
| 1035 | 3 | 3-OH-Phenyl | 2-furanyl |
| 1036 | 3 | 4-OMe-Phenyl | ethyl |
| 1037 | 3 | 4-OMe-Phenyl | n-propyl |
| 1038 | 3 | 4-OMe-Phenyl | isopropyl |
| 1039 | 3 | 4-OMe-Phenyl | —$CH_2CH(CH_3)_2$ |
| 1040 | 3 | 4-OMe-Phenyl | $CF_3$ |
| 1041 | 3 | 4-OMe-Phenyl | —$CH_2CF_3$ |
| 1042 | 3 | 4-OMe-Phenyl | —$CH_2CH_2CF_3$ |
| 1043 | 3 | 4-OMe-Phenyl | cyclopropyl |
| 1044 | 3 | 4-OMe-Phenyl | Cyclobutyl |
| 1045 | 3 | 4-OMe-Phenyl | cyclopentyl |
| 1046 | 3 | 4-OMe-Phenyl | cyclohexyl |
| 1047 | 3 | 4-OMe-Phenyl | 3-pyridyl |
| 1048 | 3 | 4-OMe-Phenyl | 1-methyl-1H-pyrazol-4-yl |
| 1049 | 3 | 4-OMe-Phenyl | 1H-imidazol-4-yl |
| 1050 | 3 | 4-OMe-Phenyl | 2-furanyl |
| 1051 | 3 | 2-OMe-Phenyl | ethyl |
| 1052 | 3 | 2-OMe-Phenyl | n-propyl |
| 1053 | 3 | 2-OMe-Phenyl | isopropyl |
| 1054 | 3 | 2-OMe-Phenyl | —$CH_2CH(CH_3)_2$ |
| 1055 | 3 | 2-OMe-Phenyl | $CF_3$ |
| 1056 | 3 | 2-OMe-Phenyl | —$CH_2CF_3$ |
| 1057 | 3 | 2-OMe-Phenyl | —$CH_2CH_2CF_3$ |
| 1058 | 3 | 2-OMe-Phenyl | cyclopropyl |
| 1059 | 3 | 2-OMe-Phenyl | Cyclobutyl |
| 1060 | 3 | 2-OMe-Phenyl | cyclopentyl |
| 1061 | 3 | 2-OMe-Phenyl | cyclohexyl |
| 1062 | 3 | 2-OMe-Phenyl | 3-pyridyl |
| 1063 | 3 | 2-OMe-Phenyl | 1-methyl-1H-pyrazol-4-yl |
| 1064 | 3 | 2-OMe-Phenyl | 1H-imidazol-4-yl |
| 1065 | 3 | 2-OMe-Phenyl | 2-furanyl |
| 1066 | 3 | 3-CN-Phenyl | ethyl |
| 1067 | 3 | 3-CN-Phenyl | n-propyl |
| 1068 | 3 | 3-CN-Phenyl | isopropyl |
| 1069 | 3 | 3-CN-Phenyl | —$CH_2CH(CH_3)_2$ |
| 1070 | 3 | 3-CN-Phenyl | $CF_3$ |
| 1071 | 3 | 3-CN-Phenyl | —$CH_2CF_3$ |
| 1072 | 3 | 3-CN-Phenyl | —$CH_2CH_2CF_3$ |
| 1073 | 3 | 3-CN-Phenyl | cyclopropyl |
| 1074 | 3 | 3-CN-Phenyl | Cyclobutyl |
| 1075 | 3 | 3-CN-Phenyl | cyclopentyl |

TABLE 32-continued

| Entry | n | $R^4$ | $R^{10c}$ |
|---|---|---|---|
| 1076 | 3 | 3-CN-Phenyl | cyclohexyl |
| 1077 | 3 | 3-CN-Phenyl | 3-pyridyl |
| 1078 | 3 | 3-CN-Phenyl | 1-methyl-1H-pyrazol-4-yl |
| 1079 | 3 | 3-CN-Phenyl | 1H-imidazol-4-yl |
| 1080 | 3 | 3-CN-Phenyl | 2-furanyl |
| 1081 | 3 | 2-F-Phenyl | ethyl |
| 1082 | 3 | 2-F-Phenyl | n-propyl |
| 1083 | 3 | 2-F-Phenyl | isopropyl |
| 1084 | 3 | 2-F-Phenyl | —$CH_2CH(CH_3)_2$ |
| 1085 | 3 | 2-F-Phenyl | $CF_3$ |
| 1086 | 3 | 2-F-Phenyl | —$CH_2CF_3$ |
| 1087 | 3 | 2-F-Phenyl | —$CH_2CH_2CF_3$ |
| 1088 | 3 | 2-F-Phenyl | cyclopropyl |
| 1089 | 3 | 2-F-Phenyl | Cyclobutyl |
| 1090 | 3 | 2-F-Phenyl | cyclopentyl |
| 1091 | 3 | 2-F-Phenyl | cyclohexyl |
| 1092 | 3 | 2-F-Phenyl | 3-pyridyl |
| 1093 | 3 | 2-F-Phenyl | 1-methyl-1H-pyrazol-4-yl |
| 1094 | 3 | 2-F-Phenyl | 1H-imidazol-4-yl |
| 1095 | 3 | 2-F-Phenyl | 2-furanyl |
| 1096 | 3 | 4-F-Phenyl | ethyl |
| 1097 | 3 | 4-F-Phenyl | n-propyl |
| 1098 | 3 | 4-F-Phenyl | isopropyl |
| 1099 | 3 | 4-F-Phenyl | —$CH_2CH(CH_3)_2$ |
| 1100 | 3 | 4-F-Phenyl | $CF_3$ |
| 1101 | 3 | 4-F-Phenyl | —$CH_2CF_3$ |
| 1102 | 3 | 4-F-Phenyl | —$CH_2CH_2CF_3$ |
| 1103 | 3 | 4-F-Phenyl | cyclopropyl |
| 1104 | 3 | 4-F-Phenyl | Cyclobutyl |
| 1105 | 3 | 4-F-Phenyl | cyclopentyl |
| 1106 | 3 | 4-F-Phenyl | cyclohexyl |
| 1107 | 3 | 4-F-Phenyl | 3-pyridyl |
| 1108 | 3 | 4-F-Phenyl | 1-methyl-1H-pyrazol-4-yl |
| 1109 | 3 | 4-F-Phenyl | 1H-imidazol-4-yl |
| 1110 | 3 | 4-F-Phenyl | 2-furanyl |
| 1111 | 3 | 3-Cl-Phenyl | ethyl |
| 1112 | 3 | 3-Cl-Phenyl | n-propyl |
| 1113 | 3 | 3-Cl-Phenyl | isopropyl |
| 1114 | 3 | 3-Cl-Phenyl | —$CH_2CH(CH_3)_2$ |
| 1115 | 3 | 3-Cl-Phenyl | $CF_3$ |
| 1116 | 3 | 3-Cl-Phenyl | —$CH_2CF_3$ |
| 1117 | 3 | 3-Cl-Phenyl | —$CH_2CH_2CF_3$ |
| 1118 | 3 | 3-Cl-Phenyl | cyclopropyl |
| 1119 | 3 | 3-Cl-Phenyl | Cyclobutyl |
| 1120 | 3 | 3-Cl-Phenyl | cyclopentyl |
| 1121 | 3 | 3-Cl-Phenyl | cyclohexyl |
| 1122 | 3 | 3-Cl-Phenyl | 3-pyridyl |
| 1123 | 3 | 3-Cl-Phenyl | 1-methyl-1H-pyrazol-4-yl |
| 1124 | 3 | 3-Cl-Phenyl | 1H-imidazol-4-yl |
| 1125 | 3 | 3-Cl-Phenyl | 2-furanyl |
| 1126 | 3 | 2-Br-Phenyl | ethyl |
| 1127 | 3 | 2-Br-Phenyl | n-propyl |
| 1128 | 3 | 2-Br-Phenyl | isopropyl |
| 1129 | 3 | 2-Br-Phenyl | —$CH_2CH(CH_3)_2$ |
| 1130 | 3 | 2-Br-Phenyl | $CF_3$ |
| 1131 | 3 | 2-Br-Phenyl | —$CH_2CF_3$ |
| 1132 | 3 | 2-Br-Phenyl | —$CH_2CH_2CF_3$ |
| 1133 | 3 | 2-Br-Phenyl | cyclopropyl |
| 1134 | 3 | 2-Br-Phenyl | Cyclobutyl |
| 1135 | 3 | 2-Br-Phenyl | cyclopentyl |
| 1136 | 3 | 2-Br-Phenyl | cyclohexyl |
| 1137 | 3 | 2-Br-Phenyl | 3-pyridyl |
| 1138 | 3 | 2-Br-Phenyl | 1-methyl-1H-pyrazol-4-yl |
| 1139 | 3 | 2-Br-Phenyl | 1H-imidazol-4-yl |
| 1140 | 3 | 2-Br-Phenyl | 2-furanyl |
| 1141 | 3 | 4-Br-Phenyl | ethyl |
| 1142 | 3 | 4-Br-Phenyl | n-propyl |
| 1143 | 3 | 4-Br-Phenyl | isopropyl |
| 1144 | 3 | 4-Br-Phenyl | —$CH_2CH(CH_3)_2$ |
| 1145 | 3 | 4-Br-Phenyl | $CF_3$ |
| 1146 | 3 | 4-Br-Phenyl | —$CH_2CF_3$ |
| 1147 | 3 | 4-Br-Phenyl | —$CH_2CH_2CF_3$ |
| 1148 | 3 | 4-Br-Phenyl | cyclopropyl |
| 1149 | 3 | 4-Br-Phenyl | Cyclobutyl |
| 1150 | 3 | 4-Br-Phenyl | cyclopentyl |
| 1151 | 3 | 4-Br-Phenyl | cyclohexyl |
| 1152 | 3 | 4-Br-Phenyl | 3-pyridyl |
| 1153 | 3 | 4-Br-Phenyl | 1-methyl-1H-pyrazol-4-yl |
| 1154 | 3 | 4-Br-Phenyl | 1H-imidazol-4-yl |
| 1155 | 3 | 4-Br-Phenyl | 2-furanyl |
| 1156 | 3 | 3-$CF_3$-Phenyl | ethyl |
| 1157 | 3 | 3-$CF_3$-Phenyl | n-propyl |
| 1158 | 3 | 3-$CF_3$-Phenyl | isopropyl |
| 1159 | 3 | 3-$CF_3$-Phenyl | —$CH_2CH(CH_3)_2$ |
| 1160 | 3 | 3-$CF_3$-Phenyl | $CF_3$ |
| 1161 | 3 | 3-$CF_3$-Phenyl | —$CH_2CF_3$ |
| 1162 | 3 | 3-$CF_3$-Phenyl | —$CH_2CH_2CF_3$ |
| 1163 | 3 | 3-$CF_3$-Phenyl | cyclopropyl |
| 1164 | 3 | 3-$CF_3$-Phenyl | Cyclobutyl |
| 1165 | 3 | 3-$CF_3$-Phenyl | cyclopentyl |
| 1166 | 3 | 3-$CF_3$-Phenyl | cyclohexyl |
| 1167 | 3 | 3-$CF_3$-Phenyl | 3-pyridyl |
| 1168 | 3 | 3-$CF_3$-Phenyl | 1-methyl-1H-pyrazol-4-yl |
| 1169 | 3 | 3-$CF_3$-Phenyl | 1H-imidazol-4-yl |
| 1170 | 3 | 3-$CF_3$-Phenyl | 2-furanyl |
| 1171 | 3 | 2-iPr-Phenyl | ethyl |
| 1172 | 3 | 2-iPr-Phenyl | n-propyl |
| 1173 | 3 | 2-iPr-Phenyl | isopropyl |
| 1174 | 3 | 2-iPr-Phenyl | —$CH_2CH(CH_3)_2$ |
| 1175 | 3 | 2-iPr-Phenyl | $CF_3$ |
| 1176 | 3 | 2-iPr-Phenyl | —$CH_2CF_3$ |
| 1177 | 3 | 2-iPr-Phenyl | —$CH_2CH_2CF_3$ |
| 1178 | 3 | 2-iPr-Phenyl | cyclopropyl |
| 1179 | 3 | 2-iPr-Phenyl | Cyclobutyl |
| 1180 | 3 | 2-iPr-Phenyl | cyclopentyl |
| 1181 | 3 | 2-iPr-Phenyl | cyclohexyl |
| 1182 | 3 | 2-iPr-Phenyl | 3-pyridyl |
| 1183 | 3 | 2-iPr-Phenyl | 1-methyl-1H-pyrazol-4-yl |
| 1184 | 3 | 2-iPr-Phenyl | 1H-imidazol-4-yl |
| 1185 | 3 | 2-iPr-Phenyl | 2-furanyl |
| 1186 | 3 | 4-iPr-Phenyl | ethyl |
| 1187 | 3 | 4-iPr-Phenyl | n-propyl |
| 1188 | 3 | 4-iPr-Phenyl | isopropyl |
| 1189 | 3 | 4-iPr-Phenyl | —$CH_2CH(CH_3)_2$ |
| 1190 | 3 | 4-iPr-Phenyl | $CF_3$ |
| 1191 | 3 | 4-iPr-Phenyl | —$CH_2CF_3$ |
| 1192 | 3 | 4-iPr-Phenyl | —$CH_2CH_2CF_3$ |
| 1193 | 3 | 4-iPr-Phenyl | cyclopropyl |
| 1194 | 3 | 4-iPr-Phenyl | Cyclobutyl |
| 1195 | 3 | 4-iPr-Phenyl | cyclopentyl |
| 1196 | 3 | 4-iPr-Phenyl | cyclohexyl |
| 1197 | 3 | 4-iPr-Phenyl | 3-pyridyl |
| 1198 | 3 | 4-iPr-Phenyl | 1-methyl-1H-pyrazol-4-yl |
| 1199 | 3 | 4-iPr-Phenyl | 1H-imidazol-4-yl |
| 1200 | 3 | 4-iPr-Phenyl | 2-furanyl |
| 1201 | 3 | 3-morpholino-phenyl | ethyl |
| 1202 | 3 | 3-morpholino-phenyl | n-propyl |
| 1203 | 3 | 3-morpholino-phenyl | isopropyl |
| 1204 | 3 | 3-morpholino-phenyl | —$CH_2CH(CH_3)_2$ |
| 1205 | 3 | 3-morpholino-phenyl | $CF_3$ |
| 1206 | 3 | 3-morpholino-phenyl | —$CH_2CF_3$ |
| 1207 | 3 | 3-morpholino-phenyl | —$CH_2CH_2CF_3$ |
| 1208 | 3 | 3-morpholino-phenyl | cyclopropyl |
| 1209 | 3 | 3-morpholino-phenyl | Cyclobutyl |
| 1210 | 3 | 3-morpholino-phenyl | cyclopentyl |
| 1211 | 3 | 3-morpholino-phenyl | cyclohexyl |
| 1212 | 3 | 3-morpholino-phenyl | 3-pyridyl |
| 1213 | 3 | 3-morpholino-phenyl | 1-methyl-1H-pyrazol-4-yl |
| 1214 | 3 | 3-morpholino-phenyl | 1H-imidazol-4-yl |
| 1215 | 3 | 3-morpholino-phenyl | 2-furanyl |
| 1216 | 3 | 4-cyano-2-morpholino-phenyl | ethyl |
| 1217 | 3 | 4-cyano-2-morpholino-phenyl | n-propyl |
| 1218 | 3 | 4-cyano-2-morpholino-phenyl | isopropyl |
| 1219 | 3 | 4-cyano-2-morpholino-phenyl | —$CH_2CH(CH_3)_2$ |
| 1220 | 3 | 4-cyano-2-morpholino-phenyl | $CF_3$ |
| 1221 | 3 | 4-cyano-2-morpholino-phenyl | —$CH_2CF_3$ |
| 1222 | 3 | 4-cyano-2-morpholino-phenyl | —$CH_2CH_2CF_3$ |
| 1223 | 3 | 4-cyano-2-morpholino-phenyl | cyclopropyl |
| 1224 | 3 | 4-cyano-2-morpholino-phenyl | Cyclobutyl |
| 1225 | 3 | 4-cyano-2-morpholino-phenyl | cyclopentyl |
| 1226 | 3 | 4-cyano-2-morpholino-phenyl | cyclohexyl |
| 1227 | 3 | 4-cyano-2-morpholino-phenyl | 3-pyridyl |
| 1228 | 3 | 4-cyano-2-morpholino-phenyl | 1-methyl-1H-pyrazol-4-yl |
| 1229 | 3 | 4-cyano-2-morpholino-phenyl | 1H-imidazol-4-yl |
| 1230 | 3 | 4-cyano-2-morpholino-phenyl | 2-furanyl |
| 1231 | 3 | 4-hydroxy-2-morpholino-phenyl | ethyl |

TABLE 32-continued

| Entry | n | $R^4$ | $R^{10c}$ |
|---|---|---|---|
| 1232 | 3 | 4-hydroxy-2-morpholino-phenyl | n-propyl |
| 1233 | 3 | 4-hydroxy-2-morpholino-phenyl | isopropyl |
| 1234 | 3 | 4-hydroxy-2-morpholino-phenyl | $—CH_2CH(CH_3)_2$ |
| 1235 | 3 | 4-hydroxy-2-morpholino-phenyl | $CF_3$ |
| 1236 | 3 | 4-hydroxy-2-morpholino-phenyl | $—CH_2CF_3$ |
| 1237 | 3 | 4-hydroxy-2-morpholino-phenyl | $—CH_2CH_2CF_3$ |
| 1238 | 3 | 4-hydroxy-2-morpholino-phenyl | cyclopropyl |
| 1239 | 3 | 4-hydroxy-2-morpholino-phenyl | Cyclobutyl |
| 1240 | 3 | 4-hydroxy-2-morpholino-phenyl | cyclopentyl |
| 1241 | 3 | 4-hydroxy-2-morpholino-phenyl | cyclohexyl |
| 1242 | 3 | 4-hydroxy-2-morpholino-phenyl | 3-pyridyl |
| 1243 | 3 | 4-hydroxy-2-morpholino-phenyl | 1-methyl-1H-pyrazol-4-yl |
| 1244 | 3 | 4-hydroxy-2-morpholino-phenyl | 1H-imidazol-4-yl |
| 1245 | 3 | 4-hydroxy-2-morpholino-phenyl | 2-furanyl |
| 1246 | 3 | $2-CH_3$-phenyl | Ethyl |
| 1247 | 3 | $2-CH_3$-phenyl | n-propyl |
| 1248 | 3 | $2-CH_3$-phenyl | Isopropyl |
| 1249 | 3 | $2-CH_3$-phenyl | $—CH_2CH(CH_3)_2$ |
| 1250 | 3 | $2-CH_3$-phenyl | $CF_3$ |
| 1251 | 3 | $2-CH_3$-phenyl | $—CH_2CF_3$ |
| 1252 | 3 | $2-CH_3$-phenyl | $—CH_2CH_2CF_3$ |
| 1253 | 3 | $2-CH_3$-phenyl | cyclopropyl |
| 1254 | 3 | $2-CH_3$-phenyl | Cyclobutyl |
| 1255 | 3 | $2-CH_3$-phenyl | cyclopentyl |
| 1256 | 3 | $2-CH_3$-phenyl | cyclohexyl |
| 1257 | 3 | $2-CH_3$-phenyl | 3-pyridyl |
| 1258 | 3 | $2-CH_3$-phenyl | 1-methyl-1H-pyrazol-4-yl |
| 1259 | 3 | $2-CH_3$-phenyl | 1H-imidazol-4-yl |
| 1260 | 3 | $2-CH_3$-phenyl | 2-furanyl |
| 1261 | 3 | 4-OH-Phenyl | Ethyl |
| 1262 | 3 | 4-OH-Phenyl | n-propyl |
| 1263 | 3 | 4-OH-Phenyl | Isopropyl |
| 1264 | 3 | 4-OH-Phenyl | $—CH_2CH(CH_3)_2$ |
| 1265 | 3 | 4-OH-Phenyl | $CF_3$ |
| 1266 | 3 | 4-OH-Phenyl | $—CH_2CF_3$ |
| 1267 | 3 | 4-OH-Phenyl | $—CH_2CH_2CF_3$ |
| 1268 | 3 | 4-OH-Phenyl | cyclopropyl |
| 1269 | 3 | 4-OH-Phenyl | Cyclobutyl |
| 1270 | 3 | 4-OH-Phenyl | cyclopentyl |
| 1271 | 3 | 4-OH-Phenyl | cyclohexyl |
| 1272 | 3 | 4-OH-Phenyl | 3-pyridyl |
| 1273 | 3 | 4-OH-Phenyl | 1-methyl-1H-pyrazol-4-yl |
| 1274 | 3 | 4-OH-Phenyl | 1H-imidazol-4-yl |
| 1275 | 3 | 4-OH-Phenyl | 2-furanyl |
| 1276 | 3 | 2-OH-Phenyl | Ethyl |
| 1277 | 3 | 2-OH-Phenyl | n-propyl |
| 1278 | 3 | 2-OH-Phenyl | Isopropyl |
| 1279 | 3 | 2-OH-Phenyl | $—CH_2CH(CH_3)_2$ |
| 1280 | 3 | 2-OH-Phenyl | $CF_3$ |
| 1281 | 3 | 2-OH-Phenyl | $—CH_2CF_3$ |
| 1282 | 3 | 2-OH-Phenyl | $—CH_2CH_2CF_3$ |
| 1283 | 3 | 2-OH-Phenyl | cyclopropyl |
| 1284 | 3 | 2-OH-Phenyl | Cyclobutyl |
| 1285 | 3 | 2-OH-Phenyl | cyclopentyl |
| 1286 | 3 | 2-OH-Phenyl | cyclohexyl |
| 1287 | 3 | 2-OH-Phenyl | 3-pyridyl |
| 1288 | 3 | 2-OH-Phenyl | 1-methyl-1H-pyrazol-4-yl |
| 1289 | 3 | 2-OH-Phenyl | 1H-imidazol-4-yl |
| 1290 | 3 | 2-OH-Phenyl | 2-furanyl |
| 1291 | 3 | 3-OMe-Phenyl | Ethyl |
| 1292 | 3 | 3-OMe-Phenyl | n-propyl |
| 1293 | 3 | 3-OMe-Phenyl | Isopropyl |
| 1294 | 3 | 3-OMe-Phenyl | $—CH_2CH(CH_3)_2$ |
| 1295 | 3 | 3-OMe-Phenyl | $CF_3$ |
| 1296 | 3 | 3-OMe-Phenyl | $—CH_2CF_3$ |
| 1297 | 3 | 3-OMe-Phenyl | $—CH_2CH_2CF_3$ |
| 1298 | 3 | 3-OMe-Phenyl | cyclopropyl |
| 1299 | 3 | 3-OMe-Phenyl | Cyclobutyl |
| 1300 | 3 | 3-OMe-Phenyl | cyclopentyl |
| 1301 | 3 | 3-OMe-Phenyl | cyclohexyl |
| 1302 | 3 | 3-OMe-Phenyl | 3-pyridyl |
| 1303 | 3 | 3-OMe-Phenyl | 1-methyl-1H-pyrazol-4-yl |
| 1304 | 3 | 3-OMe-Phenyl | 1H-imidazol-4-yl |
| 1305 | 3 | 3-OMe-Phenyl | 2-furanyl |
| 1306 | 3 | 4-CN-Phenyl | Ethyl |
| 1307 | 3 | 4-CN-Phenyl | n-propyl |
| 1308 | 3 | 4-CN-Phenyl | Isopropyl |
| 1309 | 3 | 4-CN-Phenyl | $—CH_2CH(CH_3)_2$ |
| 1310 | 3 | 4-CN-Phenyl | $CF_3$ |
| 1311 | 3 | 4-CN-Phenyl | $—CH_2CF_3$ |
| 1312 | 3 | 4-CN-Phenyl | $—CH_2CH_2CF_3$ |
| 1313 | 3 | 4-CN-Phenyl | cyclopropyl |
| 1314 | 3 | 4-CN-Phenyl | Cyclobutyl |
| 1315 | 3 | 4-CN-Phenyl | cyclopentyl |
| 1316 | 3 | 4-CN-Phenyl | cyclohexyl |
| 1317 | 3 | 4-CN-Phenyl | 3-pyridyl |
| 1318 | 3 | 4-CN-Phenyl | 1-methyl-1H-pyrazol-4-yl |
| 1319 | 3 | 4-CN-Phenyl | 1H-imidazol-4-yl |
| 1320 | 3 | 4-CN-Phenyl | 2-furanyl |
| 1321 | 3 | 2-CN-Phenyl | Ethyl |
| 1322 | 3 | 2-CN-Phenyl | n-propyl |
| 1323 | 3 | 2-CN-Phenyl | Isopropyl |
| 1324 | 3 | 2-CN-Phenyl | $—CH_2CH(CH_3)_2$ |
| 1325 | 3 | 2-CN-Phenyl | $CF_3$ |
| 1326 | 3 | 2-CN-Phenyl | $—CH_2CF_3$ |
| 1327 | 3 | 2-CN-Phenyl | $—CH_2CH_2CF_3$ |
| 1328 | 3 | 2-CN-Phenyl | cyclopropyl |
| 1329 | 3 | 2-CN-Phenyl | Cyclobutyl |
| 1330 | 3 | 2-CN-Phenyl | cyclopentyl |
| 1331 | 3 | 2-CN-Phenyl | cyclohexyl |
| 1332 | 3 | 2-CN-Phenyl | 3-pyridyl |
| 1333 | 3 | 2-CN-Phenyl | 1-methyl-1H-pyrazol-4-yl |
| 1334 | 3 | 2-CN-Phenyl | 1H-imidazol-4-yl |
| 1335 | 3 | 2-CN-Phenyl | 2-furanyl |
| 1336 | 3 | 3-F-Phenyl | Ethyl |
| 1337 | 3 | 3-F-Phenyl | n-propyl |
| 1338 | 3 | 3-F-Phenyl | Isopropyl |
| 1339 | 3 | 3-F-Phenyl | $—CH_2CH(CH_3)_2$ |
| 1340 | 3 | 3-F-Phenyl | $CF_3$ |
| 1341 | 3 | 3-F-Phenyl | $—CH_2CF_3$ |
| 1342 | 3 | 3-F-Phenyl | $—CH_2CH_2CF_3$ |
| 1343 | 3 | 3-F-Phenyl | cyclopropyl |
| 1344 | 3 | 3-F-Phenyl | Cyclobutyl |
| 1345 | 3 | 3-F-Phenyl | cyclopentyl |
| 1346 | 3 | 3-F-Phenyl | cyclohexyl |
| 1347 | 3 | 3-F-Phenyl | 3-pyridyl |
| 1348 | 3 | 3-F-Phenyl | 1-methyl-1H-pyrazol-4-yl |
| 1349 | 3 | 3-F-Phenyl | 1H-imidazol-4-yl |
| 1350 | 3 | 3-F-Phenyl | 2-furanyl |
| 1351 | 3 | 2-Cl-Phenyl | Ethyl |
| 1352 | 3 | 2-Cl-Phenyl | n-propyl |
| 1353 | 3 | 2-Cl-Phenyl | Isopropyl |
| 1354 | 3 | 2-Cl-Phenyl | $—CH_2CH(CH_3)_2$ |
| 1355 | 3 | 2-Cl-Phenyl | $CF_3$ |
| 1356 | 3 | 2-Cl-Phenyl | $—CH_2CF_3$ |
| 1357 | 3 | 2-Cl-Phenyl | $—CH_2CH_2CF_3$ |
| 1358 | 3 | 2-Cl-Phenyl | cyclopropyl |
| 1359 | 3 | 2-Cl-Phenyl | Cyclobutyl |
| 1360 | 3 | 2-Cl-Phenyl | cyclopentyl |
| 1361 | 3 | 2-Cl-Phenyl | cyclohexyl |
| 1362 | 3 | 2-Cl-Phenyl | 3-pyridyl |
| 1363 | 3 | 2-Cl-Phenyl | 1-methyl-1H-pyrazol-4-yl |
| 1364 | 3 | 2-Cl-Phenyl | 1H-imidazol-4-yl |
| 1365 | 3 | 2-Cl-Phenyl | 2-furanyl |
| 1366 | 3 | 4-Cl-Phenyl | Ethyl |
| 1367 | 3 | 4-Cl-Phenyl | n-propyl |
| 1368 | 3 | 4-Cl-Phenyl | Isopropyl |
| 1369 | 3 | 4-Cl-Phenyl | $—CH_2CH(CH_3)_2$ |
| 1370 | 3 | 4-Cl-Phenyl | $CF_3$ |
| 1371 | 3 | 4-Cl-Phenyl | $—CH_2CF_3$ |
| 1372 | 3 | 4-Cl-Phenyl | $—CH_2CH_2CF_3$ |
| 1373 | 3 | 4-Cl-Phenyl | cyclopropyl |
| 1374 | 3 | 4-Cl-Phenyl | Cyclobutyl |
| 1375 | 3 | 4-Cl-Phenyl | cyclopentyl |
| 1376 | 3 | 4-Cl-Phenyl | cyclohexyl |
| 1377 | 3 | 4-Cl-Phenyl | 3-pyridyl |
| 1378 | 3 | 4-Cl-Phenyl | 1-methyl-1H-pyrazol-4-yl |
| 1379 | 3 | 4-Cl-Phenyl | 1H-imidazol-4-yl |
| 1380 | 3 | 4-Cl-Phenyl | 2-furanyl |
| 1381 | 3 | 3-Br-Phenyl | Ethyl |
| 1382 | 3 | 3-Br-Phenyl | n-propyl |
| 1383 | 3 | 3-Br-Phenyl | Isopropyl |
| 1384 | 3 | 3-Br-Phenyl | $—CH_2CH(CH_3)_2$ |
| 1385 | 3 | 3-Br-Phenyl | $CF_3$ |
| 1386 | 3 | 3-Br-Phenyl | $—CH_2CF_3$ |
| 1387 | 3 | 3-Br-Phenyl | $—CH_2CH_2CF_3$ |

TABLE 32-continued

| Entry | n | $R^4$ | $R^{10c}$ |
|---|---|---|---|
| 1388 | 3 | 3-Br-Phenyl | cyclopropyl |
| 1389 | 3 | 3-Br-Phenyl | Cyclobutyl |
| 1390 | 3 | 3-Br-Phenyl | cyclopentyl |
| 1391 | 3 | 3-Br-Phenyl | cyclohexyl |
| 1392 | 3 | 3-Br-Phenyl | 3-pyridyl |
| 1393 | 3 | 3-Br-Phenyl | 1-methyl-1H-pyrazol-4-yl |
| 1394 | 3 | 3-Br-Phenyl | 1H-imidazol-4-yl |
| 1395 | 3 | 3-Br-Phenyl | 2-furanyl |
| 1396 | 3 | 2-$CF_3$-Phenyl | Ethyl |
| 1397 | 3 | 2-$CF_3$-Phenyl | n-propyl |
| 1398 | 3 | 2-$CF_3$-Phenyl | Isopropyl |
| 1399 | 3 | 2-$CF_3$-Phenyl | —$CH_2CH(CH_3)_2$ |
| 1400 | 3 | 2-$CF_3$-Phenyl | $CF_3$ |
| 1401 | 3 | 2-$CF_3$-Phenyl | —$CH_2CF_3$ |
| 1402 | 3 | 2-$CF_3$-Phenyl | —$CH_2CH_2CF_3$ |
| 1403 | 3 | 2-$CF_3$-Phenyl | cyclopropyl |
| 1404 | 3 | 2-$CF_3$-Phenyl | Cyclobutyl |
| 1405 | 3 | 2-$CF_3$-Phenyl | cyclopentyl |
| 1406 | 3 | 2-$CF_3$-Phenyl | cyclohexyl |
| 1407 | 3 | 2-$CF_3$-Phenyl | 3-pyridyl |
| 1408 | 3 | 2-$CF_3$-Phenyl | 1-methyl-1H-pyrazol-4-yl |
| 1409 | 3 | 2-$CF_3$-Phenyl | 1H-imidazol-4-yl |
| 1410 | 3 | 2-$CF_3$-Phenyl | 2-furanyl |
| 1411 | 3 | 4-$CF_3$-Phenyl | Ethyl |
| 1412 | 3 | 4-$CF_3$-Phenyl | n-propyl |
| 1413 | 3 | 4-$CF_3$-Phenyl | Isopropyl |
| 1414 | 3 | 4-$CF_3$-Phenyl | —$CH_2CH(CH_3)_2$ |
| 1415 | 3 | 4-$CF_3$-Phenyl | $CF_3$ |
| 1416 | 3 | 4-$CF_3$-Phenyl | —$CH_2CF_3$ |
| 1417 | 3 | 4-$CF_3$-Phenyl | —$CH_2CH_2CF_3$ |
| 1418 | 3 | 4-$CF_3$-Phenyl | cyclopropyl |
| 1419 | 3 | 4-$CF_3$-Phenyl | Cyclobutyl |
| 1420 | 3 | 4-$CF_3$-Phenyl | cyclopentyl |
| 1421 | 3 | 4-$CF_3$-Phenyl | cyclohexyl |
| 1422 | 3 | 4-$CF_3$-Phenyl | 3-pyridyl |
| 1423 | 3 | 4-$CF_3$-Phenyl | 1-methyl-1H-pyrazol-4-yl |
| 1424 | 3 | 4-$CF_3$-Phenyl | 1H-imidazol-4-yl |
| 1425 | 3 | 4-$CF_3$-Phenyl | 2-furanyl |
| 1426 | 3 | 3-iPr-Phenyl | Ethyl |
| 1427 | 3 | 3-iPr-Phenyl | n-propyl |
| 1428 | 3 | 3-iPr-Phenyl | Isopropyl |
| 1429 | 3 | 3-iPr-Phenyl | —$CH_2CH(CH_3)_2$ |
| 1430 | 3 | 3-iPr-Phenyl | $CF_3$ |
| 1431 | 3 | 3-iPr-Phenyl | —$CH_2CF_3$ |
| 1432 | 3 | 3-iPr-Phenyl | —$CH_2CH_2CF_3$ |
| 1433 | 3 | 3-iPr-Phenyl | cyclopropyl |
| 1434 | 3 | 3-iPr-Phenyl | Cyclobutyl |
| 1435 | 3 | 3-iPr-Phenyl | cyclopentyl |
| 1436 | 3 | 3-iPr-Phenyl | cyclohexyl |
| 1437 | 3 | 3-iPr-Phenyl | 3-pyridyl |
| 1438 | 3 | 3-iPr-Phenyl | 1-methyl-1H-pyrazol-4-yl |
| 1439 | 3 | 3-iPr-Phenyl | 1H-imidazol-4-yl |
| 1440 | 3 | 3-iPr-Phenyl | 2-furanyl |
| 1441 | 3 | 2-morpholino-phenyl | Ethyl |
| 1442 | 3 | 2-morpholino-phenyl | n-propyl |
| 1443 | 3 | 2-morpholino-phenyl | isopropyl |
| 1444 | 3 | 2-morpholino-phenyl | —$CH_2CH(CH_3)_2$ |
| 1445 | 3 | 2-morpholino-phenyl | $CF_3$ |
| 1446 | 3 | 2-morpholino-phenyl | —$CH_2CF_3$ |
| 1447 | 3 | 2-morpholino-phenyl | —$CH_2CH_2CF_3$ |
| 1448 | 3 | 2-morpholino-phenyl | cyclopropyl |
| 1449 | 3 | 2-morpholino-phenyl | Cyclobutyl |
| 1450 | 3 | 2-morpholino-phenyl | cyclopentyl |
| 1451 | 3 | 2-morpholino-phenyl | cyclohexyl |
| 1452 | 3 | 2-morpholino-phenyl | 3-pyridyl |
| 1453 | 3 | 2-morpholino-phenyl | 1-methyl-1H-pyrazol-4-yl |
| 1454 | 3 | 2-morpholino-phenyl | 1H-imidazol-4-yl |
| 1455 | 3 | 2-morpholino-phenyl | 2-furanyl |
| 1456 | 3 | 4-morpholino-phenyl | ethyl |
| 1457 | 3 | 4-morpholino-phenyl | n-propyl |
| 1458 | 3 | 4-morpholino-phenyl | isopropyl |
| 1459 | 3 | 4-morpholino-phenyl | —$CH_2CH(CH_3)_2$ |
| 1460 | 3 | 4-morpholino-phenyl | $CF_3$ |
| 1461 | 3 | 4-morpholino-phenyl | —$CH_2CF_3$ |
| 1462 | 3 | 4-morpholino-phenyl | —$CH_2CH_2CF_3$ |
| 1463 | 3 | 4-morpholino-phenyl | cyclopropyl |
| 1464 | 3 | 4-morpholino-phenyl | Cyclobutyl |
| 1465 | 3 | 4-morpholino-phenyl | cyclopentyl |

TABLE 32-continued

| Entry | n | $R^4$ | $R^{10c}$ |
|---|---|---|---|
| 1466 | 3 | 4-morpholino-phenyl | cyclohexyl |
| 1467 | 3 | 4-morpholino-phenyl | 3-pyridyl |
| 1468 | 3 | 4-morpholino-phenyl | 1-methyl-1H-pyrazol-4-yl |
| 1469 | 3 | 4-morpholino-phenyl | 1H-imidazol-4-yl |
| 1470 | 3 | 4-morpholino-phenyl | 2-furanyl |
| 1471 | 3 | 4-methyl-2-morpholino-phenyl | ethyl |
| 1472 | 3 | 4-methyl-2-morpholino-phenyl | n-propyl |
| 1473 | 3 | 4-methyl-2-morpholino-phenyl | isopropyl |
| 1474 | 3 | 4-methyl-2-morpholino-phenyl | —$CH_2CH(CH_3)_2$ |
| 1475 | 3 | 4-methyl-2-morpholino-phenyl | $CF_3$ |
| 1476 | 3 | 4-methyl-2-morpholino-phenyl | —$CH_2CF_3$ |
| 1477 | 3 | 4-methyl-2-morpholino-phenyl | —$CH_2CH_2CF_3$ |
| 1478 | 3 | 4-methyl-2-morpholino-phenyl | cyclopropyl |
| 1479 | 3 | 4-methyl-2-morpholino-phenyl | Cyclobutyl |
| 1480 | 3 | 4-methyl-2-morpholino-phenyl | cyclopentyl |
| 1481 | 3 | 4-methyl-2-morpholino-phenyl | cyclohexyl |
| 1482 | 3 | 4-methyl-2-morpholino-phenyl | 3-pyridyl |
| 1483 | 3 | 4-methyl-2-morpholino-phenyl | 1-methyl-1H-pyrazol-4-yl |
| 1484 | 3 | 4-methyl-2-morpholino-phenyl | 1H-imidazol-4-yl |
| 1485 | 3 | 4-methyl-2-morpholino-phenyl | 2-furanyl |
| 1486 | 4 | 4-$CH_3$-phenyl | ethyl |
| 1487 | 4 | 4-$CH_3$-phenyl | n-propyl |
| 1488 | 4 | 4-$CH_3$-phenyl | isopropyl |
| 1489 | 4 | 4-$CH_3$-phenyl | —$CH_2CH(CH_3)_2$ |
| 1490 | 4 | 4-$CH_3$-phenyl | $CF_3$ |
| 1491 | 4 | 4-$CH_3$-phenyl | —$CH_2CF_3$ |
| 1492 | 4 | 4-$CH_3$-phenyl | —$CH_2CH_2CF_3$ |
| 1493 | 4 | 4-$CH_3$-phenyl | cyclopropyl |
| 1494 | 4 | 4-$CH_3$-phenyl | Cyclobutyl |
| 1495 | 4 | 4-$CH_3$-phenyl | cyclopentyl |
| 1496 | 4 | 4-$CH_3$-phenyl | cyclohexyl |
| 1497 | 4 | 4-$CH_3$-phenyl | 3-pyridyl |
| 1498 | 4 | 4-$CH_3$-phenyl | 1-methyl-1H-pyrazol-4-yl |
| 1499 | 4 | 4-$CH_3$-phenyl | 1H-imidazol-4-yl |
| 1500 | 4 | 4-$CH_3$-phenyl | 2-furanyl |
| 1501 | 4 | 3-$CH_3$-phenyl | ethyl |
| 1502 | 4 | 3-$CH_3$-phenyl | n-propyl |
| 1503 | 4 | 3-$CH_3$-phenyl | isopropyl |
| 1504 | 4 | 3-$CH_3$-phenyl | —$CH_2CH(CH_3)_2$ |
| 1505 | 4 | 3-$CH_3$-phenyl | $CF_3$ |
| 1506 | 4 | 3-$CH_3$-phenyl | —$CH_2CF_3$ |
| 1507 | 4 | 3-$CH_3$-phenyl | —$CH_2CH_2CF_3$ |
| 1508 | 4 | 3-$CH_3$-phenyl | cyclopropyl |
| 1509 | 4 | 3-$CH_3$-phenyl | Cyclobutyl |
| 1510 | 4 | 3-$CH_3$-phenyl | cyclopentyl |
| 1511 | 4 | 3-$CH_3$-phenyl | cyclohexyl |
| 1512 | 4 | 3-$CH_3$-phenyl | 3-pyridyl |
| 1513 | 4 | 3-$CH_3$-phenyl | 1-methyl-1H-pyrazol-4-yl |
| 1514 | 4 | 3-$CH_3$-phenyl | 1H-imidazol-4-yl |
| 1515 | 4 | 3-$CH_3$-phenyl | 2-furanyl |
| 1516 | 4 | 3-OH-Phenyl | ethyl |
| 1517 | 4 | 3-OH-Phenyl | n-propyl |
| 1518 | 4 | 3-OH-Phenyl | isopropyl |
| 1519 | 4 | 3-OH-Phenyl | —$CH_2CH(CH_3)_2$ |
| 1520 | 4 | 3-OH-Phenyl | $CF_3$ |
| 1521 | 4 | 3-OH-Phenyl | —$CH_2CF_3$ |
| 1522 | 4 | 3-OH-Phenyl | —$CH_2CH_2CF_3$ |
| 1523 | 4 | 3-OH-Phenyl | cyclopropyl |
| 1524 | 4 | 3-OH-Phenyl | Cyclobutyl |
| 1525 | 4 | 3-OH-Phenyl | cyclopentyl |
| 1526 | 4 | 3-OH-Phenyl | cyclohexyl |
| 1527 | 4 | 3-OH-Phenyl | 3-pyridyl |
| 1528 | 4 | 3-OH-Phenyl | 1-methyl-1H-pyrazol-4-yl |
| 1529 | 4 | 3-OH-Phenyl | 1H-imidazol-4-yl |
| 1530 | 4 | 3-OH-Phenyl | 2-furanyl |
| 1531 | 4 | 4-OMe-Phenyl | ethyl |
| 1532 | 4 | 4-OMe-Phenyl | n-propyl |
| 1533 | 4 | 4-OMe-Phenyl | isopropyl |
| 1534 | 4 | 4-OMe-Phenyl | —$CH_2CH(CH_3)_2$ |
| 1535 | 4 | 4-OMe-Phenyl | $CF_3$ |
| 1536 | 4 | 4-OMe-Phenyl | —$CH_2CF_3$ |
| 1537 | 4 | 4-OMe-Phenyl | —$CH_2CH_2CF_3$ |
| 1538 | 4 | 4-OMe-Phenyl | cyclopropyl |
| 1539 | 4 | 4-OMe-Phenyl | Cyclobutyl |
| 1540 | 4 | 4-OMe-Phenyl | cyclopentyl |
| 1541 | 4 | 4-OMe-Phenyl | cyclohexyl |
| 1542 | 4 | 4-OMe-Phenyl | 3-pyridyl |
| 1543 | 4 | 4-OMe-Phenyl | 1-methyl-1H-pyrazol-4-yl |

TABLE 32-continued

| Entry | n | $R^4$ | $R^{10c}$ |
|---|---|---|---|
| 1544 | 4 | 4-OMe-Phenyl | 1H-imidazol-4-yl |
| 1545 | 4 | 4-OMe-Phenyl | 2-furanyl |
| 1546 | 4 | 2-OMe-Phenyl | ethyl |
| 1547 | 4 | 2-OMe-Phenyl | n-propyl |
| 1548 | 4 | 2-OMe-Phenyl | isopropyl |
| 1549 | 4 | 2-OMe-Phenyl | $—CH_2CH(CH_3)_2$ |
| 1550 | 4 | 2-OMe-Phenyl | $CF_3$ |
| 1551 | 4 | 2-OMe-Phenyl | $—CH_2CF_3$ |
| 1552 | 4 | 2-OMe-Phenyl | $—CH_2CH_2CF_3$ |
| 1553 | 4 | 2-OMe-Phenyl | cyclopropyl |
| 1554 | 4 | 2-OMe-Phenyl | Cyclobutyl |
| 1555 | 4 | 2-OMe-Phenyl | cyclopentyl |
| 1556 | 4 | 2-OMe-Phenyl | cyclohexyl |
| 1557 | 4 | 2-OMe-Phenyl | 3-pyridyl |
| 1558 | 4 | 2-OMe-Phenyl | 1-methyl-1H-pyrazol-4-yl |
| 1559 | 4 | 2-OMe-Phenyl | 1H-imidazol-4-yl |
| 1560 | 4 | 2-OMe-Phenyl | 2-furanyl |
| 1561 | 4 | 3-CN-Phenyl | ethyl |
| 1562 | 4 | 3-CN-Phenyl | n-propyl |
| 1563 | 4 | 3-CN-Phenyl | isopropyl |
| 1564 | 4 | 3-CN-Phenyl | $—CH_2CH(CH_3)_2$ |
| 1565 | 4 | 3-CN-Phenyl | $CF_3$ |
| 1566 | 4 | 3-CN-Phenyl | $—CH_2CF_3$ |
| 1567 | 4 | 3-CN-Phenyl | $—CH_2CH_2CF_3$ |
| 1568 | 4 | 3-CN-Phenyl | cyclopropyl |
| 1569 | 4 | 3-CN-Phenyl | Cyclobutyl |
| 1570 | 4 | 3-CN-Phenyl | cyclopentyl |
| 1571 | 4 | 3-CN-Phenyl | cyclohexyl |
| 1572 | 4 | 3-CN-Phenyl | 3-pyridyl |
| 1573 | 4 | 3-CN-Phenyl | 1-methyl-1H-pyrazol-4-yl |
| 1574 | 4 | 3-CN-Phenyl | 1H-imidazol-4-yl |
| 1575 | 4 | 3-CN-Phenyl | 2-furanyl |
| 1576 | 4 | 2-F-Phenyl | ethyl |
| 1577 | 4 | 2-F-Phenyl | n-propyl |
| 1578 | 4 | 2-F-Phenyl | isopropyl |
| 1579 | 4 | 2-F-Phenyl | $—CH_2CH(CH_3)_2$ |
| 1580 | 4 | 2-F-Phenyl | $CF_3$ |
| 1581 | 4 | 2-F-Phenyl | $—CH_2CF_3$ |
| 1582 | 4 | 2-F-Phenyl | $—CH_2CH_2CF_3$ |
| 1583 | 4 | 2-F-Phenyl | cyclopropyl |
| 1584 | 4 | 2-F-Phenyl | Cyclobutyl |
| 1585 | 4 | 2-F-Phenyl | cyclopentyl |
| 1586 | 4 | 2-F-Phenyl | cyclohexyl |
| 1587 | 4 | 2-F-Phenyl | 3-pyridyl |
| 1588 | 4 | 2-F-Phenyl | 1-methyl-1H-pyrazol-4-yl |
| 1589 | 4 | 2-F-Phenyl | 1H-imidazol-4-yl |
| 1590 | 4 | 2-F-Phenyl | 2-furanyl |
| 1591 | 4 | 4-F-Phenyl | ethyl |
| 1592 | 4 | 4-F-Phenyl | n-propyl |
| 1593 | 4 | 4-F-Phenyl | isopropyl |
| 1594 | 4 | 4-F-Phenyl | $—CH_2CH(CH_3)_2$ |
| 1595 | 4 | 4-F-Phenyl | $CF_3$ |
| 1596 | 4 | 4-F-Phenyl | $—CH_2CF_3$ |
| 1597 | 4 | 4-F-Phenyl | $—CH_2CH_2CF_3$ |
| 1598 | 4 | 4-F-Phenyl | cyclopropyl |
| 1599 | 4 | 4-F-Phenyl | Cyclobutyl |
| 1600 | 4 | 4-F-Phenyl | cyclopentyl |
| 1601 | 4 | 4-F-Phenyl | cyclohexyl |
| 1602 | 4 | 4-F-Phenyl | 3-pyridyl |
| 1603 | 4 | 4-F-Phenyl | 1-methyl-1H-pyrazol-4-yl |
| 1604 | 4 | 4-F-Phenyl | 1H-imidazol-4-yl |
| 1605 | 4 | 4-F-Phenyl | 2-furanyl |
| 1606 | 4 | 3-Cl-Phenyl | ethyl |
| 1607 | 4 | 3-Cl-Phenyl | n-propyl |
| 1608 | 4 | 3-Cl-Phenyl | isopropyl |
| 1609 | 4 | 3-Cl-Phenyl | $—CH_2CH(CH_3)_2$ |
| 1610 | 4 | 3-Cl-Phenyl | $CF_3$ |
| 1611 | 4 | 3-Cl-Phenyl | $—CH_2CF_3$ |
| 1612 | 4 | 3-Cl-Phenyl | $—CH_2CH_2CF_3$ |
| 1613 | 4 | 3-Cl-Phenyl | cyclopropyl |
| 1614 | 4 | 3-Cl-Phenyl | Cyclobutyl |
| 1615 | 4 | 3-Cl-Phenyl | cyclopentyl |
| 1616 | 4 | 3-Cl-Phenyl | cyclohexyl |
| 1617 | 4 | 3-Cl-Phenyl | 3-pyridyl |
| 1618 | 4 | 3-Cl-Phenyl | 1-methyl-1H-pyrazol-4-yl |
| 1619 | 4 | 3-Cl-Phenyl | 1H-imidazol-4-yl |
| 1620 | 4 | 3-Cl-Phenyl | 2-furanyl |
| 1621 | 4 | 2-Br-Phenyl | ethyl |

TABLE 32-continued

| Entry | n | $R^4$ | $R^{10c}$ |
|---|---|---|---|
| 1622 | 4 | 2-Br-Phenyl | n-propyl |
| 1623 | 4 | 2-Br-Phenyl | isopropyl |
| 1624 | 4 | 2-Br-Phenyl | $—CH_2CH(CH_3)_2$ |
| 1625 | 4 | 2-Br-Phenyl | $CF_3$ |
| 1626 | 4 | 2-Br-Phenyl | $—CH_2CF_3$ |
| 1627 | 4 | 2-Br-Phenyl | $—CH_2CH_2CF_3$ |
| 1628 | 4 | 2-Br-Phenyl | cyclopropyl |
| 1629 | 4 | 2-Br-Phenyl | Cyclobutyl |
| 1630 | 4 | 2-Br-Phenyl | cyclopentyl |
| 1631 | 4 | 2-Br-Phenyl | cyclohexyl |
| 1632 | 4 | 2-Br-Phenyl | 3-pyridyl |
| 1633 | 4 | 2-Br-Phenyl | 1-methyl-1H-pyrazol-4-yl |
| 1634 | 4 | 2-Br-Phenyl | 1H-imidazol-4-yl |
| 1635 | 4 | 2-Br-Phenyl | 2-furanyl |
| 1636 | 4 | 4-Br-Phenyl | ethyl |
| 1637 | 4 | 4-Br-Phenyl | n-propyl |
| 1638 | 4 | 4-Br-Phenyl | isopropyl |
| 1639 | 4 | 4-Br-Phenyl | $—CH_2CH(CH_3)_2$ |
| 1640 | 4 | 4-Br-Phenyl | $CF_3$ |
| 1641 | 4 | 4-Br-Phenyl | $—CH_2CF_3$ |
| 1642 | 4 | 4-Br-Phenyl | $—CH_2CH_2CF_3$ |
| 1643 | 4 | 4-Br-Phenyl | cyclopropyl |
| 1644 | 4 | 4-Br-Phenyl | Cyclobutyl |
| 1645 | 4 | 4-Br-Phenyl | cyclopentyl |
| 1646 | 4 | 4-Br-Phenyl | cyclohexyl |
| 1647 | 4 | 4-Br-Phenyl | 3-pyridyl |
| 1648 | 4 | 4-Br-Phenyl | 1-methyl-1H-pyrazol-4-yl |
| 1649 | 4 | 4-Br-Phenyl | 1H-imidazol-4-yl |
| 1650 | 4 | 4-Br-Phenyl | 2-furanyl |
| 1651 | 4 | $3-CF_3$-Phenyl | ethyl |
| 1652 | 4 | $3-CF_3$-Phenyl | n-propyl |
| 1653 | 4 | $3-CF_3$-Phenyl | isopropyl |
| 1654 | 4 | $3-CF_3$-Phenyl | $—CH_2CH(CH_3)_2$ |
| 1655 | 4 | $3-CF_3$-Phenyl | $CF_3$ |
| 1656 | 4 | $3-CF_3$-Phenyl | $—CH_2CF_3$ |
| 1657 | 4 | $3-CF_3$-Phenyl | $—CH_2CH_2CF_3$ |
| 1658 | 4 | $3-CF_3$-Phenyl | cyclopropyl |
| 1659 | 4 | $3-CF_3$-Phenyl | Cyclobutyl |
| 1660 | 4 | $3-CF_3$-Phenyl | cyclopentyl |
| 1661 | 4 | $3-CF_3$-Phenyl | cyclohexyl |
| 1662 | 4 | $3-CF_3$-Phenyl | 3-pyridyl |
| 1663 | 4 | $3-CF_3$-Phenyl | 1-methyl-1H-pyrazol-4-yl |
| 1664 | 4 | $3-CF_3$-Phenyl | 1H-imidazol-4-yl |
| 1665 | 4 | $3-CF_3$-Phenyl | 2-furanyl |
| 1666 | 4 | 2-iPr-Phenyl | ethyl |
| 1667 | 4 | 2-iPr-Phenyl | n-propyl |
| 1668 | 4 | 2-iPr-Phenyl | isopropyl |
| 1669 | 4 | 2-iPr-Phenyl | $—CH_2CH(CH_3)_2$ |
| 1670 | 4 | 2-iPr-Phenyl | $CF_3$ |
| 1671 | 4 | 2-iPr-Phenyl | $—CH_2CF_3$ |
| 1672 | 4 | 2-iPr-Phenyl | $—CH_2CH_2CF_3$ |
| 1673 | 4 | 2-iPr-Phenyl | cyclopropyl |
| 1674 | 4 | 2-iPr-Phenyl | Cyclobutyl |
| 1675 | 4 | 2-iPr-Phenyl | cyclopentyl |
| 1676 | 4 | 2-iPr-Phenyl | cyclohexyl |
| 1677 | 4 | 2-iPr-Phenyl | 3-pyridyl |
| 1678 | 4 | 2-iPr-Phenyl | 1-methyl-1H-pyrazol-4-yl |
| 1679 | 4 | 2-iPr-Phenyl | 1H-imidazol-4-yl |
| 1680 | 4 | 2-iPr-Phenyl | 2-furanyl |
| 1681 | 4 | 4-iPr-Phenyl | ethyl |
| 1682 | 4 | 4-iPr-Phenyl | n-propyl |
| 1683 | 4 | 4-iPr-Phenyl | isopropyl |
| 1684 | 4 | 4-iPr-Phenyl | $—CH_2CH(CH_3)_2$ |
| 1685 | 4 | 4-iPr-Phenyl | $CF_3$ |
| 1686 | 4 | 4-iPr-Phenyl | $—CH_2CF_3$ |
| 1687 | 4 | 4-iPr-Phenyl | $—CH_2CH_2CF_3$ |
| 1688 | 4 | 4-iPr-Phenyl | cyclopropyl |
| 1689 | 4 | 4-iPr-Phenyl | Cyclobutyl |
| 1690 | 4 | 4-iPr-Phenyl | cyclopentyl |
| 1691 | 4 | 4-iPr-Phenyl | cyclohexyl |
| 1692 | 4 | 4-iPr-Phenyl | 3-pyridyl |
| 1693 | 4 | 4-iPr-Phenyl | 1-methyl-1H-pyrazol-4-yl |
| 1694 | 4 | 4-iPr-Phenyl | 1H-imidazol-4-yl |
| 1695 | 4 | 4-iPr-Phenyl | 2-furanyl |
| 1696 | 4 | 3-morpholino-phenyl | ethyl |
| 1697 | 4 | 3-morpholino-phenyl | n-propyl |
| 1698 | 4 | 3-morpholino-phenyl | isopropyl |
| 1699 | 4 | 3-morpholino-phenyl | $—CH_2CH(CH_3)_2$ |

TABLE 32-continued

| Entry | n | $R^4$ | $R^{10c}$ |
|---|---|---|---|
| 1700 | 4 | 3-morpholino-phenyl | $CF_3$ |
| 1701 | 4 | 3-morpholino-phenyl | $—CH_2CF_3$ |
| 1702 | 4 | 3-morpholino-phenyl | $—CH_2CH_2CF_3$ |
| 1703 | 4 | 3-morpholino-phenyl | cyclopropyl |
| 1704 | 4 | 3-morpholino-phenyl | Cyclobutyl |
| 1705 | 4 | 3-morpholino-phenyl | cyclopentyl |
| 1706 | 4 | 3-morpholino-phenyl | cyclohexyl |
| 1707 | 4 | 3-morpholino-phenyl | 3-pyridyl |
| 1708 | 4 | 3-morpholino-phenyl | 1-methyl-1H-pyrazol-4-yl |
| 1709 | 4 | 3-morpholino-phenyl | 1H-imidazol-4-yl |
| 1710 | 4 | 3-morpholino-phenyl | 2-furanyl |
| 1711 | 4 | 4-cyano-2-morpholino-phenyl | ethyl |
| 1712 | 4 | 4-cyano-2-morpholino-phenyl | n-propyl |
| 1713 | 4 | 4-cyano-2-morpholino-phenyl | isopropyl |
| 1714 | 4 | 4-cyano-2-morpholino-phenyl | $—CH_2CH(CH_3)_2$ |
| 1715 | 4 | 4-cyano-2-morpholino-phenyl | $CF_3$ |
| 1716 | 4 | 4-cyano-2-morpholino-phenyl | $—CH_2CF_3$ |
| 1717 | 4 | 4-cyano-2-morpholino-phenyl | $—CH_2CH_2CF_3$ |
| 1718 | 4 | 4-cyano-2-morpholino-phenyl | cyclopropyl |
| 1719 | 4 | 4-cyano-2-morpholino-phenyl | Cyclobutyl |
| 1720 | 4 | 4-cyano-2-morpholino-phenyl | cyclopentyl |
| 1721 | 4 | 4-cyano-2-morpholino-phenyl | cyclohexyl |
| 1722 | 4 | 4-cyano-2-morpholino-phenyl | 3-pyridyl |
| 1723 | 4 | 4-cyano-2-morpholino-phenyl | 1-methyl-1H-pyrazol-4-yl |
| 1724 | 4 | 4-cyano-2-morpholino-phenyl | 1H-imidazol-4-yl |
| 1725 | 4 | 4-cyano-2-morpholino-phenyl | 2-furanyl |
| 1726 | 4 | 4-hydroxy-2-morpholino-phenyl | ethyl |
| 1727 | 4 | 4-hydroxy-2-morpholino-phenyl | n-propyl |
| 1728 | 4 | 4-hydroxy-2-morpholino-phenyl | isopropyl |
| 1729 | 4 | 4-hydroxy-2-morpholino-phenyl | $—CH_2CH(CH_3)_2$ |
| 1730 | 4 | 4-hydroxy-2-morpholino-phenyl | $CF_3$ |
| 1731 | 4 | 4-hydroxy-2-morpholino-phenyl | $—CH_2CF_3$ |
| 1732 | 4 | 4-hydroxy-2-morpholino-phenyl | $—CH_2CH_2CF_3$ |
| 1733 | 4 | 4-hydroxy-2-morpholino-phenyl | cyclopropyl |
| 1734 | 4 | 4-hydroxy-2-morpholino-phenyl | Cyclobutyl |
| 1735 | 4 | 4-hydroxy-2-morpholino-phenyl | cyclopentyl |
| 1736 | 4 | 4-hydroxy-2-morpholino-phenyl | cyclohexyl |
| 1737 | 4 | 4-hydroxy-2-morpholino-phenyl | 3-pyridyl |
| 1738 | 4 | 4-hydroxy-2-morpholino-phenyl | 1-methyl-1H-pyrazol-4-yl |
| 1739 | 4 | 4-hydroxy-2-morpholino-phenyl | 1H-imidazol-4-yl |
| 1740 | 4 | 4-hydroxy-2-morpholino-phenyl | 2-furanyl |
| 1741 | 4 | $2-CH_3$-phenyl | Ethyl |
| 1742 | 4 | $2-CH_3$-phenyl | n-propyl |
| 1743 | 4 | $2-CH_3$-phenyl | Isopropyl |
| 1744 | 4 | $2-CH_3$-phenyl | $—CH_2CH(CH_3)_2$ |
| 1745 | 4 | $2-CH_3$-phenyl | $CF_3$ |
| 1746 | 4 | $2-CH_3$-phenyl | $—CH_2CF_3$ |
| 1747 | 4 | $2-CH_3$-phenyl | $—CH_2CH_2CF_3$ |
| 1748 | 4 | $2-CH_3$-phenyl | cyclopropyl |
| 1749 | 4 | $2-CH_3$-phenyl | Cyclobutyl |
| 1750 | 4 | $2-CH_3$-phenyl | cyclopentyl |
| 1751 | 4 | $2-CH_3$-phenyl | cyclohexyl |
| 1752 | 4 | $2-CH_3$-phenyl | 3-pyridyl |
| 1753 | 4 | $2-CH_3$-phenyl | 1-methyl-1H-pyrazol-4-yl |
| 1754 | 4 | $2-CH_3$-phenyl | 1H-imidazol-4-yl |
| 1755 | 4 | $2-CH_3$-phenyl | 2-furanyl |
| 1756 | 4 | 4-OH-Phenyl | Ethyl |
| 1757 | 4 | 4-OH-Phenyl | n-propyl |
| 1758 | 4 | 4-OH-Phenyl | Isopropyl |
| 1759 | 4 | 4-OH-Phenyl | $—CH_2CH(CH_3)_2$ |
| 1760 | 4 | 4-OH-Phenyl | $CF_3$ |
| 1761 | 4 | 4-OH-Phenyl | $—CH_2CF_3$ |
| 1762 | 4 | 4-OH-Phenyl | $—CH_2CH_2CF_3$ |
| 1763 | 4 | 4-OH-Phenyl | cyclopropyl |
| 1764 | 4 | 4-OH-Phenyl | Cyclobutyl |
| 1765 | 4 | 4-OH-Phenyl | cyclopentyl |
| 1766 | 4 | 4-OH-Phenyl | cyclohexyl |
| 1767 | 4 | 4-OH-Phenyl | 3-pyridyl |
| 1768 | 4 | 4-OH-Phenyl | 1-methyl-1H-pyrazol-4-yl |
| 1769 | 4 | 4-OH-Phenyl | 1H-imidazol-4-yl |
| 1770 | 4 | 4-OH-Phenyl | 2-furanyl |
| 1771 | 4 | 2-OH-Phenyl | Ethyl |
| 1772 | 4 | 2-OH-Phenyl | n-propyl |
| 1773 | 4 | 2-OH-Phenyl | Isopropyl |
| 1774 | 4 | 2-OH-Phenyl | $—CH_2CH(CH_3)_2$ |
| 1775 | 4 | 2-OH-Phenyl | $CF_3$ |
| 1776 | 4 | 2-OH-Phenyl | $—CH_2CF_3$ |
| 1777 | 4 | 2-OH-Phenyl | $—CH_2CH_2CF_3$ |

TABLE 32-continued

| Entry | n | $R^4$ | $R^{10c}$ |
|---|---|---|---|
| 1778 | 4 | 2-OH-Phenyl | cyclopropyl |
| 1779 | 4 | 2-OH-Phenyl | Cyclobutyl |
| 1780 | 4 | 2-OH-Phenyl | cyclopentyl |
| 1781 | 4 | 2-OH-Phenyl | cyclohexyl |
| 1782 | 4 | 2-OH-Phenyl | 3-pyridyl |
| 1783 | 4 | 2-OH-Phenyl | 1-methyl-1H-pyrazol-4-yl |
| 1784 | 4 | 2-OH-Phenyl | 1H-imidazol-4-yl |
| 1785 | 4 | 2-OH-Phenyl | 2-furanyl |
| 1786 | 4 | 3-OMe-Phenyl | Ethyl |
| 1787 | 4 | 3-OMe-Phenyl | n-propyl |
| 1788 | 4 | 3-OMe-Phenyl | Isopropyl |
| 1789 | 4 | 3-OMe-Phenyl | $—CH_2CH(CH_3)_2$ |
| 1790 | 4 | 3-OMe-Phenyl | $CF_3$ |
| 1791 | 4 | 3-OMe-Phenyl | $—CH_2CF_3$ |
| 1792 | 4 | 3-OMe-Phenyl | $—CH_2CH_2CF_3$ |
| 1793 | 4 | 3-OMe-Phenyl | cyclopropyl |
| 1794 | 4 | 3-OMe-Phenyl | Cyclobutyl |
| 1795 | 4 | 3-OMe-Phenyl | cyclopentyl |
| 1796 | 4 | 3-OMe-Phenyl | cyclohexyl |
| 1797 | 4 | 3-OMe-Phenyl | 3-pyridyl |
| 1798 | 4 | 3-OMe-Phenyl | 1-methyl-1H-pyrazol-4-yl |
| 1799 | 4 | 3-OMe-Phenyl | 1H-imidazol-4-yl |
| 1800 | 4 | 3-OMe-Phenyl | 2-furanyl |
| 1801 | 4 | 4-CN-Phenyl | Ethyl |
| 1802 | 4 | 4-CN-Phenyl | n-propyl |
| 1803 | 4 | 4-CN-Phenyl | Isopropyl |
| 1804 | 4 | 4-CN-Phenyl | $—CH_2CH(CH_3)_2$ |
| 1805 | 4 | 4-CN-Phenyl | $CF_3$ |
| 1806 | 4 | 4-CN-Phenyl | $—CH_2CF_3$ |
| 1807 | 4 | 4-CN-Phenyl | $—CH_2CH_2CF_3$ |
| 1808 | 4 | 4-CN-Phenyl | cyclopropyl |
| 1809 | 4 | 4-CN-Phenyl | Cyclobutyl |
| 1810 | 4 | 4-CN-Phenyl | cyclopentyl |
| 1811 | 4 | 4-CN-Phenyl | cyclohexyl |
| 1812 | 4 | 4-CN-Phenyl | 3-pyridyl |
| 1813 | 4 | 4-CN-Phenyl | 1-methyl-1H-pyrazol-4-yl |
| 1814 | 4 | 4-CN-Phenyl | 1H-imidazol-4-yl |
| 1815 | 4 | 4-CN-Phenyl | 2-furanyl |
| 1816 | 4 | 2-CN-Phenyl | Ethyl |
| 1817 | 4 | 2-CN-Phenyl | n-propyl |
| 1818 | 4 | 2-CN-Phenyl | Isopropyl |
| 1819 | 4 | 2-CN-Phenyl | $—CH_2CH(CH_3)_2$ |
| 1820 | 4 | 2-CN-Phenyl | $CF_3$ |
| 1821 | 4 | 2-CN-Phenyl | $—CH_2CF_3$ |
| 1822 | 4 | 2-CN-Phenyl | $—CH_2CH_2CF_3$ |
| 1823 | 4 | 2-CN-Phenyl | cyclopropyl |
| 1824 | 4 | 2-CN-Phenyl | Cyclobutyl |
| 1825 | 4 | 2-CN-Phenyl | cyclopentyl |
| 1826 | 4 | 2-CN-Phenyl | cyclohexyl |
| 1827 | 4 | 2-CN-Phenyl | 3-pyridyl |
| 1828 | 4 | 2-CN-Phenyl | 1-methyl-1H-pyrazol-4-yl |
| 1829 | 4 | 2-CN-Phenyl | 1H-imidazol-4-yl |
| 1830 | 4 | 2-CN-Phenyl | 2-furanyl |
| 1831 | 4 | 3-F-Phenyl | Ethyl |
| 1832 | 4 | 3-F-Phenyl | n-propyl |
| 1833 | 4 | 3-F-Phenyl | Isopropyl |
| 1834 | 4 | 3-F-Phenyl | $—CH_2CH(CH_3)_2$ |
| 1835 | 4 | 3-F-Phenyl | $CF_3$ |
| 1836 | 4 | 3-F-Phenyl | $—CH_2CF_3$ |
| 1837 | 4 | 3-F-Phenyl | $—CH_2CH_2CF_3$ |
| 1838 | 4 | 3-F-Phenyl | cyclopropyl |
| 1839 | 4 | 3-F-Phenyl | Cyclobutyl |
| 1840 | 4 | 3-F-Phenyl | cyclopentyl |
| 1841 | 4 | 3-F-Phenyl | cyclohexyl |
| 1842 | 4 | 3-F-Phenyl | 3-pyridyl |
| 1843 | 4 | 3-F-Phenyl | 1-methyl-1H-pyrazol-4-yl |
| 1844 | 4 | 3-F-Phenyl | 1H-imidazol-4-yl |
| 1845 | 4 | 3-F-Phenyl | 2-furanyl |
| 1846 | 4 | 2-Cl-Phenyl | Ethyl |
| 1847 | 4 | 2-Cl-Phenyl | n-propyl |
| 1848 | 4 | 2-Cl-Phenyl | Isopropyl |
| 1849 | 4 | 2-Cl-Phenyl | $—CH_2CH(CH_3)_2$ |
| 1850 | 4 | 2-Cl-Phenyl | $CF_3$ |
| 1851 | 4 | 2-Cl-Phenyl | $—CH_2CF_3$ |
| 1852 | 4 | 2-Cl-Phenyl | $—CH_2CH_2CF_3$ |
| 1853 | 4 | 2-Cl-Phenyl | cyclopropyl |
| 1854 | 4 | 2-Cl-Phenyl | Cyclobutyl |
| 1855 | 4 | 2-Cl-Phenyl | cyclopentyl |

TABLE 32-continued

| Entry | n | $R^4$ | $R^{10c}$ |
|---|---|---|---|
| 1856 | 4 | 2-Cl-Phenyl | cyclohexyl |
| 1857 | 4 | 2-Cl-Phenyl | 3-pyridyl |
| 1858 | 4 | 2-Cl-Phenyl | 1-methyl-1H-pyrazol-4-yl |
| 1859 | 4 | 2-Cl-Phenyl | 1H-imidazol-4-yl |
| 1860 | 4 | 2-Cl-Phenyl | 2-furanyl |
| 1861 | 4 | 4-Cl-Phenyl | Ethyl |
| 1862 | 4 | 4-Cl-Phenyl | n-propyl |
| 1863 | 4 | 4-Cl-Phenyl | Isopropyl |
| 1864 | 4 | 4-Cl-Phenyl | $—CH_2CH(CH_3)_2$ |
| 1865 | 4 | 4-Cl-Phenyl | $CF_3$ |
| 1866 | 4 | 4-Cl-Phenyl | $—CH_2CF_3$ |
| 1867 | 4 | 4-Cl-Phenyl | $—CH_2CH_2CF_3$ |
| 1868 | 4 | 4-Cl-Phenyl | cyclopropyl |
| 1869 | 4 | 4-Cl-Phenyl | Cyclobutyl |
| 1870 | 4 | 4-Cl-Phenyl | cyclopentyl |
| 1871 | 4 | 4-Cl-Phenyl | cyclohexyl |
| 1872 | 4 | 4-Cl-Phenyl | 3-pyridyl |
| 1873 | 4 | 4-Cl-Phenyl | 1-methyl-1H-pyrazol-4-yl |
| 1874 | 4 | 4-Cl-Phenyl | 1H-imidazol-4-yl |
| 1875 | 4 | 4-Cl-Phenyl | 2-furanyl |
| 1876 | 4 | 3-Br-Phenyl | Ethyl |
| 1877 | 4 | 3-Br-Phenyl | n-propyl |
| 1878 | 4 | 3-Br-Phenyl | Isopropyl |
| 1879 | 4 | 3-Br-Phenyl | $—CH_2CH(CH_3)_2$ |
| 1880 | 4 | 3-Br-Phenyl | $CF_3$ |
| 1881 | 4 | 3-Br-Phenyl | $—CH_2CF_3$ |
| 1882 | 4 | 3-Br-Phenyl | $—CH_2CH_2CF_3$ |
| 1883 | 4 | 3-Br-Phenyl | cyclopropyl |
| 1884 | 4 | 3-Br-Phenyl | Cyclobutyl |
| 1885 | 4 | 3-Br-Phenyl | cyclopentyl |
| 1886 | 4 | 3-Br-Phenyl | cyclohexyl |
| 1887 | 4 | 3-Br-Phenyl | 3-pyridyl |
| 1888 | 4 | 3-Br-Phenyl | 1-methyl-1H-pyrazol-4-yl |
| 1889 | 4 | 3-Br-Phenyl | 1H-imidazol-4-yl |
| 1890 | 4 | 3-Br-Phenyl | 2-furanyl |
| 1891 | 4 | $2-CF_3$-Phenyl | Ethyl |
| 1892 | 4 | $2-CF_3$-Phenyl | n-propyl |
| 1893 | 4 | $2-CF_3$-Phenyl | Isopropyl |
| 1894 | 4 | $2-CF_3$-Phenyl | $—CH_2CH(CH_3)_2$ |
| 1895 | 4 | $2-CF_3$-Phenyl | $CF_3$ |
| 1896 | 4 | $2-CF_3$-Phenyl | $—CH_2CF_3$ |
| 1897 | 4 | $2-CF_3$-Phenyl | $—CH_2CH_2CF_3$ |
| 1898 | 4 | $2-CF_3$-Phenyl | cyclopropyl |
| 1899 | 4 | $2-CF_3$-Phenyl | Cyclobutyl |
| 1900 | 4 | $2-CF_3$-Phenyl | cyclopentyl |
| 1901 | 4 | $2-CF_3$-Phenyl | cyclohexyl |
| 1902 | 4 | $2-CF_3$-Phenyl | 3-pyridyl |
| 1903 | 4 | $2-CF_3$-Phenyl | 1-methyl-1H-pyrazol-4-yl |
| 1904 | 4 | $2-CF_3$-Phenyl | 1H-imidazol-4-yl |
| 1905 | 4 | $2-CF_3$-Phenyl | 2-furanyl |
| 1906 | 4 | $4-CF_3$-Phenyl | Ethyl |
| 1907 | 4 | $4-CF_3$-Phenyl | n-propyl |
| 1908 | 4 | $4-CF_3$-Phenyl | Isopropyl |
| 1909 | 4 | $4-CF_3$-Phenyl | $—CH_2CH(CH_3)_2$ |
| 1910 | 4 | $4-CF_3$-Phenyl | $CF_3$ |
| 1911 | 4 | $4-CF_3$-Phenyl | $—CH_2CF_3$ |
| 1912 | 4 | $4-CF_3$-Phenyl | $—CH_2CH_2CF_3$ |
| 1913 | 4 | $4-CF_3$-Phenyl | cyclopropyl |
| 1914 | 4 | $4-CF_3$-Phenyl | Cyclobutyl |
| 1915 | 4 | $4-CF_3$-Phenyl | cyclopentyl |
| 1916 | 4 | $4-CF_3$-Phenyl | cyclohexyl |
| 1917 | 4 | $4-CF_3$-Phenyl | 3-pyridyl |
| 1918 | 4 | $4-CF_3$-Phenyl | 1-methyl-1H-pyrazol-4-yl |
| 1919 | 4 | $4-CF_3$-Phenyl | 1H-imidazol-4-yl |
| 1920 | 4 | $4-CF_3$-Phenyl | 2-furanyl |
| 1921 | 4 | 3-iPr-Phenyl | Ethyl |
| 1922 | 4 | 3-iPr-Phenyl | n-propyl |
| 1923 | 4 | 3-iPr-Phenyl | Isopropyl |
| 1924 | 4 | 3-iPr-Phenyl | $—CH_2CH(CH_3)_2$ |
| 1925 | 4 | 3-iPr-Phenyl | $CF_3$ |
| 1926 | 4 | 3-iPr-Phenyl | $—CH_2CF_3$ |
| 1927 | 4 | 3-iPr-Phenyl | $—CH_2CH_2CF_3$ |
| 1928 | 4 | 3-iPr-Phenyl | cyclopropyl |
| 1929 | 4 | 3-iPr-Phenyl | Cyclobutyl |
| 1930 | 4 | 3-iPr-Phenyl | cyclopentyl |
| 1931 | 4 | 3-iPr-Phenyl | cyclohexyl |
| 1932 | 4 | 3-iPr-Phenyl | 3-pyridyl |
| 1933 | 4 | 3-iPr-Phenyl | 1-methyl-1H-pyrazol-4-yl |
| 1934 | 4 | 3-iPr-Phenyl | 1H-imidazol-4-yl |
| 1935 | 4 | 3-iPr-Phenyl | 2-furanyl |
| 1936 | 4 | 2-morpholino-phenyl | Ethyl |
| 1937 | 4 | 2-morpholino-phenyl | n-propyl |
| 1938 | 4 | 2-morpholino-phenyl | isopropyl |
| 1939 | 4 | 2-morpholino-phenyl | $—CH_2CH(CH_3)_2$ |
| 1940 | 4 | 2-morpholino-phenyl | $CF_3$ |
| 1941 | 4 | 2-morpholino-phenyl | $—CH_2CF_3$ |
| 1942 | 4 | 2-morpholino-phenyl | $—CH_2CH_2CF_3$ |
| 1943 | 4 | 2-morpholino-phenyl | cyclopropyl |
| 1944 | 4 | 2-morpholino-phenyl | Cyclobutyl |
| 1945 | 4 | 2-morpholino-phenyl | cyclopentyl |
| 1946 | 4 | 2-morpholino-phenyl | cyclohexyl |
| 1947 | 4 | 2-morpholino-phenyl | 3-pyridyl |
| 1948 | 4 | 2-morpholino-phenyl | 1-methyl-1H-pyrazol-4-yl |
| 1949 | 4 | 2-morpholino-phenyl | 1H-imidazol-4-yl |
| 1950 | 4 | 2-morpholino-phenyl | 2-furanyl |
| 1951 | 4 | 4-morpholino-phenyl | ethyl |
| 1952 | 4 | 4-morpholino-phenyl | n-propyl |
| 1953 | 4 | 4-morpholino-phenyl | isopropyl |
| 1954 | 4 | 4-morpholino-phenyl | $—CH_2CH(CH_3)_2$ |
| 1955 | 4 | 4-morpholino-phenyl | $CF_3$ |
| 1956 | 4 | 4-morpholino-phenyl | $—CH_2CF_3$ |
| 1957 | 4 | 4-morpholino-phenyl | $—CH_2CH_2CF_3$ |
| 1958 | 4 | 4-morpholino-phenyl | cyclopropyl |
| 1959 | 4 | 4-morpholino-phenyl | Cyclobutyl |
| 1960 | 4 | 4-morpholino-phenyl | cyclopentyl |
| 1961 | 4 | 4-morpholino-phenyl | cyclohexyl |
| 1962 | 4 | 4-morpholino-phenyl | 3-pyridyl |
| 1963 | 4 | 4-morpholino-phenyl | 1-methyl-1H-pyrazol-4-yl |
| 1964 | 4 | 4-morpholino-phenyl | 1H-imidazol-4-yl |
| 1965 | 4 | 4-morpholino-phenyl | 2-furanyl |
| 1966 | 4 | 4-methyl-2-morpholino-phenyl | ethyl |
| 1967 | 4 | 4-methyl-2-morpholino-phenyl | n-propyl |
| 1968 | 4 | 4-methyl-2-morpholino-phenyl | isopropyl |
| 1969 | 4 | 4-methyl-2-morpholino-phenyl | $—CH_2CH(CH_3)_2$ |
| 1970 | 4 | 4-methyl-2-morpholino-phenyl | $CF_3$ |
| 1971 | 4 | 4-methyl-2-morpholino-phenyl | $—CH_2CF_3$ |
| 1972 | 4 | 4-methyl-2-morpholino-phenyl | $—CH_2CH_2CF_3$ |
| 1973 | 4 | 4-methyl-2-morpholino-phenyl | cyclopropyl |
| 1974 | 4 | 4-methyl-2-morpholino-phenyl | Cyclobutyl |
| 1975 | 4 | 4-methyl-2-morpholino-phenyl | cyclopentyl |
| 1976 | 4 | 4-methyl-2-morpholino-phenyl | cyclohexyl |
| 1977 | 4 | 4-methyl-2-morpholino-phenyl | 3-pyridyl |
| 1978 | 4 | 4-methyl-2-morpholino-phenyl | 1-methyl-1H-pyrazol-4-yl |
| 1979 | 4 | 4-methyl-2-morpholino-phenyl | 1H-imidazol-4-yl |
| 1980 | 4 | 4-methyl-2-morpholino-phenyl | 2-furanyl |
| 1981 | 1 | naphthylen-1-yl | Ethyl |
| 1982 | 1 | naphthylen-1-yl | n-propyl |
| 1983 | 1 | naphthylen-1-yl | Isopropyl |
| 1984 | 1 | naphthylen-1-yl | $—CH_2CH(CH_3)_2$ |
| 1985 | 1 | naphthylen-1-yl | $CF_3$ |
| 1986 | 1 | naphthylen-1-yl | $—CH_2CF_3$ |
| 1987 | 1 | naphthylen-1-yl | $—CH_2CH_2CF_3$ |
| 1988 | 1 | naphthylen-1-yl | Cyclopropyl |
| 1989 | 1 | naphthylen-1-yl | Cyclobutyl |
| 1990 | 1 | naphthylen-1-yl | Cyclopentyl |
| 1991 | 1 | naphthylen-1-yl | Cyclohexyl |
| 1992 | 1 | naphthylen-1-yl | 3-pyridyl |
| 1993 | 1 | naphthylen-1-yl | 1-methyl-1H-pyrazol-4-yl |
| 1994 | 1 | naphthylen-1-yl | 1H-imidazol-4-yl |
| 1995 | 1 | naphthylen-1-yl | 2-furanyl |
| 1996 | 1 | naphthylen-2-yl | Ethyl |
| 1997 | 1 | naphthylen-2-yl | n-propyl |
| 1998 | 1 | naphthylen-2-yl | Isopropyl |
| 1999 | 1 | naphthylen-2-yl | $—CH_2CH(CH_3)_2$ |
| 2000 | 1 | naphthylen-2-yl | $CF_3$ |
| 2001 | 1 | naphthylen-2-yl | $—CH_2CF_3$ |
| 2002 | 1 | naphthylen-2-yl | $—CH_2CH_2CF_3$ |
| 2003 | 1 | naphthylen-2-yl | Cyclopropyl |
| 2004 | 1 | naphthylen-2-yl | Cyclobutyl |
| 2005 | 1 | naphthylen-2-yl | Cyclopentyl |
| 2006 | 1 | naphthylen-2-yl | Cyclohexyl |
| 2007 | 1 | naphthylen-2-yl | 3-pyridyl |
| 2008 | 1 | naphthylen-2-yl | 1-methyl-1H-pyrazol-4-yl |
| 2009 | 1 | naphthylen-2-yl | 1H-imidazol-4-yl |
| 2010 | 1 | naphthylen-2-yl | 2-furanyl |
| 2011 | 2 | naphthylen-1-yl | Ethyl |

TABLE 32-continued

| Entry | n | $R^4$ | $R^{10c}$ |
|---|---|---|---|
| 2012 | 2 | naphthylen-1-yl | n-propyl |
| 2013 | 2 | naphthylen-1-yl | Isopropyl |
| 2014 | 2 | naphthylen-1-yl | $—CH_2CH(CH_3)_2$ |
| 2015 | 2 | naphthylen-1-yl | $CF_3$ |
| 2016 | 2 | naphthylen-1-yl | $—CH_2CF_3$ |
| 2017 | 2 | naphthylen-1-yl | $—CH_2CH_2CF_3$ |
| 2018 | 2 | naphthylen-1-yl | Cyclopropyl |
| 2019 | 2 | naphthylen-1-yl | Cyclobutyl |
| 2020 | 2 | naphthylen-1-yl | Cyclopentyl |
| 2021 | 2 | naphthylen-1-yl | Cyclohexyl |
| 2022 | 2 | naphthylen-1-yl | 3-pyridyl |
| 2023 | 2 | naphthylen-1-yl | 1-methyl-1H-pyrazol-4-yl |
| 2024 | 2 | naphthylen-1-yl | 1H-imidazol-4-yl |
| 2025 | 2 | naphthylen-1-yl | 2-furanyl |
| 2026 | 2 | naphthylen-2-yl | Ethyl |
| 2027 | 2 | naphthylen-2-yl | n-propyl |
| 2028 | 2 | naphthylen-2-yl | Isopropyl |
| 2029 | 2 | naphthylen-2-yl | $—CH_2CH(CH_3)_2$ |
| 2030 | 2 | naphthylen-2-yl | $CF_3$ |
| 2031 | 2 | naphthylen-2-yl | $—CH_2CF_3$ |
| 2032 | 2 | naphthylen-2-yl | $—CH_2CH_2CF_3$ |
| 2033 | 2 | naphthylen-2-yl | Cyclopropyl |
| 2034 | 2 | naphthylen-2-yl | Cyclobutyl |
| 2035 | 2 | naphthylen-2-yl | Cyclopentyl |
| 2036 | 2 | naphthylen-2-yl | Cyclohexyl |
| 2037 | 2 | naphthylen-2-yl | 3-pyridyl |
| 2038 | 2 | naphthylen-2-yl | 1-methyl-1H-pyrazol-4-yl |
| 2039 | 2 | naphthylen-2-yl | 1H-imidazol-4-yl |
| 2040 | 2 | naphthylen-2-yl | 2-furanyl |
| 2041 | 3 | naphthylen-1-yl | Ethyl |
| 2042 | 3 | naphthylen-1-yl | n-propyl |
| 2043 | 3 | naphthylen-1-yl | Isopropyl |
| 2044 | 3 | naphthylen-1-yl | $—CH_2CH(CH_3)_2$ |
| 2045 | 3 | naphthylen-1-yl | $CF_3$ |
| 2046 | 3 | naphthylen-1-yl | $—CH_2CF_3$ |
| 2047 | 3 | naphthylen-1-yl | $—CH_2CH_2CF_3$ |
| 2048 | 3 | naphthylen-1-yl | Cyclopropyl |
| 2049 | 3 | naphthylen-1-yl | Cyclobutyl |
| 2050 | 3 | naphthylen-1-yl | Cyclopentyl |
| 2051 | 3 | naphthylen-1-yl | Cyclohexyl |
| 2052 | 3 | naphthylen-1-yl | 3-pyridyl |
| 2053 | 3 | naphthylen-1-yl | 1-methyl-1H-pyrazol-4-yl |
| 2054 | 3 | naphthylen-1-yl | 1H-imidazol-4-yl |
| 2055 | 3 | naphthylen-1-yl | 2-furanyl |
| 2056 | 3 | naphthylen-2-yl | Ethyl |
| 2057 | 3 | naphthylen-2-yl | n-propyl |
| 2058 | 3 | naphthylen-2-yl | Isopropyl |
| 2059 | 3 | naphthylen-2-yl | $—CH_2CH(CH_3)_2$ |
| 2060 | 3 | naphthylen-2-yl | $CF_3$ |
| 2061 | 3 | naphthylen-2-yl | $—CH_2CF_3$ |
| 2062 | 3 | naphthylen-2-yl | $—CH_2CH_2CF_3$ |
| 2063 | 3 | naphthylen-2-yl | Cyclopropyl |
| 2064 | 3 | naphthylen-2-yl | Cyclobutyl |
| 2065 | 3 | naphthylen-2-yl | Cyclopentyl |
| 2066 | 3 | naphthylen-2-yl | Cyclohexyl |
| 2067 | 3 | naphthylen-2-yl | 3-pyridyl |
| 2068 | 3 | naphthylen-2-yl | 1-methyl-1H-pyrazol-4-yl |
| 2069 | 3 | naphthylen-2-yl | 1H-imidazol-4-yl |
| 2070 | 3 | naphthylen-2-yl | 2-furanyl |
| 2071 | 4 | naphthylen-1-yl | Ethyl |
| 2072 | 4 | naphthylen-1-yl | n-propyl |
| 2073 | 4 | naphthylen-1-yl | Isopropyl |
| 2074 | 4 | naphthylen-1-yl | $—CH_2CH(CH_3)_2$ |
| 2075 | 4 | naphthylen-1-yl | $CF_3$ |
| 2076 | 4 | naphthylen-1-yl | $—CH_2CF_3$ |
| 2077 | 4 | naphthylen-1-yl | $—CH_2CH_2CF_3$ |
| 2078 | 4 | naphthylen-1-yl | Cyclopropyl |
| 2079 | 4 | naphthylen-1-yl | Cyclobutyl |
| 2080 | 4 | naphthylen-1-yl | Cyclopentyl |
| 2081 | 4 | naphthylen-1-yl | Cyclohexyl |
| 2082 | 4 | naphthylen-1-yl | 3-pyridyl |
| 2083 | 4 | naphthylen-1-yl | 1-methyl-1H-pyrazol-4-yl |
| 2084 | 4 | naphthylen-1-yl | 1H-imidazol-4-yl |
| 2085 | 4 | naphthylen-1-yl | 2-furanyl |
| 2086 | 4 | naphthylen-2-yl | Ethyl |
| 2087 | 4 | naphthylen-2-yl | n-propyl |
| 2088 | 4 | naphthylen-2-yl | Isopropyl |
| 2089 | 4 | naphthylen-2-yl | $—CH_2CH(CH_3)_2$ |
| 2090 | 4 | naphthylen-2-yl | $CF_3$ |
| 2091 | 4 | naphthylen-2-yl | $—CH_2CF_3$ |
| 2092 | 4 | naphthylen-2-yl | $—CH_2CH_2CF_3$ |
| 2093 | 4 | naphthylen-2-yl | Cyclopropyl |
| 2094 | 4 | naphthylen-2-yl | Cyclobutyl |
| 2095 | 4 | naphthylen-2-yl | Cyclopentyl |
| 2096 | 4 | naphthylen-2-yl | Cyclohexyl |
| 2097 | 4 | naphthylen-2-yl | 3-pyridyl |
| 2098 | 4 | naphthylen-2-yl | 1-methyl-1H-pyrazol-4-yl |
| 2099 | 4 | naphthylen-2-yl | 1H-imidazol-4-yl |
| 2100 | 4 | naphthylen-2-yl | 2-furanyl |

Exemplary embodiments include compounds having the formula (XXXX)

(XXXX)

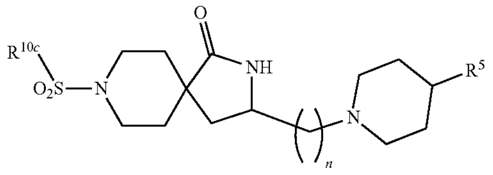

or a pharmaceutically acceptable salt form thereof defined herein below in Table 33.

TABLE 33

| Entry | n | $R^5$ | $R^{10c}$ |
|---|---|---|---|
| 1 | 1 | $4-CH_3$-phenyl | Ethyl |
| 2 | 1 | $4-CH_3$-phenyl | n-propyl |
| 3 | 1 | $4-CH_3$-phenyl | Isopropyl |
| 4 | 1 | $4-CH_3$-phenyl | $—CH_2CH(CH_3)_2$ |
| 5 | 1 | $4-CH_3$-phenyl | $CF_3$ |
| 6 | 1 | $4-CH_3$-phenyl | $—CH_2CF_3$ |
| 7 | 1 | $4-CH_3$-phenyl | $—CH_2CH_2CF_3$ |
| 8 | 1 | $4-CH_3$-phenyl | Cyclopropyl |
| 9 | 1 | $4-CH_3$-phenyl | Cyclobutyl |
| 10 | 1 | $4-CH_3$-phenyl | Cyclopentyl |
| 11 | 1 | $4-CH_3$-phenyl | Cyclohexyl |
| 12 | 1 | $4-CH_3$-phenyl | 3-pyridyl |
| 13 | 1 | $4-CH_3$-phenyl | 1-methyl-1H-pyrazol-4-yl |
| 14 | 1 | $4-CH_3$-phenyl | 1H-imidazol-4-yl |
| 15 | 1 | $4-CH_3$-phenyl | 2-furanyl |
| 16 | 1 | $3-CH_3$-phenyl | Ethyl |
| 17 | 1 | $3-CH_3$-phenyl | n-propyl |
| 18 | 1 | $3-CH_3$-phenyl | Isopropyl |
| 19 | 1 | $3-CH_3$-phenyl | $—CH_2CH(CH_3)_2$ |
| 20 | 1 | $3-CH_3$-phenyl | $CF_3$ |
| 21 | 1 | $3-CH_3$-phenyl | $—CH_2CF_3$ |
| 22 | 1 | $3-CH_3$-phenyl | $—CH_2CH_2CF_3$ |
| 23 | 1 | $3-CH_3$-phenyl | Cyclopropyl |
| 24 | 1 | $3-CH_3$-phenyl | Cyclobutyl |
| 25 | 1 | $3-CH_3$-phenyl | Cyclopentyl |
| 26 | 1 | $3-CH_3$-phenyl | cyclohexyl |
| 27 | 1 | $3-CH_3$-phenyl | 3-pyridyl |
| 28 | 1 | $3-CH_3$-phenyl | 1-methyl-1H-pyrazol-4-yl |
| 29 | 1 | $3-CH_3$-phenyl | 1H-imidazol-4-yl |
| 30 | 1 | $3-CH_3$-phenyl | 2-furanyl |
| 31 | 1 | 3-OH-Phenyl | ethyl |
| 32 | 1 | 3-OH-Phenyl | n-propyl |
| 33 | 1 | 3-OH-Phenyl | isopropyl |
| 34 | 1 | 3-OH-Phenyl | $—CH_2CH(CH_3)_2$ |
| 35 | 1 | 3-OH-Phenyl | $CF_3$ |
| 36 | 1 | 3-OH-Phenyl | $—CH_2CF_3$ |
| 37 | 1 | 3-OH-Phenyl | $—CH_2CH_2CF_3$ |
| 38 | 1 | 3-OH-Phenyl | cyclopropyl |
| 39 | 1 | 3-OH-Phenyl | Cyclobutyl |
| 40 | 1 | 3-OH-Phenyl | cyclopentyl |

TABLE 33-continued

| Entry | n | $R^5$ | $R^{10c}$ |
|---|---|---|---|
| 41 | 1 | 3-OH-Phenyl | cyclohexyl |
| 42 | 1 | 3-OH-Phenyl | 3-pyridyl |
| 43 | 1 | 3-OH-Phenyl | 1-methyl-1H-pyrazol-4-yl |
| 44 | 1 | 3-OH-Phenyl | 1H-imidazol-4-yl |
| 45 | 1 | 3-OH-Phenyl | 2-furanyl |
| 46 | 1 | 4-OMe-Phenyl | ethyl |
| 47 | 1 | 4-OMe-Phenyl | n-propyl |
| 48 | 1 | 4-OMe-Phenyl | isopropyl |
| 49 | 1 | 4-OMe-Phenyl | $—CH_2CH(CH_3)_2$ |
| 50 | 1 | 4-OMe-Phenyl | $CF_3$ |
| 51 | 1 | 4-OMe-Phenyl | $—CH_2CF_3$ |
| 52 | 1 | 4-OMe-Phenyl | $—CH_2CH_2CF_3$ |
| 53 | 1 | 4-OMe-Phenyl | cyclopropyl |
| 54 | 1 | 4-OMe-Phenyl | Cyclobutyl |
| 55 | 1 | 4-OMe-Phenyl | cyclopentyl |
| 56 | 1 | 4-OMe-Phenyl | cyclohexyl |
| 57 | 1 | 4-OMe-Phenyl | 3-pyridyl |
| 58 | 1 | 4-OMe-Phenyl | 1-methyl-1H-pyrazol-4-yl |
| 59 | 1 | 4-OMe-Phenyl | 1H-imidazol-4-yl |
| 60 | 1 | 4-OMe-Phenyl | 2-furanyl |
| 61 | 1 | 2-OMe-Phenyl | ethyl |
| 62 | 1 | 2-OMe-Phenyl | n-propyl |
| 63 | 1 | 2-OMe-Phenyl | isopropyl |
| 64 | 1 | 2-OMe-Phenyl | $—CH_2CH(CH_3)_2$ |
| 65 | 1 | 2-OMe-Phenyl | $CF_3$ |
| 66 | 1 | 2-OMe-Phenyl | $—CH_2CF_3$ |
| 67 | 1 | 2-OMe-Phenyl | $—CH_2CH_2CF_3$ |
| 68 | 1 | 2-OMe-Phenyl | cyclopropyl |
| 69 | 1 | 2-OMe-Phenyl | Cyclobutyl |
| 70 | 1 | 2-OMe-Phenyl | cyclopentyl |
| 71 | 1 | 2-OMe-Phenyl | cyclohexyl |
| 72 | 1 | 2-OMe-Phenyl | 3-pyridyl |
| 73 | 1 | 2-OMe-Phenyl | 1-methyl-1H-pyrazol-4-yl |
| 74 | 1 | 2-OMe-Phenyl | 1H-imidazol-4-yl |
| 75 | 1 | 2-OMe-Phenyl | 2-furanyl |
| 76 | 1 | 3-CN-Phenyl | ethyl |
| 77 | 1 | 3-CN-Phenyl | n-propyl |
| 78 | 1 | 3-CN-Phenyl | isopropyl |
| 79 | 1 | 3-CN-Phenyl | $—CH_2CH(CH_3)_2$ |
| 80 | 1 | 3-CN-Phenyl | $CF_3$ |
| 81 | 1 | 3-CN-Phenyl | $—CH_2CF_3$ |
| 82 | 1 | 3-CN-Phenyl | $—CH_2CH_2CF_3$ |
| 83 | 1 | 3-CN-Phenyl | cyclopropyl |
| 84 | 1 | 3-CN-Phenyl | Cyclobutyl |
| 85 | 1 | 3-CN-Phenyl | cyclopentyl |
| 86 | 1 | 3-CN-Phenyl | cyclohexyl |
| 87 | 1 | 3-CN-Phenyl | 3-pyridyl |
| 88 | 1 | 3-CN-Phenyl | 1-methyl-1H-pyrazol-4-yl |
| 89 | 1 | 3-CN-Phenyl | 1H-imidazol-4-yl |
| 90 | 1 | 3-CN-Phenyl | 2-furanyl |
| 91 | 1 | 2-F-Phenyl | ethyl |
| 92 | 1 | 2-F-Phenyl | n-propyl |
| 93 | 1 | 2-F-Phenyl | isopropyl |
| 94 | 1 | 2-F-Phenyl | $—CH_2CH(CH_3)_2$ |
| 95 | 1 | 2-F-Phenyl | $CF_3$ |
| 96 | 1 | 2-F-Phenyl | $—CH_2CF_3$ |
| 97 | 1 | 2-F-Phenyl | $—CH_2CH_2CF_3$ |
| 98 | 1 | 2-F-Phenyl | cyclopropyl |
| 99 | 1 | 2-F-Phenyl | Cyclobutyl |
| 100 | 1 | 2-F-Phenyl | cyclopentyl |
| 101 | 1 | 2-F-Phenyl | cyclohexyl |
| 102 | 1 | 2-F-Phenyl | 3-pyridyl |
| 103 | 1 | 2-F-Phenyl | 1-methyl-1H-pyrazol-4-yl |
| 104 | 1 | 2-F-Phenyl | 1H-imidazol-4-yl |
| 105 | 1 | 2-F-Phenyl | 2-furanyl |
| 106 | 1 | 4-F-Phenyl | ethyl |
| 107 | 1 | 4-F-Phenyl | n-propyl |
| 108 | 1 | 4-F-Phenyl | isopropyl |
| 109 | 1 | 4-F-Phenyl | $—CH_2CH(CH_3)_2$ |
| 110 | 1 | 4-F-Phenyl | $CF_3$ |
| 111 | 1 | 4-F-Phenyl | $—CH_2CF_3$ |
| 112 | 1 | 4-F-Phenyl | $—CH_2CH_2CF_3$ |
| 113 | 1 | 4-F-Phenyl | cyclopropyl |
| 114 | 1 | 4-F-Phenyl | Cyclobutyl |
| 115 | 1 | 4-F-Phenyl | cyclopentyl |
| 116 | 1 | 4-F-Phenyl | cyclohexyl |
| 117 | 1 | 4-F-Phenyl | 3-pyridyl |
| 118 | 1 | 4-F-Phenyl | 1-methyl-1H-pyrazol-4-yl |
| 119 | 1 | 4-F-Phenyl | 1H-imidazol-4-yl |
| 120 | 1 | 4-F-Phenyl | 2-furanyl |
| 121 | 1 | 3-Cl-Phenyl | ethyl |
| 122 | 1 | 3-Cl-Phenyl | n-propyl |
| 123 | 1 | 3-Cl-Phenyl | isopropyl |
| 124 | 1 | 3-Cl-Phenyl | $—CH_2CH(CH_3)_2$ |
| 125 | 1 | 3-Cl-Phenyl | $CF_3$ |
| 126 | 1 | 3-Cl-Phenyl | $—CH_2CF_3$ |
| 127 | 1 | 3-Cl-Phenyl | $—CH_2CH_2CF_3$ |
| 128 | 1 | 3-Cl-Phenyl | cyclopropyl |
| 129 | 1 | 3-Cl-Phenyl | Cyclobutyl |
| 130 | 1 | 3-Cl-Phenyl | cyclopentyl |
| 131 | 1 | 3-Cl-Phenyl | cyclohexyl |
| 132 | 1 | 3-Cl-Phenyl | 3-pyridyl |
| 133 | 1 | 3-Cl-Phenyl | 1-methyl-1H-pyrazol-4-yl |
| 134 | 1 | 3-Cl-Phenyl | 1H-imidazol-4-yl |
| 135 | 1 | 3-Cl-Phenyl | 2-furanyl |
| 136 | 1 | 2-Br-Phenyl | ethyl |
| 137 | 1 | 2-Br-Phenyl | n-propyl |
| 138 | 1 | 2-Br-Phenyl | isopropyl |
| 139 | 1 | 2-Br-Phenyl | $—CH_2CH(CH_3)_2$ |
| 140 | 1 | 2-Br-Phenyl | $CF_3$ |
| 141 | 1 | 2-Br-Phenyl | $—CH_2CF_3$ |
| 142 | 1 | 2-Br-Phenyl | $—CH_2CH_2CF_3$ |
| 143 | 1 | 2-Br-Phenyl | cyclopropyl |
| 144 | 1 | 2-Br-Phenyl | Cyclobutyl |
| 145 | 1 | 2-Br-Phenyl | cyclopentyl |
| 146 | 1 | 2-Br-Phenyl | cyclohexyl |
| 147 | 1 | 2-Br-Phenyl | 3-pyridyl |
| 148 | 1 | 2-Br-Phenyl | 1-methyl-1H-pyrazol-4-yl |
| 149 | 1 | 2-Br-Phenyl | 1H-imidazol-4-yl |
| 150 | 1 | 2-Br-Phenyl | 2-furanyl |
| 151 | 1 | 4-Br-Phenyl | ethyl |
| 152 | 1 | 4-Br-Phenyl | n-propyl |
| 153 | 1 | 4-Br-Phenyl | isopropyl |
| 154 | 1 | 4-Br-Phenyl | $—CH_2CH(CH_3)_2$ |
| 155 | 1 | 4-Br-Phenyl | $CF_3$ |
| 156 | 1 | 4-Br-Phenyl | $—CH_2CF_3$ |
| 157 | 1 | 4-Br-Phenyl | $—CH_2CH_2CF_3$ |
| 158 | 1 | 4-Br-Phenyl | cyclopropyl |
| 159 | 1 | 4-Br-Phenyl | Cyclobutyl |
| 160 | 1 | 4-Br-Phenyl | cyclopentyl |
| 161 | 1 | 4-Br-Phenyl | cyclohexyl |
| 162 | 1 | 4-Br-Phenyl | 3-pyridyl |
| 163 | 1 | 4-Br-Phenyl | 1-methyl-1H-pyrazol-4-yl |
| 164 | 1 | 4-Br-Phenyl | 1H-imidazol-4-yl |
| 165 | 1 | 4-Br-Phenyl | 2-furanyl |
| 166 | 1 | $3-CF_3$-Phenyl | ethyl |
| 167 | 1 | $3-CF_3$-Phenyl | n-propyl |
| 168 | 1 | $3-CF_3$-Phenyl | isopropyl |
| 169 | 1 | $3-CF_3$-Phenyl | $—CH_2CH(CH_3)_2$ |
| 170 | 1 | $3-CF_3$-Phenyl | $CF_3$ |
| 171 | 1 | $3-CF_3$-Phenyl | $—CH_2CF_3$ |
| 172 | 1 | $3-CF_3$-Phenyl | $—CH_2CH_2CF_3$ |
| 173 | 1 | $3-CF_3$-Phenyl | cyclopropyl |
| 174 | 1 | $3-CF_3$-Phenyl | Cyclobutyl |
| 175 | 1 | $3-CF_3$-Phenyl | cyclopentyl |
| 176 | 1 | $3-CF_3$-Phenyl | cyclohexyl |
| 177 | 1 | $3-CF_3$-Phenyl | 3-pyridyl |
| 178 | 1 | $3-CF_3$-Phenyl | 1-methyl-1H-pyrazol-4-yl |
| 179 | 1 | $3-CF_3$-Phenyl | 1H-imidazol-4-yl |
| 180 | 1 | $3-CF_3$-Phenyl | 2-furanyl |
| 181 | 1 | 2-iPr-Phenyl | ethyl |
| 182 | 1 | 2-iPr-Phenyl | n-propyl |
| 183 | 1 | 2-iPr-Phenyl | isopropyl |
| 184 | 1 | 2-iPr-Phenyl | $—CH_2CH(CH_3)_2$ |
| 185 | 1 | 2-iPr-Phenyl | $CF_3$ |
| 186 | 1 | 2-iPr-Phenyl | $—CH_2CF_3$ |
| 187 | 1 | 2-iPr-Phenyl | $—CH_2CH_2CF_3$ |
| 188 | 1 | 2-iPr-Phenyl | cyclopropyl |
| 189 | 1 | 2-iPr-Phenyl | Cyclobutyl |
| 190 | 1 | 2-iPr-Phenyl | cyclopentyl |
| 191 | 1 | 2-iPr-Phenyl | cyclohexyl |
| 192 | 1 | 2-iPr-Phenyl | 3-pyridyl |
| 193 | 1 | 2-iPr-Phenyl | 1-methyl-1H-pyrazol-4-yl |
| 194 | 1 | 2-iPr-Phenyl | 1H-imidazol-4-yl |
| 195 | 1 | 2-iPr-Phenyl | 2-furanyl |
| 196 | 1 | 4-iPr-Phenyl | ethyl |

TABLE 33-continued

| Entry | n | $R^5$ | $R^{10c}$ |
|---|---|---|---|
| 197 | 1 | 4-iPr-Phenyl | n-propyl |
| 198 | 1 | 4-iPr-Phenyl | isopropyl |
| 199 | 1 | 4-iPr-Phenyl | $—CH_2CH(CH_3)_2$ |
| 200 | 1 | 4-iPr-Phenyl | $CF_3$ |
| 201 | 1 | 4-iPr-Phenyl | $—CH_2CF_3$ |
| 202 | 1 | 4-iPr-Phenyl | $—CH_2CH_2CF_3$ |
| 203 | 1 | 4-iPr-Phenyl | cyclopropyl |
| 204 | 1 | 4-iPr-Phenyl | Cyclobutyl |
| 205 | 1 | 4-iPr-Phenyl | cyclopentyl |
| 206 | 1 | 4-iPr-Phenyl | cyclohexyl |
| 207 | 1 | 4-iPr-Phenyl | 3-pyridyl |
| 208 | 1 | 4-iPr-Phenyl | 1-methyl-1H-pyrazol-4-yl |
| 209 | 1 | 4-iPr-Phenyl | 1H-imidazol-4-yl |
| 210 | 1 | 4-iPr-Phenyl | 2-furanyl |
| 211 | 1 | 3-morpholino-phenyl | ethyl |
| 212 | 1 | 3-morpholino-phenyl | n-propyl |
| 213 | 1 | 3-morpholino-phenyl | isopropyl |
| 214 | 1 | 3-morpholino-phenyl | $—CH_2CH(CH_3)_2$ |
| 215 | 1 | 3-morpholino-phenyl | $CF_3$ |
| 216 | 1 | 3-morpholino-phenyl | $—CH_2CF_3$ |
| 217 | 1 | 3-morpholino-phenyl | $—CH_2CH_2CF_3$ |
| 218 | 1 | 3-morpholino-phenyl | cyclopropyl |
| 219 | 1 | 3-morpholino-phenyl | Cyclobutyl |
| 220 | 1 | 3-morpholino-phenyl | cyclopentyl |
| 221 | 1 | 3-morpholino-phenyl | cyclohexyl |
| 222 | 1 | 3-morpholino-phenyl | 3-pyridyl |
| 223 | 1 | 3-morpholino-phenyl | 1-methyl-1H-pyrazol-4-yl |
| 224 | 1 | 3-morpholino-phenyl | 1H-imidazol-4-yl |
| 225 | 1 | 3-morpholino-phenyl | 2-furanyl |
| 226 | 1 | 4-cyano-2-morpholino-phenyl | ethyl |
| 227 | 1 | 4-cyano-2-morpholino-phenyl | n-propyl |
| 228 | 1 | 4-cyano-2-morpholino-phenyl | isopropyl |
| 229 | 1 | 4-cyano-2-morpholino-phenyl | $—CH2CH(CH_3)_2$ |
| 230 | 1 | 4-cyano-2-morpholino-phenyl | $CF_3$ |
| 231 | 1 | 4-cyano-2-morpholino-phenyl | $—CH_2CF_3$ |
| 232 | 1 | 4-cyano-2-morpholino-phenyl | $—CH_2CH_2CF_3$ |
| 233 | 1 | 4-cyano-2-morpholino-phenyl | cyclopropyl |
| 234 | 1 | 4-cyano-2-morpholino-phenyl | Cyclobutyl |
| 235 | 1 | 4-cyano-2-morpholino-phenyl | cyclopentyl |
| 236 | 1 | 4-cyano-2-morpholino-phenyl | cyclohexyl |
| 237 | 1 | 4-cyano-2-morpholino-phenyl | 3-pyridyl |
| 238 | 1 | 4-cyano-2-morpholino-phenyl | 1-methyl-1H-pyrazol-4-yl |
| 239 | 1 | 4-cyano-2-morpholino-phenyl | 1H-imidazol-4-yl |
| 240 | 1 | 4-cyano-2-morpholino-phenyl | 2-furanyl |
| 241 | 1 | 4-hydroxy-2-morpholino-phenyl | ethyl |
| 242 | 1 | 4-hydroxy-2-morpholino-phenyl | n-propyl |
| 243 | 1 | 4-hydroxy-2-morpholino-phenyl | isopropyl |
| 244 | 1 | 4-hydroxy-2-morpholino-phenyl | $—CH2CH(CH_3)_2$ |
| 245 | 1 | 4-hydroxy-2-morpholino-phenyl | $CF_3$ |
| 246 | 1 | 4-hydroxy-2-morpholino-phenyl | $—CH_2CF_3$ |
| 247 | 1 | 4-hydroxy-2-morpholino-phenyl | $—CH_2CH_2CF_3$ |
| 248 | 1 | 4-hydroxy-2-morpholino-phenyl | cyclopropyl |
| 249 | 1 | 4-hydroxy-2-morpholino-phenyl | Cyclobutyl |
| 250 | 1 | 4-hydroxy-2-morpholino-phenyl | cyclopentyl |
| 251 | 1 | 4-hydroxy-2-morpholino-phenyl | cyclohexyl |
| 252 | 1 | 4-hydroxy-2-morpholino-phenyl | 3-pyridyl |
| 253 | 1 | 4-hydroxy-2-morpholino-phenyl | 1-methyl-1H-pyrazol-4-yl |
| 254 | 1 | 4-hydroxy-2-morpholino-phenyl | 1H-imidazol-4-yl |
| 255 | 1 | 4-hydroxy-2-morpholino-phenyl | 2-furanyl |
| 256 | 1 | $2-CH_3$-phenyl | Ethyl |
| 257 | 1 | $2-CH_3$-phenyl | n-propyl |
| 258 | 1 | $2-CH_3$-phenyl | Isopropyl |
| 259 | 1 | $2-CH_3$-phenyl | $—CH_2CH(CH_3)_2$ |
| 260 | 1 | $2-CH_3$-phenyl | $CF_3$ |
| 261 | 1 | $2-CH_3$-phenyl | $—CH_2CF_3$ |
| 262 | 1 | $2-CH_3$-phenyl | $—CH_2CH_2CF_3$ |
| 263 | 1 | $2-CH_3$-phenyl | cyclopropyl |
| 264 | 1 | $2-CH_3$-phenyl | Cyclobutyl |
| 265 | 1 | $2-CH_3$-phenyl | cyclopentyl |
| 266 | 1 | $2-CH_3$-phenyl | cyclohexyl |
| 267 | 1 | $2-CH_3$-phenyl | 3-pyridyl |
| 268 | 1 | $2-CH_3$-phenyl | 1-methyl-1H-pyrazol-4-yl |
| 269 | 1 | $2-CH_3$-phenyl | 1H-imidazol-4-yl |
| 270 | 1 | $2-CH_3$-phenyl | 2-furanyl |
| 271 | 1 | 4-OH-Phenyl | Ethyl |
| 272 | 1 | 4-OH-Phenyl | n-propyl |
| 273 | 1 | 4-OH-Phenyl | Isopropyl |
| 274 | 1 | 4-OH-Phenyl | $—CH_2CH(CH_3)_2$ |
| 275 | 1 | 4-OH-Phenyl | $CF_3$ |
| 276 | 1 | 4-OH-Phenyl | $—CH_2CF_3$ |
| 277 | 1 | 4-OH-Phenyl | $—CH_2CH_2CF_3$ |
| 278 | 1 | 4-OH-Phenyl | cyclopropyl |
| 279 | 1 | 4-OH-Phenyl | Cyclobutyl |
| 280 | 1 | 4-OH-Phenyl | cyclopentyl |
| 281 | 1 | 4-OH-Phenyl | cyclohexyl |
| 282 | 1 | 4-OH-Phenyl | 3-pyridyl |
| 283 | 1 | 4-OH-Phenyl | 1-methyl-1H-pyrazol-4-yl |
| 284 | 1 | 4-OH-Phenyl | 1H-imidazol-4-yl |
| 285 | 1 | 4-OH-Phenyl | 2-furanyl |
| 286 | 1 | 2-OH-Phenyl | Ethyl |
| 287 | 1 | 2-OH-Phenyl | n-propyl |
| 288 | 1 | 2-OH-Phenyl | Isopropyl |
| 289 | 1 | 2-OH-Phenyl | $—CH_2CH(CH_3)_2$ |
| 290 | 1 | 2-OH-Phenyl | CF3 |
| 291 | 1 | 2-OH-Phenyl | $—CH_2CF_3$ |
| 292 | 1 | 2-OH-Phenyl | —CH2CH2CF3 |
| 293 | 1 | 2-OH-Phenyl | cyclopropyl |
| 294 | 1 | 2-OH-Phenyl | Cyclobutyl |
| 295 | 1 | 2-OH-Phenyl | cyclopentyl |
| 296 | 1 | 2-OH-Phenyl | cyclohexyl |
| 297 | 1 | 2-OH-Phenyl | 3-pyridyl |
| 298 | 1 | 2-OH-Phenyl | 1-methyl-1H-pyrazol-4-yl |
| 299 | 1 | 2-OH-Phenyl | 1H-imidazol-4-yl |
| 300 | 1 | 2-OH-Phenyl | 2-furanyl |
| 301 | 1 | 3-OMe-Phenyl | Ethyl |
| 302 | 1 | 3-OMe-Phenyl | n-propyl |
| 303 | 1 | 3-OMe-Phenyl | Isopropyl |
| 304 | 1 | 3-OMe-Phenyl | $—CH_2CH(CH_3)_2$ |
| 305 | 1 | 3-OMe-Phenyl | $CF_3$ |
| 306 | 1 | 3-OMe-Phenyl | $—CH_2CF_3$ |
| 307 | 1 | 3-OMe-Phenyl | $—CH_2CH_2CF_3$ |
| 308 | 1 | 3-OMe-Phenyl | cyclopropyl |
| 309 | 1 | 3-OMe-Phenyl | Cyclobutyl |
| 310 | 1 | 3-OMe-Phenyl | cyclopentyl |
| 311 | 1 | 3-OMe-Phenyl | cyclohexyl |
| 312 | 1 | 3-OMe-Phenyl | 3-pyridyl |
| 313 | 1 | 3-OMe-Phenyl | 1-methyl-1H-pyrazol-4-yl |
| 314 | 1 | 3-OMe-Phenyl | 1H-imidazol-4-yl |
| 315 | 1 | 3-OMe-Phenyl | 2-furanyl |
| 316 | 1 | 4-CN-Phenyl | Ethyl |
| 317 | 1 | 4-CN-Phenyl | n-propyl |
| 318 | 1 | 4-CN-Phenyl | Isopropyl |
| 319 | 1 | 4-CN-Phenyl | $—CH_2CH(CH_3)_2$ |
| 320 | 1 | 4-CN-Phenyl | $CF_3$ |
| 321 | 1 | 4-CN-Phenyl | $—CH_2CF_3$ |
| 322 | 1 | 4-CN-Phenyl | $—CH_2CH_2CF_3$ |
| 323 | 1 | 4-CN-Phenyl | cyclopropyl |
| 324 | 1 | 4-CN-Phenyl | Cyclobutyl |
| 325 | 1 | 4-CN-Phenyl | cyclopentyl |
| 326 | 1 | 4-CN-Phenyl | cyclohexyl |
| 327 | 1 | 4-CN-Phenyl | 3-pyridyl |
| 328 | 1 | 4-CN-Phenyl | 1-methyl-1H-pyrazol-4-yl |
| 329 | 1 | 4-CN-Phenyl | 1H-imidazol-4-yl |
| 330 | 1 | 4-CN-Phenyl | 2-furanyl |
| 331 | 1 | 2-CN-Phenyl | Ethyl |
| 332 | 1 | 2-CN-Phenyl | n-propyl |
| 333 | 1 | 2-CN-Phenyl | Isopropyl |
| 334 | 1 | 2-CN-Phenyl | $—CH_2CH(CH_3)_2$ |
| 335 | 1 | 2-CN-Phenyl | $CF_3$ |
| 336 | 1 | 2-CN-Phenyl | $—CH_2CF_2$ |
| 337 | 1 | 2-CN-Phenyl | $—CH_2CH_2CF_2$ |
| 338 | 1 | 2-CN-Phenyl | cyclopropyl |
| 339 | 1 | 2-CN-Phenyl | Cyclobutyl |
| 340 | 1 | 2-CN-Phenyl | cyclopentyl |
| 341 | 1 | 2-CN-Phenyl | cyclohexyl |
| 342 | 1 | 2-CN-Phenyl | 3-pyridyl |
| 343 | 1 | 2-CN-Phenyl | 1-methyl-1H-pyrazol-4-yl |
| 344 | 1 | 2-CN-Phenyl | 1H-imidazol-4-yl |
| 345 | 1 | 2-CN-Phenyl | 2-furanyl |
| 346 | 1 | 3-F-Phenyl | Ethyl |
| 347 | 1 | 3-F-Phenyl | n-propyl |
| 348 | 1 | 3-F-Phenyl | Isopropyl |
| 349 | 1 | 3-F-Phenyl | $—CH_2CH(CH_3)_2$ |
| 350 | 1 | 3-F-Phenyl | $CF_3$ |
| 351 | 1 | 3-F-Phenyl | $—CH_2CF_2$ |
| 352 | 1 | 3-F-Phenyl | $—CH_2CH_2CF_2$ |

TABLE 33-continued

| Entry | n | $R^5$ | $R^{10c}$ |
|---|---|---|---|
| 353 | 1 | 3-F-Phenyl | cyclopropyl |
| 354 | 1 | 3-F-Phenyl | Cyclobutyl |
| 355 | 1 | 3-F-Phenyl | cyclopentyl |
| 356 | 1 | 3-F-Phenyl | cyclohexyl |
| 357 | 1 | 3-F-Phenyl | 3-pyridyl |
| 358 | 1 | 3-F-Phenyl | 1-methyl-1H-pyrazol-4-yl |
| 359 | 1 | 3-F-Phenyl | 1H-imidazol-4-yl |
| 360 | 1 | 3-F-Phenyl | 2-furanyl |
| 361 | 1 | 2-Cl-Phenyl | Ethyl |
| 362 | 1 | 2-Cl-Phenyl | n-propyl |
| 363 | 1 | 2-Cl-Phenyl | Isopropyl |
| 364 | 1 | 2-Cl-Phenyl | $—CH_2CH(CH_2)_2$ |
| 365 | 1 | 2-Cl-Phenyl | $CF_3$ |
| 366 | 1 | 2-Cl-Phenyl | $—CH_2CF_3$ |
| 367 | 1 | 2-Cl-Phenyl | $—CH_2CH_2CF_3$ |
| 368 | 1 | 2-Cl-Phenyl | cyclopropyl |
| 369 | 1 | 2-Cl-Phenyl | Cyclobutyl |
| 370 | 1 | 2-Cl-Phenyl | cyclopentyl |
| 371 | 1 | 2-Cl-Phenyl | cyclohexyl |
| 372 | 1 | 2-Cl-Phenyl | 3-pyridyl |
| 373 | 1 | 2-Cl-Phenyl | 1-methyl-1H-pyrazol-4-yl |
| 374 | 1 | 2-Cl-Phenyl | 1H-imidazol-4-yl |
| 375 | 1 | 2-Cl-Phenyl | 2-furanyl |
| 376 | 1 | 4-Cl-Phenyl | Ethyl |
| 377 | 1 | 4-Cl-Phenyl | n-propyl |
| 378 | 1 | 4-Cl-Phenyl | Isopropyl |
| 379 | 1 | 4-Cl-Phenyl | $—CH_2CH(CH_3)_2$ |
| 380 | 1 | 4-Cl-Phenyl | $CF_3$ |
| 381 | 1 | 4-Cl-Phenyl | $—CH_2CF_3$ |
| 382 | 1 | 4-Cl-Phenyl | $—CH_2CH_2CF3_3$ |
| 383 | 1 | 4-Cl-Phenyl | cyclopropyl |
| 384 | 1 | 4-Cl-Phenyl | Cyclobutyl |
| 385 | 1 | 4-Cl-Phenyl | cyclopentyl |
| 386 | 1 | 4-Cl-Phenyl | cyclohexyl |
| 387 | 1 | 4-Cl-Phenyl | 3-pyridyl |
| 388 | 1 | 4-Cl-Phenyl | 1-methyl-1H-pyrazol-4-yl |
| 389 | 1 | 4-Cl-Phenyl | 1H-imidazol-4-yl |
| 390 | 1 | 4-Cl-Phenyl | 2-furanyl |
| 391 | 1 | 3-Br-Phenyl | Ethyl |
| 392 | 1 | 3-Br-Phenyl | n-propyl |
| 393 | 1 | 3-Br-Phenyl | Isopropyl |
| 394 | 1 | 3-Br-Phenyl | $—CH_2CH(CH_3)_2$ |
| 395 | 1 | 3-Br-Phenyl | $CF_3$ |
| 396 | 1 | 3-Br-Phenyl | $—CH_2CF_3$ |
| 397 | 1 | 3-Br-Phenyl | $—CH_2CH_2CF_3$ |
| 398 | 1 | 3-Br-Phenyl | cyclopropyl |
| 399 | 1 | 3-Br-Phenyl | Cyclobutyl |
| 400 | 1 | 3-Br-Phenyl | cyclopentyl |
| 401 | 1 | 3-Br-Phenyl | cyclohexyl |
| 402 | 1 | 3-Br-Phenyl | 3-pyridyl |
| 403 | 1 | 3-Br-Phenyl | 1-methyl-1H-pyrazol-4-yl |
| 404 | 1 | 3-Br-Phenyl | 1H-imidazol-4-yl |
| 405 | 1 | 3-BrPhenyl | 2-furanyl |
| 406 | 1 | $2-CF_3$-Phenyl | Ethyl |
| 407 | 1 | $2-CF_3$-Phenyl | n-propyl |
| 408 | 1 | $2-CF_3$-Phenyl | Isopropyl |
| 409 | 1 | $2-CF_3$-Phenyl | $—CH_2CH(CH_3)_2$ |
| 410 | 1 | $2-CF_3$-Phenyl | $CF_3$ |
| 411 | 1 | $2-CF_3$-Phenyl | $—CH_2CF_3$ |
| 412 | 1 | $2-CF_3$-Phenyl | $—CH_2CH_2CF_3$ |
| 413 | 1 | $2-CF_3$-Phenyl | cyclopropyl |
| 414 | 1 | $2-CF_3$-Phenyl | Cyclobutyl |
| 415 | 1 | $2-CF_3$-Phenyl | cyclopentyl |
| 416 | 1 | $2-CF_3$-Phenyl | cyclohexyl |
| 417 | 1 | $2-CF_3$-Phenyl | 3-pyridyl |
| 418 | 1 | $2-CF_3$-Phenyl | 1-methyl-1H-pyrazol-4-yl |
| 419 | 1 | $2-CF_3$-Phenyl | 1H-imidazol-4-yl |
| 420 | 1 | $2-CF_3$-Phenyl | 2-furanyl |
| 421 | 1 | $4-CF_3$-Phenyl | Ethyl |
| 422 | 1 | $4-CF_3$-Phenyl | n-propyl |
| 423 | 1 | $4-CF_3$-Phenyl | Isopropyl |
| 424 | 1 | $4-CF_3$-Phenyl | $—CH_2CH(CH_3)_2$ |
| 425 | 1 | $4-CF_3$-Phenyl | $CF_3$ |
| 426 | 1 | $4-CF_3$-Phenyl | $—CH_2CF_3$ |
| 427 | 1 | $4-CF_3$-Phenyl | $—CH_2CH_2CF_3$ |
| 428 | 1 | $4-CF_3$-Phenyl | cyclopropyl |
| 429 | 1 | $4-CF_3$-Phenyl | Cyclobutyl |
| 430 | 1 | $4-CF_3$-Phenyl | cyclopentyl |
| 431 | 1 | $4-CF_3$-Phenyl | cyclohexyl |
| 432 | 1 | $4-CF_3$-Phenyl | 3-pyridyl |
| 433 | 1 | $4-CF_3$-Phenyl | 1-methyl-1H-pyrazol-4-yl |
| 434 | 1 | $4-CF_3$-Phenyl | 1H-imidazol-4-yl |
| 435 | 1 | $4-CF_3$-Phenyl | 2-furanyl |
| 436 | 1 | 3-iPr-Phenyl | Ethyl |
| 437 | 1 | 3-iPr-Phenyl | n-propyl |
| 438 | 1 | 3-iPr-Phenyl | Isopropyl |
| 439 | 1 | 3-iPr-Phenyl | $—CH2CH(CH_3)_2$ |
| 440 | 1 | 3-iPr-Phenyl | $CF_3$ |
| 441 | 1 | 3-iPr-Phenyl | $—CH_2CF_3$ |
| 442 | 1 | 3-iPr-Phenyl | $—CH_2CH_2CF_3$ |
| 443 | 1 | 3-iPr-Phenyl | cyclopropyl |
| 444 | 1 | 3-iPr-Phenyl | Cyclobutyl |
| 445 | 1 | 3-iPr-Phenyl | cyclopentyl |
| 446 | 1 | 3-iPr-Phenyl | cyclohexyl |
| 447 | 1 | 3-iPr-Phenyl | 3-pyridyl |
| 448 | 1 | 3-iPr-Phenyl | 1-methyl-1H-pyrazol-4-yl |
| 449 | 1 | 3-iPr-Phenyl | 1H-imidazol-4-yl |
| 450 | 1 | 3-iPr-Phenyl | 2-furanyl |
| 451 | 1 | 2-morpholino-phenyl | Ethyl |
| 452 | 1 | 2-morpholino-phenyl | n-propyl |
| 453 | 1 | 2-morpholino-phenyl | isopropyl |
| 454 | 1 | 2-morpholino-phenyl | $—CH_2CH(CH_3)_2$ |
| 455 | 1 | 2-morpholino-phenyl | $CF_3$ |
| 456 | 1 | 2-morpholino-phenyl | $—CH_2CF_3$ |
| 457 | 1 | 2-morpholino-phenyl | $—CH_2CH_2CF_3$ |
| 458 | 1 | 2-morpholino-phenyl | cyclopropyl |
| 459 | 1 | 2-morpholino-phenyl | Cyclobutyl |
| 460 | 1 | 2-morpholino-phenyl | cyclopentyl |
| 461 | 1 | 2-morpholino-phenyl | cyclohexyl |
| 462 | 1 | 2-morpholino-phenyl | 3-pyridyl |
| 463 | 1 | 2-morpholino-phenyl | 1-methyl-1H-pyrazol-4-yl |
| 464 | 1 | 2-morpholino-phenyl | 1H-imidazol-4-yl |
| 465 | 1 | 2-morpholino-phenyl | 2-furanyl |
| 466 | 1 | 4-morpholino-phenyl | ethyl |
| 467 | 1 | 4-morpholino-phenyl | n-propyl |
| 468 | 1 | 4-morpholino-phenyl | isopropyl |
| 469 | 1 | 4-morpholino-phenyl | $—CH_2CH(CH_3)_2$ |
| 470 | 1 | 4-morpholino-phenyl | $CF_3$ |
| 471 | 1 | 4-morpholino-phenyl | $—CH_2CF_3$ |
| 472 | 1 | 4-morpholino-phenyl | $—CH_2CH_2CF_3$ |
| 473 | 1 | 4-morpholino-phenyl | cyclopropyl |
| 474 | 1 | 4-morpholino-phenyl | Cyclobutyl |
| 475 | 1 | 4-morpholino-phenyl | cyclopentyl |
| 476 | 1 | 4-morpholino-phenyl | cyclohexyl |
| 477 | 1 | 4-morpholino-phenyl | 3-pyridyl |
| 478 | 1 | 4-morpholino-phenyl | 1-methyl-1H-pyrazol-4-yl |
| 479 | 1 | 4-morpholino-phenyl | 1H-imidazol-4-yl |
| 480 | 1 | 4-morpholino-phenyl | 2-furanyl |
| 481 | 1 | 4-methyl-2-morpholino-phenyl | ethyl |
| 482 | 1 | 4-methyl-2-morpholino-phenyl | n-propyl |
| 483 | 1 | 4-methyl-2-morpholino-phenyl | isopropyl |
| 484 | 1 | 4-methyl-2-morpholino-phenyl | $—CH_2CH(CH_3)_2$ |
| 485 | 1 | 4-methyl-2-morpholino-phenyl | $CF_3$ |
| 486 | 1 | 4-methyl-2-morpholino-phenyl | $—CH_2CF_3$ |
| 487 | 1 | 4-methyl-2-morpholino-phenyl | $—CH_2CH_2CF_3$ |
| 488 | 1 | 4-methyl-2-morpholino-phenyl | cyclopropyl |
| 489 | 1 | 4-methyl-2-morpholino-phenyl | Cyclobutyl |
| 490 | 1 | 4-methyl-2-morpholino-phenyl | cyclopentyl |
| 491 | 1 | 4-methyl-2-morpholino-phenyl | cyclohexyl |
| 492 | 1 | 4-methyl-2-morpholino-phenyl | 3-pyridyl |
| 493 | 1 | 4-methyl-2-morpholino-phenyl | 1-methyl-1H-pyrazol-4-yl |
| 494 | 1 | 4-methyl-2-morpholino-phenyl | 1H-imidazol-4-yl |
| 495 | 1 | 4-methyl-2-morpholino-phenyl | 2-furanyl |
| 496 | 2 | $4-CH_3$-phenyl | ethyl |
| 497 | 2 | $4-CH_3$-phenyl | n-propyl |
| 498 | 2 | $4-CH_3$-phenyl | isopropyl |
| 499 | 2 | $4-CH_3$-phenyl | $—CH_2CH(CH_3)_2$ |
| 500 | 2 | $4-CH_3$-phenyl | $CF_3$ |
| 501 | 2 | $4-CH_3$-phenyl | $—CH_2CF_3$ |
| 502 | 2 | $4-CH_3$-phenyl | $—CH_2CH_2CF_3$ |
| 503 | 2 | $4-CH_3$-phenyl | cyclopropyl |
| 504 | 2 | $4-CH_3$-phenyl | Cyclobutyl |
| 505 | 2 | $4-CH_3$-phenyl | cyclopentyl |
| 506 | 2 | $4-CH_3$-phenyl | cyclohexyl |
| 507 | 2 | $4-CH_3$-phenyl | 3-pyridyl |
| 508 | 2 | $4-CH_3$-phenyl | 1-methyl-1H-pyrazol-4-yl |

TABLE 33-continued

| Entry | n | $R^5$ | $R^{10c}$ |
|---|---|---|---|
| 509 | 2 | 4-$CH_3$-phenyl | 1H-imidazol-4-yl |
| 510 | 2 | 4-$CH_3$-phenyl | 2-furanyl |
| 511 | 2 | 3-$CH_3$-phenyl | ethyl |
| 512 | 2 | 3-$CH_3$-phenyl | n-propyl |
| 513 | 2 | 3-$CH_3$-phenyl | isopropyl |
| 514 | 2 | 3-$CH_3$-phenyl | —$CH_2CH(CH_3)_2$ |
| 515 | 2 | 3-$CH_3$-phenyl | $CF_3$ |
| 516 | 2 | 3-$CH_3$-phenyl | —$CH_2CF_3$ |
| 517 | 2 | 3-$CH_3$-phenyl | —$CH_2CH_2CF_3$ |
| 518 | 2 | 3-$CH_3$-phenyl | cyclopropyl |
| 519 | 2 | 3-$CH_3$-phenyl | Cyclobutyl |
| 520 | 2 | 3-$CH_3$-phenyl | cyclopentyl |
| 521 | 2 | 3-$CH_3$-phenyl | cyclohexyl |
| 522 | 2 | 3-$CH_3$-phenyl | 3-pyridyl |
| 523 | 2 | 3-$CH_3$-phenyl | 1-methyl-1H-pyrazol-4-yl |
| 524 | 2 | 3-$CH_3$-phenyl | 1H-imidazol-4-yl |
| 525 | 2 | 3-$CH_3$-phenyl | 2-furanyl |
| 526 | 2 | 3-OH-Phenyl | ethyl |
| 527 | 2 | 3-OH-Phenyl | n-propyl |
| 528 | 2 | 3-OH-Phenyl | isopropyl |
| 529 | 2 | 3-OH-Phenyl | —$CH_2CH(CH_3)_2$ |
| 530 | 2 | 3-OH-Phenyl | $CF_3$ |
| 531 | 2 | 3-OH-Phenyl | —$CH_2CF_3$ |
| 532 | 2 | 3-OH-Phenyl | —$CH_2CH_2CF_3$ |
| 533 | 2 | 3-OH-Phenyl | cyclopropyl |
| 534 | 2 | 3-OH-Phenyl | Cyclobutyl |
| 535 | 2 | 3-OH-Phenyl | cyclopentyl |
| 536 | 2 | 3-OH-Phenyl | cyclohexyl |
| 537 | 2 | 3-OH-Phenyl | 3-pyridyl |
| 538 | 2 | 3-OH-Phenyl | 1-methyl-1H-pyrazol-4-yl |
| 539 | 2 | 3-OH-Phenyl | 1H-imidazol-4-yl |
| 540 | 2 | 3-OH-Phenyl | 2-furanyl |
| 541 | 2 | 4-OMe-Phenyl | ethyl |
| 542 | 2 | 4-OMe-Phenyl | n-propyl |
| 543 | 2 | 4-OMe-Phenyl | isopropyl |
| 544 | 2 | 4-OMe-Phenyl | —$CH_2CH(CH_3)_2$ |
| 545 | 2 | 4-OMe-Phenyl | $CF_3$ |
| 546 | 2 | 4-OMe-Phenyl | —$CH_2CF_3$ |
| 547 | 2 | 4-OMe-Phenyl | —$CH_2CH_2CF_3$ |
| 548 | 2 | 4-OMe-Phenvl | cyclopropyl |
| 549 | 2 | 4-OMe-Phenyl | Cyclobutyl |
| 550 | 2 | 4-OMe-Phenyl | cyclopentyl |
| 551 | 2 | 4-OMe-Phenyl | cyclohexyl |
| 552 | 2 | 4-OMe-Phenyl | 3-pyridyl |
| 553 | 2 | 4-OMe-Phenyl | 1-methyl-1H-pyrazol-4-yl |
| 554 | 2 | 4-OMe-Phenyl | 1H-imidazol-4-yl |
| 555 | 2 | 4-OMe-Phenyl | 2-furanyl |
| 556 | 2 | 2-OMe-Phenyl | ethyl |
| 557 | 2 | 2-OMe-Phenyl | n-propyl |
| 558 | 2 | 2-OMe-Phenyl | isopropyl |
| 559 | 2 | 2-OMe-Phenyl | —$CH_2CH(CH_3)_2$ |
| 560 | 2 | 2-OMe-Phenyl | $CF_3$ |
| 561 | 2 | 2-OMe-Phenyl | —$CH_2CF_3$ |
| 562 | 2 | 2-OMe-Phenyl | —$CH_2CH_2CF_3$ |
| 563 | 2 | 2-OMe-Phenyl | cyclopropyl |
| 564 | 2 | 2-OMe-Phenyl | Cyclobutyl |
| 565 | 2 | 2-OMe-Phenyl | cyclopentyl |
| 566 | 2 | 2-OMe-Phenyl | cyclohexyl |
| 567 | 2 | 2-OMe-Phenyl | 3-pyridyl |
| 568 | 2 | 2-OMe-Phenyl | 1-methyl-1H-pyrazol-4-yl |
| 569 | 2 | 2-OMe-Phenyl | 1H-imidazol-4-yl |
| 570 | 2 | 2-OMe-Phenyl | 2-furanyl |
| 571 | 2 | 3-CN-Phenyl | ethyl |
| 572 | 2 | 3-CN-Phenyl | n-propyl |
| 573 | 2 | 3-CN-Phenyl | isopropyl |
| 574 | 2 | 3-CN-Phenyl | —$CH_2CH(CH_3)_2$ |
| 575 | 2 | 3-CN-Phenyl | $CF_3$ |
| 576 | 2 | 3-CN-Phenyl | —$CH_2CF_3$ |
| 577 | 2 | 3-CN-Phenyl | —$CH_2CH_2CF_3$ |
| 578 | 2 | 3-CN-Phenyl | cyclopropyl |
| 579 | 2 | 3-CN-Phenyl | Cyclobutyl |
| 580 | 2 | 3-CN-Phenyl | cyclopentyl |
| 581 | 2 | 3-CN-Phenyl | cyclohexyl |
| 582 | 2 | 3-CN-Phenyl | 3-pyridyl |
| 583 | 2 | 3-CN-Phenyl | 1-methyl-1H-pyrazol-4-yl |
| 584 | 2 | 3-CN-Phenyl | 1H-imidazol-4-yl |
| 585 | 2 | 3-CN-Phenyl | 2-furanyl |
| 586 | 2 | 2-F-Phenyl | ethyl |

TABLE 33-continued

| Entry | n | $R^5$ | $R^{10c}$ |
|---|---|---|---|
| 587 | 2 | 2-F-Phenyl | n-propyl |
| 588 | 2 | 2-F-Phenyl | isopropyl |
| 589 | 2 | 2-F-Phenyl | —$CH_2CH(CH_3)_2$ |
| 590 | 2 | 2-F-Phenyl | $CF_3$ |
| 591 | 2 | 2-F-Phenyl | —$CH_2CF_3$ |
| 592 | 2 | 2-F-Phenyl | —$CH_2CH_2CF_3$ |
| 593 | 2 | 2-F-Phenyl | cyclopropyl |
| 594 | 2 | 2-F-Phenyl | Cyclobutyl |
| 595 | 2 | 2-F-Phenyl | cyclopentyl |
| 596 | 2 | 2-F-Phenyl | cyclohexyl |
| 597 | 2 | 2-F-Phenyl | 3-pyridyl |
| 598 | 2 | 2-F-Phenyl | 1-methyl-1H-pyrazol-4-yl |
| 599 | 2 | 2-F-Phenyl | 1H-imidazol-4-yl |
| 600 | 2 | 2-F-Phenyl | 2-furanyl |
| 601 | 2 | 4-F-Phenyl | ethyl |
| 602 | 2 | 4-F-Phenyl | n-propyl |
| 603 | 2 | 4-F-Phenyl | isopropyl |
| 604 | 2 | 4-F-Phenyl | —$CH_2CH(CH_3)_2$ |
| 605 | 2 | 4-F-Phenyl | $CF_3$ |
| 606 | 2 | 4-F-Phenyl | —$CH_2CF_3$ |
| 607 | 2 | 4-F-Phenyl | —$CH_2CH_2CF_3$ |
| 608 | 2 | 4-F-Phenyl | cyclopropyl |
| 609 | 2 | 4-F-Phenyl | Cyclobutyl |
| 610 | 2 | 4-F-Phenyl | cyclopentyl |
| 611 | 2 | 4-F-Phenyl | cyclohexyl |
| 612 | 2 | 4-F-Phenyl | 3-pyridyl |
| 613 | 2 | 4-F-Phenyl | 1-methyl-1H-pyrazol-4-yl |
| 614 | 2 | 4-F-Phenyl | 1H-imidazol-4-yl |
| 615 | 2 | 4-F-Phenyl | 2-furanyl |
| 616 | 2 | 3-Cl-Phenyl | ethyl |
| 617 | 2 | 3-Cl-Phenyl | n-propyl |
| 618 | 2 | 3-Cl-Phenyl | isopropyl |
| 619 | 2 | 3-Cl-Phenyl | —$CH_2CH(CH_3)_2$ |
| 620 | 2 | 3-Cl-Phenyl | $CF_3$ |
| 621 | 2 | 3-Cl-Phenyl | —$CH_2CF_3$ |
| 622 | 2 | 3-Cl-Phenyl | —$CH_2CH_2CF_3$ |
| 623 | 2 | 3-Cl-Phenyl | cyclopropyl |
| 624 | 2 | 3-Cl-Phenyl | Cyclobutyl |
| 625 | 2 | 3-Cl-Phenyl | cyclopentyl |
| 626 | 2 | 3-Cl-Phenyl | cyclohexyl |
| 627 | 2 | 3-Cl-Phenyl | 3-pyridyl |
| 628 | 2 | 3-Cl-Phenyl | 1-methyl-1H-pyrazol-4-yl |
| 629 | 2 | 3-Cl-Phenyl | 1H-imidazol-4-yl |
| 630 | 2 | 3-Cl-Phenyl | 2-furanyl |
| 631 | 2 | 2-Br-Phenyl | ethyl |
| 632 | 2 | 2-Br-Phenyl | n-propyl |
| 633 | 2 | 2-Br-Phenyl | isopropyl |
| 634 | 2 | 2-Br-Phenyl | —$CH_2CH(CH_3)_2$ |
| 635 | 2 | 2-Br-Phenyl | $CF_3$ |
| 636 | 2 | 2-Br-Phenyl | —$CH_2CF_3$ |
| 637 | 2 | 2-Br-Phenyl | —$CH_2CH_2CF_3$ |
| 638 | 2 | 2-Br-Phenyl | cyclopropyl |
| 639 | 2 | 2-Br-Phenyl | Cyclobutyl |
| 640 | 2 | 2-Br-Phenyl | cyclopentyl |
| 641 | 2 | 2-Br-Phenyl | cyclohexyl |
| 642 | 2 | 2-Br-Phenyl | 3-pyridyl |
| 643 | 2 | 2-Br-Phenyl | 1-methyl-1H-pyrazol-4-yl |
| 644 | 2 | 2-Br-Phenyl | 1H-imidazol-4-yl |
| 645 | 2 | 2-Br-Phenyl | 2-furanyl |
| 646 | 2 | 4-Br-Phenyl | ethyl |
| 647 | 2 | 4-Br-Phenyl | n-propyl |
| 648 | 2 | 4-Br-Phenyl | isopropyl |
| 649 | 2 | 4-Br-Phenyl | —$CH_2CH(CH_3)_2$ |
| 650 | 2 | 4-Br-Phenyl | $CF_3$ |
| 651 | 2 | 4-Br-Phenyl | —$CH_2CF_3$ |
| 652 | 2 | 4-Br-Phenyl | —$CH_2CH_2CF_3$ |
| 653 | 2 | 4-Br-Phenyl | cyclopropyl |
| 654 | 2 | 4-Br-Phenyl | Cyclobutyl |
| 655 | 2 | 4-Br-Phenyl | cyclopentyl |
| 656 | 2 | 4-Br-Phenyl | cyclohexyl |
| 657 | 2 | 4-Br-Phenyl | 3-pyridyl |
| 658 | 2 | 4-Br-Phenyl | 1-methyl-1H-pyrazol-4-yl |
| 659 | 2 | 4-Br-Phenyl | 1H-imidazol-4-yl |
| 660 | 2 | 4-Br-Phenyl | 2-furanyl |
| 661 | 2 | 3-$CF_3$-Phenyl | ethyl |
| 662 | 2 | 3-$CF_3$-Phenyl | n-propyl |
| 663 | 2 | 3-$CF_3$-Phenyl | isopropyl |
| 664 | 2 | 3-$CF_3$-Phenyl | —$CH_2CH(CH_3)_2$ |

TABLE 33-continued

| Entry | n | $R^5$ | $R^{10c}$ |
|---|---|---|---|
| 665 | 2 | 3-$CF_3$-Phenyl | $CF_3$ |
| 666 | 2 | 3-$CF_3$-Phenyl | —$CH_2CF_3$ |
| 667 | 2 | 3-$CF_3$-Phenyl | —$CH_2CH_2CF_3$ |
| 668 | 2 | 3-$CF_3$-Phenyl | cyclopropyl |
| 669 | 2 | 3-$CF_3$-Phenyl | Cyclobutyl |
| 670 | 2 | 3-$CF_3$-Phenyl | cyclopentyl |
| 671 | 2 | 3-$CF_3$-Phenyl | cyclohexyl |
| 672 | 2 | 3-$CF_3$-Phenyl | 3-pyridyl |
| 673 | 2 | 3-$CF_3$-Phenyl | 1-methyl-1H-pyrazol-4-yl |
| 674 | 2 | 3-$CF_3$-Phenyl | 1H-imidazol-4-yl |
| 675 | 2 | 3-$CF_3$-Phenyl | 2-furanyl |
| 676 | 2 | 2-iPr-Phenyl | ethyl |
| 677 | 2 | 2-iPr-Phenyl | n-propyl |
| 678 | 2 | 2-iPr-Phenyl | isopropyl |
| 679 | 2 | 2-iPr-Phenyl | —$CH_2CH(CH_3)_2$ |
| 680 | 2 | 2-iPr-Phenyl | $CF_3$ |
| 681 | 2 | 2-iPr-Phenyl | —$CH_2CF_3$ |
| 682 | 2 | 2-iPr-Phenyl | —$CH_2CH_2CF_3$ |
| 683 | 2 | 2-iPr-Phenyl | cyclopropyl |
| 684 | 2 | 2-iPr-Phenyl | Cyclobutyl |
| 685 | 2 | 2-iPr-Phenyl | cyclopentyl |
| 686 | 2 | 2-iPr-Phenyl | cyclohexyl |
| 687 | 2 | 2-iPr-Phenyl | 3-pyridyl |
| 688 | 2 | 2-iPr-Phenyl | 1-methyl-1H-pyrazol-4-yl |
| 689 | 2 | 2-iPr-Phenyl | 1H-imidazol-4-yl |
| 690 | 2 | 2-iPr-Phenyl | 2-furanyl |
| 691 | 2 | 4-iPr-Phenyl | ethyl |
| 692 | 2 | 4-iPr-Phenyl | n-propyl |
| 693 | 2 | 4-iPr-Phenyl | isopropyl |
| 694 | 2 | 4-iPr-Phenyl | —$CH_2CH(CH_3)_2$ |
| 695 | 2 | 4-iPr-Phenyl | $CF_3$ |
| 696 | 2 | 4-iPr-Phenyl | —$CH_2CF_3$ |
| 697 | 2 | 4-iPr-Phenyl | —$CH_2CH_2CF_3$ |
| 698 | 2 | 4-iPr-Phenyl | cyclopropyl |
| 699 | 2 | 4-iPr-Phenyl | Cyclobutyl |
| 700 | 2 | 4-iPr-Phenyl | cyclopentyl |
| 701 | 2 | 4-iPr-Phenyl | cyclohexyl |
| 702 | 2 | 4-iPr-Phenyl | 3-pyridyl |
| 703 | 2 | 4-iPr-Phenyl | 1-methyl-1H-pyrazol-4-yl |
| 704 | 2 | 4-iPr-Phenyl | 1H-imidazol-4-yl |
| 705 | 2 | 4-iPr-Phenyl | 2-furanyl |
| 706 | 2 | 3-morpholino-phenyl | ethyl |
| 707 | 2 | 3-morpholino-phenyl | n-propyl |
| 708 | 2 | 3-morpholino-phenyl | isopropyl |
| 709 | 2 | 3-morpholino-phenyl | —$CH_2CH(CH_3)_2$ |
| 710 | 2 | 3-morpholino-phenyl | $CF_3$ |
| 711 | 2 | 3-morpholino-phenyl | —$CH_2CF_3$ |
| 712 | 2 | 3-morpholino-phenyl | —$CH_2CH_2CF_3$ |
| 713 | 2 | 3-morpholino-phenyl | cyclopropyl |
| 714 | 2 | 3-morpholino-phenyl | Cyclobutyl |
| 715 | 2 | 3-morpholino-phenyl | cyclopentyl |
| 716 | 2 | 3-morpholino-phenyl | cyclohexyl |
| 717 | 2 | 3-morpholino-phenyl | 3-pyridyl |
| 718 | 2 | 3-morpholino-phenyl | 1-methyl-1H-pyrazol-4-yl |
| 719 | 2 | 3-morpholino-phenyl | 1H-imidazol-4-yl |
| 720 | 2 | 3-morpholino-phenyl | 2-furanyl |
| 721 | 2 | 4-cyano-2-morpholino-phenyl | ethyl |
| 722 | 2 | 4-cyano-2-morpholino-phenyl | n-propyl |
| 723 | 2 | 4-cyano-2-morpholino-phenyl | isopropyl |
| 724 | 2 | 4-cyano-2-morpholino-phenyl | —$CH_2CH(CH_3)_2$ |
| 725 | 2 | 4-cyano-2-morpholino-phenyl | $CF_3$ |
| 726 | 2 | 4-cyano-2-morpholino-phenyl | —$CH_2CF_3$ |
| 727 | 2 | 4-cyano-2-morpholino-phenyl | —$CH_2CH_2CF_3$ |
| 728 | 2 | 4-cyano-2-morpholino-phenyl | cyclopropyl |
| 729 | 2 | 4-cyano-2-morpholino-phenyl | Cyclobutyl |
| 730 | 2 | 4-cyano-2-morpholino-phenyl | cyclopentyl |
| 731 | 2 | 4-cyano-2-morpholino-phenyl | cyclohexyl |
| 732 | 2 | 4-cyano-2-morpholino-phenyl | 3-pyridyl |
| 733 | 2 | 4-cyano-2-morpholino-phenyl | 1-methyl-1H-pyrazol-4-yl |
| 734 | 2 | 4-cyano-2-morpholino-phenyl | 1H-imidazol-4-yl |
| 735 | 2 | 4-cyano-2-morpholino-phenyl | 2-furanyl |
| 736 | 2 | 4-hydroxy-2-morpholino-phenyl | ethyl |
| 737 | 2 | 4-hydroxy-2-morpholino-phenyl | n-propyl |
| 738 | 2 | 4-hydroxy-2-morpholino-phenyl | isopropyl |
| 739 | 2 | 4-hydroxy-2-morpholino-phenyl | —$CH_2CH(CH_3)_2$ |
| 740 | 2 | 4-hydroxy-2-morpholino-phenyl | $CF_3$ |
| 741 | 2 | 4-hydroxy-2-morpholino-phenyl | —$CH_2CF_3$ |
| 742 | 2 | 4-hydroxy-2-morpholino-phenyl | —$CH_2CH_2CF_3$ |

TABLE 33-continued

| Entry | n | $R^5$ | $R^{10c}$ |
|---|---|---|---|
| 743 | 2 | 4-hydroxy-2-morpholino-phenyl | cyclopropyl |
| 744 | 2 | 4-hydroxy-2-morpholino-phenyl | Cyclobutyl |
| 745 | 2 | 4-hydroxy-2-morpholino-phenyl | cyclopentyl |
| 746 | 2 | 4-hydroxy-2-morpholino-phenyl | cyclohexyl |
| 747 | 2 | 4-hydroxy-2-morpholino-phenyl | 3-pyridyl |
| 748 | 2 | 4-hydroxy-2-morpholino-phenyl | 1-methyl-1H-pyrazol-4-yl |
| 749 | 2 | 4-hydroxy-2-morpholino-phenyl | 1H-imidazol-4-yl |
| 750 | 2 | 4-hydroxy-2-morpholino-phenyl | 2-furanyl |
| 751 | 2 | 2-$CH_3$-phenyl | Ethyl |
| 752 | 2 | 2-$CH_3$-phenyl | n-propyl |
| 753 | 2 | 2-$CH_3$-phenyl | Isopropyl |
| 754 | 2 | 2-$CH_3$-phenyl | —$CH_2CH(CH_3)_2$ |
| 755 | 2 | 2-$CH_3$-phenyl | $CF_3$ |
| 756 | 2 | 2-$CH_3$-phenyl | —$CH_2CF_3$ |
| 757 | 2 | 2-$CH_3$-phenyl | —$CH_2CH_2CF_3$ |
| 758 | 2 | 2-$CH_3$-phenyl | cyclopropyl |
| 759 | 2 | 2-$CH_3$-phenyl | Cyclobutyl |
| 760 | 2 | 2-$CH_3$-phenyl | cyclopentyl |
| 761 | 2 | 2-$CH_3$-phenyl | cyclohexyl |
| 762 | 2 | 2-$CH_3$-phenyl | 3-pyridyl |
| 763 | 2 | 2-$CH_3$-phenyl | 1-methyl-1H-pyrazol-4-yl |
| 764 | 2 | 2-$CH_3$-phenyl | 1H-imidazol-4-yl |
| 765 | 2 | 2-$CH_3$-phenyl | 2-furanyl |
| 766 | 2 | 4-OH-Phenyl | Ethyl |
| 767 | 2 | 4-OH-Phenyl | n-propyl |
| 768 | 2 | 4-OH-Phenyl | Isopropyl |
| 769 | 2 | 4-OH-Phenyl | —$CH_2CH(CH_3)_2$ |
| 770 | 2 | 4-OH-Phenyl | $CF_3$ |
| 771 | 2 | 4-OH-Phenyl | —$CH_2CF_3$ |
| 772 | 2 | 4-OH-Phenyl | —$CH_2CH_2CF_3$ |
| 773 | 2 | 4-OH-Phenyl | cyclopropyl |
| 774 | 2 | 4-OH-Phenyl | Cyclobutyl |
| 775 | 2 | 4-OH-Phenyl | cyclopentyl |
| 776 | 2 | 4-OH-Phenyl | cyclohexyl |
| 777 | 2 | 4-OH-Phenyl | 3-pyridyl |
| 778 | 2 | 4-OH-Phenyl | 1-methyl-1H-pyrazol-4-yl |
| 779 | 2 | 4-OH-Phenyl | 1H-imidazol-4-yl |
| 780 | 2 | 4-OH-Phenyl | 2-furanyl |
| 781 | 2 | 2-OH-Phenyl | Ethyl |
| 782 | 2 | 2-OH-Phenyl | n-propyl |
| 783 | 2 | 2-OH-Phenyl | Isopropyl |
| 784 | 2 | 2-OH-Phenyl | —$CH_2CH(CH_3)_2$ |
| 785 | 2 | 2-OH-Phenyl | $CF_3$ |
| 786 | 2 | 2-OH-Phenyl | —$CH_2CF_3$ |
| 787 | 2 | 2-OH-Phenyl | —$CH_2CH_2CF_3$ |
| 788 | 2 | 2-OH-Phenyl | cyclopropyl |
| 789 | 2 | 2-OH-Phenyl | Cyclobutyl |
| 790 | 2 | 2-OH-Phenyl | cyclopentyl |
| 791 | 2 | 2-OH-Phenyl | cyclohexyl |
| 792 | 2 | 2-OH-Phenyl | 3-pyridyl |
| 793 | 2 | 2-OH-Phenyl | 1-methyl-1H-pyrazol-4-yl |
| 794 | 2 | 2-OH-Phenyl | 1H-imidazol-4-yl |
| 795 | 2 | 2-OH-Phenyl | 2-furanyl |
| 796 | 2 | 3-OMe-Phenyl | Ethyl |
| 797 | 2 | 3-OMe-Phenyl | n-propyl |
| 798 | 2 | 3-OMe-Phenyl | Isopropyl |
| 799 | 2 | 3-OMe-Phenyl | —$CH_2CH(CH_3)_2$ |
| 800 | 2 | 3-OMe-Phenyl | $CF_3$ |
| 801 | 2 | 3-OMe-Phenyl | —$CH_2CF_3$ |
| 802 | 2 | 3-OMe-Phenyl | —$CH_2CH_2CF_3$ |
| 803 | 2 | 3-OMe-Phenyl | cyclopropyl |
| 804 | 2 | 3-OMe-Phenyl | Cyclobutyl |
| 805 | 2 | 3-OMe-Phenyl | cyclopentyl |
| 806 | 2 | 3-OMe-Phenyl | cyclohexyl |
| 807 | 2 | 3-OMe-Phenyl | 3-pyridyl |
| 808 | 2 | 3-OMe-Phenyl | 1-methyl-1H-pyrazol-4-yl |
| 809 | 2 | 3-OMe-Phenyl | 1H-imidazol-4-yl |
| 810 | 2 | 3-OMe-Phenyl | 2-furanyl |
| 811 | 2 | 4-CN-Phenyl | Ethyl |
| 812 | 2 | 4-CN-Phenyl | n-propyl |
| 813 | 2 | 4-CN-Phenyl | Isopropyl |
| 814 | 2 | 4-CN-Phenyl | —$CH_2CH(CH_3)_2$ |
| 815 | 2 | 4-CN-Phenyl | $CF_3$ |
| 816 | 2 | 4-CN-Phenyl | —$CH_2CF_3$ |
| 817 | 2 | 4-CN-Phenyl | —$CH_2CH_2CF_3$ |
| 818 | 2 | 4-CN-Phenyl | cyclopropyl |
| 819 | 2 | 4-CN-Phenyl | Cyclobutyl |
| 820 | 2 | 4-CN-Phenyl | cyclopentyl |

TABLE 33-continued

| Entry | n | $R^5$ | $R^{10c}$ |
|---|---|---|---|
| 821 | 2 | 4-CN-Phenyl | cyclohexyl |
| 822 | 2 | 4-CN-Phenyl | 3-pyridyl |
| 823 | 2 | 4-CN-Phenyl | 1-methyl-1H-pyrazol-4-yl |
| 824 | 2 | 4-CN-Phenyl | 1H-imidazol-4-yl |
| 825 | 2 | 4-CN-Phenyl | 2-furanyl |
| 826 | 2 | 2-CN-Phenyl | Ethyl |
| 827 | 2 | 2-CN-Phenyl | n-propyl |
| 828 | 2 | 2-CN-Phenyl | Isopropyl |
| 829 | 2 | 2-CN-Phenyl | —$CH_2CH(CH_3)_2$ |
| 830 | 2 | 2-CN-Phenyl | $CF_3$ |
| 831 | 2 | 2-CN-Phenyl | —$CH_2CF_3$ |
| 832 | 2 | 2-CN-Phenyl | —$CH_2CH_2CF_3$ |
| 833 | 2 | 2-CN-Phenyl | cyclopropyl |
| 834 | 2 | 2-CN-Phenyl | Cyclobutyl |
| 835 | 2 | 2-CN-Phenyl | cyclopentyl |
| 836 | 2 | 2-CN-Phenyl | cyclohexyl |
| 837 | 2 | 2-CN-Phenyl | 3-pyridyl |
| 838 | 2 | 2-CN-Phenyl | 1-methyl-1H-pyrazol-4-yl |
| 839 | 2 | 2-CN-Phenyl | 1H-imidazol-4-yl |
| 840 | 2 | 2-CN-Phenyl | 2-furanyl |
| 841 | 2 | 3-F-Phenyl | Ethyl |
| 842 | 2 | 3-F-Phenyl | n-propyl |
| 843 | 2 | 3-F-Phenyl | Isopropyl |
| 844 | 2 | 3-F-Phenyl | —$CH_2CH(CH_3)_2$ |
| 845 | 2 | 3-F-Phenyl | $CF_3$ |
| 846 | 2 | 3-F-Phenyl | —$CH_2CF_3$ |
| 847 | 2 | 3-F-Phenyl | —$CH_2CH_2CF_3$ |
| 848 | 2 | 3-F-Phenyl | cyclopropyl |
| 849 | 2 | 3-F-Phenyl | Cyclobutyl |
| 850 | 2 | 3-F-Phenyl | cyclopentyl |
| 851 | 2 | 3-F-Phenyl | cyclohexyl |
| 852 | 2 | 3-F-Phenyl | 3-pyridyl |
| 853 | 2 | 3-F-Phenyl | 1-methyl-1H-pyrazol-4-yl |
| 854 | 2 | 3-F-Phenyl | 1H-imidazol-4-yl |
| 855 | 2 | 3-F-Phenyl | 2-furanyl |
| 856 | 2 | 2-Cl-Phenyl | Ethyl |
| 857 | 2 | 2-Cl-Phenyl | n-propyl |
| 858 | 2 | 2-Cl-Phenyl | Isopropyl |
| 859 | 2 | 2-Cl-Phenyl | —$CH_2CH(CH_3)_2$ |
| 860 | 2 | 2-Cl-Phenyl | $CF_3$ |
| 861 | 2 | 2-Cl-Phenyl | —$CH_2CF_3$ |
| 862 | 2 | 2-Cl-Phenyl | —$CH_2CH_2CF_3$ |
| 863 | 2 | 2-Cl-Phenyl | cyclopropyl |
| 864 | 2 | 2-Cl-Phenyl | Cyclobutyl |
| 865 | 2 | 2-Cl-Phenyl | cyclopentyl |
| 866 | 2 | 2-Cl-Phenyl | cyclohexyl |
| 867 | 2 | 2-Cl-Phenyl | 3-pyridyl |
| 868 | 2 | 2-Cl-Phenyl | 1-methyl-1H-pyrazol-4-yl |
| 869 | 2 | 2-Cl-Phenyl | 1H-imidazol-4-yl |
| 870 | 2 | 2-Cl-Phenyl | 2-furanyl |
| 871 | 2 | 4-Cl-Phenyl | Ethyl |
| 872 | 2 | 4-Cl-Phenyl | n-propyl |
| 873 | 2 | 4-Cl-Phenyl | Isopropyl |
| 874 | 2 | 4-Cl-Phenyl | —$CH_2CH(CH_3)_2$ |
| 875 | 2 | 4-Cl-Phenyl | $CF_3$ |
| 876 | 2 | 4-Cl-Phenyl | —$CH_2CF_3$ |
| 877 | 2 | 4-Cl-Phenyl | —$CH_2CH_2CF_3$ |
| 878 | 2 | 4-Cl-Phenyl | cyclopropyl |
| 879 | 2 | 4-Cl-Phenyl | Cyclobutyl |
| 880 | 2 | 4-Cl-Phenyl | cyclopentyl |
| 881 | 2 | 4-Cl-Phenyl | cyclohexyl |
| 882 | 2 | 4-Cl-Phenyl | 3-pyridyl |
| 883 | 2 | 4-Cl-Phenyl | 1-methyl-1H-pyrazol-4-yl |
| 884 | 2 | 4-Cl-Phenyl | 1H-imidazol-4-yl |
| 885 | 2 | 4-Cl-Phenyl | 2-furanyl |
| 886 | 2 | 3-Br-Phenyl | Ethyl |
| 887 | 2 | 3-Br-Phenyl | n-propyl |
| 888 | 2 | 3-Br-Phenyl | Isopropyl |
| 889 | 2 | 3-Br-Phenyl | —$CH_2CH(CH_3)_2$ |
| 890 | 2 | 3-Br-Phenyl | $CF_3$ |
| 891 | 2 | 3-Br-Phenyl | —$CH_2CF_3$ |
| 892 | 2 | 3-Br-Phenyl | —$CH_2CH_2CF_3$ |
| 893 | 2 | 3-Br-Phenyl | cyclopropyl |
| 894 | 2 | 3-Br-Phenyl | Cyclobutyl |
| 895 | 2 | 3-Br-Phenyl | cyclopentyl |
| 896 | 2 | 3-Br-Phenyl | cyclohexyl |
| 897 | 2 | 3-Br-Phenyl | 3-pyridyl |
| 898 | 2 | 3-Br-Phenyl | 1-methyl-1H-pyrazol-4-yl |
| 899 | 2 | 3-Br-Phenyl | 1H-imidazol-4-yl |
| 900 | 2 | 3-Br-Phenyl | 2-furanyl |
| 901 | 2 | 2-$CF_3$-Phenyl | Ethyl |
| 902 | 2 | 2-$CF_3$-Phenyl | n-propyl |
| 903 | 2 | 2-$CF_3$-Phenyl | Isopropyl |
| 904 | 2 | 2-$CF_3$-Phenyl | —$CH_2CH(CH_3)_2$ |
| 905 | 2 | 2-$CF_3$-Phenyl | $CF_3$ |
| 906 | 2 | 2-$CF_3$-Phenyl | —$CH_2CF_3$ |
| 907 | 2 | 2-$CF_3$-Phenyl | —$CH_2CH_2CF_3$ |
| 908 | 2 | 2-$CF_3$-Phenyl | cyclopropyl |
| 909 | 2 | 2-$CF_3$-Phenyl | Cyclobutyl |
| 910 | 2 | 2-$CF_3$-Phenyl | cyclopentyl |
| 911 | 2 | 2-$CF_3$-Phenyl | cyclohexyl |
| 912 | 2 | 2-$CF_3$-Phenyl | 3-pyridyl |
| 913 | 2 | 2-$CF_3$-Phenyl | 1-methyl-1H-pyrazol-4-yl |
| 914 | 2 | 2-$CF_3$-Phenyl | 1H-imidazol-4-yl |
| 915 | 2 | 2-$CF_3$-Phenyl | 2-furanyl |
| 916 | 2 | 4-$CF_3$-Phenyl | Ethyl |
| 917 | 2 | 4-$CF_3$-Phenyl | n-propyl |
| 918 | 2 | 4-$CF_3$-Phenyl | Isopropyl |
| 919 | 2 | 4-$CF_3$-Phenyl | —$CH_2CH(CH_3)_2$ |
| 920 | 2 | 4-$CF_3$-Phenyl | $CF_3$ |
| 921 | 2 | 4-$CF_3$-Phenyl | —$CH_2CF_3$ |
| 922 | 2 | 4-$CF_3$-Phenyl | —$CH_2CH_2CF_3$ |
| 923 | 2 | 4-$CF_3$-Phenyl | cyclopropyl |
| 924 | 2 | 4-$CF_3$-Phenyl | Cyclobutyl |
| 925 | 2 | 4-$CF_3$-Phenyl | cyclopentyl |
| 926 | 2 | 4-$CF_3$-Phenyl | cyclohexyl |
| 927 | 2 | 4-$CF_3$-Phenyl | 3-pyridyl |
| 928 | 2 | 4-$CF_3$-Phenyl | 1-methyl-1H-pyrazol-4-yl |
| 929 | 2 | 4-$CF_3$-Phenyl | 1H-imidazol-4-yl |
| 930 | 2 | 4-$CF_3$-Phenyl | 2-furanyl |
| 931 | 2 | 3-iPr-Phenyl | Ethyl |
| 932 | 2 | 3-iPr-Phenyl | n-propyl |
| 933 | 2 | 3-iPr-Phenyl | Isopropyl |
| 934 | 2 | 3-iPr-Phenyl | —$CH_2CH(CH_3)_2$ |
| 935 | 2 | 3-iPr-Phenyl | $CF_3$ |
| 936 | 2 | 3-iPr-Phenyl | —$CH_2CF_3$ |
| 937 | 2 | 3-iPr-Phenyl | —$CH_2CH_2CF_3$ |
| 938 | 2 | 3-iPr-Phenyl | cyclopropyl |
| 939 | 2 | 3-iPr-Phenyl | Cyclobutyl |
| 940 | 2 | 3-iPr-Phenyl | cyclopentyl |
| 941 | 2 | 3-iPr-Phenyl | cyclohexyl |
| 942 | 2 | 3-iPr-Phenyl | 3-pyridyl |
| 943 | 2 | 3-iPr-Phenyl | 1-methyl-1H-pyrazol-4-yl |
| 944 | 2 | 3-iPr-Phenyl | 1H-imidazol-4-yl |
| 945 | 2 | 3-iPr-Phenyl | 2-furanyl |
| 946 | 2 | 2-morpholino-phenyl | Ethyl |
| 947 | 2 | 2-morpholino-phenyl | n-propyl |
| 948 | 2 | 2-morpholino-phenyl | isopropyl |
| 949 | 2 | 2-morpholino-phenyl | —$CH_2CH(CH_3)_2$ |
| 950 | 2 | 2-morpholino-phenyl | $CF_3$ |
| 951 | 2 | 2-morpholino-phenyl | —$CH_2CF_3$ |
| 952 | 2 | 2-morpholino-phenyl | —$CH_2CH_2CF_3$ |
| 953 | 2 | 2-morpholino-phenyl | cyclopropyl |
| 954 | 2 | 2-morpholino-phenyl | Cyclobutyl |
| 955 | 2 | 2-morpholino-phenyl | cyclopentyl |
| 956 | 2 | 2-morpholino-phenyl | cyclohexyl |
| 957 | 2 | 2-morpholino-phenyl | 3-pyridyl |
| 958 | 2 | 2-morpholino-phenyl | 1-methyl-1H-pyrazol-4-yl |
| 959 | 2 | 2-morpholino-phenyl | 1H-imidazol-4-yl |
| 960 | 2 | 2-morpholino-phenyl | 2-furanyl |
| 961 | 2 | 4-morpholino-phenyl | ethyl |
| 962 | 2 | 4-morpholino-phenyl | n-propyl |
| 963 | 2 | 4-morpholino-phenyl | isopropyl |
| 964 | 2 | 4-morpholino-phenyl | —$CH_2CH(CH_3)_2$ |
| 965 | 2 | 4-morpholino-phenyl | $CF_3$ |
| 966 | 2 | 4-morpholino-phenyl | —$CH_2CF_3$ |
| 967 | 2 | 4-morpholino-phenyl | —$CH_2CH_2CF_3$ |
| 968 | 2 | 4-morpholino-phenyl | cyclopropyl |
| 969 | 2 | 4-morpholino-phenyl | Cyclobutyl |
| 970 | 2 | 4-morpholino-phenyl | cyclopentyl |
| 971 | 2 | 4-morpholino-phenyl | cyclohexyl |
| 972 | 2 | 4-morpholino-phenyl | 3-pyridyl |
| 973 | 2 | 4-morpholino-phenyl | 1-methyl-1H-pyrazol-4-yl |
| 974 | 2 | 4-morpholino-phenyl | 1H-imidazol-4-yl |
| 975 | 2 | 4-morpholino-phenyl | 2-furanyl |
| 976 | 2 | 4-methyl-2-morpholino-phenyl | ethyl |

TABLE 33-continued

| Entry | n | $R^5$ | $R^{10c}$ |
|---|---|---|---|
| 977 | 2 | 4-methyl-2-morpholino-phenyl | n-propyl |
| 978 | 2 | 4-methyl-2-morpholino-phenyl | isopropyl |
| 979 | 2 | 4-methyl-2-morpholino-phenyl | $—CH_2CH(CH_3)_2$ |
| 980 | 2 | 4-methyl-2-morpholino-phenyl | $CF_3$ |
| 981 | 2 | 4-methyl-2-morpholino-phenyl | $—CH_2CF_3$ |
| 982 | 2 | 4-methyl-2-morpholino-phenyl | $—CH_2CH_2CF_3$ |
| 983 | 2 | 4-methyl-2-morpholino-phenyl | cyclopropyl |
| 984 | 2 | 4-methyl-2-morpholino-phenyl | Cyclobutyl |
| 985 | 2 | 4-methyl-2-morpholino-phenyl | cyclopentyl |
| 986 | 2 | 4-methyl-2-morpholino-phenyl | cyclohexyl |
| 987 | 2 | 4-methyl-2-morpholino-phenyl | 3-pyridyl |
| 988 | 2 | 4-methyl-2-morpholino-phenyl | 1-methyl-1H-pyrazol-4-yl |
| 989 | 2 | 4-methyl-2-morpholino-phenyl | 1H-imidazol-4-yl |
| 990 | 2 | 4-methyl-2-morpholino-phenyl | 2-furanyl |
| 991 | 3 | $4-CH_3$-phenyl | ethyl |
| 992 | 3 | $4-CH_3$-phenyl | n-propyl |
| 993 | 3 | $4-CH_3$-phenyl | isopropyl |
| 994 | 3 | $4-CH_3$-phenyl | $—CH_2CH(CH_3)_2$ |
| 995 | 3 | $4-CH_3$-phenyl | $CF_3$ |
| 996 | 3 | $4-CH_3$-phenyl | $—CH_2CF_3$ |
| 997 | 3 | $4-CH_3$-phenyl | $—CH_2CH_2CF_3$ |
| 998 | 3 | $4-CH_3$-phenyl | cyclopropyl |
| 999 | 3 | $4-CH_3$-phenyl | Cyclobutyl |
| 1000 | 3 | $4-CH_3$-phenyl | cyclopentyl |
| 1001 | 3 | $4-CH_3$-phenyl | cyclohexyl |
| 1002 | 3 | $4-CH_3$-phenyl | 3-pyridyl |
| 1003 | 3 | $4-CH_3$-phenyl | 1-methyl-1H-pyrazol-4-yl |
| 1004 | 3 | $4-CH_3$-phenyl | 1H-imidazol-4-yl |
| 1005 | 3 | $4-CH_3$-phenyl | 2-furanyl |
| 1006 | 3 | $3-CH_3$-phenyl | ethyl |
| 1007 | 3 | $3-CH_3$-phenyl | n-propyl |
| 1008 | 3 | $3-CH_3$-phenyl | isopropyl |
| 1009 | 3 | $3-CH_3$-phenyl | $—CH_2CH(CH_3)_2$ |
| 1010 | 3 | $3-CH_3$-phenyl | $CF_3$ |
| 1011 | 3 | $3-CH_3$-phenyl | $—CH_2CF_3$ |
| 1012 | 3 | $3-CH_3$-phenyl | $—CH_2CH_2CF_3$ |
| 1013 | 3 | $3-CH_3$-phenyl | cyclopropyl |
| 1014 | 3 | $3-CH_3$-phenyl | Cyclobutyl |
| 1015 | 3 | $3-CH_3$-phenyl | cyclopentyl |
| 1016 | 3 | $3-CH_3$-phenyl | cyclohexyl |
| 1017 | 3 | $3-CH_3$-phenyl | 3-pyridyl |
| 1018 | 3 | $3-CH_3$-phenyl | 1-methyl-1H-pyrazol-4-yl |
| 1019 | 3 | $3-CH_3$-phenyl | 1H-imidazol-4-yl |
| 1020 | 3 | $3-CH_3$-phenyl | 2-furanyl |
| 1021 | 3 | 3-OH-Phenyl | ethyl |
| 1022 | 3 | 3-OH-Phenyl | n-propyl |
| 1023 | 3 | 3-OH-Phenyl | isopropyl |
| 1024 | 3 | 3-OH-Phenyl | $—CH_2CH(CH_3)_2$ |
| 1025 | 3 | 3-OH-Phenyl | $CF_3$ |
| 1026 | 3 | 3-OH-Phenyl | $—CH_2CF_3$ |
| 1027 | 3 | 3-OH-Phenyl | $—CH_2CH_2CF_3$ |
| 1028 | 3 | 3-OH-Phenyl | cyclopropyl |
| 1029 | 3 | 3-OH-Phenyl | Cyclobutyl |
| 1030 | 3 | 3-OH-Phenyl | cyclopentyl |
| 1031 | 3 | 3-OH-Phenyl | cyclohexyl |
| 1032 | 3 | 3-OH-Phenyl | 3-pyridyl |
| 1033 | 3 | 3-OH-Phenyl | 1-methyl-1H-pyrazol-4-yl |
| 1034 | 3 | 3-OH-Phenyl | 1H-imidazol-4-yl |
| 1035 | 3 | 3-OH-Phenyl | 2-furanyl |
| 1036 | 3 | 4-OMe-Phenyl | ethyl |
| 1037 | 3 | 4-OMe-Phenyl | n-propyl |
| 1038 | 3 | 4-OMe-Phenyl | isopropyl |
| 1039 | 3 | 4-OMe-Phenyl | $—CH_2CH(CH_3)_2$ |
| 1040 | 3 | 4-OMe-Phenyl | $CF_3$ |
| 1041 | 3 | 4-OMe-Phenyl | $—CH_2CF_3$ |
| 1042 | 3 | 4-OMe-Phenyl | $—CH_2CH_2CF_3$ |
| 1043 | 3 | 4-OMe-Phenyl | cyclopropyl |
| 1044 | 3 | 4-OMe-Phenyl | Cyclobutyl |
| 1045 | 3 | 4-OMe-Phenyl | cyclopentyl |
| 1046 | 3 | 4-OMe-Phenyl | cyclohexyl |
| 1047 | 3 | 4-OMe-Phenyl | 3-pyridyl |
| 1048 | 3 | 4-OMe-Phenyl | 1-methyl-1H-pyrazol-4-yl |
| 1049 | 3 | 4-OMe-Phenyl | 1H-imidazol-4-yl |
| 1050 | 3 | 4-OMe-Phenyl | 2-furanyl |
| 1051 | 3 | 2-OMe-Phenyl | ethyl |
| 1052 | 3 | 2-OMe-Phenyl | n-propyl |
| 1053 | 3 | 2-OMe-Phenyl | isopropyl |
| 1054 | 3 | 2-OMe-Phenyl | $—CH_2CH(CH_3)_2$ |
| 1055 | 3 | 2-OMe-Phenyl | $CF_3$ |
| 1056 | 3 | 2-OMe-Phenyl | $—CH_2CF_3$ |
| 1057 | 3 | 2-OMe-Phenyl | $—CH_2CH_2CF_3$ |
| 1058 | 3 | 2-OMe-Phenyl | cyclopropyl |
| 1059 | 3 | 2-OMe-Phenyl | Cyclobutyl |
| 1060 | 3 | 2-OMe-Phenyl | cyclopentyl |
| 1061 | 3 | 2-OMe-Phenyl | cyclohexyl |
| 1062 | 3 | 2-OMe-Phenyl | 3-pyridyl |
| 1063 | 3 | 2-OMe-Phenyl | 1-methyl-1H-pyrazol-4-yl |
| 1064 | 3 | 2-OMe-Phenyl | 1H-imidazol-4-yl |
| 1065 | 3 | 2-OMe-Phenyl | 2-furanyl |
| 1066 | 3 | 3-CN-Phenyl | ethyl |
| 1067 | 3 | 3-CN-Phenyl | n-propyl |
| 1068 | 3 | 3-CN-Phenyl | isopropyl |
| 1069 | 3 | 3-CN-Phenyl | $—CH_2CH(CH_3)_2$ |
| 1070 | 3 | 3-CN-Phenyl | $CF_3$ |
| 1071 | 3 | 3-CN-Phenyl | $—CH_2CF_3$ |
| 1072 | 3 | 3-CN-Phenyl | $—CH_2CH_2CF_3$ |
| 1073 | 3 | 3-CN-Phenyl | cyclopropyl |
| 1074 | 3 | 3-CN-Phenyl | Cyclobutyl |
| 1075 | 3 | 3-CN-Phenyl | cyclopentyl |
| 1076 | 3 | 3-CN-Phenyl | cyclohexyl |
| 1077 | 3 | 3-CN-Phenyl | 3-pyridyl |
| 1078 | 3 | 3-CN-Phenyl | 1-methyl-1H-pyrazol-4-yl |
| 1079 | 3 | 3-CN-Phenyl | 1H-imidazol-4-yl |
| 1080 | 3 | 3-CN-Phenyl | 2-furanyl |
| 1081 | 3 | 2-F-Phenyl | ethyl |
| 1082 | 3 | 2-F-Phenyl | n-propyl |
| 1083 | 3 | 2-F-Phenyl | isopropyl |
| 1084 | 3 | 2-F-Phenyl | $—CH_2CH(CH_3)_2$ |
| 1085 | 3 | 2-F-Phenyl | $CF_3$ |
| 1086 | 3 | 2-F-Phenyl | $—CH_2CF_3$ |
| 1087 | 3 | 2-F-Phenyl | $—CH_2CH_2CF_3$ |
| 1088 | 3 | 2-F-Phenyl | cyclopropyl |
| 1089 | 3 | 2-F-Phenyl | Cyclobutyl |
| 1090 | 3 | 2-F-Phenyl | cyclopentyl |
| 1091 | 3 | 2-F-Phenyl | cyclohexyl |
| 1092 | 3 | 2-F-Phenyl | 3-pyridyl |
| 1093 | 3 | 2-F-Phenyl | 1-methyl-1H-pyrazol-4-yl |
| 1094 | 3 | 2-F-Phenyl | 1H-imidazol-4-yl |
| 1095 | 3 | 2-F-Phenyl | 2-furanyl |
| 1096 | 3 | 4-F-Phenyl | ethyl |
| 1097 | 3 | 4-F-Phenyl | n-propyl |
| 1098 | 3 | 4-F-Phenyl | isopropyl |
| 1099 | 3 | 4-F-Phenyl | $—CH_2CH(CH_3)_2$ |
| 1100 | 3 | 4-F-Phenyl | $CF_3$ |
| 1101 | 3 | 4-F-Phenyl | $—CH_2CF_3$ |
| 1102 | 3 | 4-F-Phenyl | $—CH_2CH_2CF_3$ |
| 1103 | 3 | 4-F-Phenyl | cyclopropyl |
| 1104 | 3 | 4-F-Phenyl | Cyclobutyl |
| 1105 | 3 | 4-F-Phenyl | cyclopentyl |
| 1106 | 3 | 4-F-Phenyl | cyclohexyl |
| 1107 | 3 | 4-F-Phenyl | 3-pyridyl |
| 1108 | 3 | 4-F-Phenyl | 1-methyl-1H-pyrazol-4-yl |
| 1109 | 3 | 4-F-Phenyl | 1H-imidazol-4-yl |
| 1110 | 3 | 4-F-Phenyl | 2-furanyl |
| 1111 | 3 | 3-Cl-Phenyl | ethyl |
| 1112 | 3 | 3-Cl-Phenyl | n-propyl |
| 1113 | 3 | 3-Cl-Phenyl | isopropyl |
| 1114 | 3 | 3-Cl-Phenyl | $—CH_2CH(CH_3)_2$ |
| 1115 | 3 | 3-Cl-Phenyl | $CF_3$ |
| 1116 | 3 | 3-Cl-Phenyl | $—CH_2CF_3$ |
| 1117 | 3 | 3-Cl-Phenyl | $—CH_2CH_2CF_3$ |
| 1118 | 3 | 3-Cl-Phenyl | cyclopropyl |
| 1119 | 3 | 3-Cl-Phenyl | Cyclobutyl |
| 1120 | 3 | 3-Cl-Phenyl | cyclopentyl |
| 1121 | 3 | 3-Cl-Phenyl | cyclohexyl |
| 1122 | 3 | 3-Cl-Phenyl | 3-pyridyl |
| 1123 | 3 | 3-Cl-Phenyl | 1-methyl-1H-pyrazol-4-yl |
| 1124 | 3 | 3-Cl-Phenyl | 1H-imidazol-4-yl |
| 1125 | 3 | 3-Cl-Phenyl | 2-furanyl |
| 1126 | 3 | 2-Br-Phenyl | ethyl |
| 1127 | 3 | 2-Br-Phenyl | n-propyl |
| 1128 | 3 | 2-Br-Phenyl | isopropyl |
| 1129 | 3 | 2-Br-Phenyl | $—CH_2CH(CH_3)_2$ |
| 1130 | 3 | 2-Br-Phenyl | $CF_3$ |
| 1131 | 3 | 2-Br-Phenyl | $—CH_2CF_3$ |
| 1132 | 3 | 2-Br-Phenyl | $—CH_2CH_2CF_3$ |

TABLE 33-continued

| Entry | n | $R^5$ | $R^{10c}$ |
|---|---|---|---|
| 1133 | 3 | 2-Br-Phenyl | cyclopropyl |
| 1134 | 3 | 2-Br-Phenyl | Cyclobutyl |
| 1135 | 3 | 2-Br-Phenyl | cyclopentyl |
| 1136 | 3 | 2-Br-Phenyl | cyclohexyl |
| 1137 | 3 | 2-Br-Phenyl | 3-pyridyl |
| 1138 | 3 | 2-Br-Phenyl | 1-methyl-1H-pyrazol-4-yl |
| 1139 | 3 | 2-Br-Phenyl | 1H-imidazol-4-yl |
| 1140 | 3 | 2-Br-Phenyl | 2-furanyl |
| 1141 | 3 | 4-Br-Phenyl | ethyl |
| 1142 | 3 | 4-Br-Phenyl | n-propyl |
| 1143 | 3 | 4-Br-Phenyl | isopropyl |
| 1144 | 3 | 4-Br-Phenyl | $—CH_2CH(CH_3)_2$ |
| 1145 | 3 | 4-Br-Phenyl | $CF_3$ |
| 1146 | 3 | 4-Br-Phenyl | $—CH_2CF_3$ |
| 1147 | 3 | 4-Br-Phenyl | $—CH_2CH_2CF_3$ |
| 1148 | 3 | 4-Br-Phenyl | cyclopropyl |
| 1149 | 3 | 4-Br-Phenyl | Cyclobutyl |
| 1150 | 3 | 4-Br-Phenyl | cyclopentyl |
| 1151 | 3 | 4-Br-Phenyl | cyclohexyl |
| 1152 | 3 | 4-Br-Phenyl | 3-pyridyl |
| 1153 | 3 | 4-Br-Phenyl | 1-methyl-1H-pyrazol-4-yl |
| 1154 | 3 | 4-Br-Phenyl | 1H-imidazol-4-yl |
| 1155 | 3 | 4-Br-Phenyl | 2-furanyl |
| 1156 | 3 | $3-CF_3$-Phenyl | ethyl |
| 1157 | 3 | $3-CF_3$-Phenyl | n-propyl |
| 1158 | 3 | $3-CF_3$-Phenyl | isopropyl |
| 1159 | 3 | $3-CF_3$-Phenyl | $—CH_2CH(CH_3)_2$ |
| 1160 | 3 | $3-CF_3$-Phenyl | $CF_3$ |
| 1161 | 3 | $3-CF_3$-Phenyl | $—CH_2CF_3$ |
| 1162 | 3 | $3-CF_3$-Phenyl | $—CH_2CH_2CF_3$ |
| 1163 | 3 | $3-CF_3$-Phenyl | cyclopropyl |
| 1164 | 3 | $3-CF_3$-Phenyl | Cyclobutyl |
| 1165 | 3 | $3-CF_3$-Phenyl | cyclopentyl |
| 1166 | 3 | $3-CF_3$-Phenyl | cyclohexyl |
| 1167 | 3 | $3-CF_3$-Phenyl | 3-pyridyl |
| 1168 | 3 | $3-CF_3$-Phenyl | 1-methyl-1H-pyrazol-4-yl |
| 1169 | 3 | $3-CF_3$-Phenyl | 1H-imidazol-4-yl |
| 1170 | 3 | $3-CF_3$-Phenyl | 2-furanyl |
| 1171 | 3 | 2-iPr-Phenyl | ethyl |
| 1172 | 3 | 2-iPr-Phenyl | n-propyl |
| 1173 | 3 | 2-iPr-Phenyl | isopropyl |
| 1174 | 3 | 2-iPr-Phenyl | $—CH_2CH(CH_3)_2$ |
| 1175 | 3 | 2-iPr-Phenyl | $CF_3$ |
| 1176 | 3 | 2-iPr-Phenyl | $—CH_2CF_3$ |
| 1177 | 3 | 2-iPr-Phenyl | $—CH_2CH_2CF_3$ |
| 1178 | 3 | 2-iPr-Phenyl | cyclopropyl |
| 1179 | 3 | 2-iPr-Phenyl | Cyclobutyl |
| 1180 | 3 | 2-iPr-Phenyl | cyclopentyl |
| 1181 | 3 | 2-iPr-Phenyl | cyclohexyl |
| 1182 | 3 | 2-iPr-Phenyl | 3-pyridyl |
| 1183 | 3 | 2-iPr-Phenyl | 1-methyl-1H-pyrazol-4-yl |
| 1184 | 3 | 2-iPr-Phenyl | 1H-imidazol-4-yl |
| 1185 | 3 | 2-iPr-Phenyl | 2-furanyl |
| 1186 | 3 | 4-iPr-Phenyl | ethyl |
| 1187 | 3 | 4-iPr-Phenyl | n-propyl |
| 1188 | 3 | 4-iPr-Phenyl | isopropyl |
| 1189 | 3 | 4-iPr-Phenyl | $—CH_2CH(CH_3)_2$ |
| 1190 | 3 | 4-iPr-Phenyl | $CF_3$ |
| 1191 | 3 | 4-iPr-Phenyl | $—CH_2CF_3$ |
| 1192 | 3 | 4-iPr-Phenyl | $—CH_2CH_2CF_3$ |
| 1193 | 3 | 4-iPr-Phenyl | cyclopropyl |
| 1194 | 3 | 4-iPr-Phenyl | Cyclobutyl |
| 1195 | 3 | 4-iPr-Phenyl | cyclopentyl |
| 1196 | 3 | 4-iPr-Phenyl | cyclohexyl |
| 1197 | 3 | 4-iPr-Phenyl | 3-pyridyl |
| 1198 | 3 | 4-iPr-Phenyl | 1-methyl-1H-pyrazol-4-yl |
| 1199 | 3 | 4-iPr-Phenyl | 1H-imidazol-4-yl |
| 1200 | 3 | 4-iPr-Phenyl | 2-furanyl |
| 1201 | 3 | 3-morpholino-phenyl | ethyl |
| 1202 | 3 | 3-morpholino-phenyl | n-propyl |
| 1203 | 3 | 3-morpholino-phenyl | isopropyl |
| 1204 | 3 | 3-morpholino-phenyl | $—CH_2CH(CH_3)_2$ |
| 1205 | 3 | 3-morpholino-phenyl | $CF_3$ |
| 1206 | 3 | 3-morpholino-phenyl | $—CH_2CF_3$ |
| 1207 | 3 | 3-morpholino-phenyl | $—CH_2CH_2CF_3$ |
| 1208 | 3 | 3-morpholino-phenyl | cyclopropyl |
| 1209 | 3 | 3-morpholino-phenyl | Cyclobutyl |
| 1210 | 3 | 3-morpholino-phenyl | cyclopentyl |
| 1211 | 3 | 3-morpholino-phenyl | cyclohexyl |
| 1212 | 3 | 3-morpholino-phenyl | 3-pyridyl |
| 1213 | 3 | 3-morpholino-phenyl | 1-methyl-1H-pyrazol-4-yl |
| 1214 | 3 | 3-morpholino-phenyl | 1H-imidazol-4-yl |
| 1215 | 3 | 3-morpholino-phenyl | 2-furanyl |
| 1216 | 3 | 4-cyano-2-morpholino-phenyl | ethyl |
| 1217 | 3 | 4-cyano-2-morpholino-phenyl | n-propyl |
| 1218 | 3 | 4-cyano-2-morpholino-phenyl | isopropyl |
| 1219 | 3 | 4-cyano-2-morpholino-phenyl | $—CH_2CH(CH_3)_2$ |
| 1220 | 3 | 4-cyano-2-morpholino-phenyl | $CF_3$ |
| 1221 | 3 | 4-cyano-2-morpholino-phenyl | $—CH_2CF_3$ |
| 1222 | 3 | 4-cyano-2-morpholino-phenyl | $—CH_2CH_2CF_3$ |
| 1223 | 3 | 4-cyano-2-morpholino-phenyl | cyclopropyl |
| 1224 | 3 | 4-cyano-2-morpholino-phenyl | Cyclobutyl |
| 1225 | 3 | 4-cyano-2-morpholino-phenyl | cyclopentyl |
| 1226 | 3 | 4-cyano-2-morpholino-phenyl | cyclohexyl |
| 1227 | 3 | 4-cyano-2-morpholino-phenyl | 3-pyridyl |
| 1228 | 3 | 4-cyano-2-morpholino-phenyl | 1-methyl-1H-pyrazol-4-yl |
| 1229 | 3 | 4-cyano-2-morpholino-phenyl | 1H-imidazol-4-yl |
| 1230 | 3 | 4-cyano-2-morpholino-phenyl | 2-furanyl |
| 1231 | 3 | 4-hydroxy-2-morpholino-phenyl | ethyl |
| 1232 | 3 | 4-hydroxy-2-morpholino-phenyl | n-propyl |
| 1233 | 3 | 4-hydroxy-2-morpholino-phenyl | isopropyl |
| 1234 | 3 | 4-hydroxy-2-morpholino-phenyl | $—CH_2CH(CH_3)_2$ |
| 1235 | 3 | 4-hydroxy-2-morpholino-phenyl | $CF_3$ |
| 1236 | 3 | 4-hydroxy-2-morpholino-phenyl | $—CH_2CF_3$ |
| 1237 | 3 | 4-hydroxy-2-morpholino-phenyl | $—CH_2CH_2CF_3$ |
| 1238 | 3 | 4-hydroxy-2-morpholino-phenyl | cyclopropyl |
| 1239 | 3 | 4-hydroxy-2-morpholino-phenyl | Cyclobutyl |
| 1240 | 3 | 4-hydroxy-2-morpholino-phenyl | cyclopentyl |
| 1241 | 3 | 4-hydroxy-2-morpholino-phenyl | cyclohexyl |
| 1242 | 3 | 4-hydroxy-2-morpholino-phenyl | 3-pyridyl |
| 1243 | 3 | 4-hydroxy-2-morpholino-phenyl | 1-methyl-1H-pyrazol-4-yl |
| 1244 | 3 | 4-hydroxy-2-morpholino-phenyl | 1H-imidazol-4-yl |
| 1245 | 3 | 4-hydroxy-2-morpholino-phenyl | 2-furanyl |
| 1246 | 3 | $2-CH_3$-phenyl | Ethyl |
| 1247 | 3 | $2-CH_3$-phenyl | n-propyl |
| 1248 | 3 | $2-CH_3$-phenyl | Isopropyl |
| 1249 | 3 | $2-CH_3$-phenyl | $—CH_2CH(CH_3)_2$ |
| 1250 | 3 | $2-CH_3$-phenyl | $CF_3$ |
| 1251 | 3 | $2-CH_3$-phenyl | $—CH_2CF_3$ |
| 1252 | 3 | $2-CH_3$-phenyl | $—CH_2CH_2CF_3$ |
| 1253 | 3 | $2-CH_3$-phenyl | cyclopropyl |
| 1254 | 3 | $2-CH_3$-phenyl | Cyclobutyl |
| 1255 | 3 | $2-CH_3$-phenyl | cyclopentyl |
| 1256 | 3 | $2-CH_3$-phenyl | cyclohexyl |
| 1257 | 3 | $2-CH_3$-phenyl | 3-pyridyl |
| 1258 | 3 | $2-CH_3$-phenyl | 1-methyl-1H-pyrazol-4-yl |
| 1259 | 3 | $2-CH_3$-phenyl | 1H-imidazol-4-yl |
| 1260 | 3 | $2-CH_3$-phenyl | 2-furanyl |
| 1261 | 3 | 4-OH-Phenyl | Ethyl |
| 1262 | 3 | 4-OH-Phenyl | n-propyl |
| 1263 | 3 | 4-OH-Phenyl | Isopropyl |
| 1264 | 3 | 4-OH-Phenyl | $—CH_2CH(CH_3)_2$ |
| 1265 | 3 | 4-OH-Phenyl | $CF_3$ |
| 1266 | 3 | 4-OH-Phenyl | $—CH_2CF_3$ |
| 1267 | 3 | 4-OH-Phenyl | $—CH_2CH_2CF_3$ |
| 1268 | 3 | 4-OH-Phenyl | cyclopropyl |
| 1269 | 3 | 4-OH-Phenyl | Cyclobutyl |
| 1270 | 3 | 4-OH-Phenyl | cyclopentyl |
| 1271 | 3 | 4-OH-Phenyl | cyclohexyl |
| 1272 | 3 | 4-OH-Phenyl | 3-pyridyl |
| 1273 | 3 | 4-OH-Phenyl | 1-methyl-1H-pyrazol-4-yl |
| 1274 | 3 | 4-OH-Phenyl | 1H-imidazol-4-yl |
| 1275 | 3 | 4-OH-Phenyl | 2-furanyl |
| 1276 | 3 | 2-OH-Phenyl | Ethyl |
| 1277 | 3 | 2-OH-Phenyl | n-propyl |
| 1278 | 3 | 2-OH-Phenyl | Isopropyl |
| 1279 | 3 | 2-OH-Phenyl | $—CH_2CH(CH_3)_2$ |
| 1280 | 3 | 2-OH-Phenyl | $CF_3$ |
| 1281 | 3 | 2-OH-Phenyl | $—CH_2CF_3$ |
| 1282 | 3 | 2-OH-Phenyl | $—CH_2CH_2CF_3$ |
| 1283 | 3 | 2-OH-Phenyl | cyclopropyl |
| 1284 | 3 | 2-OH-Phenyl | Cyclobutyl |
| 1285 | 3 | 2-OH-Phenyl | cyclopentyl |
| 1286 | 3 | 2-OH-Phenyl | cyclohexyl |
| 1287 | 3 | 2-OH-Phenyl | 3-pyridyl |
| 1288 | 3 | 2-OH-Phenyl | 1-methyl-1H-pyrazol-4-yl |

TABLE 33-continued

| Entry | n | $R^5$ | $R^{10c}$ |
|---|---|---|---|
| 1289 | 3 | 2-OH-Phenyl | 1H-imidazol-4-yl |
| 1290 | 3 | 2-OH-Phenyl | 2-furanyl |
| 1291 | 3 | 3-OMe-Phenyl | Ethyl |
| 1292 | 3 | 3-OMe-Phenyl | n-propyl |
| 1293 | 3 | 3-OMe-Phenyl | Isopropyl |
| 1294 | 3 | 3-OMe-Phenyl | $—CH_2CH(CH3)_2$ |
| 1295 | 3 | 3-OMe-Phenyl | $CF_3$ |
| 1296 | 3 | 3-OMe-Phenyl | $—CH_2CF_3$ |
| 1297 | 3 | 3-OMe-Phenyl | $—CH_2CH_2CF_3$ |
| 1298 | 3 | 3-OMe-Phenyl | cyclopropyl |
| 1299 | 3 | 3-OMe-Phenyl | Cyclobutyl |
| 1300 | 3 | 3-OMe-Phenyl | cyclopentyl |
| 1301 | 3 | 3-OMe-Phenyl | cyclohexyl |
| 1302 | 3 | 3-OMe-Phenyl | 3-pyridyl |
| 1303 | 3 | 3-OMe-Phenyl | 1-methyl-1H-pyrazol-4-yl |
| 1304 | 3 | 3-OMe-Phenyl | 1H-imidazol-4-yl |
| 1305 | 3 | 3-OMe-Phenyl | 2-furanyl |
| 1306 | 3 | 4-CN-Phenyl | Ethyl |
| 1307 | 3 | 4-CN-Phenyl | n-propyl |
| 1308 | 3 | 4-CN-Phenyl | Isopropyl |
| 1309 | 3 | 4-CN-Phenyl | $—CH_2CH(CH_3)_2$ |
| 1310 | 3 | 4-CN-Phenyl | $CF_3$ |
| 1311 | 3 | 4-CN-Phenyl | $—CH_2CF_3$ |
| 1312 | 3 | 4-CN-Phenyl | $—CH_2CH_2CF_3$ |
| 1313 | 3 | 4-CN-Phenyl | cyclopropyl |
| 1314 | 3 | 4-CN-Phenyl | Cyclobutyl |
| 1315 | 3 | 4-CN-Phenyl | cyclopentyl |
| 1316 | 3 | 4-CN-Phenyl | cyclohexyl |
| 1317 | 3 | 4-CN-Phenyl | 3-pyridyl |
| 1318 | 3 | 4-CN-Phenyl | 1-methyl-1H-pyrazol-4-yl |
| 1319 | 3 | 4-CN-Phenyl | 1H-imidazol-4-yl |
| 1320 | 3 | 4-CN-Phenyl | 2-furanyl |
| 1321 | 3 | 2-CN-Phenyl | Ethyl |
| 1322 | 3 | 2-CN-Phenyl | n-propyl |
| 1323 | 3 | 2-CN-Phenyl | Isopropyl |
| 1324 | 3 | 2-CN-Phenyl | $—CH_2CH(CH_3)_2$ |
| 1325 | 3 | 2-CN-Phenyl | $CF_3$ |
| 1326 | 3 | 2-CN-Phenyl | $—CH_2CF_3$ |
| 1327 | 3 | 2-CN-Phenyl | $—CH_2CH_2CF_3$ |
| 1328 | 3 | 2-CN-Phenyl | cyclopropyl |
| 1329 | 3 | 2-CN-Phenyl | Cyclobutyl |
| 1330 | 3 | 2-CN-Phenyl | cyclopentyl |
| 1331 | 3 | 2-CN-Phenyl | cyclohexyl |
| 1332 | 3 | 2-CN-Phenyl | 3-pyridyl |
| 1333 | 3 | 2-CN-Phenyl | 1-methyl-1H-pyrazol-4-yl |
| 1334 | 3 | 2-CN-Phenyl | 1H-imidazol-4-yl |
| 1335 | 3 | 2-CN-Phenyl | 2-furanyl |
| 1336 | 3 | 3-F-Phenyl | Ethyl |
| 1337 | 3 | 3-F-Phenyl | n-propyl |
| 1338 | 3 | 3-F-Phenyl | Isopropyl |
| 1339 | 3 | 3-F-Phenyl | $—CH_2CH(CH_3)_2$ |
| 1340 | 3 | 3-F-Phenyl | $CF_3$ |
| 1341 | 3 | 3-F-Phenyl | $—CH_2CF_3$ |
| 1342 | 3 | 3-F-Phenyl | $—CH_2CH_2CF_3$ |
| 1343 | 3 | 3-F-Phenyl | cyclopropyl |
| 1344 | 3 | 3-F-Phenyl | Cyclobutyl |
| 1345 | 3 | 3-F-Phenyl | cyclopentyl |
| 1346 | 3 | 3-F-Phenyl | cyclohexyl |
| 1347 | 3 | 3-F-Phenyl | 3-pyridyl |
| 1348 | 3 | 3-F-Phenyl | 1-methyl-1H-pyrazol-4-yl |
| 1349 | 3 | 3-F-Phenyl | 1H-imidazol-4-yl |
| 1350 | 3 | 3-F-Phenyl | 2-furanyl |
| 1351 | 3 | 2-Cl-Phenyl | Ethyl |
| 1352 | 3 | 2-Cl-Phenyl | n-propyl |
| 1353 | 3 | 2-Cl-Phenyl | Isopropyl |
| 1354 | 3 | 2-Cl-Phenyl | $—CH_2CH(CH_3)_2$ |
| 1355 | 3 | 2-Cl-Phenyl | $CF_3$ |
| 1356 | 3 | 2-Cl-Phenyl | $—CH_2CF_3$ |
| 1357 | 3 | 2-Cl-Phenyl | $—CH_2CH_2CF_3$ |
| 1358 | 3 | 2-Cl-Phenyl | cyclopropyl |
| 1359 | 3 | 2-Cl-Phenyl | Cyclobutyl |
| 1360 | 3 | 2-Cl-Phenyl | cyclopentyl |
| 1361 | 3 | 2-Cl-Phenyl | cyclohexyl |
| 1362 | 3 | 2-Cl-Phenyl | 3-pyridyl |
| 1363 | 3 | 2-Cl-Phenyl | 1-methyl-1H-pyrazol-4-yl |
| 1364 | 3 | 2-Cl-Phenyl | 1H-imidazol-4-yl |
| 1365 | 3 | 2-Cl-Phenyl | 2-furanyl |
| 1366 | 3 | 4-Cl-Phenyl | Ethyl |
| 1367 | 3 | 4-Cl-Phenyl | n-propyl |
| 1368 | 3 | 4-Cl-Phenyl | Isopropyl |
| 1369 | 3 | 4-Cl-Phenyl | $—CH_2CH(CH_3)_2$ |
| 1370 | 3 | 4-Cl-Phenyl | $CF_3$ |
| 1371 | 3 | 4-Cl-Phenyl | $—CH_2CF_3$ |
| 1372 | 3 | 4-Cl-Phenyl | $—CH_2CH_2CF_3$ |
| 1373 | 3 | 4-Cl-Phenyl | cyclopropyl |
| 1374 | 3 | 4-Cl-Phenyl | Cyclobutyl |
| 1375 | 3 | 4-Cl-Phenyl | cyclopentyl |
| 1376 | 3 | 4-Cl-Phenyl | cyclohexyl |
| 1377 | 3 | 4-Cl-Phenyl | 3-pyridyl |
| 1378 | 3 | 4-Cl-Phenyl | 1-methyl-1H-pyrazol-4-yl |
| 1379 | 3 | 4-Cl-Phenyl | 1H-imidazol-4-yl |
| 1380 | 3 | 4-Cl-Phenyl | 2-furanyl |
| 1381 | 3 | 3-Br-Phenyl | Ethyl |
| 1382 | 3 | 3-Br-Phenyl | n-propyl |
| 1383 | 3 | 3-Br-Phenyl | Isopropyl |
| 1384 | 3 | 3-Br-Phenyl | $—CH_2CH(CH_3)_2$ |
| 1385 | 3 | 3-Br-Phenyl | $CF_3$ |
| 1386 | 3 | 3-Br-Phenyl | $—CH_2CF_3$ |
| 1387 | 3 | 3-Br-Phenyl | $—CH_2CH_2CF_3$ |
| 1388 | 3 | 3-Br-Phenyl | cyclopropyl |
| 1389 | 3 | 3-Br-Phenyl | Cyclobutyl |
| 1390 | 3 | 3-Br-Phenyl | cyclopentyl |
| 1391 | 3 | 3-Br-Phenyl | cyclohexyl |
| 1392 | 3 | 3-Br-Phenyl | 3-pyridyl |
| 1393 | 3 | 3-Br-Phenyl | 1-methyl-1H-pyrazol-4-yl |
| 1394 | 3 | 3-Br-Phenyl | 1H-imidazol-4-yl |
| 1395 | 3 | 3-Br-Phenyl | 2-furanyl |
| 1396 | 3 | $2-CF_3$-Phenyl | Ethyl |
| 1397 | 3 | $2-CF_3$-Phenyl | n-propyl |
| 1398 | 3 | $2-CF_3$-Phenyl | Isopropyl |
| 1399 | 3 | $2-CF_3$-Phenyl | $—CH_2CH(CH_3)_2$ |
| 1400 | 3 | $2-CF_3$-Phenyl | $CF_3$ |
| 1401 | 3 | $2-CF_3$-Phenyl | $—CH_2CF_3$ |
| 1402 | 3 | $2-CF_3$-Phenyl | $—CH_2CH_2CF_3$ |
| 1403 | 3 | $2-CF_3$-Phenyl | cyclopropyl |
| 1404 | 3 | $2-CF_3$-Phenyl | Cyclobutyl |
| 1405 | 3 | $2-CF_3$-Phenyl | cyclopentyl |
| 1406 | 3 | $2-CF_3$-Phenyl | cyclohexyl |
| 1407 | 3 | $2-CF_3$-Phenyl | 3-pyridyl |
| 1408 | 3 | $2-CF_3$-Phenyl | 1-methyl-1H-pyrazol-4-yl |
| 1409 | 3 | $2-CF_3$-Phenyl | 1H-imidazol-4-yl |
| 1410 | 3 | $2-CF_3$-Phenyl | 2-furanyl |
| 1411 | 3 | $4-CF_3$-Phenyl | Ethyl |
| 1412 | 3 | $4-CF_3$-Phenyl | n-propyl |
| 1413 | 3 | $4-CF_3$-Phenyl | Isopropyl |
| 1414 | 3 | $4-CF_3$-Phenyl | $—CH_2CH(CH_3)_2$ |
| 1415 | 3 | $4-CF_3$-Phenyl | $CF_3$ |
| 1416 | 3 | $4-CF_3$-Phenyl | $—CH_2CF_3$ |
| 1417 | 3 | $4-CF_3$-Phenyl | $—CH_2CH_2CF_3$ |
| 1418 | 3 | $4-CF_3$-Phenyl | cyclopropyl |
| 1419 | 3 | $4-CF_3$-Phenyl | Cyclobutyl |
| 1420 | 3 | $4-CF_3$-Phenyl | cyclopentyl |
| 1421 | 3 | $4-CF_3$-Phenyl | cyclohexyl |
| 1422 | 3 | $4-CF_3$-Phenyl | 3-pyridyl |
| 1423 | 3 | $4-CF_3$-Phenyl | 1-methyl-1H-pyrazol-4-yl |
| 1424 | 3 | $4-CF_3$-Phenyl | 1H-imidazol-4-yl |
| 1425 | 3 | $4-CF_3$-Phenyl | 2-furanyl |
| 1426 | 3 | 3-iPr-Phenyl | Ethyl |
| 1427 | 3 | 3-iPr-Phenyl | n-propyl |
| 1428 | 3 | 3-iPr-Phenyl | Isopropyl |
| 1429 | 3 | 3-iPr-Phenyl | $—CH_2CH(CH_3)_2$ |
| 1430 | 3 | 3-iPr-Phenyl | $CF_3$ |
| 1431 | 3 | 3-iPr-Phenyl | $—CH_2CF_3$ |
| 1432 | 3 | 3-iPr-Phenyl | $—CH_2CH_2CF_3$ |
| 1433 | 3 | 3-iPr-Phenyl | cyclopropyl |
| 1434 | 3 | 3-iPr-Phenyl | Cyclobutyl |
| 1435 | 3 | 3-iPr-Phenyl | cyclopentyl |
| 1436 | 3 | 3-iPr-Phenyl | cyclohexyl |
| 1437 | 3 | 3-iPr-Phenyl | 3-pyridyl |
| 1438 | 3 | 3-iPr-Phenyl | 1-methyl-1H-pyrazol-4-yl |
| 1439 | 3 | 3-iPr-Phenyl | 1H-imidazol-4-yl |
| 1440 | 3 | 3-iPr-Phenyl | 2-furanyl |
| 1441 | 3 | 2-morpholino-phenyl | Ethyl |
| 1442 | 3 | 2-morpholino-phenyl | n-propyl |
| 1443 | 3 | 2-morpholino-phenyl | isopropyl |
| 1444 | 3 | 2-morpholino-phenyl | $—CH_2CH(CH_3)_2$ |

TABLE 33-continued

| Entry | n | $R^5$ | $R^{10c}$ |
|---|---|---|---|
| 1445 | 3 | 2-morpholino-phenyl | $CF_3$ |
| 1446 | 3 | 2-morpholino-phenyl | $—CH_2CF_3$ |
| 1447 | 3 | 2-morpholino-phenyl | $—CH_2CH_2CF_3$ |
| 1448 | 3 | 2-morpholino-phenyl | cyclopropyl |
| 1449 | 3 | 2-morpholino-phenyl | Cyclobutyl |
| 1450 | 3 | 2-morpholino-phenyl | cyclopentyl |
| 1451 | 3 | 2-morpholino-phenyl | cyclohexyl |
| 1452 | 3 | 2-morpholino-phenyl | 3-pyridyl |
| 1453 | 3 | 2-morpholino-phenyl | 1-methyl-1H-pyrazol-4-yl |
| 1454 | 3 | 2-morpholino-phenyl | 1H-imidazol-4-yl |
| 1455 | 3 | 2-morpholino-phenyl | 2-furanyl |
| 1456 | 3 | 4-morpholino-phenyl | ethyl |
| 1457 | 3 | 4-morpholino-phenyl | n-propyl |
| 1458 | 3 | 4-morpholino-phenyl | isopropyl |
| 1459 | 3 | 4-morpholino-phenyl | $—CH_2CH(CH_3)_2$ |
| 1460 | 3 | 4-morpholino-phenyl | $CF_3$ |
| 1461 | 3 | 4-morpholino-phenyl | $—CH_2CF_3$ |
| 1462 | 3 | 4-morpholino-phenyl | $—CH_2CH_2CF_3$ |
| 1463 | 3 | 4-morpholino-phenyl | cyclopropyl |
| 1464 | 3 | 4-morpholino-phenyl | Cyclobutyl |
| 1465 | 3 | 4-morpholino-phenyl | cyclopentyl |
| 1466 | 3 | 4-morpholino-phenyl | cyclohexyl |
| 1467 | 3 | 4-morpholino-phenyl | 3-pyridyl |
| 1468 | 3 | 4-morpholino-phenyl | 1-methyl-1H-pyrazol-4-yl |
| 1469 | 3 | 4-morpholino-phenyl | 1H-imidazol-4-yl |
| 1470 | 3 | 4-morpholino-phenyl | 2-furanyl |
| 1471 | 3 | 4-methyl-2-morpholino-phenyl | ethyl |
| 1472 | 3 | 4-methyl-2-morpholino-phenyl | n-propyl |
| 1473 | 3 | 4-methyl-2-morpholino-phenyl | isopropyl |
| 1474 | 3 | 4-methyl-2-morpholino-phenyl | $—CH_2CH(CH_3)_2$ |
| 1475 | 3 | 4-methyl-2-morpholino-phenyl | $CF_3$ |
| 1476 | 3 | 4-methyl-2-morpholino-phenyl | $—CH_2CF_3$ |
| 1477 | 3 | 4-methyl-2-morpholino-phenyl | $—CH_2CH_2CF_3$ |
| 1478 | 3 | 4-methyl-2-morpholino-phenyl | cyclopropyl |
| 1479 | 3 | 4-methyl-2-morpholino-phenyl | Cyclobutyl |
| 1480 | 3 | 4-methyl-2-morpholino-phenyl | cyclopentyl |
| 1481 | 3 | 4-methyl-2-morpholino-phenyl | cyclohexyl |
| 1482 | 3 | 4-methyl-2-morpholino-phenyl | 3-pyridyl |
| 1483 | 3 | 4-methyl-2-morpholino-phenyl | 1-methyl-1H-pyrazol-4-yl |
| 1484 | 3 | 4-methyl-2-morpholino-phenyl | 1H-imidazol-4-yl |
| 1485 | 3 | 4-methyl-2-morpholino-phenyl | 2-furanyl |
| 1486 | 4 | $4-CH_3$-phenyl | ethyl |
| 1487 | 4 | $4-CH_3$-phenyl | n-propyl |
| 1488 | 4 | $4-CH_3$-phenyl | isopropyl |
| 1489 | 4 | $4-CH_3$-phenyl | $—CH_2CH(CH_3)_2$ |
| 1490 | 4 | $4-CH_3$-phenyl | $CF_3$ |
| 1491 | 4 | $4-CH_3$-phenyl | $—CH_2CF_3$ |
| 1492 | 4 | $4-CH_3$-phenyl | $—CH_2CH_2CF_3$ |
| 1493 | 4 | $4-CH_3$-phenyl | cyclopropyl |
| 1494 | 4 | $4-CH_3$-phenyl | Cyclobutyl |
| 1495 | 4 | $4-CH_3$-phenyl | cyclopentyl |
| 1496 | 4 | $4-CH_3$-phenyl | cyclohexyl |
| 1497 | 4 | $4-CH_3$-phenyl | 3-pyridyl |
| 1498 | 4 | $4-CH_3$-phenyl | 1-methyl-1H-pyrazol-4-yl |
| 1499 | 4 | $4-CH_3$-phenyl | 1H-imidazol-4-yl |
| 1500 | 4 | $4-CH_3$-phenyl | 2-furanyl |
| 1501 | 4 | $3-CH_3$-phenyl | ethyl |
| 1502 | 4 | $3-CH_3$-phenyl | n-propyl |
| 1503 | 4 | $3-CH_3$-phenyl | isopropyl |
| 1504 | 4 | $3-CH_3$-phenyl | $—CH_2CH(CH_3)_2$ |
| 1505 | 4 | $3-CH_3$-phenyl | $CF_3$ |
| 1506 | 4 | $3-CH_3$-phenyl | $—CH_2CF_3$ |
| 1507 | 4 | $3-CH_3$-phenyl | $—CH_2CH_2CF_3$ |
| 1508 | 4 | $3-CH_3$-phenyl | cyclopropyl |
| 1509 | 4 | $3-CH_3$-phenyl | Cyclobutyl |
| 1510 | 4 | $3-CH_3$-phenyl | cyclopentyl |
| 1511 | 4 | $3-CH_3$-phenyl | cyclohexyl |
| 1512 | 4 | $3-CH_3$-phenyl | 3-pyridyl |
| 1513 | 4 | $3-CH_3$-phenyl | 1-methyl-1H-pyrazol-4-yl |
| 1514 | 4 | $3-CH_3$-phenyl | 1H-imidazol-4-yl |
| 1515 | 4 | $3-CH_3$-phenyl | 2-furanyl |
| 1516 | 4 | 3-OH-Phenyl | ethyl |
| 1517 | 4 | 3-OH-Phenyl | n-propyl |
| 1518 | 4 | 3-OH-Phenyl | isopropyl |
| 1519 | 4 | 3-OH-Phenyl | $—CH_2CH(CH_3)_2$ |
| 1520 | 4 | 3-OH-Phenyl | $CF_3$ |
| 1521 | 4 | 3-OH-Phenyl | $—CH_2CF_3$ |
| 1522 | 4 | 3-OH-Phenyl | $—CH_2CH_2CF_3$ |
| 1523 | 4 | 3-OH-Phenyl | cyclopropyl |
| 1524 | 4 | 3-OH-Phenyl | Cyclobutyl |
| 1525 | 4 | 3-OH-Phenyl | cyclopentyl |
| 1526 | 4 | 3-OH-Phenyl | cyclohexyl |
| 1527 | 4 | 3-OH-Phenyl | 3-pyridyl |
| 1528 | 4 | 3-OH-Phenyl | 1-methyl-1H-pyrazol-4-yl |
| 1529 | 4 | 3-OH-Phenyl | 1H-imidazol-4-yl |
| 1530 | 4 | 3-OH-Phenyl | 2-furanyl |
| 1531 | 4 | 4-OMe-Phenyl | ethyl |
| 1532 | 4 | 4-OMe-Phenyl | n-propyl |
| 1533 | 4 | 4-OMe-Phenyl | isopropyl |
| 1534 | 4 | 4-OMe-Phenyl | $—CH_2CH(CH_3)_2$ |
| 1535 | 4 | 4-OMe-Phenyl | $CF_3$ |
| 1536 | 4 | 4-OMe-Phenyl | $—CH_2CF_3$ |
| 1537 | 4 | 4-OMe-Phenyl | $—CH_2CH_2CF_3$ |
| 1538 | 4 | 4-OMe-Phenyl | cyclopropyl |
| 1539 | 4 | 4-OMe-Phenyl | Cyclobutyl |
| 1540 | 4 | 4-OMe-Phenyl | cyclopentyl |
| 1541 | 4 | 4-OMe-Phenyl | cyclohexyl |
| 1542 | 4 | 4-OMe-Phenyl | 3-pyridyl |
| 1543 | 4 | 4-OMe-Phenyl | 1-methyl-1H-pyrazol-4-yl |
| 1544 | 4 | 4-OMe-Phenyl | 1H-imidazol-4-yl |
| 1545 | 4 | 4-OMe-Phenyl | 2-furanyl |
| 1546 | 4 | 2-OMe-Phenyl | ethyl |
| 1547 | 4 | 2-OMe-Phenyl | n-propyl |
| 1548 | 4 | 2-OMe-Phenyl | isopropyl |
| 1549 | 4 | 2-OMe-Phenyl | $—CH_2CH(CH_3)_2$ |
| 1550 | 4 | 2-OMe-Phenyl | $CF_3$ |
| 1551 | 4 | 2-OMe-Phenyl | $—CH_2CF_3$ |
| 1552 | 4 | 2-OMe-Phenyl | $—CH_2CH_2CF_3$ |
| 1553 | 4 | 2-OMe-Phenyl | cyclopropyl |
| 1554 | 4 | 2-OMe-Phenyl | Cyclobutyl |
| 1555 | 4 | 2-OMe-Phenyl | cyclopentyl |
| 1556 | 4 | 2-OMe-Phenyl | cyclohexyl |
| 1557 | 4 | 2-OMe-Phenyl | 3-pyridyl |
| 1558 | 4 | 2-OMe-Phenyl | 1-methyl-1H-pyrazol-4-yl |
| 1559 | 4 | 2-OMe-Phenyl | 1H-imidazol-4-yl |
| 1560 | 4 | 2-OMe-Phenyl | 2-furanyl |
| 1561 | 4 | 3-CN-Phenyl | ethyl |
| 1562 | 4 | 3-CN-Phenyl | n-propyl |
| 1563 | 4 | 3-CN-Phenyl | isopropyl |
| 1564 | 4 | 3-CN-Phenyl | $—CH_2CH(CH_3)_2$ |
| 1565 | 4 | 3-CN-Phenyl | $CF_3$ |
| 1566 | 4 | 3-CN-Phenyl | $—CH_2CF_3$ |
| 1567 | 4 | 3-CN-Phenyl | $—CH_2CH_2CF_3$ |
| 1568 | 4 | 3-CN-Phenyl | cyclopropyl |
| 1569 | 4 | 3-CN-Phenyl | Cyclobutyl |
| 1570 | 4 | 3-CN-Phenyl | cyclopentyl |
| 1571 | 4 | 3-CN-Phenyl | cyclohexyl |
| 1572 | 4 | 3-CN-Phenyl | 3-pyridyl |
| 1573 | 4 | 3-CN-Phenyl | 1-methyl-1H-pyrazol-4-yl |
| 1574 | 4 | 3-CN-Phenyl | 1H-imidazol-4-yl |
| 1575 | 4 | 3-CN-Phenyl | 2-furanyl |
| 1576 | 4 | 2-F-Phenyl | ethyl |
| 1577 | 4 | 2-F-Phenyl | n-propyl |
| 1578 | 4 | 2-F-Phenyl | isopropyl |
| 1579 | 4 | 2-F-Phenyl | $—CH_2CH(CH_3)_2$ |
| 1580 | 4 | 2-F-Phenyl | $CF_3$ |
| 1581 | 4 | 2-F-Phenyl | $—CH_2CF_3$ |
| 1582 | 4 | 2-F-Phenyl | $—CH_2CH_2CF_3$ |
| 1583 | 4 | 2-F-Phenyl | cyclopropyl |
| 1584 | 4 | 2-F-Phenyl | Cyclobutyl |
| 1585 | 4 | 2-F-Phenyl | cyclopentyl |
| 1586 | 4 | 2-F-Phenyl | cyclohexyl |
| 1587 | 4 | 2-F-Phenyl | 3-pyridyl |
| 1588 | 4 | 2-F-Phenyl | 1-methyl-1H-pyrazol-4-yl |
| 1589 | 4 | 2-F-Phenyl | 1H-imidazol-4-yl |
| 1590 | 4 | 2-F-Phenyl | 2-furanyl |
| 1591 | 4 | 4-F-Phenyl | ethyl |
| 1592 | 4 | 4-F-Phenyl | n-propyl |
| 1593 | 4 | 4-F-Phenyl | isopropyl |
| 1594 | 4 | 4-F-Phenyl | $—CH_2CH(CH_3)_2$ |
| 1595 | 4 | 4-F-Phenyl | $CF_3$ |
| 1596 | 4 | 4-F-Phenyl | $—CH_2CF_3$ |
| 1597 | 4 | 4-F-Phenyl | $—CH_2CH_2CF_3$ |
| 1598 | 4 | 4-F-Phenyl | cyclopropyl |
| 1599 | 4 | 4-F-Phenyl | Cyclobutyl |
| 1600 | 4 | 4-F-Phenyl | cyclopentyl |

TABLE 33-continued

| Entry | n | $R^5$ | $R^{10c}$ |
|---|---|---|---|
| 1601 | 4 | 4-F-Phenyl | cyclohexyl |
| 1602 | 4 | 4-F-Phenyl | 3-pyridyl |
| 1603 | 4 | 4-F-Phenyl | 1-methyl-1H-pyrazol-4-yl |
| 1604 | 4 | 4-F-Phenyl | 1H-imidazol-4-yl |
| 1605 | 4 | 4-F-Phenyl | 2-furanyl |
| 1606 | 4 | 3-Cl-Phenyl | ethyl |
| 1607 | 4 | 3-Cl-Phenyl | n-propyl |
| 1608 | 4 | 3-Cl-Phenyl | isopropyl |
| 1609 | 4 | 3-Cl-Phenyl | $—CH_2CH(CH_3)_2$ |
| 1610 | 4 | 3-Cl-Phenyl | $CF_3$ |
| 1611 | 4 | 3-Cl-Phenyl | $—CH_2CF_3$ |
| 1612 | 4 | 3-Cl-Phenyl | $—CH_2CH_2CF_3$ |
| 1613 | 4 | 3-Cl-Phenyl | cyclopropyl |
| 1614 | 4 | 3-Cl-Phenyl | Cyclobutyl |
| 1615 | 4 | 3-Cl-Phenyl | cyclopentyl |
| 1616 | 4 | 3-Cl-Phenyl | cyclohexyl |
| 1617 | 4 | 3-Cl-Phenyl | 3-pyridyl |
| 1618 | 4 | 3-Cl-Phenyl | 1-methyl-1H-pyrazol-4-yl |
| 1619 | 4 | 3-Cl-Phenyl | 1H-imidazol-4-yl |
| 1620 | 4 | 3-Cl-Phenyl | 2-furanyl |
| 1621 | 4 | 2-Br-Phenyl | ethyl |
| 1622 | 4 | 2-Br-Phenyl | n-propyl |
| 1623 | 4 | 2-Br-Phenyl | isopropyl |
| 1624 | 4 | 2-Br-Phenyl | $—CH_2CH(CH_3)_2$ |
| 1625 | 4 | 2-Br-Phenyl | $CF_3$ |
| 1626 | 4 | 2-Br-Phenyl | $—CH_2CF_3$ |
| 1627 | 4 | 2-Br-Phenyl | $—CH_2CH_2CF_3$ |
| 1628 | 4 | 2-Br-Phenyl | cyclopropyl |
| 1629 | 4 | 2-Br-Phenyl | Cyclobutyl |
| 1630 | 4 | 2-Br-Phenyl | cyclopentyl |
| 1631 | 4 | 2-Br-Phenyl | cyclohexyl |
| 1632 | 4 | 2-Br-Phenyl | 3-pyridyl |
| 1633 | 4 | 2-Br-Phenyl | 1-methyl-1H-pyrazol-4-yl |
| 1634 | 4 | 2-Br-Phenyl | 1H-imidazol-4-yl |
| 1635 | 4 | 2-Br-Phenyl | 2-furanyl |
| 1636 | 4 | 4-Br-Phenyl | ethyl |
| 1637 | 4 | 4-Br-Phenyl | n-propyl |
| 1638 | 4 | 4-Br-Phenyl | isopropyl |
| 1639 | 4 | 4-Br-Phenyl | $—CH_2CH(CH_3)_2$ |
| 1640 | 4 | 4-Br-Phenyl | $CF_3$ |
| 1641 | 4 | 4-Br-Phenyl | $—CH_2CF_3$ |
| 1642 | 4 | 4-Br-Phenyl | $—CH_2CH_2CF_3$ |
| 1643 | 4 | 4-Br-Phenyl | cyclopropyl |
| 1644 | 4 | 4-Br-Phenyl | Cyclobutyl |
| 1645 | 4 | 4-Br-Phenyl | cyclopentyl |
| 1646 | 4 | 4-Br-Phenyl | cyclohexyl |
| 1647 | 4 | 4-Br-Phenyl | 3-pyridyl |
| 1648 | 4 | 4-Br-Phenyl | 1-methyl-1H-pyrazol-4-yl |
| 1649 | 4 | 4-Br-Phenyl | 1H-imidazol-4-yl |
| 1650 | 4 | 4-Br-Phenyl | 2-furanyl |
| 1651 | 4 | $3-CF_3$-Phenyl | ethyl |
| 1652 | 4 | $3-CF_3$-Phenyl | n-propyl |
| 1653 | 4 | $3-CF_3$-Phenyl | isopropyl |
| 1654 | 4 | $3-CF_3$-Phenyl | $—CH_2CH(CH_3)_2$ |
| 1655 | 4 | $3-CF_3$-Phenyl | $CF_3$ |
| 1656 | 4 | $3-CF_3$-Phenyl | $—CH_2CF_3$ |
| 1657 | 4 | $3-CF_3$-Phenyl | $—CH_2CH_2CF_3$ |
| 1658 | 4 | $3-CF_3$-Phenyl | cyclopropyl |
| 1659 | 4 | $3-CF_3$-Phenyl | Cyclobutyl |
| 1660 | 4 | $3-CF_3$-Phenyl | cyclopentyl |
| 1661 | 4 | $3-CF_3$-Phenyl | cyclohexyl |
| 1662 | 4 | $3-CF_3$-Phenyl | 3-pyridyl |
| 1663 | 4 | $3-CF_3$-Phenyl | 1-methyl-1H-pyrazol-4-yl |
| 1664 | 4 | $3-CF_3$-Phenyl | 1H-imidazol-4-yl |
| 1665 | 4 | $3-CF_3$-Phenyl | 2-furanyl |
| 1666 | 4 | 2-iPr-Phenyl | ethyl |
| 1667 | 4 | 2-iPr-Phenyl | n-propyl |
| 1668 | 4 | 2-iPr-Phenyl | isopropyl |
| 1669 | 4 | 2-iPr-Phenyl | $—CH_2CH(CH_3)_2$ |
| 1670 | 4 | 2-iPr-Phenyl | $CF_3$ |
| 1671 | 4 | 2-iPr-Phenyl | $—CH_2CF_3$ |
| 1672 | 4 | 2-iPr-Phenyl | $—CH_2CH_2CF_3$ |
| 1673 | 4 | 2-iPr-Phenyl | cyclopropyl |
| 1674 | 4 | 2-iPr-Phenyl | Cyclobutyl |
| 1675 | 4 | 2-iPr-Phenyl | cyclopentyl |
| 1676 | 4 | 2-iPr-Phenyl | cyclohexyl |
| 1677 | 4 | 2-iPr-Phenyl | 3-pyridyl |
| 1678 | 4 | 2-iPr-Phenyl | 1-methyl-1H-pyrazol-4-yl |

TABLE 33-continued

| Entry | n | $R^5$ | $R^{10c}$ |
|---|---|---|---|
| 1679 | 4 | 2-iPr-Phenyl | 1H-imidazol-4-yl |
| 1680 | 4 | 2-iPr-Phenyl | 2-furanyl |
| 1681 | 4 | 4-iPr-Phenyl | ethyl |
| 1682 | 4 | 4-iPr-Phenyl | n-propyl |
| 1683 | 4 | 4-iPr-Phenyl | isopropyl |
| 1684 | 4 | 4-iPr-Phenyl | $—CH_2CH(CH_3)_2$ |
| 1685 | 4 | 4-iPr-Phenyl | $CF_3$ |
| 1686 | 4 | 4-iPr-Phenyl | $—CH_2CF_3$ |
| 1687 | 4 | 4-iPr-Phenyl | $—CH_2CH_2CF_3$ |
| 1688 | 4 | 4-iPr-Phenyl | cyclopropyl |
| 1689 | 4 | 4-iPr-Phenyl | Cyclobutyl |
| 1690 | 4 | 4-iPr-Phenyl | cyclopentyl |
| 1691 | 4 | 4-iPr-Phenyl | cyclohexyl |
| 1692 | 4 | 4-iPr-Phenyl | 3-pyridyl |
| 1693 | 4 | 4-iPr-Phenyl | 1-methyl-1H-pyrazol-4-yl |
| 1694 | 4 | 4-iPr-Phenyl | 1H-imidazol-4-yl |
| 1695 | 4 | 4-iPr-Phenyl | 2-furanyl |
| 1696 | 4 | 3-morpholino-phenyl | ethyl |
| 1697 | 4 | 3-morpholino-phenyl | n-propyl |
| 1698 | 4 | 3-morpholino-phenyl | isopropyl |
| 1699 | 4 | 3-morpholino-phenyl | $—CH_2CH(CH_3)_2$ |
| 1700 | 4 | 3-morpholino-phenyl | $CF_3$ |
| 1701 | 4 | 3-morpholino-phenyl | $—CH_2CF_3$ |
| 1702 | 4 | 3-morpholino-phenyl | $—CH_2CH_2CF_3$ |
| 1703 | 4 | 3-morpholino-phenyl | cyclopropyl |
| 1704 | 4 | 3-morpholino-phenyl | Cyclobutyl |
| 1705 | 4 | 3-morpholino-phenyl | cyclopentyl |
| 1706 | 4 | 3-morpholino-phenyl | cyclohexyl |
| 1707 | 4 | 3-morpholino-phenyl | 3-pyridyl |
| 1708 | 4 | 3-morpholino-phenyl | 1-methyl-1H-pyrazol-4-yl |
| 1709 | 4 | 3-morpholino-phenyl | 1H-imidazol-4-yl |
| 1710 | 4 | 3-morpholino-phenyl | 2-furanyl |
| 1711 | 4 | 4-cyano-2-morpholino-phenyl | ethyl |
| 1712 | 4 | 4-cyano-2-morpholino-phenyl | n-propyl |
| 1713 | 4 | 4-cyano-2-morpholino-phenyl | isopropyl |
| 1714 | 4 | 4-cyano-2-morpholino-phenyl | $—CH_2CH(CH_3)_2$ |
| 1715 | 4 | 4-cyano-2-morpholino-phenyl | $CF_3$ |
| 1716 | 4 | 4-cyano-2-morpholino-phenyl | $—CH_2CF_3$ |
| 1717 | 4 | 4-cyano-2-morpholino-phenyl | $—CH_2CH_2CF_3$ |
| 1718 | 4 | 4-cyano-2-morpholino-phenyl | cyclopropyl |
| 1719 | 4 | 4-cyano-2-morpholino-phenyl | Cyclobutyl |
| 1720 | 4 | 4-cyano-2-morpholino-phenyl | cyclopentyl |
| 1721 | 4 | 4-cyano-2-morpholino-phenyl | cyclohexyl |
| 1722 | 4 | 4-cyano-2-morpholino-phenyl | 3-pyridyl |
| 1723 | 4 | 4-cyano-2-morpholino-phenyl | 1-methyl-1H-pyrazol-4-yl |
| 1724 | 4 | 4-cyano-2-morpholino-phenyl | 1H-imidazol-4-yl |
| 1725 | 4 | 4-cyano-2-morpholino-phenyl | 2-furanyl |
| 1726 | 4 | 4-hydroxy-2-morpholino-phenyl | ethyl |
| 1727 | 4 | 4-hydroxy-2-morpholino-phenyl | n-propyl |
| 1728 | 4 | 4-hydroxy-2-morpholino-phenyl | isopropyl |
| 1729 | 4 | 4-hydroxy-2-morpholino-phenyl | $—CH_2CH(CH_3)_2$ |
| 1730 | 4 | 4-hydroxy-2-morpholino-phenyl | $CF_3$ |
| 1731 | 4 | 4-hydroxy-2-morpholino-phenyl | $—CH_2CF_3$ |
| 1732 | 4 | 4-hydroxy-2-morpholino-phenyl | $—CH_2CH_2CF_3$ |
| 1733 | 4 | 4-hydroxy-2-morpholino-phenyl | cyclopropyl |
| 1734 | 4 | 4-hydroxy-2-morpholino-phenyl | Cyclobutyl |
| 1735 | 4 | 4-hydroxy-2-morpholino-phenyl | cyclopentyl |
| 1736 | 4 | 4-hydroxy-2-morpholino-phenyl | cyclohexyl |
| 1737 | 4 | 4-hydroxy-2-morpholino-phenyl | 3-pyridyl |
| 1738 | 4 | 4-hydroxy-2-morpholino-phenyl | 1-methyl-1H-pyrazol-4-yl |
| 1739 | 4 | 4-hydroxy-2-morpholino-phenyl | 1H-imidazol-4-yl |
| 1740 | 4 | 4-hydroxy-2-morpholino-phenyl | 2-furanyl |
| 1741 | 4 | $2-CH_3$-phenyl | Ethyl |
| 1742 | 4 | $2-CH_3$-phenyl | n-propyl |
| 1743 | 4 | $2-CH_3$-phenyl | Isopropyl |
| 1744 | 4 | $2-CH_3$-phenyl | $—CH_2CH(CH_3)_2$ |
| 1745 | 4 | $2-CH_3$-phenyl | $CF_3$ |
| 1746 | 4 | $2-CH_3$-phenyl | $—CH_2CF_3$ |
| 1747 | 4 | $2-CH_3$-phenyl | $—CH_2CH_2CF_3$ |
| 1748 | 4 | $2-CH_3$-phenyl | cyclopropyl |
| 1749 | 4 | $2-CH_3$-phenyl | Cyclobutyl |
| 1750 | 4 | $2-CH_3$-phenyl | cyclopentyl |
| 1751 | 4 | $2-CH_3$-phenyl | cyclohexyl |
| 1752 | 4 | $2-CH_3$-phenyl | 3-pyridyl |
| 1753 | 4 | $2-CH_3$-phenyl | 1-methyl-1H-pyrazol-4-yl |
| 1754 | 4 | $2-CH_3$-phenyl | 1H-imidazol-4-yl |
| 1755 | 4 | $2-CH_3$-phenyl | 2-furanyl |
| 1756 | 4 | 4-OH-Phenyl | Ethyl |

TABLE 33-continued

| Entry | n | $R^5$ | $R^{10c}$ |
|---|---|---|---|
| 1757 | 4 | 4-OH-Phenyl | n-propyl |
| 1758 | 4 | 4-OH-Phenyl | Isopropyl |
| 1759 | 4 | 4-OH-Phenyl | $—CH_2CH(CH_3)_2$ |
| 1760 | 4 | 4-OH-Phenyl | $CF_3$ |
| 1761 | 4 | 4-OH-Phenyl | $—CH_2CF_3$ |
| 1762 | 4 | 4-OH-Phenyl | $—CH_2CH_2CF_3$ |
| 1763 | 4 | 4-OH-Phenyl | cyclopropyl |
| 1764 | 4 | 4-OH-Phenyl | Cyclobutyl |
| 1765 | 4 | 4-OH-Phenyl | cyclopentyl |
| 1766 | 4 | 4-OH-Phenyl | cyclohexyl |
| 1767 | 4 | 4-OH-Phenyl | 3-pyridyl |
| 1768 | 4 | 4-OH-Phenyl | 1-methyl-1H-pyrazol-4-yl |
| 1769 | 4 | 4-OH-Phenyl | 1H-imidazol-4-yl |
| 1770 | 4 | 4-OH-Phenyl | 2-furanyl |
| 1771 | 4 | 2-OH-Phenyl | Ethyl |
| 1772 | 4 | 2-OH-Phenyl | n-propyl |
| 1773 | 4 | 2-OH-Phenyl | Isopropyl |
| 1774 | 4 | 2-OH-Phenyl | $—CH_2CH(CH_3)_2$ |
| 1775 | 4 | 2-OH-Phenyl | $CF_3$ |
| 1776 | 4 | 2-OH-Phenyl | $—CH_2CF_3$ |
| 1777 | 4 | 2-OH-Phenyl | $—CH_2CH_2CF_3$ |
| 1778 | 4 | 2-OH-Phenyl | cyclopropyl |
| 1779 | 4 | 2-OH-Phenyl | Cyclobutyl |
| 1780 | 4 | 2-OH-Phenyl | cyclopentyl |
| 1781 | 4 | 2-OH-Phenyl | cyclohexyl |
| 1782 | 4 | 2-OH-Phenyl | 3-pyridyl |
| 1783 | 4 | 2-OH-Phenyl | 1-methyl-1H-pyrazol-4-yl |
| 1784 | 4 | 2-OH-Phenyl | 1H-imidazol-4-yl |
| 1785 | 4 | 2-OH-Phenyl | 2-furanyl |
| 1786 | 4 | 3-OMe-Phenyl | Ethyl |
| 1787 | 4 | 3-OMe-Phenyl | n-propyl |
| 1788 | 4 | 3-OMe-Phenyl | Isopropyl |
| 1789 | 4 | 3-OMe-Phenyl | $—CH_2CH(CH_3)_2$ |
| 1790 | 4 | 3-OMe-Phenyl | $CF_3$ |
| 1791 | 4 | 3-OMe-Phenyl | $—CH_2CF_3$ |
| 1792 | 4 | 3-OMe-Phenyl | $—CH_2CH_2CF_3$ |
| 1793 | 4 | 3-OMe-Phenyl | cyclopropyl |
| 1794 | 4 | 3-OMe-Phenyl | Cyclobutyl |
| 1795 | 4 | 3-OMe-Phenyl | cyclopentyl |
| 1796 | 4 | 3-OMe-Phenyl | cyclohexyl |
| 1797 | 4 | 3-OMe-Phenyl | 3-pyridyl |
| 1798 | 4 | 3-OMe-Phenyl | 1-methyl-1H-pyrazol-4-yl |
| 1799 | 4 | 3-OMe-Phenyl | 1H-imidazol-4-yl |
| 1800 | 4 | 3-OMe-Phenyl | 2-furanyl |
| 1801 | 4 | 4-CN-Phenyl | Ethyl |
| 1802 | 4 | 4-CN-Phenyl | n-propyl |
| 1803 | 4 | 4-CN-Phenyl | Isopropyl |
| 1804 | 4 | 4-CN-Phenyl | $—CH_2CH(CH_3)_2$ |
| 1805 | 4 | 4-CN-Phenyl | $CF_3$ |
| 1806 | 4 | 4-CN-Phenyl | $—CH_2CF_3$ |
| 1807 | 4 | 4-CN-Phenyl | $—CH_2CH_2CF_3$ |
| 1808 | 4 | 4-CN-Phenyl | cyclopropyl |
| 1809 | 4 | 4-CN-Phenyl | Cyclobutyl |
| 1810 | 4 | 4-CN-Phenyl | cyclopentyl |
| 1811 | 4 | 4-CN-Phenyl | cyclohexyl |
| 1812 | 4 | 4-CN-Phenyl | 3-pyridyl |
| 1813 | 4 | 4-CN-Phenyl | 1-methyl-1H-pyrazol-4-yl |
| 1814 | 4 | 4-CN-Phenyl | 1H-imidazol-4-yl |
| 1815 | 4 | 4-CN-Phenyl | 2-furanyl |
| 1816 | 4 | 2-CN-Phenyl | Ethyl |
| 1817 | 4 | 2-CN-Phenyl | n-propyl |
| 1818 | 4 | 2-CN-Phenyl | Isopropyl |
| 1819 | 4 | 2-CN-Phenyl | $—CH_2CH(CH_3)_2$ |
| 1820 | 4 | 2-CN-Phenyl | $CF_3$ |
| 1821 | 4 | 2-CN-Phenyl | $—CH_2CF_3$ |
| 1822 | 4 | 2-CN-Phenyl | $—CH_2CH_2CF_3$ |
| 1823 | 4 | 2-CN-Phenyl | cyclopropyl |
| 1824 | 4 | 2-CN-Phenyl | Cyclobutyl |
| 1825 | 4 | 2-CN-Phenyl | cyclopentyl |
| 1826 | 4 | 2-CN-Phenyl | cyclohexyl |
| 1827 | 4 | 2-CN-Phenyl | 3-pyridyl |
| 1828 | 4 | 2-CN-Phenyl | 1-methyl-1H-pyrazol-4-yl |
| 1829 | 4 | 2-CN-Phenyl | 1H-imidazol-4-yl |
| 1830 | 4 | 2-CN-Phenyl | 2-furanyl |
| 1831 | 4 | 3-F-Phenyl | Ethyl |
| 1832 | 4 | 3-F-Phenyl | n-propyl |
| 1833 | 4 | 3-F-Phenyl | Isopropyl |
| 1834 | 4 | 3-F-Phenyl | $—CH_2CH(CH_3)_2$ |

TABLE 33-continued

| Entry | n | $R^5$ | $R^{10c}$ |
|---|---|---|---|
| 1835 | 4 | 3-F-Phenyl | $CF_3$ |
| 1836 | 4 | 3-F-Phenyl | $—CH_2CF_3$ |
| 1837 | 4 | 3-F-Phenyl | $—CH_2CH_2CF_3$ |
| 1838 | 4 | 3-F-Phenyl | cyclopropyl |
| 1839 | 4 | 3-F-Phenyl | Cyclobutyl |
| 1840 | 4 | 3-F-Phenyl | cyclopentyl |
| 1841 | 4 | 3-F-Phenyl | cyclohexyl |
| 1842 | 4 | 3-F-Phenyl | 3-pyridyl |
| 1843 | 4 | 3-F-Phenyl | 1-methyl-1H-pyrazol-4-yl |
| 1844 | 4 | 3-F-Phenyl | 1H-imidazol-4-yl |
| 1845 | 4 | 3-F-Phenyl | 2-furanyl |
| 1846 | 4 | 2-Cl-Phenyl | Ethyl |
| 1847 | 4 | 2-Cl-Phenyl | n-propyl |
| 1848 | 4 | 2-Cl-Phenyl | Isopropyl |
| 1849 | 4 | 2-Cl-Phenyl | $—CH_2CH(CH_3)_2$ |
| 1850 | 4 | 2-Cl-Phenyl | $CF_3$ |
| 1851 | 4 | 2-Cl-Phenyl | $—CH2CF_3$ |
| 1852 | 4 | 2-Cl-Phenyl | $—CH2CH_2CF_3$ |
| 1853 | 4 | 2-Cl-Phenyl | cyclopropyl |
| 1854 | 4 | 2-Cl-Phenyl | Cyclobutyl |
| 1855 | 4 | 2-Cl-Phenyl | cyclopentyl |
| 1856 | 4 | 2-Cl-Phenyl | cyclohexyl |
| 1857 | 4 | 2-Cl-Phenyl | 3-pyridyl |
| 1858 | 4 | 2-Cl-Phenyl | 1-methyl-1H-pyrazol-4-yl |
| 1859 | 4 | 2-Cl-Phenyl | 1H-imidazol-4-yl |
| 1860 | 4 | 2-Cl-Phenyl | 2-furanyl |
| 1861 | 4 | 4-Cl-Phenyl | Ethyl |
| 1862 | 4 | 4-Cl-Phenyl | n-propyl |
| 1863 | 4 | 4-Cl-Phenyl | Isopropyl |
| 1864 | 4 | 4-Cl-Phenyl | $—CH_2CH(CH_3)_2$ |
| 1865 | 4 | 4-Cl-Phenyl | $CF_3$ |
| 1866 | 4 | 4-Cl-Phenyl | $—CH_2CF_3$ |
| 1867 | 4 | 4-Cl-Phenyl | $—CH_2CH_2CF_3$ |
| 1868 | 4 | 4-Cl-Phenyl | cyclopropyl |
| 1869 | 4 | 4-Cl-Phenyl | Cyclobutyl |
| 1870 | 4 | 4-Cl-Phenyl | cyclopentyl |
| 1871 | 4 | 4-Cl-Phenyl | cyclohexyl |
| 1872 | 4 | 4-Cl-Phenyl | 3-pyridyl |
| 1873 | 4 | 4-Cl-Phenyl | 1-methyl-1H-pyrazol-4-yl |
| 1874 | 4 | 4-Cl-Phenyl | 1H-imidazol-4-yl |
| 1875 | 4 | 4-Cl-Phenyl | 2-furanyl |
| 1876 | 4 | 3-Br-Phenyl | Ethyl |
| 1877 | 4 | 3-Br-Phenyl | n-propyl |
| 1878 | 4 | 3-Br-Phenyl | Isopropyl |
| 1879 | 4 | 3-Br-Phenyl | $—CH_2CH(CH_3)_2$ |
| 1880 | 4 | 3-Br-Phenyl | $CF_3$ |
| 1881 | 4 | 3-Br-Phenyl | $—CH_2CF_3$ |
| 1882 | 4 | 3-Br-Phenyl | $—CH_2CH_2CF_3$ |
| 1883 | 4 | 3-Br-Phenyl | cyclopropyl |
| 1884 | 4 | 3-Br-Phenyl | Cyclobutyl |
| 1885 | 4 | 3-Br-Phenyl | cyclopentyl |
| 1886 | 4 | 3-Br-Phenyl | cyclohexyl |
| 1887 | 4 | 3-Br-Phenyl | 3-pyridyl |
| 1888 | 4 | 3-Br-Phenyl | 1-methyl-1H-pyrazol-4-yl |
| 1889 | 4 | 3-Br-Phenyl | 1H-imidazol-4-yl |
| 1890 | 4 | 3-Br-Phenyl | 2-furanyl |
| 1891 | 4 | $2-CF_3$-Phenyl | Ethyl |
| 1892 | 4 | $2-CF_3$-Phenyl | n-propyl |
| 1893 | 4 | $2-CF_3$-Phenyl | Isopropyl |
| 1894 | 4 | $2-CF_3$-Phenyl | $—CH_2CH(CH_3)_2$ |
| 1895 | 4 | $2-CF_3$-Phenyl | $CF_3$ |
| 1896 | 4 | $2-CF_3$-Phenyl | $—CH_2CF_3$ |
| 1897 | 4 | $2-CF_3$-Phenyl | $—CH_2CH_2CF_3$ |
| 1898 | 4 | $2-CF_3$-Phenyl | cyclopropyl |
| 1899 | 4 | $2-CF_3$-Phenyl | Cyclobutyl |
| 1900 | 4 | $2-CF_3$-Phenyl | cyclopentyl |
| 1901 | 4 | $2-CF_3$-Phenyl | cyclohexyl |
| 1902 | 4 | $2-CF_3$-Phenyl | 3-pyridyl |
| 1903 | 4 | $2-CF_3$-Phenyl | 1-methyl-1H-pyrazol-4-yl |
| 1904 | 4 | $2-CF_3$-Phenyl | 1H-imidazol-4-yl |
| 1905 | 4 | $2-CF_3$-Phenyl | 2-furanyl |
| 1906 | 4 | $4-CF_3$-Phenyl | Ethyl |
| 1907 | 4 | $4-CF_3$-Phenyl | n-propyl |
| 1908 | 4 | $4-CF_3$-Phenyl | Isopropyl |
| 1909 | 4 | $4-CF_3$-Phenyl | $—CH_2CH(CH_3)_2$ |
| 1910 | 4 | $4-CF_3$-Phenyl | $CF_3$ |
| 1911 | 4 | $4-CF_3$-Phenyl | $—CH_2CF_3$ |
| 1912 | 4 | $4-CF_3$-Phenyl | $—CH_2CH_2CF_3$ |

TABLE 33-continued

| Entry | n | $R^5$ | $R^{10c}$ |
|---|---|---|---|
| 1913 | 4 | 4-$CF_3$-Phenyl | cyclopropyl |
| 1914 | 4 | 4-$CF_3$-Phenyl | Cyclobutyl |
| 1915 | 4 | 4-$CF_3$-Phenyl | cyclopentyl |
| 1916 | 4 | 4-$CF_3$-Phenyl | cyclohexyl |
| 1917 | 4 | 4-$CF_3$-Phenyl | 3-pyridyl |
| 1918 | 4 | 4-$CF_3$-Phenyl | 1-methyl-1H-pyrazol-4-yl |
| 1919 | 4 | 4-$CF_3$-Phenyl | 1H-imidazol-4-yl |
| 1920 | 4 | 4-$CF_3$-Phenyl | 2-furanyl |
| 1921 | 4 | 3-iPr-Phenyl | Ethyl |
| 1922 | 4 | 3-iPr-Phenyl | n-propyl |
| 1923 | 4 | 3-iPr-Phenyl | Isopropyl |
| 1924 | 4 | 3-iPr-Phenyl | $—CH_2CH(CH_3)_2$ |
| 1925 | 4 | 3-iPr-Phenyl | $CF_3$ |
| 1926 | 4 | 3-iPr-Phenyl | $—CH_2CF_3$ |
| 1927 | 4 | 3-iPr-Phenyl | $—CH_2CH_2CF_3$ |
| 1928 | 4 | 3-iPr-Phenyl | cyclopropyl |
| 1929 | 4 | 3-iPr-Phenyl | Cyclobutyl |
| 1930 | 4 | 3-iPr-Phenyl | cyclopentyl |
| 1931 | 4 | 3-iPr-Phenyl | cyclohexyl |
| 1932 | 4 | 3-iPr-Phenyl | 3-pyridyl |
| 1933 | 4 | 3-iPr-Phenyl | 1-methyl-1H-pyrazol-4-yl |
| 1934 | 4 | 3-iPr-Phenyl | 1H-imidazol-4-yl |
| 1935 | 4 | 3-iPr-Phenyl | 2-furanyl |
| 1936 | 4 | 2-morpholino-phenyl | Ethyl |
| 1937 | 4 | 2-morpholino-phenyl | n-propyl |
| 1938 | 4 | 2-morpholino-phenyl | isopropyl |
| 1939 | 4 | 2-morpholino-phenyl | $—CH_2CH(CH_3)_2$ |
| 1940 | 4 | 2-morpholino-phenyl | $CF_3$ |
| 1941 | 4 | 2-morpholino-phenyl | $—CH_2CF_3$ |
| 1942 | 4 | 2-morpholino-phenyl | $—CH_2CH_2CF_3$ |
| 1943 | 4 | 2-morpholino-phenyl | cyclopropyl |
| 1944 | 4 | 2-morpholino-phenyl | Cyclobutyl |
| 1945 | 4 | 2-morpholino-phenyl | cyclopentyl |
| 1946 | 4 | 2-morpholino-phenyl | cyclohexyl |
| 1947 | 4 | 2-morpholino-phenyl | 3-pyridyl |
| 1948 | 4 | 2-morpholino-phenyl | 1-methyl-1H-pyrazol-4-yl |
| 1949 | 4 | 2-morpholino-phenyl | 1H-imidazol-4-yl |
| 1950 | 4 | 2-morpholino-phenyl | 2-furanyl |
| 1951 | 4 | 4-morpholino-phenyl | ethyl |
| 1952 | 4 | 4-morpholino-phenyl | n-propyl |
| 1953 | 4 | 4-morpholino-phenyl | isopropyl |
| 1954 | 4 | 4-morpholino-phenyl | $—CH_2CH(CH_3)_2$ |
| 1955 | 4 | 4-morpholino-phenyl | $CF_3$ |
| 1956 | 4 | 4-morpholino-phenyl | $—CH_2CF_3$ |
| 1957 | 4 | 4-morpholino-phenyl | $—CH_2CH_2CF_3$ |
| 1958 | 4 | 4-morpholino-phenyl | cyclopropyl |
| 1959 | 4 | 4-morpholino-phenyl | Cyclobutyl |
| 1960 | 4 | 4-morpholino-phenyl | cyclopentyl |
| 1961 | 4 | 4-morpholino-phenyl | cyclohexyl |
| 1962 | 4 | 4-morpholino-phenyl | 3-pyridyl |
| 1963 | 4 | 4-morpholino-phenyl | 1-methyl-1H-pyrazol-4-yl |
| 1964 | 4 | 4-morpholino-phenyl | 1H-imidazol-4-yl |
| 1965 | 4 | 4-morpholino-phenyl | 2-furanyl |
| 1966 | 4 | 4-methyl-2-morpholino-phenyl | ethyl |
| 1967 | 4 | 4-methyl-2-morpholino-phenyl | n-propyl |
| 1968 | 4 | 4-methyl-2-morpholino-phenyl | isopropyl |
| 1969 | 4 | 4-methyl-2-morpholino-phenyl | $—CH_2CH(CH_3)_2$ |
| 1970 | 4 | 4-methyl-2-morpholino-phenyl | $CF_3$ |
| 1971 | 4 | 4-methyl-2-morpholino-phenyl | —CH2CF3 |
| 1972 | 4 | 4-methyl-2-morpholino-phenyl | —CH2CH2CF3 |
| 1973 | 4 | 4-methyl-2-morpholino-phenyl | Cyclopropyl |
| 1974 | 4 | 4-methyl-2-morpholino-phenyl | Cyclobutyl |
| 1975 | 4 | 4-methyl-2-morpholino-phenyl | Cyclopentyl |
| 1976 | 4 | 4-methyl-2-morpholino-phenyl | Cyclohexyl |
| 1977 | 4 | 4-methyl-2-morpholino-phenyl | 3-pyridyl |
| 1978 | 4 | 4-methyl-2-morpholino-phenyl | 1-methyl-1H-pyrazol-4-yl |
| 1979 | 4 | 4-methyl-2-morpholino-phenyl | 1H-imidazol-4-yl |
| 1980 | 4 | 4-methyl-2-morpholino-phenyl | 2-furanyl |
| 1981 | 1 | naphthylen-1-yl | Ethyl |
| 1982 | 1 | naphthylen-1-yl | n-propyl |
| 1983 | 1 | naphthylen-1-yl | Isopropyl |
| 1984 | 1 | naphthylen-1-yl | $—CH_2CH(CH_3)_2$ |
| 1985 | 1 | naphthylen-1-yl | $CF_3$ |
| 1986 | 1 | naphthylen-1-yl | $—CH_2CF_3$ |
| 1987 | 1 | naphthylen-1-yl | $—CH_2CH_2CF_3$ |
| 1988 | 1 | naphthylen-1-yl | Cyclopropyl |
| 1989 | 1 | naphthylen-1-yl | Cyclobutyl |
| 1990 | 1 | naphthylen-1-yl | Cyclopentyl |

TABLE 33-continued

| Entry | n | $R^5$ | $R^{10c}$ |
|---|---|---|---|
| 1991 | 1 | naphthylen-1-yl | Cyclohexyl |
| 1992 | 1 | naphthylen-1-yl | 3-pyridyl |
| 1993 | 1 | naphthylen-1-yl | 1-methyl-1H-pyrazol-4-yl |
| 1994 | 1 | naphthylen-1-yl | 1H-imidazol-4-yl |
| 1995 | 1 | naphthylen-1-yl | 2-furanyl |
| 1996 | 1 | naphthylen-2-yl | Ethyl |
| 1997 | 1 | naphthylen-2-yl | n-propyl |
| 1998 | 1 | naphthylen-2-yl | Isopropyl |
| 1999 | 1 | naphthylen-2-yl | $—CH_2CH(CH_3)_2$ |
| 2000 | 1 | naphthylen-2-yl | $CF_3$ |
| 2001 | 1 | naphthylen-2-yl | $—CH_2CF_3$ |
| 2002 | 1 | naphthylen-2-yl | $—CH_2CH_2CF_3$ |
| 2003 | 1 | naphthylen-2-yl | Cyclopropyl |
| 2004 | 1 | naphthylen-2-yl | Cyclobutyl |
| 2005 | 1 | naphthylen-2-yl | Cyclopentyl |
| 2006 | 1 | naphthylen-2-yl | Cyclohexyl |
| 2007 | 1 | naphthylen-2-yl | 3-pyridyl |
| 2008 | 1 | naphthylen-2-yl | 1-methyl-1H-pyrazol-4-yl |
| 2009 | 1 | naphthylen-2-yl | 1H-imidazol-4-yl |
| 2010 | 1 | naphthylen-2-yl | 2-furanyl |
| 2011 | 2 | naphthylen-1-yl | Ethyl |
| 2012 | 2 | naphthylen-1-yl | n-propyl |
| 2013 | 2 | naphthylen-1-yl | Isopropyl |
| 2014 | 2 | naphthylen-1-yl | $—CH_2CH(CH_3)_2$ |
| 2015 | 2 | naphthylen-1-yl | $CF_3$ |
| 2016 | 2 | naphthylen-1-yl | $—CH_2CF_3$ |
| 2017 | 2 | naphthylen-1-yl | $—CH_2CH_2CF_3$ |
| 2018 | 2 | naphthylen-1-yl | Cyclopropyl |
| 2019 | 2 | naphthylen-1-yl | Cyclobutyl |
| 2020 | 2 | naphthylen-1-yl | Cyclopentyl |
| 2021 | 2 | naphthylen-1-yl | Cyclohexyl |
| 2022 | 2 | naphthylen-1-yl | 3-pyridyl |
| 2023 | 2 | naphthylen-1-yl | 1-methyl-1H-pyrazol-4-yl |
| 2024 | 2 | naphthylen-1-yl | 1H-imidazol-4-yl |
| 2025 | 2 | naphthylen-1-yl | 2-furanyl |
| 2026 | 2 | naphthylen-2-yl | Ethyl |
| 2027 | 2 | naphthylen-2-yl | n-propyl |
| 2028 | 2 | naphthylen-2-yl | Isopropyl |
| 2029 | 2 | naphthylen-2-yl | $—CH_2CH(CH_3)_2$ |
| 2030 | 2 | naphthylen-2-yl | $CF_3$ |
| 2031 | 2 | naphthylen-2-yl | $—CH_2CF_3$ |
| 2032 | 2 | naphthylen-2-yl | $—CH_2CH_2CF_3$ |
| 2033 | 2 | naphthylen-2-yl | Cyclopropyl |
| 2034 | 2 | naphthylen-2-yl | Cyclobutyl |
| 2035 | 2 | naphthylen-2-yl | Cyclopentyl |
| 2036 | 2 | naphthylen-2-yl | Cyclohexyl |
| 2037 | 2 | naphthylen-2-yl | 3-pyridyl |
| 2038 | 2 | naphthylen-2-yl | 1-methyl-1H-pyrazol-4-yl |
| 2039 | 2 | naphthylen-2-yl | 1H-imidazol-4-yl |
| 2040 | 2 | naphthylen-2-yl | 2-furanyl |
| 2041 | 3 | naphthylen-1-yl | Ethyl |
| 2042 | 3 | naphthylen-1-yl | n-propyl |
| 2043 | 3 | naphthylen-1-yl | Isopropyl |
| 2044 | 3 | naphthylen-1-yl | $—CH_2CH(CH_3)_2$ |
| 2045 | 3 | naphthylen-1-yl | $CF_3$ |
| 2046 | 3 | naphthylen-1-yl | $—CH_2CF_3$ |
| 2047 | 3 | naphthylen-1-yl | $—CH_2CH_2CF_3$ |
| 2048 | 3 | naphthylen-1-yl | Cyclopropyl |
| 2049 | 3 | naphthylen-1-yl | Cyclobutyl |
| 2050 | 3 | naphthylen-1-yl | Cyclopentyl |
| 2051 | 3 | naphthylen-1-yl | Cyclohexyl |
| 2052 | 3 | naphthylen-1-yl | 3-pyridyl |
| 2053 | 3 | naphthylen-1-yl | 1-methyl-1H-pyrazol-4-yl |
| 2054 | 3 | naphthylen-1-yl | 1H-imidazol-4-yl |
| 2055 | 3 | naphthylen-1-yl | 2-furanyl |
| 2056 | 3 | naphthylen-2-yl | Ethyl |
| 2057 | 3 | naphthylen-2-yl | n-propyl |
| 2058 | 3 | naphthylen-2-yl | Isopropyl |
| 2059 | 3 | naphthylen-2-yl | $—CH_2CH(CH_3)_2$ |
| 2060 | 3 | naphthylen-2-yl | $CF_3$ |
| 2061 | 3 | naphthylen-2-yl | $—CH_2CF_3$ |
| 2062 | 3 | naphthylen-2-yl | $—CH_2CH_2CF_3$ |
| 2063 | 3 | naphthylen-2-yl | Cyclopropyl |
| 2064 | 3 | naphthylen-2-yl | Cyclobutyl |
| 2065 | 3 | naphthylen-2-yl | Cyclopentyl |
| 2066 | 3 | naphthylen-2-yl | Cyclohexyl |
| 2067 | 3 | naphthylen-2-yl | 3-pyridyl |
| 2068 | 3 | naphthylen-2-yl | 1-methyl-1H-pyrazol-4-yl |

TABLE 33-continued

| Entry | n | $R^5$ | $R^{10c}$ |
|---|---|---|---|
| 2069 | 3 | naphthylen-2-yl | 1H-imidazol-4-yl |
| 2070 | 3 | naphthylen-2-yl | 2-furanyl |
| 2071 | 4 | naphthylen-1-yl | Ethyl |
| 2072 | 4 | naphthylen-1-yl | n-propyl |
| 2073 | 4 | naphthylen-1-yl | Isopropyl |
| 2074 | 4 | naphthylen-1-yl | $—CH_2CH(CH_3)_2$ |
| 2075 | 4 | naphthylen-1-yl | $CF_3$ |
| 2076 | 4 | naphthylen-1-yl | $—CH_2CF_3$ |
| 2077 | 4 | naphthylen-1-yl | $—CH_2CH_2CF_3$ |
| 2078 | 4 | naphthylen-1-yl | Cyclopropyl |
| 2079 | 4 | naphthylen-1-yl | Cyclobutyl |
| 2080 | 4 | naphthylen-1-yl | Cyclopentyl |
| 2081 | 4 | naphthylen-1-yl | Cyclohexyl |
| 2082 | 4 | naphthylen-1-yl | 3-pyridyl |
| 2083 | 4 | naphthylen-1-yl | 1-methyl-1H-pyrazol-4-yl |
| 2084 | 4 | naphthylen-1-yl | 1H-imidazol-4-yl |
| 2085 | 4 | naphthylen-1-yl | 2-furanyl |
| 2086 | 4 | naphthylen-2-yl | Ethyl |
| 2087 | 4 | naphthylen-2-yl | n-propyl |
| 2088 | 4 | naphthylen-2-yl | Isopropyl |
| 2089 | 4 | naphthylen-2-yl | $—CH_2CH(CH_3)_2$ |
| 2090 | 4 | naphthylen-2-yl | $CF_3$ |
| 2091 | 4 | naphthylen-2-yl | $—CH_2CF_3$ |
| 2092 | 4 | naphthylen-2-yl | $—CH_2CH_2CF_3$ |
| 2093 | 4 | naphthylen-2-yl | Cyclopropyl |
| 2094 | 4 | naphthylen-2-yl | Cyclobutyl |
| 2095 | 4 | naphthylen-2-yl | Cyclopentyl |
| 2096 | 4 | naphthylen-2-yl | Cyclohexyl |
| 2097 | 4 | naphthylen-2-yl | 3-pyridyl |
| 2098 | 4 | naphthylen-2-yl | 1-methyl-1H-pyrazol-4-yl |
| 2099 | 4 | naphthylen-2-yl | 1H-imidazol-4-yl |
| 2100 | 4 | naphthylen-2-yl | 2-furanyl |

For the purposes of demonstrating the manner in which the compounds of the present invention are named and referred to herein, the compound having the formula:

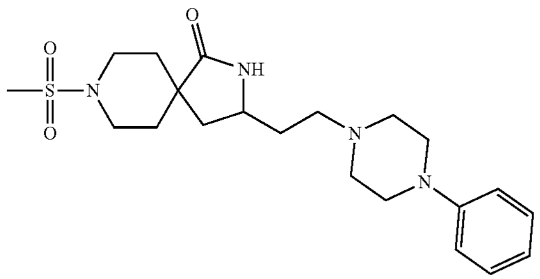 [SMILES: CS(=O)(=O)N1CCC2(CC1)CC(CCN1CCN(c3ccccc3)CC1)NC2=O]

has the chemical name 8-(methylsulfonyl)-3-(2-(4-phenylpiperazin-1-yl)ethyl)-2,8-diazaspiro[4.5]decan-1-one.

For the purposes of demonstrating the manner in which the compounds of the present invention are named and referred to herein, the compound having the formula:

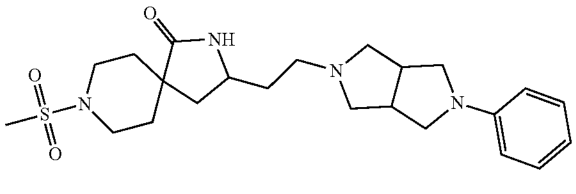 [SMILES: CS(=O)(=O)N1CCC2(CC1)CC(CCN1CC3CN(c4ccccc4)CC3C1)NC2=O]

has the chemical name 8-(methylsulfonyl)-3-(2-(5-phenylhexahydropyrrolo[3,4-c]pyrrol-2(1H)-yl)ethyl)-2,8-diazaspiro[4.5]decan-1-one.

For the purposes of demonstrating the manner in which the compounds of the present invention are named and referred to herein, the compound having the formula:

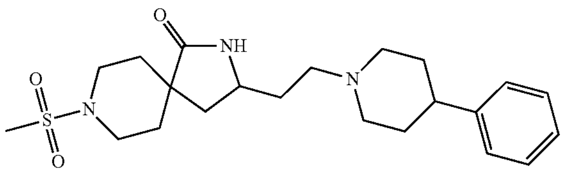

has the chemical name 8-(methylsulfonyl)-3-(2-(4-phenylpiperidin-1-yl)ethyl)-2,8-diazaspiro[4.5]decan-1-one For the purposes of the present invention, a compound depicted by the racemic formula, for example:

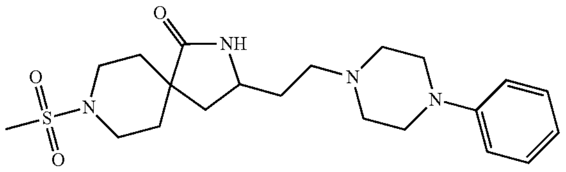 [SMILES: CS(=O)(=O)N1CCC2(CC1)CC(CCN1CCN(c3ccccc3)CC1)NC2=O]

will stand equally well for either of the two enantiomers having the formula:

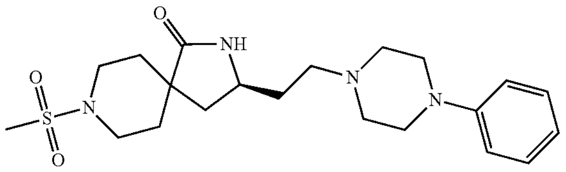 [SMILES: CS(=O)(=O)N1CCC2(CC1)C[C@H](CCN1CCN(c3ccccc3)CC1)NC2=O]

or the formula:

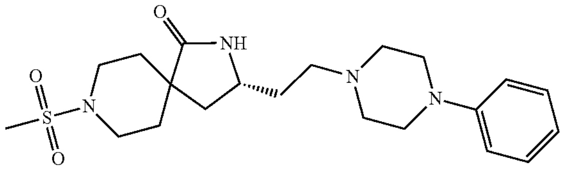 [SMILES: CS(=O)(=O)N1CCC2(CC1)C[C@@H](CCN1CCN(c3ccccc3)CC1)NC2=O]

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein. Process for preparing the 5-hydroxytryptamine receptor 7 activity modulators of the invention The present invention further relates to a process for preparing the 5-hydroxytryptamine receptor 7 activity modulators of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes. Accordingly, the invention further features any of the synthetic intermediates or processes as described herein.

Compounds of the disclosure may be prepared according to the process outlined in Scheme 1-

Scheme 1

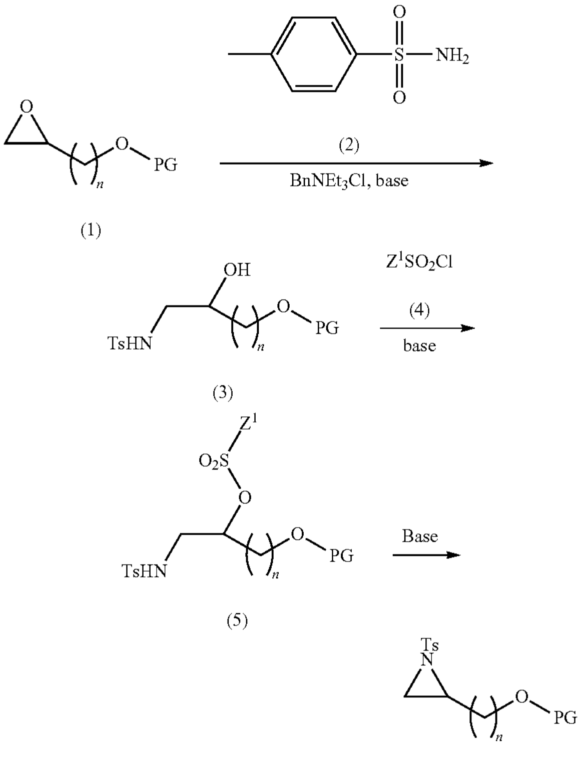

(1)

(3)

(5)

(6)

A suitably substituted compound of formula (1), a known compound or a compound prepared by known methods wherein PG is a protecting selected from the group consisting of benzyl, tert-butyl carbonate, benzyl carbonate, and tert-butyldimethylsilyl, is reacted with a compound of the formula (2), a known compound or a compound prepared by known methods, in the presence of $BnNEt_3Cl$, in the presence of a base such as potassium carbonate, sodium carbonate, cesium carbonate, lithium carbonate, sodium hydroxide, potassium hydroxide, cesium hydroxide, lithium hydroxide, and the like, in the presence of a solvent such as tetrahydrofuran, 1,4-dioxane, 1,2-dimethoxyethane, 1,2-diethoxyethane, acetonitrile, methanol, ethanol, isopropanol, N,N-dimethylformamide, N,N-dimethylacetamide, dimethylsulfoxide, and the like, optionally with heating, optionally with microwave irradiation, to provide a compounds of the formula (3). A compounds of the formula (3) is reacted with a compounds of the formula (4) a known compound or compound prepared by known methods in which $Z^1$ is selected from the group consisting of methyl, trifluoromethyl, para-tolyl, and para-$NO_2$-phenyl, in the presence of a base such as pyridine, 2,6-dimethyl pyridine, 2,6-di-tert-butyl pyridine, triethylamine, diisopropylethyl amine, and the like, in a solvent such as methylene chloride, 1,2-dichloroethane, tetrahydrofuran, 1,4-dioxane, acetonitrile, N,N-dimethylformamide, N,N-dimethylacetamide, dimethylsulfoxide, and the like, optionally with heating, optionally with microwave irradiation to provide a compound of the formula (5). A compound of the formula (5) is reacted with a base such as potassium carbonate, sodium carbonate, cesium carbonate, lithium carbonate, and the like, in a solvent such as tetrahydrofuran, 1,4-dioxane, 1,2- dimethoxyethane, 1,2-diethoxyethane, acetonitrile, N,N-dimethylformamide, N,N-dimethylacetamide, dimethylsulfoxide, and the like, optionally with heating, optionally with microwave irradiation to provide a compound of the formula (6)

Scheme 2

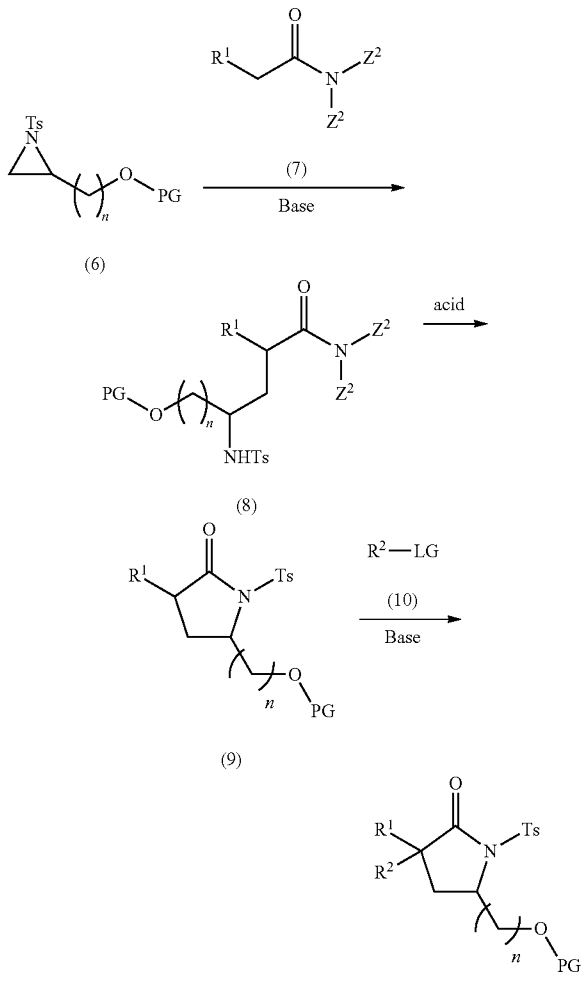

(6) (8) (9) (11)

A compound of formula (6) is reacted with a compound of the formula (7), a known compound or a compound prepared by known methods, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (8). A compound of the formula (8) is reacted with an acid such as hydrochloric acid, hydrobromic acid, sulfuric acid, para-toluenesulfonic acid, acetic acid, trifluoracetic acid, and the like, in a solvent such as benzene, toluene, para-xylene, tetrahydrofuran, 1,4-dioxane, 1,2-dimethoxyethane, 1,2-diethoxyethane, acetonitrile, N,N-dimethylformamide, N,N-dimethylacetamide, dimethylsulfoxide, and the like, optionally with heating, optionally with microwave irradiation to provide a compound of the formula (9). A compound of the formula (9) is reacted with a compound of the formula (10), a known compound or a compound prepared by known methods wherein LG is selected from the group consisting of bromine, chlorine, methansulfonate, and para-tolylsufonate, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (11).

Scheme 3

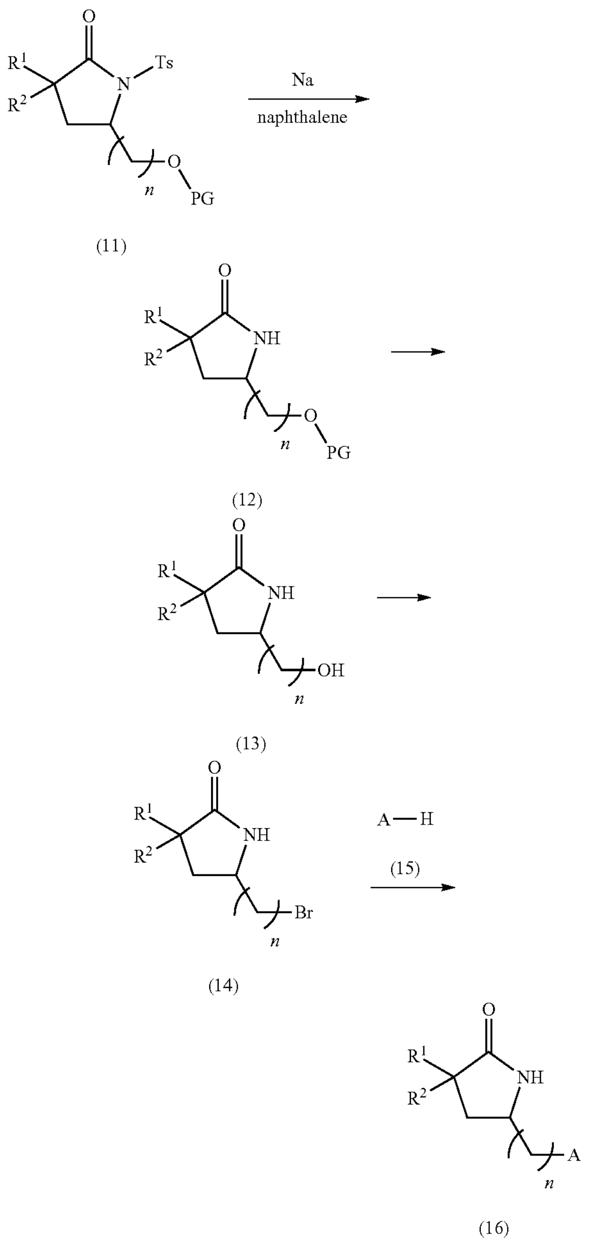

(11) (12) (13) (14) (16)

A compound of formula (11) is reacted with sodium in the presence of naphthalene in a solvent such as tetrahydrofuran, 1,4-dioxane, 1,2-dimethoxyethane, 1,2-diethoxyethane, and the like, optionally with heating, optionally with microwave irradiation to provide a compound of the formula (12). A compound of the formula (12) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis (acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (13). Alternatively, a compound of the formula (12) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (13). Alternatively, a compound of the formula (12) is reacted with tetrabutyl ammonium fluoride in the presence of a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (13). A compound of the (13) is reacted with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (14). A compound of the formula (14) is reacted with a compound of the formula (15), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (16).

Scheme 4

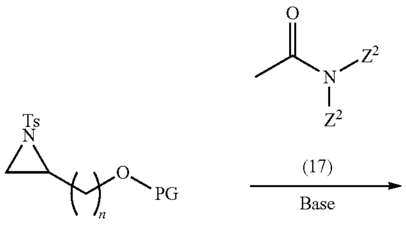

(6)

-continued

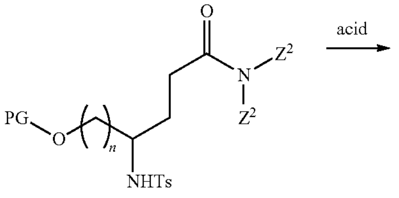

(18)

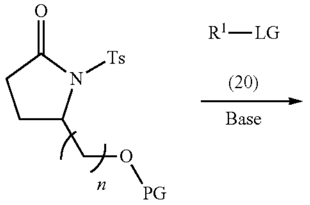

(19)

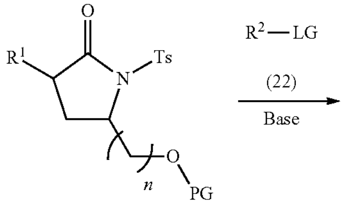

(21)

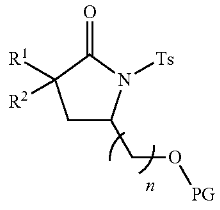

(11)

A compound of formula (6) is reacted with a compound of the formula (17), a known compound or a compound prepared by known methods, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (18). A compound of the formula (18) is reacted with an acid such as hydrochloric acid, hydrobromic acid, sulfuric acid, para-toluenesulfonic acid, acetic acid, trifluoracetic acid, and the like, in a solvent such as benzene, toluene, para-xylene, tetrahydrofuran, 1,4-dioxane, 1,2-dimethoxyethane, 1,2-diethoxyethane, acetonitrile, N,N-dimethylformamide, N,N-dimethylacetamide, dimethylsulfoxide, and the like, optionally with heating, optionally with microwave irradiation to provide a compound of the formula (19). A compound of the formula (19) is reacted with a compound of the formula (20), a known compound or a compound prepared by known methods wherein LG is selected from the group consisting of bromine, chlorine, methansulfonate, and para-tolylsufonate, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl) amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (21). A compound of the formula (21) is reacted with a compound of the formula (22), a known compound or a compound prepared by known methods wherein LG is selected from the group consisting of bromine, chlorine, methansulfonate, and para-tolylsufonate, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (11).

Scheme 5

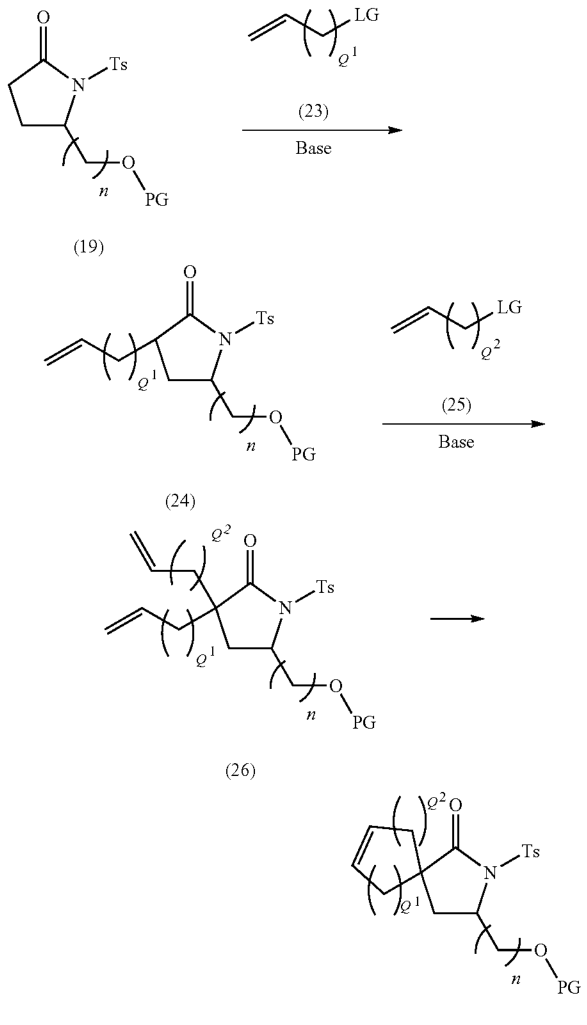

(19) (24) (26) (27)

A compound of the formula (19) is reacted with a compound of the formula (23), a known compound or a compound prepared by known methods wherein LG is selected from the group consisting of bromine, chlorine, methansulfonate, and para-tolylsufonate and wherein $Q^1$ is selected from the group consisting of 1 and 2, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (24). A compound of the formula (24) is reacted with a compound of the formula (25), a known compound or a compound prepared by known methods wherein LG is selected from the group consisting of bromine, chlorine, methansulfonate, and para-tolylsufonate and wherein $Q^2$ is selected from the group consisting of 1 and 2, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (26). A compound of the formula (26) is reacted with a ruthenium catalyst such as benzylidene-bis(tricyclohexylphosphine)dichlororuthenium, (1,3-Bis(2,4,6-trimethylphenyl)-2-imidazolidinylidene)dichloro(phenylmethylene)(tricyclohexyl phosphine)ruthenium, (1,3-bis-(2,4,6-trimethylphenyl)-2-imidazolidinylidene)dichloro(o-isopropoxy phenylmethylene)ruthenium, dichloro(2-isopropoxyphenylmethylene)(tricyclohexylphosphine) ruthenium(II), [1,3-bis(2-methylphenyl)-2-imidazolidinylidene]dichloro(phenylmethylene) (tricyclohexyl phosphine) ruthenium(II), dichloro[1,3-bis(2,4,6-trimethylphenyl)-2-imidazolidinylidene](benzylidene)bis(3-bromopyridine)ruthenium(II), dichloro[1,3-bis(2,4,6-trimethylphenyl)-2-imidazolidinylidene](3-methyl-2-butenylidene) (tricyclohexylphosphine)ruthenium(II), dichloro[1,3-bis(2-methylphenyl)-2-imidazolidinylidene] (2-isopropoxyphenylmethylene)ruthenium(II), [1,3-dimesityl-2-imidazolidinylidene]dichloro[3-(2-pyridinyl)propylidene]ruthenium(II), dichloro[1,3-bis(2,6-isopropylphenyl)-2-imidazolidinylidene](2-isopropoxyphenylmethylene)ruthenium(II), dichloro (tricyclohexylphosphine) [(tricyclohexylphosphoranyl) methylidene]ruthenium tetrafluoroborate, dichloro[1,3-bis (2,4,6-trimethyl phenyl)-2-imidazolidinylidene] [(tricyclohexylphosphoranyl)methylidene]ruthenium(II) tetrafluoroborate, [2-(1-methylethoxy-O)phenylmethyl-C] (nitrato-O,O'){rel-(2R,5R,7R)-adamantane-2,1-diyl[3-(2,4,6-trimethylphenyl)-1-imidazolidinyl-2-ylidene]}ruthenium, dichloro[1,3-bis(2,6-isopropylphenyl)-2-imidazolidinylidene](benzylidene)(tricyclohexylphosphine)ruthenium (II), [1,3-bis(2-methylphenyl)-2-imidazolidinylidene]dichloro(phenylmethylene)(tricyclohexylphosphine) ruthenium(II), dichloro[1,3-bis(2,4,6-trimethylphenyl)-2-imidazolidinylidene][3-(2-pyridinyl)propylidene]ruthenium (II), and the like in the presence of a solvent such as methylene chloride, 1,2-dichloroethane, tetrahydrofuran, 1,4-dioxane, 1,2-dimethoxyethane, 1,2-diethoxyethane, N,N-dimethylformamide, N,N-dimethylacetamide, dimethylsulfoxide, and the like, optionally with heating, optionally with microwave irradiation to provide a compound of the formula (27).

Scheme 6

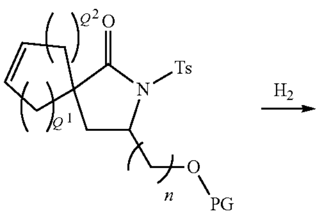

(27)

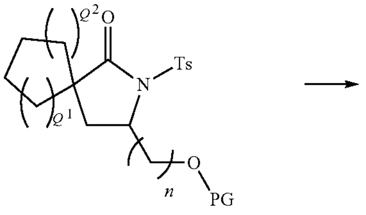

(28)

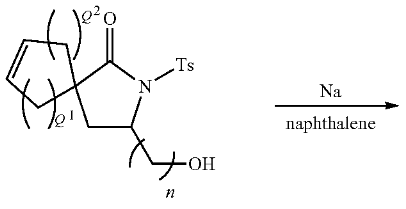

(29)

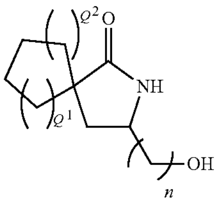

(30)

A compound of the formula (27) is reacted with hydrogen gas in the presence of a palladium catalyst such as palladium on carbon, palladium on barium sulfate, palladium (II) acetate, tetrakis(triphenylphosphine)palladium(0), dichloro-bis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (28). A compound of the formula (28) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (29). Alternatively, a compound of the formula (28) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (29). Alternatively, a compound of the formula (28) is reacted with tetrabutyl ammonium fluoride in the presence of a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (29). A compound of formula (29) is reacted with sodium in the presence of naphthalene in a solvent such as tetrahydrofuran, 1,4-dioxane, 1,2-dimethoxyethane, 1,2-diethoxyethane, and the like, optionally with heating, optionally with microwave irradiation to provide a compound of the formula (30).

Scheme 7

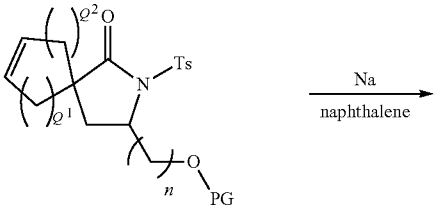

(27)

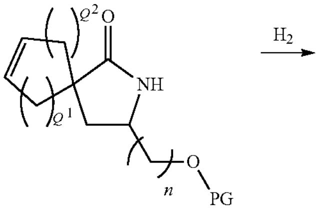

(31)

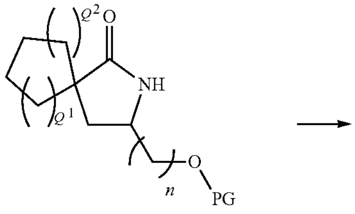

(32)

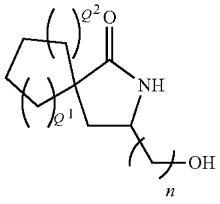

(30)

Alternatively, a compound of formula (27) is reacted with sodium in the presence of naphthalene in a solvent such as tetrahydrofuran, 1,4-dioxane, 1,2-dimethoxyethane, 1,2-diethoxyethane, and the like, optionally with heating, optionally with microwave irradiation to provide a compound of the formula (31). A compound of the formula (31) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (32). A compound of the formula (32) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile) dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (30). Alternatively, a compound of the formula (32) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (30). Alternatively, a compound of the formula (32) is reacted with tetrabutyl ammonium fluoride in the presence of a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (30).

Scheme 8

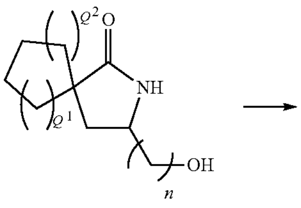

(30)

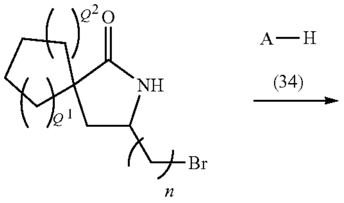

(33)

-continued

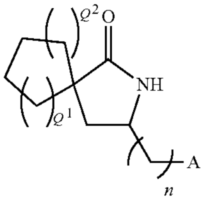

(35)

A compound of the (30) is reacted with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (33). A compound of the formula (33) is reacted with a compound of the formula (34), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (35).

Scheme 9

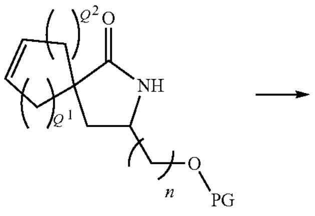

(31)

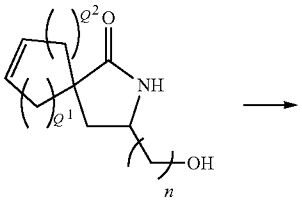

(36)

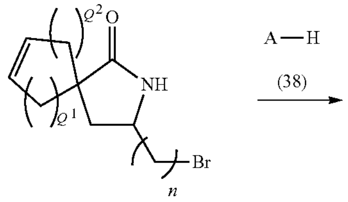

(37)

-continued

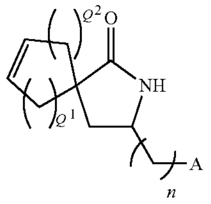

(39)

A compound of the formula (31) is reacted with hydrogen gas in the presence of a palladium catalyst such as palladium on carbon, palladium on barium sulfate, palladium (II) acetate, tetrakis(triphenylphosphine)palladium(0), dichloro-bis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (36). Alternatively, a compound of the formula (31) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (36). Alternatively, a compound of the formula (31) is reacted with tetrabutyl ammonium fluoride in the presence of a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (36). A compound of the (36) is reacted with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (37). A compound of the formula (37) is reacted with a compound of the formula (38), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (39).

Scheme 10

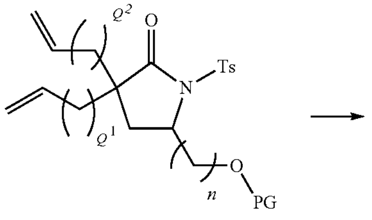

(26)

-continued

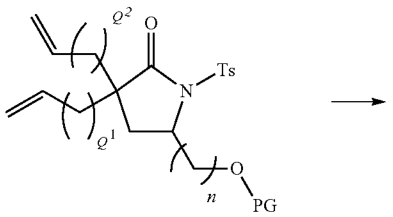

(40)

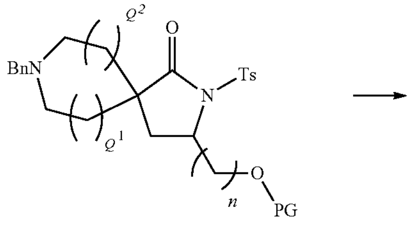

(41)

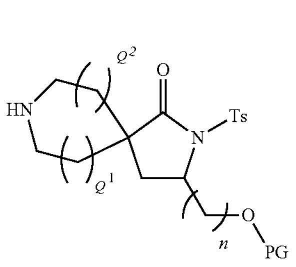

(42)

A compound of the formula (26) is reacted with a compound of the formula ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with triphenyl phosphine in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (40). Alternatively, a compound of the formula (26) is reacted with a compound of the formula ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with dimethyl sulfide in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (40). Alternatively, a compound of the formula (26) is reacted with ruthenium chloride in the presence of sodium periodate in a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally in the presence of water, optionally with heating optionally with microwave irradiation to provide a compound of the formula (40). Alternatively, a compound of the formula (26) is reacted with potassium osmate dehydrate in the presence of potassium ferricyanide, optionally in the presence of potassium carbonate, optionally in the presence of a base such as potassium hydroxide, sodium hydroxide, lithium hydroxide, and the like, in the presence of a solvent such as methanol, ethanol, isopropanol, tert-butanol, tetrahydrofuran, 1,4-dioxane, 1,2-dimethoxyethane, acetone, ethyl acetate, benzene toluene, N,N-dimethylformamide, N,N-dimethylacetamide, and the like, optionally in the presence of water, optionally with heating optionally with microwave irradiation to provide a compound of the formula (40). Alternatively, a compound of the formula (26) is reacted with osmium tetraoxide in the presence of sodium periodate, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of a base such as pyridine, 2,6-lutidine, 2,6-di-tert-butylpyridine, and the like, optionally in the presence of water, optionally with heating, optionally with microwave irradiation to provide a compound of the formula (40). Alternatively, a compound of the formula (26) is reacted with osmium tetraoxide in the presence of N-methylmorpholine N-oxide, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of water, optionally with heating, optionally with microwave irradiation to provide a compound of the formula (40). A compound of the formula (40) is reacted with benzyl amine in the presence of a reducing agent such as sodium borohydride, sodium triacetoxy borohydride, sodium cyanoborohydride, lithium borohydride, lithium triacetoxy borohydride, lithium cyanoborohydride and the like, in the presence of a solvent such as methylene chloride, 1,2-dichloroethane, methanol, ethanol, isopropanol, tert-butanol, 1,4-dioxane, tetrahydrofuran, 1,2-dimethoxtethane, benzene toluene, N,N-dimethylformamide, N,N-dimethylacetamide, and the like, optionally with heating, optionally with microwave irradiation to provide a compound of the formula (41). A compound of the formula (41) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis (acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (42).

Scheme 11

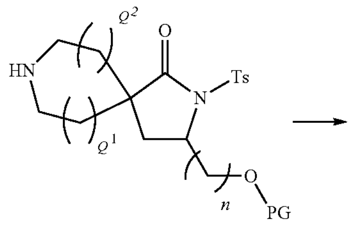

(42)

-continued

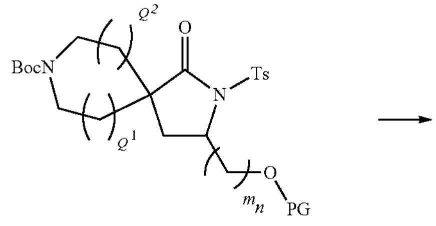

(43)

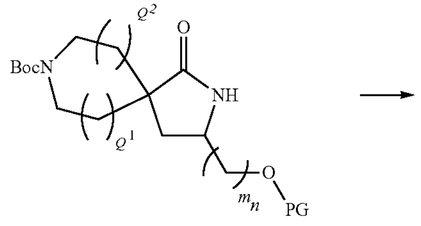

(44)

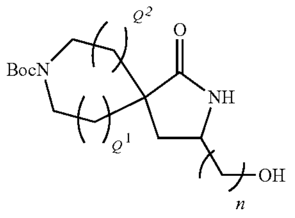

(45)

A compound of the formula (42) is reacted with Di-tert-butyl dicarbonate in the presence of a base such as such as pyridine, 2,6-lutidine, triethylamine, diisopropylethylamine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, methanol, ethanol, isopropanol, and the like, optionally with heating, optionally with microwave irradiation to provide a compound of the formula (43). A compound of formula (43) is reacted with sodium in the presence of naphthalene in a solvent such as tetrahydrofuran, 1,4-dioxane, 1,2-dimethoxyethane, 1,2-diethoxyethane, and the like, optionally with heating, optionally with microwave irradiation to provide a compound of the formula (44). A compound of the formula (44) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis (acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (45). Alternatively, a compound of the formula (44) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (45). Alternatively, a compound of the formula (44) is reacted with tetrabutyl ammonium fluoride in the presence of a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (45).

Scheme 12

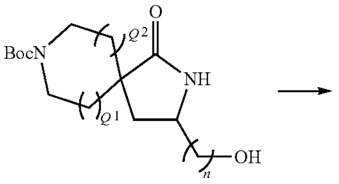

(45)

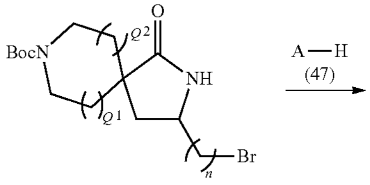

(46)

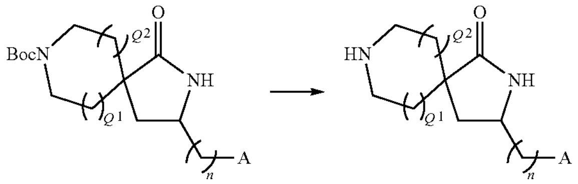

(48) (49)

A compound of the (45) is reacted with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (46). A compound of the formula (46) is reacted with a compound of the formula (47), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (48). A compound of the formula (48) is reacted with an acid such as trifluoroacetic acid, formic acid, acetic acid, hydrochloric acid, sulfuric acid, and the like, optionally in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (49).

Scheme 13

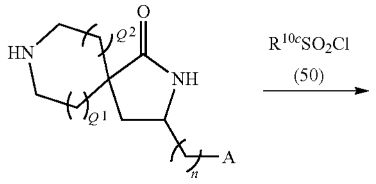

(49)

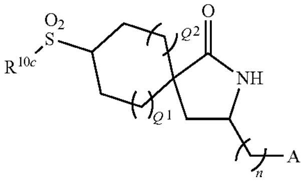

(51)

A compound of the formula (49) is reacted with a compound of the formula (50), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (51).

Scheme 14

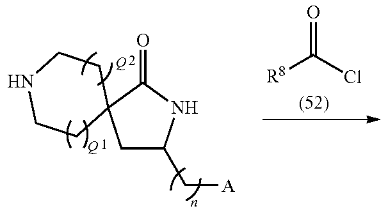

(49)

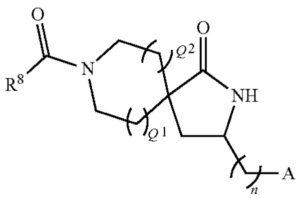

(53)

A compound of the formula (49) is reacted with a compound of the formula (52), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (53).

Scheme 15

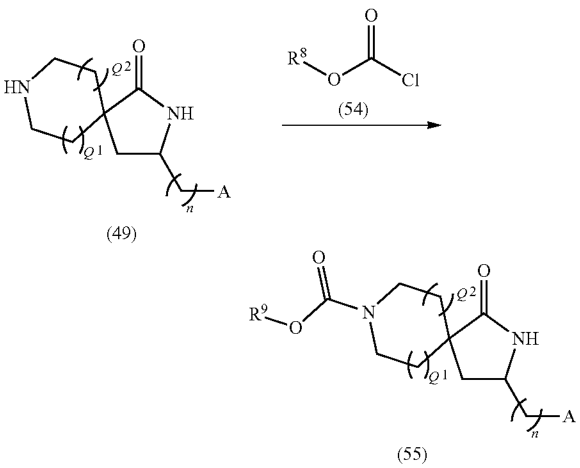

(49)

(55)

A compound of the formula (49) is reacted with a compound of the formula (54), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (55).

Scheme 16

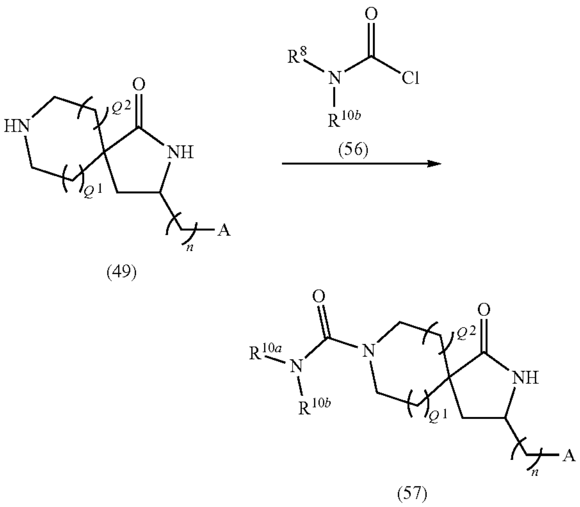

(49)

(57)

A compound of the formula (49) is reacted with a compound of the formula (56), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (57).

Scheme 17

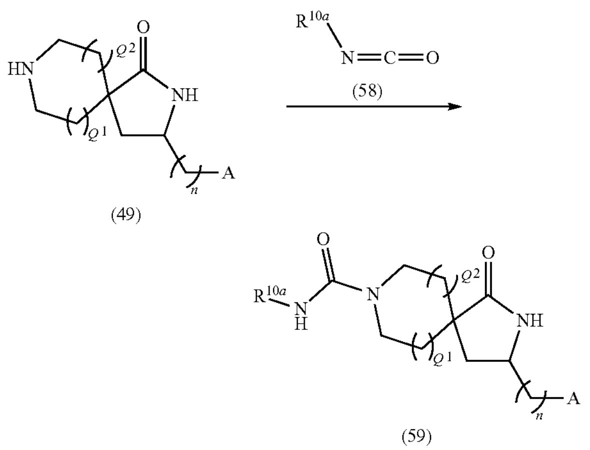

(49)

(59)

A compound of the formula (49) is reacted with a compound of the formula (58), a known compound or a compound prepared by known methods, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (59).

Scheme 18

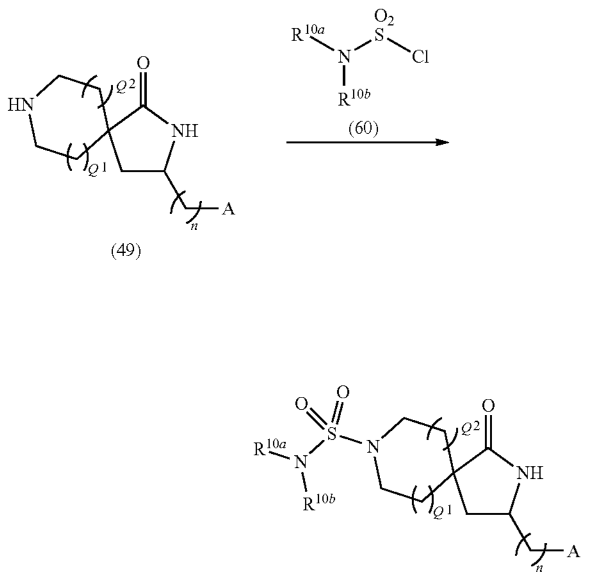

(49)

(61)

A compound of the formula (49) is reacted with a compound of the formula (60), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (61).

Scheme 19

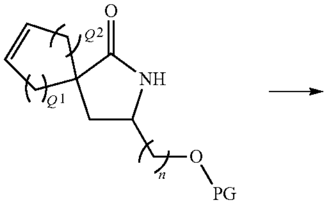

(62)

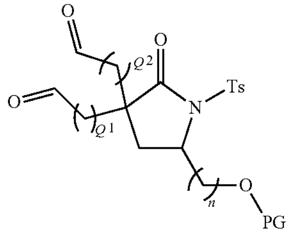

(63)

A compound of the formula (62) is reacted with a compound of the formula ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with triphenyl phosphine in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (63). Alternatively, a compound of the formula (62) is reacted with a compound of the formula ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with dimethyl sulfide in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (63). Alternatively, a compound of the formula (62) is reacted with ruthenium chloride in the presence of sodium periodate in a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally in the presence of water, optionally with heating optionally with microwave irradiation to provide a compound of the formula (63). Alternatively, a compound of the formula (62) is reacted with potassium osmate dehydrate in the presence of potassium ferricyanide, optionally in the presence of potassium carbonate, optionally in the presence of a base such as potassium hydroxide, sodium hydroxide, lithium hydroxide, and the like, in the presence of a solvent such as methanol, ethanol, isopropanol, tert-butanol, tetrahydrofuran, 1,4-dioxane, 1,2-dimethoxyethane, acetone, ethyl acetate, benzene toluene, N,N-dimethylformamide, N,N-dimethylacetamide, and the like, optionally in the presence of water, optionally with heating optionally with microwave irradiation to provide a compound of the formula (63). Alternatively, a compound of the formula (62) is reacted with osmium tetraoxide in the presence of sodium periodate, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of a base such as pyridine, 2,6-lutidine, 2,6-di-tert-butylpyridine, and the like, optionally in the presence of water, optionally with heating, optionally with microwave irradiation to provide a compound of the formula (63). Alternatively, a compound of the formula (62) is reacted with osmium tetraoxide in the presence of N-methylmorpholine N-oxide, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of water, optionally with heating, optionally with microwave irradiation to provide a compound of the formula (63).

Scheme 20

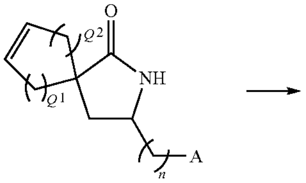

(64)

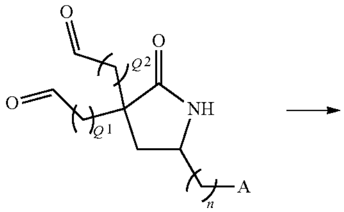

(65)

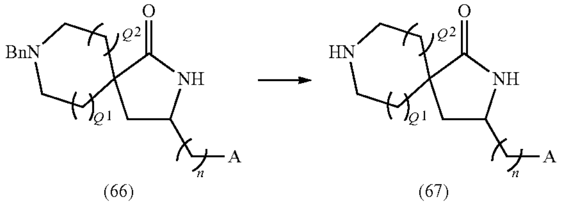

(66) (67)

A compound of the formula (64) is reacted with a compound of the formula ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with triphenyl phosphine in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (65). Alternatively, a compound of the formula (64) is reacted with a compound of the formula ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with dimethyl sulfide in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (65). Alternatively, a compound of the formula (64) is reacted with ruthenium chloride in the presence of sodium periodate in a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally in the presence of water, optionally with heating optionally with microwave irradiation to provide a compound of the formula (65). Alternatively, a compound of the formula (64) is reacted with potassium osmate dehydrate in the presence of potassium ferricyanide, optionally in the presence of potassium carbonate, optionally in the presence of a base such as potassium hydroxide, sodium hydroxide, lithium hydroxide, and the like, in the presence of a solvent such as methanol, ethanol, isopropanol, tert-butanol, tetrahydrofuran, 1,4-dioxane, 1,2-dimethoxyethane, acetone, ethyl acetate, benzene toluene, N,N-dimethylformamide, N,N-dimethylacetamide, and the like, optionally in the presence of water, optionally with heating optionally with microwave irradiation to provide a compound of the formula (65). Alternatively, a compound of the formula (64) is reacted with osmium tetraoxide in the irradiation to provide a compound of the formula (65). Alternatively, a compound of the formula (64) is reacted with osmium tetraoxide in the presence of N-methylmorpholine N-oxide, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of water, optionally with heating, optionally with microwave irradiation to provide a compound of the formula (65). A compound of the formula (65) is reacted with benzyl amine in the presence of a reducing agent such as sodium borohydride, sodium triacetoxy borohydride, sodium cyanoborohydride, lithium borohydride, lithium triacetoxy borohydride, lithium cyanoborohydride and the like, in the presence of a solvent such as methylene chloride, 1,2-dichloroethane, methanol, ethanol, isopropanol, tert-butanol, 1,4-dioxane, tetrahydrofuran, 1,2-dimethoxtethane, benzene toluene, N,N-dimethylformamide, N,N-dimethylacetamide, and the like, optionally with heating, optionally with microwave irradiation to provide a compound of the formula (66). A compound of the formula (66) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis (acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (67).

Scheme 21

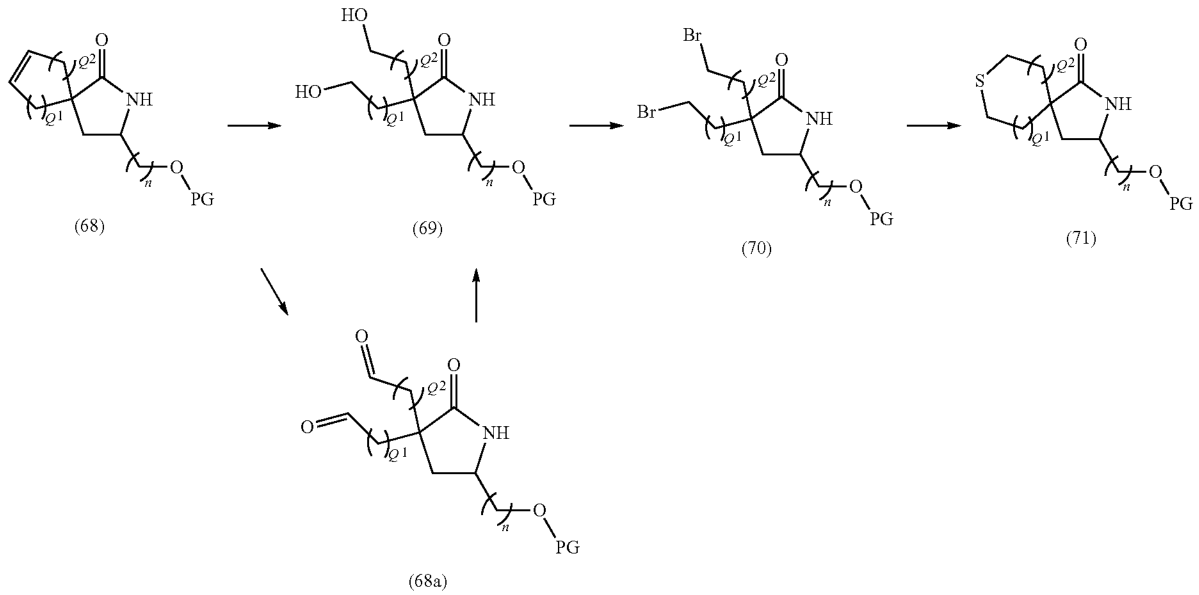

(68) (69) (70) (71) (68a)

presence of sodium periodate, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of a base such as pyridine, 2,6-lutidine, 2,6-di-tert-butylpyridine, and the like, optionally in the presence of water, optionally with heating, optionally with microwave A compound of the formula (68) is reacted with a compound of the formula ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with a reducing agent such as sodium borohydride, sodium triacetoxy borohydride, sodium cyanoborohydride, lithium borohydride, lithium triacetoxy borohydride, lithium cyanoborohydride and the like, in the presence of a solvent such as methylene chloride, 1,2-dichloroethane, methanol, ethanol, isopropanol, tert-butanol, 1,4-dioxane, tetrahydrofuran, 1,2-dimethoxtethane, benzene toluene, N,N-dimethylformamide, N,N-dimethylacetamide, and the like, optionally with heating, optionally with microwave irradiation to provide a compound of the formula (69). Alternatively, a compound of the formula (68) is reacted with a compound of the formula ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with dimethyl sulfide in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (68a). Alternatively, a compound of the formula (68) is reacted with ruthenium chloride in the presence of sodium periodate in a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally in the presence of water, optionally with heating optionally with microwave irradiation to provide a compound of the formula (68a). Alternatively, a compound of the formula (68) is reacted with potassium osmate dehydrate in the presence of potassium ferricyanide, optionally in the presence of potassium carbonate, optionally in the presence of a base such as potassium hydroxide, sodium hydroxide, lithium hydroxide, and the like, in the presence of a solvent such as methanol, ethanol, isopropanol, tert-butanol, tetrahydrofuran, 1,4-dioxane, 1,2-dimethoxyethane, acetone, ethyl acetate, benzene toluene, N,N-dimethylformamide, N,N-dimethylacetamide, and the like, optionally in the presence of water, optionally with heating optionally with microwave irradiation to provide a compound of the formula (68a). Alternatively, a compound of the formula (68) is reacted with osmium tetraoxide in the presence of sodium periodate, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of a base such as pyridine, 2,6-lutidine, 2,6-di-tert-butylpyridine, and the like, optionally in the presence of water, optionally with heating, optionally with microwave irradiation to provide a compound of the formula (68a). Alternatively, a compound of the formula (68) is reacted with osmium tetraoxide in the presence of N-methylmorpholine N-oxide, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of water, optionally with heating, optionally with microwave irradiation to provide a compound of the formula (68a). A compound of the formula (68a) is reacted with a reducing agent such as sodium borohydride, sodium triacetoxy borohydride, sodium cyanoborohydride, lithium borohydride, lithium triacetoxy borohydride, lithium cyanoborohydride and the like, in the presence of a solvent such as methylene chloride, 1,2-dichloroethane, methanol, ethanol, isopropanol, tert-butanol, 1,4-dioxane, tetrahydrofuran, 1,2-dimethoxtethane, benzene toluene, N,N-dimethylformamide, N,N-dimethylacetamide, and the like, optionally with heating, optionally with microwave irradiation to provide a compound of the formula (69). A compound of the (69) is reacted with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (70). Alternatively, a compound of the formula (69) is reacted with bromine in the presence of triphenylphosphine, in the presence of a base such as pyridine 2,6-dimethyl pyridine, 2,6-di-tert-butyl pyridine, triethylamine, diisopropylethyl amine, and the like, in a solvent such as methylene chloride, 1,2-dichloroethane, tetrahydrofuran, 1,4-dioxane, acetonitrile, N,N-dimethylformamide, N,N-dimethylacetamide, dimethylsulfoxide, and the like, optionally with heating, optionally with microwave irradiation to provide a compound of the formula (70). Alternatively, a compound of the formula (69) is reacted with dibromotriphenylphosphorane, optionally in the presence of a base such as pyridine 2,6-dimethyl pyridine, 2,6-di-tert-butyl pyridine, triethylamine, diisopropylethyl amine, and the like, in a solvent such as methylene chloride, 1,2-dichloroethane, tetrahydrofuran, 1,4-dioxane, acetonitrile, N,N-dimethylformamide, N,N-dimethylacetamide, dimethylsulfoxide, and the like, optionally with heating, optionally with microwave irradiation to provide a compound of the formula (70). A compound of the formula (70) is reacted with sodium sulfide in the presence of a solvent such as ethanol, methanol, isopropanol, N,N-dimethylformamide, N,N-dimethylacetamide, dimethylsulfoxide, and the like, optionally with heating, optionally with microwave irradiation to provide a compound of the formula (71).

Scheme 22

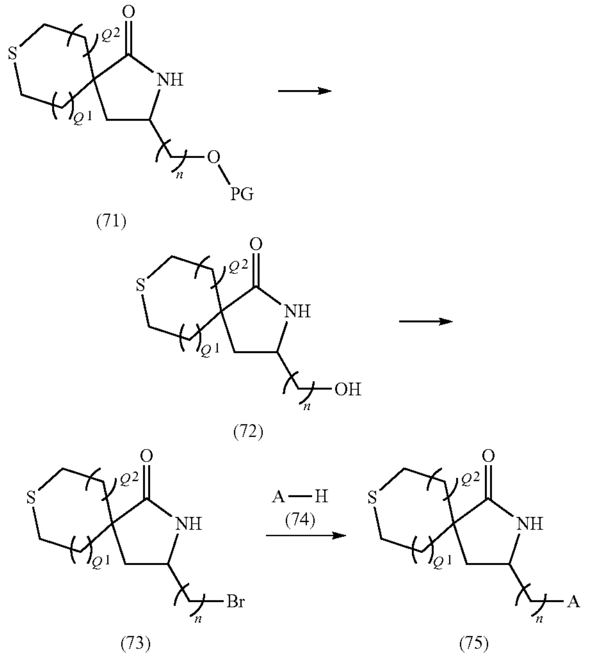

(71) (72) (73) (75)

A compound of the formula (71) is reacted with hydrogen gas in the presence of a palladium catalyst such as palladium on carbon, palladium on barium sulfate, palladium (II) acetate, tetrakis(triphenylphosphine)palladium(0), dichloro-bis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (72). Alternatively, a compound of the formula (71) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (72). Alternatively, a compound of the formula (71) is reacted with tetrabutyl ammonium fluoride in the presence of a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (72). A compound of the (72) is reacted with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (73). A compound of the formula (73) is reacted with a compound of the formula (74), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (75).

Scheme 23

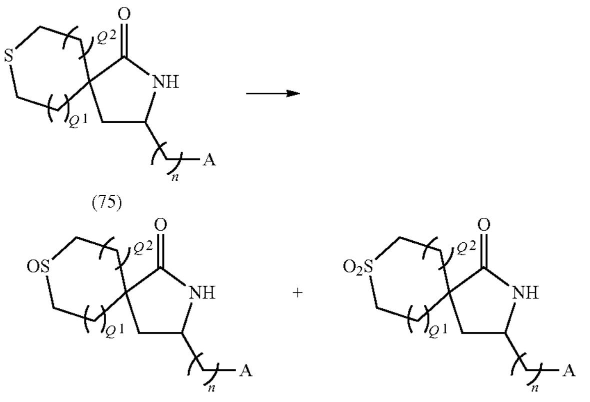

(75)

(76)

(77)

A compound of the formula (75) is reacted with an oxidizing agent such as m-chloroperoxybenzoic acid, monoperphthalic acid, peracetic acid, perpropionic acid, pertrifluoroacetic acid, potassium periodate, sodium metaperiodate, sodium perborate, potassium peroxymonosulfate (Oxone®), potassium peroxydisulfate, dimethyldioxirane, and the like, in the presence of a solvent such as tetrahydrofuran, ether, 1,4-dioxane, acetone, acetonitrile, methanol, ethanol, isopropanol, water, and the like, optionally with heating, optionally with microwave irradiation to provide compounds of the formula (76) and (77). Alternatively, a formula of the compound (75) is reacted with a sulfoxide such as diphenyl sulfoxide, dimethyl sulfoxide, and the like, in the presence of a rhenium catalyst such as $ReOCl_3(PPh_3)_2$, and the like, in a solvent such as methylene chloride, 1,2-dichloroethane, chloroform, tetrahydrofuran, ether, 1,4-dioxane, acetone, acetonitrile, and the like, optionally with heating, optionally with microwave irradiation to provide compounds of the formula (76) and (77). Alternatively, a formula of the compound (75) is reacted with a urea hydrogen peroxide complex in the presence of a rhenium catalyst such as $ReOCl_3(PPh_3)_2$, and the like, in a solvent such as methylene chloride, 1,2-dichloroethane, chloroform, tetrahydrofuran, ether, 1,4-dioxane, acetone, acetonitrile, N,N-dimethylformamide, and the like, optionally with heating, optionally with microwave irradiation to provide compounds of the formula (76) and (77). Alternatively, a compound of the formula (75) is reacted with hydrogen peroxide in the presence titanium (IV) isopropoxide-diethyltartarate, optionally in the presence of an amino alcohol such as 2-amino-3-phenylpropan-1-ol, 2-amino-4-methylpentan-1-ol, 2-amino-4-(methylthio)butan-1-ol, 2-aminopropan-1-ol, and the like, in a solvent such as methylene chloride, 1,2-dichloroethane, chloroform, tetrahydrofuran, ether, 1,4-dioxane, acetone, acetonitrile, N,N-dimethylformamide, and the like optionally with heating, optionally with microwave irradiation to provide compounds of the formula (76) and (77). It is understood that one skilled in the art would readily understand that the ratio of products (76) and (77) will be controlled by the amount of oxidant added and would adjust the amount of oxidant accordingly to produce the desired ration of products.

Scheme 24

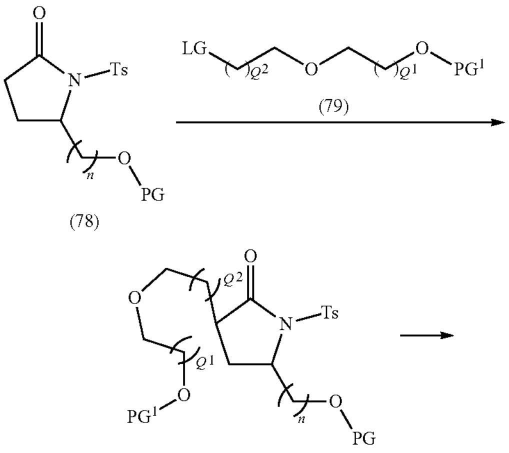

(78)

(80)

-continued

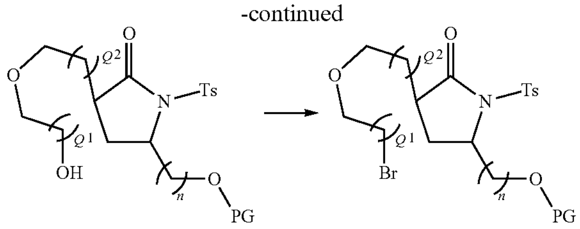

(81) (82)

A suitably substituted compound of the formula (78), a known compound or a compound prepared by known methods wherein PG is a protecting selected from the group consisting of benzyl, tert-butyl carbonate, benzyl carbonate, and tert-butyldimethylsilyl, is reacted with a compound of the formula (79), a known compound or a compound prepared by known methods in which $PG^1$ is a protecting group selected from the group consisting of benzyl, tert-butyl carbonate, benzyl carbonate, and tert-butyldimethylsilyl, and wherein the LG is selected from the group consisting of bromine, chlorine, methansulfonate, and para-tolylsufonate, in the presence of a base such as lithium diisopropylamide, sodium diisopropylamide, potassium diisopropylamide, lithium bis(trimethylsilyl)amide, sodium bis(trimethylsilyl) amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (80). A compound of the formula (80) is reacted with hydrogen gas in the presence of a palladium catalyst such as palladium on carbon, palladium on barium sulfate, palladium (II) acetate, tetrakis(triphenylphosphine) palladium(0), dichlorobis (triphenylphosphine)palladium (II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (81). Alternatively, a compound of the formula (80) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (81). Alternatively, a compound of the formula (80) is reacted with tetrabutyl ammonium fluoride in the presence of a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (81). A compound of the formula (81) is reacted with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (82). Alternatively, a compound of the formula (81) is reacted with bromine in the presence of triphenylphosphine, in the presence of a base such as pyridine 2,6-dimethyl pyridine, 2,6-di-tert-butyl pyridine, triethylamine, diisopropylethyl amine, and the like, in a solvent such as methylene chloride, 1,2-dichloroethane, tetrahydrofuran, 1,4-dioxane, acetonitrile, N,N-dimethylformamide, N,N-dimethylacetamide, dimethylsulfoxide, and the like, optionally with heating, optionally with microwave irradiation to provide a compound of the formula (82). Alternatively, a compound of the formula (81) is reacted with dibromotriphenylphosphorane, optionally in the presence of a base such as pyridine 2,6-dimethyl pyridine, 2,6-di-tert-butyl pyridine, triethylamine, diisopropylethyl amine, and the like, in a solvent such as methylene chloride, 1,2-dichloroethane, tetrahydrofuran, 1,4-dioxane, acetonitrile, N,N-dimethylformamide, N,N-dimethylacetamide, dimethylsulfoxide, and the like, optionally with heating, optionally with microwave irradiation to provide a compound of the formula (82).

Scheme 25

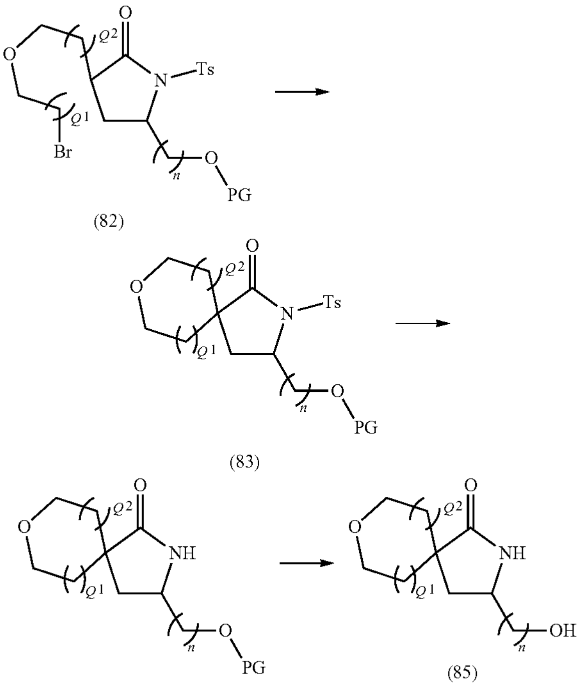

(82)

(83)

(84) (85)

A compound of the formula (82), is reacted with a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (83). A compound of formula (83) is reacted with sodium in the presence of naphthalene in a solvent such as tetrahydrofuran, 1,4-dioxane, 1,2-dimethoxyethane, 1,2-diethoxyethane, and the like, optionally with heating, optionally with microwave irradiation to provide a compound of the formula (84). A compound of the formula (84) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis (acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, optionally with heating, to provide a compound of the formula (85). Alternatively, a compound of the formula (84) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (85). Alternatively, a compound of the formula (84) is reacted with tetrabutyl ammonium fluoride in the presence of a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (85).

Scheme 26

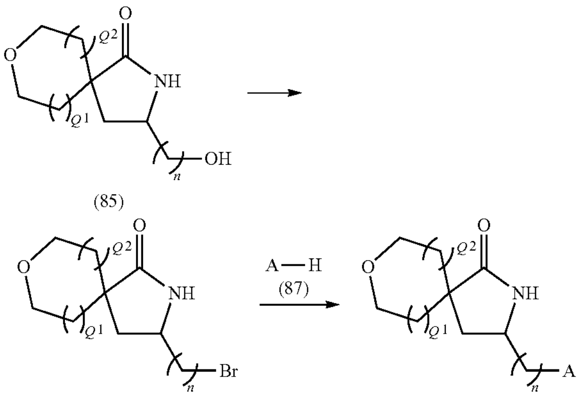

(85)

(86)

(88)

A compound of the formula (85) is reacted with carbon tetrabromide in the presence of triphenylphosphine, in a solvent such as methylene chloride, 1,2-dichloroethane, tetrahydrofuran, 1,4-dioxane, 1,2-dimethoxyethane, N,N-dimethylformamide, N,N-dimethylacetamide, and the like, optionally with heating, optionally with microwave irradiation to provide a compound of the formula (86). Alternatively, a compound of the formula (85) is reacted with bromine in the presence of triphenylphosphine, in the presence of a base such as pyridine 2,6-dimethyl pyridine, 2,6-di-tert-butyl pyridine, triethylamine, diisopropylethyl amine, and the like, in a solvent such as methylene chloride, 1,2-dichloroethane, tetrahydrofuran, 1,4-dioxane, acetonitrile, N,N-dimethylformamide, N,N-dimethylacetamide, dimethylsulfoxide, and the like, optionally with heating, optionally with microwave irradiation to provide a compound of the formula (86). Alternatively, a compound of the formula (85) is reacted with dibromotriphenylphosphorane, optionally in the presence of a base such as pyridine 2,6-dimethyl pyridine, 2,6-di-tert-butyl pyridine, triethylamine, diisopropylethyl amine, and the like, in a solvent such as methylene chloride, 1,2-dichloroethane, tetrahydrofuran, 1,4-dioxane, acetonitrile, N,N-dimethylformamide, N,N-dimethylacetamide, dimethylsulfoxide, and the like, optionally with heating, optionally with microwave irradiation to provide a compound of the formula (86). A compound of the formula (86) is reacted with a compound of the formula (87), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (88).

Scheme 26

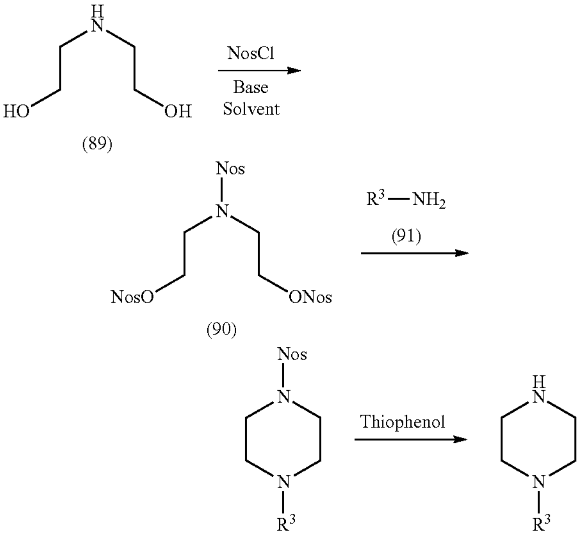

(89)

(90)

(92)

(93)

Diethanolamine (89) is reacted with 4-nitrobenzenesulfonyl chloride (NosCl) in the presence of a base such as triethylamine, diisopropylethylamine, pyridine, 2,6-lutidine, and the like in a solvent such as tetrahydrofuran, 1,4-dioxane, methylene chloride and the like to provide a compound of the formula (90). A compound of the formula (90) is then reacted with a compound of the formula (91), a known compound or one prepared by known methods, in the presence of a base such as triethylamine, diisopropylethylamine, pyridine, 2,6-lutidine, and the like, in a solvent such as acetonitrile, methanol, ethanol, dimethyl formamide, optionally with heating, optionally with microwave irradiation to provide a compound of the formula (92). A compound of the formula (92) is reacted with a thiophenol in the presence of a base such as sodium bicarbonate, potassium bicarbonate, lithium bicarbonate, sodium carbonate, potassium carbonate, lithium bicarbonate, sodium hydroxide, potassium hydroxide, lithium hydroxide, and the like, in the presence of a solvent such as tetrahydrofuran, ethyl ether, 1,4-dioxane, acetonitrile and the like, optionally in the presence of dimethylsulfoxide, optionally with heating, optionally with microwave irradiation, to provide a compound of the formula (93).

Scheme 27

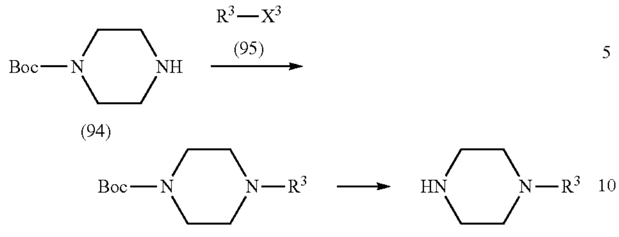

(94) (96) (97)

A compound of the formula (94), a known compound or a compound prepared by known methods, is reacted with a compound of the formula (95), a known compound or a compound prepared by known methods in which $X^3$ is selected from the group consisting of chlorine, bromine, iodine, and methanetrifluorosulfonate, in the presence of a base such as sodium tert-butoxide, lithium tert-butoxide, potassium tert-butoxide, and the like, optionally in the presence of a base such as triethylamine, diisopropylethyl amine, pyridine, 2,6-lutidine, and the like, in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), tris(dibenzylideneacetone) dipalladium(0), and the like, in the presence of a solvent such as toluene, benzene, methylene chloride, 1,2-dichloroethae, tetrahydrofuran, 1,4-dioxane, N,N-dimethylformamide, and the like, optionally with heating, optionally with microwave irradiation, to provide a compound of the formula (96). A compound of the formula (96) is reacted with an acid such as trifluoroacetic acid, formic acid, acetic acid, hydrochloric acid, sulfuric acid, and the like, optionally in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (97).

Scheme 28

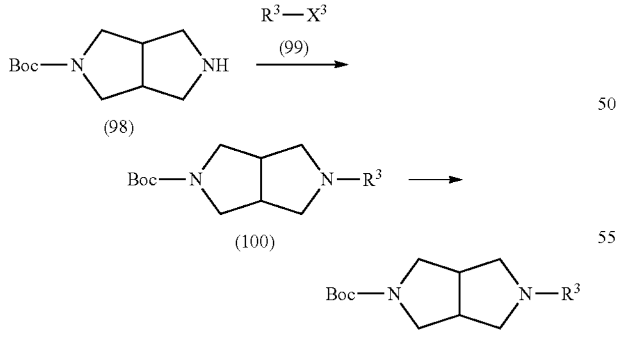

(98) (100) (101)

A compound of the formula (98), a known compound or a compound prepared by known methods, is reacted with a compound of the formula (99), a known compound or a compound prepared by known methods in which $X^3$ is selected from the group consisting of chlorine, bromine, iodine, and methanetrifluorosulfonate, in the presence of a base such as sodium tert-butoxide, lithium tert-butoxide, potassium tert-butoxide, and the like, optionally in the presence of a base such as triethylamine, diisopropylethyl amine, pyridine, 2,6-lutidine, and the like, in the presence of a palladium catalyst such as palladium (II) acetate, tetrakis (triphenylphosphine)palladium(0), dichlorobis (triphenylphosphine)palladium(II), palladium on carbon, bis(acetonitrile)dichloropalladium(II), tris(dibenzylideneacetone) dipalladium(0), and the like, in the presence of a solvent such as toluene, benzene, methylene chloride, 1,2-dichloroethae, tetrahydrofuran, 1,4-dioxane, N,N-dimethylformamide, and the like, optionally with heating, optionally with microwave irradiation, to provide a compound of the formula (100). A compound of the formula (100) is reacted with an acid such as trifluoroacetic acid, formic acid, acetic acid, hydrochloric acid, sulfuric acid, and the like, optionally in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (101).

Scheme 29

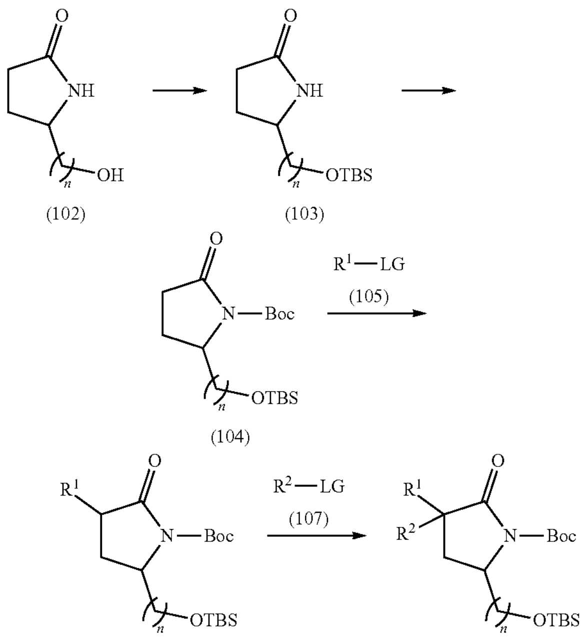

(102) (103) (104) (106) (108)

A compound of the formula (102), a known compound or a compound prepared by known methods, is reacted with tert-butylchlorodimethylsilane in the presence of a base such as imidazole, 4-dimethylaminopyridine, potassium carbonate, sodium carbonate, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (103). A compound of the formula (103) is reacted with di-tert-butyl dicarbonate in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (104). A compound of the formula (104) is reacted with a compound of the formula (105), a known compound or a compound prepared by known methods wherein LG is selected from the group consisting of bromine, chlorine, methansulfonate, and para-tolylsufonate, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (106). A compound of the formula (106) is reacted with a compound of the formula (107), a known compound or a compound prepared by known methods wherein LG is selected from the group consisting of bromine, chlorine, methansulfonate, and para-tolylsufonate, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (108).

Scheme 30

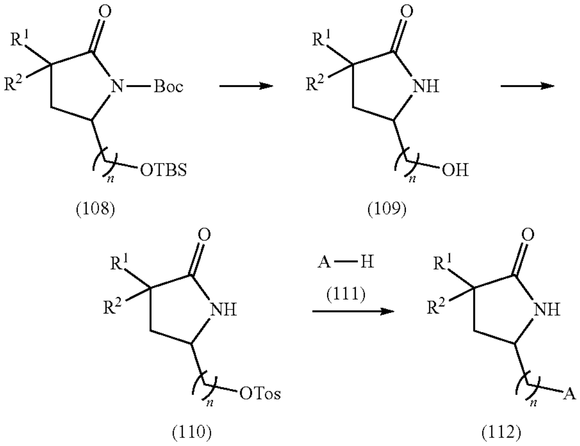

(108) (109) (110) (112)

A compound of the formula (108) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (109). A compound of the formula (109) is reacted with 4-methylbenzenesulfonyl chloride in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (110). A compound of the formula (110) is reacted with a compound of the formula (111), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (112).

Scheme 31

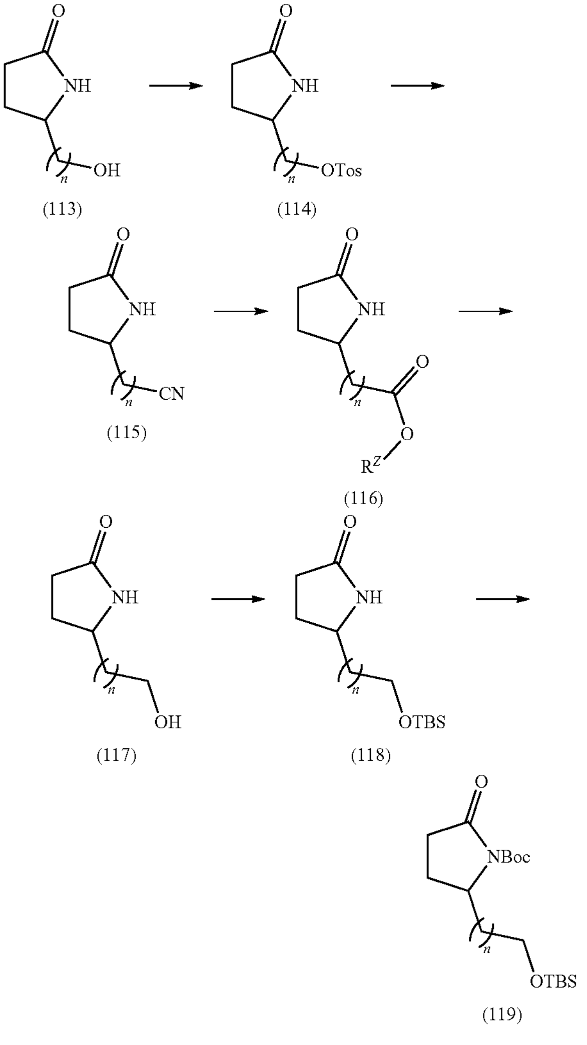

(113) (114) (115) (116) (117) (118) (119)

A compound of the formula (113), a known compound or a compound prepared by known methods, is reacted with 4-methylbenzenesulfonyl chloride in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (114). A compound of the formula (114) is reacted with a source of cyanide such as potassium cyanide, sodium cyanide, lithium cyanide, tetrabutylammonium cyanide, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (115). A compound of the formula (115) is reacted with an acid such as as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (116) where Rz is H. Alternatively, a compound of the formula of the formula (115) can be treated with acid and a suitable alcoholic solvent to provide the compound of the formula (116) that is a carboxylic acid ester (e.g., where Rz is a $C_{1-6}$ alkyl): suitable conditions include using 6M HCl in methanol to provide ester compounds of the formula (116) where Rz is methyl. A compound of the formula (116) is reacted with a reducing agent such as sodium borohydride, sodium triacetoxy borohydride, sodium cyanoborohydride, lithium borohydride, lithium triacetoxy borohydride, lithium cyanoborohydride and the like, in the presence of a solvent such as methylene chloride, 1,2-dichloroethane, methanol, ethanol, isopropanol, tert-butanol, 1,4-dioxane, tetrahydrofuran, 1,2-dimethoxtethane, benzene toluene, N,N-dimethylformamide, N,N-dimethylacetamide, and the like, optionally with heating, optionally with microwave irradiation to provide a compound of the formula (117). A compound of the formula (117) is reacted with tert-butylchlorodimethylsilane in the presence of a base such as imidazole, 4-dimethylaminopyridine, potassium carbonate, sodium carbonate, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (118). A compound of the formula (118) is reacted with di-tert-butyl dicarbonate in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (119).

Scheme 32

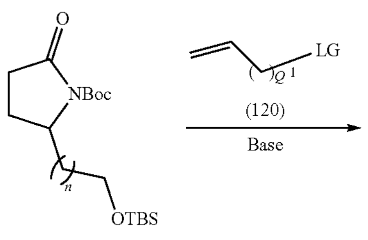

(119)

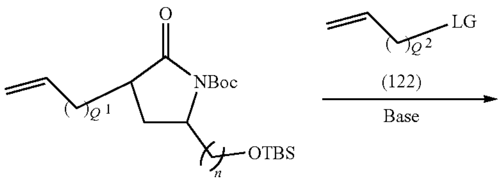

(121)

-continued

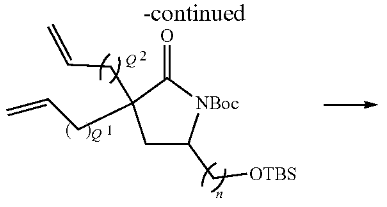

(123)

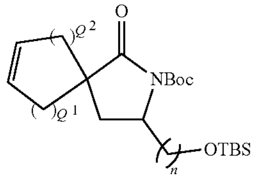

(124)

A compound of the formula (119) is reacted with a compound of the formula (120), a known compound or a compound prepared by known methods wherein LG is selected from the group consisting of bromine, chlorine, methansulfonate, and para-tolylsufonate and wherein $Q^1$ is selected from the group consisting of 1 and 2, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (121). A compound of the formula (121) is reacted with a compound of the formula (122), a known compound or a compound prepared by known methods wherein LG is selected from the group consisting of bromine, chlorine, methansulfonate, and para-tolylsufonate and wherein $Q^2$ is selected from the group consisting of 1 and 2, in the presence of a base such as lithium diisopropylamide, sodium diisopropylamide, potassium diisopropylamide, lithium bis(trimethylsilyl)amide, sodium bis(trimethylsilyl) amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (123). A compound of the formula (123) is reacted with a ruthenium catalyst such as benzylidene-bis(tricyclohexylphosphine)dichlororuthenium, (1,3-Bis(2,4,6-trimethylphenyl)-2-imidazolidinylidene)dichloro(phenylmethylene)(tricyclohexyl phosphine)ruthenium, (1,3-bis-(2,4,6-trimethylphenyl)-2-imidazolidinylidene)dichloro(o-isopropoxy phenylmethylene) ruthenium, dichloro(2-isopropoxyphenylmethylene) (tricyclohexylphosphine) ruthenium(II), [1,3-bis(2-methylphenyl)-2-imidazolidinylidene]dichloro (phenylmethylene) (tricyclohexyl phosphine) ruthenium(II), dichloro[1,3-bis(2,4,6-trimethylphenyl)-2-imidazolidinylidene](benzylidene)bis(3-bromopyridine)ruthenium(II), dichloro[1,3-bis(2,4,6-trimethylphenyl)-2-imidazolidinylidene](3-methyl-2-butenylidene) (tricyclohexylphosphine)ruthenium(II), dichloro[1,3-bis(2-methylphenyl)-2-imidazolidinylidene](2-isopropoxyphenylmethylene) ruthenium(II), [1,3-dimesityl-2-imidazolidinylidene] dichloro[3-(2-pyridinyl)propylidene]ruthenium(II), dichloro [1,3-bis(2,6-isopropylphenyl)-2-imidazolidinylidene](2- isopropoxyphenylmethylene)ruthenium(II), dichloro (tricyclohexylphosphine) [(tricyclohexylphosphoranyl) methylidene]ruthenium tetrafluoroborate, dichloro[1,3-bis (2,4,6-trimethyl phenyl)-2-imidazolidinylidene] [(tricyclohexylphosphoranyl)methylidene]ruthenium(II) tetrafluoroborate, [2-(1-methylethoxy-O)phenylmethyl-C] (nitrato-O,O'){rel-(2R,5R,7R)-adamantane-2,1-diyl[3-(2,4, 6-trimethylphenyl)-1-imidazolidinyl-2-ylidene]}ruthenium, dichloro[1,3-bis(2,6-isopropylphenyl)-2-imidazolidinylidene](benzylidene)(tricyclohexylphosphine)ruthenium (II), [1,3-bis(2-methylphenyl)-2-imidazolidinylidene]dichloro(phenylmethylene)(tricyclohexylphosphine) ruthenium(II), dichloro[1,3-bis(2,4,6-trimethylphenyl)-2-imidazolidinylidene][3-(2-pyridinyl)propylidene]ruthenium (II), and the like in the presence of a solvent such as methylene chloride, 1,2-dichloroethane, tetrahydrofuran, 1,4-dioxane, 1,2-dimethoxyethane, 1,2-diethoxyethane, N,N-dimethylformamide, N,N-dimethylacetamide, dimethylsulfoxide, and the like, optionally with heating, optionally with microwave irradiation to provide a compound of the formula (124).

Scheme 33

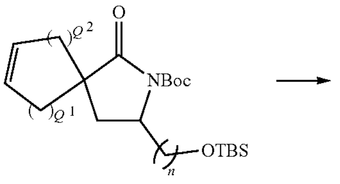

(124)

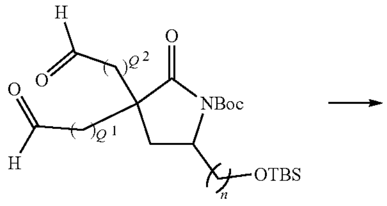

(125)

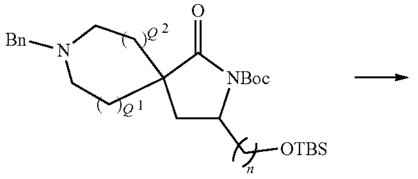

(126)

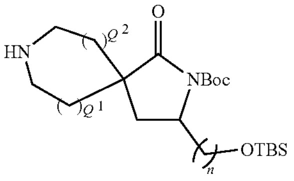

(127)

A compound of the formula (124) is reacted with ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with triphenyl phosphine in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (125). Alternatively, a compound of the formula (124) is reacted with a ozone in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation. The resulting material is then treated with dimethyl sulfide in the presence of a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally with heating optionally with microwave irradiation to provide a compound of the formula (125). Alternatively, a compound of the formula (124) is reacted with ruthenium chloride in the presence of sodium periodate in a solvent such as methylene chloride, 1,2-dichloroethane, tetrahydrofuran, 1,4-dioxane, methanol, ethanol, 1,2-dimethoxyethane, N,N-dimethylformamide, N,N-dimethylacetamide, and the like, optionally in the presence of water, optionally with heating optionally with microwave irradiation to provide a compound of the formula (125). Alternatively, a compound of the formula (124) is reacted with potassium osmate dehydrate in the presence of potassium ferricyanide, optionally in the presence of potassium carbonate, optionally in the presence of a base such as potassium hydroxide, sodium hydroxide, lithium hydroxide, and the like, in the presence of a solvent such as methanol, ethanol, isopropanol, tert-butanol, tetrahydrofuran, 1,4-dioxane, 1,2-dimethoxyethane, acetone, ethyl acetate, benzene toluene, N,N-dimethylformamide, N,N-dimethylacetamide, and the like, optionally in the presence of water, optionally with heating optionally with microwave irradiation to provide a compound of the formula (125). Alternatively, a compound of the formula (124) is reacted with osmium tetraoxide in the presence of sodium periodate, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of a base such as pyridine, 2,6-lutidine, 2,6-di-tert-butylpyridine, and the like, optionally in the presence of water, optionally with heating, optionally with microwave irradiation to provide a compound of the formula (125). Alternatively, a compound of the formula (124) is reacted with osmium tetraoxide in the presence of N-methylmorpholine N-oxide, in the presence of a solvent such as methanol, ethanol, isopropanol, tert-butanol, 1,4-dioxane, tetrahydrofuran, 1,2-dimethoxtethane, acetone, ethyl acetate, benzene toluene, N,N-dimethylformamide, N,N-dimethylacetamide, and the like, optionally in the presence of water, optionally with heating, optionally with microwave irradiation to provide a compound of the formula (125). A compound of the formula (125) is reacted with benzyl amine in the presence of a reducing agent such as sodium borohydride, sodium triacetoxy borohydride, sodium cyanoborohydride, lithium borohydride, lithium triacetoxy borohydride, lithium cyanoborohydride and the like, in the presence of a solvent such as methylene chloride, 1,2-dichloroethane, methanol, ethanol, isopropanol, tert-butanol, 1,4-dioxane, tetrahydrofuran, 1,2-dimethoxtethane, benzene toluene, N,N-dimethylformamide, N,N-dimethylacetamide, and the like, optionally with heating, optionally with microwave irradiation to provide a compound of the formula (126). A compound of the formula (126) is reacted with hydrogen gas in the presence of a palladium catalyst such as palladium on carbon, palladium on barium sulfate, palladium (II) acetate, tetrakis(triphenylphosphine)palladium(0), dichlorobis (triphenylphosphine)palladium(II), palladium on carbon, bis(acetonitrile)dichloropalladium(II), and the like, in an organic solvent such as methanol, ethanol, ethyl acetate, tetrahydrofuran, 1,4-dioxane, dichloromethane, chloroform, 1,2-dichloroethane, N,N-dimethylformamide, and the like, to provide a compound of the formula (127).

Scheme 34

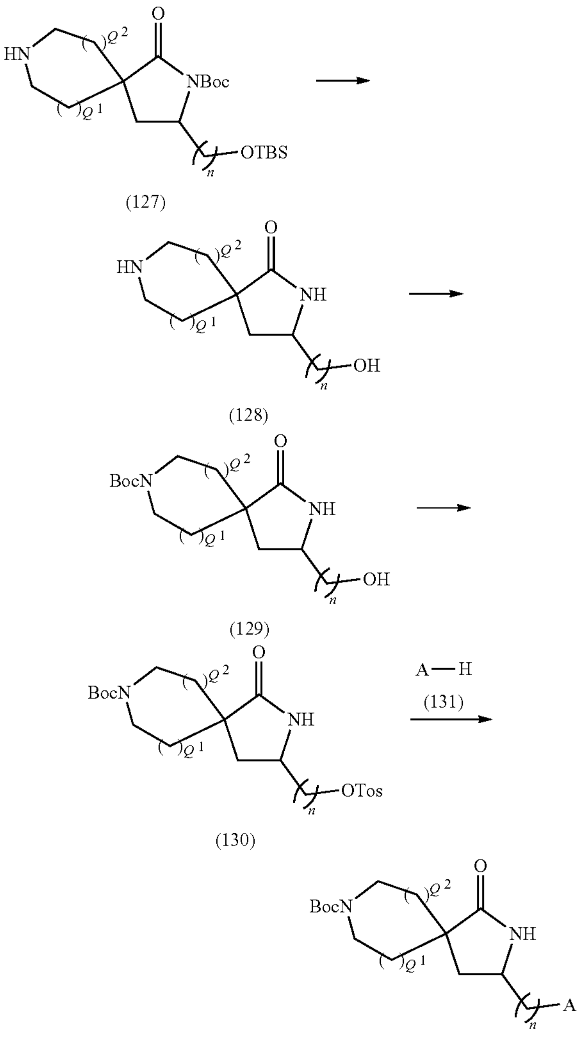

(127)

(128)

(129)

(130)

(132)

A compound of the formula (127) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (128). A compound of the formula (128) is reacted with di-tert-butyl dicarbonate in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (129). A compound of the formula (129) is reacted with 4-methylbenzenesulfonyl chloride in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (130).

Scheme 35

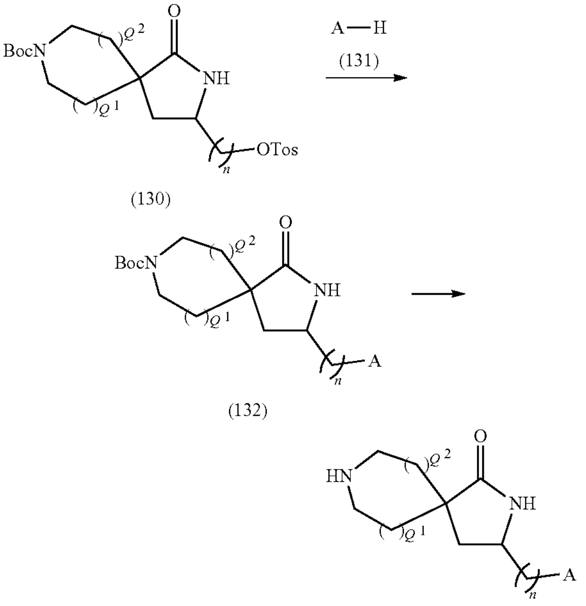

(130)

(132)

(133)

A compound of the formula (130) is reacted with a compound of the formula (131), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (132). A compound of the formula (132) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (133).

Scheme 36

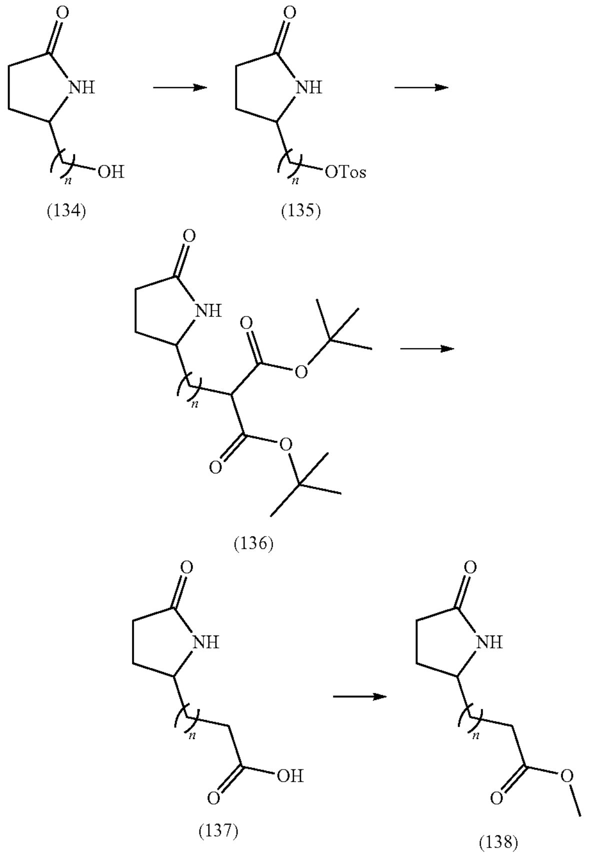

(134) (135) (136) (137) (138)

A compound of the formula (134) wherein n is selected from the group consisting 1 and 2, a known compound or a compound prepared by known methods, is reacted with 4-methylbenzenesulfonyl chloride in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (135). A compound of the formula (135) is reacted with di-tert-butyl malonate in the presence of a base such as potassium tert-butoxide, sodium tert-butoxide, lithium diisopropylamide, sodium diisopropylamide, potassium diisopropylamide, lithium bis(trimethylsilyl) amide, sodium bis(trimethylsilyl)amide, potassium bis (trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (136). A compound of the formula (136) an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (137). A compound of the formula (137) is reacted with methanol in the presence of an acid such as hydrochloric acid, sulfuric acid, and the like in a solvent such as tetrahydrofuran, 1,4-dioxane, methylene chloride, 1,2-dichloroethane, methanol, 1,2-dimethoxyethane, N,N-dimethylformamide, N,N-dimethylacetamide, and the like, optionally with heating, optionally with microwave irradiation to provide a compound of the formula (138). Alternatively, a compound of the formula (137) is reacted with methanol in the presence of a coupling agent such as 1-(3-dimethylaminopropyl)-3-ethylcarbodiimide hydrochloride, N,N'-dicyclohexylcarbodiimide, O-benzotriazole-N,N,N',N'-tetramethyl-uronium-hexafluoro-phosphate, 0-(7-azabenzotriazol-1-yl)-N,N,N',N'-tetramethyluronium hexafluorophosphate, benzotriazole-1-yl-oxy-tris-(dimethylamino)-phosphonium hexafluorophosphate, benzotriazol-1-yl-oxytripyrrolidinophosphonium hexafluorophosphate, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation to provide a compound of the formula (138). Alternatively, a compound of the formula (137) is reacted with (diazomethyl)trimethylsilane in a solvent such as tetrahydrofuran, 1,4-dioxane, methylene chloride, 1,2-dichloroethane, methanol, 1,2-dimethoxyethane, N,N-dimethylformamide, N,N-dimethylacetamide, and the like, optionally with heating, optionally with microwave irradiation to provide a compound of the formula (138).

Scheme 37

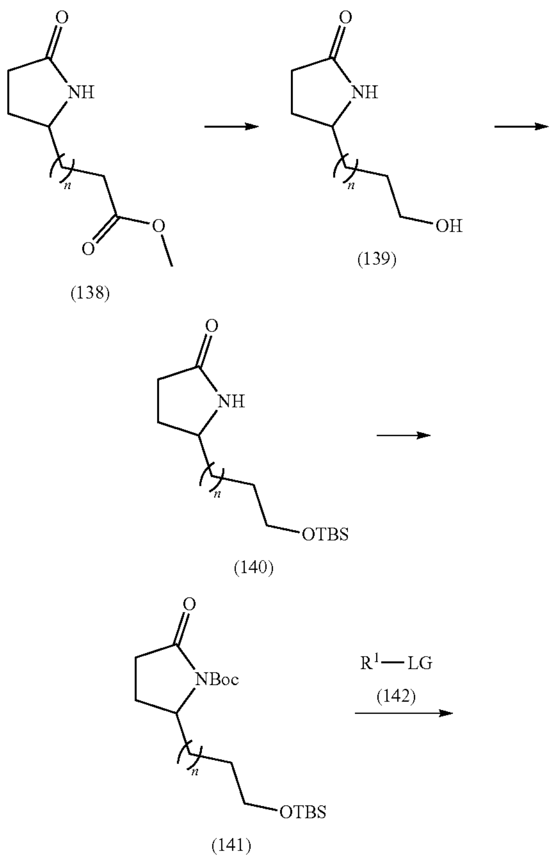

(138) (139) (140) (141)

-continued

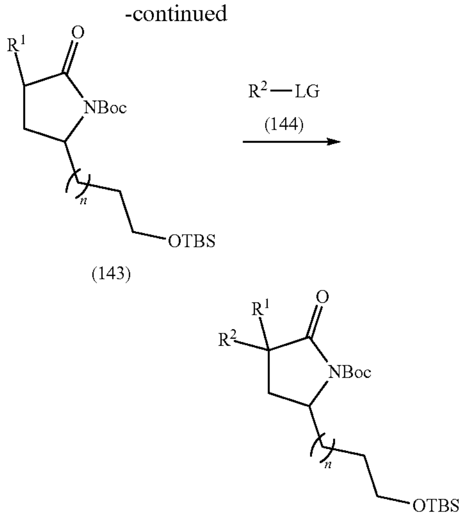

(143)

(145)

A compound of the formula (138) is reacted with a reducing agent such as sodium borohydride, sodium triacetoxy borohydride, sodium cyanoborohydride, lithium borohydride, lithium triacetoxy borohydride, lithium cyanoborohydride and the like, in the presence of a solvent such as methylene chloride, 1,2-dichloroethane, methanol, ethanol, isopropanol, tert-butanol, 1,4-dioxane, tetrahydrofuran, 1,2-dimethoxtethane, benzene toluene, N,N-dimethylformamide, N,N-dimethylacetamide, and the like, optionally with heating, optionally with microwave irradiation to provide a compound of the formula (139). A compound of the formula (139) is reacted with tert-butylchlorodimethylsilane in the presence of a base such as imidazole, 4-dimethylaminopyridine, potassium carbonate, sodium carbonate, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (140). A compound of the formula (140) is reacted with di-tert-butyl dicarbonate in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (141). A compound of the formula (141) is reacted with a compound of the formula (142), a known compound or a compound prepared by known methods wherein LG is selected from the group consisting of bromine, chlorine, methansulfonate, and para-tolylsufonate, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (143). A compound of the formula (143) is reacted with a compound of the formula (144), a known compound or a compound prepared by known methods wherein LG is selected from the group consisting of bromine, chlorine, methansulfonate, and para-tolylsufonate, in the presence of a base such as lithium diisopropylamide, sodium diisopropylamide, potassium diisopropylamide, lithium bis(trimethylsilyl)amide, sodium bis(trimethylsilyl) amide, potassium bis(trimethylsilyl)amide, sodium hydride, potassium hydride, lithium hydride, and the like in a solvent such as tetrahydrofuran, 1,4-dioxane, 1,2-dimethoxyethane, 1,2-diethoxyethane, and the like, optionally with heating, optionally with microwave irradiation to provide a compound of the formula (145).

Scheme 38

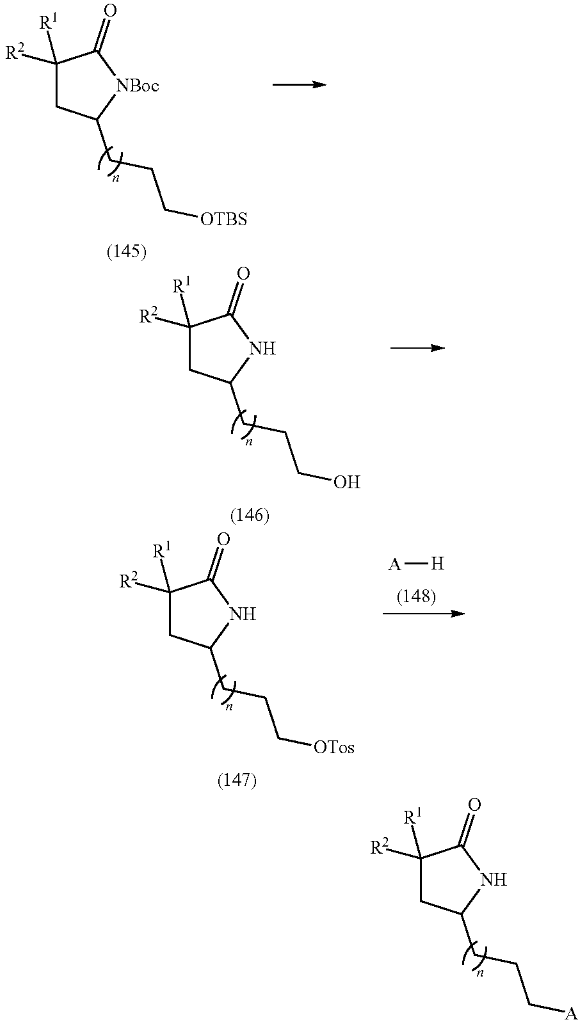

(145)

(146)

(147)

(149)

A compound of the formula (145) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (146). A compound of the formula (146) is reacted with 4-methylbenzenesulfonyl chloride in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (147). A compound of the formula (147) is reacted with a compound of the formula (148), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (149).

Scheme 39

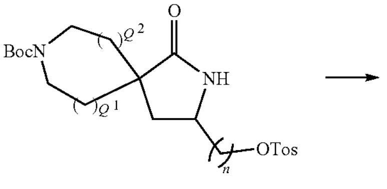

(130)

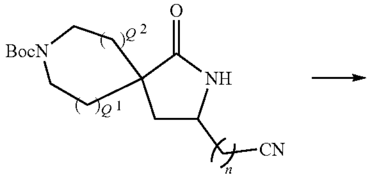

(150)

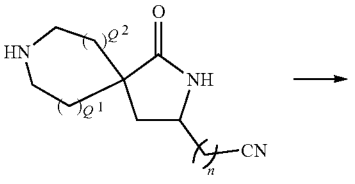

(151)

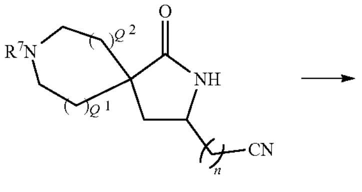

(152)

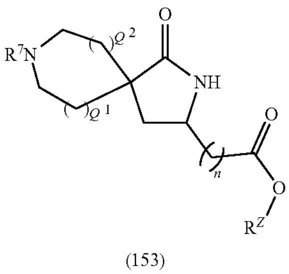

(153)

-continued

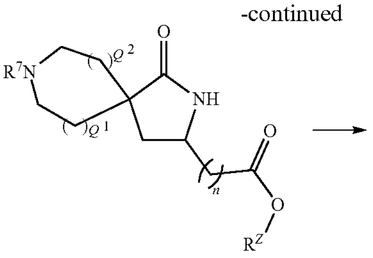

(153)

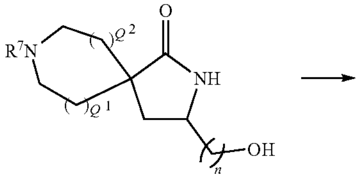

(154)

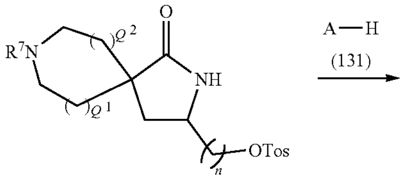

(155)

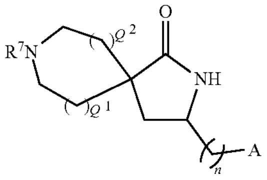

(156)

Intermediate (130) of Scheme 34 can also be used in methods that allow the further homologation of the alkylene linker group. An exemplary method is shown in Scheme 39.

A compound of the formula (130) is reacted with a source of cyanide such as potassium cyanide, sodium cyanide, lithium cyanide, tetrabutylammonium cyanide, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (150).

A compound of the formula (150) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (151).

A group corresponding to $R^7$ as described herein can be introduced according to methods known in the art (e.g., as described in Scheme 13). For example, a compound of the formula (151) can be reacted with a compound of the formula (50), a known compound or a compound prepared by known methods, in the presence of a base such as triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, and the like, optionally with heating, optionally with microwave irradiation to provide a compound of the formula (152), where $R^7$ is $SO_2R^{10c}$. Alternatively, a compound of the formula (151) can be used as a starting material in the exemplary methods of Schemes 14 and 15 to provide respectively a compound of the formula (152), where $R^7$ is $COR^8$ or $CO_2R^9$.

A compound of the formula (152) is reacted with an acid such as trifluoroacetic acid, hydrochloric acid, sulfuric acid, and the like in a solvent such as tetrahydrofuran, 1,4-dioxane, methylene chloride, 1,2-dichloroethane, methanol, ethanol, 1,2-dimethoxyethane, N,N-dimethylformamide, N,N-dimethylacetamide, and the like, optionally with heating, optionally with microwave irradiation to provide a compound of the formula (153) where Rz is H. Alternatively, a compound of the formula of the formula (152) can be treated with acid and a suitable alcoholic solvent to provide the compound of the formula (153) that is a carboxylic acid ester (e.g., where Rz is a $C_{1-6}$ alkyl): suitable conditions include using 6M HCl in methanol to provide ester compounds of the formula (153) where Rz is methyl.

A compound of the formula (153) is reacted with a reducing agent such as sodium borohydride, sodium triacetoxy borohydride, sodium cyanoborohydride, lithium borohydride, lithium triacetoxy borohydride, lithium cyanoborohydride and the like, in the presence of a solvent such as methylene chloride, 1,2-dichloroethane, methanol, ethanol, isopropanol, tert-butanol, 1,4-dioxane, tetrahydrofuran, 1,2-dimethoxtethane, benzene toluene, N,N-dimethylformamide, N,N-dimethylacetamide, and the like, optionally with heating, optionally with microwave irradiation to provide a compound of the formula (154).

A compound of the formula (154) is reacted with 4-methylbenzenesulfonyl chloride in the presence of 4-dimethylaminopyridine, in the presence of a base such as triethylamine, N,N-diisopropylethylamine, pyridine, and the like, in a solvent such as methylene chloride, 1,2-dichloroethane, tetrahydrofuran, 1,4-dioxane, acetonitrile, N,N-dimethylformamide, and the like, optionally with heating, optionally with microwave irradiation to provide a compound of the formula (155).

A compound of the formula (155) is reacted with a compound of the formula (131), a known compound or a compound prepared by known methods, in the presence of a base such as sodium carbonate, potassium carbonate, lithium carbonate, sodium bicarbonate, potassium bicarbonate, lithium bicarbonate, triethylamine, diisopropylethylamine, pyridine, and the like, in a solvent such as methylene chloride, 1,2-dichloroethane, tetrahydrofuran, 1,4-dioxane, 1,2-dimethoxyethane, N,N-dimethylformamide, N,N-dimethylacetamide, acetonitrile, methanol, ethanol, isopropanol, and the like, optionally with heating, optionally with microwave irradiation to provide a compound of the formula (156).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

Examples

The practice of the invention is illustrated by the following non-limiting examples. The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

In the examples that follow, $^1$H-NMR spectra were obtained on a Varian Mercury 300-MHz NMR. Purity (%) and mass spectral data were determined with a Waters Alliance 2695 HPLC/MS (Waters Symmetry C18, 4.6×75 mm, 3.5 μm) with a 2996 diode array detector from 210-400 nm.

Example 1: Compound Synthesis

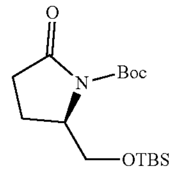 [SMILES: CC(C)(C)OC(=O)N1C(=O)CC[C@@H]1CO[Si](C)(C)C(C)(C)C]

Preparation of tert-butyl (R)-2-(((tert-butyldimethylsilyl)oxy)methyl)-5-oxopyrrolidine-1-carboxylate: To a stirred solution of (R)-(−)-5-(hydroxymethyl)-2-pyrrolidinone (1.0 g, 8.68 mmol, 1.0 equiv) and tert-butyldimethylsilyl chloride (1.44 g, 9.54 mmol, 1.1 equiv.) in dichloromethane (17.3 mL) was added imidazole (0.650 g, 9.54 mmol, 1.1 equiv.). The resulting mixture was then allowed to stirred at 23° C. for 2 hours before being diluted with deionized $H_2O$ (25 mL) and extracted with diethyl ether (3×25 mL). The combined organic layers were dried over $Na_2SO_4$ and concentrated in vacuum to give a crude intermediate which was then dissolved in acetonitrile (43 mL). To the resulting solution was added triethylamine (1.75 g, 17.3 mmol, 2 equiv.), 4-dimethylaminopyridine (0.212 g, 1.73 mmol, 0.2 equiv.) and di-tert-butyl dicarbonate (2.6 g, 16.5 mmol, 1.9 equiv.). The reaction solution was then allowed to stir at 23° C. for 2 hours before being diluted with saturated aqueous $NH_4Cl$ (25 mL) and extracted with ethyl acetate (3×25 mL). The combined organic layers were dried over $Na_2SO_4$ and concentrated in vacuum to give a crude product which was further purified by column chromatography (Ethyl acetate/Hexanes, 20%~30%). $^1$H NMR (400 MHz, $CDCl_3$) δ 4.13 (m, 1H), 3.88 (dd, J=4.0, 10.3 Hz, 1H), 3.65 (dd, J=2.2, 10.3 Hz, 1H), 2.66 (m, 1H), 2.33 (m, 1H), 2.13-1.92 (m, 2H), 1.49 (s, 9H), 0.84 (s, 9H), 0.00 (d, J=5.3 Hz, 6H).

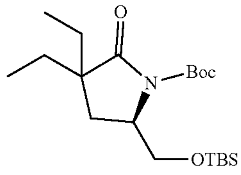 [SMILES: CCC1(CC)C[C@H](CO[Si](C)(C)C(C)(C)C)N(C(=O)OC(C)(C)C)C1=O]

Preparation of tert-butyl (R)-5-(((tert-butyldimethylsilyl)oxy)methyl)-3,3-diethyl-2-oxopyrrolidine-1-carboxylate: To a dry round bottom flask under N2 atmosphere was added tert-butyl (R)-2-(((tert-butyldimethylsilyl)oxy)methyl)-5-oxopyrrolidine-1-carboxylate (2.63 g, 7.98 mmol, 1.0 equiv.) and then dissolved in dry tetrahydrofuran (11.5 mL). The resulting solution was then cooled to −78° C. and 1 M Lithium bis(trimethylsilyl)amide solution (tetrahydrofuran, 16.8 mL, 16.8 mmol, 2.1 equiv.) was added dropwise. The resulting solution was allowed to gradually warm to −20° C.

before being cooled back to −78° C. and followed by dropwise addition of iodoethane (3.12 g, 20 mmol, 2.5 equiv.). The reaction solution was then allowed to gradually warm to 0° C. and stir at that temperature for 2 hours before being warmed to 23° C. and allowed to stir for an additional 2 hours. The resulting solution was diluted with saturated aq. $NH_4Cl$ (25 mL) and extracted with ethyl acetate (3×25 mL). The combined organic layers were dried over $Na_2SO_4$ and concentrated in vacuum to give a crude product which was further purified by column chromatography (Ethyl acetate/Hexanes, 0%~10%). $^1H$ NMR (400 MHz, $CDCl_3$) δ 3.94 (m, 1H), 3.83 (dd, J=5.2, 10.0 Hz, 1H), 3.67 (dd, J=2.5, 10.0 Hz, 1H), 1.95 (dd, J=6.3, 13.4 Hz, 1H), 1.79 (dd, J=9.0, 13.4 Hz, 1H), 1.65-1.40 (m, 13H), 0.90-0.75 (m, 15H), 0.00 (d, J=3.3 Hz, 6H).

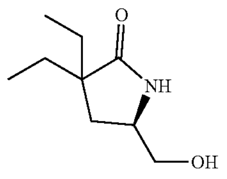

Preparation of (R)-3,3-diethyl-5-(hydroxymethyl)pyrrolidin-2-one: A 6M HCl in methanol solution was prepared via the addition of acetyl chloride (4.8 mL) to methanol (12 mL). To a small round bottom flask was added tert-butyl (R)-5-(((tert-butyldimethylsilyl)oxy)methyl)-3,3-diethyl-2-oxopyrrolidine-1-carboxylate (0.875 g, 2.65 mmol, 1.0 equiv.) and 1 mL of methanol. The prepared methanolic HCl solution was then added dropwise (12 mL) and the resulting mixture was allowed to stir at 23° C. for 30 min before being diluted with methanol and concentrated in vacuum to produce a crude product that was used in the next step without further purification. $^1H$ NMR (400 MHz, $CDCl_3$) δ 7.61 (b, 1H), 4.96 (b, 1H), 3.69-3.48 (m, 2H), 3.33 (dd, J=8.1, 11.2 Hz, 1H), 1.84 (dd, J=7.8, 13.3 Hz, 1H), 1.58-1.31 (m, 5H), 0.80 (dt, J=7.5, 21.9 Hz, 6H).

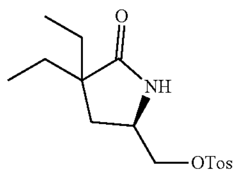

Preparation of (R)-(4,4-diethyl-5-oxopyrrolidin-2-yl) methyl 4-methylbenzenesulfonate: To a stirred solution of (R)-3,3-diethyl-5-(hydroxymethyl)pyrrolidin-2-one (0.367 g, 2.14 mmol, 1.0 equiv) and triethylamine (0.240 g, 2.36 mmol, 1.1 equiv) in dichloromethane (3.3 mL), 4-methylbenzenesulfonyl chloride (0.450 g, 2.36 mmol, 1.1 equiv) and 4-dimethylaminopyridine (0.053 g, 0.428 mmol, 0.2 equiv.) were subsequently added at 0° C. The resulting mixture was stirred at 0° C. for 10 minutes and allowed to stir overnight at 23° C. Then, the reaction mixture was diluted with dichloromethane (25 mL), washed with TN HCl (1×5 mL) and deionized $H_2O$ (2×5 mL), dried over $Na_2SO_4$ and concentrated in vacuum to give a crude product which was further purified by column chromatography (Ethyl acetate/Hexanes, 0%~100%). $^1H$ NMR (400 MHz, $CDCl_3$) δ 7.71 (d, J=8.3 Hz, 2H), 7.28 (d, J=8.1 Hz, 2H), 6.57 (b, 1H), 3.96 (dd, J=4.0, 9.6 Hz, 1H), 3.82-3.67 (m, 2H), 2.37 (s, 3H), 1.90 (dd, J=7.9, 13.5 Hz, 1H), 1.52 (dd, J=7.1, 13.6 Hz, 1H) 1.49-1.31 (m, 4H), 0.75 (dt, J=7.4, 26.5 Hz, 6H).

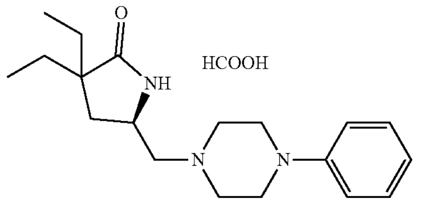 [SMILES: CCC1(CC)C[C@H](CN2CCN(c3ccccc3)CC2)NC1=O ; "HCOOH"]

Preparation of (R)-3,3-diethyl-5-((4-phenylpiperazin-1-yl)methyl)pyrrolidin-2-one formate: To a small vial was added (R)-(4,4-diethyl-5-oxopyrrolidin-2-yl)methyl 4-methylbenzenesulfonate (75 mg, 0.23 mmol, 1 equiv.) and 1-phenylpiperazine (79 mg, 0.48 mmol, 2.1 equiv.) then both were dissolved in acetonitrile (2.3 mL). Then $K_2CO_3$ (80 mg, 0.57 mmol, 2.5 equiv.) was added, the reaction mixture was allowed to stir at 80° C. for 3 days, and then cooled to 23° C. The mixture was filtered, washed with acetonitrile, and the filtrate was concentrated in vacuum to give a crude product which was further purified by HPLC ($CH_3CN/H_2O$, 0.1% Formic acid), 0%~100%). $^1H$ NMR (400 MHz, $CDCl_3$) δ 7.19 (m, 2H), 6.85 (d, J=8.3 Hz, 2H), 6.79 (t, J=7.0 Hz, 1H), 6.42 (b, 1H), 3.70 (m, 1H), 3.12 (m, 4H), 2.70 (m, 2H), 2.50 (m, 2H), 2.41 (dd, J=3.6, 12.4 Hz, 1H), 2.29 (dd, J=9.8, 12.4 Hz, 1H), 1.93 (dd, J=7.6, 13.5 Hz, 1H), 1.57-1.37 (m, 5H), 0.84 (dt, J=7.4, 19.6 Hz, 6H). LC/MS [M+H]=m/z 316.2.

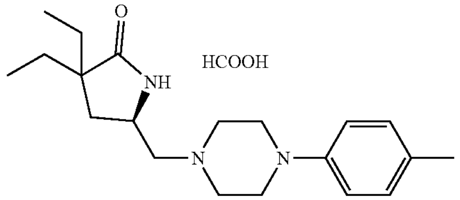 [SMILES: CCC1(CC)C[C@H](CN2CCN(c3ccc(C)cc3)CC2)NC1=O ; "HCOOH"]

Preparation of (R)-3,3-diethyl-5-((4-(p-tolyl)piperazin-1-yl)methyl)pyrrolidin-2-one formate: The title compound was prepared according to the procedure for (R)-3,3-diethyl-5-((4-phenylpiperazin-1-yl)methyl)pyrrolidin-2-one formate, except 1-(4-methylphenyl)piperazine was substituted for 1-phenylpiperazine. $^1H$ NMR (400 MHz, $CDCl_3$) δ 7.09 (d, J=8.2 Hz, 2H), 6.85 (d, J=8.5 Hz, 2H), 6.47 (b, 1H), 3.78 (m, 1H), 3.15 (m, 4H), 2.78 (m, 2H), 2.59 (m, 2H), 2.49 (dd, J=3.6, 12.4 Hz, 1H), 2.38 (dd, J=9.9, 12.4 Hz, 1H), 2.28 (s, 3H), 2.01 (dd, J=7.6, 13.1 Hz, 1H), 1.67-1.45 (m, 5H), 0.93 (dt, J=7.4, 19.6 Hz, 6H). LC/MS [M+H]=m/z 330.2.

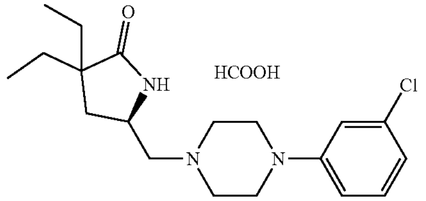 [SMILES: CCC1(CC)C[C@H](CN2CCN(c3cccc(Cl)c3)CC2)NC1=O ; "HCOOH"]

Preparation of (R)-5-((4-(3-chlorophenyl)piperazin-1-yl)methyl)-3,3-diethylpyrrolidin-2-one: The title compound was prepared according to the procedure for (R)-3,3-diethyl- 5-((4-phenylpiperazin-1-yl)methyl)pyrrolidin-2-one formate, except 1-(3-chlorophenyl)piperazine hydrochloride was substituted for 1-phenylpiperazine and 5 equiv. of $K_2CO_3$ used instead of 2.5 equiv. $^1$H NMR (400 MHz, $CDCl_3$) δ 7.09 (t, J=8.1 Hz, 1H), 6.79 (t, J=2.0 Hz, 1H), 6.74 (dd, J=1.8, 7.7 Hz, 1H), 6.70 (dd, J=2.3, 8.3 Hz, 1H), 6.36 (b, 1H), 3.69 (m, 1H), 3.11 (m, 4H), 2.67 (m, 2H), 2.47 (m, 2H), 2.39 (dd, J=3.5, 12.3 Hz, 1H), 2.28 (dd, J=10.0, 12.4 Hz, 1H), 1.92 (dd, J=7.8, 13.2 Hz, 1H), 1.58-1.38 (m, 5H), 0.84 (dt, J=7.5, 20.2 Hz, 6H). LC/MS [M+H]=m/z 350.2.

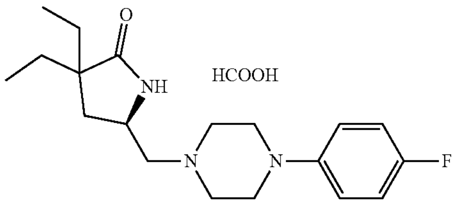 [SMILES: CCC1(CC)C[C@H](CN2CCN(c3ccc(F)cc3)CC2)NC1=O ; "HCOOH"]

Preparation of (R)-3,3-diethyl-5-((4-(4-fluorophenyl)piperazin-1-yl)methyl)pyrrolidin-2-one formate: The title compound was prepared according to the procedure for (R)-3,3-diethyl-5-((4-phenylpiperazin-1-yl)methyl)pyrrolidin-2-one formate, except 1-(4-fluorophenyl)piperazine was substituted for 1-phenylpiperazine. $^1$H NMR (400 MHz, $CDCl_3$) δ 6.97 (m, 2H), 6.92-6.77 (m, 3H), 3.81 (m, 1H), 3.15 (m, 4H), 2.82 (m, 2H), 2.65 (m, 2H), 2.53 (dd, J=3.5, 12.4 Hz, 1H), 2.44 (dd, J=9.6, 12.4 Hz, 1H), 2.03 (dd, J=7.6, 13.3 Hz, 1H), 1.68-1.44 (m, 5H), 0.92 (dt, J=7.5, 18.9 Hz, 6H). LC/MS [M+H]=m/z 334.2.

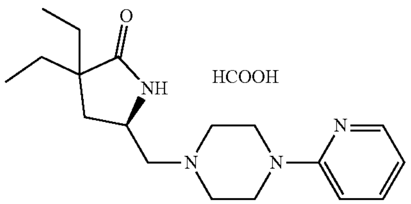 [SMILES: CCC1(CC)C[C@H](CN2CCN(c3ccccn3)CC2)NC1=O ; "HCOOH"]

Preparation of (R)-3,3-diethyl-5-((4-(pyridin-2-yl)piperazin-1-yl)methyl)pyrrolidin-2-one formate: The title compound was prepared according to the procedure for (R)-3,3-diethyl-5-((4-phenylpiperazin-1-yl)methyl)pyrrolidin-2-one formate, except 1-(2-pyridyl)piperazine was substituted for 1-phenylpiperazine. $^1$H NMR (400 MHz, $CDCl_3$) δ 8.19 (m, 1H), 7.50 (m, 1H), 6.86 (b, 1H) 6.65 (m, 2H), 3.81 (m, 1H), 3.57 (m, 4H), 2.77 (m, 2H), 2.59 (m, 2H), 2.51 (dd, J=3.8, 12.6 Hz, 1H), 2.43 (dd, J=9.4, 12.5 Hz, 1H), 2.02 (dd, J=7.7, 13.2 Hz, 1H), 1.66-1.44 (m, 5H), 0.90 (dt, J=7.4, 20.0 Hz, 6H). LC/MS [M+H]=m/z 317.2.

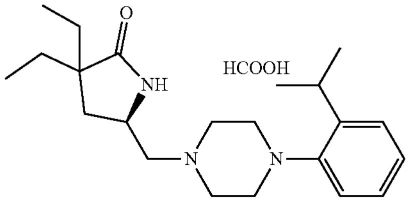 [SMILES: CCC1(CC)C[C@H](CN2CCN(c3ccccc3C(C)C)CC2)NC1=O ; "HCOOH"]

Preparation of (R)-3,3-diethyl-5-((4-(2-isopropylphenyl)piperazin-1-yl)methyl)pyrrolidin-2-one formate: The title compound was prepared according to the procedure for (R)-3,3-diethyl-5-((4-phenylpiperazin-1-yl)methyl)pyrrolidin-2-one formate, except 1-(2-isopropylphenyl)piperazine was substituted for 1-phenylpiperazine. $^1$H NMR (400 MHz, $CDCl_3$) δ 7.18 (m, 1H), 7.12-6.99 (m, 3H), 6.34 (b, 1H), 3.71 (m, 1H), 3.40 (sept, J=6.8 Hz, 1H), 2.83 (m, 4H), 2.71 (b, 2H), 2.60-2.39 (b, 3H), 2.32 (m, 1H), 1.94 (dd, J=7.5, 13.2 Hz, 1H), 1.60-1.36 (m, 5H), 1.12 (d, J=6.9 Hz, 6H), 0.84 (dt, J=7.4, 18.3 Hz, 6H). LC/MS [M+H]=m/z 358.2.

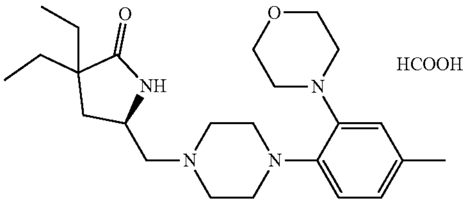 [SMILES: CCC1(CC)C[C@H](CN2CCN(c3ccc(C)cc3N3CCOCC3)CC2)NC1=O ; "HCOOH"]

Preparation of (R)-3,3-diethyl-5-((4-(4-methyl-2-morpholinophenyl)piperazin-1-yl)methyl)pyrrolidin-2-one formate: The title compound was prepared according to the procedure for (R)-3,3-diethyl-5-((4-phenylpiperazin-1-yl)methyl)pyrrolidin-2-one formate, except 1-(4-methyl-2-morpholinophenyl)piperazine was substituted for 1-phenylpiperazine. $^1$H NMR (400 MHz, $CDCl_3$) δ 6.73 (m, 2H), 6.63 (b, 1H), 6.45 (b, 1H) 3.82-3.64 (m, 5H), 3.31-2.84 (b, 8H), 2.68 (b, 2H), 2.57-2.38 (b, 3H), 2.32 (m, 1H), 2.21 (s, 3H), 1.94 (dd, J=7.4, 13.0 Hz, 1H), 1.59-1.38 (m, 5H), 0.84 (dt, J=7.4, 18.8 Hz, 6H). LC/MS [M+H]=m/z 415.2.

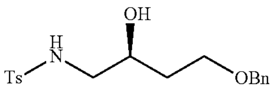 [SMILES: Cc1ccc(S(=O)(=O)NC[C@@H](O)CCOCc2ccccc2)cc1]

Preparation of (S)-N-(4-(benzyloxy)-2-hydroxybutyl)-4-methylbenzenesulfonamide: To a stirred solution of (S)-2-(2-(benzyloxy)ethyl)oxirane (0.5 g, 2.8 mmo, 1.0 equiv.) in 1,4-dioxane (11.25 mL) was added p-toluenesulfonamide (0.96 g, 5.6 mmol, 2.0 equiv.), benzyltriethylammonium chloride (0.064 g, 0.28 mmol, 0.1 equiv.) and $Cs_2CO_3$ (0.092 g, 0.28 mmol, 0.1 equiv.). The resulting mixture was then stirred at 90° C. for 48 hours. The reaction was then allowed to cool to 23° C. and concentrated in vacuum to give a crude product which was further purified by HPLC ($CH_3CN/H_2O$, 0.1% Formic acid), 0%~100%). Desired fractions were further purified by column chromatography (Ethyl acetate/Hexanes, 10%~100%). $^1$H NMR (400 MHz, $CDCl_3$) δ 7.73 (d, J=8.2 Hz, 2H), 7.44-7.22 (m, 7H), 5.00 (t, J=6.2 Hz, 1H), 4.50 (s, 2H), 3.93 (m, 1H), 3.66 (m, 2H), 3.07 (m, 1H), 2.87 (m, 1H), 2.43 (s, 3H), 1.83 (m, 1H), 1.70 (m, 1H).

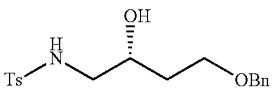

Preparation of (R)-N-(4-(benzyloxy)-2-hydroxybutyl)-4-methylbenzenesulfonamide: The title compound was prepared according to the procedure for (S)-N-(4-(benzyloxy)-2-hydroxybutyl)-4-methylbenzenesulfonamide, except (R)-2-(2-(benzyloxy)ethyl)oxirane was substituted for (S)-2-(2-(benzyloxy)ethyl)oxirane. $^1$H NMR (400 MHz, $CDCl_3$) δ

7.64 (d, J=8.2 Hz, 2H), 7.31-7.16 (m, 7H), 4.90 (t, J=6.1 Hz, 1H), 4.41 (s, 2H), 3.84 (m, 1H), 3.57 (m, 2H), 2.98 (m, 1H), 2.78 (m, 1H), 2.34 (s, 3H), 1.74 (m, 1H), 1.60 (m, 1H).

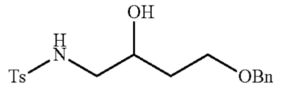 [SMILES: Cc1ccc(S(=O)(=O)NCC(O)CCOCc2ccccc2)cc1]

Preparation of N-(4-(benzyloxy)-2-hydroxybutyl)-4-methylbenzenesulfonamide: The title compound was prepared according to the procedure for (S)-N-(4-(benzyloxy)-2-hydroxybutyl)-4-methylbenzenesulfonamide, except (rac)-2-(2-(benzyloxy)ethyl)oxirane was substituted for (S)-2-(2-(benzyloxy)ethyl)oxirane. $^1$H NMR (400 MHz, $CDCl_3$) δ 7.66 (d, J=8.2 Hz, 2H), 7.35-7.18 (m, 7H), 4.92 (t, J=6.1 Hz, 1H), 4.43 (s, 2H), 3.89 (m, 1H), 3.60 (m, 2H), 3.02 (m, 1H), 2.80 (m, 1H), 2.38 (s, 3H), 1.77 (m, 1H), 1.63 (m, 1H).

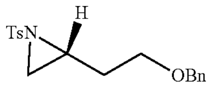 [SMILES: Cc1ccc(S(=O)(=O)N2C[C@H]2CCOCc2ccccc2)cc1]

Preparation of (R)-2-(2-(benzyloxy)ethyl)-1-tosylaziridine: This reaction was performed in oven-dried glassware under a nitrogen atmosphere. To a stirred solution of pyridine (1.57 g, 19.9 mmol, 5.0 equiv.) and methanesulfonyl chloride (2.28 g, 19.9 mmol, 5.0 equiv.) in dry dichloromethane (22.5 mL) at 0° C. was added a solution of (S)-N-(4-(benzyloxy)-2-hydroxybutyl)-4-methylbenzenesulfonamide (1.4 g, 3.99 mmol, 1.0 equiv.) in dry dichloromethane (22.5 mL). The resulting solution was stirred at reflux overnight, cooled to 23° C., and washed with brine (50 mL). The organic layer was dried over $Na_2SO_4$ and concentrated in vacuo to give crude mesylate which was further purified by column chromatography (Ethyl acetate/Hexanes, 10%~50%).

The purified mesylate was then dissolved in acetonitrile (45 mL) and $K_2CO_3$ (2.22 g, 16.0 mmol, 4.0 equiv.) was added. The resulting mixture was allowed to stir at 45° C. overnight before being cooled to 23° C. and filtered. The filtrate was concentrated in vacuo to give crude product which was purified by column chromatography (Ethyl acetate/Hexanes, 10% 20%). $^1$H NMR (400 MHz, $CDCl_3$) δ 7.84 (d, J=8.2 Hz, 2H), 7.45-7.19 (m, 7H), 4.39 (s, 2H), 3.46 (dt, J=3.7, 9.2 Hz, 1H), 3.35 (m, 1H), 2.93 (m, 1H), 2.70 (d, J=7.1 Hz, 1H), 2.45 (s, 3H), 2.15 (d, J=4.6 Hz, 1H), 1.94 (m, 1H), 1.58 (m, 1H).

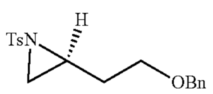 [SMILES: Cc1ccc(S(=O)(=O)N2C[C@@H]2CCOCc2ccccc2)cc1]

Preparation of (S)-2-(2-(benzyloxy)ethyl)-1-tosylaziridine: The title compound was prepared according to the procedure for (R)-2-(2-(benzyloxy)ethyl)-1-tosylaziridine, except (R)-N-(4-(benzyloxy)-2-hydroxybutyl)-4-methylbenzenesulfonamide was substituted for (S)-N-(4-(benzyloxy)-2-hydroxybutyl)-4-methylbenzenesulfonamide. $^1$H NMR (400 MHz, $CDCl_3$) δ 7.84 (d, J=8.3 Hz, 2H), 7.43-7.23 (m, 7H), 4.39 (s, 2H), 3.46 (dt, J=3.8, 9.3 Hz, 1H), 3.35 (m, 1H), 2.93 (m, 1H), 2.69 (d, J=7.0 Hz, 1H), 2.45 (s, 3H), 2.15 (d, J=4.5 Hz, 1H), 1.94 (m, 1H), 1.59 (m, 1H).

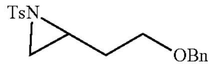 [SMILES: Cc1ccc(S(=O)(=O)N2CC2CCOCc2ccccc2)cc1]

Preparation of 2-(2-(benzyloxy)ethyl)-1-tosylaziridine: The title compound was prepared according to the procedure for (R)-2-(2-(benzyloxy)ethyl)-1-tosylaziridine, except (rac)-N-(4-(benzyloxy)-2-hydroxybutyl)-4-methylbenzenesulfonamide was substituted for (S)-N-(4-(benzyloxy)-2-hydroxybutyl)-4-methylbenzenesulfonamide. $^1$H NMR (400 MHz, $CDCl_3$) δ 7.84 (d, J=8.3 Hz, 2H), 7.41-7.26 (m, 7H), 4.39 (s, 2H), 3.46 (dt, J=3.8, 9.3 Hz, 1H), 3.35 (m, 1H), 2.93 (m, 1H), 2.69 (d, J=7.0 Hz, 1H), 2.45 (s, 3H), 2.15 (d, J=4.6 Hz, 1H), 1.93 (m, 1H), 1.59 (m, 1H).

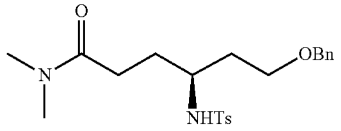

Preparation of (S)-6-(benzyloxy)-N,N-dimethyl-4-((4-methylphenyl)sulfonamido) hexanamide: This reaction was performed in oven-dried glassware under a nitrogen atmosphere. To a cooled solution of dry N, N-dimethylacetamide (0.527 g, 6.05 mmol, 1.1 equiv.) and dry tetrahydrofuran (18 mL) at −78° C. was added dropwise a 1M Lithium diisopropylamide solution (tetrahydrofuran/Hexanes, 7.26 mL, 7.26 mmol, 1.3 equiv.). The resulting solution was then stirred at −78° C. for 30 minutes before being allowed to warm to 0° C. At 0° C., a solution of (R)-2-(2-(benzyloxy)ethyl)-1-tosylaziridine (1.82 g, 5.5 mmol, 1.0 equiv.) in dry tetrahydrofuran (18 mL) was added to the solution. The reaction was stirred at 0° C. for 20 minutes and then allowed to warm to 23° C. and stir overnight. The reaction was quenched with sat. $NH_4Cl$ (40 mL) and extracted with ethyl acetate (3×30 mL). The combined organic layers were dried over $Na_2SO_4$ and concentrated in vacuum to give a crude product which was further purified by column chromatography (Ethyl acetate/Hexanes, 40%~100%). $^1$H NMR (400 MHz, $CDCl_3$) δ 7.72 (d, J=8.2 Hz, 2H), 7.41-7.19 (m, 7H), 5.91 (d, J=7.5 Hz, 1H), 4.40 (q, J=9.3 Hz, 2H), 3.56 (m, 1H), 3.40 (m, 2H), 2.93 (s, 3H), 2.90 (s, 3H), 2.48-2.35 (m, 4H), 2.21 (dt, J=6.6, 16.6 Hz, 1H), 1.88-1.69 (m, 2H), 1.68-1.55 (n, 2H).

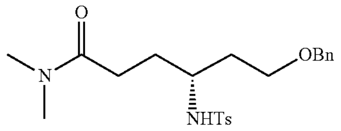

Preparation of (R)-6-(benzyloxy)-N,N-dimethyl-4-((4-methylphenyl)sulfonamido) hexanamide: The title compound was prepared according to the procedure for (S)-6-(benzyloxy)-N,N-dimethyl-4-((4-methylphenyl) sulfonamido)hexanamide, except (S)-2-(2-(benzyloxy) ethyl)-1-tosylaziridine was substituted for (R)-2-(2-(benzyloxy)ethyl)-1-tosylaziridine. $^1$H NMR (400 MHz, $CDCl_3$) δ 7.71 (d, J=8.2 Hz, 2H), 7.41-7.18 (m, 7H), 5.91 (d, J=7.5 Hz, 1H), 4.40 (q, J=8.9 Hz, 2H), 3.54 (m, 1H), 3.40 (m, 2H), 2.94 (s, 3H), 2.91 (s, 3H), 2.47-2.35 (m, 4H), 2.21 (dt, J=6.6, 16.6 Hz, 1H), 1.87-1.68 (m, 2H), 1.67-1.52 (m, 2H).

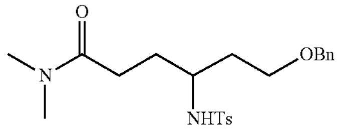

Preparation of 6-(benzyloxy)-N,N-dimethyl-4-((4-methylphenyl)sulfonamido) hexanamide: The title compound was prepared according to the procedure for (S)-6-(benzyloxy)-N,N-dimethyl-4-((4-methylphenyl)sulfonamido) hexanamide, except (rac)-2-(2-(benzyloxy)ethyl)-1-tosylaziridine was substituted for (R)-2-(2-(benzyloxy)ethyl)-1-tosylaziridine. $^1$H NMR (400 MHz, $CDCl_3$) δ 7.72 (d, J=8.2 Hz, 2H), 7.42-7.21 (m, 7H), 5.90 (d, J=7.5 Hz, 1H), 4.41 (q, J=9.3 Hz, 2H), 3.57 (m, 1H), 3.40 (m, 2H), 2.95 (s, 3H), 2.93 (s, 3H), 2.50-2.36 (m, 4H), 2.23 (dt, J=6.6, 16.6 Hz, 1H), 1.88-1.70 (m, 2H), 1.69-1.57 (m, 2H).

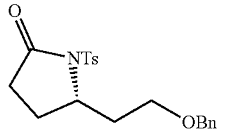 [SMILES: Cc1ccc(S(=O)(=O)N2C(=O)CC[C@H]2CCOCc2ccccc2)cc1]

Preparation of (S)-5-(2-(benzyloxy)ethyl)-1-tosylpyrrolidin-2-one: (S)-6-(benzyloxy)-N,N-dimethyl-4-((4-methylphenyl)sulfonamido)hexanamide (0.565 g, 1.35 mmol, 1.0 equiv.) was mixed with p-toluenesulfonic acid monohydrate (0.282 g, 1.48 mmol, 1.1 equiv.) and toluene (5.65 mL) in a microwave vial. The mixture was then heated in a microwave reactor at 190° C. for 2 hours. The mixture was then neutralized with sat. $NaHCO_3$ and extracted with ethyl acetate (3×15 mL). The combined organic phase was dried over $Na_2SO_4$ and concentrated in vacuum to give a crude product which was further purified by column chromatography (Ethyl acetate/Hexanes, 0%~40%). $^1$H NMR (400 MHz, $CDCl_3$) δ 7.96 (d, J=8.2 Hz, 2H), 7.42-7.26 (m, 7H), 4.59-4.42 (m, 3H), 3.65-3.54 (m, 2H), 2.62-2.50 (m, 1H), 2.45 (s, 3H), 2.42-2.27 (m, 2H), 2.25-2.12 (m, 1H), 2.11-1.89 (m, 2H).

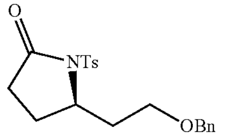 [SMILES: Cc1ccc(S(=O)(=O)N2C(=O)CC[C@@H]2CCOCc2ccccc2)cc1]

Preparation of (R)-5-(2-(benzyloxy)ethyl)-1-tosylpyrrolidin-2-one: The title compound was prepared according to the procedure for (S)-5-(2-(benzyloxy)ethyl)-1-tosylpyrrolidin-2-one, except (R)-6-(benzyloxy)-N,N-dimethyl-4-((4-methylphenyl)sulfonamido)hexanamide was substituted for (S)-6-(benzyloxy)-N,N-dimethyl-4-((4-methylphenyl)sulfonamido)hexanamide. $^1$H NMR (400 MHz, $CDCl_3$) δ 7.95 (d, J=8.4 Hz, 2H), 7.39-7.25 (m, 7H), 4.59-4.42 (m, 3H), 3.67-3.53 (m, 2H), 2.61-2.47 (m, 1H), 2.42 (s, 3H), 2.40-2.23 (m, 2H), 2.22-2.09 (m, 1H), 2.07-1.89 (m, 2H).

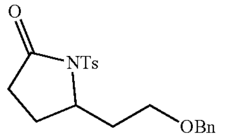 [SMILES: Cc1ccc(S(=O)(=O)N2C(=O)CCC2CCOCc2ccccc2)cc1]

Preparation of 5-(2-(benzyloxy)ethyl)-1-tosylpyrrolidin-2-one: The title compound was prepared according to the procedure for (S)-5-(2-(benzyloxy)ethyl)-1-tosylpyrrolidin-2-one, except (rac)-6-(benzyloxy)-N,N-dimethyl-4-((4-methylphenyl)sulfonamido)hexanamide was substituted for (S)-6-(benzyloxy)-N,N-dimethyl-4-((4-methylphenyl)sulfonamido)hexanamide. $^1$H NMR (400 MHz, $CDCl_3$) δ 7.96 (d, J=8.3 Hz, 2H), 7.41-7.25 (m, 7H), 4.60-4.42 (m, 3H), 3.64-3.54 (m, 2H), 2.62-2.49 (m, 1H), 2.44 (s, 3H), 2.42-2.26 (m, 2H), 2.24-2.11 (m, 1H), 2.10-1.88 (m, 2H).

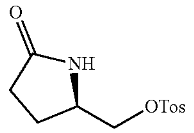

Preparation of (R)-(5-oxopyrrolidin-2-yl)methyl 4-methylbenzenesulfonate: To a cooled mixture of (R)-(−)-5-(hydroxymethyl)-2-pyrrolidinone (10.0 g, 87 mmol, 1.0 equiv.) and triethylamine (9.68 g, 95.7 mmol, 1.1 equiv.) in methylene chloride (134 mL) at 0° C. was added 4-toluenesulfonyl chloride (18.25 g, 95.7 mmol, 1.1 equiv.) followed by 4-dimethylaminopyridine (2.12 g, 17.3 mmol, 0.2 equiv.). The resulting reaction mixture was stirred at 0° C. for 5 minutes before being warmed to 23° C. and allowed to stir overnight. Then, the reaction mixture was diluted with dichloromethane (200 mL), washed with 1N HCl (1×200 mL) and deionized $H_2O$ (2×150 mL), dried over $Na_2SO_4$ and concentrated in vacuum to give a crude product which used in the next step without further purification. $^1$H NMR (400 MHz, $CDCl_3$) δ 7.77 (d, J=8.2 Hz, 2H), 7.35 (d, J=8.2 Hz, 2H), 6.76 (b, 1H), 4.01 (dd, J=3.6, 9.7 Hz, 1H), 3.86 (m, 1H), 3.80 (dd, J=7.4, 9.6 Hz, 1H), 2.44 (s, 3H), 2.37-2.12 (m, 3H), 1.77 (m, 1H)

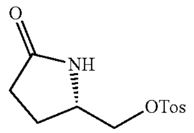

Preparation of (S)-(5-oxopyrrolidin-2-yl)methyl 4-methylbenzenesulfonate: The title compound was prepared according to the procedure for (R)-(5-oxopyrrolidin-2-yl) methyl 4-methylbenzenesulfonate, except L-pyroglutaminol was substituted for (R)-(−)-5-(hydroxymethyl)-2-pyrrolidinone. $^1$H NMR (400 MHz, $CDCl_3$) δ 7.71 (d, J=8.3 Hz, 2H), 7.30 (d, J=8.2 Hz, 2H), 5.77 (b, 1H), 3.99 (dd, J=3.5, 9.7 Hz, 1H), 3.86 (m, 1H), 3.79 (dd, J=7.4, 9.6 Hz, 1H), 2.39 (s, 3H), 2.29-2.11 (m, 3H), 1.69 (m, 1H).

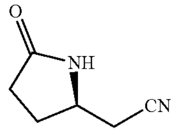

Preparation of (R)-2-(5-oxopyrrolidin-2-yl)acetonitrile: To a solution of (R)-(5-oxopyrrolidin-2-yl)methyl 4-methylbenzenesulfonate (21.25 g, 79 mmol, 1.0 equiv.) in acetonitrile (335 mL) was added potassium cyanide (12.86 g, 197 mmol, 2.5 equiv.). The resulting reaction mixture was then heated to reflux and allowed to reflux overnight. After cooling to 23° C., the reaction mixture was filtered thru a plug of Celite and concentrated in vacuum to give a crude product which was further purified by column chromatography (MeOH/Ethyl acetate, 10%). $^1H$ NMR (400 MHz, $CDCl_3$) δ 7.23 (b, 1H), 3.93 (m, 1H), 2.54 (d, J=5.7 Hz, 2H), 2.48-2.24 (m, 3H), 1.88 (m, 1H).

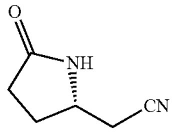

Preparation of (S)-2-(5-oxopyrrolidin-2-yl)acetonitrile: The title compound was prepared according to the procedure for (R)-2-(5-oxopyrrolidin-2-yl)acetonitrile, except (S)-(5-oxopyrrolidin-2-yl)methyl 4-methylbenzenesulfonate was substituted for (R)-(5-oxopyrrolidin-2-yl)methyl 4-methylbenzenesulfonate. $^1H$ NMR (400 MHz, $CDCl_3$) δ 7.47 (b, 1H), 3.92 (m, 1H), 2.55 (d, J=5.6 Hz, 2H), 2.47-2.24 (m, 3H), 1.86 (m, 1H).

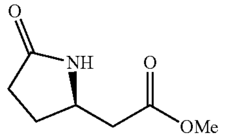 [SMILES: COC(=O)C[C@H]1CCC(=O)N1]

Preparation of methyl (R)-2-(5-oxopyrrolidin-2-yl)acetate: A 6 M HCl in methanol solution was prepared via the addition of acetyl chloride (33 mL) to methanol (77 mL). (R)-2-(5-oxopyrrolidin-2-yl)acetonitrile (4.73 g, 38 mmol, 1.0 equiv.) was dissolved in the prepared 6 M methanolic HCl solution (77 mL) and stirred at 23° C. overnight. The reaction mixture was diluted with deionized $H_2O$ (100 mL) and methylene chloride (100 mL) and layers were seperated. The aqueous layer was backwashed with methylene chloride (8×100 mL). The combined organic phase was dried over $Na_2SO_4$ and concentrated in vacuum to give a crude product that was used in the next step without further purification. $^1H$ NMR (400 MHz, $CDCl_3$) δ 6.40 (b, 1H), 3.94 (m, 1H), 3.64 (s, 3H), 2.52 (dd, J=4.5, 16.5 Hz, 1H), 2.43 (dd, J=9.0, 16.5 Hz, 1H), 2.35-2.19 (m, 3H), 1.68 (m, 1H).

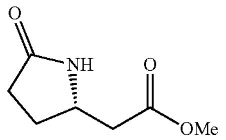 [SMILES: COC(=O)C[C@@H]1CCC(=O)N1]

Preparation of methyl (S)-2-(5-oxopyrrolidin-2-yl)acetate: The title compound was prepared according to the procedure for methyl (R)-2-(5-oxopyrrolidin-2-yl)acetate, except (S)-2-(5-oxopyrrolidin-2-yl)acetonitrile was substituted for (R)-2-(5-oxopyrrolidin-2-yl)acetonitrile. $^1H$ NMR (400 MHz, $CDCl_3$) δ 6.25 (b, 1H), 3.94 (m, 1H), 3.64 (s, 3H), 2.52 (dd, J=4.3, 16.4 Hz, 1H), 2.42 (dd, J=9.2, 16.5 Hz, 1H), 2.32-2.23 (m, 3H), 1.68 (m, 1H).

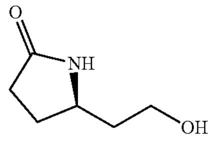

Preparation of (R)-5-(2-hydroxyethyl)pyrrolidin-2-one: To a stirred solution of methyl (R)-2-(5-oxopyrrolidin-2-yl)acetate (0.525 g, 3.3 mmol, 1.0 equiv.) in ethanol (13.4 mL) was added NaBH4 (0.380 g, 10 mmol, 3.0 equiv.) and the resulting mixture was stirred at 23° C. for 5 minutes then at reflux for 1 hour. After cooling to 23° C., the reaction mixture was quenched with 1 mL of acetic acid and the filtered while washing with methanol. The filtrate was concentrated in vacuum to give a crude product which was further purified by column chromatography (MeOH/methanol, 10%). $^1H$ NMR (400 MHz, $CDCl_3$) δ 7.36 (b, 1H), 4.86-4.09 (b, 1H), 3.82-3.54 (m, 3H), 2.32-2.14 (m, 3H), 1.74-1.53 (m, 3H).

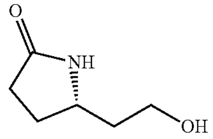

Preparation of (S)-5-(2-hydroxyethyl)pyrrolidin-2-one: The title compound was prepared according to the procedure for (R)-5-(2-hydroxyethyl)pyrrolidin-2-one, except methyl (S)-2-(5-oxopyrrolidin-2-yl)acetate was substituted for methyl (R)-2-(5-oxopyrrolidin-2-yl)acetate. $^1H$ NMR (400 MHz, $CDCl_3$) δ 7.04 (b, 1H), 3.81-3.59 (m, 3H), 3.35-2.88 (b, 1H), 2.31-2.14 (m, 3H), 1.75-1.57 (m, 3H).

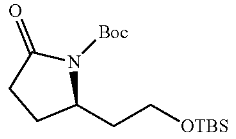 [SMILES: CC(C)(C)OC(=O)N1C(=O)CC[C@@H]1CCO[Si](C)(C)C(C)(C)C]

Preparation of tert-butyl (R)-2-(2-((tert-butyldimethylsilyl)oxy)ethyl)-5-oxopyrrolidine-1-carboxylate: To a stirred solution of (R)-5-(2-hydroxyethyl)pyrrolidin-2-one (3.41 g, 26.4 mmol, 1.0 equiv.) in methylene chloride (50 mL) was added tert-butylchlorodimethylsilane (4.37 g, 29 mmol, 1.1 equiv.) followed by imidazole (1.98 g, 29 mmol, 1.1 equiv.). The resulting mixture was then stirred at 23° C. for 2 hr before being diluted with diethyl ether (100 mL) and washed with deionized $H_2O$ (50 mL). The aqueous layer was backwashed with diethyl ether (2×20 mL). The combined organic phase was dried over $Na_2SO_4$ and concentrated in vacuum to give a crude intermediate that was dissolved in acetonitrile (132 mL). Triethylamine (5.34 g, 52.8 mmol, 2.0 equiv.), di-tert-butyl dicarbonate (10.95 g, 50.2 mmol, 1.9 equiv.) and 4-dimethylaminopyridine (0.645 g, 5.28 mmol, 0.2 equiv.) were then added and the resulting solution was stirred at 23° C. for 2 hrs. The reaction was diluted with ethyl acetate (200 mL) and washed with sat. $NH_4Cl$ (100 mL). The aqueous layer was backwashed with ethyl acetate (2×20 mL) and the combined organic phase was dried over $Na_2SO_4$ and concentrated in vacuum to give a crude product which was further purified by column chromatography (Ethyl acetate/Hexanes, 20-30%). $^1$H NMR (400 MHz, $CDCl_3$) δ 4.18 (m, 1H), 3.66 (t, J=6.2 Hz, 2H), 2.54 (ddd, J=9.2, 11.3, 17.6 Hz, 1H), 2.36 (ddd, J=2.4, 9.2, 17.6 Hz, 1H), 2.13-1.82 (m, 3H), 1.66 (m, 1H), 1.47 (s, 9H), 0.83 (s, 9H), 0.00 (s, 6H).

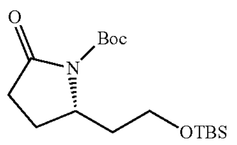 [SMILES: CC(C)(C)OC(=O)N1C(=O)CC[C@H]1CCO[Si](C)(C)C(C)(C)C]

Preparation of tert-butyl (S)-2-(2-((tert-butyldimethylsilyl)oxy)ethyl)-5-oxopyrrolidine-1-carboxylate: The title compound was prepared according to the procedure for tert-butyl (R)-2-(2-((tert-butyldimethylsilyl)oxy)ethyl)-5-oxopyrrolidine-1-carboxylate, except (S)-5-(2-hydroxyethyl)pyrrolidin-2-one was substituted for (R)-5-(2-hydroxyethyl)pyrrolidin-2-one. $^1$H NMR (400 MHz, $CDCl_3$) δ 4.18 (m, 1H), 3.66 (t, J=6.3 Hz, 2H), 2.54 (ddd, J=9.1, 11.3, 17.6 Hz, 1H), 2.36 (ddd, J=2.4, 9.2, 17.6 Hz, 1H), 2.12-1.85 (m, 3H), 1.66 (m, 1H), 1.47 (s, 9H), 0.83 (s, 9H), 0.00 (s, 6H).

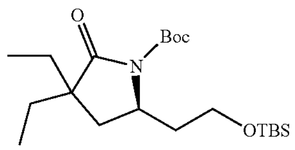 [SMILES: CCC1(CC)C[C@H](CCO[Si](C)(C)C(C)(C)C)N(C(=O)OC(C)(C)C)C1=O]

Preparation of tert-butyl (R)-5-(2-((tert-butyldimethylsilyl)oxy)ethyl)-3,3-diethyl-2-oxopyrrolidine-1-carboxylate: This reaction was performed in oven-dried glassware under a nitrogen atmosphere. A stirred solution of tert-butyl (R)-2-(2-((tert-butyldimethylsilyl)oxy)ethyl)-5-oxopyrrolidine-1-carboxylate (8.0 g, 23.2 mmol, 1.0 equiv.) in dry tetrahydrofuran (35 mL) was cooled to −78° C. and 1M lithium bis(trimethylsilyl)amide solution (tetrahydrofuran, 51 mL, 51 mmol, 2.2 equiv.) was added dropwise while maintaining the reaction temperature below −70° C. The resulting solution was allowed to slowly warm to -30° C. before being cooled back to −78° C. at which iodoethane (8.48 g, 50.5 mmol, 2.15 equiv.) was slowly added dropwise. The resulting solution was slowly warmed to −15° C. and allowed to stir at this temperature for 2 hr before being warmed to 23° C. and allowed to stir for an additional 2.5 hr. The reaction was quenched with sat. $NH_4Cl$ (40 mL) and extracted with ethyl acetate (3×50 mL). The combined organic layers were dried over $Na_2SO_4$ and concentrated in vacuum to give a crude product which was further purified by column chromatography (Ethyl acetate/Hexanes, 0%~10%). $^1$H NMR (400 MHz, $CDCl_3$) δ 3.97 (m, 1H), 3.65 (t, J=5.9 Hz, 2H), 2.23 (m, 1H), 1.95 (dd, J=8.6, 13.5 Hz, 1H), 1.66 (dd, J=6.1, 13.5 Hz, 1H), 1.58-1.39 (m, 14H), 0.90-0.74 (m, 15H), 0.00 (s, 3H).

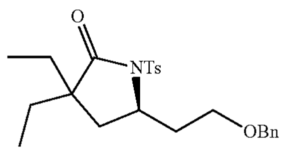 [SMILES: CCC1(CC)C[C@H](CCOCc2ccccc2)N(S(=O)(=O)c2ccc(C)cc2)C1=O]

Preparation of (R)-5-(2-(benzyloxy)ethyl)-3,3-diethyl-1-tosylpyrrolidin-2-one: The title compound was prepared according to the procedure for tert-butyl (R)-5-(2-((tert-butyldimethylsilyl)oxy)ethyl)-3,3-diethyl-2-oxopyrrolidine-1-carboxylate, except (R)-5-(2-(benzyloxy)ethyl)-1-tosylpyrrolidin-2-one was substituted for tert-butyl (R)-2-(2-((tert-butyldimethylsilyl)oxy)ethyl)-5-oxopyrrolidine-1-carboxylate. $^1$H NMR (400 MHz, $CDCl_3$) δ 7.84 (d, J=8.4 Hz, 2H), 7.33-7.16 (m, 7H), 4.44 (dd, J=12.0, 32.0 Hz, 2H), 4.21 (m, 1H), 3.54 (t, J=5.5 Hz, 2H), 2.69 (m, 1H), 2.34 (s, 3H), 1.95 (dd, J=8.1, 13.5 Hz, 1H), 1.81-1.64 (m, 2H), 1.41 (q, J=7.5 Hz, 2H), 1.33-1.13 (m, 2H), 0.71 (t, J=7.5 Hz, 3H), 0.48 (t, J=7.5 Hz, 3H).

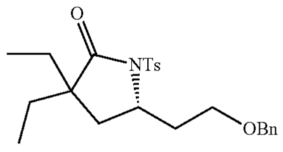 [SMILES: CCC1(CC)C[C@@H](CCOCc2ccccc2)N(S(=O)(=O)c2ccc(C)cc2)C1=O]

Preparation of (S)-5-(2-(benzyloxy)ethyl)-3,3-diethyl-1-tosylpyrrolidin-2-one: The title compound was prepared according to the procedure for tert-butyl (R)-5-(2-((tert-butyldimethylsilyl)oxy)ethyl)-3,3-diethyl-2-oxopyrrolidine-1-carboxylate, except (S)-5-(2-(benzyloxy)ethyl)-1-tosylpyrrolidin-2-one was substituted for tert-butyl (R)-2-(2-((tert-butyldimethylsilyl)oxy)ethyl)-5-oxopyrrolidine-1-carboxylate. $^1$H NMR (400 MHz, $CDCl_3$) δ 7.93 (d, J=8.2 Hz, 2H), 7.40-7.24 (m, 7H), 4.53 (dd, J=11.9, 32.6 Hz, 2H), 4.31 (m, 1H), 3.63 (t, J=5.8 Hz, 2H), 2.78 (m, 1H), 2.42 (s, 3H), 2.04 (dd, J=8.6, 13.5 Hz, 1H), 1.90-1.74 (m, 2H), 1.50 (q, J=7.7 Hz, 2H), 1.44-1.23 (m, 2H), 0.80 (t, J=7.4 Hz, 3H), 0.57 (t, J=7.4 Hz, 3H).

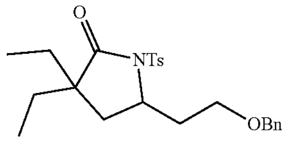 [SMILES: CCC1(CC)CC(CCOCc2ccccc2)N(S(=O)(=O)c2ccc(C)cc2)C1=O]

Preparation of 5-(2-(benzyloxy)ethyl)-3,3-diethyl-1-tosylpyrrolidin-2-one: The title compound was prepared according to the procedure for tert-butyl (R)-5-(2-((tert-butyldimethylsilyl)oxy)ethyl)-3,3-diethyl-2-oxopyrrolidine-1-carboxylate, except (rac)-5-(2-(benzyloxy)ethyl)-1-tosylpyrrolidin-2-one was substituted for tert-butyl (R)-2-(2-((tert-butyldimethylsilyl)oxy)ethyl)-5-oxopyrrolidine-1-carboxylate. $^1$H NMR (400 MHz, $CDCl_3$) δ 7.93 (d, J=8.3 Hz, 2H), 7.41-7.24 (m, 7H), 4.52 (dd, J=12.0, 32.4 Hz, 2H), 4.30 (m, 1H), 3.62 (t, J=5.7 Hz, 2H), 2.78 (m, 1H), 2.41 (s, 3H), 2.04 (dd, J=8.6, 13.5 Hz, 1H), 1.89-1.72 (m, 2H), 1.49 (q, J=7.6 Hz, 2H), 1.43-1.19 (m, 2H), 0.80 (t, J=7.4 Hz, 3H), 0.56 (t, J=7.4 Hz, 3H).

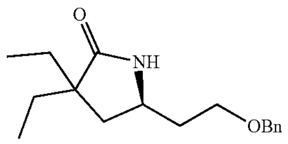 [SMILES: CCC1(CC)C[C@H](CCOCc2ccccc2)NC1=O]

Preparation of (R)-5-(2-(benzyloxy)ethyl)-3,3-diethylpyrrolidin-2-one: This reaction was performed in oven-dried glassware under a nitrogen atmosphere. A mixture of Na metal (800 mg) and dry tetrahydrofuran (100 mL) was stirred at 23° C. for 45 minutes. The reaction mixture was cooled to −78° C. followed by the addition of a solution of (R)-5-(2-(benzyloxy)ethyl)-3,3-diethyl-1-tosylpyrrolidin-2-one (1.48 g, 3.45 mmol, 1.0 equiv.) in dry tetrahydrofuran (51 mL). The resulting mixture was allowed to stir at −78° C. for 1.5 hours before being quenched with sat. $NH_4Cl$ (50 mL) and extracted with ethyl acetate (3×40 mL). The combined organic layers were dried over $Na_2SO_4$ and concentrated in vacuum to give a crude product which was further purified by column chromatography (Ethyl acetate/Hexanes, 0% 100%). $^1H$ NMR (400 MHz, $CDCl_3$) δ 7.31-7.14 (m, 5H), 6.59 (b, 1H), 4.40 (s, 2H), 3.60-3.37 (m, 3H), 1.93 (dd, J=7.5, 13.3 Hz, 1H), 1.75-1.58 (m, 2H), 1.57-1.32 (m, 5H), 0.80 (dt, J=7.6, 18.3 Hz, 6H).

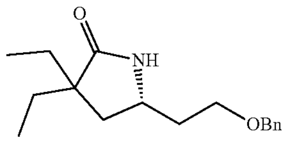

Preparation of (S)-5-(2-(benzyloxy)ethyl)-3,3-diethylpyrrolidin-2-one: The title compound was prepared according to the procedure for (R)-5-(2-(benzyloxy)ethyl)-3,3-diethylpyrrolidin-2-one, except (S)-5-(2-(benzyloxy)ethyl)-3,3-diethyl-1-tosylpyrrolidin-2-one was substituted for (R)-5-(2-(benzyloxy)ethyl)-3,3-diethyl-1-tosylpyrrolidin-2-one. $^1H$ NMR (400 MHz, $CDCl_3$) δ 7.35-7.13 (m, 5H), 6.06 (b, 1H), 4.42 (s, 2H), 3.62-3.36 (m, 3H), 1.95 (dd, J=7.5, 13.3 Hz, 1H), 1.75-1.59 (m, 2H), 1.57-1.36 (m, 5H), 0.80 (dt, J=7.6, 18.3 Hz, 6H)

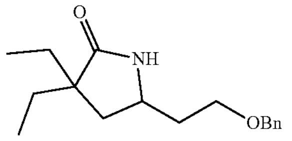

Preparation of 5-(2-(benzyloxy)ethyl)-3,3-diethylpyrrolidin-2-one: The title compound was prepared according to the procedure for (R)-5-(2-(benzyloxy)ethyl)-3,3-diethylpyrrolidin-2-one, except (rac)-5-(2-(benzyloxy)ethyl)-3,3-diethyl-1-tosylpyrrolidin-2-one was substituted for (R)-5-(2-(benzyloxy)ethyl)-3,3-diethyl-1-tosylpyrrolidin-2-one. $^1H$ NMR (400 MHz, $CDCl_3$) δ 7.28-7.10 (m, 5H), 6.17 (b, 1H), 4.36 (s, 2H), 3.58-3.32 (m, 3H), 1.89 (dd, J=7.3, 13.3 Hz, 1H), 1.68-1.53 (m, 2H), 1.52-1.28 (m, 5H), 0.76 (dt, J=7.4, 19.8 Hz, 6H)

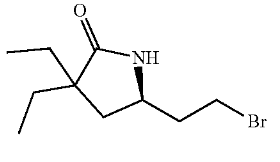

Preparation of (R)-5-(2-bromoethyl)-3,3-diethylpyrrolidin-2-one: To a round bottom flask was added 10% Pd/C (175 mg, 20% wt) followed by a solution of (R)-5-(2-(benzyloxy)ethyl)-3,3-diethylpyrrolidin-2-one (876 mg, 3.19 mmol, 1 equiv.) in ethanol (17 mL). The system was put under $H_2$ (1 atm) using a balloon and allowed to stir at 23° C. under a $H_2$ atmosphere overnight. The reaction was filtered through a plug of Celite and concentrated under reduced pressure. The crude alcohol was dissolved in tetrahydrofuran (12.8 mL) and then triphenylphosphine (1.35 g, 5.13 mmol, 1.6 equiv.) and carbon tetrabromide (1.70 g, 5.13 mmol, 1.6 equiv.) were sequentially added and the reaction was allowed to stir at 23° C. for −3 hours. The resulting mixture was filtered and concentrated in vacuum to give a crude product which was further purified by column chromatography (100% Hexanes then Ethyl acetate/Hexanes, 30%~50%). $^1H$ NMR (400 MHz, $CDCl_3$) δ 7.31 (b, 1H), 3.65 (p, J=6.8 Hz, 1H), 3.38 (t, J=6.7 Hz, 2H), 2.12-1.85 (m, 3H), 1.62-1.32 (m, 5H), 0.82 (dt, J=7.5, 17.8 Hz, 6H).

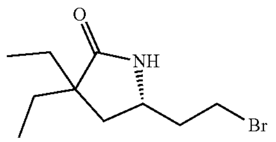

Preparation of (S)-5-(2-bromoethyl)-3,3-diethylpyrrolidin-2-one: The title compound was prepared according to the procedure for (R)-5-(2-bromoethyl)-3,3-diethylpyrrolidin-2-one, except (S)-5-(2-(benzyloxy)ethyl)-3,3-diethylpyrrolidin-2-one was substituted for (R)-5-(2-(benzyloxy)ethyl)-3,3-diethylpyrrolidin-2-one. $^1H$ NMR (400 MHz, $CDCl_3$) δ 7.16 (b, 1H), 3.66 (p, J=6.8 Hz, 1H), 3.38 (t, J=6.8 Hz, 2H), 2.08-1.88 (m, 3H), 1.59-1.35 (m, 5H), 0.82 (dt, J=7.5, 17.8 Hz, 6H).

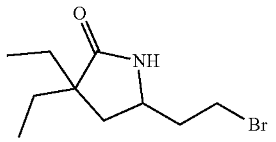

Preparation of 5-(2-bromoethyl)-3,3-diethylpyrrolidin-2-one: The title compound was prepared according to the procedure for (R)-5-(2-bromoethyl)-3,3-diethylpyrrolidin-2-one, except 5-(2-(benzyloxy)ethyl)-3,3-diethylpyrrolidin-2-one was substituted for (R)-5-(2-(benzyloxy)ethyl)-3,3-diethylpyrrolidin-2-one. $^1H$ NMR (400 MHz, $CDCl_3$) δ 8.06 (b, 1H), 3.64 (p, J=6.5 Hz, 1H), 3.40 (t, J=6.8 Hz, 2H), 2.06-1.86 (m, 3H), 1.58-1.34 (m, 5H), 0.81 (dt, J=7.5, 16.8 Hz, 6H).

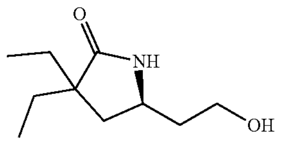

Preparation of (R)-3,3-diethyl-5-(2-hydroxyethyl)pyrrolidin-2-one: A 6M HCl in methanol solution was prepared via the addition of acetyl chloride (18 mL) to methanol (45 mL). tert-Butyl (R)-5-(2-((tert-butyldimethylsilyl)oxy)ethyl)-3,3-diethyl-2-oxopyrrolidine-1-carboxylate (3.98 g, 10 mmol, 1.0 equiv.) was dissolved in the prepared 6M methanolic HCl solution (45 mL) and stirred at 23° C. for 30 minutes. The resulting reaction solution was diluted with methanol and then concentrated in vacuo to give a crude product which used in the next step without further purification. $^1$H NMR (400 MHz, $CDCl_3$) δ 7.28 (b, 1H), 3.82 (m, 2H), 3.68 (m, 1H), 2.07 (dd, J=7.7, 13.4 Hz, 1H), 1.70 (m, 2H), 1.61 (dd, J=7.7, 13.3 Hz, 1H), 1.57-1.39 (m, 4H), 0.84 (dt, J=7.5, 18.0 Hz, 6H).

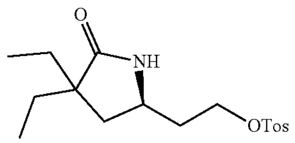

Preparation of (R)-2-(4,4-diethyl-5-oxopyrrolidin-2-yl) ethyl 4-methylbenzenesulfonate: To a cooled solution of (R)-3,3-diethyl-5-(2-hydroxyethyl)pyrrolidin-2-one (1.85 g, 10 mmol, 1.0 equiv.) and triethylamine (2.02 g, 20 mmol, 2.0 equiv.) in tetrahydrofuran/methylene chloride (50 mL:50 mL) at 0° C. was added 4-toluenesulfonyl chloride (2.85 g, 15 mmol, 1.5 equiv.) followed by 4-dimethylaminopyridine (0.122 g, 1 mmol, 0.2 equiv.). The resulting reaction mixture was stirred at 0° C. for 5 minutes before being warmed to 23° C. and allowed to stir for 72 hours. Then, the reaction mixture was diluted with dichloromethane (50 mL), washed with 1N HCl (1×50 mL) and deionized $H_2O$ (2×50 mL), dried over $Na_2SO_4$ and concentrated in vacuo to give a crude product which was further purified by column chromatography (Ethyl acetate/Hexanes, 20%~75%). $^1$H NMR (400 MHz, $CDCl_3$) δ 7.22 (d, J=8.2 Hz, 2H), 7.29 (d, J=7.9 Hz, 2H), 6.05 (b, 1H), 4.04 (t, J=5.8 Hz, 2H), 3.53 (p, J=6.8 Hz, 1H), 2.38 (s, 3H), 1.94 (dd, J=7.6, 13.2 Hz, 1H), 1.75 (q, J=6.0 Hz, 2H), 1.53-1.32 (m, 5H), 0.78 (dt, J=7.5, 21.5 Hz, 6H).

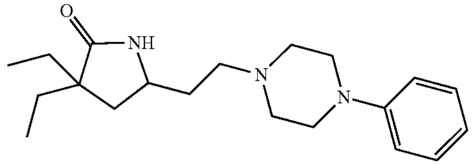 [SMILES: CCC1(CC)CC(CCN2CCN(c3ccccc3)CC2)NC1=O]

Preparation of 3,3-diethyl-5-(2-(4-phenylpiperazin-1-yl) ethyl)pyrrolidin-2-one: To a small vial was added 5-(2-bromoethyl)-3,3-diethylpyrrolidin-2-one (50 mg, 0.201 mmol, 1 equiv.), 1-phenylpiperazine (69 mg, 0.422 mmol, 2.1 eq.) and tetrahydrofuran (3.5 mL). The reaction mixture was allowed to reflux overnight was then cooled to 23° C. The mixture was filtered, washed with tetrahydrofuran, and the filtrate was concentrated in vacuo to give a crude product which was further purified by column chromatography (MeOH/DCM, 0%~10%). $^1$H NMR (400 MHz, $CDCl_3$) δ 7.26 (m, 2H), 6.93 (d, J=8.1 Hz, 2H), 6.86 (t, J=7.2 Hz, 1H), 6.76 (b, 1H), 3.58 (m, 1H), 3.22 (t, J=5.0 Hz, 4H), 2.69 (m, 2H), 2.60-2.40 (m, 4H), 2.06 (dd, J=7.2, 13.1 Hz, 1H), 1.78-1.43 (m, 7H), 0.91 (dt, J=7.5, 13.5 Hz, 6H). LC/MS [M+H]=m/z 330.2

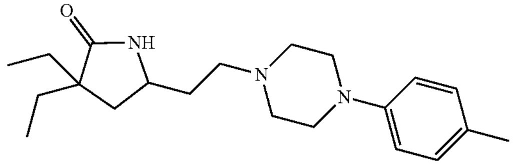 [SMILES: CCC1(CC)CC(CCN2CCN(c3ccc(C)cc3)CC2)NC1=O]

Preparation of 3,3-diethyl-5-(2-(4-(p-tolyl)piperazin-1-yl)ethyl)pyrrolidin-2-one: The title compound was prepared according to the procedure for 3,3-diethyl-5-(2-(4-phenylpiperazin-1-yl)ethyl)pyrrolidin-2-one, except 1-(4-methylphenyl)piperazine was substituted for 1-phenylpiperazine. $^1$H NMR (400 MHz, $CDCl_3$) δ 7.07 (d, J=8.1 Hz, 2H), 6.84 (d, J=8.6 Hz, 2H), 6.74 (b, 1H), 3.58 (m, 1H), 3.16 (t, J=5.0 Hz, 4H), 2.69 (m, 2H), 2.56-2.40 (m, 4H), 2.27 (s, 3H), 2.05 (dd, J=7.3, 13.3 Hz, 1H), 1.78-1.43 (m, 7H), 0.91 (dt, J=7.4, 13.8 Hz, 6H). LC/MS [M+H]=m/z 344.2

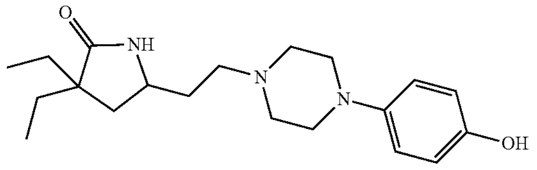 [SMILES: CCC1(CC)CC(CCN2CCN(c3ccc(O)cc3)CC2)NC1=O]

Preparation of 3,3-diethyl-5-(2-(4-(4-hydroxyphenyl)piperazin-1-yl)ethyl)pyrrolidin-2-one: The title compound was prepared according to the procedure for 3,3-diethyl-5-(2-(4-phenylpiperazin-1-yl)ethyl)pyrrolidin-2-one, except 1-(4-hydroxyphenyl)piperazine was substituted for 1-phenylpiperazine. $^1$H NMR (400 MHz, $CDCl_3$) δ 7.23 (b, 1H), 6.73 (d, J=9.1 Hz, 2H), 6.68 (d, J=9.0 Hz, 2H), 3.59 (m, 1H), 3.04-2.87 (b, 4H), 2.69 (m, 2H), 2.57 (m, 1H), 2.45 (m, 3H), 2.06 (dd, J=7.4, 13.2 Hz, 1H), 1.75-1.43 (m, 7H), 0.91 (dt, J=7.5, 14.3 Hz, 6H). LC/MS [M+H]=m/z 346.2

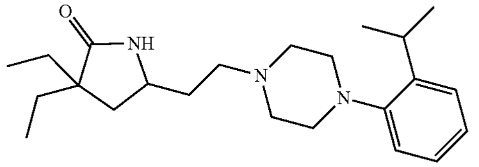 [SMILES: CCC1(CC)CC(CCN2CCN(c3ccccc3C(C)C)CC2)NC1=O]

Preparation of 3,3-diethyl-5-(2-(4-(2-isopropylphenyl) piperazin-1-yl)ethyl)pyrrolidin-2-one: The title compound was prepared according to the procedure for 3,3-diethyl-5-(2-(4-phenylpiperazin-1-yl)ethyl)pyrrolidin-2-one, except 1-(2-isopropylphenyl)piperazine was substituted for 1-phenylpiperazine. $^1$H NMR (400 MHz, $CDCl_3$) δ 7.26 (d, J=7.5 Hz, 1H), 7.20-7.04 (m, 3H), 6.79 (b, 1H), 3.59 (m, 1H), 3.49 (sept. J=6.8 Hz, 1H), 2.93 (t, J=4.6 Hz, 4H), 2.83-2.60 (b, 2H), 2.60-2.42 (m, 4H), 2.07 (dd, J=7.4, 13.1 Hz, 1H), 1.78-1.45 (m, 7H), 1.23 (dd, J=2.4, 6.9 Hz, 6H), 0.92 (dt, J=7.4, 18.3 Hz, 6H). LC/MS [M+H]=m/z 372.2

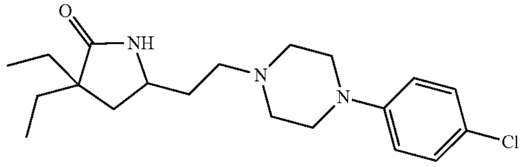 [SMILES: CCC1(CC)CC(CCN2CCN(c3ccc(Cl)cc3)CC2)NC1=O]

Preparation of 5-(2-(4-(4-chlorophenyl)piperazin-1-yl) ethyl)-3,3-diethylpyrrolidin-2-one: The title compound was prepared according to the procedure for 3,3-diethyl-5-(2-(4-phenylpiperazin-1-yl)ethyl)pyrrolidin-2-one, except 1-(4-chlorophenyl)piperazine was substituted for 1-phenylpiperazine. $^1$H NMR (400 MHz, $CDCl_3$) δ 7.19 (d, J=9.0 Hz, 2H), 6.83 (d, J=9.0 Hz, 2H), 6.73 (b, 1H), 3.57 (m, 1H), 3.17

(t, J=5.0 Hz, 4H), 2.68 (m, 2H), 2.58-2.40 (m, 4H), 2.05 (dd, J=7.4, 13.2 Hz, 1H), 1.76-1.42 (m, 7H), 0.90 (dt, J=7.4, 13.7 Hz, 6H). LC/MS [M+H]=m/z 364.2

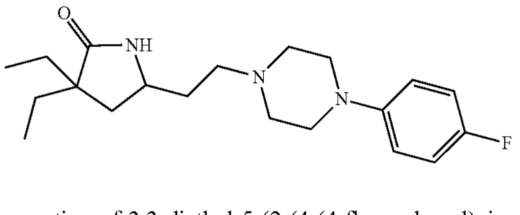

Preparation of 3,3-diethyl-5-(2-(4-(4-fluorophenyl)piperazin-1-yl)ethyl)pyrrolidin-2-one: The title compound was prepared according to the procedure for 3,3-diethyl-5-(2-(4-phenylpiperazin-1-yl)ethyl)pyrrolidin-2-one, except 1-(4-fluorophenyl)piperazine was substituted for 1-phenylpiperazine. $^1$H NMR (400 MHz, $CDCl_3$) δ 6.99-6.90 (m, 2H), 6.89-6.83 (m, 2H), 6.79 (b, 1H), 3.56 (m, 1H), 3.12 (t, J=4.9 Hz, 4H), 2.68 (m, 2H), 2.58-2.39 (m, 4H), 2.04 (dd, J=7.5, 13.2 Hz, 1H), 1.74-1.42 (m, 7H), 0.89 (dt, J=7.4, 13.9 Hz, 6H). LC/MS [M+H]=m/z 348.2

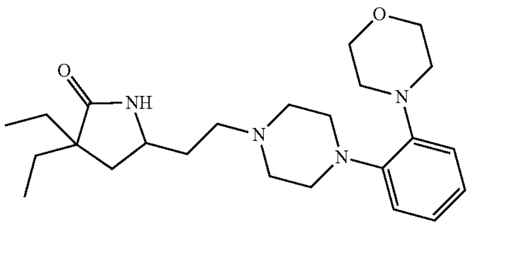 [SMILES: CCC1(CC)CC(CCN2CCN(c3ccccc3N3CCOCC3)CC2)NC1=O]

Preparation of 3,3-diethyl-5-(2-(4-(2-morpholinophenyl)piperazin-1-yl)ethyl)pyrrolidin-2-one: The title compound was prepared according to the procedure for 3,3-diethyl-5-(2-(4-phenylpiperazin-1-yl)ethyl)pyrrolidin-2-one, except 4-(2-(piperazin-1-yl)phenyl)morpholine was substituted for 1-phenylpiperazine. $^1$H NMR (400 MHz, $CDCl_3$) δ 6.91-6.84 (m, 2H), 6.84-6.74 (m, 2H), 6.51 (b, 1H), 3.71 (t, J=4.8 Hz, 4H), 3.46 (m, 1H), 3.36-2.77 (b, 8H), 2.74-2.07 (b, 6H), 1.94 (dd, J=7.5, 13.2 Hz, 1H), 1.65-1.31 (m, 7H), 0.79 (dt, J=7.3, 15.9 Hz, 6H). LC/MS [M+H]=m/z 415.2

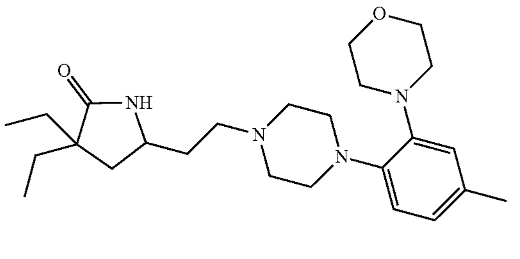 [SMILES: CCC1(CC)CC(CCN2CCN(c3ccc(C)cc3N3CCOCC3)CC2)NC1=O]

Preparation of 3,3-diethyl-5-(2-(4-(4-methyl-2-morpholinophenyl)piperazin-1-yl)ethyl)pyrrolidin-2-one: The title compound was prepared according to the procedure for 3,3-diethyl-5-(2-(4-phenylpiperazin-1-yl)ethyl)pyrrolidin-2-one, except 4-(5-methyl-2-(piperazin-1-yl)phenyl)morpholine was substituted for 1-phenylpiperazine. $^1$H NMR (400 MHz, $CDCl_3$) δ 6.88-6.78 (m, 2H), 6.77-6.67 (m, 2H), 3.84 (t, J=4.6 Hz, 4H), 3.59 (m, 1H), 3.42-2.86 (b, 8H), 2.80-2.32 (b, 6H), 2.29 (s, 3H), 2.06 (dd, J=7.5, 13.3 Hz, 1H), 1.78-1.44 (m, 7H), 0.92 (dt, J=7.4, 15.6 Hz, 6H). LC/MS [M+H]=m/z 429.2

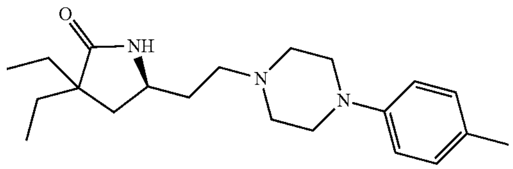 [SMILES: CCC1(CC)C[C@H](CCN2CCN(c3ccc(C)cc3)CC2)NC1=O]

Preparation of (R)-3,3-diethyl-5-(2-(4-(p-tolyl)piperazin-1-yl)ethyl)pyrrolidin-2-one: The title compound was prepared according to the procedure for 3,3-diethyl-5-(2-(4-phenylpiperazin-1-yl)ethyl)pyrrolidin-2-one, except (R)-5-(2-bromoethyl)-3,3-diethylpyrrolidin-2-one was substituted 5-(2-bromoethyl)-3,3-diethylpyrrolidin-2-one and 1-(4-methylphenyl)piperazine was substituted for 1-phenylpiperazine. $^1$H NMR (400 MHz, $CDCl_3$) δ 7.07 (d, J=8.2 Hz, 2H), 6.84 (d, J=8.5 Hz, 2H), 6.41 (b, 1H), 3.57 (m, 1H), 3.16 (t, J=4.9 Hz, 4H), 2.69 (m, 2H), 2.58-2.40 (m, 4H), 2.27 (s, 3H), 2.05 (dd, J=7.3, 13.1 Hz, 1H), 1.77-1.43 (m, 7H), 0.91 (dt, J=7.4, 13.7 Hz, 6H). LC/MS [M+H]=m/z 344.2

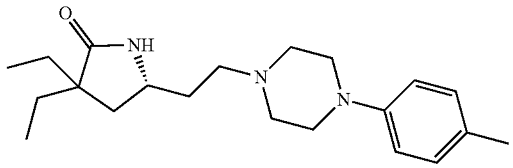 [SMILES: CCC1(CC)C[C@@H](CCN2CCN(c3ccc(C)cc3)CC2)NC1=O]

Preparation of (S)-3,3-diethyl-5-(2-(4-(p-tolyl)piperazin-1-yl)ethyl)pyrrolidin-2-one: The title compound was prepared according to the procedure for 3,3-diethyl-5-(2-(4-phenylpiperazin-1-yl)ethyl)pyrrolidin-2-one, except (S)-5-(2-bromoethyl)-3,3-diethylpyrrolidin-2-one was substituted 5-(2-bromoethyl)-3,3-diethylpyrrolidin-2-one and 1-(4-methylphenyl)piperazine was substituted for 1-phenylpiperazine. $^1$H NMR (400 MHz, $CDCl_3$) δ 7.00 (d, J=8.5 Hz, 2H), 6.76 (d, J=8.5 Hz, 2H), 6.41 (b, 1H), 3.50 (m, 1H), 3.09 (t, J=5.1 Hz, 4H), 2.64 (m, 2H), 2.54-2.32 (m, 4H), 2.19 (s, 3H), 1.98 (dd, J=7.3, 13.1 Hz, 1H), 1.69-1.69 (m, 7H), 0.83 (dt, J=7.4, 14.5 Hz, 6H). LC/MS [M+H]=m/z 344.2

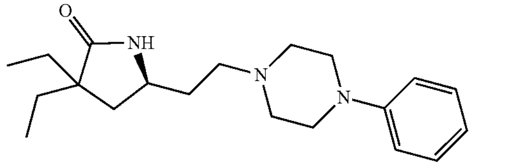 [SMILES: CCC1(CC)C[C@H](CCN2CCN(c3ccccc3)CC2)NC1=O]

Preparation of (R)-3,3-diethyl-5-(2-(4-phenylpiperazin-1-yl)ethyl)pyrrolidin-2-one: To a small vial was added (R)-2-(4,4-diethyl-5-oxopyrrolidin-2-yl)ethyl 4-methylbenzenesulfonate (75 mg, 0.22 mmol, 1 equiv.) and 1-phenylpiperazine (76 mg, 0.46 mmol, 2.1 equiv.) then both were dissolved in acetonitrile (2.2 mL). Then $K_2CO_3$ (77 mg, 0.55 mmol, 2.5 equiv.) was added, the reaction was allowed to stir at 80° C. overnight, and then cooled to 23° C. The mixture was filtered, washed with acetonitrile and the filtrate was concentrated in vacuo to give a crude product which was by further purified by column chromatography (MeOH/DCM, 0%~10%). $^1$H NMR (400 MHz, $CDCl_3$) δ 7.27 (m, 2H), 6.94 (d, J=8.1 Hz, 2H), 6.87 (t, J=7.2 Hz, 1H), 6.65 (b, 1H), 3.59 (m, 1H), 3.23 (t, J=5.0 Hz, 4H), 2.71 (m, 2H), 2.61-2.41 (m, 4H), 2.07 (dd, J=7.4, 13.1 Hz, 1H), 1.77-1.45 (m, 7H), 0.92 (dt, J=7.4, 14.0 Hz, 6H). LC/MS [M+H]=m/z 330.2.

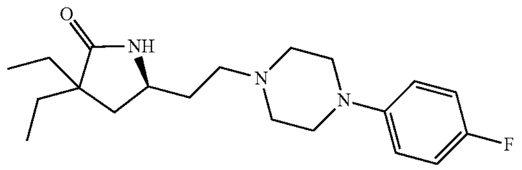 [SMILES: CCC1(CC)C[C@H](CCN2CCN(c3ccc(F)cc3)CC2)NC1=O]

Preparation of (R)-3,3-diethyl-5-(2-(4-(4-fluorophenyl)piperazin-1-yl)ethyl)pyrrolidin-2-one: The title compound was prepared according to the procedure for (R)-3,3-diethyl-5-(2-(4-phenylpiperazin-1-yl)ethyl)pyrrolidin-2-one, except 1-(4-fluorophenyl)piperazine was substituted for 1-phenylpiperazine. $^1$H NMR (400 MHz, $CDCl_3$) δ 7.00-6.91 (m, 2H), 6.91-6.82 (m, 2H), 6.74 (b, 1H), 3.57 (m, 1H), 3.13 (t, J=5.0 Hz, 4H), 2.70 (m, 2H), 2.60-2.41 (m, 4H), 2.05 (dd, J=7.3, 13.1 Hz, 1H), 1.76-1.44 (m, 7H), 0.90 (dt, J=7.5, 14.1 Hz, 6H). LC/MS [M+H]=m/z 348.2

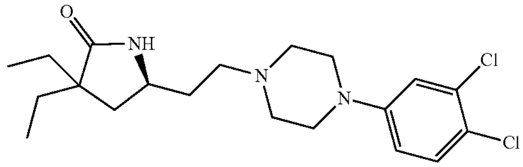 [SMILES: CCC1(CC)C[C@H](CCN2CCN(c3ccc(Cl)c(Cl)c3)CC2)NC1=O]

Preparation of (R)-5-(2-(4-(3,4-dichlorophenyl)piperazin-1-yl)ethyl)-3,3-diethylpyrrolidin-2-one: The title compound was prepared according to the procedure for (R)-3,3-diethyl-5-(2-(4-phenylpiperazin-1-yl)ethyl)pyrrolidin-2-one, except 1-(3,4-dichlorophenyl)piperazine was substituted for 1-phenylpiperazine. $^1$H NMR (400 MHz, $CDCl_3$) δ 7.26 (d, J=9.0 Hz, 1H), 6.95 (d, J=2.9 Hz, 1H), 6.79-2.67 (b, 2H), 3.58 (m, 1H), 3.18 (t, J=5.0 Hz, 4H), 2.67 (m, 2H), 2.59-2.39 (m, 4H), 2.05 (dd, J=7.4, 13.1 Hz, 1H), 1.75-1.42 (m, 7H), 0.90 (dt, J=7.4, 13.7 Hz, 6H). LC/MS [M+H]=m/z 398.2.

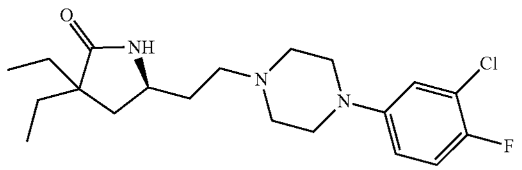 [SMILES: CCC1(CC)C[C@H](CCN2CCN(c3ccc(F)c(Cl)c3)CC2)NC1=O]

Preparation of (R)-5-(2-(4-(3-chloro-4-fluorophenyl)piperazin-1-yl)ethyl)-3,3-diethylpyrrolidin-2-one: The title compound was prepared according to the procedure for (R)-3,3-diethyl-5-(2-(4-phenylpiperazin-1-yl)ethyl)pyrrolidin-2-one, except 1-(3-chloro-4-fluorophenyl)piperazine was substituted for 1-phenylpiperazine. $^1$H NMR (400 MHz, $CDCl_3$) δ 7.01 (t, J=8.8 Hz, 1H), 6.91 (dd, J=2.9, 6.2 Hz, 1H), 6.79-6.66 (b, 2H), 3.57 (m, 1H), 3.14 (t, J=5.0 Hz, 4H), 2.68 (m, 2H), 2.60-2.40 (m, 4H), 2.05 (dd, J=7.5, 13.2 Hz, 1H), 1.75-1.43 (m, 7H), 0.90 (dt, J=7.3, 13.9 Hz, 6H). LC/MS [M+H]=m/z 382.2.

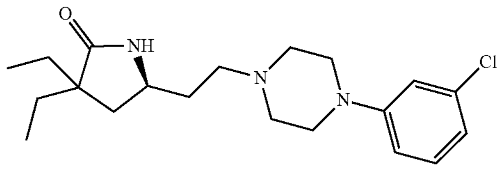 [SMILES: CCC1(CC)C[C@H](CCN2CCN(c3cccc(Cl)c3)CC2)NC1=O]

Preparation of (R)-5-(2-(4-(3-chlorophenyl)piperazin-1-yl)ethyl)-3,3-diethylpyrrolidin-2-one: The title compound was prepared according to the procedure for (R)-3,3-diethyl-5-(2-(4-phenylpiperazin-1-yl)ethyl)pyrrolidin-2-one, except 1-(3-chlorophenyl)piperazine was substituted for 1-phenylpiperazine. $^1$H NMR (400 MHz, $CDCl_3$) δ 7.16 (t, J=8.1 Hz, 1H), 6.87 (t, J=2.1 Hz, 1H), 6.83-6.75 (m, 2H), 6.71 (b, 1H), 3.58 (m, 1H), 3.21 (t, J=5.0 Hz, 4H), 2.68 (m, 2H), 2.60-2.40 (m, 4H), 2.06 (dd, J=7.2, 13.1 Hz, 1H), 1.76-1.44 (m, 7H), 0.91 (dt, J=7.4, 13.8 Hz, 6H). LC/MS [M+H]=m/z 364.2

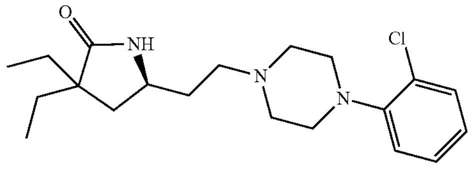 [SMILES: CCC1(CC)C[C@H](CCN2CCN(c3ccccc3Cl)CC2)NC1=O]

Preparation of (R)-5-(2-(4-(2-chlorophenyl)piperazin-1-yl)ethyl)-3,3-diethylpyrrolidin-2-one: The title compound was prepared according to the procedure for (R)-3,3-diethyl-5-(2-(4-phenylpiperazin-1-yl)ethyl)pyrrolidin-2-one, except 1-(2-chlorophenyl)piperazine was substituted for 1-phenylpiperazine. $^1$H NMR (400 MHz, $CDCl_3$) δ 7.27 (dd, J=1.5, 7.9 Hz, 1H), 7.14 (td, J=1.5, 7.7 Hz, 1H), 6.98 (dd, J=1.5, 8.0 Hz, 1H), 6.89 (td, J=1.5, 7.7 Hz, 1H), 6.63 (b, 1H), 3.50 (m, 1H), 3.18-2.83 (b, 4H), 2.77-2.56 (b, 2H), 2.55-2.31 (m, 4H), 1.98 (dd, J=7.4, 13.1 Hz, 1H), 1.69-1.36 (m, 7H), 0.83 (dt, J=7.4, 16.9 Hz, 6H). LC/MS [M+H]=m/z 364.2

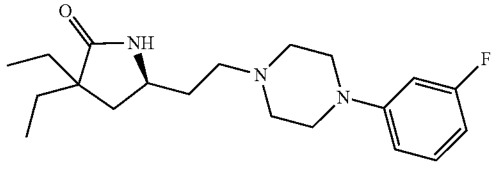 [SMILES: CCC1(CC)C[C@H](CCN2CCN(c3cccc(F)c3)CC2)NC1=O]

Preparation of (R)-5-(2-(4-(3-fluorophenyl)piperazin-1-yl)ethyl)-3,3-diethylpyrrolidin-2-one: The title compound was prepared according to the procedure for (R)-3,3-diethyl-5-(2-(4-phenylpiperazin-1-yl)ethyl)pyrrolidin-2-one, except 1-(3-fluorophenyl)piperazine was substituted for 1-phenylpiperazine. $^1$H NMR (400 MHz, $CDCl_3$) δ 7.10 (m, 1H), 6.64-6.54 (b, 2H), 6.50 (dt, J=2.4, 12.4 Hz, 1H), 6.45 (td, J=2.3, 8.2 Hz, 1H), 3.50 (m, 1H), 3.14 (t, J=5.0 Hz, 4H), 2.60 (m, 2H), 2.51-2.30 (m, 4H), 1.98 (dd, J=7.3, 13.2 Hz, 1H), 1.67-1.36 (m, 7H), 0.83 (dt, J=7.3, 14.0 Hz, 6H). LC/MS [M+H]=m/z 348.2

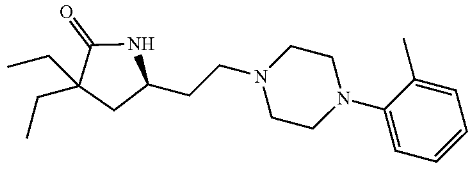 [SMILES: CCC1(CC)C[C@H](CCN2CCN(c3ccccc3C)CC2)NC1=O]

Preparation of (R)-5-(2-(4-(2-methylphenyl)piperazin-1-yl)ethyl)-3,3-diethylpyrrolidin-2-one: The title compound was prepared according to the procedure for (R)-3,3-diethyl-5-(2-(4-phenylpiperazin-1-yl)ethyl)pyrrolidin-2-one, except 1-(2-methylphenyl)piperazine was substituted for 1-phenylpiperazine. $^1$H NMR (400 MHz, $CDCl_3$) δ 7.17 (m, 2H), 7.04 (dd, J=1.2, 8.5 Hz, 1H), 6.99 (td, J=1.2, 7.4 Hz, 1H), 6.73 (b, 1H), 3.59 (m, 1H), 3.03-2.89 (b, 4H), 2.83-2.62 (b, 2H), 2.62-2.38 (m, 4H), 2.31 (s, 3H), 2.07 (dd, J=7.5, 13.1 Hz, 1H), 1.77-1.45 (m, 7H), 0.92 (dt, J=7.5, 17.5 Hz, 6H). LC/MS [M+H]=m/z 344.2

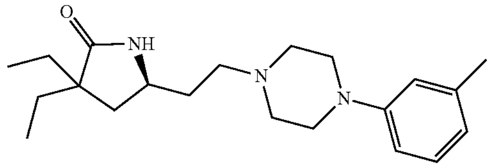 [SMILES: CCC1(CC)C[C@H](CCN2CCN(c3cccc(C)c3)CC2)NC1=O]

Preparation of (R)-5-(2-(4-(3-methylphenyl)piperazin-1-yl)ethyl)-3,3-diethylpyrrolidin-2-one: The title compound was prepared according to the procedure for (R)-3,3-diethyl-5-(2-(4-phenylpiperazin-1-yl)ethyl)pyrrolidin-2-one, except 1-(3-methylphenyl)piperazine was substituted for 1-phenylpiperazine. $^1$H NMR (400 MHz, $CDCl_3$) δ 7.16 (t, J=7.8 Hz, 1H), 6.80-6.68 (m, 3H), 6.63 (b, 1H), 3.59 (m, 1H), 3.22 (t, J=5.0 Hz, 4H), 2.71 (m, 2H), 2.61-2.41 (m, 4H), 2.33 (s, 3H), 2.07 (dd, J=7.4, 13.2 Hz, 1H), 1.78-1.45 (m, 7H), 0.92 (dt, J=7.4, 14.0 Hz, 6H). LC/MS [M+H]=m/z 344.2

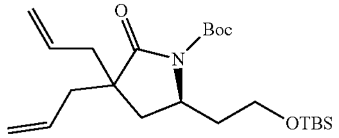 [SMILES: C=CCC1(CC=C)C[C@H](CCO[Si](C)(C)C(C)(C)C)N(C(=O)OC(C)(C)C)C1=O]

Preparation of tert-butyl (R)-3,3-diallyl-5-(2-((tert-butyldimethylsilyl)oxy)ethyl)-2-oxopyrrolidine-1-carboxylate: This reaction was performed in oven-dried glassware under a nitrogen atmosphere. A stirred solution of tert-butyl (R)-2-(2-((tert-butyldimethylsilyl)oxy)ethyl)-5-oxopyrrolidine-1-carboxylate (10.0 g, 29.0 mmol, 1.0 equiv.) in dry tetrahydrofuran (43 mL) was cooled to −78° C. and 1M lithium bis(trimethylsilyl)amide solution (tetrahydrofuran, 63.8 mL, 63.8 mmol, 2.2 equiv.) was added dropwise while maintaining the reaction temperature below −70° C. The resulting solution was allowed to slowly warm to −30° C. before being cooled back to −78° C. at which time allyl iodide (10.71 g, 63.8 mmol, 2.2 equiv.) was slowly added dropwise. The resulting solution was slowly warmed to −20° C. and then quenched with sat. $NH_4Cl$ (75 mL) and extracted with ethyl acetate (3×75 mL). The combined organic layers were dried over $Na_2SO_4$ and concentrated in vacuo to give a crude product which was further purified by column chromatography (Ethyl acetate/Hexanes, 0% 10%). $^1$H NMR (400 MHz, $CDCl_3$) δ 5.77-5.58 (m, 2H), 5.12-4.99 (m, 4H), 3.96 (m, 1H), 3.63 (t, J=6.2 Hz, 2H), 2.40-2.09 (m, 5H), 2.01 (dd, J=8.6, 13.6 Hz, 1H), 1.70 (dd, J=6.4, 13.6 Hz, 1H), 1.57-1.42 (m, 10H), 0.84 (s, 9H), 0.00 (s, 6H).

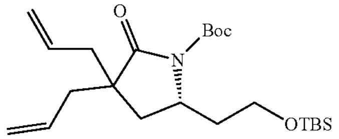 [SMILES: C=CCC1(CC=C)C[C@@H](CCO[Si](C)(C)C(C)(C)C)N(C(=O)OC(C)(C)C)C1=O]

Preparation of tert-butyl (S)-3,3-diallyl-5-(2-((tert-butyldimethylsilyl)oxy)ethyl)-2-oxopyrrolidine-1-carboxylate: The title compound was prepared according to the procedure for tert-butyl (R)-3,3-diallyl-5-(2-((tert-butyldimethylsilyl)oxy)ethyl)-2-oxopyrrolidine-1-carboxylate, except tert-butyl (S)-2-(2-((tert-butyldimethylsilyl)oxy) ethyl)-5-oxopyrrolidine-1-carboxylate was substituted for tert-butyl (R)-2-(2-((tert-butyldimethylsilyl)oxy)ethyl)-5-oxopyrrolidine-1-carboxylate. $^1$H NMR (400 MHz, $CDCl_3$) δ 5.79-5.60 (m, 2H), 5.13-4.98 (m, 4H), 3.96 (m, 1H), 3.62 (t, J=6.2 Hz, 2H), 2.40-2.10 (m, 5H), 2.00 (dd, J=8.6, 13.6 Hz, 1H), 1.69 (dd, J=6.3, 13.6 Hz, 1H), 1.58-1.42 (m, 10H), 0.83 (s, 9H), 0.00 (s, 6H).

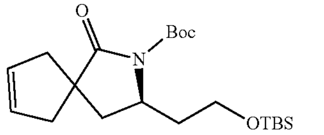 [SMILES: CC(C)(C)OC(=O)N1C(=O)C2(CC=CC2)C[C@@H]1CCO[Si](C)(C)C(C)(C)C]

Preparation of tert-butyl (R)-3-(2-((tert-butyldimethylsilyl)oxy)ethyl)-1-oxo-2-azaspiro[4.4]non-7-ene-2-carboxylate: To a stirred solution of tert-butyl (R)-3,3-diallyl-5-(2-((tert-butyldimethylsilyl)oxy)ethyl)-2-oxopyrrolidine-1-carboxylate (10.03 g, 23.6 mmol, 1.0 equiv.) in methylene chloride (200 mL) was added benzylidene-bis(tricyclohexyl (phophine)dichlororuthenium (0.388 g, 0.472 mmol, 2 mol %). The resulting solution was allowed to stir at 23° C. for 4 hours before being concentrated in vacuo to give a crude product which was further purified by column chromatography (Ethyl acetate/Hexanes, 0%~20%). $^1$H NMR (400 MHz, $CDCl_3$) δ 5.56 (m, 2H), 4.08 (m, 1H), 3.66 (t, J=6.1 Hz, 2H), 2.86 (m, 2H), 2.36 (m, 1H), 2.29-2.14 (m, 2H), 2.09 (dd, J=8.0, 13.0 Hz, 1H), 1.98 (dd, J=3.9, 13.0 Hz, 1H), 1.60 (m, 1H), 1.48 (s, 9H), 0.83 (s, 9H), 0.00 (s, 6H).

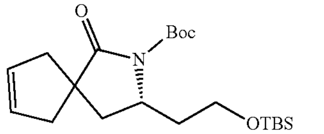 [SMILES: CC(C)(C)OC(=O)N1C(=O)C2(CC=CC2)C[C@H]1CCO[Si](C)(C)C(C)(C)C]

Preparation of tert-butyl (S)-3-(2-((tert-butyldimethylsilyl)oxy)ethyl)-1-oxo-2-azaspiro[4.4]non-7-ene-2-carboxylate: The title compound was prepared according to the procedure for tert-butyl (R)-3-(2-((tert-butyldimethylsilyl) oxy)ethyl)-1-oxo-2-azaspiro[4.4]non-7-ene-2-carboxylate, except tert-butyl (S)-3,3-diallyl-5-(2-((tert-butyldimethylsilyl)oxy)ethyl)-2-oxopyrrolidine-1-carboxylate was substituted for tert-butyl (R)-3,3-diallyl-5-(2-((tert-butyldimethylsilyl)oxy)ethyl)-2-oxopyrrolidine-1-carboxylate. $^1$H NMR (400 MHz, $CDCl_3$) δ 5.56 (m, 2H), 4.08 (m, 1H), 3.66 (t, J=6.1 Hz, 2H), 2.87 (m, 2H), 2.36 (m, 1H), 2.30-2.14 (m, 2H), 2.09 (dd, J=8.0, 13.1 Hz, 1H), 1.98 (dd, J=3.9, 13.1 Hz, 1H), 1.60 (m, 1H), 1.48 (s, 9H), 0.83 (s, 9H), 0.00 (s, 6H).

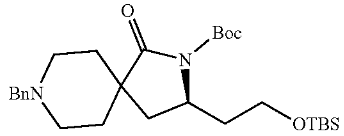 [SMILES: CC(C)(C)OC(=O)N1C(=O)C2(CCN(Cc3ccccc3)CC2)C[C@@H]1CCO[Si](C)(C)C(C)(C)C]

Preparation of tert-butyl (R)-8-benzyl-3-(2-((tert-butyldimethylsilyl)oxy)ethyl)-1-oxo-2,8-diazaspiro[4.5]decane-2-carboxylate: A stirred solution of tert-butyl (R)-3-(2-((tert-butyldimethylsilyl)oxy)ethyl)-1-oxo-2-azaspiro[4.4]non-7-ene-2-carboxylate (9.04 g, 22.8 mmol, 1.0 equiv.) in methylene chloride (235 mL) and methanol (7.7 mL) was cooled to −78° C. and a gaseous stream of $O_3/O_2$ was bubbled through the solution until the color developed a purple tint (45 minutes). Residual 03 was removed by bubbling $O_2$ through the solution for 10 minutes. At -78° C., $NaBH(OAc)_3$ (4.93 g, 23.2 mmol, 1.02 equiv.) was added and the reaction mixture was allowed to warm to 23° C. and stir for 45 minutes. Next, $BnNH_2$ (2.70 g, 25.2 mmol, 1.1 equiv.) and $NaBH(OAc)_3$ (9.72 g, 45.8 mmol, 2.0 equiv.) were sequentially added and the reaction was stirred at 23° C. overnight. The resulting mixture was filtered and concentrated in vacuo to give a crude product which was further purified by column chromatography (2M Ammonia in MeOH/methylene chloride, 0%~2%). $^1H$ NMR (400 MHz, $CDCl_3$) δ 7.34-7.19 (m, 5H), 4.03 (m, 1H), 3.65 (t, J=5.9 Hz, 2H) 3.54 (b, 2H), 2.94 (b, 2H), 2.41 (b, 2H), 2.19 (m, 1H), 2.08-1.86 (m, 3H), 1.79 (dd, J=4.7, 13.5 Hz, 1H), 1.60-1.40 (m, 12H), 0.84 (s, 9H), 0.00 (s, 6H).

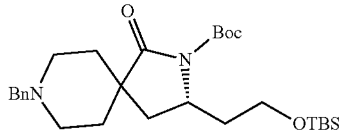 [SMILES: CC(C)(C)OC(=O)N1C(=O)C2(CCN(Cc3ccccc3)CC2)C[C@H]1CCO[Si](C)(C)C(C)(C)C]

Preparation of tert-butyl (S)-8-benzyl-3-(2-((tert-butyldimethylsilyl)oxy)ethyl)-1-oxo-2,8-diazaspiro[4.5]decane-2-carboxylate: The title compound was prepared according to the procedure for tert-butyl (R)-8-benzyl-3-(2-((tert-butyldimethylsilyl)oxy)ethyl)-1-oxo-2,8-diazaspiro[4.5]decane-2-carboxylate, except tert-butyl (S)-3-(2-((tert-butyldimethylsilyl)oxy)ethyl)-1-oxo-2-azaspiro[4.4]non-7-ene-2-carboxylate was substituted for tert-butyl (R)-3-(2-((tert-butyldimethylsilyl)oxy)ethyl)-1-oxo-2-azaspiro[4.4]non-7-ene-2-carboxylate. $^1H$ NMR (400 MHz, $CDCl_3$) δ 7.32-7.14 (m, 5H), 4.02 (m, 1H), 3.65 (t, J=5.9 Hz, 2H) 3.54 (b, 2H), 2.84 (b, 2H), 2.41 (b, 2H), 2.19 (m, 1H), 2.05-1.86 (m, 3H), 1.80 (dd, J=4.7, 13.3 Hz, 1H), 1.60-1.39 (m, 12H), 0.84 (s, 9H), 0.00 (s, 6H).

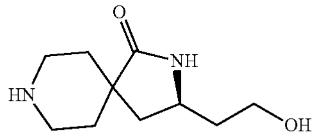 [SMILES: O=C1N[C@@H](CCO)CC12CCNCC2]

Preparation of (R)-3-(2-hydroxyethyl)-2,8-diazaspiro[4.5]decan-1-one: To a round bottom flask was added 10% Pd/C (1.27 g, 20% by weight) followed by a solution of tert-butyl (R)-8-benzyl-3-(2-((tert-butyldimethylsilyl)oxy)ethyl)-1-oxo-2,8-diazaspiro[4.5]decane-2-carboxylate (6.32 g, 12.5 mmol, 1 equiv.) in methanol (83 mL). The reaction was put under $H_2$ (1 atm) using a balloon and stirred at 23° C. overnight. The reaction was filtered through a plug of Celite and concentrated filtrate under reduced pressure to give a crude intermediate.

A 6M HCl in methanol solution was prepared via the addition of acetyl chloride (60 mL) to methanol (160 mL). The crude intermediate was dissolved in the prepared 6M methanolic HCl solution (160 mL) and stirred at 23° C. for 30 minutes before being diluted with methanol and concentrated in vacuo to produce a crude product as an HCl salt. The product was free based by stirring with Amberlite IRN-78 base resin in methanol (~150 mL) for 15 minutes followed by filtration and concentrated in vacuo to produce a crude product that was used in the next step without further purification. $^1H$ NMR (400 MHz, MeOD) δ 3.82-3.61 (m, 3H), 3.02 (m, 2H), 2.76 (td, J=2.9, 12.9 Hz, 1H), 2.64 (td, J=2.9, 12.9 Hz, 1H), 2.46 (dd, J=7.0, 13.0 Hz, 1H), 1.93 (td, J=4.4, 12.7 Hz, 1H), 1.86-1.74 (m, 1H), 1.74-1.64 (m, 2H), 1.60 (dd, J=8.2, 12.9 Hz, 1H), 1.49 (d, J=13.2 Hz, 1H), 1.36 (d, J=13.6 Hz, 1H).

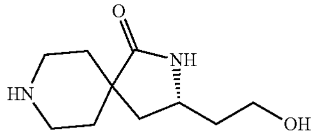 [SMILES: O=C1N[C@H](CCO)CC12CCNCC2]

Preparation of (S)-3-(2-hydroxyethyl)-2,8-diazaspiro[4.5]decan-1-one: The title compound was prepared according to the procedure for (R)-3-(2-hydroxyethyl)-2,8-diazaspiro[4.5]decan-1-one, except tert-butyl (R)-8-benzyl-3-(2-((tert-butyldimethylsilyl)oxy)ethyl)-1-oxo-2,8-diazaspiro[4.5]decane-2-carboxylate was substituted for tert-butyl (S)-8-benzyl-3-(2-((tert-butyldimethylsilyl)oxy)ethyl)-1-oxo-2,8-diazaspiro[4.5]decane-2-carboxylate. $^1H$ NMR (400 MHz, MeOD) δ 3.82-3.60 (m, 3H), 3.02 (m, 2H), 2.76 (td, J=2.9, 12.9 Hz, 1H), 2.64 (td, J=2.9, 12.9 Hz, 1H), 2.46 (dd, J=7.1, 13.2 Hz, 1H), 1.93 (td, J=3.7, 12.3 Hz, 1H), 1.86-1.75 (m, 1H), 1.75-1.64 (m, 2H), 1.60 (dd, J=8.0, 12.7 Hz, 1H), 1.49 (d, J=13.1 Hz, 1H), 1.37 (d, J=13.0 Hz, 1H).

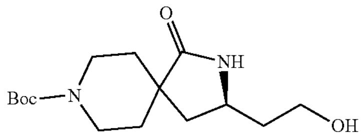 [SMILES: CC(C)(C)OC(=O)N1CCC2(CC1)C[C@H](CCO)NC2=O]

Preparation of tert-butyl (R)-3-(2-hydroxyethyl)-1-oxo-2,8-diazaspiro[4.5]decane-8-carboxylate: To a solution of (R)-3-(2-hydroxyethyl)-2,8-diazaspiro[4.5]decan-1-one (2.2 g, 11.0 mmol, 1.0 equiv.) and triethylamine (1.12 g, 11.0 mmol, 1.0 equiv.) in methylene chloride (113 mL) and methanol (3 mL) was added di-tert-butyl dicarbonate (2.4 g, 11.0 mmol, 1.0 equiv.). The resulting solution was allowed to stir at 23° C. overnight before being concentrated in vacuo to produce a crude product that was used in the next step without further purification. $^1H$ NMR (400 MHz, $CDCl_3$) δ 6.93 (b, 1H), 4.15-3.55 (b, 6H), 3.15-2.74 (m, 2H), 2.29 (dd, J=6.7, 12.5H, 1H), 2.00-1.82 (m, 1H), 1.80-1.60 (m, 3H), 1.58-1.29 (m, 12).

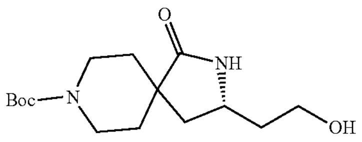 [SMILES: CC(C)(C)OC(=O)N1CCC2(CC1)C[C@@H](CCO)NC2=O]

Preparation of tert-butyl (S)-3-(2-hydroxyethyl)-1-oxo-2,8-diazaspiro[4.5]decane-8-carboxylate: The title compound was prepared according to the procedure for (tert-butyl (R)-3-(2-hydroxyethyl)-1-oxo-2,8-diazaspiro[4.5]decane-8-carboxylate, except (S)-3-(2-hydroxyethyl)-2,8-diazaspiro[4.5]decan-1-one was substituted for (R)-3-(2-hydroxyethyl)-2,8-diazaspiro[4.5]decan-1-one. $^1$H NMR (400 MHz, $CDCl_3$) δ 6.53 (b, 1H), 4.06-3.56 (b, 6H), 3.05-2.77 (m, 2H), 2.25 (dd, J=6.7, 12.9H, 1H), 1.93-1.80 (m, 1H), 1.74-1.56 (m, 3H), 1.52-1.24 (m, 12).

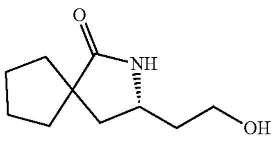 [SMILES: O=C1N[C@H](CCO)CC12CCCC2]

Preparation of (S)-3-(2-hydroxyethyl)-2-azaspiro[4.4]nonan-1-one: To a round bottom flask was added 10% Pd/C (0.60 g, 20% by wieght) followed by a solution of tert-butyl (S)-3-(2-((tert-butyldimethylsilyl)oxy)ethyl)-1-oxo-2-azaspiro[4.4]non-7-ene-2-carboxylate (0.30 g, 0.758 mmol, 1 equiv.) in methanol (7.5 mL). The reaction was put under $H_2$ (1 atm) using a balloon and stirred at 23° C. for 4 hrs. The reaction was filtered through a plug of Celite and concentrated filtrate under reduced pressure to give a crude intermediate.

A 6M HCl in methanol solution was prepared via the addition of acetyl chloride (3 mL) to methanol (7.5 mL). The crude intermediate was dissolved in the prepared 6M methanolic HCl solution (7.5 mL) and stirred at 23° C. for 30 minutes before being diluted with methanol and concentrated in vacuo to produce a crude product was used in the next step without further purification. $^1$H NMR (400 MHz, $CDCl_3$) δ 6.95 (b, 1H), 3.99 (b, 1H), 3.76 (m, 1H), 3.64 (m, 2H), 2.09 (dd, J=6.6, 12.6 Hz, 1H), 2.01 (m, 1H), 1.81-1.45 (m, 9H), 1.37 (m, 1H).

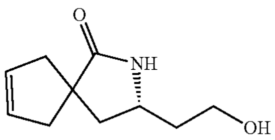 [SMILES: O=C1N[C@H](CCO)CC12CC=CC2]

Preparation of (S)-3-(2-hydroxyethyl)-2-azaspiro[4.4]non-7-en-1-one: A 6M HCl in methanol solution was prepared via the addition of acetyl chloride (3 mL) to methanol (7.5 mL). tert-Butyl (S)-3-(2-((tert-butyldimethylsilyl)oxy)ethyl)-1-oxo-2-azaspiro[4.4]non-7-ene-2-carboxylate (0.30 g, 0.758 mmol, 1 equiv.) was dissolved in the prepared 6M methanolic HCl solution (7.5 mL) and stirred at 23° C. for ~30 minutes before being diluted with methanol and concentrated in vacuo to produce a crude product was used in the next step without further purification. $^1$H NMR (400 MHz, $CDCl_3$) δ 7.04 (b, 1H), 5.62 (m, 1H), 5.52 (m, 1H), 3.83-3.71 (m, 2H), 3.70-3.57 (m, 2H), 2.90 (dp, J=2.4, 16.6 Hz, 1H), 2.58 (dp, J=2.4, 16.3 Hz, 1H), 2.33 (d, J=16.4 Hz, 1H), 2.22 (dd, J=6.2, 12.4 Hz, 1H), 2.14 (d, J=16.2 Hz, 1H), 1.71-1.54 (m, 3H).

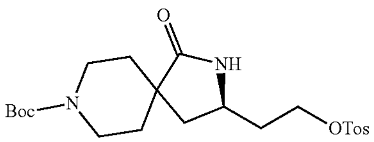

Preparation of tert-butyl (R)-1-oxo-3-(2-(tosyloxy)ethyl)-2,8-diazaspiro[4.5]decane-8-carboxylate: To a cooled solution of tert-butyl (R)-3-(2-hydroxyethyl)-1-oxo-2,8-diazaspiro[4.5]decane-8-carboxylate (3.2 g, 10.7 mmol, 1.0 equiv.) and triethylamine (2.16 g, 21.4 mmol, 2.0 equiv.) in tetrahydrofuran/methylene chloride (46 mL:46 mL) at 0° C. was added 4-toluenesulfonyl chloride (3.06 g, 16 mmol, 1.5 equiv.) followed by 4-dimethylaminopyridine (0.131 g, 1.07 mmol, 0.2 equiv.). The resulting reaction mixture was stirred at 0° C. for 5 minutes before being warmed to 23° C. and allowed to stir overnight. Then, the reaction mixture was diluted with dichloromethane (50 mL) and washed with deionized $H_2O$ (1×50 mL). The aqueous layer was back-washed with methylene chloride (2×50 mL). The combined organic phase was dried over $Na_2SO_4$ and concentrated in vacuo to give a crude product which was further purified by HPLC ($CH_3CN/H_2O$, 0.1% Formic acid), 0%~100%). $^1$H NMR (400 MHz, $CDCl_3$) δ 7.81 (d, J=8.3 Hz, 2H), 7.38 (d, J=8.2 Hz, 2H), 6.11 (b, 1H), 4.14 (m, 2H), 4.07-3.89 (b, 2H), 3.72 (p, J=6.8 Hz, 1H), 2.97 (m, 2H), 2.48 (s, 3H), 2.28 (dd, J=6.9, 12.8 Hz, 1H), 1.97-1.83 (m, 3H), 1.75 (m, 1H), 1.56-1.30 (m, 12H).

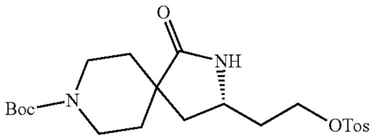

Preparation of tert-butyl (S)-1-oxo-3-(2-(tosyloxy)ethyl)-2,8-diazaspiro[4.5]decane-8-carboxylate: The title compound was prepared according to the procedure for tert-butyl (R)-1-oxo-3-(2-(tosyloxy)ethyl)-2,8-diazaspiro[4.5]decane-8-carboxylate, except tert-butyl (S)-3-(2-hydroxyethyl)-1-oxo-2,8-diazaspiro[4.5]decane-8-carboxylate was substituted for tert-butyl (R)-3-(2-hydroxyethyl)-1-oxo-2,8-diazaspiro[4.5]decane-8-carboxylate. $^1$H NMR (400 MHz, $CDCl_3$) δ 7.77 (d, J=8.3 Hz, 2H), 7.34 (d, J=8.2 Hz, 2H), 7.05 (b, 1H), 4.11 (m, 2H), 4.05-3.78 (b, 2H), 3.68 (p, J=6.8 Hz, 1H), 2.92 (m, 2H), 2.43 (s, 3H), 2.22 (dd, J=6.8, 12.9 Hz, 1H), 1.93-1.76 (m, 3H), 1.68 (m, 1H), 1.53-1.24 (m, 12H).

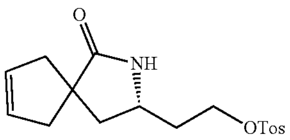

Preparation of (S)-2-(1-oxo-2-azaspiro[4.4]non-7-en-3-yl)ethyl 4-methylbenzenesulfonate: To a cooled solution of (S)-3-(2-hydroxyethyl)-2-azaspiro[4.4]non-7-en-1-one (0.140 g, 0.758 mmol, 1.0 equiv.) and N-methylimidazole (0.312 g, 3.8 mmol, 5.0 equiv.) in methylene chloride (2.5 mL) at 0° C. was added a solution of 4-toluenesulfonyl chloride (0.217 g, 1.14 mmol, 1.5 equiv.) in methylene chloride (3.5 mL). The resulting reaction mixture was stirred at 0° C. for 5 min utesbefore being warmed to 23° C. and allowed to stir overnight. Then, the reaction mixture was quenched with 1N HCl (1×5 mL) and extracted with methylene chloride (3×15 mL). The combined organic phase was dried over $Na_2SO_4$ and concentrated in vacuo to give a crude product which was further by column chromatography (Ethyl acetate/Hexanes, 40%~100%). $^1$H NMR (400 MHz, $CDCl_3$) δ 7.71 (d, J=8.3 Hz, 2H), 7.27 (d, J=8.1 Hz, 2H), 6.97 (b, 1H), 5.58 (m, 1H), 5.51 (m, 1H), 4.04 (m, 2H), 3.58 (p, J=6.8 Hz, 1H), 2.86 (dp, J=2.3, 16.5 Hz, 1H), 2.58 (dp, J=2.3, 16.3 Hz, 1H), 2.37 (s, 3H), 2.25 (d, J=16.1 Hz, 1H), 2.19-2.04 (m, 2H), 1.86-1.67 (m, 2H), 1.54 (dd, J=7.7, 12.5 Hz, 1H).

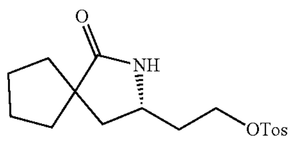

Preparation of (S)-2-(1-oxo-2-azaspiro[4.4]nonan-3-yl) ethyl 4-methylbenzenesulfonate: The title compound was prepared according to the procedure for (S)-2-(1-oxo-2-azaspiro[4.4]non-7-en-3-yl)ethyl 4-methylbenzenesulfonate, except (S)-3-(2-hydroxyethyl)-2-azaspiro[4.4]nonan-1-one was substituted for (S)-3-(2-hydroxyethyl)-2-azaspiro[4.4]non-7-en-1-one. $^1$H NMR (400 MHz, $CDCl_3$) δ 7.78 (d, J=8.2 Hz, 2H), 7.34 (d, J=8.1 Hz, 2H), 6.87 (b, 1H), 4.10 (m, 2H), 3.60 (p, J=6.7 Hz, 1H), 2.44 (s, 3H), 2.12-1.97 (m, 2H), 1.94-1.68 (m, 5H), 1.66-1.45 (m, 4H), 1.40 (m, 1H).

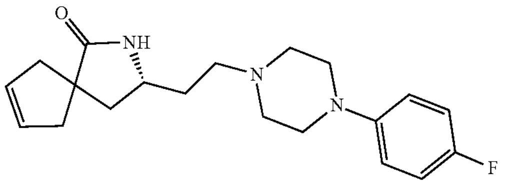 [SMILES: O=C1N[C@H](CCN2CCN(c3ccc(F)cc3)CC2)CC12CC=CC2]

Preparation of (S)-3-(2-(4-(4-fluorophenyl)piperazin-1-yl)ethyl)-2-azaspiro[4.4]non-7-en-1-one: To a small vial was added (S)-2-(1-oxo-2-azaspiro[4.4]non-7-en-3-yl)ethyl 4-methylbenzenesulfonate (50 mg, 0.15 mmol, 1 equiv.) and 1-(4-fluorophenyl)piperazine (57 mg, 0.31 mmol, 2.1 equiv.) then both were dissolved in acetonitrile (1.5 mL). Then $K_2CO_3$ (52 mg, 0.37 mmol, 2.5 equiv.) was added, the reaction was allowed to stir at 80° C. overnight, and then cooled to 23° C. The mixture was filtered, washed with acetonitrile and filtrate was concentrated in vacuo to give a crude product which was by further purified by column chromatography (MeOH/methylene chloride, 0%~10%). $^1$H NMR (400 MHz, $CDCl_3$) δ 7.00-6.82 (m, 5H), 5.70 (m, 1H), 5.59 (m, 1H), 3.63 (m, 1H), 3.13 (t, J=4.9 Hz, 4H), 3.02 (dp, J=2.5, 16.5 Hz, 1H), 2.76-2.62 (m, 3H), 2.61-2.43 (m, 4H), 2.39 (d, J=16.6 Hz, 1H), 2.29 (dd, J=6.1, 12.4 Hz, 1H), 2.20 (d, J=16.4 Hz, 1H), 1.80-1.57 (m, 3H). LC/MS [M+H]=m/z 344.2

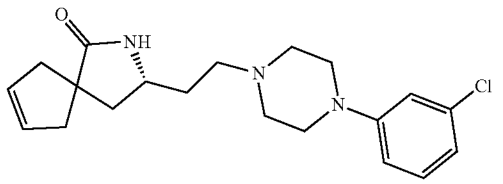 [SMILES: O=C1N[C@H](CCN2CCN(c3cccc(Cl)c3)CC2)CC12CC=CC2]

Preparation of (S)-3-(2-(4-(3-chlorophenyl)piperazin-1-yl)ethyl)-2-azaspiro[4.4]non-7-en-1-one: The title compound was prepared according to the procedure for (S)-3-(2-(4-(4-fluorophenyl)piperazin-1-yl)ethyl)-2-azaspiro[4.4]non-7-en-1-one, except 1-(3-chlorophenyl)piperazine was substituted for 1-(4-fluorophenyl)piperazine. $^1$H NMR (400 MHz, $CDCl_3$) δ 7.08 (t, J=8.0 Hz, 1H), 6.79 (t, J=2.1 Hz, 1H), 6.77-6.65 (m, 3H). 5.60 (m, 1H), 5.51 (m, 1H), 3.56 (m, 1H), 3.13 (t, J=5.1 Hz, 4H), 2.95 (dp, J=2.4, 16.6 Hz, 1H), 2.68-2.54 (m, 3H), 2.54-2.35 (m, 4H), 2.31 (d, J=16.0 Hz, 1H), 2.22 (dd, J=6.1, 12.3 Hz, 1H), 2.13 (d, J=16.5 Hz, 1H), 1.72-1.49 (m, 3H). LC/MS [M+H]=m/z 360.2.

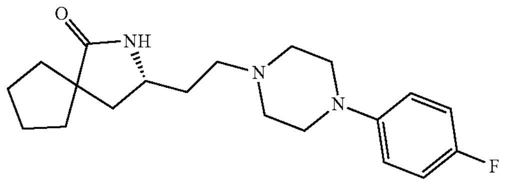 [SMILES: O=C1N[C@H](CCN2CCN(c3ccc(F)cc3)CC2)CC12CCCC2]

Preparation of (S)-3-(2-(4-(4-fluorophenyl)piperazin-1-yl)ethyl)-2-azaspiro[4.4]nonan-1-one: The title compound was prepared according to the procedure for (S)-3-(2-(4-(4-fluorophenyl)piperazin-1-yl)ethyl)-2-azaspiro[4.4]non-7-en-1-one, except (S)-2-(1-oxo-2-azaspiro[4.4]nonan-3-yl) ethyl 4-methylbenzenesulfonate was substituted for (S)-2-(1-oxo-2-azaspiro[4.4]non-7-en-3-yl)ethyl 4-methylbenzenesulfonate. $^1$H NMR (400 MHz, $CDCl_3$) δ 7.00-6.91 (m, 2H), 6.90-6.74 (m, 3H), 3.59 (m, 1H), 3.12 (t, J=4.9 Hz, 4H), 2.69 (m, 2H), 2.60-2.44 (m, 4H), 2.19-2.06 (m, 2H), 1.86-1.51 (m, 9H), 1.44 (m, 1H). LC/MS [M+H] =m/z 346.2.

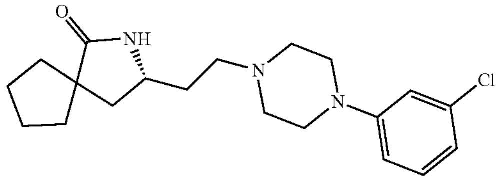 [SMILES: O=C1N[C@H](CCN2CCN(c3cccc(Cl)c3)CC2)CC12CCCC2]

Preparation of (S)-3-(2-(4-(3-chlorophenyl)piperazin-1-yl)ethyl)-2-azaspiro[4.4]nonan-1-one: The title compound was prepared according to the procedure for (S)-3-(2-(4-(4-fluorophenyl)piperazin-1-yl)ethyl)-2-azaspiro[4.4]non-7-en-1-one, except (S)-2-(1-oxo-2-azaspiro[4.4]nonan-3-yl) ethyl 4-methylbenzenesulfonate was substituted for (S)-2-(1-oxo-2-azaspiro[4.4]non-7-en-3-yl)ethyl 4-methylbenzenesulfonate and 1-(3-chlorophenyl)piperazine was substituted for 1-(4-fluorophenyl)piperazine. $^1$H NMR (400 MHz, $CDCl_3$) δ 7.16 (t, J=8.0 Hz, 1H), 6.88 (t, J=2.1 Hz, 1H), 6.81 (dd, J=1.7, 7.8 Hz, 1H), 6.78 (dd, J=2.3, 8.3 Hz, 1H), 6.69 (b, 1H), 3.60 (m, 1H), 3.22 (t, J=5.0 Hz, 4H), 2.69 (m, 2H), 2.61-2.39 (m, 4H), 2.23-2.08 (m, 2H), 1.87-1.55 (m, 9H), 1.46 (m, 1H). LC/MS [M+H]=m/z 362.2.

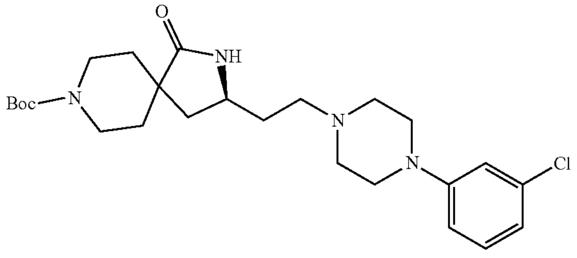 [SMILES: CC(C)(C)OC(=O)N1CCC2(CC1)C[C@H](CCN1CCN(c3cccc(Cl)c3)CC1)NC2=O]

Preparation of tert-butyl (R)-3-(2-(4-(3-chlorophenyl)piperazin-1-yl)ethyl)-1-oxo-2,8-diazaspiro[4.5]decane-8-carboxylate: The title compound was prepared according to the procedure for (S)-3-(2-(4-(4-fluorophenyl)piperazin-1-yl)ethyl)-2-azaspiro[4.4]non-7-en-1-one, except tert-butyl (R)-1-oxo-3-(2-(tosyloxy)ethyl)-2,8-diazaspiro[4.5]decane-8-carboxylate was substituted for (S)-2-(1-oxo-2-azaspiro[4.4]non-7-en-3-yl)ethyl 4-methylbenzenesulfonate and 1-(3-chlorophenyl)piperazine was substituted for 1-(4-fluorophenyl)piperazine. $^1H$ NMR (400 MHz, $CDCl_3$) δ 7.15 (t, J=7.9 Hz, 1H), 7.06 (b, 1H), 6.84 (t, J=2.0 Hz, 1H), 6.79 (dd, J=1.6, 7.6 Hz, 1H), 6.74 (dd, J=2.1, 8.3 Hz, 1H), 4.13-3.82 (b, 2H), 3.63 (p, J=7.0 Hz, 1H), 3.20 (t, J=4.8 Hz, 4H), 3.10-2.83 (m, 2H), 2.67 (m, 2H), 2.60-2.40 (m, 4H), 2.29 (dd, J=6.7, 12.8 Hz, 1H), 1.96 (m, 1H), 1.80-1.62 (m, 3H), 1.58-1.30 (m, 12H). LC/MS [M+H]=m/z 478.2.

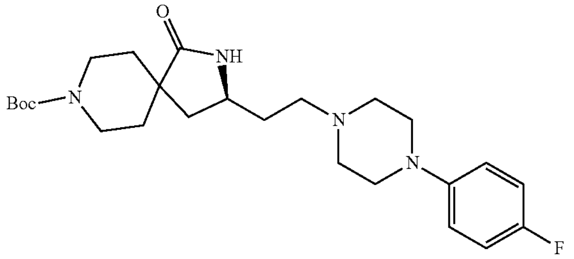 [SMILES: CC(C)(C)OC(=O)N1CCC2(CC1)C[C@H](CCN1CCN(c3ccc(F)cc3)CC1)NC2=O]

Preparation of tert-butyl (R)-3-(2-(4-(4-fluorophenyl)piperazin-1-yl)ethyl)-1-oxo-2,8-diazaspiro[4.5]decane-8-carboxylate: The title compound was prepared according to the procedure for (S)-3-(2-(4-(4-fluorophenyl)piperazin-1-yl)ethyl)-2-azaspiro[4.4]non-7-en-1-one, except tert-butyl (R)-1-oxo-3-(2-(tosyloxy)ethyl)-2,8-diazaspiro[4.5]decane-8-carboxylate was substituted for (S)-2-(1-oxo-2-azaspiro[4.4]non-7-en-3-yl)ethyl 4-methylbenzenesulfonate. $^1H$ NMR (400 MHz, $CDCl_3$) δ 7.02 (b, 1H), 6.97-6.90 (m, 2H), 6.90-6.80 (m, 2H), 4.23-3.78 (b, 2H), 3.63 (p, J=6.5 Hz, 1H), 3.12 (t, J=4.7 Hz, 4H), 3.07-2.82 (m, 2H), 2.68 (m, 2H), 2.60-2.40 (m, 4H), 2.28 (dd, J=6.7, 12.7 Hz, 1H), 1.95 (m, 1H), 1.80-1.61 (m, 3H), 1.58-1.29 (m, 12H). LC/MS [M+H]=m/z 461.2.

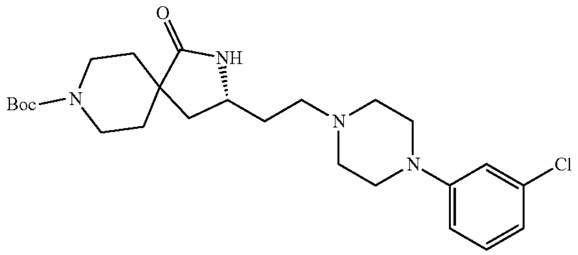 [SMILES: CC(C)(C)OC(=O)N1CCC2(CC1)C[C@@H](CCN1CCN(c3cccc(Cl)c3)CC1)NC2=O]

Preparation of tert-butyl (S)-3-(2-(4-(3-chlorophenyl)piperazin-1-yl)ethyl)-1-oxo-2,8-diazaspiro[4.5]decane-8-carboxylate: The title compound was prepared according to the procedure for (S)-3-(2-(4-(4-fluorophenyl)piperazin-1-yl)ethyl)-2-azaspiro[4.4]non-7-en-1-one, except tert-butyl (S)-1-oxo-3-(2-(tosyloxy)ethyl)-2,8-diazaspiro[4.5]decane-8-carboxylate was substituted for (S)-2-(1-oxo-2-azaspiro[4.4]non-7-en-3-yl)ethyl 4-methylbenzenesulfonate and 1-(3-chlorophenyl)piperazine was substituted for 1-(4-fluorophenyl)piperazine. $^1H$ NMR (400 MHz, $CDCl_3$) δ 7.14 (t, J=8.0 Hz, 1H), 7.04 (b, 1H), 6.85 (t, J=2.0 Hz, 1H), 6.79 (dd, J=1.6, 7.7 Hz, 1H), 6.76 (dd, J=2.1, 8.3 Hz, 1H), 4.13-3.83 (b, 2H), 3.63 (p, J=7.0 Hz, 1H), 3.19 (t, J=4.8 Hz, 4H), 3.09-2.80 (m, 2H), 2.67 (m, 2H), 2.60-2.39 (m, 4H), 2.29 (dd, J=6.6, 12.8 Hz, 1H), 1.95 (m, 1H), 1.80-1.63 (m, 3H), 1.57-1.30 (m, 12H). LC/MS [M+H]=m/z 478.2

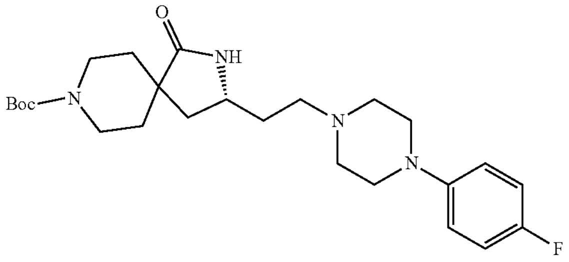 [SMILES: CC(C)(C)OC(=O)N1CCC2(CC1)C[C@@H](CCN1CCN(c3ccc(F)cc3)CC1)NC2=O]

Preparation of tert-butyl (S)-3-(2-(4-(4-fluorophenyl)piperazin-1-yl)ethyl)-1-oxo-2,8-diazaspiro[4.5]decane-8-carboxylate: The title compound was prepared according to the procedure for (S)-3-(2-(4-(4-fluorophenyl)piperazin-1-yl)ethyl)-2-azaspiro[4.4]non-7-en-1-one, except tert-butyl (S)-1-oxo-3-(2-(tosyloxy)ethyl)-2,8-diazaspiro[4.5]decane-8-carboxylate was substituted for (S)-2-(1-oxo-2-azaspiro[4.4]non-7-en-3-yl)ethyl 4-methylbenzenesulfonate. $^1H$ NMR (400 MHz, $CDCl_3$) δ 7.01 (b, 1H), 6.97-6.89 (m, 2H), 6.89-6.80 (m, 2H), 4.21-3.76 (b, 2H), 3.63 (p, J=6.5 Hz, 1H), 3.11 (t, J=4.7 Hz, 4H), 3.06-2.82 (m, 2H), 2.69 (m, 2H), 2.61-2.41 (m, 4H), 2.29 (dd, J=6.7, 12.8 Hz, 1H), 1.94 (m, 1H), 1.80-1.60 (m, 3H), 1.57-1.28 (m, 12H). LC/MS [M+H]=m/z 461.

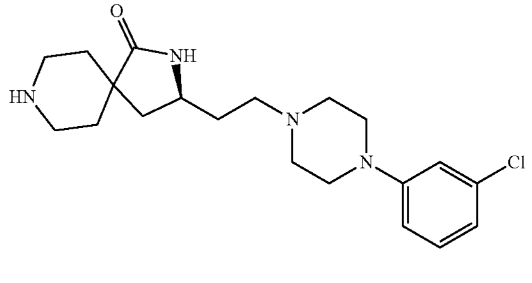 [SMILES: O=C1N[C@@H](CCN2CCN(c3cccc(Cl)c3)CC2)CC12CCNCC2]

Preparation of (R)-3-(2-(4-(3-chlorophenyl)piperazin-1-yl)ethyl)-2,8-diazaspiro[4.5]decan-1-one: A 6M HCl in methanol solution was prepared via the addition of acetyl chloride (1.2 mL) to methanol (3 mL). tert-Butyl (R)-3-(2-(4-(3-chlorophenyl)piperazin-1-yl)ethyl)-1-oxo-2,8-diazaspiro[4.5]decane-8-carboxylate (0.127 g, 0.266 mmol, 1.0 equiv.) was dissolved in the prepared 6M methanolic HCl solution (3 mL) and let stir at 23° C. for 30 minutes before being diluted with methanol and concentrated in vacuo to produce a crude product as an HCl salt. The product was free based by stirring with Amberlite IRN-78 base resin in methanol (~10 mL) for 15 minutes followed by filtration and concentrated in vacuo to produce a crude product that was used in the next step without further purification. $^1$H NMR (400 MHz, MeOD) δ 7.21 (t, J=8.3 Hz, 1H), 6.95 (s, 1H), 6.88 (d, J=8.5 Hz, 1H), 6.81 (d, J=7.7 Hz, 1H), 3.68 (m, 1H), 3.29-3.13 (m, 4H), 3.01 (m, 2H), 2.81-2.38 (m, 9H), 1.93 (m, 1H), 1.86-1.64 (m, 3H), 1.60 (dd, J=7.6, 12.7 Hz, 1H), 1.49 (d, J=13.2 Hz, 1H), 1.38 (d, J=12.8 Hz, 1H). LC/MS [M+H]=m/z 377.

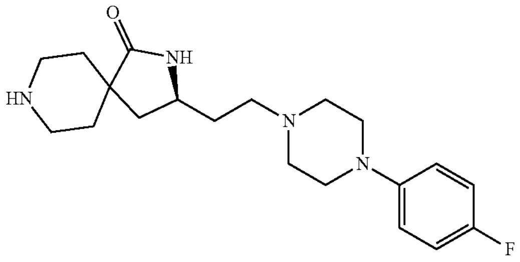 [SMILES: O=C1N[C@@H](CCN2CCN(c3ccc(F)cc3)CC2)CC12CCNCC2]

Preparation of (R)-3-(2-(4-(4-fluorophenyl)piperazin-1-yl)ethyl)-2,8-diazaspiro[4.5]decan-1-one: The title compound was prepared according to the procedure for (R)-3-(2-(4-(3-chlorophenyl)piperazin-1-yl)ethyl)-2,8-diazaspiro[4.5]decan-1-one, except tert-butyl (R)-3-(2-(4-(4-fluorophenyl)piperazin-1-yl)ethyl)-1-oxo-2,8-diazaspiro[4.5]decane-8-carboxylate was substituted for tert-butyl (R)-3-(2-(4-(3-chlorophenyl)piperazin-1-yl)ethyl)-1-oxo-2,8-diazaspiro[4.5]decane-8-carboxylate. $^1$H NMR (400 MHz, MeOD) δ 7.08-6.92 (m, 4H), 3.68 (m, 1H), 3.23-3.09 (m, 4H), 3.01 (m, 2H), 2.81-2.38 (m, 9H), 1.93 (m, 1H), 1.86-1.62 (m, 3H), 1.60 (dd, J=7.6, 12.5 Hz, 1H), 1.48 (d, J=13.5 Hz, 1H), 1.37 (d, J=13.5 Hz, 1H). LC/MS [M+H]=m/z 361.

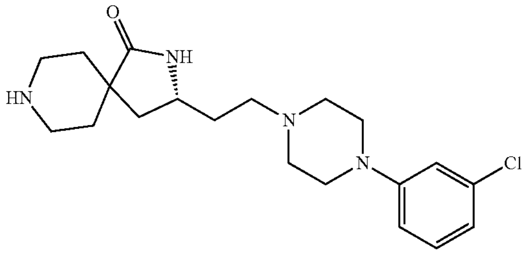 [SMILES: O=C1N[C@H](CCN2CCN(c3cccc(Cl)c3)CC2)CC12CCNCC2]

Preparation of (S)-3-(2-(4-(3-chlorophenyl)piperazin-1-yl)ethyl)-2,8-diazaspiro[4.5]decan-1-one: The title compound was prepared according to the procedure for (R)-3-(2-(4-(3-chlorophenyl)piperazin-1-yl)ethyl)-2,8-diazaspiro[4.5]decan-1-one, except tert-butyl (S)-3-(2-(4-(3-chlorophenyl)piperazin-1-yl)ethyl)-2,8-diazaspiro[4.5]decan-1-one was substituted for tert-butyl (R)-3-(2-(4-(3-chlorophenyl)piperazin-1-yl)ethyl)-1-oxo-2,8-diazaspiro[4.5]decane-8-carboxylate. $^1$H NMR (400 MHz, MeOD) δ 7.20 (t, J=8.2 Hz, 1H), 6.94 (s, 1H), 6.88 (d, J=8.5 Hz, 1H), 6.80 (d, J=7.7 Hz, 1H), 3.68 (m, 1H), 3.28-3.13 (m, 4H), 3.02 (m, 2H), 2.80-2.36 (m, 9H), 1.93 (m, 1H), 1.85-1.64 (m, 3H), 1.59 (dd, J=7.6, 12.7 Hz, 1H), 1.48 (d, J=13.2 Hz, 1H), 1.37 (d, J=12.8 Hz, 1H). LC/MS [M+H]=m/z 377.

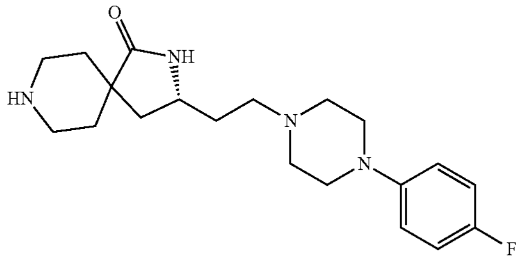 [SMILES: O=C1N[C@H](CCN2CCN(c3ccc(F)cc3)CC2)CC12CCNCC2]

Preparation of (S)-3-(2-(4-(4-fluorophenyl)piperazin-1-yl)ethyl)-2,8-diazaspiro[4.5]decan-1-one: The title compound was prepared according to the procedure for (R)-3-(2-(4-(3-chlorophenyl)piperazin-1-yl)ethyl)-2,8-diazaspiro[4.5]decan-1-one, except tert-butyl (S)-3-(2-(4-(4-fluorophenyl)piperazin-1-yl)ethyl)-1-oxo-2,8-diazaspiro[4.5]decane-8-carboxylate was substituted for tert-butyl (R)-3-(2-(4-(3-chlorophenyl)piperazin-1-yl)ethyl)-1-oxo-2,8-diazaspiro[4.5]decane-8-carboxylate. $^1$H NMR (400 MHz, MeOD) δ 7.07-6.91 (m, 4H), 3.68 (m, 1H), 3.22-3.09 (m, 4H), 3.02 (m, 2H), 2.81-2.37 (m, 9H), 1.93 (m, 1H), 1.86-1.63 (m, 3H), 1.59 (dd, J=7.6, 12.5 Hz, 1H), 1.48 (d, J=13.5 Hz, 1H), 1.38 (d, J=13.5 Hz, 1H). LC/MS [M+H]=m/z 361.2.

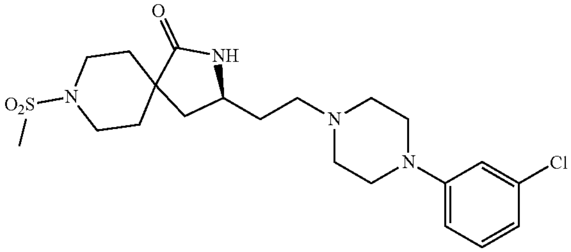 [SMILES: CS(=O)(=O)N1CCC2(CC1)C[C@H](CCN1CCN(c3cccc(Cl)c3)CC1)NC2=O]

Preparation of (R)-3-(2-(4-(3-chlorophenyl)piperazin-1-yl)ethyl)-8-(methylsulfonyl)-2,8-diazaspiro[4.5]decan-1-one: A solution of (R)-3-(2-(4-(3-chlorophenyl)piperazin-1-yl)ethyl)-2,8-diazaspiro[4.5]decan-1-one (28 mg, 0.074 mmol, 1 equiv.), dichloromethane (0.85 mL) and triethylamine (15.7 mg, 0.155 mmol, 2.1 eq.) was cooled to 0° C. before methanesulfonyl chloride (12.7 mg. 0.111 mmol, 1.5 equiv.) was added to the solution. The reaction solution was allowed to warm to 23° C. and stir for 15 minutes. The reaction was diluted with methanol (~2 mL), concentrated in vacuo and further purified by flash column chromatography (methanol/dichloromethane, 0%~10%). $^1$H NMR (400 MHz, $CDCl_3$) δ 7.17 (t, J=8.2 Hz, 1H), 6.88 (t, J=2.1 Hz, 1H), 6.83 (dd, J=1.7, 7.8 Hz, 1H), 6.81-6.72 (m, 2H), 3.81-3.61 (m, 2H), 3.50 (m, 1H), 3.32-3.11 (m, 6H), 2.82 (s, 3H), 2.73 (m, 2H), 2.66-2.42 (m, 4H), 2.20 (dd, J=6.5, 12.7 Hz, 1H), 2.04 (m, 1H), 1.96 (m, 1H), 1.79-1.50 (m, 5H); MS (LC/MS, M+H$^+$): 456.2.

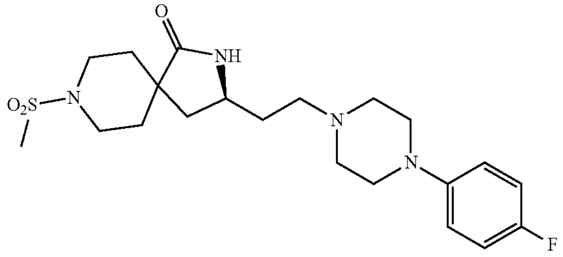 [SMILES: CS(=O)(=O)N1CCC2(CC1)C[C@H](CCN1CCN(c3ccc(F)cc3)CC1)NC2=O]

Preparation of (R)-3-(2-(4-(4-fluorophenyl)piperazin-1-yl)ethyl)-8-(methylsulfonyl)-2,8-diazaspiro[4.5]decan-1-one: The title compound was prepared according to the procedure for (R)-3-(2-(4-(3-chlorophenyl)piperazin-1-yl)ethyl)-8-(methylsulfonyl)-2,8-diazaspiro[4.5]decan-1-one, except (R)-3-(2-(4-(4-fluorophenyl)piperazin-1-yl)ethyl)-2,8-diazaspiro[4.5]decan-1-one was substituted for (R)-3-(2-(4-(3-chlorophenyl)piperazin-1-yl)ethyl)-2,8-diazaspiro[4.5]decan-1-one. $^1$H NMR (400 MHz, $CDCl_3$) δ 7.07-6.93 (m, 2H), 6.92-6.84 (m, 2H), 6.80 (b, 1H), 3.80-3.62 (m, 2H), 3.49 (m, 1H), 3.27 (m, 1H), 3.22-3.08 (m, 5H), 2.82 (s, 3H), 2.75 (m, 2H), 2.66-2.43 (m, 4H), 2.20 (dd, J=6.4, 12.7 Hz, 1H), 2.04 (m, 1H), 1.96 (m, 1H), 1.79-1.48 (m, 5H); MS (LC/MS, M+H$^+$): 439.2.

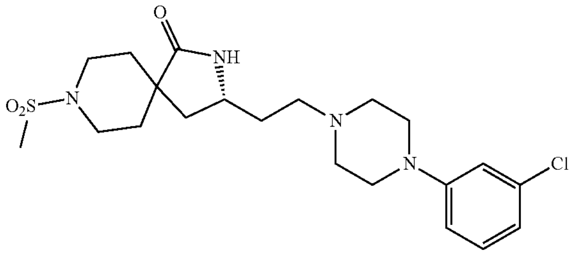 [SMILES: CS(=O)(=O)N1CCC2(CC1)C[C@@H](CCN1CCN(c3cccc(Cl)c3)CC1)NC2=O]

Preparation of (S)-3-(2-(4-(3-chlorophenyl)piperazin-1-yl)ethyl)-8-(methylsulfonyl)-2,8-diazaspiro[4.5]decan-1-one: The title compound was prepared according to the procedure for (R)-3-(2-(4-(3-chlorophenyl)piperazin-1-yl)ethyl)-8-(methylsulfonyl)-2,8-diazaspiro[4.5]decan-1-one, except (S)-3-(2-(4-(3-chlorophenyl)piperazin-1-yl)ethyl)-2,8-diazaspiro[4.5]decan-1-one was substituted for (R)-3-(2-(4-(3-chlorophenyl)piperazin-1-yl)ethyl)-2,8-diazaspiro[4.5]decan-1-one. $^1$H NMR (400 MHz, $CDCl_3$) δ 7.09 (t, J=8.1 Hz, 1H), 6.79 (t, J=2.1 Hz, 1H), 6.74 (dd, J=1.7, 7.7 Hz, 1H), 6.72-6.65 (m, 2H), 3.72-3.53 (m, 2H), 3.41 (m, 1H), 3.23-3.04 (m, 6H), 2.73 (s, 3H), 2.64 (m, 2H), 2.57-2.33 (m, 4H), 2.12 (dd, J=6.4, 12.8 Hz, 1H), 1.95 (m, 1H), 1.88 (m, 1H), 1.70-1.42 (m, 5H); MS (LC/MS, M+H$^+$): 456.2.

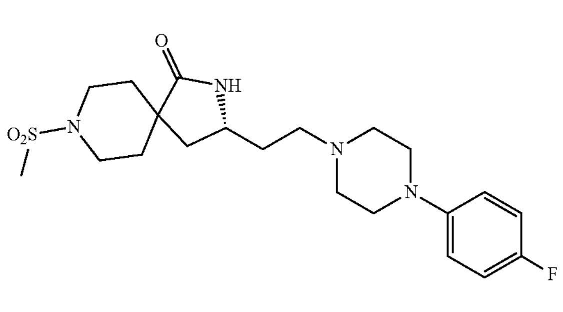 [SMILES: CS(=O)(=O)N1CCC2(CC1)C[C@@H](CCN1CCN(c3ccc(F)cc3)CC1)NC2=O]

Preparation of (S)-3-(2-(4-(4-fluorophenyl)piperazin-1-yl)ethyl)-8-(methylsulfonyl)-2,8-diazaspiro[4.5]decan-1-one: The title compound was prepared according to the procedure for (R)-3-(2-(4-(3-chlorophenyl)piperazin-1-yl)ethyl)-8-(methylsulfonyl)-2,8-diazaspiro[4.5]decan-1-one, except (S)-3-(2-(4-(4-fluorophenyl)piperazin-1-yl)ethyl)-2,8-diazaspiro[4.5]decan-1-one was substituted for (R)-3-(2-(4-(3-chlorophenyl)piperazin-1-yl)ethyl)-2,8-diazaspiro[4.5]decan-1-one. $^1$H NMR (400 MHz, $CDCl_3$) δ 6.94-6.84 (m, 2H), 6.83-6.76 (m, 2H), 6.74 (b, 1H), 3.71-3.54 (m, 2H), 3.41 (m, 1H), 3.17 (m, 1H), 3.13-2.99 (m, 5H), 2.73 (s, 3H), 2.65 (m, 2H), 2.57-2.34 (m, 4H), 2.11 (dd, J=6.4, 12.7 Hz, 1H), 1.95 (m, 1H), 1.87 (m, 1H), 1.70-1.39 (m, 5H); MS (LC/MS, M+H$^+$): 439.2

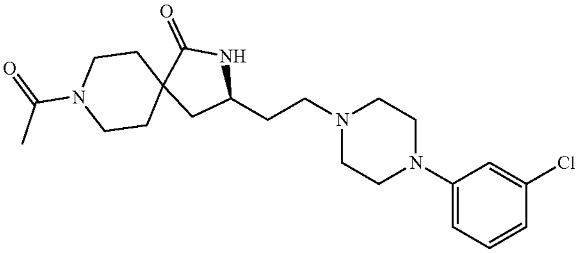 [SMILES: CC(=O)N1CCC2(CC1)C[C@H](CCN1CCN(c3cccc(Cl)c3)CC1)NC2=O]

Preparation of (R)-8-acetyl-3-(2-(4-(3-chlorophenyl)piperazin-1-yl)ethyl)-2,8-diazaspiro[4.5]decan-1-one: A solution of(R)-3-(2-(4-(3-chlorophenyl)piperazin-1-yl)ethyl)-2,8-diazaspiro[4.5]decan-1-one (21 mg, 0.056 mmol, 1 equiv.), dichloromethane (0.725 mL) and triethylamine (12 mg, 0.118 mmol, 2.1 eq.) was cooled to 0° C. before acetyl chloride (12.7 mg. 0.057 mmol, 1.01 equiv.) was added to the solution. The reaction solution was allowed to warm to 23° C. and stir for 15 minutes. The reaction was diluted with methanol (~2 mL), concentrated in vacuo and further purified by flash column chromatography (methanol/methylene chloride, 0%~10%). $^1$H NMR (400 MHz, $CDCl_3$) δ 7.09 (t, J=8.1 Hz, 1H), 6.80 (t, J=2.2 Hz, 1H), 6.77-6.65 (m, 3H), 4.26 (dt, J=4.8, 13.4 Hz, 0.5H), 4.12 (dt, J=5.0, 13.8 Hz, 0.5H), 3.82 (dt, J=4.5, 13.5 Hz, 0.5H), 3.69 (dt, J=4.9, 13.8 Hz, 0.5H), 3.60 (m, 1H), 3.27-3.03 (m, 5.5H), 2.97 (m, 0.5H), 2.63 (m, 2H), 2.57-2.31 (m, 4H), 2.23 (m, 1H), 2.02 (s, 3H), 1.98-1.80 (m, 1H), 1.80-1.56 (m, 3H), 1.55-1.29 (m, 3H); MS (LC/MS, M+H$^+$): 419.2

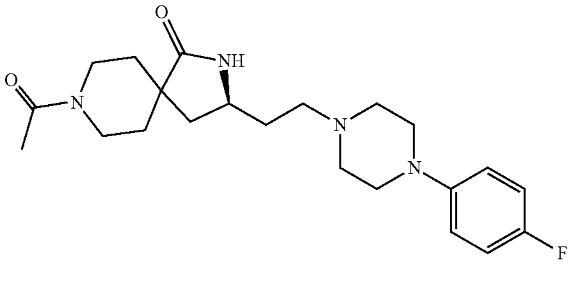 [SMILES: CC(=O)N1CCC2(CC1)C[C@H](CCN1CCN(c3ccc(F)cc3)CC1)NC2=O]

Preparation of (R)-8-acetyl-3-(2-(4-(4-fluorophenyl)piperazin-1-yl)ethyl)-2,8-diazaspiro[4.5]decan-1-one: The title compound was prepared according to the procedure for (R)-8-acetyl-3-(2-(4-(3-chlorophenyl)piperazin-1-yl)ethyl)-2,8-diazaspiro[4.5]decan-1-one, except (R)-3-(2-(4-(4-fluorophenyl)piperazin-1-yl)ethyl)-2,8-diazaspiro[4.5]decan-1-one was substituted for (R)-3-(2-(4-(3-chlorophenyl)piperazin-1-yl)ethyl)-2,8-diazaspiro[4.5]decan-1-one. $^1$H NMR (400 MHz, $CDCl_3$) δ 6.93-6.84 (m, 2H), 6.83-6.70 (m, 3H), 4.26 (dt, J=5.2, 13.5 Hz, 0.5H), 4.12 (dt, J=5.0, 13.5 Hz, 0.5H), 3.82 (dt, J=5.0, 13.7 Hz, 0.5H), 3.69 (dt, J=5.0, 13.7 Hz, 0.5H), 3.59 (m, 1H), 3.27-2.91 (m, 6H), 2.65 (m, 2H), 2.58-2.33 (m, 4H), 2.23 (m, 1H), 2.02 (s, 3H), 1.99-1.82 (m, 1H), 1.80-1.55 (m, 3H), 1.54-1.30 (m, 3H); MS (LC/MS, $M+H^+$): 403.2

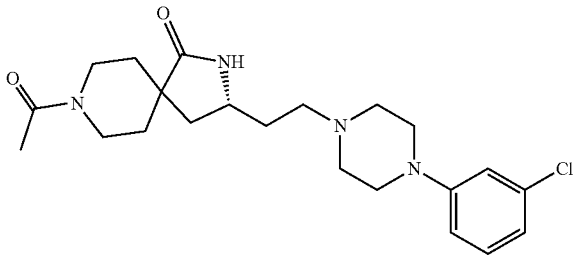 [SMILES: CC(=O)N1CCC2(CC1)C[C@@H](CCN1CCN(c3cccc(Cl)c3)CC1)NC2=O]

Preparation of (S)-8-acetyl-3-(2-(4-(3-chlorophenyl)piperazin-1-yl)ethyl)-2,8-diazaspiro[4.5]decan-1-one: The title compound was prepared according to the procedure for (R)-8-acetyl-3-(2-(4-(3-chlorophenyl)piperazin-1-yl)ethyl)-2,8-diazaspiro[4.5]decan-1-one, except (S)-3-(2-(4-(3-chlorophenyl)piperazin-1-yl)ethyl)-2,8-diazaspiro[4.5]decan-1-one was substituted for (R)-3-(2-(4-(3-chlorophenyl) piperazin-1-yl)ethyl)-2,8-diazaspiro[4.5]decan-1-one. $^1H$ NMR (400 MHz, $CDCl_3$) δ 7.09 (t, J=8.1 Hz, 1H), 6.80 (t, J=2.2 Hz, 1H), 6.77-6.66 (m, 3H), 4.26 (dt, J=4.8, 13.4 Hz, 0.5H), 4.12 (dt, J=5.0, 13.8 Hz, 0.5H), 3.82 (dt, J=4.5, 13.5 Hz, 0.5H), 3.69 (dt, J=4.9, 13.8 Hz, 0.5H), 3.60 (m, 1H), 3.25-3.08 (m, 5.5H), 2.98 (m, 0.5H), 2.63 (m, 2H), 2.56-2.34 (m, 4H), 2.23 (m, 1H), 2.02 (s, 3H), 1.98-1.83 (m, 1H), 1.81-1.56 (m, 3H), 1.54-1.30 (m, 3H); MS (LC/MS, $M+H^+$): 419.2

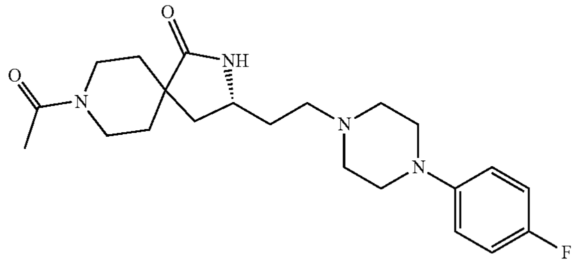 [SMILES: CC(=O)N1CCC2(CC1)C[C@@H](CCN1CCN(c3ccc(F)cc3)CC1)NC2=O]

Preparation of (S)-8-acetyl-3-(2-(4-(4-fluorophenyl)piperazin-1-yl)ethyl)-2,8-diazaspiro[4.5]decan-1-one: The title compound was prepared according to the procedure for (R)-8-acetyl-3-(2-(4-(3-chlorophenyl)piperazin-1-yl)ethyl)-2,8-diazaspiro[4.5]decan-1-one, except (S)-3-(2-(4-(4-fluorophenyl)piperazin-1-yl)ethyl)-2,8-diazaspiro[4.5]decan-1-one was substituted for (R)-3-(2-(4-(3-chlorophenyl) piperazin-1-yl)ethyl)-2,8-diazaspiro[4.5]decan-1-one. $^1H$ NMR (400 MHz, $CDCl_3$) δ 6.93-6.84 (m, 2H), 6.83-6.73 (m, 3H), 4.26 (dt, J=5.2, 13.5 Hz, 0.5H), 4.12 (dt, J=5.0, 13.5 Hz, 0.5H), 3.82 (dt, J=5.0, 13.7 Hz, 0.5H), 3.69 (dt, J=5.0, 13.7 Hz, 0.5H), 3.59 (m, 1H), 3.26-2.91 (m, 6H), 2.65 (m, 2H), 2.57-2.32 (m, 4H), 2.23 (m, 1H), 2.02 (s, 3H), 1.98-1.82 (m, 1H), 1.81-1.55 (m, 3H), 1.54-1.30 (m, 3H); MS (LC/MS, $M+H^+$): 403.2

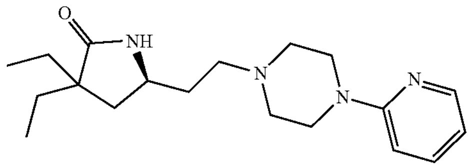 [SMILES: CCC1(CC)C[C@H](CCN2CCN(c3ccccn3)CC2)NC1=O]

Preparation of (R)-3,3-diethyl-5-(2-(4-(pyridin-2-yl)piperazin-1-yl)ethyl)pyrrolidin-2-one: The title compound was prepared according to the procedure for (R)-3,3-diethyl-5-(2-(4-phenylpiperazin-1-yl)ethyl)pyrrolidin-2-one, except 1-(2-pyridyl)piperazine was substituted for 1-phenylpiperazine. $^1H$ NMR (400 MHz, $CDCl_3$) δ 8.18 (dd, J=2.1, 4.8 Hz, 1H), 7.47 (m, 1H), 6.73 (b, 1H), 6.66-6.57 (m, 2H), 3.64-3.47 (m, 5H), 2.63 (m, 2H), 2.58-2.36 (m, 4H), 2.05 (dd, J=7.4, 13.0 Hz, 1H), 1.76-1.43 (m, 7H), 0.90 (dt, J=7.4, 14.5 Hz, 6H). LC/MS [M+H]=m/z 331.2

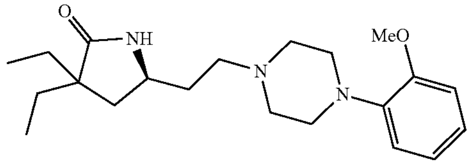 [SMILES: CCC1(CC)C[C@H](CCN2CCN(c3ccccc3OC)CC2)NC1=O]

Preparation of (R)-3,3-diethyl-5-(2-(4-(2-methoxyphenyl)piperazin-1-yl)ethyl)pyrrolidin-2-one: The title compound was prepared according to the procedure for (R)-3,3-diethyl-5-(2-(4-phenylpiperazin-1-yl)ethyl)pyrrolidin-2-one, except 1-(2-methoxyphenyl)piperazine was substituted for 1-phenylpiperazine. $^1H$ NMR (400 MHz, $CDCl_3$) δ 7.04-6.88 (m, 3H), 6.85 (dd, J=1.1, 8.0 Hz, 1H), 6.72 (b, 1H), 3.86 (s, 3H), 3.58 (m, 1H), 3.28-2.90 (b, 4H), 2.84-2.65 (b, 2H), 2.64-2.41 (m, 4H), 2.05 (dd, J=7.3, 13.1 Hz, 1H), 1.76-1.43 (m, 7H), 0.91 (dt, J=7.5, 16.1 Hz, 6H). LC/MS [M+H]=m/z 360.2

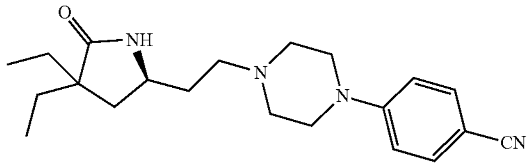 [SMILES: CCC1(CC)C[C@H](CCN2CCN(c3ccc(C#N)cc3)CC2)NC1=O]

Preparation of (R)-4-(4-(2-(4,4-diethyl-5-oxopyrrolidin-2-yl)ethyl)piperazin-1-yl)benzonitrile: The title compound was prepared according to the procedure for (R)-3,3-diethyl-5-(2-(4-phenylpiperazin-1-yl)ethyl)pyrrolidin-2-one, except 1-(4-cyanophenyl)piperazine was substituted for 1-phenylpiperazine. $^1H$ NMR (400 MHz, $CDCl_3$) δ 7.48 (d, J=9.0 Hz, 2H), 6.85 (d, J=9.0 Hz, 2H), 6.73 (b, 1H), 3.58 (m, 1H), 3.34 (t, J=5.1 Hz, 4H), 2.67 (m, 2H), 2.60-2.38 (m, 4H), 2.06 (dd, J=7.6, 13.2 Hz, 1H), 1.75-1.42 (m, 7H), 0.90 (dt, J=7.4, 14.0 Hz, 6H). LC/MS [M+H]=m/z 355.2

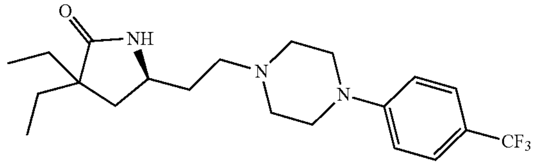 [SMILES: CCC1(CC)C[C@H](CCN2CCN(c3ccc(C(F)(F)F)cc3)CC2)NC1=O]

Preparation of (R)-3,3-diethyl-5-(2-(4-(4-(trifluoromethyl)phenyl)piperazin-1-yl)ethyl)pyrrolidin-2-one: The title compound was prepared according to the procedure for (R)-3,3-diethyl-5-(2-(4-phenylpiperazin-1-yl)ethyl)pyrrolidin-2-one, except 1-(4-(trifluoromethyl)phenyl)piperazine was substituted for 1-phenylpiperazine. $^1$H NMR (400 MHz, $CDCl_3$) δ 7.36 (d, J=8.6 Hz, 2H), 6.80 (d, J=8.6 Hz, 2H), 6.58 (b, 1H), 3.47 (m, 1H), 3.18 (t, J=5.0 Hz, 4H), 2.57 (m, 2H), 2.49-2.28 (m, 4H), 1.95 (dd, J=7.4, 13.1 Hz, 1H), 1.64-1.32 (m, 7H), 0.79 (dt, J=7.3, 13.8 Hz, 6H). LC/MS [M+H]=m/z 398.2

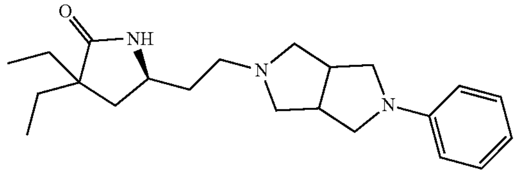 [SMILES: CCC1(CC)C[C@H](CCN2CC3CN(c4ccccc4)CC3C2)NC1=O]

Preparation of (5R)-3,3-diethyl-5-(2-(5-phenylhexahydropyrrolo[3,4-c]pyrrol-2(1H)-yl)ethyl)pyrrolidin-2-one: The title compound was prepared according to the procedure for (R)-3,3-diethyl-5-(2-(4-phenylpiperazin-1-yl)ethyl)pyrrolidin-2-one, except 2-phenyloctahydropyrrolo[3,4-c]pyrrole was substituted for 1-phenylpiperazine. $^1$H NMR (400 MHz, $CDCl_3$) δ 7.11 (m, 2H), 6.61 (t, J=7.4 Hz, 1H), 6.56 (d, J=8.6 Hz, 2H), 6.44 (b, 1H), 3.42 (m, 1H), 3.20-3.05 (m, 4H), 2.91 (m, 1H), 2.87-2.70 (m, 3H), 2.51 (m, 1H), 2.34-2.15 (m, 2H), 2.07 (dd, J=4.7, 8.5 Hz, 1H), 1.91 (dd, J=7.4, 13.1 Hz, 1H), 1.58-1.28 (m, 7H), 0.77 (m, 6H). LC/MS [M+H]=m/z 356.2

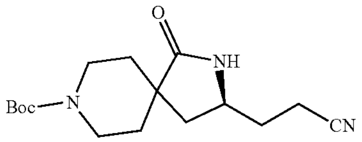 [SMILES: CC(C)(C)OC(=O)N1CCC2(CC1)C[C@H](CCC#N)NC2=O]

Preparation of tert-butyl (S)-3-(2-cyanoethyl)-1-oxo-2,8-diazaspiro[4.5]decane-8-carboxylate: To a solution of tert-butyl (R)-1-oxo-3-(2-(tosyloxy)ethyl)-2,8-diazaspiro[4.5] decane-8-carboxylate (0.2 g, 0.44 mmol, 1.0 equiv.) in acetonitrile (1.9 mL) was added potassium cyanide (0.72 g, 1.1 mmol, 2.5 equiv.). The resulting reaction mixture was then allowed to reflux for 16 hours. After cooling to 23° C., the reaction mixture was filtered thru a plug of Celite and concentrated in vacuo to give a crude product which was further purified by column chromatography (MeOH/dichloromethane, 0%~10%). $^1$H NMR (400 MHz, $CDCl_3$) δ 8.08 (b, 1H), 4.11-3.79 (b, 2H), 3.72 (p, J=6.6 Hz, 1H), 3.00 (t, J=11.3 Hz, 1H), 2.91 (t, J=11.3 Hz, 1H), 2.49 (td, J=1.2, 7.4 Hz, 2H), 2.32 (dd, J=7.0, 13.0 Hz, 1H), 1.97-1.78 (m, 3H), 1.72 (m, 1H), 1.52 (dd, J=7.8, 12.9 Hz, 1H), 1.48-1.29 (m, 11H).

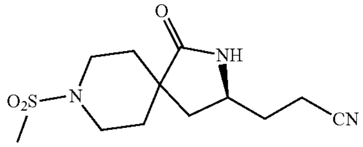 [SMILES: CS(=O)(=O)N1CCC2(CC1)C[C@H](CCC#N)NC2=O]

Preparation of (S)-3-(8-(methylsulfonyl)-1-oxo-2,8-diazaspiro[4.5]decan-3-yl)propanenitrile: To a solution of tert-butyl (S)-3-(2-cyanoethyl)-1-oxo-2,8-diazaspiro[4.5]decane-8-carboxylate (0.1 g, 0.35 mmol, 1.0 equiv.) in dichloromethane (2.75 mL) was added trifluoroacetic acid (0.5 mL). The resulting solution was allowed to stir at 23° C. for 45 minutes before being concentrated in vacuo. The residue was dissolved in MeOH (5 mL) followed by the addition of Amberlite IRN-78 base resin (0.5 g). This mixture was stirred vigorously for 15 minutes, filtered and the filtrate was concentrated in vacuo to give a crude intermediate that was then dissolved in dichloromethane (3.75 mL). The resulting solution was then cooled to 0° C. before the sequential addition of triethylamine (0.72 g, 0.70 mmol, 2.0 eq.) and methanesulfonyl chloride (0.6 g. 0.53 mmol, 1.5 equiv.). The reaction solution was allowed to warm to 23° C. and stir for 15 minutes. The reaction was diluted with MeOH (2 mL), concentrated in vacuo and further purified by flash column chromatography (MeOH w/2M ammonia/dichloromethane, 0%-10%). $^1$H NMR (400 MHz, $CDCl_3$) δ 6.56 (b, 1H), 3.81 (p, J=6.8 Hz, 1H), 3.72 (m, 1H), 3.53 (m, 1H), 3.32-3.15 (m, 2H), 2.83 (s, 3H), 2.49 (t, J=6.8 Hz, 2H), 2.29 (dd, J=6.9, 12.9 Hz, 1H), 2.09-1.82 (m, 4H), 1.75-1.59 (m, 3H).

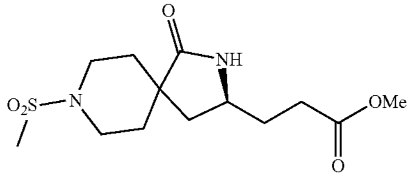 [SMILES: COC(=O)CC[C@H]1CC2(CCN(S(C)(=O)=O)CC2)C(=O)N1]

Preparation of methyl (S)-3-(8-(methylsulfonyl)-1-oxo-2,8-diazaspiro[4.5]decan-3-yl)propanoate: A 6M HCl in methanol solution was prepared via the addition of acetyl chloride (0.48 mL) to MeOH (1 mL). (S)-3-(8-(methylsulfonyl)-1-oxo-2,8-diazaspiro[4.5]decan-3-yl)propanenitrile (91 mg, 0.32 mmol, 1.0 equiv.) was dissolved in the prepared 6M methanolic HCl solution (0.64 mL) and stirred at 23° C. overnight. The reaction mixture was diluted with MeOH (1 mL) and concentrated in vacuo. The resulting residue was suspended in sat. aqueous $NaHCO_3$ and extracted with dichloromethane (4×15 mL). The combined organic phase was dried over $Na_2SO_4$ and concentrated in vacuo to give a crude product that was used in the next step without further purification. $^1$H NMR (400 MHz, $CDCl_3$) δ 7.13 (b, 1H), 3.75-3.57 (m, 5H), 3.50 (m, 1H), 3.23-3.02 (m, 2H), 2.79 (s, 3H), 2.40 (td, J=1.7, 7.2 Hz, 2H), 2.18 (dd, J=6.8, 13.0 Hz, 1H), 2.01 (m, 1H), 1.92 (m, 1H), 1.83 (q, J=6.9 Hz, 2H), 1.68-1.45 (m, 3H).

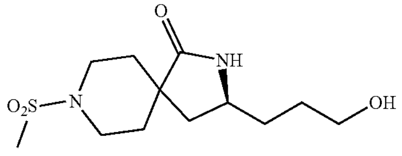 [SMILES: CS(=O)(=O)N1CCC2(CC1)C[C@H](CCCO)NC2=O]

Preparation of (S)-3-(3-hydroxypropyl)-8-(methylsulfonyl)-2,8-diazaspiro[4.5]decan-1-one: This reaction was performed in oven-dried glassware under a nitrogen atmosphere. To a stirred solution of methyl (S)-3-(8-(methylsulfonyl)-1-oxo-2,8-diazaspiro[4.5]decan-3-yl) propanoate (80 mg, 0.25 mmol, 1.0 equiv.) in dry tetrahydrofuran (1.2 mL) at 0° C. was added $LiBH_4$ (2M in tetrahydrofuran, 0.25 mL, 0.5 mmol, 2.0 equiv.) and the resulting solution was stirred at 23° C. for 6 hours. The reaction was then quenched with 0.5 mL of acetic acid and then filtered while washing with MeOH. The filtrate was concentrated in vacuo to give a crude product which was further purified by column chromatography (MeOH/dichloromethane, 10%). $^1H$ NMR (400 MHz, MeOD) δ 3.74-3.55 (m, 5H), 3.02 (td, J=3.0, 11.2 Hz, 1H), 2.92 (td, J=2.9, 11.5 Hz, 1H), 2.86 (s, 3H), 2.39 (dd, J=7.0, 13.1 Hz, 1H), 2.08-1.97 (m, 1H), 1.89-1.78 (m, 1H), 1.71-1.50 (m, 7H).

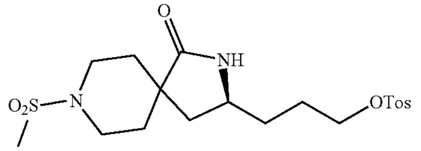

Preparation of (S)-3-(8-(methylsulfonyl)-1-oxo-2,8-diazaspiro[4.5]decan-3-yl)propyl 4-methylbenzenesulfonate: To a cooled mixture of (S)-3-(3-hydroxypropyl)-8-(methylsulfonyl)-2,8-diazaspiro[4.5]decan-1-one (55 mg, 0.19 mmol, 1.0 equiv.) and triethylamine (40 mg, 0.38 mmol, 2.0 equiv.) in dichloromethane:dimethylformamide (2.0 mL:0.2 mL) at 0° C. was added 4-toluenesulfonyl chloride (55 mg, 0.28 mmol, 1.5 equiv.) followed by 4-dimethylaminopyridine (3 mg, 0.02 mmol, 0.1 equiv.). The resulting reaction mixture was stirred at 0° C. for 5 minutes before being warmed to 23° C. and allowed to stir for 24 hours. Then, the reaction mixture was diluted with dichloromethane (5 mL), washed with 1N HCl (1×5 mL). The aqueous layer was backwashed with dichloromethane (2×5 mL). The combined organic layers were dried over $Na_2SO_4$ and concentrated in vacuo to give a crude product which was further purified by HPLC ($CH_3CN/H_2O$, 0.1% Formic acid), 0%~100%). $^1H$ NMR (400 MHz, $CDCl_3$) δ 7.78 (d, J=8.2 Hz, 2H), 7.37 (d, J=8.0 Hz, 2H), 6.84 (b, 1H), 4.04 (t, J=5.9 Hz, 2H), 3.70 (m, 1H), 3.64-3.44 (m, 2H), 3.21-3.00 (m, 2H), 2.80 (s, 3H), 2.46 (s, 3H), 2.17 (dd, J=6.8, 12.8 Hz, 1H), 2.01 (m, 1H), 1.91 (m, 1H), 1.81-1.66 (m, 2H), 1.66-1.44 (m, 5H).

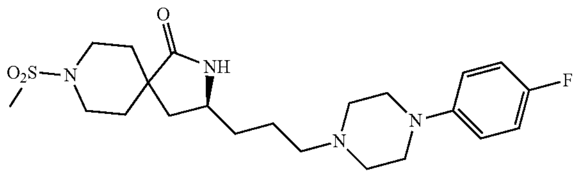 [SMILES: CS(=O)(=O)N1CCC2(CC1)C[C@H](CCCN1CCN(c3ccc(F)cc3)CC1)NC2=O]

Preparation of (S)-3-(3-(4-(4-fluorophenyl)piperazin-1-yl)propyl)-8-(methylsulfonyl)-2,8-diazaspiro[4.5]decan-1-one: To a small vial was added (S)-3-(8-(methylsulfonyl)-1-oxo-2,8-diazaspiro[4.5]decan-3-yl)propyl 4-methylbenzenesulfonate (16 mg, 0.036 mmol, 1 equiv.) and 1-(4-fluorophenyl)piperazine (13.5 mg, 0.75 mmol, 2.1 equiv.) then both were dissolved in acetonitrile (0.4 mL). Then $K_2CO_3$ (13 mg, 0.089 mmol, 2.5 equiv.) was added and the reaction mixture was stirred at 80° C. overnight and then cooled to 23° C. The mixture was filtered, washed with acetonitrile and filtrate was concentrated in vacuo to give a crude product which was by further purified by column chromatography (MeOH/dichloromethane, 0%~10%). $^1H$ NMR (400 MHz, $CDCl_3$) δ 7.02-6.92 (m, 3H), 6.92-6.84 (m, 2H), 3.72 (m, 1H), 3.59 (m, 1H), 3.50 (m, 1H), 3.31-3.09 (m, 6H), 2.81 (s, 3H), 2.74-2.56 (m, 4H), 2.46 (t, J=6.2 Hz, 2H), 2.18 (dd, J=6.6, 12.8 Hz, 1H), 2.09-1.90 (m, 2H), 1.74-1.43 (m, 7H). LC/MS [M+H]=m/z 453.2

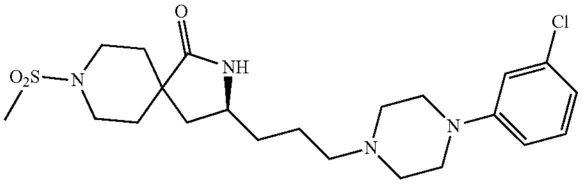 [SMILES: CS(=O)(=O)N1CCC2(CC1)C[C@H](CCCN1CCN(c3cccc(Cl)c3)CC1)NC2=O]

Preparation of (S)-3-(3-(4-(3-chlorophenyl)piperazin-1-yl)propyl)-8-(methylsulfonyl)-2,8-diazaspiro[4.5]decan-1-one: The title compound was prepared according to the procedure for (S)-3-(3-(4-(4-fluorophenyl)piperazin-1-yl) propyl)-8-(methylsulfonyl)-2,8-diazaspiro[4.5]decan-1-one, except 1-(3-chlorophenyl)piperazine was substituted for 1-(4-fluorophenyl)piperazine. $^1H$ NMR (400 MHz, $CDCl_3$) δ 7.17 (t, J=8.2 Hz, 1H), 6.92-6.85 (m, 2H), 6.84-6.76 (m, 2H), 3.72 (m, 1H), 3.60 (m, 1H), 3.50 (m, 1H), 3.32-3.13 (m, 6H), 2.81 (s, 3H), 2.71-2.55 (m, 4H), 2.45 (t, J=6.3 Hz, 2H), 2.19 (dd, J=6.7, 12.8 Hz, 1H), 2.09-1.90 (m, 2H), 1.73-1.44 (m, 7H). LC/MS [M+H]=m/z 469.2

Example 2: Exemplary Formulations

The present invention also relates to compositions or formulations which comprise the 5-hydroxytryptamine receptor 7 activity modulators according to the present invention. In general, the compositions of the present invention comprise an effective amount of one or more compounds of the disclosure and salts thereof according to the present invention which are effective for providing modulation of 5-hydroxytryptamine receptor 7 activity; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, PA (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known 5-hydroxytryptamine receptor 7 activity modulators. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound (s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and *arachis* oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.]

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more compounds of the disclosure according to the present invention and one or more excipients; from about 0.01 mg to about 100 mg of one or more compounds of the disclosure according to the present invention and one or more excipients; and from about 0.1 mg to about 10 mg of one or more compounds of the disclosure according to the present invention; and one or more excipients.

Example 3: General Biochemical Procedures

The following procedures can be utilized in evaluating and selecting compounds as 5-hydroxytryptamine receptor 7 activity modulators.

Radiolabel Binding Studies for Serotonin 5HT7 Receptors, Method 1:

A solution of the compound of the disclosure to be tested is prepared as a 1-mg/ml stock in Assay Buffer or DMSO according to its solubility. A similar stock of the reference compound chlorpromazine is also prepared as a positive control. Eleven dilutions (5×assay concentration) of the compound of the disclosure and chlorpromazine are prepared in the Assay Buffer by serial dilution to yield final corresponding assay concentrations ranging from 10 pM to 10 μM.

A stock concentration of 5 nM [$^3$H]LSD (lysergic acid diethyl amide) is prepared in 50 mM Tris-HCl, 10 mM $MgCl_2$, 1 mM EDTA, pH 7.4 (Assay Buffer). Aliquots (50 μl) of radioligand are dispensed into the wells of a 96-well plate containing 100 μl of Assay Buffer. Duplicate 50-μl aliquots of the compound of the disclosure test and chlorpromazine positive control reference compound serial dilutions are added.

Membrane fractions of cells expressing recombinant $5HT_7$ receptors (50 μL) are dispensed into each well. The membranes are prepared from stably transfected cell lines expressing $5HT_7$ receptors cultured on 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; the membrane preparations are resuspended in 3 ml of chilled Assay Buffer and homogenized by several passages through a 26 gauge needle before using in the assay.

The 250-μl reactions are incubated at room temperature for 1.5 hours, then harvested by rapid filtration onto 0.3% polyethyleneimine-treated, 96-well filter mats using a 96-well Filtermate harvester. Four rapid 500-μl washes are performed with chilled Assay Buffer to reduce non-specific binding. The filter mats are dried, then scintillant is added to the filters and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y=\text{bottom}+[(top\text{-bottom})/(1+10x-\log IC_{50})]$$

where bottom equals the residual radioligand binding measured in the presence of 10 μM reference compound (i.e., non-specific binding) and top equals the total radioligand binding observed in the absence of competitor. The log $IC_{50}$ (i.e., the log of the ligand concentration that reduces radioligand binding by 50%) is thus estimated from the data and used to obtain the Ki by applying the Cheng-Prusoff approximation:

$$Ki=IC_{50}/(1+[\text{ligand}]/KD)$$

where [ligand] equals the assay radioligand concentration and KD equals the affinity constant of the radioligand for the target receptor.

Compounds of the disclosure are also screened at a single concentration of 10 μM using the same method described for the Radiolabel Binding Studies for Serotonin $5HT_7$ receptors to determine the percent inhibition of [$^3$H]LSD binding.

Radiolabel Binding Studies for Serotonin 5-HT7 Receptors, Method 2:

A solution of the compound of the disclosure to be tested is prepared as a 1-mg/ml stock in Assay Buffer or DMSO according to its solubility. A similar stock of the reference compound chlorpromazine is also prepared as a positive control. Eleven dilutions (5× assay concentration) of the compound of the disclosure and chlorpromazine are prepared in the Assay Buffer by serial dilution to yield final corresponding assay concentrations ranging from 10 μM to 10 μM.

A stock concentration of 5 nM [$^3$H]-5-Hydroxytryptamine ([$^3$H]-5HT) is prepared in 50 mM Tris-HCl, 10 mM $MgCl_2$, 1 mM EDTA, pH 7.4 (Assay Buffer). Aliquots (50 μl) of radioligand are dispensed into the wells of a 96-well plate containing 100 μl of Assay Buffer. Duplicate 50-μl aliquots of the compound of the disclosure test and chlorpromazine positive control reference compound serial dilutions are added.

Membrane fractions of cells expressing recombinant $5HT_7$ receptors (50 μL) are dispensed into each well. The membranes are prepared from stably transfected cell lines expressing $5HT_7$ receptors cultured on 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; the membrane preparations are resuspended in 3 ml of chilled Assay Buffer and homogenized by several passages through a 26 gauge needle before using in the assay.

The 250-μl reactions are incubated at room temperature for 1.5 hours, then harvested by rapid filtration onto 0.3% polyethyleneimine-treated, 96-well filter mats using a 96-well Filtermate harvester. Four rapid 500-μl washes are performed with chilled Assay Buffer to reduce non-specific binding. The filter mats are dried, then scintillant is added to the filters and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y=\text{bottom}+[(top\text{-bottom})/(1+10x-\log IC_{50})]$$

where bottom equals the residual radioligand binding measured in the presence of 10 μM reference compound (i.e., non-specific binding) and top equals the total radioligand binding observed in the absence of competitor. The log $IC_{50}$ (i.e., the log of the ligand concentration that reduces radioligand binding by 50%) is thus estimated from the data and used to obtain the Ki by applying the Cheng-Prusoff approximation:

$$Ki=IC_{50}/(1+[\text{ligand}]/KD)$$

where [ligand] equals the assay radioligand concentration and KD equals the affinity constant of the radioligand for the target receptor.

Compounds of the disclosure are also screened at a single concentration of 10 μM using the same method described for the Radiolabel Binding Studies for Serotonin $5HT_7$ receptors to determine the percent inhibition of [$^3$H]-5HT binding.

Functional Serotonin $5HT_7$ Assay, Method 1:

Cell lines stably expressing human 5HT7 receptors are seeded in 96-well, poly-L-lysine-coated plates 48 hours prior to the assay (40,000 cells per well) in Dulbecco's Modified Eagle Medium (DMEM) containing 5% dialyzed serum. Twenty hours prior to the assay, the medium is changed to serum-free DMEM. On the day of the assay, the DMEM is washed and replaced with 30 μl of assay buffer (1× Krebs-Ringer bicarbonate glucose buffer, 0.75 mM IBMX, pH 7.4). A 10-min pre-incubation is performed in a 37-degree centigrade, humidified incubator. Then, the cells are stimulated by addition of 30 μl of 2× dilutions of compounds of the disclosure or chlorpromazine (final concentrations ranging from 0.1 nM to 10 μM, each concentration assayed in triplicate). A positive control (100 μM forskolin) is also included. Accumulation of cAMP is allowed to continue for 15 min, after which the buffer is removed and the cells are lysed with Cell Lysis Buffer (CatchPoint cAMP Assay Kit, Molecular Devices). Next, the lysates are transferred to 96-well, glass-bottom plates coated with goat anti-rabbit IgG and adsorbed with rabbit anti-cAMP (Molecular Devices). Following a 5 minute incubation, horseradish peroxidase-cAMP conjugate is added (Molecular Devices) and a 2-hour incubation is performed at room temperature. Then, after three washes with Wash Buffer (Molecular Devices), Stoplight Red substrate (Molecular Devices), reconstituted in Substrate Buffer (Molecular Devices) containing freshly-added 1 mM $H_2O_2$, is added and, after a 15-min incubation at room temperature, fluorescence is measured (excitation 510-545 nm, emission 565-625 nm). For each assay, a cAMP calibration curve is generated and controls without lysate and without antibody are included.

For agonist tests, raw data (maximum fluorescence, fluorescence units) for each concentration of the compounds of the disclosure or chlorpromazine are normalized to the basal (vehicle-stimulated) fluorescence (reported as fold increase over basal) and plotted as a function of the logarithm of the molar concentration of the drug (i.e., test or reference compound). Non-linear regression of the normalized data is performed in Prism 4.0 (GraphPad Software) using the built-in three parameter logistic model (i.e., sigmoidal concentration-response) describing agonist-stimulated activation of one receptor population:

$$y=\text{bottom}+[(top\text{-bottom})/(1+10\text{x}-\text{logEC50})]$$

where bottom equals the best-fit basal fluorescence and top equals the best-fit maximal fluorescence stimulated by the compound of the disclosure or chlorpromazine. The log $EC_{50}$ (i.e., the log of the drug concentration that increases fluorescence by 50% of the maximum fluorescence observed for the compound of the disclosure or chlorpromazine is thus estimated from the data, and the $EC_{50}$ (agonist potency) is obtained. To obtain an estimate of the relative efficacy of the test compound (Rel. Emax), its best-fit top is compared to and expressed as a ratio of that for the chlorpromazine (Rel. Emax of the reference agonist is 1.00).

To ascertain whether compounds of the disclosure are antagonists, a double-addition paradigm is employed. First, 30 μl of a compound of the disclosure (20 μM) is added (10 μM final concentration) and a 15 minute incubation is performed. Then, 30 μl of chlorpromazine (3×; $EC_{90}$) is added (final concentration of agonist is EC30) and cAMP accumulation is allowed to proceed for 15 minutes. The samples are then processed for cAMP measurements as detailed above. Measurements of chlorpromazine -induced cAMP accumulation are compared to the signals elicited by the chlorpromazine following addition of vehicle instead of test compound and expressed as a ratio. 'Hits' (compounds that antagonize chlorpromazine -stimulated increases in baseline-normalized fluorescence by at least 50%) are then characterized by a modified Schild analysis.

For modified Schild analysis, a family of chlorpromazine concentration-response isotherms is generated in the absence and presence of graded concentrations of test compound (added 15 min prior to reference agonist). Theoretically, compounds that are competitive antagonists cause a dextral shift of agonist concentration-response isotherms without reducing the maximum response to agonist (i.e., surmountable antagonism). However, on occasion, factors such as non-competitive antagonism, hemiequilibria, and/or receptor reserve cause apparent insurmountable antagonism. To account for such deviations, we apply the modified Lew-Angus method to ascertain antagonist potency (Christopoulos et al., 1999). Briefly, equieffective concentrations of agonist (concentrations of agonist that elicit a response equal to the $EC_{25\%}$ of the agonist control curve) are plotted as a function of the compound of the disclosure concentration present in the wells in which they were measured. Non-linear regression of the baseline-normalized data is performed in Prism 4.0 using the following equation:

$$pEC25\%=-\log\ ([B]+10\text{-}pK)-\log\ c$$

where EC25% equals the concentration of agonist that elicits a response equal to 25% of the maximum agonist control curve response and [B] equals the antagonist concentration; K, c, and s are fit parameters. The parameter s is equal to the Schild slope factor. If s is not significantly different from unity, pK equals pKB; otherwise, pA2 is calculated (pA2=pK/s). The parameter c equals the ratio $EC_{25\%}$/[B].

Functional Efficacy Assay for 5-$HT_7$ Receptors Method 2:

Functional efficacy of the compounds of the disclosure on 5-$HT_7$ serotonin receptors were measured in a cell based cAMP enzyme fragment complementation assay using the HitHunter cAMP assay (DiscoveRx). Cells stably expressing human 5$HT_7$ receptors were plated in 96-well plates at 4000 cells/well, 16-20 hours prior to assay in growth media (Ultraculture medium, 2 mM GlutaMax and G418 1 mg/mL. Serial dilutions of the agonist, 5-Carboxamidotryptamine (5-CT), were prepared in a final concentration range of 10 μM to 10 nM. Compounds of the disclosure were prepared in 3-fold serial dilutions to obtain a final concentration range of 10 μM to 0.1 nM. Compounds of the disclosure are tested for agonist activity in the absence of 5-CT and antagonist activity in the presence of 5-CT. For the cAMP assay, the protocol was followed according to the instructions provided by the supplier. Briefly, cells were incubated with a compound of the disclosure for 30 minutes at 37° C. prior to addition of EC70 concentration of 5-CT. After an additional 30 minutes, cAMP antibody/cell lysis solution was added (20 μL/well) and incubated for 60 minutes at room temperature. cAMP XS+EA reagent is added (20 μL/well) and incubated for 2 hours at room temperature. Luminescence was read on the Envision Multilabel plate reader.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Example 4: Biochemical Experiments

Methods:

[1]Radiolabeled Binding ($IC_{50}$ and $K_1$)

A solution of the compound of the disclosure to be tested was prepared as a 1-mg/ml stock in Assay Buffer or DMSO according to its solubility. A similar stock of the reference compound chlorpromazine was also prepared as a positive control. Eleven dilutions (5× assay concentration) of the compound of the disclosure and chlorpromazine were prepared in the Assay Buffer by serial dilution to yield final corresponding assay concentrations ranging from 10 μM to 10 μM.

A stock concentration of 5 nM [$^3$H]LSD (lysergic acid diethyl amide) was prepared in 50 mM Tris-HCl, 10 mM $MgCl_2$, 1 mM EDTA, pH 7.4 (Assay Buffer). Aliquots (50 μl) of radioligand were dispensed into the wells of a 96-well plate containing 100 μl of Assay Buffer. Duplicate 50-μl aliquots of the compound of the disclosure test and chlorpromazine positive control reference compound serial dilutions were added.

Membrane fractions of cells expressing recombinant $5HT_7$ receptors (50 μL) were dispensed into each well. The membranes were prepared from stably transfected cell lines expressing $5HT_7$ receptors cultured on 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; the membrane preparations were resuspended in 3 ml of chilled Assay Buffer and homogenized by several passages through a 26 gauge needle before using in the assay.

The 250-μl reactions were incubated at room temperature for 1.5 hours, then harvested by rapid filtration onto 0.3% polyethyleneimine-treated, 96-well filter mats using a 96-well Filtermate harvester. Four rapid 500-μl washes were performed with chilled Assay Buffer to reduce non-specific binding. The filter mats were dried, then scintillant is added to the filters and the radioactivity retained on the filters was counted in a Microbeta scintillation counter.

Raw data (dpm) representing total radioligand binding (i.e., specific+non-specific binding) was plotted as a function of the logarithm of the molar concentration of the competitor (i.e., test or reference compound). Non-linear regression of the normalized (i.e., percent radioligand binding compared to that observed in the absence of test or reference compound) raw data was performed in Prism 4.0 (GraphPad Software) using the built-in three parameter logistic model describing ligand competition binding to radioligand-labeled sites:

$$y=\text{bottom}+[(top\text{-bottom})/(1+10x-\log IC_{50})]$$

where bottom equals the residual radioligand binding measured in the presence of 10 μM reference compound (i.e., non-specific binding) and top equals the total radioligand binding observed in the absence of competitor. The log $IC_{50}$ (i.e., the log of the ligand concentration that reduces radioligand binding by 50%) was thus estimated from the data and used to obtain the Ki by applying the Cheng-Prusoff approximation:

$$Ki=IC_{50}/(1+[\text{ligand}]/KD)$$

where [ligand] equals the assay radioligand concentration and KD equals the affinity constant of the radioligand for the target receptor.

Functional Data (Kb)

Functional efficacy of the compounds of the disclosure on 5-$HT_7$ serotonin receptors were measured in a cell based cAMP enzyme fragment complementation assay using the HitHunter cAMP assay (DiscoveRx). Cells stably expressing human $5HT_7$ receptors were plated in 96-well plates at 4000 cells/well, 16-20 hours prior to assay in growth media (Ultraculture medium, 2 mM GlutaMax and G418 1 mg/mL. Serial dilutions of the agonist, 5-hydroxytryptamine (5-HT), were prepared in a final concentration range of 10 μM to 10 nM. Compounds of the disclosure were prepared in 3-fold serial dilutions to obtain a final concentration range of 10 μM to 0.1 nM. Compounds of the disclosure are tested for agonist activity in the absence of 5-HT and antagonist activity in the presence of 5-HT. For the cAMP assay, the protocol was followed according to the instructions provided by the supplier. Briefly, cells were incubated with a compound of the disclosure for 30 minutes at 37° C. prior to addition of $EC_{70}$ concentration of 5-HT. After an additional 30 minutes, cAMP antibody/cell lysis solution was added (20 μL/well) and incubated for 60 minutes at room temperature. cAMP XS+EA reagent is added (20 μL/well) and incubated for 2 hours at room temperature. Luminescence was read on the Envision Multilabel plate reader.

Results

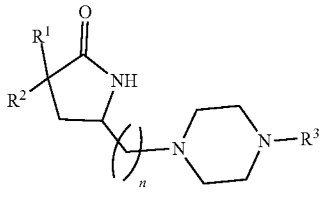

(XLI)

TABLE 34

| n | $R^1$ | $R^2$ | $R^3$ | $IC_{50}$ (nM)[1] | $K_i$ (nM)[1] | $K_b$ (nM)[2] | TPSA |
|---|---|---|---|---|---|---|---|
| 2 | Ethyl | Ethyl | 4-F-Phenyl | | 8.5 | 8.98 | 35.6 |
| 2 | Ethyl | Ethyl | 4-Cl-Phenyl | | 13 | 54.6 | 35.6 |
| 2 | Ethyl | Ethyl | 2-iPr-phenyl | | 23 | 163 | 35.6 |
| 2 | Ethyl | Ethyl | 2-morpholino-phenyl | | 24 | 32.3 | 48.1 |
| 2 | Ethyl | Ethyl | 4-Me-Phenyl | | 28 | 24.1 | 35.6 |
| 2 | Ethyl | Ethyl | 4-OH-Phenyl | | 34 | 50 | 55.8 |
| 2 | Ethyl | Ethyl | Phenyl | | 68 | 17.8 | 35.6 |
| 2 | Ethyl | Ethyl | 4-Me-2-morpholino-phenyl | | 74 | 59.3 | 48.1 |

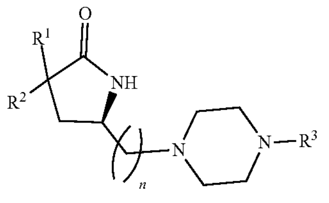

(XLII)

TABLE 35

| n | $R^1$ | $R^2$ | $R^3$ | $IC_{50}$ (nM)[1] | $K_i$ (nM)[1] | $K_b$ (nM)[2] | TPSA |
|---|---|---|---|---|---|---|---|
| 1 | Ethyl | Ethyl | 2-iPr-phenyl | | 121 | | 35.6 |
| 1 | Ethyl | Ethyl | 4-Me-2-morpholino-phenyl | | 132 | 43.8 | 48.1 |
| 1 | Ethyl | Ethyl | 4-F-Phenyl | | 243 | | 35.6 |
| 1 | Ethyl | Ethyl | 4-Me-Phenyl | | 249 | | 35.6 |
| 1 | Ethyl | Ethyl | 2-pyridyl | | 669 | | 48.5 |
| 1 | Ethyl | Ethyl | Phenyl | | 819 | | 35.6 |
| 1 | Ethyl | Ethyl | 3-Cl-Phenyl | | 1087 | | 35.6 |
| 2 | Ethyl | Ethyl | 4-Me-Phenyl | | 11 | 8.43 | 35.6 |
| 2 | Ethyl | Ethyl | 4-F-Phenyl | 12.34 | | 0.81 | 35.6 |
| 2 | Ethyl | Ethyl | 3,4-di-Cl-Phenyl | 82.8 | | 6.19 | 35.6 |
| 2 | Ethyl | Ethyl | 4-F-3-Cl-Phenyl | 8.7 | | 1.92 | 35.6 |
| 2 | Ethyl | Ethyl | 3-Cl-Phenyl | 9.9 | | 1.38 | 35.6 |
| 2 | Ethyl | Ethyl | Phenyl | | | 6.59 | 35.6 |
| 2 | Ethyl | Ethyl | 2-Cl-Phenyl | | | 109 | 35.6 |
| 2 | Ethyl | Ethyl | 3-F-Phenyl | | | 9.89 | 35.6 |
| 2 | Ethyl | Ethyl | 2-Me-Phenyl | | | 127 | 35.6 |
| 2 | Ethyl | Ethyl | 3-Me-Phenyl | | | 1.65 | 35.6 |
| 2 | Ethyl | Ethyl | 2-pyridyl | | | 4.91 | 48.5 |
| 2 | Ethyl | Ethyl | 2-OMe-Phenyl | | | 230 | 44.8 |
| 2 | Ethyl | Ethyl | 4-CN-Phenyl | | | 544 | 59.4 |
| 2 | Ethyl | Ethyl | $4-CF_3$-Phenyl | | | 137 | 35.6 |

(XLIII)

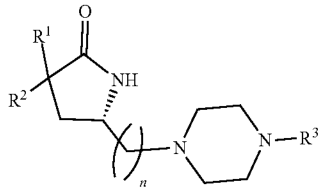

TABLE 36

| n | $R^1$ | $R^2$ | $R^3$ | $IC_{50}$ (nM)[1] | $K_i$ (nM)[1] | $K_b$ (nM)[2] | TPSA |
|---|---|---|---|---|---|---|---|
| 2 | Ethyl | Ethyl | 4-Me-Phenyl | | 79 | 58.1 | 35.6 |
| 2 | $—CH_2CH{=}CHCH_2—$ | | 4-F-Phenyl | | | 46.2 | 35.6 |
| 2 | $—CH_2CH{=}CHCH_2—$ | | 3-Cl-Phenyl | | | 36.3 | 35.6 |
| 2 | $—CH_2CH_2CH_2CH_2—$ | | 4-F-Phenyl | | | 52.6 | 35.6 |
| 2 | $—CH_2CH_2CH_2CH_2—$ | | 3-Cl-Phenyl | | | 48.4 | 35.6 |

(XLIV)

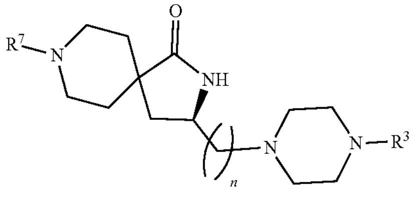

TABLE 37

| n | $R^3$ | $R^7$ | $IC_{50}$ (nM)[1] | $K_i$ (nM)[1] | $K_b$ (nM)[2] | TPSA |
|---|---|---|---|---|---|---|
| 2 | 3-Cl-Phenyl | Acetyl | | 63 | 5.04 | 55.9 |
| 2 | 4-F-Phenyl | Acetyl | | 76 | 14.4 | 55.9 |
| 2 | 4-F-Phenyl | $MeSO_2$ | | 89 | 30.7 | 81.3 |
| 2 | 3-Cl-Phenyl | $MeSO_2$ | | 107 | 13.5 | 81.3 |

TABLE 37-continued

| n | $R^3$ | $R^7$ | $IC_{50}$ (nM)[1] | $K_i$ (nM)[1] | $K_b$ (nM)[2] | TPSA |
|---|---|---|---|---|---|---|
| 3 | 3-Cl-Phenyl | $MeSO_2$ | | | 321 | 81.3 |
| 3 | 4-F-Phenyl | $MeSO_2$ | | | 526 | 81.3 |

(XLV)

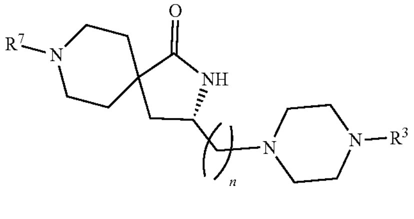

TABLE 38

| n | $R^3$ | $R^7$ | $IC_{50}$ (nM)[1] | $K_i$ (nM)[1] | $K_b$ (nM)[2] | TPSA |
|---|---|---|---|---|---|---|
| 2 | 3-Cl-Phenyl | $MeSO_2$ | | 117 | | 81.3 |
| 2 | 4-F-Phenyl | $MeSO_2$ | | 167 | 74.2 | 81.3 |
| 2 | 3-Cl-Phenyl | Acetyl | | 214 | | 55.9 |
| 2 | 4-F-Phenyl | Acetyl | | 325 | | 55.9 |

(XLVI)

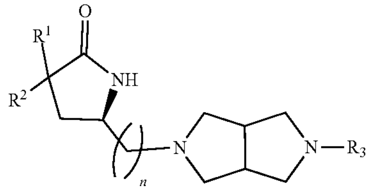

TABLE 39

| n | $R^1$ | $R^2$ | $R^3$ | $IC_{50}$ (nM)[1] | $K_i$ (nM)[1] | $K_b$ (nM)[2] | TPSA |
|---|---|---|---|---|---|---|---|
| 2 | Ethyl | Ethyl | Phenyl | | | 144 | 35.6 |

From the foregoing description, one skilled in the art can easily ascertain the essential characteristics of this invention, and without departing from the spirit and scope thereof, can make various changes and modifications of the invention to adapt it to various usages and conditions.

All references, patents or applications, U.S. or foreign, cited in the application are hereby incorporated by reference as if written herein in their entireties. Where any inconsistencies arise, material literally disclosed herein controls.

What is claimed is:

1. A compound having a structure according to Formula (XLIIIb):

(XLIIIb)

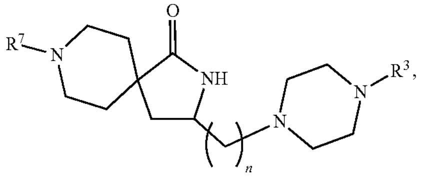

or a pharmaceutically acceptable salt thereof, wherein:

$R^3$ is phenyl or substituted phenyl, wherein the substituents are selected from the group consisting of hydroxyl, halo, cyano, $C_{1-6}$ alkoxy, $C_{1-6}$ linear alkyl, $C_{3-7}$ branched alkyl, $C_{1-6}$ haloalkyl, and heterocyclyl;

$R^7$ is selected from the group consisting of H, $COR^8$, $CO_2R^9$, and $SO_2R^{10c}$;

$R^8$ is selected from the group consisting of H, $C_{1-6}$ linear alkyl, $C_{3-7}$ branched alkyl, and $C_{3-7}$ cycloalkyl;

$R^9$ is selected from the group consisting of $C_{1-6}$ linear alkyl, $C_{3-7}$ branched alkyl, and $C_{3-7}$ cycloalkyl;

$R^{10c}$ is $C_{1-6}$ linear alkyl or $C_{3-7}$ branched alkyl; and n is 1, 2, 3, or 4.

2. A compound having a structure according to Formula (II), (II)

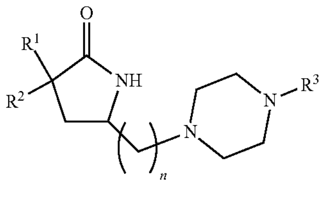

, or a pharmaceutically acceptable salt thereof, wherein:

$R^1$ and $R^2$ are each $C_{1-6}$ linear alkyl;

$R^3$ is phenyl or substituted phenyl, wherein the substituents are selected from the group consisting of hydroxyl, halo, cyano, $C_{1-6}$ alkoxy, $C_{1-6}$ linear alkyl, $C_{3-7}$ branched alkyl, $C_{1-6}$ haloalkyl, and heterocyclyl; and n is 1, 2, 3, or 4.

3. The compound of claim 1, having the Formula (XLIV):

(XLIV)

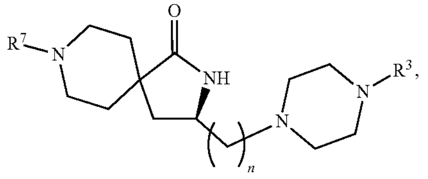

Formula (XLV):

(XLV)

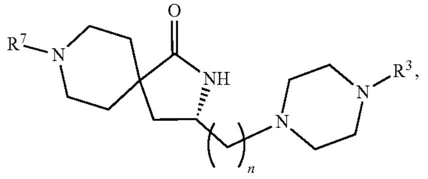

or a pharmaceutically acceptable salt thereof.

4. A composition comprising an effective amount of at least one compound according to claim 1, or a pharmaceutically acceptable salt thereof, optionally further comprising at least one excipient.

5. The compound of claim 2, or a pharmaceutically acceptable salt thereof, wherein each of $R^1$ and $R^2$ is ethyl and/or n is 2.

6. The compound of claim 2, wherein $R^3$ is selected from the group consisting of hydroxylphenyl, fluorophenyl, chlorophenyl, bromophenyl, cyanophenyl, tolyl, methoxylphenyl, difluorophenyl, dichlorophenyl, chloro-fluorophenyl, dimethylphenyl, trifluoromethylphenyl, di(trifluoromethyl) phenyl.

7. The compound of claim 2, wherein $R^3$ is selected from the group consisting of 4-hydroxyphenyl, 3-fluorophenyl, 4-fluorophenyl, 3-chlorophenyl, 4-chlorophenyl, 3,4-dichlorophenyl, 4-fluoro-3-chlorophenyl, 4-cyanophenyl, 2-methoxyphenyl, 2-methylphenyl, 3-methylphenyl, 4-methylphenyl, 2-isopropylphenyl, 4-trifluoromethylphenyl, 2-morpholinophenyl, and 4-methyl-2-morpholinophenyl.

8. The compound of claim 7, wherein $R^3$ is 4-fluorophenyl.

9. The compound of claim 1, wherein $R^8$, $R^9$, or $R^{10}$ is $C_{1-6}$ linear alkyl.

10. The compound of claim 9, wherein $R^7$ is $COR^8$.

11. The compound of claim 9, wherein $R^7$ is $CO_2R^9$.

12. The compound of claim 9, wherein $R^7$ is $SO_2R^{10C}$.

13. The compound of claim 1, wherein $R^3$ is selected from the group consisting of 4-hydroxyphenyl, 3-fluorophenyl, 4-fluorophenyl, 3-chlorophenyl, 4-chlorophenyl, 3,4-dichlorophenyl, 4-fluoro-3-chlorophenyl, 4-cyanophenyl, 2-methoxyphenyl, 2-methylphenyl, 3-methylphenyl, 4-methyphenyl, 2-isopropylphenyl, 4-trifluoromethyphenyl, 2-morpholinophenyl, and 4-methyl-2-morpholinophenyl.

14. The compound of claim 13, wherein $R^3$ is 4-fluorophenyl.

15. The compound of claim 2, wherein the compound is selected from the compounds described in Table 1:

TABLE 1

| Entry | $R^1$ | $R^2$ | n | $R^3$ |
|---|---|---|---|---|
| 1 | Methyl | Methyl | 1 | Phenyl |
| 2 | Methyl | Methyl | 2 | Phenyl |
| 3 | Methyl | Methyl | 3 | Phenyl |
| 4 | Methyl | Methyl | 4 | Phenyl |
| 5 | Methyl | Methyl | 1 | 4-OH-Phenyl |
| 6 | Methyl | Methyl | 2 | 4-OH-Phenyl |
| 7 | Methyl | Methyl | 3 | 4-OH-Phenyl |
| 8 | Methyl | Methyl | 4 | 4-OH-Phenyl |
| 9 | Methyl | Methyl | 1 | 3-OH-Phenyl |
| 10 | Methyl | Methyl | 2 | 3-OH-Phenyl |
| 11 | Methyl | Methyl | 3 | 3-OH-Phenyl |
| 12 | Methyl | Methyl | 4 | 3-OH-Phenyl |
| 13 | Methyl | Methyl | 1 | 2-OH-Phenyl |
| 14 | Methyl | Methyl | 2 | 2-OH-Phenyl |
| 15 | Methyl | Methyl | 3 | 2-OH-Phenyl |
| 16 | Methyl | Methyl | 4 | 2-OH-Phenyl |
| 17 | Methyl | Methyl | 1 | 4-OMe-Phenyl |
| 18 | Methyl | Methyl | 2 | 4-OMe-Phenyl |
| 19 | Methyl | Methyl | 3 | 4-OMe-Phenyl |
| 20 | Methyl | Methyl | 4 | 4-OMe-Phenyl |
| 21 | Methyl | Methyl | 1 | 3-OMe-Phenyl |
| 22 | Methyl | Methyl | 2 | 3-OMe-Phenyl |
| 23 | Methyl | Methyl | 3 | 3-OMe-Phenyl |
| 24 | Methyl | Methyl | 4 | 3-OMe-Phenyl |
| 25 | Methyl | Methyl | 1 | 2-OMe-Phenyl |
| 26 | Methyl | Methyl | 2 | 2-OMe-Phenyl |
| 27 | Methyl | Methyl | 3 | 2-OMe-Phenyl |
| 28 | Methyl | Methyl | 4 | 2-OMe-Phenyl |
| 29 | Methyl | Methyl | 1 | 4-CN-Phenyl |
| 30 | Methyl | Methyl | 2 | 4-CN-Phenyl |
| 31 | Methyl | Methyl | 3 | 4-CN-Phenyl |
| 32 | Methyl | Methyl | 4 | 4-CN-Phenyl |
| 33 | Methyl | Methyl | 1 | 3-CN-Phenyl |
| 34 | Methyl | Methyl | 2 | 3-CN-Phenyl |
| 35 | Methyl | Methyl | 3 | 3-CN-Phenyl |
| 36 | Methyl | Methyl | 4 | 3-CN-Phenyl |
| 37 | Methyl | Methyl | 1 | 2-CN-Phenyl |
| 38 | Methyl | Methyl | 2 | 2-CN-Phenyl |
| 39 | Methyl | Methyl | 3 | 2-CN-Phenyl |
| 40 | Methyl | Methyl | 4 | 2-CN-Phenyl |
| 41 | Methyl | Methyl | 1 | 4-Me-Phenyl |
| 42 | Methyl | Methyl | 2 | 4-Me-Phenyl |
| 43 | Methyl | Methyl | 3 | 4-Me-Phenyl |
| 44 | Methyl | Methyl | 4 | 4-Me-Phenyl |
| 45 | Methyl | Methyl | 1 | 3-Me-Phenyl |
| 46 | Methyl | Methyl | 2 | 3-Me-Phenyl |
| 47 | Methyl | Methyl | 3 | 3-Me-Phenyl |
| 48 | Methyl | Methyl | 4 | 3-Me-Phenyl |
| 49 | Methyl | Methyl | 1 | 2-Me-Phenyl |
| 50 | Methyl | Methyl | 2 | 2-Me-Phenyl |
| 51 | Methyl | Methyl | 3 | 2-Me-Phenyl |
| 52 | Methyl | Methyl | 4 | 2-Me-Phenyl |
| 53 | Methyl | Methyl | 1 | 4-F-Phenyl |
| 54 | Methyl | Methyl | 2 | 4-F-Phenyl |
| 55 | Methyl | Methyl | 3 | 4-F-Phenyl |
| 56 | Methyl | Methyl | 4 | 4-F-Phenyl |
| 57 | Methyl | Methyl | 1 | 3-F-Phenyl |
| 58 | Methyl | Methyl | 2 | 3-F-Phenyl |
| 59 | Methyl | Methyl | 3 | 3-F-Phenyl |
| 60 | Methyl | Methyl | 4 | 3-F-Phenyl |
| 61 | Methyl | Methyl | 1 | 2-F-Phenyl |
| 62 | Methyl | Methyl | 2 | 2-F-Phenyl |
| 63 | Methyl | Methyl | 3 | 2-F-Phenyl |
| 64 | Methyl | Methyl | 4 | 2-F-Phenyl |
| 65 | Methyl | Methyl | 1 | 4-Cl-Phenyl |
| 66 | Methyl | Methyl | 2 | 4-Cl-Phenyl |
| 67 | Methyl | Methyl | 3 | 4-Cl-Phenyl |
| 68 | Methyl | Methyl | 4 | 4-Cl-Phenyl |
| 69 | Methyl | Methyl | 1 | 3-Cl-Phenyl |
| 70 | Methyl | Methyl | 2 | 3-Cl-Phenyl |
| 71 | Methyl | Methyl | 3 | 3-Cl-Phenyl |
| 72 | Methyl | Methyl | 4 | 3-Cl-Phenyl |

TABLE 1-continued

| Entry | $R^1$ | $R^2$ | n | $R^3$ |
|---|---|---|---|---|
| 73 | Methyl | Methyl | 1 | 2-Cl-Phenyl |
| 74 | Methyl | Methyl | 2 | 2-Cl-Phenyl |
| 75 | Methyl | Methyl | 3 | 2-Cl-Phenyl |
| 76 | Methyl | Methyl | 4 | 2-Cl-Phenyl |
| 77 | Methyl | Methyl | 1 | 4-Br-Phenyl |
| 78 | Methyl | Methyl | 2 | 4-Br-Phenyl |
| 79 | Methyl | Methyl | 3 | 4-Br-Phenyl |
| 80 | Methyl | Methyl | 4 | 4-Br-Phenyl |
| 81 | Methyl | Methyl | 1 | 3-Br-Phenyl |
| 82 | Methyl | Methyl | 2 | 3-Br-Phenyl |
| 83 | Methyl | Methyl | 3 | 3-Br-Phenyl |
| 84 | Methyl | Methyl | 4 | 3-Br-Phenyl |
| 85 | Methyl | Methyl | 1 | 2-Br-Phenyl |
| 86 | Methyl | Methyl | 2 | 2-Br-Phenyl |
| 87 | Methyl | Methyl | 3 | 2-Br-Phenyl |
| 88 | Methyl | Methyl | 4 | 2-Br-Phenyl |
| 89 | Methyl | Methyl | 1 | 4-$CF_3$-Phenyl |
| 90 | Methyl | Methyl | 2 | 4-$CF_3$-Phenyl |
| 91 | Methyl | Methyl | 3 | 4-$CF_3$-Phenyl |
| 92 | Methyl | Methyl | 4 | 4-$CF_3$-Phenyl |
| 93 | Methyl | Methyl | 1 | 3-$CF_3$-Phenyl |
| 94 | Methyl | Methyl | 2 | 3-$CF_3$-Phenyl |
| 95 | Methyl | Methyl | 3 | 3-$CF_3$-Phenyl |
| 96 | Methyl | Methyl | 4 | 3-$CF_3$-Phenyl |
| 97 | Methyl | Methyl | 1 | 2-$CF_3$-Phenyl |
| 98 | Methyl | Methyl | 2 | 2-$CF_3$-Phenyl |
| 99 | Methyl | Methyl | 3 | 2-$CF_3$-Phenyl |
| 100 | Methyl | Methyl | 4 | 2-$CF_3$-Phenyl |
| 101 | Methyl | Methyl | 1 | 4-iPr-Phenyl |
| 102 | Methyl | Methyl | 2 | 4-iPr-Phenyl |
| 103 | Methyl | Methyl | 3 | 4-iPr-Phenyl |
| 104 | Methyl | Methyl | 4 | 4-iPr-Phenyl |
| 105 | Methyl | Methyl | 1 | 3-iPr-Phenyl |
| 106 | Methyl | Methyl | 2 | 3-iPr-Phenyl |
| 107 | Methyl | Methyl | 3 | 3-iPr-Phenyl |
| 108 | Methyl | Methyl | 4 | 3-iPr-Phenyl |
| 109 | Methyl | Methyl | 1 | 2-iPr-Phenyl |
| 110 | Methyl | Methyl | 2 | 2-iPr-Phenyl |
| 111 | Methyl | Methyl | 3 | 2-iPr-Phenyl |
| 112 | Methyl | Methyl | 4 | 2-iPr-Phenyl |
| 125 | Methyl | Methyl | 1 | 2,3-di-Me-Phenyl |
| 126 | Methyl | Methyl | 2 | 2,3-di-Me-Phenyl |
| 127 | Methyl | Methyl | 3 | 2,3-di-Me-Phenyl |
| 128 | Methyl | Methyl | 4 | 2,3-di-Me-Phenyl |
| 129 | Methyl | Methyl | 1 | 2,4-di-Me-Phenyl |
| 130 | Methyl | Methyl | 2 | 2,4-di-Me-Phenyl |
| 131 | Methyl | Methyl | 3 | 2,4-di-Me-Phenyl |
| 132 | Methyl | Methyl | 4 | 2,4-di-Me-Phenyl |
| 133 | Methyl | Methyl | 1 | 2,5-di-Me-Phenyl |
| 134 | Methyl | Methyl | 2 | 2,5-di-Me-Phenyl |
| 135 | Methyl | Methyl | 3 | 2,5-di-Me-Phenyl |
| 136 | Methyl | Methyl | 4 | 2,5-di-Me-Phenyl |
| 137 | Methyl | Methyl | 1 | 2,6-di-Me-Phenyl |
| 138 | Methyl | Methyl | 2 | 2,6-di-Me-Phenyl |
| 139 | Methyl | Methyl | 3 | 2,6-di-Me-Phenyl |
| 140 | Methyl | Methyl | 4 | 2,6-di-Me-Phenyl |
| 141 | Methyl | Methyl | 1 | 2,6-di-iPr-Phenyl |
| 142 | Methyl | Methyl | 2 | 2,6-di-iPr-Phenyl |
| 143 | Methyl | Methyl | 3 | 2,6-di-iPr-Phenyl |
| 144 | Methyl | Methyl | 4 | 2,6-di-iPr-Phenyl |
| 145 | Methyl | Methyl | 1 | 2-morpholino-phenyl |
| 146 | Methyl | Methyl | 2 | 2-morpholino-phenyl |
| 147 | Methyl | Methyl | 3 | 2-morpholino-phenyl |
| 148 | Methyl | Methyl | 4 | 2-morpholino-phenyl |
| 149 | Methyl | Methyl | 1 | 3-morpholino-phenyl |
| 150 | Methyl | Methyl | 2 | 3-morpholino-phenyl |
| 151 | Methyl | Methyl | 3 | 3-morpholino-phenyl |
| 152 | Methyl | Methyl | 4 | 3-morpholino-phenyl |
| 153 | Methyl | Methyl | 1 | 4-morpholino-phenyl |
| 154 | Methyl | Methyl | 2 | 4-morpholino-phenyl |
| 155 | Methyl | Methyl | 3 | 4-morpholino-phenyl |
| 156 | Methyl | Methyl | 4 | 4-morpholino-phenyl |
| 157 | Methyl | Methyl | 1 | 4-CN-2-morpholino-phenyl |
| 158 | Methyl | Methyl | 2 | 4-CN-2-morpholino-phenyl |
| 159 | Methyl | Methyl | 3 | 4-CN-2-morpholino-phenyl |
| 160 | Methyl | Methyl | 4 | 4-CN-2-morpholino-phenyl |
| 161 | Methyl | Methyl | 1 | 4-$CH_3$-2-morpholino-phenyl |
| 162 | Methyl | Methyl | 2 | 4-$CH_3$-2-morpholino-phenyl |

TABLE 1-continued

| Entry | $R^1$ | $R^2$ | n | $R^3$ |
|---|---|---|---|---|
| 163 | Methyl | Methyl | 3 | 4-$CH_3$-2-morpholino-phenyl |
| 164 | Methyl | Methyl | 4 | 4-$CH_3$-2-morpholino-phenyl |
| 165 | Methyl | Methyl | 1 | 4-OH-2-morpholino-phenyl |
| 166 | Methyl | Methyl | 2 | 4-OH-2-morpholino-phenyl |
| 167 | Methyl | Methyl | 3 | 4-OH-2-morpholino-phenyl |
| 168 | Methyl | Methyl | 4 | 4-OH-2-morpholino-phenyl |
| 177 | Ethyl | Ethyl | 1 | Phenyl |
| 178 | Ethyl | Ethyl | 2 | Phenyl |
| 179 | Ethyl | Ethyl | 3 | Phenyl |
| 180 | Ethyl | Ethyl | 4 | Phenyl |
| 181 | Ethyl | Ethyl | 1 | 4-OH-Phenyl |
| 182 | Ethyl | Ethyl | 2 | 4-OH-Phenyl |
| 183 | Ethyl | Ethyl | 3 | 4-OH-Phenyl |
| 184 | Ethyl | Ethyl | 4 | 4-OH-Phenyl |
| 185 | Ethyl | Ethyl | 1 | 3-OH-Phenyl |
| 186 | Ethyl | Ethyl | 2 | 3-OH-Phenyl |
| 187 | Ethyl | Ethyl | 3 | 3-OH-Phenyl |
| 188 | Ethyl | Ethyl | 4 | 3-OH-Phenyl |
| 189 | Ethyl | Ethyl | 1 | 2-OH-Phenyl |
| 190 | Ethyl | Ethyl | 2 | 2-OH-Phenyl |
| 191 | Ethyl | Ethyl | 3 | 2-OH-Phenyl |
| 192 | Ethyl | Ethyl | 4 | 2-OH-Phenyl |
| 193 | Ethyl | Ethyl | 1 | 4-OMe-Phenyl |
| 194 | Ethyl | Ethyl | 2 | 4-OMe-Phenyl |
| 195 | Ethyl | Ethyl | 3 | 4-OMe-Phenyl |
| 196 | Ethyl | Ethyl | 4 | 4-OMe-Phenyl |
| 197 | Ethyl | Ethyl | 1 | 3-OMe-Phenyl |
| 198 | Ethyl | Ethyl | 2 | 3-OMe-Phenyl |
| 199 | Ethyl | Ethyl | 3 | 3-OMe-Phenyl |
| 200 | Ethyl | Ethyl | 4 | 3-OMe-Phenyl |
| 201 | Ethyl | Ethyl | 1 | 2-OMe-Phenyl |
| 202 | Ethyl | Ethyl | 2 | 2-OMe-Phenyl |
| 203 | Ethyl | Ethyl | 3 | 2-OMe-Phenyl |
| 204 | Ethyl | Ethyl | 4 | 2-OMe-Phenyl |
| 205 | Ethyl | Ethyl | 1 | 4-CN-Phenyl |
| 206 | Ethyl | Ethyl | 2 | 4-CN-Phenyl |
| 207 | Ethyl | Ethyl | 3 | 4-CN-Phenyl |
| 208 | Ethyl | Ethyl | 4 | 4-CN-Phenyl |
| 209 | Ethyl | Ethyl | 1 | 3-CN-Phenyl |
| 210 | Ethyl | Ethyl | 2 | 3-CN-Phenyl |
| 211 | Ethyl | Ethyl | 3 | 3-CN-Phenyl |
| 212 | Ethyl | Ethyl | 4 | 3-CN-Phenyl |
| 213 | Ethyl | Ethyl | 1 | 2-CN-Phenyl |
| 214 | Ethyl | Ethyl | 2 | 2-CN-Phenyl |
| 215 | Ethyl | Ethyl | 3 | 2-CN-Phenyl |
| 216 | Ethyl | Ethyl | 4 | 2-CN-Phenyl |
| 217 | Ethyl | Ethyl | 1 | 4-Me-Phenyl |
| 218 | Ethyl | Ethyl | 2 | 4-Me-Phenyl |
| 219 | Ethyl | Ethyl | 3 | 4-Me-Phenyl |
| 220 | Ethyl | Ethyl | 4 | 4-Me-Phenyl |
| 221 | Ethyl | Ethyl | 1 | 3-Me-Phenyl |
| 222 | Ethyl | Ethyl | 2 | 3-Me-Phenyl |
| 223 | Ethyl | Ethyl | 3 | 3-Me-Phenyl |
| 224 | Ethyl | Ethyl | 4 | 3-Me-Phenyl |
| 225 | Ethyl | Ethyl | 1 | 2-Me-Phenyl |
| 226 | Ethyl | Ethyl | 2 | 2-Me-Phenyl |
| 227 | Ethyl | Ethyl | 3 | 2-Me-Phenyl |
| 228 | Ethyl | Ethyl | 4 | 2-Me-Phenyl |
| 229 | Ethyl | Ethyl | 1 | 4-F-Phenyl |
| 230 | Ethyl | Ethyl | 2 | 4-F-Phenyl |
| 231 | Ethyl | Ethyl | 3 | 4-F-Phenyl |
| 232 | Ethyl | Ethyl | 4 | 4-F-Phenyl |
| 233 | Ethyl | Ethyl | 1 | 3-F-Phenyl |
| 234 | Ethyl | Ethyl | 2 | 3-F-Phenyl |
| 235 | Ethyl | Ethyl | 3 | 3-F-Phenyl |
| 236 | Ethyl | Ethyl | 4 | 3-F-Phenyl |
| 237 | Ethyl | Ethyl | 1 | 2-F-Phenyl |
| 238 | Ethyl | Ethyl | 2 | 2-F-Phenyl |
| 239 | Ethyl | Ethyl | 3 | 2-F-Phenyl |
| 240 | Ethyl | Ethyl | 4 | 2-F-Phenyl |
| 241 | Ethyl | Ethyl | 1 | 4-Cl-Phenyl |
| 242 | Ethyl | Ethyl | 2 | 4-Cl-Phenyl |
| 243 | Ethyl | Ethyl | 3 | 4-Cl-Phenyl |
| 244 | Ethyl | Ethyl | 4 | 4-Cl-Phenyl |
| 245 | Ethyl | Ethyl | 1 | 3-Cl-Phenyl |
| 246 | Ethyl | Ethyl | 2 | 3-Cl-Phenyl |
| 247 | Ethyl | Ethyl | 3 | 3-Cl-Phenyl |
| 248 | Ethyl | Ethyl | 4 | 3-Cl-Phenyl |

TABLE 1-continued

| Entry | $R^1$ | $R^2$ | n | $R^3$ |
|---|---|---|---|---|
| 249 | Ethyl | Ethyl | 1 | 2-Cl-Phenyl |
| 250 | Ethyl | Ethyl | 2 | 2-Cl-Phenyl |
| 251 | Ethyl | Ethyl | 3 | 2-Cl-Phenyl |
| 252 | Ethyl | Ethyl | 4 | 2-Cl-Phenyl |
| 253 | Ethyl | Ethyl | 1 | 4-Br-Phenyl |
| 254 | Ethyl | Ethyl | 2 | 4-Br-Phenyl |
| 255 | Ethyl | Ethyl | 3 | 4-Br-Phenyl |
| 256 | Ethyl | Ethyl | 4 | 4-Br-Phenyl |
| 257 | Ethyl | Ethyl | 1 | 3-Br-Phenyl |
| 258 | Ethyl | Ethyl | 2 | 3-Br-Phenyl |
| 259 | Ethyl | Ethyl | 3 | 3-Br-Phenyl |
| 260 | Ethyl | Ethyl | 4 | 3-Br-Phenyl |
| 261 | Ethyl | Ethyl | 1 | 2-Br-Phenyl |
| 262 | Ethyl | Ethyl | 2 | 2-Br-Phenyl |
| 263 | Ethyl | Ethyl | 3 | 2-Br-Phenyl |
| 264 | Ethyl | Ethyl | 4 | 2-Br-Phenyl |
| 265 | Ethyl | Ethyl | 1 | 4-$CF_3$-Phenyl |
| 266 | Ethyl | Ethyl | 2 | 4-$CF_3$-Phenyl |
| 267 | Ethyl | Ethyl | 3 | 4-$CF_3$-Phenyl |
| 268 | Ethyl | Ethyl | 4 | 4-$CF_3$-Phenyl |
| 269 | Ethyl | Ethyl | 1 | 3-$CF_3$-Phenyl |
| 270 | Ethyl | Ethyl | 2 | 3-$CF_3$-Phenyl |
| 271 | Ethyl | Ethyl | 3 | 3-$CF_3$-Phenyl |
| 272 | Ethyl | Ethyl | 4 | 3-$CF_3$-Phenyl |
| 273 | Ethyl | Ethyl | 1 | 2-$CF_3$-Phenyl |
| 274 | Ethyl | Ethyl | 2 | 2-$CF_3$-Phenyl |
| 275 | Ethyl | Ethyl | 3 | 2-$CF_3$-Phenyl |
| 276 | Ethyl | Ethyl | 4 | 2-$CF_3$-Phenyl |
| 277 | Ethyl | Ethyl | 1 | 4-iPr-Phenyl |
| 278 | Ethyl | Ethyl | 2 | 4-iPr-Phenyl |
| 279 | Ethyl | Ethyl | 3 | 4-iPr-Phenyl |
| 280 | Ethyl | Ethyl | 4 | 4-iPr-Phenyl |
| 281 | Ethyl | Ethyl | 1 | 3-iPr-Phenyl |
| 282 | Ethyl | Ethyl | 2 | 3-iPr-Phenyl |
| 283 | Ethyl | Ethyl | 3 | 3-iPr-Phenyl |
| 284 | Ethyl | Ethyl | 4 | 3-iPr-Phenyl |
| 285 | Ethyl | Ethyl | 1 | 2-iPr-Phenyl |
| 286 | Ethyl | Ethyl | 2 | 2-iPr-Phenyl |
| 287 | Ethyl | Ethyl | 3 | 2-iPr-Phenyl |
| 288 | Ethyl | Ethyl | 4 | 2-iPr-Phenyl |
| 301 | Ethyl | Ethyl | 1 | 2,3-di-Me-Phenyl |
| 302 | Ethyl | Ethyl | 2 | 2,3-di-Me-Phenyl |
| 303 | Ethyl | Ethyl | 3 | 2,3-di-Me-Phenyl |
| 304 | Ethyl | Ethyl | 4 | 2,3-di-Me-Phenyl |
| 305 | Ethyl | Ethyl | 1 | 2,4-di-Me-Phenyl |
| 306 | Ethyl | Ethyl | 2 | 2,4-di-Me-Phenyl |
| 307 | Ethyl | Ethyl | 3 | 2,4-di-Me-Phenyl |
| 308 | Ethyl | Ethyl | 4 | 2,4-di-Me-Phenyl |
| 309 | Ethyl | Ethyl | 1 | 2,5-di-Me-Phenyl |
| 310 | Ethyl | Ethyl | 2 | 2,5-di-Me-Phenyl |
| 311 | Ethyl | Ethyl | 3 | 2,5-di-Me-Phenyl |
| 312 | Ethyl | Ethyl | 4 | 2,5-di-Me-Phenyl |
| 313 | Ethyl | Ethyl | 1 | 2,6-di-Me-Phenyl |
| 314 | Ethyl | Ethyl | 2 | 2,6-di-Me-Phenyl |
| 315 | Ethyl | Ethyl | 3 | 2,6-di-Me-Phenyl |
| 316 | Ethyl | Ethyl | 4 | 2,6-di-Me-Phenyl |
| 317 | Ethyl | Ethyl | 1 | 2,6-di-iPr-Phenyl |
| 318 | Ethyl | Ethyl | 2 | 2,6-di-iPr-Phenyl |
| 319 | Ethyl | Ethyl | 3 | 2,6-di-iPr-Phenyl |
| 320 | Ethyl | Ethyl | 4 | 2,6-di-iPr-Phenyl |
| 321 | Ethyl | Ethyl | 1 | 2-morpholino-phenyl |
| 322 | Ethyl | Ethyl | 2 | 2-morpholino-phenyl |
| 323 | Ethyl | Ethyl | 3 | 2-morpholino-phenyl |
| 324 | Ethyl | Ethyl | 4 | 2-morpholino-phenyl |
| 325 | Ethyl | Ethyl | 1 | 3-morpholino-phenyl |
| 326 | Ethyl | Ethyl | 2 | 3-morpholino-phenyl |
| 327 | Ethyl | Ethyl | 3 | 3-morpholino-phenyl |
| 328 | Ethyl | Ethyl | 4 | 3-morpholino-phenyl |
| 329 | Ethyl | Ethyl | 1 | 4-morpholino-phenyl |
| 330 | Ethyl | Ethyl | 2 | 4-morpholino-phenyl |
| 331 | Ethyl | Ethyl | 3 | 4-morpholino-phenyl |
| 332 | Ethyl | Ethyl | 4 | 4-morpholino-phenyl |
| 333 | Ethyl | Ethyl | 1 | 4-CN-2-morpholino-phenyl |
| 334 | Ethyl | Ethyl | 2 | 4-CN-2-morpholino-phenyl |
| 335 | Ethyl | Ethyl | 3 | 4-CN-2-morpholino-phenyl |
| 336 | Ethyl | Ethyl | 4 | 4-CN-2-morpholino-phenyl |
| 337 | Ethyl | Ethyl | 1 | 4-$CH_3$-2-morpholino-phenyl |
| 338 | Ethyl | Ethyl | 2 | 4-$CH_3$-2-morpholino-phenyl |

TABLE 1-continued

| Entry | $R^1$ | $R^2$ | n | $R^3$ |
|---|---|---|---|---|
| 339 | Ethyl | Ethyl | 3 | 4-$CH_3$-2-morpholino-phenyl |
| 340 | Ethyl | Ethyl | 4 | 4-$CH_3$-2-morpholino-phenyl |
| 341 | Ethyl | Ethyl | 1 | 4-OH-2-morpholino-phenyl |
| 342 | Ethyl | Ethyl | 2 | 4-OH-2-morpholino-phenyl |
| 343 | Ethyl | Ethyl | 3 | 4-OH-2-morpholino-phenyl |
| 344 | Ethyl | Ethyl | 4 | 4-OH-2-morpholino-phenyl |

or a pharmaceutically acceptable salt thereof.

16. The compound of claim 15, wherein each of $R^1$ and $R^2$ is ethyl.

17. A compound of Formula (XXII), having a structure as described in Table 16:

(XXII)

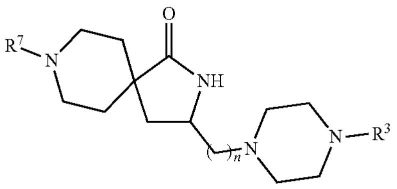

TABLE 16

| Entry | n | $R^7$ | $R^3$ |
|---|---|---|---|
| 1 | 1 | H | Phenyl |
| 2 | 2 | H | Phenyl |
| 3 | 3 | H | Phenyl |
| 4 | 4 | H | Phenyl |
| 13 | 1 | COMe | Phenyl |
| 14 | 2 | COMe | Phenyl |
| 15 | 3 | COMe | Phenyl |
| 16 | 4 | COMe | Phenyl |
| 17 | 1 | $CO_2Me$ | Phenyl |
| 18 | 2 | $CO_2Me$ | Phenyl |
| 19 | 3 | $CO_2Me$ | Phenyl |
| 20 | 4 | $CO_2Me$ | Phenyl |
| 21 | 1 | $CO_2tBu$ | Phenyl |
| 22 | 2 | $CO_2tBu$ | Phenyl |
| 23 | 3 | $CO_2tBu$ | Phenyl |
| 24 | 4 | $CO_2tBu$ | Phenyl |
| 29 | 1 | $SO_2Me$ | Phenyl |
| 30 | 2 | $SO_2Me$ | Phenyl |
| 31 | 3 | $SO_2Me$ | Phenyl |
| 32 | 4 | $SO_2Me$ | Phenyl |
| 37 | 1 | H | 3-OH-Phenyl |
| 38 | 2 | H | 3-OH-Phenyl |
| 39 | 3 | H | 3-OH-Phenyl |
| 40 | 4 | H | 3-OH-Phenyl |
| 49 | 1 | COMe | 3-OH-Phenyl |
| 50 | 2 | COMe | 3-OH-Phenyl |
| 51 | 3 | COMe | 3-OH-Phenyl |
| 52 | 4 | COMe | 3-OH-Phenyl |
| 53 | 1 | $CO_2Me$ | 3-OH-Phenyl |
| 54 | 2 | $CO_2Me$ | 3-OH-Phenyl |
| 55 | 3 | $CO_2Me$ | 3-OH-Phenyl |
| 56 | 4 | $CO_2Me$ | 3-OH-Phenyl |
| 57 | 1 | $CO_2tBu$ | 3-OH-Phenyl |
| 58 | 2 | $CO_2tBu$ | 3-OH-Phenyl |
| 59 | 3 | $CO_2tBu$ | 3-OH-Phenyl |
| 60 | 4 | $CO_2tBu$ | 3-OH-Phenyl |
| 65 | 1 | $SO_2Me$ | 3-OH-Phenyl |
| 66 | 2 | $SO_2Me$ | 3-OH-Phenyl |
| 67 | 3 | $SO_2Me$ | 3-OH-Phenyl |
| 68 | 4 | $SO_2Me$ | 3-OH-Phenyl |
| 109 | 1 | H | 3-OMe-Phenyl |
| 110 | 2 | H | 3-OMe-Phenyl |
| 111 | 3 | H | 3-OMe-Phenyl |
| 112 | 4 | H | 3-OMe-Phenyl |
| 121 | 1 | COMe | 3-OMe-Phenyl |

TABLE 16-continued

| Entry | n | $R^7$ | $R^3$ |
|---|---|---|---|
| 122 | 2 | COMe | 3-OMe-Phenyl |
| 123 | 3 | COMe | 3-OMe-Phenyl |
| 124 | 4 | COMe | 3-OMe-Phenyl |
| 125 | 1 | $CO_2Me$ | 3-OMe-Phenyl |
| 126 | 2 | $CO_2Me$ | 3-OMe-Phenyl |
| 127 | 3 | $CO_2Me$ | 3-OMe-Phenyl |
| 128 | 4 | $CO_2Me$ | 3-OMe-Phenyl |
| 129 | 1 | $CO_2tBu$ | 3-OMe-Phenyl |
| 130 | 2 | $CO_2tBu$ | 3-OMe-Phenyl |
| 131 | 3 | $CO_2tBu$ | 3-OMe-Phenyl |
| 132 | 4 | $CO_2tBu$ | 3-OMe-Phenyl |
| 137 | 1 | $SO_2Me$ | 3-OMe-Phenyl |
| 138 | 2 | $SO_2Me$ | 3-OMe-Phenyl |
| 139 | 3 | $SO_2Me$ | 3-OMe-Phenyl |
| 140 | 4 | $SO_2Me$ | 3-OMe-Phenyl |
| 145 | 1 | H | 4-CN-Phenyl |
| 146 | 2 | H | 4-CN-Phenyl |
| 147 | 3 | H | 4-CN-Phenyl |
| 148 | 4 | H | 4-CN-Phenyl |
| 157 | 1 | COMe | 4-CN-Phenyl |
| 158 | 2 | COMe | 4-CN-Phenyl |
| 159 | 3 | COMe | 4-CN-Phenyl |
| 160 | 4 | COMe | 4-CN-Phenyl |
| 161 | 1 | $CO_2Me$ | 4-CN-Phenyl |
| 162 | 2 | $CO_2Me$ | 4-CN-Phenyl |
| 163 | 3 | $CO_2Me$ | 4-CN-Phenyl |
| 164 | 4 | $CO_2Me$ | 4-CN-Phenyl |
| 165 | 1 | $CO_2tBu$ | 4-CN-Phenyl |
| 166 | 2 | $CO_2tBu$ | 4-CN-Phenyl |
| 167 | 3 | $CO_2tBu$ | 4-CN-Phenyl |
| 168 | 4 | $CO_2tBu$ | 4-CN-Phenyl |
| 173 | 1 | $SO_2Me$ | 4-CN-Phenyl |
| 174 | 2 | $SO_2Me$ | 4-CN-Phenyl |
| 175 | 3 | $SO_2Me$ | 4-CN-Phenyl |
| 176 | 4 | $SO_2Me$ | 4-CN-Phenyl |
| 181 | 1 | H | 2-CN-Phenyl |
| 182 | 2 | H | 2-CN-Phenyl |
| 183 | 3 | H | 2-CN-Phenyl |
| 184 | 4 | H | 2-CN-Phenyl |
| 193 | 1 | COMe | 2-CN-Phenyl |
| 194 | 2 | COMe | 2-CN-Phenyl |
| 195 | 3 | COMe | 2-CN-Phenyl |
| 196 | 4 | COMe | 2-CN-Phenyl |
| 197 | 1 | $CO_2Me$ | 2-CN-Phenyl |
| 198 | 2 | $CO_2Me$ | 2-CN-Phenyl |
| 199 | 3 | $CO_2Me$ | 2-CN-Phenyl |
| 200 | 4 | $CO_2Me$ | 2-CN-Phenyl |
| 201 | 1 | $CO_2tBu$ | 2-CN-Phenyl |
| 202 | 2 | $CO_2tBu$ | 2-CN-Phenyl |
| 203 | 3 | $CO_2tBu$ | 2-CN-Phenyl |
| 204 | 4 | $CO_2tBu$ | 2-CN-Phenyl |
| 209 | 1 | $SO_2Me$ | 2-CN-Phenyl |
| 210 | 2 | $SO_2Me$ | 2-CN-Phenyl |
| 211 | 3 | $SO_2Me$ | 2-CN-Phenyl |
| 212 | 4 | $SO_2Me$ | 2-CN-Phenyl |
| 217 | 1 | H | 3-Me-Phenyl |
| 218 | 2 | H | 3-Me-Phenyl |
| 219 | 3 | H | 3-Me-Phenyl |
| 220 | 4 | H | 3-Me-Phenyl |
| 229 | 1 | COMe | 3-Me-Phenyl |
| 230 | 2 | COMe | 3-Me-Phenyl |
| 231 | 3 | COMe | 3-Me-Phenyl |
| 232 | 4 | COMe | 3-Me-Phenyl |
| 233 | 1 | $CO_2Me$ | 3-Me-Phenyl |
| 234 | 2 | $CO_2Me$ | 3-Me-Phenyl |
| 235 | 3 | $CO_2Me$ | 3-Me-Phenyl |
| 236 | 4 | $CO_2Me$ | 3-Me-Phenyl |
| 237 | 1 | $CO_2tBu$ | 3-Me-Phenyl |
| 238 | 2 | $CO_2tBu$ | 3-Me-Phenyl |
| 239 | 3 | $CO_2tBu$ | 3-Me-Phenyl |
| 240 | 4 | $CO_2tBu$ | 3-Me-Phenyl |
| 245 | 1 | $SO_2Me$ | 3-Me-Phenyl |
| 246 | 2 | $SO_2Me$ | 3-Me-Phenyl |
| 247 | 3 | $SO_2Me$ | 3-Me-Phenyl |
| 248 | 4 | $SO_2Me$ | 3-Me-Phenyl |
| 253 | 1 | H | 2-F-Phenyl |
| 254 | 2 | H | 2-F-Phenyl |
| 255 | 3 | H | 2-F-Phenyl |

TABLE 16-continued

| Entry | n | $R^7$ | $R^3$ |
|---|---|---|---|
| 256 | 4 | H | 2-F-Phenyl |
| 266 | 2 | COMe | 2-F-Phenyl |
| 267 | 3 | COMe | 2-F-Phenyl |
| 268 | 4 | COMe | 2-F-Phenyl |
| 269 | 1 | $CO_2Me$ | 2-F-Phenyl |
| 270 | 2 | $CO_2Me$ | 2-F-Phenyl |
| 271 | 3 | $CO_2Me$ | 2-F-Phenyl |
| 272 | 4 | $CO_2Me$ | 2-F-Phenyl |
| 273 | 1 | $CO_2tBu$ | 2-F-Phenyl |
| 274 | 2 | $CO_2tBu$ | 2-F-Phenyl |
| 275 | 3 | $CO_2tBu$ | 2-F-Phenyl |
| 276 | 4 | $CO_2tBu$ | 2-F-Phenyl |
| 281 | 1 | $SO_2Me$ | 2-F-Phenyl |
| 282 | 2 | $SO_2Me$ | 2-F-Phenyl |
| 283 | 3 | $SO_2Me$ | 2-F-Phenyl |
| 284 | 4 | $SO_2Me$ | 2-F-Phenyl |
| 289 | 1 | H | 4-F-Phenyl |
| 290 | 2 | H | 4-F-Phenyl |
| 291 | 3 | H | 4-F-Phenyl |
| 292 | 4 | H | 4-F-Phenyl |
| 301 | 1 | COMe | 4-F-Phenyl |
| 302 | 2 | COMe | 4-F-Phenyl |
| 303 | 3 | COMe | 4-F-Phenyl |
| 304 | 4 | COMe | 4-F-Phenyl |
| 305 | 1 | $CO_2Me$ | 4-F-Phenyl |
| 306 | 2 | $CO_2Me$ | 4-F-Phenyl |
| 307 | 3 | $CO_2Me$ | 4-F-Phenyl |
| 308 | 4 | $CO_2Me$ | 4-F-Phenyl |
| 309 | 1 | $CO_2tBu$ | 4-F-Phenyl |
| 310 | 2 | $CO_2tBu$ | 4-F-Phenyl |
| 311 | 3 | $CO_2tBu$ | 4-F-Phenyl |
| 312 | 4 | $CO_2tBu$ | 4-F-Phenyl |
| 317 | 1 | $SO_2Me$ | 4-F-Phenyl |
| 318 | 2 | $SO_2Me$ | 4-F-Phenyl |
| 319 | 3 | $SO_2Me$ | 4-F-Phenyl |
| 320 | 4 | $SO_2Me$ | 4-F-Phenyl |
| 325 | 1 | H | 3-Cl-Phenyl |
| 326 | 2 | H | 3-Cl-Phenyl |
| 327 | 3 | H | 3-Cl-Phenyl |
| 328 | 4 | H | 3-Cl-Phenyl |
| 337 | 1 | COMe | 3-Cl-Phenyl |
| 338 | 2 | COMe | 3-Cl-Phenyl |
| 339 | 3 | COMe | 3-Cl-Phenyl |
| 340 | 4 | COMe | 3-Cl-Phenyl |
| 341 | 1 | $CO_2Me$ | 3-Cl-Phenyl |
| 342 | 2 | $CO_2Me$ | 3-Cl-Phenyl |
| 343 | 3 | $CO_2Me$ | 3-Cl-Phenyl |
| 344 | 4 | $CO_2Me$ | 3-Cl-Phenyl |
| 345 | 1 | $CO_2tBu$ | 3-Cl-Phenyl |
| 346 | 2 | $CO_2tBu$ | 3-Cl-Phenyl |
| 347 | 3 | $CO_2tBu$ | 3-Cl-Phenyl |
| 348 | 4 | $CO_2tBu$ | 3-Cl-Phenyl |
| 353 | 1 | $SO_2Me$ | 3-Cl-Phenyl |
| 354 | 2 | $SO_2Me$ | 3-Cl-Phenyl |
| 355 | 3 | $SO_2Me$ | 3-Cl-Phenyl |
| 356 | 4 | $SO_2Me$ | 3-Cl-Phenyl |
| 361 | 1 | H | 2-Br-Phenyl |
| 362 | 2 | H | 2-Br-Phenyl |
| 363 | 3 | H | 2-Br-Phenyl |
| 364 | 4 | H | 2-Br-Phenyl |
| 373 | 1 | COMe | 2-Br-Phenyl |
| 374 | 2 | COMe | 2-Br-Phenyl |
| 375 | 3 | COMe | 2-Br-Phenyl |
| 376 | 4 | COMe | 2-Br-Phenyl |
| 377 | 1 | $CO_2Me$ | 2-Br-Phenyl |
| 378 | 2 | $CO_2Me$ | 2-Br-Phenyl |
| 379 | 3 | $CO_2Me$ | 2-Br-Phenyl |
| 380 | 4 | $CO_2Me$ | 2-Br-Phenyl |
| 381 | 1 | $CO_2tBu$ | 2-Br-Phenyl |
| 382 | 2 | $CO_2tBu$ | 2-Br-Phenyl |
| 383 | 3 | $CO_2tBu$ | 2-Br-Phenyl |
| 384 | 4 | $CO_2tBu$ | 2-Br-Phenyl |
| 389 | 1 | $SO_2Me$ | 2-Br-Phenyl |
| 390 | 2 | $SO_2Me$ | 2-Br-Phenyl |
| 391 | 3 | $SO_2Me$ | 2-Br-Phenyl |
| 392 | 4 | $SO_2Me$ | 2-Br-Phenyl |
| 397 | 1 | H | 4-Br-Phenyl |
| 398 | 2 | H | 4-Br-Phenyl |

TABLE 16-continued

| Entry | n | $R^7$ | $R^3$ |
|---|---|---|---|
| 399 | 3 | H | 4-Br-Phenyl |
| 400 | 4 | H | 4-Br-Phenyl |
| 409 | 1 | COMe | 4-Br-Phenyl |
| 410 | 2 | COMe | 4-Br-Phenyl |
| 411 | 3 | COMe | 4-Br-Phenyl |
| 412 | 4 | COMe | 4-Br-Phenyl |
| 413 | 1 | $CO_2Me$ | 4-Br-Phenyl |
| 414 | 2 | $CO_2Me$ | 4-Br-Phenyl |
| 415 | 3 | $CO_2Me$ | 4-Br-Phenyl |
| 416 | 4 | $CO_2Me$ | 4-Br-Phenyl |
| 417 | 1 | $CO_2tBu$ | 4-Br-Phenyl |
| 418 | 2 | $CO_2tBu$ | 4-Br-Phenyl |
| 419 | 3 | $CO_2tBu$ | 4-Br-Phenyl |
| 420 | 4 | $CO_2tBu$ | 4-Br-Phenyl |
| 425 | 1 | $SO_2Me$ | 4-Br-Phenyl |
| 426 | 2 | $SO_2Me$ | 4-Br-Phenyl |
| 427 | 3 | $SO_2Me$ | 4-Br-Phenyl |
| 428 | 4 | $SO_2Me$ | 4-Br-Phenyl |
| 433 | 1 | H | 3-$CF_3$-Phenyl |
| 434 | 2 | H | 3-$CF_3$-Phenyl |
| 435 | 3 | H | 3-$CF_3$-Phenyl |
| 436 | 4 | H | 3-$CF_3$-Phenyl |
| 445 | 1 | COMe | 3-$CF_3$-Phenyl |
| 446 | 2 | COMe | 3-$CF_3$-Phenyl |
| 447 | 3 | COMe | 3-$CF_3$-Phenyl |
| 448 | 4 | COMe | 3-$CF_3$-Phenyl |
| 449 | 1 | $CO_2Me$ | 3-$CF_3$-Phenyl |
| 450 | 2 | $CO_2Me$ | 3-$CF_3$-Phenyl |
| 451 | 3 | $CO_2Me$ | 3-$CF_3$-Phenyl |
| 452 | 4 | $CO_2Me$ | 3-$CF_3$-Phenyl |
| 453 | 1 | $CO_2tBu$ | 3-$CF_3$-Phenyl |
| 454 | 2 | $CO_2tBu$ | 3-$CF_3$-Phenyl |
| 455 | 3 | $CO_2tBu$ | 3-$CF_3$-Phenyl |
| 456 | 4 | $CO_2tBu$ | 3-$CF_3$-Phenyl |
| 461 | 1 | $SO_2Me$ | 3-$CF_3$-Phenyl |
| 462 | 2 | $SO_2Me$ | 3-$CF_3$-Phenyl |
| 463 | 3 | $SO_2Me$ | 3-$CF_3$-Phenyl |
| 464 | 4 | $SO_2Me$ | 3-$CF_3$-Phenyl |
| 469 | 1 | H | 2-iPr-Phenyl |
| 470 | 2 | H | 2-iPr-Phenyl |
| 471 | 3 | H | 2-iPr-Phenyl |
| 472 | 4 | H | 2-iPr-Phenyl |
| 481 | 1 | COMe | 2-iPr-Phenyl |
| 482 | 2 | COMe | 2-iPr-Phenyl |
| 483 | 3 | COMe | 2-iPr-Phenyl |
| 484 | 4 | COMe | 2-iPr-Phenyl |
| 485 | 1 | $CO_2Me$ | 2-iPr-Phenyl |
| 486 | 2 | $CO_2Me$ | 2-iPr-Phenyl |
| 487 | 3 | $CO_2Me$ | 2-iPr-Phenyl |
| 488 | 4 | $CO_2Me$ | 2-iPr-Phenyl |
| 489 | 1 | $CO_2tBu$ | 2-iPr-Phenyl |
| 490 | 2 | $CO_2tBu$ | 2-iPr-Phenyl |
| 491 | 3 | $CO_2tBu$ | 2-iPr-Phenyl |
| 492 | 4 | $CO_2tBu$ | 2-iPr-Phenyl |
| 497 | 1 | $SO_2Me$ | 2-iPr-Phenyl |
| 498 | 2 | $SO_2Me$ | 2-iPr-Phenyl |
| 499 | 3 | $SO_2Me$ | 2-iPr-Phenyl |
| 500 | 4 | $SO_2Me$ | 2-iPr-Phenyl |
| 505 | 1 | H | 4-iPr-Phenyl |
| 506 | 2 | H | 4-iPr-Phenyl |
| 507 | 3 | H | 4-iPr-Phenyl |
| 508 | 4 | H | 4-iPr-Phenyl |
| 517 | 1 | COMe | 4-iPr-Phenyl |
| 518 | 2 | COMe | 4-iPr-Phenyl |
| 519 | 3 | COMe | 4-iPr-Phenyl |
| 520 | 4 | COMe | 4-iPr-Phenyl |
| 521 | 1 | $CO_2Me$ | 4-iPr-Phenyl |
| 522 | 2 | $CO_2Me$ | 4-iPr-Phenyl |
| 523 | 3 | $CO_2Me$ | 4-iPr-Phenyl |
| 524 | 4 | $CO_2Me$ | 4-iPr-Phenyl |
| 525 | 1 | $CO_2tBu$ | 4-iPr-Phenyl |
| 526 | 2 | $CO_2tBu$ | 4-iPr-Phenyl |
| 527 | 3 | $CO_2tBu$ | 4-iPr-Phenyl |
| 528 | 4 | $CO_2tBu$ | 4-iPr-Phenyl |
| 533 | 1 | $SO_2Me$ | 4-iPr-Phenyl |
| 534 | 2 | $SO_2Me$ | 4-iPr-Phenyl |
| 535 | 3 | $SO_2Me$ | 4-iPr-Phenyl |
| 536 | 4 | $SO_2Me$ | 4-iPr-Phenyl |

TABLE 16-continued

| Entry | n | $R^7$ | $R^3$ |
|---|---|---|---|
| 577 | 1 | H | 2,4-di-Me-Phenyl |
| 578 | 2 | H | 2,4-di-Me-Phenyl |
| 579 | 3 | H | 2,4-di-Me-Phenyl |
| 580 | 4 | H | 2,4-di-Me-Phenyl |
| 589 | 1 | COMe | 2,4-di-Me-Phenyl |
| 590 | 2 | COMe | 2,4-di-Me-Phenyl |
| 591 | 3 | COMe | 2,4-di-Me-Phenyl |
| 592 | 4 | COMe | 2,4-di-Me-Phenyl |
| 593 | 1 | $CO_2Me$ | 2,4-di-Me-Phenyl |
| 594 | 2 | $CO_2Me$ | 2,4-di-Me-Phenyl |
| 595 | 3 | $CO_2Me$ | 2,4-di-Me-Phenyl |
| 596 | 4 | $CO_2Me$ | 2,4-di-Me-Phenyl |
| 597 | 1 | $CO_2tBu$ | 2,4-di-Me-Phenyl |
| 598 | 2 | $CO_2tBu$ | 2,4-di-Me-Phenyl |
| 599 | 3 | $CO_2tBu$ | 2,4-di-Me-Phenyl |
| 600 | 4 | $CO_2tBu$ | 2,4-di-Me-Phenyl |
| 605 | 1 | $SO_2Me$ | 2,4-di-Me-Phenyl |
| 606 | 2 | $SO_2Me$ | 2,4-di-Me-Phenyl |
| 607 | 3 | $SO_2Me$ | 2,4-di-Me-Phenyl |
| 608 | 4 | $SO_2Me$ | 2,4-di-Me-Phenyl |
| 613 | 1 | H | 2,6-di-iPr-Phenyl |
| 614 | 2 | H | 2,6-di-iPr-Phenyl |
| 615 | 3 | H | 2,6-di-iPr-Phenyl |
| 616 | 4 | H | 2,6-di-iPr-Phenyl |
| 625 | 1 | COMe | 2,6-di-iPr-Phenyl |
| 626 | 2 | COMe | 2,6-di-iPr-Phenyl |
| 627 | 3 | COMe | 2,6-di-iPr-Phenyl |
| 628 | 4 | COMe | 2,6-di-iPr-Phenyl |
| 629 | 1 | $CO_2Me$ | 2,6-di-iPr-Phenyl |
| 630 | 2 | $CO_2Me$ | 2,6-di-iPr-Phenyl |
| 631 | 3 | $CO_2Me$ | 2,6-di-iPr-Phenyl |
| 632 | 4 | $CO_2Me$ | 2,6-di-iPr-Phenyl |
| 633 | 1 | $CO_2tBu$ | 2,6-di-iPr-Phenyl |
| 634 | 2 | $CO_2tBu$ | 2,6-di-iPr-Phenyl |
| 635 | 3 | $CO_2tBu$ | 2,6-di-iPr-Phenyl |
| 636 | 4 | $CO_2tBu$ | 2,6-di-iPr-Phenyl |
| 641 | 1 | $SO_2Me$ | 2,6-di-iPr-Phenyl |
| 642 | 2 | $SO_2Me$ | 2,6-di-iPr-Phenyl |
| 643 | 3 | $SO_2Me$ | 2,6-di-iPr-Phenyl |
| 644 | 4 | $SO_2Me$ | 2,6-di-iPr-Phenyl |
| 685 | 1 | H | 2-morpholino-phenyl |
| 686 | 2 | H | 2-morpholino-phenyl |
| 687 | 3 | H | 2-morpholino-phenyl |
| 688 | 4 | H | 2-morpholino-phenyl |
| 697 | 1 | COMe | 2-morpholino-phenyl |
| 698 | 2 | COMe | 2-morpholino-phenyl |
| 699 | 3 | COMe | 2-morpholino-phenyl |
| 700 | 4 | COMe | 2-morpholino-phenyl |
| 701 | 1 | $CO_2Me$ | 2-morpholino-phenyl |
| 702 | 2 | $CO_2Me$ | 2-morpholino-phenyl |
| 703 | 3 | $CO_2Me$ | 2-morpholino-phenyl |
| 704 | 4 | $CO_2Me$ | 2-morpholino-phenyl |
| 705 | 1 | $CO_2tBu$ | 2-morpholino-phenyl |
| 706 | 2 | $CO_2tBu$ | 2-morpholino-phenyl |
| 707 | 3 | $CO_2tBu$ | 2-morpholino-phenyl |
| 708 | 4 | CO2tBu | 2-morpholino-phenyl |
| 713 | 1 | $SO_2Me$ | 2-morpholino-phenyl |
| 714 | 2 | $SO_2Me$ | 2-morpholino-phenyl |
| 715 | 3 | $SO_2Me$ | 2-morpholino-phenyl |
| 716 | 4 | $SO_2Me$ | 2-morpholino-phenyl |
| 721 | 1 | H | 4-morpholino-phenyl |
| 722 | 2 | H | 4-morpholino-phenyl |
| 723 | 3 | H | 4-morpholino-phenyl |
| 724 | 4 | H | 4-morpholino-phenyl |
| 729 | 1 | $CO_2Me$ | 4-morpholino-phenyl |
| 730 | 2 | $CO_2Me$ | 4-morpholino-phenyl |
| 731 | 3 | $CO_2Me$ | 4-morpholino-phenyl |
| 732 | 4 | $CO_2Me$ | 4-morpholino-phenyl |
| 779 | 1 | H | 4-OH-Phenyl |
| 780 | 2 | H | 4-OH-Phenyl |
| 781 | 3 | H | 4-OH-Phenyl |
| 782 | 4 | H | 4-OH-Phenyl |
| 791 | 1 | COMe | 4-OH-Phenyl |
| 792 | 2 | COMe | 4-OH-Phenyl |
| 793 | 3 | COMe | 4-OH-Phenyl |
| 794 | 4 | COMe | 4-OH-Phenyl |
| 795 | 1 | $CO_2Me$ | 4-OH-Phenyl |
| 796 | 2 | $CO_2Me$ | 4-OH-Phenyl |

TABLE 16-continued

| Entry | n | $R^7$ | $R^3$ |
|---|---|---|---|
| 797 | 3 | $CO_2Me$ | 4-OH-Phenyl |
| 798 | 4 | $CO_2Me$ | 4-OH-Phenyl |
| 799 | 1 | $CO_2tBu$ | 4-OH-Phenyl |
| 800 | 2 | $CO_2tBu$ | 4-OH-Phenyl |
| 801 | 3 | $CO_2tBu$ | 4-OH-Phenyl |
| 802 | 4 | $CO_2tBu$ | 4-OH-Phenyl |
| 807 | 1 | $SO_2Me$ | 4-OH-Phenyl |
| 808 | 2 | $SO_2Me$ | 4-OH-Phenyl |
| 809 | 3 | $SO_2Me$ | 4-OH-Phenyl |
| 810 | 4 | $SO_2Me$ | 4-OH-Phenyl |
| 815 | 1 | H | 2-OH-Phenyl |
| 816 | 2 | H | 2-OH-Phenyl |
| 817 | 3 | H | 2-OH-Phenyl |
| 818 | 4 | H | 2-OH-Phenyl |
| 827 | 1 | COMe | 2-OH-Phenyl |
| 828 | 2 | COMe | 2-OH-Phenyl |
| 829 | 3 | COMe | 2-OH-Phenyl |
| 830 | 4 | COMe | 2-OH-Phenyl |
| 831 | 1 | $CO_2Me$ | 2-OH-Phenyl |
| 832 | 2 | $CO_2Me$ | 2-OH-Phenyl |
| 833 | 3 | $CO_2Me$ | 2-OH-Phenyl |
| 834 | 4 | $CO_2Me$ | 2-OH-Phenyl |
| 835 | 1 | $CO_2tBu$ | 2-OH-Phenyl |
| 836 | 2 | $CO_2tBu$ | 2-OH-Phenyl |
| 837 | 3 | $CO_2tBu$ | 2-OH-Phenyl |
| 838 | 4 | $CO_2tBu$ | 2-OH-Phenyl |
| 843 | 1 | $SO_2Me$ | 2-OH-Phenyl |
| 844 | 2 | $SO_2Me$ | 2-OH-Phenyl |
| 845 | 3 | $SO_2Me$ | 2-OH-Phenyl |
| 846 | 4 | $SO_2Me$ | 2-OH-Phenyl |
| 863 | 1 | COMe | 4-OMe-Phenyl |
| 864 | 2 | COMe | 4-OMe-Phenyl |
| 865 | 3 | COMe | 4-OMe-Phenyl |
| 866 | 4 | COMe | 4-OMe-Phenyl |
| 867 | 1 | $CO_2Me$ | 4-OMe-Phenyl |
| 868 | 2 | $CO_2Me$ | 4-OMe-Phenyl |
| 869 | 3 | $CO_2Me$ | 4-OMe-Phenyl |
| 870 | 4 | $CO_2Me$ | 4-OMe-Phenyl |
| 871 | 1 | $CO_2tBu$ | 4-OMe-Phenyl |
| 872 | 2 | $CO_2tBu$ | 4-OMe-Phenyl |
| 873 | 3 | $CO_2tBu$ | 4-OMe-Phenyl |
| 874 | 4 | $CO_2tBu$ | 4-OMe-Phenyl |
| 879 | 1 | $SO_2Me$ | 4-OMe-Phenyl |
| 880 | 2 | $SO_2Me$ | 4-OMe-Phenyl |
| 881 | 3 | $SO_2Me$ | 4-OMe-Phenyl |
| 882 | 4 | $SO_2Me$ | 4-OMe-Phenyl |
| 887 | 1 | H | 2-OMe-Phenyl |
| 888 | 2 | H | 2-OMe-Phenyl |
| 889 | 3 | H | 2-OMe-Phenyl |
| 890 | 4 | H | 2-OMe-Phenyl |
| 899 | 1 | COMe | 2-OMe-Phenyl |
| 900 | 2 | COMe | 2-OMe-Phenyl |
| 901 | 3 | COMe | 2-OMe-Phenyl |
| 902 | 4 | COMe | 2-OMe-Phenyl |
| 903 | 1 | $CO_2Me$ | 2-OMe-Phenyl |
| 904 | 2 | $CO_2Me$ | 2-OMe-Phenyl |
| 905 | 3 | $CO_2Me$ | 2-OMe-Phenyl |
| 906 | 4 | $CO_2Me$ | 2-OMe-Phenyl |
| 907 | 1 | $CO_2tBu$ | 2-OMe-Phenyl |
| 908 | 2 | $CO_2tBu$ | 2-OMe-Phenyl |
| 909 | 3 | $CO_2tBu$ | 2-OMe-Phenyl |
| 910 | 4 | $CO_2tBu$ | 2-OMe-Phenyl |
| 915 | 1 | $SO_2Me$ | 2-OMe-Phenyl |
| 916 | 2 | $SO_2Me$ | 2-OMe-Phenyl |
| 917 | 3 | $SO_2Me$ | 2-OMe-Phenyl |
| 918 | 4 | $SO_2Me$ | 2-OMe-Phenyl |
| 923 | 1 | H | 3-CN-Phenyl |
| 924 | 2 | H | 3-CN-Phenyl |
| 925 | 3 | H | 3-CN-Phenyl |
| 926 | 4 | H | 3-CN-Phenyl |
| 935 | 1 | COMe | 3-CN-Phenyl |
| 936 | 2 | COMe | 3-CN-Phenyl |
| 937 | 3 | COMe | 3-CN-Phenyl |
| 938 | 4 | COMe | 3-CN-Phenyl |
| 939 | 1 | $CO_2Me$ | 3-CN-Phenyl |
| 940 | 2 | $CO_2Me$ | 3-CN-Phenyl |
| 941 | 3 | $CO_2Me$ | 3-CN-Phenyl |
| 942 | 4 | $CO_2Me$ | 3-CN-Phenyl |

TABLE 16-continued

| Entry | n | $R^7$ | $R^3$ |
|---|---|---|---|
| 943 | 1 | $CO_2tBu$ | 3-CN-Phenyl |
| 944 | 2 | $CO_2tBu$ | 3-CN-Phenyl |
| 945 | 3 | $CO_2tBu$ | 3-CN-Phenyl |
| 946 | 4 | $CO_2tBu$ | 3-CN-Phenyl |
| 951 | 1 | $SO_2Me$ | 3-CN-Phenyl |
| 952 | 2 | $SO_2Me$ | 3-CN-Phenyl |
| 953 | 3 | $SO_2Me$ | 3-CN-Phenyl |
| 954 | 4 | $SO_2Me$ | 3-CN-Phenyl |
| 959 | 1 | H | 2-Me-Phenyl |
| 960 | 2 | H | 2-Me-Phenyl |
| 961 | 3 | H | 2-Me-Phenyl |
| 962 | 4 | H | 2-Me-Phenyl |
| 971 | 1 | COMe | 2-Me-Phenyl |
| 972 | 2 | COMe | 2-Me-Phenyl |
| 973 | 3 | COMe | 2-Me-Phenyl |
| 974 | 4 | COMe | 2-Me-Phenyl |
| 975 | 1 | $CO_2Me$ | 2-Me-Phenyl |
| 976 | 2 | $CO_2Me$ | 2-Me-Phenyl |
| 977 | 3 | $CO_2Me$ | 2-Me-Phenyl |
| 978 | 4 | $CO_2Me$ | 2-CN-Phenyl |
| 979 | 1 | $CO_2tBu$ | 2-Me-Phenyl |
| 980 | 2 | $CO_2tBu$ | 2-Me-Phenyl |
| 981 | 3 | $CO_2tBu$ | 2-Me-Phenyl |
| 982 | 4 | $CO_2tBu$ | 2-Me-Phenyl |
| 987 | 1 | $SO_2Me$ | 2-Me-Phenyl |
| 988 | 2 | $SO_2Me$ | 2-Me-Phenyl |
| 989 | 3 | $SO_2Me$ | 2-Me-Phenyl |
| 990 | 4 | $SO_2Me$ | 2-Me-Phenyl |
| 995 | 1 | H | 4-Me-Phenyl |
| 996 | 2 | H | 4-Me-Phenyl |
| 997 | 3 | H | 4-Me-Phenyl |
| 998 | 4 | H | 4-Me-Phenyl |
| 1007 | 1 | COMe | 4-Me-Phenyl |
| 1008 | 2 | COMe | 4-Me-Phenyl |
| 1009 | 3 | COMe | 4-Me-Phenyl |
| 1010 | 4 | COMe | 4-Me-Phenyl |
| 1011 | 1 | $CO_2Me$ | 4-Me-Phenyl |
| 1012 | 2 | $CO_2Me$ | 4-Me-Phenyl |
| 1013 | 3 | $CO_2Me$ | 4-Me-Phenyl |
| 1014 | 4 | $CO_2Me$ | 4-Me-Phenyl |
| 1015 | 1 | $CO_2tBu$ | 4-Me-Phenyl |
| 1016 | 2 | $CO_2tBu$ | 4-Me-Phenyl |
| 1017 | 3 | $CO_2tBu$ | 4-Me-Phenyl |
| 1018 | 4 | $CO_2tBu$ | 4-Me-Phenyl |
| 1023 | 1 | $SO_2Me$ | 4-Me-Phenyl |
| 1024 | 2 | $SO_2Me$ | 4-Me-Phenyl |
| 1025 | 3 | $SO_2Me$ | 4-Me-Phenyl |
| 1026 | 4 | $SO_2Me$ | 4-Me-Phenyl |
| 1031 | 1 | H | 3-F-Phenyl |
| 1032 | 2 | H | 3-F-Phenyl |
| 1033 | 3 | H | 3-F-Phenyl |
| 1034 | 4 | H | 3-F-Phenyl |
| 1044 | 2 | COMe | 3-F-Phenyl |
| 1045 | 3 | COMe | 3-F-Phenyl |
| 1046 | 4 | COMe | 3-F-Phenyl |
| 1047 | 1 | $CO_2Me$ | 3-F-Phenyl |
| 1048 | 2 | $CO_2Me$ | 3-F-Phenyl |
| 1049 | 3 | $CO_2Me$ | 3-F-Phenyl |
| 1050 | 4 | $CO_2Me$ | 3-F-Phenyl |
| 1051 | 1 | $CO_2tBu$ | 3-F-Phenyl |
| 1052 | 2 | $CO_2tBu$ | 3-F-Phenyl |
| 1053 | 3 | $CO_2tBu$ | 3-F-Phenyl |
| 1054 | 4 | $CO_2tBu$ | 3-F-Phenyl |
| 1059 | 1 | $SO_2Me$ | 3-F-Phenyl |
| 1060 | 2 | $SO_2Me$ | 3-F-Phenyl |
| 1061 | 3 | $SO_2Me$ | 3-F-Phenyl |
| 1062 | 4 | $SO_2Me$ | 3-F-Phenyl |
| 1067 | 1 | H | 2-Cl-Phenyl |
| 1068 | 2 | H | 2-Cl-Phenyl |
| 1069 | 3 | H | 2-Cl-Phenyl |
| 1070 | 4 | H | 2-Cl-Phenyl |
| 1079 | 1 | COMe | 2-Cl-Phenyl |
| 1080 | 2 | COMe | 2-Cl-Phenyl |
| 1081 | 3 | COMe | 2-Cl-Phenyl |
| 1082 | 4 | COMe | 2-Cl-Phenyl |
| 1083 | 1 | $CO_2Me$ | 2-Cl-Phenyl |
| 1084 | 2 | $CO_2Me$ | 2-Cl-Phenyl |
| 1085 | 3 | $CO_2Me$ | 2-Cl-Phenyl |

TABLE 16-continued

| Entry | n | $R^7$ | $R^3$ |
|---|---|---|---|
| 1086 | 4 | $CO_2Me$ | 2-Cl-Phenyl |
| 1087 | 1 | $CO_2tBu$ | 2-Cl-Phenyl |
| 1088 | 2 | $CO_2tBu$ | 2-Cl-Phenyl |
| 1089 | 3 | $CO_2tBu$ | 2-Cl-Phenyl |
| 1090 | 4 | $CO_2tBu$ | 2-Cl-Phenyl |
| 1095 | 1 | $SO_2Me$ | 2-Cl-Phenyl |
| 1096 | 2 | $SO_2Me$ | 2-Cl-Phenyl |
| 1097 | 3 | $SO_2Me$ | 2-Cl-Phenyl |
| 1098 | 4 | $SO_2Me$ | 2-Cl-Phenyl |
| 1103 | 1 | H | 4-Cl-Phenyl |
| 1104 | 2 | H | 4-Cl-Phenyl |
| 1105 | 3 | H | 4-Cl-Phenyl |
| 1106 | 4 | H | 4-Cl-Phenyl |
| 1115 | 1 | COMe | 4-Cl-Phenyl |
| 1116 | 2 | COMe | 4-Cl-Phenyl |
| 1117 | 3 | COMe | 4-Cl-Phenyl |
| 1118 | 4 | COMe | 4-Cl-Phenyl |
| 1119 | 1 | $CO_2Me$ | 4-Cl-Phenyl |
| 1120 | 2 | $CO_2Me$ | 4-Cl-Phenyl |
| 1121 | 3 | $CO_2Me$ | 4-Cl-Phenyl |
| 1122 | 4 | $CO_2Me$ | 4-Cl-Phenyl |
| 1123 | 1 | $CO_2tBu$ | 4-Cl-Phenyl |
| 1124 | 2 | $CO_2tBu$ | 4-Cl-Phenyl |
| 1125 | 3 | $CO_2tBu$ | 4-Cl-Phenyl |
| 1126 | 4 | $CO_2tBu$ | 4-Cl-Phenyl |
| 1131 | 1 | $SO_2Me$ | 4-Cl-Phenyl |
| 1132 | 2 | $SO_2Me$ | 4-Cl-Phenyl |
| 1133 | 3 | $SO_2Me$ | 4-Cl-Phenyl |
| 1134 | 4 | $SO_2Me$ | 4-Cl-Phenyl |
| 1139 | 1 | H | 3-Br-Phenyl |
| 1140 | 2 | H | 3-Br-Phenyl |
| 1141 | 3 | H | 3-Br-Phenyl |
| 1142 | 4 | H | 3-Br-Phenyl |
| 1151 | 1 | COMe | 3-Br-Phenyl |
| 1152 | 2 | COMe | 3-Br-Phenyl |
| 1153 | 3 | COMe | 3-Br-Phenyl |
| 1154 | 4 | COMe | 3-Br-Phenyl |
| 1155 | 1 | $CO_2Me$ | 3-Br-Phenyl |
| 1156 | 2 | $CO_2Me$ | 3-Br-Phenyl |
| 1157 | 3 | $CO_2Me$ | 3-Br-Phenyl |
| 1158 | 4 | $CO_2Me$ | 3-Br-Phenyl |
| 1159 | 1 | $CO_2tBu$ | 3-Br-Phenyl |
| 1160 | 2 | $CO_2tBu$ | 3-Br-Phenyl |
| 1161 | 3 | $CO_2tBu$ | 3-Br-Phenyl |
| 1162 | 4 | $CO_2tBu$ | 3-Br-Phenyl |
| 1167 | 1 | $SO_2Me$ | 3-Br-Phenyl |
| 1168 | 2 | $SO_2Me$ | 3-Br-Phenyl |
| 1169 | 3 | $SO_2Me$ | 3-Br-Phenyl |
| 1170 | 4 | $SO_2Me$ | 3-Br-Phenyl |
| 1175 | 1 | H | 3-$CF_3$-Phenyl |
| 1176 | 2 | H | 3-$CF_3$-Phenyl |
| 1177 | 3 | H | 3-$CF_3$-Phenyl |
| 1178 | 4 | H | 3-$CF_3$-Phenyl |
| 1187 | 1 | COMe | 3-$CF_3$-Phenyl |
| 1188 | 2 | COMe | 3-$CF_3$-Phenyl |
| 1189 | 3 | COMe | 3-$CF_3$-Phenyl |
| 1190 | 4 | COMe | 3-$CF_3$-Phenyl |
| 1191 | 1 | $CO_2Me$ | 3-$CF_3$-Phenyl |
| 1192 | 2 | $CO_2Me$ | 3-$CF_3$-Phenyl |
| 1193 | 3 | $CO_2Me$ | 3-$CF_3$-Phenyl |
| 1194 | 4 | $CO_2Me$ | 3-$CF_3$-Phenyl |
| 1195 | 1 | $CO_2tBu$ | 3-$CF_3$-Phenyl |
| 1196 | 2 | $CO_2tBu$ | 3-$CF_3$-Phenyl |
| 1197 | 3 | $CO_2tBu$ | 3-$CF_3$-Phenyl |
| 1198 | 4 | $CO_2tBu$ | 3-$CF_3$-Phenyl |
| 1203 | 1 | $SO_2Me$ | 3-$CF_3$-Phenyl |
| 1204 | 2 | $SO_2Me$ | 3-$CF_3$-Phenyl |
| 1205 | 3 | $SO_2Me$ | 3-$CF_3$-Phenyl |
| 1206 | 4 | $SO_2Me$ | 3-$CF_3$-Phenyl |
| 1211 | 1 | H | 3-$CF_3$-Phenyl |
| 1212 | 2 | H | 3-$CF_3$-Phenyl |
| 1213 | 3 | H | 3-$CF_3$-Phenyl |
| 1214 | 4 | H | 3-$CF_3$-Phenyl |
| 1223 | 1 | COMe | 3-$CF_3$-Phenyl |
| 1224 | 2 | COMe | 3-$CF_3$-Phenyl |
| 1225 | 3 | COMe | 3-$CF_3$-Phenyl |
| 1226 | 4 | COMe | 3-$CF_3$-Phenyl |
| 1227 | 1 | $CO_2Me$ | 3-$CF_3$-Phenyl |

TABLE 16-continued

| Entry | n | $R^7$ | $R^3$ |
|---|---|---|---|
| 1228 | 2 | $CO_2Me$ | 3-$CF_3$-Phenyl |
| 1229 | 3 | $CO_2Me$ | 3-$CF_3$-Phenyl |
| 1230 | 4 | $CO_2Me$ | 3-$CF_3$-Phenyl |
| 1231 | 1 | $CO_2tBu$ | 3-$CF_3$-Phenyl |
| 1232 | 2 | $CO_2tBu$ | 3-$CF_3$-Phenyl |
| 1233 | 3 | $CO_2tBu$ | 3-$CF_3$-Phenyl |
| 1234 | 4 | $CO_2tBu$ | 3-$CF_3$-Phenyl |
| 1239 | 1 | $SO_2Me$ | 3-$CF_3$-Phenyl |
| 1240 | 2 | $SO_2Me$ | 3-$CF_3$-Phenyl |
| 1241 | 3 | $SO_2Me$ | 3-$CF_3$-Phenyl |
| 1242 | 4 | $SO_2Me$ | 3-$CF_3$-Phenyl |
| 1247 | 1 | H | 3-iPr-Phenyl |
| 1248 | 2 | H | 3-iPr-Phenyl |
| 1249 | 3 | H | 3-iPr-Phenyl |
| 1250 | 4 | H | 3-iPr-Phenyl |
| 1259 | 1 | COMe | 3-iPr-Phenyl |
| 1260 | 2 | COMe | 3-iPr-Phenyl |
| 1261 | 3 | COMe | 3-iPr-Phenyl |
| 1262 | 4 | COMe | 3-iPr-Phenyl |
| 1263 | 1 | $CO_2Me$ | 3-iPr-Phenyl |
| 1264 | 2 | $CO_2Me$ | 3-iPr-Phenyl |
| 1265 | 3 | $CO_2Me$ | 3-iPr-Phenyl |
| 1266 | 4 | $CO_2Me$ | 3-iPr-Phenyl |
| 1267 | 1 | $CO_2tBu$ | 3-iPr-Phenyl |
| 1268 | 2 | $CO_2tBu$ | 3-iPr-Phenyl |
| 1269 | 3 | $CO_2tBu$ | 3-iPr-Phenyl |
| 1270 | 4 | $CO_2tBu$ | 3-iPr-Phenyl |
| 1275 | 1 | $SO_2Me$ | 3-iPr-Phenyl |
| 1276 | 2 | $SO_2Me$ | 3-iPr-Phenyl |
| 1277 | 3 | $SO_2Me$ | 3-iPr-Phenyl |
| 1278 | 4 | $SO_2Me$ | 3-iPr-Phenyl |
| 1355 | 1 | H | 2,6-di-Me-Phenyl |
| 1356 | 2 | H | 2,6-di-Me-Phenyl |
| 1357 | 3 | H | 2,6-di-Me-Phenyl |
| 1358 | 4 | H | 2,6-di-Me-Phenyl |
| 1367 | 1 | COMe | 2,6-di-Me-Phenyl |
| 1368 | 2 | COMe | 2,6-di-Me-Phenyl |
| 1369 | 3 | COMe | 2,6-di-Me-Phenyl |
| 1370 | 4 | COMe | 2,6-di-Me-Phenyl |
| 1371 | 1 | $CO_2Me$ | 2,6-di-Me-Phenyl |
| 1372 | 2 | $CO_2Me$ | 2,6-di-Me-Phenyl |
| 1373 | 3 | $CO_2Me$ | 2,6-di-Me-Phenyl |
| 1374 | 4 | $CO_2Me$ | 2,6-di-Me-Phenyl |
| 1375 | 1 | $CO_2tBu$ | 2,6-di-Me-Phenyl |
| 1376 | 2 | $CO_2tBu$ | 2,6-di-Me-Phenyl |
| 1377 | 3 | $CO_2tBu$ | 2,6-di-Me-Phenyl |
| 1378 | 4 | $CO_2tBu$ | 2,6-di-Me-Phenyl |
| 1383 | 1 | $SO_2Me$ | 2,6-di-Me-Phenyl |
| 1384 | 2 | $SO_2Me$ | 2,6-di-Me-Phenyl |
| 1385 | 3 | $SO_2Me$ | 2,6-di-Me-Phenyl |
| 1386 | 4 | $SO_2Me$ | 2,6-di-Me-Phenyl |
| 1463 | 1 | H | 3-morpholino-phenyl |
| 1464 | 2 | H | 3-morpholino-phenyl |
| 1465 | 3 | H | 3-morpholino-phenyl |
| 1466 | 4 | H | 3-morpholino-phenyl |
| 1475 | 1 | COMe | 3-morpholino-phenyl |
| 1476 | 2 | COMe | 3-morpholino-phenyl |
| 1477 | 3 | COMe | 3-morpholino-phenyl |
| 1478 | 4 | COMe | 3-morpholino-phenyl |
| 1479 | 1 | $CO_2Me$ | 3-morpholino-phenyl |
| 1480 | 2 | $CO_2Me$ | 3-morpholino-phenyl |
| 1481 | 3 | $CO_2Me$ | 3-morpholino-phenyl |
| 1482 | 4 | $CO_2Me$ | 3-morpholino-phenyl |
| 1483 | 1 | $CO_2tBu$ | 3-morpholino-phenyl |
| 1484 | 2 | $CO_2tBu$ | 3-morpholino-phenyl |
| 1485 | 3 | $CO_2tBu$ | 3-morpholino-phenyl |
| 1486 | 4 | $CO_2tBu$ | 3-morpholino-phenyl |
| 1491 | 1 | $SO_2Me$ | 3-morpholino-phenyl |
| 1492 | 2 | $SO_2Me$ | 3-morpholino-phenyl |
| 1493 | 3 | $SO_2Me$ | 3-morpholino-phenyl |
| 1494 | 4 | $SO_2Me$ | 3-morpholino-phenyl |
| 1503 | 1 | COMe | 4-morpholino-phenyl |
| 1504 | 2 | COMe | 4-morpholino-phenyl |
| 1505 | 3 | COMe | 4-morpholino-phenyl |
| 1506 | 4 | COMe | 4-morpholino-phenyl |
| 1507 | 1 | $CO_2tBu$ | 4-morpholino-phenyl |
| 1508 | 2 | $CO_2tBu$ | 4-morpholino-phenyl |
| 1509 | 3 | $CO_2tBu$ | 4-morpholino-phenyl |

TABLE 16-continued

| Entry | n | $R^7$ | $R^3$ |
|---|---|---|---|
| 1510 | 4 | $CO_2tBu$ | 4-morpholino-phenyl |
| 1511 | 1 | $SO_2Me$ | 4-morpholino-phenyl |
| 1512 | 2 | $SO_2Me$ | 4-morpholino-phenyl |
| 1513 | 3 | $SO_2Me$ | 4-morpholino-phenyl |
| 1514 | 4 | $SO_2Me$ | 4-morpholino-phenyl |

or a pharmaceutically acceptable salt thereof.

18. The compound of claim 1, wherein the compound is selected from the compounds described in Tables 37 or 38:

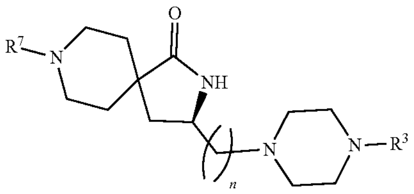

(XLIV)

TABLE 37

| n | $R^3$ | $R^7$ |
|---|---|---|
| 2 | 3-Cl-Phenyl | Acetyl |
| 2 | 4-F-Phenyl | Acetyl |
| 2 | 4-F-Phenyl | $MeSO_2$ |
| 2 | 3-Cl-Phenyl | $MeSO_2$ |
| 3 | 3-Cl-Phenyl | $MeSO_2$ |
| 3 | 4-F-Phenyl | $MeSO_2$ |

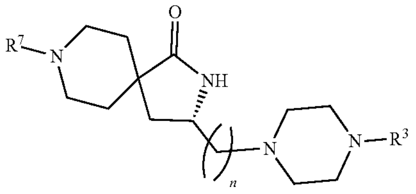

(XLV)

TABLE 38

| n | $R^3$ | $R^7$ |
|---|---|---|
| 2 | 3-Cl-Phenyl | $MeSO_2$ |
| 2 | 4-F-Phenyl | $MeSO_2$ |
| 2 | 3-Cl-Phenyl | Acetyl |
| 2 | 4-F-Phenyl | Acetyl |

or a pharmaceutically acceptable salt thereof.

19. The compound of claim 2, wherein the compound is selected from the compounds described in any one of Tables 34-36:

(XLI)

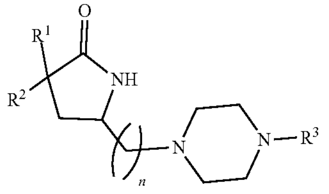

TABLE 34

| n | $R^1$ | $R^2$ | $R^3$ |
|---|---|---|---|
| 2 | Ethyl | Ethyl | 4-F-Phenyl |
| 2 | Ethyl | Ethyl | 4-Cl-Phenyl |
| 2 | Ethyl | Ethyl | 2-iPr-phenyl |
| 2 | Ethyl | Ethyl | 2-morpholino-phenyl |
| 2 | Ethyl | Ethyl | 4-Me-Phenyl |
| 2 | Ethyl | Ethyl | 4-OH-Phenyl |
| 2 | Ethyl | Ethyl | Phenyl |
| 2 | Ethyl | Ethyl | 4-Me-2-morpholino-phenyl |

(XLII)

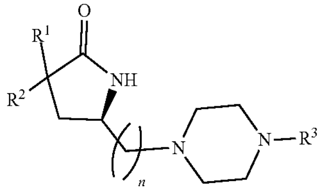

TABLE 35

| n | $R^1$ | $R^2$ | $R^3$ |
|---|---|---|---|
| 1 | Ethyl | Ethyl | 2-iPr-phenyl |
| 1 | Ethyl | Ethyl | 4-Me-2-morpholino-phenyl |

TABLE 35-continued

| n | $R^1$ | $R^2$ | $R^3$ |
|---|---|---|---|
| 1 | Ethyl | Ethyl | 4-F-Phenyl |
| 1 | Ethyl | Ethyl | 4-Me-Phenyl |
| 1 | Ethyl | Ethyl | Phenyl |
| 1 | Ethyl | Ethyl | 3-Cl-Phenyl |
| 2 | Ethyl | Ethyl | 4-Me-Phenyl |
| 2 | Ethyl | Ethyl | 4-F-Phenyl |
| 2 | Ethyl | Ethyl | 3,4-di-Cl-Phenyl |
| 2 | Ethyl | Ethyl | 4-F-3-Cl-Phenyl |
| 2 | Ethyl | Ethyl | 3-Cl-Phenyl |
| 2 | Ethyl | Ethyl | Phenyl |
| 2 | Ethyl | Ethyl | 2-Cl-Phenyl |
| 2 | Ethyl | Ethyl | 3-F-Phenyl |
| 2 | Ethyl | Ethyl | 2-Me-Phenyl |
| 2 | Ethyl | Ethyl | 3-Me-Phenyl |
| 2 | Ethyl | Ethyl | 2-OMe-Phenyl |
| 2 | Ethyl | Ethyl | 4-CN-Phenyl |
| 2 | Ethyl | Ethyl | 4-$CF_3$-Phenyl |

(XLIII)

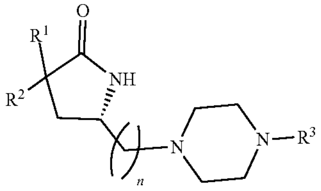

TABLE 36

| n | $R^1$ | $R^2$ | $R^3$ |
|---|---|---|---|
| 2 | Ethyl | Ethyl | 4-Me-Phenyl |

or a pharmaceutically acceptable salt thereof.

* * * * *